US012630533B2

(12) United States Patent
Stock et al.

(10) Patent No.: US 12,630,533 B2

(45) Date of Patent: May 19, 2026

(54) HETEROCYCLIC COMPOUNDS USEFUL AS KCNT1 INHIBITORS

(71) Applicant: Actio Biosciences, Inc., San Diego, CA (US)

(72) Inventors: Nicholas Simon Stock, Encinitas, CA (US); Steven Govek, San Diego, CA (US); Ashley Katana, Fairview Park, OH (US)

(73) Assignee: Actio Biosciences, Inc., San Diego, CA (US)

(*) Notice: Subject to any disclaimer, the term of this patent is extended or adjusted under 35 U.S.C. 154(b) by 0 days.

(21) Appl. No.: 19/242,489

(22) Filed: Jun. 18, 2025

(65) Prior Publication Data

US 2025/0313548 A1 Oct. 9, 2025

Related U.S. Application Data

(63) Continuation of application No. PCT/US2024/057646, filed on Nov. 27, 2024.

(60) Provisional application No. 63/553,526, filed on Feb. 14, 2024, provisional application No. 63/604,173, filed on Nov. 29, 2023.

(51) Int. Cl.

| | |
|---|---|
| ***C07D 401/14*** | (2006.01) |
| ***A61K 31/422*** | (2006.01) |
| ***A61K 31/4245*** | (2006.01) |
| ***A61K 31/437*** | (2006.01) |
| ***A61K 31/4439*** | (2006.01) |
| ***A61K 31/444*** | (2006.01) |
| ***A61K 31/4709*** | (2006.01) |
| ***A61K 31/4725*** | (2006.01) |
| ***A61K 31/497*** | (2006.01) |
| ***A61K 31/498*** | (2006.01) |
| ***A61K 31/501*** | (2006.01) |
| ***A61K 31/502*** | (2006.01) |
| ***A61K 31/5025*** | (2006.01) |
| ***A61K 31/506*** | (2006.01) |
| ***A61K 31/517*** | (2006.01) |
| ***A61K 31/519*** | (2006.01) |
| ***A61K 31/5365*** | (2006.01) |
| ***A61K 31/55*** | (2006.01) |
| ***C07D 401/04*** | (2006.01) |
| ***C07D 409/14*** | (2006.01) |
| ***C07D 413/04*** | (2006.01) |
| ***C07D 413/14*** | (2006.01) |
| ***C07D 417/14*** | (2006.01) |
| ***C07D 471/04*** | (2006.01) |
| ***C07D 487/04*** | (2006.01) |
| ***C07D 519/00*** | (2006.01) |

(52) U.S. Cl.

CPC .......... *C07D 401/14* (2013.01); *A61K 31/422* (2013.01); *A61K 31/4245* (2013.01); *A61K 31/437* (2013.01); *A61K 31/4439* (2013.01); *A61K 31/444* (2013.01); *A61K 31/4709* (2013.01); *A61K 31/4725* (2013.01); *A61K 31/497* (2013.01); *A61K 31/498* (2013.01); *A61K 31/501* (2013.01); *A61K 31/502* (2013.01); *A61K 31/5025* (2013.01); *A61K 31/506* (2013.01); *A61K 31/517* (2013.01); *A61K 31/519* (2013.01); *A61K 31/5365* (2013.01); *A61K 31/55* (2013.01); *C07D 401/04* (2013.01); *C07D 409/14* (2013.01); *C07D 413/04* (2013.01); *C07D 413/14* (2013.01); *C07D 417/14* (2013.01); *C07D 471/04* (2013.01); *C07D 487/04* (2013.01); *C07D 519/00* (2013.01)

(58) Field of Classification Search

None

See application file for complete search history.

(56) References Cited

U.S. PATENT DOCUMENTS

| | | | |
|---|---|---|---|
| 5,034,311 | A | 7/1991 | Slusarek et al. |
| 8,378,096 | B2 | 2/2013 | Liotta et al. |
| 10,765,116 | B2 | 9/2020 | Kausch-Busies et al. |
| 2007/0043057 | A1 | 2/2007 | Matteucci et al. |
| 2009/0099143 | A1 | 4/2009 | Lagu et al. |
| 2010/0009969 | A1 | 1/2010 | Denonne et al. |
| 2022/0259193 | A1 | 8/2022 | Martinez Botella et al. |
| 2022/0280476 | A1 | 9/2022 | Martinez Botella et al. |
| 2023/0234940 | A1 | 7/2023 | Lee et al. |
| 2023/0348416 | A1 | 11/2023 | Bucknell et al. |
| 2024/0000951 | A1 | 1/2024 | Ryu et al. |
| 2024/0317711 | A1 | 9/2024 | Ryu et al. |

FOREIGN PATENT DOCUMENTS

| | | | |
|---|---|---|---|
| CN | 104016979 | A | 9/2014 |
| CN | 106749193 | A | 5/2017 |
| DE | 19518054 | A1 | 9/1996 |
| JP | 2011-246389 | A | 12/2011 |
| JP | 5765229 | B2 | 8/2015 |
| WO | WO-2001/025241 | A2 | 4/2001 |

(Continued)

OTHER PUBLICATIONS

WO 2023/244788 A1 pp. 1-126 (Year: 2023).*

(Continued)

*Primary Examiner* — Adam C Milligan

*Assistant Examiner* — Jed A Kucharczk

(74) *Attorney, Agent, or Firm* — Choate, Hall & Stewart LLP; Kristen C. Buteau

(57) ABSTRACT

The present disclosure provides compounds and pharmaceutical compositions thereof, and methods of using the same.

30 Claims, No Drawings

(56) References Cited

FOREIGN PATENT DOCUMENTS

| | | | | | |
|---|---|---|---|---|---|
| WO | WO-2003/048155 | A1 | | 6/2003 | |
| WO | WO-2006/057946 | A2 | | 6/2006 | |
| WO | WO-2006/065233 | A1 | | 6/2006 | |
| WO | WO-2007/011626 | A2 | | 1/2007 | |
| WO | WO-2007/038036 | A1 | | 4/2007 | |
| WO | WO-2008/014307 | A2 | | 1/2008 | |
| WO | WO-2008/089307 | A2 | | 7/2008 | |
| WO | WO-2008/115671 | A1 | | 9/2008 | |
| WO | WO-2008/115705 | A2 | | 9/2008 | |
| WO | WO-2008/115705 | A3 | | 1/2009 | |
| WO | WO-2010/045764 | A1 | | 4/2010 | |
| WO | WO-2011/043254 | A1 | | 4/2011 | |
| WO | WO-2011/097717 | A1 | | 8/2011 | |
| WO | WO-2012/006958 | A1 | | 1/2012 | |
| WO | WO-2012/020131 | A2 | | 2/2012 | |
| WO | WO-2012/020133 | A1 | | 2/2012 | |
| WO | WO-2012/076639 | A1 | | 6/2012 | |
| WO | WO-2014/089324 | A1 | | 6/2014 | |
| WO | WO-2014/165263 | A1 | | 10/2014 | |
| WO | WO-2015/187542 | A1 | | 12/2015 | |
| WO | WO-2017/196982 | A1 | | 11/2017 | |
| WO | WO-2020/236586 | A1 | | 11/2020 | |
| WO | WO-2021/191883 | A1 | | 9/2021 | |
| WO | WO-2021/229583 | A1 | | 11/2021 | |
| WO | WO-2021/247606 | A1 | | 12/2021 | |
| WO | WO-2021/263082 | A2 | | 12/2021 | |
| WO | WO-2022/119362 | A1 | | 6/2022 | |
| WO | WO-2022/270987 | A1 | | 12/2022 | |
| WO | WO-2023/018682 | A1 | | 2/2023 | |
| WO | WO-2023244788 | A1 | * | 12/2023 | ........... C07D 513/04 |
| WO | WO-2025/117662 | A1 | | 6/2025 | |

OTHER PUBLICATIONS

International Search Report for PCT/US2024/057646, 4 pages, (mailed Mar. 17, 2025).

Qunies, A.M. and Emmitte, K.A., Small-Molecule Inhibitors of Slack Potassium Channels As Potential Therapeutics for Childhood Epilepsies, Pharmaceutical Patent Analysis, 11(2):45-56 (2022).

Written Opinion for PCT/US2024/057646, 7 pages, (mailed Mar. 17, 2025).

Defendants' Opening Brief in Support of Motion to Dismiss Plaintiff's Complaint Under Fed. R. Civ. P. 12(b)(1) and/or 12(b)(6), *Praxis Precision Medicines, Inc*., v. *David B. Goldstein and Actio Biosciences*, C.A. No. 25-1256-RGA, 26 pages, (2025).

Defendants' Reply Brief in Support of Motion to Dismiss Plaintiff's Complaint Under Fed. R. Civ. P. 12(b)(1) and/or 12(b)(6), *Praxis Precision Medicines, Inc*., v. *David B. Goldstein and Actio Biosciences*, C.A. No. 25-1256-RGA, 15 pages, (2026).

Griffin, A.M et al., Discovery of the First Orally Available, Selective KNa1.1 Inhibitor: In Vitro and In Vivo Activity of an Oxadiazole Series, ACS Med. Chem. Lett., 12(4):593-602 (2021).

Plaintiff's Answering Brief in Opposition to Defendant's Motion to Dismiss, *Praxis Precision Medicines, Inc*., v. *David B. Goldstein and Actio Biosciences*, C.A. No. 25-1256-RGA, 26 pages, (2026).

* cited by examiner

HETEROCYCLIC COMPOUNDS USEFUL AS KCNT1 INHIBITORS

BACKGROUND OF THE DISCLOSURE

KCNT1 encodes an outwardly rectifying sodium-activated potassium channel (potassium channel, subfamily T, member 1) commonly known as Slack (Sequence like a calcium-activated $K^+$ channel), or as Slo2.2 or $K_{Ca}4.1$. These channels are expressed in central and peripheral neurons and play an important role in neuronal excitability. Gain of function (GoF) mutations in, KCNT1 that increase channel activity have been associated with certain diseases or conditions for which there are no existing cures.

SUMMARY OF THE DISCLOSURE

Pathogenic mutations in, KCNT1 cause several early onset epilepsies, including epilepsy of infancy with migrating focal seizures (EIMFS) and Autosomal Dominant Nocturnal Frontal Lobe Epilepsy (ADNFLE), now termed Sleep-Related Hypermotor Epilepsy (SHE). In some embodiments, the present disclosure provides the insight that pharmaceutical compounds that selectively modulate abnormal, KCNT1 function are useful in treating a neurological disease, disorder or condition related to excessive neuronal excitability and/or, KCNT1 gain-of-function mutations.

In some embodiments, the present disclosure provides inhibitors of, KCNT1 that are useful for treating conditions requiring modulation of the activity of the potassium channel encoded by, KCNT1. In some embodiments, a condition modulated by, KCNT1 is a neurological disease. In some such embodiments, a neurological disease is associated with one or more, KCNT1 activating mutations. In some embodiments, a neurological disease is selected from epilepsy of infancy with migrating focal seizures (EIMFS), also called migrating focal seizures of infancy (MFSI), and Frontal Lobe Epilepsy, also known as Autosomal Dominant Nocturnal Frontal Lobe Epilepsy (ADNFLE) or Sleep-Related Hypermotor Epilepsy (SHE). In some embodiments, a KCNT1 inhibitor provided herein is useful for treating SHE due to causes other than activating mutations in, KCNT1, including those due to mutations in nicotinic acetylcholine receptor genes or other genetic or non-genetic causes. In some embodiments, a, KCNT1 inhibitor provided herein is useful for treating epilepsy and refractory epilepsy including epileptic encephalopathies, generalized epilepsies, focal epilepsies, and post traumatic epilepsy. In some embodiments, a KCNT1 inhibitor provided herein is useful for treating, among other things, muscle disorders or psychiatric disorders including but not limited to hyperactivity and anxiety. In some embodiments, a neurological disease is a disease that affects a patient who is a child (e.g., a patient who is less than 18 years of age, a patient who is less than or about 12 years of age, or a patient who is less than or about 6 years of age).

In some embodiments, the present disclosure provides a compound of formula I':

I'

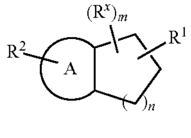

or a pharmaceutically acceptable salt thereof, wherein each of Ring A, $R^1$, $R^2$, $R^x$, m, and n is defined and described herein.

In some embodiments, the present disclosure provides a pharmaceutical composition comprising a compound of formula I or formula I', or a pharmaceutically acceptable salt thereof, and one or more pharmaceutically acceptable excipients, carriers, or diluents.

In some embodiments, the present disclosure provides synthetic intermediates and synthetic processes useful for preparing compounds of formula I or formula I', or a pharmaceutically acceptable salt thereof.

In some embodiments, the present disclosure provides a method of treating a disease associated with aberrant (e.g., loss of function, gain of function, etc.), KCNT1 activity, or a mutant thereof, the method comprising administering to a patient in need thereof a compound of formula I or formula I', or a pharmaceutically acceptable salt thereof.

In some embodiments, the present disclosure provides a method of inhibiting one or more mutants of, KCNT1, the method comprising contacting a biological sample (e.g., a protein, a cell, a sample derived or obtained from a patient, etc.) with a compound of formula I or formula I', or a pharmaceutically acceptable salt thereof.

In some embodiments, the present disclosure provides a method of inhibiting activity of, KCNT1, or a mutant thereof, in a patient comprising the step of administering to said patient a compound of formula I or formula I', or a pharmaceutically acceptable salt thereof.

In some embodiments, the present disclosure provides a compound of formula I or formula I', or a pharmaceutically acceptable salt thereof, for use in medical therapy.

In some embodiments, the present disclosure provides a compound of formula I or formula I', or a pharmaceutically acceptable salt thereof, for the prophylactic or therapeutic treatment of a disease associated with aberrant, KCNT1 activity, or a mutant thereof.

In some embodiments, the present disclosure provides the use of a compound of formula I or formula I', or a pharmaceutically acceptable salt thereof, in the preparation of a medicament useful for treating a disease associated with aberrant, KCNT1 activity, or a mutant thereof in an animal (e.g., a human).

DETAILED DESCRIPTION OF CERTAIN EMBODIMENTS

1. General Description of Compounds of the Disclosure

In certain embodiments, the present disclosure provides a compound of formula I:

I

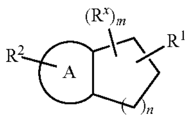

or a pharmaceutically acceptable salt thereof, wherein:

Ring A is a 5- to 6-membered heteroaryl ring having 1-3 heteroatoms independently selected from nitrogen, oxygen, and sulfur;

$R^1$ is selected from

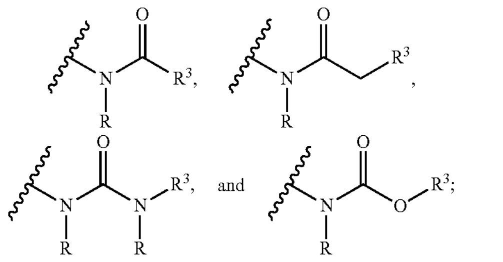

$R^2$ is a 5- to 6-membered heteroaryl ring having 1-3 heteroatoms independently selected from nitrogen, oxygen, and sulfur or a 9- to 10-membered heteroaryl ring having 1-4 heteroatoms independently selected from nitrogen, oxygen, and sulfur, wherein $R^2$ is substituted with 0-3 instances of $R^y$;

$R^3$ is selected from $C_{1-6}$ aliphatic, a 3- to 6-membered saturated or partially unsaturated carbocyclic ring, phenyl, a 10-membered aryl ring, a 5- to 6-membered heteroaryl ring having 1-3 heteroatoms independently selected from nitrogen, oxygen, and sulfur, and a 9- to 10-membered heteroaryl ring having 1-4 heteroatoms independently selected from nitrogen, oxygen, and sulfur, wherein $R^3$ is substituted with 0-4 instances of $R^z$;

each $R^x$ is selected from optionally substituted $C_{1-6}$ aliphatic, —N(R)$_2$, and —OR;

each $R^y$ is independently selected from oxo, —CN, —N(R)$_2$, —OR, —$CO_2$R, or an optionally substituted group selected from $C_{1-4}$ aliphatic and a 3- to 7-membered saturated or partially unsaturated carbocyclic ring;

each $R^z$ is independently selected from —CN, halogen, —OR, —$SO_2$R, and an optionally substituted group selected from $C_{1-6}$ aliphatic and a 3- to 7-membered saturated or partially unsaturated carbocyclic ring;

each R is independently selected from hydrogen or an optionally substituted group selected from $C_{1-6}$ aliphatic, phenyl, a 3- to 7-membered saturated or partially unsaturated carbocyclic ring, a 3- to 7-membered saturated or partially unsaturated heterocyclic ring having 1-3 heteroatoms independently selected from nitrogen, oxygen, and sulfur, and a 5- to 6-membered heteroaryl ring having 1-4 heteroatoms independently selected from nitrogen, oxygen, and sulfur;

m is 0-2; and n is 1-3.

In certain embodiments, the present disclosure provides a compound of formula I':

I'

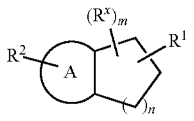

or a pharmaceutically acceptable salt thereof, wherein:

Ring A is a 5- to 6-membered heteroaryl ring having 1-3 heteroatoms independently selected from nitrogen, oxygen, and sulfur;

$R^1$ is selected from

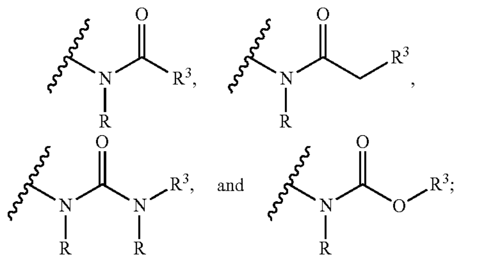

$R^2$ is a 5- to 6-membered heteroaryl ring having 1-3 heteroatoms independently selected from nitrogen, oxygen, and sulfur or a 9- to 10-membered heteroaryl ring having 1-4 heteroatoms independently selected from nitrogen, oxygen, and sulfur, wherein $R^2$ is substituted with 0-3 instances of $R^y$;

$R^3$ is selected from $C_{1-6}$ aliphatic, a 3- to 6-membered saturated or partially unsaturated carbocyclic ring, a 5- to 7-membered bridged bicyclic carbocyclic ring, a 6- to 8-membered spirocyclic carbocyclic ring, phenyl, a 10-membered aryl ring, a 5- to 6-membered heteroaryl ring having 1-3 heteroatoms independently selected from nitrogen, oxygen, and sulfur, and an 8- to 10-membered heteroaryl ring having 1-4 heteroatoms independently selected from nitrogen, oxygen, and sulfur, wherein $R^3$ is substituted with 0-4 instances of $R^z$;

each $R^x$ is selected from optionally substituted $C_{1-6}$ aliphatic, —N(R)$_2$, and —OR;

each $R^y$ is independently selected from oxo, —CN, —N(R)$_2$, —OR, —$CO_2$R, or an optionally substituted group selected from $C_{1-4}$ aliphatic and a 3- to 7-membered saturated or partially unsaturated carbocyclic ring;

each $R^z$ is independently selected from —CN, halogen, —OR, —$SO_2$R, and an optionally substituted group selected from $C_{1-6}$ aliphatic, phenyl, and a 3- to 7-membered saturated or partially unsaturated carbocyclic ring;

each R is independently selected from hydrogen or an optionally substituted group selected from $C_{1-6}$ aliphatic, phenyl, a 3- to 7-membered saturated or partially unsaturated carbocyclic ring, a 3- to 7-membered saturated or partially unsaturated heterocyclic ring having 1-3 heteroatoms independently selected from nitrogen, oxygen, and sulfur, and a 5- to 6-membered heteroaryl ring having 1-4 heteroatoms independently selected from nitrogen, oxygen, and sulfur;

m is 0-2; and n is 1-3.

2. Compounds and Definitions

Compounds of this disclosure include those described generally above, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.:

Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched hydrocarbon chain that is completely saturated or that contains one or more units of unsaturation. Unless otherwise specified, aliphatic groups contain 1-6 carbon atoms. In some embodiments, aliphatic groups contain 1-5 carbon atoms. In other embodiments, aliphatic groups contain 1-4 carbon atoms. In still other embodiments, aliphatic groups contain 1-3 carbon atoms, and in yet other embodiments, aliphatic groups contain 1-2 carbon atoms. Suitable aliphatic groups include, but are not limited to, linear or branched alkyl, alkenyl, and alkynyl.

The term "alkyl" means a monovalent straight-chain (i.e., unbranched) or branched hydrocarbon chain that is completely saturated. Suitable alkyl groups include methyl, ethyl, n-propyl, isopropyl, n-butyl, sec-butyl, iso-butyl, tert-butyl, etc.

The term "alkenyl" means a monovalent straight-chain (i.e., unbranched) or branched hydrocarbon chain that contains at least one carbon-carbon double bond in the chain. Suitable alkenyl groups include vinyl, allyl, 1,3-butadienyl, etc.

The term "alkynyl" means a monovalent straight-chain (i.e., unbranched) or branched hydrocarbon chain that contains at least one carbon-carbon triple bond in the chain. Suitable alkynyl groups include ethynyl (also known as acetylenyl), prop-1-ynyl, etc.

The term "carbocyclic" ("cycloaliphatic", or "carbocycle" or "cycloalkyl") refers to a monocyclic $C_3$-$C_7$ hydrocarbon that is completely saturated or that contains one or more units of unsaturation, but which is not aromatic, where the radical or point of attachment is on the carbocyclic ring.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR (as in

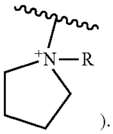

).

The term "unsaturated", as used herein, means that a moiety has one or more units of unsaturation (e.g., a carbon-carbon double bond or a carbon-carbon triple bond).

The term "halogen" means F, Cl, Br, or I.

The term "aryl" refers to monocyclic, bicyclic or tricyclic ring systems having a total of five to fourteen carbon ring members, wherein at least one ring in the system is aromatic and wherein each ring in the system contains three to seven ring members, and where the radical or point of attachment is on the aromatic ring. The term "aryl" may be used interchangeably with the term "aryl ring". In certain embodiments of the present disclosure, "aryl" refers to an aromatic ring system which includes, but is not limited to, phenyl, biphenyl, naphthyl, anthracyl and the like. Examples of aryl rings fused to one or more non-aromatic rings include indanyl, phthalimidyl, naphthimidyl, phenanthridinyl, or tetrahydronaphthyl, and the like, wherein the point of attachment is on the aryl ring.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 $\pi$ electrons shared in a cyclic array, and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaryl ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, and phenoxazinyl. A heteroaryl group may be mono- or bicyclic. The term "heteroaryl" may be used interchangeably with the terms "heteroaryl ring", "heteroaryl group", or "heteroaromatic", any of which terms include rings. The term "heteroaralkyl" refers to an alkyl group substituted by a heteroaryl.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a nitrogen that may bear one or more substituents as context and valency permit. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in

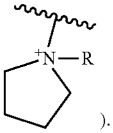

).

A heterocyclic ring can be attached to its pendant group at any heteroatom or carbon atom that results in a stable structure. Examples of such saturated or partially unsaturated heterocyclic radicals include, without limitation, tetrahydrofuranyl, tetrahydrothiophenyl pyrrolidinyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, tetrahydroquinolinyl, or tetrahydroisoquinolinyl, where the radical or point of attachment is on the heterocyclyl ring. A heterocyclyl group may be mono- or bicyclic unless otherwise specified. The term "heterocyclylalkyl" refers to an alkyl group substituted by a heterocyclyl.

As used herein, the term "partially unsaturated" refers to a ring moiety that includes at least one double or triple bond. The term "partially unsaturated" is intended to encompass rings having multiple sites of unsaturation but is not intended to include aryl or heteroaryl moieties, as herein defined.

As described herein, compounds of the disclosure may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R°$; $—(CH_2)_{0-4}OR°$; $—O(CH_2)_{0-4}R°$, $—O—(CH_2)_{0-4}C(O)OR°$; $—(CH_2)_{0-4}CH(OR°)_2$; $—(CH_2)_{0-4}SR°$; $—(CH_2)_{0-4}Ph$, which may be substituted with R°; $—(CH_2)_{0-4}O(CH_2)_{0-1}Ph$ which may be substituted with R°; —CH═CHPh, which may be substituted with R°; $—(CH_2)_{0-4}O(CH_2)_{0-1}$-pyridyl which may be substituted with R°; $—NO_2$; —CN; $—N_3$; $—(CH_2)_{0-4}N(R°)_2$; $—(CH_2)_{0-4}N(R°)C(O)R°$; —N(R°)C(S)R°; $—(CH_2)_{0-4}N(R°)C(O)NR°_2$; $—N(R°)C(S)NR°_2$; $—(CH_2)_{0-4}N(R°)C(O)OR°$; —N(R°)N(R°)C(O)R°; $—N(R°)N(R°)C(O)NR°_2$; —N(R°)N(R°)C(O)OR°; $—(CH_2)_{0-4}C(O)R°$; —C(S)R°; $—(CH_2)_{0-4}C(O)OR°$; $—(CH_2)_{0-4}C(O)SR°$; $—(CH_2)_{0-4}C(O)OSiR°_3$; $—(CH_2)_{0-4}OC(O)R°$; $—OC(O)(CH_2)_{0-4}SR°$, SC(S)SR°; $—(CH_2)_{0-4}SC(O)R°$; $—(CH_2)_{0-4}C(O)NR°_2$; $—C(S)NR°_2$; —C(S)SR°; —SC(S)SR°, $—(CH_2)_{0-4}OC(O)NR°_2$; —C(O)N(OR°)R°; —C(O)C(O)R°; $—C(O)CH_2C(O)R°$; —C(NOR°)R°; $—(CH_2)_{0-4}SSR°$; $—(CH_2)_{0-4}S(O)_2R°$; $—(CH_2)_{0-4}S(O)_2OR°$; $—(CH_2)_{0-4}OS(O)_2R°$; $—S(O)_2NR°_2$; $—(CH_2)_{0-4}S(O)R°$; $—N(R°)S(O)_2NR°_2$; $—N(R°)S(O)_2R°$; —N(OR°)R°; $—C(NH)NR°_2$; $—P(O)_2R°$; $—P(O)R°_2$; $—OP(O)R°_2$; $—OP(O)(OR°)_2$; $SiR°_3$; $—(C_{1-4}$ straight or branched alkylene)O—N(R°)$_2$; or $—(C_{1-4}$ straight or branched alkylene)C(O)O—N(R°)$_2$, wherein each R° may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, $—(CH_2)_{0-2}R^●$, -(haloR$^●$), $—(CH_2)_{0-2}OH$, $—(CH_2)_{0-2}OR^●$, $—(CH_2)_{0-2}CH(OR^●)_2$; —O(haloR$^●$), —CN, $—N_3$, $—(CH_2)_{0-2}C(O)R^●$, $—(CH_2)_{0-2}C(O)OH$, $—(CH_2)_{0-2}C(O)OR^●$, $—(CH_2)_{0-2}SR^●$, $—(CH_2)_{0-2}SH$, $—(CH_2)_{0-2}NH_2$, $—(CH_2)_{0-2}NHR^●$, $—(CH_2)_{0-2}NR^●_2$, $—NO_2$, $—SiR^●_3$, $—OSiR^●_3$, $—C(O)SR^●$, $—(C_{1-4}$ straight or branched alkylene)C(O)OR$^●$, or —SSR$^●$ wherein each R$^●$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O, ═S, $═NNR^●_2$, ═NNHC(O)R*, ═NNHC(O)OR*, $═NNHS(O)_2R*$, ═NR*, ═NOR*, $—O(C(R*_2))_{2-3}O—$, or $—S(C(R*_2))_{2-3}S—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR*_2)_{2-3}O—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $—R^●$, -(haloR$^●$), —OH, $—OR^●$, —O(haloR$^●$), —CN, —C(O)OH, $—C(O)OR^●$, $—NH_2$, $—NHR^●$, $–NR^●_2$, or $—NO_2$, wherein each R$^●$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $—R^†$, $–NR^†_2$, $—C(O)R^†$, —C(O)OR†, $—C(O)C(O)R^†$, $—C(O)CH_2C(O)R^†$, $—S(O)_2R^†$, $—S(O)_2NR^†_2$, $—C(S)NR^†_2$, $—C(NH)NR^†_2$, or $—N(R^†)S(O)_2R^†$; wherein each RT is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R\ are independently halogen, $—R^●$, -(haloR$^●$), —OH, $—OR^●$, —O(haloR$^●$), —CN, —C(O)OH, $—C(O)OR^●$, $—NH_2$, $—NHR^●$, $–NR^●_2$, or $—NO_2$, wherein each R$^●$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. When a bond in a compound or formula provided herein is drawn in a non-stereochemical manner (e.g., flat), the atom to which the bond is attached includes all stereochemical possibilities. Bold-rectangles () and dashed-rectangles () designate relative stereochemistry. When a bond in a compound or formula provided herein is drawn as a bold-wedge () or a dashed-wedge (), it is to be understood that the atom to which the bond is attached has the stereochemistry as designated and the compound is said to have absolute stereochemistry. In some embodiments, the present disclosure provides a composition comprising a mixture of two stereoisomers of a compound. A composition that comprises a 50:50 mixture of two stereoisomers is a racemic mixture. In some embodiments, the present disclosure provides a racemic mixture of two stereoisomeric compounds. In some embodiments, a composition comprising a mixture of two stereoisomers is said to be enriched when the composition comprises a greater amount of one stereoisomer. In some embodiments, the composition is enriched by at least 51% of the absolute stereoisomer depicted. In some embodiments, the composition is enriched by at least 60% of the absolute stereoisomer depicted. In some embodiments, the composition is enriched by at least 80% of the absolute stereoisomer depicted. In some embodiments, the composition is enriched by at least 90% of the absolute stereoisomer depicted. In some embodiments, the composition is enriched by at least 95% of the absolute stereoisomer depicted. In some embodiments, the composition is enriched by at least 99% of the absolute stereoisomer depicted. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this disclosure. Such compounds are useful, for example, as analytical tools, as probes in biological assays, or as therapeutic agents in accordance with the present disclosure.

As used herein, the term "inhibitor" is defined as a compound that binds to and/or inhibits the target protein with measurable affinity. In certain embodiments, an inhibitor has an $IC_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in activity of, KCNT1, or a mutant thereof, between a sample comprising a compound of the present disclosure, or composition thereof, and, KCNT1, or a mutant thereof, and an equivalent sample comprising, KCNT1, or a mutant thereof, in the absence of said compound, or composition thereof.

3. Description of Exemplary Compounds

According to one aspect, the present disclosure provides a compound of formula I:

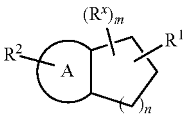

I or a pharmaceutically acceptable salt thereof, wherein:

Ring A is a 5- to 6-membered heteroaryl ring having 1-3 heteroatoms independently selected from nitrogen, oxygen, and sulfur;

$R^1$ is selected from

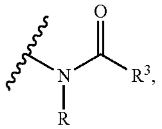

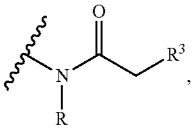

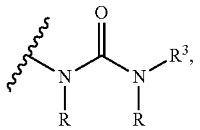

and

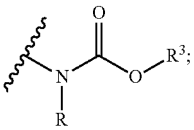

$R^2$ is a 5- to 6-membered heteroaryl ring having 1-3 heteroatoms independently selected from nitrogen, oxygen, and sulfur or a 9- to 10-membered heteroaryl ring having 1-4 heteroatoms independently selected from nitrogen, oxygen, and sulfur, wherein $R^2$ is substituted with 0-3 instances of $R^y$;

$R^3$ is selected from $C_{1-6}$ aliphatic, a 3- to 6-membered saturated or partially unsaturated carbocyclic ring, phenyl, a 10-membered aryl ring, a 5- to 6-membered heteroaryl ring having 1-3 heteroatoms independently selected from nitrogen, oxygen, and sulfur, and a 9- to 10-membered heteroaryl ring having 1-4 heteroatoms independently selected from nitrogen, oxygen, and sulfur, wherein $R^3$ is substituted with 0-4 instances of $R^z$;

each $R^x$ is selected from optionally substituted $C_{1-6}$ aliphatic, —N(R)$_2$, and —OR;

each $R^y$ is independently selected from oxo, —CN, —N(R)$_2$, —OR, —CO$_2$R, or an optionally substituted group selected from $C_{1-4}$ aliphatic and a 3- to 7-membered saturated or partially unsaturated carbocyclic ring;

each $R^z$ is independently selected from —CN, halogen, —OR, —SO$_2$R, and an optionally substituted group selected from $C_{1-6}$ aliphatic and a 3- to 7-membered saturated or partially unsaturated carbocyclic ring;

each R is independently selected from hydrogen or an optionally substituted group selected from $C_{1-6}$ aliphatic, phenyl, a 3- to 7-membered saturated or partially unsaturated carbocyclic ring, a 3- to 7-membered saturated or partially unsaturated heterocyclic ring having 1-3 heteroatoms independently selected from nitrogen, oxygen, and sulfur, and a 5- to 6-membered heteroaryl ring having 1-4 heteroatoms independently selected from nitrogen, oxygen, and sulfur;

m is 0-2; and n is 1-3.

In certain embodiments, the present disclosure provides a compound of formula I':

I'

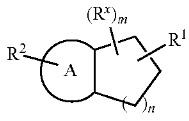

or a pharmaceutically acceptable salt thereof, wherein:

Ring A is a 5- to 6-membered heteroaryl ring having 1-3 heteroatoms independently selected from nitrogen, oxygen, and sulfur;

$R^1$ is selected from

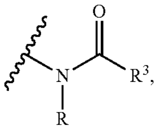 , 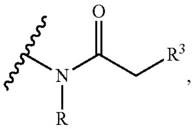 ,

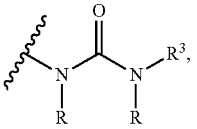 , and 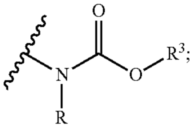 ;

$R^2$ is a 5- to 6-membered heteroaryl ring having 1-3 heteroatoms independently selected from nitrogen, oxygen, and sulfur or a 9- to 10-membered heteroaryl ring having 1-4 heteroatoms independently selected from nitrogen, oxygen, and sulfur, wherein $R^2$ is substituted with 0-3 instances of $R^y$;

$R^3$ is selected from $C_{1-6}$ aliphatic, a 3- to 6-membered saturated or partially unsaturated carbocyclic ring, a 5- to 7-membered bridged bicyclic carbocyclic ring, a 6- to 8-membered spirocyclic carbocyclic ring, phenyl, a 10-membered aryl ring, a 5- to 6-membered heteroaryl ring having 1-3 heteroatoms independently selected from nitrogen, oxygen, and sulfur, and an 8- to 10-membered heteroaryl ring having 1-4 heteroatoms independently selected from nitrogen, oxygen, and sulfur, wherein $R^3$ is substituted with 0-4 instances of $R^z$;

each $R^x$ is selected from optionally substituted $C_{1-6}$ aliphatic, —N(R)$_2$, and —OR;

each $R^y$ is independently selected from oxo, —CN, —N(R)$_2$, —OR, —CO$_2$R, or an optionally substituted group selected from $C_{1-4}$ aliphatic and a 3- to 7-membered saturated or partially unsaturated carbocyclic ring;

each $R^z$ is independently selected from —CN, halogen, —OR, —SO$_2$R, and an optionally substituted group selected from $C_{1-6}$ aliphatic, phenyl, and a 3- to 7-membered saturated or partially unsaturated carbocyclic ring;

each R is independently selected from hydrogen or an optionally substituted group selected from $C_{1-6}$ aliphatic, phenyl, a 3- to 7-membered saturated or partially unsaturated carbocyclic ring, a 3- to 7-membered saturated or partially unsaturated heterocyclic ring having 1-3 heteroatoms independently selected from nitrogen, oxygen, and sulfur, and a 5- to 6-membered heteroaryl ring having 1-4 heteroatoms independently selected from nitrogen, oxygen, and sulfur;

m is 0-2; and n is 1-3.

As defined generally above, Ring A is a 5- to 6-membered heteroaryl ring having 1-3 heteroatoms independently selected from nitrogen, oxygen, and sulfur. It will be appreciated that when Ring A comprises a nitrogen atom, that nitrogen atom is —N= or —N(R)— as valency permits. In some such embodiments, a nitrogen atom in Ring A is selected from —N= and —N(R)—, wherein R is as defined above and described herein. In some embodiments, Ring A is a 5-membered heteroaryl ring having 1-3 heteroatoms independently selected from nitrogen, oxygen, and sulfur. In some embodiments, Ring A is a 5-membered heteroaryl ring having 1-2 heteroatoms independently selected from nitrogen, oxygen, and sulfur. In some embodiments, Ring A is a 5-membered heteroaryl ring having 2 heteroatoms independently selected from nitrogen, oxygen, and sulfur. In some embodiments, Ring A is a 5-membered heteroaryl ring having 1 heteroatom selected from nitrogen, oxygen, and sulfur. In some embodiments, Ring A is a 5-membered heteroaryl ring having 1-2 nitrogen atoms. In some embodiments, Ring A is a 5-membered heteroaryl ring having 1 nitrogen atom. In some embodiments, Ring A is a 5-membered heteroaryl ring having 2 nitrogen atoms.

In some embodiments, Ring A is a 6-membered heteroaryl ring having 1-3 nitrogen atoms. In some embodiments, Ring A is a 6-membered heteroaryl ring having 1-2 nitrogen atoms. In some embodiments, Ring A is a 6-membered heteroaryl ring having 1 nitrogen atom.

In some embodiments, Ring A is selected from
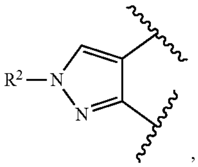,
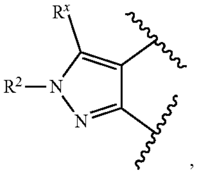,
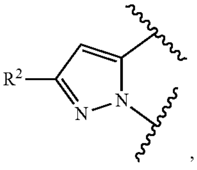,
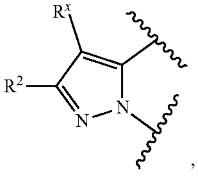,
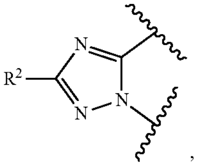,
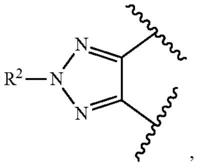,
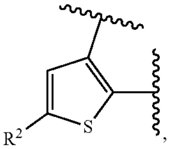,
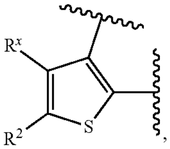,
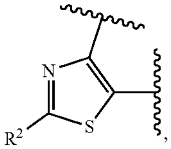,
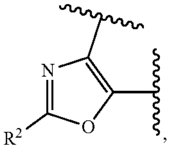,
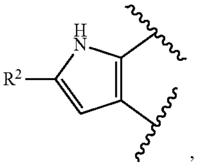,
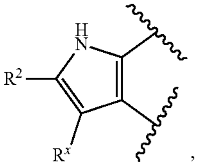,
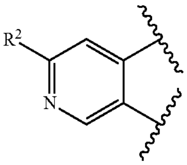,
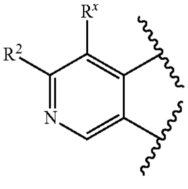,
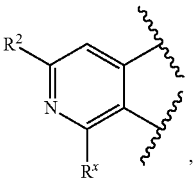,
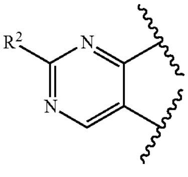,
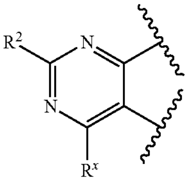,
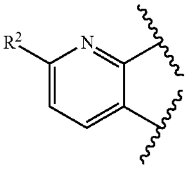,
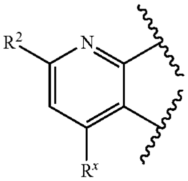,
-continued
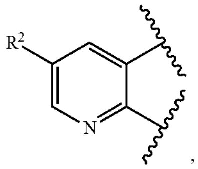,
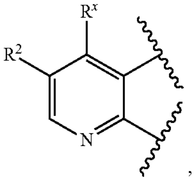, and
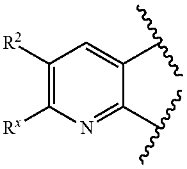.
In some embodiments, Ring A is selected from
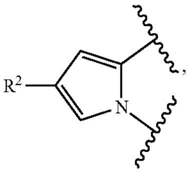,
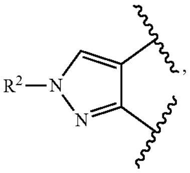,
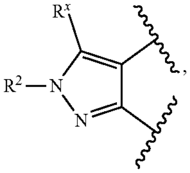,
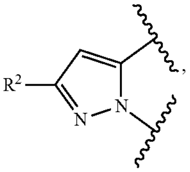,
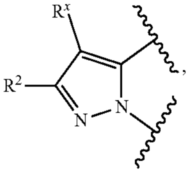,
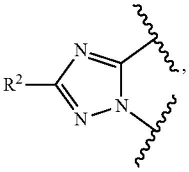,
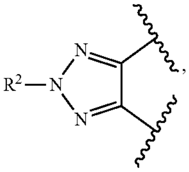,
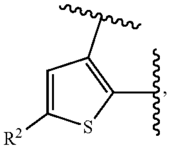,
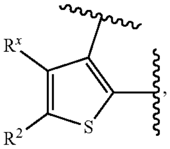,
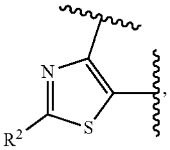,
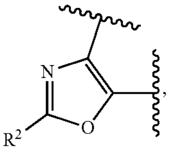,
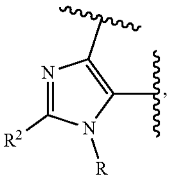,
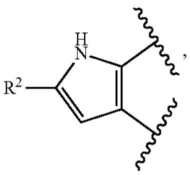, -continued
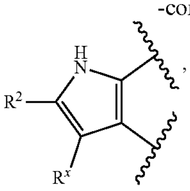,
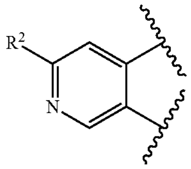,
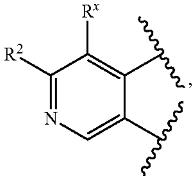,
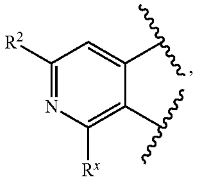,
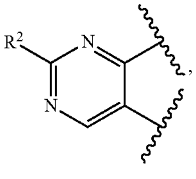,
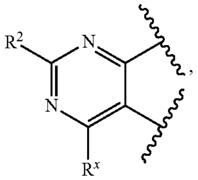,
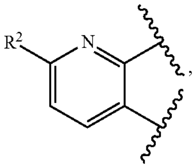,
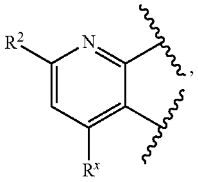,
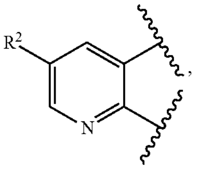,
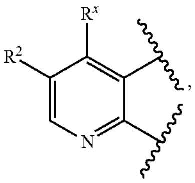, and
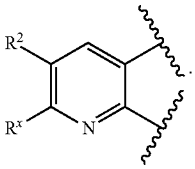.
In some embodiments, Ring A is selected from
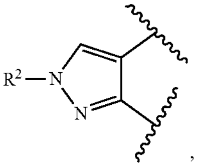,
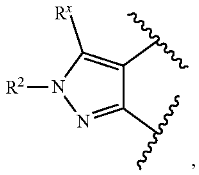,
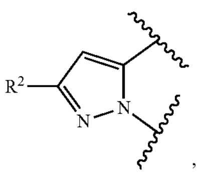,
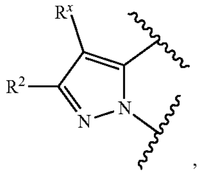,
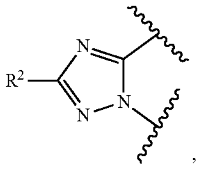,
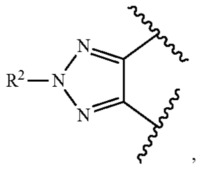,
-continued
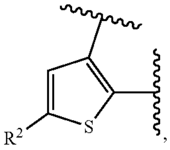,
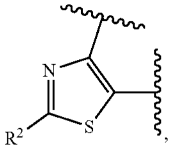,
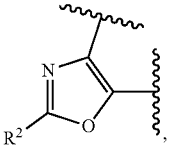,
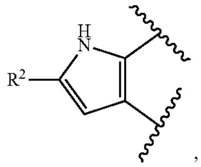,
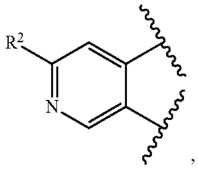,
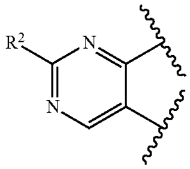,
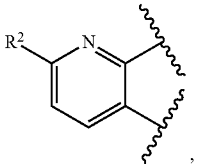, and
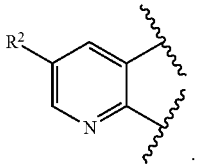.
In some embodiments, Ring A is selected from
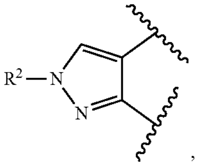,
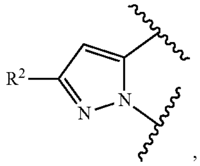,
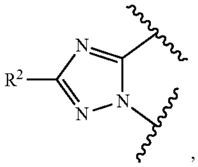,
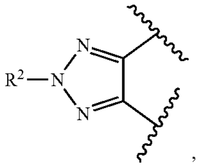,
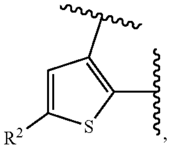,
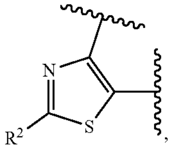,
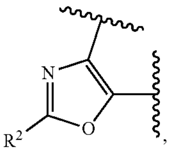,
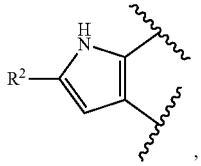,
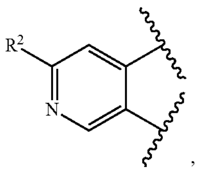,
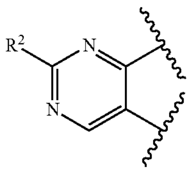, -continued
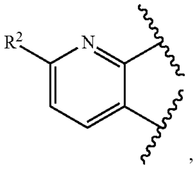
, and
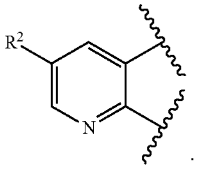
.
In some embodiments, Ring A is selected from
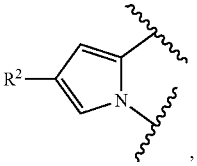
,
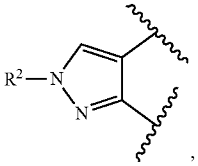
,
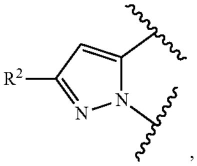
,
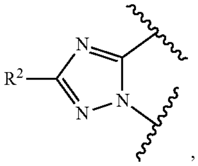
,
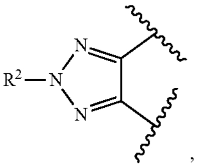
,
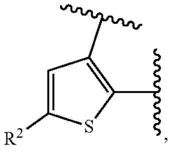
,
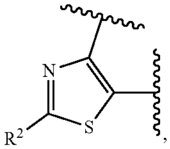
,
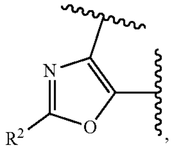
,
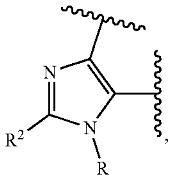
,
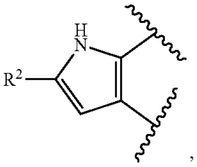
,
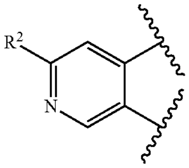
,
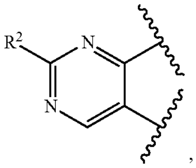
,
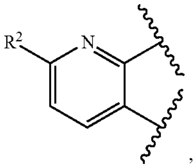
, and
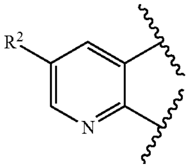
.
As defined generally above, $R^1$ is selected from
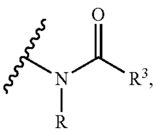
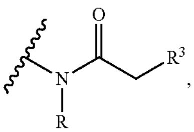
,
-continued
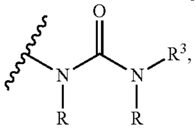
and
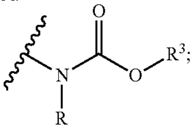
In some embodiments, $R^1$ is
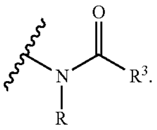
In some embodiments, $R^1$ is
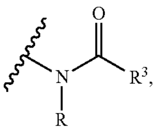
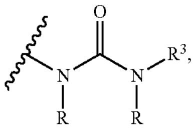
and
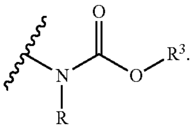
In some embodiments, $R^1$ is
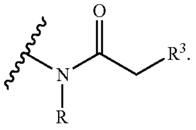
In some embodiments, $R^1$ is
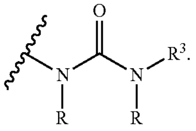
In some embodiments, $R^1$ is
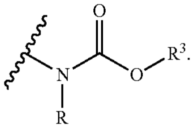
In some embodiments, $R^1$ is
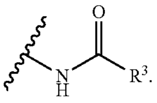

In some embodiments, $R^1$ is

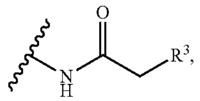

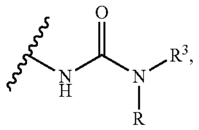

or

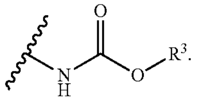

In some embodiments, $R^1$ is

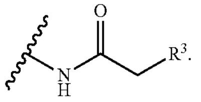

In some embodiments, $R^1$ is

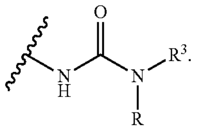

In some embodiments, $R^1$ is

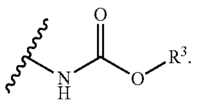

As defined generally above, $R^2$ is a 5- to 6-membered heteroaryl ring having 1-3 heteroatoms independently selected from nitrogen, oxygen, and sulfur or a 9- to 10-membered heteroaryl ring having 1-4 heteroatoms independently selected from nitrogen, oxygen, and sulfur, wherein $R^2$ is substituted with 0-3 instances of $R^y$. In some embodiments, $R^2$ is substituted with 0-2 instances of $R^y$. In some embodiments, $R^2$ is substituted with 0-1 instances of $R^y$. In some embodiments, $R^2$ is substituted with 1-3 instances of $R^y$. In some embodiments, $R^2$ is substituted with 1-2 instances of $R^y$. In some embodiments, $R^2$ is substituted with 2-3 instances of $R^y$.

In some embodiments, $R^2$ is a 5- to 6-membered heteroaryl ring having 1-3 heteroatoms independently selected from nitrogen, oxygen, and sulfur. In some embodiments, $R^2$ is a 5-membered heteroaryl ring having 1-3 heteroatoms independently selected from nitrogen, oxygen, and sulfur. In some embodiments, $R^2$ is a 5-membered heteroaryl ring having 1-2 heteroatoms independently selected from nitrogen, oxygen, and sulfur. In some embodiments, $R^2$ is a 5-membered heteroaryl ring having 2 heteroatoms independently selected from nitrogen, oxygen, and sulfur. In some embodiments, $R^2$ is a 5-membered heteroaryl ring having 1 heteroatom selected from nitrogen, oxygen, and sulfur.

In some embodiments, $R^2$ is a 6-membered heteroaryl ring having 1-3 nitrogen atoms. In some embodiments, $R^2$ is a 6-membered heteroaryl ring having 1-2 nitrogen atoms. In some embodiments, $R^2$ is a 6-membered heteroaryl ring having 2 nitrogen atoms. In some embodiments, $R^2$ is a 6-membered heteroaryl ring having 1 nitrogen atom.

In some embodiments, $R^2$ is a 9- to 10-membered heteroaryl ring having 1-4 heteroatoms independently selected from nitrogen, oxygen, and sulfur. In some embodiments, $R^2$ is a 9-membered heteroaryl ring having 1-4 heteroatoms independently selected from nitrogen, oxygen, and sulfur. In some embodiments, $R^2$ is a 9-membered heteroaryl ring having 1-3 heteroatoms independently selected from nitrogen, oxygen, and sulfur. In some embodiments, $R^2$ is a 9-membered heteroaryl ring having 1-2 heteroatoms independently selected from nitrogen, oxygen, and sulfur. In some embodiments, $R^2$ is a 9-membered heteroaryl ring having 2 heteroatoms independently selected from nitrogen, oxygen, and sulfur. In some embodiments, $R^2$ is a 9-membered heteroaryl ring having 1 heteroatom selected from nitrogen, oxygen, and sulfur.

In some embodiments, $R^2$ is a 10-membered heteroaryl ring having 1-4 nitrogen atoms. In some embodiments, $R^2$ is a 10-membered heteroaryl ring having 1-3 nitrogen atoms. In some embodiments, $R^2$ is a 10-membered heteroaryl ring having 1-2 nitrogen atoms. In some embodiments, $R^2$ is a 10-membered heteroaryl ring having 2 nitrogen atoms. In some embodiments, $R^2$ is a 10-membered heteroaryl ring having 1 nitrogen atom.

In some embodiments, $R^2$ is selected from

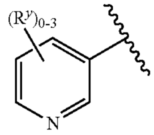
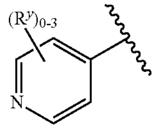
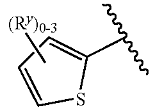
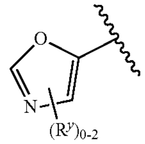
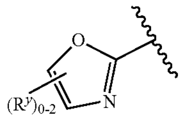
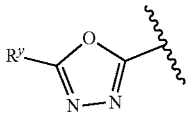
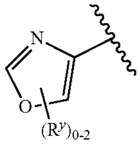
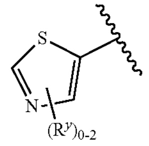
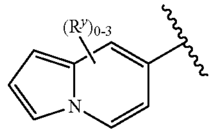
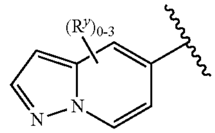
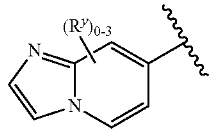

In some embodiments, $R^2$ is selected from

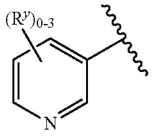
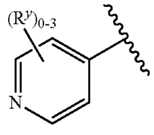
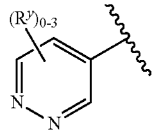
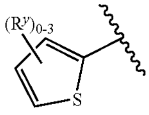
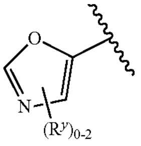
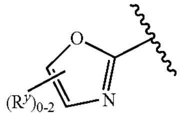

-continued
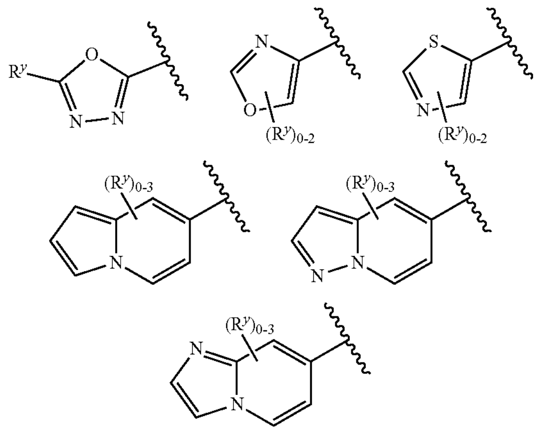
In some embodiments, $R^2$ is selected from
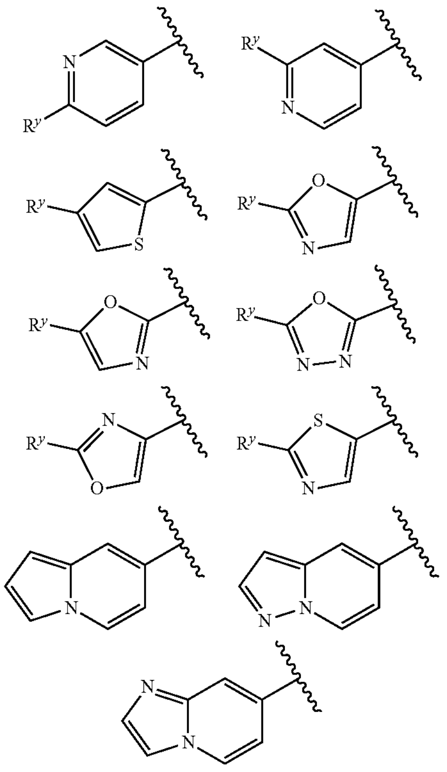
In some embodiments, $R^2$ is selected from
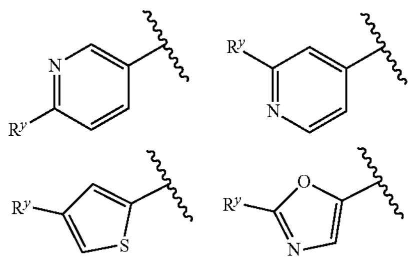
-continued
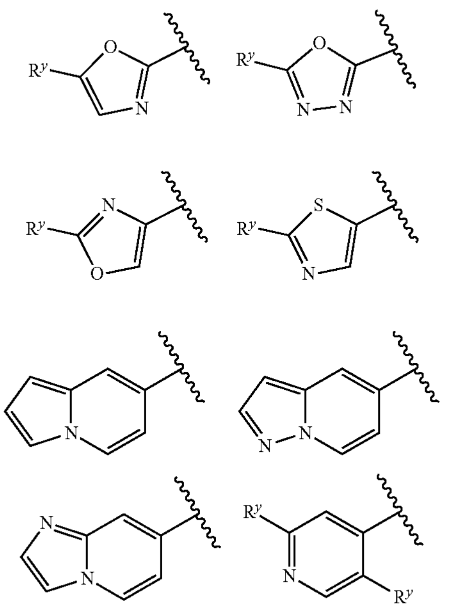
In some embodiments, $R^2$ is selected from
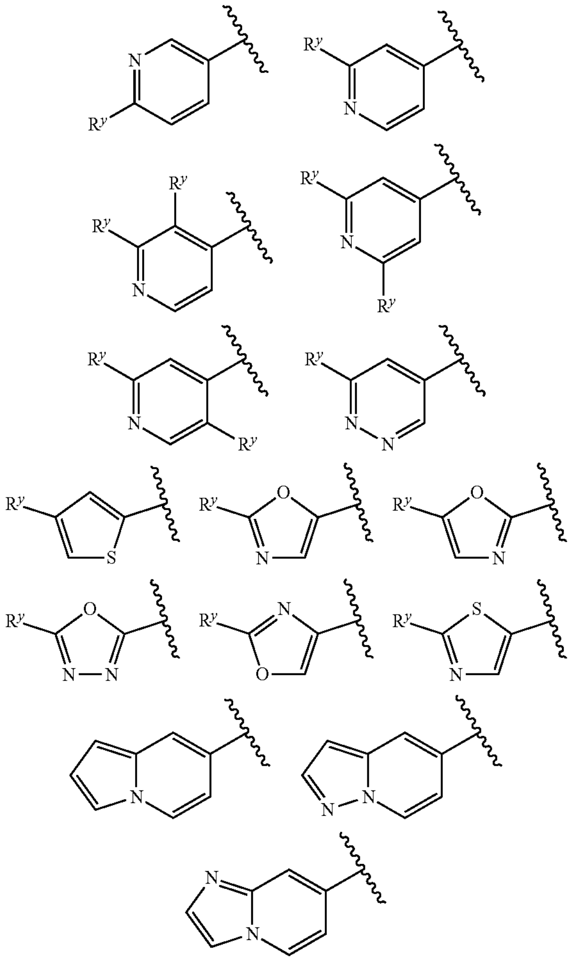

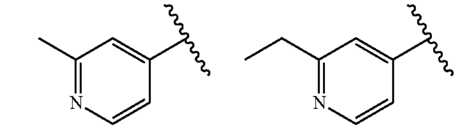
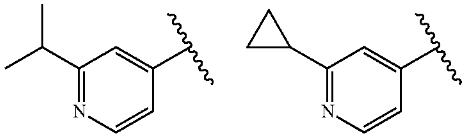
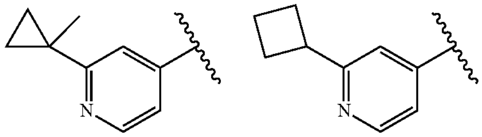
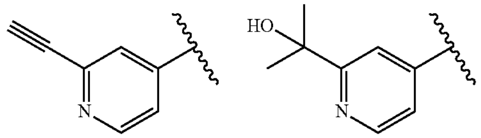
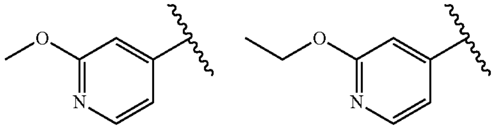
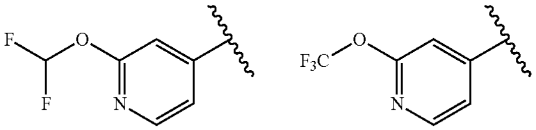
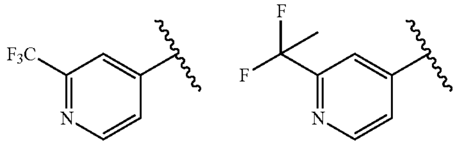
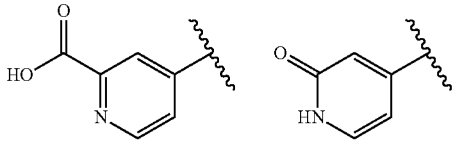
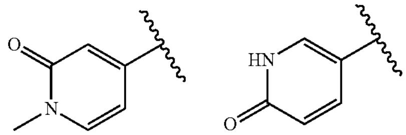
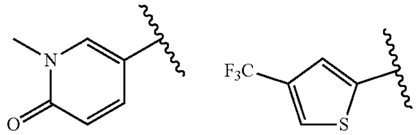
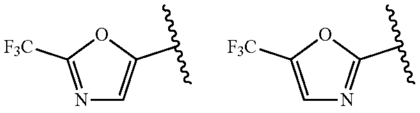
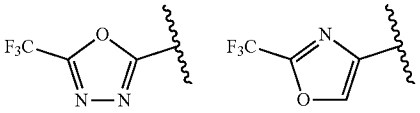
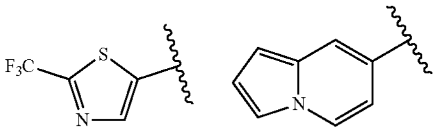
-continued
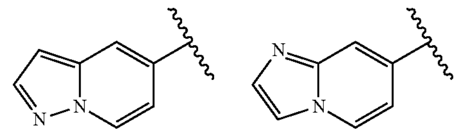
In some embodiments, $R^2$ is selected from
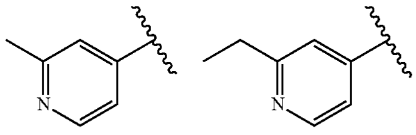
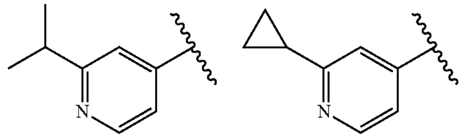
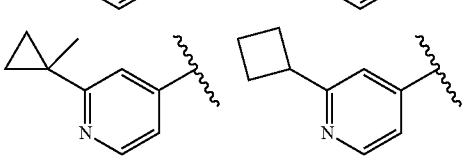
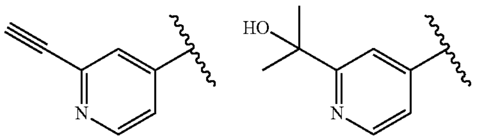
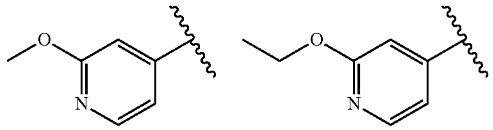
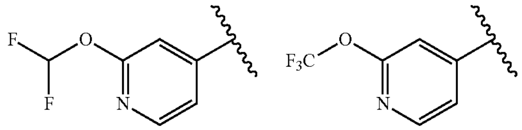
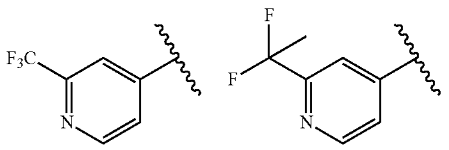
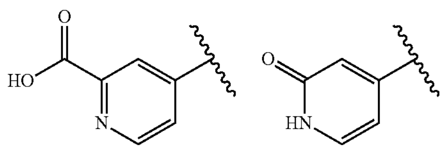
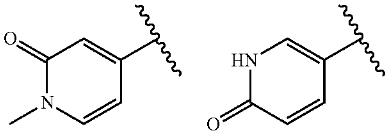
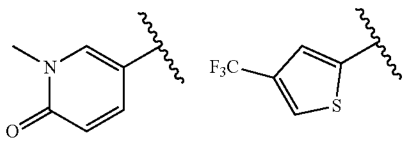

-continued
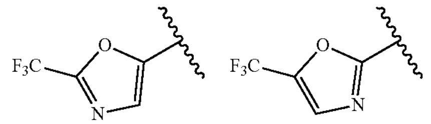
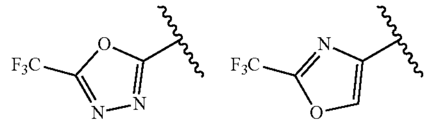
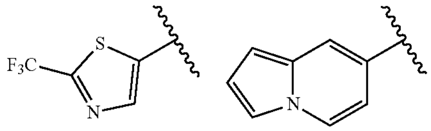
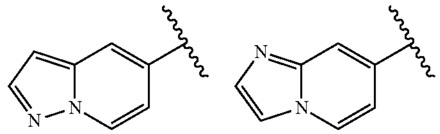
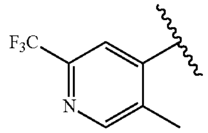
In some embodiments $R^2$ is selected from
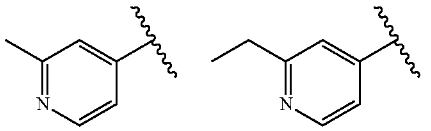
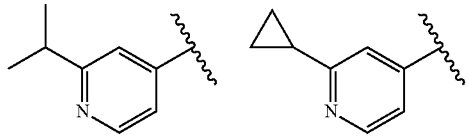
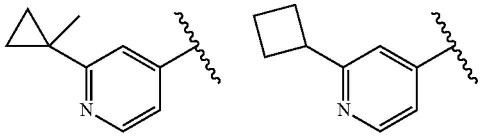
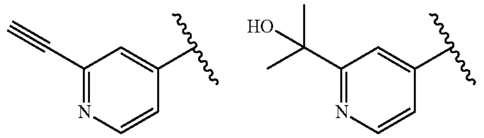
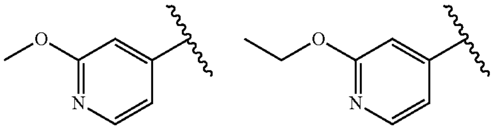
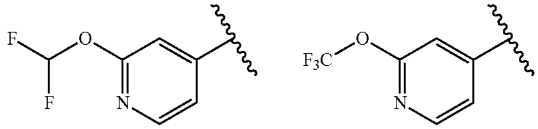
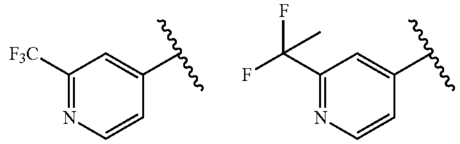
-continued
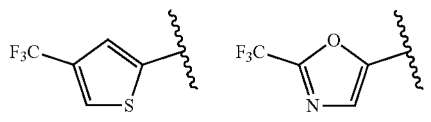
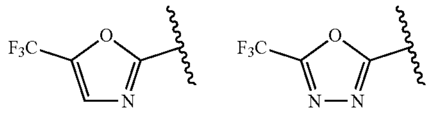
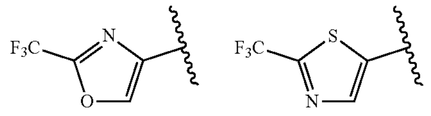
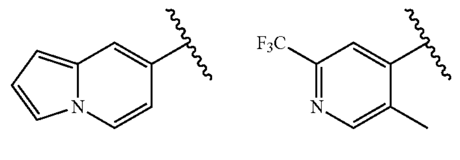
In some embodiments, $R^2$ is selected from
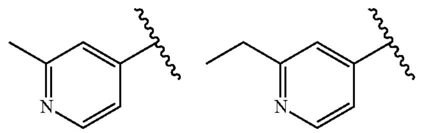
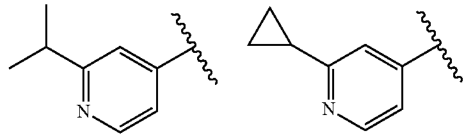
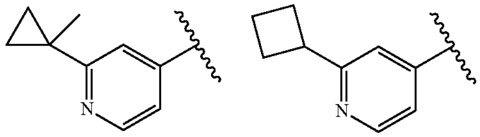
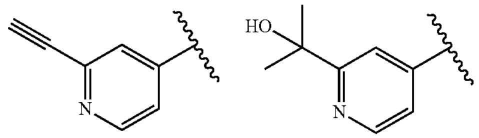
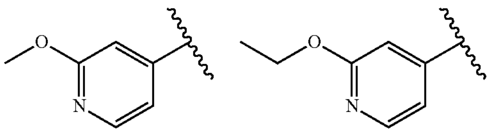
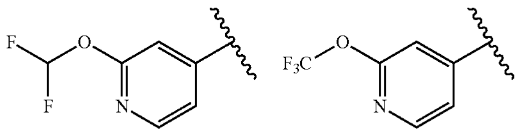
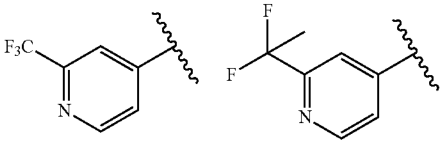
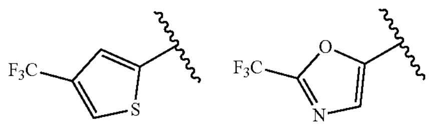

-continued

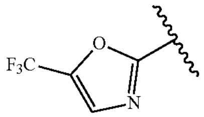
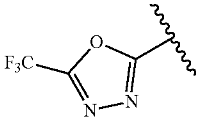
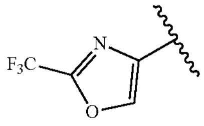
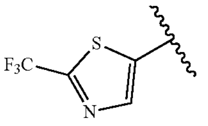
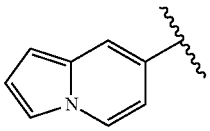
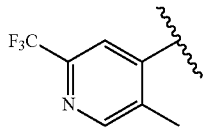
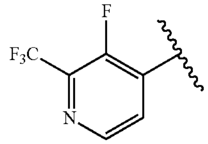
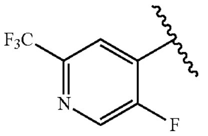
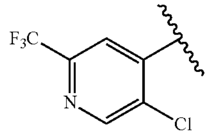
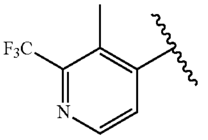
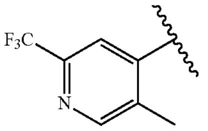
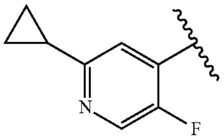
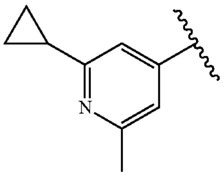
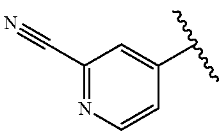
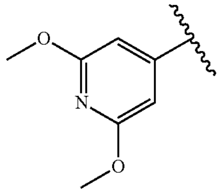
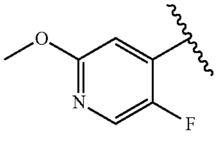
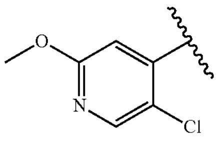
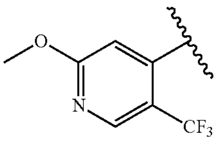
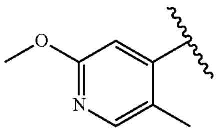
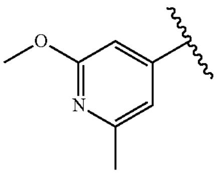
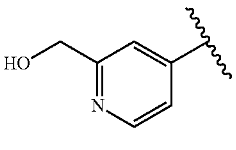
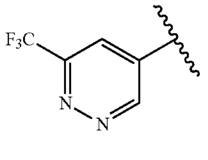

-continued

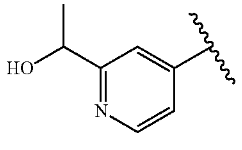
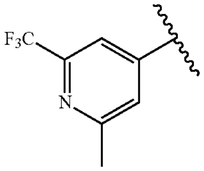
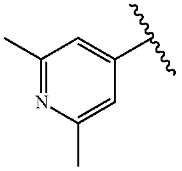
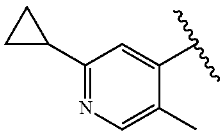
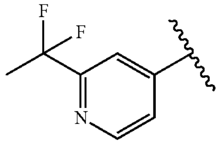

As defined generally above, $R^3$ is selected from $C_{1-6}$ aliphatic, a 3- to 6-membered saturated or partially unsaturated carbocyclic ring, phenyl, a 10-membered aryl ring, a 5- to 6-membered heteroaryl ring having 1-3 heteroatoms independently selected from nitrogen, oxygen, and sulfur, and a 9- to 10-membered heteroaryl ring having 1-4 heteroatoms independently selected from nitrogen, oxygen, and sulfur, wherein $R^3$ is substituted with 0-4 instances of $R^z$. In some embodiments, $R^3$ is substituted with 0-3 instances of $R^z$. In some embodiments, $R^3$ is substituted with 0-2 instances of $R^z$. In some embodiments, $R^3$ is substituted with 0-1 instances of $R^z$. In some embodiments, $R^3$ is substituted with 1-4 instances of $R^z$. In some embodiments, $R^3$ is substituted with 1-3 instances of $R^z$. In some embodiments, $R^3$ is substituted with 1-2 instances of $R^z$. In some embodiments, $R^3$ is substituted with 2-4 instances of $R^z$. In some embodiments, $R^3$ is substituted with 2-3 instances of $R^z$. In some embodiments, $R^3$ is substituted with 3-4 instances of $R^z$.

In some embodiments, $R^3$ is $C_{1-6}$ aliphatic. In some embodiments, $R^3$ is $C_{1-4}$ aliphatic. In some embodiments, $R^3$ is $C_{1-2}$ aliphatic. In some embodiments, $R^3$ is $C_{3-6}$ aliphatic. In some embodiments, $R^3$ is $C_{4-6}$ aliphatic. In some embodiments, $R^3$ is $C_{4-5}$ aliphatic.

In some embodiments, $R^3$ is a 3- to 6-membered saturated or partially unsaturated carbocyclic ring. In some embodiments, $R^3$ is a 3- to 4-membered saturated carbocyclic ring. In some embodiments, $R^3$ is a 4- to 6-membered saturated or partially unsaturated carbocyclic ring. In some embodiments, $R^3$ is a 4- to 6-membered saturated carbocyclic ring. In some embodiments, $R^3$ is a 5- to 6-membered saturated or partially unsaturated carbocyclic ring. In some embodiments, $R^3$ is a 5- to 6-membered saturated carbocyclic ring. In some embodiments, $R^3$ is a cyclobutyl ring.

In some embodiments of Formula I', $R^3$ is a 5- to 7-membered bridged bicyclic carbocyclic ring or a 6- to 8-membered spirocyclic carbocyclic ring. In some embodiments of Formula I', $R^3$ is a 5-membered bridged bicyclic carbocyclic ring. In some embodiments of Formula I', $R^3$ is a 6-membered bridged bicyclic carbocyclic ring. In some embodiments of Formula I', $R^3$ is a 7-membered bridged bicyclic carbocyclic ring. In some embodiments of Formula I', $R^3$ is a bicyclopentanyl ring.

In some embodiments, $R^3$ is a 6- to 8-membered spirocyclic carbocyclic ring. In some embodiments, $R^3$ is a spiro[2.3]hexanyl ring.

In some embodiments, $R^3$ is phenyl.

In some embodiments, $R^3$ is a 10-membered aryl ring.

In some embodiments, $R^3$ is a 5- to 6-membered heteroaryl ring having 1-3 heteroatoms independently selected from nitrogen, oxygen, and sulfur. In some embodiments, $R^3$ is a 5-membered heteroaryl ring having 1-3 heteroatoms independently selected from nitrogen, oxygen, and sulfur. In some embodiments, $R^3$ is a 5-membered heteroaryl ring having 1-2 heteroatoms independently selected from nitrogen, oxygen, and sulfur. In some embodiments, $R^3$ is a 5-membered heteroaryl ring having 2 heteroatoms independently selected from nitrogen, oxygen, and sulfur. In some embodiments, $R^3$ is a 5-membered heteroaryl ring having 1 heteroatom selected from nitrogen, oxygen, and sulfur. In some embodiments, $R^3$ is pyrazolyl or oxazolyl. In some embodiments, $R^3$ is 1,2,4-triazolyl.

In some embodiments, $R^3$ is a 6-membered heteroaryl ring having 1-3 nitrogen atoms. In some embodiments, $R^3$ is a 6-membered heteroaryl ring having 1-2 nitrogen atoms. In some embodiments, $R^3$ is a 6-membered heteroaryl ring having 2 nitrogen atoms. In some embodiments, $R^3$ is a 6-membered heteroaryl ring having 1 nitrogen atom. In some embodiments, $R^3$ is pyridyl, pyrimidinyl, or pyrazinyl.

In some embodiments, $R^3$ is a 9- to 10-membered heteroaryl ring having 1-4 heteroatoms independently selected from nitrogen, oxygen, and sulfur. In some embodiments, $R^3$ is a 9-membered heteroaryl ring having 1-4 heteroatoms independently selected from nitrogen, oxygen, and sulfur. In some embodiments, $R^3$ is a 9-membered heteroaryl ring having 1-3 heteroatoms independently selected from nitrogen, oxygen, and sulfur. In some embodiments, $R^3$ is a 9-membered heteroaryl ring having 1-2 heteroatoms independently selected from nitrogen, oxygen, and sulfur. In some embodiments, $R^3$ is a 9-membered heteroaryl ring having 2 heteroatoms independently selected from nitrogen, oxygen, and sulfur. In some embodiments, $R^3$ is a 9-membered heteroaryl ring having 1 heteroatom selected from nitrogen, oxygen, and sulfur.

In some embodiments, $R^3$ is a 10-membered heteroaryl ring having 1-4 nitrogen atoms. In some embodiments, $R^3$ is a 10-membered heteroaryl ring having 1-3 nitrogen atoms. In some embodiments, $R^3$ is a 10-membered heteroaryl ring having 1-2 nitrogen atoms. In some embodiments, $R^3$ is a 10-membered heteroaryl ring having 2 nitrogen atoms. In some embodiments, $R^3$ is a 10-membered heteroaryl ring having 1 nitrogen atom. In some embodiments, $R^3$ is pyrrolo[1,2-b]pyridazinyl or quinoxalinyl.

In some embodiments of Formula I', $R^3$ is an 8- to 10-membered heteroaryl ring having 1-4 heteroatoms independently selected from nitrogen, oxygen, and sulfur, wherein $R^3$ is substituted with 0-4 instances of $R^z$. In some embodiments of Formula I', $R^3$ is an 8-membered heteroaryl ring having 1-4 heteroatoms independently selected from nitrogen, oxygen, and sulfur, wherein $R^3$ is substituted with 0-4 instances of $R^z$.

In some embodiments, $R^3$ is selected from

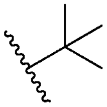 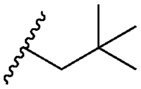 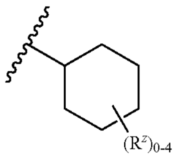

-continued

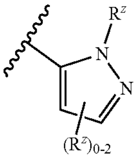 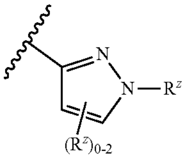 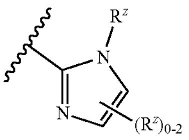

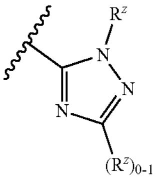 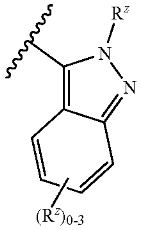 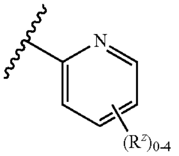

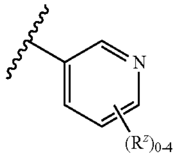 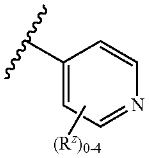 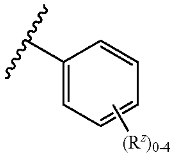

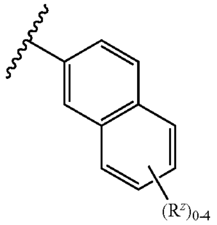

In some embodiments, $R^3$ is selected from

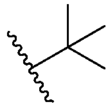 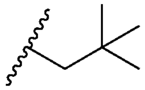 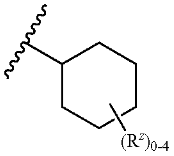

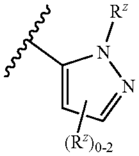 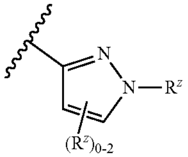 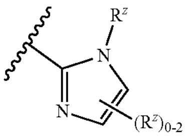

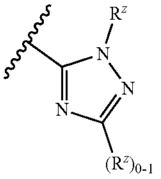 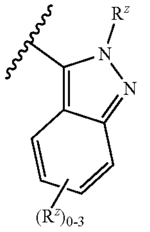 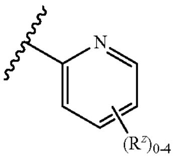

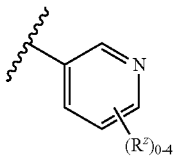 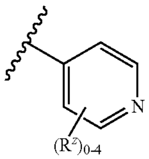 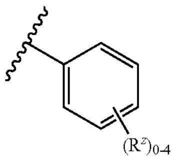

-continued
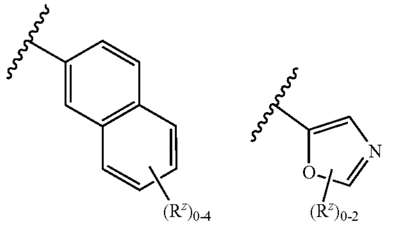
In some embodiments, $R^3$ is selected from
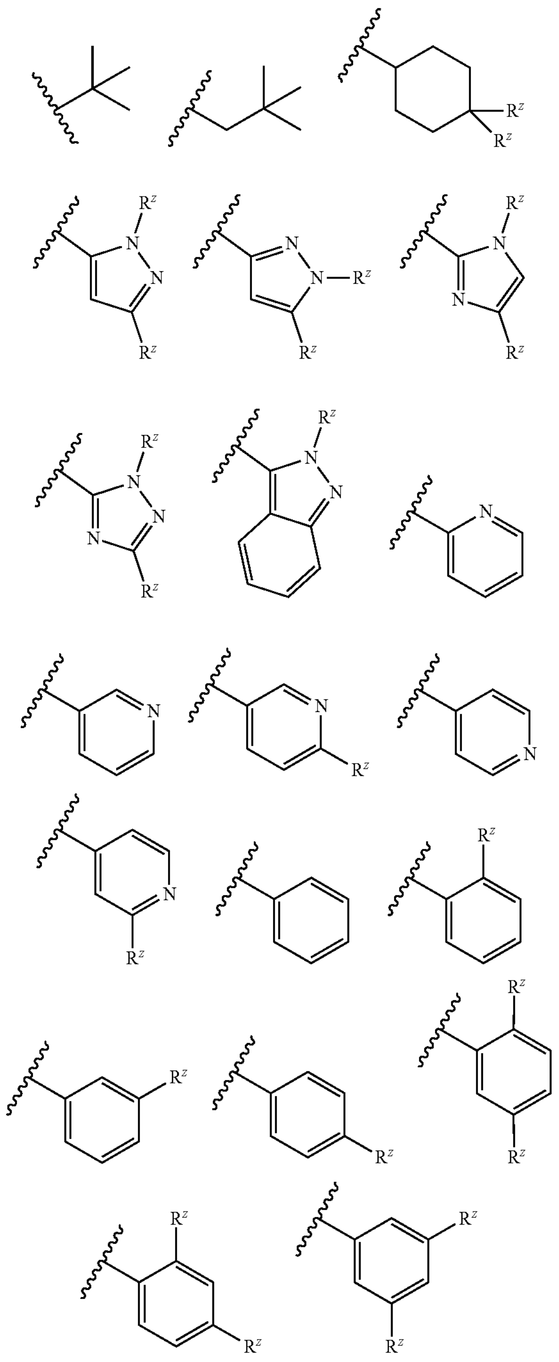
-continued
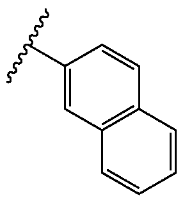
In some embodiments, $R^3$ is selected from
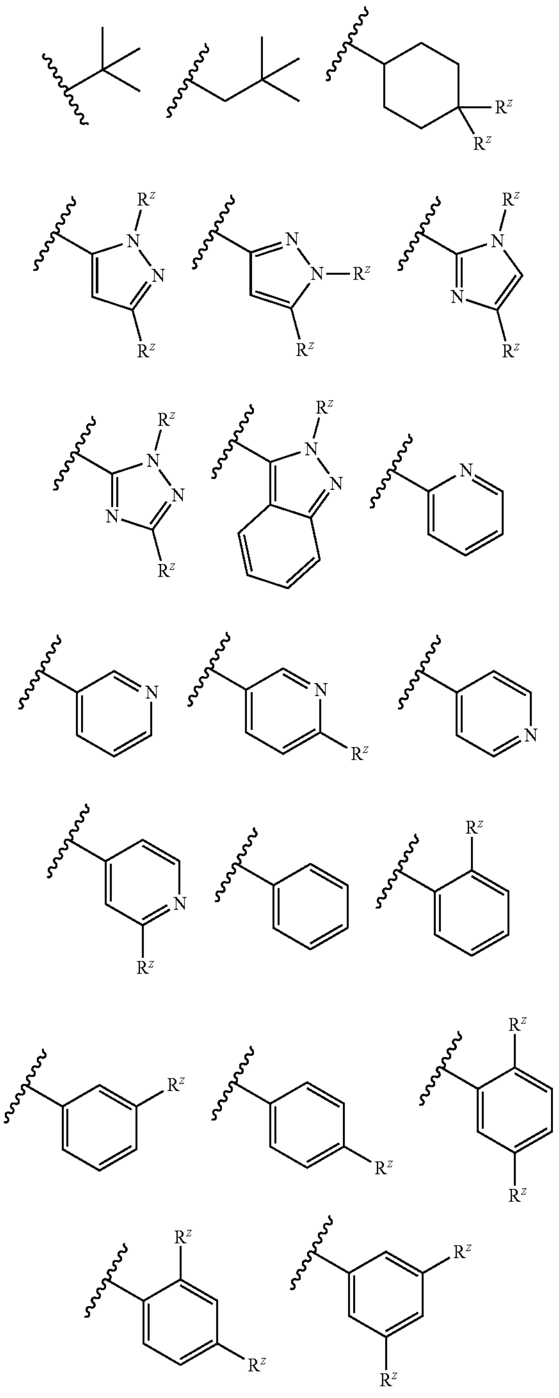

-continued
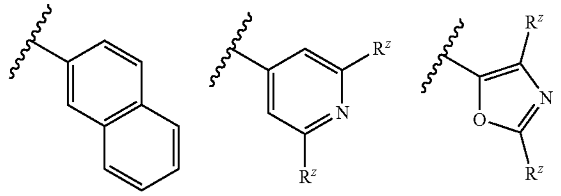
In some embodiments, $R^3$ is selected from
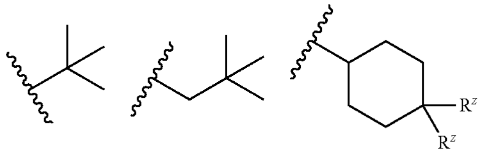
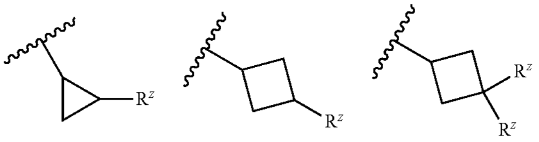
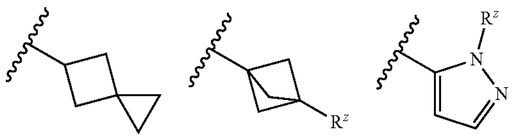
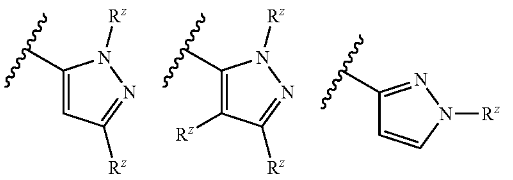
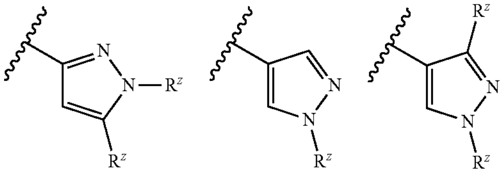
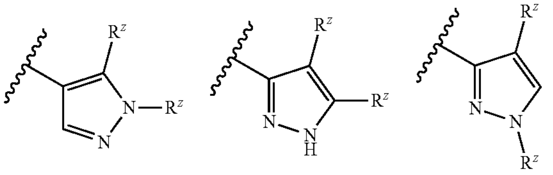
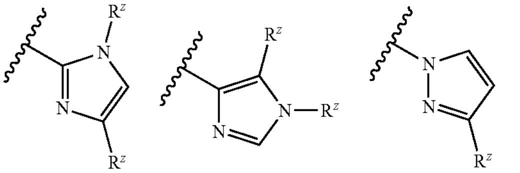
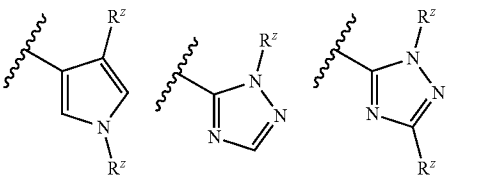
-continued
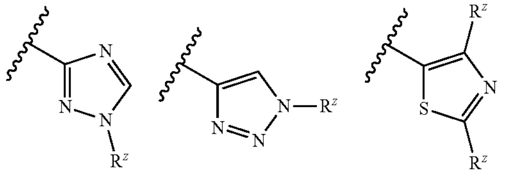
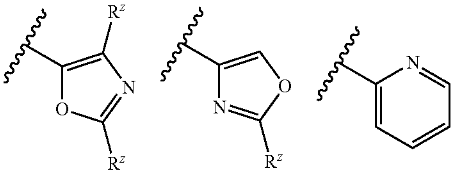
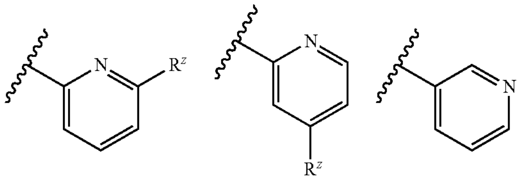
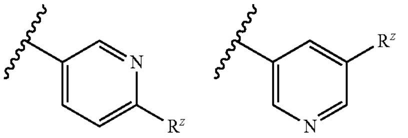
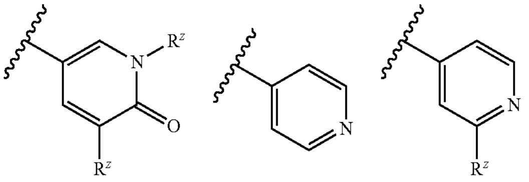
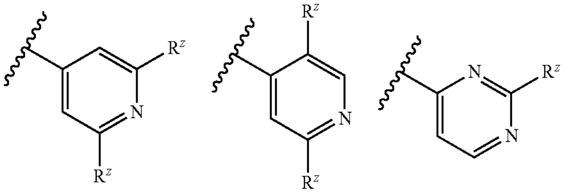
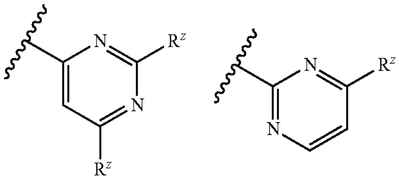
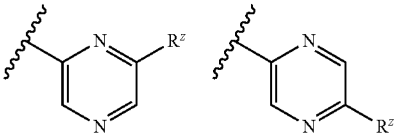
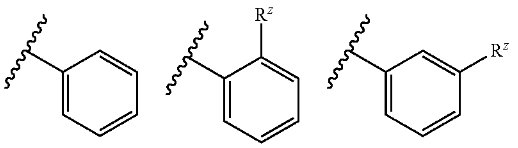
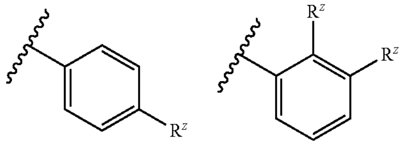

-continued
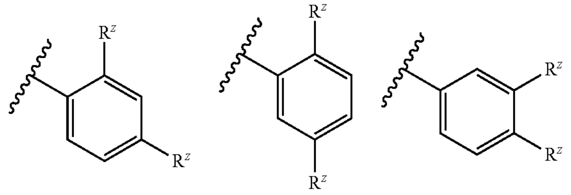
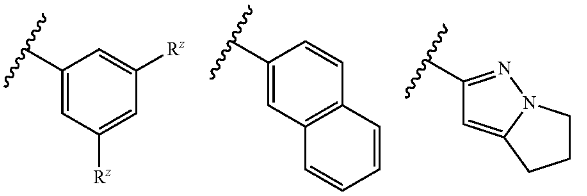
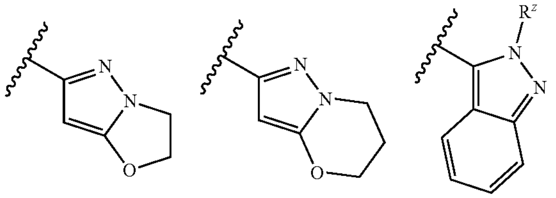
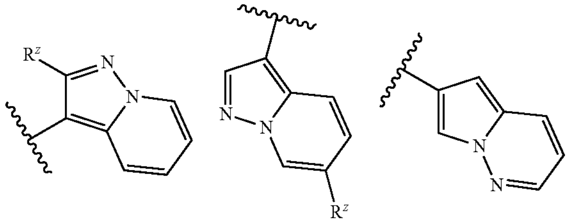
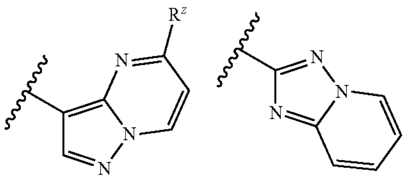
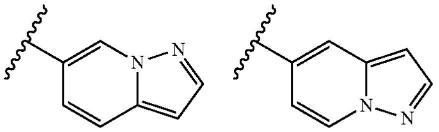
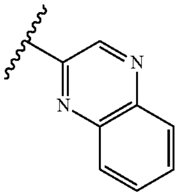
In some embodiments, $R^3$ is selected from
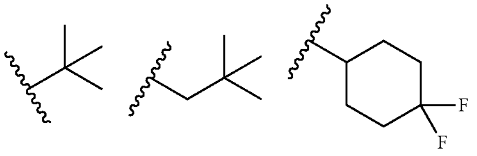
-continued
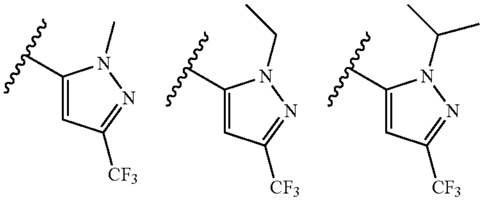
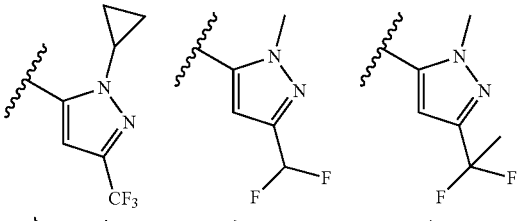
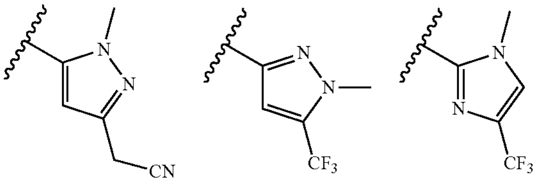
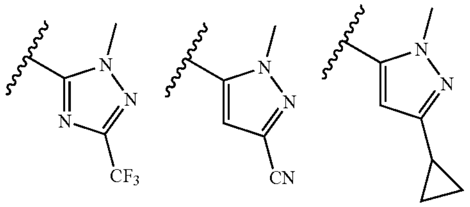
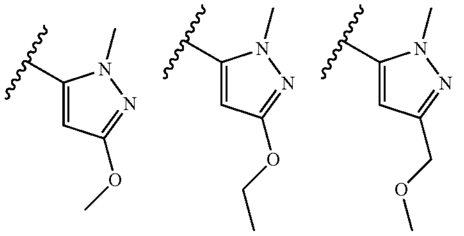
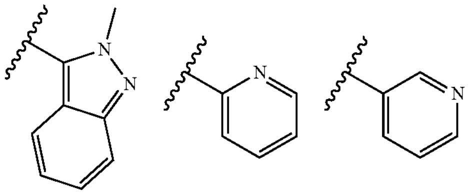
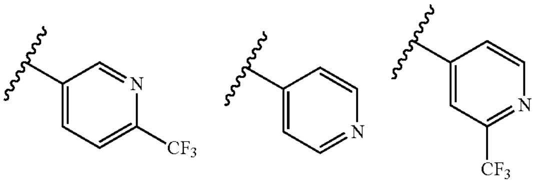
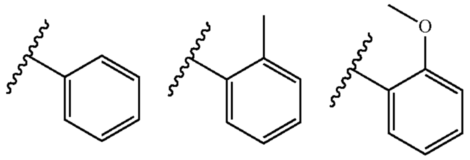
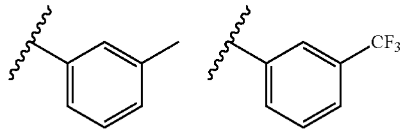

-continued
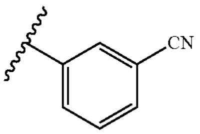
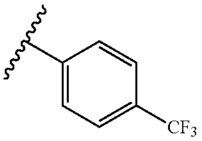
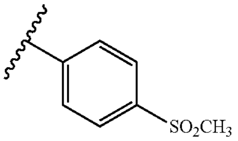
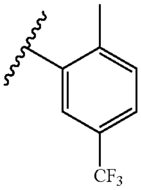
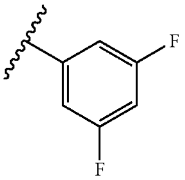
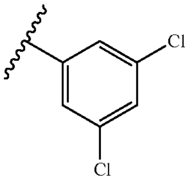
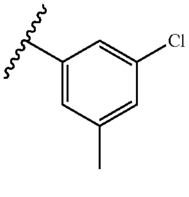
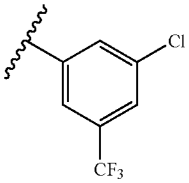
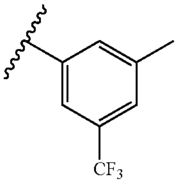
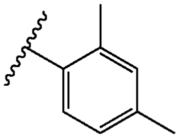
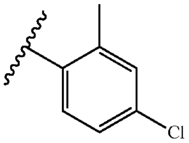
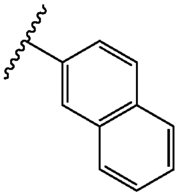
In some embodiments, $R^3$ is selected from
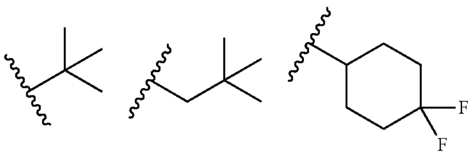
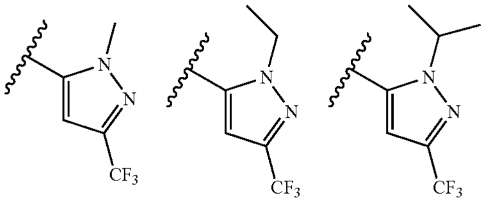
-continued
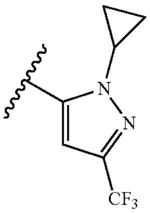
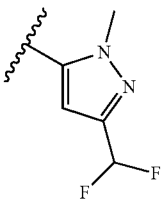
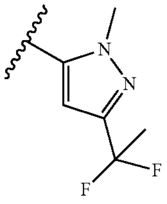
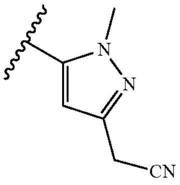
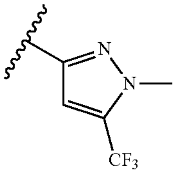
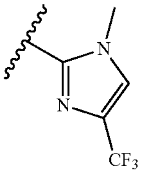
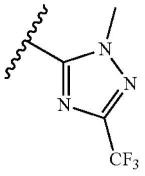
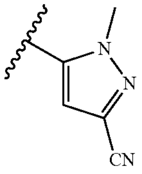
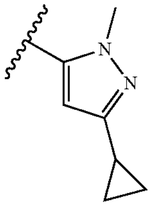
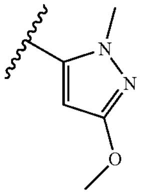
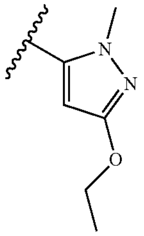
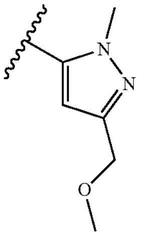
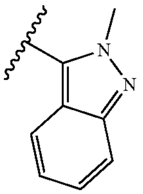
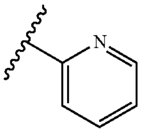
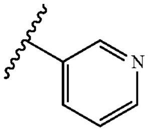
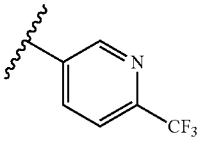
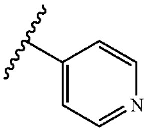
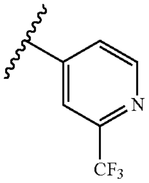
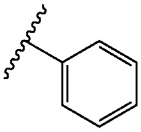
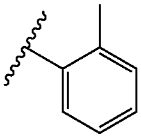
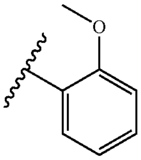
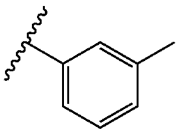
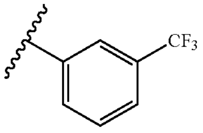
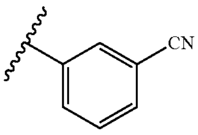
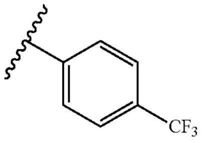

-continued
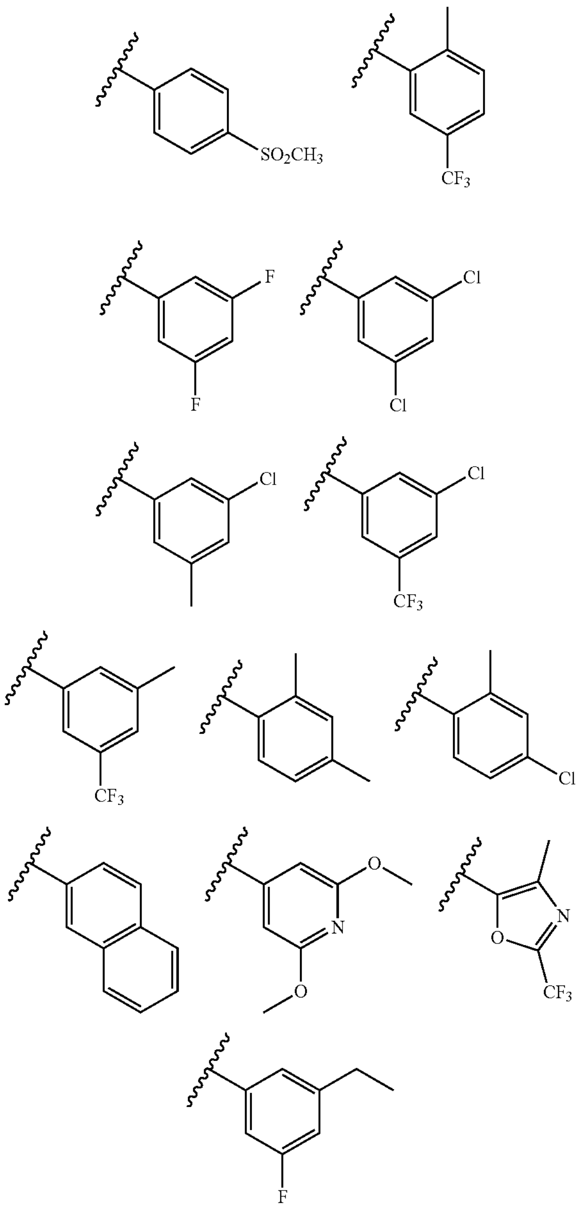
In some embodiments, $R^3$ is selected from
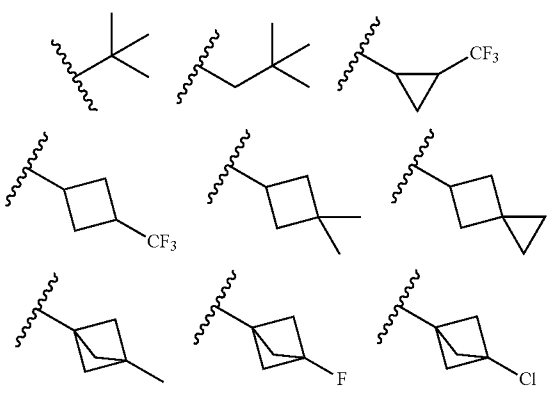
-continued
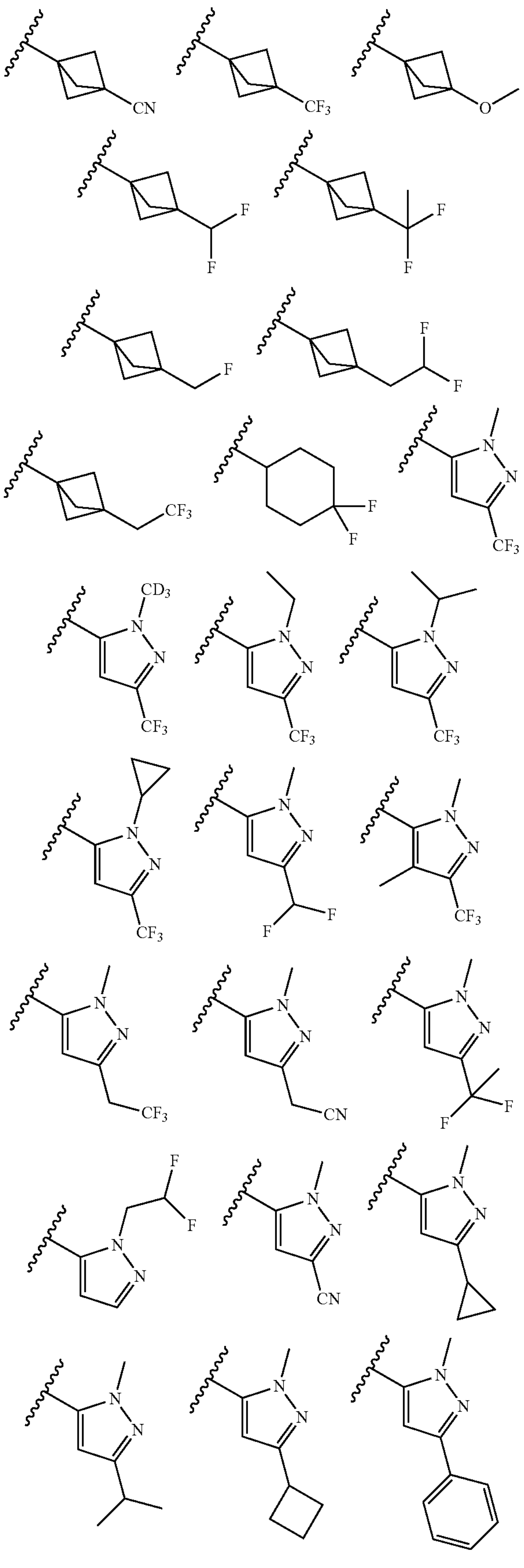

-continued
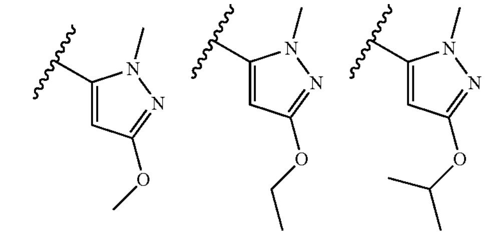
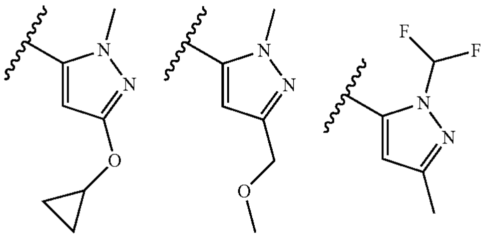
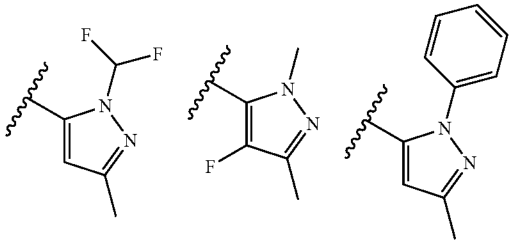
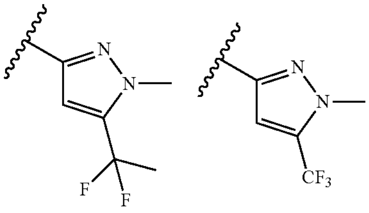
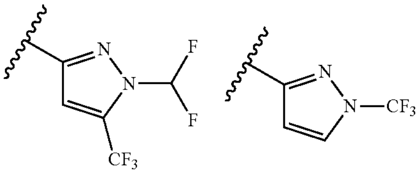
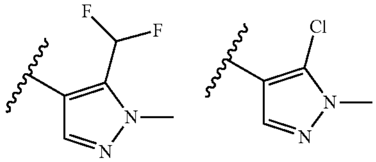
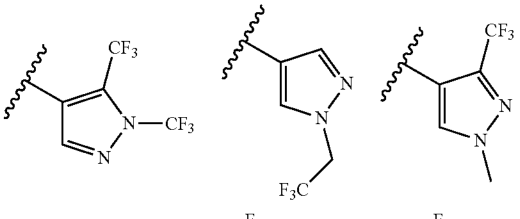
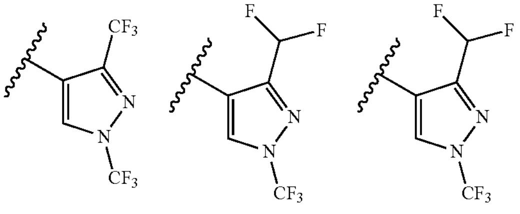
-continued
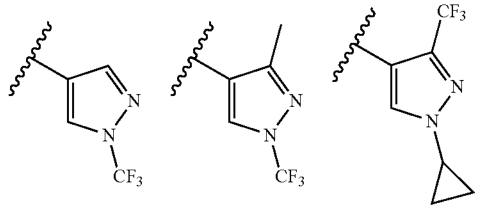
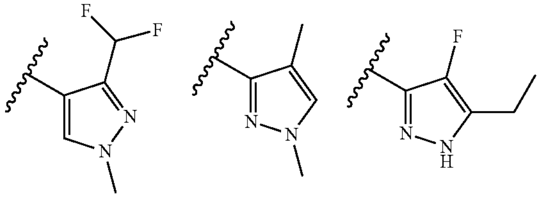
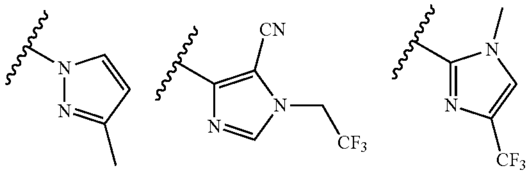
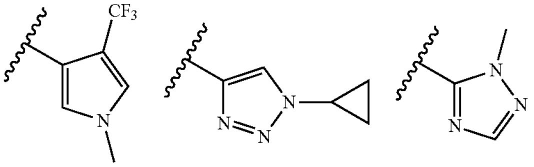
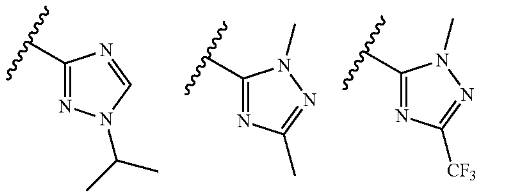
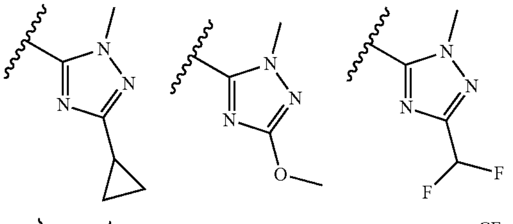
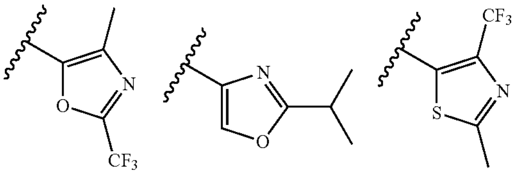
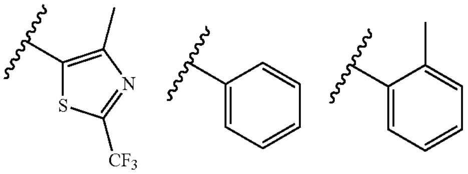
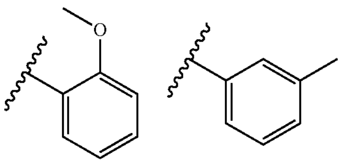

-continued
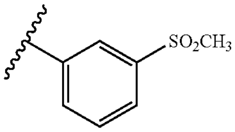
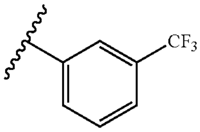
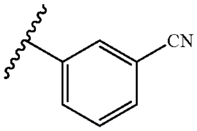
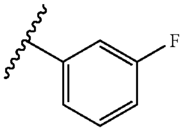
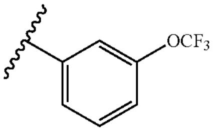
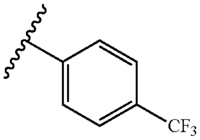
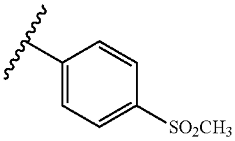
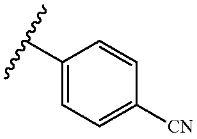
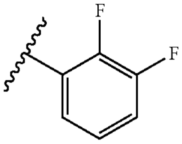
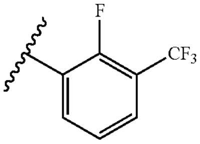
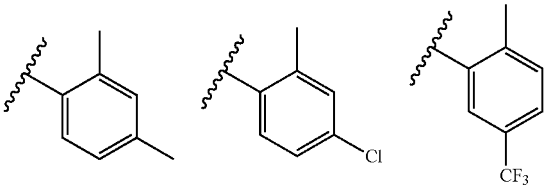
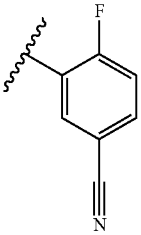
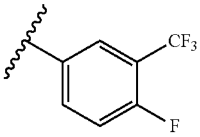
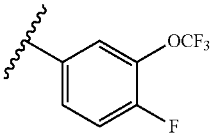
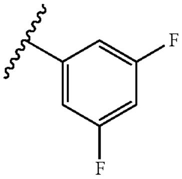
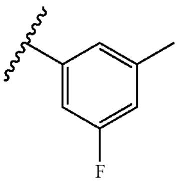
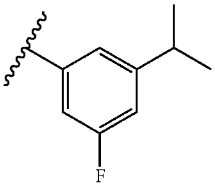
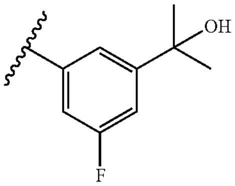
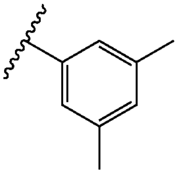
-continued
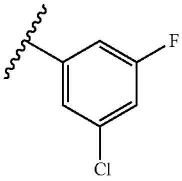
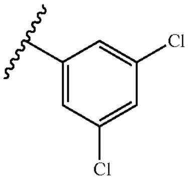
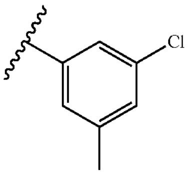
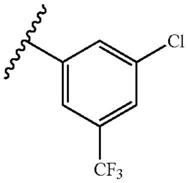
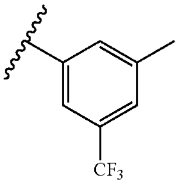
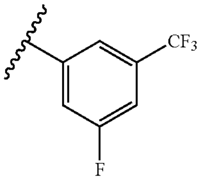
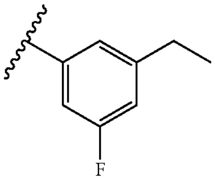
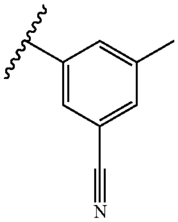
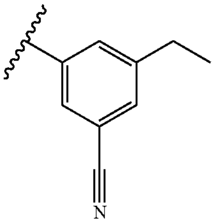
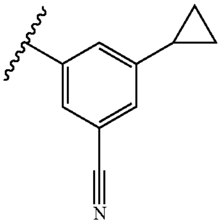
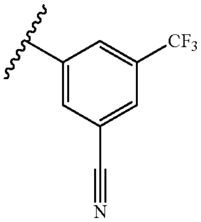
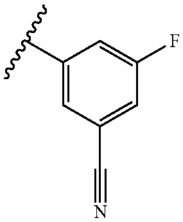
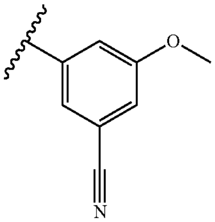
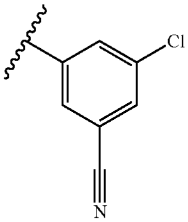
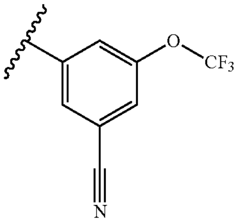
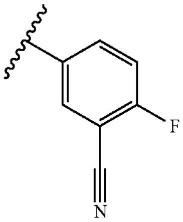

-continued
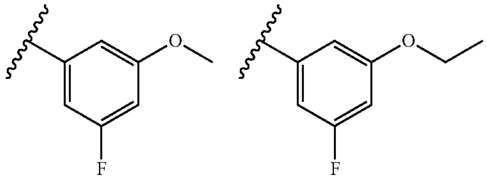
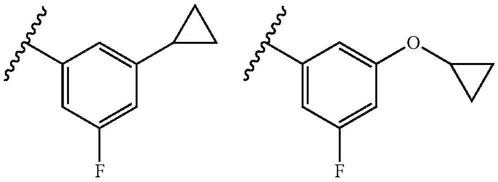
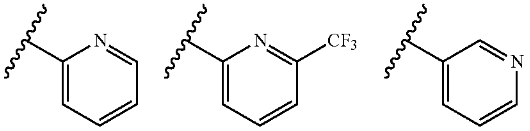
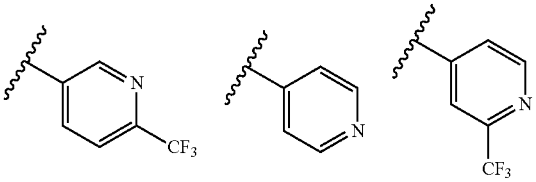
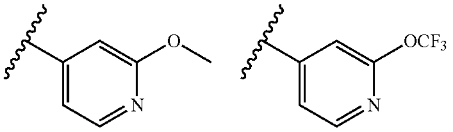
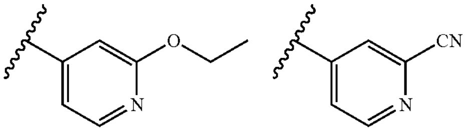
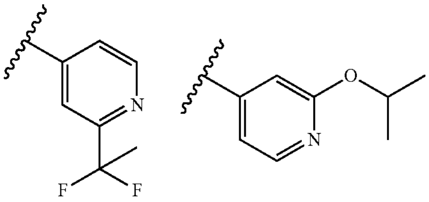
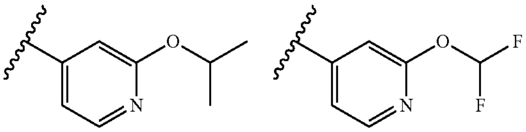
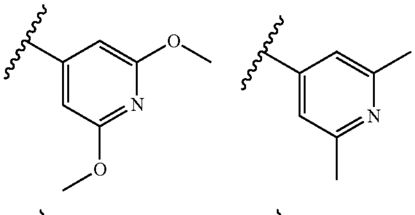
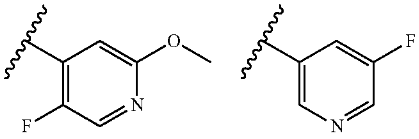
-continued
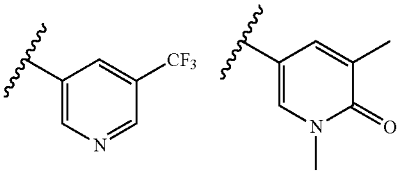
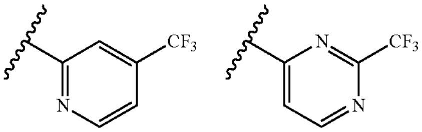
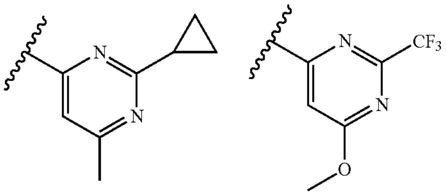
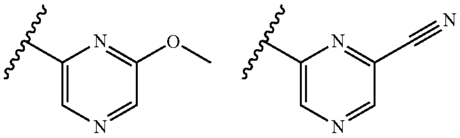
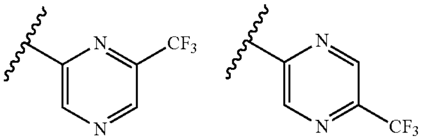
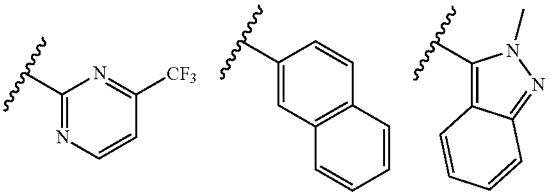
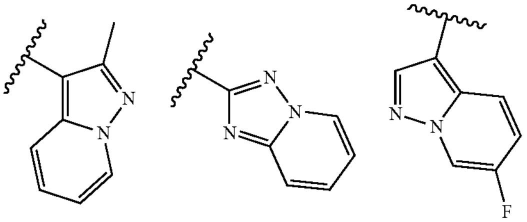
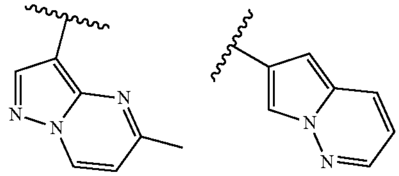
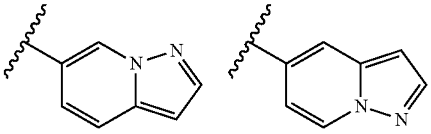
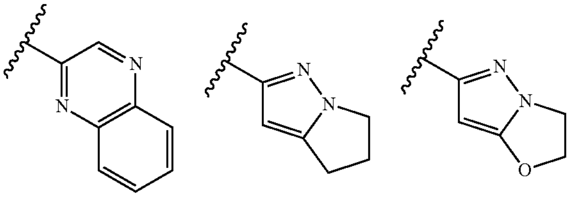

-continued

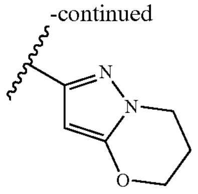

As defined generally above, each $R^x$ is selected from optionally substituted $C_{1-6}$ aliphatic, —$N(R)_2$, and —OR. In some embodiments, $R^x$ is $C_{1-6}$ aliphatic. In some embodiments, $R^x$ is $C_{1-4}$ aliphatic. In some embodiments, $R^x$ is $C_{1-2}$ aliphatic. In some embodiments, $R^x$ is —$CH_3$, —$CH_2CH_3$, or —$CH(CH_3)_2$. In some embodiments, at least one $R^x$ is $C_{1-6}$ aliphatic. In some embodiments, $R^x$ is optionally substituted $C_{1-6}$ aliphatic. In some embodiments, $R^x$ is $C_{1-6}$ aliphatic optionally substituted with halogen (e.g., fluoro). In some embodiments, $R^x$ is $C_{1-4}$ aliphatic optionally substituted with halogen (e.g., fluoro). In some embodiments, $R^x$ is $C_{1-2}$ aliphatic optionally substituted with halogen (e.g., fluoro). In some such embodiments, $R^x$ is —$CF_3$, —$CF_2H$, —$CHF_2$, $CF_2CH_3$, or $CH_2CF_3$.

In some embodiments, $R^x$ is —$N(R)_2$. In some embodiments, $R^x$ is —NHR. In some embodiments, $R^x$ is —$NH_2$. In some embodiments, $R^x$ is —$NHCH_3$. In some embodiments, $R^x$ is —$N(CH_3)_2$.

In some embodiments, $R^x$ is —OR. In some embodiments, $R^x$ is —$OCH_3$. In some embodiments, $R^x$ is —OR, wherein R is $C_{1-6}$ aliphatic optionally substituted with halogen (e.g., fluoro). In some embodiments, $R^x$ is —OR, wherein R is $C_{1-4}$ aliphatic optionally substituted with halogen (e.g., fluoro). In some embodiments, $R^x$ is —OR, wherein R is $C_{1-2}$ aliphatic optionally substituted with halogen (e.g., fluoro). In some embodiments, $R^x$ is —$OCH_2F$. In some embodiments, $R^x$ is —$OCF_2H$. In some embodiments, $R^x$ is —$OCF_3$.

As defined generally above, each $R^y$ is independently selected from oxo, —CN, —$N(R)_2$, —OR, —$CO_2R$, or an optionally substituted group selected from $C_{1-4}$ aliphatic, and a 3- to 7-membered saturated or partially unsaturated carbocyclic ring. In some embodiments, R is selected from —CN, —$N(R)_2$, —OR and —$CO_2R$. In some embodiments, $R^y$ is an optionally substituted group selected from $C_{1-4}$ aliphatic and a 3- to 7-membered saturated or partially unsaturated carbocyclic ring. In some embodiments, $R^y$ is —CN. In some embodiments, $R^y$ is —$N(R)_2$. In some embodiments, $R^y$ is selected from —$NH_2$, —$NHCH_3$, and —$N(CH_3)_2$. In some embodiments, $R^y$ is —OR. In some embodiments, $R^y$ is —OR, wherein R is $C_{1-6}$ aliphatic optionally substituted with halogen (e.g., fluoro). In some embodiments, $R^y$ is —OR, wherein R is $C_{1-4}$ aliphatic optionally substituted with halogen (e.g., fluoro). In some embodiments, $R^y$ is —OR, wherein R is $C_{1-2}$ aliphatic optionally substituted with halogen (e.g., fluoro). In some embodiments, $R^y$ is selected from —OH, —$OCH_3$, —$OCH_2CH_3$, —$OCHF_2$, —$OCF_2H$, and —$OCF_3$. In some embodiments, $R^y$ is —$CO_2R$. In some embodiments, $R^y$ is —$CO_2H$. It will be appreciated that, in certain instances, $R^2$ can be drawn in one or more tautomeric forms when, for example, $R^y$ is —OH on a carbon atom adjacent to a nitrogen atom of $R^2$. For example, when $R^2$ is

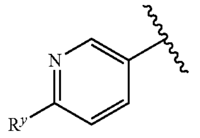

and $R^y$ is —OH, $R^2$ can be drawn as

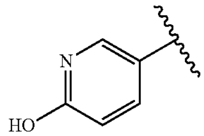

or

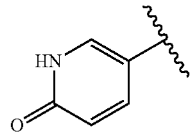

Similarly, when $R^2$ is

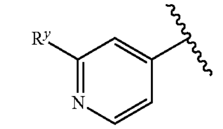

and $R^y$ is —OH, $R^2$ can be drawn as

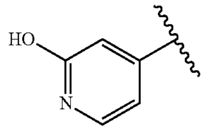

or

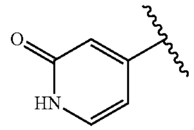

.

All tautomeric forms of a moiety are contemplated by this disclosure.

In some embodiments, $R^y$ is an optionally substituted group selected from $C_{1-4}$ aliphatic and a 3- to 7-membered saturated or partially unsaturated carbocyclic ring. In some embodiments, $R^y$ is optionally substituted $C_{1-4}$ aliphatic. In some embodiments, $R^y$ is $C_{1-4}$ aliphatic optionally substituted with halogen (e.g., fluoro) or —$(CH_2)_{0-4}OR°$. In some embodiments, $R^y$ is $C_{1-4}$ aliphatic optionally substituted with halogen (e.g., fluoro) or —OR°. In some such embodiments, R° is hydrogen or —$CH_3$. In some embodiments, $R^y$ is optionally substituted $C_{1-3}$ aliphatic. In some such embodiments, $R^y$ is —$CH_3$, —$CH_2CH_3$, —$CH(CH_3)_2$, —$CF_3$, —$CH_2F$, —$CF_2H$, —$CF_2CH_3$, —$C(OH)(CH_3)_2$, and —C≡CH. In some embodiments, $R^y$ is —$CH_3$, —$CH_2CH_3$, —$CH(CH_3)_2$, —$CF_3$, —$CH_2F$, —$CF_2H$, —$CF_2CH_3$, —$CH_2OH$, —$C(OH)(CH_3)_2$, and —C≡CH.

In some embodiments, $R^y$ is an optionally substituted 3- to 7-membered saturated or partially unsaturated carbocyclic ring. In some embodiments, $R^y$ is an optionally substituted 3- to 7-membered saturated carbocyclic ring. In some embodiments, $R^y$ is an optionally substituted 3- to 5-membered saturated carbocyclic ring. In some embodiments, $R^y$ is an optionally substituted 3- to 4-membered saturated carbocyclic ring. In some embodiments, R is an optionally substituted 5- to 7-membered saturated carbocyclic ring. In some embodiments, R is an optionally substituted 5- to 6-membered saturated carbocyclic ring. In some embodiments, $R^y$ is a 3- to 4-membered saturated carbocyclic ring optionally substituted with —$(CH_2)_{0-4}R°$. In some embodiments, $R^y$ is a 3- to 4-membered saturated carbocyclic ring optionally substituted with —R°. In some such embodiments, R° is —$CH_3$.

In some embodiments, $R^y$ is selected from

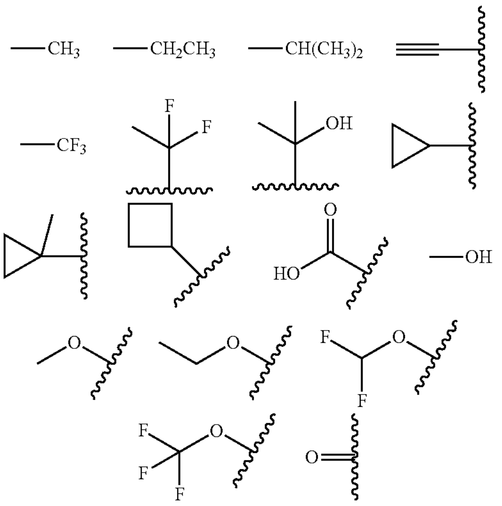

In some embodiments, $R^y$ is selected from halogen (e.g., fluoro or chloro)

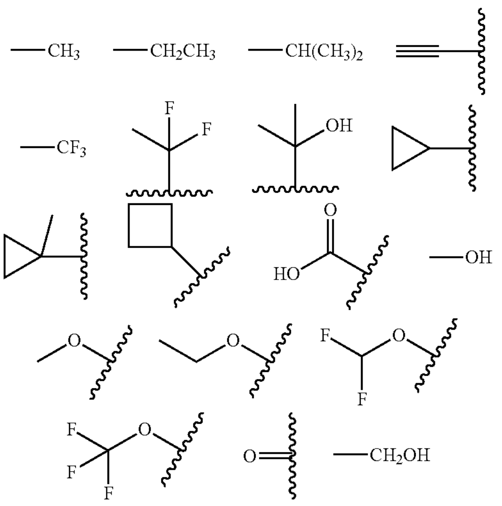

As defined generally above, each $R^z$ is independently selected from —CN, halogen, —OR, —$SO_2$R, and an optionally substituted group selected from $C_{1-6}$ aliphatic and a 3- to 7-membered saturated or partially unsaturated carbocyclic ring. In some embodiments, $R^z$ is selected from —CN, halogen, —OR, and —$SO_2$R. In some embodiments, $R^z$ is halogen. In some embodiments, $R^z$ is —CN. In some embodiments, $R^z$ is —OR. In some embodiments, $R^z$ is —$SO_2$R.

In some embodiments, $R^z$ is an optionally substituted group selected from $C_{1-4}$ aliphatic and a 3- to 7-membered saturated or partially unsaturated carbocyclic ring. In some embodiments, $R^z$ is optionally substituted $C_{1-4}$ aliphatic. In some embodiments, $R^z$ is optionally substituted $C_{1-3}$ aliphatic. In some embodiments, $R^z$ is $C_{1-4}$ aliphatic optionally substituted with halogen (e.g., fluoro), —$(CH_2)_{0-4}$OR° or —CN. In some embodiments, $R^z$ is $C_{1-4}$ aliphatic optionally substituted with halogen (e.g., fluoro), —OR° or —CN, wherein R° is hydrogen or —$CH_3$. In some such embodiments, $R^z$ is —$CH_3$, —$CH_2CH_3$, —$CH(CH_3)_2$, —$CF_3$, —$CH_2F$, —$CF_2H$, —$CF_2CH_3$, —$CH_2CN$, and —$CH_2OCH_3$.

In some embodiments, at least one $R^z$ is —$CF_3$. In some embodiments, at least one $R^z$ is —$CF_3$ and at least one additional $R^z$ is selected from halogen (e.g., Cl), —$CH_3$, —$CH_2CH_3$, —$CH(CH_3)_2$, and cyclopropyl. In some embodiments, at least one $R^z$ is —$CH_3$. In some embodiments, at least one $R^z$ is —$CH_3$ and at least one additional $R^z$ is selected from —CN, —$CH_3$, —$CF_3$, halogen (e.g., Cl), —$CF_2H$, —$CF_2CH_3$, —$CH_2CN$, —$CH_2OCH_3$, cyclopropyl, —$OCH_3$, —$OCH_2CH_3$, and cyclopropyl. In some embodiments, at least one $R^z$ is —$CH_3$. In some embodiments, at least one $R^z$ is —$CH_3$ and at least one additional $R^z$ is selected from —CN, —$CH_3$, —$CH_2CH_3$, —$CF_3$, halogen (e.g., Cl), —$CF_2H$, —$CF_2CH_3$, —$CH_2CN$, —$CH_2OCH_3$, cyclopropyl, —$OCH_3$, —$OCH_2CH_3$, and cyclopropyl. In some embodiments, at least one $R^z$ is —$CH_3$ and at least one additional $R^z$ is selected from —CN, —$CH_3$, —$CH_2CH_3$, —$CF_3$, halogen (e.g., Cl), —$CF_2H$, —$CF_2CH_3$, —$CH_2CN$, —$CH_2OCH_3$, cyclopropyl, —$OCH_3$, —$OCF_3$, —$OCH_2CH_3$, —$OCH(CH_3)_2$,

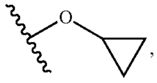, and cyclopropyl.

In some embodiments, $R^z$ is selected from halogen (e.g, F or Cl), —CN, —$SO_2CH_3$, —$OCH_3$, —$OCH_2CH_3$, —$CH_3$, —$CH_2CH_3$, —$CH(CH_3)_2$, —$CF_3$, —$CF_2H$, —$CF_2CH_3$, —$CH_2CN$, —$CH_2OCH_3$, and cyclopropyl. In some embodiments, $R^z$ is selected from halogen (e.g,. F or Cl), —CN, —$SO_2CH_3$, —$OCH_3$, —$OCHF_2$, —$OCF_3$, —$OCH_2CH_3$, —$OCH(CH_3)_2$,

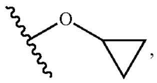,

—$CH_3$, —$CD_3$, —$CH_2CH_3$, —$CH(CH_3)_2$, —$CF_3$, —$CF_2H$, —$CF_2CH_3$, —$CH_2F$, —$CH_2CN$, —$CH_2CHF_2$, —$CH_2CF_3$, —$CH_2OCH_3$, —$C(CH_3)_2$OH, and cyclopropyl.

In some embodiments, $R^z$ is an optionally substituted 3- to 7-membered saturated or partially unsaturated carbocyclic ring. In some embodiments, $R^z$ is an optionally substituted 3- to 7-membered saturated carbocyclic ring. In some embodiments, $R^z$ is an optionally substituted 3- to 5-membered saturated carbocyclic ring. In some embodiments, $R^z$ is an optionally substituted 3- to 4-membered saturated carbocyclic ring. In some embodiments, $R^z$ is an optionally substituted 5- to 7-membered saturated carbocyclic ring. In some embodiments, $R^z$ is an optionally substituted 5- to 6-membered saturated carbocyclic ring. In some embodiments, $R^z$ is a 5- to 6-membered saturated carbocyclic ring optionally substituted with halogen (e.g., fluoro).

In some embodiments of Formula I', $R^z$ is phenyl.

As defined generally above, each R is independently selected from hydrogen or an optionally substituted group selected from $C_{1-6}$ aliphatic, phenyl, a 3- to 7-membered saturated or partially unsaturated carbocyclic ring, a 3- to 7-membered saturated or partially unsaturated heterocyclic ring having 1-3 heteroatoms independently selected from nitrogen, oxygen, and sulfur, and a 5- to 6-membered heteroaryl ring having 1-4 heteroatoms independently selected from nitrogen, oxygen, and sulfur. In some embodiments, each R is hydrogen. In some embodiments, each R is an optionally substituted group selected from $C_{1-6}$ aliphatic, phenyl, a 3- to 7-membered saturated or partially unsaturated carbocyclic ring, a 3- to 7-membered saturated or partially unsaturated heterocyclic ring having 1-3 heteroatoms independently selected from nitrogen, oxygen, and sulfur, and a 5- to 6-membered heteroaryl ring having 1-4 heteroatoms independently selected from nitrogen, oxygen, and sulfur. In some embodiments, at least one R is optionally substituted $C_{1-6}$ aliphatic. In some embodiments, at least one R is optionally substituted $C_{1-4}$ aliphatic. In some embodiments, at least one R is optionally substituted $C_{1-2}$ aliphatic. In some embodiments, at least one R is $C_{1-6}$ aliphatic optionally substituted with halogen (e.g., fluoro), —CN, $-(CH_2)_{0-4}R^{\circ}$, or $-(CH_2)_{0-4}OR^{\circ}$. In some embodiments, at least one R is $C_{1-4}$ aliphatic optionally substituted with halogen (e.g., fluoro), —CN, $-(CH_2)_{0-4}R^{\circ}$, or $-(CH_2)_{0-4}OR^{\circ}$. In some embodiments, at least one R is $C_{1-2}$ aliphatic optionally substituted with halogen (e.g., fluoro), —CN, $-(CH_2)_{0-4}R^{\circ}$, or $-(CH_2)_{0-4}OR^{\circ}$. In some embodiments, $R^{\circ}$ is hydrogen or $-CH_3$. In some embodiments, at least one R is $-CH_3$, $-CF_3$, $-CF_2H$, $-CH_2F$, $-CH_2CH_3$, $-CF_2CH_3$, $-CH_2CF_3$, or $-CH(CH_3)_2$.

In some embodiments, at least one R is optionally substituted phenyl. In some embodiments, at least one R is an optionally substituted 3- to 7-membered saturated or partially unsaturated carbocyclic ring. In some embodiments, at least one R is an optionally substituted 3- to 5-membered saturated carbocyclic ring. In some embodiments, at least one R is an optionally substituted 3- to 4-membered saturated carbocyclic ring. In some embodiments, at least one R is an optionally substituted 5- to 7-membered saturated or partially unsaturated carbocyclic ring. In some embodiments, at least one R is an optionally substituted 5- to 7-membered saturated carbocyclic ring.

In some embodiments, at least one R is an optionally substituted 3- to 7-membered saturated or partially unsaturated heterocyclic ring having 1-3 heteroatoms independently selected from nitrogen, oxygen, and sulfur. In some embodiments, at least one R is an optionally substituted 3- to 5-membered saturated heterocyclic ring having 1-3 heteroatoms independently selected from nitrogen, oxygen, and sulfur. In some embodiments, at least one R is an optionally substituted 3- to 4-membered saturated heterocyclic ring having 1-3 heteroatoms independently selected from nitrogen, oxygen, and sulfur. In some embodiments, at least one R is an optionally substituted 5- to 7-membered saturated or partially unsaturated heterocyclic ring having 1-3 heteroatoms independently selected from nitrogen, oxygen, and sulfur. In some embodiments, at least one R is an optionally substituted 5- to 7-membered saturated heterocyclic ring having 1-3 heteroatoms independently selected from nitrogen, oxygen, and sulfur.

In some embodiments, at least one R is an optionally substituted 5- to 6-membered heteroaryl ring having 1-4 heteroatoms independently selected from nitrogen, oxygen, and sulfur. In some embodiments, at least one R is an optionally substituted 5-membered heteroaryl ring having 1-4 heteroatoms independently selected from nitrogen, oxygen, and sulfur. In some embodiments, at least one R is an optionally substituted 5-membered heteroaryl ring having 1-3 heteroatoms independently selected from nitrogen, oxygen, and sulfur. In some embodiments, at least one R is an optionally substituted 5-membered heteroaryl ring having 1-2 heteroatoms independently selected from nitrogen, oxygen, and sulfur.

In some embodiments, at least one R is an optionally substituted 6-membered heteroaryl ring having 1-3 nitrogen atoms. In some embodiments, at least one R is an optionally substituted 6-membered heteroaryl ring having 1-2 nitrogen atoms.

In some embodiments, at least one R is hydrogen. In some embodiments, each R group of $R^1$ is hydrogen (i.e., the R group of any of

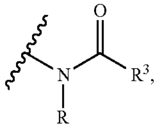
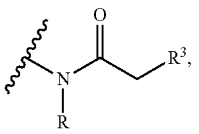
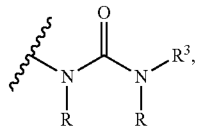
and
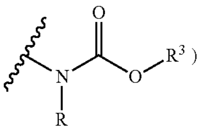

is hydrogen. In some embodiments, the R group of $R^y$ is hydrogen. In some embodiments, the R group of R is $-CH_3$. In some embodiments, the R group of $R^z$ is hydrogen. In some embodiments, the R group of $R^z$ is $-CH_3$.

As defined generally above, m is 0-2. In some embodiments, m is 0. In some embodiments, m is 0-1. In some embodiments, m is 1-2. In some embodiments, m is 1. In some embodiments, m is 2.

As defined generally above, n is 1-3. In some embodiments, n is 1. In some embodiments, n is 2. In some embodiments, n is 3.

In some embodiments, the present disclosure provides a compound of any of formulae I-a, I-b, I-c, I-d, I-e, I-f, I-g, I-h, I-i, I-j, I-k, I-l, I-m, I-n, I-o, I-p, I-q, I-r, I-s, and I-t:

I-a

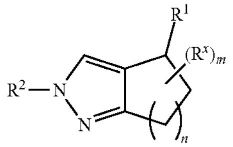

I-b

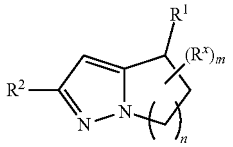

I-c

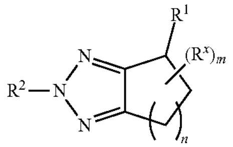

-continued

I-d

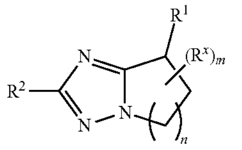

I-e

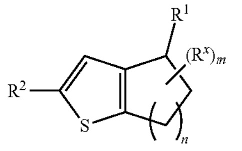

I-f

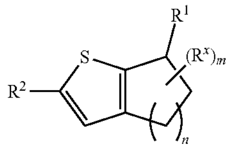

I-g

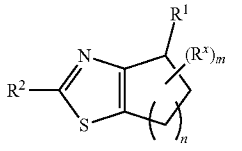

I-h

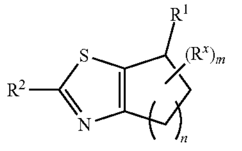

I-i

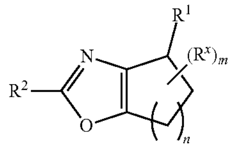

I-j

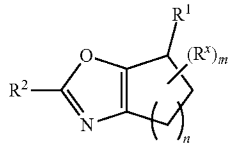

I-k

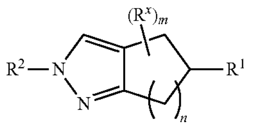

I-l

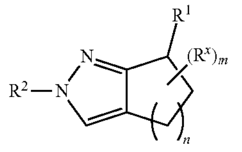

I-m

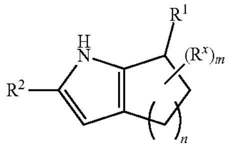

-continued

I-n

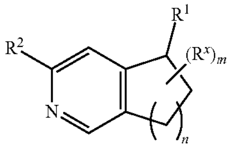

I-o

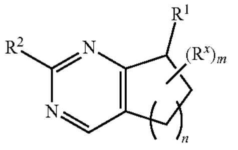

I-p

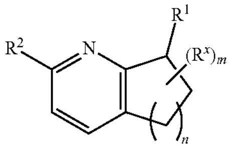

I-q

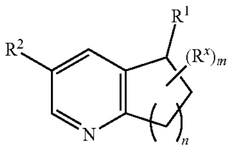

I-r

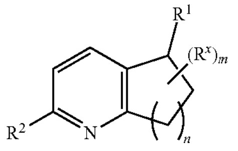

I-s

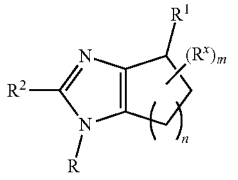

I-t

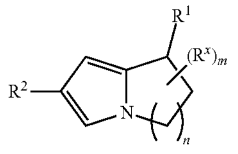

or a pharmaceutically acceptable salt thereof, wherein each of $R^1$, $R^2$, $R^x$, m, and n is as defined in any of the above embodiments, and combinations thereof.

In some embodiments, the present disclosure provides a compound of any of formulae I-a-i, I-b-i, I-c-i, I-d-i, I-e-i, I-f-i, I-g-i, I-h-i, I-i-i, I-j-i, I-k-i, I-l-i, I-m-i, I-n-i, I-o-i, I-p-i, I-q-i, I-r-i, I-s-i, and I-t-i:

I-a-i

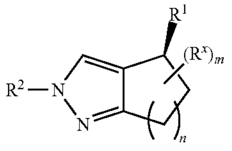

-continued

I-b-i

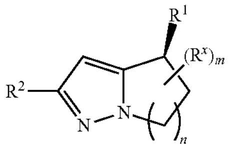

I-c-i

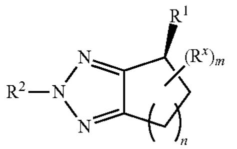

I-d-i

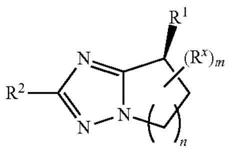

I-e-i

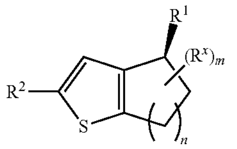

I-f-i

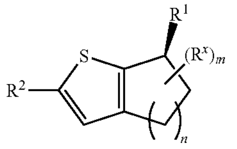

I-g-i

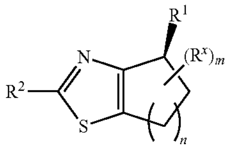

I-h-i

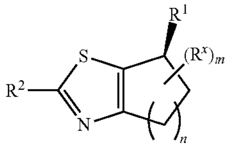

I-i-i

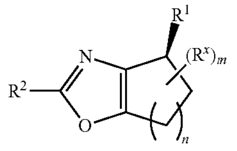

I-j-i

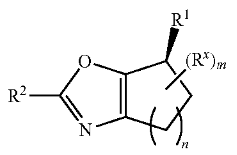

I-k-i

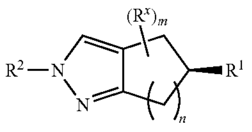

-continued

I-l-i

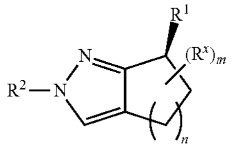

I-m-i

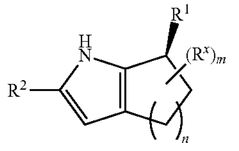

I-n-i

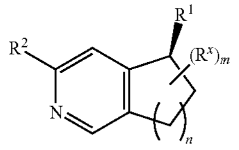

I-o-i

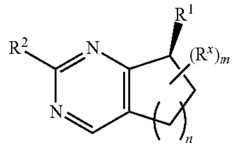

I-p-i

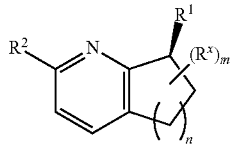

I-q-i

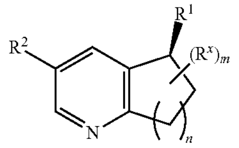

I-r-i

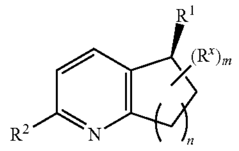

I-s-i

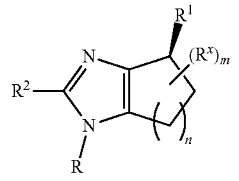

I-t-i

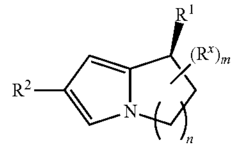

or a pharmaceutically acceptable salt thereof, wherein each of $R^1$, $R^2$, $R^x$, m, and n is as defined in any of the above embodiments, and combinations thereof.

In some embodiments, the present disclosure provides a compound of any of formulae II-a, II-b, II-c, II-d, II-e, III-a, III-b, III-c, III-d, III-e, III-f, III-g, III-h, III-i, III-j, III-k, III-l, III-m, III-n, III-o, III-p, III-q, IV-a, IV-b, IV-c, IV-d, IV-e, IV-f, IV-g, IV-h, V-a, V-b, V-c, V-d, V-e, VI-a, VI-b, VI-c, VI-d, VI-e, VI-f, VI-g, and VII-a:
II-a
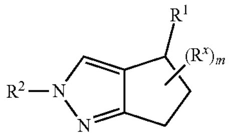
II-b
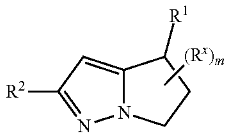
II-c
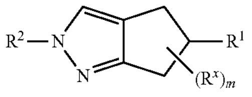
II-d
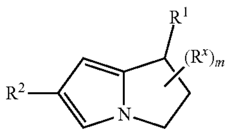
II-e
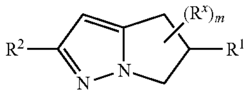
III-a
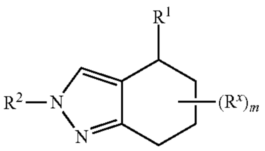
III-b
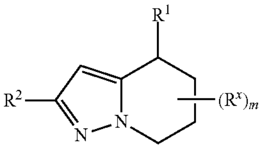
III-c
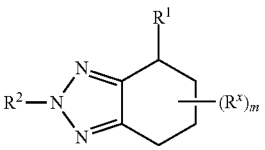
III-d
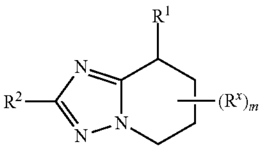
III-e
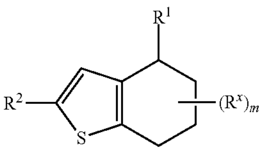
-continued
III-f
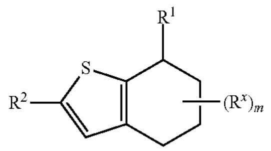
III-g
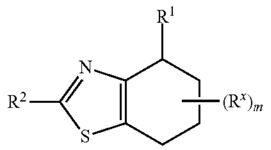
III-h
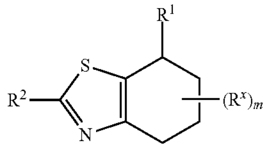
III-i
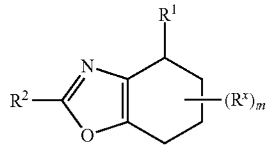
III-j
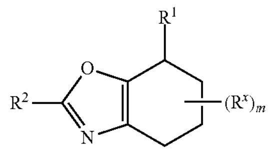
III-k
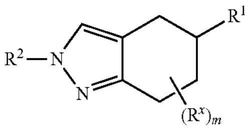
III-l
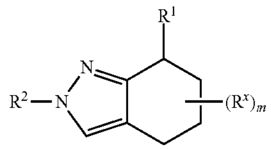
III-m
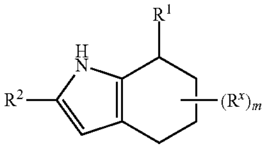
III-n
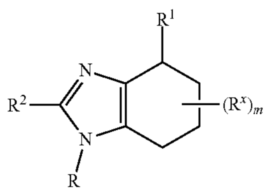
III-o
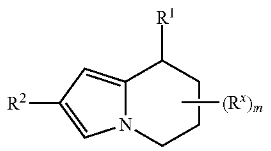

-continued
III-p
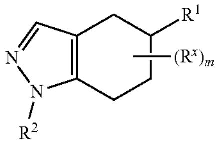
III-q
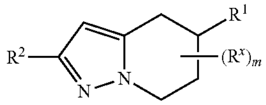
IV-a
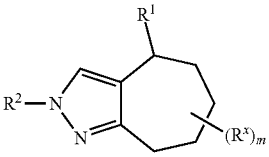
IV-b
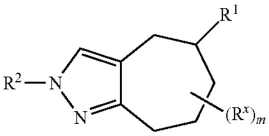
IV-c
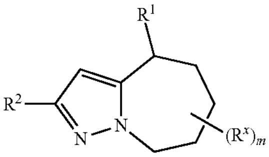
IV-d
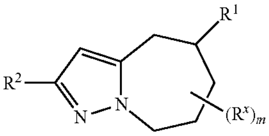
IV-e
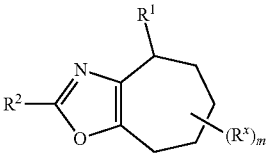
IV-f
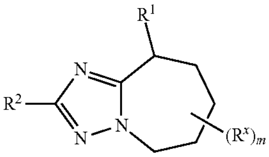
IV-g
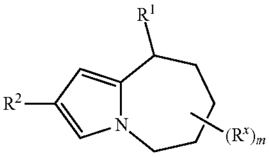
IV-h
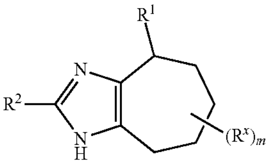
-continued
V-a
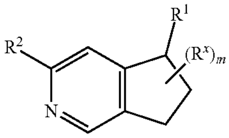
V-b
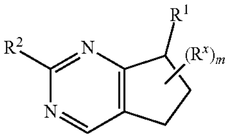
V-c
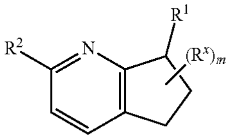
V-d
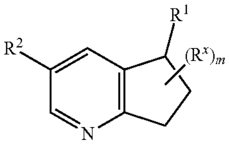
V-e
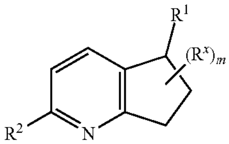
VI-a
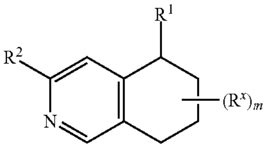
VI-b
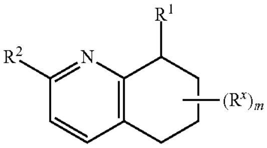
VI-c
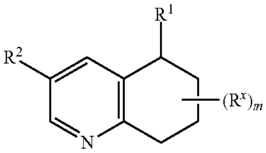
VI-d
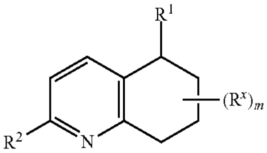
VI-e
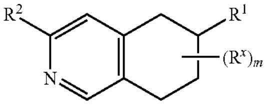

-continued

VI-f

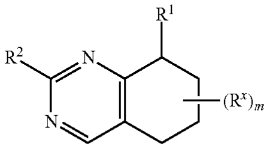

VI-g

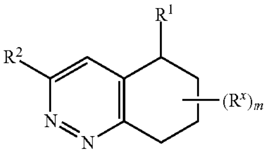

VII-a

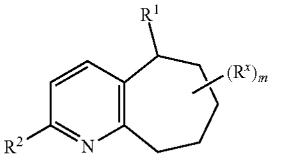

or a pharmaceutically acceptable salt thereof, wherein each of $R^1$, $R^2$, $R^x$, and m is as defined in any of the above embodiments, and combinations thereof.

In some embodiments, the present disclosure provides a compound of any of formulae II-a-i, II-b-i, II-c-i, II-d-i, II-e-i, III-a-i, III-b-i, III-c-i, III-d-i, III-e-i, III-f-i, III-g-i, III-h-i, III-i-i, III-j-i, III-k-i, III-l-i, III-m-i, III-n-i, III-o-i, III-p-i, III-q-i, IV-a-i, IV-b-i, IV-c-i, IV-d-i, IV-e-i, IV-f-i, IV-g-i, IV-h-i, V-a-i, V-b-i, V-c-i, V-d-i, V-e-i, VI-a-i, VI-b-i, VI-c-i, VI-d-i, VI-e-i, VI-f-i, VI-g-i, and VII-a-i.

II-a-i

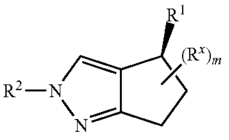

II-b-i

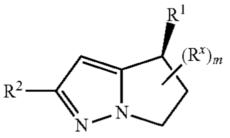

II-c-i

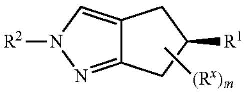

II-d-i

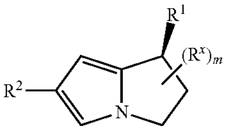

II-e-i

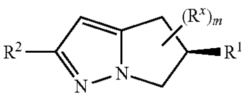

III-a-i

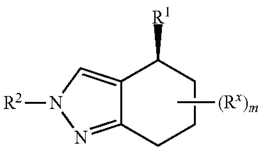

-continued

III-b-i

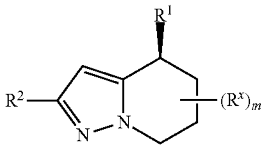

III-c-i

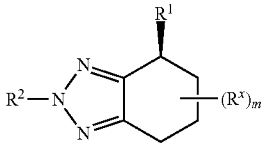

III-d-i

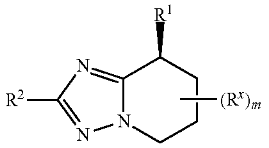

III-e-i

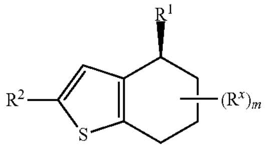

III-f-i

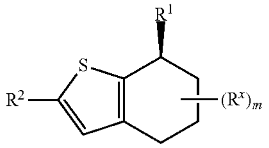

III-g-i

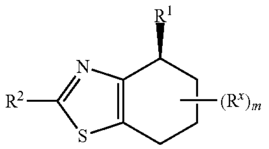

III-h-i

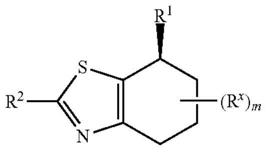

III-i-i

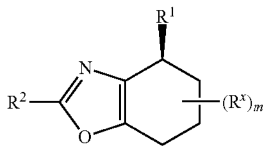

III-j-i

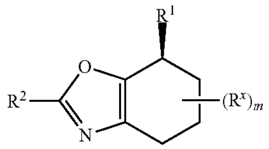

III-k-i

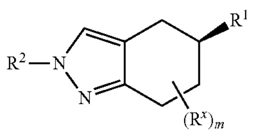

-continued
III-l-i
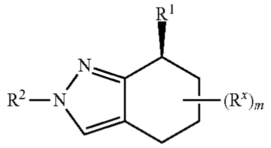
III-m-i
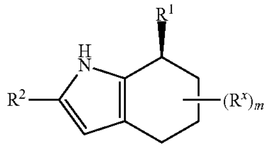
III-n-i
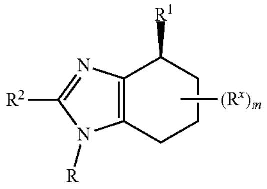
III-o-i
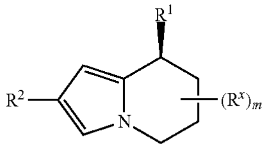
III-p-i
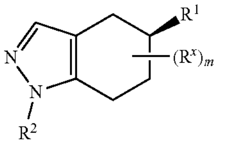
III-q-i
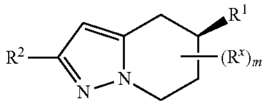
IV-a-i
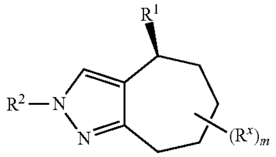
IV-b-i
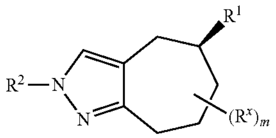
IV-c-i
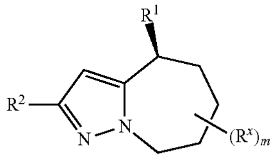
IV-d-i
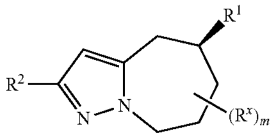
-continued
IV-e-i
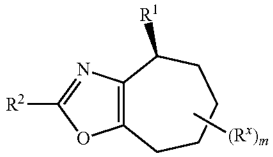
IV-f-i
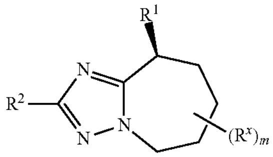
IV-g-i
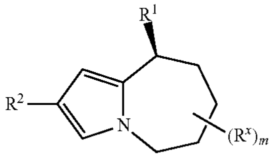
IV-h-i
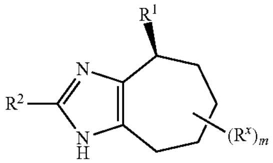
V-a-i
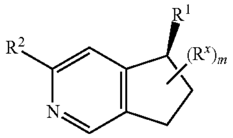
V-b-i
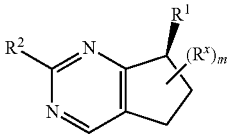
V-c-i
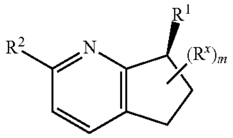
V-d-i
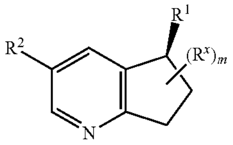
V-e-i
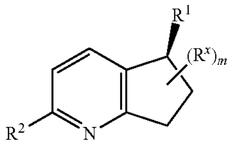
VI-a-i
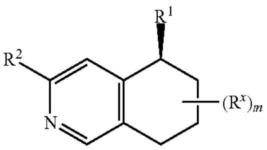

-continued
VI-b-i
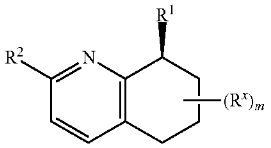
VI-c-i
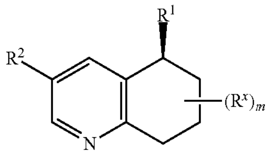
VI-d-i
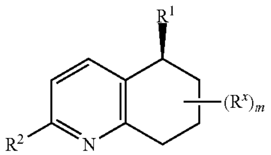
VI-e-i
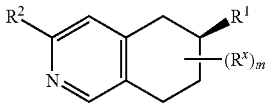
-continued
VI-f-i
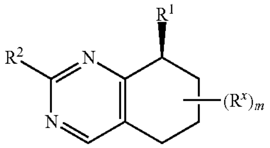
VI-g-i
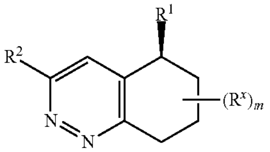
VII-a-i
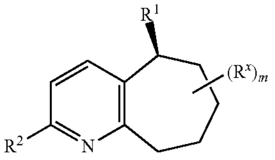
or a pharmaceutically acceptable salt thereof, wherein each of $R^1$, $R^2$, $R^x$, and m is as defined in any of the above embodiments, and combinations thereof.
In some embodiments, the present disclosure provides a compound selected from Table 1:
TABLE 1
I-1
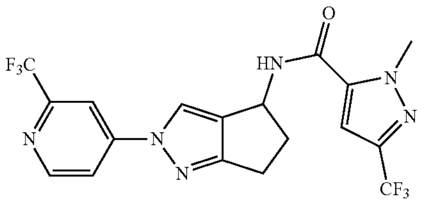 [SMILES: Cn1nc(C(F)(F)F)cc1C(=O)NC1CCc2nn(-c3ccnc(C(F)(F)F)c3)cc21]
I-1a
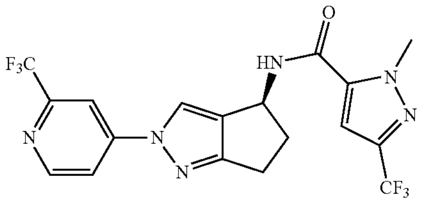 [SMILES: Cn1nc(C(F)(F)F)cc1C(=O)N[C@H]1CCc2nn(-c3ccnc(C(F)(F)F)c3)cc21]
I-1b
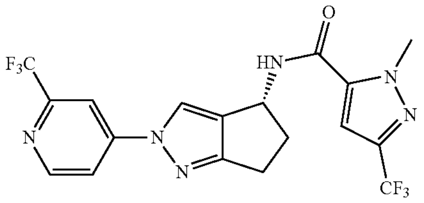
I-2
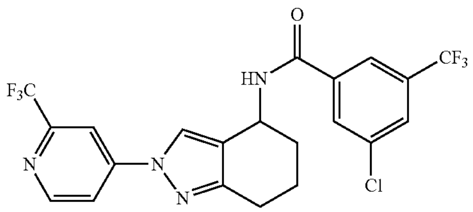 [SMILES: O=C(NC1CCCc2nn(-c3ccnc(C(F)(F)F)c3)cc21)c1cc(Cl)cc(C(F)(F)F)c1]

TABLE 1-continued
I-2a
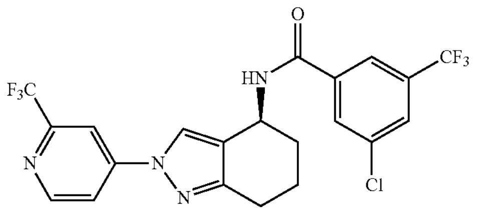
I-2b
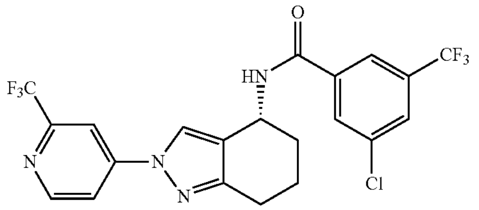 [SMILES: O=C(N[C@@H]1CCCc2nn(-c3ccnc(C(F)(F)F)c3)cc21)c1cc(Cl)cc(C(F)(F)F)c1]
I-3
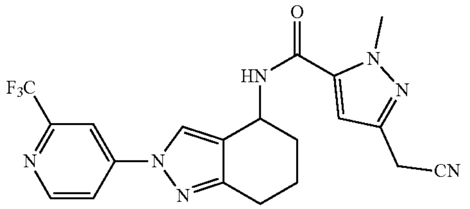 [SMILES: Cn1nc(CC#N)cc1C(=O)N[C@@H]1CCCc2nn(-c3ccnc(C(F)(F)F)c3)cc21]
I-3a
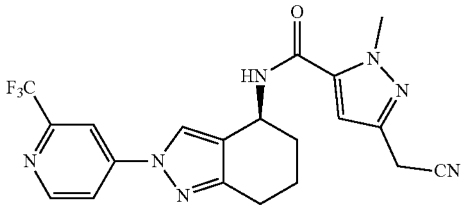
I-3b
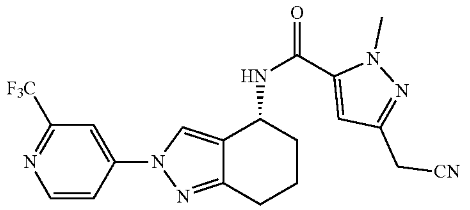
I-4
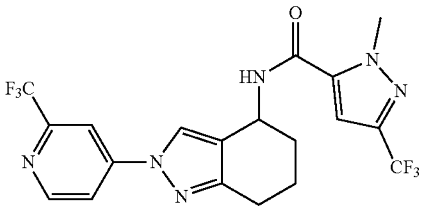
I-4a
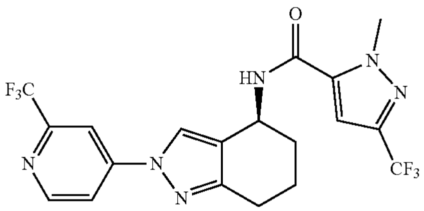

TABLE 1-continued
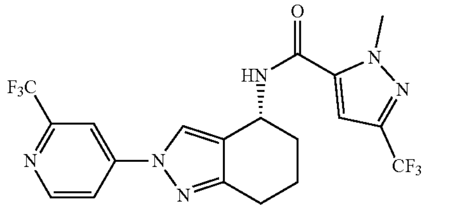
I-4b
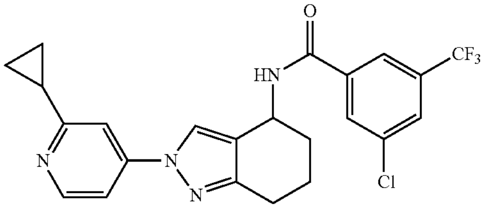 [SMILES: O=C(NC1CCCc2nn(-c3ccnc(C4CC4)c3)cc21)c1cc(Cl)cc(C(F)(F)F)c1]
I-5
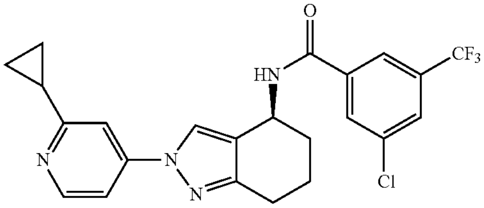 [SMILES: O=C(N[C@H]1CCCc2nn(-c3ccnc(C4CC4)c3)cc21)c1cc(Cl)cc(C(F)(F)F)c1]
I-5a
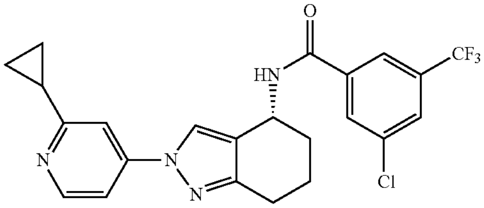 [SMILES: O=C(N[C@@H]1CCCc2nn(-c3ccnc(C4CC4)c3)cc21)c1cc(Cl)cc(C(F)(F)F)c1]
I-5b
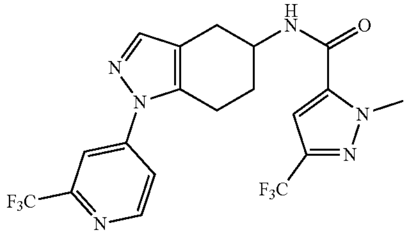 [SMILES: Cn1nc(C(F)(F)F)cc1C(=O)NC1CCc2c(cnn2-c2ccnc(C(F)(F)F)c2)C1]
I-6
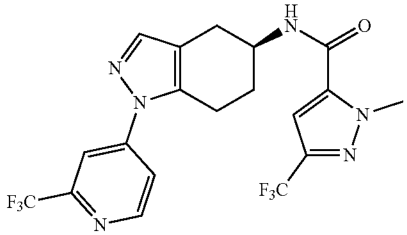 [SMILES: Cn1nc(C(F)(F)F)cc1C(=O)N[C@H]1CCc2c(cnn2-c2ccnc(C(F)(F)F)c2)C1]
I-6a
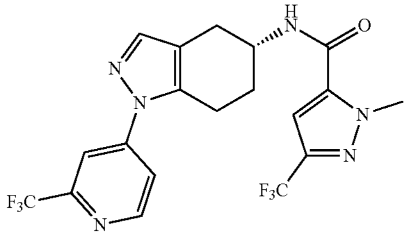 [SMILES: Cn1nc(C(F)(F)F)cc1C(=O)N[C@@H]1CCc2c(cnn2-c2ccnc(C(F)(F)F)c2)C1]
I-6b TABLE 1-continued
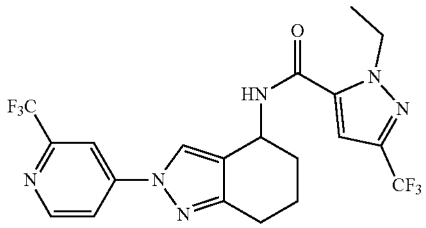
I-7
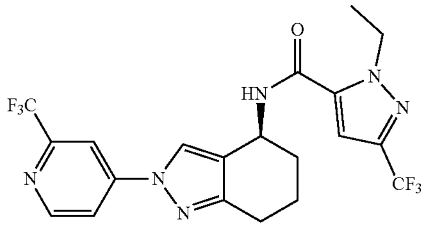
I-7a
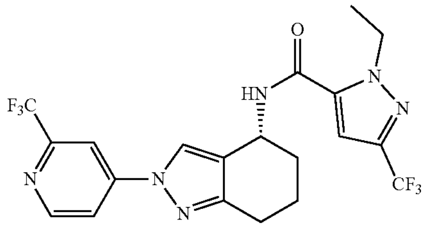
I-7b
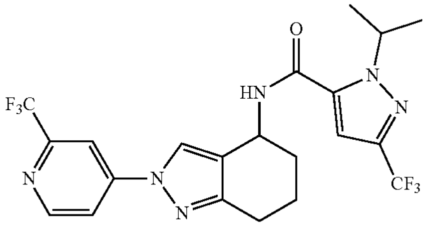 [SMILES: CC(C)n1nc(C(F)(F)F)cc1C(=O)NC1CCCc2nn(-c3ccnc(C(F)(F)F)c3)cc21]
I-8
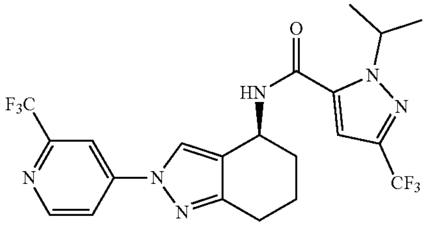 [SMILES: CC(C)n1nc(C(F)(F)F)cc1C(=O)N[C@H]1CCCc2nn(-c3ccnc(C(F)(F)F)c3)cc21]
I-8a
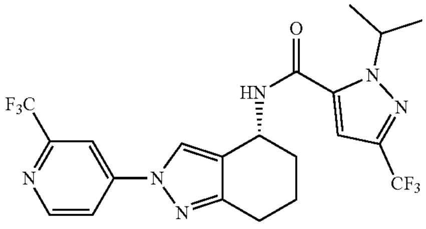
I-8b TABLE 1-continued
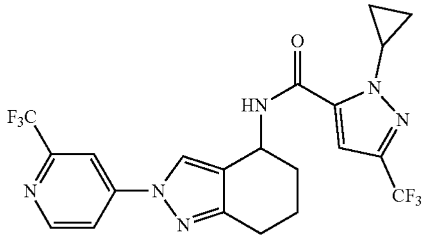 [SMILES: O=C(NC1CCCc2nn(-c3ccnc(C(F)(F)F)c3)cc21)c1cc(C(F)(F)F)nn1C1CC1]
I-9
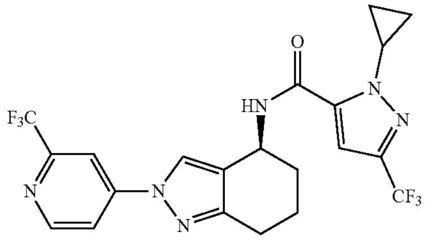 [SMILES: O=C(N[C@H]1CCCc2nn(-c3ccnc(C(F)(F)F)c3)cc21)c1cc(C(F)(F)F)nn1C1CC1]
I-9a
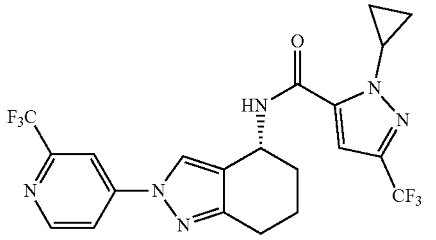 [SMILES: O=C(N[C@@H]1CCCc2nn(-c3ccnc(C(F)(F)F)c3)cc21)c1cc(C(F)(F)F)nn1C1CC1]
I-9b
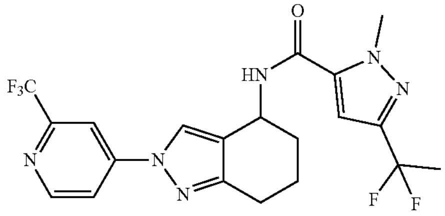
I-10
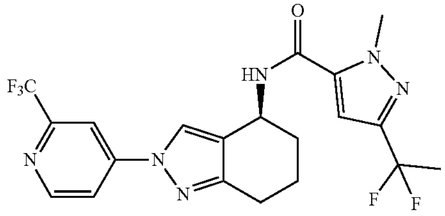 [SMILES: Cn1nc(C(C)(F)F)cc1C(=O)N[C@H]1CCCc2nn(-c3ccnc(C(F)(F)F)c3)cc21]
I-10a
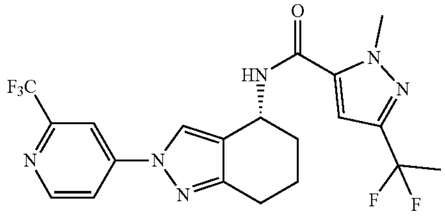
I-10b
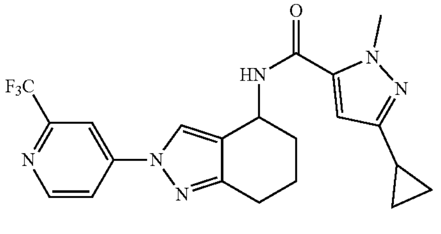 [SMILES: Cn1nc(C2CC2)cc1C(=O)NC1CCCc2nn(-c3ccnc(C(F)(F)F)c3)cc21]
I-11

TABLE 1-continued
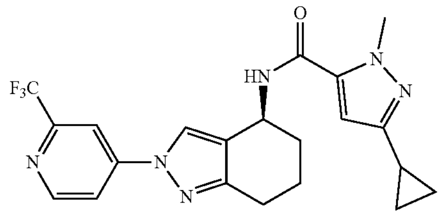 [SMILES: Cn1nc(C2CC2)cc1C(=O)N[C@H]1CCCc2nn(-c3ccnc(C(F)(F)F)c3)cc21]
I-11a
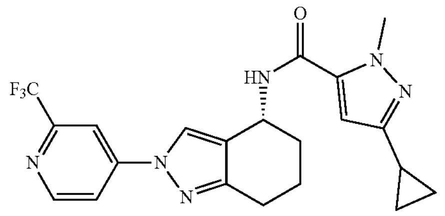
I-11b
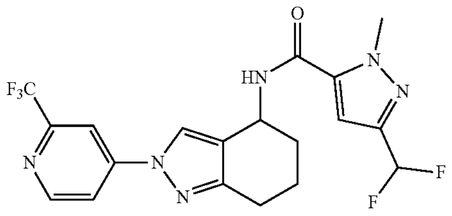 [SMILES: Cn1nc(C(F)F)cc1C(=O)NC1CCCc2nn(-c3ccnc(C(F)(F)F)c3)cc21]
I-12
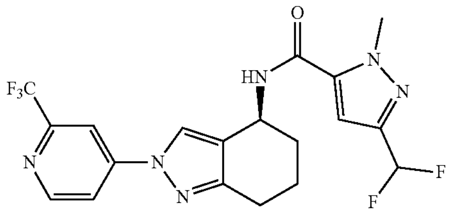 [SMILES: Cn1nc(C(F)F)cc1C(=O)N[C@H]1CCCc2nn(-c3ccnc(C(F)(F)F)c3)cc21]
I-12a
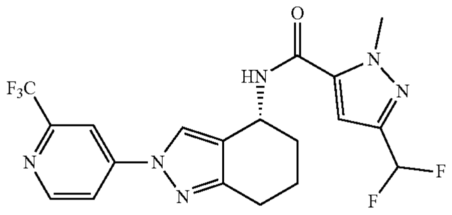
I-12b
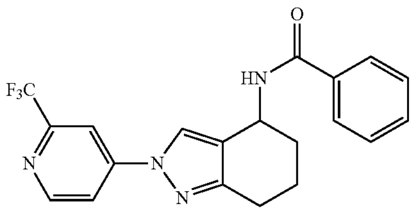
I-13
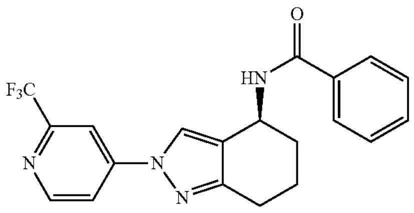
I-13a TABLE 1-continued
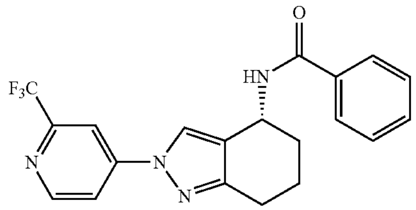
I-13b
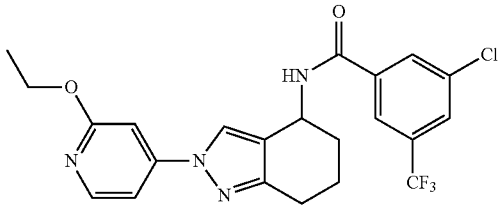 [SMILES: CCOc1cc(-n2cc3c(n2)CCCC3NC(=O)c2cc(Cl)cc(C(F)(F)F)c2)ccn1]
I-14
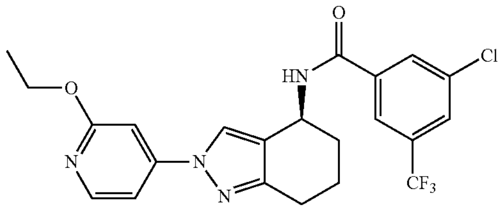 [SMILES: CCOc1cc(-n2cc3c(n2)CCC[C@@H]3NC(=O)c2cc(Cl)cc(C(F)(F)F)c2)ccn1]
I-14a
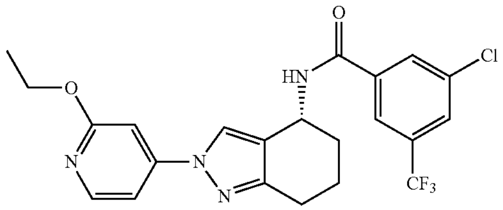 [SMILES: CCOc1cc(-n2cc3c(n2)CCC[C@H]3NC(=O)c2cc(Cl)cc(C(F)(F)F)c2)ccn1]
I-14b
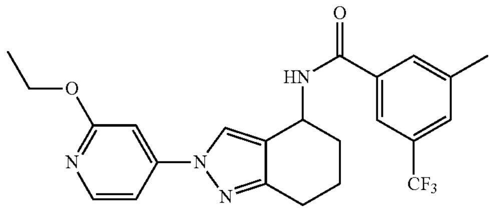 [SMILES: CCOc1cc(-n2cc3c(n2)CCCC3NC(=O)c2cc(C)cc(C(F)(F)F)c2)ccn1]
I-15
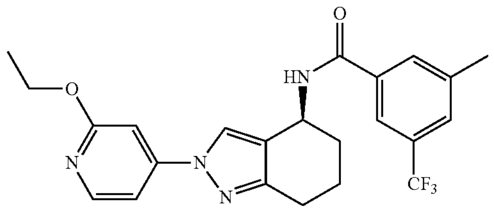 [SMILES: CCOc1cc(-n2cc3c(n2)CCC[C@@H]3NC(=O)c2cc(C)cc(C(F)(F)F)c2)ccn1]
I-15a
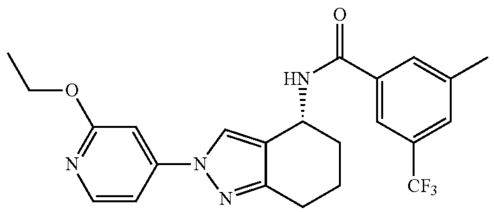 [SMILES: CCOc1cc(-n2cc3c(n2)CCC[C@H]3NC(=O)c2cc(C)cc(C(F)(F)F)c2)ccn1]
I-15b TABLE 1-continued
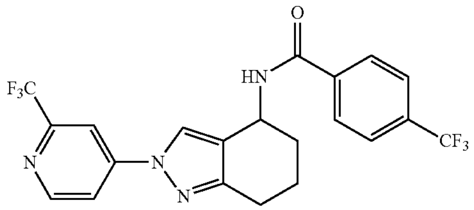
I-16
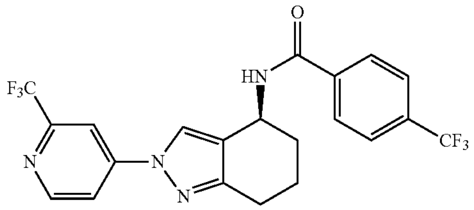
I-16a
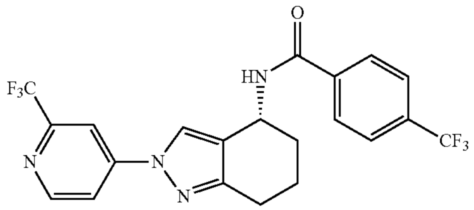
I-16b
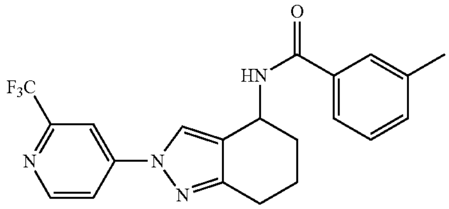
I-17
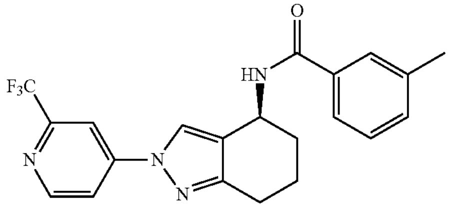
I-17a
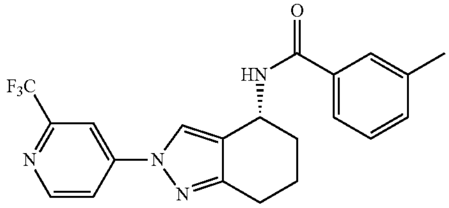
I-17b
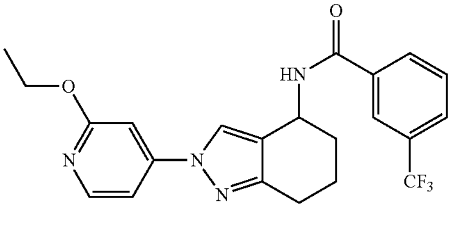 [SMILES: CCOc1cc(-n2cc3c(n2)CCCC3NC(=O)c2cccc(C(F)(F)F)c2)ccn1]
I-18

TABLE 1-continued
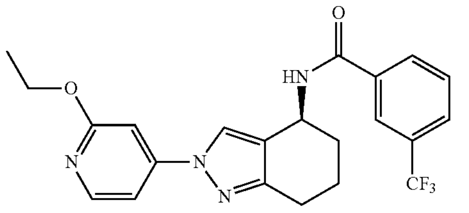 [SMILES: CCOc1cc(-n2cc3c(n2)CCC[C@@H]3NC(=O)c2cccc(C(F)(F)F)c2)ccn1]
I-18a
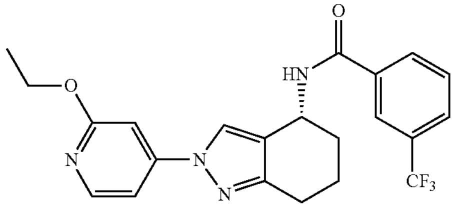 [SMILES: CCOc1cc(-n2cc3c(n2)CCC[C@H]3NC(=O)c2cccc(C(F)(F)F)c2)ccn1]
I-18b
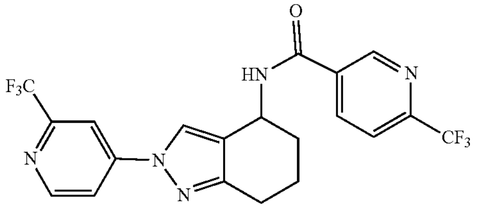
I-19
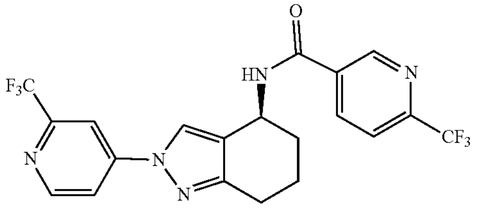 [SMILES: O=C(N[C@H]1CCCc2nn(-c3ccnc(C(F)(F)F)c3)cc21)c1ccc(C(F)(F)F)nc1]
I-19a
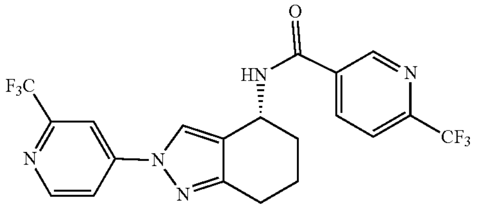 [SMILES: O=C(N[C@@H]1CCCc2nn(-c3ccnc(C(F)(F)F)c3)cc21)c1ccc(C(F)(F)F)nc1]
I-19b
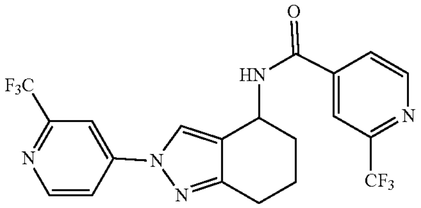 [SMILES: O=C(NC1CCCc2nn(-c3ccnc(C(F)(F)F)c3)cc21)c1ccnc(C(F)(F)F)c1]
I-20
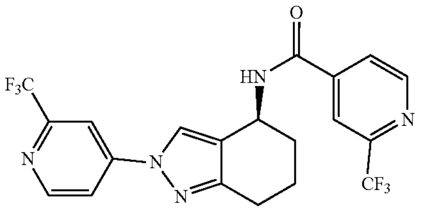 [SMILES: O=C(N[C@H]1CCCc2nn(-c3ccnc(C(F)(F)F)c3)cc21)c1ccnc(C(F)(F)F)c1]
I-20a TABLE 1-continued
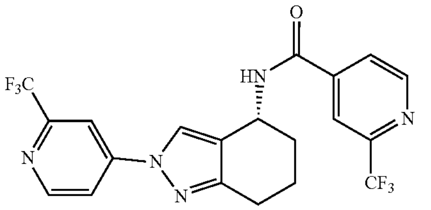 [SMILES: O=C(N[C@@H]1CCCc2nn(-c3ccnc(C(F)(F)F)c3)cc21)c1ccnc(C(F)(F)F)c1]
I-20b
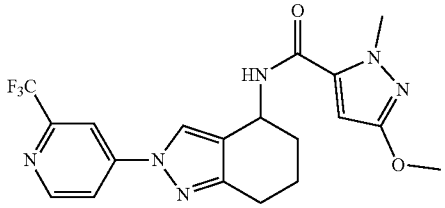 [SMILES: COc1cc(C(=O)NC2CCCc3nn(-c4ccnc(C(F)(F)F)c4)cc32)n(C)n1]
I-21
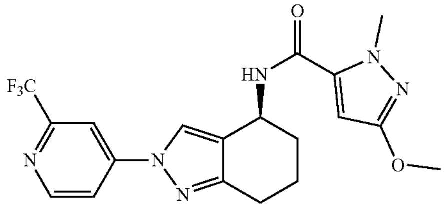 [SMILES: COc1cc(C(=O)N[C@H]2CCCc3nn(-c4ccnc(C(F)(F)F)c4)cc32)n(C)n1]
I-21a
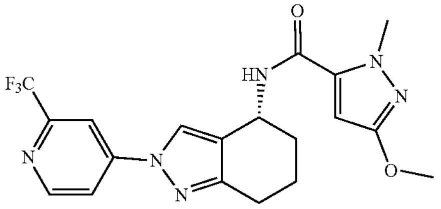 [SMILES: COc1cc(C(=O)N[C@@H]2CCCc3nn(-c4ccnc(C(F)(F)F)c4)cc32)n(C)n1]
I-21b
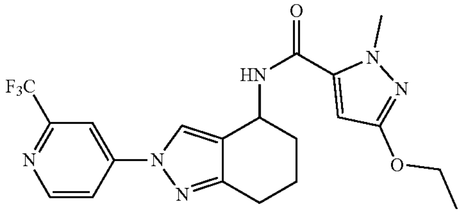 [SMILES: CCOc1cc(C(=O)NC2CCCc3nn(-c4ccnc(C(F)(F)F)c4)cc32)n(C)n1]
I-22
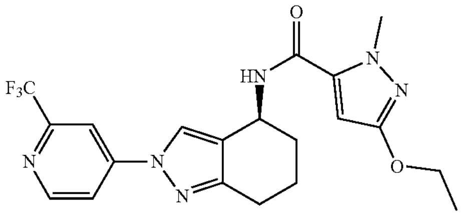 [SMILES: CCOc1cc(C(=O)N[C@H]2CCCc3nn(-c4ccnc(C(F)(F)F)c4)cc32)n(C)n1]
I-22a
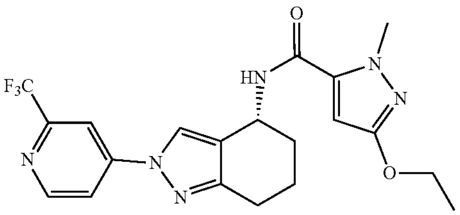 [SMILES: CCOc1cc(C(=O)N[C@@H]2CCCc3nn(-c4ccnc(C(F)(F)F)c4)cc32)n(C)n1]
I-22b TABLE 1-continued
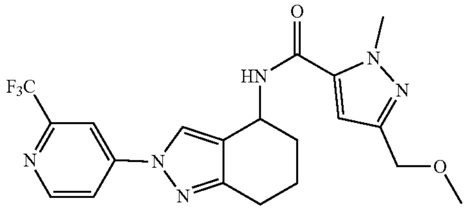 [SMILES: COCc1cc(C(=O)NC2CCCc3nn(-c4ccnc(C(F)(F)F)c4)cc32)n(C)n1]
I-23
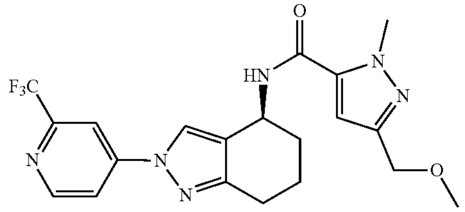 [SMILES: COCc1cc(C(=O)N[C@H]2CCCc3nn(-c4ccnc(C(F)(F)F)c4)cc32)n(C)n1]
I-23a
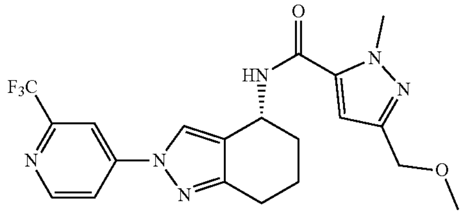 [SMILES: COCc1cc(C(=O)N[C@@H]2CCCc3nn(-c4ccnc(C(F)(F)F)c4)cc32)n(C)n1]
I-23b
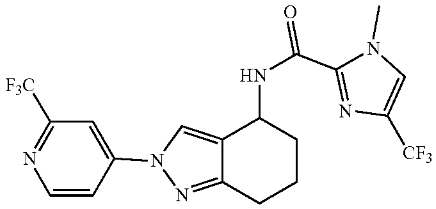 [SMILES: Cn1cc(C(F)(F)F)nc1C(=O)NC1CCCc2nn(-c3ccnc(C(F)(F)F)c3)cc21]
I-24
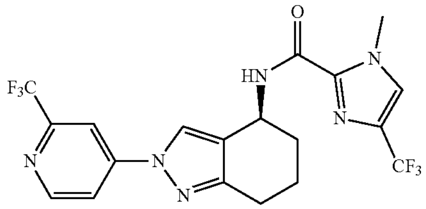 [SMILES: Cn1cc(C(F)(F)F)nc1C(=O)N[C@H]1CCCc2nn(-c3ccnc(C(F)(F)F)c3)cc21]
I-24a
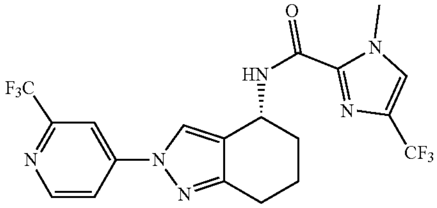 [SMILES: Cn1cc(C(F)(F)F)nc1C(=O)N[C@@H]1CCCc2nn(-c3ccnc(C(F)(F)F)c3)cc21]
I-24b
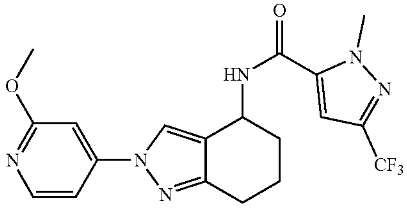
I-25

TABLE 1-continued
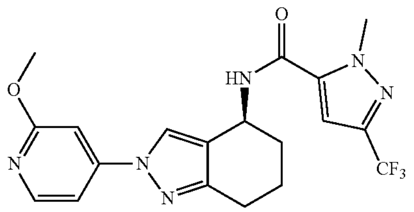 [SMILES: COc1cc(-n2cc3c(n2)CCC[C@@H]3NC(=O)c2cc(C(F)(F)F)nn2C)ccn1]
I-25a
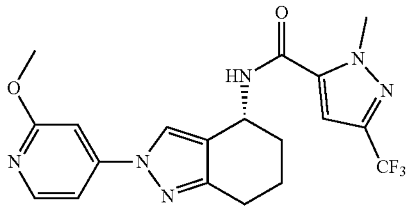
I-25b
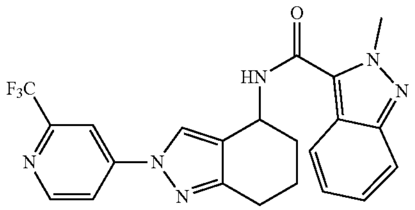 [SMILES: Cn1nc2ccccc2c1C(=O)NC1CCCc2nn(-c3ccnc(C(F)(F)F)c3)cc21]
I-26
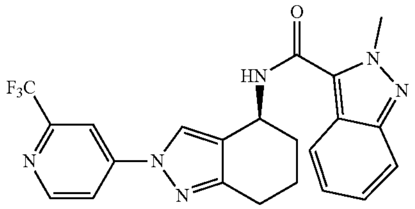 [SMILES: Cn1nc2ccccc2c1C(=O)N[C@H]1CCCc2nn(-c3ccnc(C(F)(F)F)c3)cc21]
I-26a
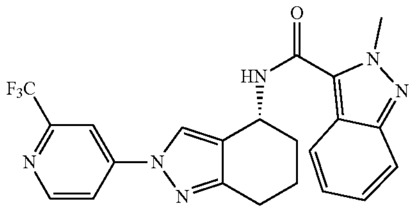 [SMILES: Cn1nc2ccccc2c1C(=O)N[C@@H]1CCCc2nn(-c3ccnc(C(F)(F)F)c3)cc21]
I-26b
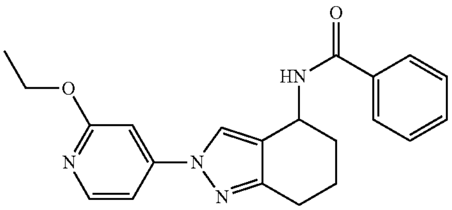
I-27
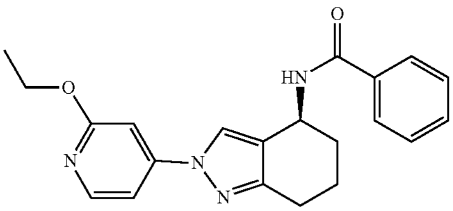 [SMILES: CCOc1cc(-n2cc3c(n2)CCC[C@@H]3NC(=O)c2ccccc2)ccn1]
I-27a TABLE 1-continued
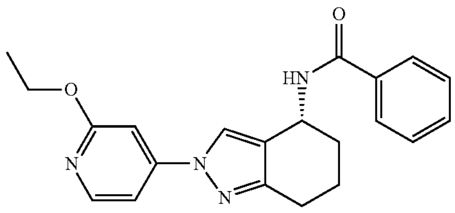 [SMILES: CCOc1cc(-n2cc3c(n2)CCC[C@H]3NC(=O)c2ccccc2)ccn1]
I-27b
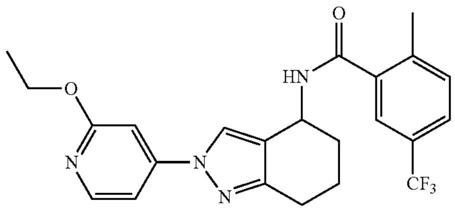 [SMILES: CCOc1cc(-n2cc3c(n2)CCCC3NC(=O)c2cc(C(F)(F)F)ccc2C)ccn1]
I-28
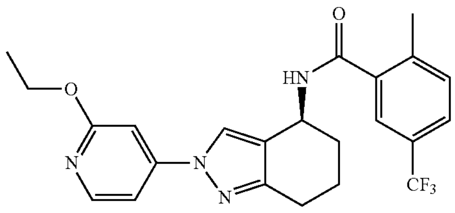
I-28a
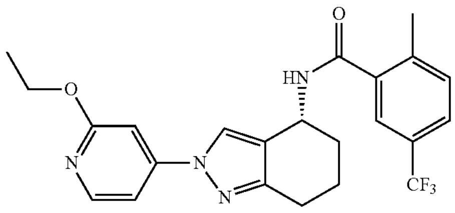 [SMILES: CCOc1cc(-n2cc3c(n2)CCC[C@H]3NC(=O)c2cc(C(F)(F)F)ccc2C)ccn1]
I-28b
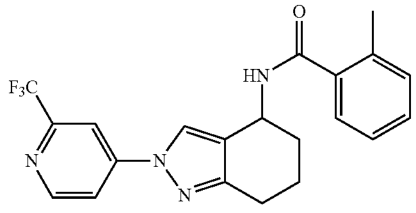 [SMILES: Cc1ccccc1C(=O)NC1CCCc2nn(-c3ccnc(C(F)(F)F)c3)cc21]
I-29
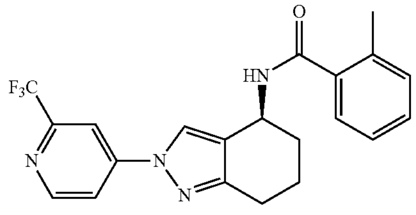 [SMILES: Cc1ccccc1C(=O)N[C@H]1CCCc2nn(-c3ccnc(C(F)(F)F)c3)cc21]
I-29a
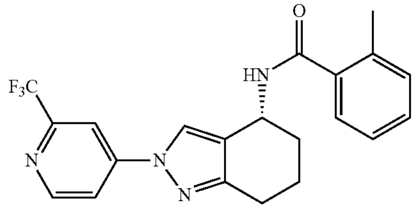
I-29b TABLE 1-continued
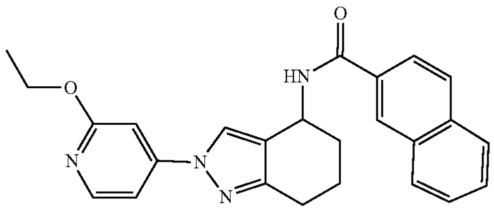 [SMILES: CCOc1cc(-n2cc3c(n2)CCCC3NC(=O)c2ccc3ccccc3c2)ccn1]
I-30
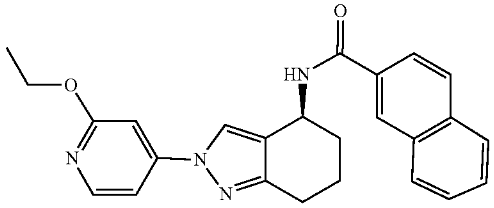 [SMILES: CCOc1cc(-n2cc3c(n2)CCC[C@@H]3NC(=O)c2ccc3ccccc3c2)ccn1]
I-30a
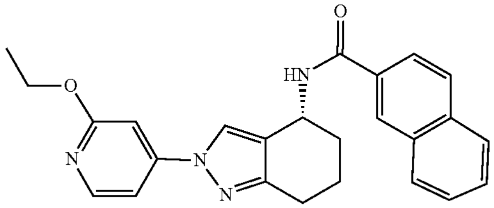 [SMILES: CCOc1cc(-n2cc3c(n2)CCC[C@H]3NC(=O)c2ccc3ccccc3c2)ccn1]
I-30b
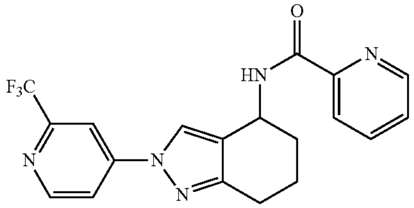 [SMILES: O=C(NC1CCCc2nn(-c3ccnc(C(F)(F)F)c3)cc21)c1ccccn1]
I-31
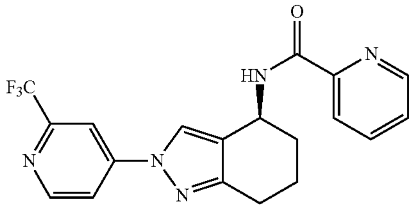 [SMILES: O=C(N[C@H]1CCCc2nn(-c3ccnc(C(F)(F)F)c3)cc21)c1ccccn1]
I-31a
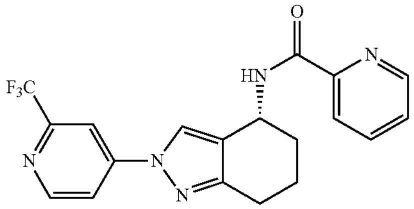
I-31b
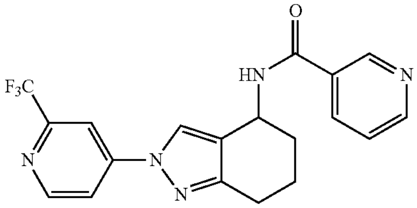
I-32

TABLE 1-continued
I-32a
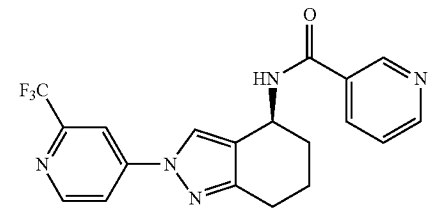 [SMILES: O=C(N[C@H]1CCCc2nn(-c3ccnc(C(F)(F)F)c3)cc21)c1cccnc1]
I-32b
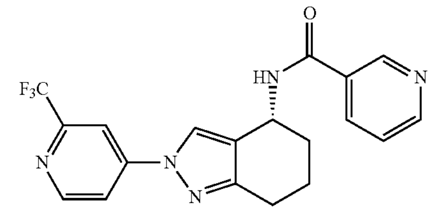
I-33
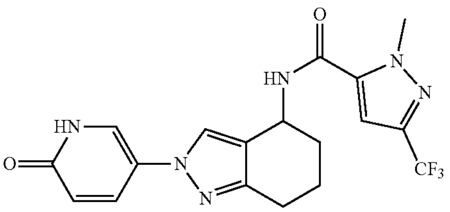 [SMILES: Cn1nc(C(F)(F)F)cc1C(=O)NC1CCCc2nn(-c3ccc(=O)[nH]c3)cc21]
I-33a
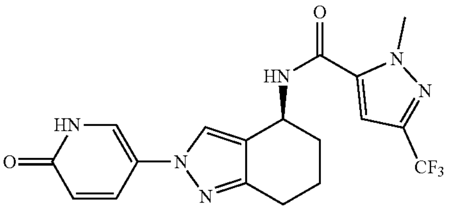 [SMILES: Cn1nc(C(F)(F)F)cc1C(=O)N[C@H]1CCCc2nn(-c3ccc(=O)[nH]c3)cc21]
I-33b
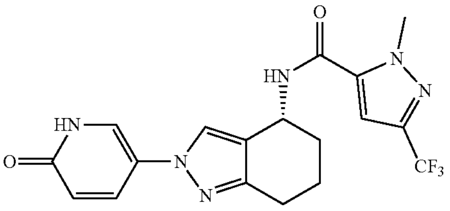 [SMILES: Cn1nc(C(F)(F)F)cc1C(=O)N[C@@H]1CCCc2nn(-c3ccc(=O)[nH]c3)cc21]
I-34
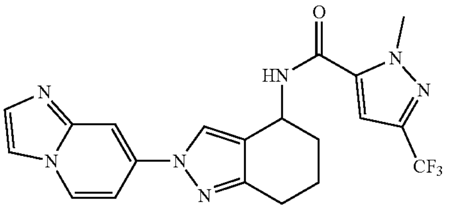 [SMILES: Cn1nc(C(F)(F)F)cc1C(=O)NC1CCCc2nn(-c3ccn4ccnc4c3)cc21]
I-34a
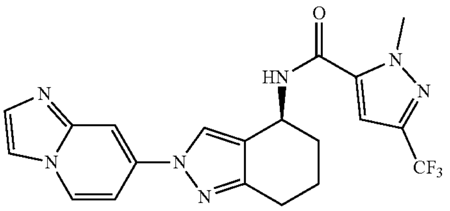 [SMILES: Cn1nc(C(F)(F)F)cc1C(=O)N[C@H]1CCCc2nn(-c3ccn4ccnc4c3)cc21]

TABLE 1-continued
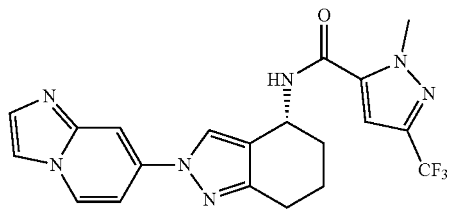
I-34b
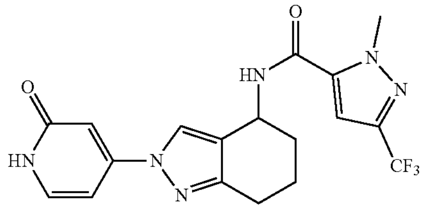 [SMILES: Cn1nc(C(F)(F)F)cc1C(=O)NC1CCCc2nn(-c3cc[nH]c(=O)c3)cc21]
I-35
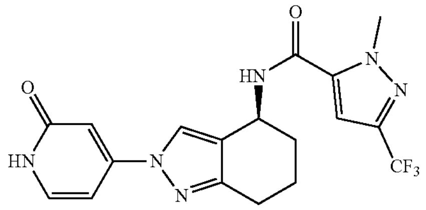 [SMILES: Cn1nc(C(F)(F)F)cc1C(=O)N[C@H]1CCCc2nn(-c3cc[nH]c(=O)c3)cc21]
I-35a
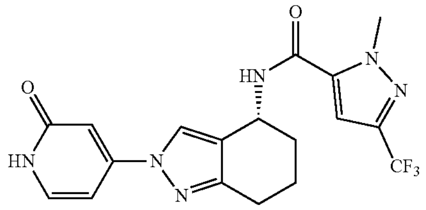 [SMILES: Cn1nc(C(F)(F)F)cc1C(=O)N[C@@H]1CCCc2nn(-c3cc[nH]c(=O)c3)cc21]
I-35b
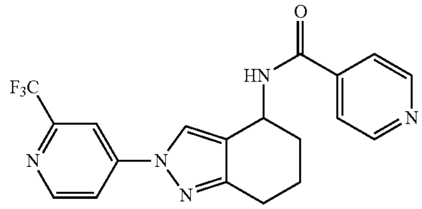 [SMILES: O=C(NC1CCCc2nn(-c3ccnc(C(F)(F)F)c3)cc21)c1ccncc1]
I-36
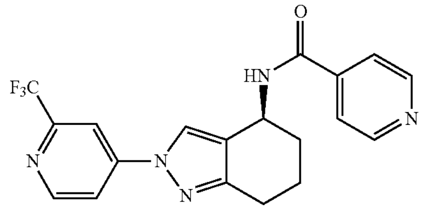 [SMILES: O=C(N[C@H]1CCCc2nn(-c3ccnc(C(F)(F)F)c3)cc21)c1ccncc1]
I-36a
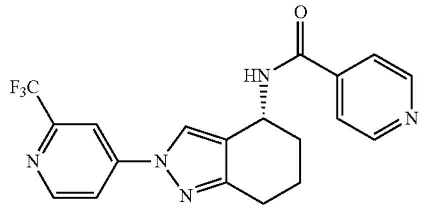
I-36b TABLE 1-continued
I-37
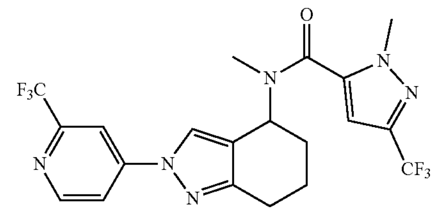 [SMILES: CN(C(=O)c1cc(C(F)(F)F)nn1C)C1CCCc2nn(-c3ccnc(C(F)(F)F)c3)cc21]
I-37a
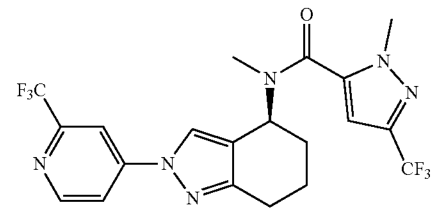 [SMILES: CN(C(=O)c1cc(C(F)(F)F)nn1C)[C@H]1CCCc2nn(-c3ccnc(C(F)(F)F)c3)cc21]
I-37b
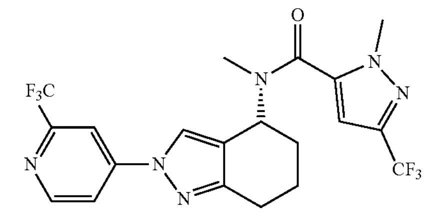
I-38
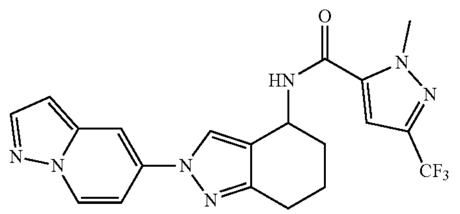 [SMILES: Cn1nc(C(F)(F)F)cc1C(=O)NC1CCCc2nn(-c3ccn4nccc4c3)cc21]
I-38a
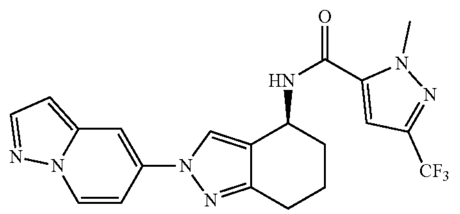 [SMILES: Cn1nc(C(F)(F)F)cc1C(=O)N[C@H]1CCCc2nn(-c3ccn4nccc4c3)cc21]
I-38b
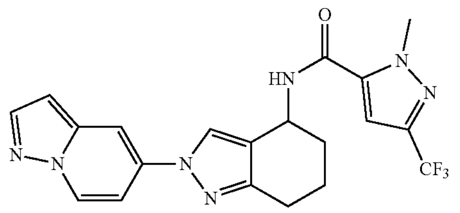
I-39
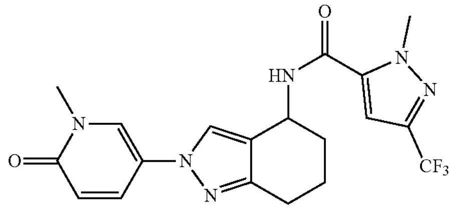 [SMILES: Cn1nc(C(F)(F)F)cc1C(=O)NC1CCCc2nn(-c3ccc(=O)n(C)c3)cc21]

TABLE 1-continued
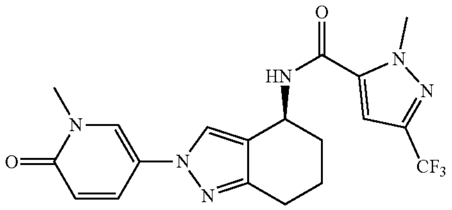 [SMILES: Cn1nc(C(F)(F)F)cc1C(=O)N[C@H]1CCCc2nn(-c3ccc(=O)n(C)c3)cc21]
I-39a
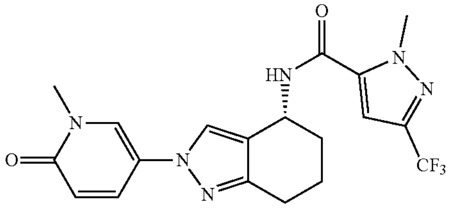 [SMILES: Cn1nc(C(F)(F)F)cc1C(=O)N[C@@H]1CCCc2nn(-c3ccc(=O)n(C)c3)cc21]
I-39b
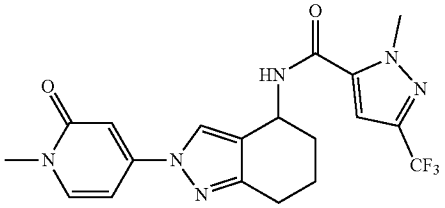 [SMILES: Cn1nc(C(F)(F)F)cc1C(=O)NC1CCCc2nn(-c3ccn(C)c(=O)c3)cc21]
I-40
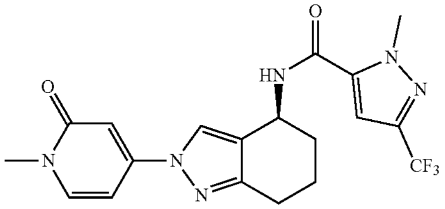 [SMILES: Cn1nc(C(F)(F)F)cc1C(=O)N[C@H]1CCCc2nn(-c3ccn(C)c(=O)c3)cc21]
I-40a
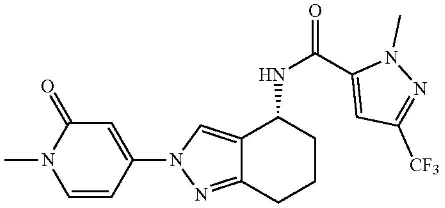
I-40b
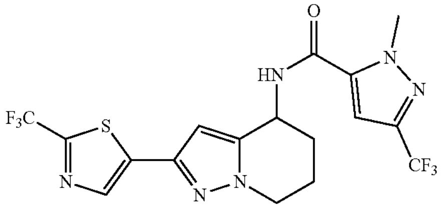 [SMILES: Cn1nc(C(F)(F)F)cc1C(=O)NC1CCCn2nc(-c3cnc(C(F)(F)F)s3)cc21]
I-41
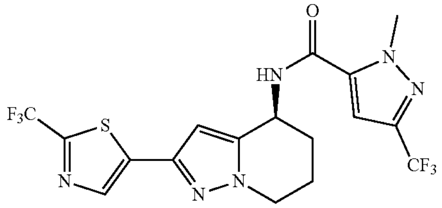
I-41a TABLE 1-continued
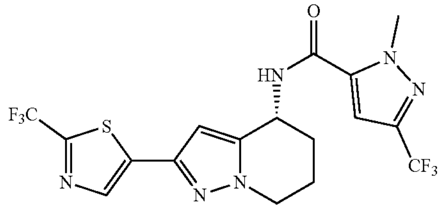
I-41b
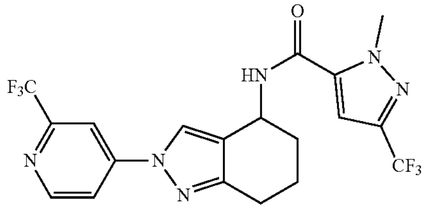 [SMILES: Cn1nc(C(F)(F)F)cc1C(=O)NC1CCCc2nn(-c3ccnc(C(F)(F)F)c3)cc21]
I-42
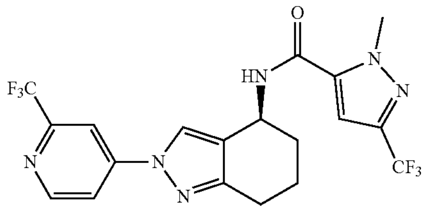 [SMILES: Cn1nc(C(F)(F)F)cc1C(=O)N[C@H]1CCCc2nn(-c3ccnc(C(F)(F)F)c3)cc21]
I-42a
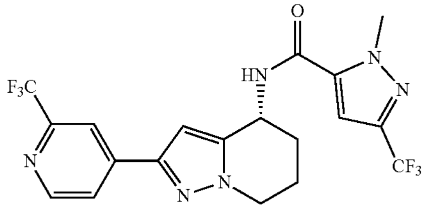 [SMILES: Cn1nc(C(F)(F)F)cc1C(=O)N[C@@H]1CCCn2nc(-c3ccnc(C(F)(F)F)c3)cc21]
I-42b
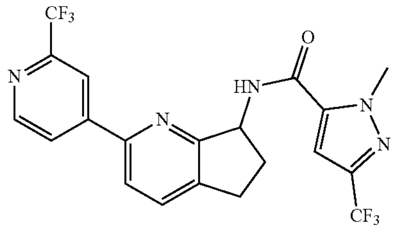 [SMILES: Cn1nc(C(F)(F)F)cc1C(=O)NC1CCc2ccc(-c3ccnc(C(F)(F)F)c3)nc21]
I-43
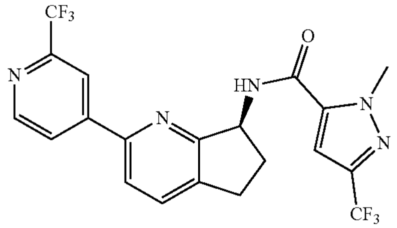 [SMILES: Cn1nc(C(F)(F)F)cc1C(=O)N[C@H]1CCc2ccc(-c3ccnc(C(F)(F)F)c3)nc21]
I-43a
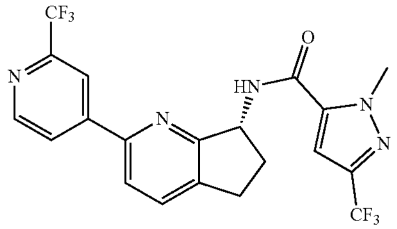 [SMILES: Cn1nc(C(F)(F)F)cc1C(=O)N[C@@H]1CCc2ccc(-c3ccnc(C(F)(F)F)c3)nc21]
I-43b TABLE 1-continued
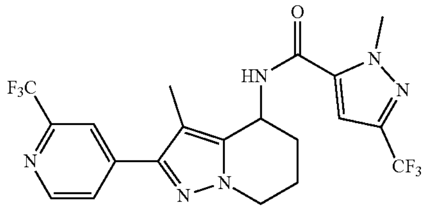 [SMILES: Cc1c(-c2ccnc(C(F)(F)F)c2)nn2c1C(NC(=O)c1cc(C(F)(F)F)nn1C)CCC2]
I-44
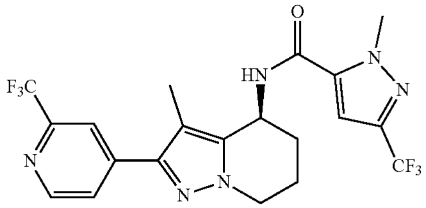 [SMILES: Cc1c(-c2ccnc(C(F)(F)F)c2)nn2c1[C@@H](NC(=O)c1cc(C(F)(F)F)nn1C)CCC2]
I-44a
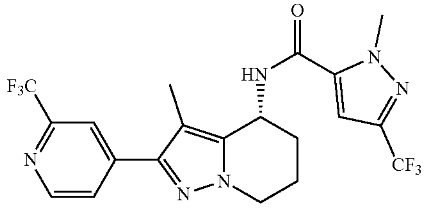
I-44b
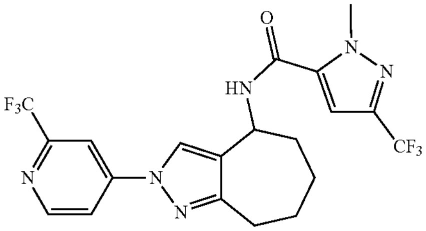 [SMILES: Cn1nc(C(F)(F)F)cc1C(=O)NC1CCCCc2nn(-c3ccnc(C(F)(F)F)c3)cc21]
I-45
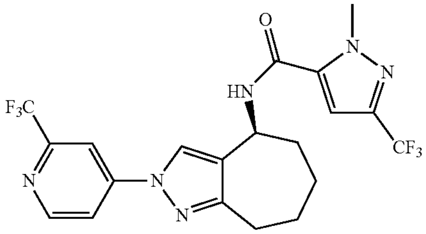 [SMILES: Cn1nc(C(F)(F)F)cc1C(=O)N[C@H]1CCCCc2nn(-c3ccnc(C(F)(F)F)c3)cc21]
I-45a
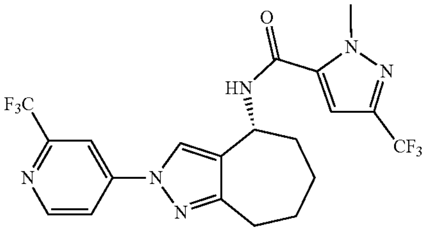 [SMILES: Cn1nc(C(F)(F)F)cc1C(=O)N[C@@H]1CCCCc2nn(-c3ccnc(C(F)(F)F)c3)cc21]
I-45b
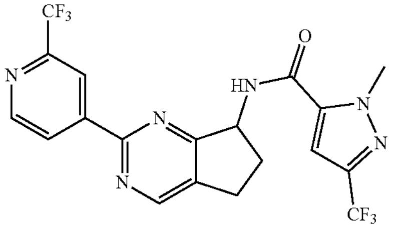
I-46

TABLE 1-continued
I-46a
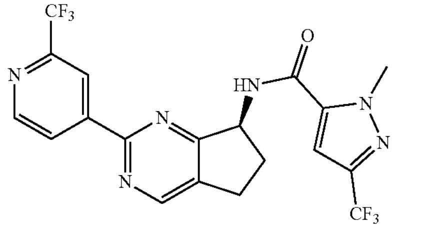
I-46b
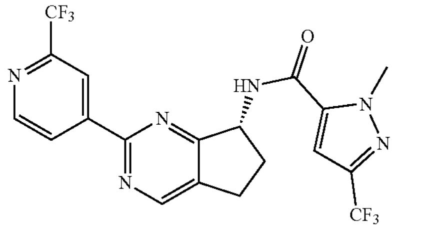
I-47
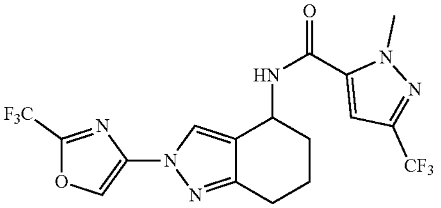 [SMILES: Cn1nc(C(F)(F)F)cc1C(=O)NC1CCCc2nn(-c3coc(C(F)(F)F)n3)cc21]
I-47a
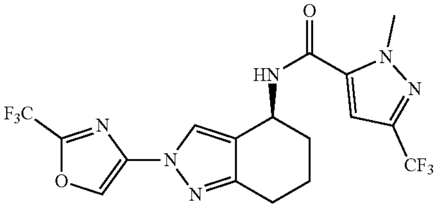 [SMILES: Cn1nc(C(F)(F)F)cc1C(=O)N[C@H]1CCCc2nn(-c3coc(C(F)(F)F)n3)cc21]
I-47b
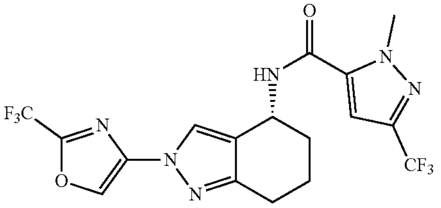 [SMILES: Cn1nc(C(F)(F)F)cc1C(=O)N[C@@H]1CCCc2nn(-c3coc(C(F)(F)F)n3)cc21]
I-48
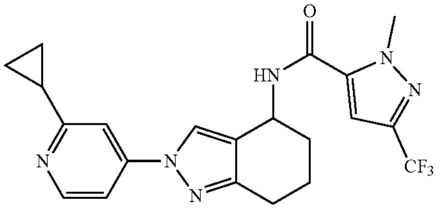 [SMILES: Cn1nc(C(F)(F)F)cc1C(=O)NC1CCCc2nn(-c3ccnc(C4CC4)c3)cc21]
I-48a
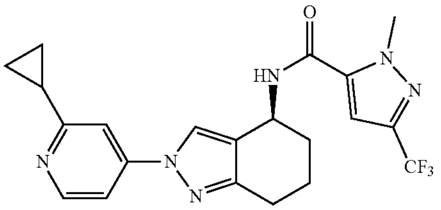 [SMILES: Cn1nc(C(F)(F)F)cc1C(=O)N[C@H]1CCCc2nn(-c3ccnc(C4CC4)c3)cc21]

TABLE 1-continued
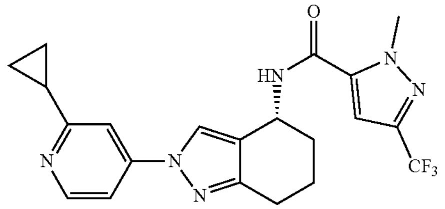 [SMILES: Cn1nc(C(F)(F)F)cc1C(=O)N[C@@H]1CCCc2nn(-c3ccnc(C4CC4)c3)cc21]
I-48b
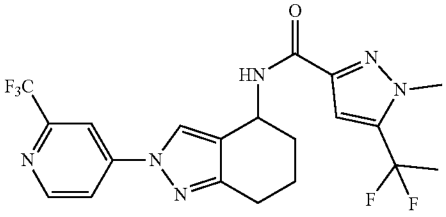
I-49
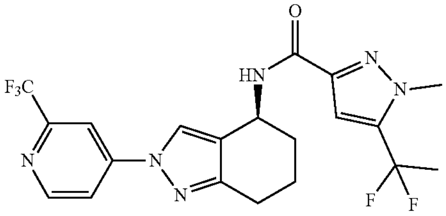 [SMILES: Cn1nc(C(=O)N[C@H]2CCCc3nn(-c4ccnc(C(F)(F)F)c4)cc32)cc1C(C)(F)F]
I-49a
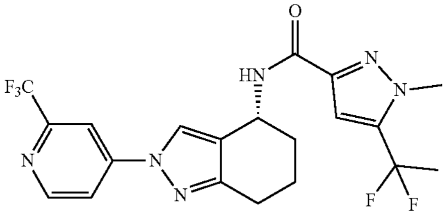 [SMILES: Cn1nc(C(=O)N[C@@H]2CCCc3nn(-c4ccnc(C(F)(F)F)c4)cc32)cc1C(C)(F)F]
I-49b
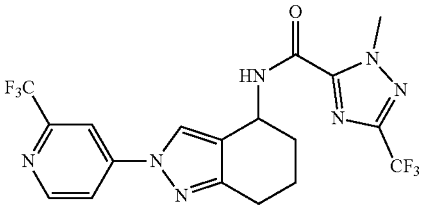
I-50
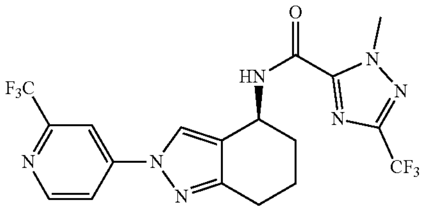
I-50a
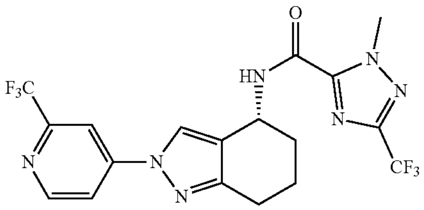
I-50b TABLE 1-continued
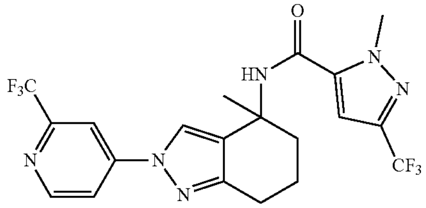 [SMILES: Cn1nc(C(F)(F)F)cc1C(=O)NC1(C)CCCc2nn(-c3ccnc(C(F)(F)F)c3)cc21]
I-51
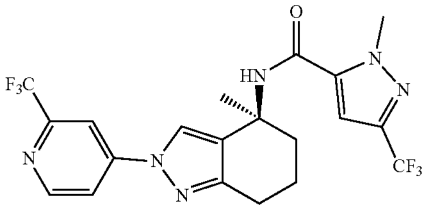 [SMILES: Cn1nc(C(F)(F)F)cc1C(=O)N[C@@]1(C)CCCc2nn(-c3ccnc(C(F)(F)F)c3)cc21]
I-51a
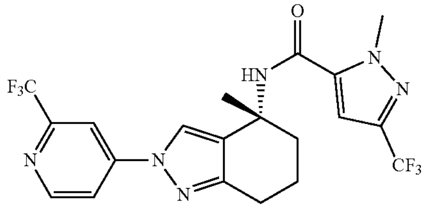 [SMILES: Cn1nc(C(F)(F)F)cc1C(=O)N[C@]1(C)CCCc2nn(-c3ccnc(C(F)(F)F)c3)cc21]
I-51b
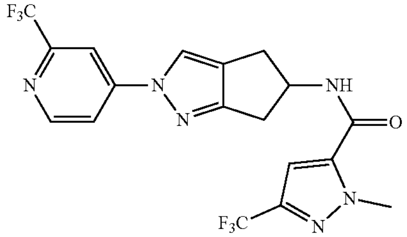
I-52
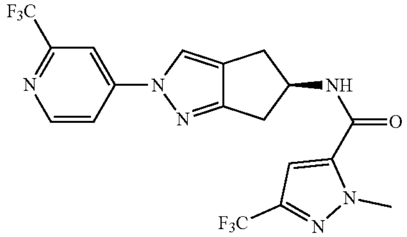 [SMILES: Cn1nc(C(F)(F)F)cc1C(=O)N[C@@H]1Cc2cn(-c3ccnc(C(F)(F)F)c3)nc2C1]
I-52a
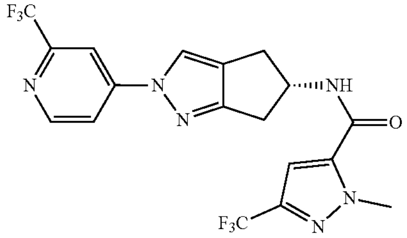 [SMILES: Cn1nc(C(F)(F)F)cc1C(=O)N[C@H]1Cc2cn(-c3ccnc(C(F)(F)F)c3)nc2C1]
I-52b
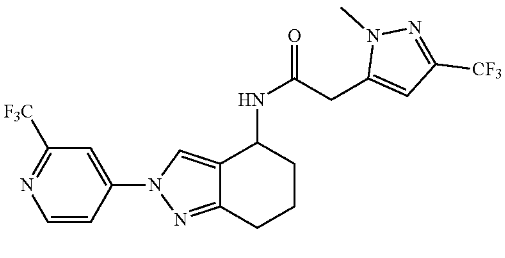 [SMILES: Cn1nc(C(F)(F)F)cc1CC(=O)NC1CCCc2nn(-c3ccnc(C(F)(F)F)c3)cc21]
I-53

TABLE 1-continued
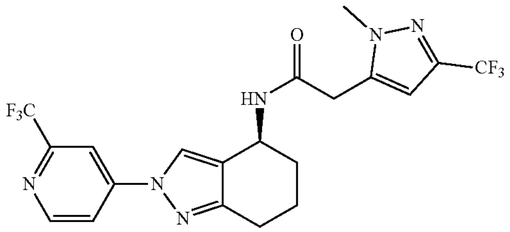 [SMILES: Cn1nc(C(F)(F)F)cc1CC(=O)N[C@H]1CCCc2nn(-c3ccnc(C(F)(F)F)c3)cc21]
I-53a
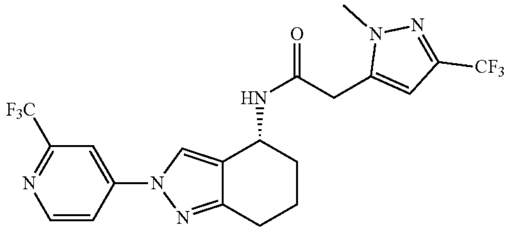
I-53b
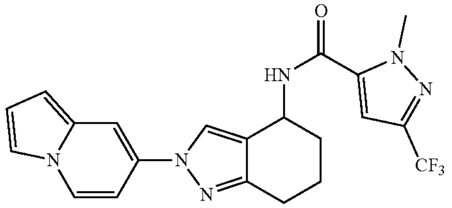 [SMILES: Cn1nc(C(F)(F)F)cc1C(=O)NC1CCCc2nn(-c3ccn4cccc4c3)cc21]
I-54
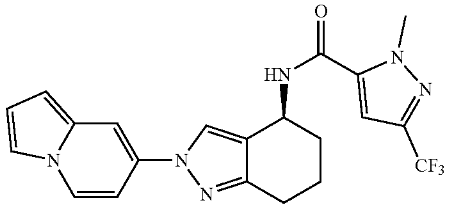 [SMILES: Cn1nc(C(F)(F)F)cc1C(=O)N[C@H]1CCCc2nn(-c3ccn4cccc4c3)cc21]
I-54a
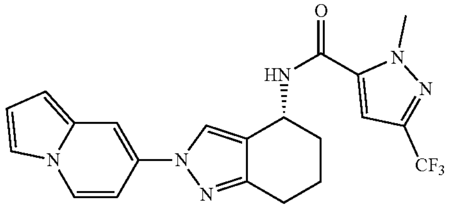 [SMILES: Cn1nc(C(F)(F)F)cc1C(=O)N[C@@H]1CCCc2nn(-c3ccn4cccc4c3)cc21]
I-54b
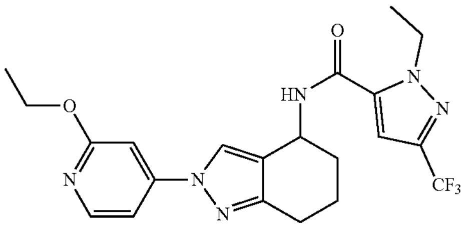 [SMILES: CCOc1cc(-n2cc3c(n2)CCCC3NC(=O)c2cc(C(F)(F)F)nn2CC)ccn1]
I-55
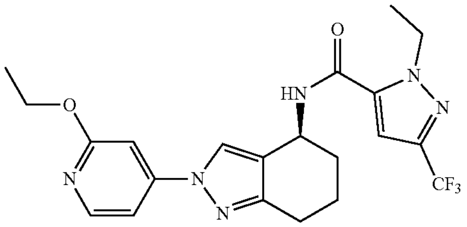
I-55a TABLE 1-continued
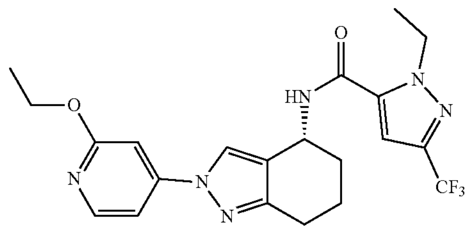 [SMILES: CCOc1cc(-n2cc3c(n2)CCC[C@H]3NC(=O)c2cc(C(F)(F)F)nn2CC)ccn1]
I-55b
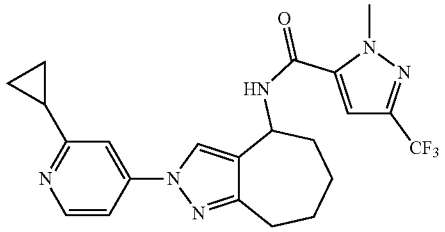 [SMILES: Cn1nc(C(F)(F)F)cc1C(=O)NC1CCCCc2nn(-c3ccnc(C4CC4)c3)cc21]
I-56
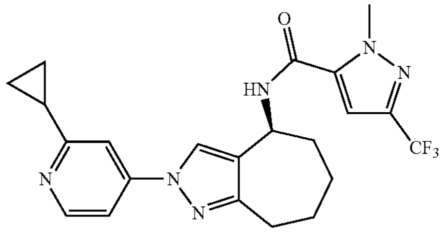 [SMILES: Cn1nc(C(F)(F)F)cc1C(=O)N[C@H]1CCCCc2nn(-c3ccnc(C4CC4)c3)cc21]
I-56a
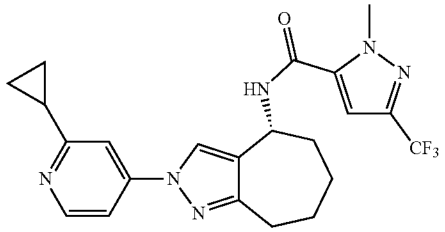 [SMILES: Cn1nc(C(F)(F)F)cc1C(=O)N[C@@H]1CCCCc2nn(-c3ccnc(C4CC4)c3)cc21]
I-56b
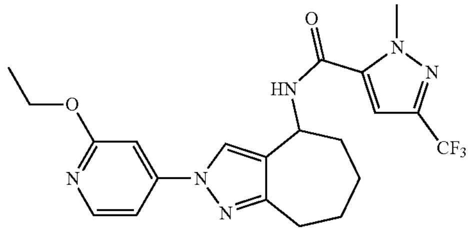
I-57
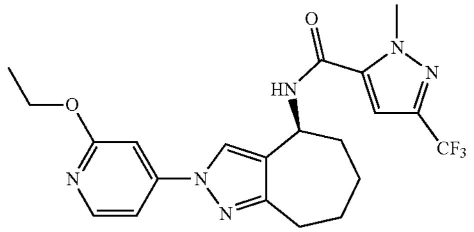 [SMILES: CCOc1cc(-n2cc3c(n2)CCCC[C@@H]3NC(=O)c2cc(C(F)(F)F)nn2C)ccn1]
I-57a TABLE 1-continued
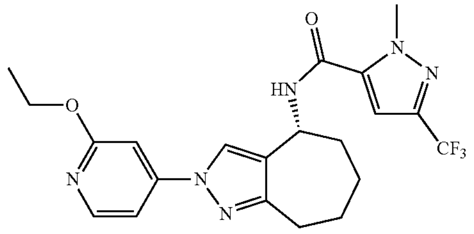
I-57b
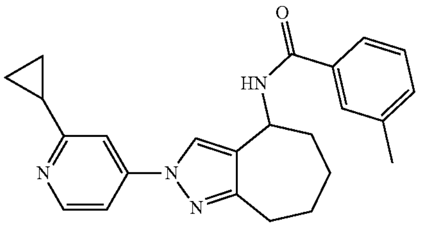 [SMILES: Cc1cccc(C(=O)NC2CCCCc3nn(-c4ccnc(C5CC5)c4)cc32)c1]
I-58
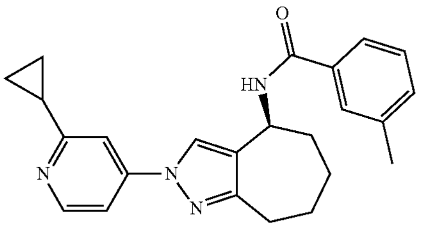 [SMILES: Cc1cccc(C(=O)N[C@H]2CCCCc3nn(-c4ccnc(C5CC5)c4)cc32)c1]
I-58a
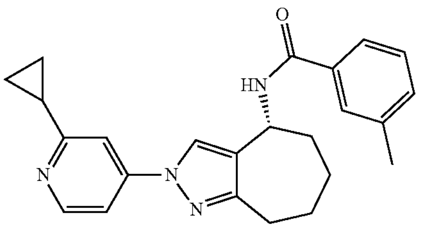 [SMILES: Cc1cccc(C(=O)N[C@@H]2CCCCc3nn(-c4ccnc(C5CC5)c4)cc32)c1]
I-58b
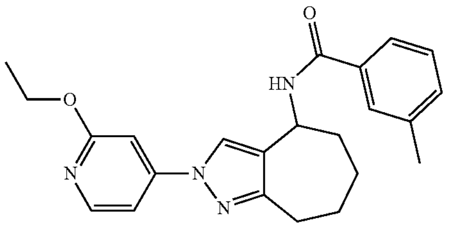 [SMILES: CCOc1cc(-n2cc3c(n2)CCCCC3NC(=O)c2cccc(C)c2)ccn1]
I-59
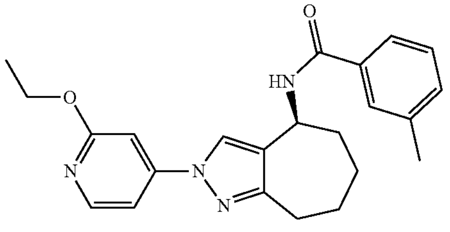 [SMILES: CCOc1cc(-n2cc3c(n2)CCCC[C@@H]3NC(=O)c2cccc(C)c2)ccn1]
I-59a
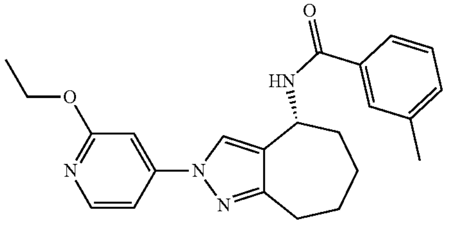 [SMILES: CCOc1cc(-n2cc3c(n2)CCCC[C@H]3NC(=O)c2cccc(C)c2)ccn1]
I-59b TABLE 1-continued
I-60
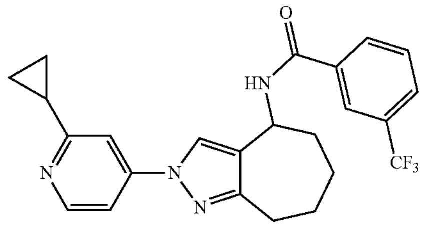 [SMILES: O=C(NC1CCCCc2nn(-c3ccnc(C4CC4)c3)cc21)c1cccc(C(F)(F)F)c1]
I-60a
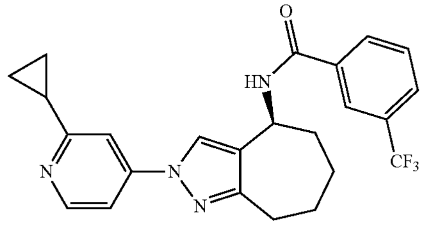 [SMILES: O=C(N[C@H]1CCCCc2nn(-c3ccnc(C4CC4)c3)cc21)c1cccc(C(F)(F)F)c1]
I-60b
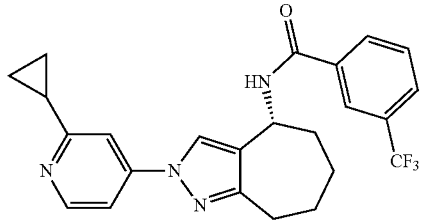 [SMILES: O=C(N[C@@H]1CCCCc2nn(-c3ccnc(C4CC4)c3)cc21)c1cccc(C(F)(F)F)c1]
I-61
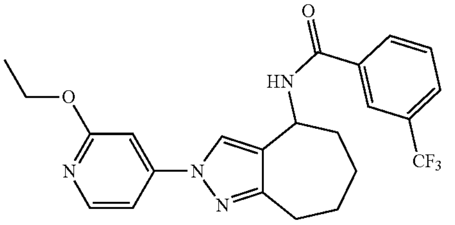 [SMILES: CCOc1cc(-n2cc3c(n2)CCCCC3NC(=O)c2cccc(C(F)(F)F)c2)ccn1]
I-61a
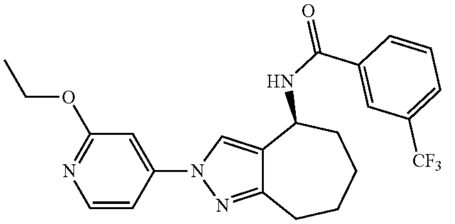 [SMILES: CCOc1cc(-n2cc3c(n2)CCCC[C@@H]3NC(=O)c2cccc(C(F)(F)F)c2)ccn1]
I-61b
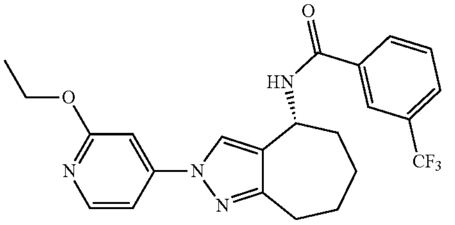 [SMILES: CCOc1cc(-n2cc3c(n2)CCCC[C@H]3NC(=O)c2cccc(C(F)(F)F)c2)ccn1]
I-62
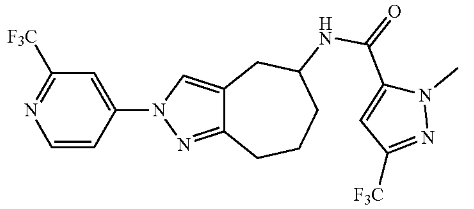 [SMILES: Cn1nc(C(F)(F)F)cc1C(=O)NC1CCCc2nn(-c3ccnc(C(F)(F)F)c3)cc2C1]

TABLE 1-continued
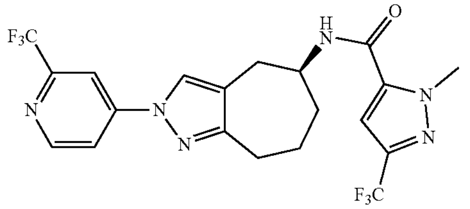 [SMILES: Cn1nc(C(F)(F)F)cc1C(=O)N[C@H]1CCCc2nn(-c3ccnc(C(F)(F)F)c3)cc2C1]
I-62a
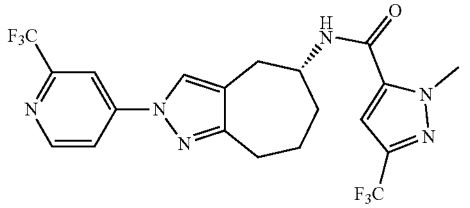
I-62b
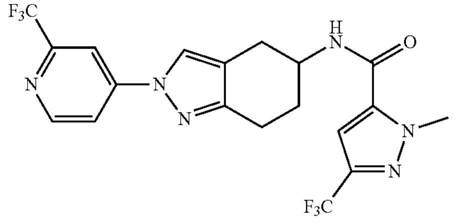 [SMILES: Cn1nc(C(F)(F)F)cc1C(=O)NC1CCc2nn(-c3ccnc(C(F)(F)F)c3)cc2C1]
I-63
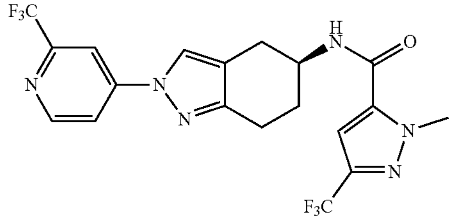 [SMILES: Cn1nc(C(F)(F)F)cc1C(=O)N[C@H]1CCc2nn(-c3ccnc(C(F)(F)F)c3)cc2C1]
I-63a
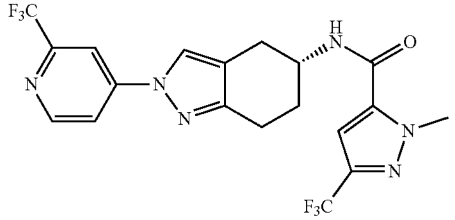
I-63b
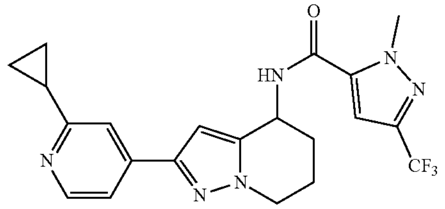
I-64
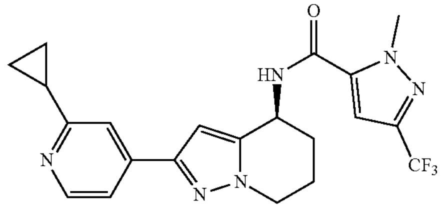
I-64a TABLE 1-continued
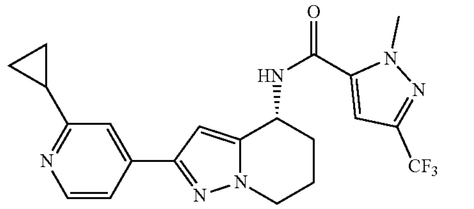
I-64b
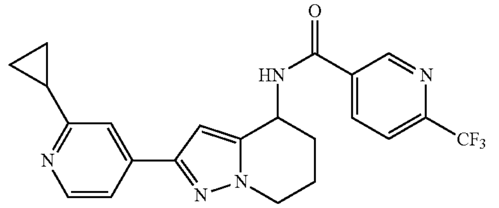
I-65
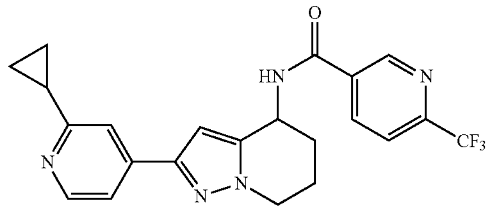
I-65a
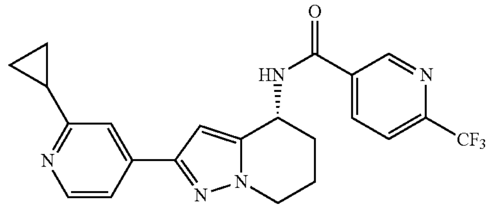 [SMILES: O=C(N[C@@H]1CCCn2nc(-c3ccnc(C4CC4)c3)cc21)c1ccc(C(F)(F)F)nc1]
I-65b
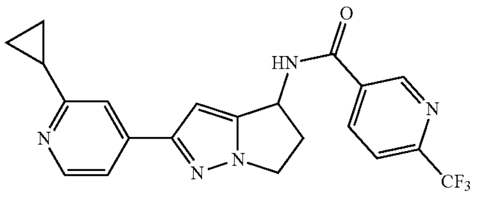 [SMILES: O=C(NC1CCn2nc(-c3ccnc(C4CC4)c3)cc21)c1ccc(C(F)(F)F)nc1]
I-66
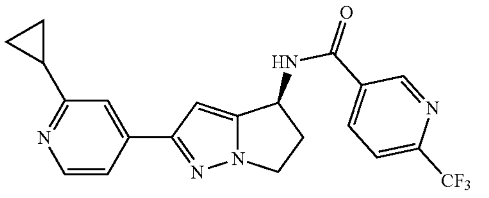 [SMILES: O=C(N[C@H]1CCn2nc(-c3ccnc(C4CC4)c3)cc21)c1ccc(C(F)(F)F)nc1]
I-66a
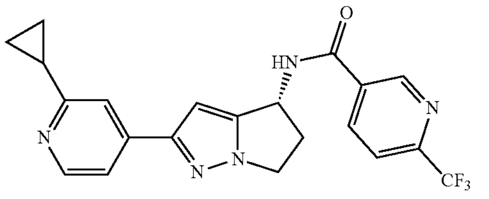 [SMILES: O=C(N[C@@H]1CCn2nc(-c3ccnc(C4CC4)c3)cc21)c1ccc(C(F)(F)F)nc1]
I-66b TABLE 1-continued
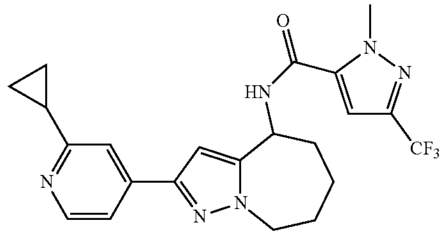 [SMILES: Cn1nc(C(F)(F)F)cc1C(=O)NC1CCCCn2nc(-c3ccnc(C4CC4)c3)cc21]
I-67
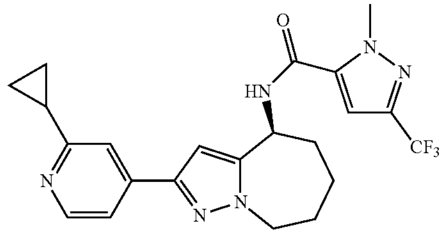 [SMILES: Cn1nc(C(F)(F)F)cc1C(=O)N[C@H]1CCCCn2nc(-c3ccnc(C4CC4)c3)cc21]
I-67a
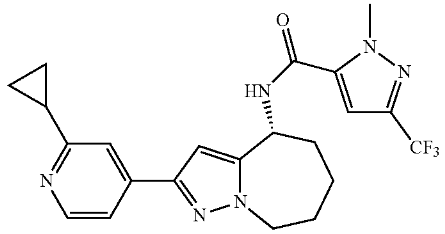 [SMILES: Cn1nc(C(F)(F)F)cc1C(=O)N[C@@H]1CCCCn2nc(-c3ccnc(C4CC4)c3)cc21]
I-67b
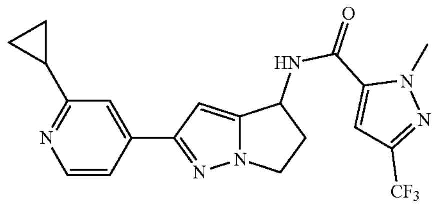 [SMILES: Cn1nc(C(F)(F)F)cc1C(=O)NC1CCn2nc(-c3ccnc(C4CC4)c3)cc21]
I-68
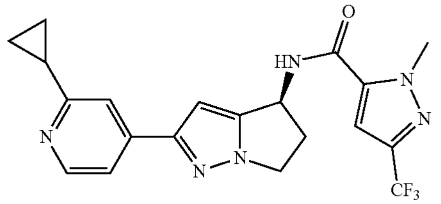 [SMILES: Cn1nc(C(F)(F)F)cc1C(=O)N[C@H]1CCn2nc(-c3ccnc(C4CC4)c3)cc21]
I-68a
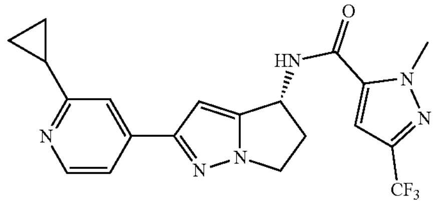 [SMILES: Cn1nc(C(F)(F)F)cc1C(=O)N[C@@H]1CCn2nc(-c3ccnc(C4CC4)c3)cc21]
I-68b
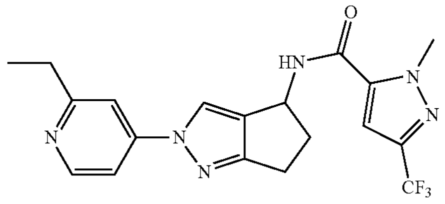 [SMILES: CCc1cc(-n2cc3c(n2)CCC3NC(=O)c2cc(C(F)(F)F)nn2C)ccn1]
I-69

TABLE 1-continued
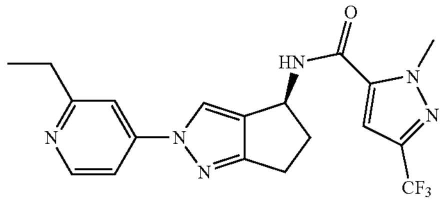
I-69a
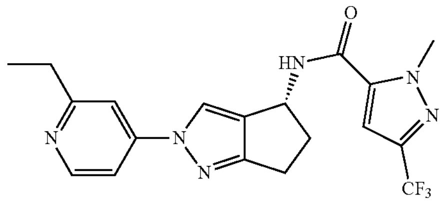
I-69b
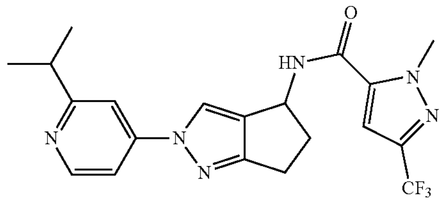
I-70
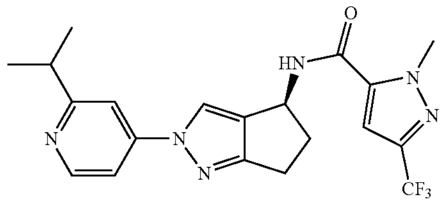
I-70a
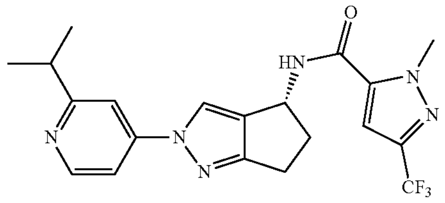 [SMILES: CC(C)c1cc(-n2cc3c(n2)CCC3NC(=O)c2cc(C(F)(F)F)nn2C)ccn1]
I-70b
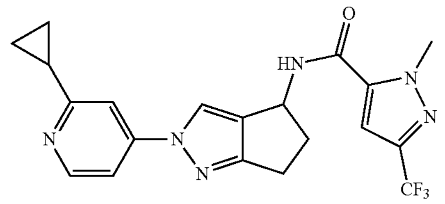
I-71
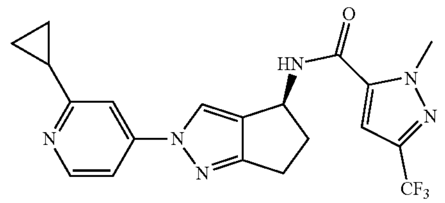 [SMILES: Cn1nc(C(F)(F)F)cc1C(=O)N[C@H]1CCc2nn(-c3ccnc(C4CC4)c3)cc21]
I-71a TABLE 1-continued
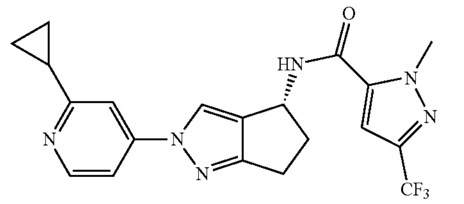 [SMILES: Cn1nc(C(F)(F)F)cc1C(=O)N[C@@H]1CCc2nn(-c3ccnc(C4CC4)c3)cc21]
I-71b
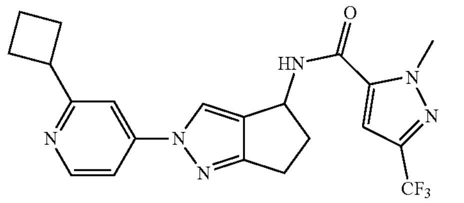
I-72
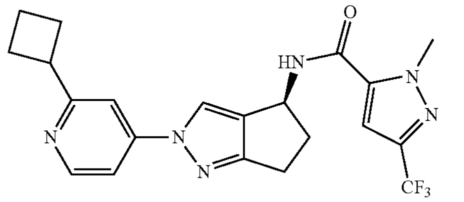
I-72a
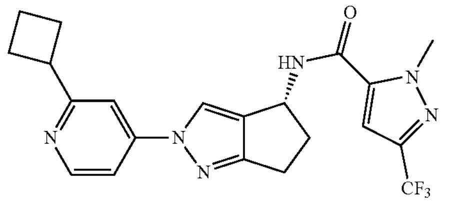 [SMILES: Cn1nc(C(F)(F)F)cc1C(=O)NC1CCc2nn(-c3ccnc(C4CCC4)c3)cc21]
I-72b
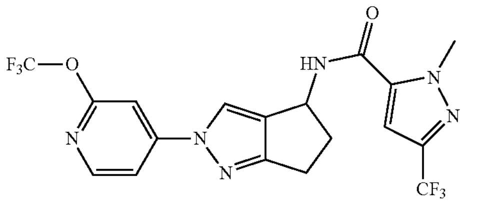 [SMILES: Cn1nc(C(F)(F)F)cc1C(=O)NC1CCc2nn(-c3ccnc(OC(F)(F)F)c3)cc21]
I-73
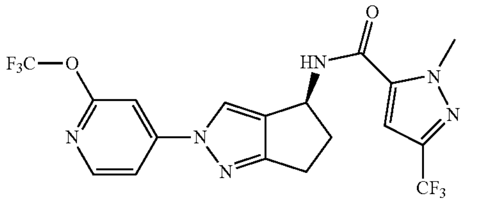 [SMILES: Cn1nc(C(F)(F)F)cc1C(=O)N[C@H]1CCc2nn(-c3ccnc(OC(F)(F)F)c3)cc21]
I-73a
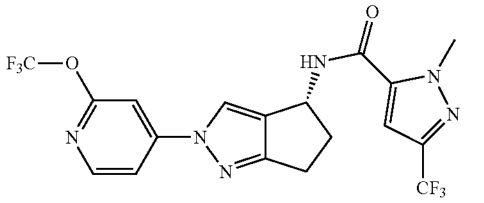 [SMILES: Cn1nc(C(F)(F)F)cc1C(=O)N[C@@H]1CCc2nn(-c3ccnc(OC(F)(F)F)c3)cc21]
I-73b TABLE 1-continued
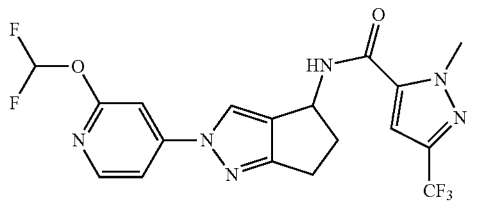
I-74
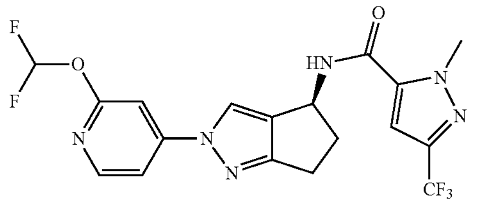
I-74a
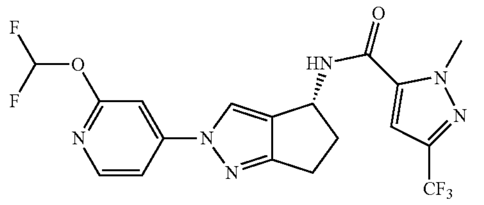 [SMILES: Cn1nc(C(F)(F)F)cc1C(=O)N[C@@H]1CCc2nn(-c3ccnc(OC(F)F)c3)cc21]
I-74b
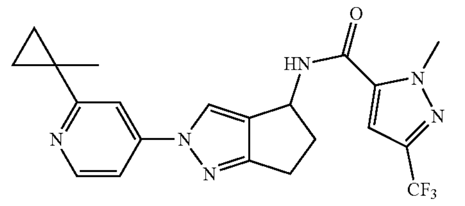 [SMILES: Cn1nc(C(F)(F)F)cc1C(=O)NC1CCc2nn(-c3ccnc(C4(C)CC4)c3)cc21]
I-75
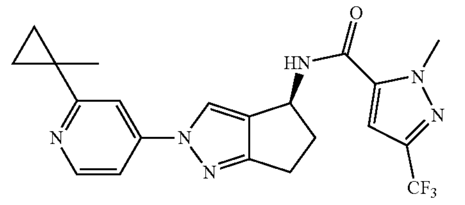 [SMILES: Cn1nc(C(F)(F)F)cc1C(=O)N[C@H]1CCc2nn(-c3ccnc(C4(C)CC4)c3)cc21]
I-75a
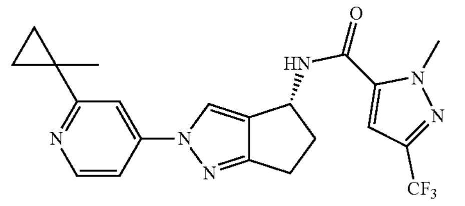
I-75b
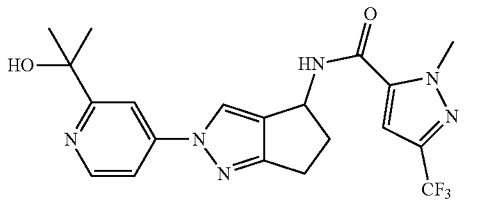 [SMILES: Cn1nc(C(F)(F)F)cc1C(=O)NC1CCc2nn(-c3ccnc(C(C)(C)O)c3)cc21]
I-76

TABLE 1-continued
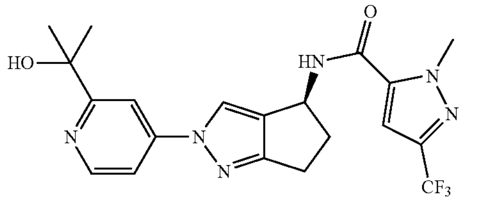 [SMILES: Cn1nc(C(F)(F)F)cc1C(=O)N[C@H]1CCc2nn(-c3ccnc(C(C)(C)O)c3)cc21]
I-76a
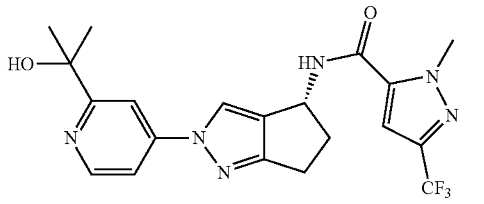 [SMILES: Cn1nc(C(F)(F)F)cc1C(=O)N[C@@H]1CCc2nn(-c3ccnc(C(C)(C)O)c3)cc21]
I-76b
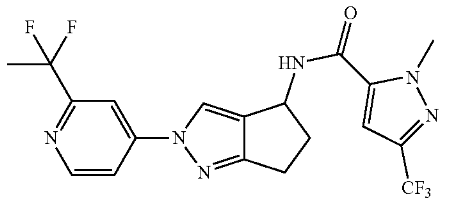 [SMILES: Cn1nc(C(F)(F)F)cc1C(=O)NC1CCc2nn(-c3ccnc(C(C)(F)F)c3)cc21]
I-77
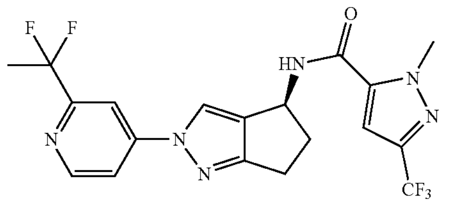
I-77a
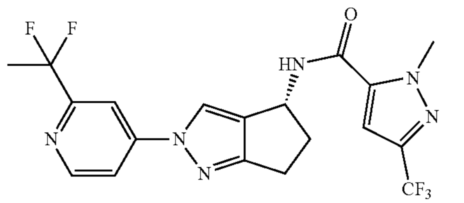 [SMILES: Cn1nc(C(F)(F)F)cc1C(=O)N[C@@H]1CCc2nn(-c3ccnc(C(C)(F)F)c3)cc21]
I-77b
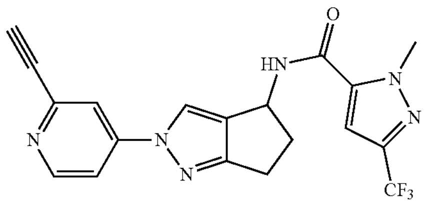 [SMILES: C#Cc1cc(-n2cc3c(n2)CCC3NC(=O)c2cc(C(F)(F)F)nn2C)ccn1]
I-78
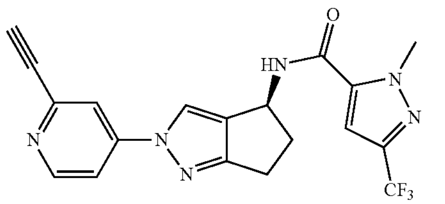 [SMILES: C#Cc1cc(-n2cc3c(n2)CC[C@@H]3NC(=O)c2cc(C(F)(F)F)nn2C)ccn1]
I-78a TABLE 1-continued
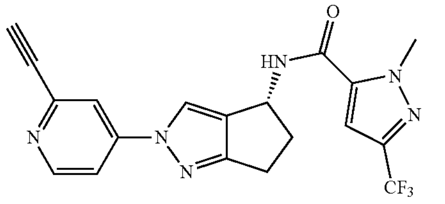 [SMILES: C#Cc1cc(-n2cc3c(n2)CC[C@H]3NC(=O)c2cc(C(F)(F)F)nn2C)ccn1]
I-78b
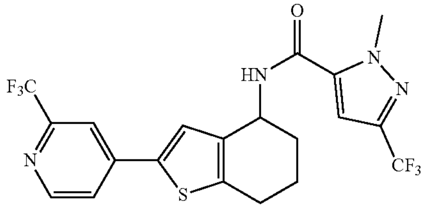
I-79
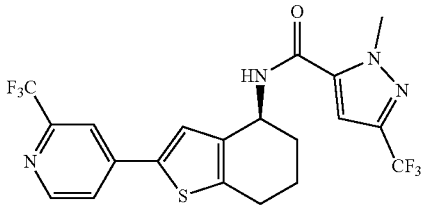
I-79a
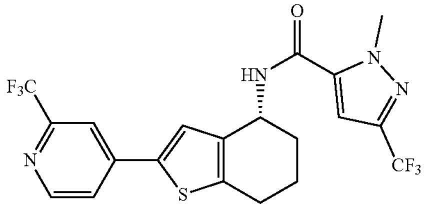
I-79b
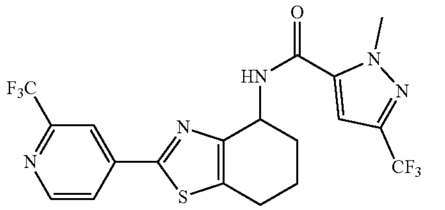 [SMILES: Cn1nc(C(F)(F)F)cc1C(=O)NC1CCCc2sc(-c3ccnc(C(F)(F)F)c3)nc21]
I-80
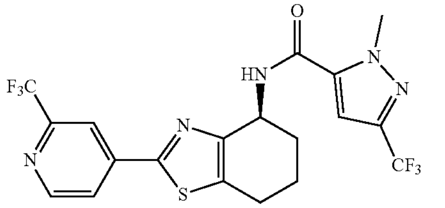 [SMILES: Cn1nc(C(F)(F)F)cc1C(=O)N[C@H]1CCCc2sc(-c3ccnc(C(F)(F)F)c3)nc21]
I-80a
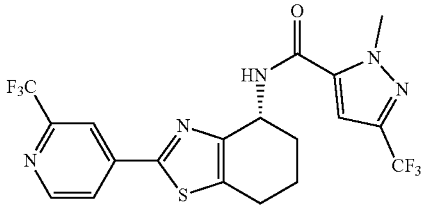 [SMILES: Cn1nc(C(F)(F)F)cc1C(=O)N[C@@H]1CCCc2sc(-c3ccnc(C(F)(F)F)c3)nc21]
I-80b TABLE 1-continued
I-81
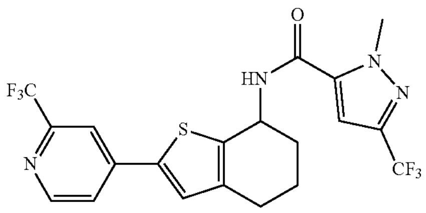 [SMILES: Cn1nc(C(F)(F)F)cc1C(=O)NC1CCCc2cc(-c3ccnc(C(F)(F)F)c3)sc21]
I-81a
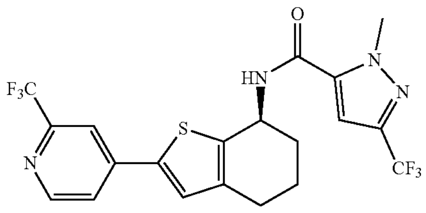
I-81b
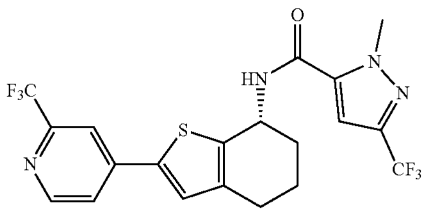
I-82
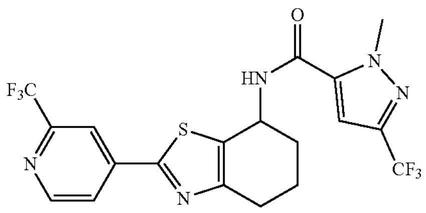 [SMILES: Cn1nc(C(F)(F)F)cc1C(=O)NC1CCCc2nc(-c3ccnc(C(F)(F)F)c3)sc21]
I-82a
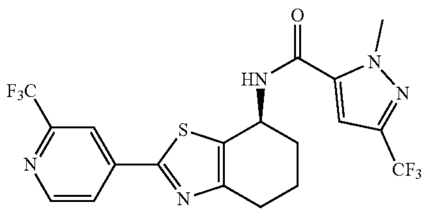
I-82b
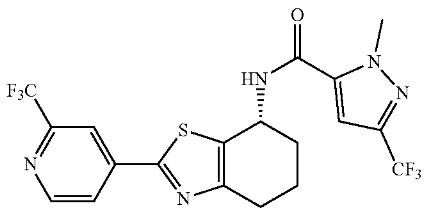 [SMILES: Cn1nc(C(F)(F)F)cc1C(=O)N[C@@H]1CCCc2nc(-c3ccnc(C(F)(F)F)c3)sc21]
I-83
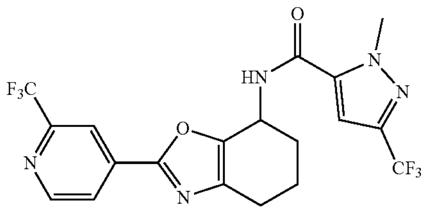 [SMILES: Cn1nc(C(F)(F)F)cc1C(=O)NC1CCCc2nc(-c3ccnc(C(F)(F)F)c3)oc21]

TABLE 1-continued
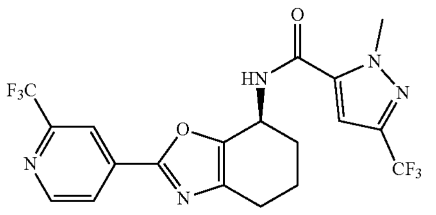
I-83a
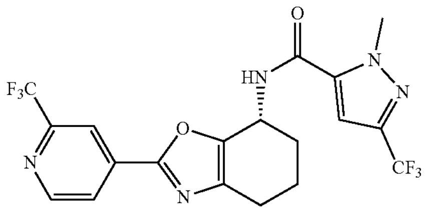 [SMILES: Cn1nc(C(F)(F)F)cc1C(=O)N[C@@H]1CCCc2nc(-c3ccnc(C(F)(F)F)c3)oc21]
I-83b
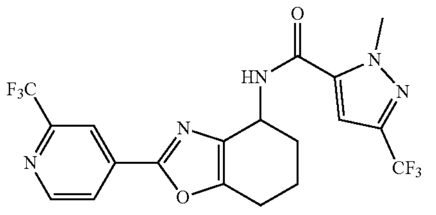
I-84
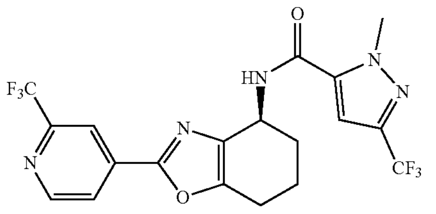
I-84a
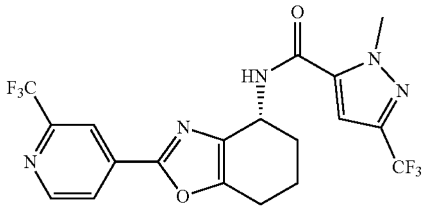
I-84b
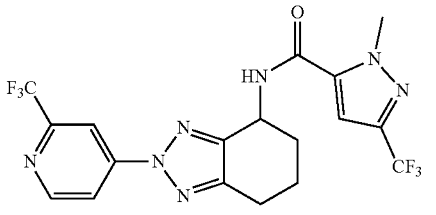
I-85
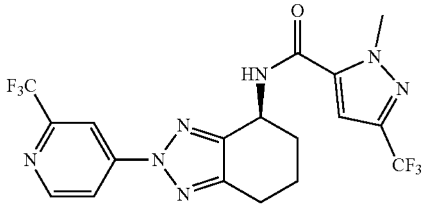
I-85a TABLE 1-continued
I-85b
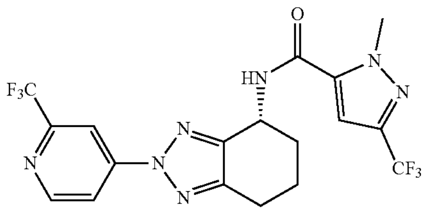
I-86
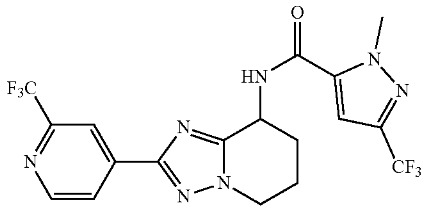
I-86a
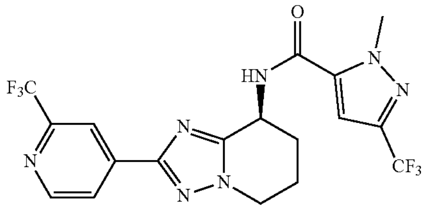
I-86b
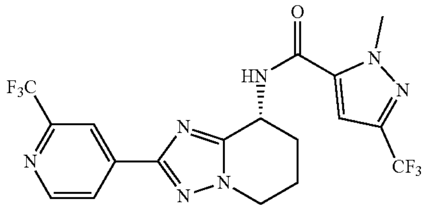
I-87
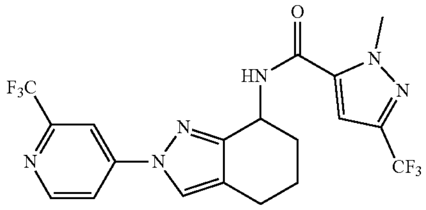
I-87a
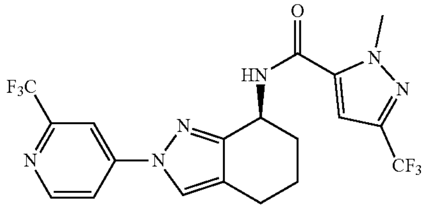 [SMILES: Cn1nc(C(F)(F)F)cc1C(=O)N[C@H]1CCCc2cn(-c3ccnc(C(F)(F)F)c3)nc21]
I-87b
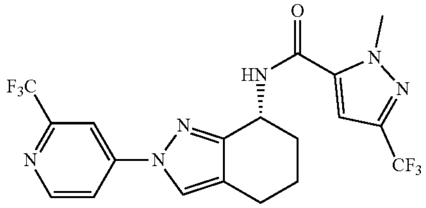 [SMILES: Cn1nc(C(F)(F)F)cc1C(=O)N[C@@H]1CCCc2cn(-c3ccnc(C(F)(F)F)c3)nc21]

TABLE 1-continued
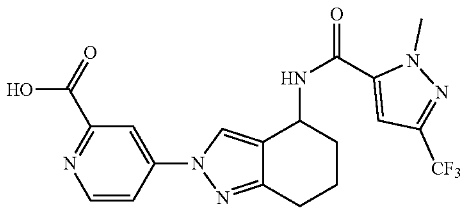 [SMILES: Cn1nc(C(F)(F)F)cc1C(=O)NC1CCCc2nn(-c3ccnc(C(=O)O)c3)cc21]
I-88
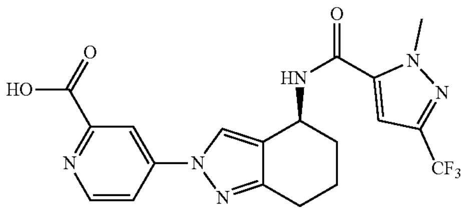 [SMILES: Cn1nc(C(F)(F)F)cc1C(=O)N[C@H]1CCCc2nn(-c3ccnc(C(=O)O)c3)cc21]
I-88a
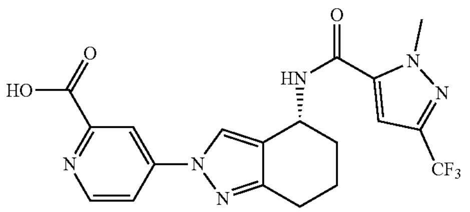 [SMILES: Cn1nc(C(F)(F)F)cc1C(=O)N[C@@H]1CCCc2nn(-c3ccnc(C(=O)O)c3)cc21]
I-88b
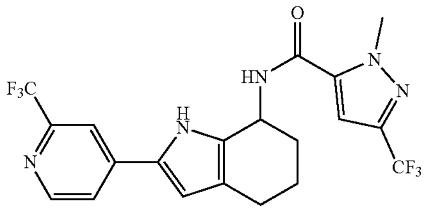 [SMILES: Cn1nc(C(F)(F)F)cc1C(=O)NC1CCCc2cc(-c3ccnc(C(F)(F)F)c3)[nH]c21]
I-89
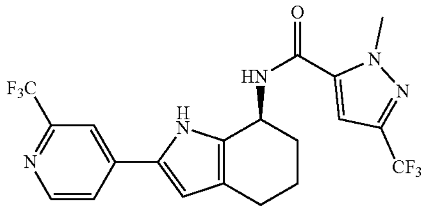 [SMILES: Cn1nc(C(F)(F)F)cc1C(=O)N[C@H]1CCCc2cc(-c3ccnc(C(F)(F)F)c3)[nH]c21]
I-89a
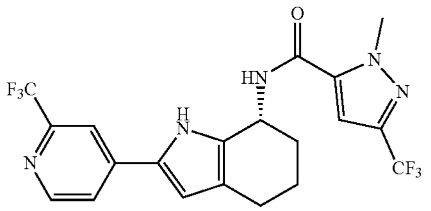 [SMILES: Cn1nc(C(F)(F)F)cc1C(=O)N[C@@H]1CCCc2cc(-c3ccnc(C(F)(F)F)c3)[nH]c21]
I-89b
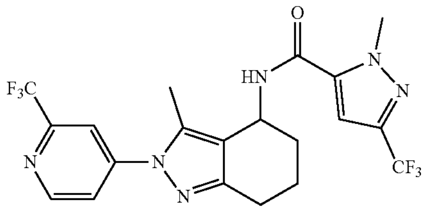 [SMILES: Cc1c2c(nn1-c1ccnc(C(F)(F)F)c1)CCCC2NC(=O)c1cc(C(F)(F)F)nn1C]
I-90

TABLE 1-continued
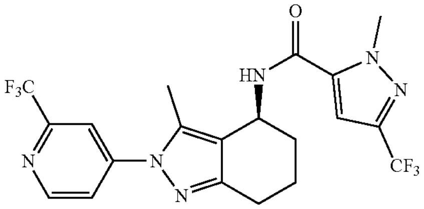 [SMILES: Cc1c2c(nn1-c1ccnc(C(F)(F)F)c1)CCC[C@@H]2NC(=O)c1cc(C(F)(F)F)nn1C]
I-90a
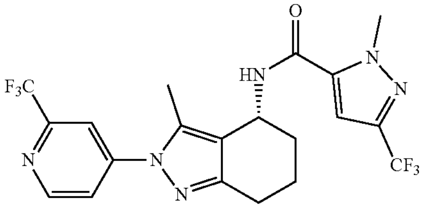 [SMILES: Cc1c2c(nn1-c1ccnc(C(F)(F)F)c1)CCC[C@H]2NC(=O)c1cc(C(F)(F)F)nn1C]
I-90b
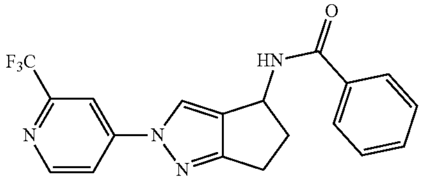
I-91
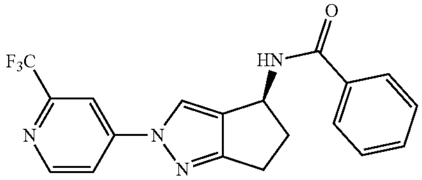
I-91a
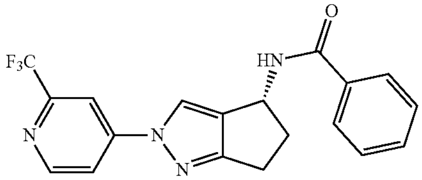
I-91b
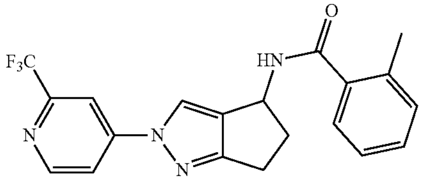
I-92
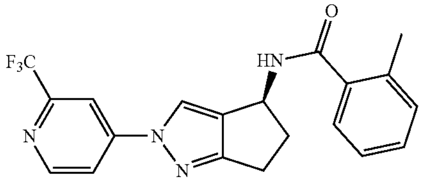 [SMILES: O=C(N[C@H]1CCc2nn(-c3ccnc(C(F)(F)F)c3)cc21)c1ccccc1]
I-92a
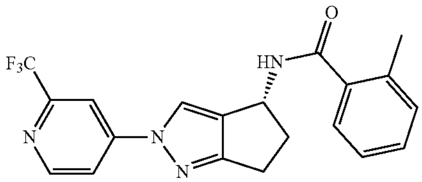 [SMILES: O=C(N[C@@H]1CCc2nn(-c3ccnc(C(F)(F)F)c3)cc21)c1ccccc1]
I-92b TABLE 1-continued
I-93
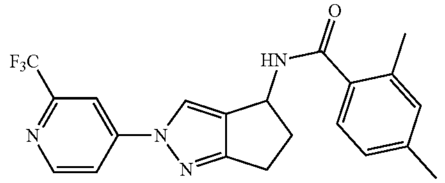 [SMILES: Cc1ccc(C(=O)NC2CCc3nn(-c4ccnc(C(F)(F)F)c4)cc32)c(C)c1]
I-93a
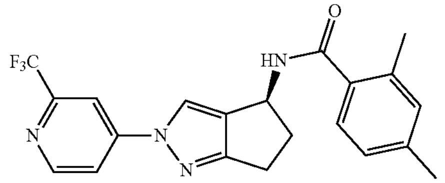 [SMILES: Cc1ccc(C(=O)N[C@H]2CCc3nn(-c4ccnc(C(F)(F)F)c4)cc32)c(C)c1]
I-93b
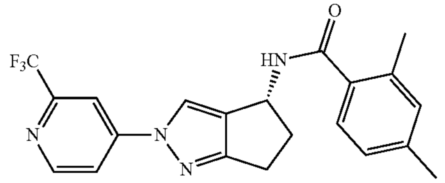 [SMILES: Cc1ccc(C(=O)N[C@@H]2CCc3nn(-c4ccnc(C(F)(F)F)c4)cc32)c(C)c1]
I-94
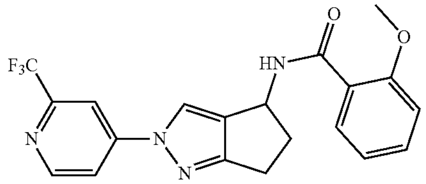 [SMILES: COc1ccccc1C(=O)NC1CCc2nn(-c3ccnc(C(F)(F)F)c3)cc21]
I-94a
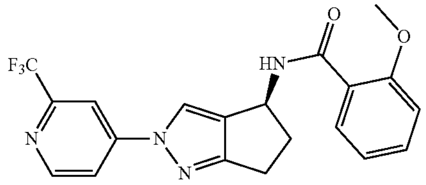 [SMILES: COc1ccccc1C(=O)N[C@H]1CCc2nn(-c3ccnc(C(F)(F)F)c3)cc21]
I-94b
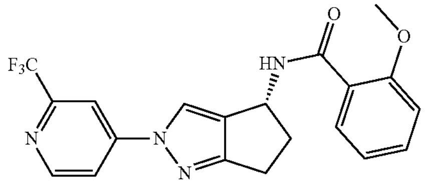 [SMILES: COc1ccccc1C(=O)N[C@@H]1CCc2nn(-c3ccnc(C(F)(F)F)c3)cc21]
I-95
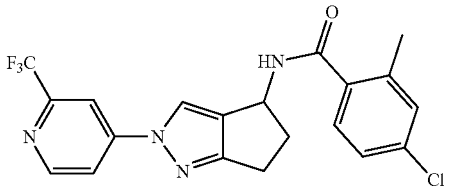 [SMILES: Cc1cc(Cl)ccc1C(=O)NC1CCc2nn(-c3ccnc(C(F)(F)F)c3)cc21]
I-95a
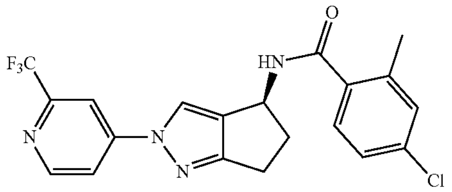 [SMILES: Cc1cc(Cl)ccc1C(=O)N[C@H]1CCc2nn(-c3ccnc(C(F)(F)F)c3)cc21]

TABLE 1-continued
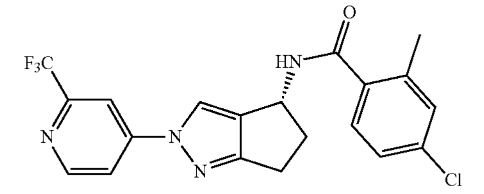 [SMILES: Cc1cc(Cl)ccc1C(=O)N[C@@H]1CCc2nn(-c3ccnc(C(F)(F)F)c3)cc21]
I-95b
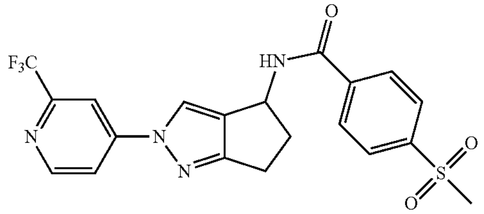 [SMILES: CS(=O)(=O)c1ccc(C(=O)NC2CCc3nn(-c4ccnc(C(F)(F)F)c4)cc32)cc1]
I-96
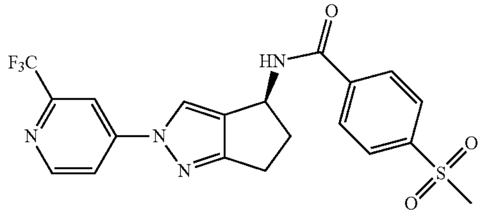 [SMILES: CS(=O)(=O)c1ccc(C(=O)N[C@H]2CCc3nn(-c4ccnc(C(F)(F)F)c4)cc32)cc1]
I-96a
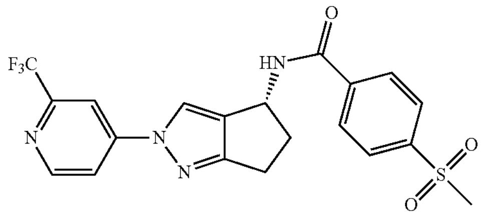 [SMILES: CS(=O)(=O)c1ccc(C(=O)N[C@@H]2CCc3nn(-c4ccnc(C(F)(F)F)c4)cc32)cc1]
I-96b
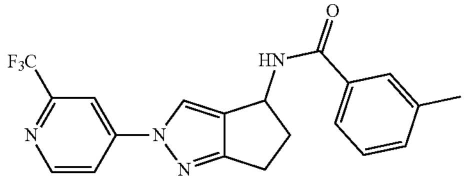 [SMILES: Cc1cccc(C(=O)NC2CCc3nn(-c4ccnc(C(F)(F)F)c4)cc32)c1]
I-97
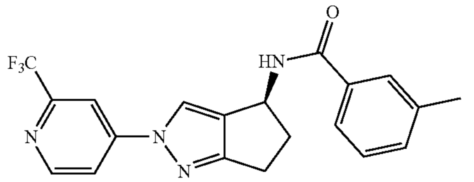 [SMILES: Cc1cccc(C(=O)N[C@H]2CCc3nn(-c4ccnc(C(F)(F)F)c4)cc32)c1]
I-97a
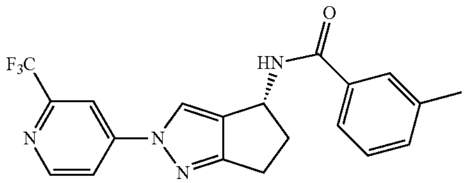 [SMILES: Cc1cccc(C(=O)N[C@@H]2CCc3nn(-c4ccnc(C(F)(F)F)c4)cc32)c1]
I-97b TABLE 1-continued
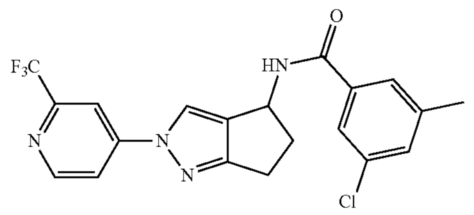
I-98
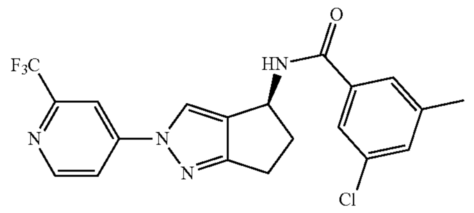 [SMILES: Cc1cc(Cl)cc(C(=O)N[C@H]2CCc3nn(-c4ccnc(C(F)(F)F)c4)cc32)c1]
I-98a
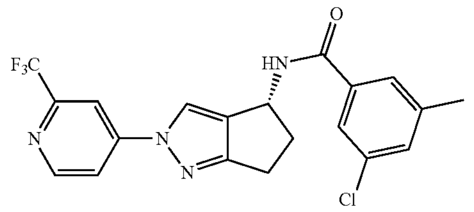 [SMILES: Cc1cc(Cl)cc(C(=O)N[C@@H]2CCc3nn(-c4ccnc(C(F)(F)F)c4)cc32)c1]
I-98b
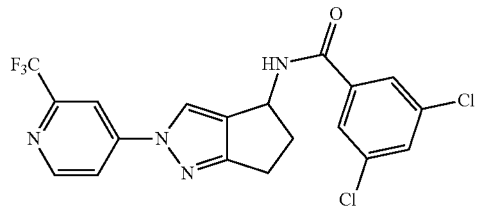 [SMILES: O=C(NC1CCc2nn(-c3ccnc(C(F)(F)F)c3)cc21)c1cc(Cl)cc(Cl)c1]
I-99
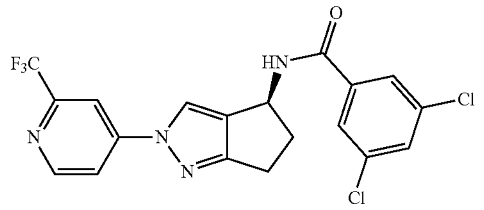 [SMILES: O=C(N[C@H]1CCc2nn(-c3ccnc(C(F)(F)F)c3)cc21)c1cc(Cl)cc(Cl)c1]
I-99a
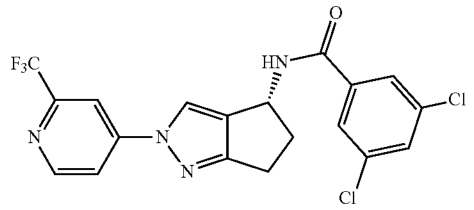 [SMILES: O=C(N[C@@H]1CCc2nn(-c3ccnc(C(F)(F)F)c3)cc21)c1cc(Cl)cc(Cl)c1]
I-99b
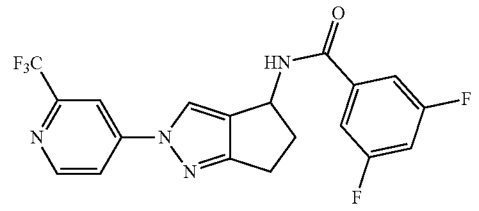 [SMILES: O=C(NC1CCc2nn(-c3ccnc(C(F)(F)F)c3)cc21)c1cc(F)cc(F)c1]
I-100

TABLE 1-continued
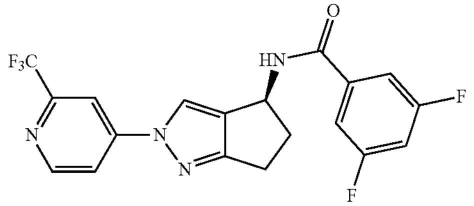 [SMILES: O=C(N[C@H]1CCc2nn(-c3ccnc(C(F)(F)F)c3)cc21)c1cc(F)cc(F)c1]
I-100a
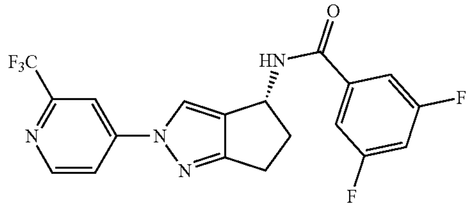 [SMILES: O=C(N[C@@H]1CCc2nn(-c3ccnc(C(F)(F)F)c3)cc21)c1cc(F)cc(F)c1]
I-100b
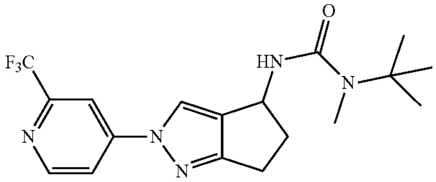 [SMILES: CN(C(=O)NC1CCc2nn(-c3ccnc(C(F)(F)F)c3)cc21)C(C)(C)C]
I-101
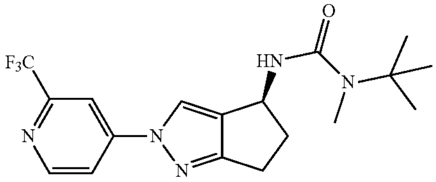 [SMILES: CN(C(=O)N[C@H]1CCc2nn(-c3ccnc(C(F)(F)F)c3)cc21)C(C)(C)C]
I-101a
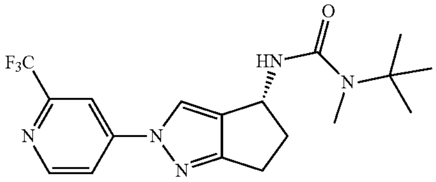 [SMILES: CN(C(=O)N[C@@H]1CCc2nn(-c3ccnc(C(F)(F)F)c3)cc21)C(C)(C)C]
I-101b
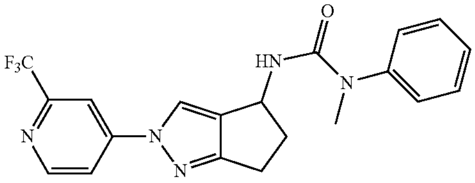 [SMILES: CN(C(=O)NC1CCc2nn(-c3ccnc(C(F)(F)F)c3)cc21)c1ccccc1]
I-102
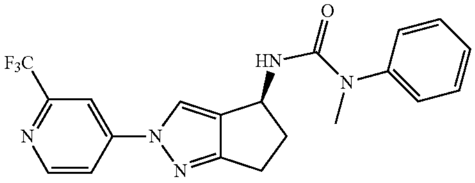 [SMILES: CN(C(=O)N[C@H]1CCc2nn(-c3ccnc(C(F)(F)F)c3)cc21)c1ccccc1]
I-102a
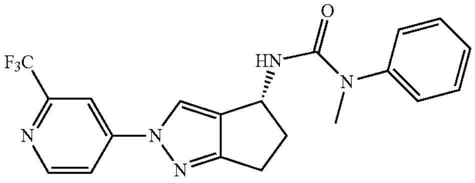 [SMILES: CN(C(=O)N[C@@H]1CCc2nn(-c3ccnc(C(F)(F)F)c3)cc21)c1ccccc1]
I-102b TABLE 1-continued
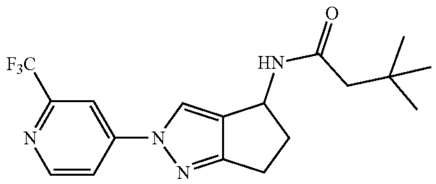 [SMILES: CC(C)(C)CC(=O)NC1CCc2nn(-c3ccnc(C(F)(F)F)c3)cc21]
I-103
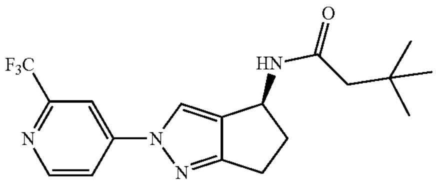 [SMILES: CC(C)(C)CC(=O)N[C@H]1CCc2nn(-c3ccnc(C(F)(F)F)c3)cc21]
I-103a
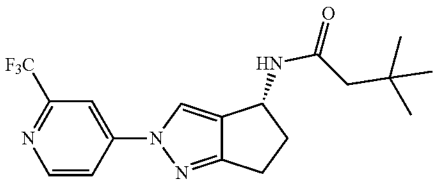 [SMILES: CC(C)(C)CC(=O)N[C@@H]1CCc2nn(-c3ccnc(C(F)(F)F)c3)cc21]
I-103b
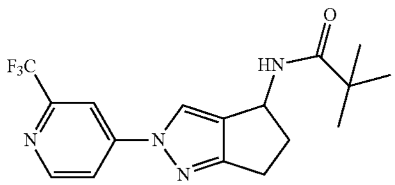 [SMILES: CC(C)(C)C(=O)NC1CCc2nn(-c3ccnc(C(F)(F)F)c3)cc21]
I-104
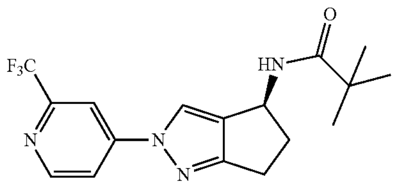 [SMILES: CC(C)(C)C(=O)N[C@H]1CCc2nn(-c3ccnc(C(F)(F)F)c3)cc21]
I-104a
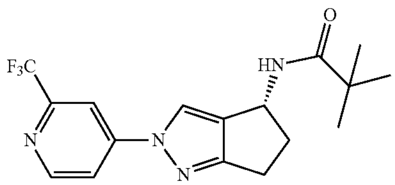 [SMILES: CC(C)(C)C(=O)N[C@@H]1CCc2nn(-c3ccnc(C(F)(F)F)c3)cc21]
I-104b
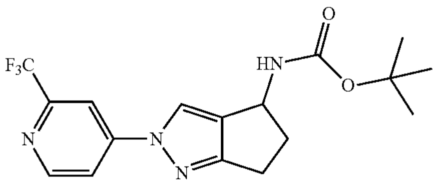 [SMILES: CC(C)(C)OC(=O)NC1CCc2nn(-c3ccnc(C(F)(F)F)c3)cc21]
I-105
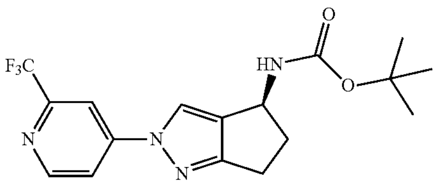 [SMILES: CC(C)(C)OC(=O)N[C@H]1CCc2nn(-c3ccnc(C(F)(F)F)c3)cc21]
I-105a TABLE 1-continued
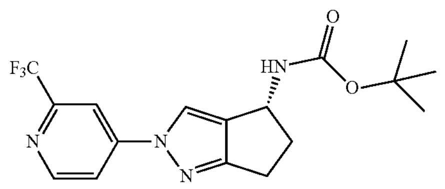 [SMILES: CC(C)(C)OC(=O)N[C@@H]1CCc2nn(-c3ccnc(C(F)(F)F)c3)cc21]
I-105b
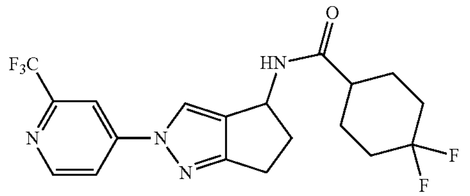 [SMILES: O=C(NC1CCc2nn(-c3ccnc(C(F)(F)F)c3)cc21)C1CCC(F)(F)CC1]
I-106
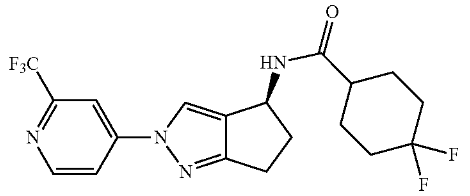 [SMILES: O=C(N[C@H]1CCc2nn(-c3ccnc(C(F)(F)F)c3)cc21)C1CCC(F)(F)CC1]
I-106a
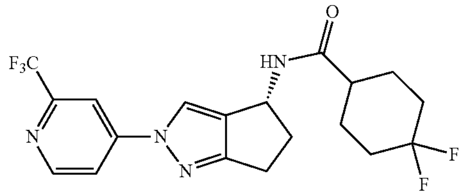 [SMILES: O=C(N[C@@H]1CCc2nn(-c3ccnc(C(F)(F)F)c3)cc21)C1CCC(F)(F)CC1]
I-106b
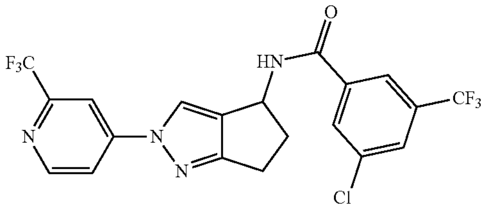 [SMILES: O=C(NC1CCc2nn(-c3ccnc(C(F)(F)F)c3)cc21)c1cc(Cl)cc(C(F)(F)F)c1]
I-107
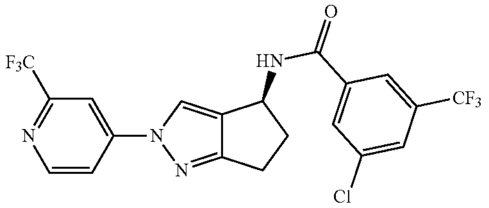 [SMILES: O=C(N[C@H]1CCc2nn(-c3ccnc(C(F)(F)F)c3)cc21)c1cc(Cl)cc(C(F)(F)F)c1]
I-107a
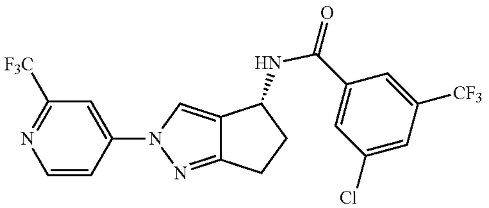 [SMILES: O=C(N[C@@H]1CCc2nn(-c3ccnc(C(F)(F)F)c3)cc21)c1cc(Cl)cc(C(F)(F)F)c1]
I-107b TABLE 1-continued
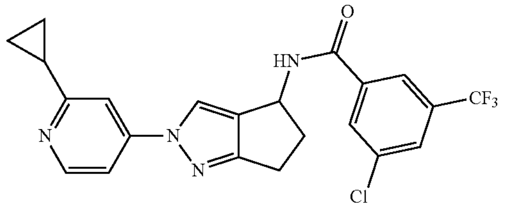 [SMILES: O=C(NC1CCc2nn(-c3ccnc(C4CC4)c3)cc21)c1cc(Cl)cc(C(F)(F)F)c1]
I-108
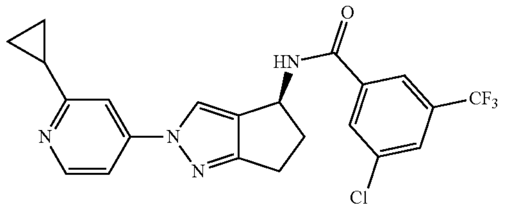 [SMILES: O=C(N[C@H]1CCc2nn(-c3ccnc(C4CC4)c3)cc21)c1cc(Cl)cc(C(F)(F)F)c1]
I-108a
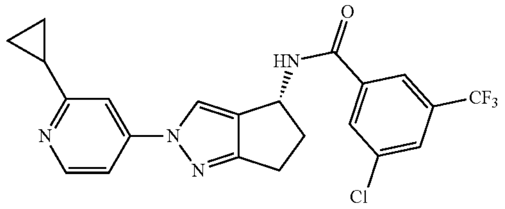 [SMILES: O=C(N[C@@H]1CCc2nn(-c3ccnc(C4CC4)c3)cc21)c1cc(Cl)cc(C(F)(F)F)c1]
I-108b
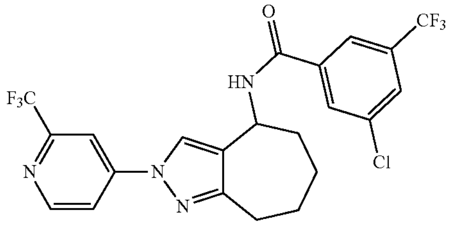 [SMILES: O=C(NC1CCCCc2nn(-c3ccnc(C(F)(F)F)c3)cc21)c1cc(Cl)cc(C(F)(F)F)c1]
I-109
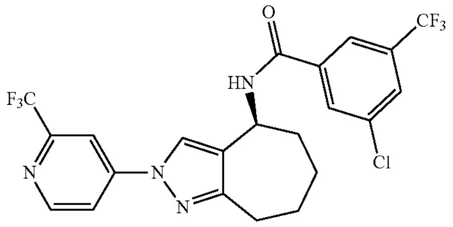 [SMILES: O=C(N[C@H]1CCCCc2nn(-c3ccnc(C(F)(F)F)c3)cc21)c1cc(Cl)cc(C(F)(F)F)c1]
I-109a
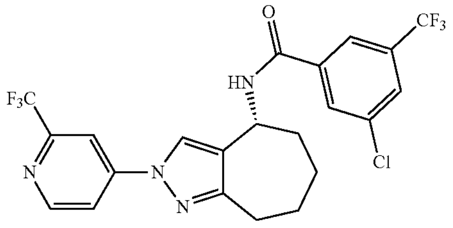 [SMILES: O=C(N[C@@H]1CCCCc2nn(-c3ccnc(C(F)(F)F)c3)cc21)c1cc(Cl)cc(C(F)(F)F)c1]
I-109b
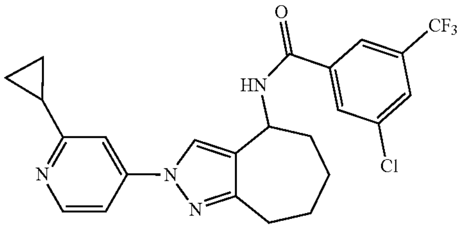 [SMILES: O=C(NC1CCCCc2nn(-c3ccnc(C4CC4)c3)cc21)c1cc(Cl)cc(C(F)(F)F)c1]
I-110

TABLE 1-continued
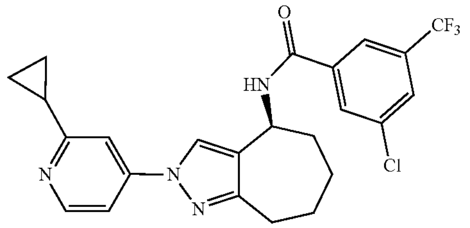 [SMILES: O=C(N[C@H]1CCCCc2nn(-c3ccnc(C4CC4)c3)cc21)c1cc(Cl)cc(C(F)(F)F)c1]
I-110a
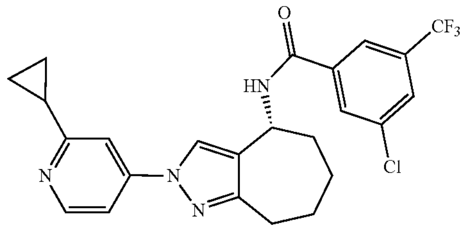 [SMILES: O=C(N[C@@H]1CCCCc2nn(-c3ccnc(C4CC4)c3)cc21)c1cc(Cl)cc(C(F)(F)F)c1]
I-110b
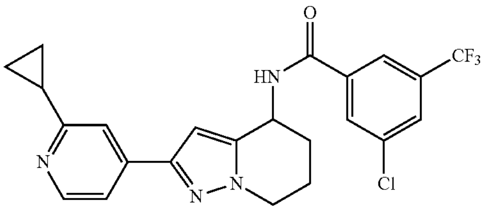 [SMILES: O=C(NC1CCCn2nc(-c3ccnc(C4CC4)c3)cc21)c1cc(Cl)cc(C(F)(F)F)c1]
I-111
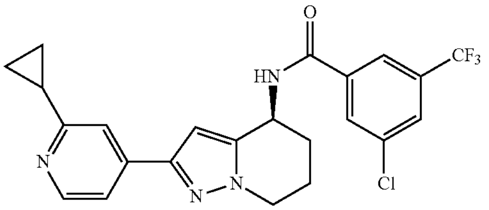 [SMILES: O=C(N[C@H]1CCCn2nc(-c3ccnc(C4CC4)c3)cc21)c1cc(Cl)cc(C(F)(F)F)c1]
I-111a
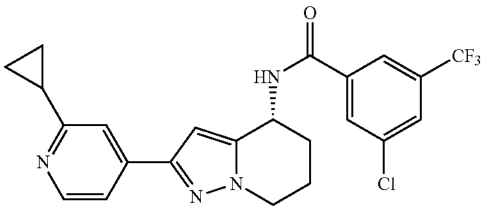
I-111b
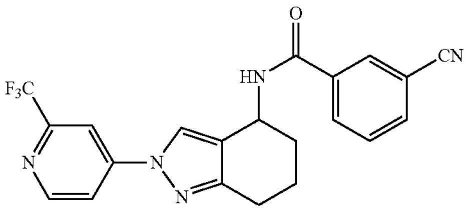 [SMILES: N#Cc1cccc(C(=O)NC2CCCc3nn(-c4ccnc(C(F)(F)F)c4)cc32)c1]
I-112
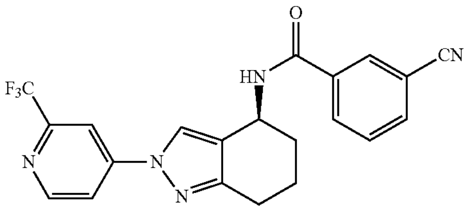 [SMILES: N#Cc1cccc(C(=O)N[C@H]2CCCc3nn(-c4ccnc(C(F)(F)F)c4)cc32)c1]
I-112a TABLE 1-continued
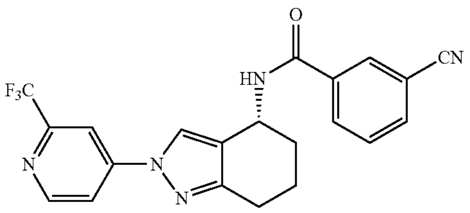 [SMILES: N#Cc1cccc(C(=O)N[C@@H]2CCCc3nn(-c4ccnc(C(F)(F)F)c4)cc32)c1]
I-112b
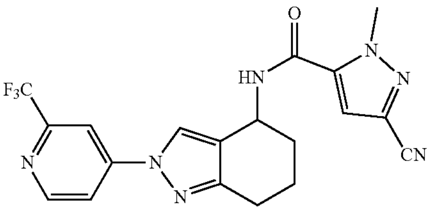 [SMILES: Cn1nc(C#N)cc1C(=O)NC1CCCc2nn(-c3ccnc(C(F)(F)F)c3)cc21]
I-113
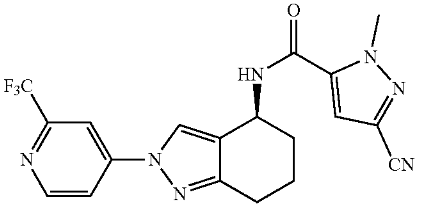 [SMILES: Cn1nc(C#N)cc1C(=O)N[C@H]1CCCc2nn(-c3ccnc(C(F)(F)F)c3)cc21]
I-113a
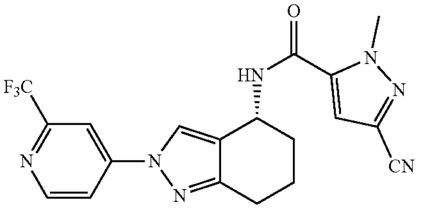 [SMILES: Cn1nc(C#N)cc1C(=O)N[C@@H]1CCCc2nn(-c3ccnc(C(F)(F)F)c3)cc21]
I-113b
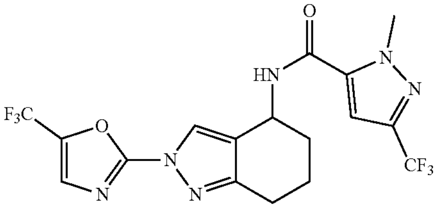
I-114
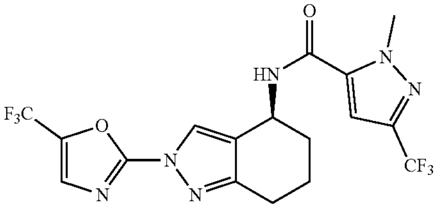
I-114a
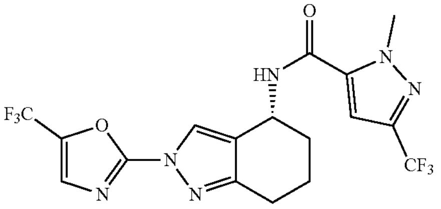
I-114b TABLE 1-continued
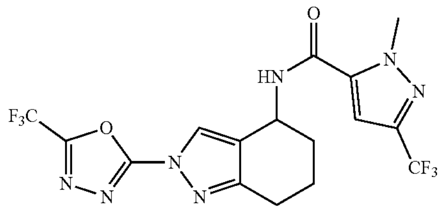
I-115
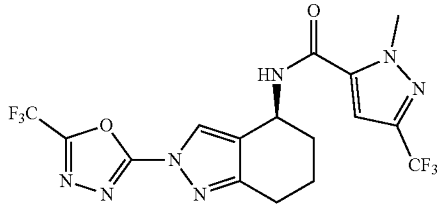
I-115a
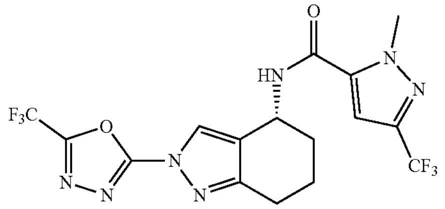
I-115b
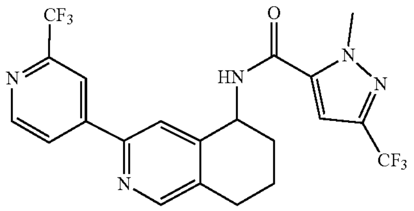 [SMILES: Cn1nc(C(F)(F)F)cc1C(=O)NC1CCCc2cnc(-c3ccnc(C(F)(F)F)c3)cc21]
I-116
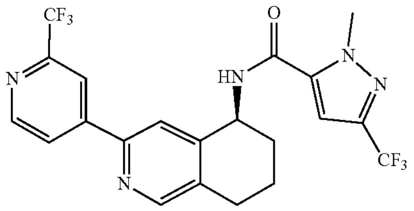 [SMILES: Cn1nc(C(F)(F)F)cc1C(=O)N[C@H]1CCCc2cnc(-c3ccnc(C(F)(F)F)c3)cc21]
I-116a
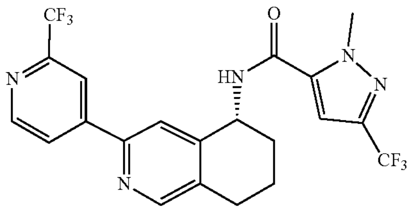
I-116b
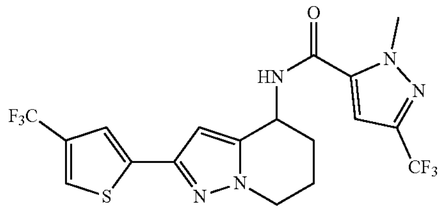
I-117

TABLE 1-continued
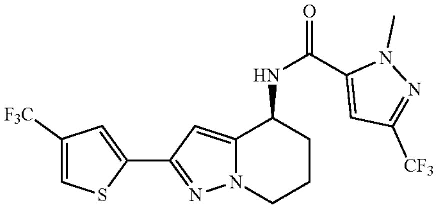
I-117a
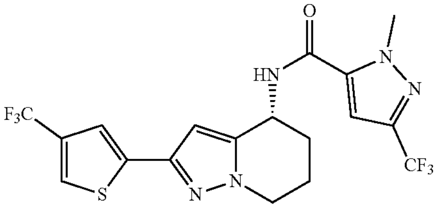
I-117b
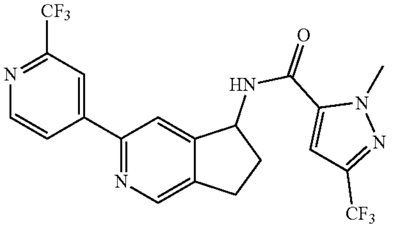 [SMILES: Cn1nc(C(F)(F)F)cc1C(=O)NC1CCc2cnc(-c3ccnc(C(F)(F)F)c3)cc21]
I-118
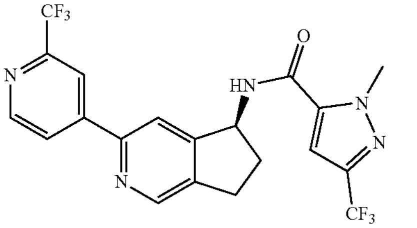 [SMILES: Cn1nc(C(F)(F)F)cc1C(=O)N[C@H]1CCc2cnc(-c3ccnc(C(F)(F)F)c3)cc21]
I-118a
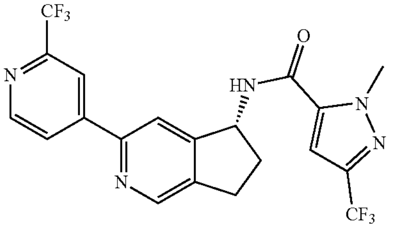 [SMILES: Cn1nc(C(F)(F)F)cc1C(=O)N[C@@H]1CCc2cnc(-c3ccnc(C(F)(F)F)c3)cc21]
I-118b
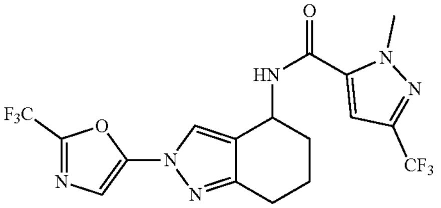
I-119
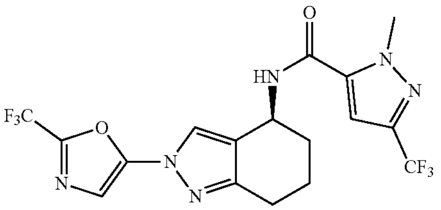 [SMILES: Cn1nc(C(F)(F)F)cc1C(=O)N[C@H]1CCCc2nn(-c3cnc(C(F)(F)F)o3)cc21]
I-119a TABLE 1-continued
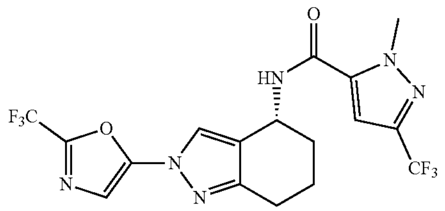 [SMILES: Cn1nc(C(F)(F)F)cc1C(=O)N[C@@H]1CCCc2nn(-c3cnc(C(F)(F)F)o3)cc21]
I-119b
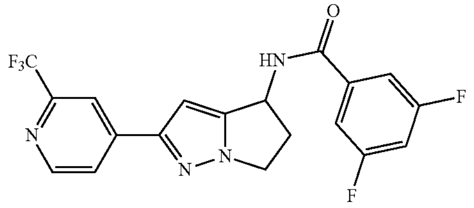 [SMILES: O=C(NC1CCn2nc(-c3ccnc(C(F)(F)F)c3)cc21)c1cc(F)cc(F)c1]
I-120
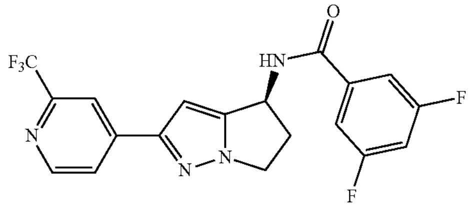 [SMILES: O=C(N[C@H]1CCn2nc(-c3ccnc(C(F)(F)F)c3)cc21)c1cc(F)cc(F)c1]
I-120a
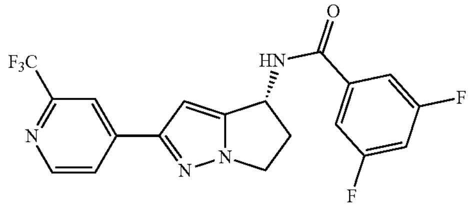
I-120b
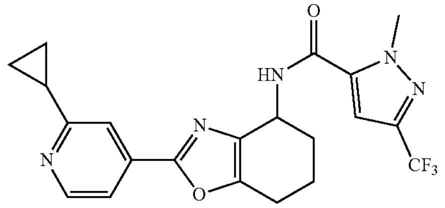
I-121
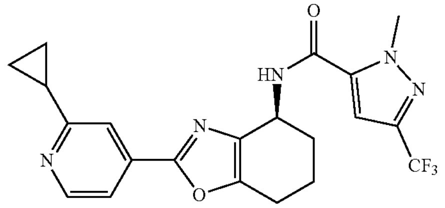
I-121a
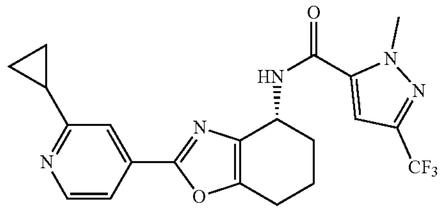
I-121b TABLE 1-continued
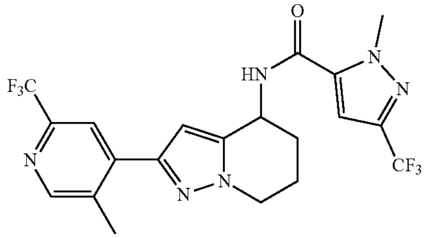 [SMILES: Cc1cnc(C(F)(F)F)cc1-c1cc2n(n1)CCCC2NC(=O)c1cc(C(F)(F)F)nn1C]
I-122
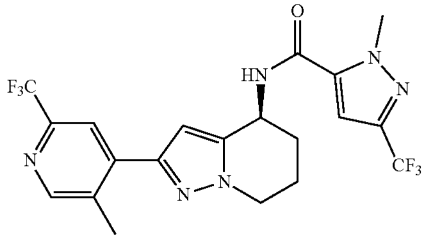 [SMILES: Cc1cnc(C(F)(F)F)cc1-c1cc2n(n1)CCC[C@@H]2NC(=O)c1cc(C(F)(F)F)nn1C]
I-122a
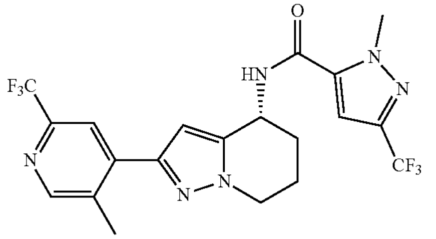 [SMILES: Cc1cnc(C(F)(F)F)cc1-c1cc2n(n1)CCC[C@H]2NC(=O)c1cc(C(F)(F)F)nn1C]
I-122b
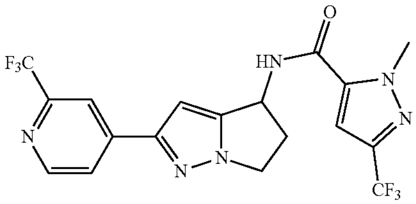 [SMILES: Cn1nc(C(F)(F)F)cc1C(=O)NC1CCn2nc(-c3ccnc(C(F)(F)F)c3)cc21]
I-123
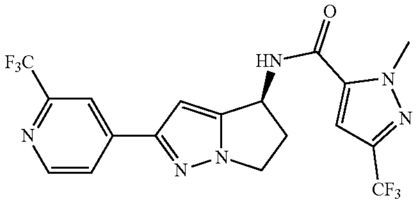 [SMILES: Cn1nc(C(F)(F)F)cc1C(=O)N[C@H]1CCn2nc(-c3ccnc(C(F)(F)F)c3)cc21]
I-123a
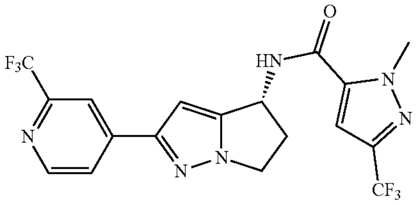
I-123b
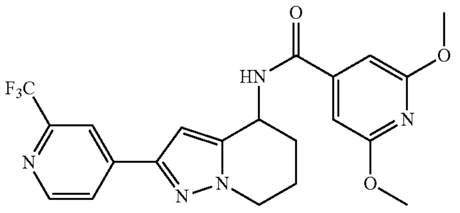 [SMILES: COc1cc(C(=O)NC2CCCn3nc(-c4ccnc(C(F)(F)F)c4)cc32)cc(OC)n1]
I-124

TABLE 1-continued
I-124a
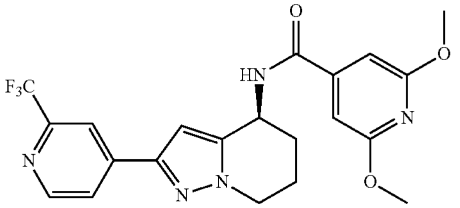 [SMILES: COc1cc(C(=O)N[C@H]2CCCn3nc(-c4ccnc(C(F)(F)F)c4)cc32)cc(OC)n1]
I-124b
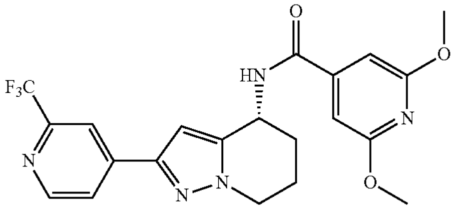 [SMILES: COc1cc(C(=O)N[C@@H]2CCCn3nc(-c4ccnc(C(F)(F)F)c4)cc32)cc(OC)n1]
I-125
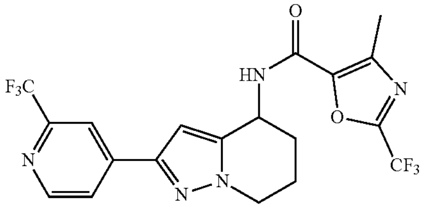 [SMILES: Cc1nc(C(F)(F)F)oc1C(=O)NC1CCCn2nc(-c3ccnc(C(F)(F)F)c3)cc21]
I-125a
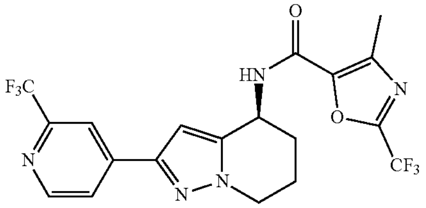 [SMILES: Cc1nc(C(F)(F)F)oc1C(=O)N[C@H]1CCCn2nc(-c3ccnc(C(F)(F)F)c3)cc21]
I-125b
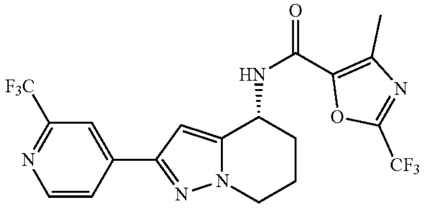 [SMILES: Cc1nc(C(F)(F)F)oc1C(=O)N[C@@H]1CCCn2nc(-c3ccnc(C(F)(F)F)c3)cc21]
I-126
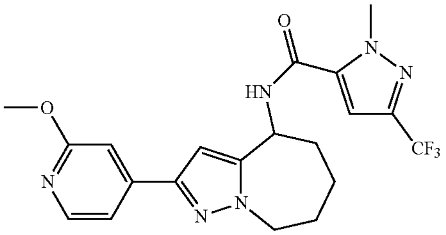 [SMILES: COc1cc(-c2cc3n(n2)CCCCC3NC(=O)c2cc(C(F)(F)F)nn2C)ccn1]
I-126a
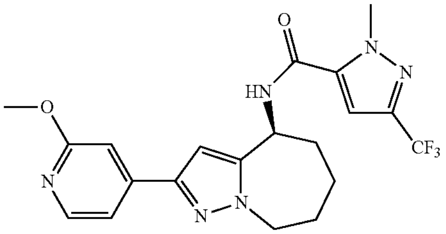 [SMILES: COc1cc(-c2cc3n(n2)CCCC[C@@H]3NC(=O)c2cc(C(F)(F)F)nn2C)ccn1]

TABLE 1-continued
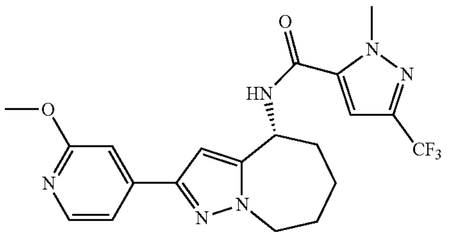 [SMILES: COc1cc(-c2cc3n(n2)CCCC[C@H]3NC(=O)c2cc(C(F)(F)F)nn2C)ccn1]
I-126b
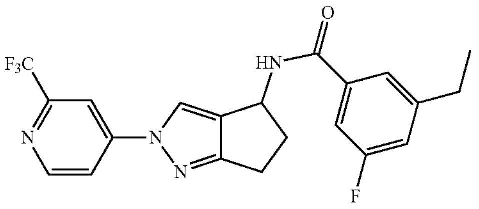 [SMILES: CCc1cc(F)cc(C(=O)NC2CCc3nn(-c4ccnc(C(F)(F)F)c4)cc32)c1]
I-127
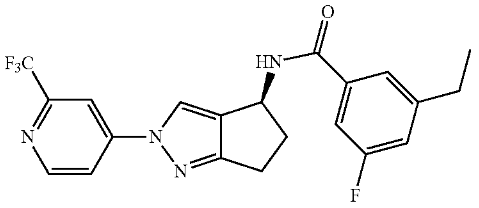 [SMILES: CCc1cc(F)cc(C(=O)N[C@H]2CCc3nn(-c4ccnc(C(F)(F)F)c4)cc32)c1]
I-127a
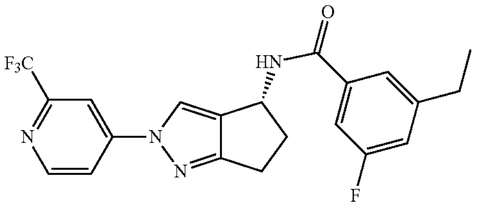 [SMILES: CCc1cc(F)cc(C(=O)N[C@@H]2CCc3nn(-c4ccnc(C(F)(F)F)c4)cc32)c1]
I-127b
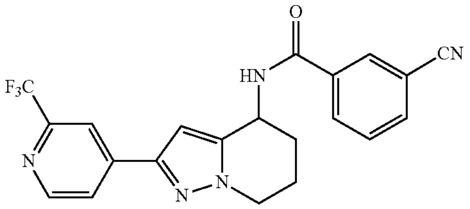 [SMILES: N#Cc1cccc(C(=O)NC2CCCn3nc(-c4ccnc(C(F)(F)F)c4)cc32)c1]
I-128
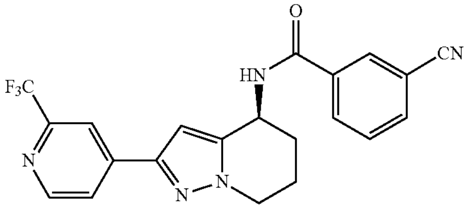
I-128a
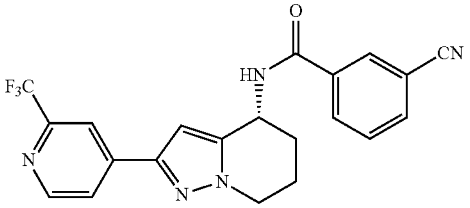 [SMILES: N#Cc1cccc(C(=O)N[C@@H]2CCCn3nc(-c4ccnc(C(F)(F)F)c4)cc32)c1]
I-128b TABLE 1-continued
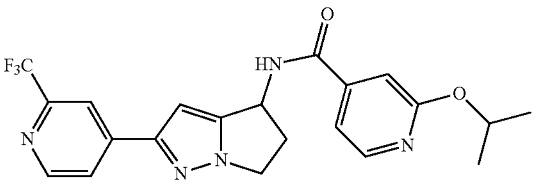 [SMILES: CC(C)Oc1cc(C(=O)NC2CCn3nc(-c4ccnc(C(F)(F)F)c4)cc32)ccn1]
I-129
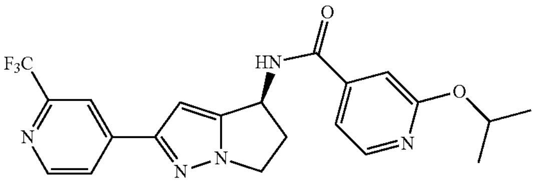 [SMILES: CC(C)Oc1cc(C(=O)N[C@H]2CCn3nc(-c4ccnc(C(F)(F)F)c4)cc32)ccn1]
I-129a
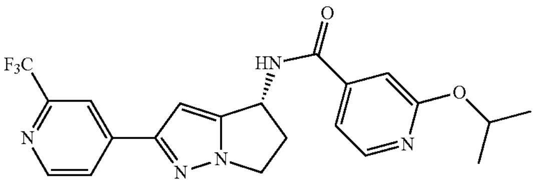 [SMILES: CC(C)Oc1cc(C(=O)N[C@@H]2CCn3nc(-c4ccnc(C(F)(F)F)c4)cc32)ccn1]
I-129b
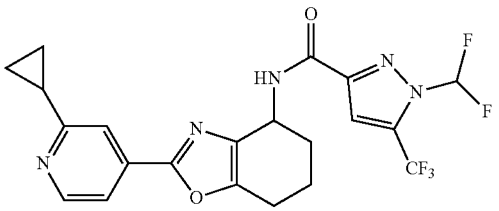 [SMILES: O=C(NC1CCCc2oc(-c3ccnc(C4CC4)c3)nc21)c1cc(C(F)(F)F)n(C(F)F)n1]
I-130
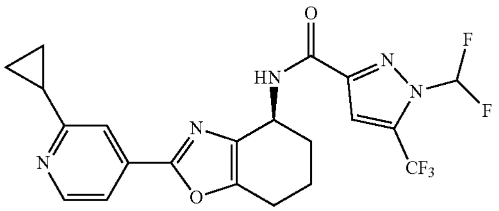 [SMILES: O=C(N[C@H]1CCCc2oc(-c3ccnc(C4CC4)c3)nc21)c1cc(C(F)(F)F)n(C(F)F)n1]
I-130a
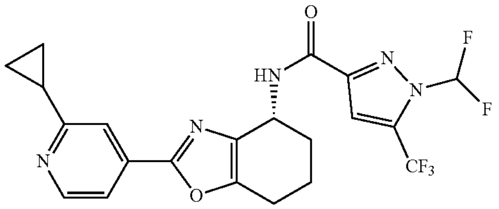 [SMILES: O=C(N[C@@H]1CCCc2oc(-c3ccnc(C4CC4)c3)nc21)c1cc(C(F)(F)F)n(C(F)F)n1]
I-130b
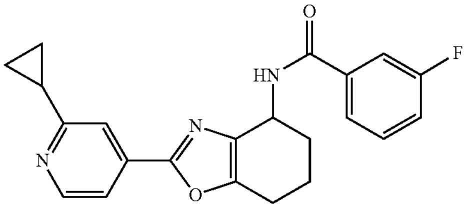 [SMILES: O=C(NC1CCCc2oc(-c3ccnc(C4CC4)c3)nc21)c1cccc(F)c1]
I-131

TABLE 1-continued
I-131a
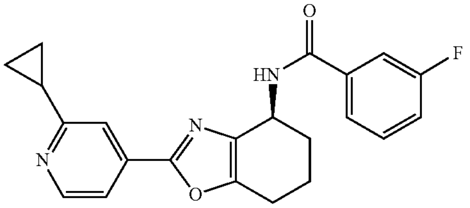 [SMILES: O=C(N[C@H]1CCCc2oc(-c3ccnc(C4CC4)c3)nc21)c1cccc(F)c1]
I-131b
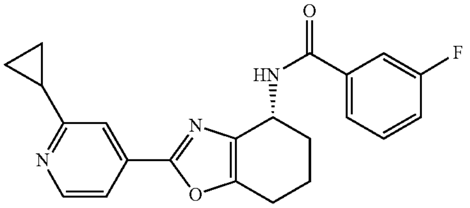
I-132
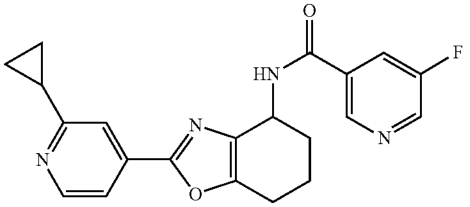 [SMILES: O=C(NC1CCCc2oc(-c3ccnc(C4CC4)c3)nc21)c1cncc(F)c1]
I-132a
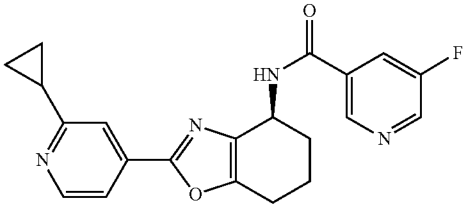 [SMILES: O=C(N[C@H]1CCCc2oc(-c3ccnc(C4CC4)c3)nc21)c1cncc(F)c1]
I-132b
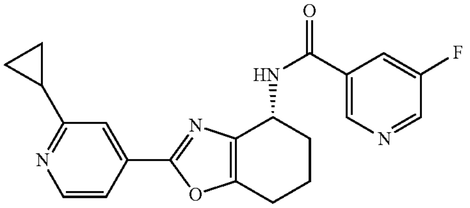
I-133
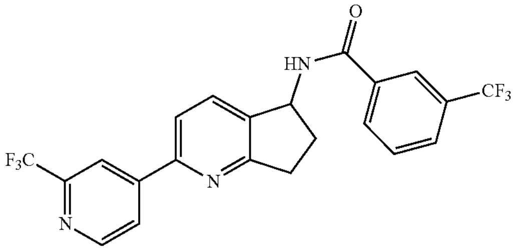 [SMILES: O=C(NC1CCc2nc(-c3ccnc(C(F)(F)F)c3)ccc21)c1cccc(C(F)(F)F)c1]
I-133a
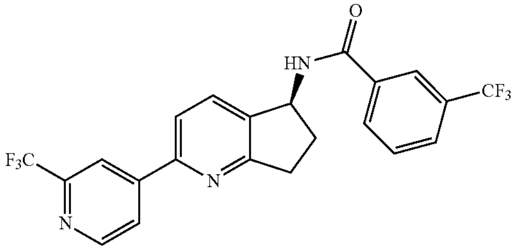 [SMILES: O=C(N[C@H]1CCc2nc(-c3ccnc(C(F)(F)F)c3)ccc21)c1cccc(C(F)(F)F)c1]

TABLE 1-continued
I-133b
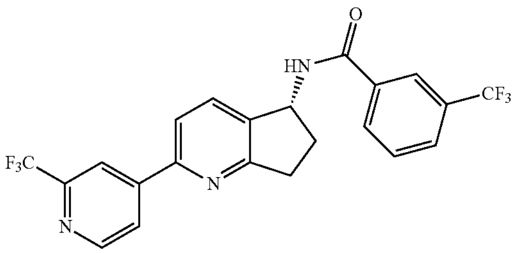 [SMILES: O=C(N[C@@H]1CCc2nc(-c3ccnc(C(F)(F)F)c3)ccc21)c1cccc(C(F)(F)F)c1]
I-134
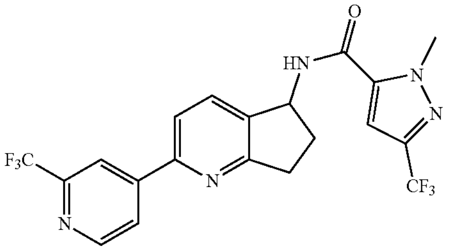 [SMILES: Cn1nc(C(F)(F)F)cc1C(=O)NC1CCc2nc(-c3ccnc(C(F)(F)F)c3)ccc21]
I-134a
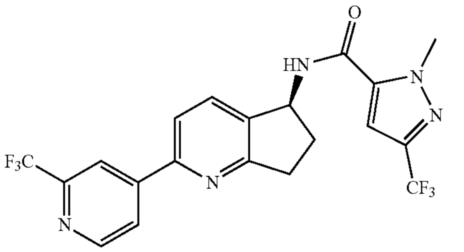 [SMILES: Cn1nc(C(F)(F)F)cc1C(=O)N[C@H]1CCc2nc(-c3ccnc(C(F)(F)F)c3)ccc21]
I-134b
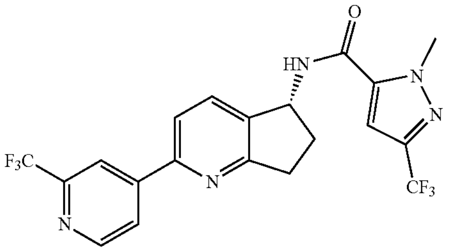 [SMILES: Cn1nc(C(F)(F)F)cc1C(=O)N[C@@H]1CCc2nc(-c3ccnc(C(F)(F)F)c3)ccc21]
I-135
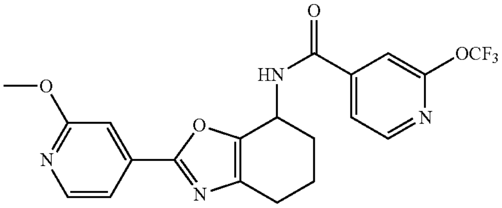 [SMILES: COc1cc(-c2nc3c(o2)C(NC(=O)c2ccnc(OC(F)(F)F)c2)CCC3)ccn1]
I-135a
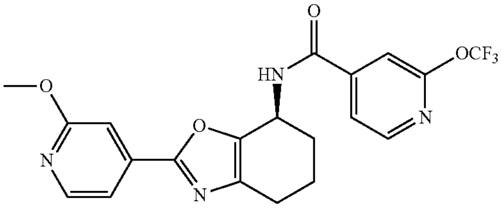 [SMILES: COc1cc(-c2nc3c(o2)[C@@H](NC(=O)c2ccnc(OC(F)(F)F)c2)CCC3)ccn1]

TABLE 1-continued
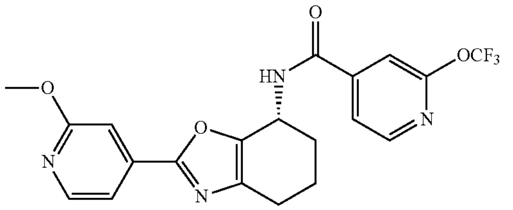 [SMILES: COc1cc(-c2nc3c(o2)[C@H](NC(=O)c2ccnc(OC(F)(F)F)c2)CCC3)ccn1]
I-135b
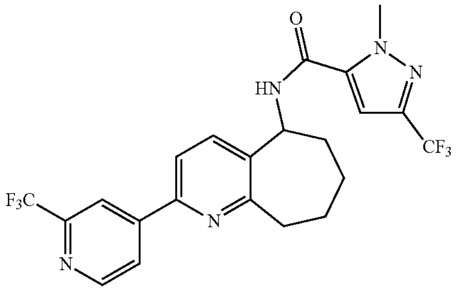 [SMILES: Cn1nc(C(F)(F)F)cc1C(=O)NC1CCCCc2nc(-c3ccnc(C(F)(F)F)c3)ccc21]
I-136
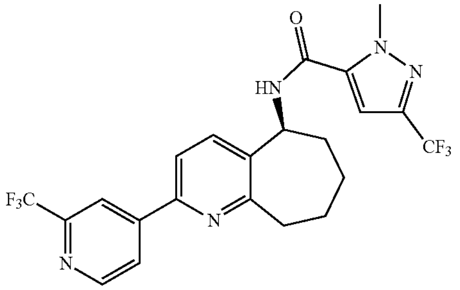 [SMILES: Cn1nc(C(F)(F)F)cc1C(=O)N[C@H]1CCCCc2nc(-c3ccnc(C(F)(F)F)c3)ccc21]
I-136a
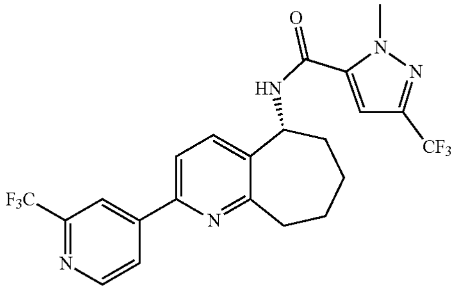 [SMILES: Cn1nc(C(F)(F)F)cc1C(=O)N[C@@H]1CCCCc2nc(-c3ccnc(C(F)(F)F)c3)ccc21]
I-136b
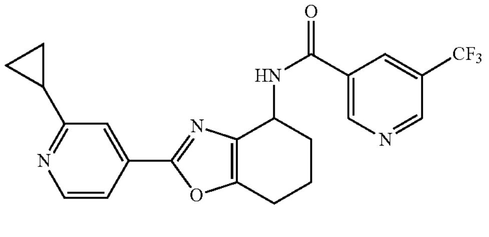 [SMILES: O=C(NC1CCCc2oc(-c3ccnc(C4CC4)c3)nc21)c1cncc(C(F)(F)F)c1]
I-137
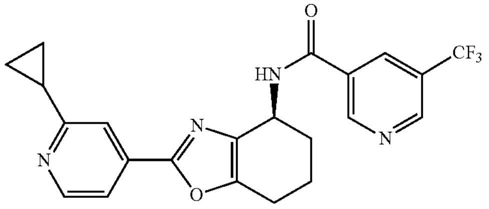 [SMILES: O=C(N[C@H]1CCCc2oc(-c3ccnc(C4CC4)c3)nc21)c1cncc(C(F)(F)F)c1]
I-137a TABLE 1-continued
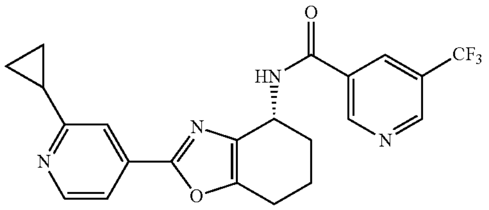 [SMILES: O=C(N[C@@H]1CCCc2oc(-c3ccnc(C4CC4)c3)nc21)c1cncc(C(F)(F)F)c1]
I-137b
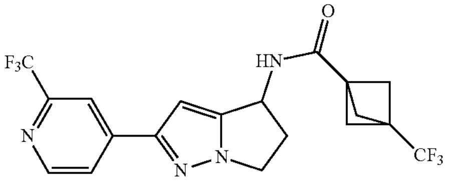 [SMILES: O=C(NC1CCn2nc(-c3ccnc(C(F)(F)F)c3)cc21)C12CC(C(F)(F)F)(C1)C2]
I-138
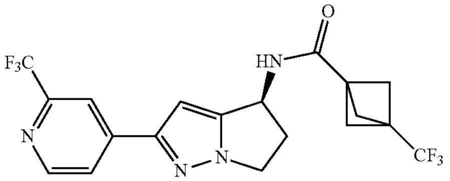 [SMILES: O=C(N[C@H]1CCn2nc(-c3ccnc(C(F)(F)F)c3)cc21)C12CC(C(F)(F)F)(C1)C2]
I-138a
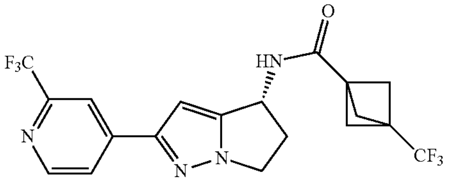 [SMILES: O=C(N[C@@H]1CCn2nc(-c3ccnc(C(F)(F)F)c3)cc21)C12CC(C(F)(F)F)(C1)C2]
I-138b
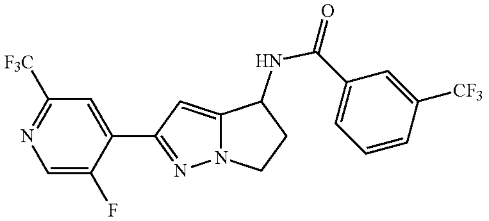 [SMILES: O=C(NC1CCn2nc(-c3cc(C(F)(F)F)ncc3F)cc21)c1cccc(C(F)(F)F)c1]
I-139
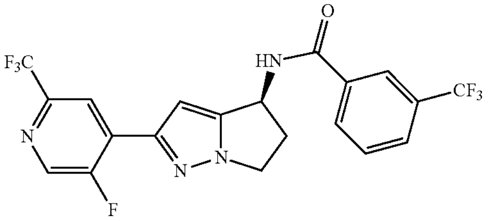 [SMILES: O=C(N[C@H]1CCn2nc(-c3cc(C(F)(F)F)ncc3F)cc21)c1cccc(C(F)(F)F)c1]
I-139a
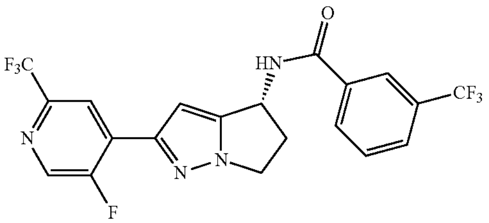 [SMILES: O=C(N[C@@H]1CCn2nc(-c3cc(C(F)(F)F)ncc3F)cc21)c1cccc(C(F)(F)F)c1]
I-139b TABLE 1-continued
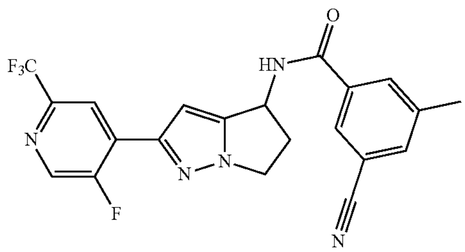 [SMILES: Cc1cc(C#N)cc(C(=O)NC2CCn3nc(-c4cc(C(F)(F)F)ncc4F)cc32)c1]
I-140
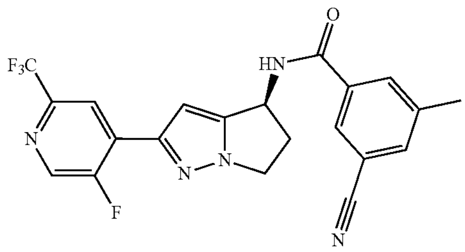 [SMILES: Cc1cc(C#N)cc(C(=O)N[C@H]2CCn3nc(-c4cc(C(F)(F)F)ncc4F)cc32)c1]
I-140a
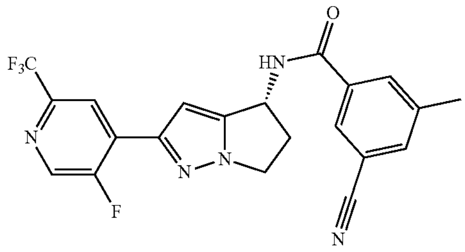 [SMILES: Cc1cc(C#N)cc(C(=O)N[C@@H]2CCn3nc(-c4cc(C(F)(F)F)ncc4F)cc32)c1]
I-140b
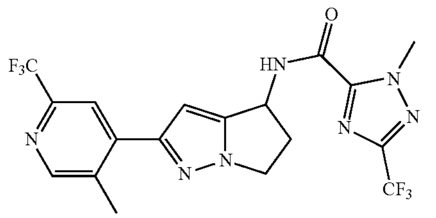 [SMILES: Cc1cnc(C(F)(F)F)cc1-c1cc2n(n1)CCC2NC(=O)c1nc(C(F)(F)F)nn1C]
I-141
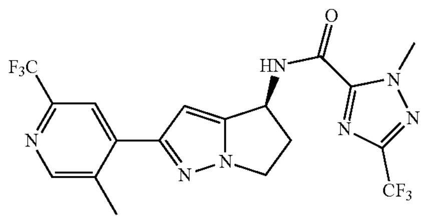 [SMILES: Cc1cnc(C(F)(F)F)cc1-c1cc2n(n1)CC[C@@H]2NC(=O)c1nc(C(F)(F)F)nn1C]
I-141a
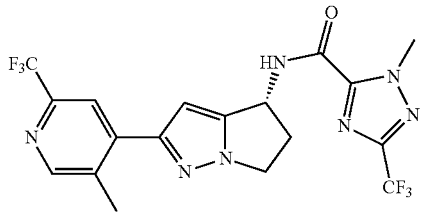 [SMILES: Cc1cnc(C(F)(F)F)cc1-c1cc2n(n1)CC[C@H]2NC(=O)c1nc(C(F)(F)F)nn1C]
I-141b TABLE 1-continued
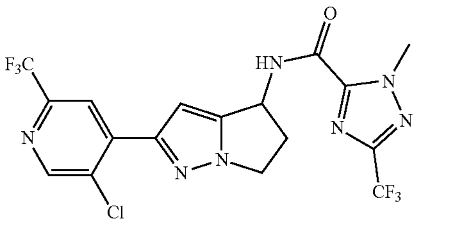
I-142
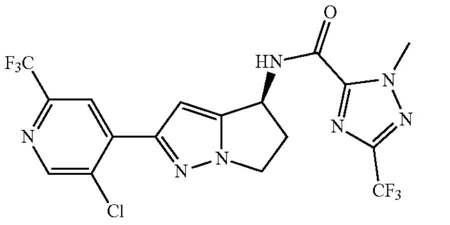
I-142a
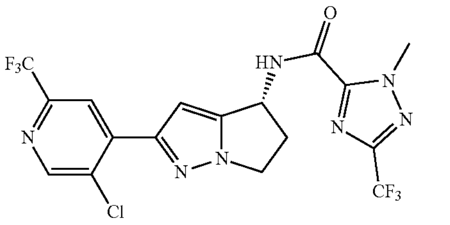
I-142b
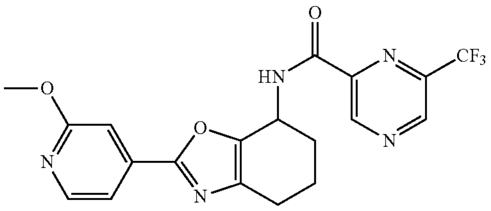
I-143
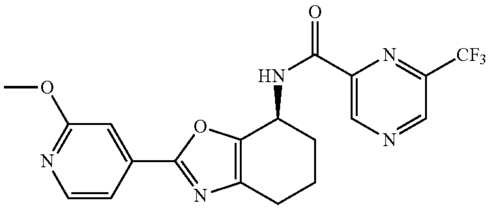
I-143a
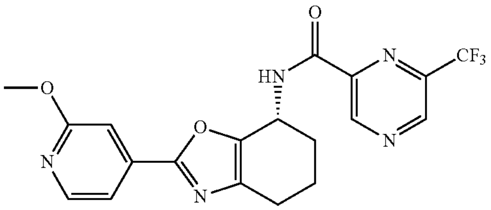
I-143b
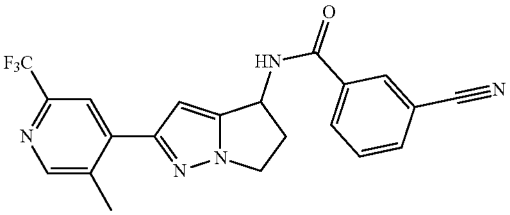 [SMILES: Cc1cnc(C(F)(F)F)cc1-c1cc2n(n1)CCC2NC(=O)c1cccc(C#N)c1]
I-144

TABLE 1-continued
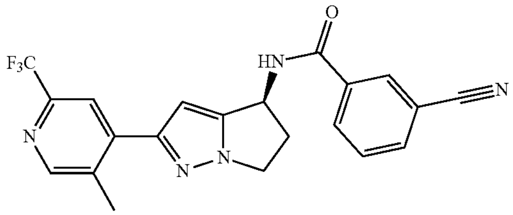 [SMILES: Cc1cnc(C(F)(F)F)cc1-c1cc2n(n1)CC[C@@H]2NC(=O)c1cccc(C#N)c1]
I-144a
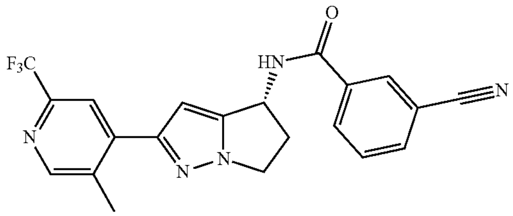 [SMILES: Cc1cnc(C(F)(F)F)cc1-c1cc2n(n1)CC[C@H]2NC(=O)c1cccc(C#N)c1]
I-144b
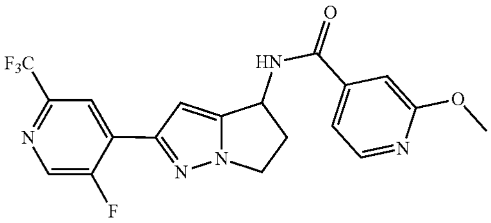 [SMILES: COc1cc(C(=O)NC2CCn3nc(-c4cc(C(F)(F)F)ncc4F)cc32)ccn1]
I-145
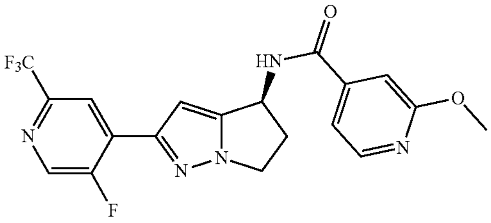 [SMILES: COc1cc(C(=O)N[C@H]2CCn3nc(-c4cc(C(F)(F)F)ncc4F)cc32)ccn1]
I-145a
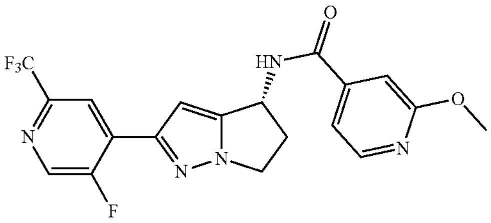 [SMILES: COc1cc(C(=O)N[C@@H]2CCn3nc(-c4cc(C(F)(F)F)ncc4F)cc32)ccn1]
I-145b
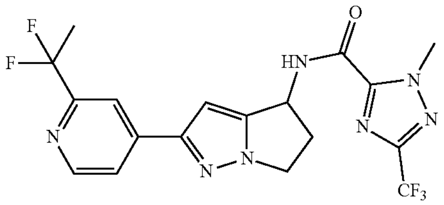 [SMILES: Cn1nc(C(F)(F)F)nc1C(=O)NC1CCn2nc(-c3ccnc(C(C)(F)F)c3)cc21]
I-146
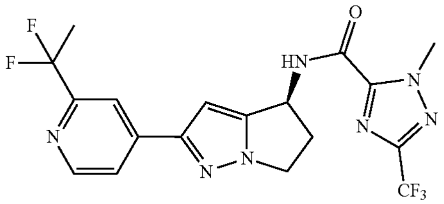 [SMILES: Cn1nc(C(F)(F)F)nc1C(=O)N[C@H]1CCn2nc(-c3ccnc(C(C)(F)F)c3)cc21]
I-146a TABLE 1-continued
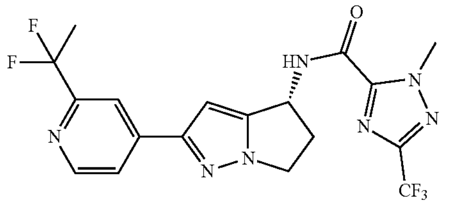
I-146b
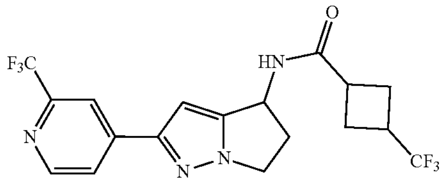 [SMILES: O=C(NC1CCn2nc(-c3ccnc(C(F)(F)F)c3)cc21)C1CC(C(F)(F)F)C1]
I-147
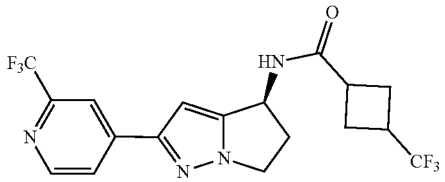 [SMILES: O=C(N[C@H]1CCn2nc(-c3ccnc(C(F)(F)F)c3)cc21)C1CC(C(F)(F)F)C1]
I-147a
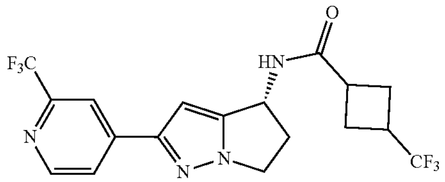 [SMILES: O=C(N[C@@H]1CCn2nc(-c3ccnc(C(F)(F)F)c3)cc21)C1CC(C(F)(F)F)C1]
I-147b
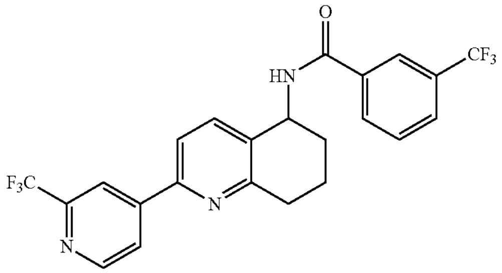 [SMILES: O=C(NC1CCCc2nc(-c3ccnc(C(F)(F)F)c3)ccc21)c1cccc(C(F)(F)F)c1]
I-148
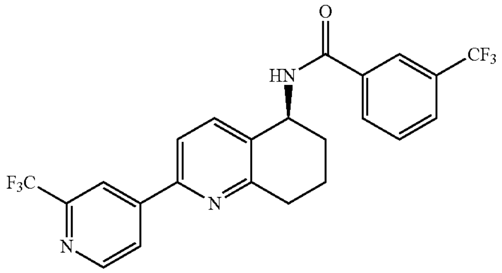 [SMILES: O=C(N[C@H]1CCCc2nc(-c3ccnc(C(F)(F)F)c3)ccc21)c1cccc(C(F)(F)F)c1]
I-148a
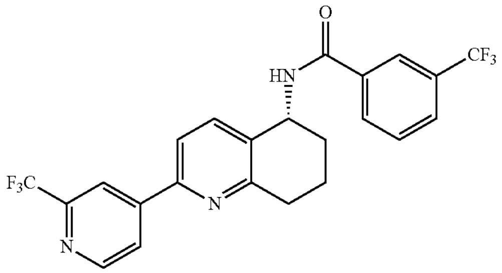 [SMILES: O=C(N[C@@H]1CCCc2nc(-c3ccnc(C(F)(F)F)c3)ccc21)c1cccc(C(F)(F)F)c1]
I-148b TABLE 1-continued
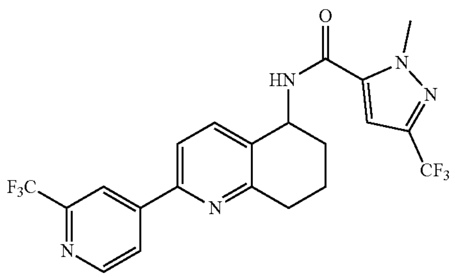 [SMILES: Cn1nc(C(F)(F)F)cc1C(=O)NC1CCCc2nc(-c3ccnc(C(F)(F)F)c3)ccc21]
I-149
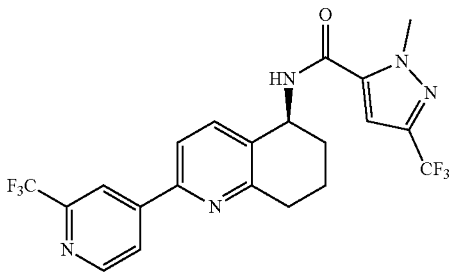 [SMILES: Cn1nc(C(F)(F)F)cc1C(=O)N[C@H]1CCCc2nc(-c3ccnc(C(F)(F)F)c3)ccc21]
I-149a
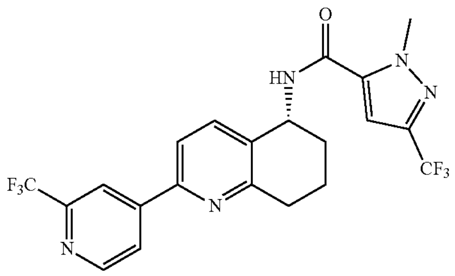 [SMILES: Cn1nc(C(F)(F)F)cc1C(=O)N[C@@H]1CCCc2nc(-c3ccnc(C(F)(F)F)c3)ccc21]
I-149b
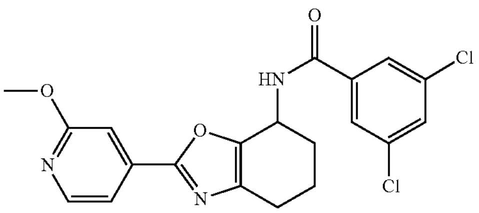 [SMILES: COc1cc(-c2nc3c(o2)C(NC(=O)c2cc(Cl)cc(Cl)c2)CCC3)ccn1]
I-150
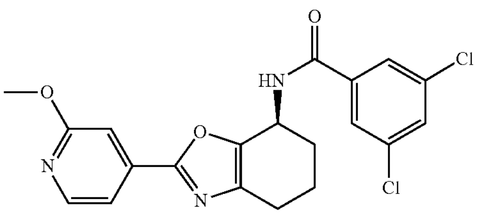 [SMILES: COc1cc(-c2nc3c(o2)[C@@H](NC(=O)c2cc(Cl)cc(Cl)c2)CCC3)ccn1]
I-150a
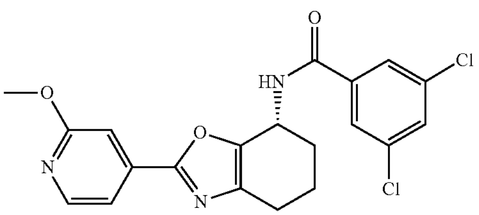 [SMILES: COc1cc(-c2nc3c(o2)[C@H](NC(=O)c2cc(Cl)cc(Cl)c2)CCC3)ccn1]
I-150b TABLE 1-continued
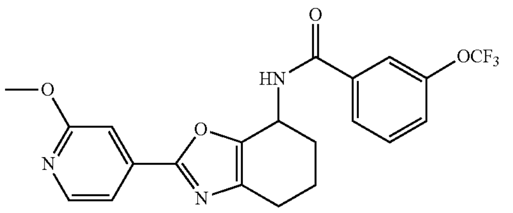
I-151
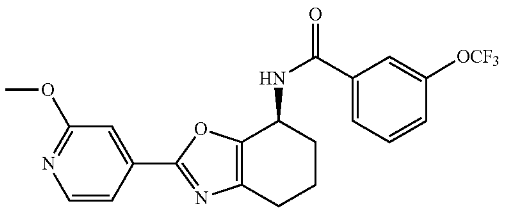
I-151a
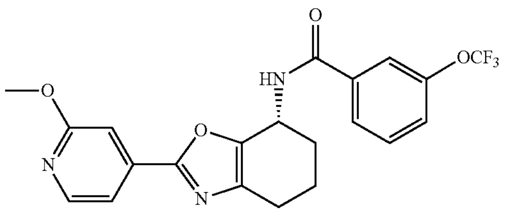
I-151b
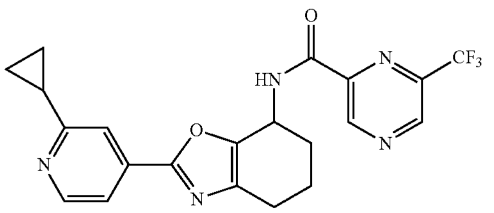 [SMILES: O=C(NC1CCCc2nc(-c3ccnc(C4CC4)c3)oc21)c1cncc(C(F)(F)F)n1]
I-152
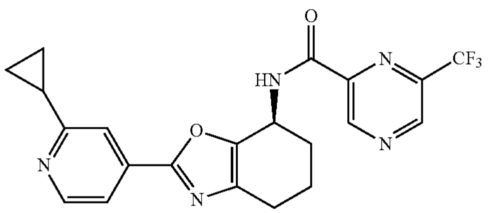
I-152a
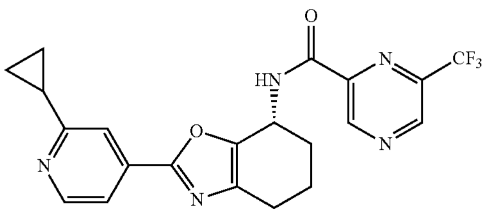
I-152b
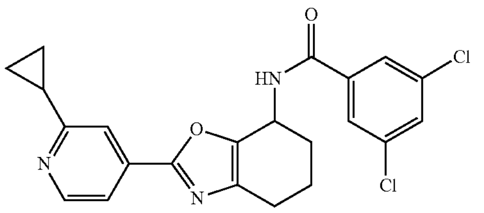 [SMILES: O=C(NC1CCCc2nc(-c3ccnc(C4CC4)c3)oc21)c1cc(Cl)cc(Cl)c1]
I-153

TABLE 1-continued
I-153a
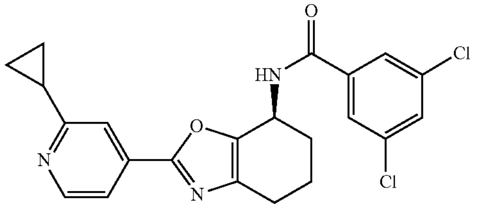 [SMILES: O=C(N[C@H]1CCCc2nc(-c3ccnc(C4CC4)c3)oc21)c1cc(Cl)cc(Cl)c1]
I-153b
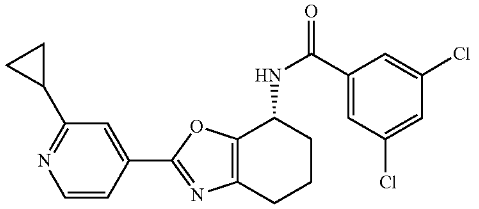 [SMILES: O=C(N[C@@H]1CCCc2nc(-c3ccnc(C4CC4)c3)oc21)c1cc(Cl)cc(Cl)c1]
I-154
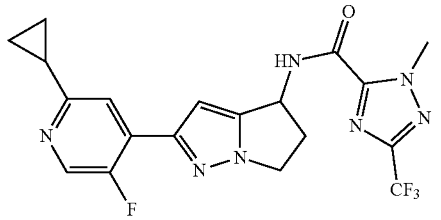 [SMILES: Cn1nc(C(F)(F)F)nc1C(=O)NC1CCn2nc(-c3cc(C4CC4)ncc3F)cc21]
I-154a
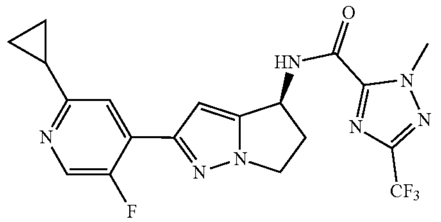 [SMILES: Cn1nc(C(F)(F)F)nc1C(=O)N[C@H]1CCn2nc(-c3cc(C4CC4)ncc3F)cc21]
I-154b
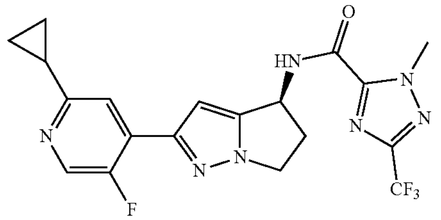 [SMILES: Cn1nc(C(F)(F)F)nc1C(=O)N[C@H]1CCn2nc(-c3cc(C4CC4)ncc3F)cc21]
I-155
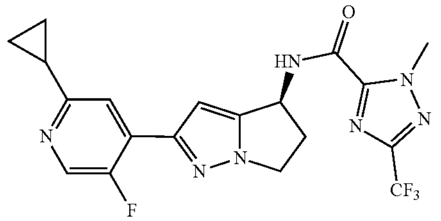 [SMILES: Cn1nc(C(F)(F)F)nc1C(=O)N[C@H]1CCn2nc(-c3cc(C4CC4)ncc3F)cc21]
I-155a
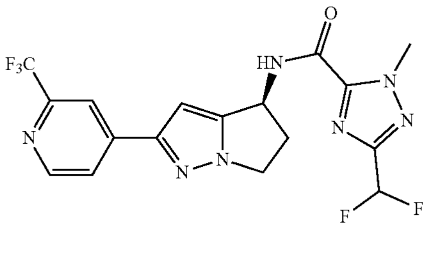 [SMILES: Cn1nc(C(F)F)nc1C(=O)N[C@H]1CCn2nc(-c3ccnc(C(F)(F)F)c3)cc21]

TABLE 1-continued
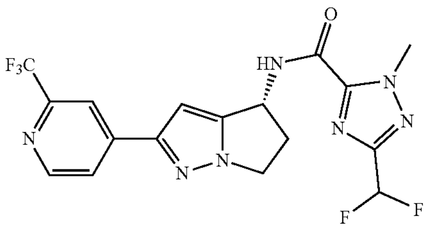 [SMILES: Cn1nc(C(F)F)nc1C(=O)N[C@@H]1CCn2nc(-c3ccnc(C(F)(F)F)c3)cc21]
I-155b
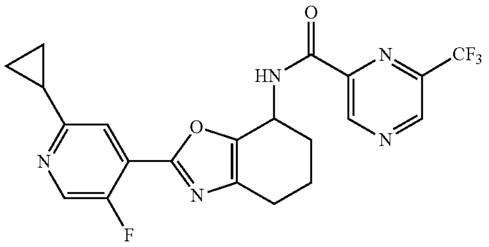 [SMILES: O=C(NC1CCCc2nc(-c3cc(C4CC4)ncc3F)oc21)c1cncc(C(F)(F)F)n1]
I-156
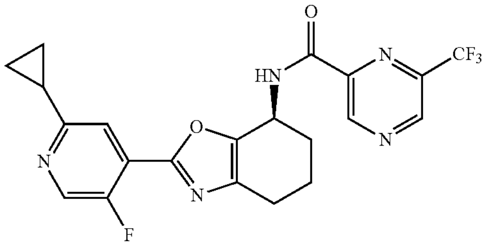 [SMILES: O=C(N[C@H]1CCCc2nc(-c3cc(C4CC4)ncc3F)oc21)c1cncc(C(F)(F)F)n1]
I-156a
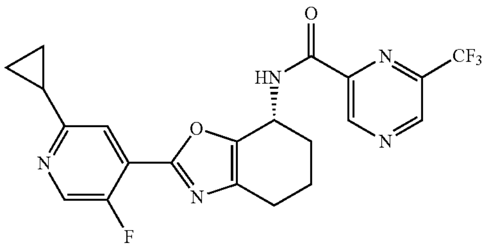 [SMILES: O=C(N[C@@H]1CCCc2nc(-c3cc(C4CC4)ncc3F)oc21)c1cncc(C(F)(F)F)n1]
I-156b
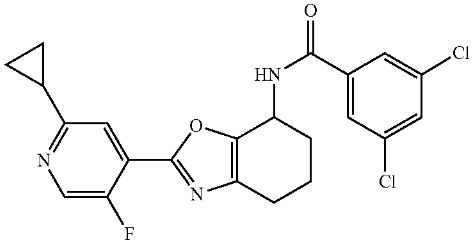 [SMILES: O=C(NC1CCCc2nc(-c3cc(C4CC4)ncc3F)oc21)c1cc(Cl)cc(Cl)c1]
I-157
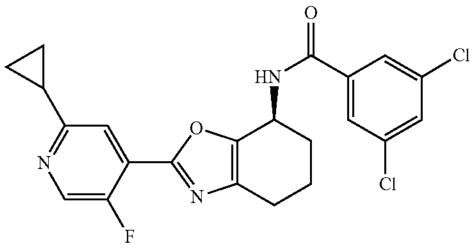 [SMILES: O=C(N[C@H]1CCCc2nc(-c3cc(C4CC4)ncc3F)oc21)c1cc(Cl)cc(Cl)c1]
I-157a TABLE 1-continued
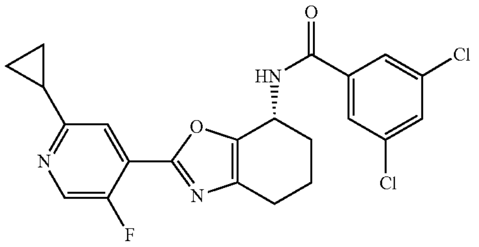 [SMILES: O=C(N[C@@H]1CCCc2nc(-c3cc(C4CC4)ncc3F)oc21)c1cc(Cl)cc(Cl)c1]
I-157b
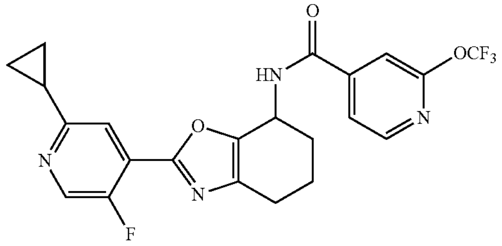 [SMILES: O=C(NC1CCCc2nc(-c3cc(C4CC4)ncc3F)oc21)c1ccnc(OC(F)(F)F)c1]
I-158
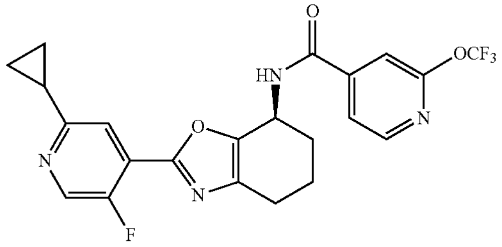 [SMILES: O=C(N[C@H]1CCCc2nc(-c3cc(C4CC4)ncc3F)oc21)c1ccnc(OC(F)(F)F)c1]
I-158a
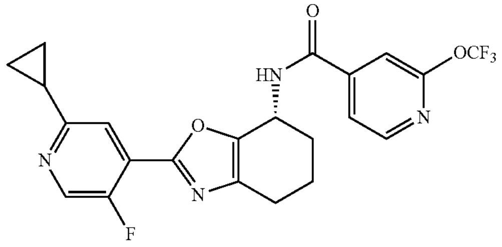 [SMILES: O=C(N[C@@H]1CCCc2nc(-c3cc(C4CC4)ncc3F)oc21)c1ccnc(OC(F)(F)F)c1]
I-158b
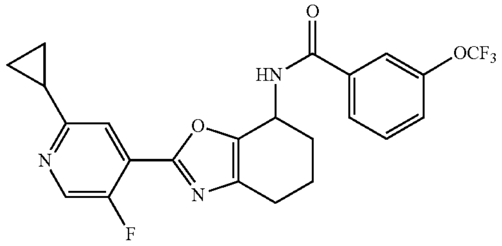 [SMILES: O=C(NC1CCCc2nc(-c3cc(C4CC4)ncc3F)oc21)c1cccc(OC(F)(F)F)c1]
I-159
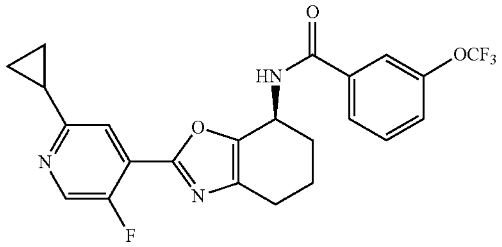 [SMILES: O=C(N[C@H]1CCCc2nc(-c3cc(C4CC4)ncc3F)oc21)c1cccc(OC(F)(F)F)c1]
I-159a TABLE 1-continued
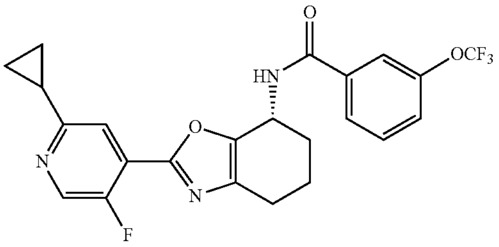 [SMILES: O=C(N[C@@H]1CCCc2nc(-c3cc(C4CC4)ncc3F)oc21)c1cccc(OC(F)(F)F)c1]
I-159b
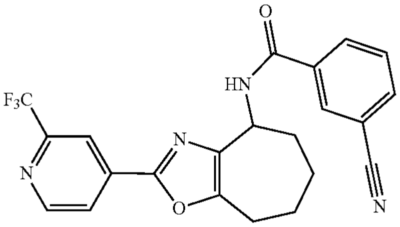 [SMILES: N#Cc1cccc(C(=O)NC2CCCCc3oc(-c4ccnc(C(F)(F)F)c4)nc32)c1]
I-160
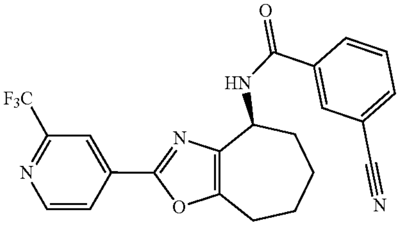 [SMILES: N#Cc1cccc(C(=O)N[C@H]2CCCCc3oc(-c4ccnc(C(F)(F)F)c4)nc32)c1]
I-160a
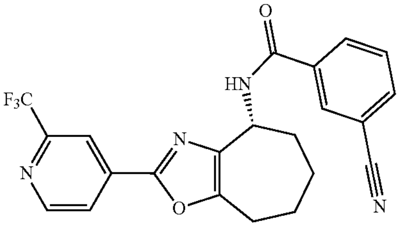 [SMILES: N#Cc1cccc(C(=O)N[C@@H]2CCCCc3oc(-c4ccnc(C(F)(F)F)c4)nc32)c1]
I-160b
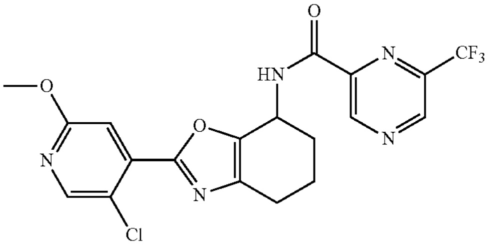 [SMILES: COc1cc(-c2nc3c(o2)C(NC(=O)c2cncc(C(F)(F)F)n2)CCC3)c(Cl)cn1]
I-161
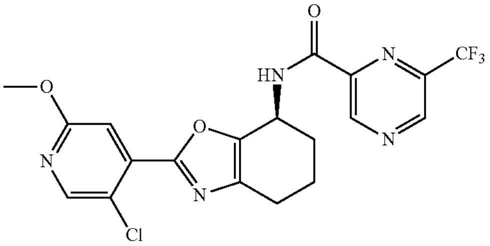
I-161a TABLE 1-continued
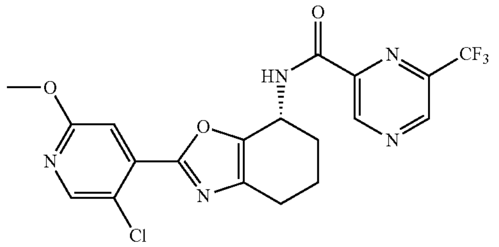 [SMILES: COc1cc(-c2nc3c(o2)[C@H](NC(=O)c2cncc(C(F)(F)F)n2)CCC3)c(Cl)cn1]
I-161b
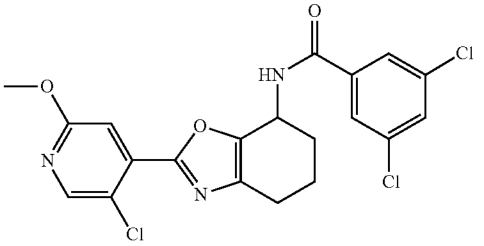
I-162
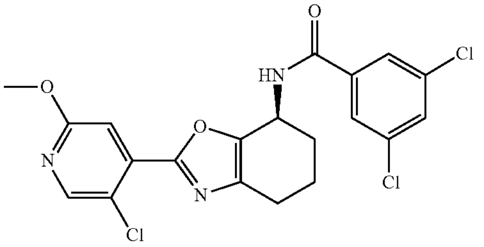
I-162a
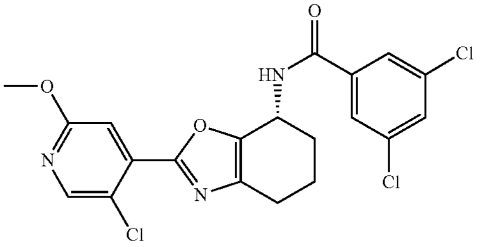
I-162b
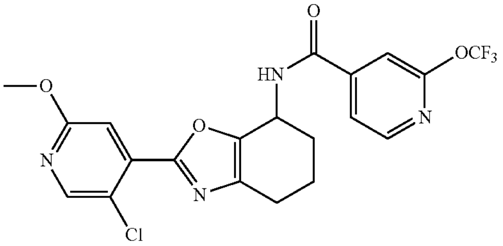 [SMILES: COc1cc(-c2nc3c(o2)C(NC(=O)c2ccnc(OC(F)(F)F)c2)CCC3)c(Cl)cn1]
I-163
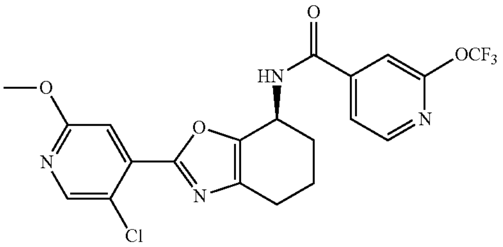
I-163a TABLE 1-continued
I-163b
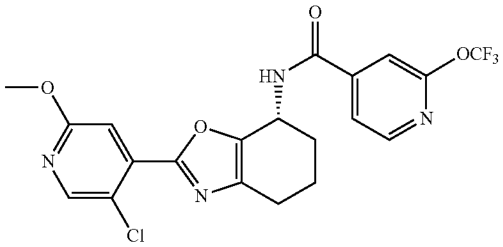 [SMILES: COc1cc(-c2nc3c(o2)[C@H](NC(=O)c2ccnc(OC(F)(F)F)c2)CCC3)c(Cl)cn1]
I-164
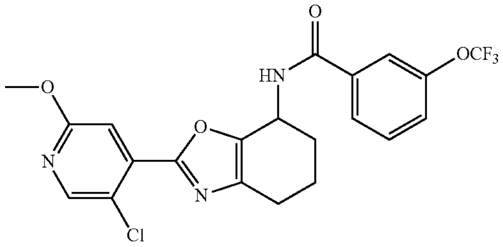
I-164a
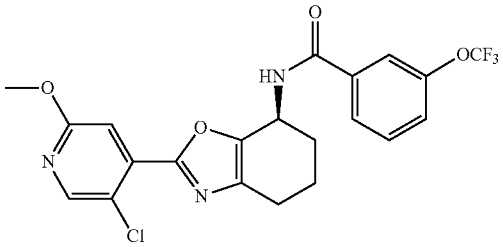
I-164b
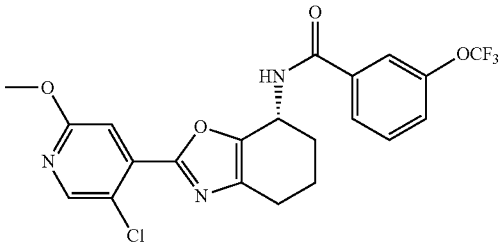
I-165
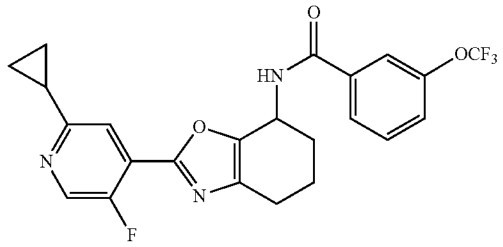 [SMILES: O=C(NC1CCCc2nc(-c3cc(C4CC4)ncc3F)oc21)c1cccc(OC(F)(F)F)c1]
I-165a
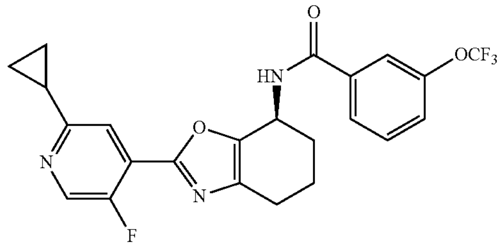 [SMILES: O=C(N[C@H]1CCCc2nc(-c3cc(C4CC4)ncc3F)oc21)c1cccc(OC(F)(F)F)c1]

TABLE 1-continued
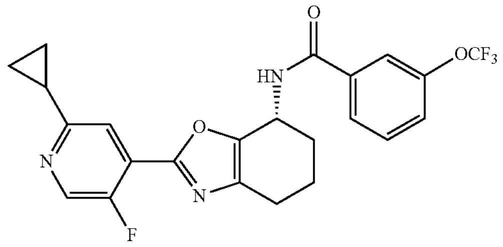 [SMILES: O=C(N[C@@H]1CCCc2nc(-c3cc(C4CC4)ncc3F)oc21)c1cccc(OC(F)(F)F)c1]
I-165b
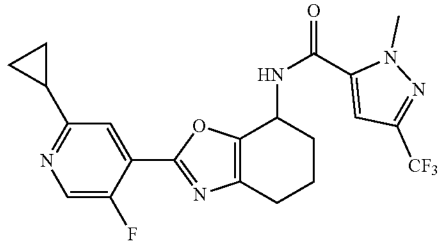 [SMILES: Cn1nc(C(F)(F)F)cc1C(=O)NC1CCCc2nc(-c3cc(C4CC4)ncc3F)oc21]
I-166
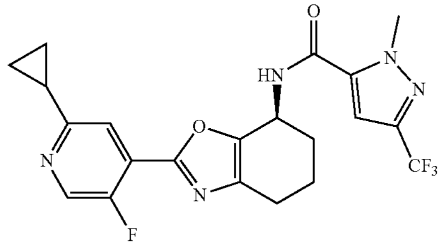 [SMILES: Cn1nc(C(F)(F)F)cc1C(=O)N[C@H]1CCCc2nc(-c3cc(C4CC4)ncc3F)oc21]
I-166a
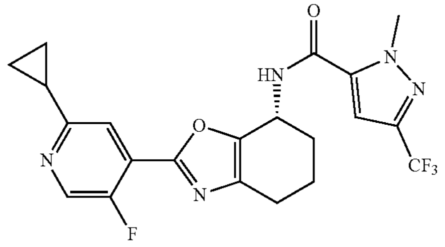 [SMILES: Cn1nc(C(F)(F)F)cc1C(=O)N[C@@H]1CCCc2nc(-c3cc(C4CC4)ncc3F)oc21]
I-166b
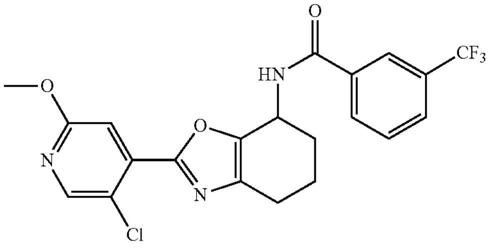 [SMILES: COc1cc(-c2nc3c(o2)C(NC(=O)c2cccc(C(F)(F)F)c2)CCC3)c(Cl)cn1]
I-167
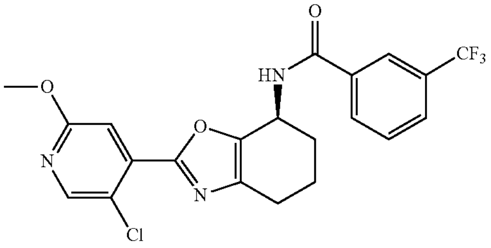
I-167a TABLE 1-continued
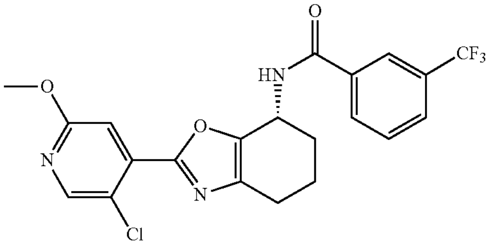
I-167b
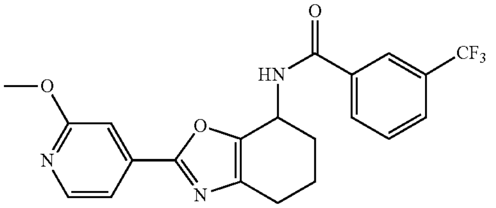 [SMILES: COc1cc(-c2nc3c(o2)C(NC(=O)c2cccc(C(F)(F)F)c2)CCC3)ccn1]
I-168
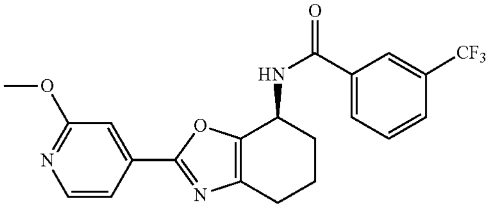 [SMILES: COc1cc(-c2nc3c(o2)[C@@H](NC(=O)c2cccc(C(F)(F)F)c2)CCC3)ccn1]
I-168a
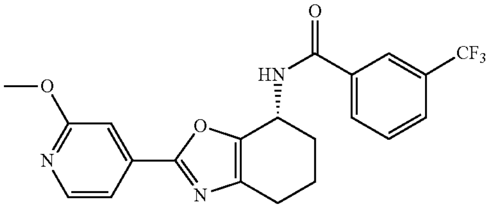 [SMILES: COc1cc(-c2nc3c(o2)[C@H](NC(=O)c2cccc(C(F)(F)F)c2)CCC3)ccn1]
I-168b
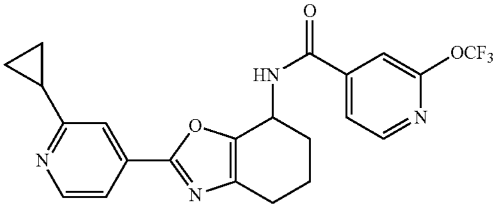 [SMILES: O=C(NC1CCCc2nc(-c3ccnc(C4CC4)c3)oc21)c1ccnc(OC(F)(F)F)c1]
I-169
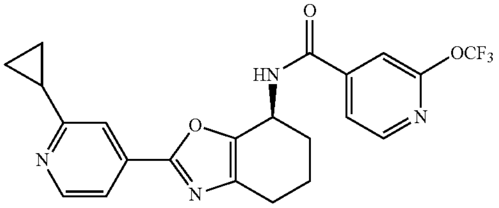 [SMILES: O=C(N[C@H]1CCCc2nc(-c3ccnc(C4CC4)c3)oc21)c1ccnc(OC(F)(F)F)c1]
I-169a
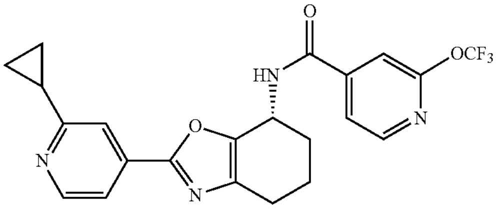 [SMILES: O=C(N[C@@H]1CCCc2nc(-c3ccnc(C4CC4)c3)oc21)c1ccnc(OC(F)(F)F)c1]
I-169b TABLE 1-continued
I-170
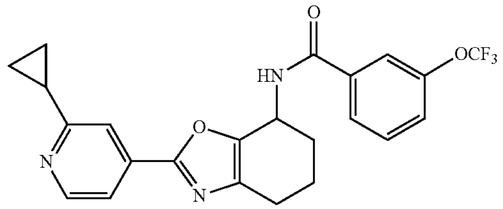 [SMILES: O=C(NC1CCCc2nc(-c3ccnc(C4CC4)c3)oc21)c1cccc(OC(F)(F)F)c1]
I-170a
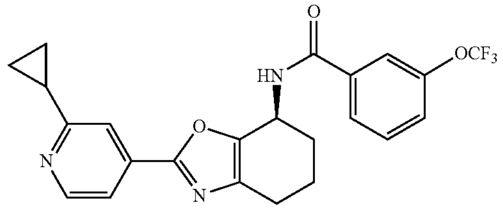 [SMILES: O=C(N[C@H]1CCCc2nc(-c3ccnc(C4CC4)c3)oc21)c1cccc(OC(F)(F)F)c1]
I-170b
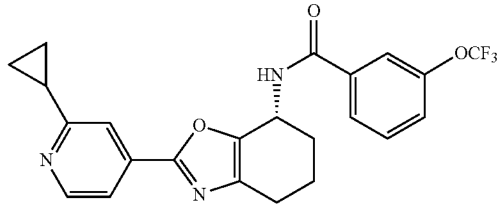 [SMILES: O=C(N[C@@H]1CCCc2nc(-c3ccnc(C4CC4)c3)oc21)c1cccc(OC(F)(F)F)c1]
I-171
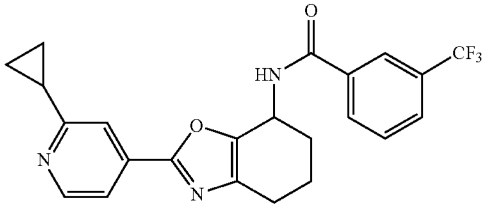 [SMILES: O=C(NC1CCCc2nc(-c3ccnc(C4CC4)c3)oc21)c1cccc(C(F)(F)F)c1]
I-171a
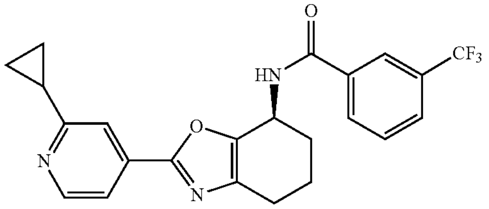 [SMILES: O=C(N[C@H]1CCCc2nc(-c3ccnc(C4CC4)c3)oc21)c1cccc(C(F)(F)F)c1]
I-171b
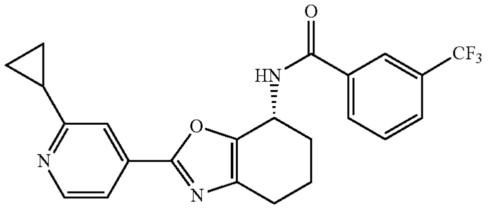 [SMILES: O=C(N[C@@H]1CCCc2nc(-c3ccnc(C4CC4)c3)oc21)c1cccc(C(F)(F)F)c1]
I-172
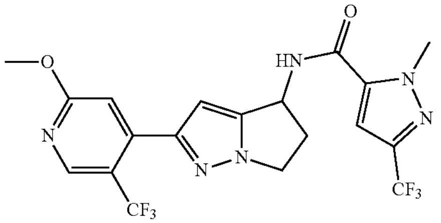

TABLE 1-continued
I-172a
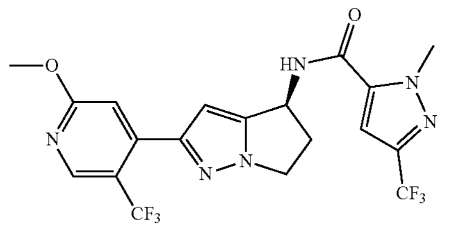
I-172b
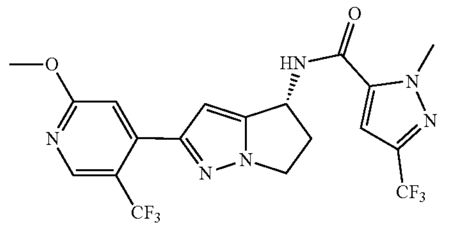
I-173
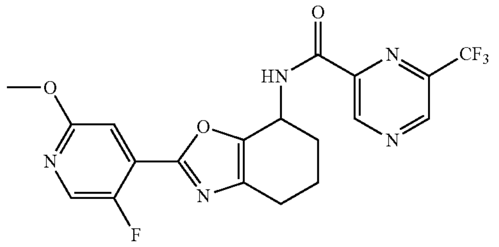 [SMILES: COc1cc(-c2nc3c(o2)C(NC(=O)c2cncc(C(F)(F)F)n2)CCC3)c(F)cn1]
I-173a
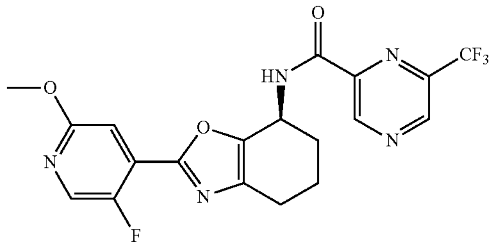
I-173b
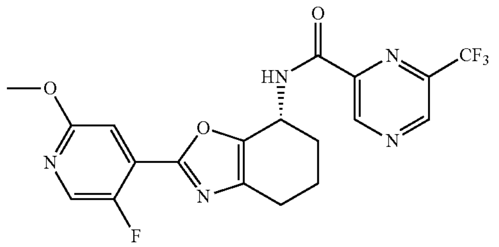
I-174
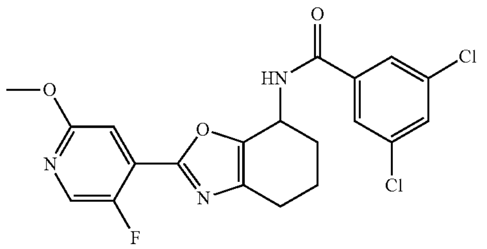 [SMILES: COc1cc(-c2nc3c(o2)C(NC(=O)c2cc(Cl)cc(Cl)c2)CCC3)c(F)cn1]

TABLE 1-continued
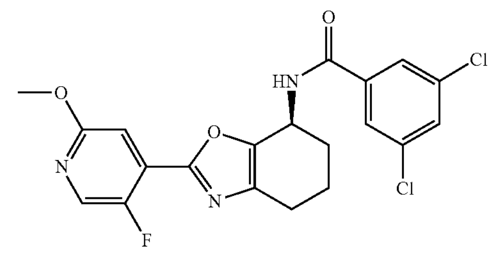 [SMILES: COc1cc(-c2nc3c(o2)[C@@H](NC(=O)c2cc(Cl)cc(Cl)c2)CCC3)c(F)cn1]
I-174a
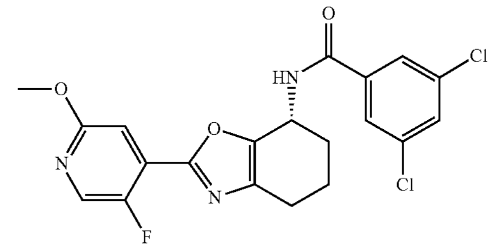 [SMILES: COc1cc(-c2nc3c(o2)[C@H](NC(=O)c2cc(Cl)cc(Cl)c2)CCC3)c(F)cn1]
I-174b
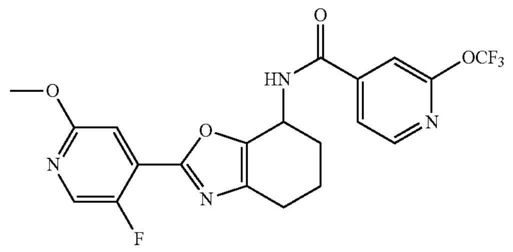 [SMILES: COc1cc(-c2nc3c(o2)C(NC(=O)c2ccnc(OC(F)(F)F)c2)CCC3)c(F)cn1]
I-175
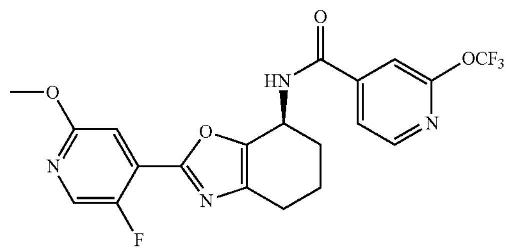 [SMILES: COc1cc(-c2nc3c(o2)[C@@H](NC(=O)c2ccnc(OC(F)(F)F)c2)CCC3)c(F)cn1]
I-175a
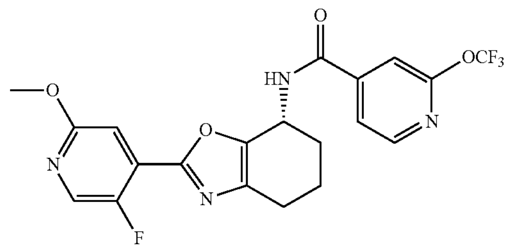 [SMILES: COc1cc(-c2nc3c(o2)[C@H](NC(=O)c2ccnc(OC(F)(F)F)c2)CCC3)c(F)cn1]
I-175b
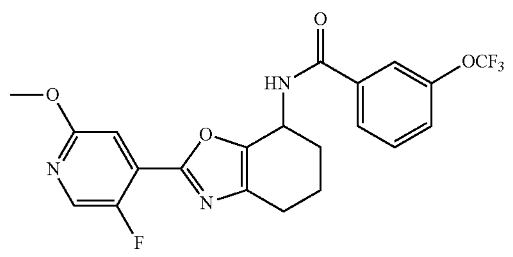 [SMILES: COc1cc(-c2nc3c(o2)C(NC(=O)c2cccc(OC(F)(F)F)c2)CCC3)c(F)cn1]
I-176

TABLE 1-continued
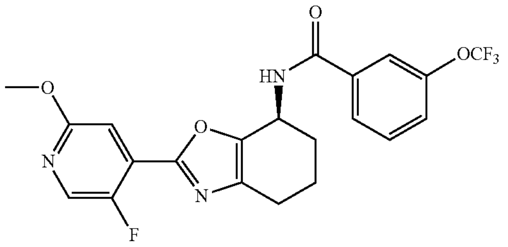 [SMILES: COc1cc(-c2nc3c(o2)[C@@H](NC(=O)c2cccc(OC(F)(F)F)c2)CCC3)c(F)cn1]
I-176a
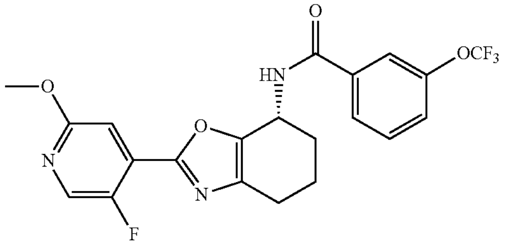 [SMILES: COc1cc(-c2nc3c(o2)[C@H](NC(=O)c2cccc(OC(F)(F)F)c2)CCC3)c(F)cn1]
I-176b
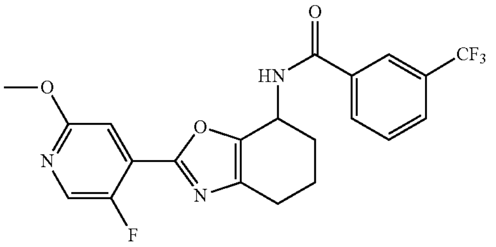 [SMILES: COc1cc(-c2nc3c(o2)C(NC(=O)c2cccc(C(F)(F)F)c2)CCC3)c(F)cn1]
I-177
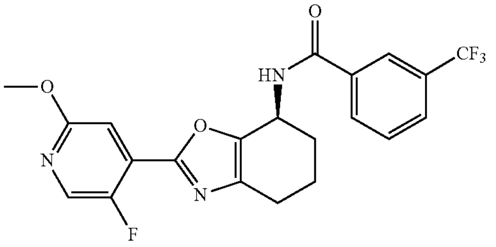 [SMILES: COc1cc(-c2nc3c(o2)[C@@H](NC(=O)c2cccc(C(F)(F)F)c2)CCC3)c(F)cn1]
I-177a
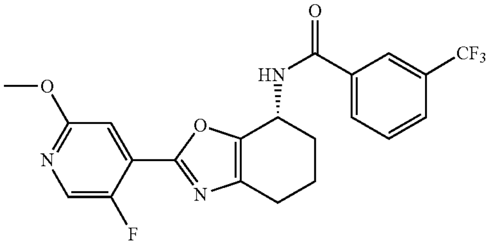
I-177b
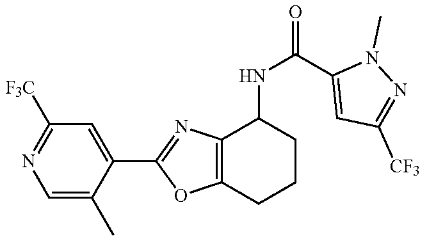 [SMILES: Cc1cnc(C(F)(F)F)cc1-c1nc2c(o1)CCCC2NC(=O)c1cc(C(F)(F)F)nn1C]
I-178

TABLE 1-continued
I-178a
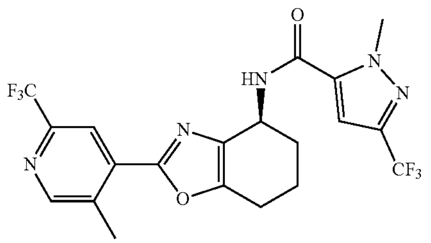 [SMILES: Cc1cnc(C(F)(F)F)cc1-c1nc2c(o1)CCC[C@@H]2NC(=O)c1cc(C(F)(F)F)nn1C]
I-178b
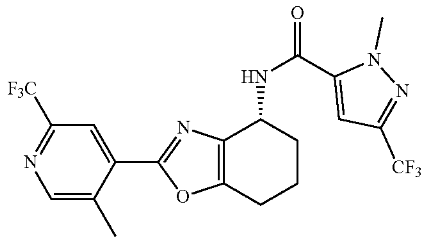 [SMILES: Cc1cnc(C(F)(F)F)cc1-c1nc2c(o1)CCC[C@H]2NC(=O)c1cc(C(F)(F)F)nn1C]
I-179
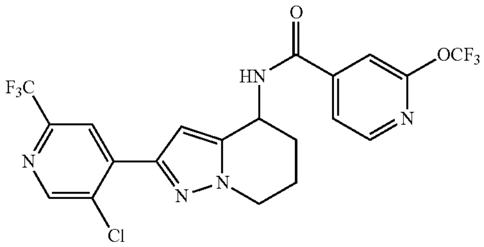 [SMILES: O=C(NC1CCCn2nc(-c3cc(C(F)(F)F)ncc3Cl)cc21)c1ccnc(OC(F)(F)F)c1]
I-179a
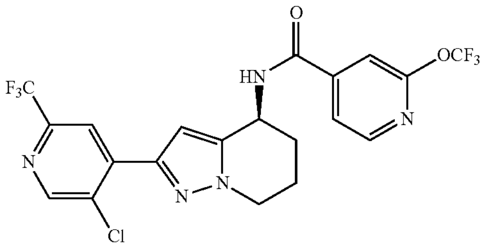
I-179b
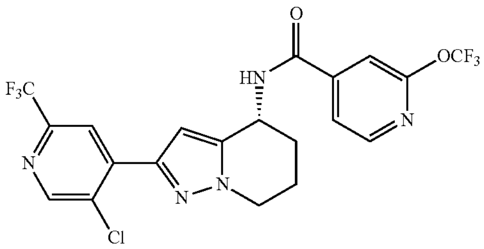 [SMILES: O=C(N[C@@H]1CCCn2nc(-c3cc(C(F)(F)F)ncc3Cl)cc21)c1ccnc(OC(F)(F)F)c1]
I-180
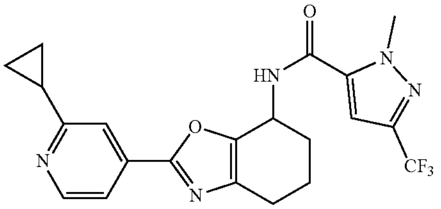 [SMILES: Cn1nc(C(F)(F)F)cc1C(=O)NC1CCCc2nc(-c3ccnc(C4CC4)c3)oc21]

TABLE 1-continued
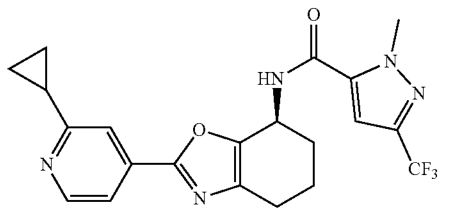 [SMILES: Cn1nc(C(F)(F)F)cc1C(=O)N[C@H]1CCCc2nc(-c3ccnc(C4CC4)c3)oc21]
I-180a
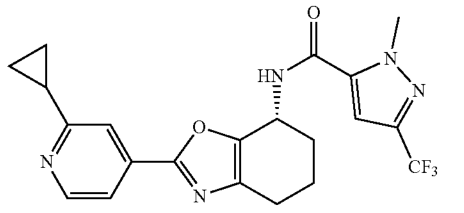 [SMILES: Cn1nc(C(F)(F)F)cc1C(=O)N[C@@H]1CCCc2nc(-c3ccnc(C4CC4)c3)oc21]
I-180b
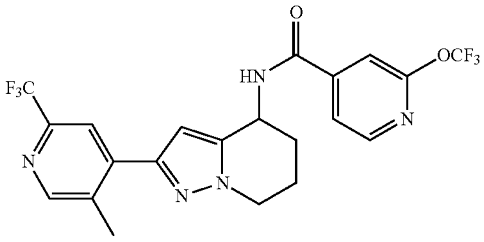 [SMILES: Cc1cnc(C(F)(F)F)cc1-c1cc2n(n1)CCCC2NC(=O)c1ccnc(OC(F)(F)F)c1]
I-181
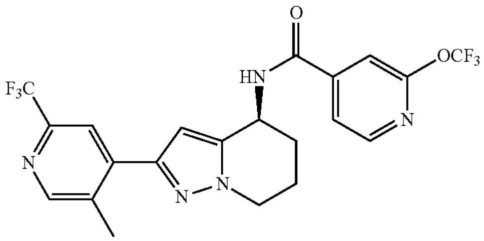 [SMILES: Cc1cnc(C(F)(F)F)cc1-c1cc2n(n1)CCC[C@@H]2NC(=O)c1ccnc(OC(F)(F)F)c1]
I-181a
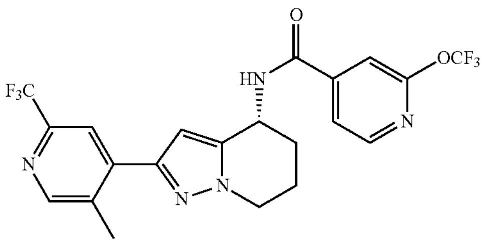
I-181b
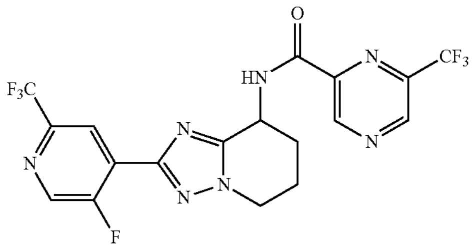 [SMILES: O=C(NC1CCCn2nc(-c3cc(C(F)(F)F)ncc3F)nc21)c1cncc(C(F)(F)F)n1]
I-182

TABLE 1-continued
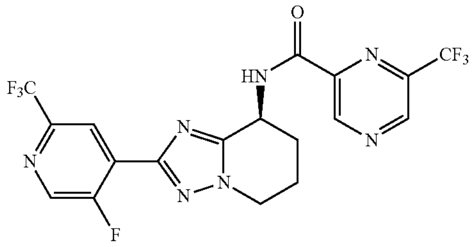 [SMILES: O=C(N[C@H]1CCCn2nc(-c3cc(C(F)(F)F)ncc3F)nc21)c1cncc(C(F)(F)F)n1]
I-182a
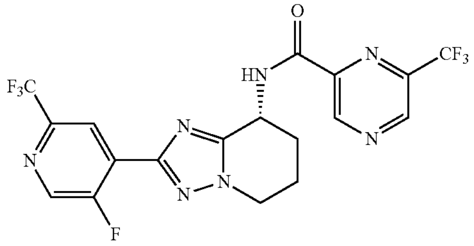 [SMILES: O=C(N[C@@H]1CCCn2nc(-c3cc(C(F)(F)F)ncc3F)nc21)c1cncc(C(F)(F)F)n1]
I-182b
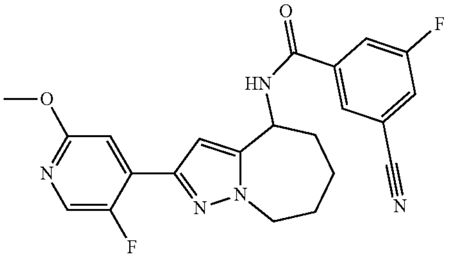 [SMILES: COc1cc(-c2cc3n(n2)CCCCC3NC(=O)c2cc(F)cc(C#N)c2)c(F)cn1]
I-183
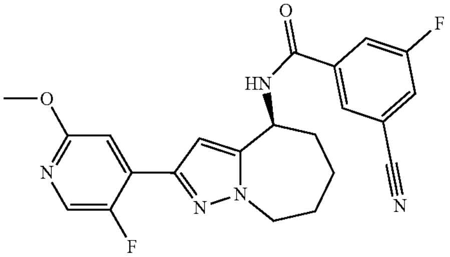 [SMILES: COc1cc(-c2cc3n(n2)CCCC[C@@H]3NC(=O)c2cc(F)cc(C#N)c2)c(F)cn1]
I-183a
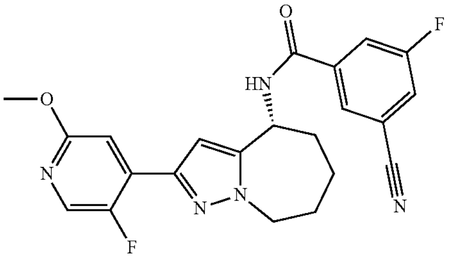 [SMILES: COc1cc(-c2cc3n(n2)CCCC[C@H]3NC(=O)c2cc(F)cc(C#N)c2)c(F)cn1]
I-183b
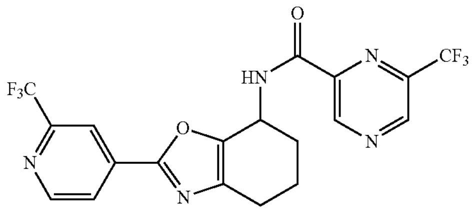 [SMILES: O=C(NC1CCCc2nc(-c3ccnc(C(F)(F)F)c3)oc21)c1cncc(C(F)(F)F)n1]
I-184

TABLE 1-continued
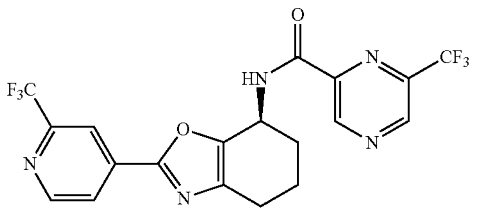 [SMILES: O=C(N[C@H]1CCCc2nc(-c3ccnc(C(F)(F)F)c3)oc21)c1cncc(C(F)(F)F)n1]
I-184a
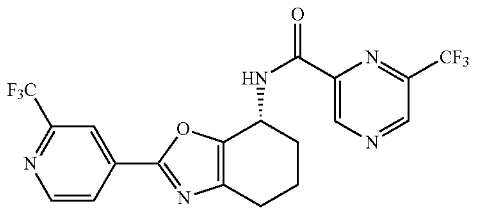 [SMILES: O=C(N[C@@H]1CCCc2nc(-c3ccnc(C(F)(F)F)c3)oc21)c1cncc(C(F)(F)F)n1]
I-184b
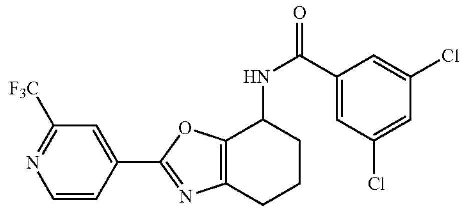 [SMILES: O=C(NC1CCCc2nc(-c3ccnc(C(F)(F)F)c3)oc21)c1cc(Cl)cc(Cl)c1]
I-185
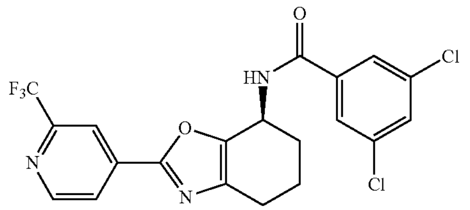 [SMILES: O=C(N[C@H]1CCCc2nc(-c3ccnc(C(F)(F)F)c3)oc21)c1cc(Cl)cc(Cl)c1]
I-185a
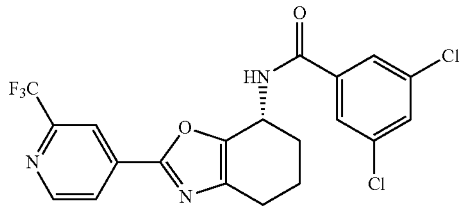 [SMILES: O=C(N[C@@H]1CCCc2nc(-c3ccnc(C(F)(F)F)c3)oc21)c1cc(Cl)cc(Cl)c1]
I-185b
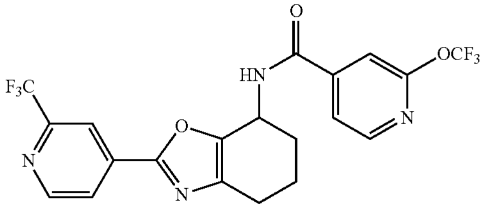 [SMILES: O=C(NC1CCCc2nc(-c3ccnc(C(F)(F)F)c3)oc21)c1ccnc(OC(F)(F)F)c1]
I-186
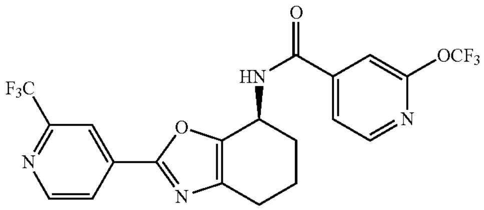 [SMILES: O=C(N[C@H]1CCCc2nc(-c3ccnc(C(F)(F)F)c3)oc21)c1ccnc(OC(F)(F)F)c1]
I-186a TABLE 1-continued
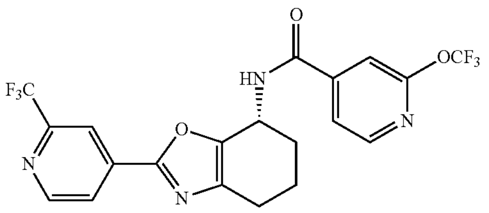
I-186b
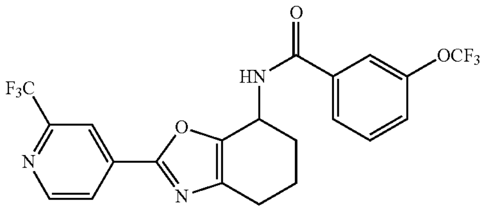 [SMILES: O=C(NC1CCCc2nc(-c3ccnc(C(F)(F)F)c3)oc21)c1cccc(OC(F)(F)F)c1]
I-187
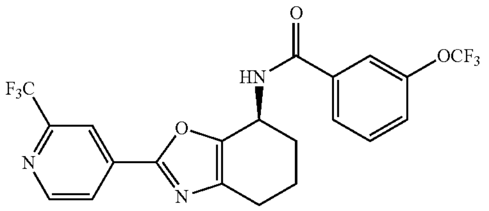 [SMILES: O=C(N[C@H]1CCCc2nc(-c3ccnc(C(F)(F)F)c3)oc21)c1cccc(OC(F)(F)F)c1]
I-187a
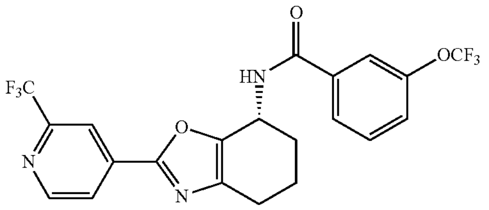 [SMILES: O=C(N[C@@H]1CCCc2nc(-c3ccnc(C(F)(F)F)c3)oc21)c1cccc(OC(F)(F)F)c1]
I-187b
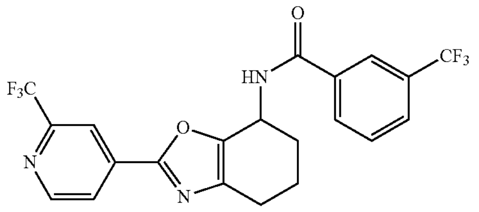 [SMILES: O=C(NC1CCCc2nc(-c3ccnc(C(F)(F)F)c3)oc21)c1cccc(C(F)(F)F)c1]
I-188
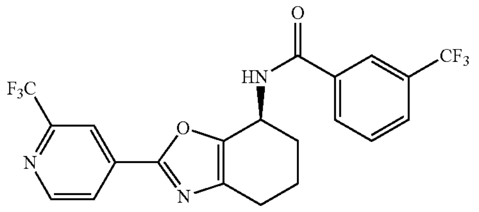 [SMILES: O=C(N[C@H]1CCCc2nc(-c3ccnc(C(F)(F)F)c3)oc21)c1cccc(C(F)(F)F)c1]
I-188a
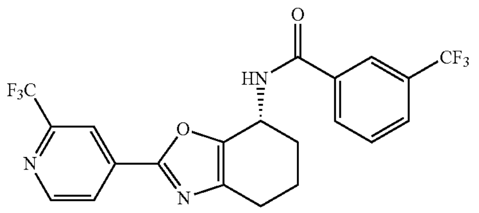 [SMILES: O=C(N[C@@H]1CCCc2nc(-c3ccnc(C(F)(F)F)c3)oc21)c1cccc(C(F)(F)F)c1]
I-188b TABLE 1-continued
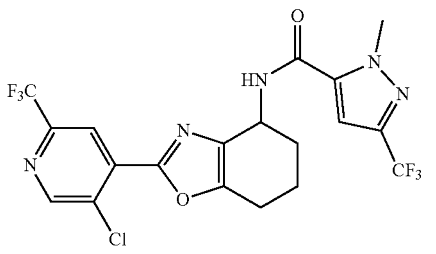 [SMILES: Cn1nc(C(F)(F)F)cc1C(=O)NC1CCCc2oc(-c3cc(C(F)(F)F)ncc3Cl)nc21]
I-189
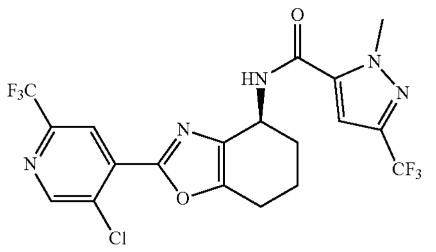
I-189a
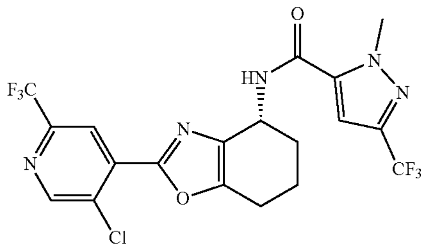 [SMILES: Cn1nc(C(F)(F)F)cc1C(=O)N[C@@H]1CCCc2oc(-c3cc(C(F)(F)F)ncc3Cl)nc21]
I-189b
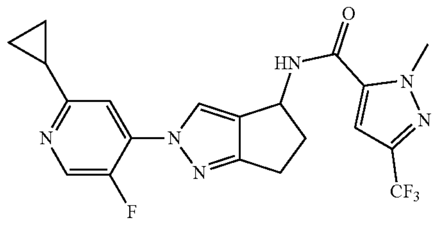 [SMILES: Cn1nc(C(F)(F)F)cc1C(=O)NC1CCc2nn(-c3cc(C4CC4)ncc3F)cc21]
I-190
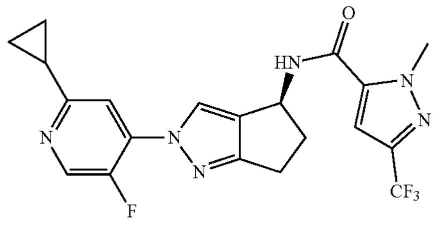 [SMILES: Cn1nc(C(F)(F)F)cc1C(=O)N[C@H]1CCc2nn(-c3cc(C4CC4)ncc3F)cc21]
I-190a
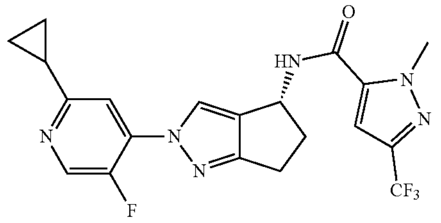 [SMILES: Cn1nc(C(F)(F)F)cc1C(=O)N[C@@H]1CCc2nn(-c3cc(C4CC4)ncc3F)cc21]
I-190b TABLE 1-continued
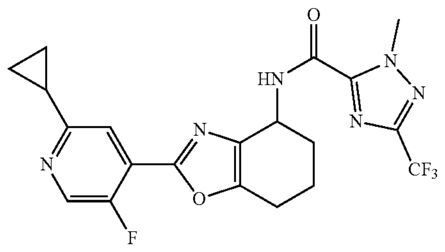 [SMILES: Cn1nc(C(F)(F)F)nc1C(=O)NC1CCCc2oc(-c3cc(C4CC4)ncc3F)nc21]
I-191
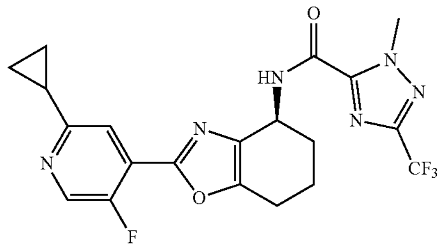 [SMILES: Cn1nc(C(F)(F)F)nc1C(=O)N[C@H]1CCCc2oc(-c3cc(C4CC4)ncc3F)nc21]
I-191a
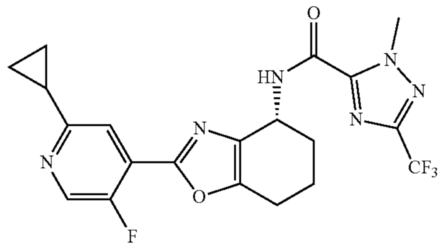 [SMILES: Cn1nc(C(F)(F)F)nc1C(=O)N[C@@H]1CCCc2oc(-c3cc(C4CC4)ncc3F)nc21]
I-191b
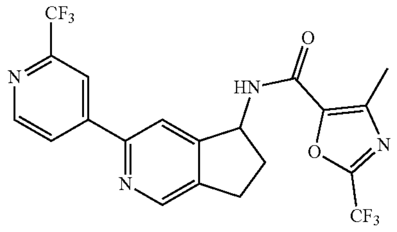 [SMILES: Cc1nc(C(F)(F)F)oc1C(=O)NC1CCc2cnc(-c3ccnc(C(F)(F)F)c3)cc21]
I-192
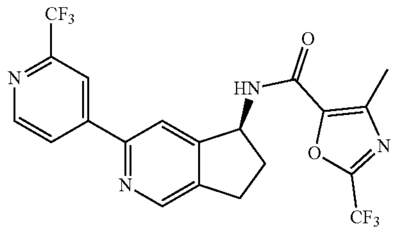 [SMILES: Cc1nc(C(F)(F)F)oc1C(=O)N[C@H]1CCc2cnc(-c3ccnc(C(F)(F)F)c3)cc21]
I-192a
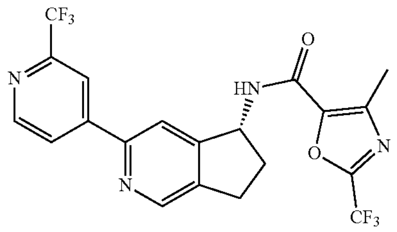
I-192b TABLE 1-continued
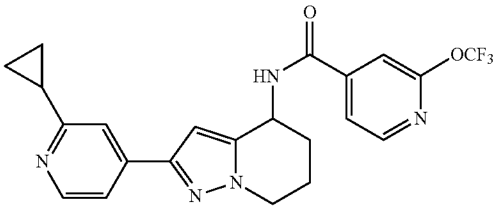 [SMILES: O=C(NC1CCCn2nc(-c3ccnc(C4CC4)c3)cc21)c1ccnc(OC(F)(F)F)c1]
I-193
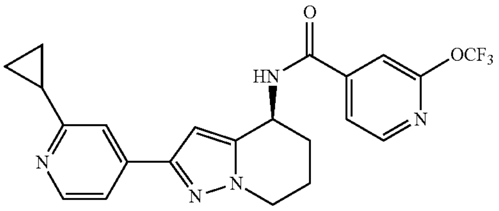 [SMILES: O=C(N[C@H]1CCCn2nc(-c3ccnc(C4CC4)c3)cc21)c1ccnc(OC(F)(F)F)c1]
I-193a
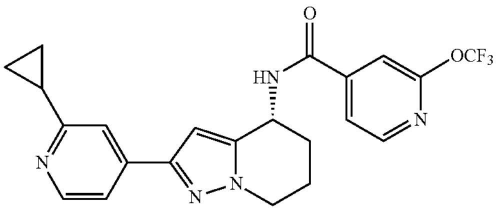 [SMILES: O=C(N[C@@H]1CCCn2nc(-c3ccnc(C4CC4)c3)cc21)c1ccnc(OC(F)(F)F)c1]
I-193b
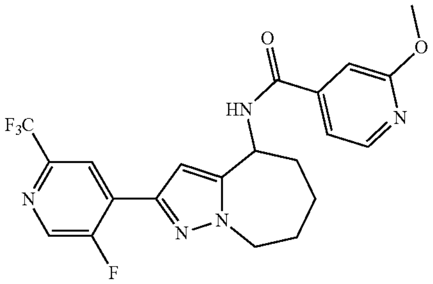 [SMILES: COc1cc(C(=O)NC2CCCCn3nc(-c4cc(C(F)(F)F)ncc4F)cc32)ccn1]
I-194
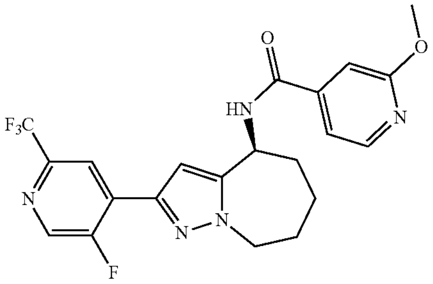 [SMILES: COc1cc(C(=O)N[C@H]2CCCCn3nc(-c4cc(C(F)(F)F)ncc4F)cc32)ccn1]
I-194a
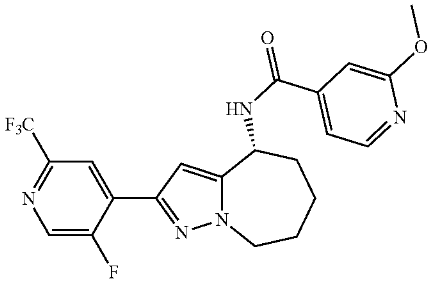 [SMILES: COc1cc(C(=O)N[C@@H]2CCCCn3nc(-c4cc(C(F)(F)F)ncc4F)cc32)ccn1]
I-194b TABLE 1-continued
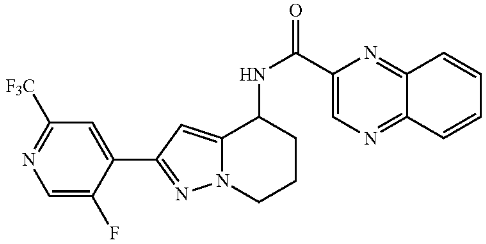 [SMILES: O=C(NC1CCCn2nc(-c3cc(C(F)(F)F)ncc3F)cc21)c1cnc2ccccc2n1]
I-195
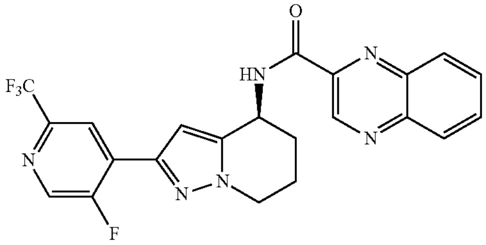 [SMILES: O=C(N[C@H]1CCCn2nc(-c3cc(C(F)(F)F)ncc3F)cc21)c1cnc2ccccc2n1]
I-195a
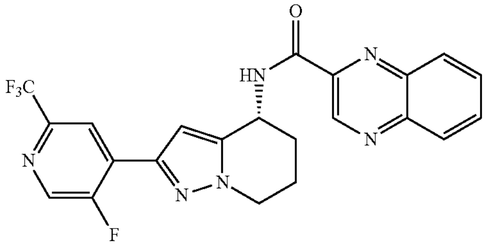 [SMILES: O=C(N[C@@H]1CCCn2nc(-c3cc(C(F)(F)F)ncc3F)cc21)c1cnc2ccccc2n1]
I-195b
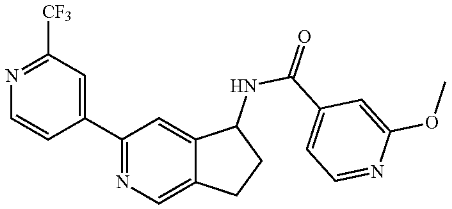 [SMILES: COc1cc(C(=O)NC2CCc3cnc(-c4ccnc(C(F)(F)F)c4)cc32)ccn1]
I-196
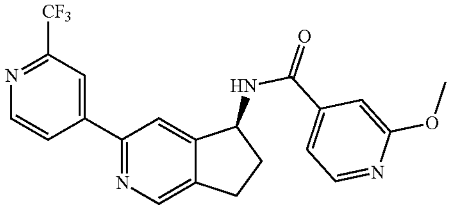 [SMILES: COc1cc(C(=O)N[C@H]2CCc3cnc(-c4ccnc(C(F)(F)F)c4)cc32)ccn1]
I-196a
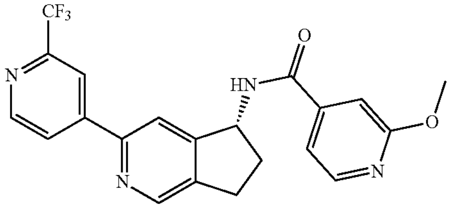 [SMILES: COc1cc(C(=O)N[C@@H]2CCc3cnc(-c4ccnc(C(F)(F)F)c4)cc32)ccn1]
I-196b
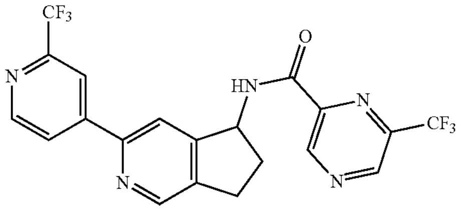 [SMILES: O=C(NC1CCc2cnc(-c3ccnc(C(F)(F)F)c3)cc21)c1cncc(C(F)(F)F)n1]
I-197

TABLE 1-continued
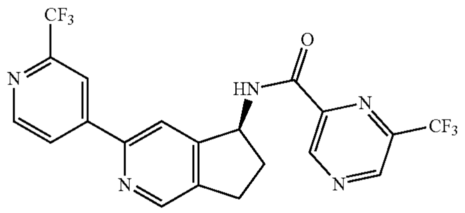 [SMILES: O=C(N[C@H]1CCc2cnc(-c3ccnc(C(F)(F)F)c3)cc21)c1cncc(C(F)(F)F)n1]
I-197a
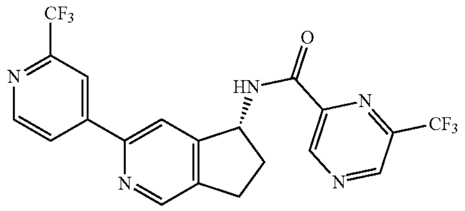
I-197b
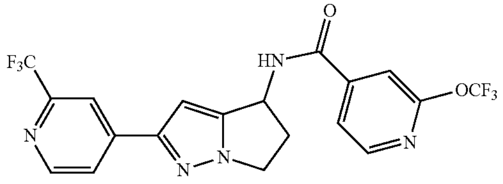 [SMILES: O=C(NC1CCn2nc(-c3ccnc(C(F)(F)F)c3)cc21)c1ccnc(OC(F)(F)F)c1]
I-198
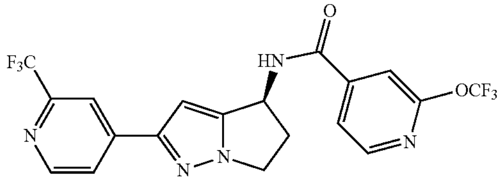 [SMILES: O=C(N[C@H]1CCn2nc(-c3ccnc(C(F)(F)F)c3)cc21)c1ccnc(OC(F)(F)F)c1]
I-198a
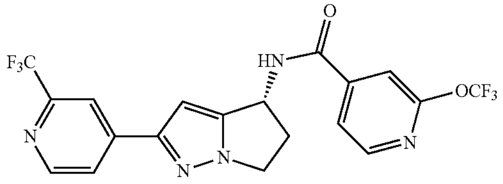 [SMILES: O=C(N[C@@H]1CCn2nc(-c3ccnc(C(F)(F)F)c3)cc21)c1ccnc(OC(F)(F)F)c1]
I-198b
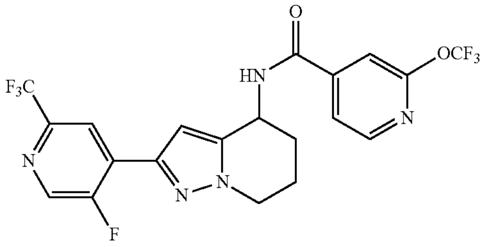 [SMILES: O=C(NC1CCCn2nc(-c3cc(C(F)(F)F)ncc3F)cc21)c1ccnc(OC(F)(F)F)c1]
I-199
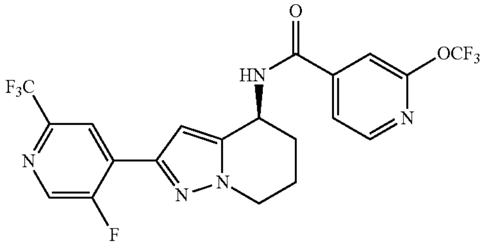 [SMILES: O=C(N[C@H]1CCCn2nc(-c3cc(C(F)(F)F)ncc3F)cc21)c1ccnc(OC(F)(F)F)c1]
I-199a TABLE 1-continued
I-199b
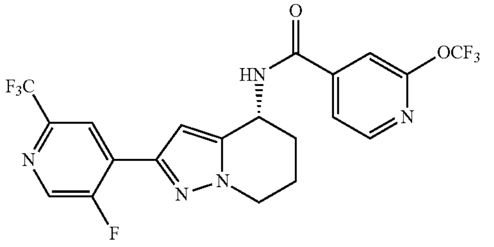
I-200
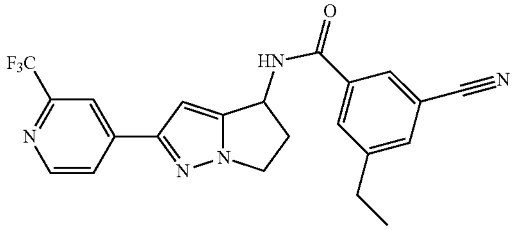 [SMILES: CCc1cc(C#N)cc(C(=O)NC2CCn3nc(-c4ccnc(C(F)(F)F)c4)cc32)c1]
I-200a
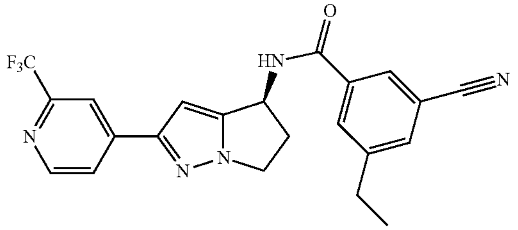 [SMILES: CCc1cc(C#N)cc(C(=O)N[C@H]2CCn3nc(-c4ccnc(C(F)(F)F)c4)cc32)c1]
I-200b
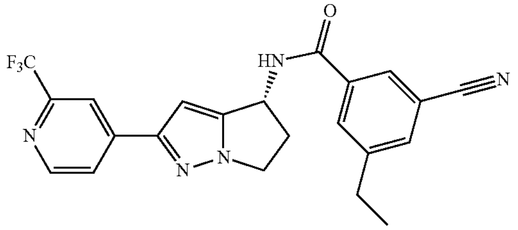 [SMILES: CCc1cc(C#N)cc(C(=O)N[C@@H]2CCn3nc(-c4ccnc(C(F)(F)F)c4)cc32)c1]
I-201
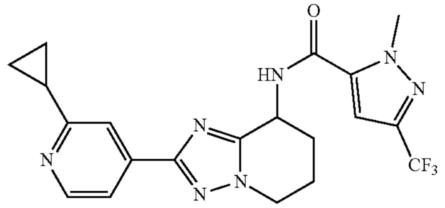 [SMILES: Cn1nc(C(F)(F)F)cc1C(=O)NC1CCCn2nc(-c3ccnc(C4CC4)c3)nc21]
I-201a
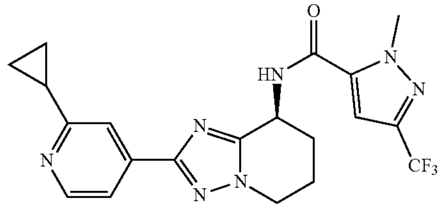 [SMILES: Cn1nc(C(F)(F)F)cc1C(=O)N[C@H]1CCCn2nc(-c3ccnc(C4CC4)c3)nc21]
I-201b
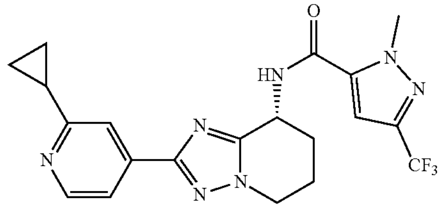 [SMILES: Cn1nc(C(F)(F)F)cc1C(=O)N[C@@H]1CCCn2nc(-c3ccnc(C4CC4)c3)nc21]

TABLE 1-continued
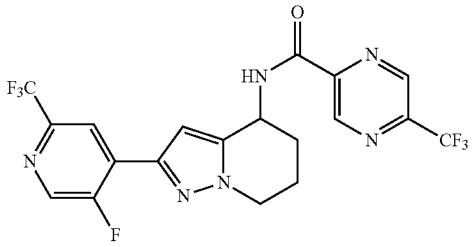 [SMILES: O=C(NC1CCCn2nc(-c3cc(C(F)(F)F)ncc3F)cc21)c1cnc(C(F)(F)F)cn1]
I-202
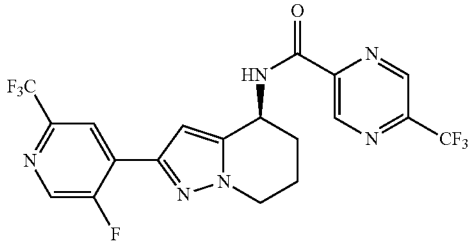 [SMILES: O=C(N[C@H]1CCCn2nc(-c3cc(C(F)(F)F)ncc3F)cc21)c1cnc(C(F)(F)F)cn1]
I-202a
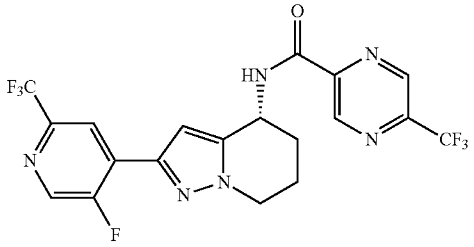 [SMILES: O=C(N[C@@H]1CCCn2nc(-c3cc(C(F)(F)F)ncc3F)cc21)c1cnc(C(F)(F)F)cn1]
I-202b
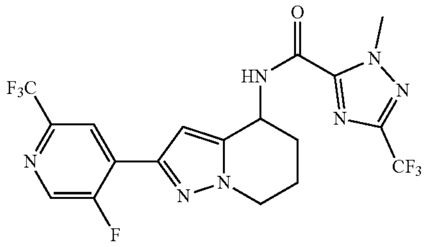 [SMILES: Cn1nc(C(F)(F)F)nc1C(=O)NC1CCCn2nc(-c3cc(C(F)(F)F)ncc3F)cc21]
I-203
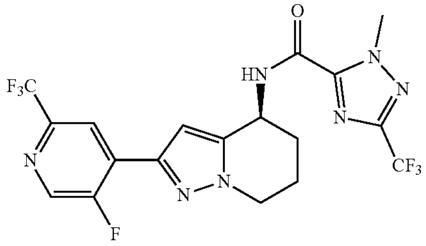 [SMILES: Cn1nc(C(F)(F)F)nc1C(=O)N[C@H]1CCCn2nc(-c3cc(C(F)(F)F)ncc3F)cc21]
I-203a
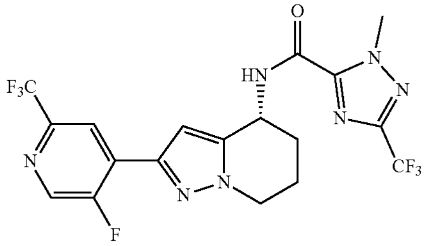 [SMILES: Cn1nc(C(F)(F)F)nc1C(=O)N[C@@H]1CCCn2nc(-c3cc(C(F)(F)F)ncc3F)cc21]
I-203b TABLE 1-continued
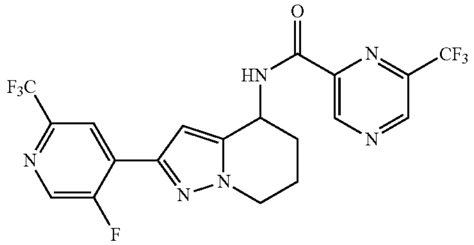 [SMILES: O=C(NC1CCCn2nc(-c3cc(C(F)(F)F)ncc3F)cc21)c1cncc(C(F)(F)F)n1]
I-204
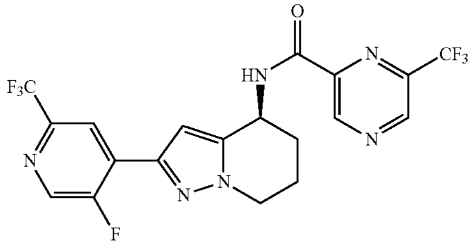 [SMILES: O=C(N[C@H]1CCCn2nc(-c3cc(C(F)(F)F)ncc3F)cc21)c1cncc(C(F)(F)F)n1]
I-204a
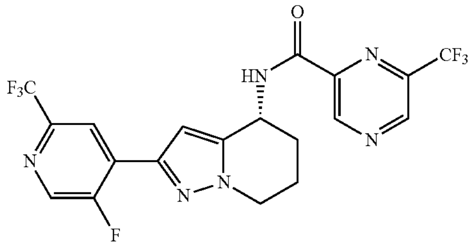 [SMILES: O=C(N[C@@H]1CCCn2nc(-c3cc(C(F)(F)F)ncc3F)cc21)c1cncc(C(F)(F)F)n1]
I-204b
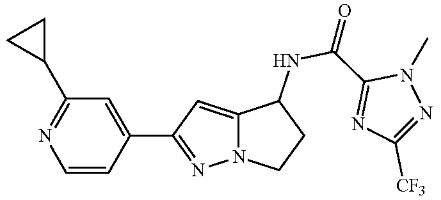 [SMILES: Cn1nc(C(F)(F)F)nc1C(=O)NC1CCn2nc(-c3ccnc(C4CC4)c3)cc21]
I-205
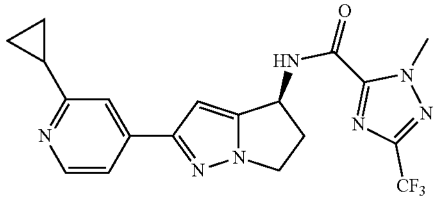 [SMILES: Cn1nc(C(F)(F)F)nc1C(=O)N[C@H]1CCn2nc(-c3ccnc(C4CC4)c3)cc21]
I-205a
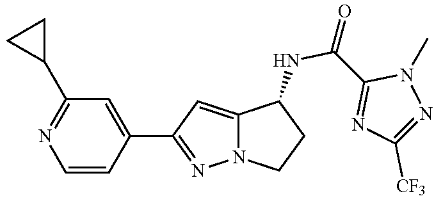 [SMILES: Cn1nc(C(F)(F)F)nc1C(=O)N[C@@H]1CCn2nc(-c3ccnc(C4CC4)c3)cc21]
I-205b
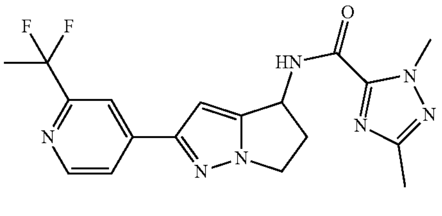 [SMILES: Cc1nc(C(=O)NC2CCn3nc(-c4ccnc(C(C)(F)F)c4)cc32)n(C)n1]
I-206

TABLE 1-continued
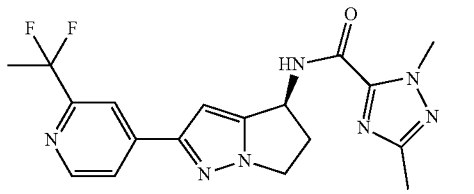 [SMILES: Cc1nc(C(=O)N[C@H]2CCn3nc(-c4ccnc(C(C)(F)F)c4)cc32)n(C)n1]
I-206a
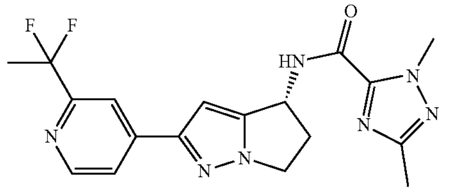 [SMILES: Cc1nc(C(=O)N[C@@H]2CCn3nc(-c4ccnc(C(C)(F)F)c4)cc32)n(C)n1]
I-206b
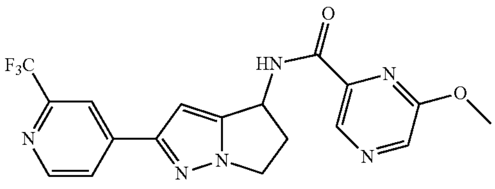 [SMILES: COc1cncc(C(=O)NC2CCn3nc(-c4ccnc(C(F)(F)F)c4)cc32)n1]
I-207
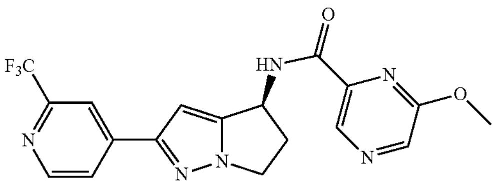 [SMILES: COc1cncc(C(=O)N[C@H]2CCn3nc(-c4ccnc(C(F)(F)F)c4)cc32)n1]
I-207a
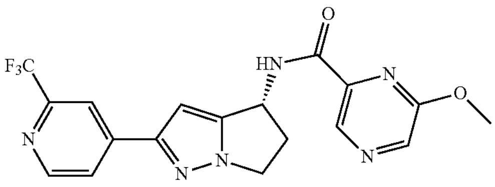 [SMILES: COc1cncc(C(=O)N[C@@H]2CCn3nc(-c4ccnc(C(F)(F)F)c4)cc32)n1]
I-207b
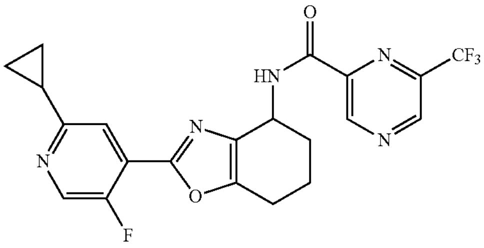
I-208
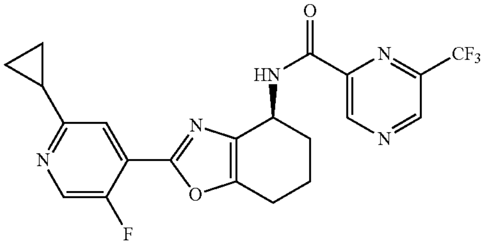 [SMILES: O=C(N[C@H]1CCCc2oc(-c3cc(C4CC4)ncc3F)nc21)c1cncc(C(F)(F)F)n1]
I-208a TABLE 1-continued
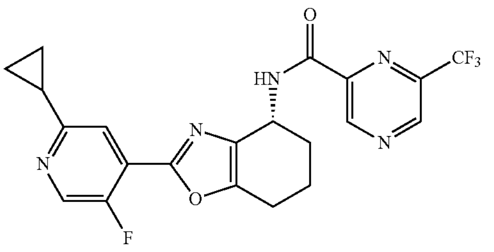 [SMILES: O=C(N[C@@H]1CCCc2oc(-c3cc(C4CC4)ncc3F)nc21)c1cncc(C(F)(F)F)n1]
I-208b
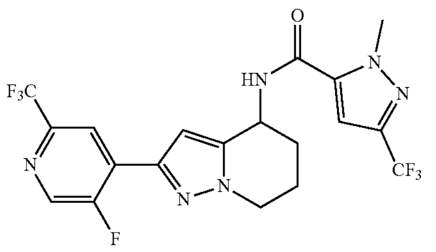 [SMILES: Cn1nc(C(F)(F)F)cc1C(=O)NC1CCCn2nc(-c3cc(C(F)(F)F)ncc3F)cc21]
I-209
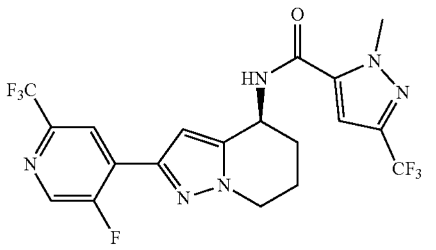 [SMILES: Cn1nc(C(F)(F)F)cc1C(=O)N[C@H]1CCCn2nc(-c3cc(C(F)(F)F)ncc3F)cc21]
I-209a
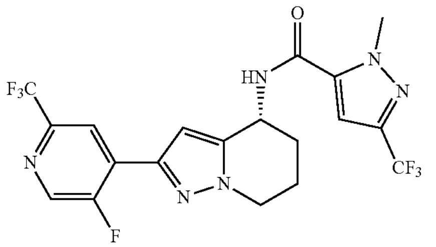 [SMILES: Cn1nc(C(F)(F)F)cc1C(=O)N[C@@H]1CCCn2nc(-c3cc(C(F)(F)F)ncc3F)cc21]
I-209b
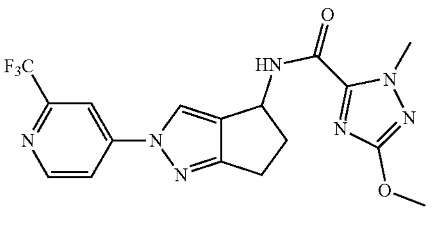 [SMILES: COc1nc(C(=O)NC2CCc3nn(-c4ccnc(C(F)(F)F)c4)cc32)n(C)n1]
I-210
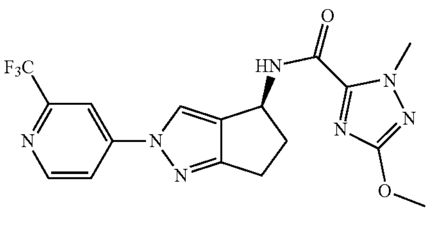 [SMILES: COc1nc(C(=O)N[C@H]2CCc3nn(-c4ccnc(C(F)(F)F)c4)cc32)n(C)n1]
I-210a TABLE 1-continued
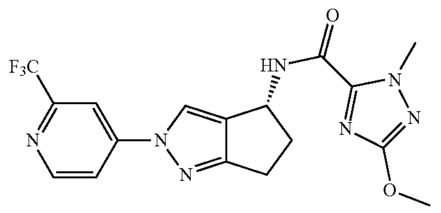 [SMILES: COc1nc(C(=O)N[C@@H]2CCc3nn(-c4ccnc(C(F)(F)F)c4)cc32)n(C)n1]
I-210b
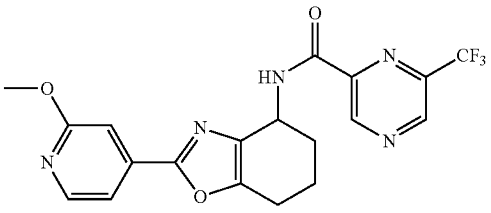 [SMILES: COc1cc(-c2nc3c(o2)CCCC3NC(=O)c2cncc(C(F)(F)F)n2)ccn1]
I-211
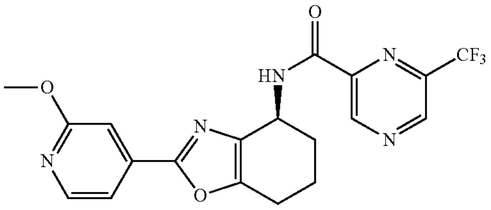
I-211a
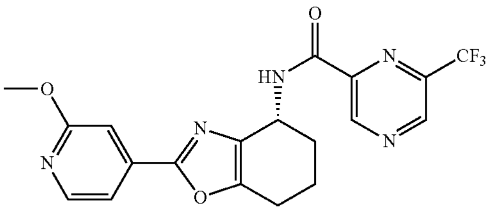
I-211b
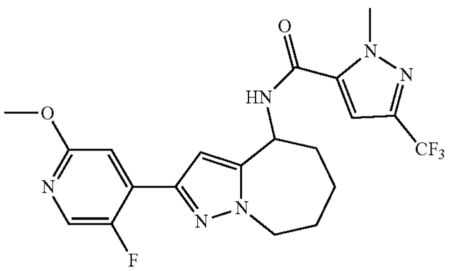 [SMILES: COc1cc(-c2cc3n(n2)CCCCC3NC(=O)c2cc(C(F)(F)F)nn2C)c(F)cn1]
I-212
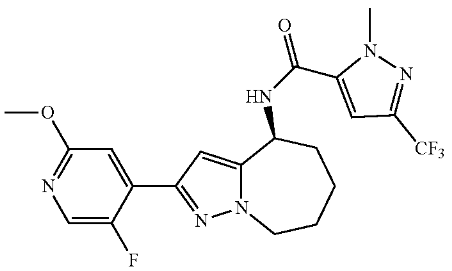 [SMILES: COc1cc(-c2cc3n(n2)CCCC[C@@H]3NC(=O)c2cc(C(F)(F)F)nn2C)c(F)cn1]
I-212a TABLE 1-continued
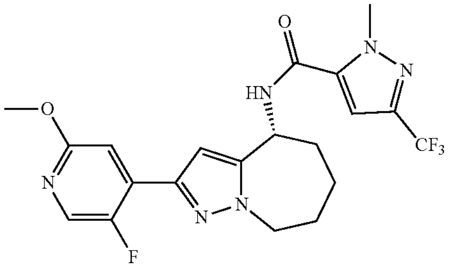 [SMILES: COc1cc(-c2cc3n(n2)CCCC[C@H]3NC(=O)c2cc(C(F)(F)F)nn2C)c(F)cn1]
I-212b
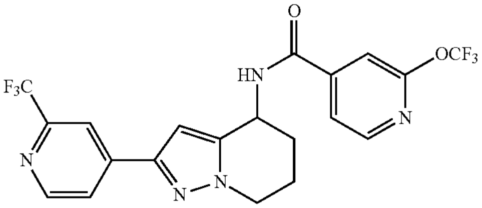 [SMILES: O=C(NC1CCCn2nc(-c3ccnc(C(F)(F)F)c3)cc21)c1ccnc(OC(F)(F)F)c1]
I-213
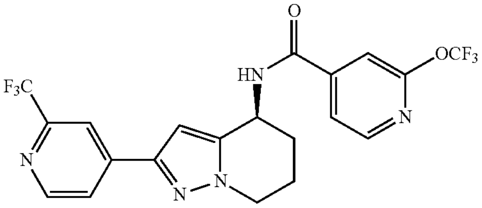 [SMILES: O=C(N[C@H]1CCCn2nc(-c3ccnc(C(F)(F)F)c3)cc21)c1ccnc(OC(F)(F)F)c1]
I-213a
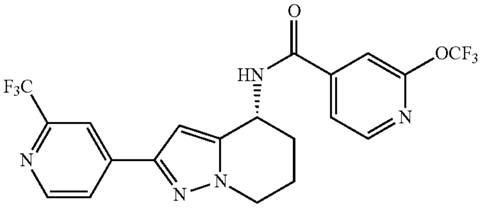
I-213b
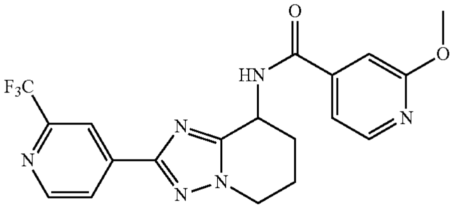
I-214
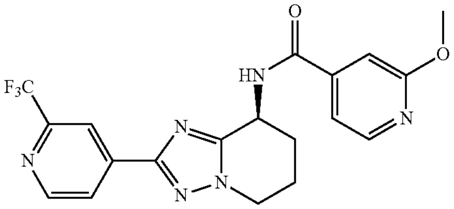
I-214a
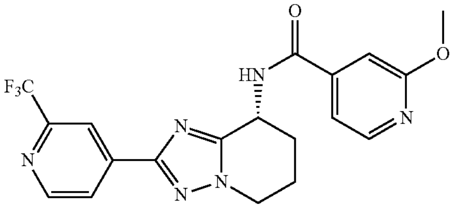
I-214b TABLE 1-continued
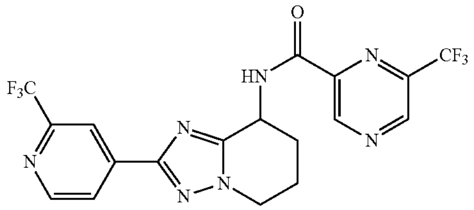 [SMILES: O=C(NC1CCCn2nc(-c3ccnc(C(F)(F)F)c3)nc21)c1cncc(C(F)(F)F)n1]
I-215
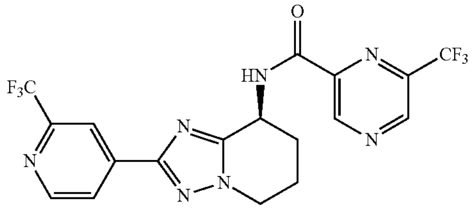 [SMILES: O=C(N[C@H]1CCCn2nc(-c3ccnc(C(F)(F)F)c3)nc21)c1cncc(C(F)(F)F)n1]
I-215a
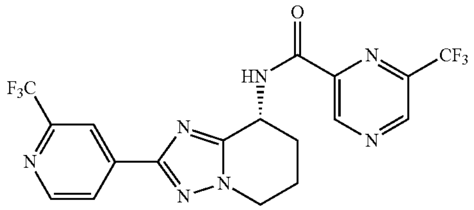 [SMILES: O=C(N[C@@H]1CCCn2nc(-c3ccnc(C(F)(F)F)c3)nc21)c1cncc(C(F)(F)F)n1]
I-215b
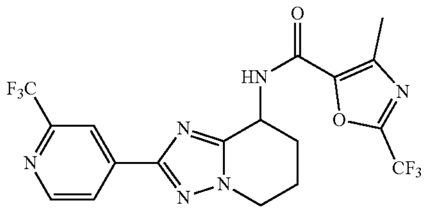 [SMILES: Cc1nc(C(F)(F)F)oc1C(=O)NC1CCCn2nc(-c3ccnc(C(F)(F)F)c3)nc21]
I-216
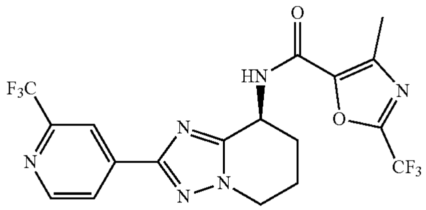
I-216a
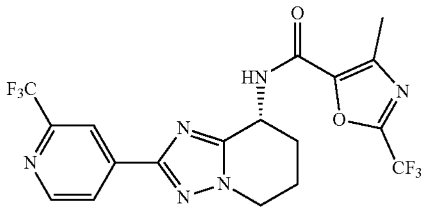 [SMILES: Cc1nc(C(F)(F)F)oc1C(=O)N[C@@H]1CCCn2nc(-c3ccnc(C(F)(F)F)c3)nc21]
I-216b
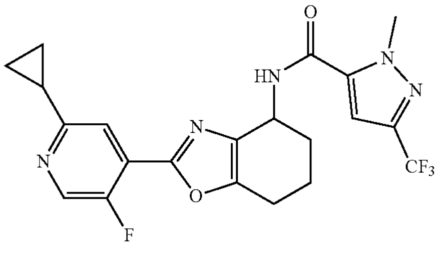
I-217

TABLE 1-continued
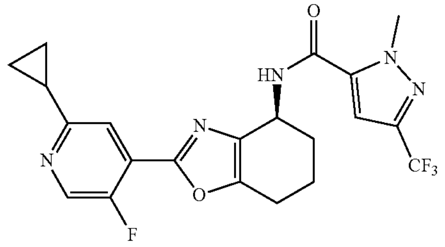
I-217a
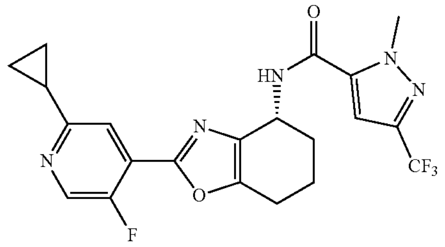
I-217b
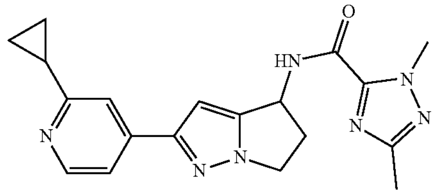 [SMILES: Cc1nc(C(=O)NC2CCn3nc(-c4ccnc(C5CC5)c4)cc32)n(C)n1]
I-218
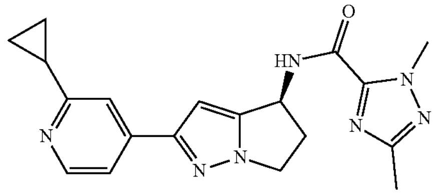 [SMILES: Cc1nc(C(=O)N[C@H]2CCn3nc(-c4ccnc(C5CC5)c4)cc32)n(C)n1]
I-218a
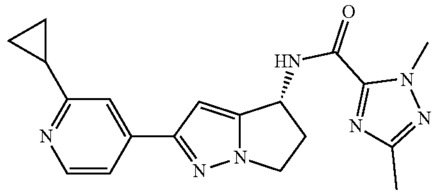 [SMILES: Cc1nc(C(=O)N[C@@H]2CCn3nc(-c4ccnc(C5CC5)c4)cc32)n(C)n1]
I-218b
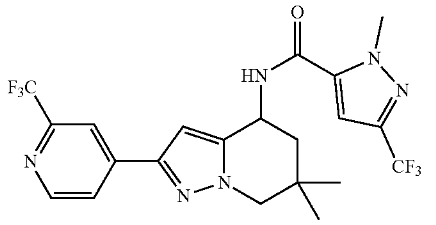 [SMILES: Cn1nc(C(F)(F)F)cc1C(=O)NC1CC(C)(C)Cn2nc(-c3ccnc(C(F)(F)F)c3)cc21]
I-219
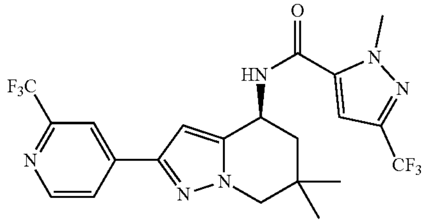 [SMILES: Cn1nc(C(F)(F)F)cc1C(=O)N[C@H]1CC(C)(C)Cn2nc(-c3ccnc(C(F)(F)F)c3)cc21]
I-219a TABLE 1-continued
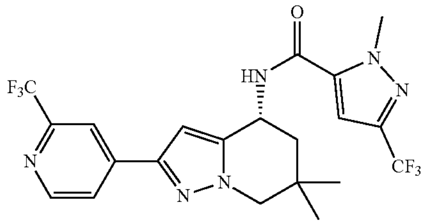 [SMILES: Cn1nc(C(F)(F)F)cc1C(=O)N[C@@H]1CC(C)(C)Cn2nc(-c3ccnc(C(F)(F)F)c3)cc21]
I-219b
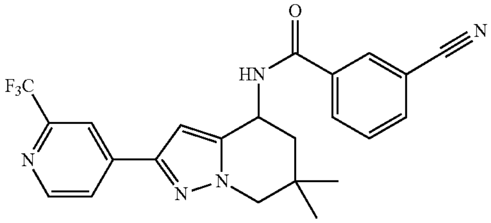 [SMILES: CC1(C)CC(NC(=O)c2cccc(C#N)c2)c2cc(-c3ccnc(C(F)(F)F)c3)nn2C1]
I-220
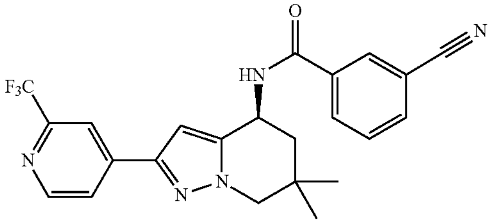 [SMILES: CC1(C)C[C@H](NC(=O)c2cccc(C#N)c2)c2cc(-c3ccnc(C(F)(F)F)c3)nn2C1]
I-220a
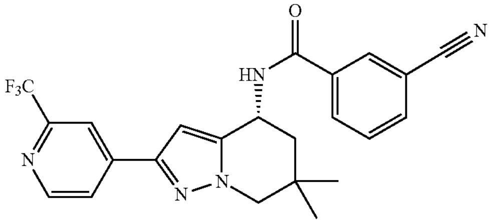 [SMILES: CC1(C)C[C@@H](NC(=O)c2cccc(C#N)c2)c2cc(-c3ccnc(C(F)(F)F)c3)nn2C1]
I-220b
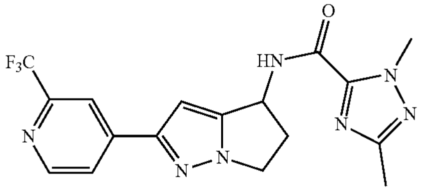 [SMILES: Cc1nc(C(=O)NC2CCn3nc(-c4ccnc(C(F)(F)F)c4)cc32)n(C)n1]
I-221
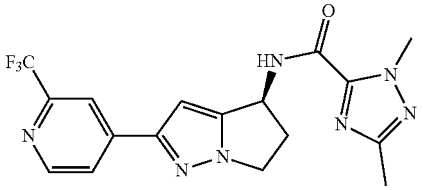 [SMILES: Cc1nc(C(=O)N[C@H]2CCn3nc(-c4ccnc(C(F)(F)F)c4)cc32)n(C)n1]
I-221a
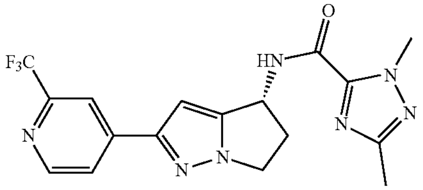 [SMILES: Cc1nc(C(=O)N[C@@H]2CCn3nc(-c4ccnc(C(F)(F)F)c4)cc32)n(C)n1]
I-221b TABLE 1-continued
I-222
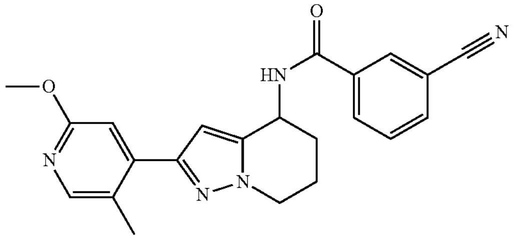 [SMILES: COc1cc(-c2cc3n(n2)CCCC3NC(=O)c2cccc(C#N)c2)c(C)cn1]
I-222a
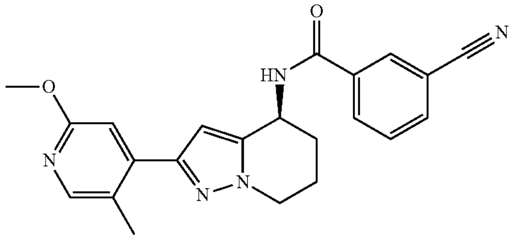 [SMILES: COc1cc(-c2cc3n(n2)CCC[C@@H]3NC(=O)c2cccc(C#N)c2)c(C)cn1]
I-222b
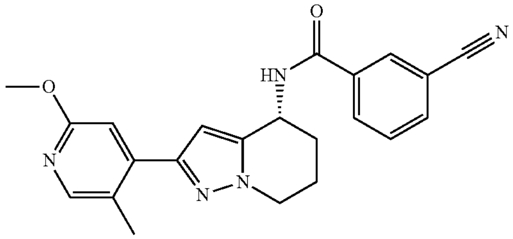 [SMILES: COc1cc(-c2cc3n(n2)CCC[C@H]3NC(=O)c2cccc(C#N)c2)c(C)cn1]
I-223
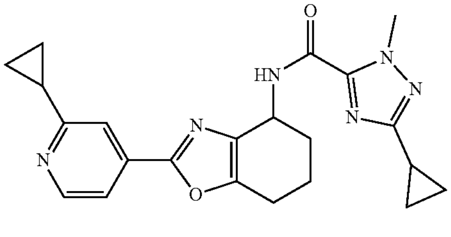 [SMILES: Cn1nc(C2CC2)nc1C(=O)NC1CCCc2oc(-c3ccnc(C4CC4)c3)nc21]
I-223a
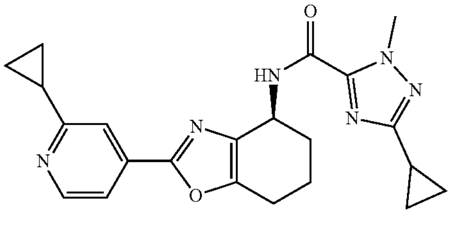 [SMILES: Cn1nc(C2CC2)nc1C(=O)N[C@H]1CCCc2oc(-c3ccnc(C4CC4)c3)nc21]
I-223b
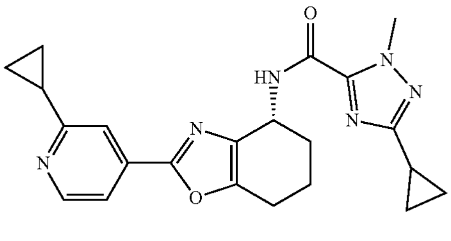

TABLE 1-continued
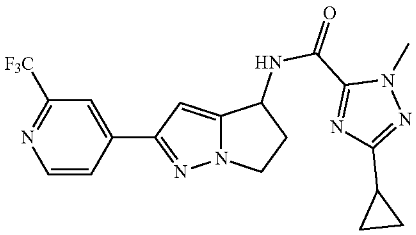 [SMILES: Cn1nc(C2CC2)nc1C(=O)NC1CCn2nc(-c3ccnc(C(F)(F)F)c3)cc21]
I-224
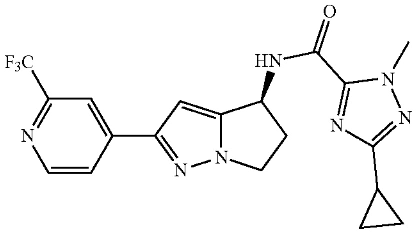 [SMILES: Cn1nc(C2CC2)nc1C(=O)N[C@H]1CCn2nc(-c3ccnc(C(F)(F)F)c3)cc21]
I-224a
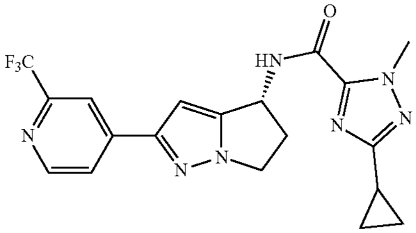 [SMILES: Cn1nc(C2CC2)nc1C(=O)N[C@@H]1CCn2nc(-c3ccnc(C(F)(F)F)c3)cc21]
I-224b
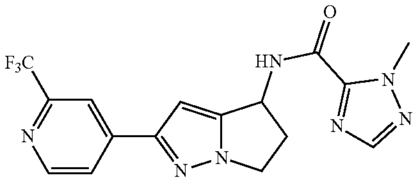 [SMILES: Cn1ncnc1C(=O)NC1CCn2nc(-c3ccnc(C(F)(F)F)c3)cc21]
I-225
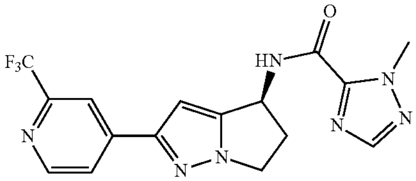 [SMILES: Cn1ncnc1C(=O)N[C@H]1CCn2nc(-c3ccnc(C(F)(F)F)c3)cc21]
I-225a
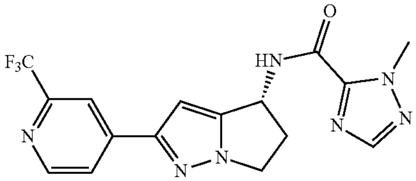 [SMILES: Cn1ncnc1C(=O)N[C@@H]1CCn2nc(-c3ccnc(C(F)(F)F)c3)cc21]
I-225b
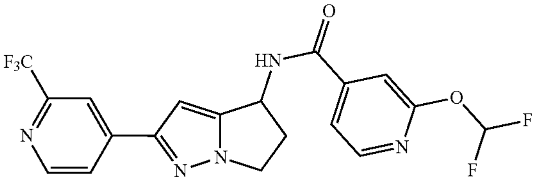 [SMILES: O=C(NC1CCn2nc(-c3ccnc(C(F)(F)F)c3)cc21)c1ccnc(OC(F)F)c1]
I-226

TABLE 1-continued
I-226a
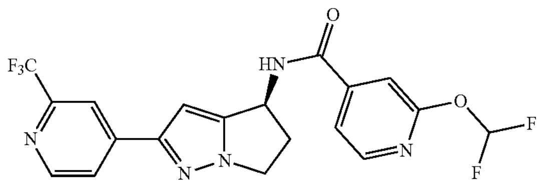 [SMILES: O=C(N[C@H]1CCn2nc(-c3ccnc(C(F)(F)F)c3)cc21)c1ccnc(OC(F)F)c1]
I-226b
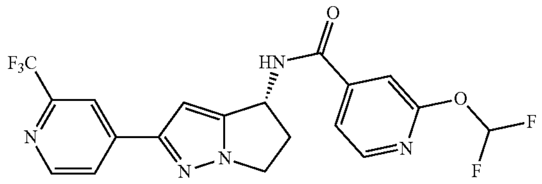 [SMILES: O=C(N[C@@H]1CCn2nc(-c3ccnc(C(F)(F)F)c3)cc21)c1ccnc(OC(F)F)c1]
I-227
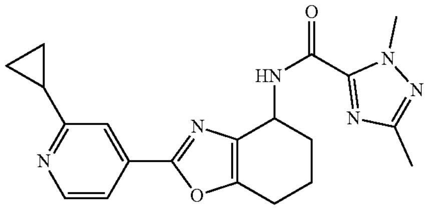 [SMILES: Cc1nc(C(=O)NC2CCCc3oc(-c4ccnc(C5CC5)c4)nc32)n(C)n1]
I-227a
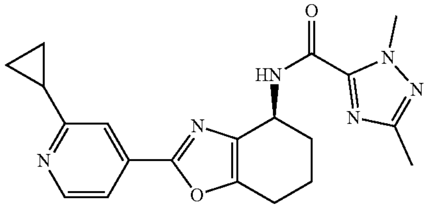 [SMILES: Cc1nc(C(=O)N[C@H]2CCCc3oc(-c4ccnc(C5CC5)c4)nc32)n(C)n1]
I-227b
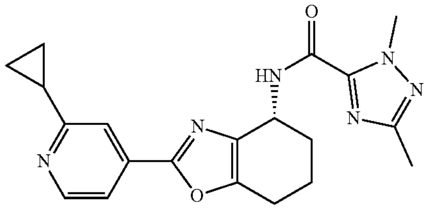 [SMILES: Cc1nc(C(=O)N[C@@H]2CCCc3oc(-c4ccnc(C5CC5)c4)nc32)n(C)n1]
I-228
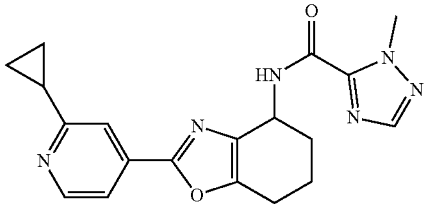 [SMILES: Cn1ncnc1C(=O)NC1CCCc2oc(-c3ccnc(C4CC4)c3)nc21]
I-228a
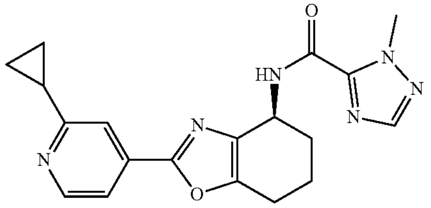 [SMILES: Cn1ncnc1C(=O)N[C@H]1CCCc2oc(-c3ccnc(C4CC4)c3)nc21]

TABLE 1-continued
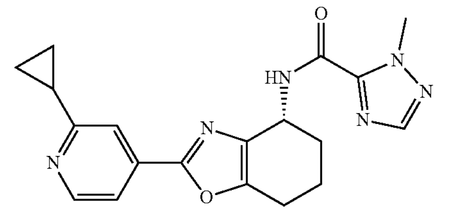 [SMILES: Cn1ncnc1C(=O)N[C@@H]1CCCc2oc(-c3ccnc(C4CC4)c3)nc21]
I-228b
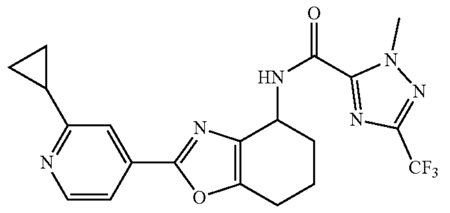
I-229
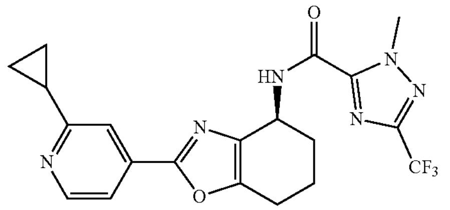
I-229a
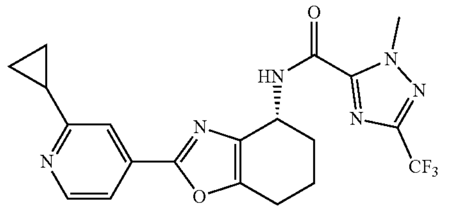
I-229b
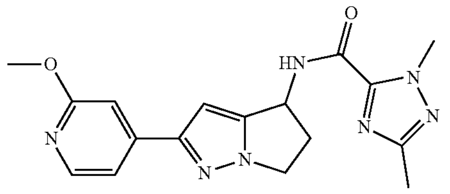
I-230
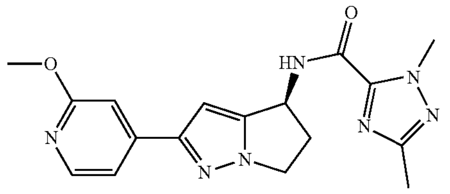
I-230a
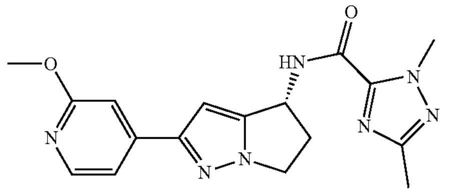
I-230b TABLE 1-continued
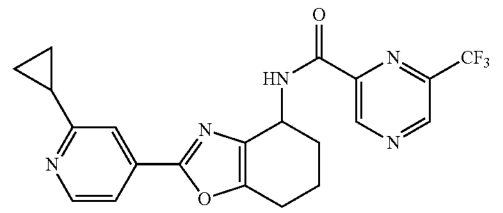
I-231
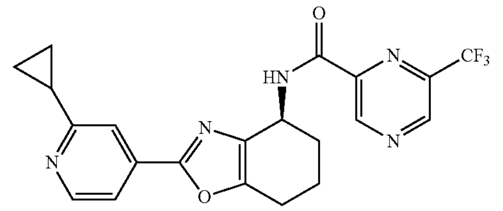 [SMILES: O=C(N[C@H]1CCCc2oc(-c3ccnc(C4CC4)c3)nc21)c1cncc(C(F)(F)F)n1]
I-231a
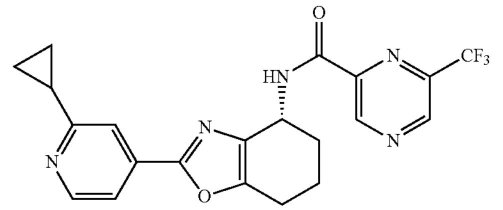 [SMILES: O=C(N[C@@H]1CCCc2oc(-c3ccnc(C4CC4)c3)nc21)c1cncc(C(F)(F)F)n1]
I-231b
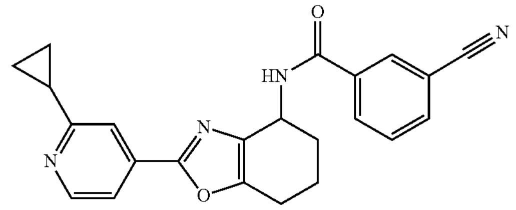 [SMILES: N#Cc1cccc(C(=O)NC2CCCc3oc(-c4ccnc(C5CC5)c4)nc32)c1]
I-232
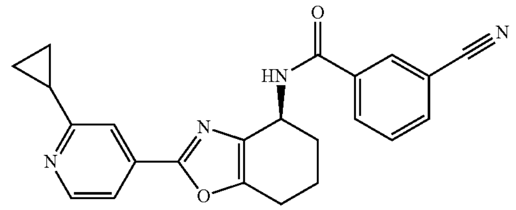 [SMILES: N#Cc1cccc(C(=O)N[C@H]2CCCc3oc(-c4ccnc(C5CC5)c4)nc32)c1]
I-232a
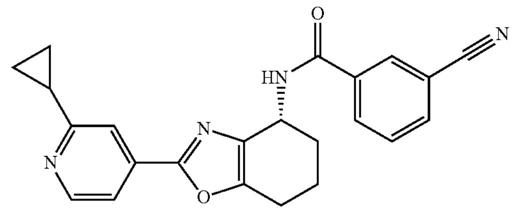 [SMILES: N#Cc1cccc(C(=O)N[C@@H]2CCCc3oc(-c4ccnc(C5CC5)c4)nc32)c1]
I-232b
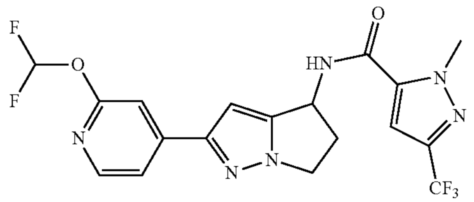 [SMILES: Cn1nc(C(F)(F)F)cc1C(=O)NC1CCn2nc(-c3ccnc(OC(F)F)c3)cc21]
I-233

TABLE 1-continued
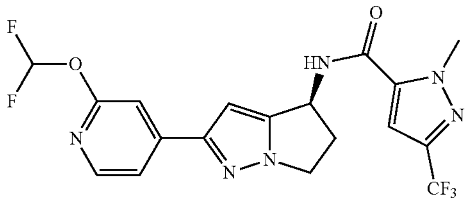 [SMILES: Cn1nc(C(F)(F)F)cc1C(=O)N[C@H]1CCn2nc(-c3ccnc(OC(F)F)c3)cc21]
I-233a
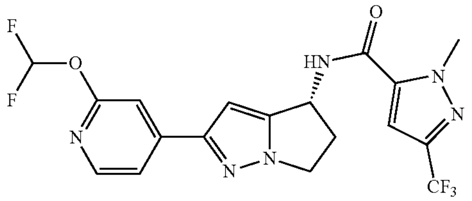 [SMILES: Cn1nc(C(F)(F)F)cc1C(=O)N[C@@H]1CCn2nc(-c3ccnc(OC(F)F)c3)cc21]
I-233b
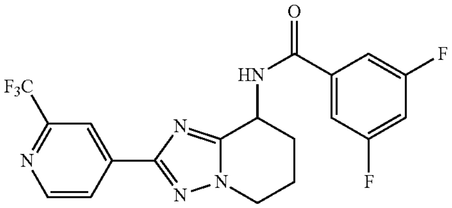 [SMILES: O=C(NC1CCCn2nc(-c3ccnc(C(F)(F)F)c3)nc21)c1cc(F)cc(F)c1]
I-234
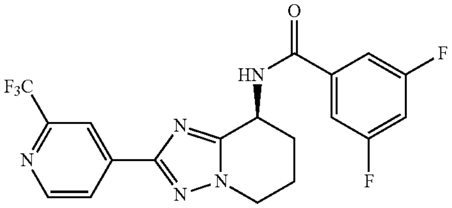 [SMILES: O=C(N[C@H]1CCCn2nc(-c3ccnc(C(F)(F)F)c3)nc21)c1cc(F)cc(F)c1]
I-234a
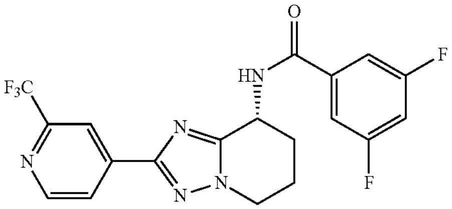
I-234b
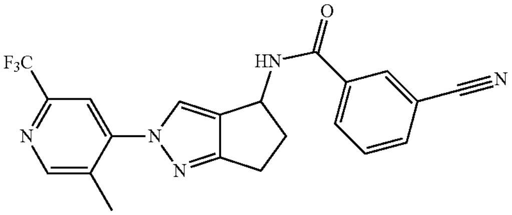 [SMILES: Cc1cnc(C(F)(F)F)cc1-n1cc2c(n1)CCC2NC(=O)c1cccc(C#N)c1]
I-235
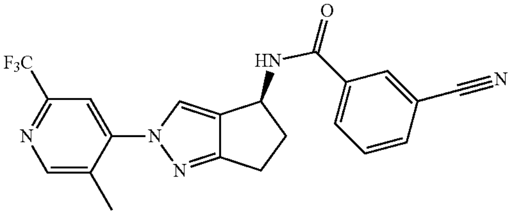 [SMILES: Cc1cnc(C(F)(F)F)cc1-n1cc2c(n1)CC[C@@H]2NC(=O)c1cccc(C#N)c1]
I-235a TABLE 1-continued
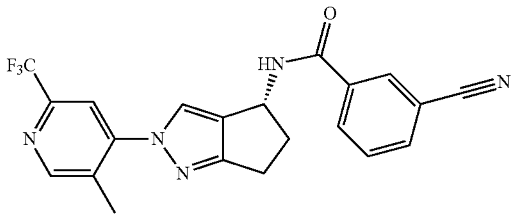 [SMILES: Cc1cnc(C(F)(F)F)cc1-n1cc2c(n1)CC[C@H]2NC(=O)c1cccc(C#N)c1]
I-235b
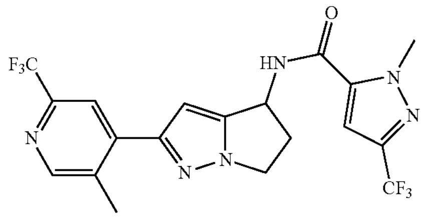
I-236
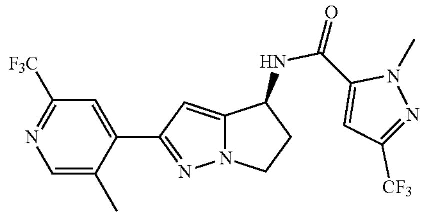
I-236a
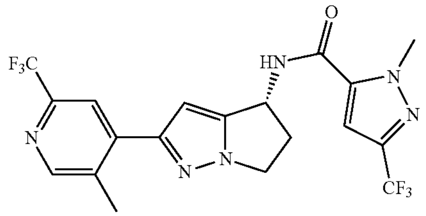 [SMILES: Cc1cnc(C(F)(F)F)cc1-c1cc2n(n1)CC[C@H]2NC(=O)c1cc(C(F)(F)F)nn1C]
I-236b
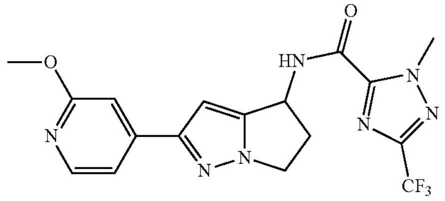
I-237
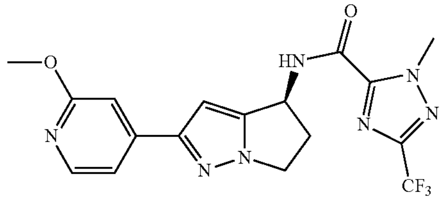
I-237a
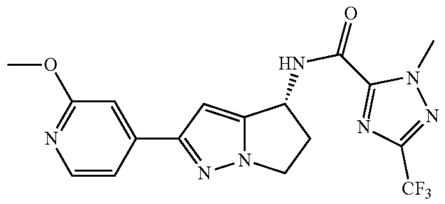
I-237b TABLE 1-continued
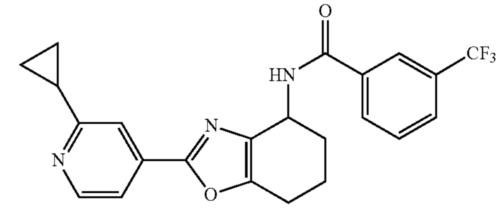 [SMILES: O=C(NC1CCCc2oc(-c3ccnc(C4CC4)c3)nc21)c1cccc(C(F)(F)F)c1]
I-238
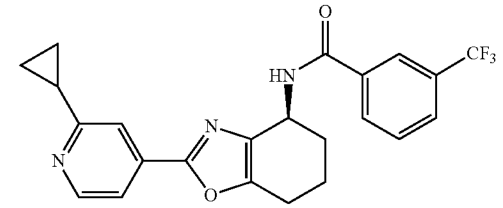 [SMILES: O=C(N[C@H]1CCCc2oc(-c3ccnc(C4CC4)c3)nc21)c1cccc(C(F)(F)F)c1]
I-238a
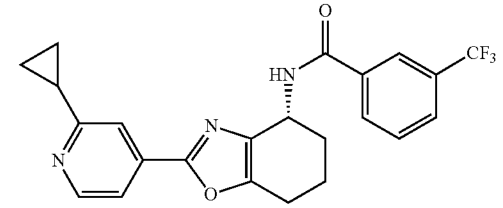 [SMILES: O=C(N[C@@H]1CCCc2oc(-c3ccnc(C4CC4)c3)nc21)c1cccc(C(F)(F)F)c1]
I-238b
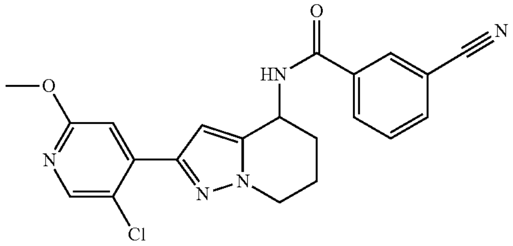 [SMILES: COc1cc(-c2cc3n(n2)CCCC3NC(=O)c2cccc(C#N)c2)c(Cl)cn1]
I-239
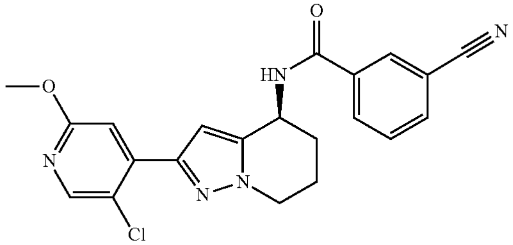 [SMILES: COc1cc(-c2cc3n(n2)CCC[C@@H]3NC(=O)c2cccc(C#N)c2)c(Cl)cn1]
I-239a
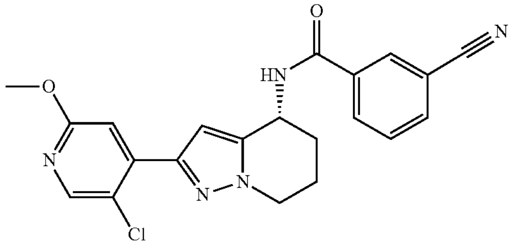
I-239b
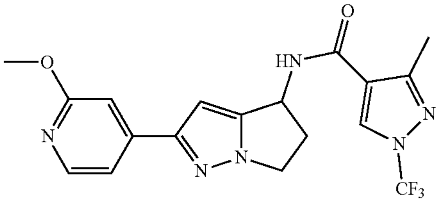
I-240

TABLE 1-continued
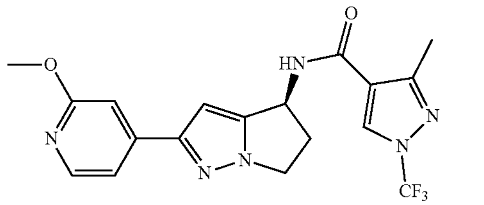
I-240a
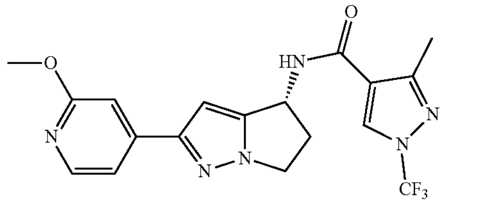
I-240b
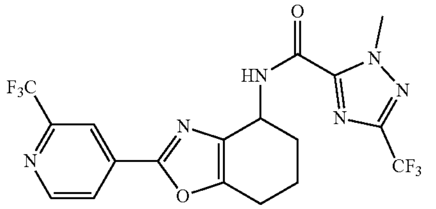
I-241
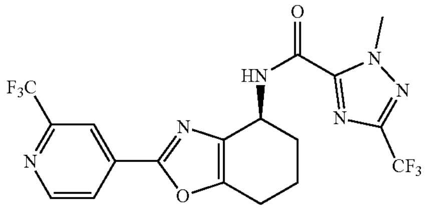
I-241a
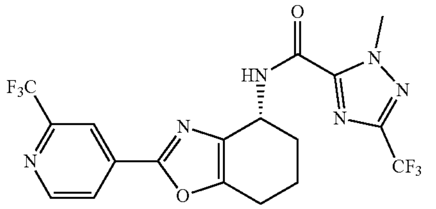
I-241b
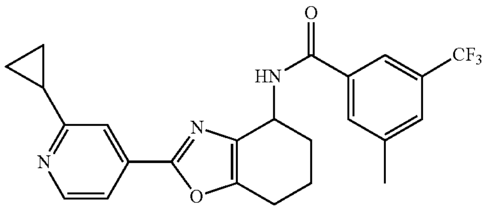 [SMILES: Cc1cc(C(=O)NC2CCCc3oc(-c4ccnc(C5CC5)c4)nc32)cc(C(F)(F)F)c1]
I-242
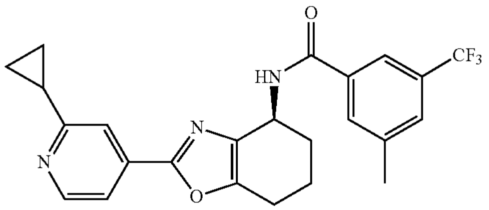 [SMILES: Cc1cc(C(=O)N[C@H]2CCCc3oc(-c4ccnc(C5CC5)c4)nc32)cc(C(F)(F)F)c1]
I-242a TABLE 1-continued
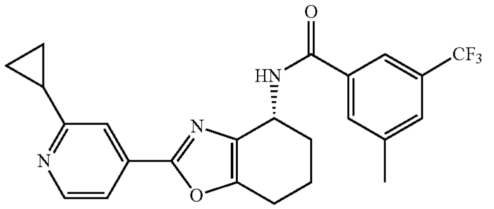
I-242b
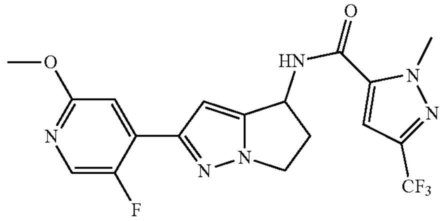
I-243
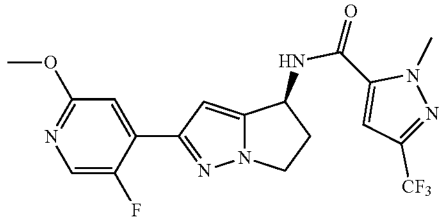
I-243a
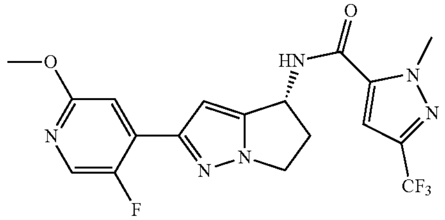
I-243b
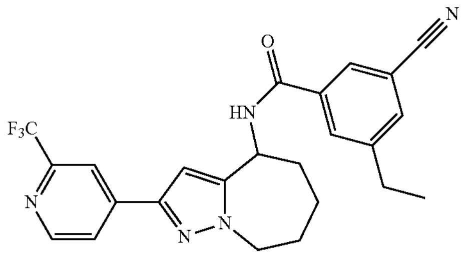 [SMILES: CCc1cc(C#N)cc(C(=O)NC2CCCCn3nc(-c4ccnc(C(F)(F)F)c4)cc32)c1]
I-244
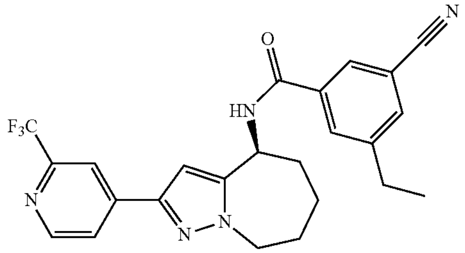 [SMILES: CCc1cc(C#N)cc(C(=O)N[C@H]2CCCCn3nc(-c4ccnc(C(F)(F)F)c4)cc32)c1]
I-244a TABLE 1-continued
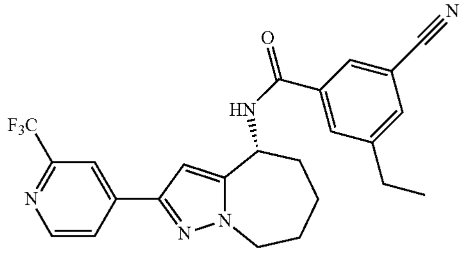 [SMILES: CCc1cc(C#N)cc(C(=O)N[C@@H]2CCCCn3nc(-c4ccnc(C(F)(F)F)c4)cc32)c1]
I-244b
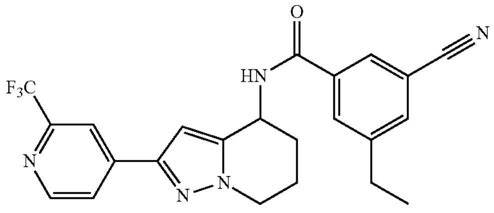
I-245
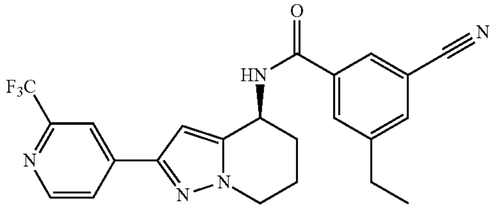
I-245a
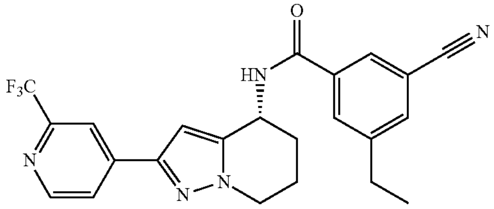 [SMILES: CCc1cc(C#N)cc(C(=O)NC2CCCn3nc(-c4ccnc(C(F)(F)F)c4)cc32)c1]
I-245b
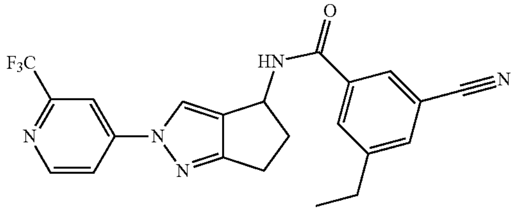 [SMILES: CCc1cc(C#N)cc(C(=O)NC2CCc3nn(-c4ccnc(C(F)(F)F)c4)cc32)c1]
I-246
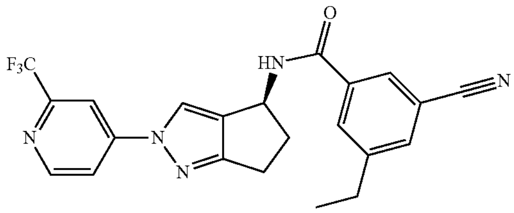 [SMILES: CCc1cc(C#N)cc(C(=O)N[C@H]2CCc3nn(-c4ccnc(C(F)(F)F)c4)cc32)c1]
I-246a
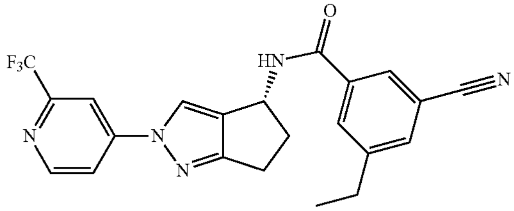 [SMILES: CCc1cc(C#N)cc(C(=O)N[C@@H]2CCc3nn(-c4ccnc(C(F)(F)F)c4)cc32)c1]
I-246b TABLE 1-continued
I-247
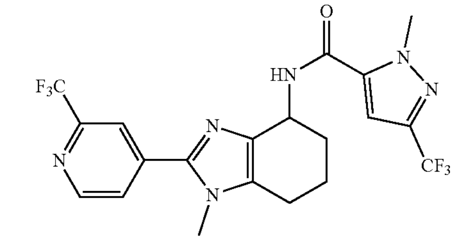 [SMILES: Cn1nc(C(F)(F)F)cc1C(=O)NC1CCCc2c1nc(-c1ccnc(C(F)(F)F)c1)n2C]
I-247a
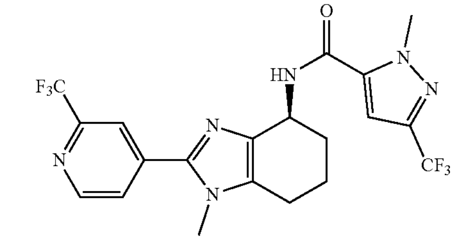 [SMILES: Cn1nc(C(F)(F)F)cc1C(=O)N[C@H]1CCCc2c1nc(-c1ccnc(C(F)(F)F)c1)n2C]
I-247b
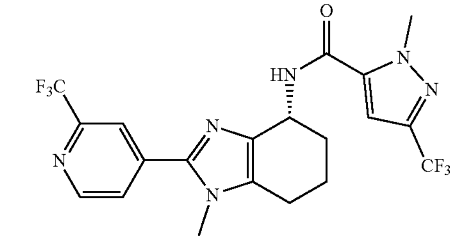 [SMILES: Cn1nc(C(F)(F)F)cc1C(=O)N[C@@H]1CCCc2c1nc(-c1ccnc(C(F)(F)F)c1)n2C]
I-248
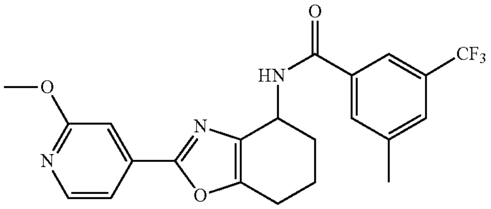 [SMILES: COc1cc(-c2nc3c(o2)CCCC3NC(=O)c2cc(C)cc(C(F)(F)F)c2)ccn1]
I-248a
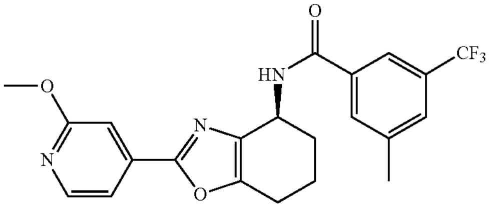 [SMILES: COc1cc(-c2nc3c(o2)CCC[C@@H]3NC(=O)c2cc(C)cc(C(F)(F)F)c2)ccn1]
I-248b
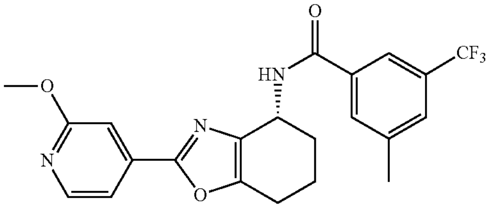
I-249
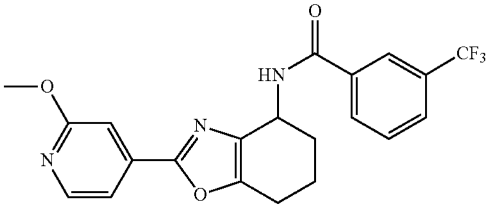 [SMILES: COc1cc(-c2nc3c(o2)CCCC3NC(=O)c2cccc(C(F)(F)F)c2)ccn1]

TABLE 1-continued
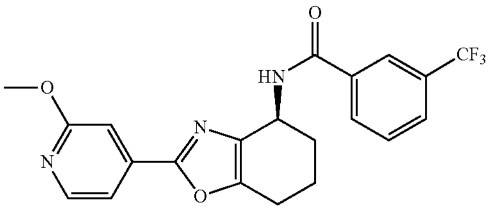 [SMILES: COc1cc(-c2nc3c(o2)CCC[C@@H]3NC(=O)c2cccc(C(F)(F)F)c2)ccn1]
I-249a
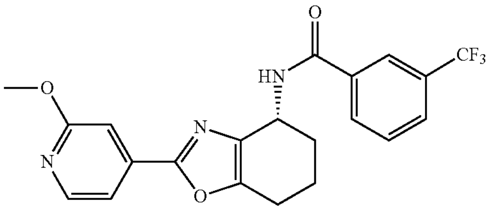
I-249b
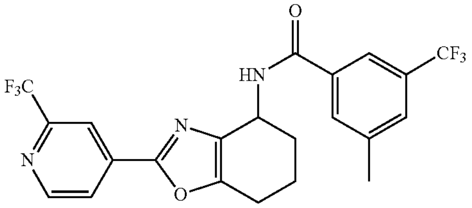 [SMILES: Cc1cc(C(=O)NC2CCCc3oc(-c4ccnc(C(F)(F)F)c4)nc32)cc(C(F)(F)F)c1]
I-250
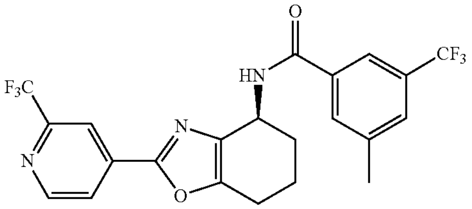 [SMILES: Cc1cc(C(=O)N[C@H]2CCCc3oc(-c4ccnc(C(F)(F)F)c4)nc32)cc(C(F)(F)F)c1]
I-250a
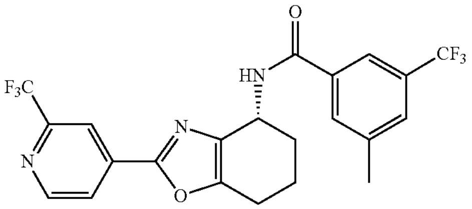 [SMILES: Cc1cc(C(=O)N[C@@H]2CCCc3oc(-c4ccnc(C(F)(F)F)c4)nc32)cc(C(F)(F)F)c1]
I-250b
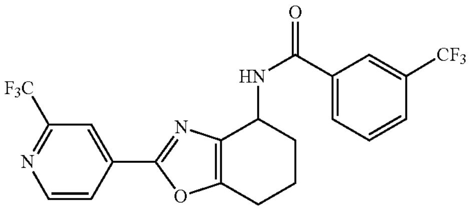 [SMILES: O=C(NC1CCCc2oc(-c3ccnc(C(F)(F)F)c3)nc21)c1cccc(C(F)(F)F)c1]
I-251
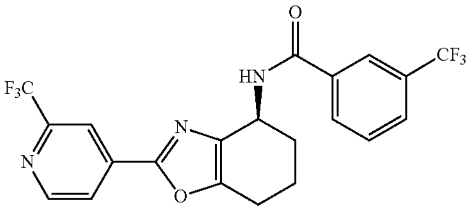 [SMILES: O=C(N[C@H]1CCCc2oc(-c3ccnc(C(F)(F)F)c3)nc21)c1cccc(C(F)(F)F)c1]
I-251a TABLE 1-continued
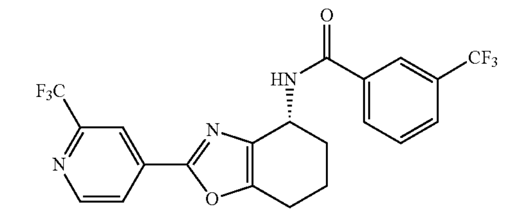 [SMILES: O=C(N[C@@H]1CCCc2oc(-c3ccnc(C(F)(F)F)c3)nc21)c1cccc(C(F)(F)F)c1]
I-251b
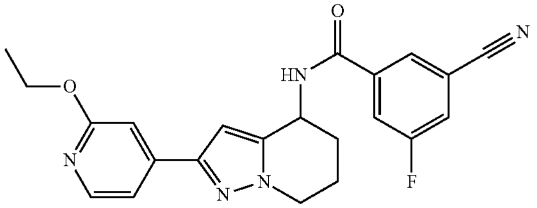 [SMILES: CCOc1cc(-c2cc3n(n2)CCCC3NC(=O)c2cc(F)cc(C#N)c2)ccn1]
I-252
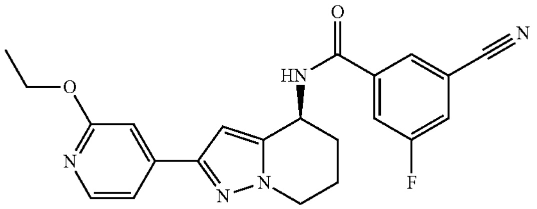 [SMILES: CCOc1cc(-c2cc3n(n2)CCC[C@@H]3NC(=O)c2cc(F)cc(C#N)c2)ccn1]
I-252a
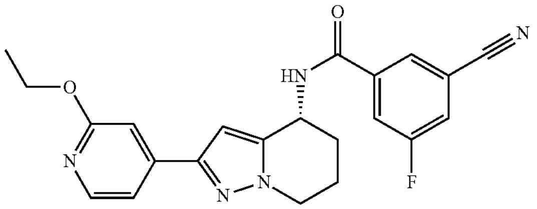 [SMILES: CCOc1cc(-c2cc3n(n2)CCC[C@H]3NC(=O)c2cc(F)cc(C#N)c2)ccn1]
I-252b
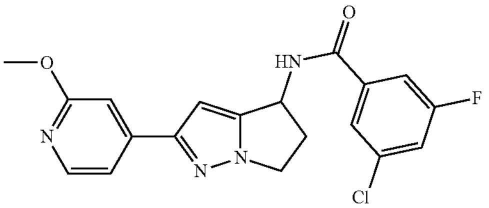 [SMILES: COc1cc(-c2cc3n(n2)CCC3NC(=O)c2cc(F)cc(Cl)c2)ccn1]
I-253
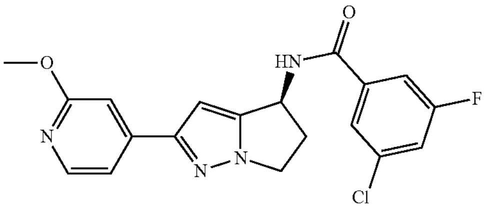 [SMILES: COc1cc(-c2cc3n(n2)CC[C@@H]3NC(=O)c2cc(F)cc(Cl)c2)ccn1]
I-253a
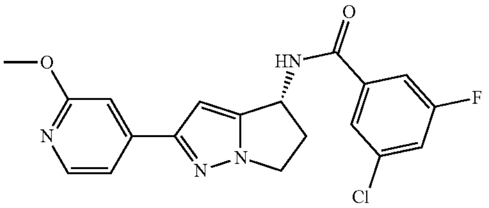 [SMILES: COc1cc(-c2cc3n(n2)CC[C@H]3NC(=O)c2cc(F)cc(Cl)c2)ccn1]
I-253b TABLE 1-continued
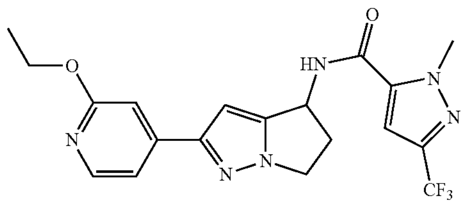 [SMILES: CCOc1cc(-c2cc3n(n2)CCC3NC(=O)c2cc(C(F)(F)F)nn2C)ccn1]
I-254
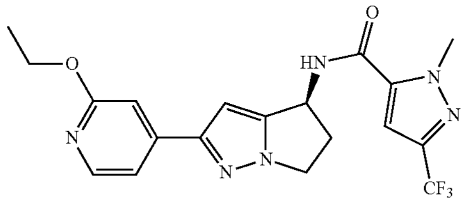 [SMILES: CCOc1cc(-c2cc3n(n2)CC[C@@H]3NC(=O)c2cc(C(F)(F)F)nn2C)ccn1]
I-254a
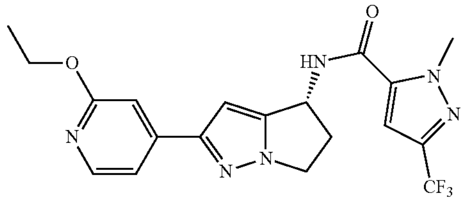 [SMILES: CCOc1cc(-c2cc3n(n2)CC[C@H]3NC(=O)c2cc(C(F)(F)F)nn2C)ccn1]
I-254b
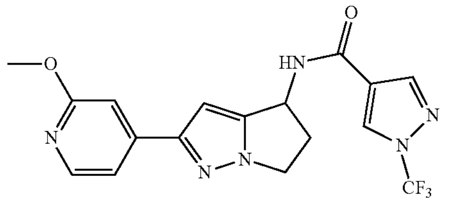 [SMILES: COc1cc(-c2cc3n(n2)CCC3NC(=O)c2cnn(C(F)(F)F)c2)ccn1]
I-255
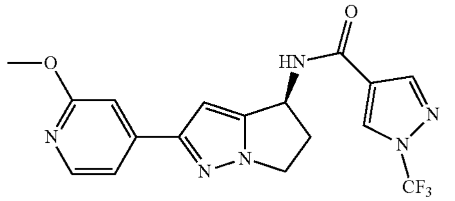 [SMILES: COc1cc(-c2cc3n(n2)CC[C@@H]3NC(=O)c2cnn(C(F)(F)F)c2)ccn1]
I-255a
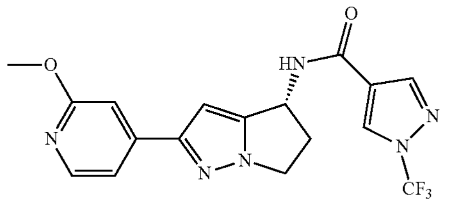
I-255b
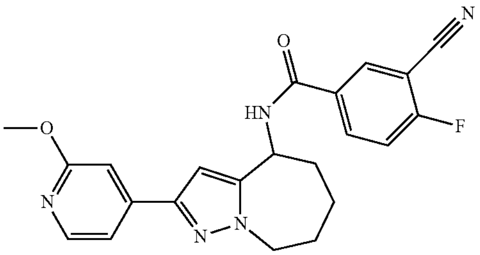 [SMILES: COc1cc(-c2cc3n(n2)CCCCC3NC(=O)c2ccc(F)c(C#N)c2)ccn1]
I-256

TABLE 1-continued
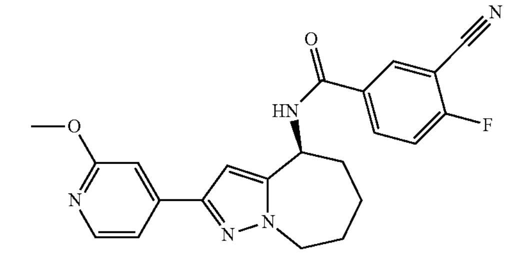 [SMILES: COc1cc(-c2cc3n(n2)CCCC[C@@H]3NC(=O)c2ccc(F)c(C#N)c2)ccn1]
I-256a
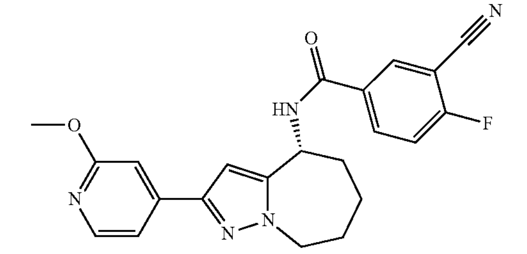 [SMILES: COc1cc(-c2cc3n(n2)CCCC[C@H]3NC(=O)c2ccc(F)c(C#N)c2)ccn1]
I-256b
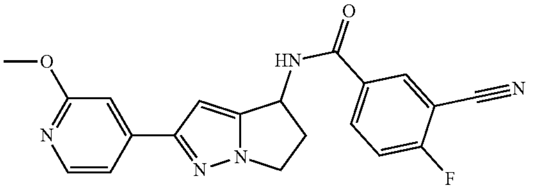 [SMILES: COc1cc(-c2cc3n(n2)CCC3NC(=O)c2ccc(F)c(C#N)c2)ccn1]
I-257
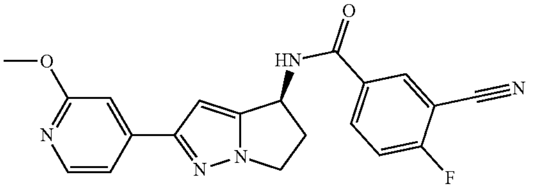 [SMILES: COc1cc(-c2cc3n(n2)CC[C@@H]3NC(=O)c2ccc(F)c(C#N)c2)ccn1]
I-257a
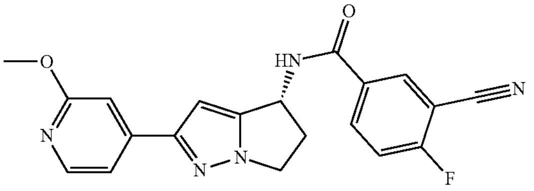 [SMILES: COc1cc(-c2cc3n(n2)CC[C@H]3NC(=O)c2ccc(F)c(C#N)c2)ccn1]
I-257b
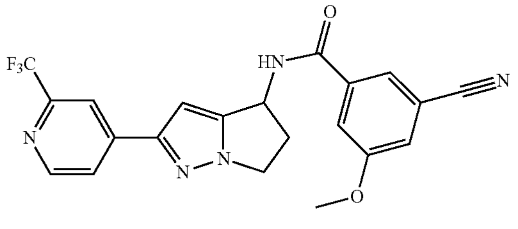 [SMILES: COc1cc(C#N)cc(C(=O)NC2CCn3nc(-c4ccnc(C(F)(F)F)c4)cc32)c1]
I-258
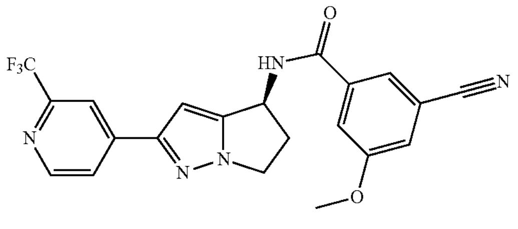 [SMILES: COc1cc(C#N)cc(C(=O)N[C@H]2CCn3nc(-c4ccnc(C(F)(F)F)c4)cc32)c1]
I-258a TABLE 1-continued
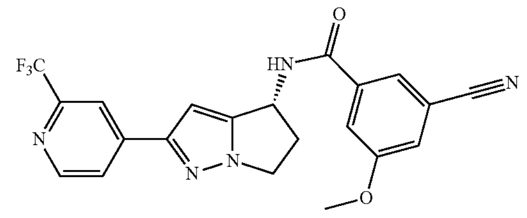 [SMILES: COc1cc(C#N)cc(C(=O)N[C@@H]2CCn3nc(-c4ccnc(C(F)(F)F)c4)cc32)c1]
I-258b
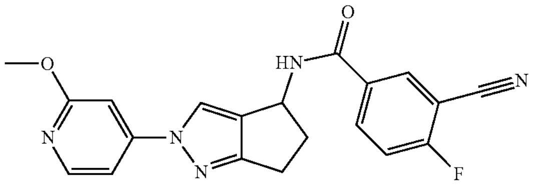 [SMILES: COc1cc(-n2cc3c(n2)CCC3NC(=O)c2ccc(F)c(C#N)c2)ccn1]
I-259
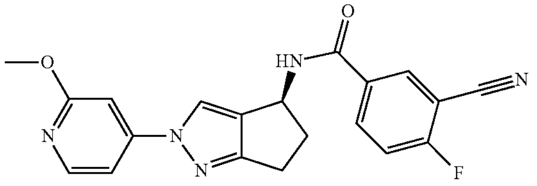 [SMILES: COc1cc(-n2cc3c(n2)CC[C@@H]3NC(=O)c2ccc(F)c(C#N)c2)ccn1]
I-259a
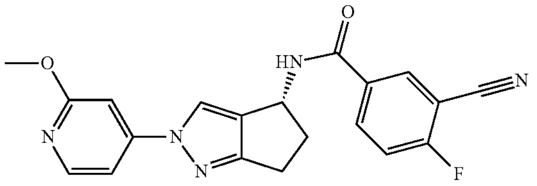 [SMILES: COc1cc(-n2cc3c(n2)CC[C@H]3NC(=O)c2ccc(F)c(C#N)c2)ccn1]
I-259b
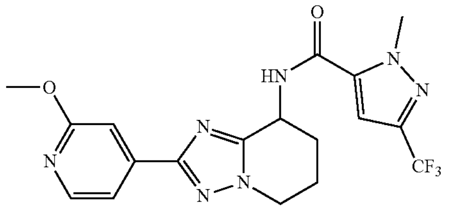
I-260
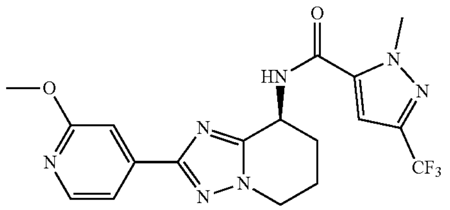 [SMILES: COc1cc(-c2nc3n(n2)CCC[C@@H]3NC(=O)c2cc(C(F)(F)F)nn2C)ccn1]
I-260a
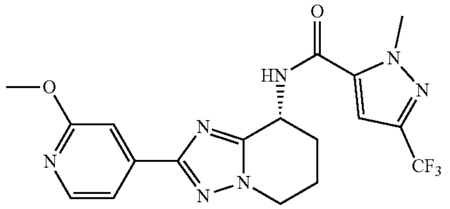
I-260b TABLE 1-continued
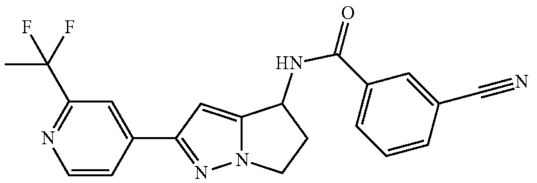 [SMILES: CC(F)(F)c1cc(-c2cc3n(n2)CCC3NC(=O)c2cccc(C#N)c2)ccn1]
I-261
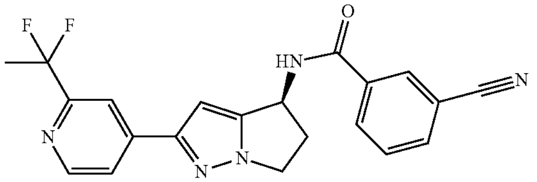 [SMILES: CC(F)(F)c1cc(-c2cc3n(n2)CC[C@@H]3NC(=O)c2cccc(C#N)c2)ccn1]
I-261a
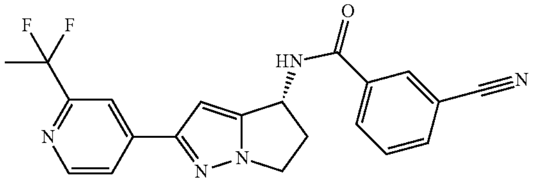 [SMILES: CC(F)(F)c1cc(-c2cc3n(n2)CC[C@H]3NC(=O)c2cccc(C#N)c2)ccn1]
I-261b
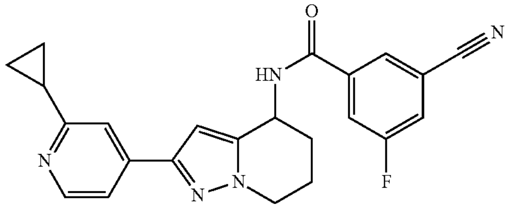 [SMILES: N#Cc1cc(F)cc(C(=O)NC2CCCn3nc(-c4ccnc(C5CC5)c4)cc32)c1]
I-262
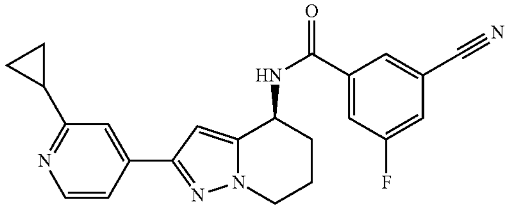 [SMILES: N#Cc1cc(F)cc(C(=O)N[C@H]2CCCn3nc(-c4ccnc(C5CC5)c4)cc32)c1]
I-262a
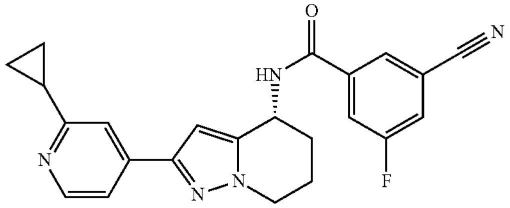 [SMILES: N#Cc1cc(F)cc(C(=O)N[C@@H]2CCCn3nc(-c4ccnc(C5CC5)c4)cc32)c1]
I-262b
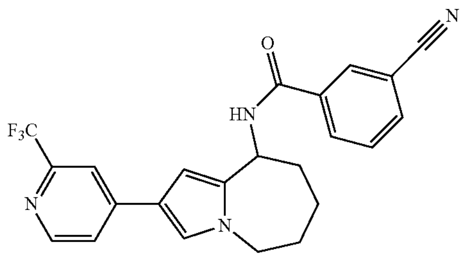 [SMILES: N#Cc1cccc(C(=O)NC2CCCCn3cc(-c4ccnc(C(F)(F)F)c4)cc32)c1]
I-263

TABLE 1-continued
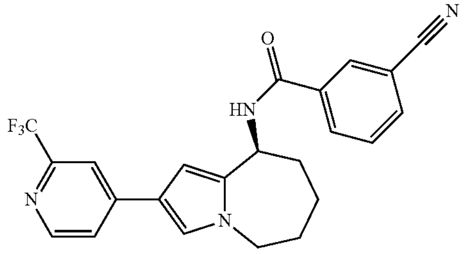 [SMILES: N#Cc1cccc(C(=O)N[C@H]2CCCCn3cc(-c4ccnc(C(F)(F)F)c4)cc32)c1]
I-263a
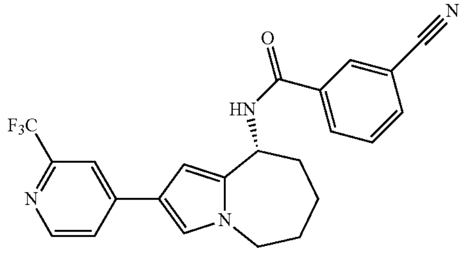 [SMILES: N#Cc1cccc(C(=O)N[C@@H]2CCCCn3cc(-c4ccnc(C(F)(F)F)c4)cc32)c1]
I-263b
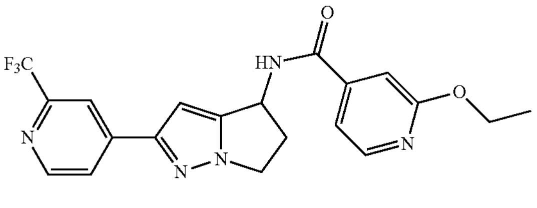 [SMILES: CCOc1cc(C(=O)NC2CCn3nc(-c4ccnc(C(F)(F)F)c4)cc32)ccn1]
I-264
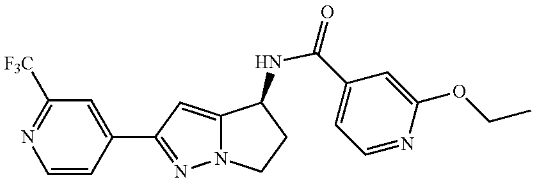 [SMILES: CCOc1cc(C(=O)N[C@H]2CCn3nc(-c4ccnc(C(F)(F)F)c4)cc32)ccn1]
I-264a
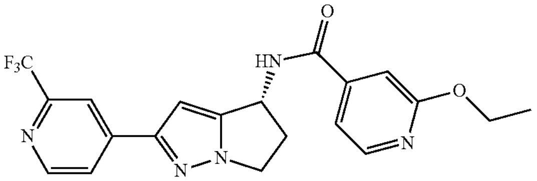 [SMILES: CCOc1cc(C(=O)N[C@@H]2CCn3nc(-c4ccnc(C(F)(F)F)c4)cc32)ccn1]
I-264b
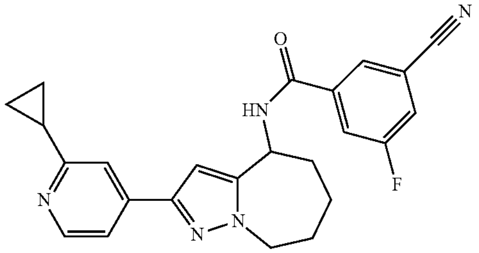 [SMILES: N#Cc1cc(F)cc(C(=O)NC2CCCCn3nc(-c4ccnc(C5CC5)c4)cc32)c1]
I-265
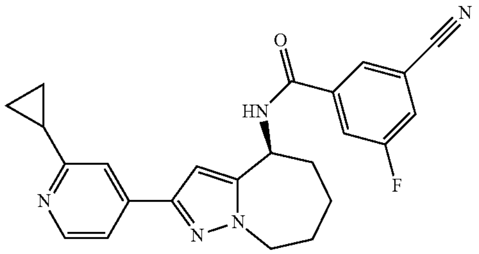 [SMILES: N#Cc1cc(F)cc(C(=O)N[C@H]2CCCCn3nc(-c4ccnc(C5CC5)c4)cc32)c1]
I-265a TABLE 1-continued
I-265b
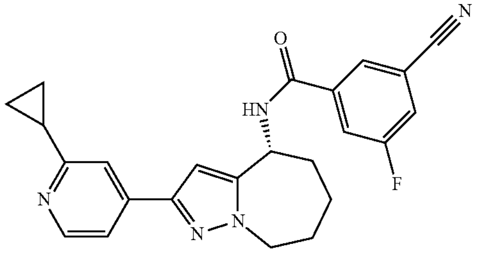 [SMILES: N#Cc1cc(F)cc(C(=O)N[C@@H]2CCCCn3nc(-c4ccnc(C5CC5)c4)cc32)c1]
I-266
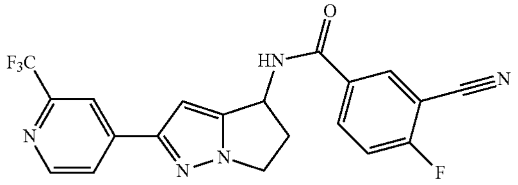 [SMILES: N#Cc1cc(C(=O)NC2CCn3nc(-c4ccnc(C(F)(F)F)c4)cc32)ccc1F]
I-266a
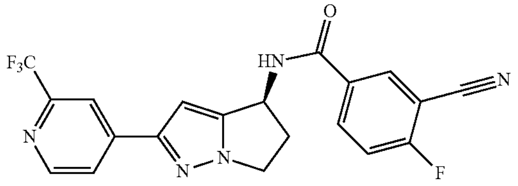 [SMILES: N#Cc1cc(C(=O)N[C@H]2CCn3nc(-c4ccnc(C(F)(F)F)c4)cc32)ccc1F]
I-266b
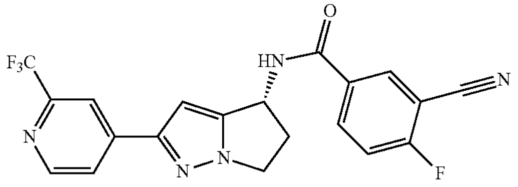 [SMILES: N#Cc1cc(C(=O)N[C@@H]2CCn3nc(-c4ccnc(C(F)(F)F)c4)cc32)ccc1F]
I-267
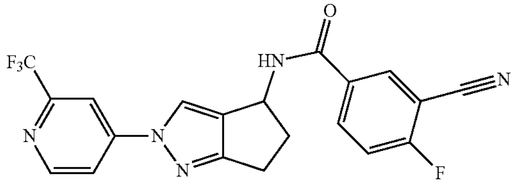 [SMILES: N#Cc1cc(C(=O)NC2CCc3nn(-c4ccnc(C(F)(F)F)c4)cc32)ccc1F]
I-267a
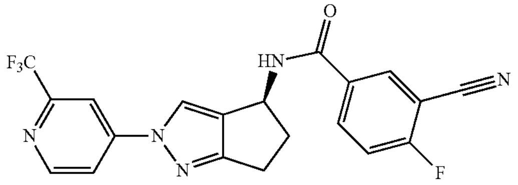 [SMILES: N#Cc1cc(C(=O)N[C@H]2CCc3nn(-c4ccnc(C(F)(F)F)c4)cc32)ccc1F]
I-267b
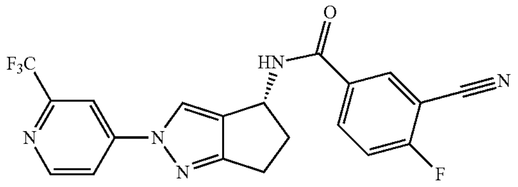 [SMILES: N#Cc1cc(C(=O)N[C@@H]2CCc3nn(-c4ccnc(C(F)(F)F)c4)cc32)ccc1F]
I-268
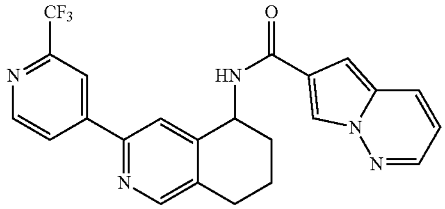 [SMILES: O=C(NC1CCCc2cnc(-c3ccnc(C(F)(F)F)c3)cc21)c1cc2cccnn2c1]

TABLE 1-continued
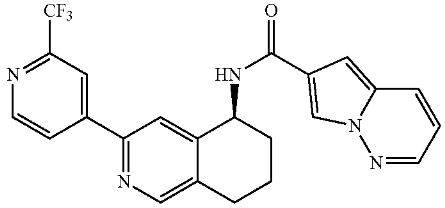 [SMILES: O=C(N[C@H]1CCCc2cnc(-c3ccnc(C(F)(F)F)c3)cc21)c1cc2cccnn2c1]
I-268a
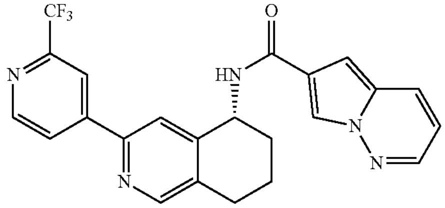
I-268b
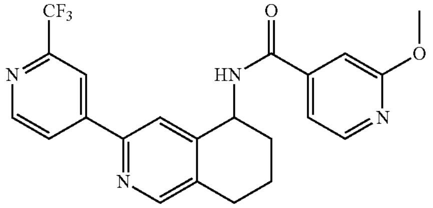 [SMILES: COc1cc(C(=O)NC2CCCc3cnc(-c4ccnc(C(F)(F)F)c4)cc32)ccn1]
I-269
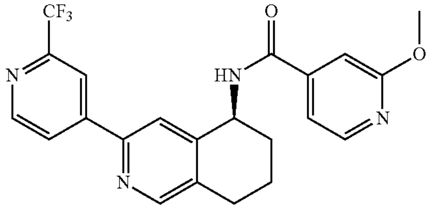 [SMILES: COc1cc(C(=O)N[C@H]2CCCc3cnc(-c4ccnc(C(F)(F)F)c4)cc32)ccn1]
I-269a
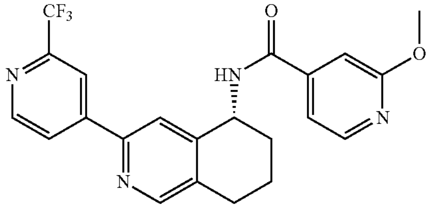
I-269b
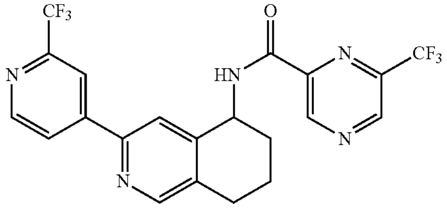 [SMILES: O=C(NC1CCCc2cnc(-c3ccnc(C(F)(F)F)c3)cc21)c1cncc(C(F)(F)F)n1]
I-270
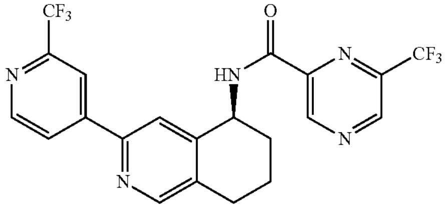 [SMILES: O=C(N[C@H]1CCCc2cnc(-c3ccnc(C(F)(F)F)c3)cc21)c1cncc(C(F)(F)F)n1]
I-270a TABLE 1-continued
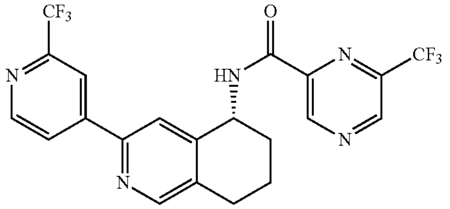 [SMILES: O=C(N[C@@H]1CCCc2cnc(-c3ccnc(C(F)(F)F)c3)cc21)c1cncc(C(F)(F)F)n1]
I-270b
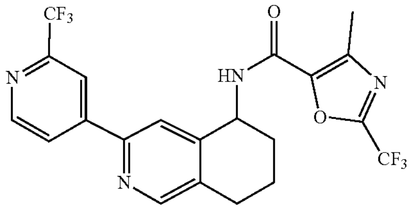 [SMILES: Cc1nc(C(F)(F)F)oc1C(=O)NC1CCCc2cnc(-c3ccnc(C(F)(F)F)c3)cc21]
I-271
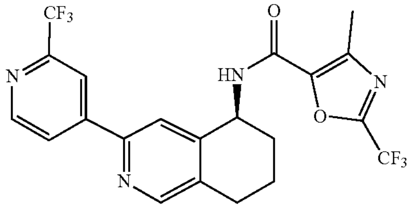 [SMILES: Cc1nc(C(F)(F)F)oc1C(=O)N[C@H]1CCCc2cnc(-c3ccnc(C(F)(F)F)c3)cc21]
I-271a
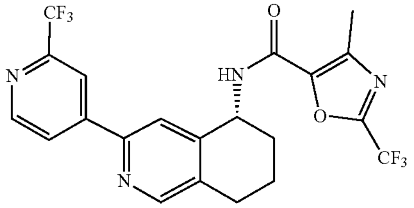
I-271b
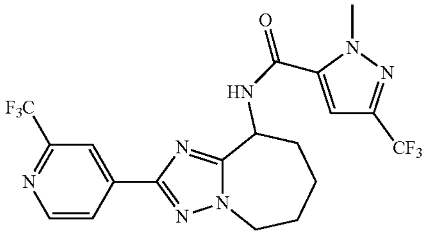 [SMILES: Cn1nc(C(F)(F)F)cc1C(=O)NC1CCCCn2nc(-c3ccnc(C(F)(F)F)c3)nc21]
I-272
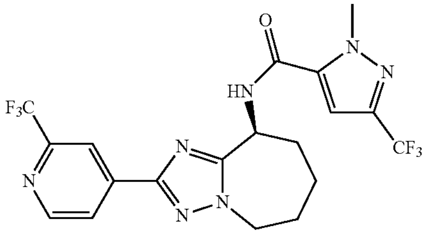 [SMILES: Cn1nc(C(F)(F)F)cc1C(=O)N[C@H]1CCCCn2nc(-c3ccnc(C(F)(F)F)c3)nc21]
I-272a
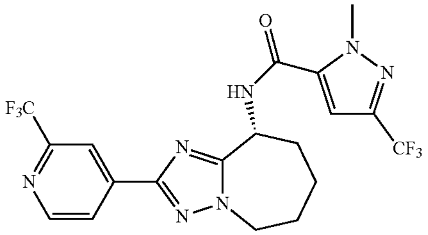 [SMILES: Cn1nc(C(F)(F)F)cc1C(=O)N[C@@H]1CCCCn2nc(-c3ccnc(C(F)(F)F)c3)nc21]
I-272b TABLE 1-continued
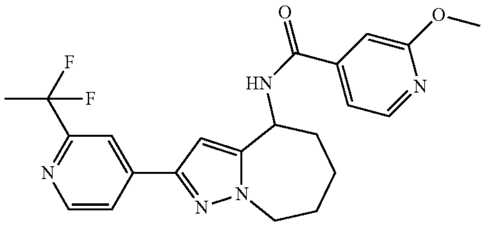 [SMILES: COc1cc(C(=O)NC2CCCCn3nc(-c4ccnc(C(C)(F)F)c4)cc32)ccn1]
I-273
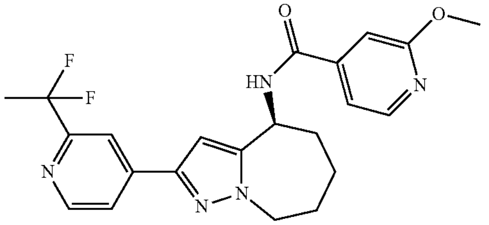 [SMILES: COc1cc(C(=O)N[C@H]2CCCCn3nc(-c4ccnc(C(C)(F)F)c4)cc32)ccn1]
I-273a
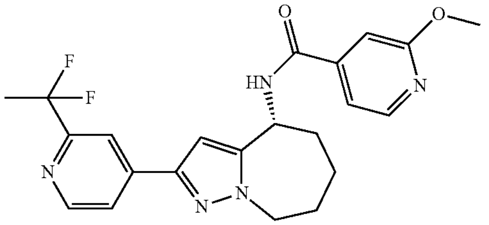 [SMILES: COc1cc(C(=O)N[C@@H]2CCCCn3nc(-c4ccnc(C(C)(F)F)c4)cc32)ccn1]
I-273b
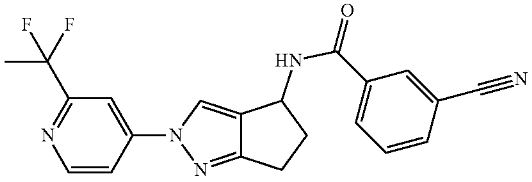 [SMILES: CC(F)(F)c1cc(-n2cc3c(n2)CCC3NC(=O)c2cccc(C#N)c2)ccn1]
I-274
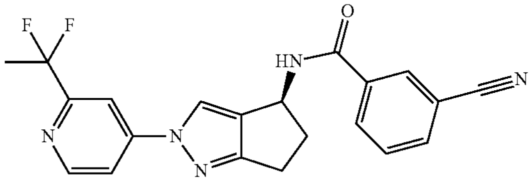 [SMILES: CC(F)(F)c1cc(-n2cc3c(n2)CC[C@@H]3NC(=O)c2cccc(C#N)c2)ccn1]
I-274a
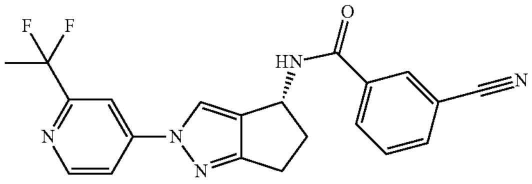 [SMILES: CC(F)(F)c1cc(-n2cc3c(n2)CC[C@H]3NC(=O)c2cccc(C#N)c2)ccn1]
I-274b
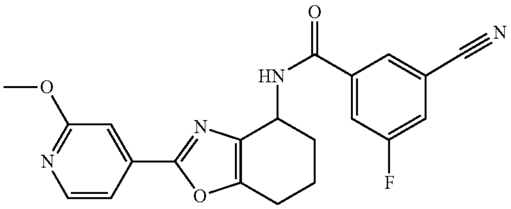 [SMILES: COc1cc(-c2nc3c(o2)CCCC3NC(=O)c2cc(F)cc(C#N)c2)ccn1]
I-275

TABLE 1-continued
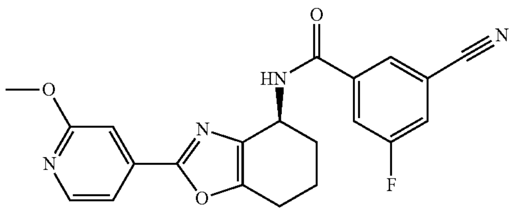 [SMILES: COc1cc(-c2nc3c(o2)CCC[C@@H]3NC(=O)c2cc(F)cc(C#N)c2)ccn1]
I-275a
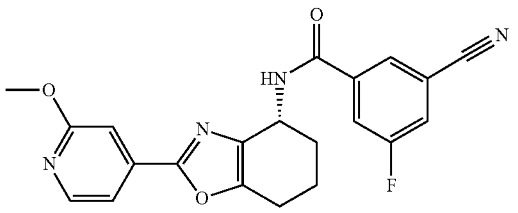 [SMILES: COc1cc(-c2nc3c(o2)CCC[C@H]3NC(=O)c2cc(F)cc(C#N)c2)ccn1]
I-275b
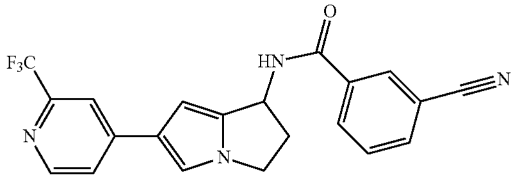 [SMILES: N#Cc1cccc(C(=O)NC2CCn3cc(-c4ccnc(C(F)(F)F)c4)cc32)c1]
I-276
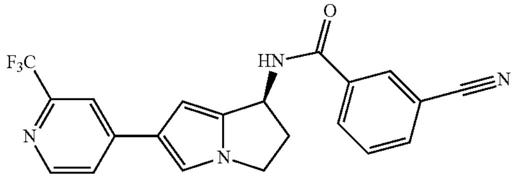 [SMILES: N#Cc1cccc(C(=O)N[C@H]2CCn3cc(-c4ccnc(C(F)(F)F)c4)cc32)c1]
I-276a
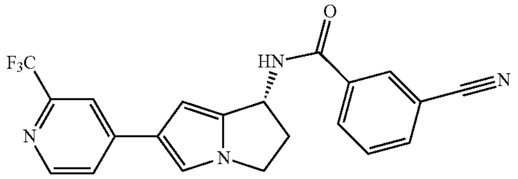 [SMILES: N#Cc1cccc(C(=O)N[C@@H]2CCn3cc(-c4ccnc(C(F)(F)F)c4)cc32)c1]
I-276b
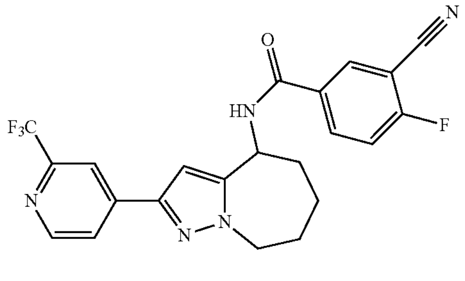 [SMILES: N#Cc1cc(C(=O)NC2CCCCn3nc(-c4ccnc(C(F)(F)F)c4)cc32)ccc1F]
I-277
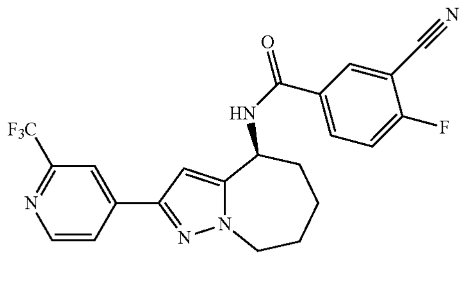 [SMILES: N#Cc1cc(C(=O)N[C@H]2CCCCn3nc(-c4ccnc(C(F)(F)F)c4)cc32)ccc1F]
I-277a TABLE 1-continued
I-277b
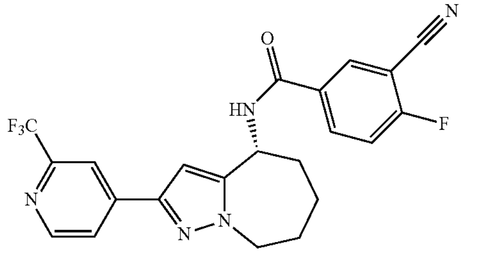 [SMILES: N#Cc1cc(C(=O)N[C@@H]2CCCCn3nc(-c4ccnc(C(F)(F)F)c4)cc32)ccc1F]
I-278
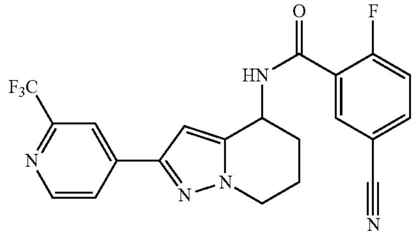 [SMILES: N#Cc1ccc(F)c(C(=O)NC2CCCn3nc(-c4ccnc(C(F)(F)F)c4)cc32)c1]
I-278a
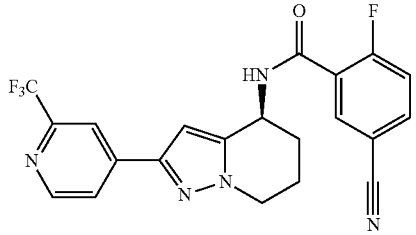 [SMILES: N#Cc1ccc(F)c(C(=O)N[C@H]2CCCn3nc(-c4ccnc(C(F)(F)F)c4)cc32)c1]
I-278b
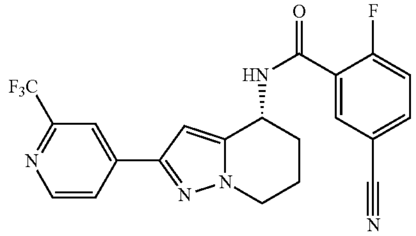 [SMILES: N#Cc1ccc(F)c(C(=O)N[C@@H]2CCCn3nc(-c4ccnc(C(F)(F)F)c4)cc32)c1]
I-279
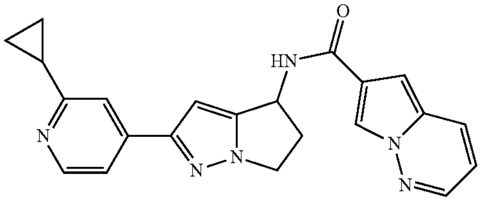 [SMILES: O=C(NC1CCn2nc(-c3ccnc(C4CC4)c3)cc21)c1cc2cccnn2c1]
I-279a
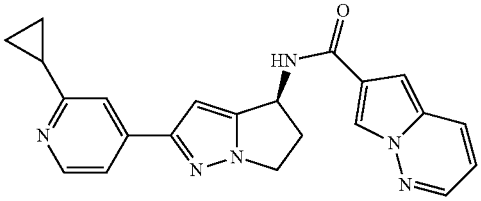 [SMILES: O=C(N[C@H]1CCn2nc(-c3ccnc(C4CC4)c3)cc21)c1cc2cccnn2c1]
I-279b
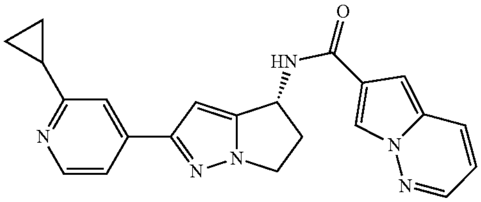 [SMILES: O=C(N[C@@H]1CCn2nc(-c3ccnc(C4CC4)c3)cc21)c1cc2cccnn2c1]

TABLE 1-continued
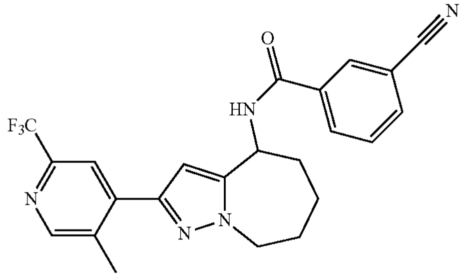 [SMILES: Cc1cnc(C(F)(F)F)cc1-c1cc2n(n1)CCCCC2NC(=O)c1cccc(C#N)c1]
I-280
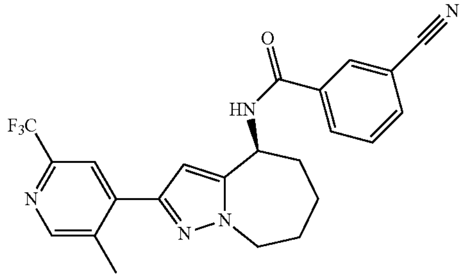 [SMILES: Cc1cnc(C(F)(F)F)cc1-c1cc2n(n1)CCCC[C@@H]2NC(=O)c1cccc(C#N)c1]
I-280a
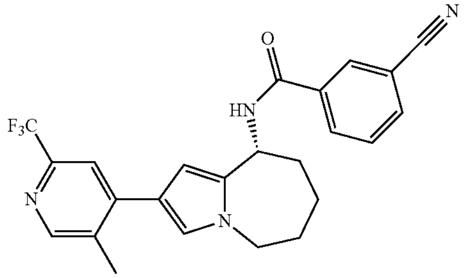 [SMILES: Cc1cnc(C(F)(F)F)cc1-c1cc2n(c1)CCCC[C@H]2NC(=O)c1cccc(C#N)c1]
I-280b
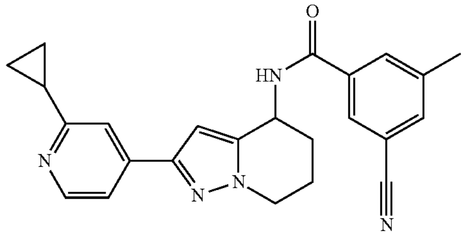 [SMILES: Cc1cc(C#N)cc(C(=O)NC2CCCn3nc(-c4ccnc(C5CC5)c4)cc32)c1]
I-281
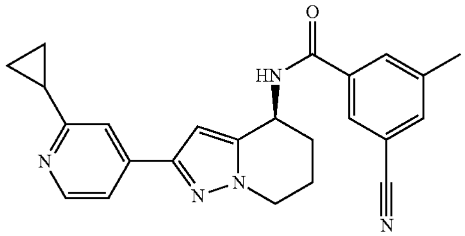 [SMILES: Cc1cc(C#N)cc(C(=O)N[C@H]2CCCn3nc(-c4ccnc(C5CC5)c4)cc32)c1]
I-281a
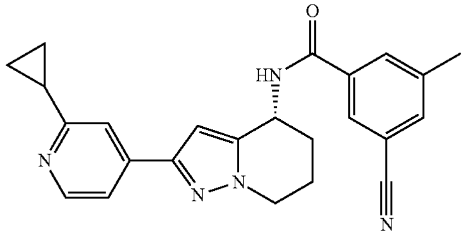 [SMILES: Cc1cc(C#N)cc(C(=O)N[C@@H]2CCCn3nc(-c4ccnc(C5CC5)c4)cc32)c1]
I-281b TABLE 1-continued
I-282
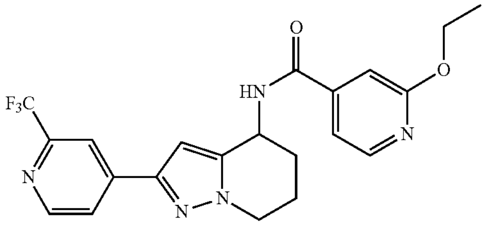 [SMILES: CCOc1cc(C(=O)NC2CCCn3nc(-c4ccnc(C(F)(F)F)c4)cc32)ccn1]
I-282a
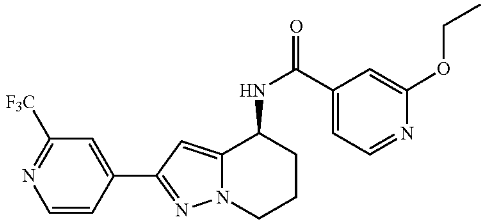 [SMILES: CCOc1cc(C(=O)N[C@H]2CCCn3nc(-c4ccnc(C(F)(F)F)c4)cc32)ccn1]
I-282b
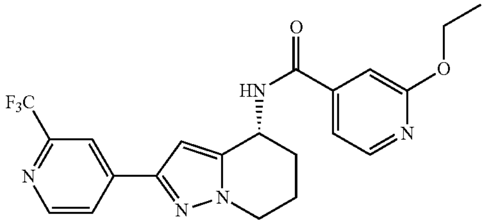 [SMILES: CCOc1cc(C(=O)N[C@@H]2CCCn3nc(-c4ccnc(C(F)(F)F)c4)cc32)ccn1]
I-283
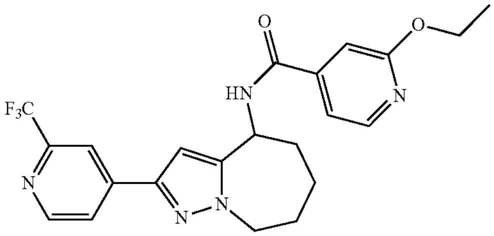 [SMILES: CCOc1cc(C(=O)NC2CCCCn3nc(-c4ccnc(C(F)(F)F)c4)cc32)ccn1]
I-283a
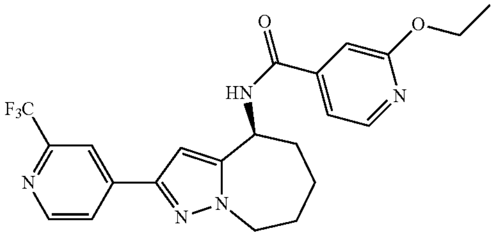 [SMILES: CCOc1cc(C(=O)N[C@H]2CCCCn3nc(-c4ccnc(C(F)(F)F)c4)cc32)ccn1]
I-283b
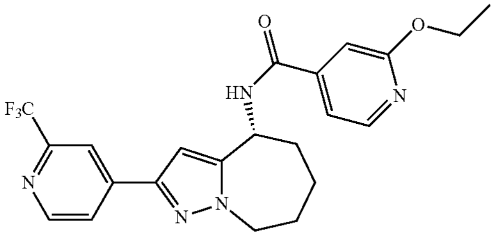 [SMILES: CCOc1cc(C(=O)N[C@@H]2CCCCn3nc(-c4ccnc(C(F)(F)F)c4)cc32)ccn1]

TABLE 1-continued
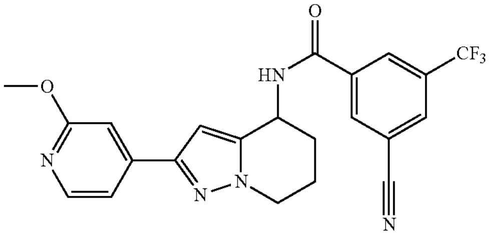 [SMILES: COc1cc(-c2cc3n(n2)CCCC3NC(=O)c2cc(C#N)cc(C(F)(F)F)c2)ccn1]
I-284
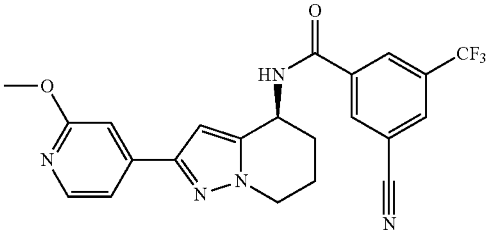 [SMILES: COc1cc(-c2cc3n(n2)CCC[C@@H]3NC(=O)c2cc(C#N)cc(C(F)(F)F)c2)ccn1]
I-284a
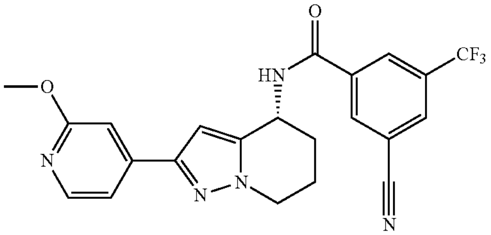 [SMILES: COc1cc(-c2cc3n(n2)CCC[C@H]3NC(=O)c2cc(C#N)cc(C(F)(F)F)c2)ccn1]
I-284b
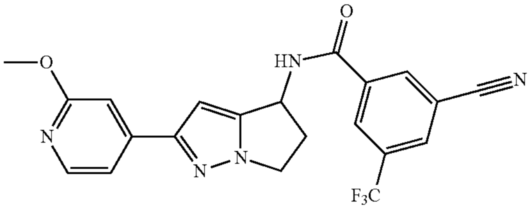 [SMILES: COc1cc(-c2cc3n(n2)CCC3NC(=O)c2cc(C#N)cc(C(F)(F)F)c2)ccn1]
I-285
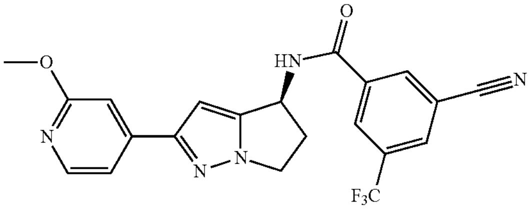 [SMILES: COc1cc(-c2cc3n(n2)CC[C@@H]3NC(=O)c2cc(C#N)cc(C(F)(F)F)c2)ccn1]
I-285a
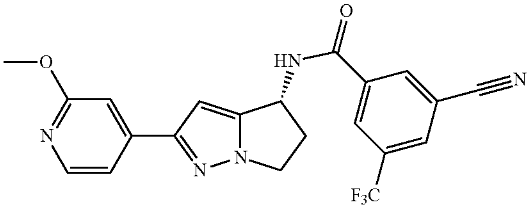 [SMILES: COc1cc(-c2cc3n(n2)CC[C@H]3NC(=O)c2cc(C#N)cc(C(F)(F)F)c2)ccn1]
I-285b
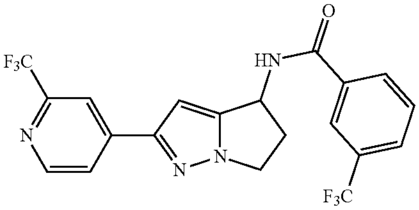
I-286

TABLE 1-continued
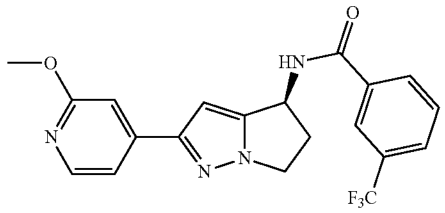 [SMILES: COc1cc(-c2cc3n(n2)CC[C@@H]3NC(=O)c2cccc(C(F)(F)F)c2)ccn1]
I-286a
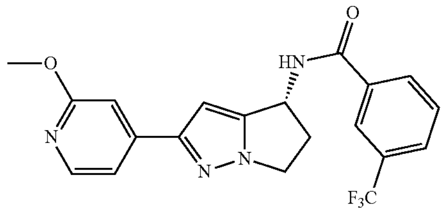 [SMILES: COc1cc(-c2cc3n(n2)CC[C@H]3NC(=O)c2cccc(C(F)(F)F)c2)ccn1]
I-286b
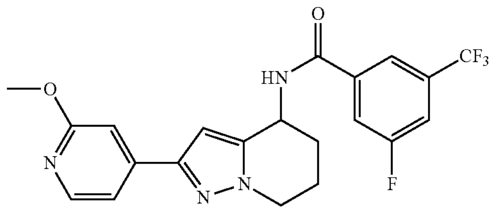 [SMILES: COc1cc(-c2cc3n(n2)CCCC3NC(=O)c2cc(F)cc(C(F)(F)F)c2)ccn1]
I-287
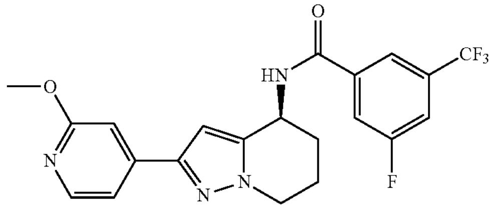 [SMILES: COc1cc(-c2cc3n(n2)CCC[C@@H]3NC(=O)c2cc(F)cc(C(F)(F)F)c2)ccn1]
I-287a
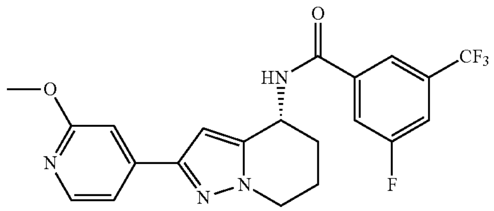 [SMILES: COc1cc(-c2cc3n(n2)CCC[C@H]3NC(=O)c2cc(F)cc(C(F)(F)F)c2)ccn1]
I-287b
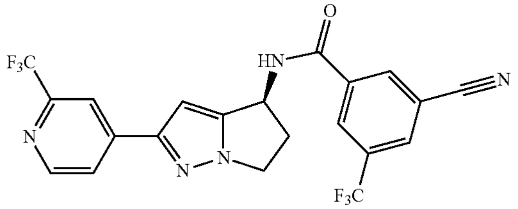 [SMILES: N#Cc1cc(C(=O)N[C@H]2CCn3nc(-c4ccnc(C(F)(F)F)c4)cc32)cc(C(F)(F)F)c1]
I-288
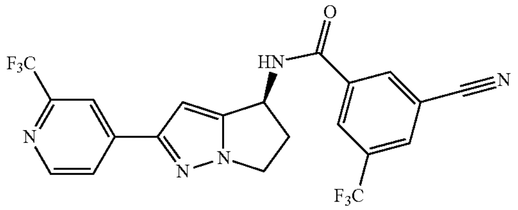 [SMILES: N#Cc1cc(C(=O)N[C@H]2CCn3nc(-c4ccnc(C(F)(F)F)c4)cc32)cc(C(F)(F)F)c1]
I-288a TABLE 1-continued
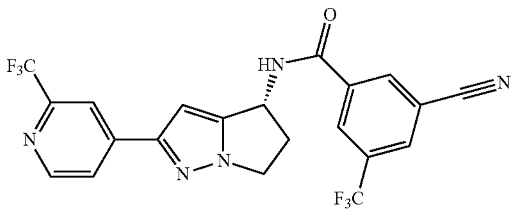 [SMILES: N#Cc1cc(C(=O)N[C@@H]2CCn3nc(-c4ccnc(C(F)(F)F)c4)cc32)cc(C(F)(F)F)c1]
I-288b
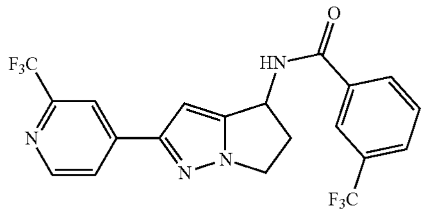 [SMILES: O=C(NC1CCn2nc(-c3ccnc(C(F)(F)F)c3)cc21)c1cccc(C(F)(F)F)c1]
I-289
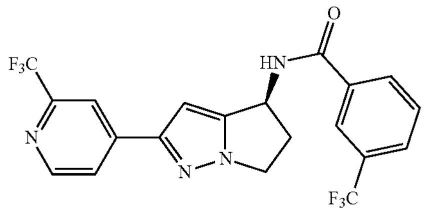 [SMILES: O=C(N[C@H]1CCn2nc(-c3ccnc(C(F)(F)F)c3)cc21)c1cccc(C(F)(F)F)c1]
I-289a
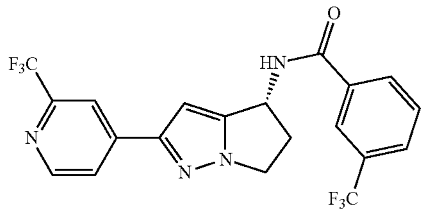 [SMILES: O=C(N[C@@H]1CCn2nc(-c3ccnc(C(F)(F)F)c3)cc21)c1cccc(C(F)(F)F)c1]
I-289b
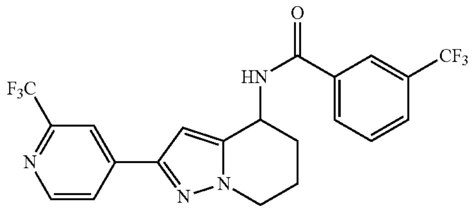 [SMILES: O=C(NC1CCCn2nc(-c3ccnc(C(F)(F)F)c3)cc21)c1cccc(C(F)(F)F)c1]
I-290
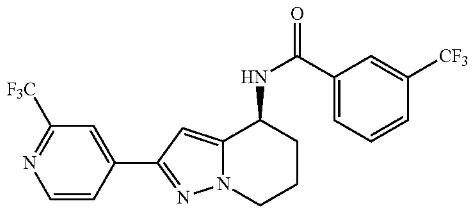 [SMILES: O=C(N[C@H]1CCCn2nc(-c3ccnc(C(F)(F)F)c3)cc21)c1cccc(C(F)(F)F)c1]
I-290a
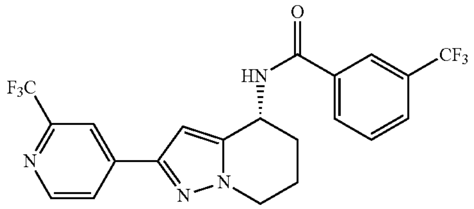 [SMILES: O=C(N[C@@H]1CCCn2nc(-c3ccnc(C(F)(F)F)c3)cc21)c1cccc(C(F)(F)F)c1]
I-290b TABLE 1-continued
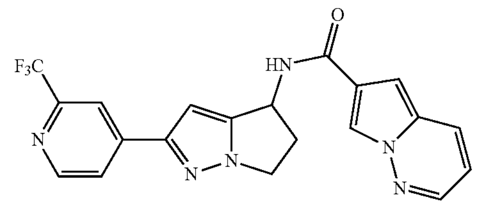 [SMILES: O=C(NC1CCn2nc(-c3ccnc(C(F)(F)F)c3)cc21)c1cc2cccnn2c1]
I-291
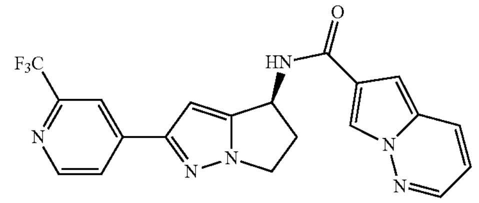 [SMILES: O=C(N[C@H]1CCn2nc(-c3ccnc(C(F)(F)F)c3)cc21)c1cc2cccnn2c1]
I-291a
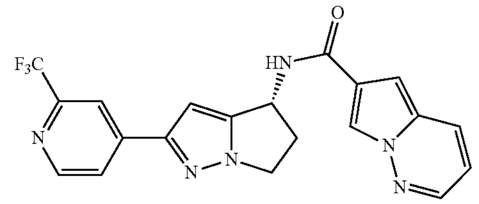 [SMILES: O=C(N[C@@H]1CCn2nc(-c3ccnc(C(F)(F)F)c3)cc21)c1cc2cccnn2c1]
I-291b
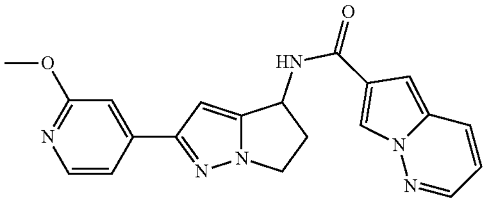 [SMILES: COc1cc(-c2cc3n(n2)CCC3NC(=O)c2cc3cccnn3c2)ccn1]
I-292
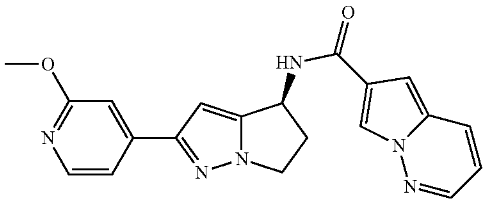 [SMILES: COc1cc(-c2cc3n(n2)CC[C@@H]3NC(=O)c2cc3cccnn3c2)ccn1]
I-292a
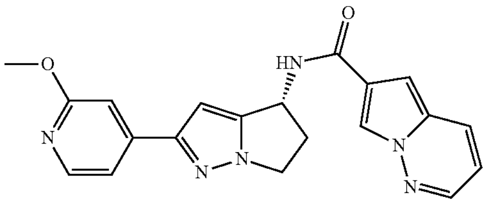 [SMILES: COc1cc(-c2cc3n(n2)CC[C@H]3NC(=O)c2cc3cccnn3c2)ccn1]
I-292b
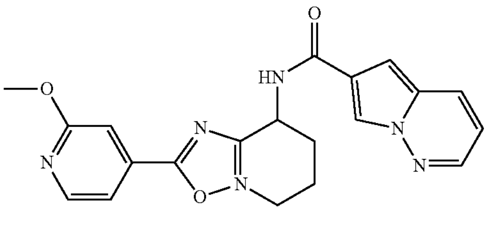
I-293

TABLE 1-continued
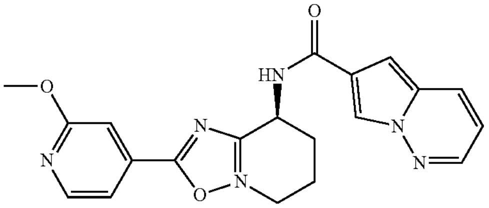
I-293a
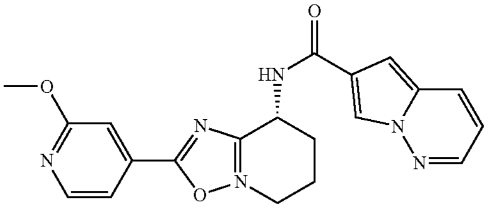
I-293b
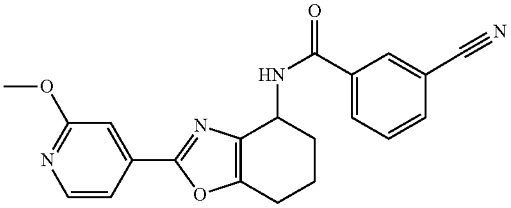 [SMILES: COc1cc(-c2nc3c(o2)CCCC3NC(=O)c2cccc(C#N)c2)ccn1]
I-294
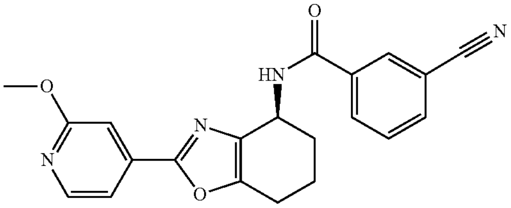 [SMILES: COc1cc(-c2nc3c(o2)CCC[C@@H]3NC(=O)c2cccc(C#N)c2)ccn1]
I-294a
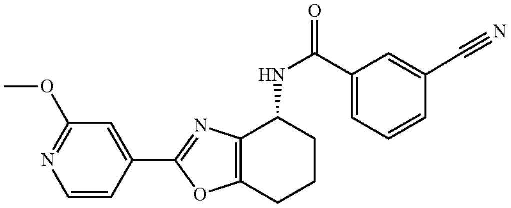 [SMILES: COc1cc(-c2nc3c(o2)CCC[C@H]3NC(=O)c2cccc(C#N)c2)ccn1]
I-294b
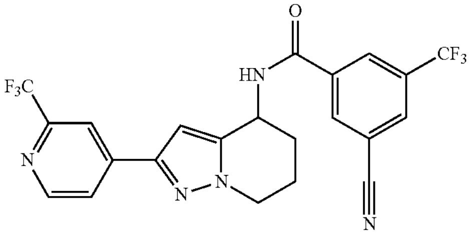 [SMILES: N#Cc1cc(C(=O)NC2CCCn3nc(-c4ccnc(C(F)(F)F)c4)cc32)cc(C(F)(F)F)c1]
I-295
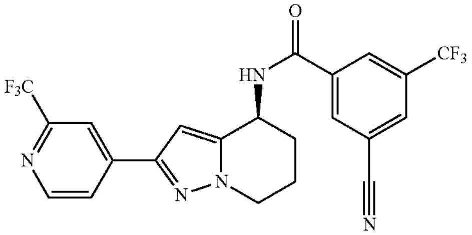 [SMILES: N#Cc1cc(C(=O)N[C@H]2CCCn3nc(-c4ccnc(C(F)(F)F)c4)cc32)cc(C(F)(F)F)c1]
I-295a TABLE 1-continued
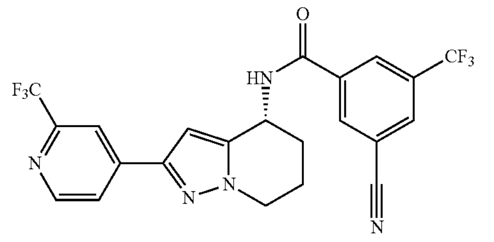 [SMILES: N#Cc1cc(C(=O)N[C@@H]2CCCn3nc(-c4ccnc(C(F)(F)F)c4)cc32)cc(C(F)(F)F)c1]
I-295b
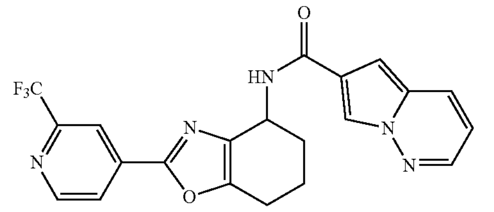 [SMILES: O=C(NC1CCCc2oc(-c3ccnc(C(F)(F)F)c3)nc21)c1cc2cccnn2c1]
I-296
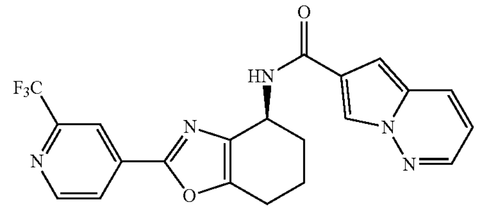 [SMILES: O=C(N[C@H]1CCCc2oc(-c3ccnc(C(F)(F)F)c3)nc21)c1cc2cccnn2c1]
I-296a
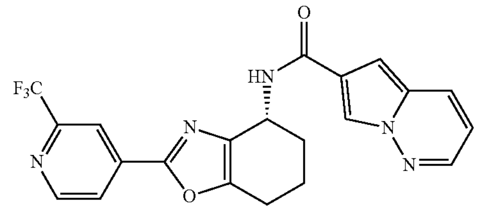 [SMILES: O=C(N[C@@H]1CCCc2oc(-c3ccnc(C(F)(F)F)c3)nc21)c1cc2cccnn2c1]
I-296b
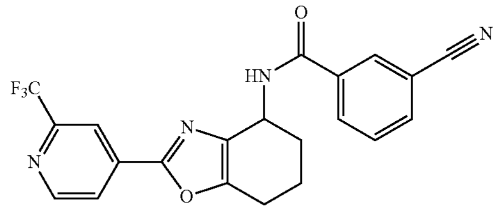 [SMILES: N#Cc1cccc(C(=O)NC2CCCc3oc(-c4ccnc(C(F)(F)F)c4)nc32)c1]
I-297
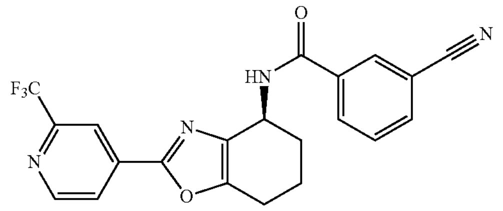 [SMILES: N#Cc1cccc(C(=O)N[C@H]2CCCc3oc(-c4ccnc(C(F)(F)F)c4)nc32)c1]
I-297a
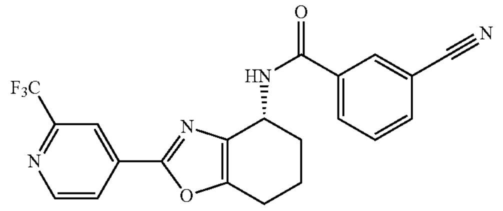 [SMILES: N#Cc1cccc(C(=O)N[C@@H]2CCCc3oc(-c4ccnc(C(F)(F)F)c4)nc32)c1]
I-297b TABLE 1-continued
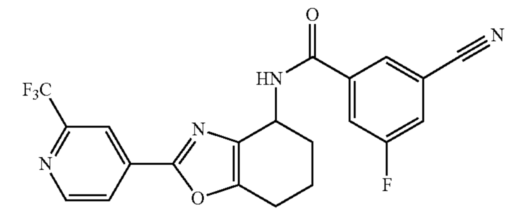 [SMILES: N#Cc1cc(F)cc(C(=O)NC2CCCc3oc(-c4ccnc(C(F)(F)F)c4)nc32)c1]
I-298
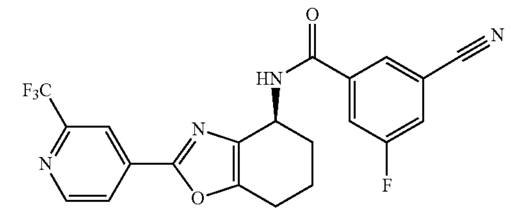 [SMILES: N#Cc1cc(F)cc(C(=O)N[C@H]2CCCc3oc(-c4ccnc(C(F)(F)F)c4)nc32)c1]
I-298a
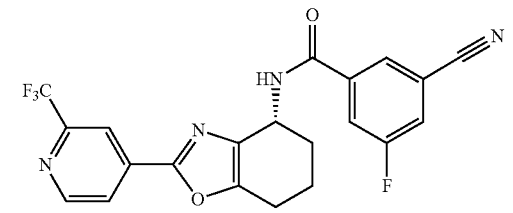
I-298b
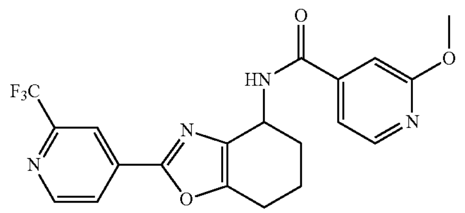 [SMILES: COc1cc(C(=O)NC2CCCc3oc(-c4ccnc(C(F)(F)F)c4)nc32)ccn1]
I-299
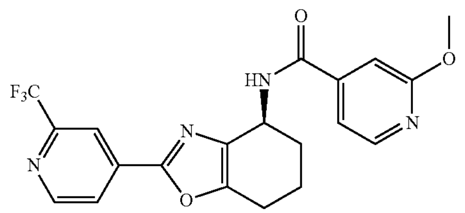 [SMILES: COc1cc(C(=O)N[C@H]2CCCc3oc(-c4ccnc(C(F)(F)F)c4)nc32)ccn1]
I-299a
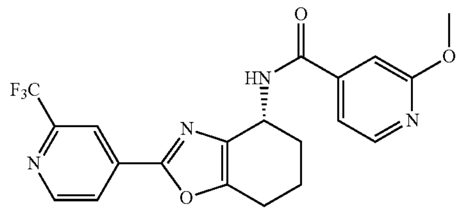 [SMILES: COc1cc(C(=O)N[C@@H]2CCCc3oc(-c4ccnc(C(F)(F)F)c4)nc32)ccn1]
I-299b
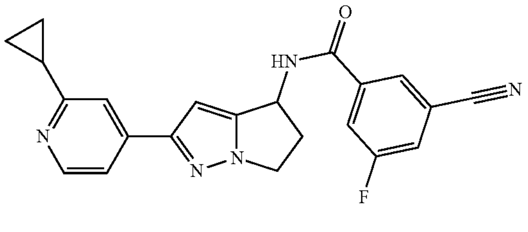 [SMILES: N#Cc1cc(F)cc(C(=O)NC2CCn3nc(-c4ccnc(C5CC5)c4)cc32)c1]
I-300

TABLE 1-continued
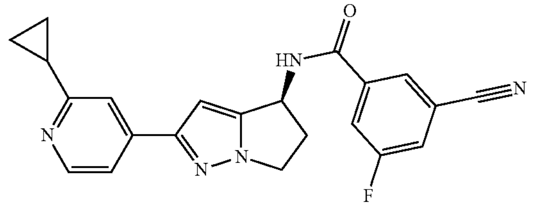 [SMILES: N#Cc1cc(F)cc(C(=O)N[C@H]2CCn3nc(-c4ccnc(C5CC5)c4)cc32)c1]
I-300a
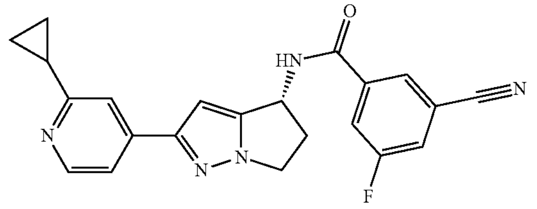 [SMILES: N#Cc1cc(F)cc(C(=O)N[C@@H]2CCn3nc(-c4ccnc(C5CC5)c4)cc32)c1]
I-300b
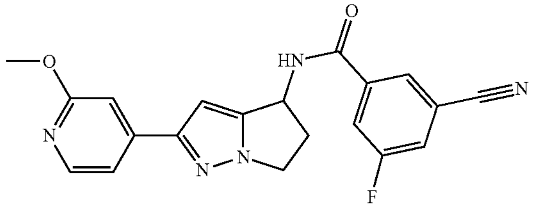 [SMILES: COc1cc(-c2cc3n(n2)CCC3NC(=O)c2cc(F)cc(C#N)c2)ccn1]
I-301
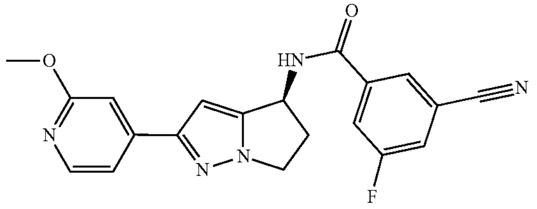 [SMILES: COc1cc(-c2cc3n(n2)CC[C@@H]3NC(=O)c2cc(F)cc(C#N)c2)ccn1]
I-301a
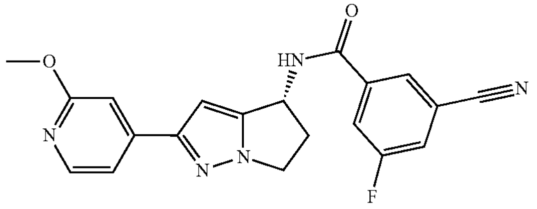 [SMILES: COc1cc(-c2cc3n(n2)CC[C@H]3NC(=O)c2cc(F)cc(C#N)c2)ccn1]
I-301b
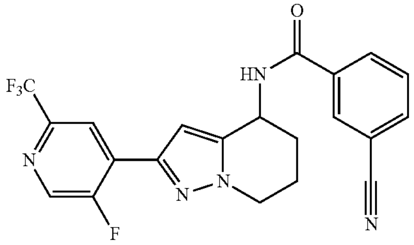 [SMILES: N#Cc1cccc(C(=O)NC2CCCn3nc(-c4cc(C(F)(F)F)ncc4F)cc32)c1]
I-302
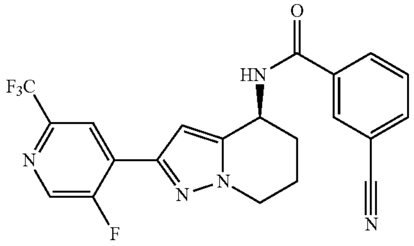 [SMILES: N#Cc1cccc(C(=O)N[C@H]2CCCn3nc(-c4cc(C(F)(F)F)ncc4F)cc32)c1]
I-302a TABLE 1-continued
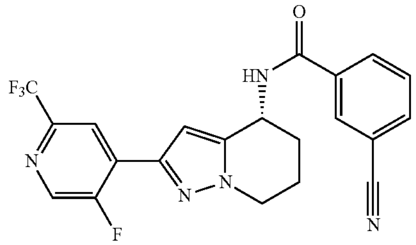
I-302b
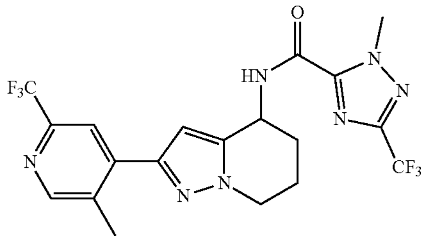 [SMILES: Cc1cnc(C(F)(F)F)cc1-c1cc2n(n1)CCCC2NC(=O)c1nc(C(F)(F)F)nn1C]
I-303
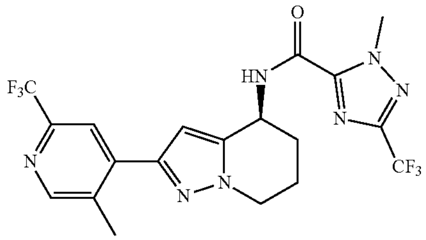 [SMILES: Cc1cnc(C(F)(F)F)cc1-c1cc2n(n1)CCC[C@@H]2NC(=O)c1nc(C(F)(F)F)nn1C]
I-303a
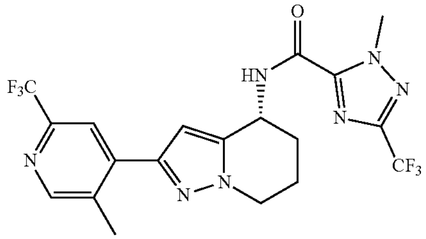 [SMILES: Cc1cnc(C(F)(F)F)cc1-c1cc2n(n1)CCC[C@H]2NC(=O)c1nc(C(F)(F)F)nn1C]
I-303b
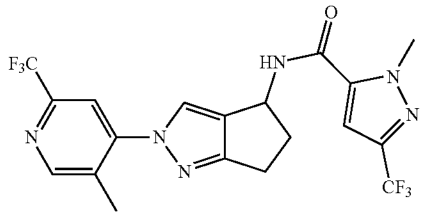 [SMILES: Cc1cnc(C(F)(F)F)cc1-n1cc2c(n1)CCC2NC(=O)c1cc(C(F)(F)F)nn1C]
I-304
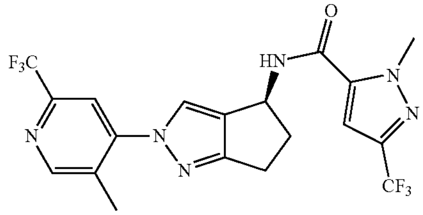 [SMILES: Cc1cnc(C(F)(F)F)cc1-n1cc2c(n1)CC[C@@H]2NC(=O)c1cc(C(F)(F)F)nn1C]
I-304a TABLE 1-continued
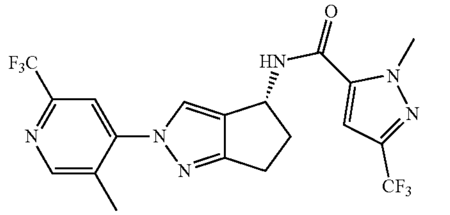 [SMILES: Cc1cnc(C(F)(F)F)cc1-n1cc2c(n1)CC[C@H]2NC(=O)c1cc(C(F)(F)F)nn1C]
I-304b
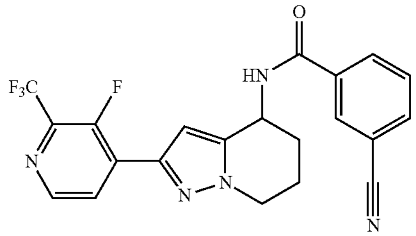 [SMILES: N#Cc1cccc(C(=O)NC2CCCn3nc(-c4ccnc(C(F)(F)F)c4F)cc32)c1]
I-305
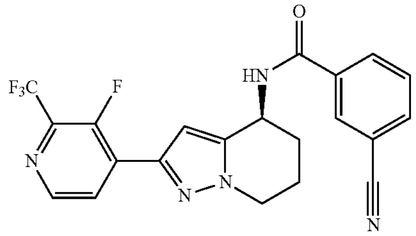 [SMILES: N#Cc1cccc(C(=O)N[C@H]2CCCn3nc(-c4ccnc(C(F)(F)F)c4F)cc32)c1]
I-305a
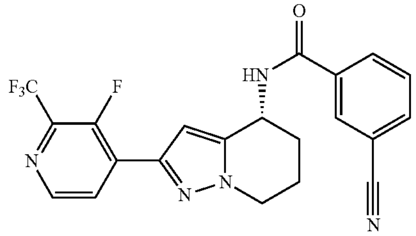 [SMILES: N#Cc1cccc(C(=O)N[C@@H]2CCCn3nc(-c4ccnc(C(F)(F)F)c4F)cc32)c1]
I-305b
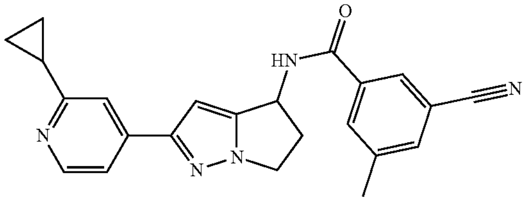 [SMILES: Cc1cc(C#N)cc(C(=O)NC2CCn3nc(-c4ccnc(C5CC5)c4)cc32)c1]
I-306
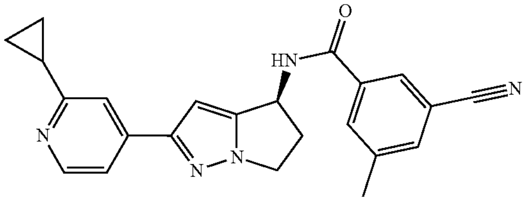 [SMILES: Cc1cc(C#N)cc(C(=O)N[C@H]2CCn3nc(-c4ccnc(C5CC5)c4)cc32)c1]
I-306a
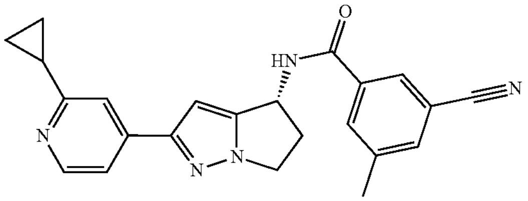 [SMILES: Cc1cc(C#N)cc(C(=O)N[C@@H]2CCn3nc(-c4ccnc(C5CC5)c4)cc32)c1]
I-306b TABLE 1-continued
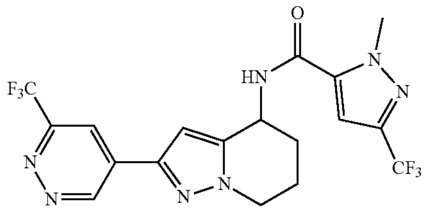
I-307
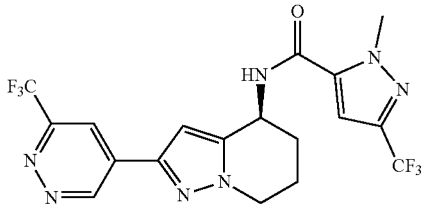
I-307a
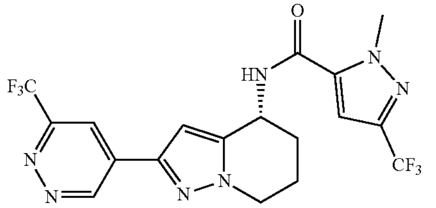
I-307b
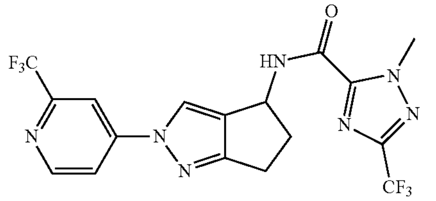
I-308
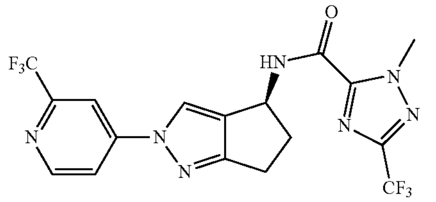
I-308a
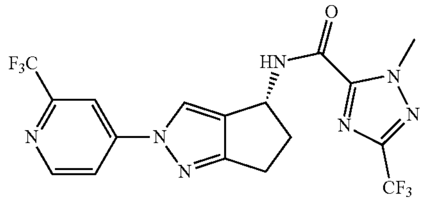
I-308b
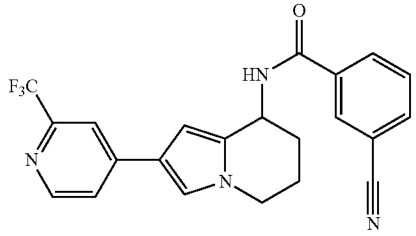 [SMILES: N#Cc1cccc(C(=O)NC2CCCn3cc(-c4ccnc(C(F)(F)F)c4)cc32)c1]
I-309

TABLE 1-continued
I-309a
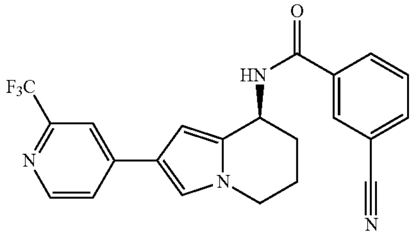 [SMILES: N#Cc1cccc(C(=O)N[C@H]2CCCn3cc(-c4ccnc(C(F)(F)F)c4)cc32)c1]
I-309b
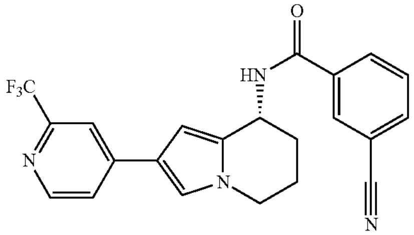 [SMILES: N#Cc1cccc(C(=O)N[C@@H]2CCCn3cc(-c4ccnc(C(F)(F)F)c4)cc32)c1]
I-310
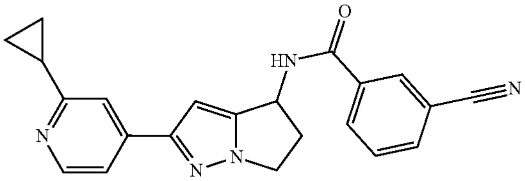 [SMILES: N#Cc1cccc(C(=O)NC2CCn3nc(-c4ccnc(C5CC5)c4)cc32)c1]
I-310a
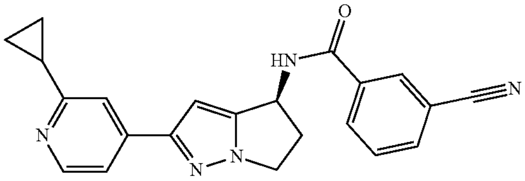 [SMILES: N#Cc1cccc(C(=O)N[C@H]2CCn3nc(-c4ccnc(C5CC5)c4)cc32)c1]
I-310b
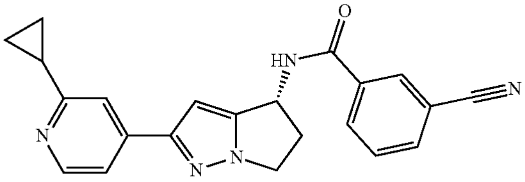 [SMILES: N#Cc1cccc(C(=O)N[C@@H]2CCn3nc(-c4ccnc(C5CC5)c4)cc32)c1]
I-311
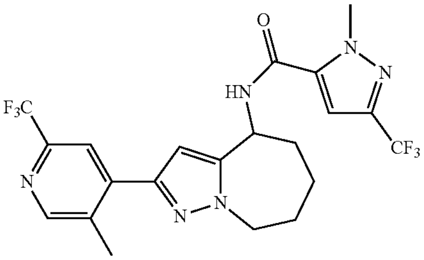 [SMILES: Cc1cnc(C(F)(F)F)cc1-c1cc2n(n1)CCCCC2NC(=O)c1cc(C(F)(F)F)nn1C]
I-311a
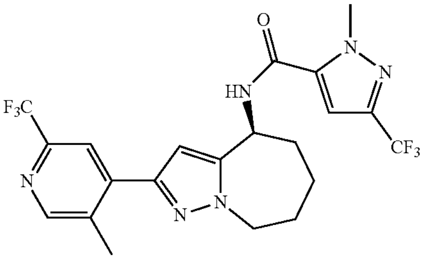 [SMILES: Cc1cnc(C(F)(F)F)cc1-c1cc2n(n1)CCCC[C@@H]2NC(=O)c1cc(C(F)(F)F)nn1C]

TABLE 1-continued
I-311b
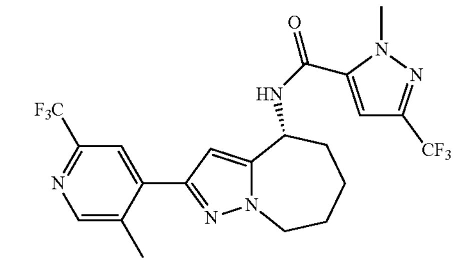 [SMILES: Cc1cnc(C(F)(F)F)cc1-c1cc2n(n1)CCCC[C@H]2NC(=O)c1cc(C(F)(F)F)nn1C]
I-312
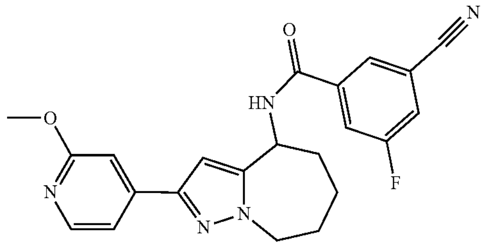 [SMILES: COc1cc(-c2cc3n(n2)CCCCC3NC(=O)c2cc(F)cc(C#N)c2)ccn1]
I-312a
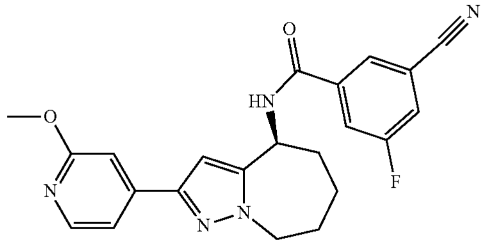 [SMILES: COc1cc(-c2cc3n(n2)CCCC[C@@H]3NC(=O)c2cc(F)cc(C#N)c2)ccn1]
I-312b
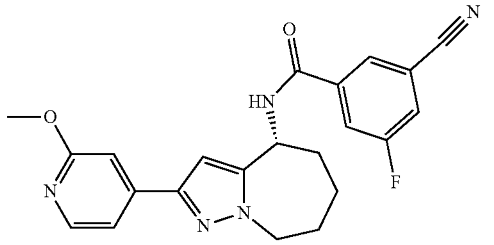 [SMILES: COc1cc(-c2cc3n(n2)CCCC[C@H]3NC(=O)c2cc(F)cc(C#N)c2)ccn1]
I-313
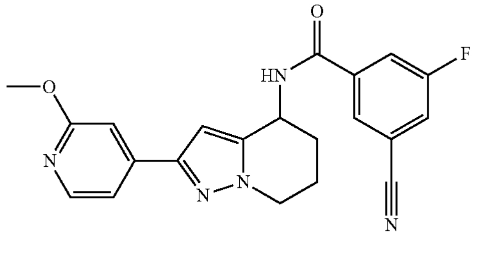 [SMILES: COc1cc(-c2cc3n(n2)CCCC3NC(=O)c2cc(F)cc(C#N)c2)ccn1]
I-313a
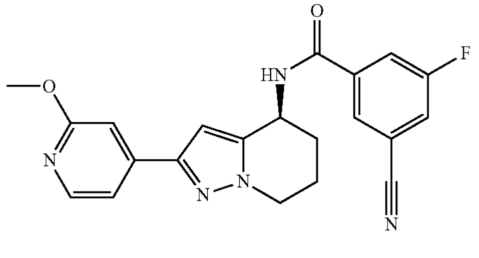 [SMILES: COc1cc(-c2cc3n(n2)CCC[C@@H]3NC(=O)c2cc(F)cc(C#N)c2)ccn1]

TABLE 1-continued
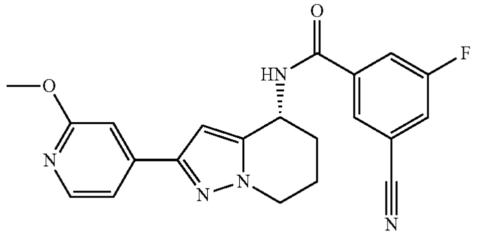 [SMILES: COc1cc(-c2cc3n(n2)CCC[C@H]3NC(=O)c2cc(F)cc(C#N)c2)ccn1]
I-313b
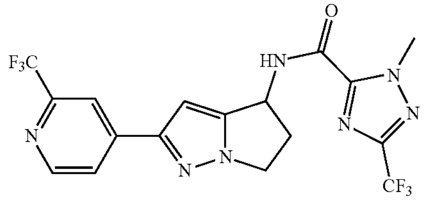 [SMILES: Cn1nc(C(F)(F)F)nc1C(=O)NC1CCn2nc(-c3ccnc(C(F)(F)F)c3)cc21]
I-314
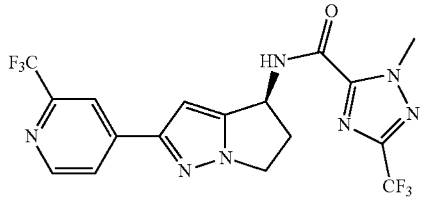 [SMILES: Cn1nc(C(F)(F)F)nc1C(=O)N[C@H]1CCn2nc(-c3ccnc(C(F)(F)F)c3)cc21]
I-314a
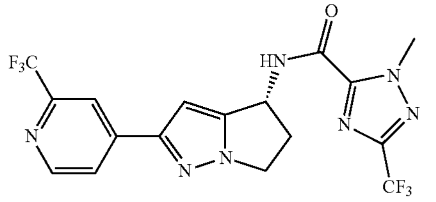 [SMILES: Cn1nc(C(F)(F)F)nc1C(=O)N[C@@H]1CCn2nc(-c3ccnc(C(F)(F)F)c3)cc21]
I-314b
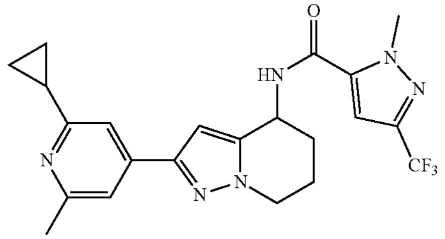 [SMILES: Cc1cc(-c2cc3n(n2)CCCC3NC(=O)c2cc(C(F)(F)F)nn2C)cc(C2CC2)n1]
I-315
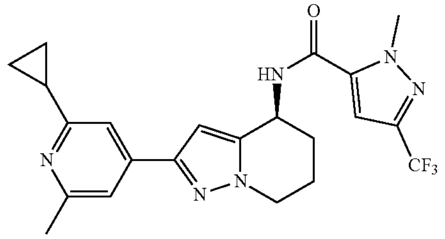 [SMILES: Cc1cc(-c2cc3n(n2)CCC[C@@H]3NC(=O)c2cc(C(F)(F)F)nn2C)cc(C2CC2)n1]
I-315a
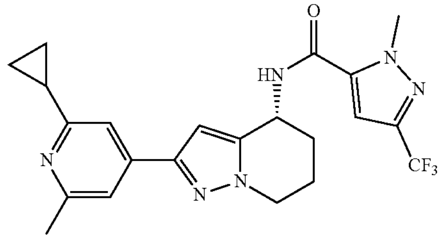 [SMILES: Cc1cc(-c2cc3n(n2)CCC[C@H]3NC(=O)c2cc(C(F)(F)F)nn2C)cc(C2CC2)n1]
I-315b TABLE 1-continued
I-316
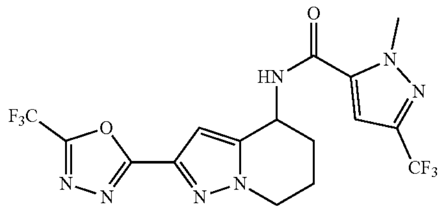
I-316a
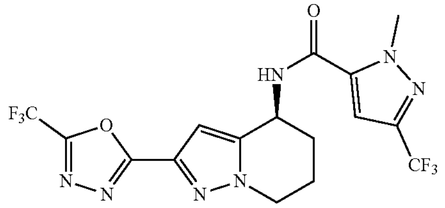 [SMILES: Cn1nc(C(F)(F)F)cc1C(=O)N[C@H]1CCCn2nc(-c3nnc(C(F)(F)F)o3)cc21]
I-316b
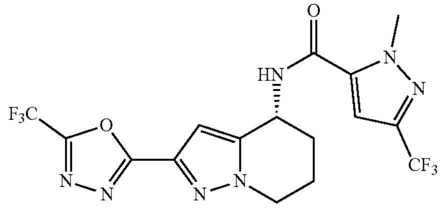 [SMILES: Cn1nc(C(F)(F)F)cc1C(=O)N[C@@H]1CCCn2nc(-c3nnc(C(F)(F)F)o3)cc21]
I-317
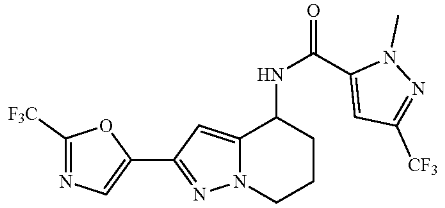
I-317a
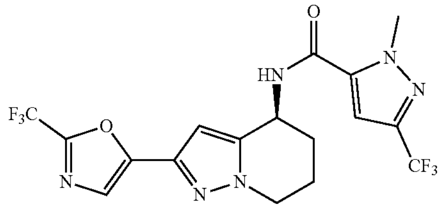 [SMILES: Cn1nc(C(F)(F)F)cc1C(=O)N[C@H]1CCCn2nc(-c3cnc(C(F)(F)F)o3)cc21]
I-317b
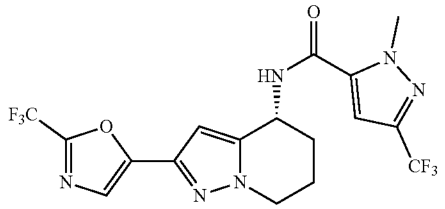 [SMILES: Cn1nc(C(F)(F)F)cc1C(=O)N[C@@H]1CCCn2nc(-c3cnc(C(F)(F)F)o3)cc21]
I-318
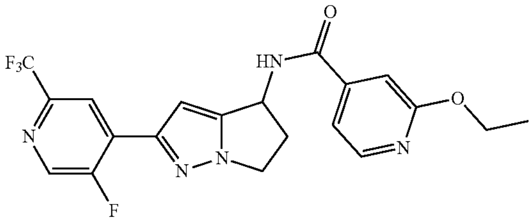 [SMILES: CCOc1cc(C(=O)NC2CCn3nc(-c4cc(C(F)(F)F)ncc4F)cc32)ccn1]

TABLE 1-continued
I-318a
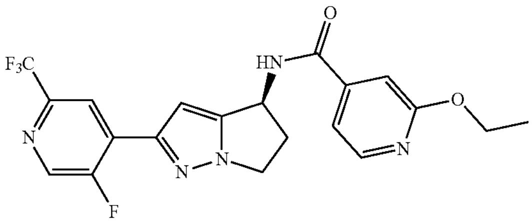 [SMILES: CCOc1cc(C(=O)N[C@H]2CCn3nc(-c4cc(C(F)(F)F)ncc4F)cc32)ccn1]
I-318b
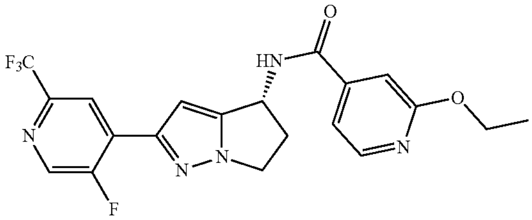
I-319
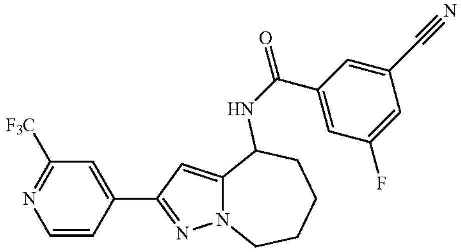 [SMILES: N#Cc1cc(F)cc(C(=O)NC2CCCCn3nc(-c4ccnc(C(F)(F)F)c4)cc32)c1]
I-319a
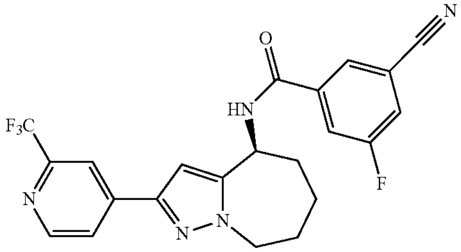 [SMILES: N#Cc1cc(F)cc(C(=O)N[C@H]2CCCCn3nc(-c4ccnc(C(F)(F)F)c4)cc32)c1]
I-319b
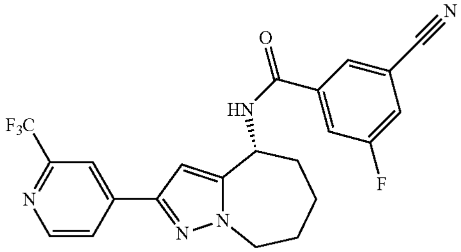 [SMILES: N#Cc1cc(F)cc(C(=O)N[C@@H]2CCCCn3nc(-c4ccnc(C(F)(F)F)c4)cc32)c1]
I-320
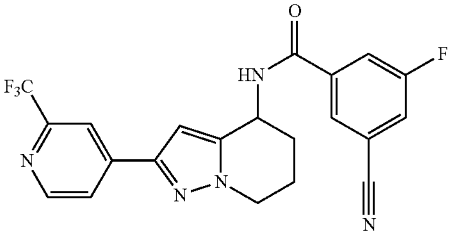 [SMILES: N#Cc1cc(F)cc(C(=O)NC2CCCn3nc(-c4ccnc(C(F)(F)F)c4)cc32)c1]

TABLE 1-continued
I-320a
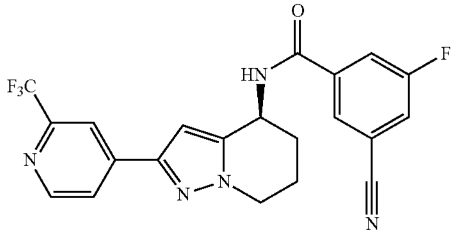 [SMILES: N#Cc1cc(F)cc(C(=O)N[C@H]2CCCn3nc(-c4ccnc(C(F)(F)F)c4)cc32)c1]
I-320b
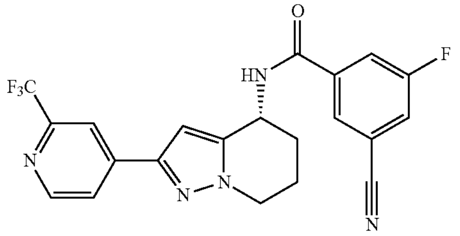 [SMILES: N#Cc1cc(F)cc(C(=O)N[C@@H]2CCCn3nc(-c4ccnc(C(F)(F)F)c4)cc32)c1]
I-321
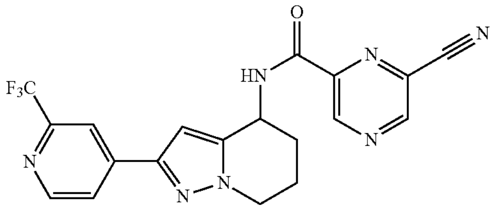 [SMILES: N#Cc1cncc(C(=O)NC2CCCn3nc(-c4ccnc(C(F)(F)F)c4)cc32)n1]
I-321a
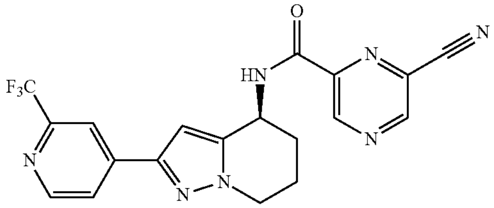
I-321b
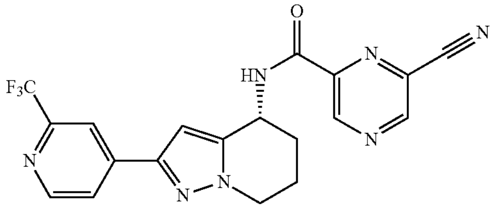 [SMILES: N#Cc1cncc(C(=O)N[C@@H]2CCCn3nc(-c4ccnc(C(F)(F)F)c4)cc32)n1]
I-322
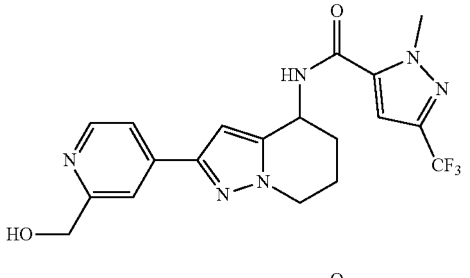
I-322a
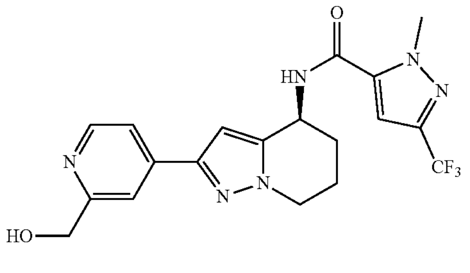 [SMILES: Cn1nc(C(F)(F)F)cc1C(=O)N[C@H]1CCCn2nc(-c3ccnc(CO)c3)cc21]

TABLE 1-continued
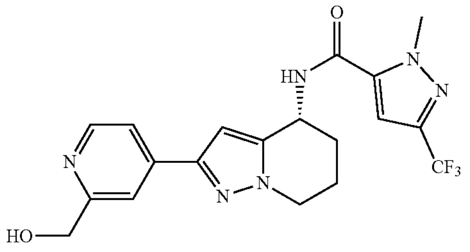 [SMILES: Cn1nc(C(F)(F)F)cc1C(=O)N[C@@H]1CCCn2nc(-c3ccnc(CO)c3)cc21]
I-322b
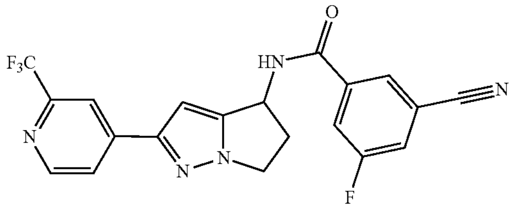 [SMILES: N#Cc1cc(F)cc(C(=O)NC2CCn3nc(-c4ccnc(C(F)(F)F)c4)cc32)c1]
I-323
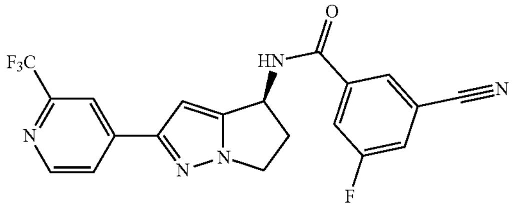 [SMILES: N#Cc1cc(F)cc(C(=O)N[C@H]2CCn3nc(-c4ccnc(C(F)(F)F)c4)cc32)c1]
I-323a
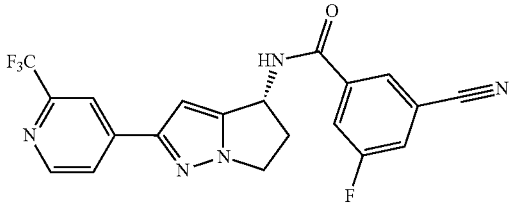 [SMILES: N#Cc1cc(F)cc(C(=O)N[C@@H]2CCn3nc(-c4ccnc(C(F)(F)F)c4)cc32)c1]
I-323b
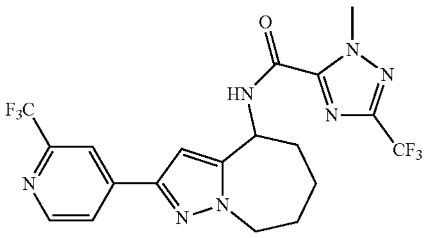 [SMILES: Cn1nc(C(F)(F)F)nc1C(=O)NC1CCCCn2nc(-c3ccnc(C(F)(F)F)c3)cc21]
I-324
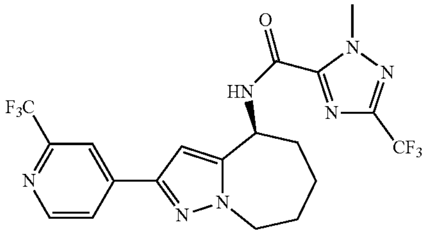 [SMILES: Cn1nc(C(F)(F)F)nc1C(=O)N[C@H]1CCCCn2nc(-c3ccnc(C(F)(F)F)c3)cc21]
I-324a
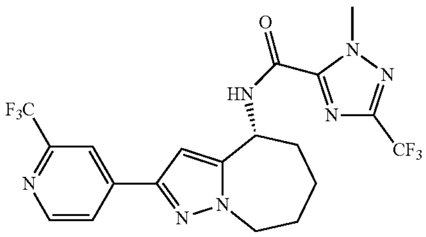 [SMILES: Cn1nc(C(F)(F)F)nc1C(=O)N[C@@H]1CCCCn2nc(-c3ccnc(C(F)(F)F)c3)cc21]
I-324b TABLE 1-continued
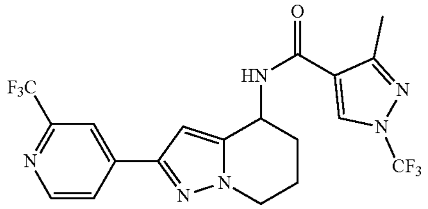
I-325
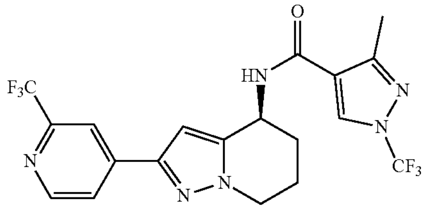
I-325a
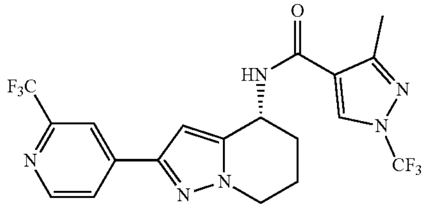
I-325b
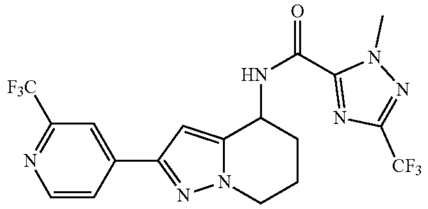
I-326
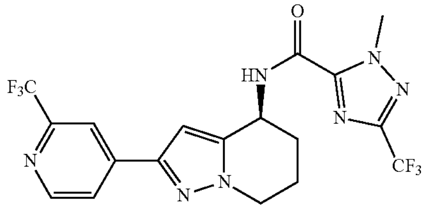
I-326a
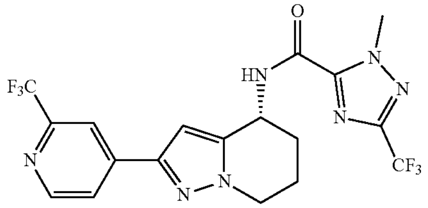
I-326b
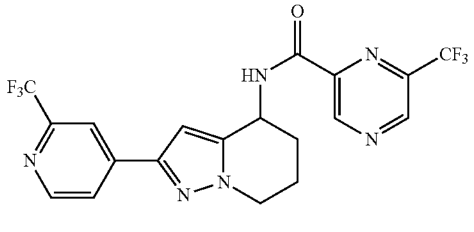
I-327

TABLE 1-continued
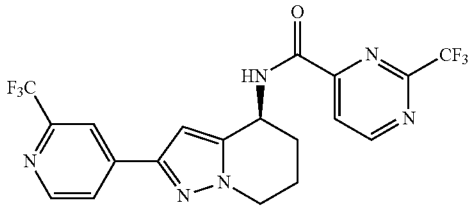 [SMILES: O=C(N[C@H]1CCCn2nc(-c3ccnc(C(F)(F)F)c3)cc21)c1ccnc(C(F)(F)F)n1]
I-327a
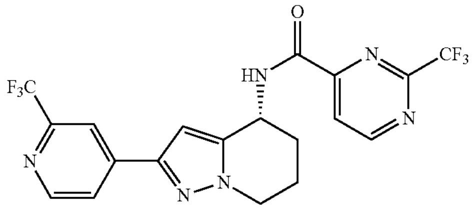 [SMILES: O=C(N[C@@H]1CCCn2nc(-c3ccnc(C(F)(F)F)c3)cc21)c1ccnc(C(F)(F)F)n1]
I-327b
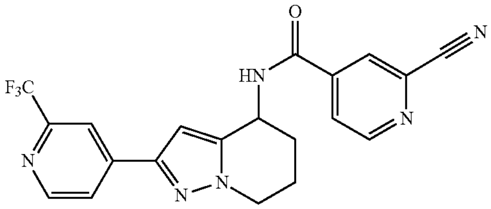 [SMILES: N#Cc1cc(C(=O)NC2CCCn3nc(-c4ccnc(C(F)(F)F)c4)cc32)ccn1]
I-328
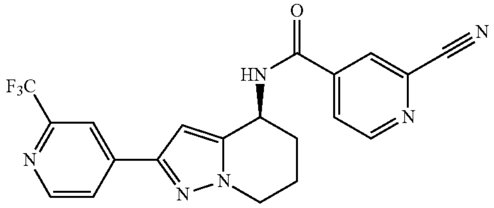 [SMILES: N#Cc1cc(C(=O)N[C@H]2CCCn3nc(-c4ccnc(C(F)(F)F)c4)cc32)ccn1]
I-328a
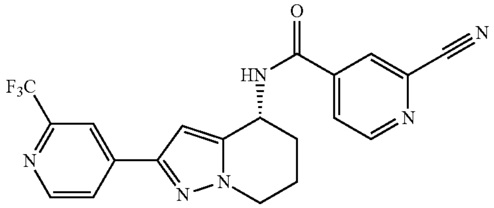 [SMILES: N#Cc1cc(C(=O)N[C@@H]2CCCn3nc(-c4ccnc(C(F)(F)F)c4)cc32)ccn1]
I-328b
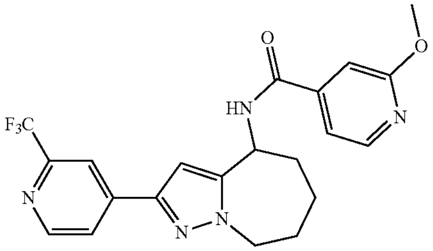
I-329
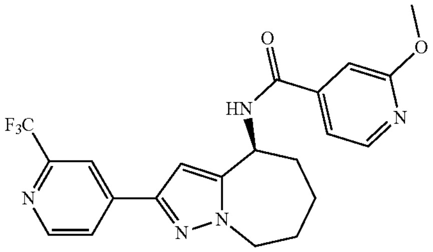 [SMILES: COc1cc(C(=O)N[C@H]2CCCCn3nc(-c4ccnc(C(F)(F)F)c4)cc32)ccn1]
I-329a TABLE 1-continued
I-329b
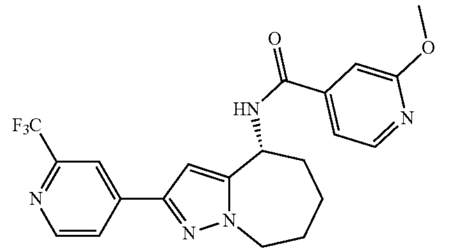 [SMILES: COc1cc(C(=O)N[C@@H]2CCCCn3nc(-c4ccnc(C(F)(F)F)c4)cc32)ccn1]
I-330
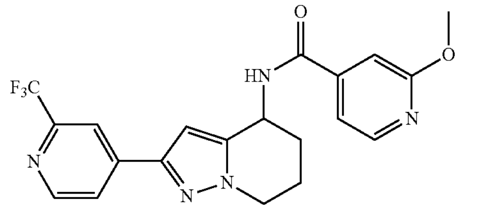 [SMILES: COc1cc(C(=O)NC2CCCn3nc(-c4ccnc(C(F)(F)F)c4)cc32)ccn1]
I-330a
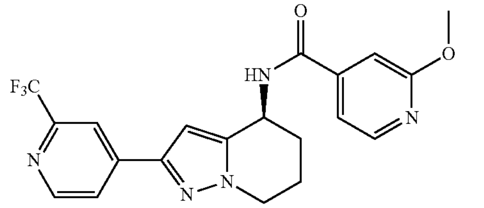 [SMILES: COc1cc(C(=O)N[C@H]2CCCn3nc(-c4ccnc(C(F)(F)F)c4)cc32)ccn1]
I-330b
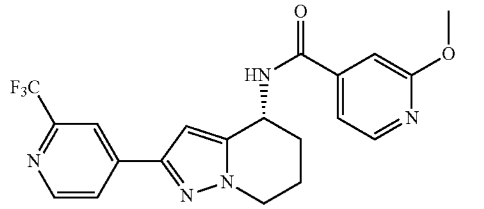
I-331
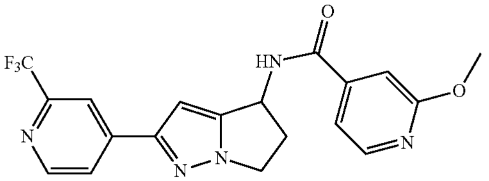 [SMILES: COc1cc(C(=O)NC2CCn3nc(-c4ccnc(C(F)(F)F)c4)cc32)ccn1]
I-331a
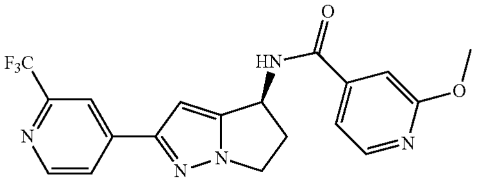 [SMILES: COc1cc(C(=O)N[C@H]2CCn3nc(-c4ccnc(C(F)(F)F)c4)cc32)ccn1]
I-331b
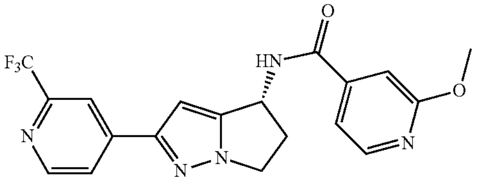 [SMILES: COc1cc(C(=O)N[C@@H]2CCn3nc(-c4ccnc(C(F)(F)F)c4)cc32)ccn1]

TABLE 1-continued
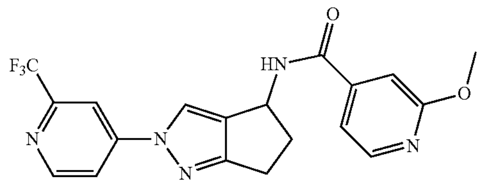 [SMILES: COc1cc(C(=O)NC2CCc3nn(-c4ccnc(C(F)(F)F)c4)cc32)ccn1]
I-332
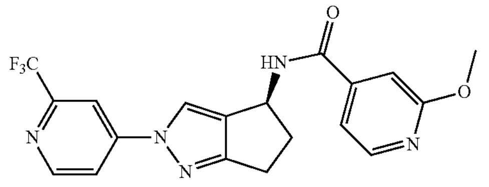 [SMILES: COc1cc(C(=O)N[C@H]2CCc3nn(-c4ccnc(C(F)(F)F)c4)cc32)ccn1]
I-332a
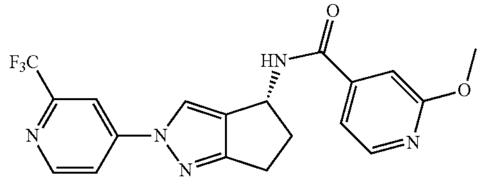 [SMILES: COc1cc(C(=O)N[C@@H]2CCc3nn(-c4ccnc(C(F)(F)F)c4)cc32)ccn1]
I-332b
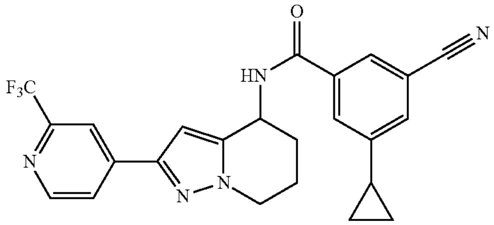 [SMILES: N#Cc1cc(C(=O)NC2CCCn3nc(-c4ccnc(C(F)(F)F)c4)cc32)cc(C2CC2)c1]
I-333
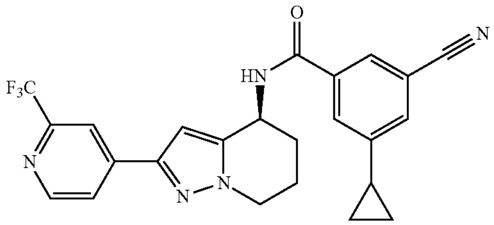 [SMILES: N#Cc1cc(C(=O)N[C@H]2CCCn3nc(-c4ccnc(C(F)(F)F)c4)cc32)cc(C2CC2)c1]
I-333a
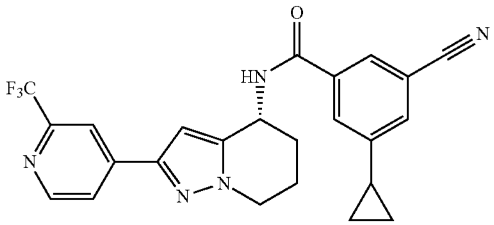
I-333b
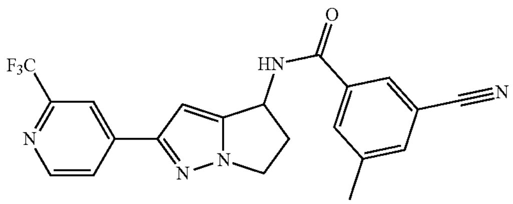 [SMILES: Cc1cc(C#N)cc(C(=O)NC2CCn3nc(-c4ccnc(C(F)(F)F)c4)cc32)c1]
I-334

TABLE 1-continued
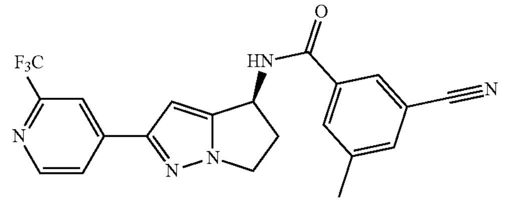 [SMILES: Cc1cc(C#N)cc(C(=O)N[C@H]2CCn3nc(-c4ccnc(C(F)(F)F)c4)cc32)c1]
I-334a
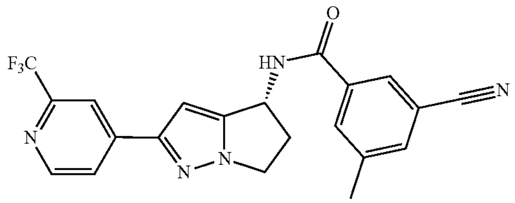 [SMILES: Cc1cc(C#N)cc(C(=O)N[C@@H]2CCn3nc(-c4ccnc(C(F)(F)F)c4)cc32)c1]
I-334b
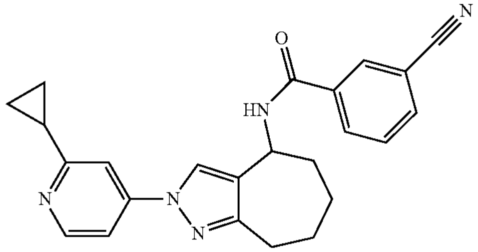 [SMILES: N#Cc1cccc(C(=O)NC2CCCCc3nn(-c4ccnc(C5CC5)c4)cc32)c1]
I-335
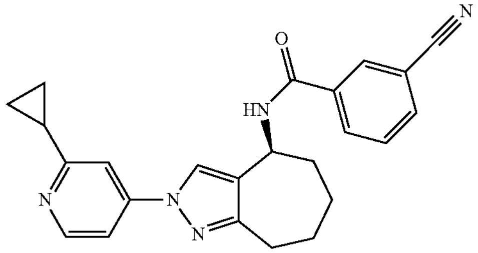 [SMILES: N#Cc1cccc(C(=O)N[C@H]2CCCCc3nn(-c4ccnc(C5CC5)c4)cc32)c1]
I-335a
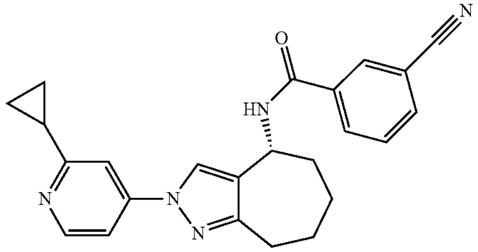 [SMILES: N#Cc1cccc(C(=O)N[C@@H]2CCCCc3nn(-c4ccnc(C5CC5)c4)cc32)c1]
I-335b
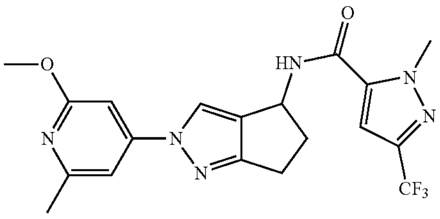
I-336
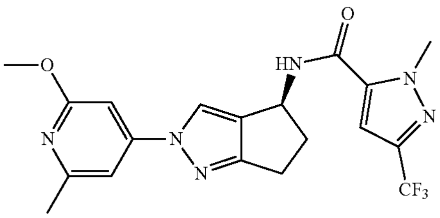
I-336a TABLE 1-continued
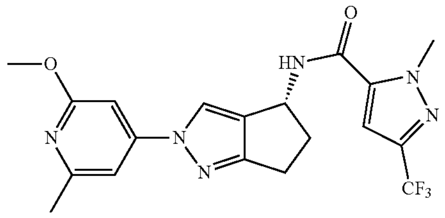
I-336b
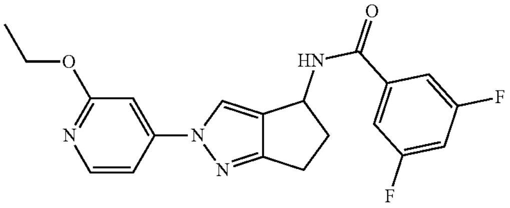
I-337
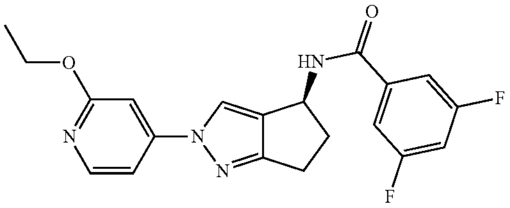 [SMILES: CCOc1cc(-n2cc3c(n2)CC[C@@H]3NC(=O)c2cc(F)cc(F)c2)ccn1]
I-337a
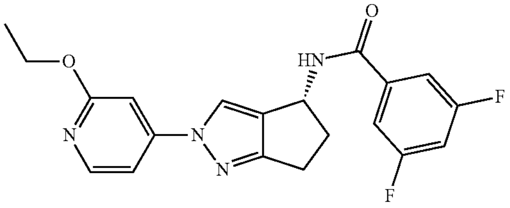 [SMILES: CCOc1cc(-n2cc3c(n2)CC[C@H]3NC(=O)c2cc(F)cc(F)c2)ccn1]
I-337b
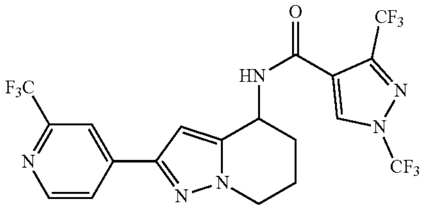 [SMILES: O=C(NC1CCCn2nc(-c3ccnc(C(F)(F)F)c3)cc21)c1cn(C(F)(F)F)nc1C(F)(F)F]
I-338
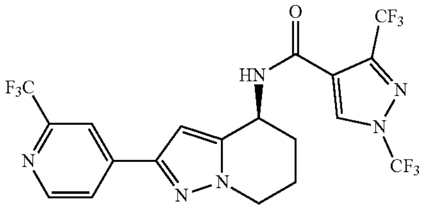 [SMILES: O=C(N[C@H]1CCCn2nc(-c3ccnc(C(F)(F)F)c3)cc21)c1cn(C(F)(F)F)nc1C(F)(F)F]
I-338a
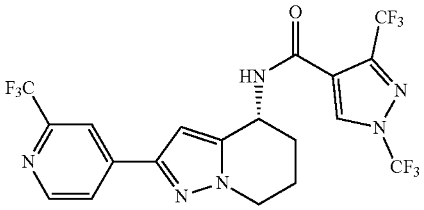 [SMILES: O=C(N[C@@H]1CCCn2nc(-c3ccnc(C(F)(F)F)c3)cc21)c1cn(C(F)(F)F)nc1C(F)(F)F]
I-338b TABLE 1-continued
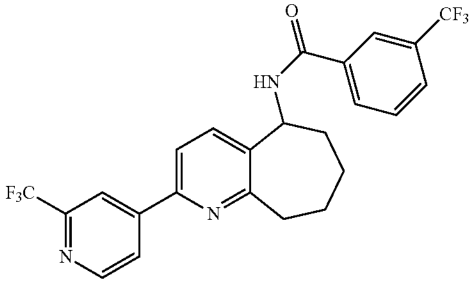 [SMILES: O=C(NC1CCCCc2nc(-c3ccnc(C(F)(F)F)c3)ccc21)c1cccc(C(F)(F)F)c1]
I-339
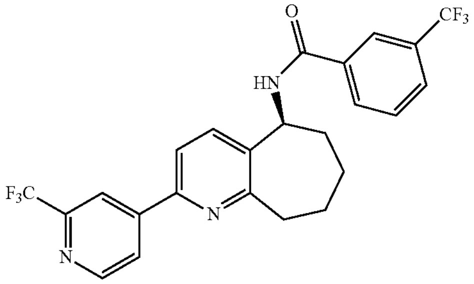 [SMILES: O=C(N[C@H]1CCCCc2nc(-c3ccnc(C(F)(F)F)c3)ccc21)c1cccc(C(F)(F)F)c1]
I-339a
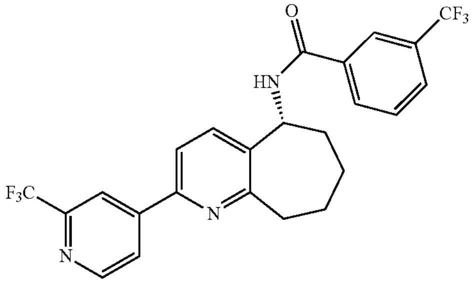 [SMILES: O=C(N[C@@H]1CCCCc2nc(-c3ccnc(C(F)(F)F)c3)ccc21)c1cccc(C(F)(F)F)c1]
I-339b
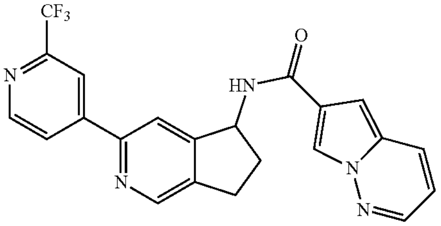 [SMILES: O=C(NC1CCc2cnc(-c3ccnc(C(F)(F)F)c3)cc21)c1cc2cccnn2c1]
I-340
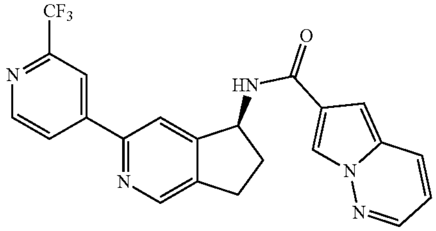 [SMILES: O=C(N[C@H]1CCc2cnc(-c3ccnc(C(F)(F)F)c3)cc21)c1cc2cccnn2c1]
I-340a
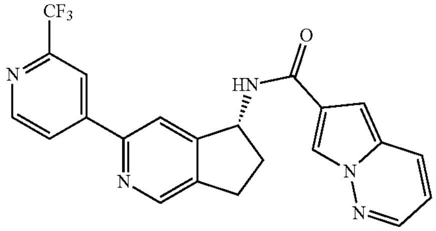 [SMILES: O=C(N[C@@H]1CCc2cnc(-c3ccnc(C(F)(F)F)c3)cc21)c1cc2cccnn2c1]
I-340b TABLE 1-continued
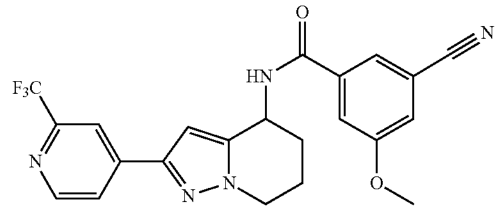 [SMILES: COc1cc(C#N)cc(C(=O)NC2CCCn3nc(-c4ccnc(C(F)(F)F)c4)cc32)c1]
I-341
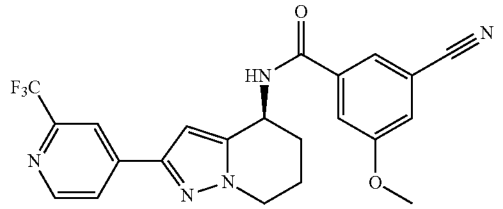 [SMILES: COc1cc(C#N)cc(C(=O)N[C@H]2CCCn3nc(-c4ccnc(C(F)(F)F)c4)cc32)c1]
I-341a
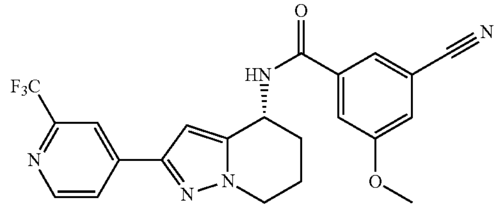
I-341b
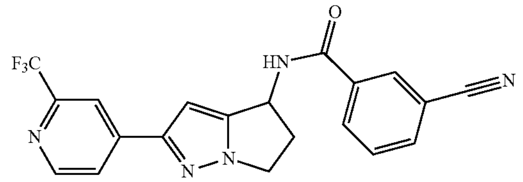
I-342
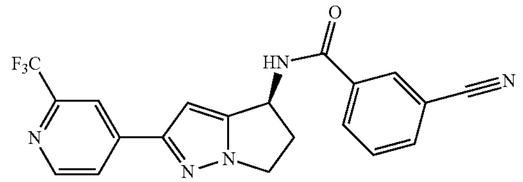 [SMILES: N#Cc1cccc(C(=O)N[C@H]2CCn3nc(-c4ccnc(C(F)(F)F)c4)cc32)c1]
I-342a
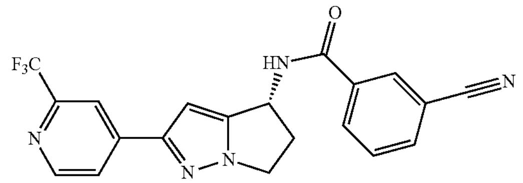 [SMILES: N#Cc1cccc(C(=O)N[C@@H]2CCn3nc(-c4ccnc(C(F)(F)F)c4)cc32)c1]
I-342b
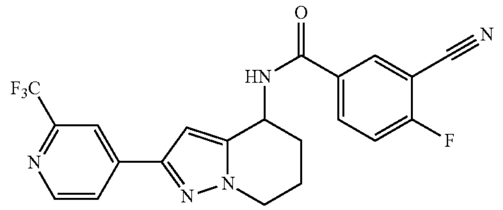
I-343

TABLE 1-continued
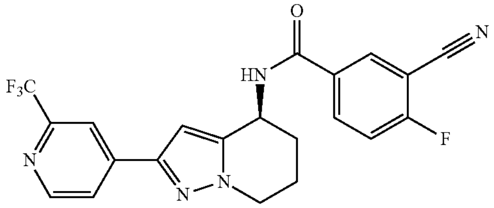
I-343a
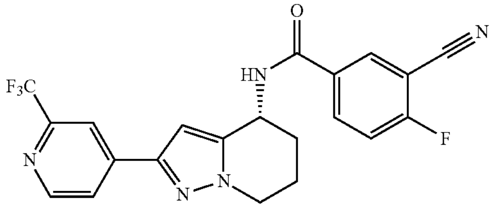 [SMILES: N#Cc1cc(C(=O)NC2CCCn3nc(-c4ccnc(C(F)(F)F)c4)cc32)ccc1F]
I-343b
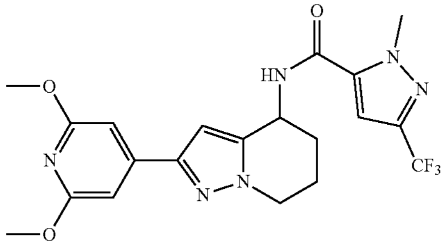 [SMILES: COc1cc(-c2cc3n(n2)CCCC3NC(=O)c2cc(C(F)(F)F)nn2C)cc(OC)n1]
I-344
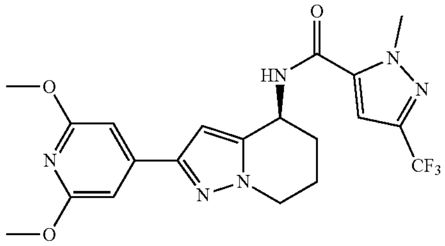 [SMILES: COc1cc(-c2cc3n(n2)CCC[C@@H]3NC(=O)c2cc(C(F)(F)F)nn2C)cc(OC)n1]
I-344a
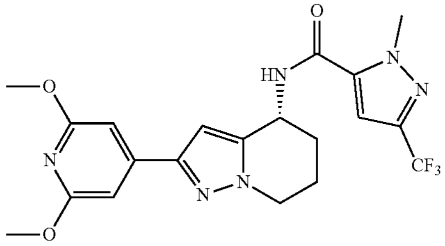 [SMILES: COc1cc(-c2cc3n(n2)CCC[C@H]3NC(=O)c2cc(C(F)(F)F)nn2C)cc(OC)n1]
I-344b
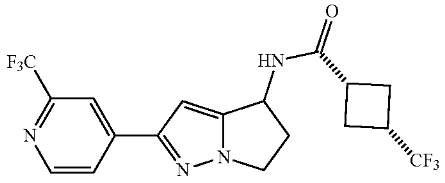
I-345
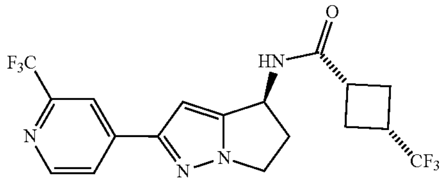
I-345a TABLE 1-continued
I-345b
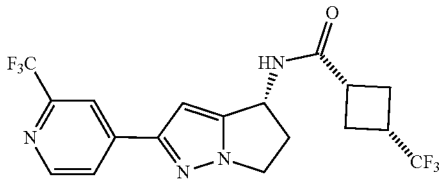
I-346
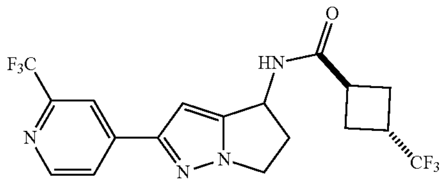
I-346a
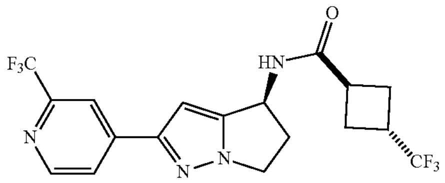
I-346b
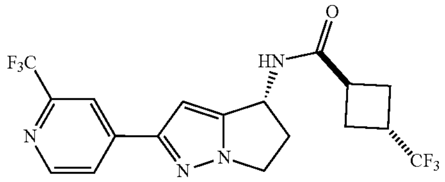
I-347
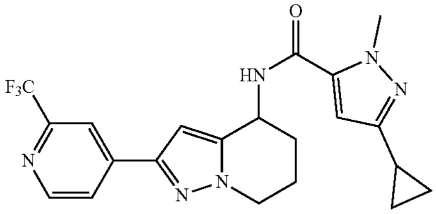
I-347a
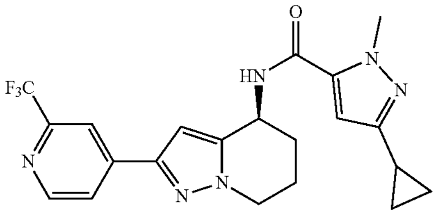 [SMILES: Cn1nc(C2CC2)cc1C(=O)N[C@H]1CCCn2nc(-c3ccnc(C(F)(F)F)c3)cc21]
I-347b
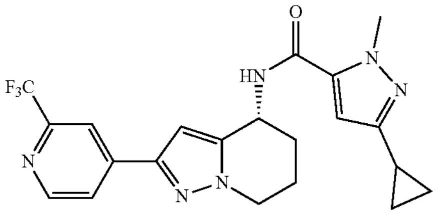 [SMILES: Cn1nc(C2CC2)cc1C(=O)N[C@@H]1CCCn2nc(-c3ccnc(C(F)(F)F)c3)cc21]

TABLE 1-continued
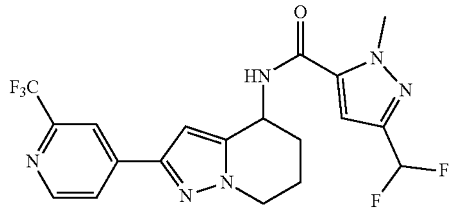 [SMILES: Cn1nc(C(F)F)cc1C(=O)NC1CCCn2nc(-c3ccnc(C(F)(F)F)c3)cc21]
I-348
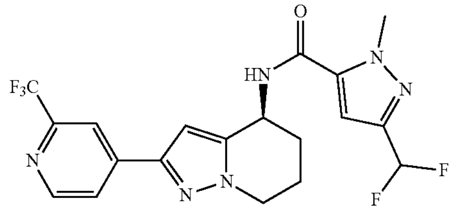 [SMILES: Cn1nc(C(F)F)cc1C(=O)N[C@H]1CCCn2nc(-c3ccnc(C(F)(F)F)c3)cc21]
I-348a
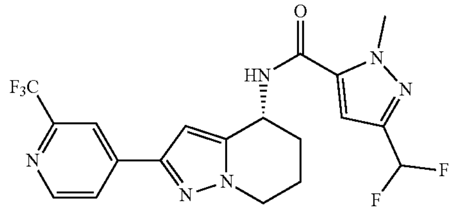
I-348b
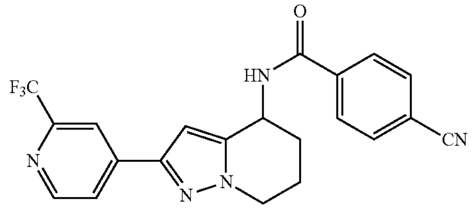
I-349
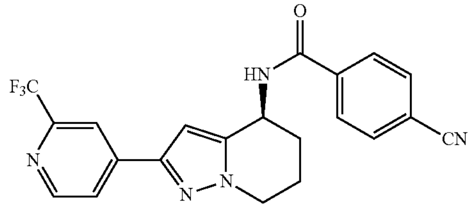 [SMILES: N#Cc1ccc(C(=O)N[C@H]2CCCn3nc(-c4ccnc(C(F)(F)F)c4)cc32)cc1]
I-349a
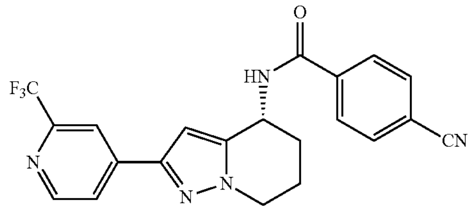 [SMILES: N#Cc1ccc(C(=O)N[C@@H]2CCCn3nc(-c4ccnc(C(F)(F)F)c4)cc32)cc1]
I-349b
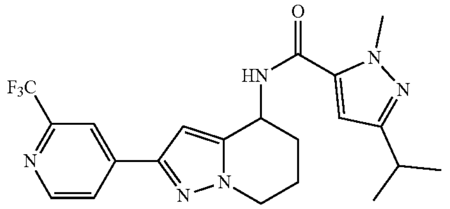 [SMILES: CC(C)c1cc(C(=O)NC2CCCn3nc(-c4ccnc(C(F)(F)F)c4)cc32)n(C)n1]
I-350

TABLE 1-continued
I-350a
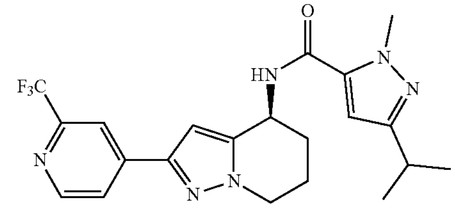 [SMILES: CC(C)c1cc(C(=O)N[C@H]2CCCn3nc(-c4ccnc(C(F)(F)F)c4)cc32)n(C)n1]
I-350b
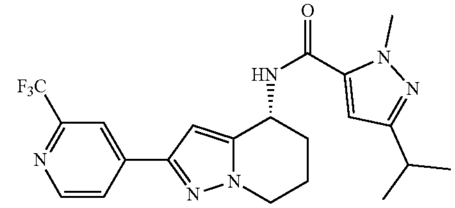
I-351
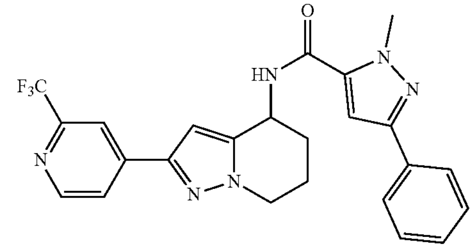 [SMILES: Cn1nc(-c2ccccc2)cc1C(=O)NC1CCCn2nc(-c3ccnc(C(F)(F)F)c3)cc21]
I-351a
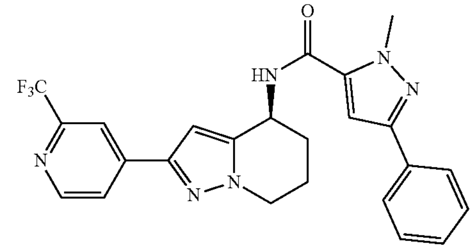 [SMILES: Cn1nc(-c2ccccc2)cc1C(=O)N[C@H]1CCCn2nc(-c3ccnc(C(F)(F)F)c3)cc21]
I-351b
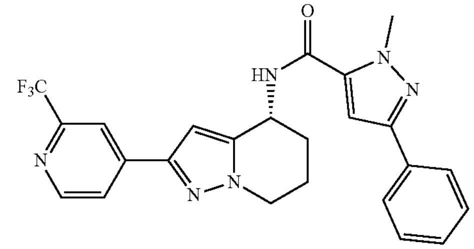
I-352
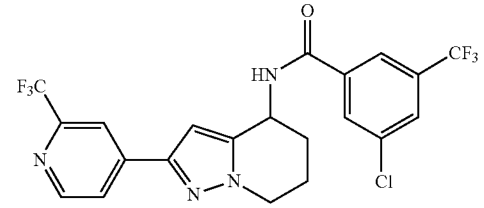 [SMILES: O=C(NC1CCCn2nc(-c3ccnc(C(F)(F)F)c3)cc21)c1cc(Cl)cc(C(F)(F)F)c1]
I-352a
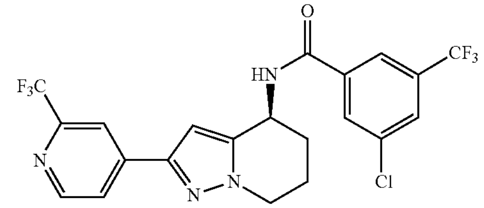 [SMILES: O=C(N[C@H]1CCCn2nc(-c3ccnc(C(F)(F)F)c3)cc21)c1cc(Cl)cc(C(F)(F)F)c1]

TABLE 1-continued
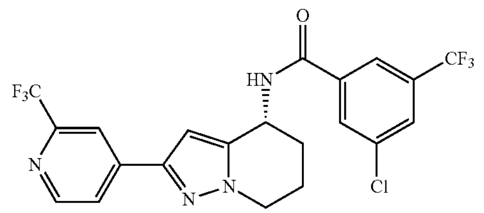
I-352b
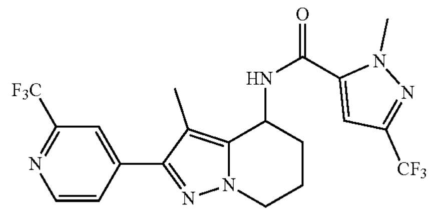
I-353
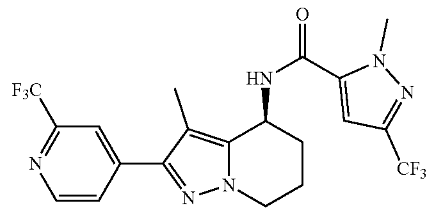 [SMILES: Cc1c(-c2ccnc(C(F)(F)F)c2)nn2c1[C@@H](NC(=O)c1cc(C(F)(F)F)nn1C)CCC2]
I-353a
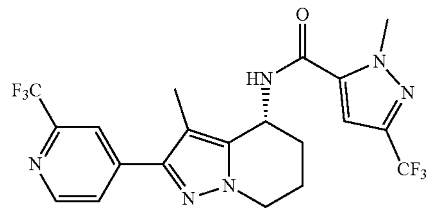
I-353b
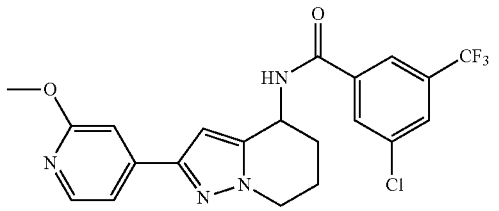 [SMILES: COc1cc(-c2cc3n(n2)CCCC3NC(=O)c2cc(Cl)cc(C(F)(F)F)c2)ccn1]
I-354
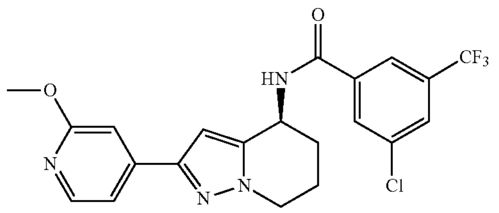 [SMILES: COc1cc(-c2cc3n(n2)CCC[C@@H]3NC(=O)c2cc(Cl)cc(C(F)(F)F)c2)ccn1]
I-354a
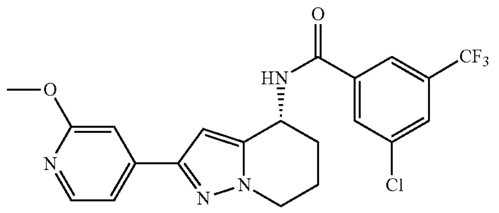
I-354b TABLE 1-continued
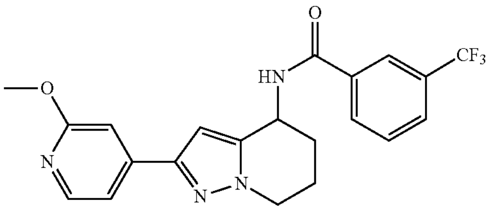
I-355
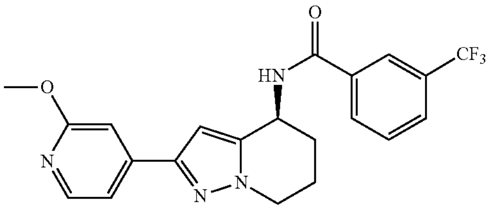
I-355a
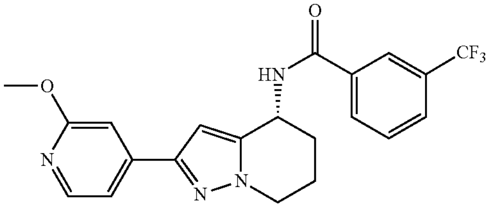
I-355b
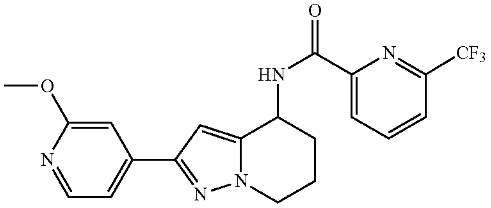 [SMILES: COc1cc(-c2cc3n(n2)CCCC3NC(=O)c2cccc(C(F)(F)F)n2)ccn1]
I-356
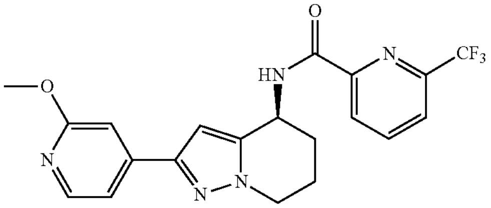 [SMILES: COc1cc(-c2cc3n(n2)CCC[C@@H]3NC(=O)c2cccc(C(F)(F)F)n2)ccn1]
I-356a
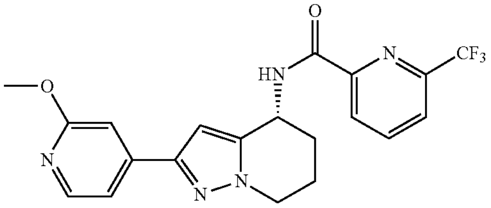
I-356b
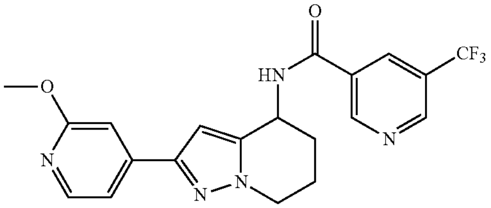 [SMILES: COc1cc(-c2cc3n(n2)CCCC3NC(=O)c2cncc(C(F)(F)F)c2)ccn1]
I-357

TABLE 1-continued
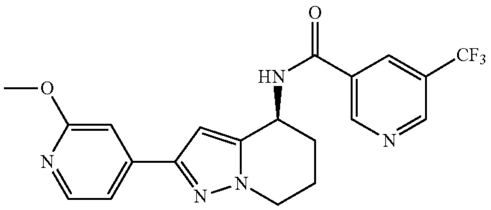 [SMILES: COc1cc(-c2cc3n(n2)CCC[C@@H]3NC(=O)c2cncc(C(F)(F)F)c2)ccn1]
I-357a
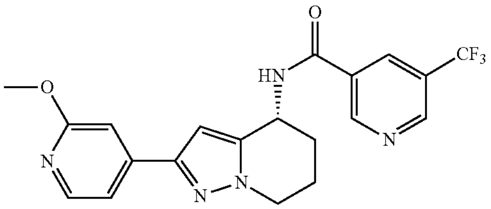 [SMILES: COc1cc(-c2cc3n(n2)CCC[C@H]3NC(=O)c2cncc(C(F)(F)F)c2)ccn1]
I-357b
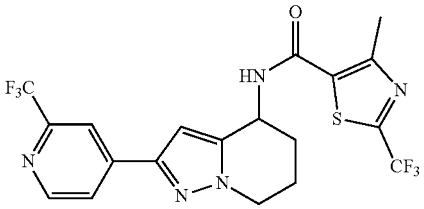
I-358
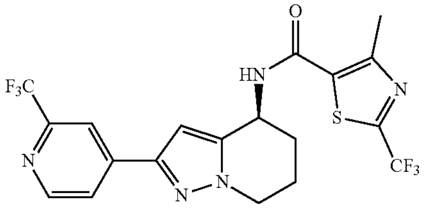 [SMILES: Cc1nc(C(F)(F)F)sc1C(=O)N[C@H]1CCCn2nc(-c3ccnc(C(F)(F)F)c3)cc21]
I-358a
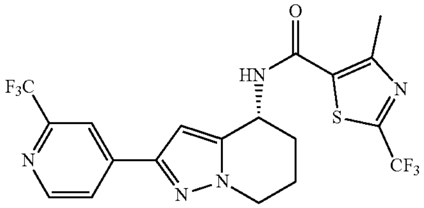 [SMILES: Cc1nc(C(F)(F)F)sc1C(=O)N[C@@H]1CCCn2nc(-c3ccnc(C(F)(F)F)c3)cc21]
I-358b
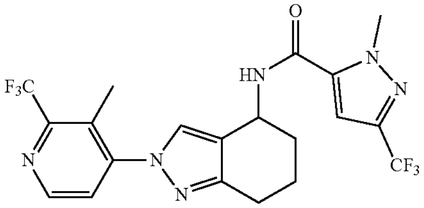 [SMILES: Cc1c(-n2cc3c(n2)CCCC3NC(=O)c2cc(C(F)(F)F)nn2C)ccnc1C(F)(F)F]
I-359
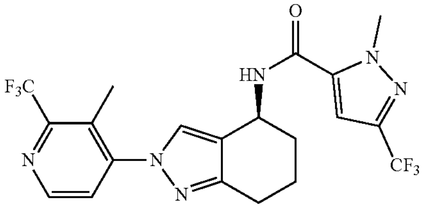 [SMILES: Cc1c(-n2cc3c(n2)CCC[C@@H]3NC(=O)c2cc(C(F)(F)F)nn2C)ccnc1C(F)(F)F]
I-359a TABLE 1-continued
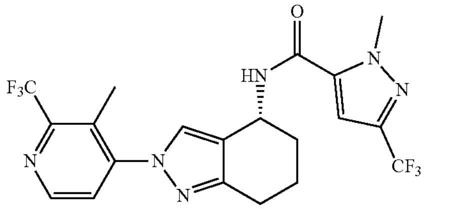 [SMILES: Cc1c(-n2cc3c(n2)CCC[C@H]3NC(=O)c2cc(C(F)(F)F)nn2C)ccnc1C(F)(F)F]
I-359b
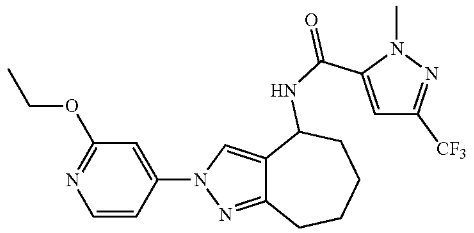 [SMILES: CCOc1cc(-n2cc3c(n2)CCCCC3NC(=O)c2cc(C(F)(F)F)nn2C)ccn1]
I-360
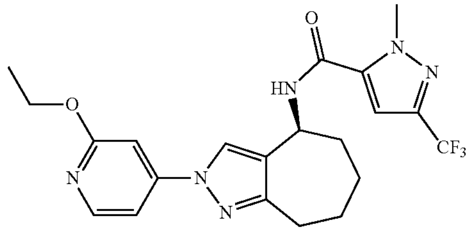 [SMILES: CCOc1cc(-n2cc3c(n2)CCCC[C@@H]3NC(=O)c2cc(C(F)(F)F)nn2C)ccn1]
I-360a
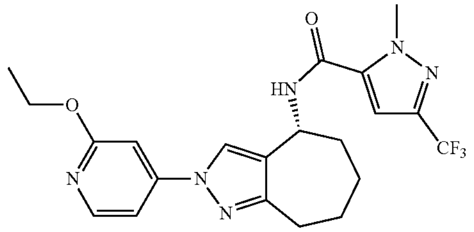 [SMILES: CCOc1cc(-n2cc3c(n2)CCCC[C@H]3NC(=O)c2cc(C(F)(F)F)nn2C)ccn1]
I-360b
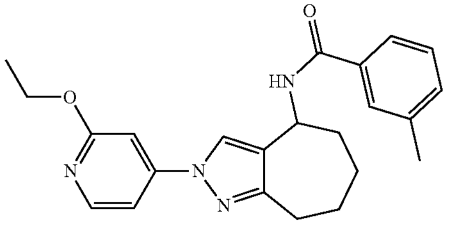 [SMILES: CCOc1cc(-n2cc3c(n2)CCCCC3NC(=O)c2cccc(C)c2)ccn1]
I-361
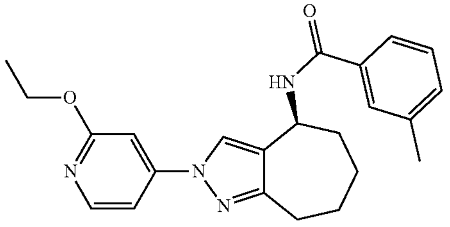 [SMILES: CCOc1cc(-n2cc3c(n2)CCCC[C@@H]3NC(=O)c2cccc(C)c2)ccn1]
I-361a
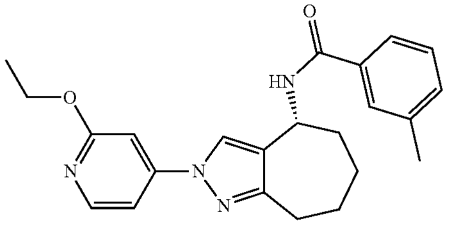 [SMILES: CCOc1cc(-n2cc3c(n2)CCCC[C@H]3NC(=O)c2cccc(C)c2)ccn1]
I-361b TABLE 1-continued
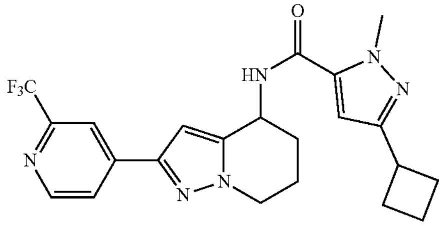 [SMILES: Cn1nc(C2CCC2)cc1C(=O)NC1CCCn2nc(-c3ccnc(C(F)(F)F)c3)cc21]
I-362
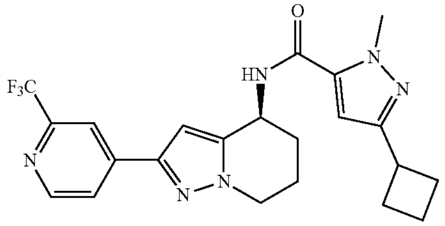 [SMILES: Cn1nc(C2CCC2)cc1C(=O)N[C@H]1CCCn2nc(-c3ccnc(C(F)(F)F)c3)cc21]
I-362a
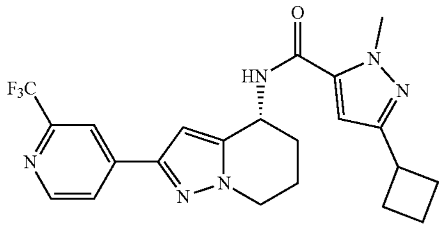 [SMILES: Cn1nc(C2CCC2)cc1C(=O)N[C@@H]1CCCn2nc(-c3ccnc(C(F)(F)F)c3)cc21]
I-362b
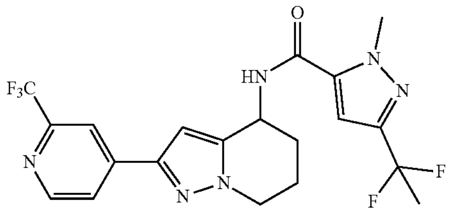
I-363
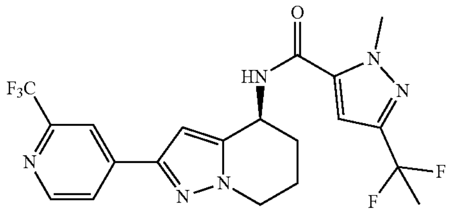 [SMILES: Cn1nc(C(C)(F)F)cc1C(=O)N[C@H]1CCCn2nc(-c3ccnc(C(F)(F)F)c3)cc21]
I-363a
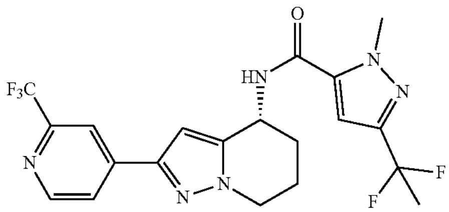 [SMILES: Cn1nc(C(C)(F)F)cc1C(=O)N[C@@H]1CCCn2nc(-c3ccnc(C(F)(F)F)c3)cc21]
I-363b
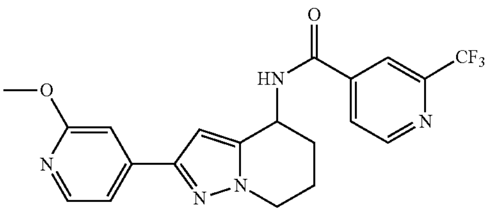 [SMILES: COc1cc(-c2cc3n(n2)CCCC3NC(=O)c2ccnc(C(F)(F)F)c2)ccn1]
I-364

TABLE 1-continued
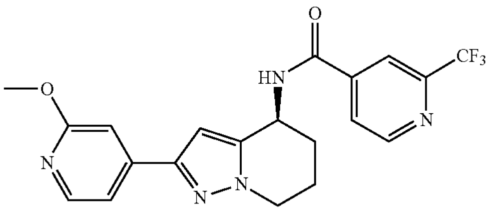 [SMILES: COc1cc(-c2cc3n(n2)CCC[C@@H]3NC(=O)c2ccnc(C(F)(F)F)c2)ccn1]
I-364a
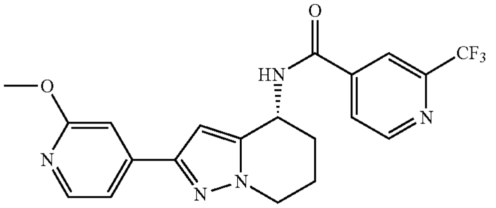
I-364b
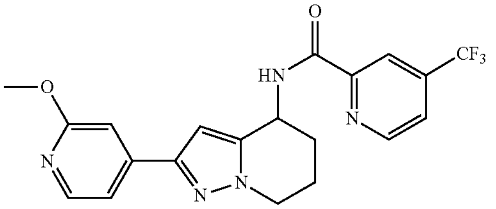 [SMILES: COc1cc(-c2cc3n(n2)CCCC3NC(=O)c2cc(C(F)(F)F)ccn2)ccn1]
I-365
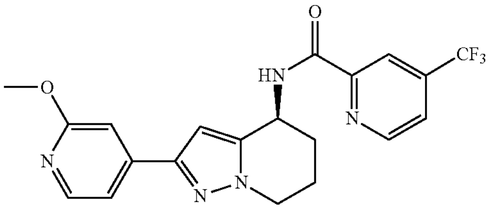 [SMILES: COc1cc(-c2cc3n(n2)CCC[C@@H]3NC(=O)c2cc(C(F)(F)F)ccn2)ccn1]
I-365a
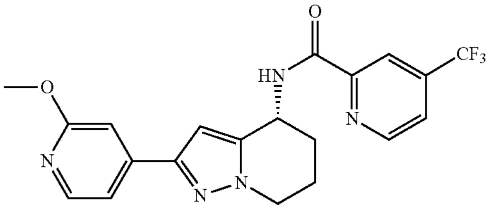
I-365b
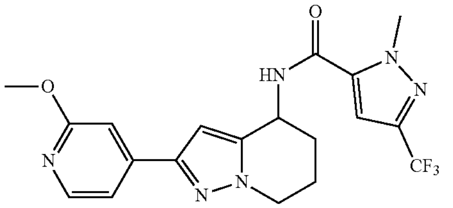 [SMILES: COc1cc(-c2cc3n(n2)CCCC3NC(=O)c2cc(C(F)(F)F)nn2C)ccn1]
I-366
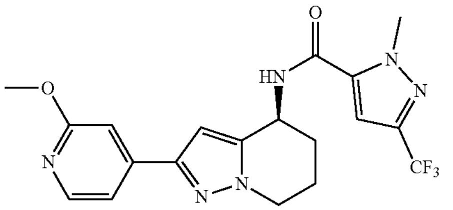 [SMILES: COc1cc(-c2cc3n(n2)CCC[C@@H]3NC(=O)c2cc(C(F)(F)F)nn2C)ccn1]
I-366a TABLE 1-continued
I-366b
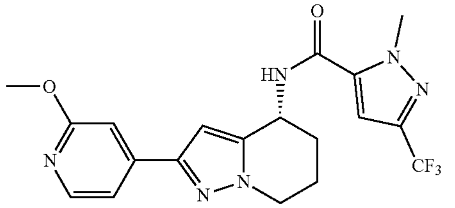 [SMILES: COc1cc(-c2cc3n(n2)CCC[C@H]3NC(=O)c2cc(C(F)(F)F)nn2C)ccn1]
I-367
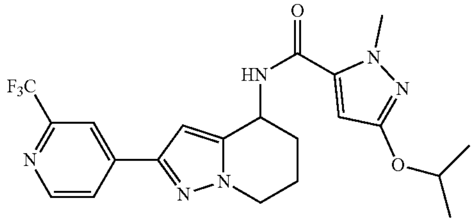 [SMILES: CC(C)Oc1cc(C(=O)NC2CCCn3nc(-c4ccnc(C(F)(F)F)c4)cc32)n(C)n1]
I-367a
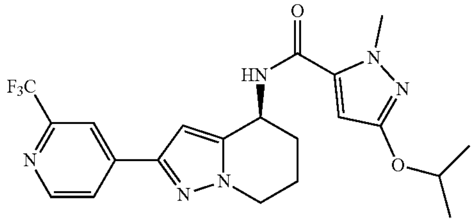 [SMILES: CC(C)Oc1cc(C(=O)N[C@H]2CCCn3nc(-c4ccnc(C(F)(F)F)c4)cc32)n(C)n1]
I-367b
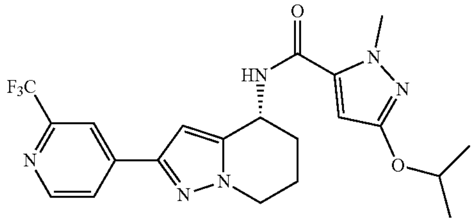 [SMILES: CC(C)Oc1cc(C(=O)N[C@@H]2CCCn3nc(-c4ccnc(C(F)(F)F)c4)cc32)n(C)n1]
I-368
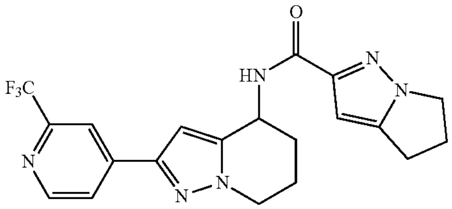 [SMILES: O=C(NC1CCCn2nc(-c3ccnc(C(F)(F)F)c3)cc21)c1cc2n(n1)CCC2]
I-368a
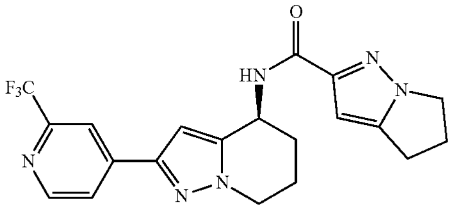 [SMILES: O=C(N[C@H]1CCCn2nc(-c3ccnc(C(F)(F)F)c3)cc21)c1cc2n(n1)CCC2]
I-368b
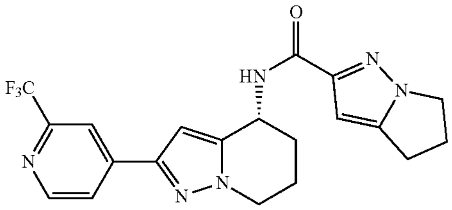 [SMILES: O=C(N[C@@H]1CCCn2nc(-c3ccnc(C(F)(F)F)c3)cc21)c1cc2n(n1)CCC2]

TABLE 1-continued
I-369
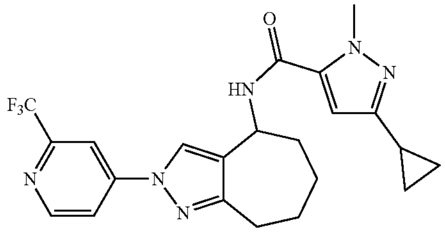 [SMILES: Cn1nc(C2CC2)cc1C(=O)NC1CCCCc2nn(-c3ccnc(C(F)(F)F)c3)cc21]
I-369a
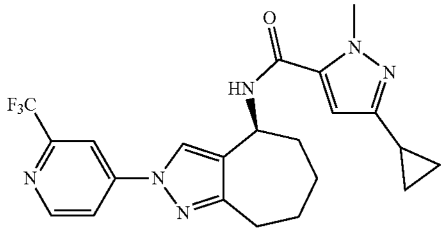 [SMILES: Cn1nc(C2CC2)cc1C(=O)N[C@H]1CCCCc2nn(-c3ccnc(C(F)(F)F)c3)cc21]
I-369b
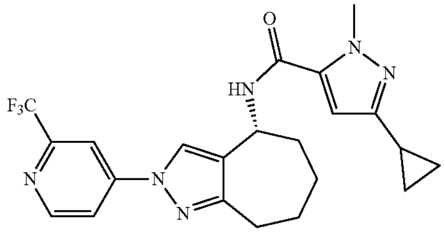 [SMILES: Cn1nc(C2CC2)cc1C(=O)N[C@@H]1CCCCc2nn(-c3ccnc(C(F)(F)F)c3)cc21]
I-370
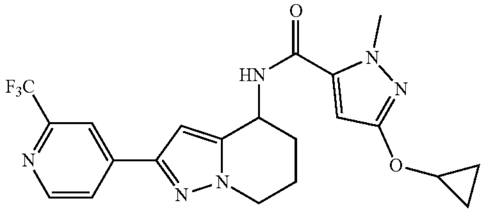 [SMILES: Cn1nc(OC2CC2)cc1C(=O)NC1CCCn2nc(-c3ccnc(C(F)(F)F)c3)cc21]
I-370a
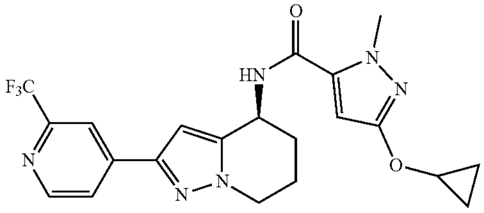 [SMILES: Cn1nc(OC2CC2)cc1C(=O)N[C@H]1CCCn2nc(-c3ccnc(C(F)(F)F)c3)cc21]
I-370b
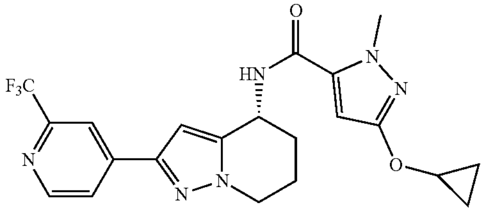 [SMILES: Cn1nc(OC2CC2)cc1C(=O)N[C@@H]1CCCn2nc(-c3ccnc(C(F)(F)F)c3)cc21]
I-371
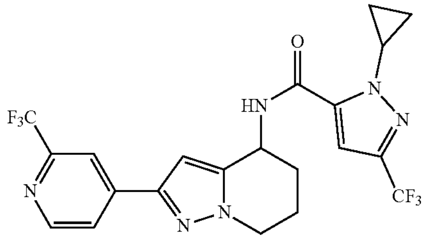 [SMILES: O=C(NC1CCCn2nc(-c3ccnc(C(F)(F)F)c3)cc21)c1cc(C(F)(F)F)nn1C1CC1]

TABLE 1-continued
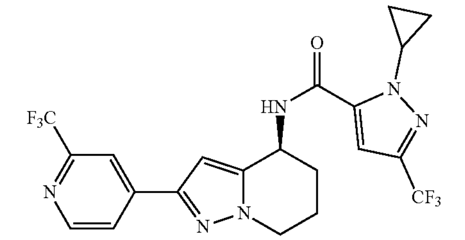 [SMILES: O=C(N[C@H]1CCCn2nc(-c3ccnc(C(F)(F)F)c3)cc21)c1cc(C(F)(F)F)nn1C1CC1]
I-371a
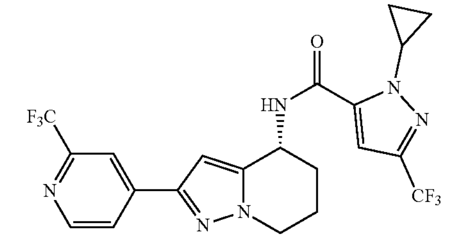 [SMILES: O=C(N[C@@H]1CCCn2nc(-c3ccnc(C(F)(F)F)c3)cc21)c1cc(C(F)(F)F)nn1C1CC1]
I-371b
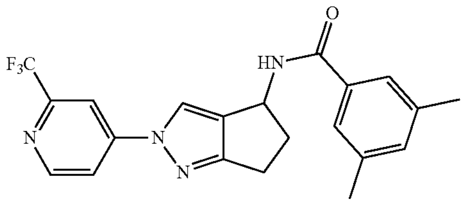 [SMILES: Cc1cc(C)cc(C(=O)NC2CCc3nn(-c4ccnc(C(F)(F)F)c4)cc32)c1]
I-372
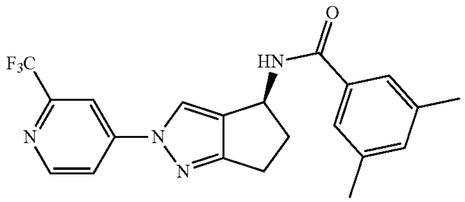 [SMILES: Cc1cc(C)cc(C(=O)N[C@H]2CCc3nn(-c4ccnc(C(F)(F)F)c4)cc32)c1]
I-372a
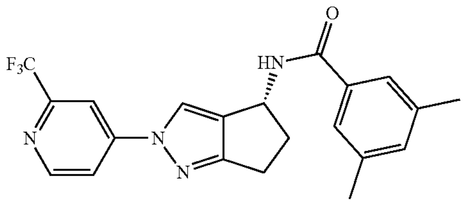 [SMILES: Cc1cc(C)cc(C(=O)N[C@@H]2CCc3nn(-c4ccnc(C(F)(F)F)c4)cc32)c1]
I-372b
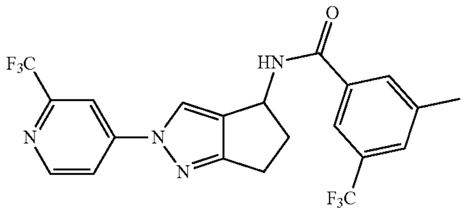 [SMILES: Cc1cc(C(=O)NC2CCc3nn(-c4ccnc(C(F)(F)F)c4)cc32)cc(C(F)(F)F)c1]
I-373
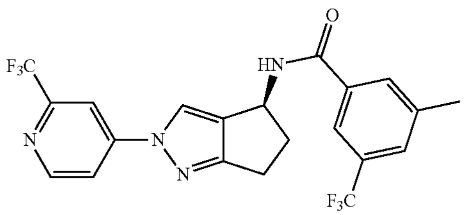 [SMILES: Cc1cc(C(=O)N[C@H]2CCc3nn(-c4ccnc(C(F)(F)F)c4)cc32)cc(C(F)(F)F)c1]
I-373a TABLE 1-continued
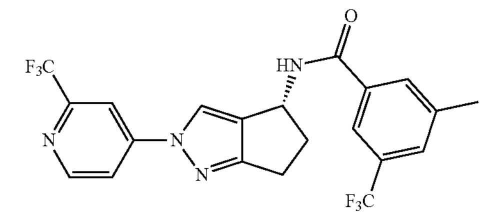 [SMILES: Cc1cc(C(=O)N[C@@H]2CCc3nn(-c4ccnc(C(F)(F)F)c4)cc32)cc(C(F)(F)F)c1]
I-373b
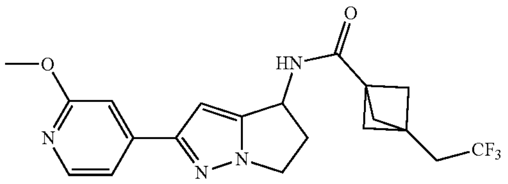 [SMILES: COc1cc(-c2cc3n(n2)CCC3NC(=O)C23CC(CC(F)(F)F)(C2)C3)ccn1]
I-374
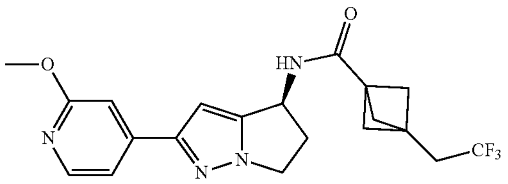 [SMILES: COc1cc(-c2cc3n(n2)CC[C@@H]3NC(=O)C23CC(CC(F)(F)F)(C2)C3)ccn1]
I-374a
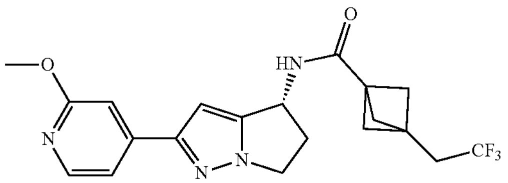 [SMILES: COc1cc(-c2cc3n(n2)CC[C@H]3NC(=O)C23CC(CC(F)(F)F)(C2)C3)ccn1]
I-374b
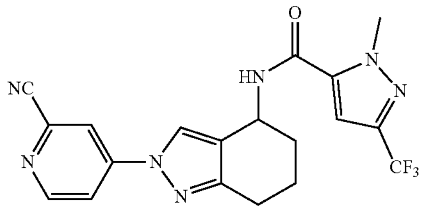 [SMILES: Cn1nc(C(F)(F)F)cc1C(=O)NC1CCCc2nn(-c3ccnc(C#N)c3)cc21]
I-375
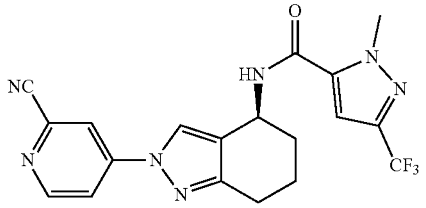 [SMILES: Cn1nc(C(F)(F)F)cc1C(=O)N[C@H]1CCCc2nn(-c3ccnc(C#N)c3)cc21]
I-375a
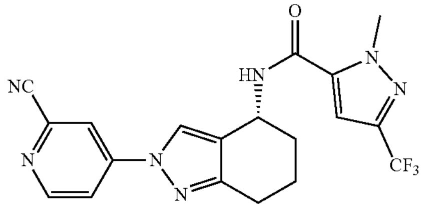 [SMILES: Cn1nc(C(F)(F)F)cc1C(=O)N[C@@H]1CCCc2nn(-c3ccnc(C#N)c3)cc21]
I-375b TABLE 1-continued
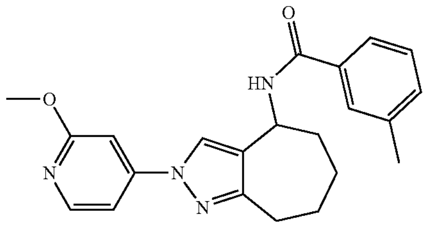 [SMILES: COc1cc(-n2cc3c(n2)CCCCC3NC(=O)c2cccc(C)c2)ccn1]
I-376
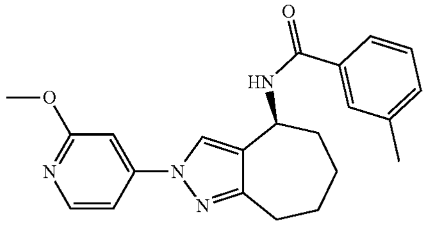 [SMILES: COc1cc(-n2cc3c(n2)CCCC[C@@H]3NC(=O)c2cccc(C)c2)ccn1]
I-376a
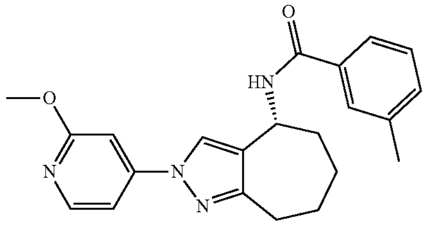 [SMILES: COc1cc(-n2cc3c(n2)CCCC[C@H]3NC(=O)c2cccc(C)c2)ccn1]
I-376b
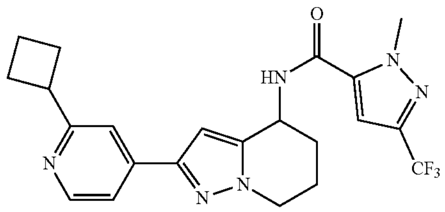 [SMILES: Cn1nc(C(F)(F)F)cc1C(=O)NC1CCCn2nc(-c3ccnc(C4CCC4)c3)cc21]
I-377
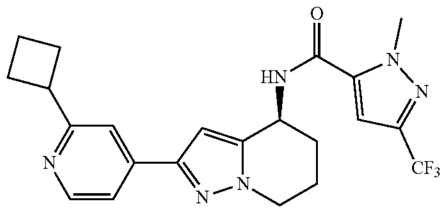 [SMILES: Cn1nc(C(F)(F)F)cc1C(=O)N[C@H]1CCCn2nc(-c3ccnc(C4CCC4)c3)cc21]
I-377a
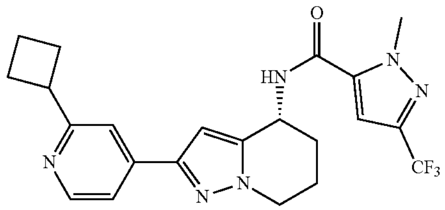
I-377b
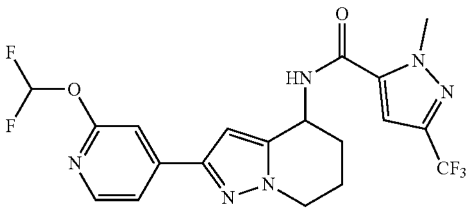 [SMILES: Cn1nc(C(F)(F)F)cc1C(=O)NC1CCCn2nc(-c3ccnc(OC(F)F)c3)cc21]
I-378

TABLE 1-continued
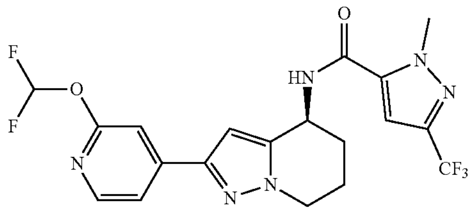 [SMILES: Cn1nc(C(F)(F)F)cc1C(=O)N[C@H]1CCCn2nc(-c3ccnc(OC(F)F)c3)cc21]
I-378a
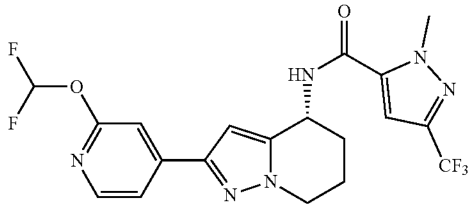
I-378b
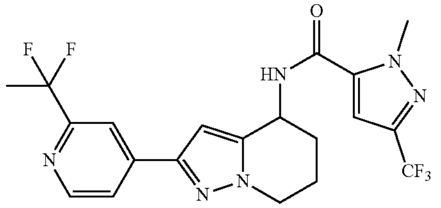 [SMILES: Cn1nc(C(F)(F)F)cc1C(=O)NC1CCCn2nc(-c3ccnc(C(C)(F)F)c3)cc21]
I-379
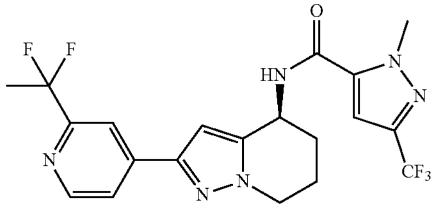 [SMILES: Cn1nc(C(F)(F)F)cc1C(=O)N[C@H]1CCCn2nc(-c3ccnc(C(C)(F)F)c3)cc21]
I-379a
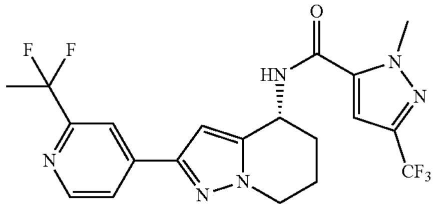 [SMILES: Cn1nc(C(F)(F)F)cc1C(=O)N[C@@H]1CCCn2nc(-c3ccnc(C(C)(F)F)c3)cc21]
I-379b
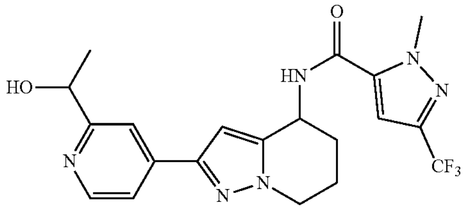 [SMILES: CC(O)c1cc(-c2cc3n(n2)CCCC3NC(=O)c2cc(C(F)(F)F)nn2C)ccn1]
I-380
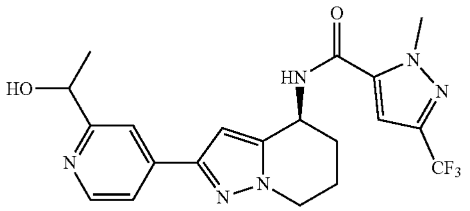 [SMILES: CC(O)c1cc(-c2cc3n(n2)CCC[C@@H]3NC(=O)c2cc(C(F)(F)F)nn2C)ccn1]
I-380a TABLE 1-continued
I-380b
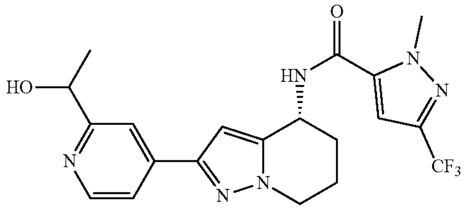 [SMILES: CC(O)c1cc(-c2cc3n(n2)CCC[C@H]3NC(=O)c2cc(C(F)(F)F)nn2C)ccn1]
I-381
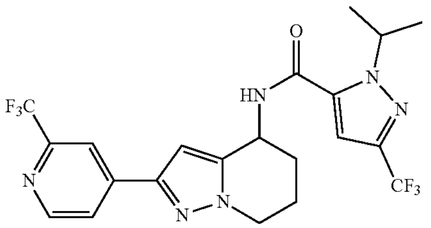 [SMILES: CC(C)n1nc(C(F)(F)F)cc1C(=O)NC1CCCn2nc(-c3ccnc(C(F)(F)F)c3)cc21]
I-381a
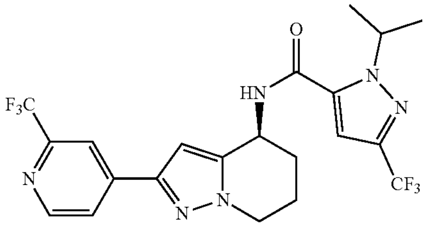 [SMILES: CC(C)n1nc(C(F)(F)F)cc1C(=O)N[C@H]1CCCn2nc(-c3ccnc(C(F)(F)F)c3)cc21]
I-381b
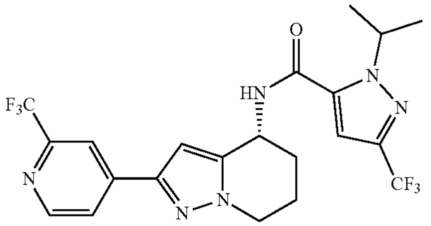 [SMILES: CC(C)n1nc(C(F)(F)F)cc1C(=O)N[C@@H]1CCCn2nc(-c3ccnc(C(F)(F)F)c3)cc21]
I-382
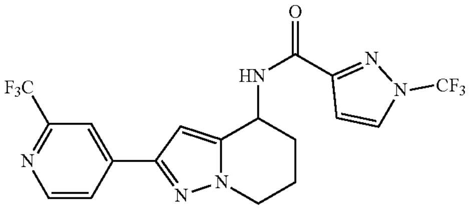 [SMILES: O=C(NC1CCCn2nc(-c3ccnc(C(F)(F)F)c3)cc21)c1ccn(C(F)(F)F)n1]
I-382a
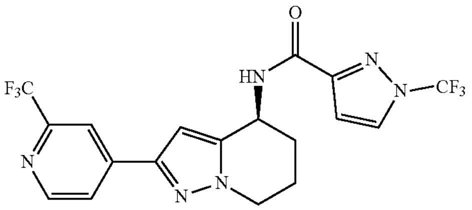 [SMILES: O=C(N[C@H]1CCCn2nc(-c3ccnc(C(F)(F)F)c3)cc21)c1ccn(C(F)(F)F)n1]
I-382b
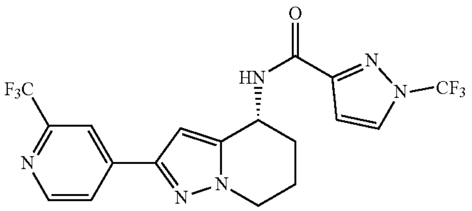

TABLE 1-continued
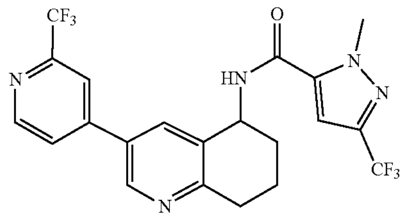 [SMILES: Cn1nc(C(F)(F)F)cc1C(=O)NC1CCCc2ncc(-c3ccnc(C(F)(F)F)c3)cc21]
I-383
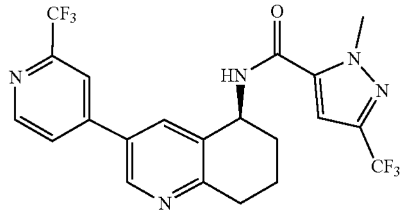 [SMILES: Cn1nc(C(F)(F)F)cc1C(=O)N[C@H]1CCCc2ncc(-c3ccnc(C(F)(F)F)c3)cc21]
I-383a
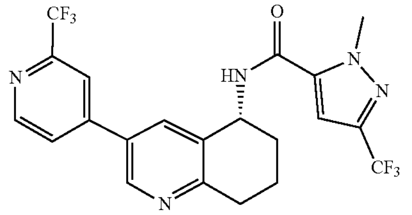 [SMILES: Cn1nc(C(F)(F)F)cc1C(=O)N[C@@H]1CCCc2ncc(-c3ccnc(C(F)(F)F)c3)cc21]
I-383b
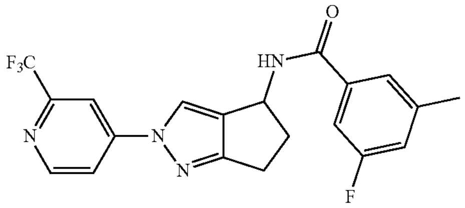
I-384
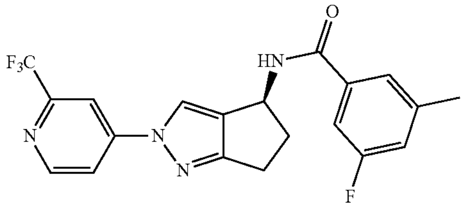 [SMILES: Cc1cc(F)cc(C(=O)N[C@H]2CCc3nn(-c4ccnc(C(F)(F)F)c4)cc32)c1]
I-384a
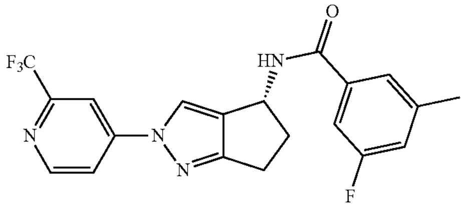
I-384b
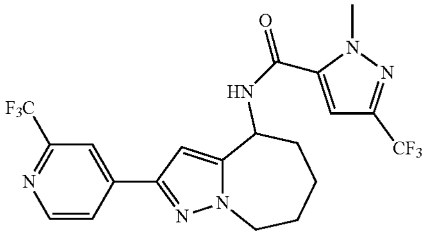 [SMILES: Cn1nc(C(F)(F)F)cc1C(=O)NC1CCCCn2nc(-c3ccnc(C(F)(F)F)c3)cc21]
I-385

TABLE 1-continued
I-385a
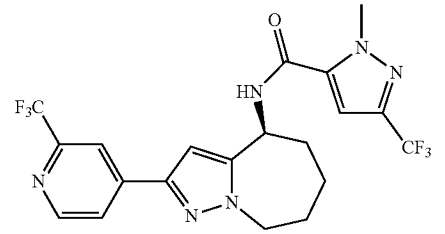 [SMILES: Cn1nc(C(F)(F)F)cc1C(=O)N[C@H]1CCCCn2nc(-c3ccnc(C(F)(F)F)c3)cc21]
I-385b
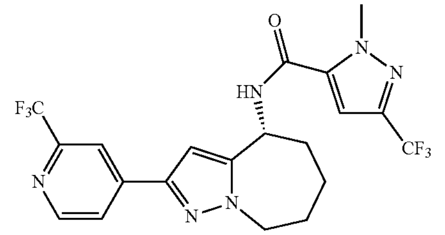
I-386
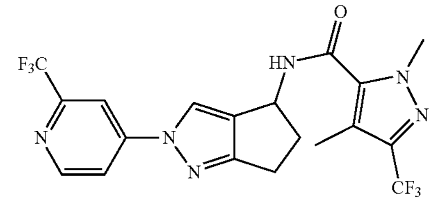
I-386a
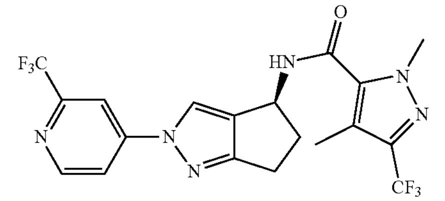 [SMILES: Cc1c(C(F)(F)F)nn(C)c1C(=O)N[C@H]1CCc2nn(-c3ccnc(C(F)(F)F)c3)cc21]
I-386b
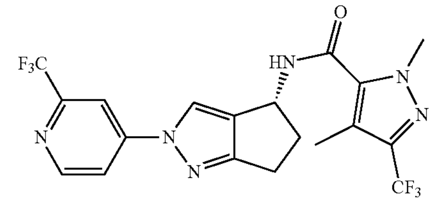 [SMILES: Cc1c(C(F)(F)F)nn(C)c1C(=O)N[C@@H]1CCc2nn(-c3ccnc(C(F)(F)F)c3)cc21]
I-387
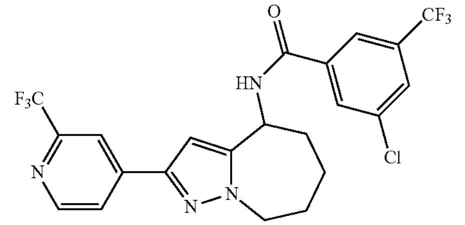 [SMILES: O=C(NC1CCCCn2nc(-c3ccnc(C(F)(F)F)c3)cc21)c1cc(Cl)cc(C(F)(F)F)c1]
I-387a
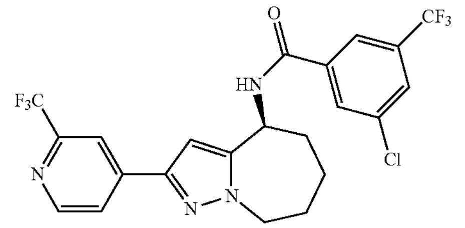 [SMILES: O=C(N[C@H]1CCCCn2nc(-c3ccnc(C(F)(F)F)c3)cc21)c1cc(Cl)cc(C(F)(F)F)c1]

TABLE 1-continued
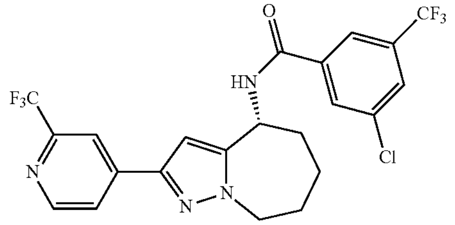 [SMILES: O=C(N[C@@H]1CCCCn2nc(-c3ccnc(C(F)(F)F)c3)cc21)c1cc(Cl)cc(C(F)(F)F)c1]
I-387b
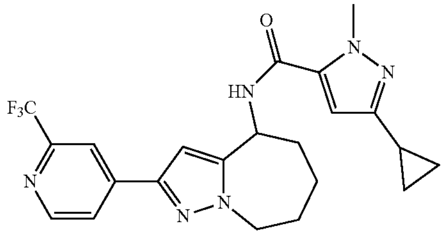 [SMILES: Cn1nc(C2CC2)cc1C(=O)NC1CCCCn2nc(-c3ccnc(C(F)(F)F)c3)cc21]
I-388
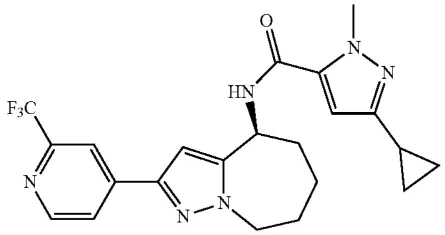 [SMILES: Cn1nc(C2CC2)cc1C(=O)N[C@H]1CCCCn2nc(-c3ccnc(C(F)(F)F)c3)cc21]
I-388a
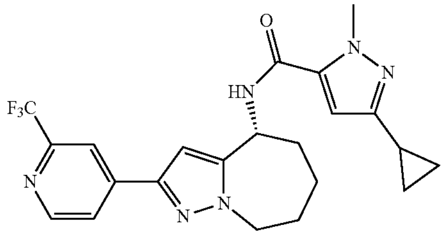 [SMILES: Cn1nc(C2CC2)cc1C(=O)N[C@@H]1CCCCn2nc(-c3ccnc(C(F)(F)F)c3)cc21]
I-388b
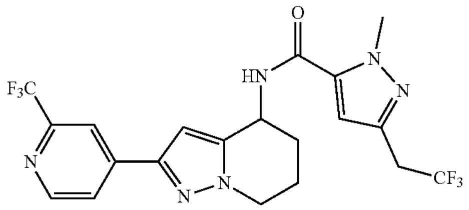 [SMILES: Cn1nc(CC(F)(F)F)cc1C(=O)NC1CCCn2nc(-c3ccnc(C(F)(F)F)c3)cc21]
I-389
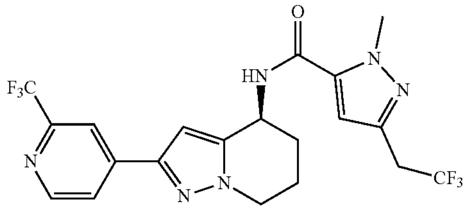 [SMILES: Cn1nc(CC(F)(F)F)cc1C(=O)N[C@H]1CCCn2nc(-c3ccnc(C(F)(F)F)c3)cc21]
I-389a
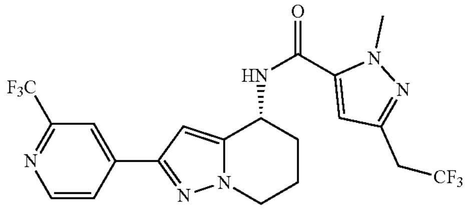
I-389b TABLE 1-continued
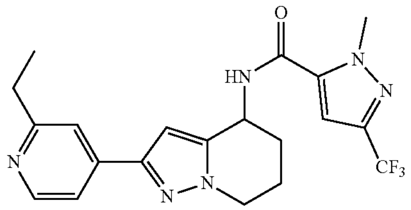 [SMILES: CCc1cc(-c2cc3n(n2)CCCC3NC(=O)c2cc(C(F)(F)F)nn2C)ccn1]
I-390
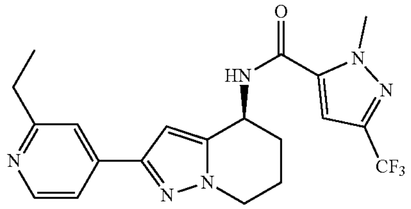 [SMILES: CCc1cc(-c2cc3n(n2)CCC[C@@H]3NC(=O)c2cc(C(F)(F)F)nn2C)ccn1]
I-390a
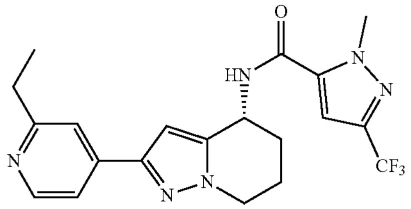 [SMILES: CCc1cc(-c2cc3n(n2)CCC[C@H]3NC(=O)c2cc(C(F)(F)F)nn2C)ccn1]
I-390b
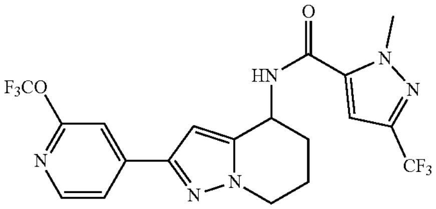 [SMILES: Cn1nc(C(F)(F)F)cc1C(=O)NC1CCCn2nc(-c3ccnc(OC(F)(F)F)c3)cc21]
I-391
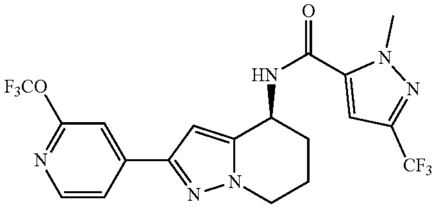 [SMILES: Cn1nc(C(F)(F)F)cc1C(=O)N[C@H]1CCCn2nc(-c3ccnc(OC(F)(F)F)c3)cc21]
I-391a
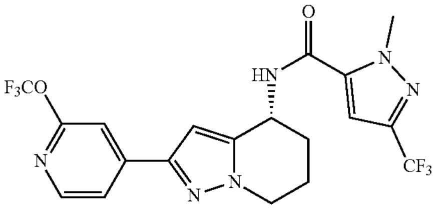 [SMILES: Cn1nc(C(F)(F)F)cc1C(=O)N[C@@H]1CCCn2nc(-c3ccnc(OC(F)(F)F)c3)cc21]
I-391b
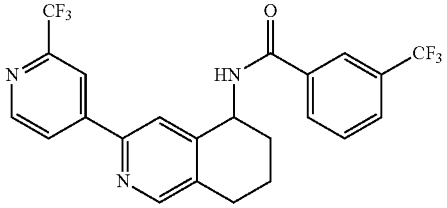
I-392

TABLE 1-continued
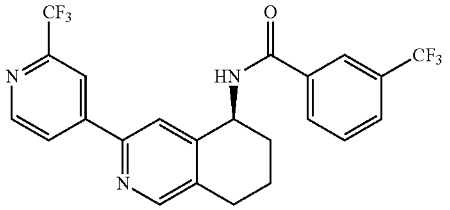 [SMILES: O=C(N[C@H]1CCCc2cnc(-c3ccnc(C(F)(F)F)c3)cc21)c1cccc(C(F)(F)F)c1]
I-392a
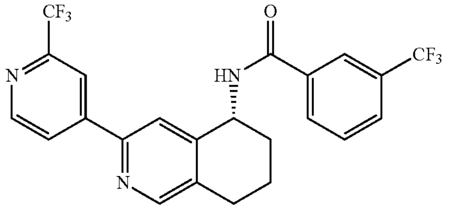 [SMILES: O=C(N[C@@H]1CCCc2cnc(-c3ccnc(C(F)(F)F)c3)cc21)c1cccc(C(F)(F)F)c1]
I-392b
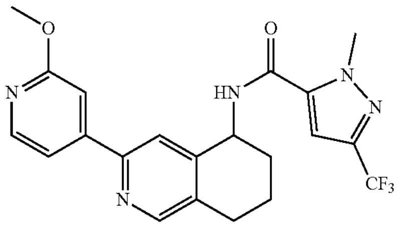 [SMILES: COc1cc(-c2cc3c(cn2)CCCC3NC(=O)c2cc(C(F)(F)F)nn2C)ccn1]
I-393
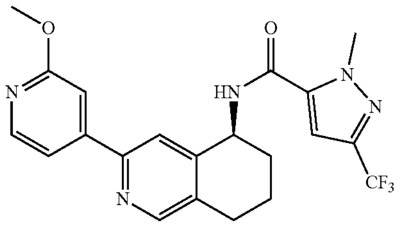 [SMILES: COc1cc(-c2cc3c(cn2)CCC[C@@H]3NC(=O)c2cc(C(F)(F)F)nn2C)ccn1]
I-393a
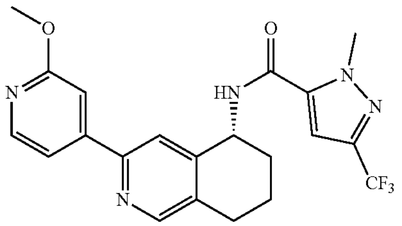 [SMILES: COc1cc(-c2cc3c(cn2)CCC[C@H]3NC(=O)c2cc(C(F)(F)F)nn2C)ccn1]
I-393b
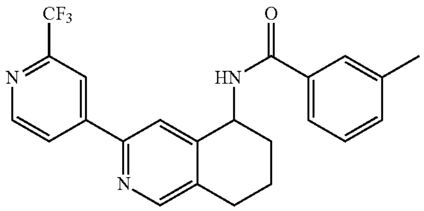 [SMILES: Cc1cccc(C(=O)NC2CCCc3cnc(-c4ccnc(C(F)(F)F)c4)cc32)c1]
I-394
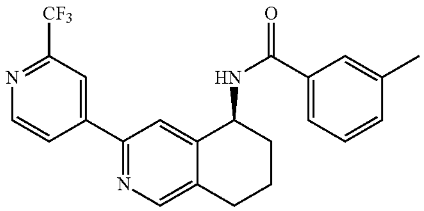 [SMILES: Cc1cccc(C(=O)N[C@H]2CCCc3cnc(-c4ccnc(C(F)(F)F)c4)cc32)c1]
I-394a TABLE 1-continued
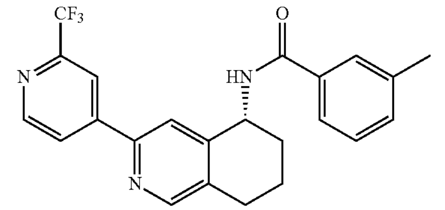 [SMILES: Cc1cccc(C(=O)N[C@@H]2CCCc3cnc(-c4ccnc(C(F)(F)F)c4)cc32)c1]
I-394b
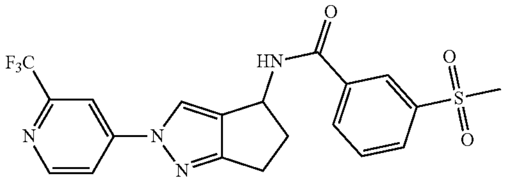 [SMILES: CS(=O)(=O)c1cccc(C(=O)NC2CCc3nn(-c4ccnc(C(F)(F)F)c4)cc32)c1]
I-395
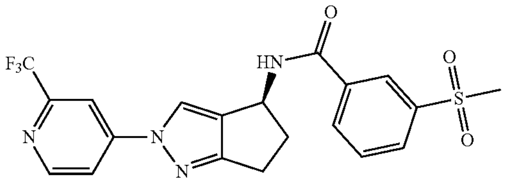 [SMILES: CS(=O)(=O)c1cccc(C(=O)N[C@H]2CCc3nn(-c4ccnc(C(F)(F)F)c4)cc32)c1]
I-395a
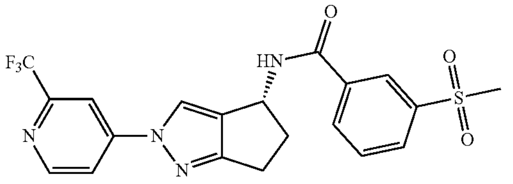 [SMILES: CS(=O)(=O)c1cccc(C(=O)N[C@@H]2CCc3nn(-c4ccnc(C(F)(F)F)c4)cc32)c1]
I-395b
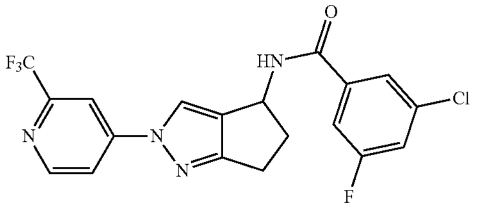
I-396
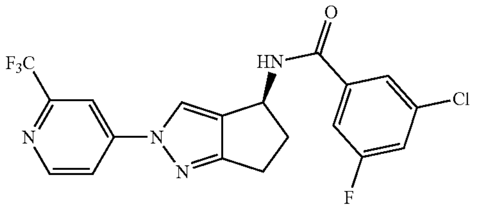
I-396a
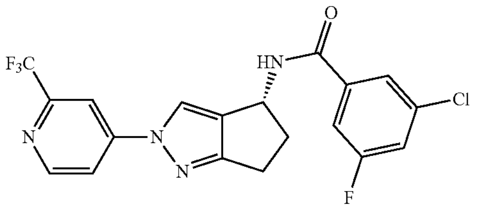
I-396b TABLE 1-continued
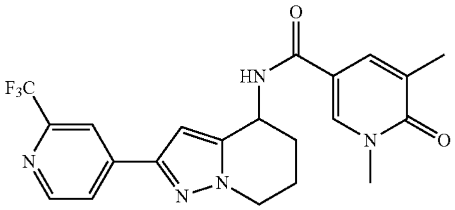 [SMILES: Cc1cc(C(=O)NC2CCCn3nc(-c4ccnc(C(F)(F)F)c4)cc32)cn(C)c1=O]
I-397
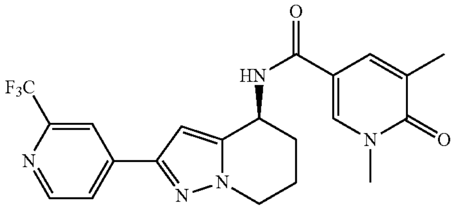 [SMILES: Cc1cc(C(=O)N[C@H]2CCCn3nc(-c4ccnc(C(F)(F)F)c4)cc32)cn(C)c1=O]
I-397a
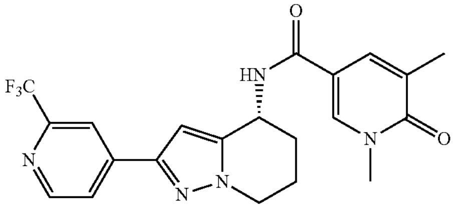 [SMILES: Cc1cc(C(=O)N[C@@H]2CCCn3nc(-c4ccnc(C(F)(F)F)c4)cc32)cn(C)c1=O]
I-397b
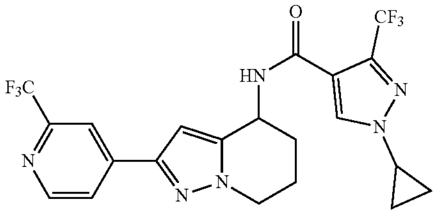 [SMILES: O=C(NC1CCCn2nc(-c3ccnc(C(F)(F)F)c3)cc21)c1cn(C2CC2)nc1C(F)(F)F]
I-398
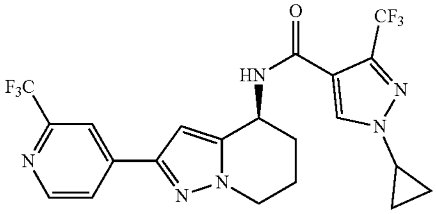 [SMILES: O=C(N[C@H]1CCCn2nc(-c3ccnc(C(F)(F)F)c3)cc21)c1cn(C2CC2)nc1C(F)(F)F]
I-398a
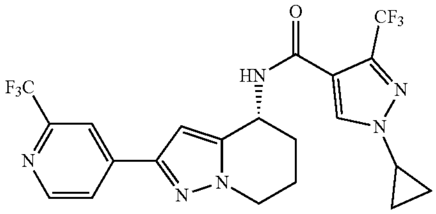 [SMILES: O=C(N[C@@H]1CCCn2nc(-c3ccnc(C(F)(F)F)c3)cc21)c1cn(C2CC2)nc1C(F)(F)F]
I-398b
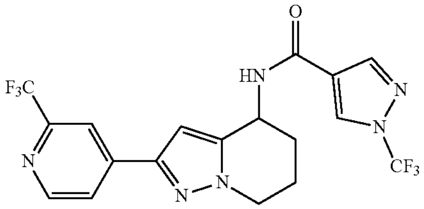 [SMILES: O=C(NC1CCCn2nc(-c3ccnc(C(F)(F)F)c3)cc21)c1cnn(C(F)(F)F)c1]
I-399

TABLE 1-continued
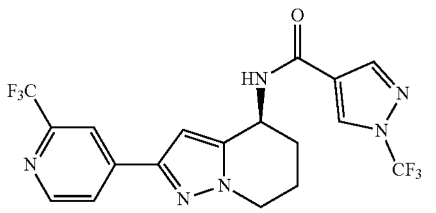
I-399a
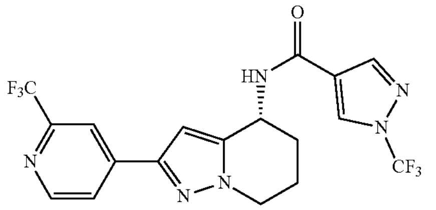 [SMILES: O=C(N[C@@H]1CCCn2nc(-c3ccnc(C(F)(F)F)c3)cc21)c1cnn(C(F)(F)F)c1]
I-399b
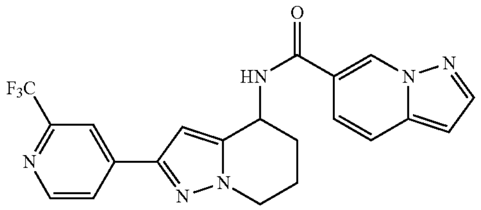 [SMILES: O=C(NC1CCCn2nc(-c3ccnc(C(F)(F)F)c3)cc21)c1ccc2ccnn2c1]
I-400
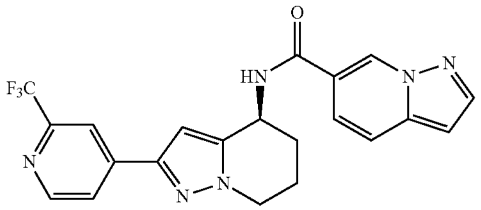 [SMILES: O=C(N[C@H]1CCCn2nc(-c3ccnc(C(F)(F)F)c3)cc21)c1ccc2ccnn2c1]
I-400a
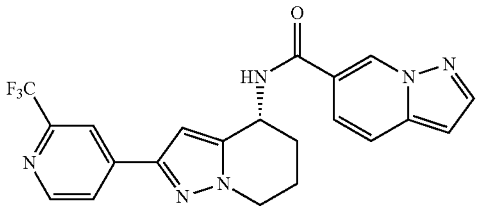 [SMILES: O=C(N[C@@H]1CCCn2nc(-c3ccnc(C(F)(F)F)c3)cc21)c1ccc2ccnn2c1]
I-400b
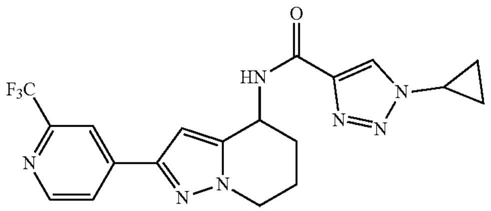 [SMILES: O=C(NC1CCCn2nc(-c3ccnc(C(F)(F)F)c3)cc21)c1cn(C2CC2)nn1]
I-401
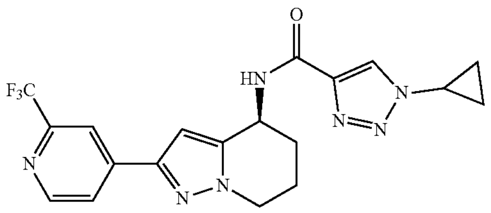 [SMILES: O=C(N[C@H]1CCCn2nc(-c3ccnc(C(F)(F)F)c3)cc21)c1cn(C2CC2)nn1]
I-401a TABLE 1-continued
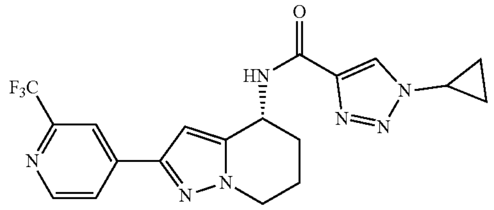 [SMILES: O=C(N[C@@H]1CCCn2nc(-c3ccnc(C(F)(F)F)c3)cc21)c1cn(C2CC2)nn1]
I-401b
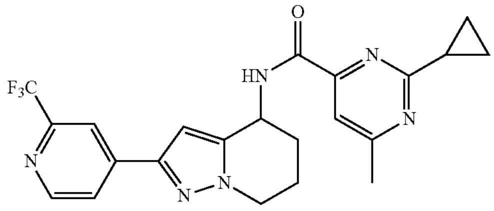
I-402
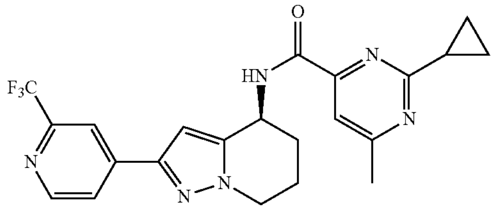 [SMILES: Cc1cc(C(=O)N[C@H]2CCCn3nc(-c4ccnc(C(F)(F)F)c4)cc32)nc(C2CC2)n1]
I-402a
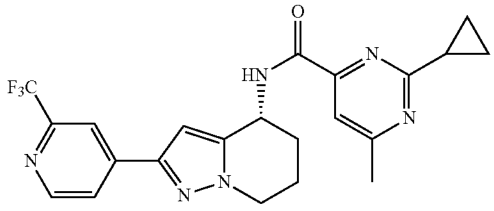 [SMILES: Cc1cc(C(=O)N[C@@H]2CCCn3nc(-c4ccnc(C(F)(F)F)c4)cc32)nc(C2CC2)n1]
I-402b
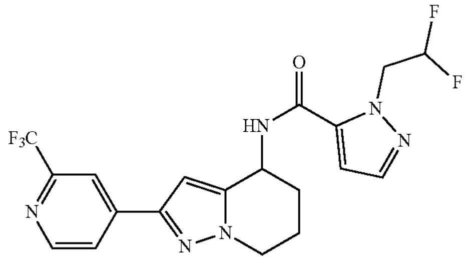 [SMILES: O=C(NC1CCCn2nc(-c3ccnc(C(F)(F)F)c3)cc21)c1ccnn1CC(F)F]
I-403
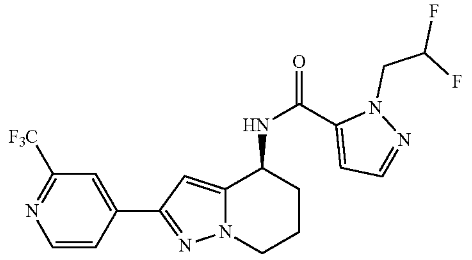 [SMILES: O=C(N[C@H]1CCCn2nc(-c3ccnc(C(F)(F)F)c3)cc21)c1ccnn1CC(F)F]
I-403a TABLE 1-continued
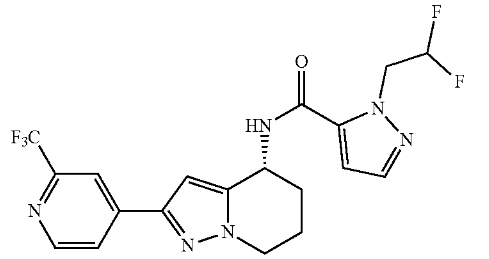 [SMILES: O=C(N[C@@H]1CCCn2nc(-c3ccnc(C(F)(F)F)c3)cc21)c1ccnn1CC(F)F]
I-403b
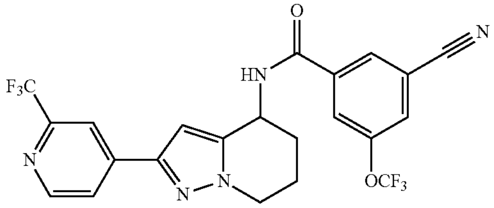 [SMILES: N#Cc1cc(OC(F)(F)F)cc(C(=O)NC2CCCn3nc(-c4ccnc(C(F)(F)F)c4)cc32)c1]
I-404
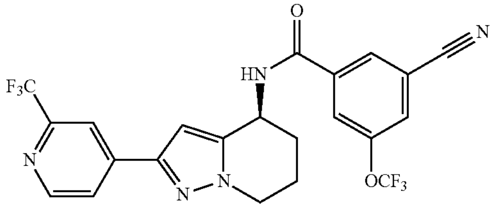 [SMILES: N#Cc1cc(OC(F)(F)F)cc(C(=O)N[C@H]2CCCn3nc(-c4ccnc(C(F)(F)F)c4)cc32)c1]
I-404a
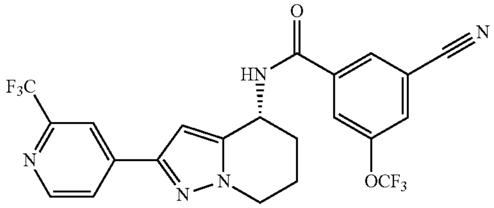
I-404b
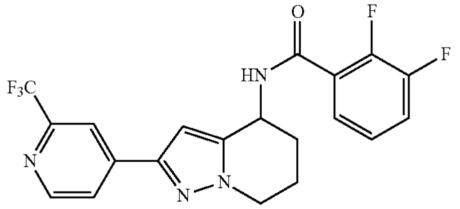 [SMILES: O=C(NC1CCCn2nc(-c3ccnc(C(F)(F)F)c3)cc21)c1cccc(F)c1F]
I-405
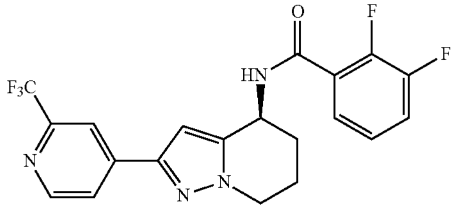 [SMILES: O=C(N[C@H]1CCCn2nc(-c3ccnc(C(F)(F)F)c3)cc21)c1cccc(F)c1F]
I-405a
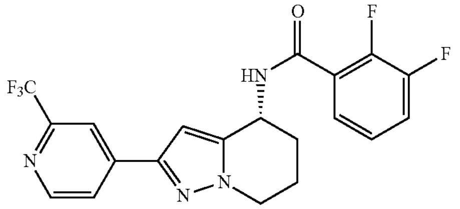
I-405b TABLE 1-continued
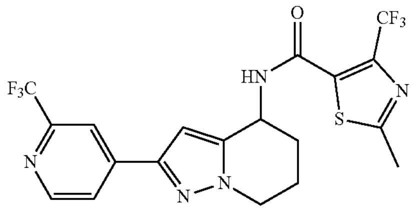 [SMILES: Cc1nc(C(F)(F)F)c(C(=O)NC2CCCn3nc(-c4ccnc(C(F)(F)F)c4)cc32)s1]
I-406
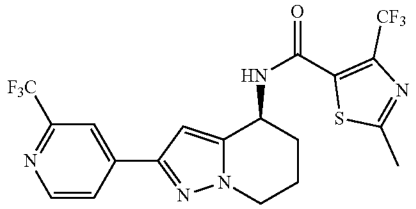 [SMILES: Cc1nc(C(F)(F)F)c(C(=O)N[C@H]2CCCn3nc(-c4ccnc(C(F)(F)F)c4)cc32)s1]
I-406a
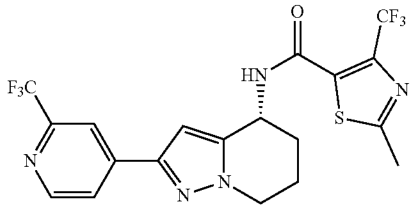 [SMILES: Cc1nc(C(F)(F)F)c(C(=O)N[C@@H]2CCCn3nc(-c4ccnc(C(F)(F)F)c4)cc32)s1]
I-406b
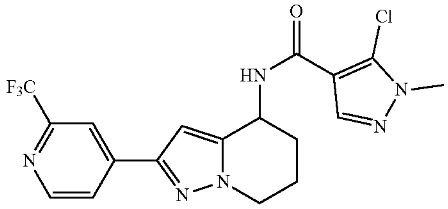 [SMILES: Cn1ncc(C(=O)NC2CCCn3nc(-c4ccnc(C(F)(F)F)c4)cc32)c1Cl]
I-407
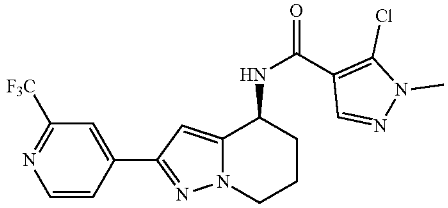 [SMILES: Cn1ncc(C(=O)N[C@H]2CCCn3nc(-c4ccnc(C(F)(F)F)c4)cc32)c1Cl]
I-407a
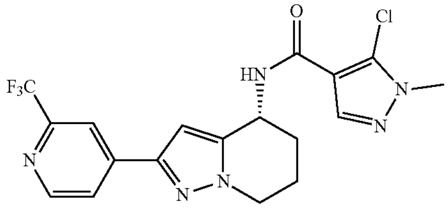 [SMILES: Cn1ncc(C(=O)N[C@@H]2CCCn3nc(-c4ccnc(C(F)(F)F)c4)cc32)c1Cl]
I-407b
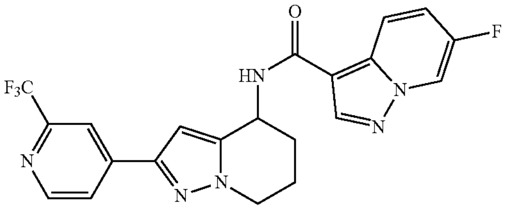 [SMILES: O=C(NC1CCCn2nc(-c3ccnc(C(F)(F)F)c3)cc21)c1cnn2cc(F)ccc12]
I-408

TABLE 1-continued
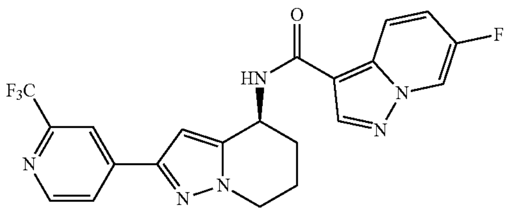 [SMILES: O=C(N[C@H]1CCCn2nc(-c3ccnc(C(F)(F)F)c3)cc21)c1cnn2cc(F)ccc12]
I-408a
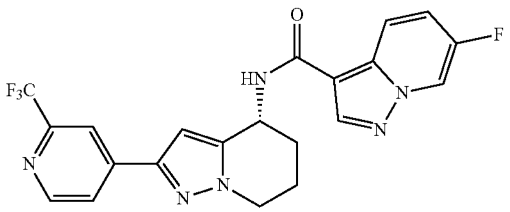 [SMILES: O=C(N[C@@H]1CCCn2nc(-c3ccnc(C(F)(F)F)c3)cc21)c1cnn2cc(F)ccc12]
I-408b
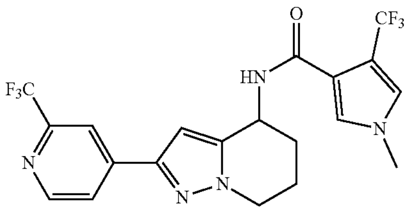 [SMILES: Cn1cc(C(=O)NC2CCCn3nc(-c4ccnc(C(F)(F)F)c4)cc32)c(C(F)(F)F)c1]
I-409
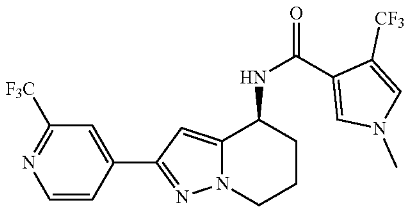 [SMILES: Cn1cc(C(=O)N[C@H]2CCCn3nc(-c4ccnc(C(F)(F)F)c4)cc32)c(C(F)(F)F)c1]
I-409a
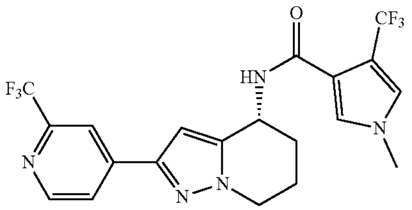 [SMILES: Cn1cc(C(=O)N[C@@H]2CCCn3nc(-c4ccnc(C(F)(F)F)c4)cc32)c(C(F)(F)F)c1]
I-409b
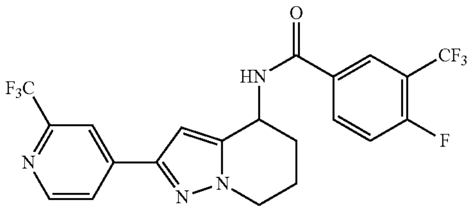 [SMILES: O=C(NC1CCCn2nc(-c3ccnc(C(F)(F)F)c3)cc21)c1ccc(F)c(C(F)(F)F)c1]
I-410
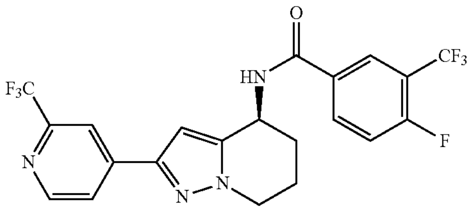 [SMILES: O=C(N[C@H]1CCCn2nc(-c3ccnc(C(F)(F)F)c3)cc21)c1ccc(F)c(C(F)(F)F)c1]
I-410a TABLE 1-continued
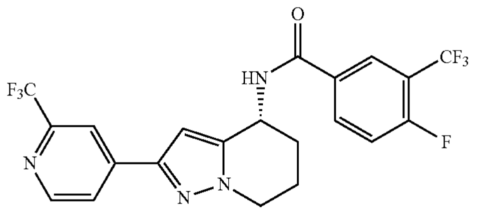 [SMILES: O=C(N[C@@H]1CCCn2nc(-c3ccnc(C(F)(F)F)c3)cc21)c1ccc(F)c(C(F)(F)F)c1]
I-410b
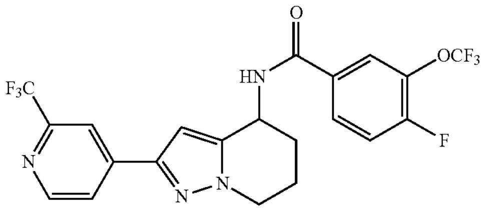 [SMILES: O=C(NC1CCCn2nc(-c3ccnc(C(F)(F)F)c3)cc21)c1ccc(F)c(OC(F)(F)F)c1]
I-411
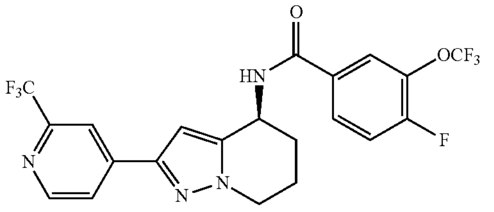 [SMILES: O=C(N[C@H]1CCCn2nc(-c3ccnc(C(F)(F)F)c3)cc21)c1ccc(F)c(OC(F)(F)F)c1]
I-411a
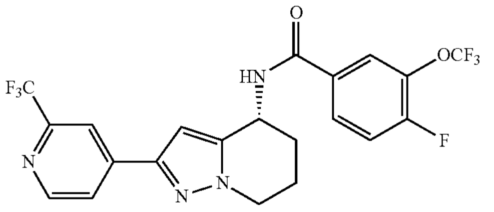 [SMILES: O=C(N[C@@H]1CCCn2nc(-c3ccnc(C(F)(F)F)c3)cc21)c1ccc(F)c(OC(F)(F)F)c1]
I-411b
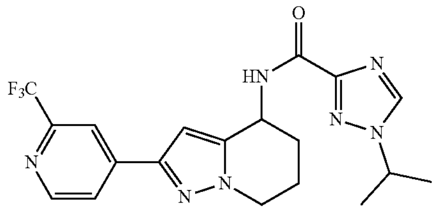 [SMILES: CC(C)n1cnc(C(=O)NC2CCCn3nc(-c4ccnc(C(F)(F)F)c4)cc32)n1]
I-412
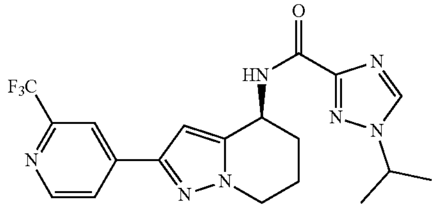 [SMILES: CC(C)n1cnc(C(=O)N[C@H]2CCCn3nc(-c4ccnc(C(F)(F)F)c4)cc32)n1]
I-412a
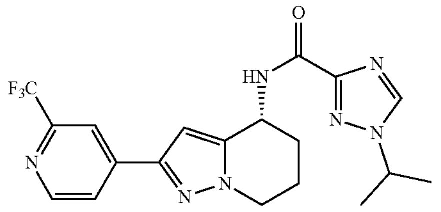
I-412b TABLE 1-continued
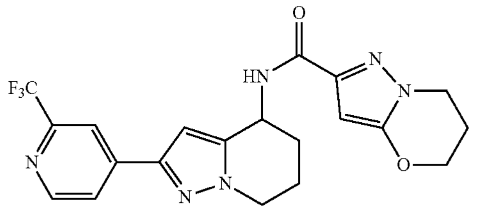 [SMILES: O=C(NC1CCCn2nc(-c3ccnc(C(F)(F)F)c3)cc21)c1cc2n(n1)CCCO2]
I-413
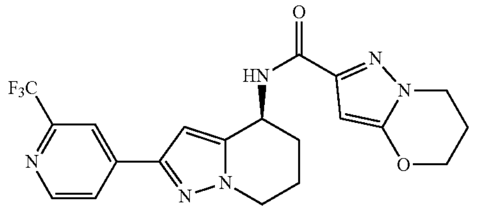 [SMILES: O=C(N[C@H]1CCCn2nc(-c3ccnc(C(F)(F)F)c3)cc21)c1cc2n(n1)CCCO2]
I-413a
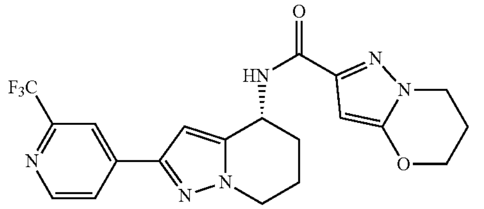 [SMILES: O=C(N[C@@H]1CCCn2nc(-c3ccnc(C(F)(F)F)c3)cc21)c1cc2n(n1)CCCO2]
I-413b
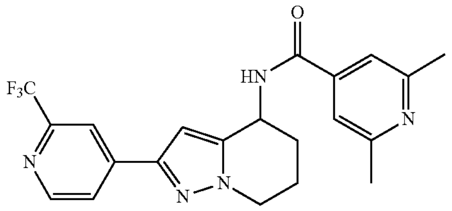 [SMILES: Cc1cc(C(=O)NC2CCCn3nc(-c4ccnc(C(F)(F)F)c4)cc32)cc(C)n1]
I-414
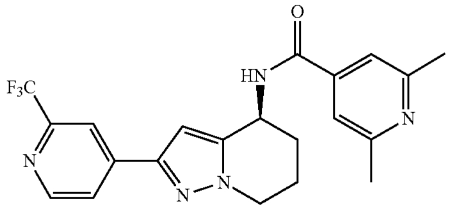 [SMILES: Cc1cc(C(=O)N[C@H]2CCCn3nc(-c4ccnc(C(F)(F)F)c4)cc32)cc(C)n1]
I-414a
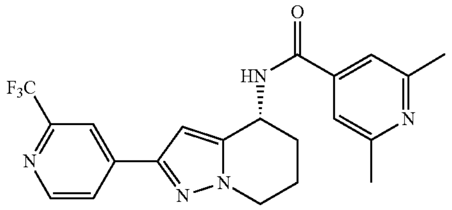 [SMILES: Cc1cc(C(=O)N[C@@H]2CCCn3nc(-c4ccnc(C(F)(F)F)c4)cc32)cc(C)n1]
I-414b
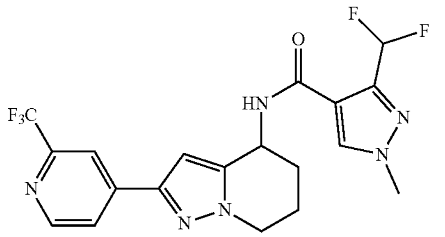 [SMILES: Cn1cc(C(=O)NC2CCCn3nc(-c4ccnc(C(F)(F)F)c4)cc32)c(C(F)F)n1]
I-415

TABLE 1-continued
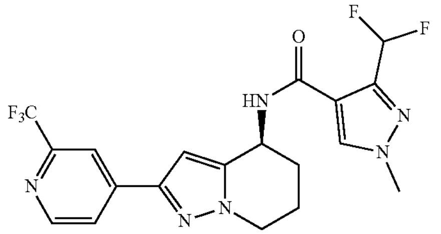 [SMILES: Cn1cc(C(=O)N[C@H]2CCCn3nc(-c4ccnc(C(F)(F)F)c4)cc32)c(C(F)F)n1]
I-415a
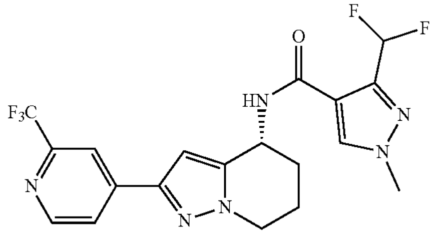 [SMILES: Cn1cc(C(=O)N[C@@H]2CCCn3nc(-c4ccnc(C(F)(F)F)c4)cc32)c(C(F)F)n1]
I-415b
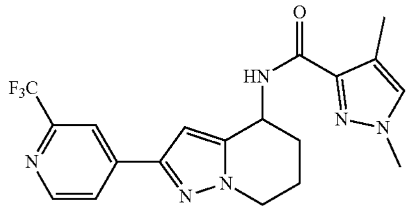 [SMILES: Cc1cn(C)nc1C(=O)NC1CCCn2nc(-c3ccnc(C(F)(F)F)c3)cc21]
I-416
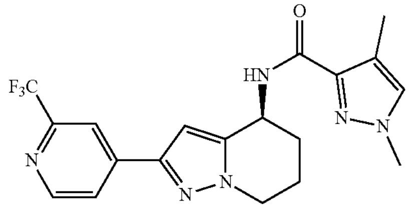 [SMILES: Cc1cn(C)nc1C(=O)N[C@H]1CCCn2nc(-c3ccnc(C(F)(F)F)c3)cc21]
I-416a
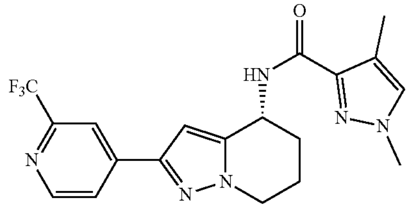
I-416b
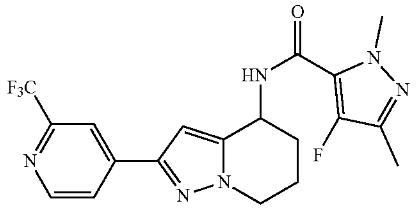 [SMILES: Cc1nn(C)c(C(=O)NC2CCCn3nc(-c4ccnc(C(F)(F)F)c4)cc32)c1F]
I-417
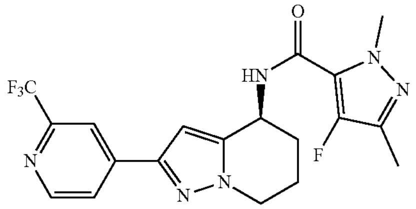 [SMILES: Cc1nn(C)c(C(=O)N[C@H]2CCCn3nc(-c4ccnc(C(F)(F)F)c4)cc32)c1F]
I-417a TABLE 1-continued
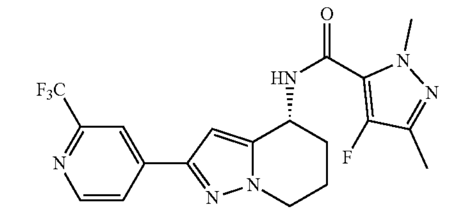
I-417b
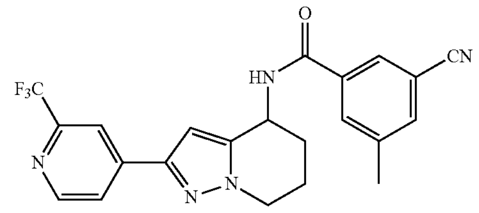
I-418
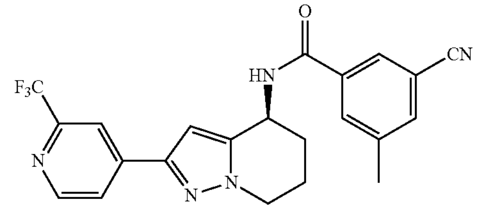
I-418a
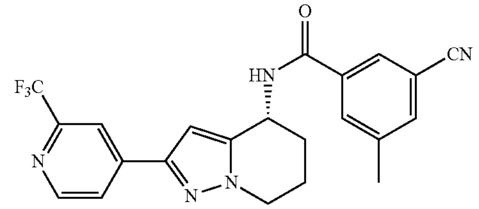 [SMILES: Cc1cc(C#N)cc(C(=O)N[C@@H]2CCCn3nc(-c4ccnc(C(F)(F)F)c4)cc32)c1]
I-418b
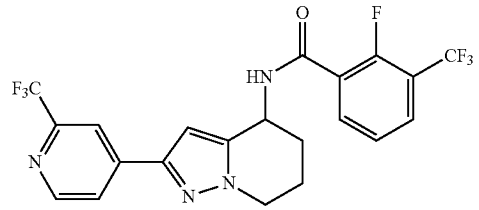 [SMILES: O=C(NC1CCCn2nc(-c3ccnc(C(F)(F)F)c3)cc21)c1cccc(C(F)(F)F)c1F]
I-419
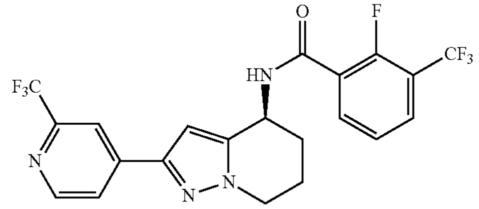 [SMILES: O=C(N[C@H]1CCCn2nc(-c3ccnc(C(F)(F)F)c3)cc21)c1cccc(C(F)(F)F)c1F]
I-419a
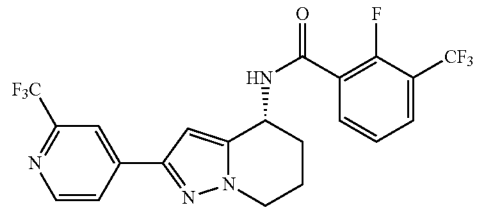 [SMILES: O=C(N[C@@H]1CCCn2nc(-c3ccnc(C(F)(F)F)c3)cc21)c1cccc(C(F)(F)F)c1F]
I-419b TABLE 1-continued
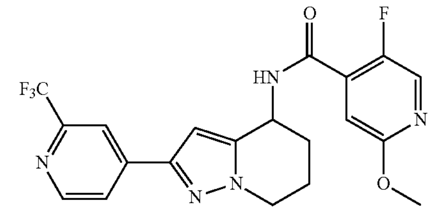 [SMILES: COc1cc(C(=O)NC2CCCn3nc(-c4ccnc(C(F)(F)F)c4)cc32)c(F)cn1]
I-420
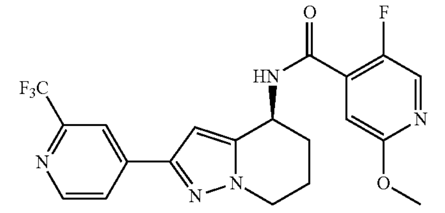 [SMILES: COc1cc(C(=O)N[C@H]2CCCn3nc(-c4ccnc(C(F)(F)F)c4)cc32)c(F)cn1]
I-420a
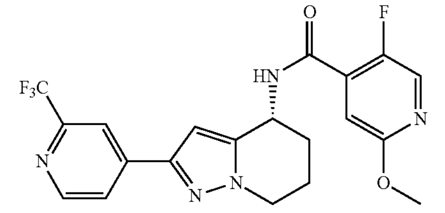
I-420b
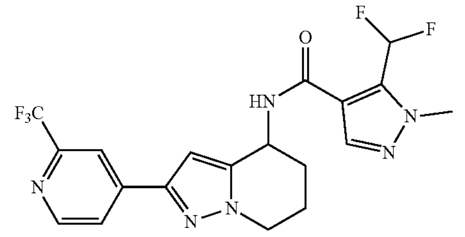 [SMILES: Cn1ncc(C(=O)NC2CCCn3nc(-c4ccnc(C(F)(F)F)c4)cc32)c1C(F)F]
I-421
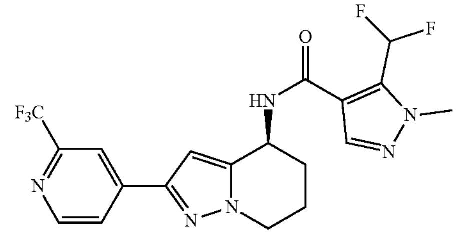 [SMILES: Cn1ncc(C(=O)N[C@H]2CCCn3nc(-c4ccnc(C(F)(F)F)c4)cc32)c1C(F)F]
I-421a
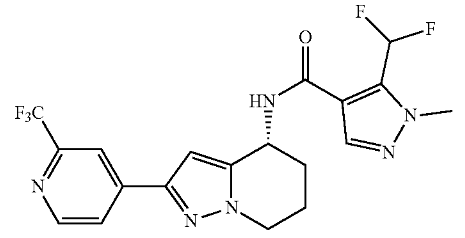 [SMILES: Cn1ncc(C(=O)N[C@@H]2CCCn3nc(-c4ccnc(C(F)(F)F)c4)cc32)c1C(F)F]
I-421b
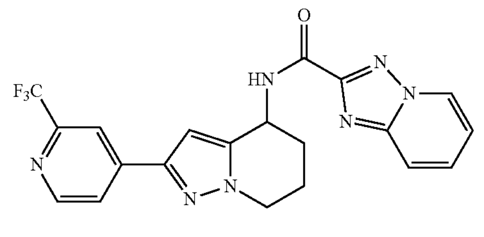 [SMILES: O=C(NC1CCCn2nc(-c3ccnc(C(F)(F)F)c3)cc21)c1nc2ccccn2n1]
I-422

TABLE 1-continued
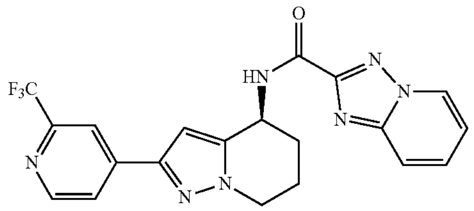 [SMILES: O=C(N[C@H]1CCCn2nc(-c3ccnc(C(F)(F)F)c3)cc21)c1nc2ccccn2n1]
I-422a
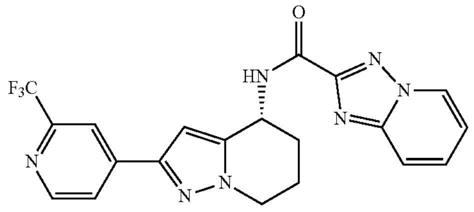 [SMILES: O=C(N[C@@H]1CCCn2nc(-c3ccnc(C(F)(F)F)c3)cc21)c1nc2ccccn2n1]
I-422b
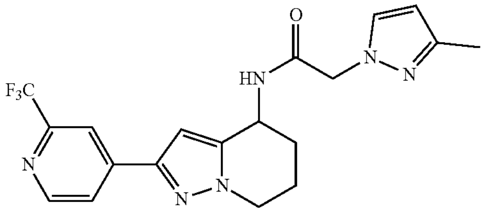 [SMILES: Cc1ccn(CC(=O)NC2CCCn3nc(-c4ccnc(C(F)(F)F)c4)cc32)n1]
I-423
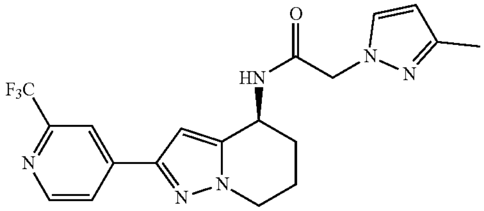 [SMILES: Cc1ccn(CC(=O)N[C@H]2CCCn3nc(-c4ccnc(C(F)(F)F)c4)cc32)n1]
I-423a
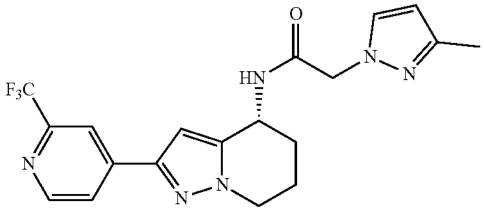 [SMILES: Cc1ccn(CC(=O)N[C@@H]2CCCn3nc(-c4ccnc(C(F)(F)F)c4)cc32)n1]
I-423b
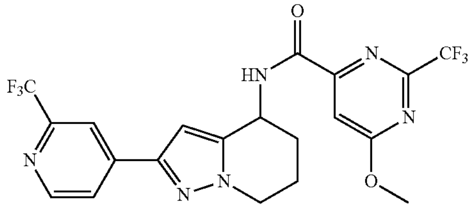 [SMILES: COc1cc(C(=O)NC2CCCn3nc(-c4ccnc(C(F)(F)F)c4)cc32)nc(C(F)(F)F)n1]
I-424
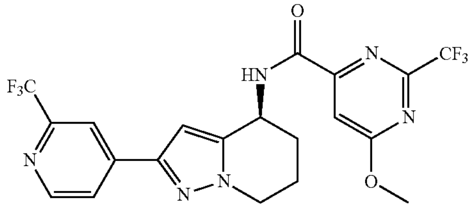 [SMILES: COc1cc(C(=O)N[C@H]2CCCn3nc(-c4ccnc(C(F)(F)F)c4)cc32)nc(C(F)(F)F)n1]
I-424a TABLE 1-continued
I-424b
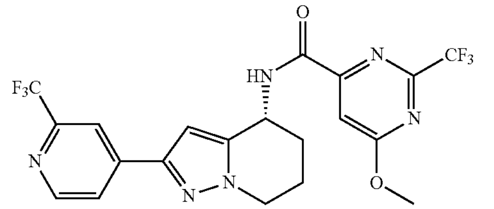 [SMILES: COc1cc(C(=O)N[C@@H]2CCCn3nc(-c4ccnc(C(F)(F)F)c4)cc32)nc(C(F)(F)F)n1]
I-425
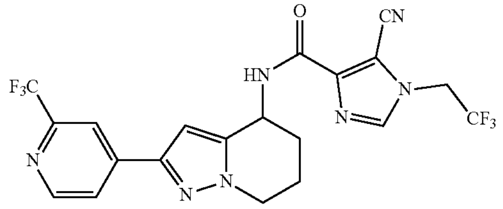 [SMILES: N#Cc1c(C(=O)NC2CCCn3nc(-c4ccnc(C(F)(F)F)c4)cc32)ncn1CC(F)(F)F]
I-425a
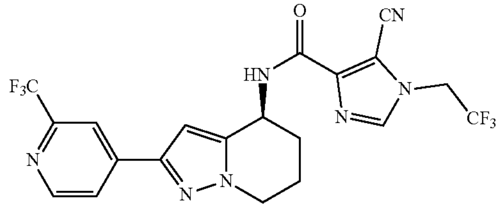 [SMILES: N#Cc1c(C(=O)N[C@H]2CCCn3nc(-c4ccnc(C(F)(F)F)c4)cc32)ncn1CC(F)(F)F]
I-425b
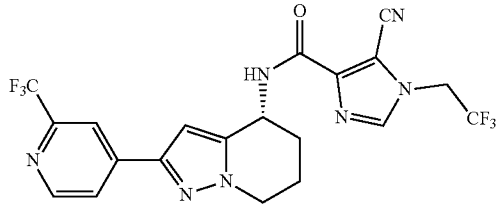 [SMILES: N#Cc1c(C(=O)N[C@@H]2CCCn3nc(-c4ccnc(C(F)(F)F)c4)cc32)ncn1CC(F)(F)F]
I-426
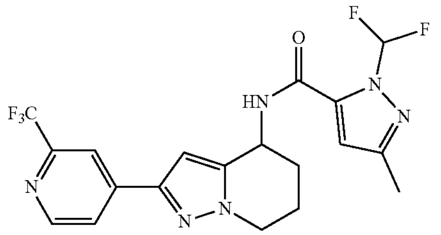 [SMILES: Cc1cc(C(=O)NC2CCCn3nc(-c4ccnc(C(F)(F)F)c4)cc32)n(C(F)F)n1]
I-426a
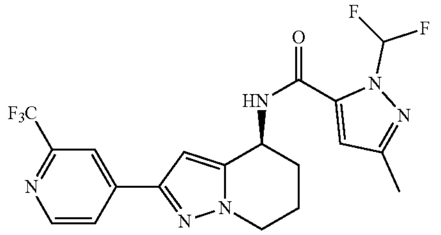 [SMILES: Cc1cc(C(=O)N[C@H]2CCCn3nc(-c4ccnc(C(F)(F)F)c4)cc32)n(C(F)F)n1]
I-426b
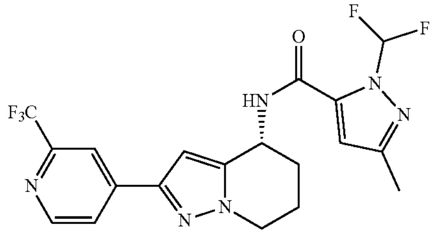 [SMILES: Cc1cc(C(=O)N[C@@H]2CCCn3nc(-c4ccnc(C(F)(F)F)c4)cc32)n(C(F)F)n1]

TABLE 1-continued
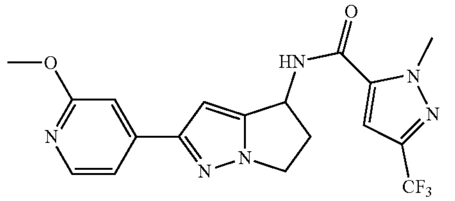
I-427
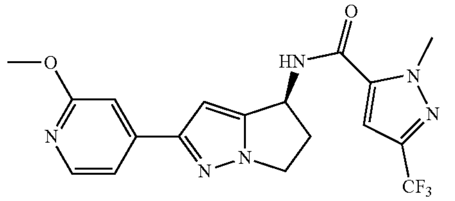
I-427a
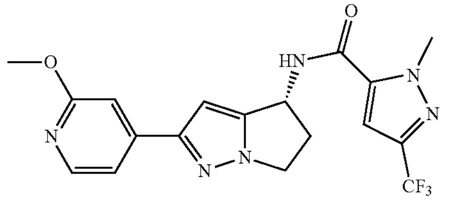
I-427b
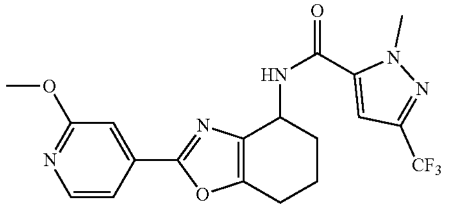
I-428
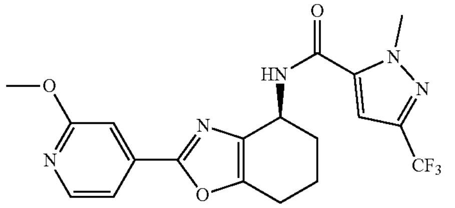 [SMILES: COc1cc(-c2nc3c(o2)CCC[C@@H]3NC(=O)c2cc(C(F)(F)F)nn2C)ccn1]
I-428a
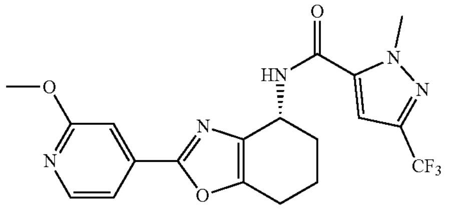 [SMILES: COc1cc(-c2nc3c(o2)CCC[C@H]3NC(=O)c2cc(C(F)(F)F)nn2C)ccn1]
I-428b
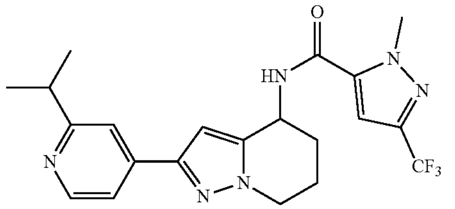 [SMILES: CC(C)c1cc(-c2cc3n(n2)CCCC3NC(=O)c2cc(C(F)(F)F)nn2C)ccn1]
I-429

TABLE 1-continued
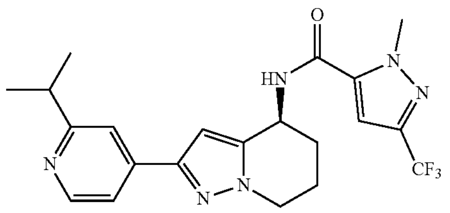
I-429a
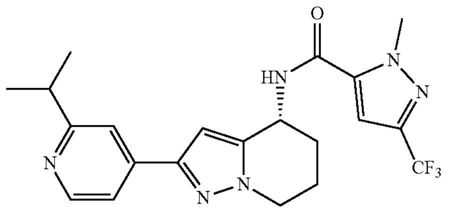
I-429b
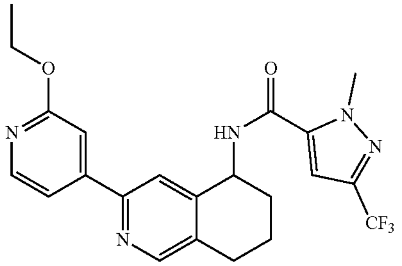
I-430
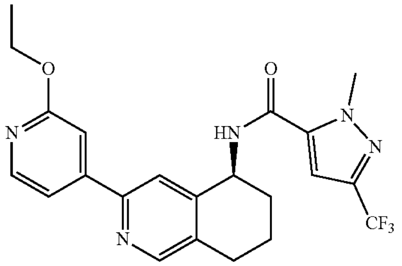 [SMILES: CCOc1cc(-c2cc3c(cn2)CCC[C@@H]3NC(=O)c2cc(C(F)(F)F)nn2C)ccn1]
I-430a
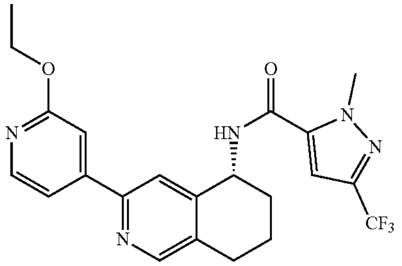 [SMILES: CCOc1cc(-c2cc3c(cn2)CCC[C@H]3NC(=O)c2cc(C(F)(F)F)nn2C)ccn1]
I-430b
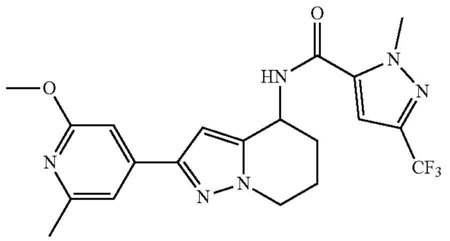 [SMILES: COc1cc(-c2cc3n(n2)CCCC3NC(=O)c2cc(C(F)(F)F)nn2C)cc(C)n1]
I-431

TABLE 1-continued
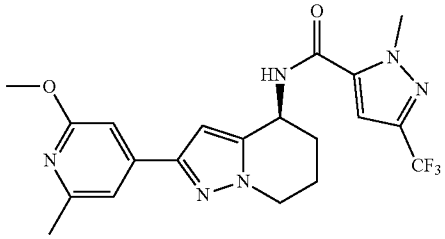 [SMILES: COc1cc(-c2cc3n(n2)CCC[C@@H]3NC(=O)c2cc(C(F)(F)F)nn2C)cc(C)n1]
I-431a
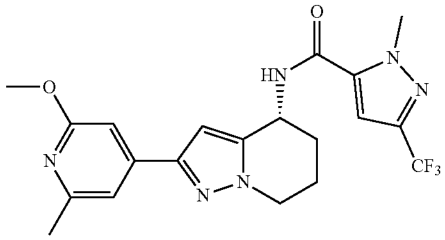
I-431b
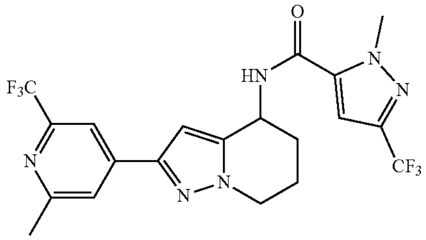 [SMILES: Cc1cc(-c2cc3n(n2)CCCC3NC(=O)c2cc(C(F)(F)F)nn2C)cc(C(F)(F)F)n1]
I-432
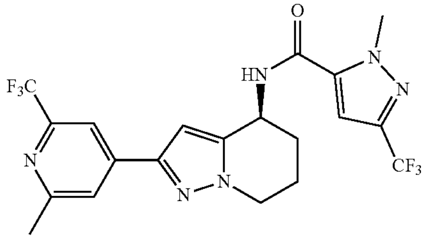 [SMILES: Cc1cc(-c2cc3n(n2)CCC[C@@H]3NC(=O)c2cc(C(F)(F)F)nn2C)cc(C(F)(F)F)n1]
I-432a
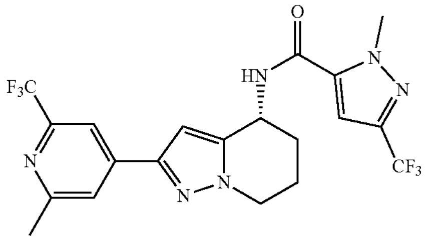
I-432b
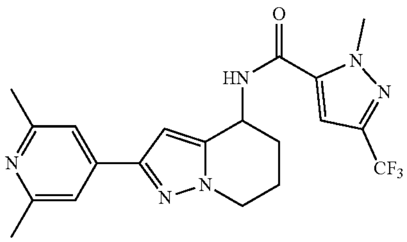 [SMILES: Cc1cc(-c2cc3n(n2)CCCC3NC(=O)c2cc(C(F)(F)F)nn2C)cc(C)n1]
I-433

TABLE 1-continued
I-433a
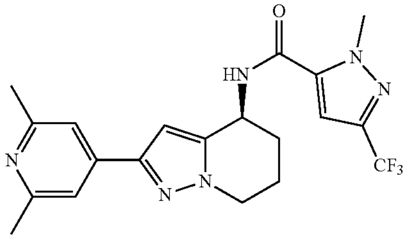 [SMILES: Cc1cc(-c2cc3n(n2)CCC[C@@H]3NC(=O)c2cc(C(F)(F)F)nn2C)cc(C)n1]
I-433b
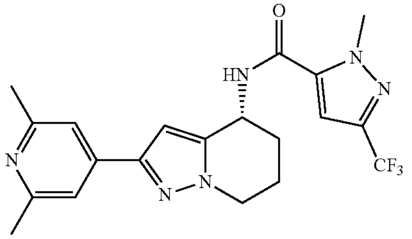 [SMILES: Cc1cc(-c2cc3n(n2)CCC[C@H]3NC(=O)c2cc(C(F)(F)F)nn2C)cc(C)n1]
I-434
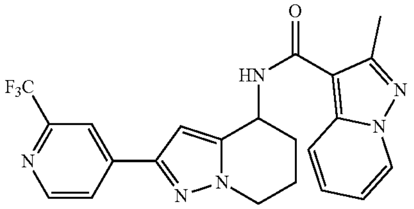 [SMILES: Cc1nn2ccccc2c1C(=O)NC1CCCn2nc(-c3ccnc(C(F)(F)F)c3)cc21]
I-434a
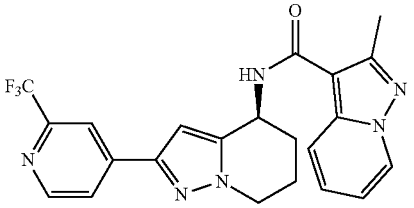 [SMILES: Cc1nn2ccccc2c1C(=O)N[C@H]1CCCn2nc(-c3ccnc(C(F)(F)F)c3)cc21]
I-434b
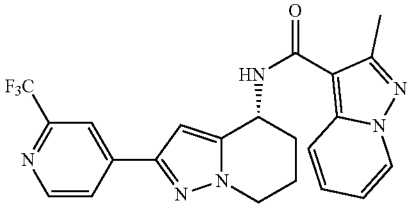 [SMILES: Cc1nn2ccccc2c1C(=O)N[C@@H]1CCCn2nc(-c3ccnc(C(F)(F)F)c3)cc21]
I-435
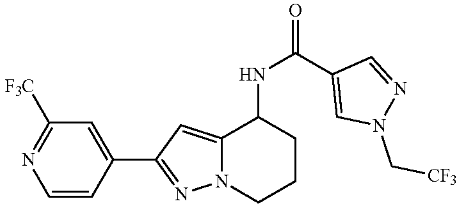
I-435a
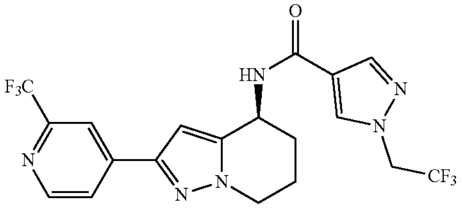

TABLE 1-continued
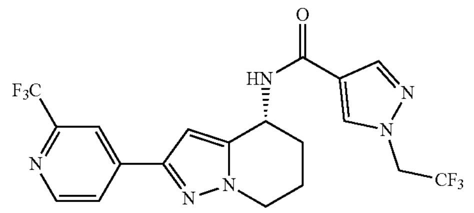 [SMILES: O=C(N[C@@H]1CCCn2nc(-c3ccnc(C(F)(F)F)c3)cc21)c1cnn(CC(F)(F)F)c1]
I-435b
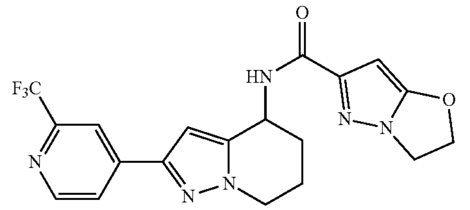 [SMILES: O=C(NC1CCCn2nc(-c3ccnc(C(F)(F)F)c3)cc21)c1cc2n(n1)CCO2]
I-436
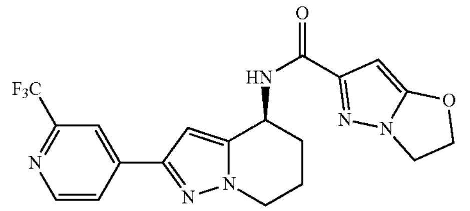 [SMILES: O=C(N[C@H]1CCCn2nc(-c3ccnc(C(F)(F)F)c3)cc21)c1cc2n(n1)CCO2]
I-436a
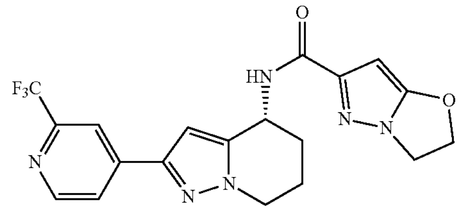 [SMILES: O=C(N[C@@H]1CCCn2nc(-c3ccnc(C(F)(F)F)c3)cc21)c1cc2n(n1)CCO2]
I-436b
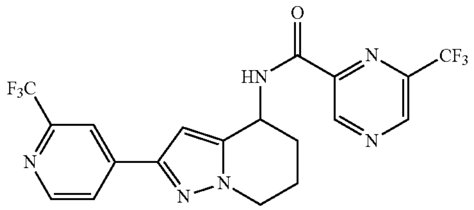 [SMILES: O=C(NC1CCCn2nc(-c3ccnc(C(F)(F)F)c3)cc21)c1cncc(C(F)(F)F)n1]
I-437
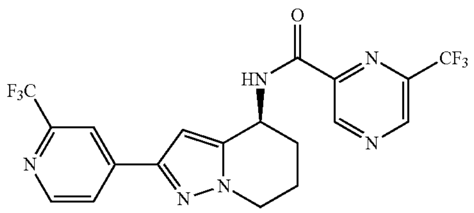 [SMILES: O=C(N[C@H]1CCCn2nc(-c3ccnc(C(F)(F)F)c3)cc21)c1cncc(C(F)(F)F)n1]
I-437a
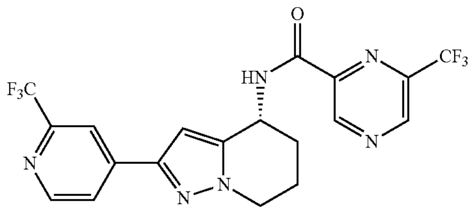
I-437b TABLE 1-continued
I-438
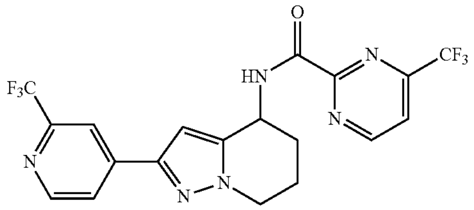
I-438a
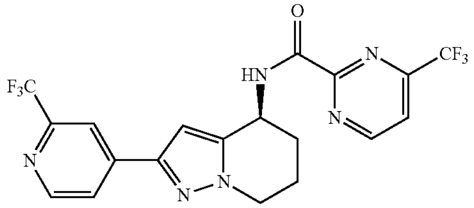 [SMILES: O=C(N[C@H]1CCCn2nc(-c3ccnc(C(F)(F)F)c3)cc21)c1nccc(C(F)(F)F)n1]
I-438b
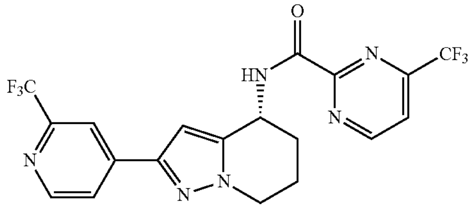 [SMILES: O=C(N[C@@H]1CCCn2nc(-c3ccnc(C(F)(F)F)c3)cc21)c1nccc(C(F)(F)F)n1]
I-439
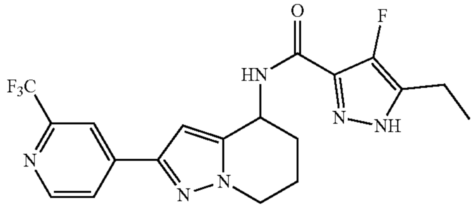 [SMILES: CCc1[nH]nc(C(=O)NC2CCCn3nc(-c4ccnc(C(F)(F)F)c4)cc32)c1F]
I-439a
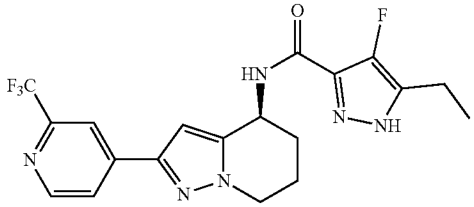 [SMILES: CCc1[nH]nc(C(=O)N[C@H]2CCCn3nc(-c4ccnc(C(F)(F)F)c4)cc32)c1F]
I-439b
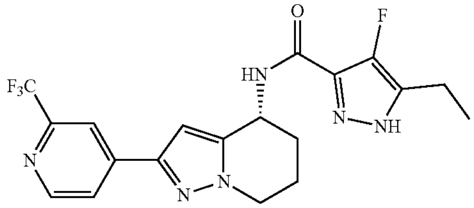
I-440
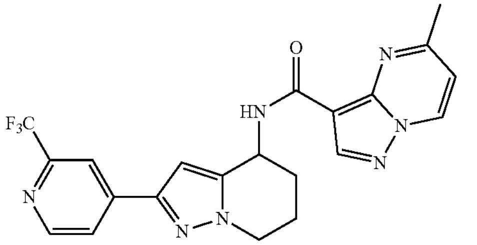 [SMILES: Cc1ccn2ncc(C(=O)NC3CCCn4nc(-c5ccnc(C(F)(F)F)c5)cc43)c2n1]

TABLE 1-continued
I-440a
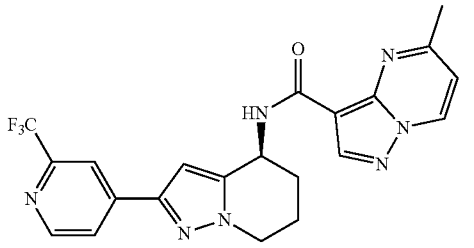 [SMILES: Cc1ccn2ncc(C(=O)N[C@H]3CCCn4nc(-c5ccnc(C(F)(F)F)c5)cc43)c2n1]
I-440b
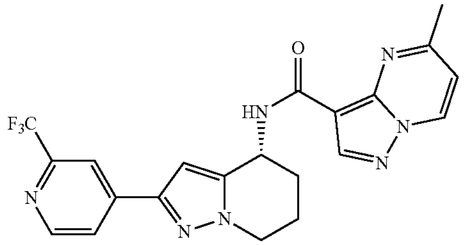 [SMILES: Cc1ccn2ncc(C(=O)N[C@@H]3CCCn4nc(-c5ccnc(C(F)(F)F)c5)cc43)c2n1]
I-441
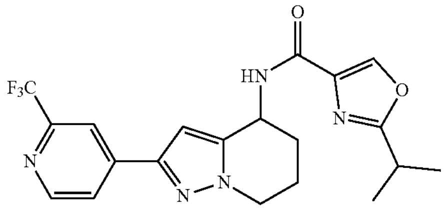
I-441a
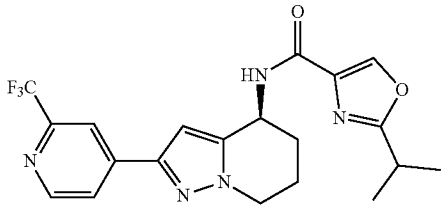 [SMILES: CC(C)c1nc(C(=O)N[C@H]2CCCn3nc(-c4ccnc(C(F)(F)F)c4)cc32)co1]
I-441b
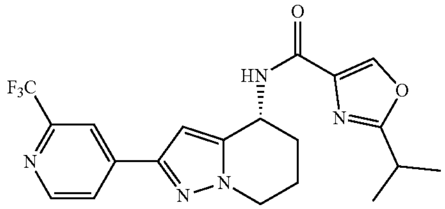 [SMILES: CC(C)c1nc(C(=O)N[C@@H]2CCCn3nc(-c4ccnc(C(F)(F)F)c4)cc32)co1]
I-442
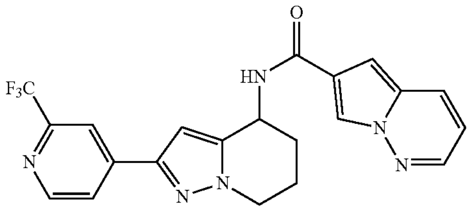 [SMILES: O=C(NC1CCCn2nc(-c3ccnc(C(F)(F)F)c3)cc21)c1cc2cccnn2c1]
I-442a
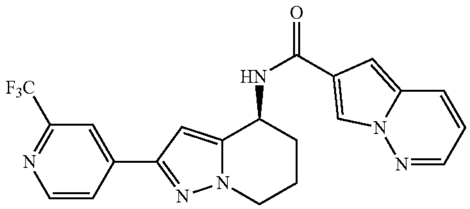 [SMILES: O=C(N[C@H]1CCCn2nc(-c3ccnc(C(F)(F)F)c3)cc21)c1cc2cccnn2c1]

TABLE 1-continued
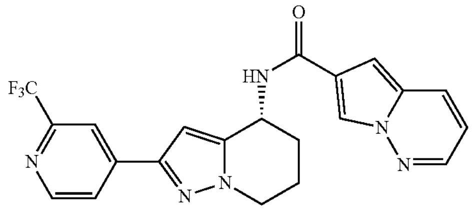 [SMILES: O=C(N[C@@H]1CCCn2nc(-c3ccnc(C(F)(F)F)c3)cc21)c1cc2cccnn2c1]
I-442b
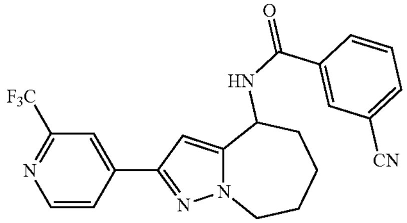
I-443
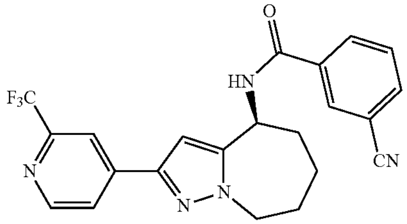
I-443a
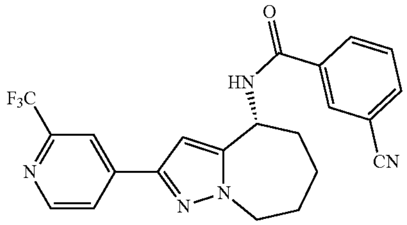 [SMILES: N#Cc1cccc(C(=O)NC2CCCCn3nc(-c4ccnc(C(F)(F)F)c4)cc32)c1]
I-443b
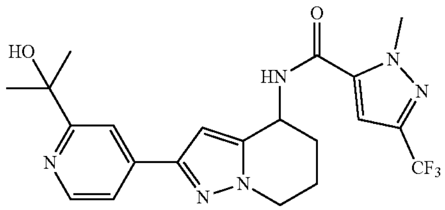 [SMILES: Cn1nc(C(F)(F)F)cc1C(=O)NC1CCCn2nc(-c3ccnc(C(C)(C)O)c3)cc21]
I-444
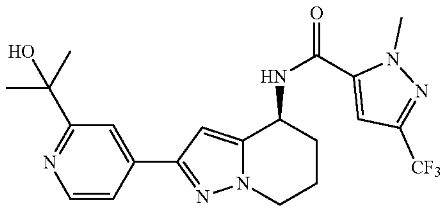 [SMILES: Cn1nc(C(F)(F)F)cc1C(=O)N[C@H]1CCCn2nc(-c3ccnc(C(C)(C)O)c3)cc21]
I-444a
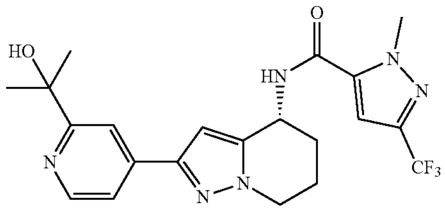 [SMILES: Cn1nc(C(F)(F)F)cc1C(=O)N[C@@H]1CCCn2nc(-c3ccnc(C(C)(C)O)c3)cc21]
I-444b TABLE 1-continued
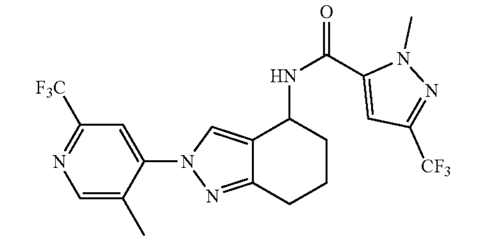 [SMILES: Cc1cnc(C(F)(F)F)cc1-n1cc2c(n1)CCCC2NC(=O)c1cc(C(F)(F)F)nn1C]
I-445
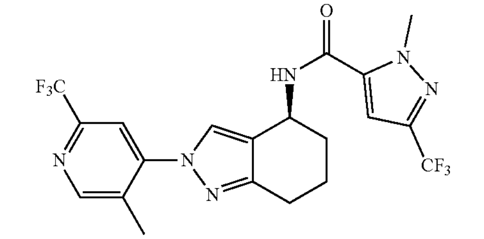 [SMILES: Cc1cnc(C(F)(F)F)cc1-n1cc2c(n1)CCC[C@@H]2NC(=O)c1cc(C(F)(F)F)nn1C]
I-445a
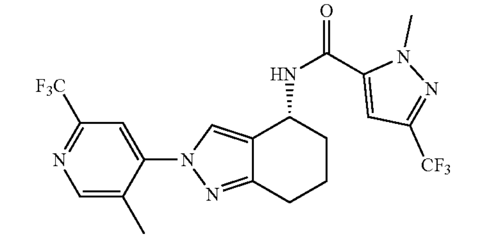 [SMILES: Cc1cnc(C(F)(F)F)cc1-n1cc2c(n1)CCC[C@H]2NC(=O)c1cc(C(F)(F)F)nn1C]
I-445b
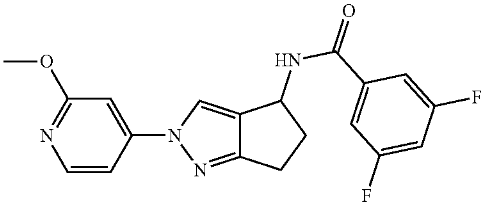 [SMILES: COc1cc(-n2cc3c(n2)CCC3NC(=O)c2cc(F)cc(F)c2)ccn1]
I-446
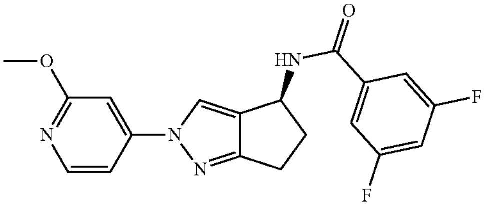 [SMILES: COc1cc(-n2cc3c(n2)CC[C@@H]3NC(=O)c2cc(F)cc(F)c2)ccn1]
I-446a
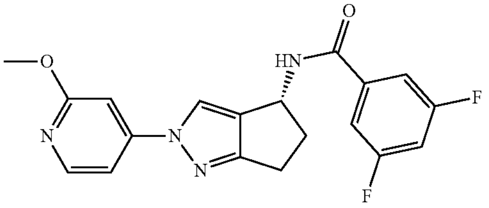 [SMILES: COc1cc(-n2cc3c(n2)CC[C@H]3NC(=O)c2cc(F)cc(F)c2)ccn1]
I-446b
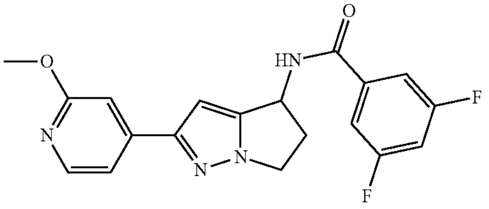 [SMILES: COc1cc(-c2cc3n(n2)CCC3NC(=O)c2cc(F)cc(F)c2)ccn1]
I-447

TABLE 1-continued
I-447a
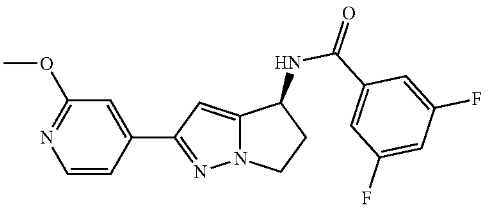 [SMILES: COc1cc(-c2cc3n(n2)CC[C@@H]3NC(=O)c2cc(F)cc(F)c2)ccn1]
I-447b
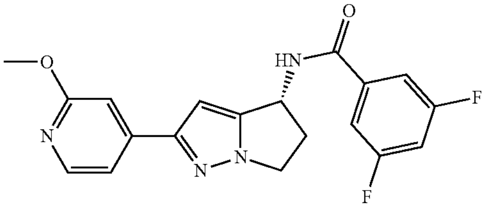 [SMILES: COc1cc(-c2cc3n(n2)CC[C@H]3NC(=O)c2cc(F)cc(F)c2)ccn1]
I-448
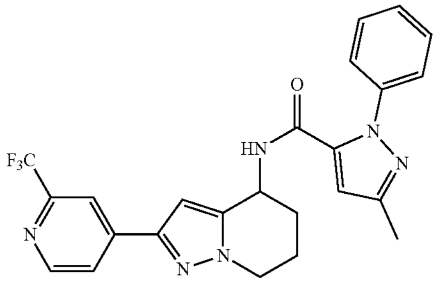 [SMILES: Cc1cc(C(=O)NC2CCCn3nc(-c4ccnc(C(F)(F)F)c4)cc32)n(-c2ccccc2)n1]
I-448a
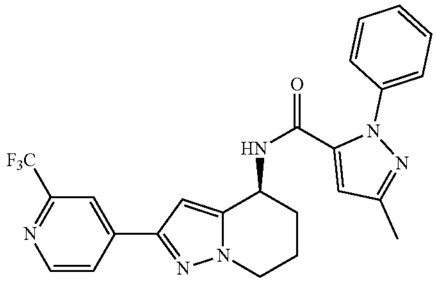 [SMILES: Cc1cc(C(=O)N[C@H]2CCCn3nc(-c4ccnc(C(F)(F)F)c4)cc32)n(-c2ccccc2)n1]
I-448b
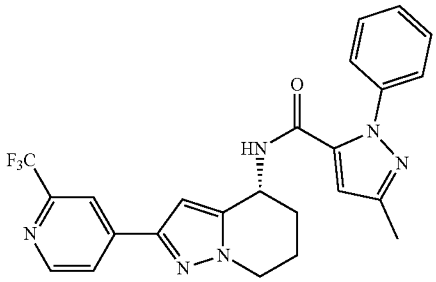 [SMILES: Cc1cc(C(=O)N[C@@H]2CCCn3nc(-c4ccnc(C(F)(F)F)c4)cc32)n(-c2ccccc2)n1]
I-449
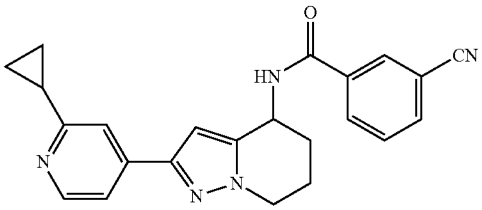 [SMILES: N#Cc1cccc(C(=O)NC2CCCn3nc(-c4ccnc(C5CC5)c4)cc32)c1]

TABLE 1-continued
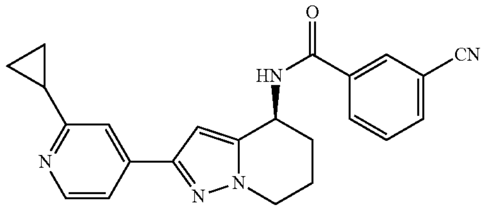 [SMILES: N#Cc1cccc(C(=O)N[C@H]2CCCn3nc(-c4ccnc(C5CC5)c4)cc32)c1]
I-449a
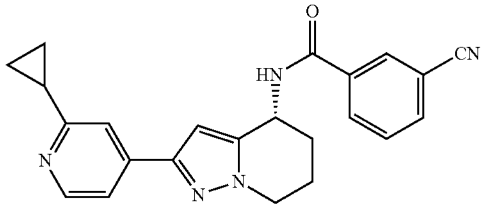 [SMILES: N#Cc1cccc(C(=O)N[C@@H]2CCCn3nc(-c4ccnc(C5CC5)c4)cc32)c1]
I-449b
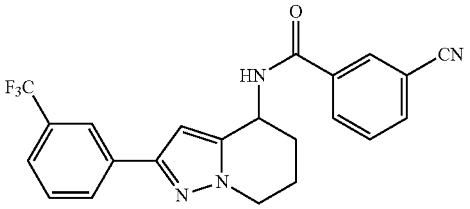 [SMILES: N#Cc1cccc(C(=O)NC2CCCn3nc(-c4cccc(C(F)(F)F)c4)cc32)c1]
I-450
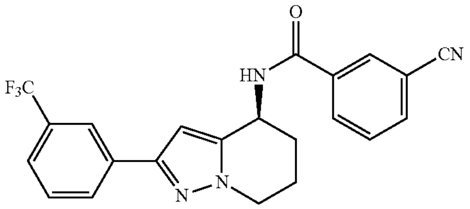 [SMILES: N#Cc1cccc(C(=O)N[C@H]2CCCn3nc(-c4cccc(C(F)(F)F)c4)cc32)c1]
I-450a
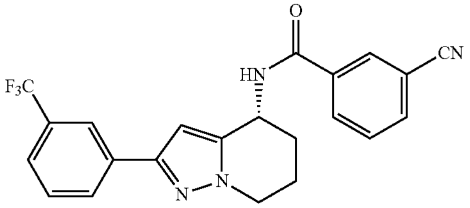 [SMILES: N#Cc1cccc(C(=O)N[C@@H]2CCCn3nc(-c4cccc(C(F)(F)F)c4)cc32)c1]
I-450b
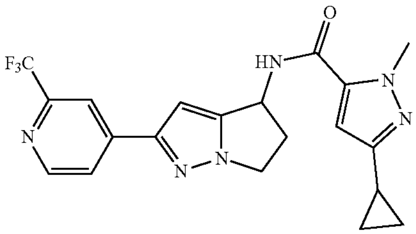
I-450
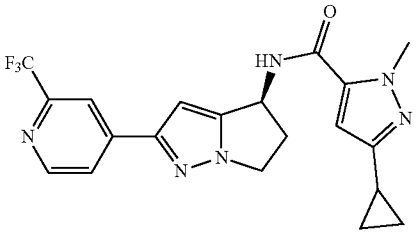
I-450a TABLE 1-continued
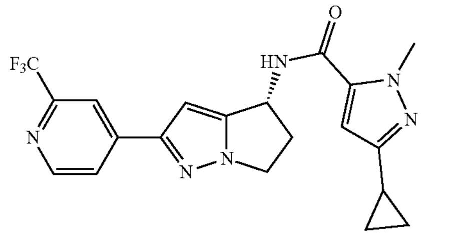
I-450b
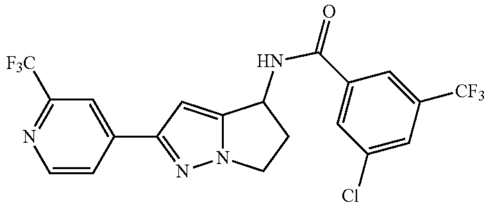 [SMILES: O=C(NC1CCn2nc(-c3ccnc(C(F)(F)F)c3)cc21)c1cc(Cl)cc(C(F)(F)F)c1]
I-451
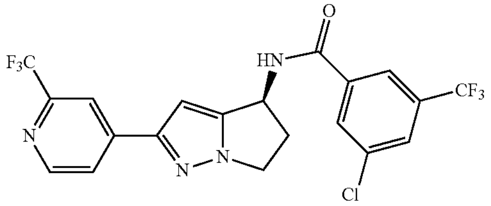 [SMILES: O=C(N[C@H]1CCn2nc(-c3ccnc(C(F)(F)F)c3)cc21)c1cc(Cl)cc(C(F)(F)F)c1]
I-451a
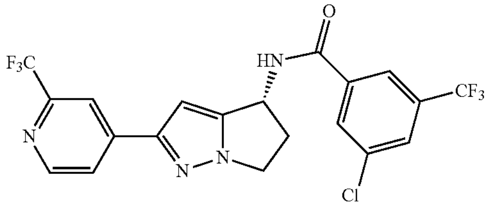 [SMILES: O=C(N[C@@H]1CCn2nc(-c3ccnc(C(F)(F)F)c3)cc21)c1cc(Cl)cc(C(F)(F)F)c1]
I-451b
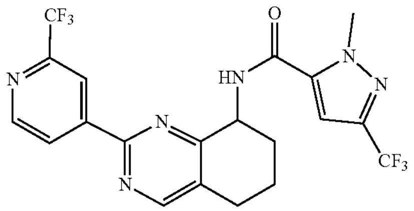 [SMILES: Cn1nc(C(F)(F)F)cc1C(=O)NC1CCCc2cnc(-c3ccnc(C(F)(F)F)c3)nc21]
I-452
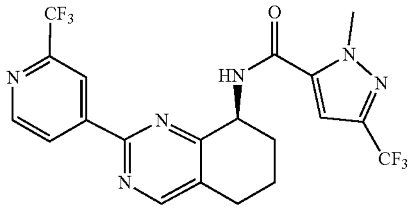 [SMILES: Cn1nc(C(F)(F)F)cc1C(=O)N[C@H]1CCCc2cnc(-c3ccnc(C(F)(F)F)c3)nc21]
I-452a
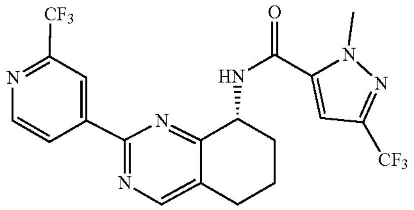 [SMILES: Cn1nc(C(F)(F)F)cc1C(=O)N[C@@H]1CCCc2cnc(-c3ccnc(C(F)(F)F)c3)nc21]
I-452b TABLE 1-continued
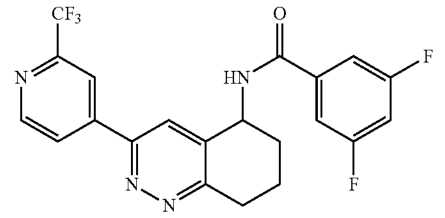 [SMILES: O=C(NC1CCCc2nnc(-c3ccnc(C(F)(F)F)c3)cc21)c1cc(F)cc(F)c1]
I-453
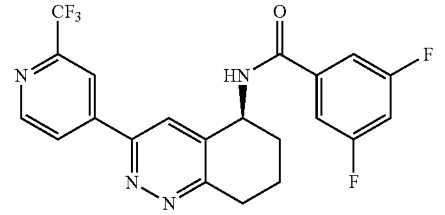 [SMILES: O=C(N[C@H]1CCCc2nnc(-c3ccnc(C(F)(F)F)c3)cc21)c1cc(F)cc(F)c1]
I-453a
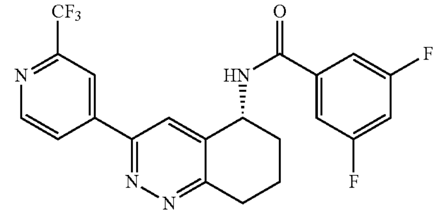
I-453b
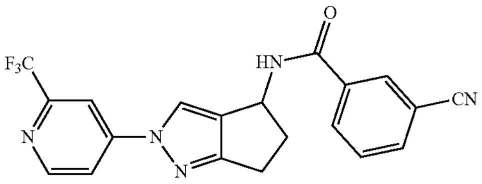 [SMILES: N#Cc1cccc(C(=O)NC2CCc3nn(-c4ccnc(C(F)(F)F)c4)cc32)c1]
I-454
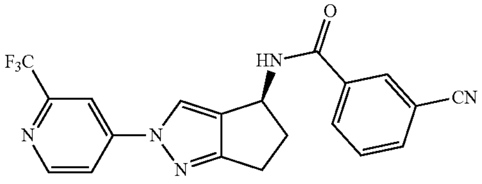 [SMILES: N#Cc1cccc(C(=O)N[C@H]2CCc3nn(-c4ccnc(C(F)(F)F)c4)cc32)c1]
I-454a
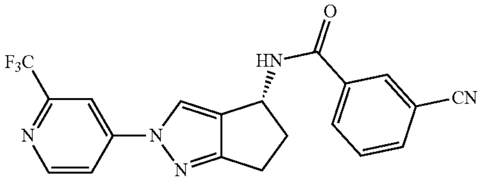 [SMILES: N#Cc1cccc(C(=O)N[C@@H]2CCc3nn(-c4ccnc(C(F)(F)F)c4)cc32)c1]
I-454b
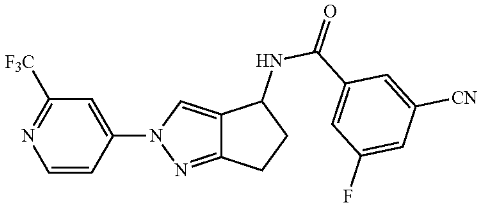 [SMILES: N#Cc1cc(F)cc(C(=O)NC2CCc3nn(-c4ccnc(C(F)(F)F)c4)cc32)c1]
I-455

TABLE 1-continued
I-455a
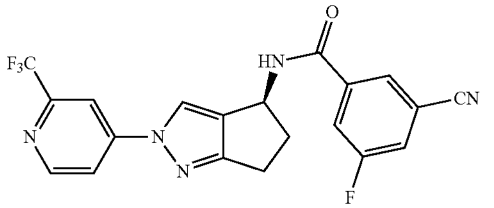
I-455b
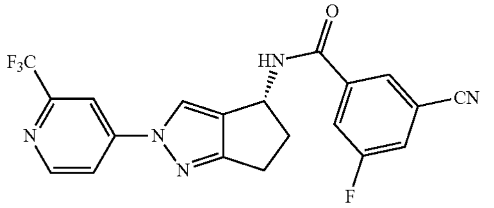 [SMILES: N#Cc1cc(F)cc(C(=O)N[C@@H]2CCc3nn(-c4ccnc(C(F)(F)F)c4)cc32)c1]
I-456
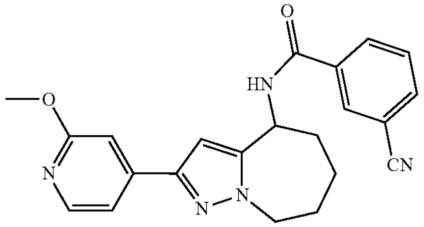 [SMILES: COc1cc(-c2cc3n(n2)CCCCC3NC(=O)c2cccc(C#N)c2)ccn1]
I-456a
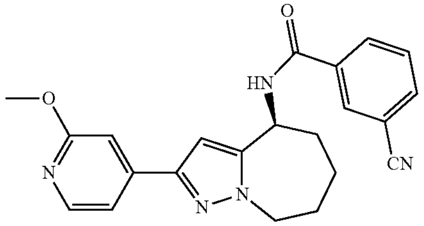 [SMILES: COc1cc(-c2cc3n(n2)CCCC[C@@H]3NC(=O)c2cccc(C#N)c2)ccn1]
I-456b
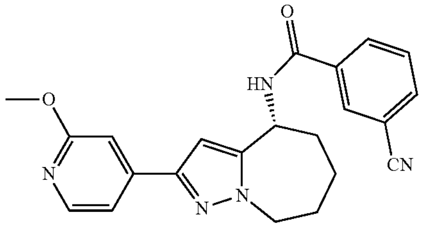 [SMILES: COc1cc(-c2cc3n(n2)CCCC[C@H]3NC(=O)c2cccc(C#N)c2)ccn1]
I-457
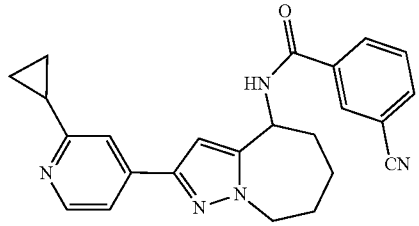 [SMILES: N#Cc1cccc(C(=O)NC2CCCCn3nc(-c4ccnc(C5CC5)c4)cc32)c1]
I-457a
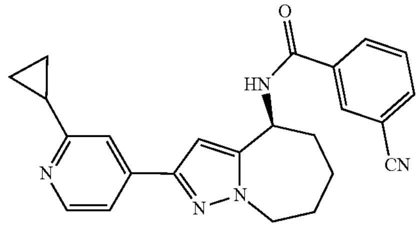 [SMILES: N#Cc1cccc(C(=O)N[C@H]2CCCCn3nc(-c4ccnc(C5CC5)c4)cc32)c1]

TABLE 1-continued
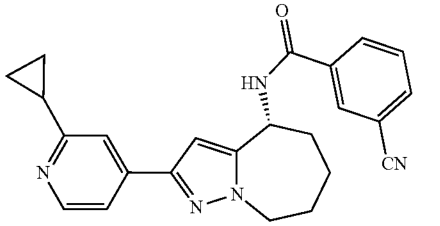 [SMILES: N#Cc1cccc(C(=O)N[C@@H]2CCCCn3nc(-c4ccnc(C5CC5)c4)cc32)c1]
I-457b
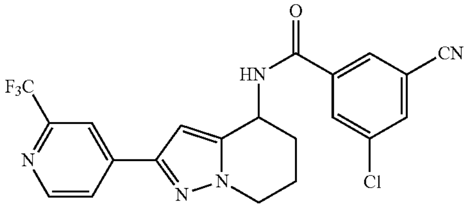 [SMILES: N#Cc1cc(Cl)cc(C(=O)NC2CCCn3nc(-c4ccnc(C(F)(F)F)c4)cc32)c1]
I-458
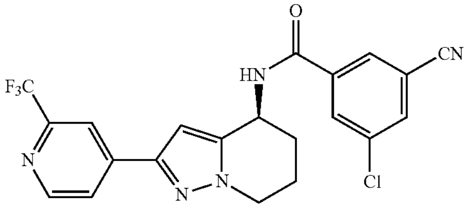 [SMILES: N#Cc1cc(Cl)cc(C(=O)N[C@H]2CCCn3nc(-c4ccnc(C(F)(F)F)c4)cc32)c1]
I-458a
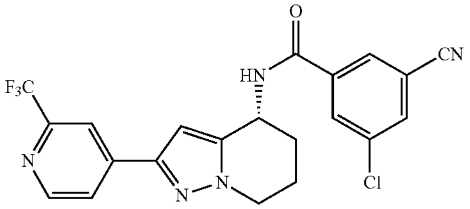 [SMILES: N#Cc1cc(Cl)cc(C(=O)N[C@@H]2CCCn3nc(-c4ccnc(C(F)(F)F)c4)cc32)c1]
I-458b
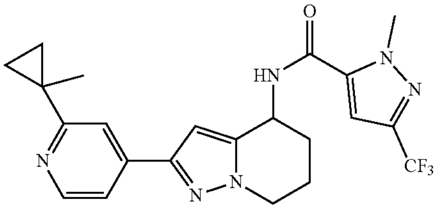
I-459
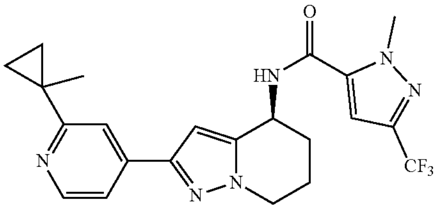 [SMILES: Cn1nc(C(F)(F)F)cc1C(=O)N[C@H]1CCCn2nc(-c3ccnc(C4(C)CC4)c3)cc21]
I-459a
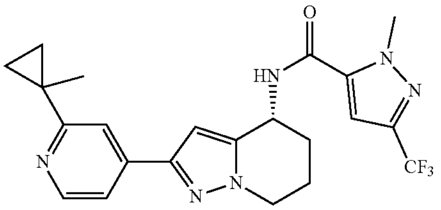
I-459b TABLE 1-continued
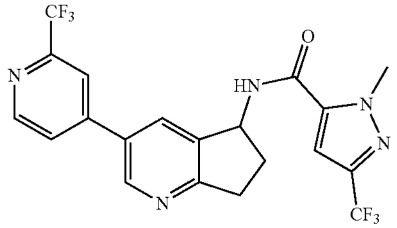 [SMILES: Cn1nc(C(F)(F)F)cc1C(=O)NC1CCc2ncc(-c3ccnc(C(F)(F)F)c3)cc21]
I-460
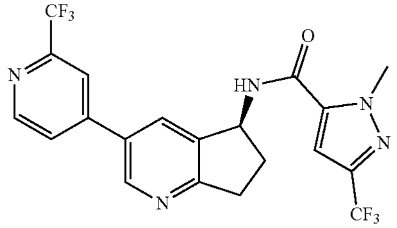
I-460a
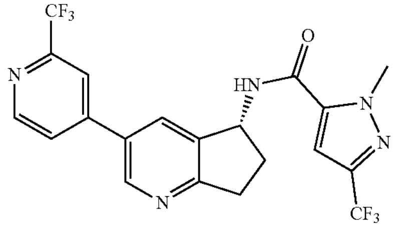
I-460b
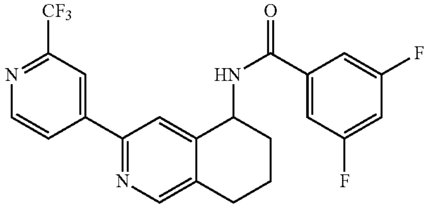 [SMILES: O=C(NC1CCCc2cnc(-c3ccnc(C(F)(F)F)c3)cc21)c1cc(F)cc(F)c1]
I-461
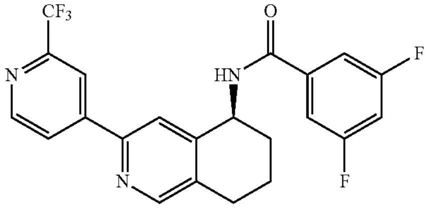 [SMILES: O=C(N[C@H]1CCCc2cnc(-c3ccnc(C(F)(F)F)c3)cc21)c1cc(F)cc(F)c1]
I-461a
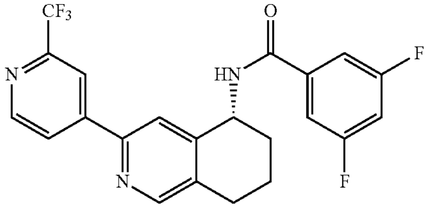 [SMILES: O=C(N[C@@H]1CCCc2cnc(-c3ccnc(C(F)(F)F)c3)cc21)c1cc(F)cc(F)c1]
I-461b
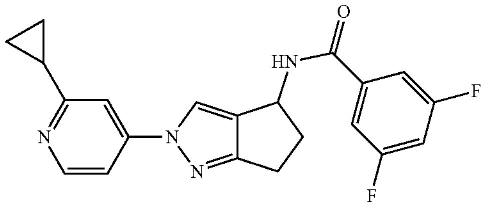 [SMILES: O=C(NC1CCc2nn(-c3ccnc(C4CC4)c3)cc21)c1cc(F)cc(F)c1]
I-462

TABLE 1-continued
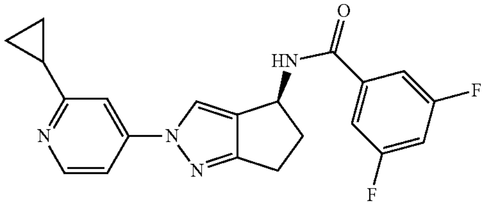 [SMILES: O=C(N[C@H]1CCc2nn(-c3ccnc(C4CC4)c3)cc21)c1cc(F)cc(F)c1]
I-462a
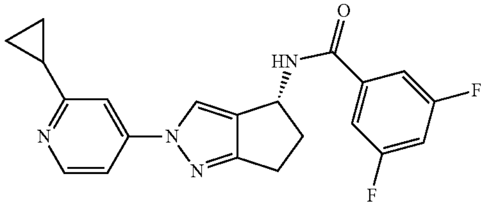 [SMILES: O=C(N[C@@H]1CCc2nn(-c3ccnc(C4CC4)c3)cc21)c1cc(F)cc(F)c1]
I-462b
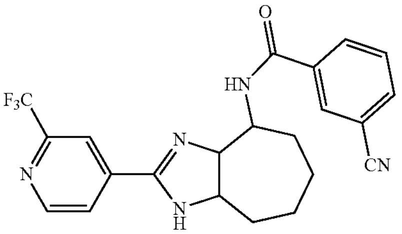 [SMILES: N#Cc1cccc(C(=O)NC2CCCCC3NC(c4ccnc(C(F)(F)F)c4)=NC23)c1]
I-463
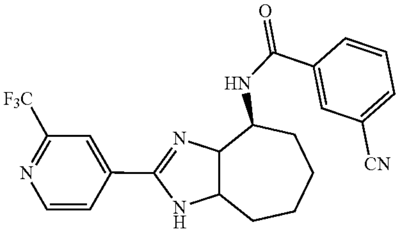 [SMILES: N#Cc1cccc(C(=O)N[C@H]2CCCCC3NC(c4ccnc(C(F)(F)F)c4)=NC32)c1]
I-463a
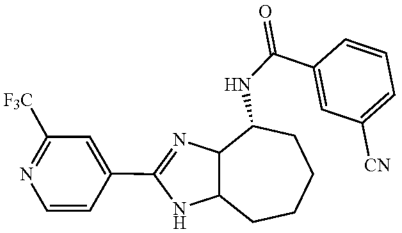 [SMILES: N#Cc1cccc(C(=O)N[C@@H]2CCCCC3NC(c4ccnc(C(F)(F)F)c4)=NC32)c1]
I-463b
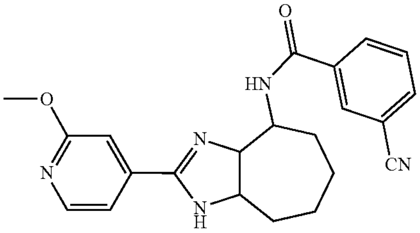 [SMILES: COc1cc(C2=NC3C(NC(=O)c4cccc(C#N)c4)CCCCC3N2)ccn1]
I-464
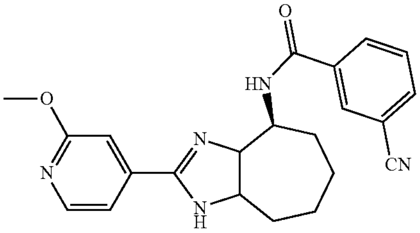 [SMILES: COc1cc(C2=NC3C(CCCC[C@@H]3NC(=O)c3cccc(C#N)c3)N2)ccn1]
I-464a TABLE 1-continued
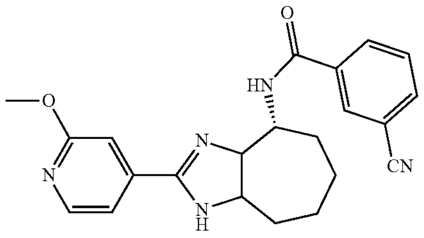 [SMILES: COc1cc(C2=NC3C(CCCC[C@H]3NC(=O)c3cccc(C#N)c3)N2)ccn1]
I-464b
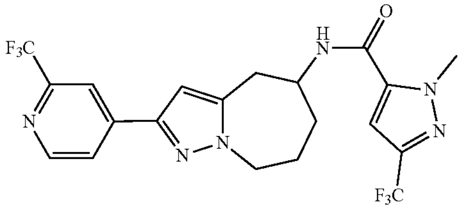 [SMILES: Cn1nc(C(F)(F)F)cc1C(=O)NC1CCCn2nc(-c3ccnc(C(F)(F)F)c3)cc2C1]
I-465
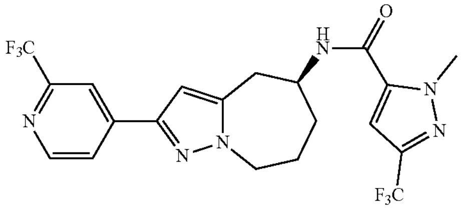 [SMILES: Cn1nc(C(F)(F)F)cc1C(=O)N[C@H]1CCCn2nc(-c3ccnc(C(F)(F)F)c3)cc2C1]
I-465a
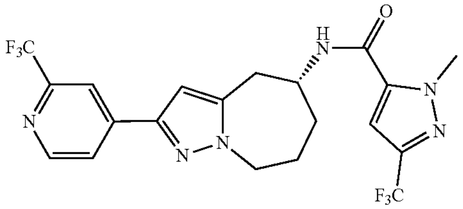 [SMILES: Cn1nc(C(F)(F)F)cc1C(=O)N[C@@H]1CCCn2nc(-c3ccnc(C(F)(F)F)c3)cc2C1]
I-465b
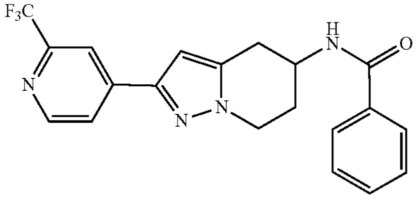 [SMILES: O=C(NC1CCn2nc(-c3ccnc(C(F)(F)F)c3)cc2C1)c1ccccc1]
I-466
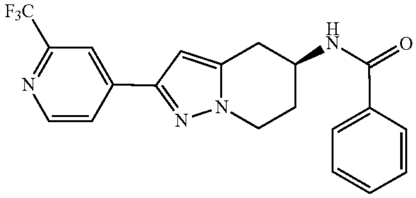 [SMILES: O=C(N[C@H]1CCn2nc(-c3ccnc(C(F)(F)F)c3)cc2C1)c1ccccc1]
I-466a
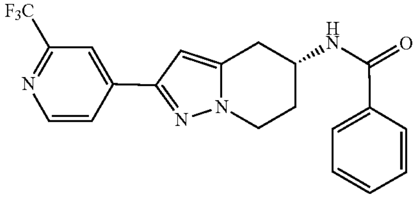 [SMILES: O=C(N[C@@H]1CCn2nc(-c3ccnc(C(F)(F)F)c3)cc2C1)c1ccccc1]
I-466b TABLE 1-continued
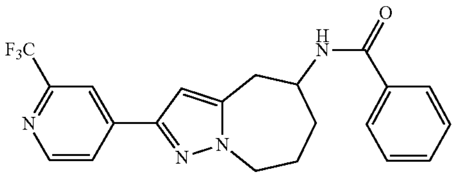 [SMILES: O=C(NC1CCCn2nc(-c3ccnc(C(F)(F)F)c3)cc2C1)c1ccccc1]
I-467
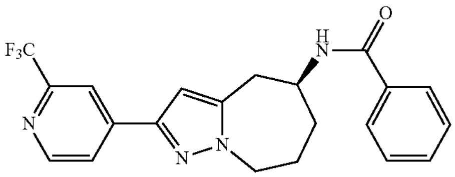 [SMILES: O=C(N[C@H]1CCCn2nc(-c3ccnc(C(F)(F)F)c3)cc2C1)c1ccccc1]
I-467a
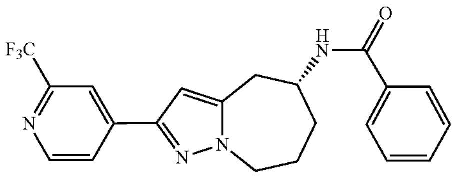 [SMILES: O=C(N[C@@H]1CCCn2nc(-c3ccnc(C(F)(F)F)c3)cc2C1)c1ccccc1]
I-467b
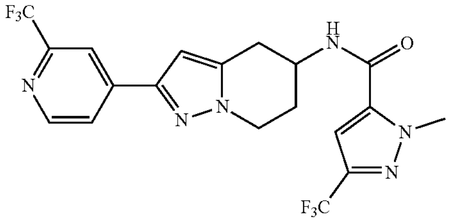 [SMILES: Cn1nc(C(F)(F)F)cc1C(=O)NC1CCn2nc(-c3ccnc(C(F)(F)F)c3)cc2C1]
I-468
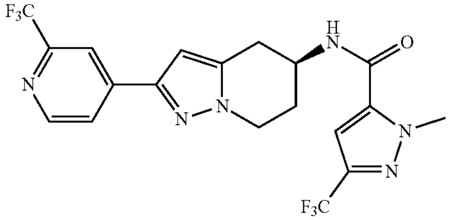 [SMILES: Cn1nc(C(F)(F)F)cc1C(=O)N[C@H]1CCn2nc(-c3ccnc(C(F)(F)F)c3)cc2C1]
I-468a
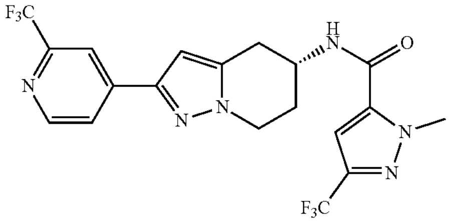 [SMILES: Cn1nc(C(F)(F)F)cc1C(=O)N[C@@H]1CCn2nc(-c3ccnc(C(F)(F)F)c3)cc2C1]
I-468b
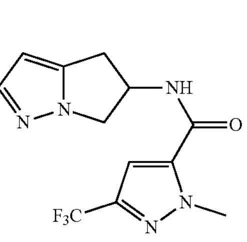
I-469

TABLE 1-continued
I-469a
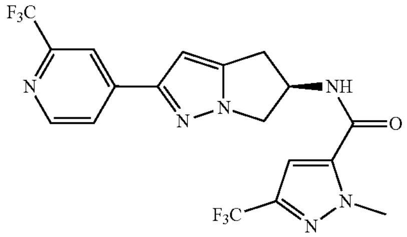 [SMILES: Cn1nc(C(F)(F)F)cc1C(=O)N[C@@H]1Cc2cc(-c3ccnc(C(F)(F)F)c3)nn2C1]
I-469b
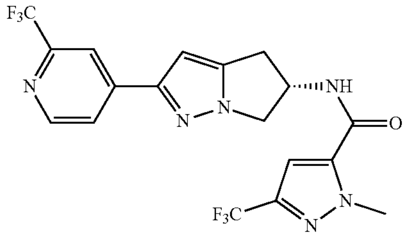 [SMILES: Cn1nc(C(F)(F)F)cc1C(=O)N[C@H]1Cc2cc(-c3ccnc(C(F)(F)F)c3)nn2C1]
I-470
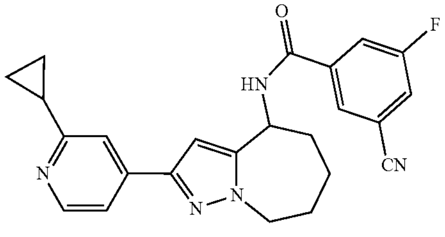 [SMILES: N#Cc1cc(F)cc(C(=O)NC2CCCCn3nc(-c4ccnc(C5CC5)c4)cc32)c1]
I-470a
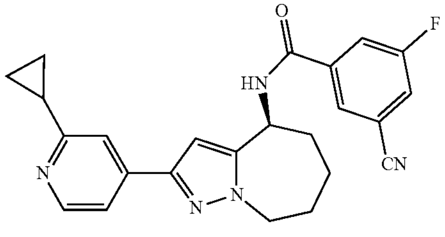 [SMILES: N#Cc1cc(F)cc(C(=O)N[C@H]2CCCCn3nc(-c4ccnc(C5CC5)c4)cc32)c1]
I-470b
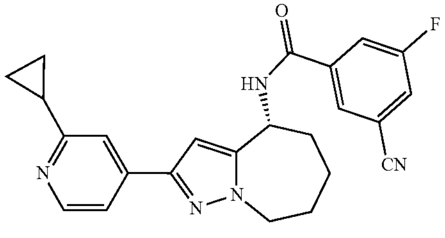 [SMILES: N#Cc1cc(F)cc(C(=O)N[C@@H]2CCCCn3nc(-c4ccnc(C5CC5)c4)cc32)c1]
I-471
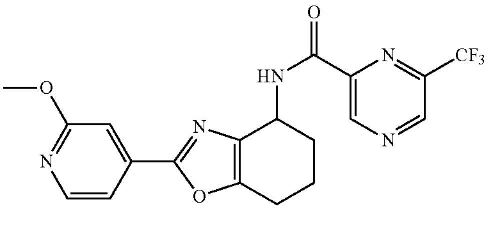 [SMILES: COc1cc(-c2nc3c(o2)CCCC3NC(=O)c2cncc(C(F)(F)F)n2)ccn1]
I-471a
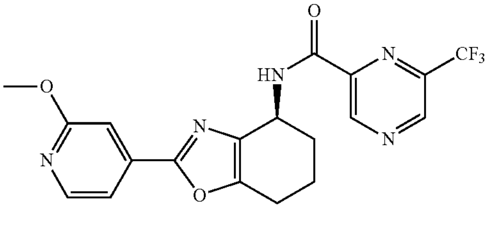 [SMILES: COc1cc(-c2nc3c(o2)CCC[C@@H]3NC(=O)c2cncc(C(F)(F)F)n2)ccn1]

TABLE 1-continued
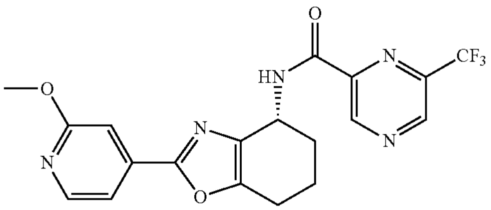
I-471b
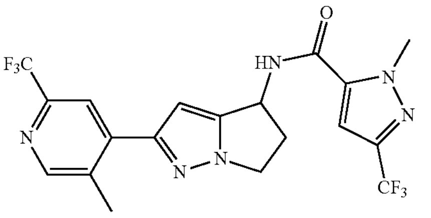
I-472
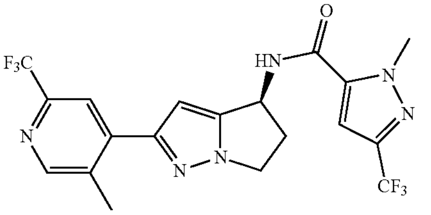 [SMILES: Cc1cnc(C(F)(F)F)cc1-c1cc2n(n1)CC[C@@H]2NC(=O)c1cc(C(F)(F)F)nn1C]
I-472a
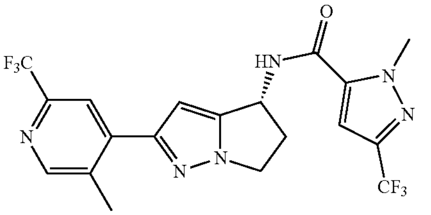
I-472b
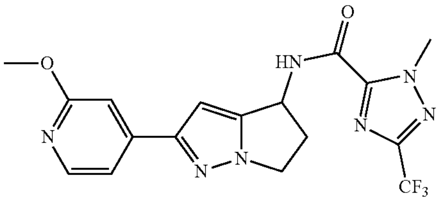
I-473
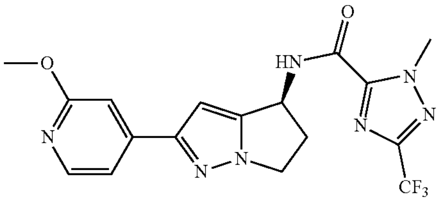
I-473a
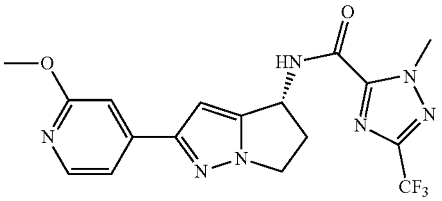
I-473b TABLE 1-continued
I-474
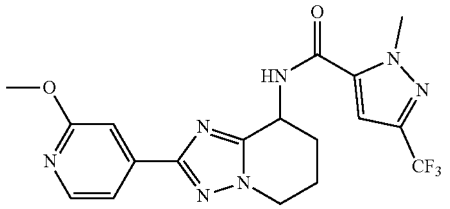 [SMILES: COc1cc(-c2nc3n(n2)CCCC3NC(=O)c2cc(C(F)(F)F)nn2C)ccn1]
I-474a
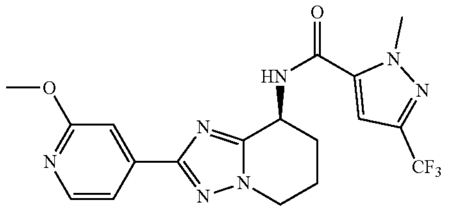 [SMILES: COc1cc(-c2nc3n(n2)CCC[C@@H]3NC(=O)c2cc(C(F)(F)F)nn2C)ccn1]
I-474b
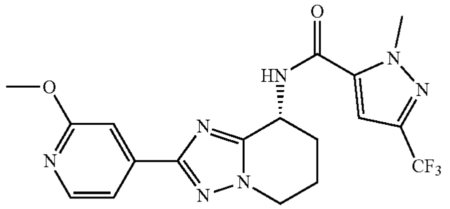
I-475
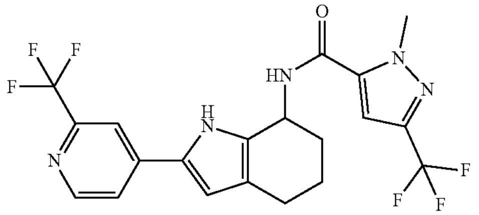 [SMILES: Cn1nc(C(F)(F)F)cc1C(=O)NC1CCCc2cc(-c3ccnc(C(F)(F)F)c3)[nH]c21]
I-475a
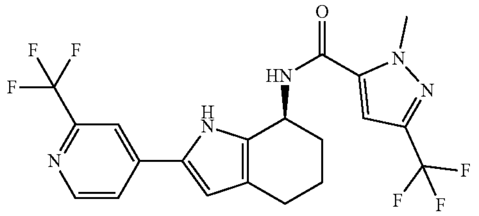 [SMILES: Cn1nc(C(F)(F)F)cc1C(=O)N[C@H]1CCCc2cc(-c3ccnc(C(F)(F)F)c3)[nH]c21]
I-475b
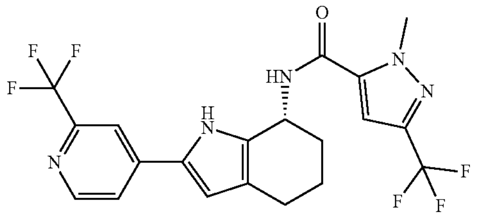 [SMILES: Cn1nc(C(F)(F)F)cc1C(=O)N[C@@H]1CCCc2cc(-c3ccnc(C(F)(F)F)c3)[nH]c21]
I-476
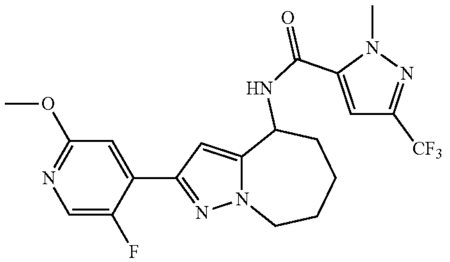 [SMILES: COc1cc(-c2cc3n(n2)CCCCC3NC(=O)c2cc(C(F)(F)F)nn2C)c(F)cn1]

TABLE 1-continued
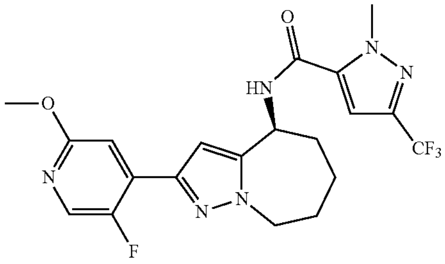 [SMILES: COc1cc(-c2cc3n(n2)CCCC[C@@H]3NC(=O)c2cc(C(F)(F)F)nn2C)c(F)cn1]
I-476a
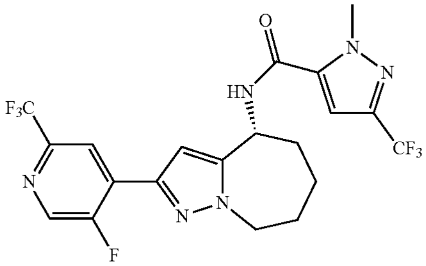 [SMILES: Cn1nc(C(F)(F)F)cc1C(=O)N[C@@H]1CCCCn2nc(-c3cc(C(F)(F)F)ncc3F)cc21]
I-476b
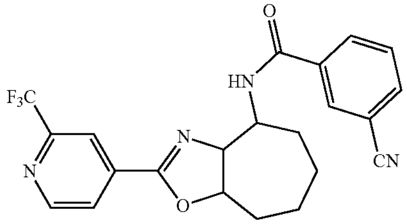 [SMILES: N#Cc1cccc(C(=O)NC2CCCCC3OC(c4ccnc(C(F)(F)F)c4)=NC23)c1]
I-477
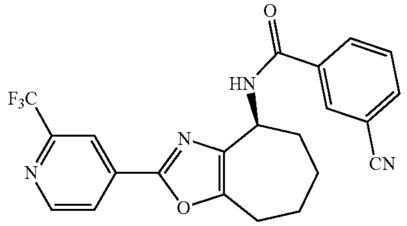 [SMILES: N#Cc1cccc(C(=O)N[C@H]2CCCCc3oc(-c4ccnc(C(F)(F)F)c4)nc32)c1]
I-477a
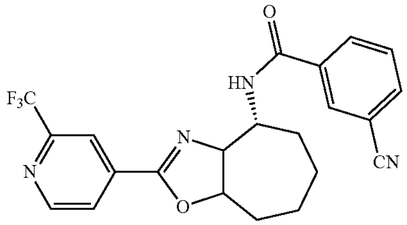 [SMILES: N#Cc1cccc(C(=O)N[C@@H]2CCCCC3OC(c4ccnc(C(F)(F)F)c4)=NC32)c1]
I-477b
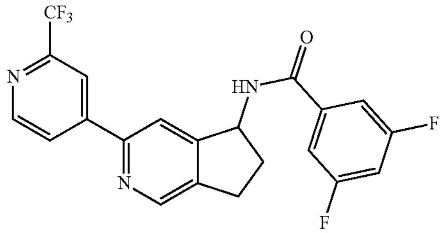 [SMILES: O=C(NC1CCc2cnc(-c3ccnc(C(F)(F)F)c3)cc21)c1cc(F)cc(F)c1]
I-478

TABLE 1-continued
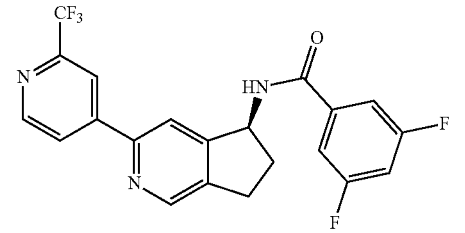 [SMILES: O=C(N[C@H]1CCc2cnc(-c3ccnc(C(F)(F)F)c3)cc21)c1cc(F)cc(F)c1]
I-478a
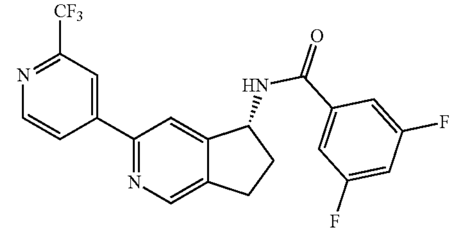 [SMILES: O=C(N[C@@H]1CCc2cnc(-c3ccnc(C(F)(F)F)c3)cc21)c1cc(F)cc(F)c1]
I-478b
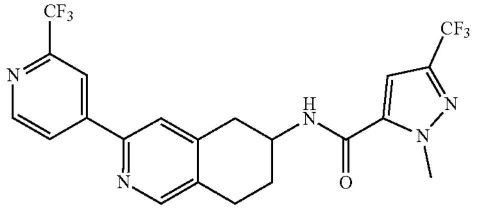 [SMILES: Cn1nc(C(F)(F)F)cc1C(=O)NC1CCc2cnc(-c3ccnc(C(F)(F)F)c3)cc2C1]
I-479
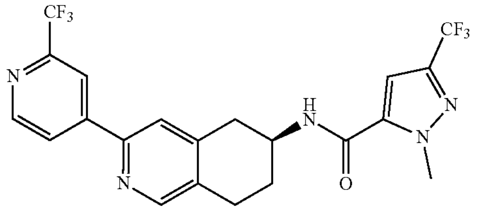 [SMILES: Cn1nc(C(F)(F)F)cc1C(=O)N[C@H]1CCc2cnc(-c3ccnc(C(F)(F)F)c3)cc2C1]
I-479a
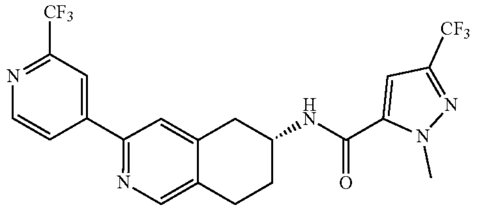 [SMILES: Cn1nc(C(F)(F)F)cc1C(=O)N[C@@H]1CCc2cnc(-c3ccnc(C(F)(F)F)c3)cc2C1]
I-479b
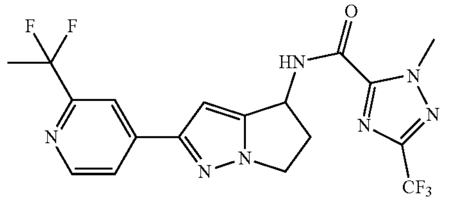
I-480
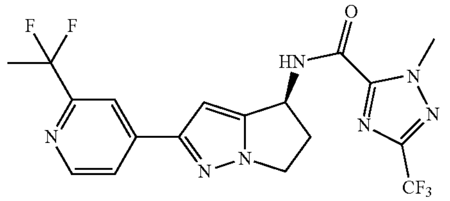
I-480a TABLE 1-continued
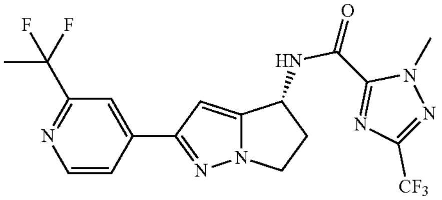 [SMILES: Cn1nc(C(F)(F)F)nc1C(=O)NC1CCn2nc(-c3ccnc(C(C)(F)F)c3)cc21]
I-480b
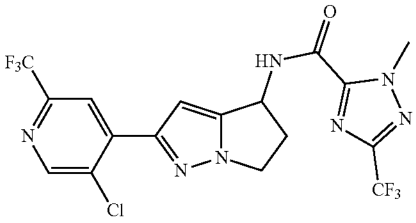
I-481
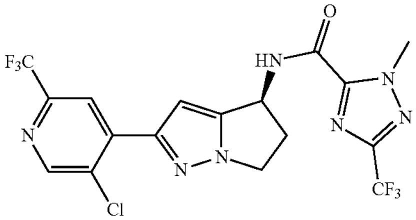
I-481a
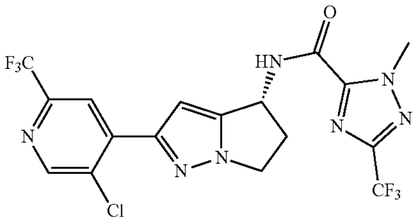
I-481b
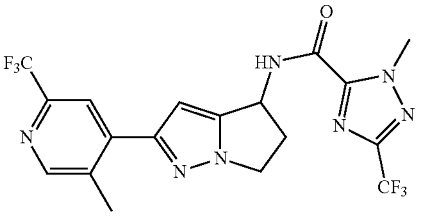 [SMILES: Cc1cnc(C(F)(F)F)cc1-c1cc2n(n1)CCC2NC(=O)c1nc(C(F)(F)F)nn1C]
I-482
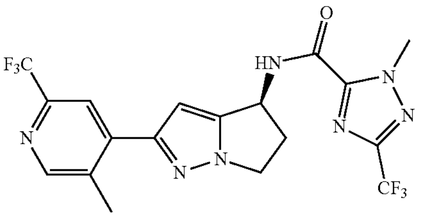 [SMILES: Cc1cnc(C(F)(F)F)cc1-c1cc2n(n1)CC[C@@H]2NC(=O)c1nc(C(F)(F)F)nn1C]
I-482a
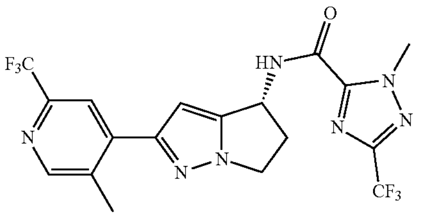 [SMILES: Cc1cnc(C(F)(F)F)cc1-c1cc2n(n1)CC[C@H]2NC(=O)c1nc(C(F)(F)F)nn1C]
I-482b TABLE 1-continued
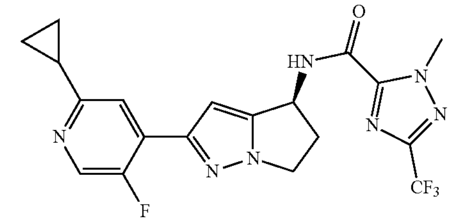
I-483
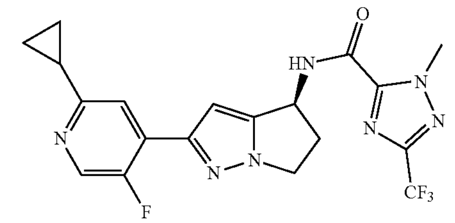 [SMILES: Cn1nc(C(F)(F)F)nc1C(=O)N[C@H]1CCn2nc(-c3cc(C4CC4)ncc3F)cc21]
I-483a
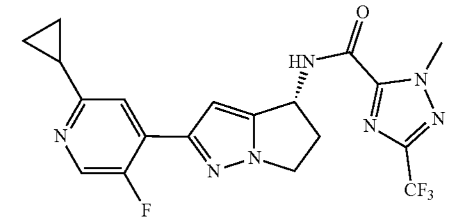 [SMILES: Cn1nc(C(F)(F)F)nc1C(=O)N[C@@H]1CCn2nc(-c3cc(C4CC4)ncc3F)cc21]
I-483b
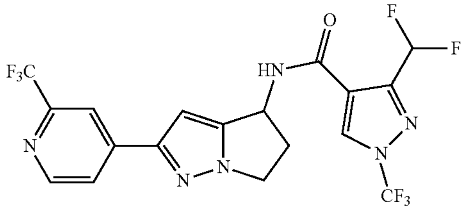 [SMILES: O=C(NC1CCn2nc(-c3ccnc(C(F)(F)F)c3)cc21)c1cn(C(F)(F)F)nc1C(F)F]
I-484
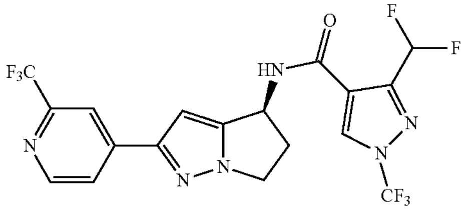 [SMILES: O=C(N[C@H]1CCn2nc(-c3ccnc(C(F)(F)F)c3)cc21)c1cn(C(F)(F)F)nc1C(F)F]
I-484a
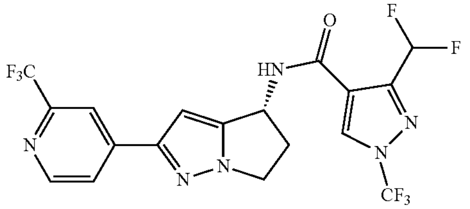 [SMILES: O=C(N[C@@H]1CCn2nc(-c3ccnc(C(F)(F)F)c3)cc21)c1cn(C(F)(F)F)nc1C(F)F]
I-484b
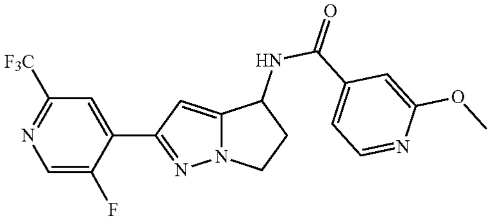 [SMILES: COc1cc(C(=O)NC2CCn3nc(-c4cc(C(F)(F)F)ncc4F)cc32)ccn1]
I-485

TABLE 1-continued
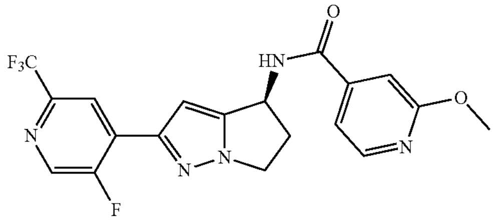 [SMILES: COc1cc(C(=O)N[C@H]2CCn3nc(-c4cc(C(F)(F)F)ncc4F)cc32)ccn1]
I-485a
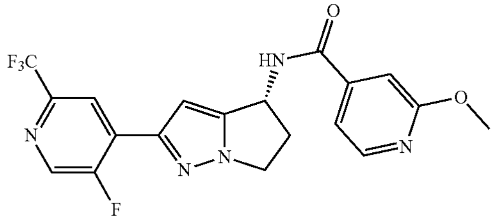 [SMILES: COc1cc(C(=O)N[C@@H]2CCn3nc(-c4cc(C(F)(F)F)ncc4F)cc32)ccn1]
I-485b
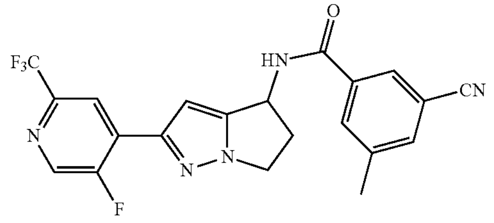 [SMILES: Cc1cc(C#N)cc(C(=O)NC2CCn3nc(-c4cc(C(F)(F)F)ncc4F)cc32)c1]
I-486
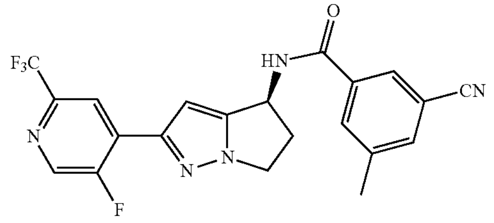 [SMILES: Cc1cc(C#N)cc(C(=O)N[C@H]2CCn3nc(-c4cc(C(F)(F)F)ncc4F)cc32)c1]
I-486a
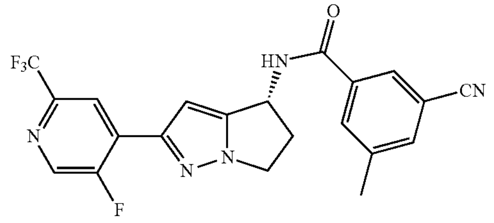
I-486b
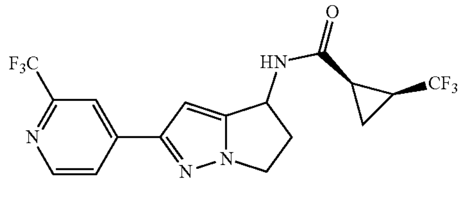
I-487
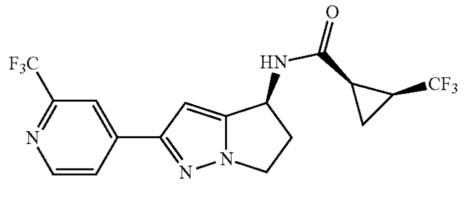 [SMILES: O=C(N[C@H]1CCn2nc(-c3ccnc(C(F)(F)F)c3)cc21)[C@@H]1C[C@@H]1C(F)(F)F]
I-487a TABLE 1-continued
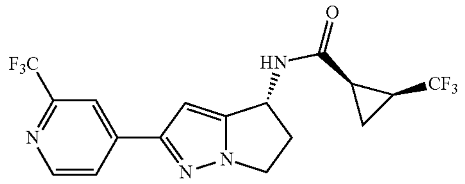 [SMILES: O=C(N[C@@H]1CCn2nc(-c3ccnc(C(F)(F)F)c3)cc21)[C@@H]1C[C@@H]1C(F)(F)F]
I-487b
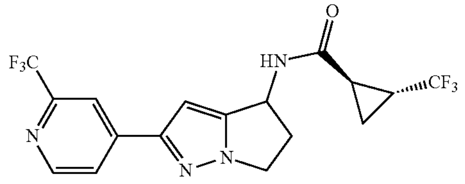
I-488
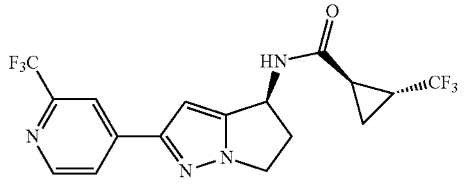 [SMILES: O=C(N[C@H]1CCn2nc(-c3ccnc(C(F)(F)F)c3)cc21)[C@@H]1C[C@H]1C(F)(F)F]
I-488a
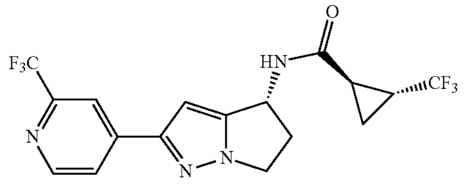 [SMILES: O=C(N[C@@H]1CCn2nc(-c3ccnc(C(F)(F)F)c3)cc21)[C@@H]1C[C@H]1C(F)(F)F]
I-488b
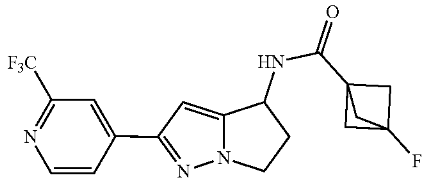 [SMILES: O=C(NC1CCn2nc(-c3ccnc(C(F)(F)F)c3)cc21)C12CC(F)(C1)C2]
I-489
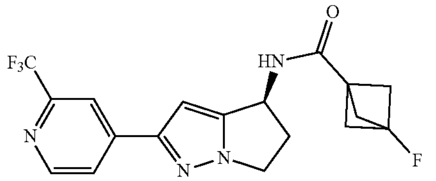 [SMILES: O=C(N[C@H]1CCn2nc(-c3ccnc(C(F)(F)F)c3)cc21)C12CC(F)(C1)C2]
I-489a
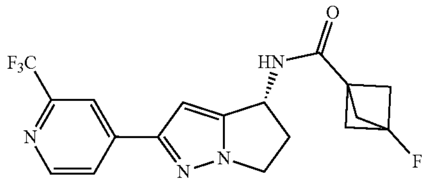 [SMILES: O=C(N[C@@H]1CCn2nc(-c3ccnc(C(F)(F)F)c3)cc21)C12CC(F)(C1)C2]
I-489b
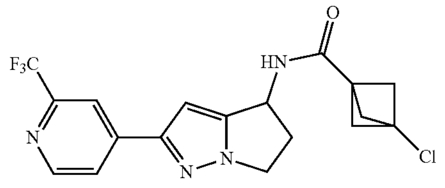 [SMILES: O=C(NC1CCn2nc(-c3ccnc(C(F)(F)F)c3)cc21)C12CC(Cl)(C1)C2]
I-490

TABLE 1-continued
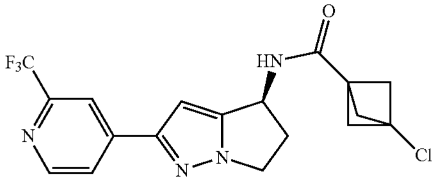 [SMILES: O=C(N[C@H]1CCn2nc(-c3ccnc(C(F)(F)F)c3)cc21)C12CC(Cl)(C1)C2]
I-490a
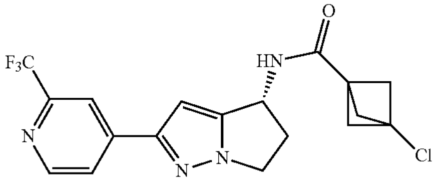 [SMILES: O=C(N[C@@H]1CCn2nc(-c3ccnc(C(F)(F)F)c3)cc21)C12CC(Cl)(C1)C2]
I-490b
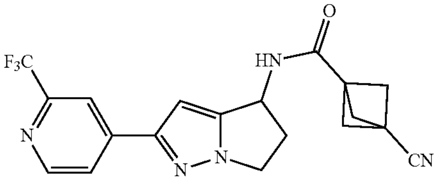 [SMILES: N#CC12CC(C(=O)NC3CCn4nc(-c5ccnc(C(F)(F)F)c5)cc43)(C1)C2]
I-491
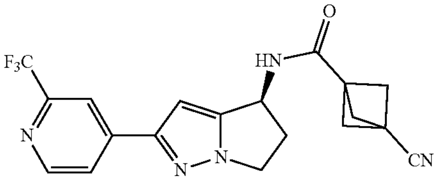 [SMILES: N#CC12CC(C(=O)N[C@H]3CCn4nc(-c5ccnc(C(F)(F)F)c5)cc43)(C1)C2]
I-491a
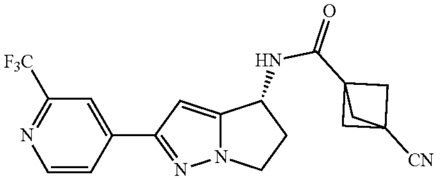 [SMILES: N#CC12CC(C(=O)N[C@@H]3CCn4nc(-c5ccnc(C(F)(F)F)c5)cc43)(C1)C2]
I-491b
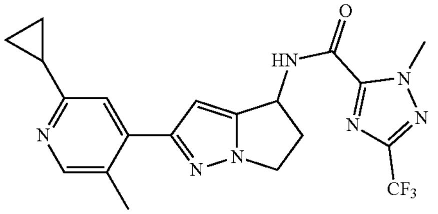 [SMILES: Cc1cnc(C2CC2)cc1-c1cc2n(n1)CCC2NC(=O)c1nc(C(F)(F)F)nn1C]
I-492
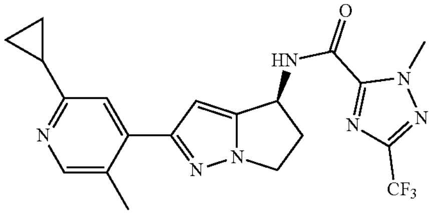 [SMILES: Cc1cnc(C2CC2)cc1-c1cc2n(n1)CC[C@@H]2NC(=O)c1nc(C(F)(F)F)nn1C]
I-492a
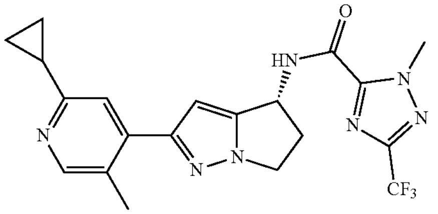 [SMILES: Cc1cnc(C2CC2)cc1-c1cc2n(n1)CC[C@H]2NC(=O)c1nc(C(F)(F)F)nn1C]
I-492b TABLE 1-continued
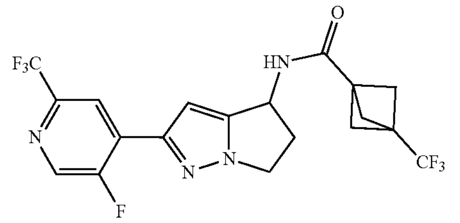 [SMILES: O=C(NC1CCn2nc(-c3cc(C(F)(F)F)ncc3F)cc21)C12CC(C(F)(F)F)(C1)C2]
I-493
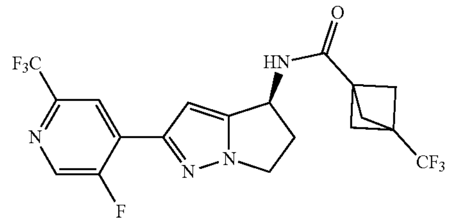 [SMILES: O=C(N[C@H]1CCn2nc(-c3cc(C(F)(F)F)ncc3F)cc21)C12CC(C(F)(F)F)(C1)C2]
I-493a
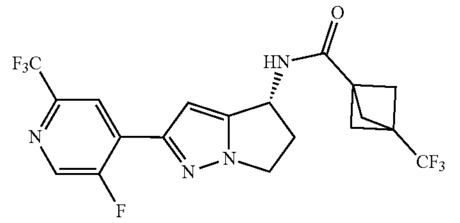
I-493b
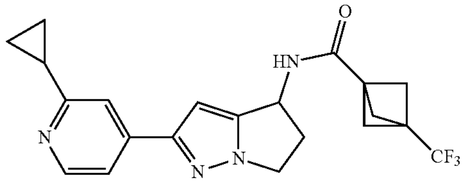 [SMILES: O=C(NC1CCn2nc(-c3ccnc(C4CC4)c3)cc21)C12CC(C(F)(F)F)(C1)C2]
I-494
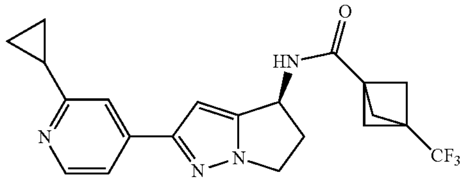 [SMILES: O=C(N[C@H]1CCn2nc(-c3ccnc(C4CC4)c3)cc21)C12CC(C(F)(F)F)(C1)C2]
I-494a
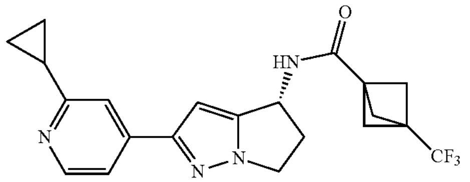 [SMILES: O=C(N[C@@H]1CCn2nc(-c3ccnc(C4CC4)c3)cc21)C12CC(C(F)(F)F)(C1)C2]
I-494b
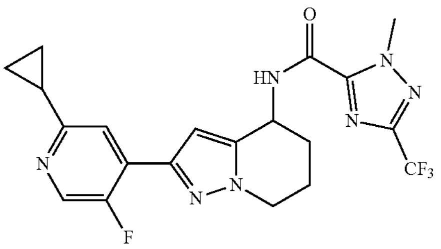 [SMILES: Cn1nc(C(F)(F)F)nc1C(=O)NC1CCCn2nc(-c3cc(C4CC4)ncc3F)cc21]
I-495

TABLE 1-continued
I-495a
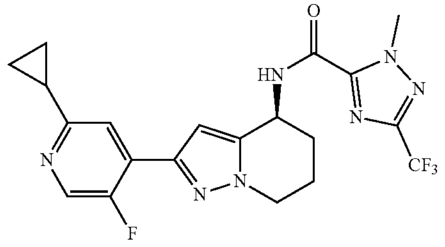 [SMILES: Cn1nc(C(F)(F)F)nc1C(=O)N[C@H]1CCCn2nc(-c3cc(C4CC4)ncc3F)cc21]
I-495b
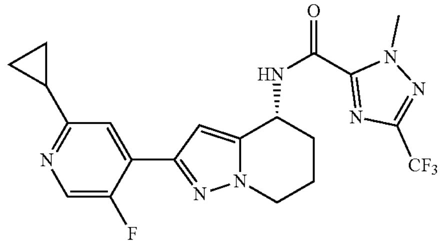 [SMILES: Cn1nc(C(F)(F)F)nc1C(=O)N[C@@H]1CCCn2nc(-c3cc(C4CC4)ncc3F)cc21]
I-496
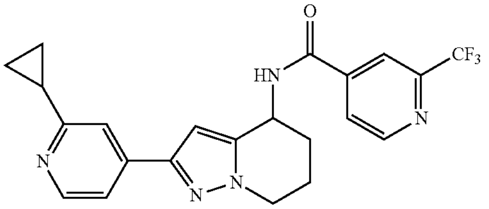 [SMILES: O=C(NC1CCCn2nc(-c3ccnc(C4CC4)c3)cc21)c1ccnc(C(F)(F)F)c1]
I-496a
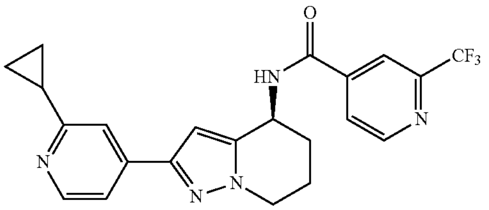 [SMILES: O=C(N[C@H]1CCCn2nc(-c3ccnc(C4CC4)c3)cc21)c1ccnc(C(F)(F)F)c1]
I-496b
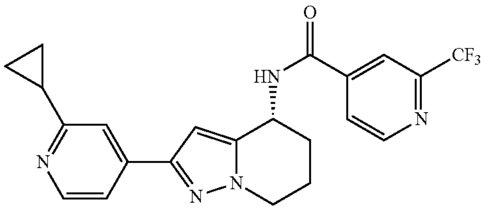 [SMILES: O=C(N[C@@H]1CCCn2nc(-c3ccnc(C4CC4)c3)cc21)c1ccnc(C(F)(F)F)c1]
I-497
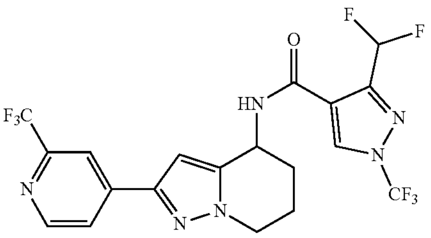
I-497a
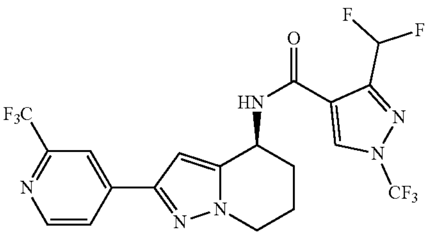 [SMILES: O=C(N[C@H]1CCCn2nc(-c3ccnc(C(F)(F)F)c3)cc21)c1cn(C(F)(F)F)nc1C(F)F]

TABLE 1-continued
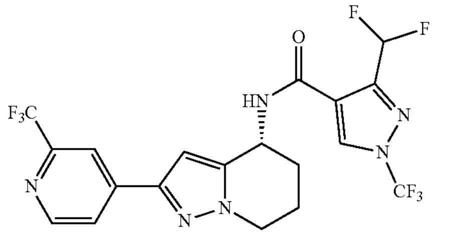 [SMILES: O=C(N[C@@H]1CCCn2nc(-c3ccnc(C(F)(F)F)c3)cc21)c1cn(C(F)(F)F)nc1C(F)F]
I-497b
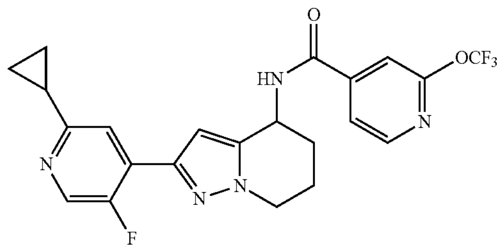 [SMILES: O=C(NC1CCCn2nc(-c3cc(C4CC4)ncc3F)cc21)c1ccnc(OC(F)(F)F)c1]
I-498
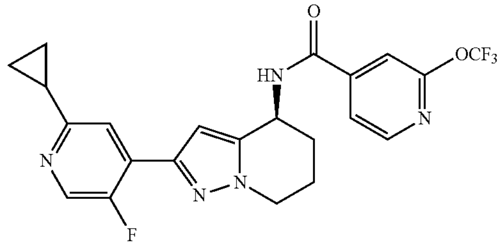 [SMILES: O=C(N[C@H]1CCCn2nc(-c3cc(C4CC4)ncc3F)cc21)c1ccnc(OC(F)(F)F)c1]
I-498a
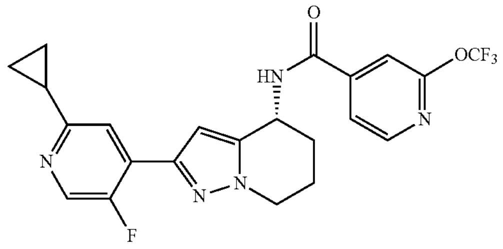
I-498b
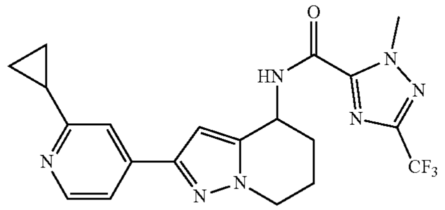 [SMILES: Cn1nc(C(F)(F)F)nc1C(=O)NC1CCCn2nc(-c3ccnc(C4CC4)c3)cc21]
I-499
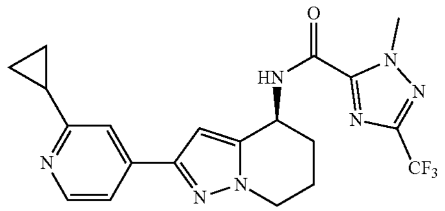
I-499a TABLE 1-continued
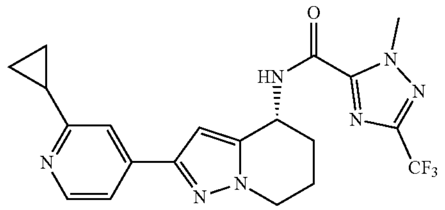
I-499b
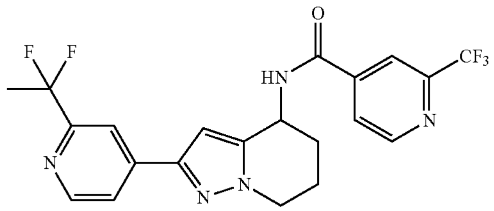 [SMILES: CC(F)(F)c1cc(-c2cc3n(n2)CCCC3NC(=O)c2ccnc(C(F)(F)F)c2)ccn1]
I-500
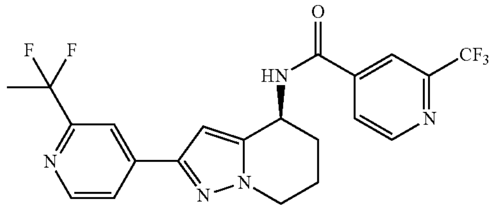 [SMILES: CC(F)(F)c1cc(-c2cc3n(n2)CCC[C@@H]3NC(=O)c2ccnc(C(F)(F)F)c2)ccn1]
I-500a
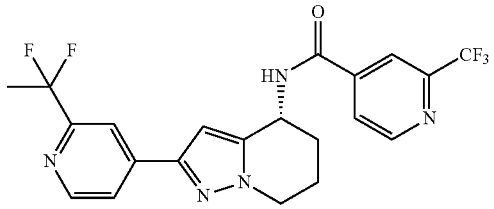
I-500b
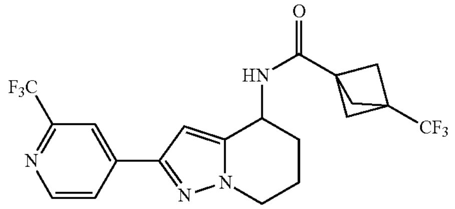 [SMILES: O=C(NC1CCCn2nc(-c3ccnc(C(F)(F)F)c3)cc21)C12CC(C(F)(F)F)(C1)C2]
I-501
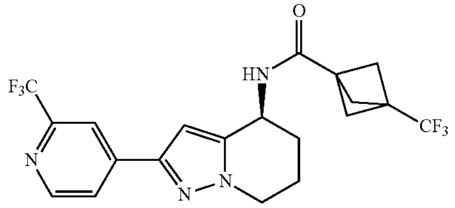 [SMILES: O=C(N[C@H]1CCCn2nc(-c3ccnc(C(F)(F)F)c3)cc21)C12CC(C(F)(F)F)(C1)C2]
I-501a
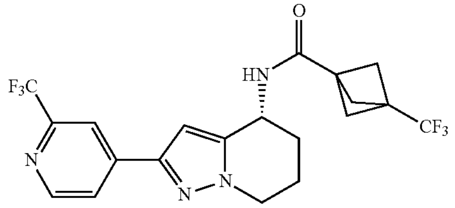 [SMILES: O=C(N[C@@H]1CCCn2nc(-c3ccnc(C(F)(F)F)c3)cc21)C12CC(C(F)(F)F)(C1)C2]
I-501b TABLE 1-continued
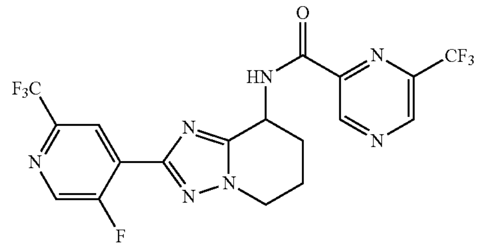 [SMILES: O=C(NC1CCCn2nc(-c3cc(C(F)(F)F)ncc3F)nc21)c1cncc(C(F)(F)F)n1]
I-502
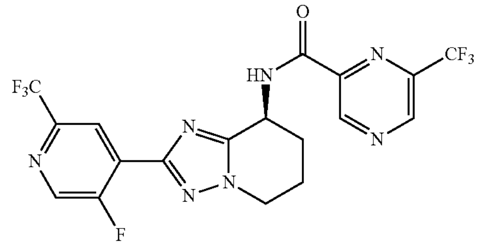 [SMILES: O=C(N[C@H]1CCCn2nc(-c3cc(C(F)(F)F)ncc3F)nc21)c1cncc(C(F)(F)F)n1]
I-502a
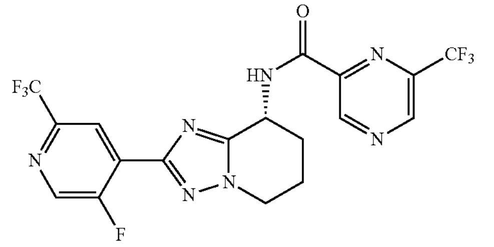 [SMILES: O=C(N[C@@H]1CCCn2nc(-c3cc(C(F)(F)F)ncc3F)nc21)c1cncc(C(F)(F)F)n1]
I-502b
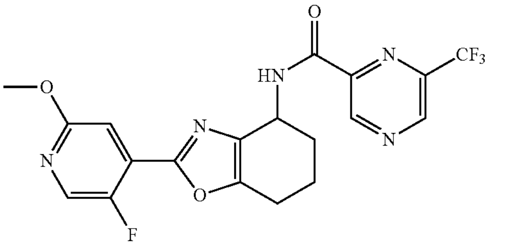 [SMILES: COc1cc(-c2nc3c(o2)CCCC3NC(=O)c2cncc(C(F)(F)F)n2)c(F)cn1]
I-503
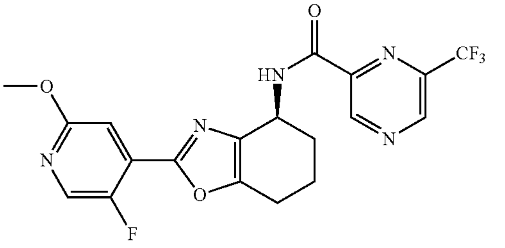 [SMILES: COc1cc(-c2nc3c(o2)CCC[C@@H]3NC(=O)c2cncc(C(F)(F)F)n2)c(F)cn1]
I-503a
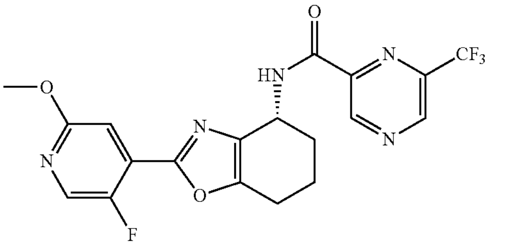 [SMILES: COc1cc(-c2nc3c(o2)CCC[C@H]3NC(=O)c2cncc(C(F)(F)F)n2)c(F)cn1]
I-503b TABLE 1-continued
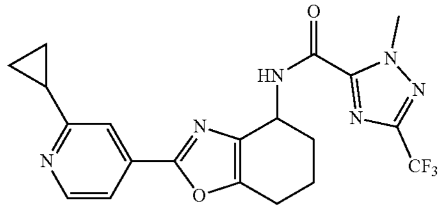 [SMILES: Cn1nc(C(F)(F)F)nc1C(=O)NC1CCCc2oc(-c3ccnc(C4CC4)c3)nc21]
I-504
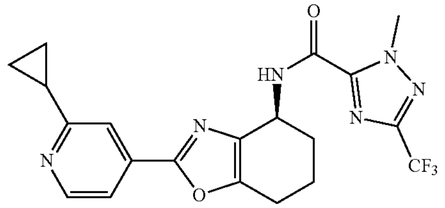 [SMILES: Cn1nc(C(F)(F)F)nc1C(=O)N[C@H]1CCCc2oc(-c3ccnc(C4CC4)c3)nc21]
I-504a
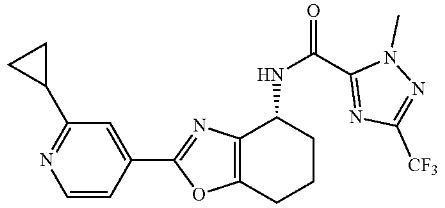 [SMILES: Cn1nc(C(F)(F)F)nc1C(=O)N[C@@H]1CCCc2oc(-c3ccnc(C4CC4)c3)nc21]
I-504b
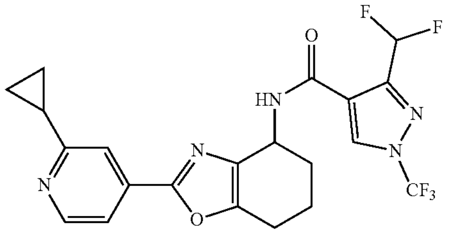 [SMILES: O=C(NC1CCCc2oc(-c3ccnc(C4CC4)c3)nc21)c1cn(C(F)(F)F)nc1C(F)F]
I-505
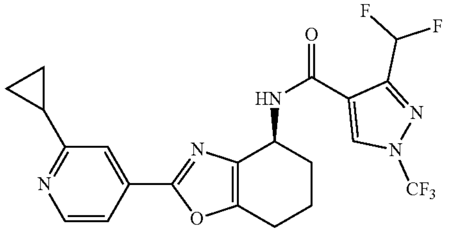 [SMILES: O=C(N[C@H]1CCCc2oc(-c3ccnc(C4CC4)c3)nc21)c1cn(C(F)(F)F)nc1C(F)F]
I-505a
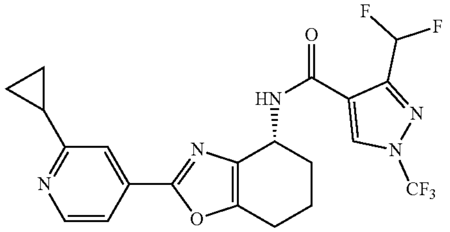 [SMILES: O=C(N[C@@H]1CCCc2oc(-c3ccnc(C4CC4)c3)nc21)c1cn(C(F)(F)F)nc1C(F)F]
I-505b
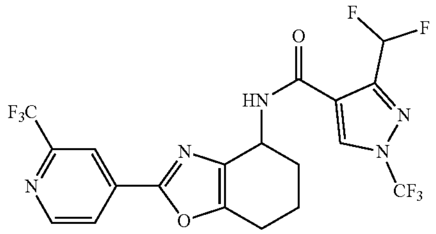 [SMILES: O=C(NC1CCCc2oc(-c3ccnc(C(F)(F)F)c3)nc21)c1cn(C(F)(F)F)nc1C(F)F]
I-506

TABLE 1-continued
I-506a
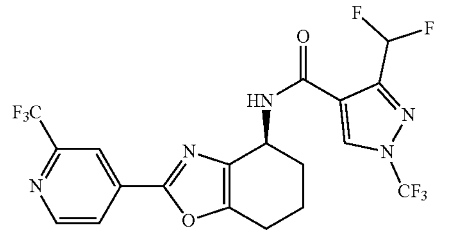 [SMILES: O=C(N[C@H]1CCCc2oc(-c3ccnc(C(F)(F)F)c3)nc21)c1cn(C(F)(F)F)nc1C(F)F]
I-506b
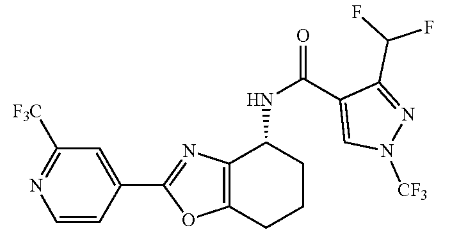 [SMILES: O=C(N[C@@H]1CCCc2oc(-c3ccnc(C(F)(F)F)c3)nc21)c1cn(C(F)(F)F)nc1C(F)F]
I-507
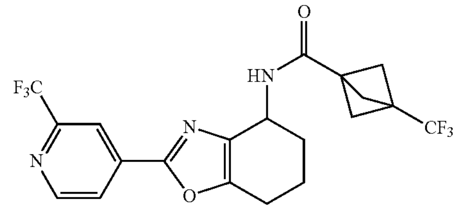 [SMILES: O=C(NC1CCCc2oc(-c3ccnc(C(F)(F)F)c3)nc21)C12CC(C(F)(F)F)(C1)C2]
I-507a
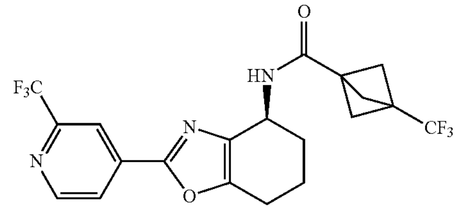 [SMILES: O=C(N[C@H]1CCCc2oc(-c3ccnc(C(F)(F)F)c3)nc21)C12CC(C(F)(F)F)(C1)C2]
I-507b
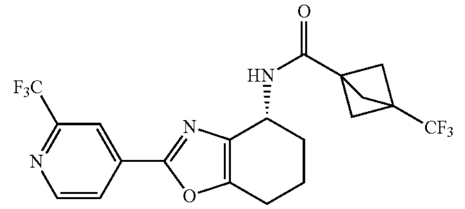
I-508
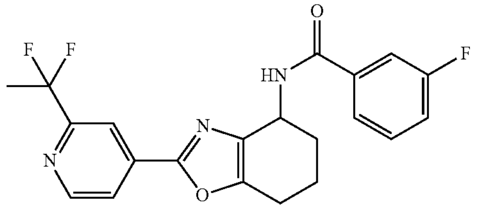
I-508a
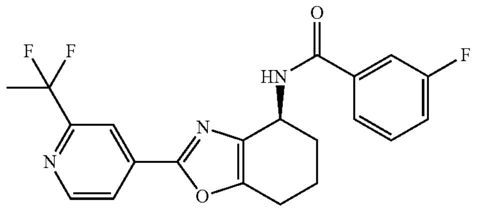 [SMILES: CC(F)(F)c1cc(-c2nc3c(o2)CCC[C@@H]3NC(=O)c2cccc(F)c2)ccn1]

TABLE 1-continued
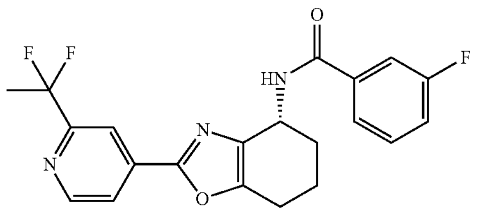 [SMILES: CC(F)(F)c1cc(-c2nc3c(o2)CCC[C@H]3NC(=O)c2cccc(F)c2)ccn1]
I-508b
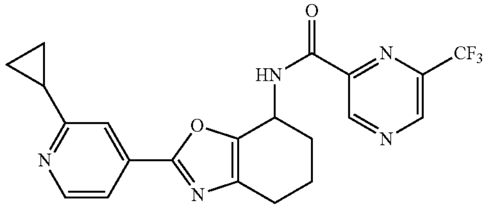 [SMILES: O=C(NC1CCCc2nc(-c3ccnc(C4CC4)c3)oc21)c1cncc(C(F)(F)F)n1]
I-509
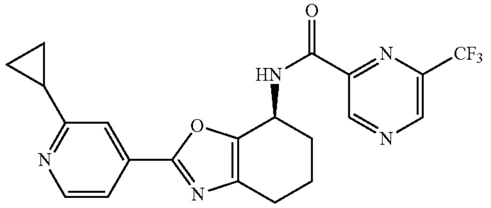 [SMILES: O=C(N[C@H]1CCCc2nc(-c3ccnc(C4CC4)c3)oc21)c1cncc(C(F)(F)F)n1]
I-509a
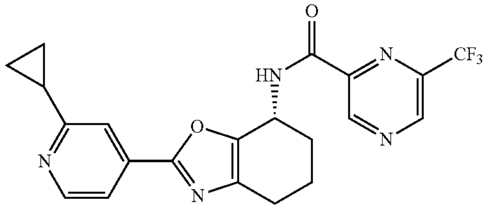 [SMILES: O=C(N[C@@H]1CCCc2nc(-c3ccnc(C4CC4)c3)oc21)c1cncc(C(F)(F)F)n1]
I-509b
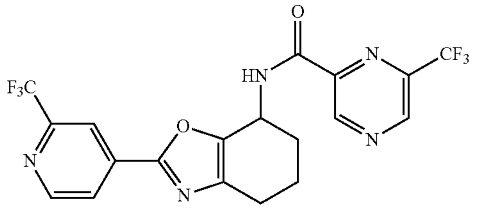 [SMILES: O=C(NC1CCCc2nc(-c3ccnc(C(F)(F)F)c3)oc21)c1cncc(C(F)(F)F)n1]
I-510
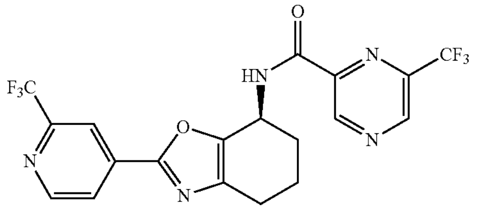 [SMILES: O=C(N[C@H]1CCCc2nc(-c3ccnc(C(F)(F)F)c3)oc21)c1cncc(C(F)(F)F)n1]
I-510a
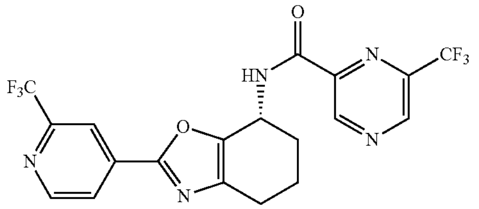 [SMILES: O=C(N[C@@H]1CCCc2nc(-c3ccnc(C(F)(F)F)c3)oc21)c1cncc(C(F)(F)F)n1]
I-510b TABLE 1-continued
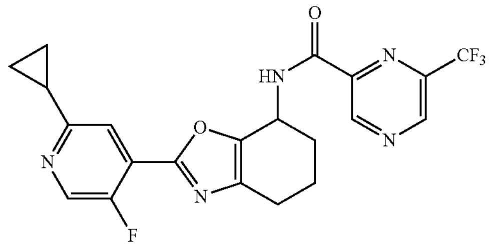 [SMILES: O=C(NC1CCCc2nc(-c3cc(C4CC4)ncc3F)oc21)c1cncc(C(F)(F)F)n1]
I-511
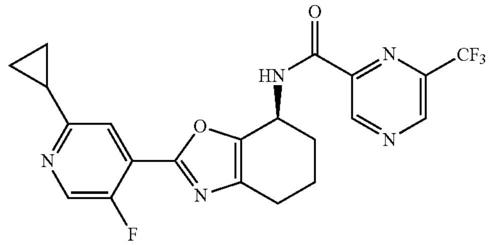 [SMILES: O=C(N[C@H]1CCCc2nc(-c3cc(C4CC4)ncc3F)oc21)c1cncc(C(F)(F)F)n1]
I-511a
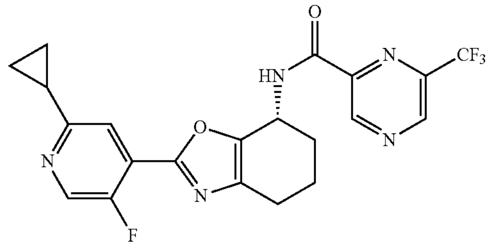 [SMILES: O=C(N[C@@H]1CCCc2nc(-c3cc(C4CC4)ncc3F)oc21)c1cncc(C(F)(F)F)n1]
I-511b
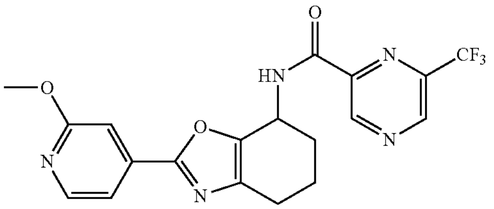 [SMILES: COc1cc(-c2nc3c(o2)C(NC(=O)c2cncc(C(F)(F)F)n2)CCC3)ccn1]
I-512
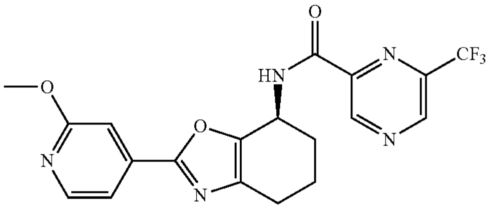 [SMILES: COc1cc(-c2nc3c(o2)[C@@H](NC(=O)c2cncc(C(F)(F)F)n2)CCC3)ccn1]
I-512a
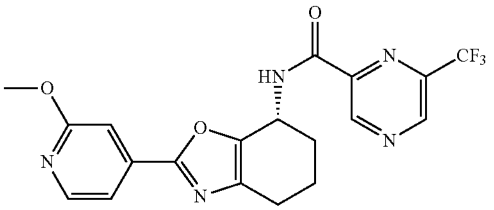 [SMILES: COc1cc(-c2nc3c(o2)[C@H](NC(=O)c2cncc(C(F)(F)F)n2)CCC3)ccn1]
I-512b TABLE 1-continued
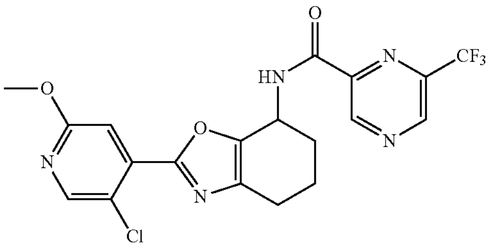 [SMILES: COc1cc(-c2nc3c(o2)C(NC(=O)c2cncc(C(F)(F)F)n2)CCC3)c(Cl)cn1]
I-513
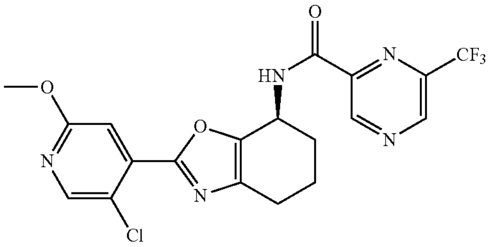 [SMILES: COc1cc(-c2nc3c(o2)[C@@H](NC(=O)c2cncc(C(F)(F)F)n2)CCC3)c(Cl)cn1]
I-513a
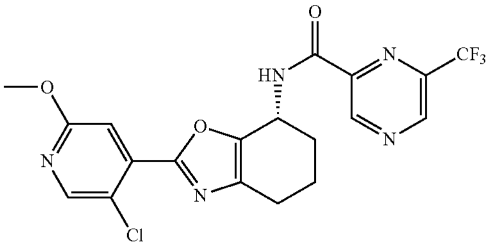 [SMILES: COc1cc(-c2nc3c(o2)[C@H](NC(=O)c2cncc(C(F)(F)F)n2)CCC3)c(Cl)cn1]
I-513b
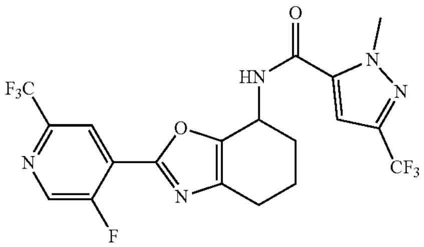 [SMILES: Cn1nc(C(F)(F)F)cc1C(=O)NC1CCCc2nc(-c3cc(C(F)(F)F)ncc3F)oc21]
I-514
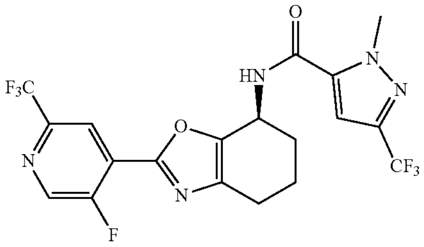 [SMILES: Cn1nc(C(F)(F)F)cc1C(=O)N[C@H]1CCCc2nc(-c3cc(C(F)(F)F)ncc3F)oc21]
I-514a
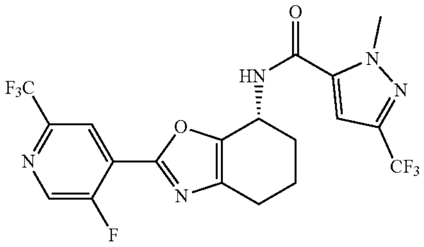 [SMILES: Cn1nc(C(F)(F)F)cc1C(=O)N[C@@H]1CCCc2nc(-c3cc(C(F)(F)F)ncc3F)oc21]
I-514b TABLE 1-continued
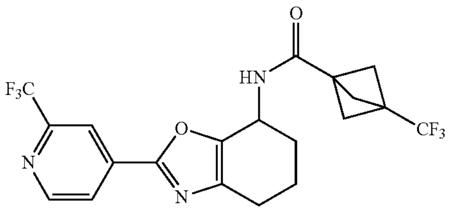 [SMILES: O=C(NC1CCCc2nc(-c3ccnc(C(F)(F)F)c3)oc21)C12CC(C(F)(F)F)(C1)C2]
I-515
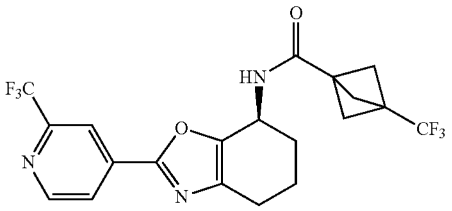 [SMILES: O=C(N[C@H]1CCCc2nc(-c3ccnc(C(F)(F)F)c3)oc21)C12CC(C(F)(F)F)(C1)C2]
I-515a
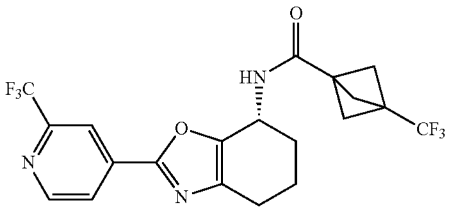 [SMILES: O=C(N[C@@H]1CCCc2nc(-c3ccnc(C(F)(F)F)c3)oc21)C12CC(C(F)(F)F)(C1)C2]
I-515b
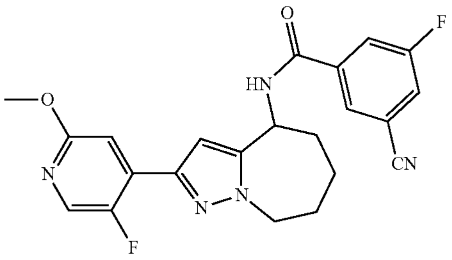 [SMILES: COc1cc(-c2cc3n(n2)CCCCC3NC(=O)c2cc(F)cc(C#N)c2)c(F)cn1]
I-516
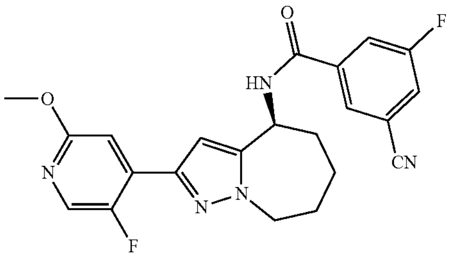 [SMILES: COc1cc(-c2cc3n(n2)CCCC[C@@H]3NC(=O)c2cc(F)cc(C#N)c2)c(F)cn1]
I-516a
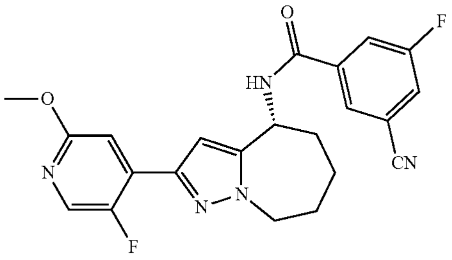 [SMILES: COc1cc(-c2cc3n(n2)CCCC[C@H]3NC(=O)c2cc(F)cc(C#N)c2)c(F)cn1]
I-516b TABLE 1-continued
I-517
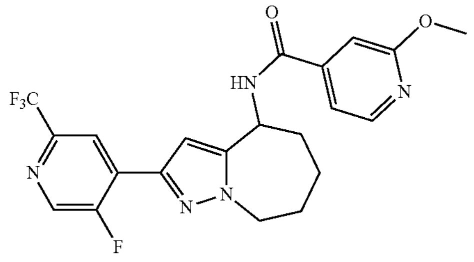 [SMILES: COc1cc(C(=O)NC2CCCCn3nc(-c4cc(C(F)(F)F)ncc4F)cc32)ccn1]
I-517a
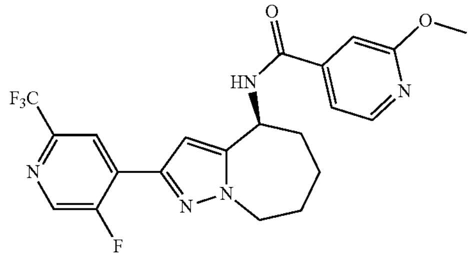 [SMILES: COc1cc(C(=O)N[C@H]2CCCCn3nc(-c4cc(C(F)(F)F)ncc4F)cc32)ccn1]
I-517b
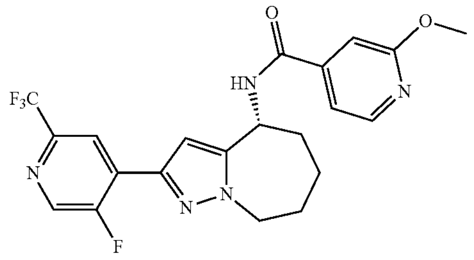 [SMILES: COc1cc(C(=O)N[C@@H]2CCCCn3nc(-c4cc(C(F)(F)F)ncc4F)cc32)ccn1]
I-518
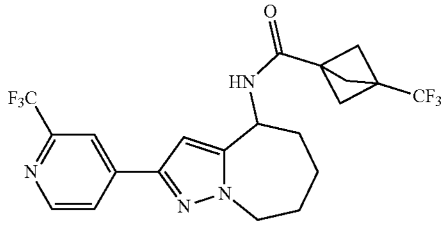 [SMILES: O=C(NC1CCCCn2nc(-c3ccnc(C(F)(F)F)c3)cc21)C12CC(C(F)(F)F)(C1)C2]
I-518a
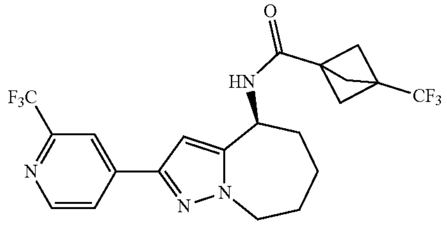 [SMILES: O=C(N[C@H]1CCCCn2nc(-c3ccnc(C(F)(F)F)c3)cc21)C12CC(C(F)(F)F)(C1)C2]
I-518b
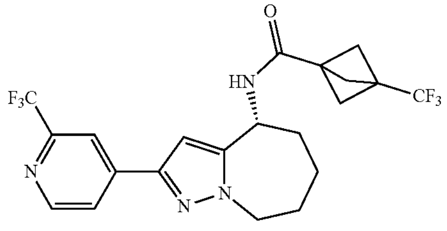 [SMILES: O=C(N[C@@H]1CCCCn2nc(-c3ccnc(C(F)(F)F)c3)cc21)C12CC(C(F)(F)F)(C1)C2]

TABLE 1-continued
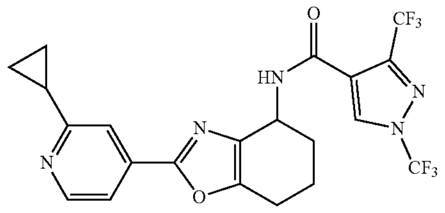 [SMILES: O=C(NC1CCCc2oc(-c3ccnc(C4CC4)c3)nc21)c1cn(C(F)(F)F)nc1C(F)(F)F]
I-519
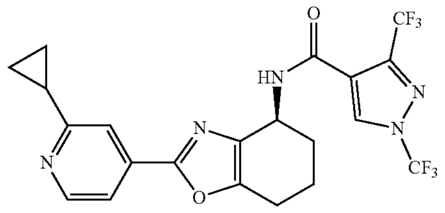 [SMILES: O=C(N[C@H]1CCCc2oc(-c3ccnc(C4CC4)c3)nc21)c1cn(C(F)(F)F)nc1C(F)(F)F]
I-519a
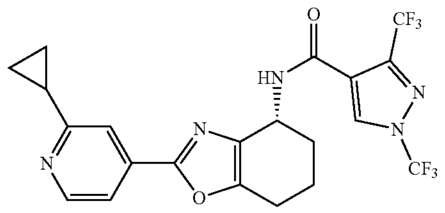 [SMILES: O=C(N[C@@H]1CCCc2oc(-c3ccnc(C4CC4)c3)nc21)c1cn(C(F)(F)F)nc1C(F)(F)F]
I-519b
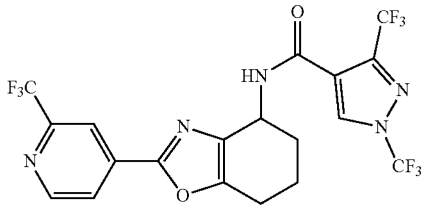 [SMILES: O=C(NC1CCCc2oc(-c3ccnc(C(F)(F)F)c3)nc21)c1cn(C(F)(F)F)nc1C(F)(F)F]
I-520
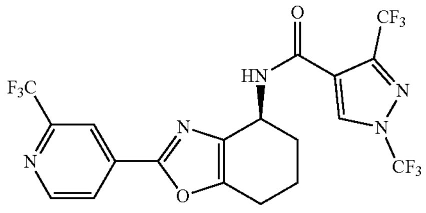
I-520a
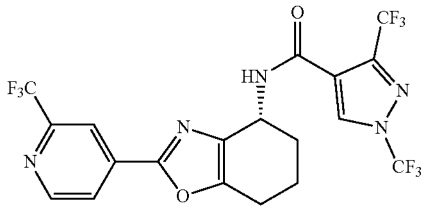 [SMILES: O=C(N[C@@H]1CCCc2oc(-c3ccnc(C(F)(F)F)c3)nc21)c1cn(C(F)(F)F)nc1C(F)(F)F]
I-520b
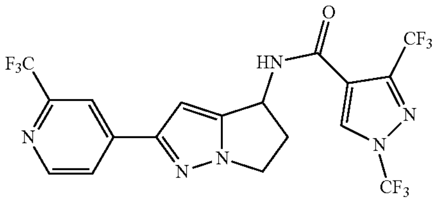 [SMILES: O=C(NC1CCn2nc(-c3ccnc(C(F)(F)F)c3)cc21)c1cn(C(F)(F)F)nc1C(F)(F)F]
I-521

TABLE 1-continued
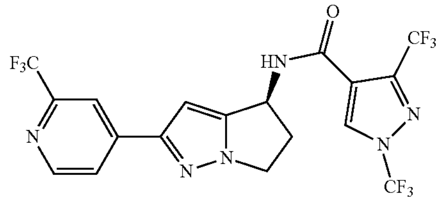 [SMILES: O=C(N[C@H]1CCn2nc(-c3ccnc(C(F)(F)F)c3)cc21)c1cn(C(F)(F)F)nc1C(F)(F)F]
I-521a
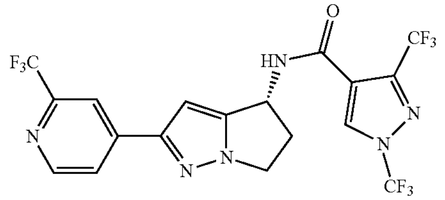
I-521b
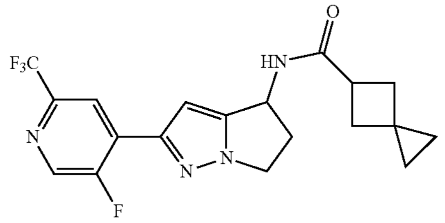 [SMILES: O=C(NC1CCn2nc(-c3cc(C(F)(F)F)ncc3F)cc21)C1CC2(CC2)C1]
I-522
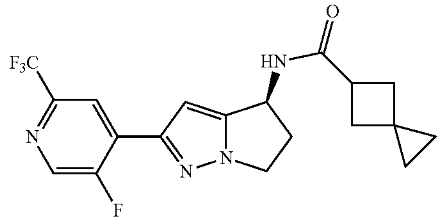 [SMILES: O=C(N[C@H]1CCn2nc(-c3cc(C(F)(F)F)ncc3F)cc21)C1CC2(CC2)C1]
I-522a
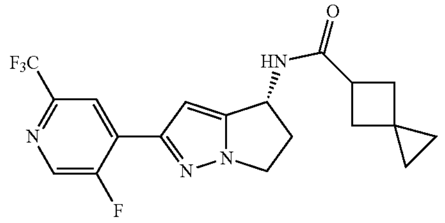 [SMILES: O=C(N[C@@H]1CCn2nc(-c3cc(C(F)(F)F)ncc3F)cc21)C1CC2(CC2)C1]
I-522b
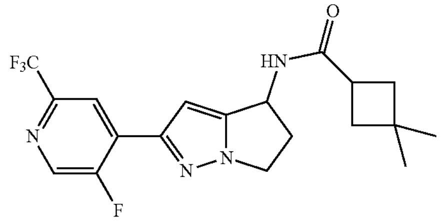 [SMILES: CC1(C)CC(C(=O)NC2CCn3nc(-c4cc(C(F)(F)F)ncc4F)cc32)C1]
I-523
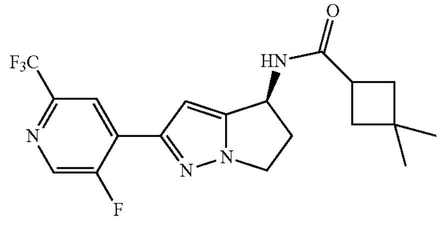 [SMILES: CC1(C)CC(C(=O)N[C@H]2CCn3nc(-c4cc(C(F)(F)F)ncc4F)cc32)C1]
I-523a TABLE 1-continued
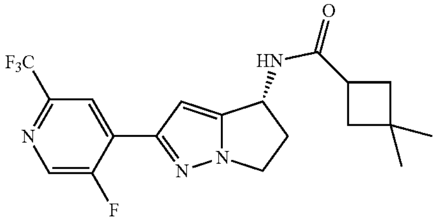 [SMILES: CC1(C)CC(C(=O)N[C@@H]2CCn3nc(-c4cc(C(F)(F)F)ncc4F)cc32)C1]
I-523b
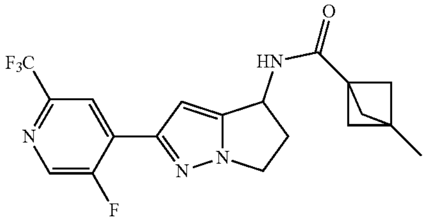 [SMILES: CC12CC(C(=O)NC3CCn4nc(-c5cc(C(F)(F)F)ncc5F)cc43)(C1)C2]
I-524
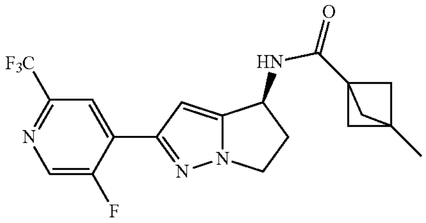 [SMILES: CC12CC(C(=O)N[C@H]3CCn4nc(-c5cc(C(F)(F)F)ncc5F)cc43)(C1)C2]
I-524a
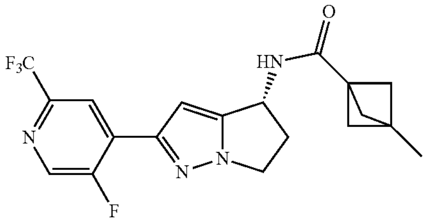 [SMILES: CC12CC(C(=O)N[C@@H]3CCn4nc(-c5cc(C(F)(F)F)ncc5F)cc43)(C1)C2]
I-524b
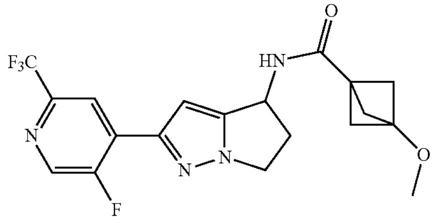 [SMILES: COC12CC(C(=O)NC3CCn4nc(-c5cc(C(F)(F)F)ncc5F)cc43)(C1)C2]
I-525
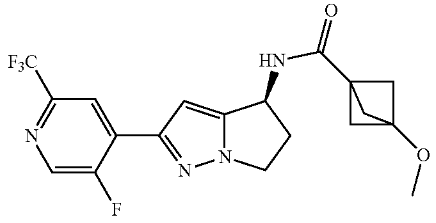 [SMILES: COC12CC(C(=O)N[C@H]3CCn4nc(-c5cc(C(F)(F)F)ncc5F)cc43)(C1)C2]
I-525a
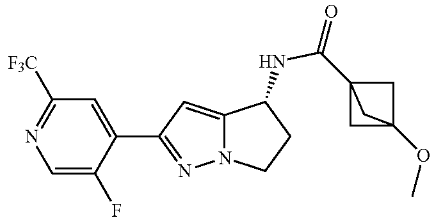 [SMILES: COC12CC(C(=O)N[C@@H]3CCn4nc(-c5cc(C(F)(F)F)ncc5F)cc43)(C1)C2]
I-525b TABLE 1-continued
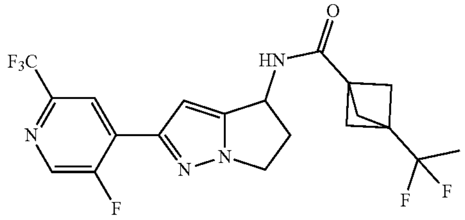 [SMILES: CC(F)(F)C12CC(C(=O)NC3CCn4nc(-c5cc(C(F)(F)F)ncc5F)cc43)(C1)C2]
I-526
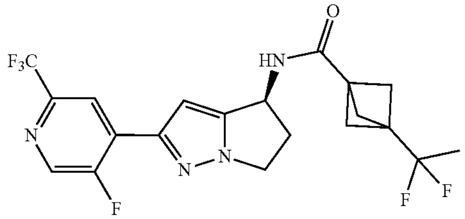 [SMILES: CC(F)(F)C12CC(C(=O)N[C@H]3CCn4nc(-c5cc(C(F)(F)F)ncc5F)cc43)(C1)C2]
I-526a
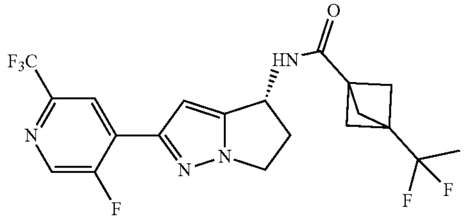 [SMILES: CC(F)(F)C12CC(C(=O)N[C@@H]3CCn4nc(-c5cc(C(F)(F)F)ncc5F)cc43)(C1)C2]
I-526b
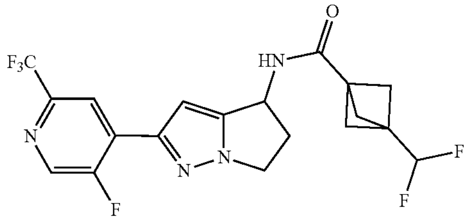 [SMILES: O=C(NC1CCn2nc(-c3cc(C(F)(F)F)ncc3F)cc21)C12CC(C(F)F)(C1)C2]
I-527
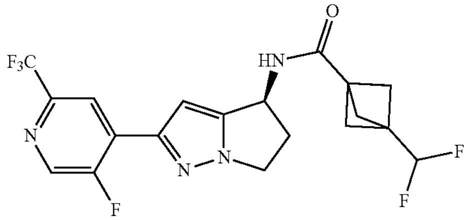 [SMILES: O=C(N[C@H]1CCn2nc(-c3cc(C(F)(F)F)ncc3F)cc21)C12CC(C(F)F)(C1)C2]
I-527a
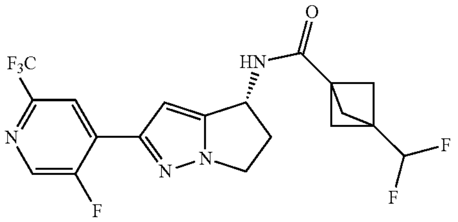 [SMILES: O=C(N[C@@H]1CCn2nc(-c3cc(C(F)(F)F)ncc3F)cc21)C12CC(C(F)F)(C1)C2]
I-527b
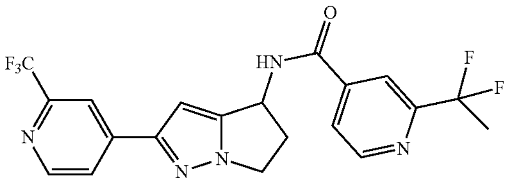 [SMILES: CC(F)(F)c1cc(C(=O)NC2CCn3nc(-c4ccnc(C(F)(F)F)c4)cc32)ccn1]
I-528

TABLE 1-continued
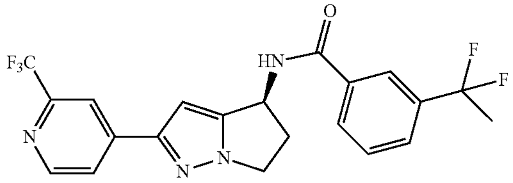 [SMILES: CC(F)(F)c1cccc(C(=O)N[C@H]2CCn3nc(-c4ccnc(C(F)(F)F)c4)cc32)c1]
I-528a
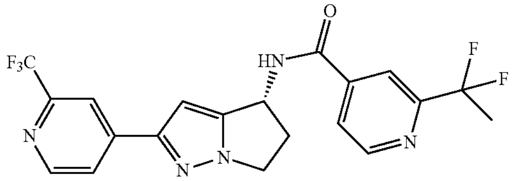 [SMILES: CC(F)(F)c1cc(C(=O)N[C@@H]2CCn3nc(-c4ccnc(C(F)(F)F)c4)cc32)ccn1]
I-528b
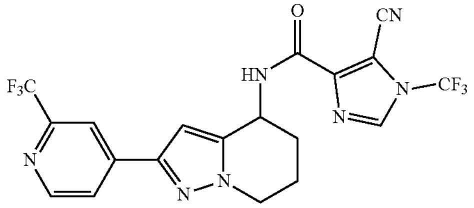 [SMILES: N#Cc1c(C(=O)NC2CCCn3nc(-c4ccnc(C(F)(F)F)c4)cc32)ncn1C(F)(F)F]
I-529
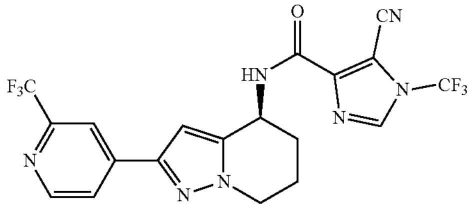 [SMILES: N#Cc1c(C(=O)N[C@H]2CCCn3nc(-c4ccnc(C(F)(F)F)c4)cc32)ncn1C(F)(F)F]
I-529a
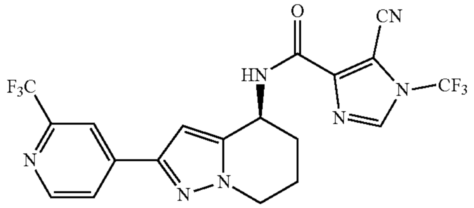 [SMILES: N#Cc1c(C(=O)N[C@H]2CCCn3nc(-c4ccnc(C(F)(F)F)c4)cc32)ncn1C(F)(F)F]
I-529b
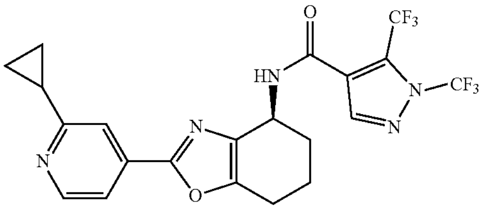 [SMILES: O=C(N[C@H]1CCCc2oc(-c3ccnc(C4CC4)c3)nc21)c1cnn(C(F)(F)F)c1C(F)(F)F]
I-530
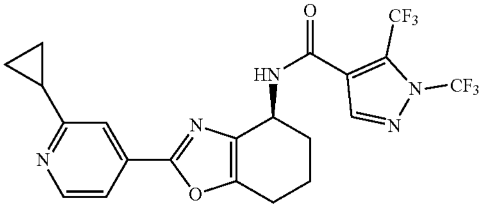 [SMILES: O=C(N[C@H]1CCCc2oc(-c3ccnc(C4CC4)c3)nc21)c1cnn(C(F)(F)F)c1C(F)(F)F]
I-530a TABLE 1-continued
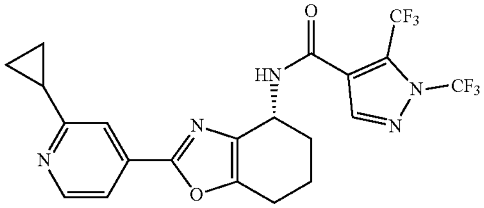 [SMILES: O=C(N[C@@H]1CCCc2oc(-c3ccnc(C4CC4)c3)nc21)c1cnn(C(F)(F)F)c1C(F)(F)F]
I-530b
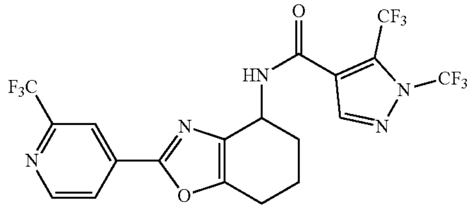 [SMILES: O=C(NC1CCCc2oc(-c3ccnc(C(F)(F)F)c3)nc21)c1cnn(C(F)(F)F)c1C(F)(F)F]
I-531
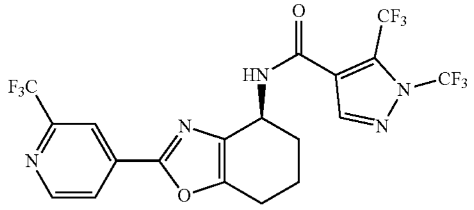 [SMILES: O=C(N[C@H]1CCCc2oc(-c3ccnc(C(F)(F)F)c3)nc21)c1cnn(C(F)(F)F)c1C(F)(F)F]
I-531a
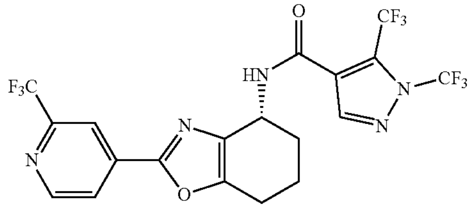 [SMILES: O=C(N[C@@H]1CCCc2oc(-c3ccnc(C(F)(F)F)c3)nc21)c1cnn(C(F)(F)F)c1C(F)(F)F]
I-531b
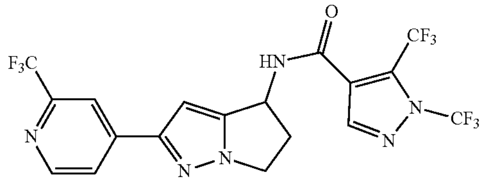 [SMILES: O=C(NC1CCn2nc(-c3ccnc(C(F)(F)F)c3)cc21)c1cnn(C(F)(F)F)c1C(F)(F)F]
I-532
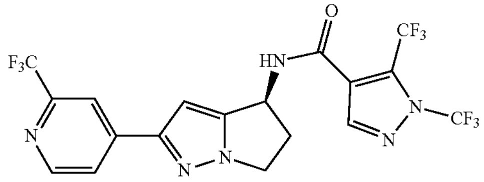 [SMILES: O=C(N[C@H]1CCn2nc(-c3ccnc(C(F)(F)F)c3)cc21)c1cnn(C(F)(F)F)c1C(F)(F)F]
I-532a
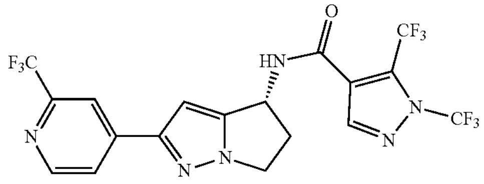 [SMILES: O=C(N[C@@H]1CCn2nc(-c3ccnc(C(F)(F)F)c3)cc21)c1cnn(C(F)(F)F)c1C(F)(F)F]
I-532b TABLE 1-continued
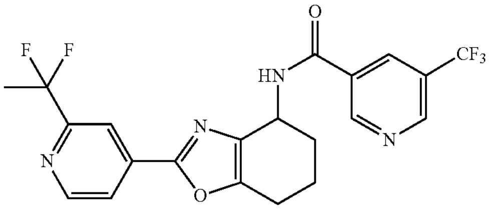 [SMILES: CC(F)(F)c1cc(-c2nc3c(o2)CCCC3NC(=O)c2cncc(C(F)(F)F)c2)ccn1]
I-533
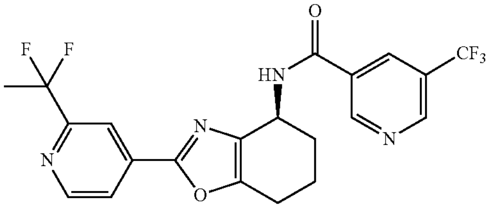 [SMILES: CC(F)(F)c1cc(-c2nc3c(o2)CCC[C@@H]3NC(=O)c2cncc(C(F)(F)F)c2)ccn1]
I-533a
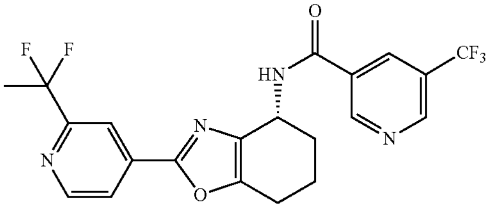 [SMILES: CC(F)(F)c1cc(-c2nc3c(o2)CCC[C@H]3NC(=O)c2cncc(C(F)(F)F)c2)ccn1]
I-533b
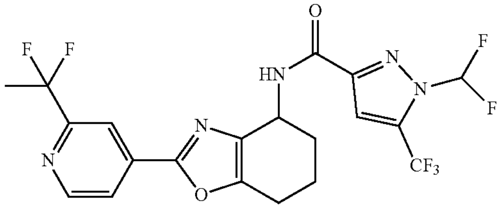 [SMILES: CC(F)(F)c1cc(-c2nc3c(o2)CCCC3NC(=O)c2cc(C(F)(F)F)n(C(F)F)n2)ccn1]
I-534
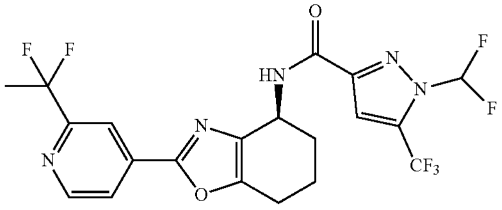 [SMILES: CC(F)(F)c1cc(-c2nc3c(o2)CCC[C@@H]3NC(=O)c2cc(C(F)(F)F)n(C(F)F)n2)ccn1]
I-534a
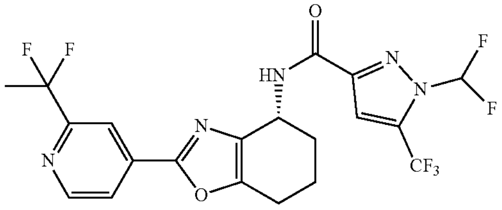
I-534b
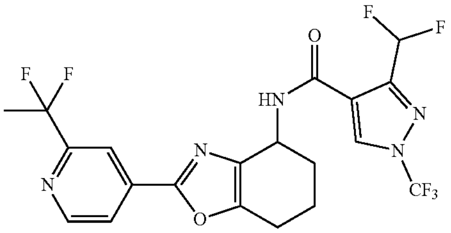 [SMILES: CC(F)(F)c1cc(-c2nc3c(o2)CCCC3NC(=O)c2cn(C(F)(F)F)nc2C(F)F)ccn1]
I-535

TABLE 1-continued
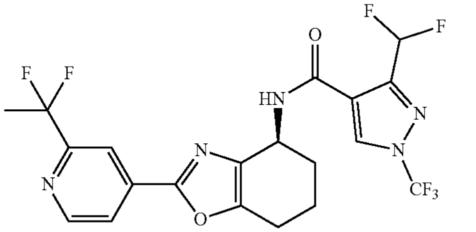 [SMILES: CC(F)(F)c1cc(-c2nc3c(o2)CCC[C@@H]3NC(=O)c2cn(C(F)(F)F)nc2C(F)F)ccn1]
I-535a
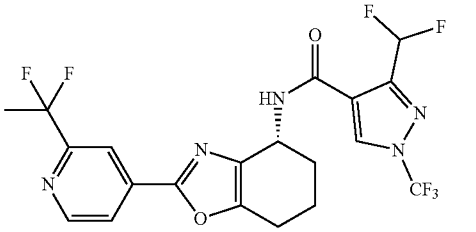
I-535b
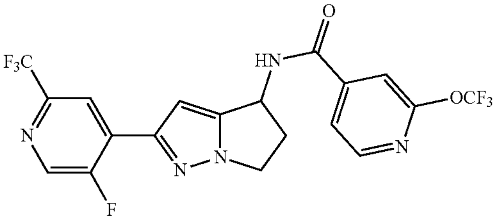 [SMILES: O=C(NC1CCn2nc(-c3cc(C(F)(F)F)ncc3F)cc21)c1ccnc(OC(F)(F)F)c1]
I-536
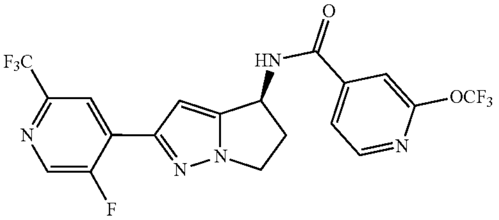 [SMILES: O=C(N[C@H]1CCn2nc(-c3cc(C(F)(F)F)ncc3F)cc21)c1ccnc(OC(F)(F)F)c1]
I-536a
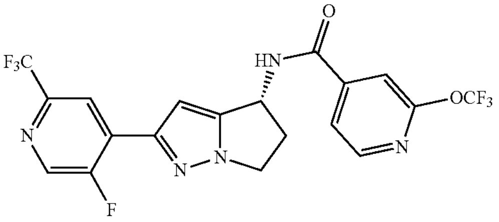 [SMILES: O=C(N[C@@H]1CCn2nc(-c3cc(C(F)(F)F)ncc3F)cc21)c1ccnc(OC(F)(F)F)c1]
I-536b
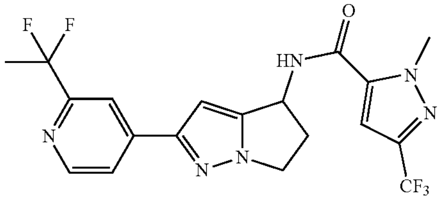
I-537
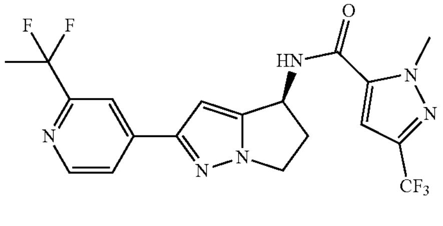
I-537a TABLE 1-continued
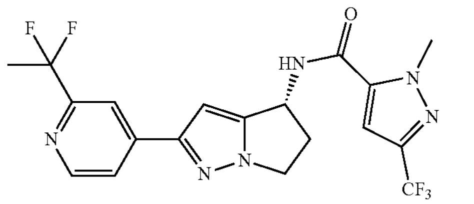
I-537b
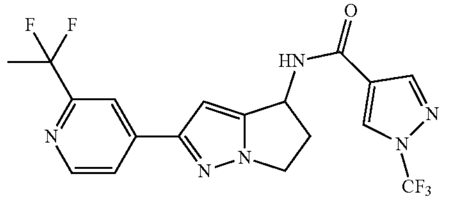
I-538
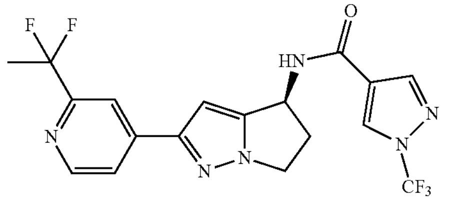 [SMILES: CC(F)(F)c1cc(-c2cc3n(n2)CC[C@@H]3NC(=O)c2cnn(C(F)(F)F)c2)ccn1]
I-538a
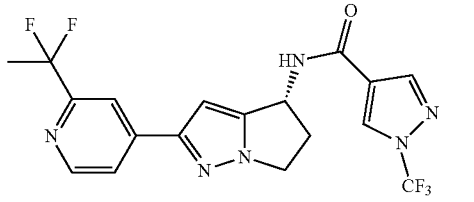
I-538b
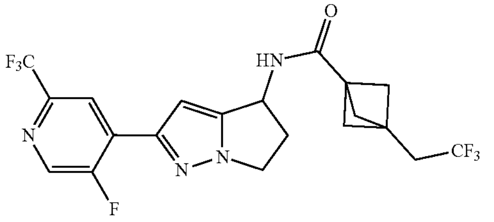 [SMILES: O=C(NC1CCn2nc(-c3cc(C(F)(F)F)ncc3F)cc21)C12CC(CC(F)(F)F)(C1)C2]
I-539
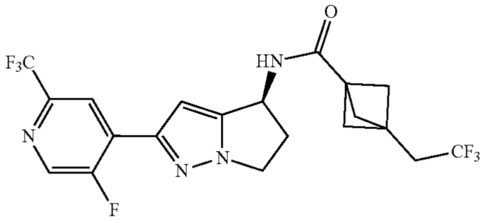 [SMILES: O=C(N[C@H]1CCn2nc(-c3cc(C(F)(F)F)ncc3F)cc21)C12CC(CC(F)(F)F)(C1)C2]
I-539a
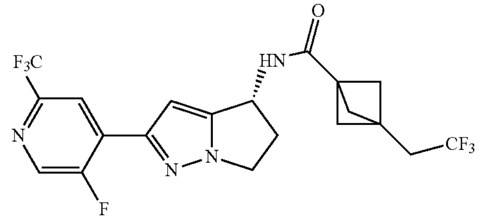 [SMILES: O=C(N[C@@H]1CCn2nc(-c3cc(C(F)(F)F)ncc3F)cc21)C12CC(CC(F)(F)F)(C1)C2]
I-539b TABLE 1-continued
I-540
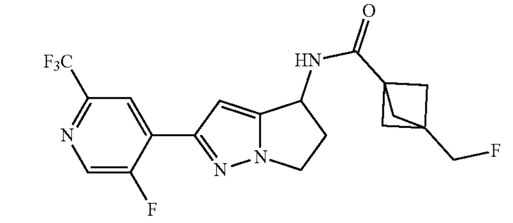 [SMILES: O=C(NC1CCn2nc(-c3cc(C(F)(F)F)ncc3F)cc21)C12CC(CF)(C1)C2]
I-540a
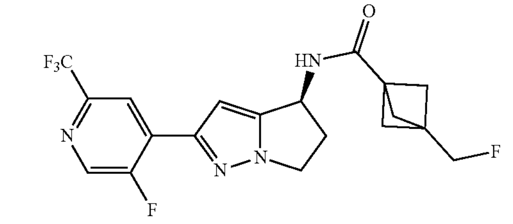 [SMILES: O=C(N[C@H]1CCn2nc(-c3cc(C(F)(F)F)ncc3F)cc21)C12CC(CF)(C1)C2]
I-540b
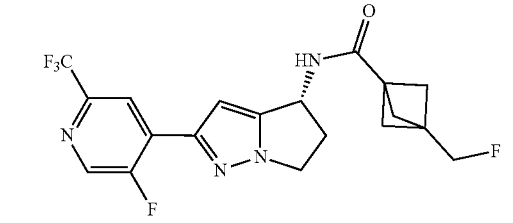 [SMILES: O=C(N[C@@H]1CCn2nc(-c3cc(C(F)(F)F)ncc3F)cc21)C12CC(CF)(C1)C2]
I-541
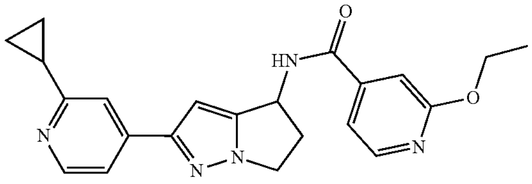 [SMILES: CCOc1cc(C(=O)NC2CCn3nc(-c4ccnc(C5CC5)c4)cc32)ccn1]
I-541a
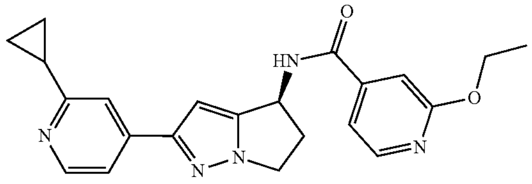 [SMILES: CCOc1cc(C(=O)N[C@H]2CCn3nc(-c4ccnc(C5CC5)c4)cc32)ccn1]
I-541b
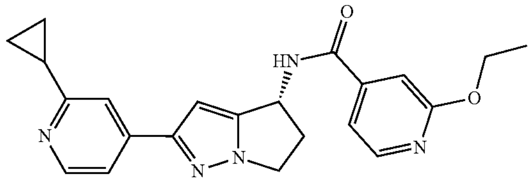 [SMILES: CCOc1cc(C(=O)N[C@@H]2CCn3nc(-c4ccnc(C5CC5)c4)cc32)ccn1]
I-542
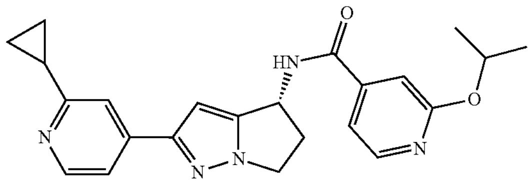 [SMILES: CC(C)Oc1cc(C(=O)N[C@@H]2CCn3nc(-c4ccnc(C5CC5)c4)cc32)ccn1]
I-542a
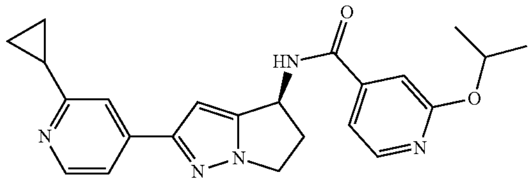 [SMILES: CC(C)Oc1cc(C(=O)N[C@H]2CCn3nc(-c4ccnc(C5CC5)c4)cc32)ccn1]

TABLE 1-continued
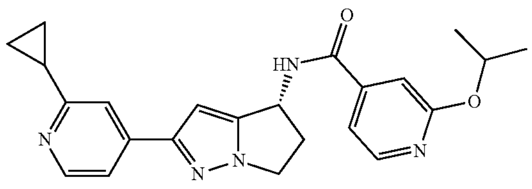 [SMILES: CC(C)Oc1cc(C(=O)N[C@@H]2CCn3nc(-c4ccnc(C5CC5)c4)cc32)ccn1]
I-542b
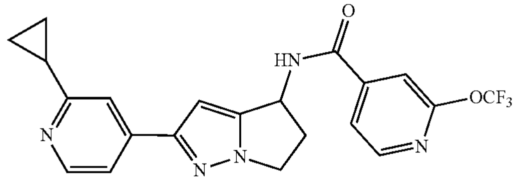 [SMILES: O=C(NC1CCn2nc(-c3ccnc(C4CC4)c3)cc21)c1ccnc(OC(F)(F)F)c1]
I-543
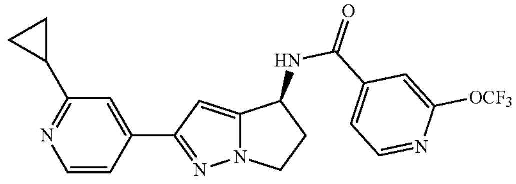 [SMILES: O=C(N[C@H]1CCn2nc(-c3ccnc(C4CC4)c3)cc21)c1ccnc(OC(F)(F)F)c1]
I-543a
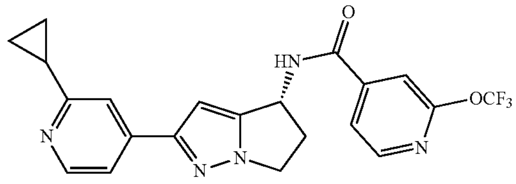 [SMILES: O=C(N[C@@H]1CCn2nc(-c3ccnc(C4CC4)c3)cc21)c1ccnc(OC(F)(F)F)c1]
I-543b
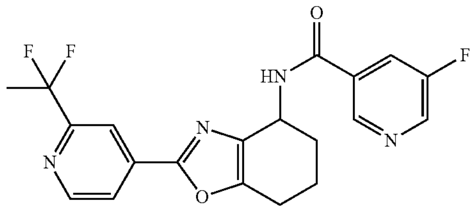 [SMILES: CC(F)(F)c1cc(-c2nc3c(o2)CCCC3NC(=O)c2cncc(F)c2)ccn1]
I-544
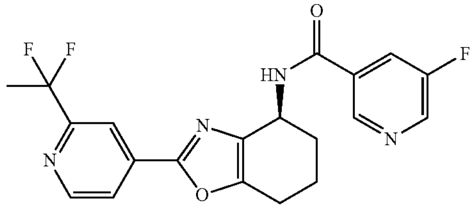 [SMILES: CC(F)(F)c1cc(-c2nc3c(o2)CCC[C@@H]3NC(=O)c2cncc(F)c2)ccn1]
I-544a
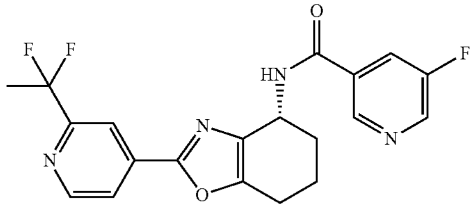 [SMILES: CC(F)(F)c1cc(-c2nc3c(o2)CCC[C@H]3NC(=O)c2cncc(F)c2)ccn1]
I-544b TABLE 1-continued
I-545
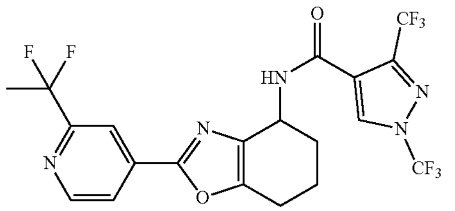 [SMILES: CC(F)(F)c1cc(-c2nc3c(o2)CCCC3NC(=O)c2cn(C(F)(F)F)nc2C(F)(F)F)ccn1]
I-545a
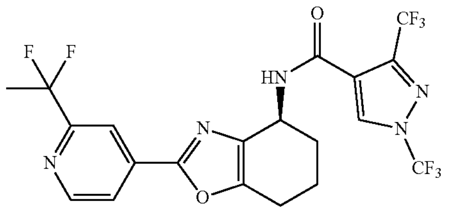 [SMILES: CC(F)(F)c1cc(-c2nc3c(o2)CCC[C@@H]3NC(=O)c2cn(C(F)(F)F)nc2C(F)(F)F)ccn1]
I-545b
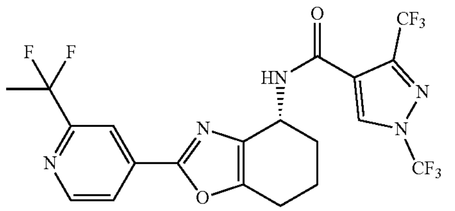 [SMILES: CC(F)(F)c1cc(-c2nc3c(o2)CCC[C@H]3NC(=O)c2cn(C(F)(F)F)nc2C(F)(F)F)ccn1]
I-546
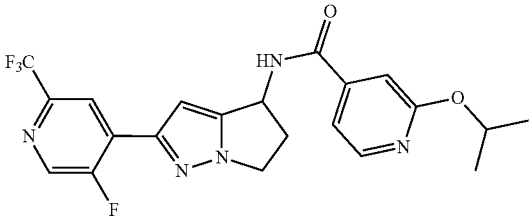 [SMILES: CC(C)Oc1cc(C(=O)NC2CCn3nc(-c4cc(C(F)(F)F)ncc4F)cc32)ccn1]
I-546a
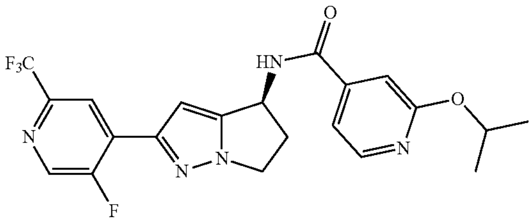 [SMILES: CC(C)Oc1cc(C(=O)N[C@H]2CCn3nc(-c4cc(C(F)(F)F)ncc4F)cc32)ccn1]
I-546b
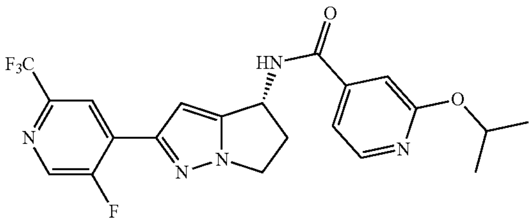 [SMILES: CC(C)Oc1cc(C(=O)N[C@@H]2CCn3nc(-c4cc(C(F)(F)F)ncc4F)cc32)ccn1]
I-547
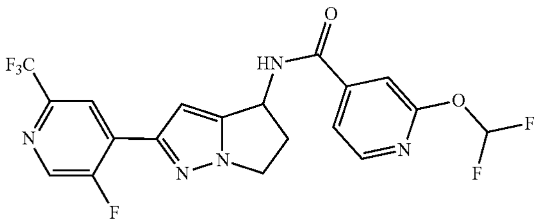 [SMILES: O=C(NC1CCn2nc(-c3cc(C(F)(F)F)ncc3F)cc21)c1ccnc(OC(F)F)c1]

TABLE 1-continued
I-547a
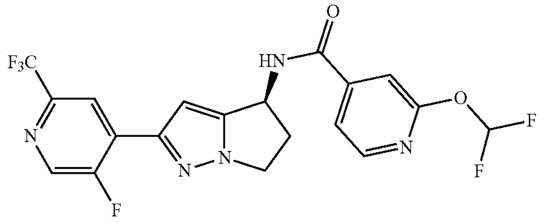 [SMILES: O=C(N[C@H]1CCn2nc(-c3cc(C(F)(F)F)ncc3F)cc21)c1ccnc(OC(F)F)c1]
I-547b
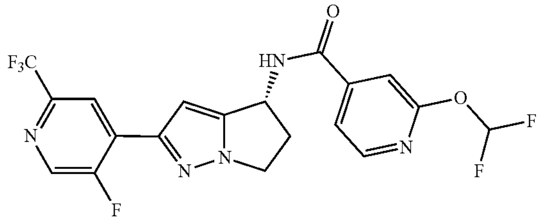 [SMILES: O=C(N[C@@H]1CCn2nc(-c3cc(C(F)(F)F)ncc3F)cc21)c1ccnc(OC(F)F)c1]
I-548
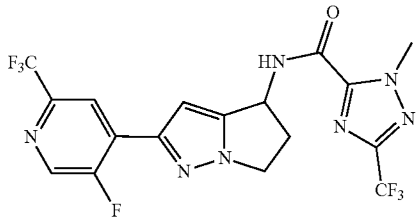 [SMILES: Cn1nc(C(F)(F)F)nc1C(=O)NC1CCn2nc(-c3cc(C(F)(F)F)ncc3F)cc21]
I-548a
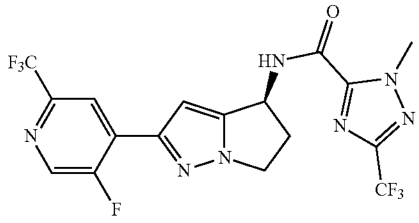 [SMILES: Cn1nc(C(F)(F)F)nc1C(=O)N[C@H]1CCn2nc(-c3cc(C(F)(F)F)ncc3F)cc21]
I-548b
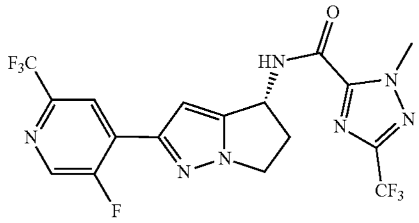 [SMILES: Cn1nc(C(F)(F)F)nc1C(=O)N[C@@H]1CCn2nc(-c3cc(C(F)(F)F)ncc3F)cc21]
I-549
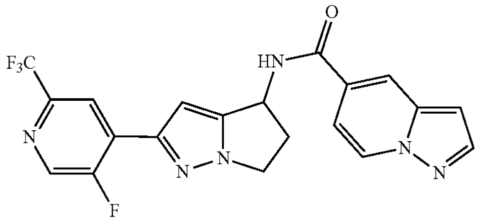 [SMILES: O=C(NC1CCn2nc(-c3cc(C(F)(F)F)ncc3F)cc21)c1ccn2nccc2c1]
I-549a
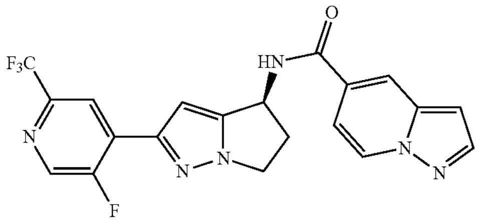 [SMILES: O=C(N[C@H]1CCn2nc(-c3cc(C(F)(F)F)ncc3F)cc21)c1ccn2nccc2c1]

TABLE 1-continued
I-549b
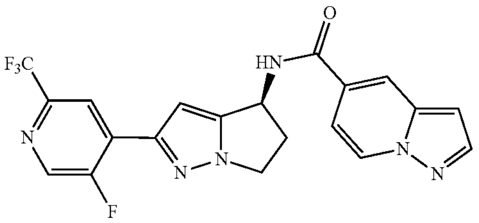 [SMILES: O=C(N[C@H]1CCn2nc(-c3cc(C(F)(F)F)ncc3F)cc21)c1ccn2nccc2c1]
I-550
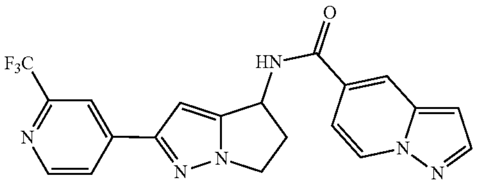 [SMILES: O=C(NC1CCn2nc(-c3ccnc(C(F)(F)F)c3)cc21)c1ccn2nccc2c1]
I-550a
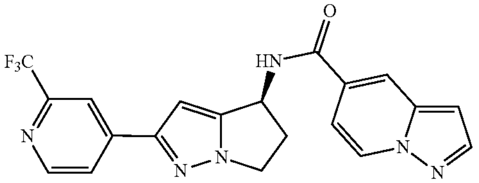 [SMILES: O=C(N[C@H]1CCn2nc(-c3ccnc(C(F)(F)F)c3)cc21)c1ccn2nccc2c1]
I-550b
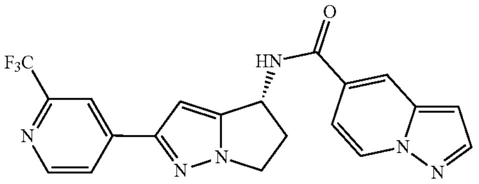 [SMILES: O=C(N[C@@H]1CCn2nc(-c3ccnc(C(F)(F)F)c3)cc21)c1ccn2nccc2c1]
I-551
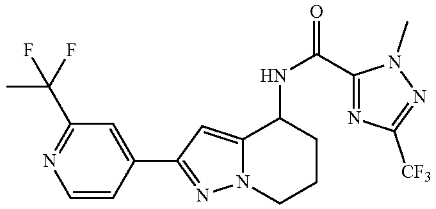 [SMILES: Cn1nc(C(F)(F)F)nc1C(=O)NC1CCCn2nc(-c3ccnc(C(C)(F)F)c3)cc21]
I-551a
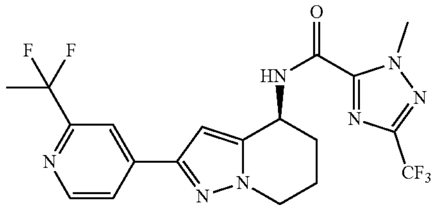 [SMILES: Cn1nc(C(F)(F)F)nc1C(=O)N[C@H]1CCCn2nc(-c3ccnc(C(C)(F)F)c3)cc21]
I-551b
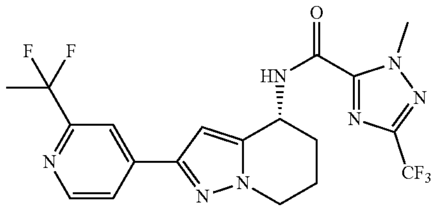 [SMILES: Cn1nc(C(F)(F)F)nc1C(=O)N[C@@H]1CCCn2nc(-c3ccnc(C(C)(F)F)c3)cc21]

TABLE 1-continued
I-552
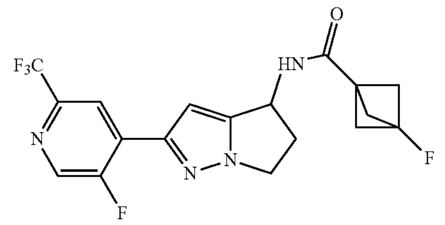 [SMILES: O=C(NC1CCn2nc(-c3cc(C(F)(F)F)ncc3F)cc21)C12CC(F)(C1)C2]
I-552a
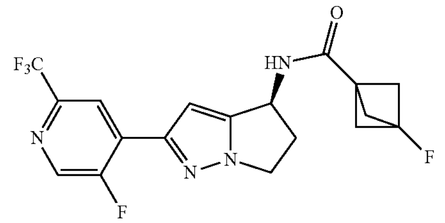 [SMILES: O=C(N[C@H]1CCn2nc(-c3cc(C(F)(F)F)ncc3F)cc21)C12CC(F)(C1)C2]
I-552b
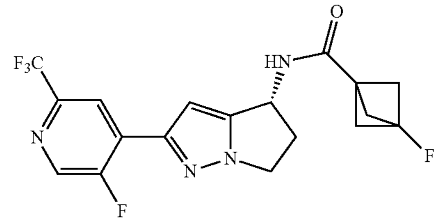 [SMILES: O=C(N[C@@H]1CCn2nc(-c3cc(C(F)(F)F)ncc3F)cc21)C12CC(F)(C1)C2]
I-553
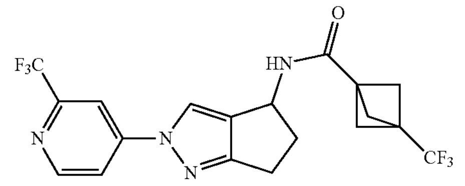 [SMILES: O=C(NC1CCc2nn(-c3ccnc(C(F)(F)F)c3)cc21)C12CC(C(F)(F)F)(C1)C2]
I-553a
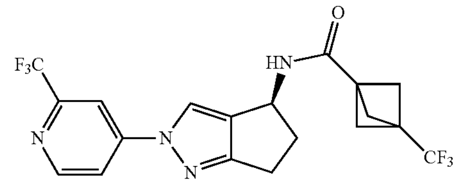 [SMILES: O=C(N[C@H]1CCc2nn(-c3ccnc(C(F)(F)F)c3)cc21)C12CC(C(F)(F)F)(C1)C2]
I-553b
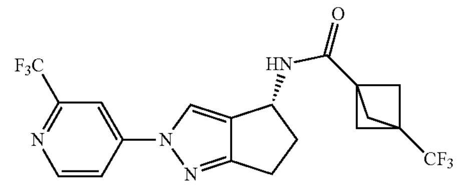 [SMILES: O=C(N[C@@H]1CCc2nn(-c3ccnc(C(F)(F)F)c3)cc21)C12CC(C(F)(F)F)(C1)C2]
I-554
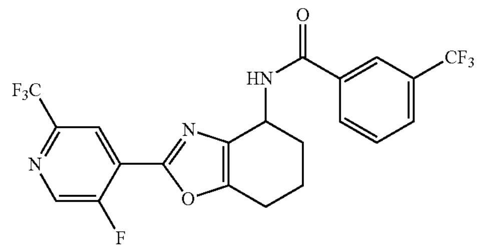 [SMILES: O=C(NC1CCCc2oc(-c3cc(C(F)(F)F)ncc3F)nc21)c1cccc(C(F)(F)F)c1]

TABLE 1-continued
I-554a
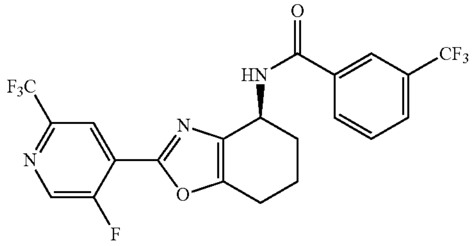 [SMILES: O=C(N[C@H]1CCCc2oc(-c3cc(C(F)(F)F)ncc3F)nc21)c1cccc(C(F)(F)F)c1]
I-554b
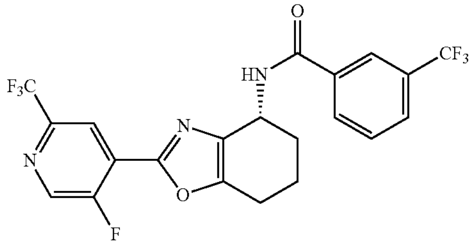 [SMILES: O=C(N[C@@H]1CCCc2oc(-c3cc(C(F)(F)F)ncc3F)nc21)c1cccc(C(F)(F)F)c1]
I-555
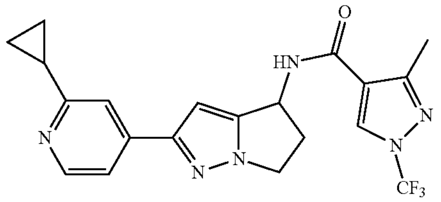
I-555a
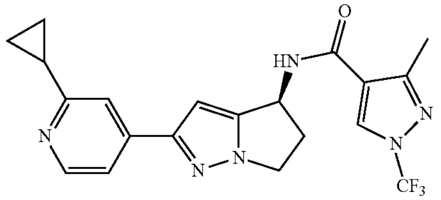 [SMILES: Cc1nn(C(F)(F)F)cc1C(=O)N[C@H]1CCn2nc(-c3ccnc(C4CC4)c3)cc21]
I-555b
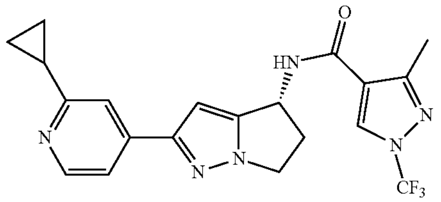 [SMILES: Cc1nn(C(F)(F)F)cc1C(=O)N[C@@H]1CCn2nc(-c3ccnc(C4CC4)c3)cc21]
I-556
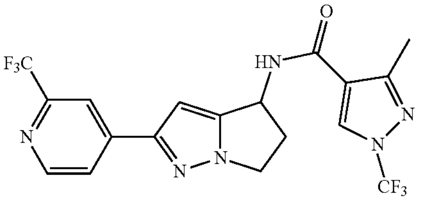
I-556a
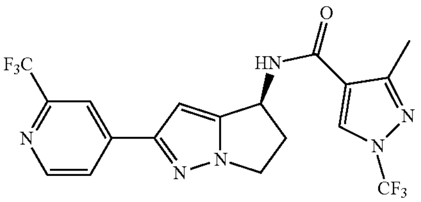

TABLE 1-continued
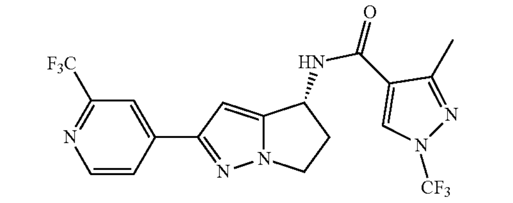 [SMILES: Cc1nn(C(F)(F)F)cc1C(=O)N[C@@H]1CCn2nc(-c3ccnc(C(F)(F)F)c3)cc21]
I-556b
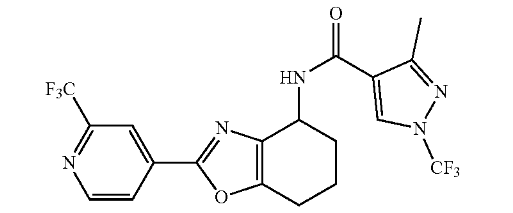 [SMILES: Cc1nn(C(F)(F)F)cc1C(=O)NC1CCCc2oc(-c3ccnc(C(F)(F)F)c3)nc21]
I-557
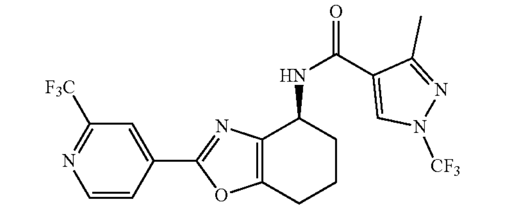 [SMILES: Cc1nn(C(F)(F)F)cc1C(=O)N[C@H]1CCCc2oc(-c3ccnc(C(F)(F)F)c3)nc21]
I-557a
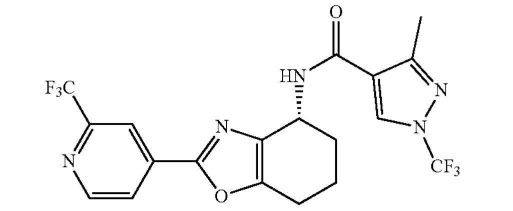 [SMILES: Cc1nn(C(F)(F)F)cc1C(=O)N[C@@H]1CCCc2oc(-c3ccnc(C(F)(F)F)c3)nc21]
I-557b
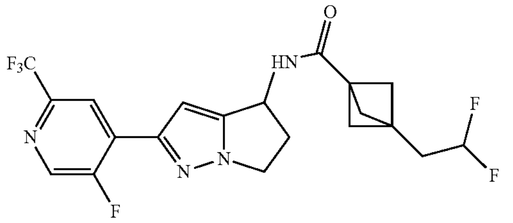 [SMILES: O=C(NC1CCn2nc(-c3cc(C(F)(F)F)ncc3F)cc21)C12CC(CC(F)F)(C1)C2]
I-558
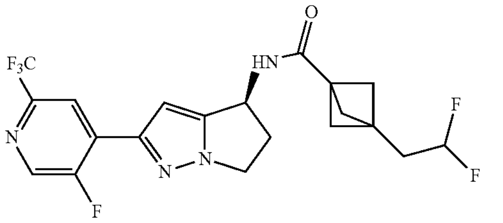 [SMILES: O=C(N[C@H]1CCn2nc(-c3cc(C(F)(F)F)ncc3F)cc21)C12CC(CC(F)F)(C1)C2]
I-558a
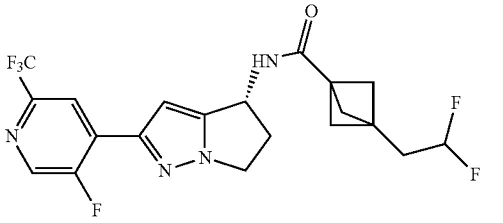 [SMILES: O=C(N[C@@H]1CCn2nc(-c3cc(C(F)(F)F)ncc3F)cc21)C12CC(CC(F)F)(C1)C2]
I-558b TABLE 1-continued
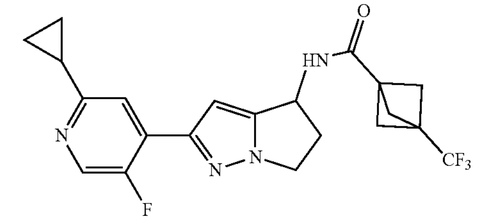 [SMILES: O=C(NC1CCn2nc(-c3cc(C4CC4)ncc3F)cc21)C12CC(C(F)(F)F)(C1)C2]
I-559
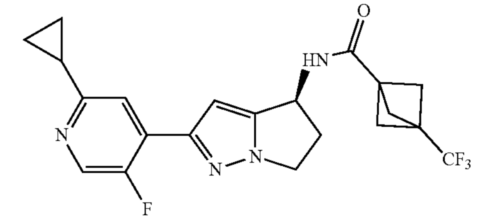 [SMILES: O=C(N[C@H]1CCn2nc(-c3cc(C4CC4)ncc3F)cc21)C12CC(C(F)(F)F)(C1)C2]
I-559a
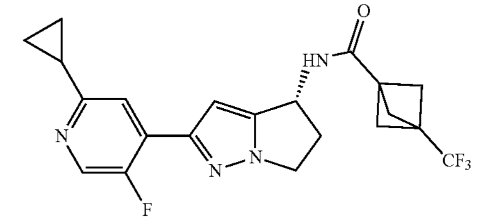
I-559b
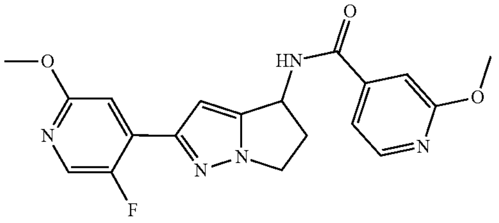
I-560
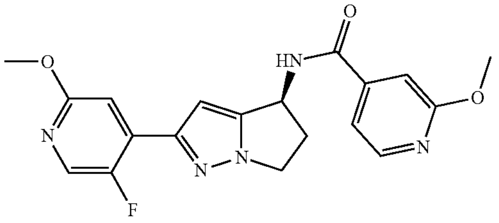
I-560a
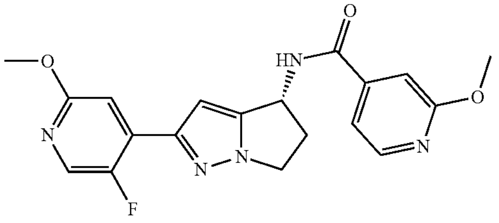
I-560b
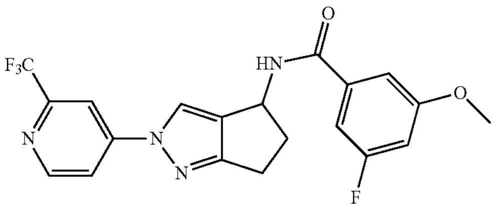 [SMILES: COc1cc(F)cc(C(=O)NC2CCc3nn(-c4ccnc(C(F)(F)F)c4)cc32)c1]
I-561

TABLE 1-continued
I-561a
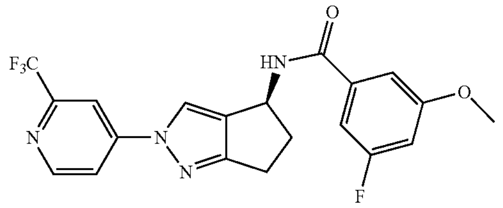 [SMILES: COc1cc(F)cc(C(=O)N[C@H]2CCc3nn(-c4ccnc(C(F)(F)F)c4)cc32)c1]
I-561b
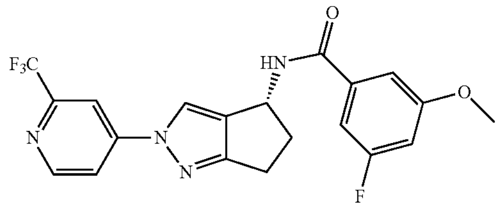 [SMILES: COc1cc(F)cc(C(=O)N[C@@H]2CCc3nn(-c4ccnc(C(F)(F)F)c4)cc32)c1]
I-562
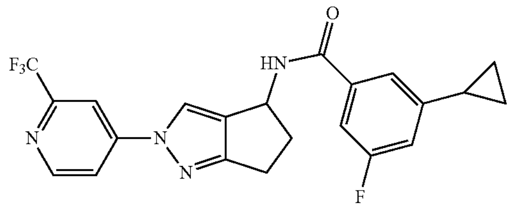 [SMILES: O=C(NC1CCc2nn(-c3ccnc(C(F)(F)F)c3)cc21)c1cc(F)cc(C2CC2)c1]
I-562a
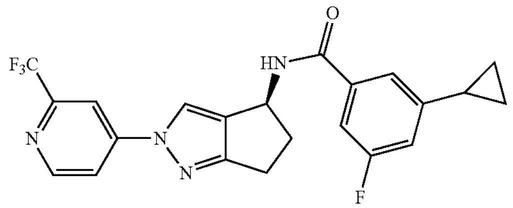 [SMILES: O=C(N[C@H]1CCc2nn(-c3ccnc(C(F)(F)F)c3)cc21)c1cc(F)cc(C2CC2)c1]
I-562b
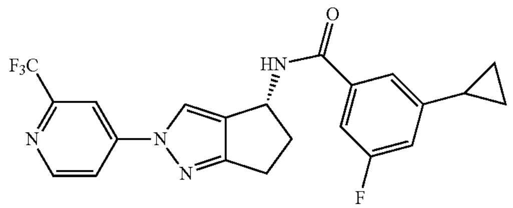 [SMILES: O=C(N[C@@H]1CCc2nn(-c3ccnc(C(F)(F)F)c3)cc21)c1cc(F)cc(C2CC2)c1]
I-563
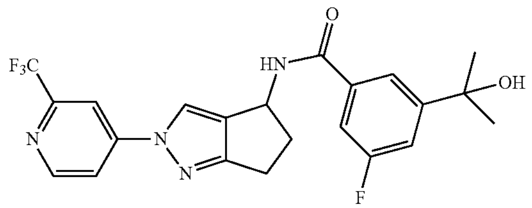 [SMILES: CC(C)(O)c1cc(F)cc(C(=O)NC2CCc3nn(-c4ccnc(C(F)(F)F)c4)cc32)c1]
I-563a
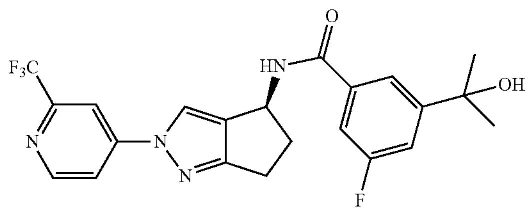 [SMILES: CC(C)(O)c1cc(F)cc(C(=O)N[C@H]2CCc3nn(-c4ccnc(C(F)(F)F)c4)cc32)c1]

TABLE 1-continued
I-563b
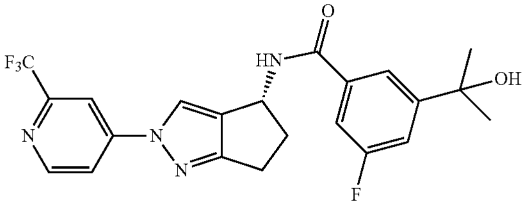 [SMILES: CC(C)(O)c1cc(F)cc(C(=O)N[C@@H]2CCc3nn(-c4ccnc(C(F)(F)F)c4)cc32)c1]
I-564
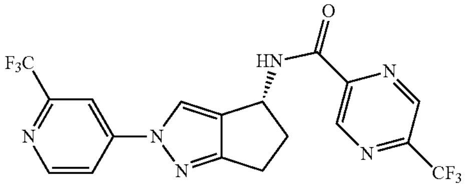 [SMILES: O=C(N[C@@H]1CCc2nn(-c3ccnc(C(F)(F)F)c3)cc21)c1cnc(C(F)(F)F)cn1]
I-564a
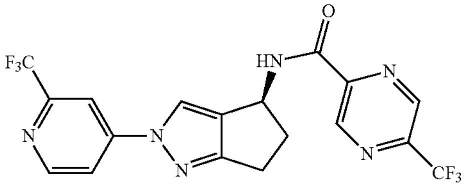 [SMILES: O=C(N[C@H]1CCc2nn(-c3ccnc(C(F)(F)F)c3)cc21)c1cnc(C(F)(F)F)cn1]
I-564b
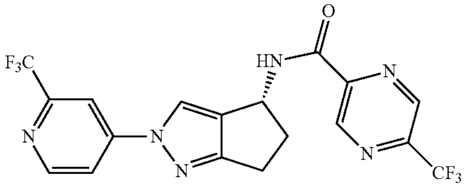 [SMILES: O=C(N[C@@H]1CCc2nn(-c3ccnc(C(F)(F)F)c3)cc21)c1cnc(C(F)(F)F)cn1]
I-565
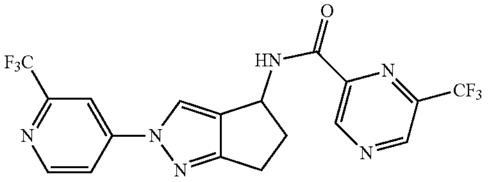 [SMILES: O=C(NC1CCc2nn(-c3ccnc(C(F)(F)F)c3)cc21)c1cncc(C(F)(F)F)n1]
I-565a
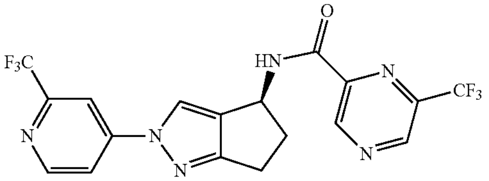 [SMILES: O=C(N[C@H]1CCc2nn(-c3ccnc(C(F)(F)F)c3)cc21)c1cncc(C(F)(F)F)n1]
I-565b
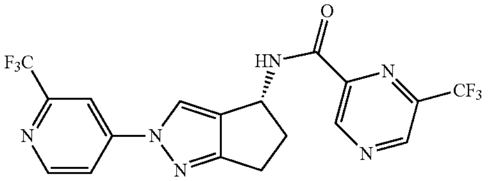 [SMILES: O=C(N[C@@H]1CCc2nn(-c3ccnc(C(F)(F)F)c3)cc21)c1cncc(C(F)(F)F)n1]
I-566
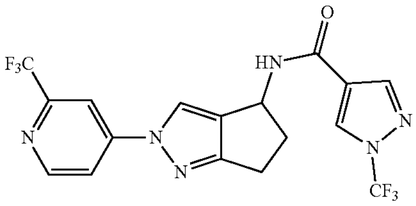 [SMILES: O=C(NC1CCc2nn(-c3ccnc(C(F)(F)F)c3)cc21)c1cnn(C(F)(F)F)c1]

TABLE 1-continued
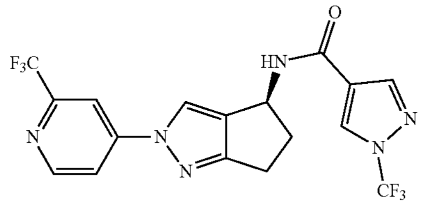
I-566a
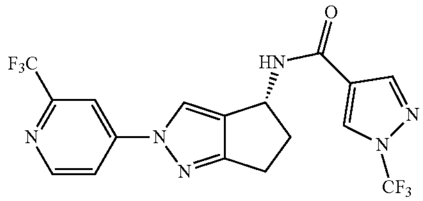 [SMILES: O=C(N[C@@H]1CCc2nn(-c3ccnc(C(F)(F)F)c3)cc21)c1cnn(C(F)(F)F)c1]
I-566b
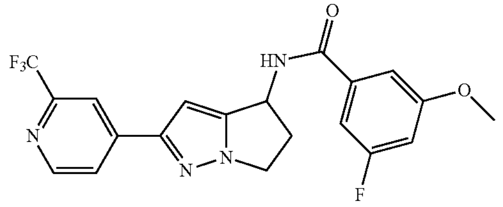 [SMILES: COc1cc(F)cc(C(=O)NC2CCn3nc(-c4ccnc(C(F)(F)F)c4)cc32)c1]
I-567
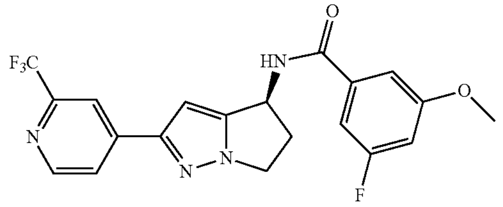 [SMILES: COc1cc(F)cc(C(=O)N[C@H]2CCn3nc(-c4ccnc(C(F)(F)F)c4)cc32)c1]
I-567a
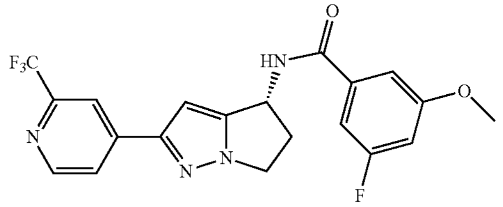 [SMILES: COc1cc(F)cc(C(=O)N[C@@H]2CCn3nc(-c4ccnc(C(F)(F)F)c4)cc32)c1]
I-567b
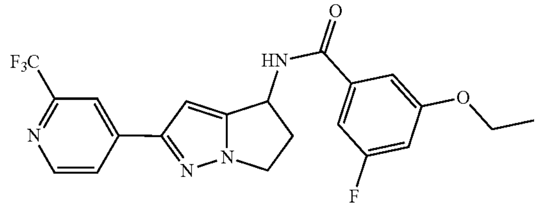 [SMILES: CCOc1cc(F)cc(C(=O)NC2CCn3nc(-c4ccnc(C(F)(F)F)c4)cc32)c1]
I-568
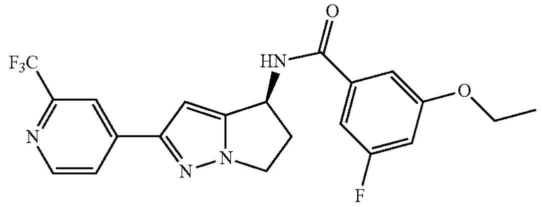 [SMILES: CCOc1cc(F)cc(C(=O)N[C@H]2CCn3nc(-c4ccnc(C(F)(F)F)c4)cc32)c1]
I-568a TABLE 1-continued
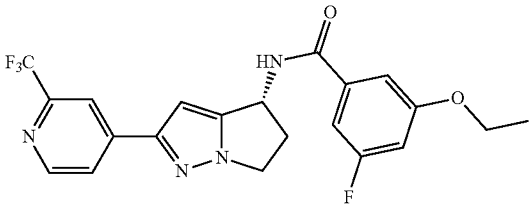 [SMILES: CCOc1cc(F)cc(C(=O)N[C@@H]2CCn3nc(-c4ccnc(C(F)(F)F)c4)cc32)c1]
I-568b
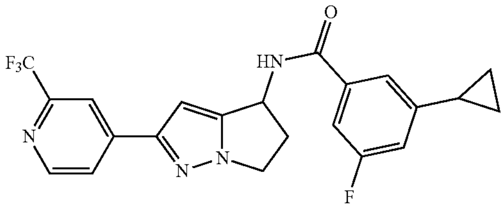 [SMILES: O=C(NC1CCn2nc(-c3ccnc(C(F)(F)F)c3)cc21)c1cc(F)cc(C2CC2)c1]
I-569
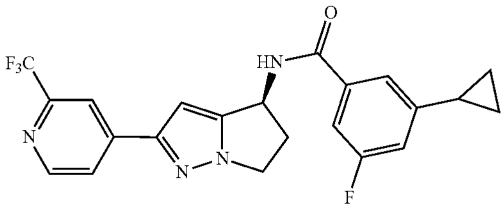 [SMILES: O=C(N[C@H]1CCn2nc(-c3ccnc(C(F)(F)F)c3)cc21)c1cc(F)cc(C2CC2)c1]
I-569a
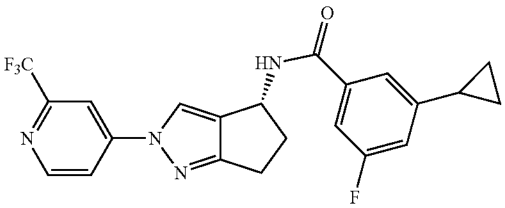 [SMILES: O=C(N[C@@H]1CCc2nn(-c3ccnc(C(F)(F)F)c3)cc21)c1cc(F)cc(C2CC2)c1]
I-569b
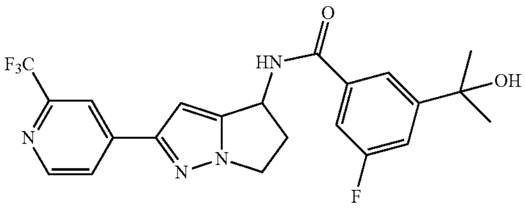 [SMILES: CC(C)(O)c1cc(F)cc(C(=O)NC2CCn3nc(-c4ccnc(C(F)(F)F)c4)cc32)c1]
I-570
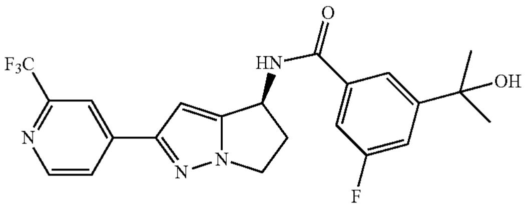 [SMILES: CC(C)(O)c1cc(F)cc(C(=O)N[C@H]2CCn3nc(-c4ccnc(C(F)(F)F)c4)cc32)c1]
I-570a
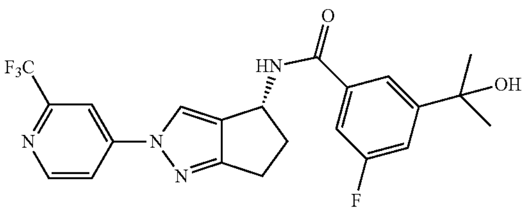 [SMILES: CC(C)(O)c1cc(F)cc(C(=O)N[C@@H]2CCc3nn(-c4ccnc(C(F)(F)F)c4)cc32)c1]
I-570b TABLE 1-continued
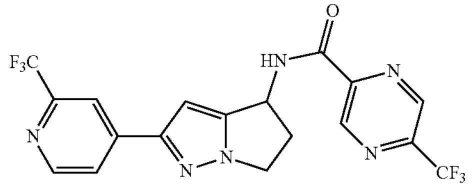 [SMILES: O=C(NC1CCn2nc(-c3ccnc(C(F)(F)F)c3)cc21)c1cnc(C(F)(F)F)cn1]
I-571
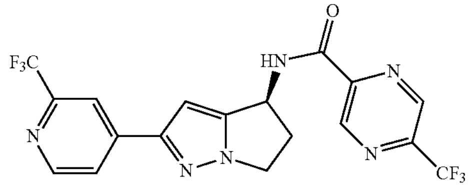 [SMILES: O=C(N[C@H]1CCn2nc(-c3ccnc(C(F)(F)F)c3)cc21)c1cnc(C(F)(F)F)cn1]
I-571a
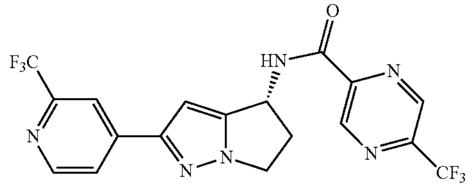 [SMILES: O=C(N[C@@H]1CCn2nc(-c3ccnc(C(F)(F)F)c3)cc21)c1cnc(C(F)(F)F)cn1]
I-571b
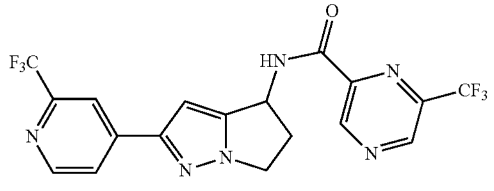 [SMILES: O=C(NC1CCn2nc(-c3ccnc(C(F)(F)F)c3)cc21)c1cncc(C(F)(F)F)n1]
I-572
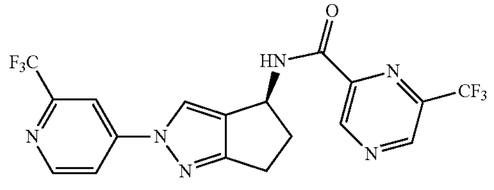 [SMILES: O=C(N[C@H]1CCc2nn(-c3ccnc(C(F)(F)F)c3)cc21)c1cncc(C(F)(F)F)n1]
I-572a
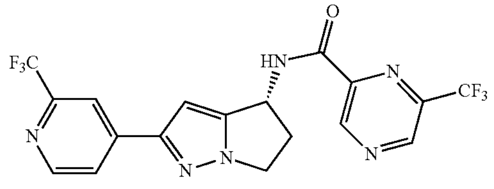 [SMILES: O=C(N[C@@H]1CCn2nc(-c3ccnc(C(F)(F)F)c3)cc21)c1cncc(C(F)(F)F)n1]
I-572b
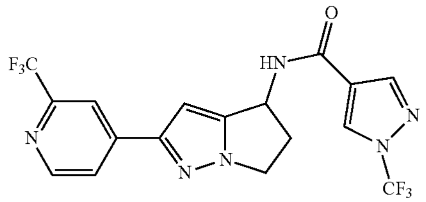 [SMILES: O=C(NC1CCn2nc(-c3ccnc(C(F)(F)F)c3)cc21)c1cnn(C(F)(F)F)c1]
I-573
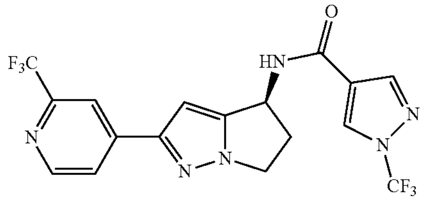 [SMILES: O=C(N[C@H]1CCn2nc(-c3ccnc(C(F)(F)F)c3)cc21)c1cnn(C(F)(F)F)c1]
I-573a TABLE 1-continued
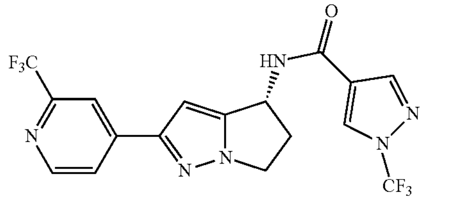 [SMILES: O=C(N[C@@H]1CCn2nc(-c3ccnc(C(F)(F)F)c3)cc21)c1cnn(C(F)(F)F)c1]
I-573b
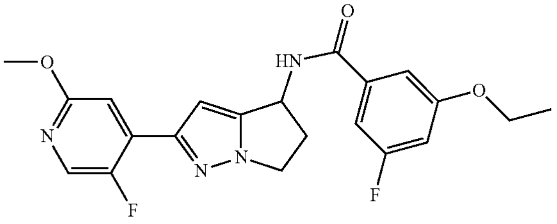 [SMILES: CCOc1cc(F)cc(C(=O)NC2CCn3nc(-c4cc(OC)ncc4F)cc32)c1]
I-574
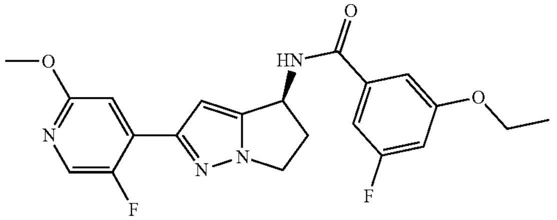 [SMILES: CCOc1cc(F)cc(C(=O)N[C@H]2CCn3nc(-c4cc(OC)ncc4F)cc32)c1]
I-574a
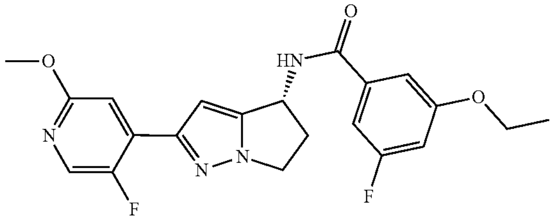 [SMILES: CCOc1cc(F)cc(C(=O)N[C@@H]2CCn3nc(-c4cc(OC)ncc4F)cc32)c1]
I-574b
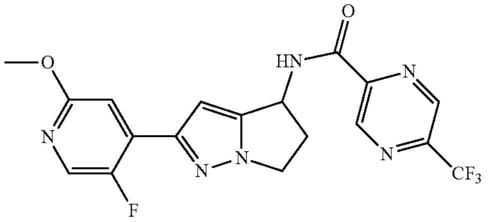 [SMILES: COc1cc(-c2cc3n(n2)CCC3NC(=O)c2cnc(C(F)(F)F)cn2)c(F)cn1]
I-575
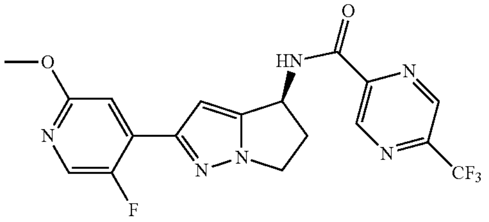 [SMILES: COc1cc(-c2cc3n(n2)CC[C@@H]3NC(=O)c2cnc(C(F)(F)F)cn2)c(F)cn1]
I-575a
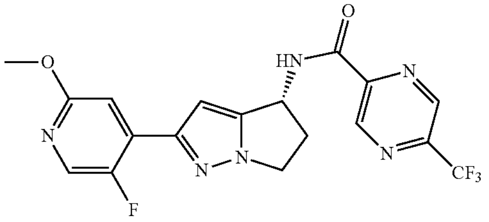
I-575b TABLE 1-continued
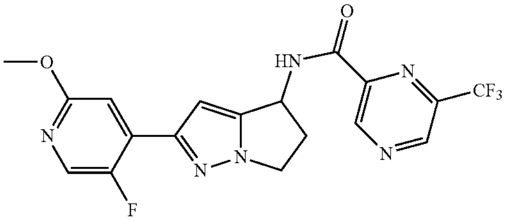
I-576
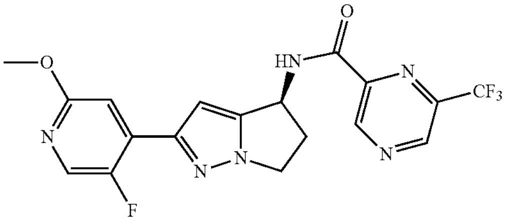 [SMILES: COc1cc(-c2cc3n(n2)CC[C@@H]3NC(=O)c2cncc(C(F)(F)F)n2)c(F)cn1]
I-576a
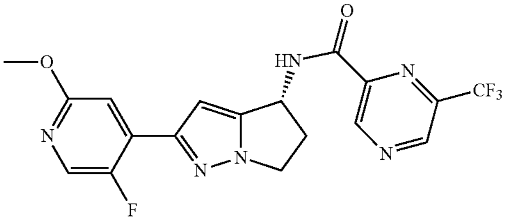 [SMILES: COc1cc(-c2cc3n(n2)CC[C@H]3NC(=O)c2cncc(C(F)(F)F)n2)c(F)cn1]
I-576b
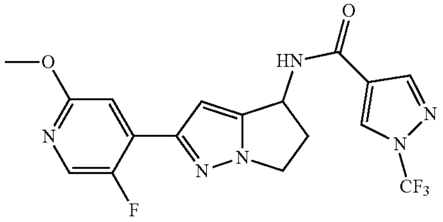 [SMILES: COc1cc(-c2cc3n(n2)CCC3NC(=O)c2cnn(C(F)(F)F)c2)c(F)cn1]
I-577
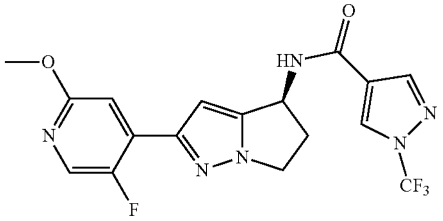 [SMILES: COc1cc(-c2cc3n(n2)CC[C@@H]3NC(=O)c2cnn(C(F)(F)F)c2)c(F)cn1]
I-577a
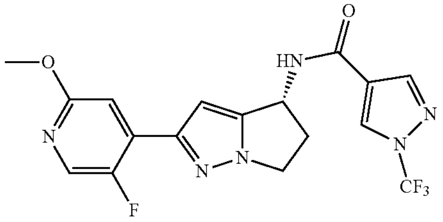 [SMILES: COc1cc(-c2cc3n(n2)CC[C@H]3NC(=O)c2cnn(C(F)(F)F)c2)c(F)cn1]
I-577b
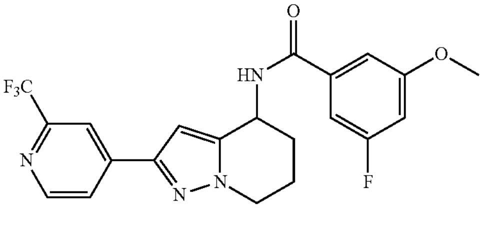 [SMILES: COc1cc(F)cc(C(=O)NC2CCCn3nc(-c4ccnc(C(F)(F)F)c4)cc32)c1]
I-578

TABLE 1-continued
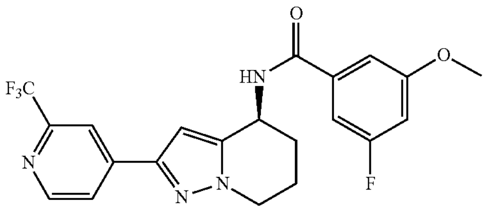 [SMILES: COc1cc(F)cc(C(=O)N[C@H]2CCCn3nc(-c4ccnc(C(F)(F)F)c4)cc32)c1]
I-578a
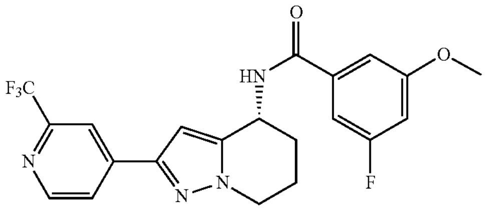
I-578b
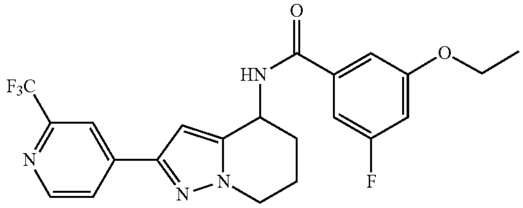 [SMILES: CCOc1cc(F)cc(C(=O)NC2CCCn3nc(-c4ccnc(C(F)(F)F)c4)cc32)c1]
I-579
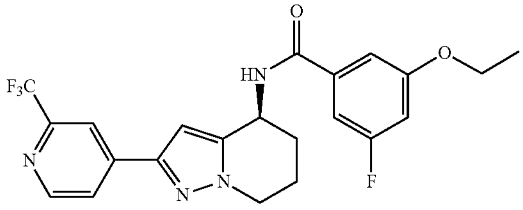 [SMILES: CCOc1cc(F)cc(C(=O)N[C@H]2CCCn3nc(-c4ccnc(C(F)(F)F)c4)cc32)c1]
I-579a
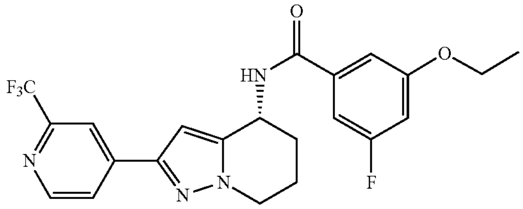
I-579b
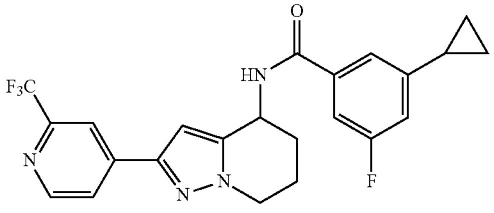 [SMILES: O=C(NC1CCCn2nc(-c3ccnc(C(F)(F)F)c3)cc21)c1cc(F)cc(C2CC2)c1]
I-580
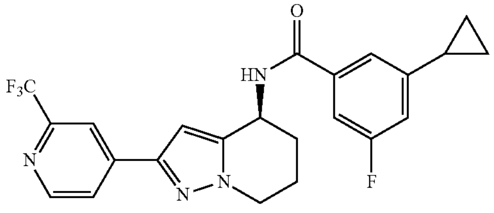 [SMILES: O=C(N[C@H]1CCCn2nc(-c3ccnc(C(F)(F)F)c3)cc21)c1cc(F)cc(C2CC2)c1]
I-580a TABLE 1-continued
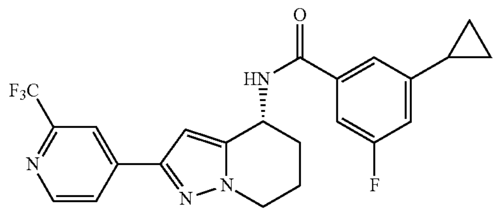
I-580b
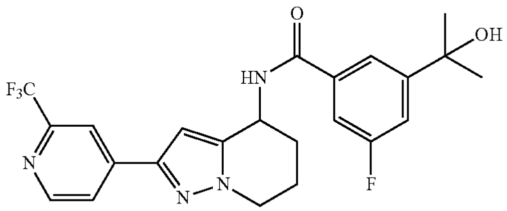 [SMILES: CC(C)(O)c1cc(F)cc(C(=O)NC2CCCn3nc(-c4ccnc(C(F)(F)F)c4)cc32)c1]
I-581
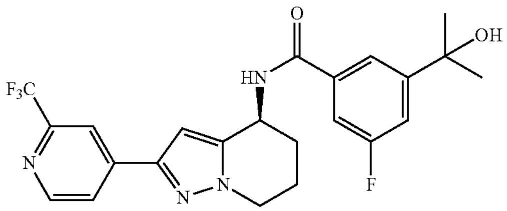 [SMILES: CC(C)(O)c1cc(F)cc(C(=O)N[C@H]2CCCn3nc(-c4ccnc(C(F)(F)F)c4)cc32)c1]
I-581a
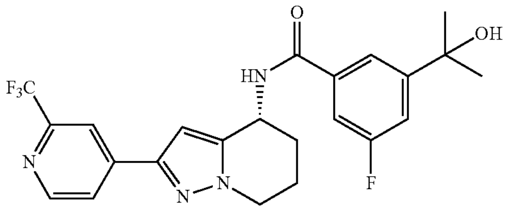 [SMILES: CC(C)(O)c1cc(F)cc(C(=O)N[C@@H]2CCCn3nc(-c4ccnc(C(F)(F)F)c4)cc32)c1]
I-581b
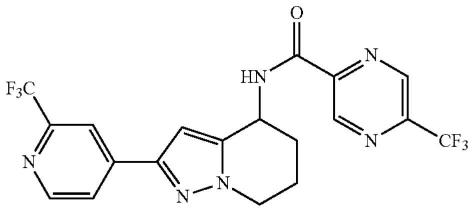
I-582
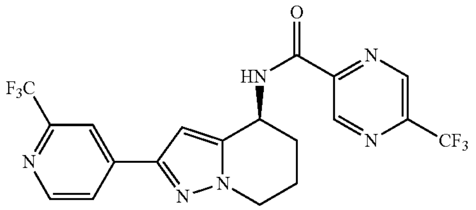
I-582a
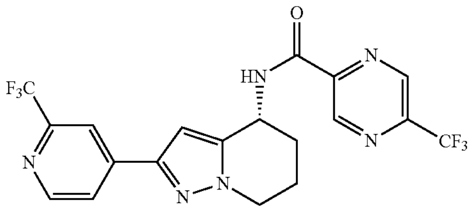 [SMILES: O=C(N[C@@H]1CCCn2nc(-c3ccnc(C(F)(F)F)c3)cc21)c1cnc(C(F)(F)F)cn1]
I-582b TABLE 1-continued
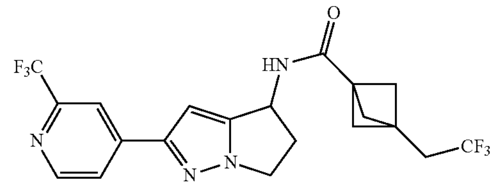 [SMILES: O=C(NC1CCn2nc(-c3ccnc(C(F)(F)F)c3)cc21)C12CC(CC(F)(F)F)(C1)C2]
I-583
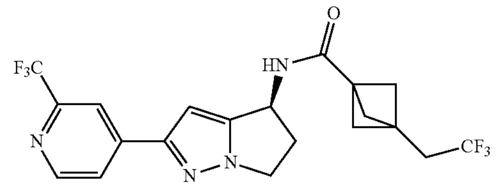 [SMILES: O=C(N[C@H]1CCn2nc(-c3ccnc(C(F)(F)F)c3)cc21)C12CC(CC(F)(F)F)(C1)C2]
I-583a
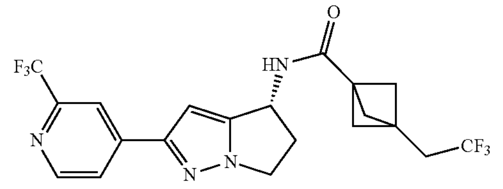 [SMILES: O=C(N[C@@H]1CCn2nc(-c3ccnc(C(F)(F)F)c3)cc21)C12CC(CC(F)(F)F)(C1)C2]
I-583b
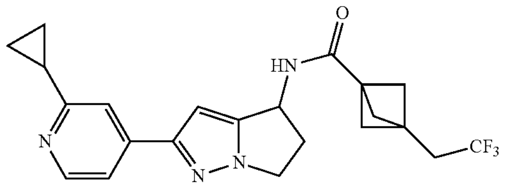 [SMILES: O=C(NC1CCn2nc(-c3ccnc(C4CC4)c3)cc21)C12CC(CC(F)(F)F)(C1)C2]
I-584
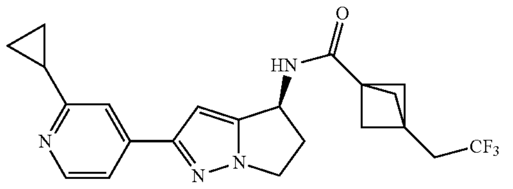 [SMILES: O=C(N[C@H]1CCn2nc(-c3ccnc(C4CC4)c3)cc21)C12CC(CC(F)(F)F)(C1)C2]
I-584a
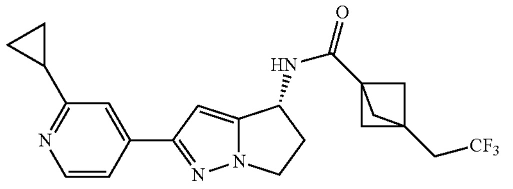
I-584b
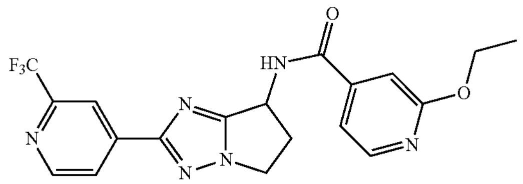 [SMILES: CCOc1cc(C(=O)NC2CCn3nc(-c4ccnc(C(F)(F)F)c4)nc32)ccn1]
I-585
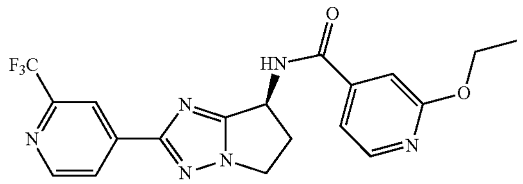 [SMILES: CCOc1cc(C(=O)N[C@H]2CCn3nc(-c4ccnc(C(F)(F)F)c4)nc32)ccn1]
I-585a TABLE 1-continued
I-585b
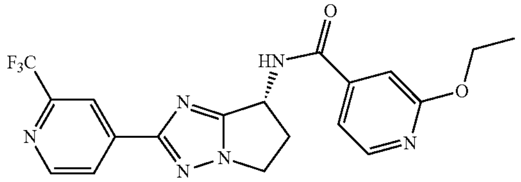 [SMILES: CCOc1cc(C(=O)N[C@@H]2CCn3nc(-c4ccnc(C(F)(F)F)c4)nc32)ccn1]
I-586
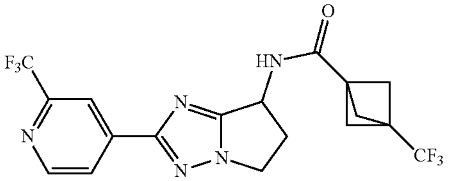 [SMILES: O=C(NC1CCn2nc(-c3ccnc(C(F)(F)F)c3)nc21)C12CC(C(F)(F)F)(C1)C2]
I-586a
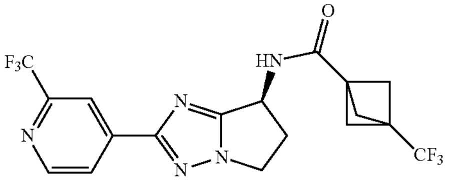
I-586b
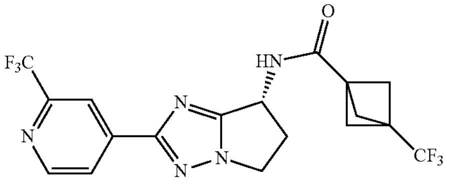 [SMILES: O=C(N[C@@H]1CCn2nc(-c3ccnc(C(F)(F)F)c3)nc21)C12CC(C(F)(F)F)(C1)C2]
I-587
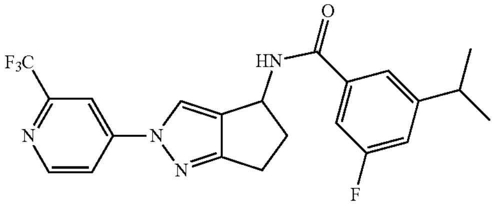 [SMILES: CC(C)c1cc(F)cc(C(=O)NC2CCc3nn(-c4ccnc(C(F)(F)F)c4)cc32)c1]
I-587a
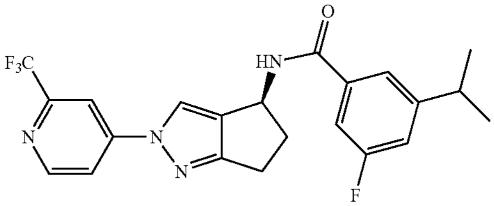 [SMILES: CC(C)c1cc(F)cc(C(=O)N[C@H]2CCc3nn(-c4ccnc(C(F)(F)F)c4)cc32)c1]
I-587b
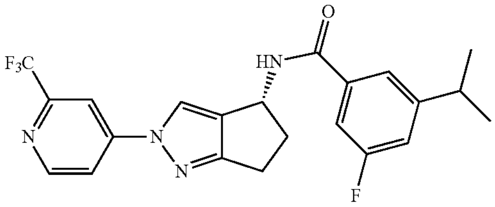 [SMILES: CC(C)c1cc(F)cc(C(=O)N[C@@H]2CCc3nn(-c4ccnc(C(F)(F)F)c4)cc32)c1]
I-588
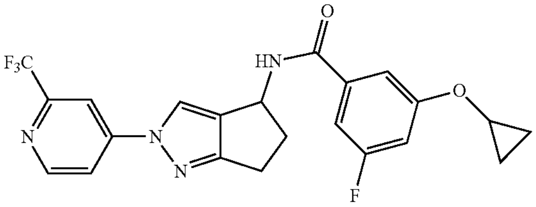 [SMILES: O=C(NC1CCc2nn(-c3ccnc(C(F)(F)F)c3)cc21)c1cc(F)cc(OC2CC2)c1]

TABLE 1-continued
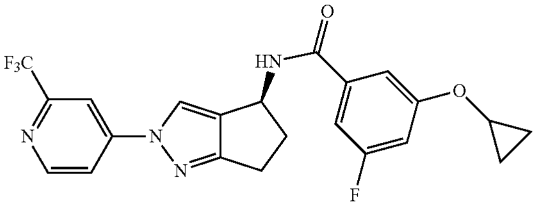 [SMILES: O=C(N[C@H]1CCc2nn(-c3ccnc(C(F)(F)F)c3)cc21)c1cc(F)cc(OC2CC2)c1]
I-588a
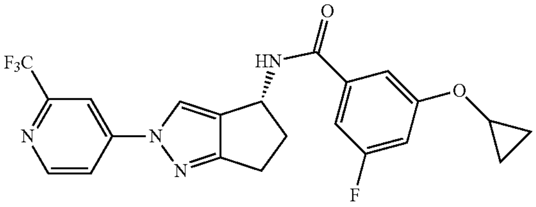 [SMILES: O=C(N[C@@H]1CCc2nn(-c3ccnc(C(F)(F)F)c3)cc21)c1cc(F)cc(OC2CC2)c1]
I-588b
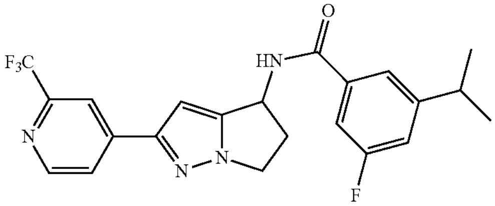 [SMILES: CC(C)c1cc(F)cc(C(=O)NC2CCn3nc(-c4ccnc(C(F)(F)F)c4)cc32)c1]
I-589
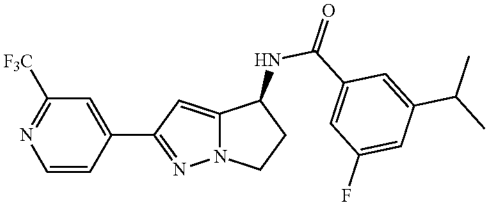 [SMILES: CC(C)c1cc(F)cc(C(=O)N[C@H]2CCn3nc(-c4ccnc(C(F)(F)F)c4)cc32)c1]
I-589a
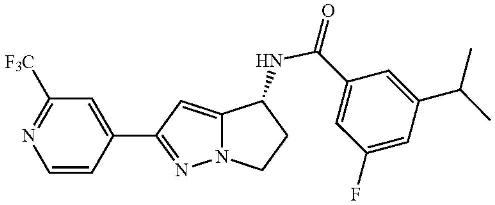 [SMILES: CC(C)c1cc(F)cc(C(=O)N[C@@H]2CCn3nc(-c4ccnc(C(F)(F)F)c4)cc32)c1]
I-589b
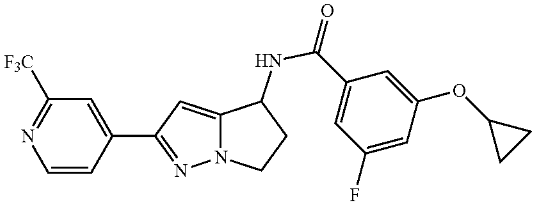 [SMILES: O=C(NC1CCn2nc(-c3ccnc(C(F)(F)F)c3)cc21)c1cc(F)cc(OC2CC2)c1]
I-590
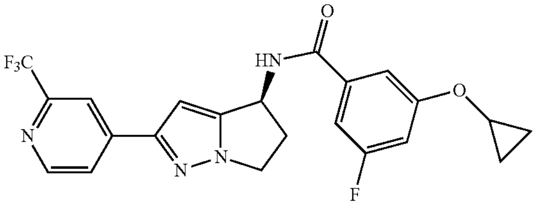 [SMILES: O=C(N[C@H]1CCn2nc(-c3ccnc(C(F)(F)F)c3)cc21)c1cc(F)cc(OC2CC2)c1]
I-590a TABLE 1-continued
I-590b
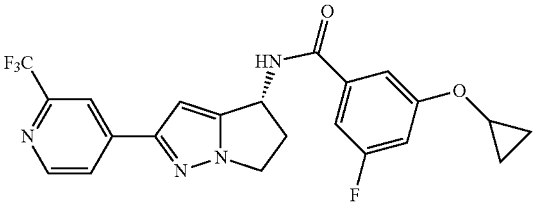 [SMILES: O=C(N[C@@H]1CCn2nc(-c3ccnc(C(F)(F)F)c3)cc21)c1cc(F)cc(OC2CC2)c1]
I-591
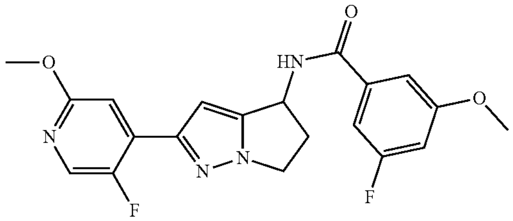
I-591a
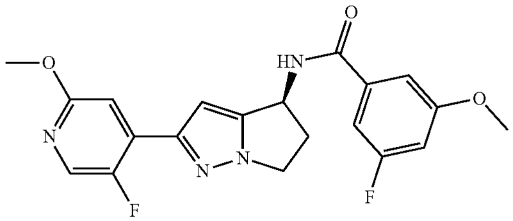
I-591b
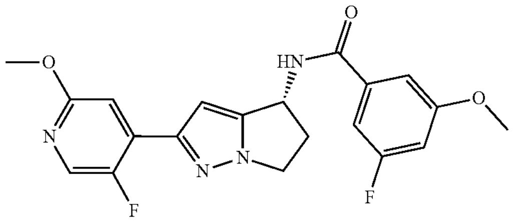
I-592
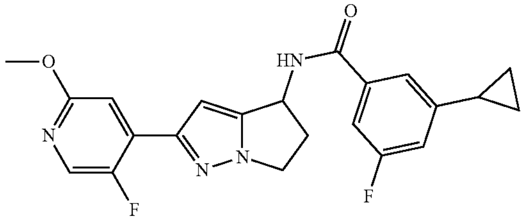 [SMILES: COc1cc(-c2cc3n(n2)CCC3NC(=O)c2cc(F)cc(C3CC3)c2)c(F)cn1]
I-592a
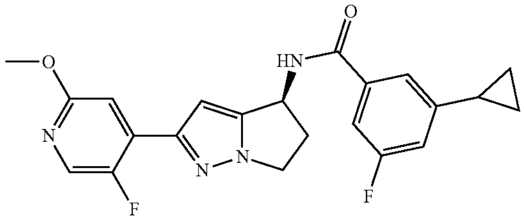 [SMILES: COc1cc(-c2cc3n(n2)CC[C@@H]3NC(=O)c2cc(F)cc(C3CC3)c2)c(F)cn1]
I-592b
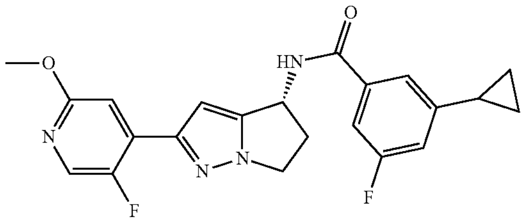 [SMILES: COc1cc(-c2cc3n(n2)CC[C@H]3NC(=O)c2cc(F)cc(C3CC3)c2)c(F)cn1]

TABLE 1-continued
I-593
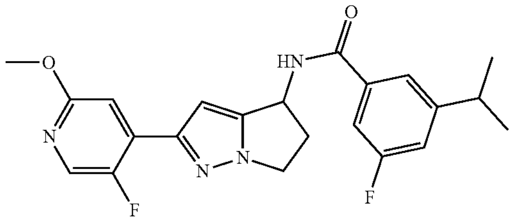 [SMILES: COc1cc(-c2cc3n(n2)CCC3NC(=O)c2cc(F)cc(C(C)C)c2)c(F)cn1]
I-593a
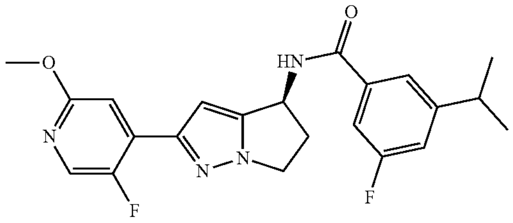 [SMILES: COc1cc(-c2cc3n(n2)CC[C@@H]3NC(=O)c2cc(F)cc(C(C)C)c2)c(F)cn1]
I-593b
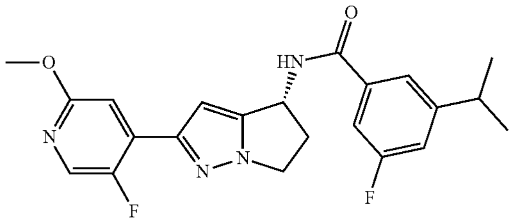
I-594
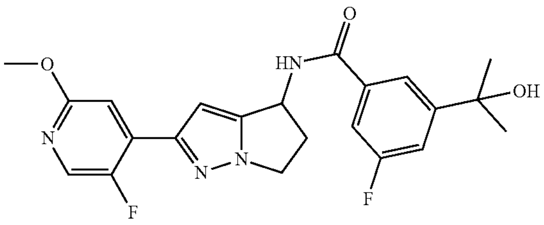 [SMILES: COc1cc(-c2cc3n(n2)CCC3NC(=O)c2cc(F)cc(C(C)(C)O)c2)c(F)cn1]
I-594a
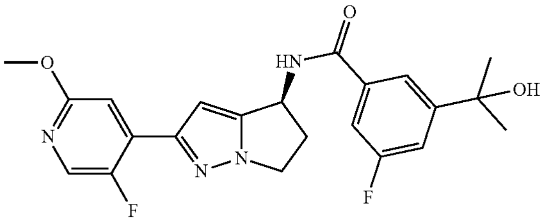 [SMILES: COc1cc(-c2cc3n(n2)CC[C@@H]3NC(=O)c2cc(F)cc(C(C)(C)O)c2)c(F)cn1]
I-594b
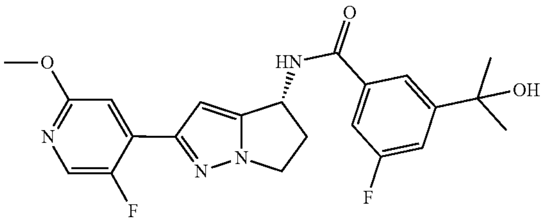 [SMILES: COc1cc(-c2cc3n(n2)CC[C@H]3NC(=O)c2cc(F)cc(C(C)(C)O)c2)c(F)cn1]
I-595
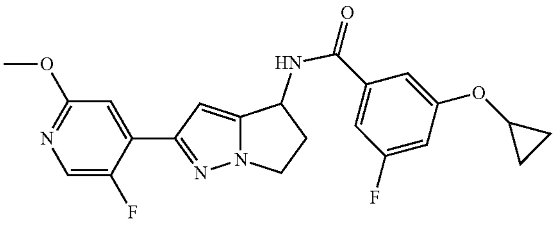 [SMILES: COc1cc(-c2cc3n(n2)CCC3NC(=O)c2cc(F)cc(OC3CC3)c2)c(F)cn1]

TABLE 1-continued
I-595a
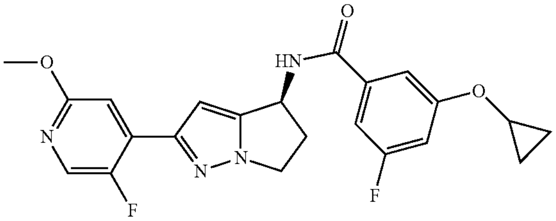 [SMILES: COc1cc(-c2cc3n(n2)CC[C@@H]3NC(=O)c2cc(F)cc(OC3CC3)c2)c(F)cn1]
I-595b
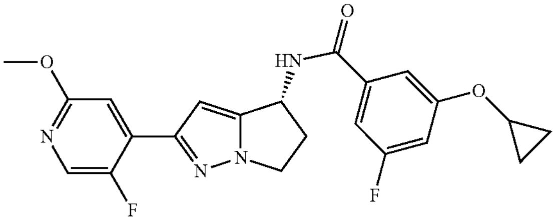 [SMILES: COc1cc(-c2cc3n(n2)CC[C@H]3NC(=O)c2cc(F)cc(OC3CC3)c2)c(F)cn1]
I-596
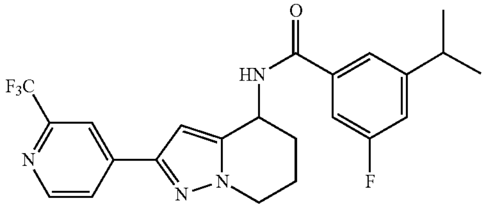 [SMILES: CC(C)c1cc(F)cc(C(=O)NC2CCCn3nc(-c4ccnc(C(F)(F)F)c4)cc32)c1]
I-596a
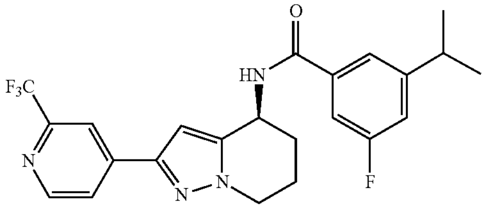 [SMILES: CC(C)c1cc(F)cc(C(=O)N[C@H]2CCCn3nc(-c4ccnc(C(F)(F)F)c4)cc32)c1]
I-596b
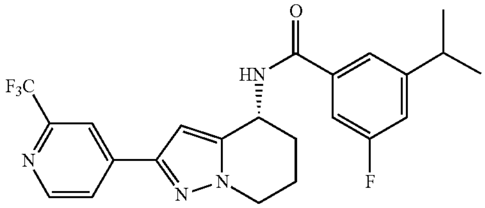 [SMILES: CC(C)c1cc(F)cc(C(=O)N[C@@H]2CCCn3nc(-c4ccnc(C(F)(F)F)c4)cc32)c1]
I-597
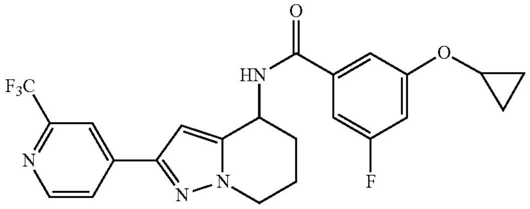 [SMILES: O=C(NC1CCCn2nc(-c3ccnc(C(F)(F)F)c3)cc21)c1cc(F)cc(OC2CC2)c1]
I-597a
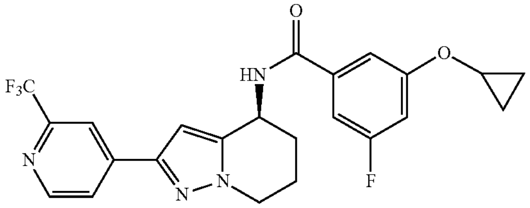 [SMILES: O=C(N[C@H]1CCCn2nc(-c3ccnc(C(F)(F)F)c3)cc21)c1cc(F)cc(OC2CC2)c1]

TABLE 1-continued
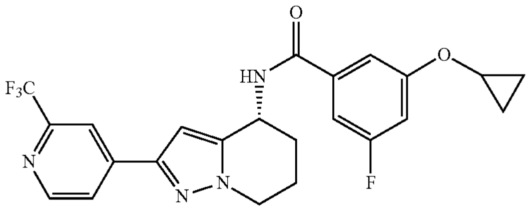 [SMILES: O=C(N[C@@H]1CCCn2nc(-c3ccnc(C(F)(F)F)c3)cc21)c1cc(F)cc(OC2CC2)c1]
I-597b
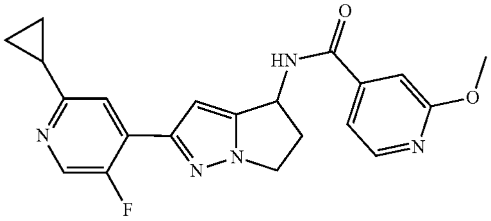 [SMILES: COc1cc(C(=O)NC2CCn3nc(-c4cc(C5CC5)ncc4F)cc32)ccn1]
I-598
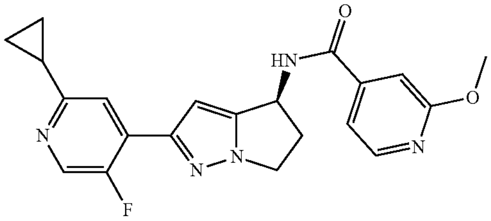 [SMILES: COc1cc(C(=O)N[C@H]2CCn3nc(-c4cc(C5CC5)ncc4F)cc32)ccn1]
I-598a
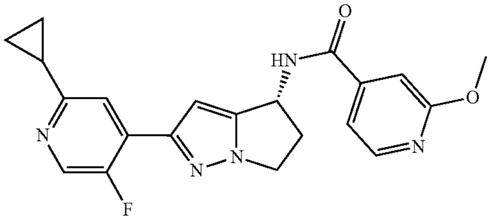 [SMILES: COc1cc(C(=O)N[C@@H]2CCn3nc(-c4cc(C5CC5)ncc4F)cc32)ccn1]
I-598b
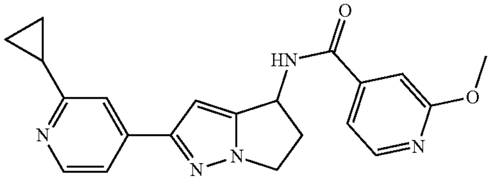 [SMILES: COc1cc(C(=O)NC2CCn3nc(-c4ccnc(C5CC5)c4)cc32)ccn1]
I-599
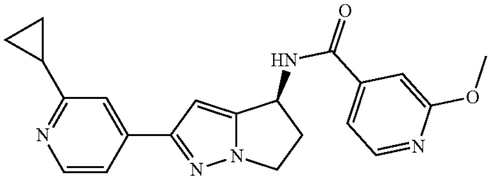 [SMILES: COc1cc(C(=O)N[C@H]2CCn3nc(-c4ccnc(C5CC5)c4)cc32)ccn1]
I-599a
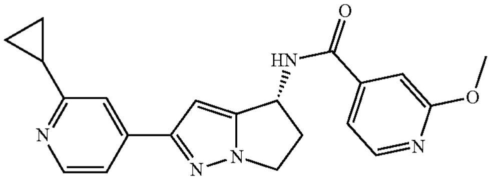 [SMILES: COc1cc(C(=O)N[C@@H]2CCn3nc(-c4ccnc(C5CC5)c4)cc32)ccn1]
I-599b TABLE 1-continued

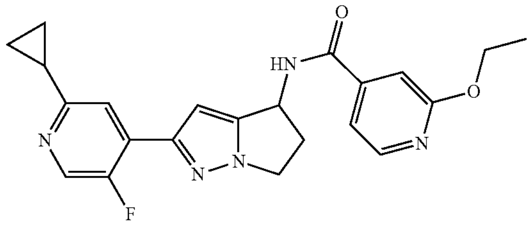 [SMILES: CCOc1cc(C(=O)NC2CCn3nc(-c4cc(C5CC5)ncc4F)cc32)ccn1]
I-600

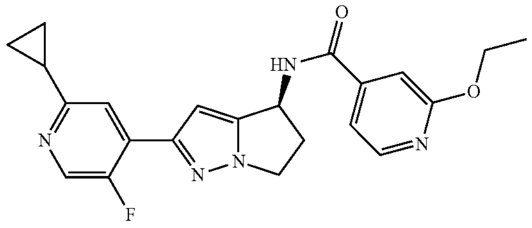 [SMILES: CCOc1cc(C(=O)N[C@H]2CCn3nc(-c4cc(C5CC5)ncc4F)cc32)ccn1]
I-600a

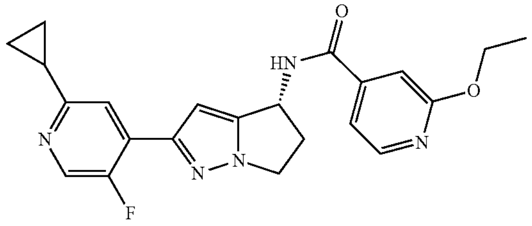 [SMILES: CCOc1cc(C(=O)N[C@@H]2CCn3nc(-c4cc(C5CC5)ncc4F)cc32)ccn1]
I-600b or a pharmaceutically acceptable salt thereof.

4. Uses, Formulation and Administration Pharmaceutically Acceptable Compositions According to another embodiment, the invention provides a composition comprising a compound described herein or a pharmaceutically acceptable derivative (e.g., a pharmaceutically acceptable salt) thereof and a pharmaceutically acceptable carrier, adjuvant, or vehicle. The amount of compound in provided compositions is such that is effective to measurably inhibit KCNT1, or a mutant thereof, in a biological sample or in a patient. In certain embodiments, the amount of compound in provided compositions is such that is effective to measurably inhibit KCNT1, or a mutant thereof, in a biological sample or in a patient. In certain embodiments, a provided composition is formulated for administration to a patient in need of such composition. In some embodiments, a provided composition is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of, KCNT1, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compounds of the present disclosure that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present disclosure in the composition will also depend upon the particular compound in the composition.

Uses of Compounds and Pharmaceutically Acceptable Compositions

Compounds and compositions described herein are generally useful for the inhibition of activity of, KCNT1, or a mutant thereof. In some embodiments, a provided compound inhibits one or more gain-of-function (GoF), KCNT1 mutants. In some embodiments, a provided compound inhibits a, KCNT1 mutant selected from, KCNT1$^{G288S}$, KCNT1$^{R398}$Q, KCNT1$^{A934T}$, KCNT1$^{R950Q}$, KCNT1$^{R961H}$, KCNT1$^{R474H}$, KCNT1$^{R25w}$, KCNT1$^{R428Q}$, KCNT1$^{R100W}$, KCNT1$^{R356Q}$, KCNT1$^{A966T}$, KCNT1$^{R262Q}$, KCNT1$^{R262W}$, KCNT1$^{F346L}$, KCNT1$^{R356W}$, KCNT1$^{S379N}$, KCNT1$^{L437I}$, KCNT1$^{L437F}$, KCNT1$^{R474C}$, KCNT1$^{R928C}$, KCNT1$^{A259T}$, KCNT1$^{M267T}$, KCNT1$^{Q270K}$, KCNT1$^{Q270E}$, KCNT1$^{V271F}$, KCNT1$^{L281F}$, KCNT1$^{L2811}$, KCNT1$^{G288C}$, KCNT1$^{A295V}$, KCNT1$^{L339R}$, KCNT1$^{M354R}$ KCNT1$^{R398W}$, KCNT1$^{P409S}$, KCNT1$^{P409L}$, KCNT1$^{H469P}$, KCNT1$^{H469L}$, KCNT1$^{R474L}$, KCNT1$^{R474S}$, KCNT1$^{W476R}$, KCNT1$^{A477T}$, KCNT1$^{R484Q}$, KCNT1$^{H499R}$, KCNT1$^{F502S}$, KCNT1$^{M516V}$, KCNT1$^{R538C}$, KCNT1$^{G554E}$, KCNT1$^{K629Q}$, KCNT1$^{K629E}$, KCNT1$^{T6711}$, KCNT1$^{1760F}$, KCNT1$^{1760M}$, KCNT1$^{L781V}$, KCNT1$^{Y796H}$, KCNT1$^{G797V}$, KCNT1$^{P820L}$, KCNT1$^{E893K}$, KCNT1$^{E893V}$, KCNT1$^{M896I}$, KCNT1$^{M896K}$, KCNT1$^{M896R}$, KCNT1$^{M896V}$, KCNT1$^{Q906R}$, KCNT1$^{F9321}$, KCNT1$^{R933G}$, KCNT1$^{R933H}$, KCNT1$^{A934S}$, KCNT1$^{A934V}$, KCNT1$^{Y938C}$, KCNT1$^{L942F}$, KCNT1$^{K947E}$, KCNT1$^{R950L}$, KCNT1$^{S982P}$, KCNT1$^{T1001S}$ and, KCNT1$^{A1113D}$. In some embodiments, a provided compound inhibits a, KCNT1 mutant selected from, KCNT1$^{G288S}$, KCNT1$^{R398Q}$, KCNT1$^{A934T}$, KCNT1$^{R950Q}$, KCNT1$^{R961H}$, KCNT1$^{R474H}$, KCNT1$^{R25W}$, KCNT1$^{R428Q}$, KCNT1$^{R100W}$, KCNT1$^{R356Q}$, KCNT1$^{A966T}$, KCNT1$^{R262Q}$, KCNT1$^{R262W}$, KCNT1$^{F346L}$, KCNT1$^{R356W}$, KCNT1$^{S379N}$, KCNT1$^{L437I}$, KCNT1$^{L437F}$, KCNT1$^{R474C}$, KCNT1$^{R928C}$ and, KCNT1$^{P924L}$. In some embodiments, a provided compound inhibits substantially all gain-of-function, KCNT1 mutants. In some embodiments, a provided compound inhibits at least 90%, at least 91%, at least 92%, at least 93%, at least 94%, at least 95%, at least 96%, at least 97%, at least 98%, or at least 99% of gain-of-function, KCNT1 mutants.

The compounds and compositions described herein can be used to treat a neurological disease or disorder or a disease or condition associated with excessive neuronal excitability and/or a gain-of-function mutation in a gene (e.g., KCNT1), also referred to herein as a disease or disorder mediated by, KCNT1. In some embodiments, the present disclosure provides a compound for use in treating a disease or disorder mediated by, KCNT1. In some such embodiments, such compound is a compound provided herein. In some embodiments, the present disclosure provides a use of a compound provided herein (e.g., a compound of formula I) in the treatment of a disease or disorder mediated by, KCNT1. In some embodiments, the present disclosure provides a use of a compound provided herein (e.g., a compound of formula I) in a method of treating a disease or disorder mediated by, KCNT1. Exemplary diseases, disorders, or conditions mediated by, KCNT1 include epilepsy and other encephalopathies (e.g., epilepsy of infancy with migrating focal seizures (MMFSI, EIMFS)), autosomal dominant nocturnal frontal lobe epilepsy (ADNFLE), West syndrome, infantile spasms, epileptic encephalopathy, developmental and epileptic encephalopathy (DEE), early infantile epileptic encephalopathy (EIEE), generalized epilepsy, focal epilepsy, multifocal epilepsy, temporal lobe epilepsy, Ohtahara syndrome, early myoclonic encephalopathy and Lennox Gastaut syndrome, drug resistant epilepsy, seizures (e.g., frontal lobe seizures, generalized tonic-clonic seizures, asymmetric tonic seizures, focal seizures), leukodystrophy, hypomyelinating leukodystrophy, leukoencephalopathy, and sudden unexpected death in epilepsy, cardiac dysfunctions (e.g., cardiac arrhythmia, Brugada syndrome, myocardial infarction), pulmonary vasculopathy/hemorrhage, pain and related conditions (e.g., neuropathic pain, acute/chronic pain, migraine, etc.), muscle disorders (e.g., myotonia, neuromyotonia, cramp muscle spasms, spasticity), itch and pruritis, movement disorders (e.g., ataxia and cerebellar ataxias), psychiatric disorders (e.g., major depression, anxiety, bipolar disorder, schizophrenia, attention-deficit hyperactivity disorder), neurodevelopmental disorder, learning disorders, intellectual disability, Fragile X, neuronal plasticity, and autism spectrum disorders. In some embodiments, a disease, disorder, or condition mediated by, KCNT1 is an epilepsy or other neuropsychiatric disease associated with reduced activity of inhibitory interneurons. In some embodiments, a disease, disorder, or condition mediated by, KCNT1 is an epilepsy or other neuropsychiatric disease associated with an imbalance in excitatory and inhibitory neuron activity. Without wishing to be bound by any particular theory, it is believed that inhibitory interneurons prevent instability of the brain system by inhibition. Such diseases include Dravet syndrome, which is a genetic epilepsy characterized by temperature-sensitive/febrile seizures, myoclonic atonic epilepsy, Lennox-Gastaut syndrome, myoclonic epilepsy of infancy, PCDH19-associated epilepsy, benign myoclonic epilepsy (BME), severe infantile multifocal epilepsy (SIMFE), and myoclonic-astatic epilepsy (MAE).

In some embodiments, the neurological disease or disorder or the disease or condition associated with excessive neuronal excitability and/or a gain-of-function mutation in a gene (e.g., KCNT1) is selected from EIMFS, ADNFLE and West syndrome. In some embodiments, the neurological disease or disorder or the disease or condition associated with excessive neuronal excitability and/or a gain-of-function mutation in a gene (e.g., KCNT1) is selected from infantile spasms, epileptic encephalopathy, focal epilepsy, Ohtahara syndrome, developmental and epileptic encephalopathy and Lennox Gastaut syndrome. In some embodiments, the neurological disease or disorder or the disease or condition associated with excessive neuronal excitability and/or a gain-of-function mutation in a gene (e.g., KCNT1) is seizure. In some embodiments, the neurological disease or disorder or the disease or condition associated with excessive neuronal excitability and/or a gain-of-function mutation in a gene (e.g., KCNT1) is selected from cardiac arrhythmia, Brugada syndrome, and myocardial infarction.

In some embodiments, the neurological disease or disorder or the disease or condition associated with excessive neuronal excitability and/or a gain-of-function mutation in a gene (e.g., KCNT1) is selected from the group consisting of the learning disorders, Fragile X, intellectual function, neuronal plasticity, psychiatric disorders, and autism spectrum disorders.

Accordingly, the compounds and compositions thereof can be administered to a subject with a neurological disease or disorder or a disease or condition associated with excessive neuronal excitability and/or a gain-of-function mutation in a gene such as, KCNT1 (e.g., EIMFS, ADNFLE, West syndrome, infantile spasms, epileptic encephalopathy, focal epilepsy, Ohtahara syndrome, developmental and epileptic encephalopathy, and Lennox Gastaut syndrome, seizures, cardiac arrhythmia, Brugada syndrome, and myocardial infarction). EIMFS is a rare and debilitating genetic condition characterized by an early onset (e.g., before 6 months of age) of almost continuous heterogeneous focal seizures, where seizures appear to migrate from one brain region and hemisphere to another. Patients with EIMFS are generally intellectually impaired, non-verbal and non-ambulatory. While several genes have been implicated to date, the gene that is most commonly associated with EIMFS is, KCNT1. Several de novo mutations in, KCNT1 have been identified in patients with EIMFS, including V271F, G288S, R428Q, R474Q, R474H, R474C, 1760M, A934T, P924L, G243S, H257D, A259D, R262Q, Q270E, L2741, F346L, C377S, R398Q, P409S, A477T, F502V, M516V, Q550del, K629E, K629N, 1760F, E893K, M896K, R933G, R950Q, K1154Q (Barcia et al. (2012) *Nat Genet.* 44: 1255-1260; Ishii et al. (2013) *Gene* 531:467-471; McTague et al. (2013) *Brain.* 136: 1578-1591; Epi4K Consortium & Epilepsy Phenome/Genome Project. (2013) *Nature* 501:217-221; Lim et al. *J Med Genet* 2016; 53:217-225; Ohba et al. (2015) *Epilepsia* 56:e121-e128; Zhou et al. (2018) *Genes Brain Behav.* e12456; Moller et al. (2015) *Epilepsia.* e114-20; Numis et al. (2018) *Epilepsia.* 1889-1898; Madaan et al. *Brain Dev.* 40(3):229-232; McTague et al. (2018) *Neurology.* 90(1):e55-e66; Kawasaki et al. (2017) *J Pediatr.* 191:270-274; Kim et al. (2014) *Cell Rep.* 9(5):1661-1672; Ohba et al. (2015) *Epilepsia.* 56(9):e121-8; Rizzo et al. (2016) *Mol Cell Neurosci.* 72:54-63; Zhang et al. (2017) *Clin Genet.* 91(5):717-724; Mikati et al. (2015) *Ann Neurol.* 78(6):995-9; Baumer et al. (2017) *Neurology.* 89(21):2212; Dilena et al. (2018) *Neurotherapeutics.* 15(4):1112-1126). These mutations are gain-of-function, missense mutations that are dominant (i.e., present on only one allele) and result in change in function of the encoded potassium channel that causes a marked increase in whole cell current when tested in *Xenopus* oocyte or mammalian expression systems (see, e.g., Milligan et al. (2015) *Ann Neurol.* 75(4): 581-590; Barcia et al. (2012) *Nat Genet.* 44(11): 1255-1259; and Mikati et al. (2015) *Ann Neurol.* 78(6): 995-999).

ADNFLE has a later onset than EIMFS, generally in mid-childhood, and is generally a less severe condition. It is characterized by nocturnal frontal lobe seizures and can result in psychiatric, behavioral and cognitive disabilities in patients with the condition. While ADNFLE is associated with genes encoding several neuronal nicotinic acetylcholine receptor subunits, mutations in the, KCNT1 gene have been implicated in more severe cases of the disease (Heron et al. (2012) *Nat Genet.* 44: 1188-1190). Functional studies of the mutated, KCNT1 genes associated with ADNFLE indicated that the underlying mutations (M896I, R398Q, Y796H, and R928C) were dominant, gain-of-function mutations (Milligan et al. (2015) *Ann Neurol.* 75(4): 581-590; Mikati et al. (2015) *Ann Neurol.* 78(6): 995-999).

West syndrome is a severe form of epilepsy composed of a triad of infantile spasms, an interictal electroencephalogram (EEG) pattern termed hypsarrhythmia, and mental retardation, although a diagnosis can be made one of these elements is missing. Mutations in, KCNT1, including G652V and R474H, have been associated with West syndrome (Fukuoka et al. (2017) *Brain Dev* 39:80-83 and Ohba et al. (2015) *Epilepsia* 56:e121-e128). Treatment targeting the KCNT1 channel suggests that these mutations are gain-of-function mutations (Fukuoka et al. (2017) *Brain Dev* 39:80-83).

In some embodiments, the present disclosure provides a method of treating a disease or condition associated with excessive neuronal excitability and/or a gain-of-function mutation in a gene such as, KCNT1 (for example, epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy (DEE), and Lennox Gastaut syndrome, seizures, leukodystrophy, leukoencephalopathy, intellectual disability, multifocal epilepsy, generalized tonic-clonic seizures, drug resistant epilepsy, temporal lobe epilepsy, cerebellar ataxia, asymmetric tonic seizures) and cardiac dysfunctions (e.g., cardiac arrhythmia, Brugada syndrome, sudden unexpected death in epilepsy, myocardial infarction), pain and related conditions (e.g., neuropathic pain, acute/chronic pain, migraine, etc.), muscle disorders (e.g., myotonia, neuromyotonia, cramp muscle spasms, spasticity), itch and pruritis, ataxia and cerebellar ataxias, psychiatric disorders (e.g., major depression, anxiety, bipolar disorder, schizophrenia), learning disorders, Fragile X, neuronal plasticity, and autism spectrum disorders) comprising administering to a patient in need thereof a compound disclosed herein (e.g., a compound of Formula I, I-a, I-b, I-c, I-d, I-e, I-f, I-g, I-h, I-i, I-j, I-k, I-l, I-m, I-n, I-o, I-p, I-q, I-r, I-s, I-t, I-a-i, I-b-i, I-c-i, I-d-i, I-e-i, I-f-i, I-g-i, I-h-i, I-i-i, I-j-i, I-k-i, I-l-i, I-m-i, I-n-i, I-o-i, I-p-i, I-q-i, I-r-i, I-s-i, I-t-i, II-a, II-b, II-c, II-d, III-a, III-b, III-c, III-d, III-e, III-f, III-g, III-h, III-i, III-j, III-k, III-l, III-m, III-n, III-o, IV-a, IV-b, IV-c, IV-d, IV-e, IV-f, IV-g, V-a, V-b, V-c, V-d, V-e, VI-a, VI-b, VI-c, VI-d, VII-a, II-a-i, II-b-i, II-c-i, II-d-i, III-a-i, III-b-i, III-c-i, III-d-i, III-e-i, III-f-i, III-g-i, III-h-i, III-i-i, III-j-i, III-k-i, III-l-i, III-m-i, III-n-i, III-o-i, IV-a-i, IV-b-i, IV-c-i, IV-d-i, IV-e-i, IV-f-i, IV-g-i, V-a-i, V-b-i, V-c-i, V-d-i, V-e-i, VI-a-i, VI-b-i, VI-c-i, VI-d-i, or VII-a-i, or a pharmaceutically acceptable salt thereof), or a pharmaceutical composition disclosed herein (e.g., a pharmaceutical composition comprising a compound disclosed herein (e.g., a compound of Formula I, I-a, I-b, I-c, I-d, I-e, I-f, I-g, I-h, I-i, I-j, I-k, I-l, I-m, I-n, I-o, I-p, I-q, I-r, I-s, I-t, I-a-i, I-b-i, I-c-i, I-d-i, I-e-i, I-f-i, I-g-i, I-h-i, I-i-i, I-j-i, I-k-i, I-l-i, I-m-i, I-n-i, I-o-i, I-p-i, I-q-i, I-r-i, I-s-i, I-t-i, II-a, II-b, II-c, II-d, III-a, III-b, III-c, III-d, III-e, III-f, III-g, III-h, III-i, III-j, III-k, III-l, III-m, III-n, III-o, IV-a, IV-b, IV-c, IV-d, IV-e, IV-f, IV-g, V-a, V-b, V-c, V-d, V-e, VI-a, VI-b, VI-c, VI-d, VII-a, II-a-i, II-b-i, II-c-i, II-d-i, III-a-i, III-b-i, III-c-i, III-d-i, III-e-i, III-f-i, III-g-i, III-h-i, III-i-i, III-j-i, III-k-i, III-l-i, III-m-i, III-n-i, III-o-i, IV-a-i, IV-b-i, IV-c-i, IV-d-i, IV-e-i, IV-f-i, IV-g-i, V-a-i, V-b-i, V-c-i, V-d-i, V-e-i, VI-a-i, VI-b-i, VI-c-i, VI-d-i, or VII-a-i, or a pharmaceutically acceptable salt thereof), and a pharmaceutically acceptable excipient).

In some examples, a patient presenting with a disease or condition that is or may be associated with a gain-of-function mutation in, KCNT1 is genotyped to confirm the presence of a known gain-of-function mutation in, KCNT1 prior to administration of the compounds and compositions thereof. For example, whole exome sequencing can be performed on the patient. Gain-of-function mutations associated with EIMFS may include, but are not limited to, V271F, G288S, R428Q, R474Q, R474H, R474C, I760M, A934T, P924L, G243S, H257D, A259D, R262Q, Q270E, L2741, F346L, C377S, R398Q, P409S, A477T, F502V, M516V, Q550del, K629E, K629N, I760F, E893K, M896K, R933G, R950Q, and K1154Q. Gain-of-function mutations associated with ADNFLE may include, but are not limited to, M896I, R398Q, Y796H, R928C, and G288S. Gain-of-function mutations associated with West syndrome may include, but are not limited to, G652V and R474H. Gain-of-function mutations associated with temporal lobe epilepsy may include, but are not limited to, R133H and R565H. Gain-of-function mutations associated with Lennox-Gastaut may include, but are not limited to, R209C. Gain-of-function mutations associated with seizures may include, but are not limited to, A259D, G288S, R474C, and R474H. Gain-of-function mutations associated with leukodystrophy may include, but are not limited to, G288S and Q906H.

Gain-of-function mutations associated with Multifocal Epilepsy may include, but are not limited to, V340M. Gain-of-function mutations associated with EOE may include, but are not limited to, F346L and A934T. Gain-of-function mutations associated with early-onset epileptic encephalopathies (EOEE) may include, but are not limited to, R428Q. Gain-of-function mutations associated with developmental and epileptic encephalopathies may include, but are not limited to, F346L, R474H, and A934T. Gain-of-function mutations associated with epileptic encephalopathies may include, but are not limited to, L437F, Y796H, P924L, and R961H. Gain-of-function mutations associated with Early Infantile Epileptic Encephalopathy (EIEE) may include, but are not limited to, M896K. Gain-of-function mutations associated with drug resistant epilepsy and generalized tonic-clonic seizure may include, but are not limited to, F346L. Gain-of-function mutations associated with migrating partial seizures of infancy may include, but are not limited to, R428Q. Gain-of-function mutations associated with leukoencephalopathy may include, but are not limited to, F932I.

Gain-of-function mutations associated with NFLE may include, but are not limited to, A934T and R950Q. Gain-of-function mutations associated with Ohtahara syndrome may include, but are not limited to, A966T. Gain-of-function mutations associated with infantile spasms may include, but are not limited to, P924L. Gain-of-function mutations associated with Brugada syndrome may include, but are not limited to, R1106Q. Gain-of-function mutations associated with Brugada syndrome may include, but are not limited to, R474H.

In other examples, the patient is first genotyped to identify the presence of a mutation in, KCNT1 and this mutation is then confirmed to be a gain-of-function mutation using standard in vitro assays, such as those described in Milligan et al. (2015) *Ann Neurol.* 75(4): 581-590. Typically, the presence of a gain-of-function mutation is confirmed when the expression of the mutated, KCNT1 allele results an increase in whole cell current compared to the whole cell current resulting from expression of wild-type, KCNT1 as assessed using whole-cell electrophysiology (such as described in Milligan et al. (2015) *Ann Neurol.* 75(4): 581-590; Barcia et al. (2012) *Nat Genet.* 44(11): 1255-1259; Mikati et al. (2015) *Ann Neurol.* 78(6): 995-999; or Rizzo et al. *Mol Cell Neurosci.* (2016) 72:54-63). This increase of whole cell current can be, for example, an increase of at least about 50%, 100%, 150%, 200%, 250%, 300%, 350%, 400% or more. The subject can then be confirmed to have a disease or condition associated with a gain-of-function mutation in, KCNT1.

In some embodiments, the patient is confirmed as having a, KCNT1 allele containing a gain-of-function mutation (e.g., V271F, G288S, R398Q, R428Q, R474Q, R474H, R474C, G652V, I760M, Y796H, M896I, P924L, R928C or A934T).

The compounds and compositions, according to methods described herein, may be administered using any amount and any route of administration effective for treating or lessening the severity of a neurological disease or disorder or the disease or condition associated with excessive neuronal excitability and/or a gain-of-function mutation in a gene (e.g., KCNT1). The exact amount required will vary from subject to subject, depending on the species, age, and general condition of the subject, the severity of the infection, the particular agent, its mode of administration, and the like. Compounds described herein are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the disclosure may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present disclosure, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting the activity of, KCNT1, or a mutant thereof, in a biological sample comprising the step of contacting said biological sample with a compound of this disclosure, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

In some embodiments, the present disclosure provides a method of inhibiting activity of, KCNT1, or a mutant thereof, in a patient comprising the step of administering to said patient a compound of the present disclosure, or a composition comprising said compound.

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated."

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Compound numbers utilized in the Examples below correspond to compound numbers set forth in Table 1, supra.

Example 1. Synthesis of Exemplary Compounds

Compounds of formula I can be made according to any of Schemes A, B, C, D, E and F:

Scheme A

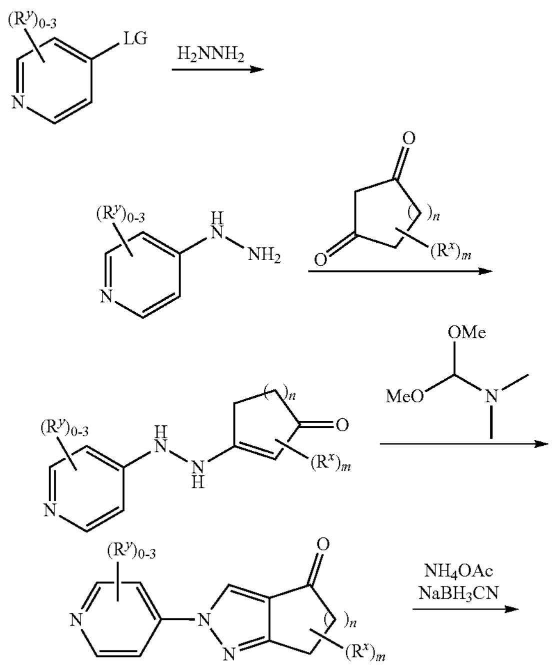

-continued
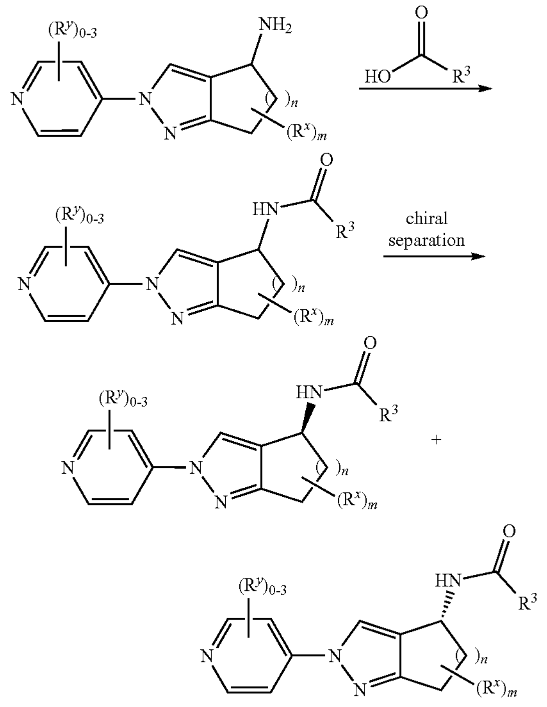
Scheme B
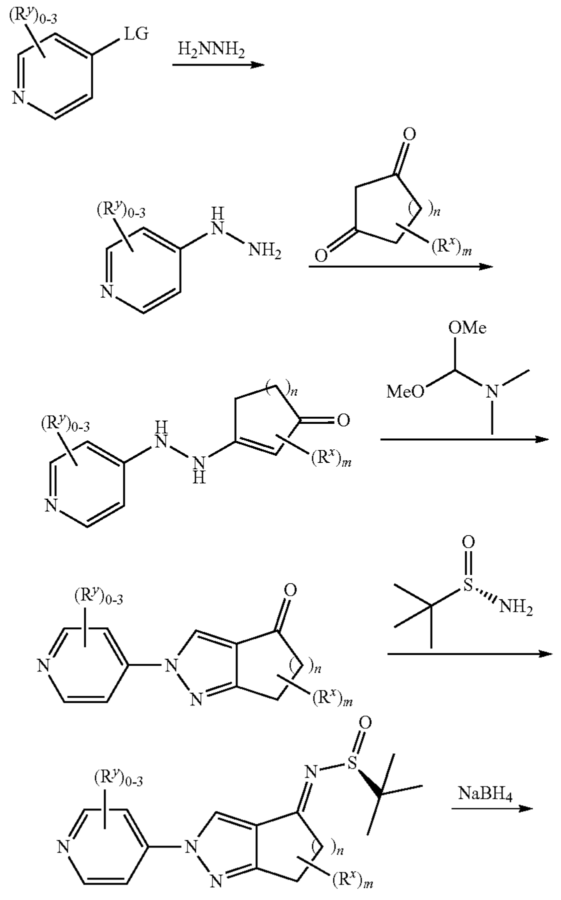
-continued
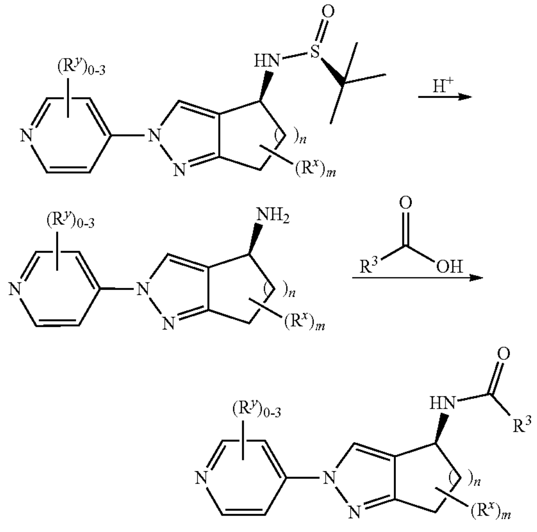
Scheme C
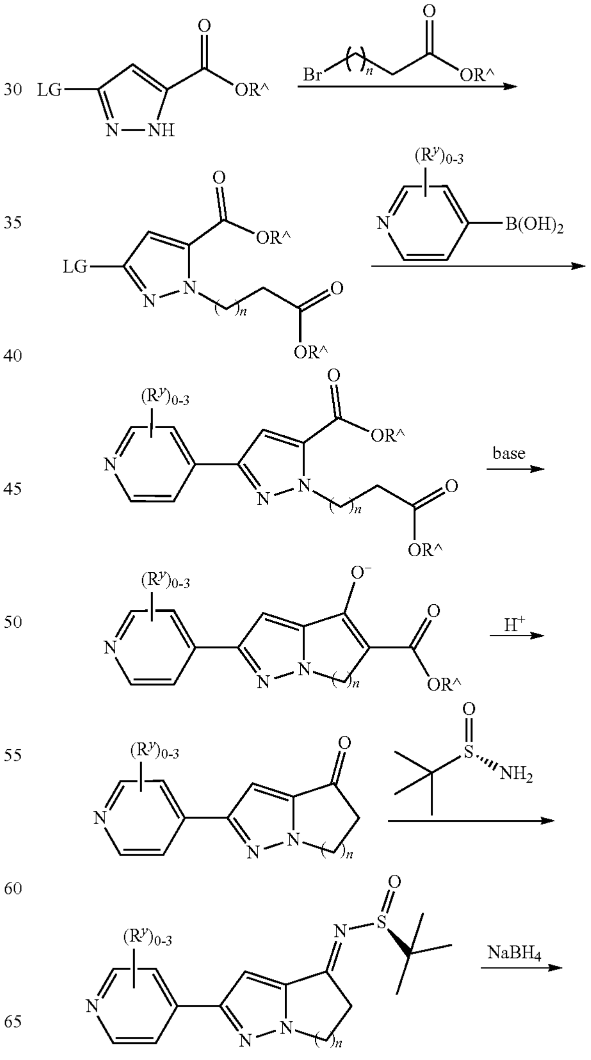

-continued
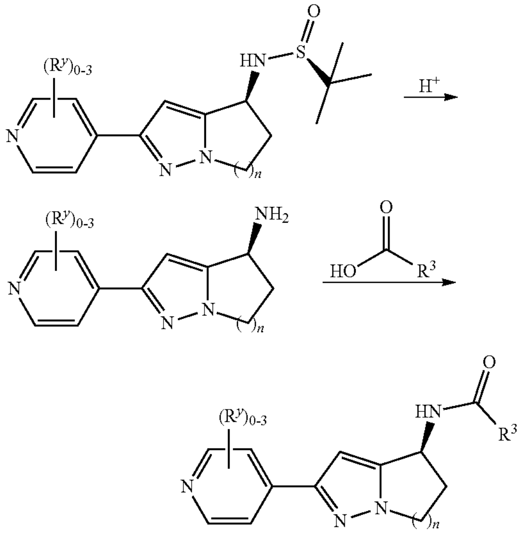
Scheme D
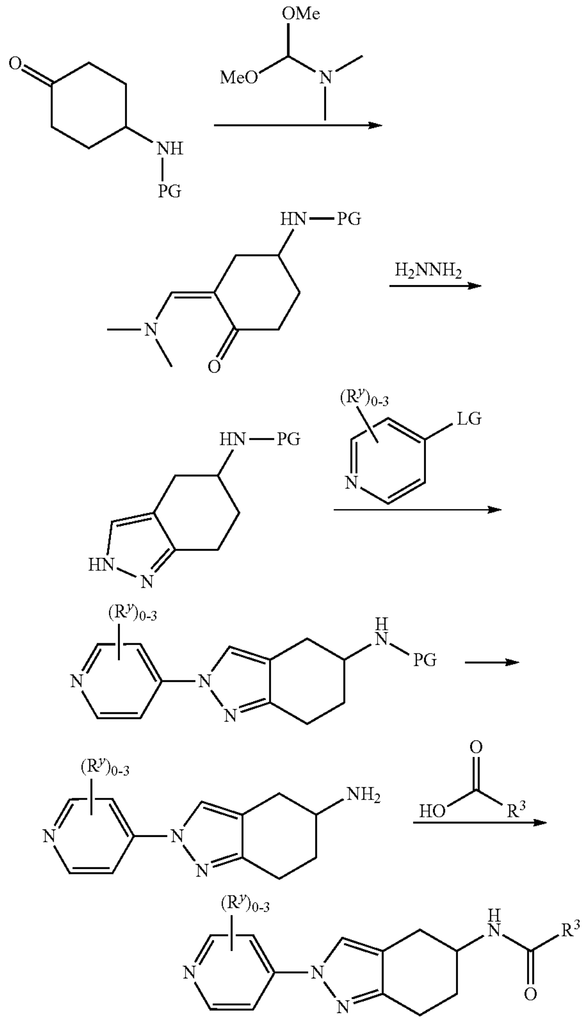
Scheme E
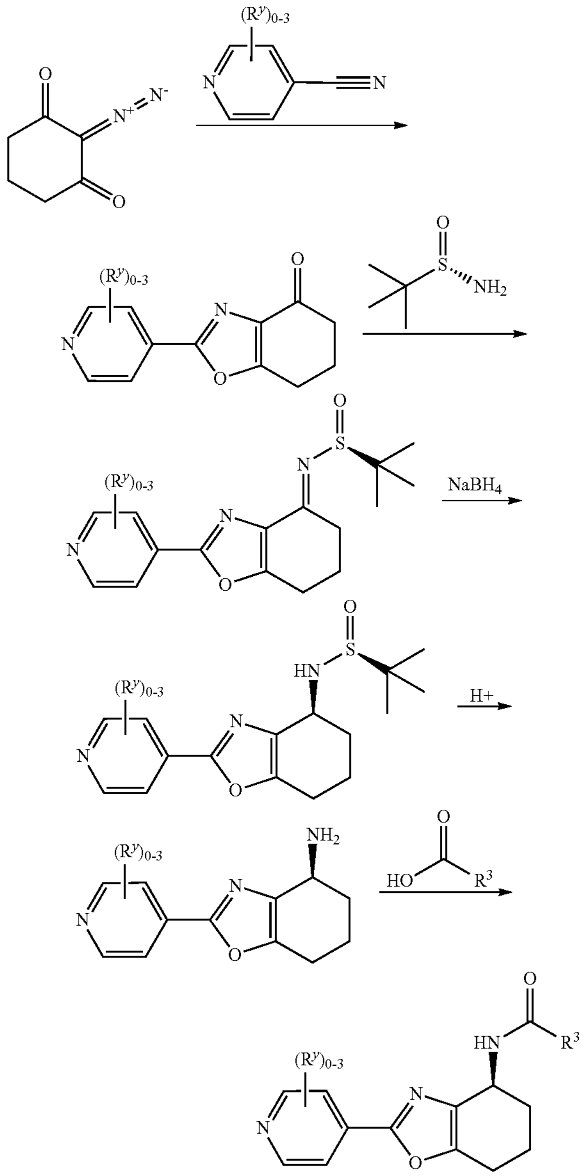
Scheme F
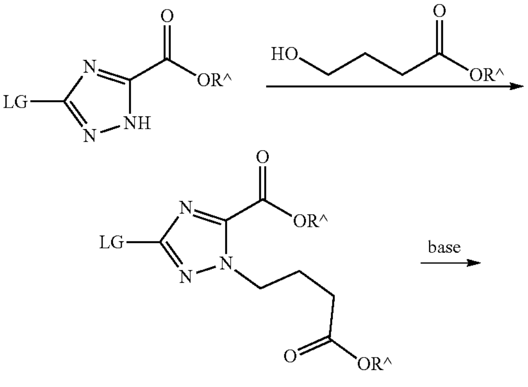

-continued

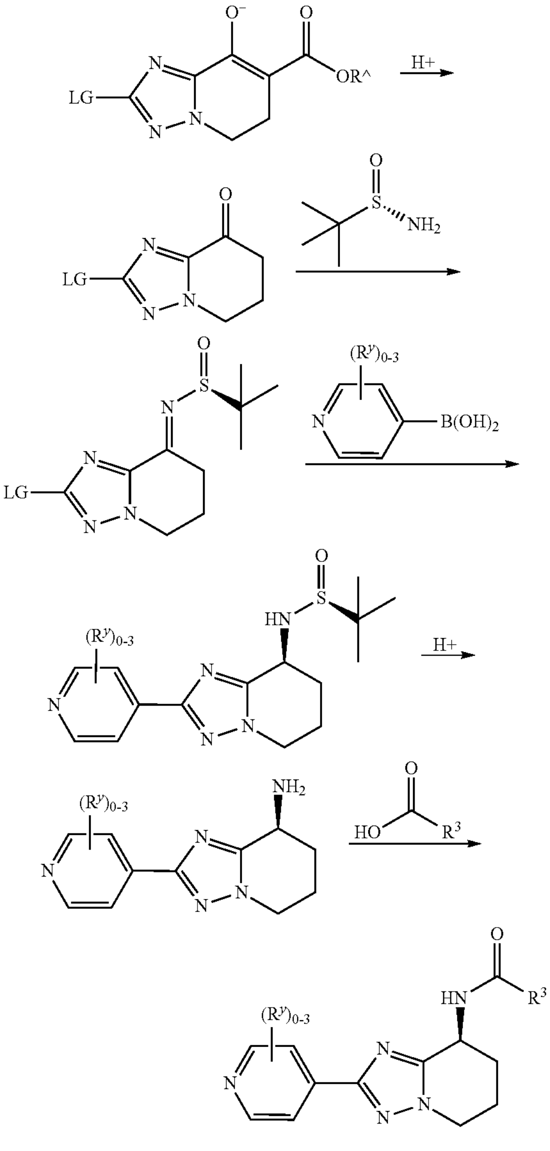

In Schemes A-F, $R^x$, $R^y$, $R^3$, m and n are as defined above for formula I, LG is a suitable leaving group such as, for example, halogen (e.g., Cl, Br, or I) and R^ is $C_{1-4}$ alkyl.

Example 1.1. Synthesis of (S)-1-Methyl-3-(trifluoromethyl)-N-(2-(2-(trifluoromethyl)pyridin-4-yl)-4,5,6,7-tetrahydro-2H-indazol-4-yl)-1H-pyrazole-5-carboxamide (I-4a)

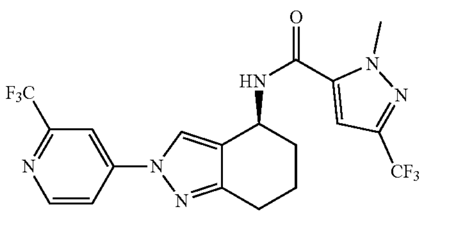 [SMILES: Cn1nc(C(F)(F)F)cc1C(=O)N[C@H]1CCCc2nn(-c3ccnc(C(F)(F)F)c3)cc21]

Step 1—Synthesis of 4-Hydrazinyl-2-(trifluoromethyl)pyridine

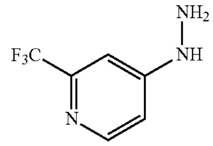

To a solution of 4-chloro-2-(trifluoromethyl)pyridine (50 g, 275.5 mmol) in i-PrOH (300 mL) was added $N_2H_4 \cdot H_2O$ (47.5 mL, 825.3 mmol). The mixture was stirred at 110° C. for 16 h. After cooling to room temperature, the reaction mixture was concentrated in vacuo and diluted with EtOH (50 mL). The mixture was filtered and the filter cake was washed with EtOH (30 mL), then the filter cake was concentrated in vacuo to give the title compound (32 g, crude) as a white solid that was used without further purification. LCMS (ESI) m/z: 178.1 $[M+H]^+$.

Step 2—Synthesis of 3-(2-(2-(Trifluoromethyl)pyridin-4-yl)hydrazinyl)cyclohex-2-en-1-one

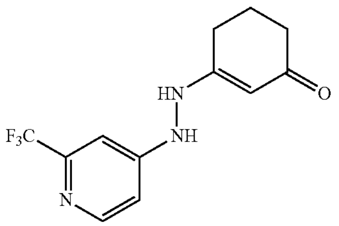 [SMILES: O=C1C=C(NNc2ccnc(C(F)(F)F)c2)CCC1]

To a solution of 4-hydrazinyl-2-(trifluoromethyl)pyridine (20 g, 112.9 mmol) in EtOH (100 mL) and $H_2O$ (100 mL) was added cyclohexane-1,3-dione (13.5 g, 132.2 mmol) at 0° C. The mixture was stirred at 25° C. for 3 h. The reaction mixture was concentrated in vacuo and diluted with water (100 mL) and extracted with ethyl acetate (100 mL×2). The combined organic layers were washed with brine (50 mL), dried over anhydrous $Na_2SO_4$, filtered and concentrated in vacuo. The crude residue was purified by silica gel chromatography (solvent gradient: 0-30% EtOAc in petroleum ether) to give the title compound (21 g, 49%) as a brown solid. $^1H$ NMR (400 MHz, DMSO-$d_6$) δ 9.10 (s, 1H), 8.95 (s, 1H), 8.31 (d, J=5.6 Hz, 1H), 6.98 (s, 1H), 6.90-6.73 (m, 1H), 4.90 (s, 1H), 2.46-2.36 (m, 2H), 2.18-2.08 (m, 2H), 1.94-1.83 (m, 2H). LCMS (ESI) m/z: 272.1 $[M+H]^+$.

Step 3—Synthesis of 2-(2-(Trifluoromethyl)pyridin-4-yl)-2,5,6,7-tetrahydro-4H-indazol-4-one

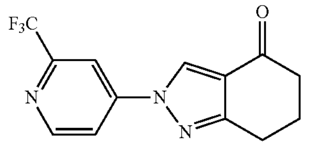

To a solution of 3-[2-[2-(trifluoromethyl)-4-pyridyl]hydrazino]cyclohex-2-en-1-one (21 g, 77.4 mmol) in THE (175 mL) was added DMF-DMA (31 mL, 232.36 mmol). The mixture was stirred at 70° C. for 16 h. After cooling to room temperature, the reaction was concentrated in vacuo and diluted with ethyl acetate (50 mL). The organic phase was washed with brine (50 mL), dried over anhydrous $Na_2SO_4$, filtered and concentrated in vacuo. The crude residue was purified by silica gel chromatography (solvent gradient: 0-30% EtOAc in petroleum ether) to give the title compound (12 g, 55%) as a yellow solid. $^1H$ NMR (400 MHz, DMSO-$d_6$) δ 9.43 (s, 1H), 8.86 (d, J=5.6 Hz, 1H), 8.43 (d, J=2.0 Hz, 1H), 8.27-8.22 (m, 1H), 2.97-2.84 (m, 2H), 2.54-2.51 (m, 2H), 2.15-2.03 (m, 2H). LCMS (ESI) m/z: 282.0 $[M+H]^+$.

Step 4—Synthesis of (S,E)-2-Methyl-N-(2-(2-(trifluoromethyl)pyridin-4-yl)-2,5,6,7-tetrahydro-4H-indazol-4-ylidene)propane-2-sulfinamide

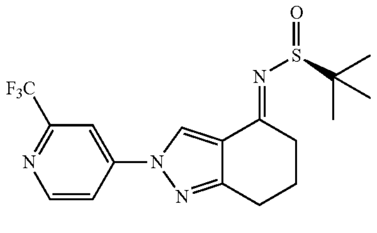 [SMILES: CC(C)(C)[S@](=O)/N=C1\CCCc2nn(-c3ccnc(C(F)(F)F)c3)cc21]

To a solution of 2-(2-(trifluoromethyl)pyridin-4-yl)-2,5,6,7-tetrahydro-4H-indazol-4-one (6.4 g, 22.8 mmol), (S)-2-methylpropane-2-sulfinamide (13.8 g, 113.8 mmol) in THE (50 mL) was added Ti(i-PrO)$_4$ (16.79 mL, 56.9 mmol). The reaction mixture was stirred at 60° C. for 16 h under a nitrogen atmosphere. After cooling to room temperature, the mixture was quenched with $H_2O$ (40 mL), and then filtered. The filtrate was extracted with ethyl acetate (30 mL×2). The combined organic layers were washed with brine (50 mL), dried over anhydrous $Na_2SO_4$, filtered and concentrated in vacuo. The residue was purified by silica gel chromatography (solvent gradient: 0-50% EtOAc in petroleum ether) to give the title compound (2 g, 23%) as a yellow solid. $^1H$ NMR (400 MHz, DMSO-$d_6$) δ 9.32 (s, 1H), 8.84 (d, J=5.6 Hz, 1H), 8.45 (d, J=1.6 Hz, 1H), 8.34-8.18 (m, 1H), 3.14-3.02 (m, 1H), 2.95-2.86 (m, 1H), 2.85-2.79 (m, 2H), 2.04-1.97 (m, 2H), 1.22 (s, 9H). LCMS (ESI) m/z: 385.0 $[M+H]^+$.

Step 5—Synthesis of (S)-2-Methyl-N—((S)-2-(2-(trifluoromethyl)pyridin-4-yl)-4,5,6,7-tetrahydro-2H-indazol-4-yl)propane-2-sulfinamide

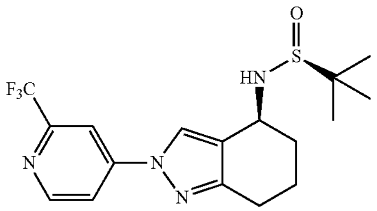 [SMILES: CC(C)(C)[S@](=O)N[C@H]1CCCc2nn(-c3ccnc(C(F)(F)F)c3)cc21]

To a solution of (S,E)-2-methyl-N-(2-(2-(trifluoromethyl)pyridin-4-yl)-2,5,6,7-tetrahydro-4H-indazol-4-ylidene)propane-2-sulfinamide (2 g, 5.2 mmol) in THE (25 mL) at 0° C. was added $NaBH_4$ (236 mg, 6.2 mmol). The reaction mixture was stirred at 25° C. for 1 h. The mixture was quenched with sat. aq. $NH_4Cl$ (2 mL), and water (30 mL) was added. The mixture was extracted with EtOAc (50 mL×2). The combined organic layers were washed with brine (50 mL×2), dried over anhydrous $Na_2SO_4$, filtered and concentrated in vacuo. The crude residue was purified by silica gel chromatography (solvent gradient: 0-50% EtOAc in petroleum ether) to give the title compound (1.5 g, 75%) as a yellow solid. $^1H$ NMR (400 MHz, DMSO-$d_6$) δ 8.76 (d, J=5.2 Hz, 1H), 8.62 (s, 1H), 8.17 (d, J=2.0 Hz, 1H), 8.12-7.99 (m, 1H), 5.46 (d, J=7.2 Hz, 1H), 4.40-4.35 (m, 1H), 2.72-2.58 (m, 2H), 2.11-1.87 (m, 2H), 1.76-1.60 (m, 2H), 1.15 (s, 9H). LCMS (ESI) m/z: 387.1 $[M+H]^+$.

Step 6—Synthesis of (S)-2-(2-(Trifluoromethyl)pyridin-4-yl)-4,5,6,7-tetrahydro-2H-indazol-4-amine hydrochloride salt

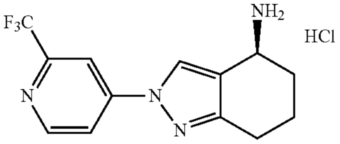 [SMILES: N[C@H]1CCCc2nn(-c3ccnc(C(F)(F)F)c3)cc21 ; Cl]

To a solution of (S)-2-methyl-N-[(4S)-2-[2-(trifluoromethyl)-4-pyridyl]-4,5,6,7-tetrahydroindazol-4-yl]propane-2-sulfinamide (1.5 g, 3.9 mmol) in dioxane (5 mL) was added hydrochloric acid in dioxane (2 M, 20 mL). The mixture was stirred at room temperature for 2 h. The mixture was concentrated in vacuo to give the title compound (2.5 g, crude) as yellow oil that was used without further purification. LCMS (ESI) m/z: 283.2 $[M+H]^+$.

Step 7—Synthesis of (S)-1-Methyl-3-(trifluoromethyl)-N-(2-(2-(trifluoromethyl)pyridin-4-yl)-4,5,6,7-tetrahydro-2H-indazol-4-yl)-1H-pyrazole-5-carboxamide (I-4a)

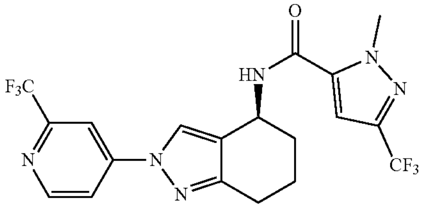

To a solution of (4S)-2-[2-(trifluoromethyl)-4-pyridyl]-4,5,6,7-tetrahydroindazol-4-amine HCl salt (1.20 g, 4.3 mmol), 1-methyl-3-(trifluoromethyl)-1H-pyrazole-5-carboxylic acid (990 mg, 5.1 mmol) and DIEA (2.22 mL, 12.8 mmol) in DCM (20 mL) was added HATU (1.94 g, 5.1 mmol). The reaction mixture was stirred at 25° C. for 1 h. The reaction was diluted with $H_2O$ (30 mL), and then extracted with DCM (30 mL×2). The combined organic layers were washed with brine (20 mL×2), dried over anhydrous $Na_2SO_4$, filtered and concentrated in vacuo. The residue was purified by reverse phase chromatography (acetonitrile 50-90%/0.225% formic acid in water) to give the title compound (1.12 g, 58%) as a white solid. $^1H$ NMR (400 MHz, DMSO-$d_6$) δ 8.96 (d, J=8.0 Hz, 1H), 8.76 (d, J=5.6 Hz, 1H), 8.74 (s, 1H), 8.27 (d, J=2.0 Hz, 1H), 8.14-8.09 (m, 1H), 7.40 (s, 1H), 5.20-5.13 (m, 1H), 4.20 (s, 3H), 2.76-2.52 (m, 2H), 2.10-1.99 (m, 2H), 1.84-1.69 (m, 2H). LCMS (ESI) m/z: 459.1 $[M+H]^+$.

Example 1.2. Synthesis of (S)-1-Methyl-3-(trifluoromethyl)-N-(2-(2-(trifluoromethyl)pyridin-4-yl)-4,5,6,7-tetrahydro-2H-indazol-4-yl)-1H-pyrazole-5-carboxamide (I-4a) and (R)-1-Methyl-3-(trifluoromethyl)-N-(2-(2-(trifluoromethyl)pyridin-4-yl)-4,5,6,7-tetrahydro-2H-indazol-4-yl)-1H-pyrazole-5-carboxamide (I-4b)

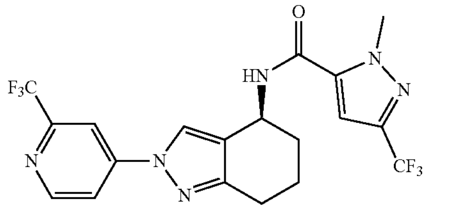 [SMILES: Cn1nc(C(F)(F)F)cc1C(=O)N[C@H]1CCCc2nn(-c3ccnc(C(F)(F)F)c3)cc21]

and

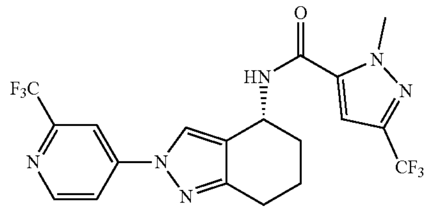

Step 1—Synthesis of 2-(2-(Trifluoromethyl)pyridin-4-yl)-4,5,6,7-tetrahydro-2H-indazol-4-amine

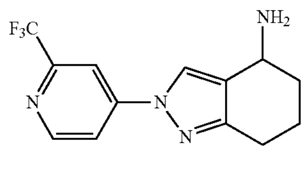 [SMILES: NC1CCCc2nn(-c3ccnc(C(F)(F)F)c3)cc21]

To a solution of 2-[2-(trifluoromethyl)-4-pyridyl]-6,7-dihydro-5H-indazol-4-one (2.8 g, 10.0 mmol) in MeOH (60 mL) was added $NH_4OAc$ (7.67 g, 99.6 mmol) and $NaBH_3CN$ (1.88 g, 29.9 mmol). The mixture was stirred at room temperature for 2 h. The mixture was concentrated in vacuo. The crude residue was purified by silica gel chromatography (solvent gradient: 0-100% EtOAc in petroleum ether) to give the title compound (2.3 g, 83%) as a white solid. LCMS (ESI) m/z: 283.2 $[M+H]^+$.

Step 2—Synthesis of (rac)-1-Methyl-3-(trifluoromethyl)-N-(2-(2-(trifluoromethyl)pyridin-4-yl)-4,5,6,7-tetrahydro-2H-indazol-4-yl)-1H-pyrazole-5-carboxamide

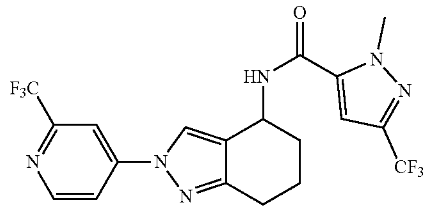 [SMILES: Cn1nc(C(F)(F)F)cc1C(=O)NC1CCCc2nn(-c3ccnc(C(F)(F)F)c3)cc21]

To a solution of (4S)-2-[2-(trifluoromethyl)-4-pyridyl]-4,5,6,7-tetrahydroindazol-4-amine (200 mg, 708.6 μmol), 1-methyl-3-(trifluoromethyl)-1H-pyrazole-5-carboxylic acid (151 mg, 779.4 μmol) and DIEA (0.37 mL, 2.1 mmol) in DCM (5 mL) was added HATU (350 mg, 921.1 μmol). The reaction mixture was stirred at 25° C. for 1 h. The reaction was diluted with $H_2O$ (30 mL), and then extracted with DCM (30 mL×2). The combined organic layers were washed with brine (20 mL×2), dried over anhydrous $Na_2SO_4$, filtered and concentrated in vacuo. The residue was purified by reverse phase chromatography (acetonitrile 51-81%/0.225% formic acid in water) to give the title compound (1.12 g, 58%) as a white solid. LCMS (ESI) m/z: 459.1 $[M+H]^+$.

Step 3—Synthesis of (S)-1-Methyl-3-(trifluoromethyl)-N-(2-(2-(trifluoromethyl)pyridin-4-yl)-4,5,6,7-tetrahydro-2H-indazol-4-yl)-1H-pyrazole-5-carboxamide (I-4a) and (R)-1-Methyl-3-(trifluoromethyl)-N-(2-(2-(trifluoromethyl)pyridin-4-yl)-4,5,6,7-tetrahydro-2H-indazol-4-yl)-1H-pyrazole-5-carboxamide (I-4b)

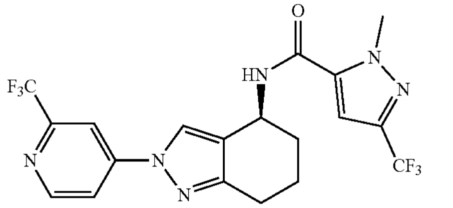 [SMILES: Cn1nc(C(F)(F)F)cc1C(=O)N[C@H]1CCCc2nn(-c3ccnc(C(F)(F)F)c3)cc21]

and

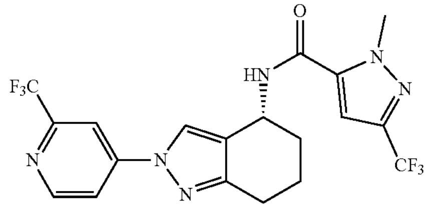

(rac)-1-Methyl-3-(trifluoromethyl)-N-(2-(2-(trifluoromethyl)pyridin-4-yl)-4,5,6,7-tetrahydro-2H-indazol-4-yl)-1H-pyrazole-5-carboxamide (100 mg, 227 μmol) was separated by using chiral SFC (DAICEL CHIRALCEL OJ (250 mm*30 mm, 10 μm); Supercritical $CO_2$/EtOH+0.1% $NH_3 \cdot H_2O$=70/30; 60 mL/min) to afford (S)-1-methyl-3-(trifluoromethyl)-N-(2-(2-(trifluoromethyl)pyridin-4-yl)-4,5,6,7-tetrahydro-2H-indazol-4-yl)-1H-pyrazole-5-carboxamide (48 mg, first peak) and (R)-1-methyl-3-

(trifluoromethyl)-N-(2-(2-(trifluoromethyl)pyridin-4-yl)-4,5,6,7-tetrahydro-2H-indazol-4-yl)-1H-pyrazole-5-carboxamide (43 mg, second peak) both as white solids. First peak: (I-4a): $^1$H NMR (400 MHz, DMSO-$d_6$) δ 8.97 (d, J=8.0 Hz, 1H), 8.76 (d, J=5.6 Hz, 1H), 8.74 (s, 1H), 8.27 (d, J=2.0 Hz, 1H), 8.14-8.09 (m, 1H), 7.40 (s, 1H), 5.25-5.09 (m, 1H), 4.20 (s, 3H), 2.84-2.63 (m, 2H), 2.13-1.97 (m, 2H), 1.87-1.60 (m, 2H). LCMS (ESI) m/z: 459.1 $[M+H]^+$. Second peak: (I-4b): $^1$H NMR (400 MHz, DMSO-$d_6$) δ 8.97 (d, J=8.0 Hz, 1H), 8.76 (d, J=5.6 Hz, 1H), 8.74 (s, 1H), 8.27 (d, J=2.0 Hz, 1H), 8.14-8.09 (m, 1H), 7.40 (s, 1H), 5.25-5.09 (m, 1H), 4.20 (s, 3H), 2.84-2.63 (m, 2H), 2.13-1.97 (m, 2H), 1.87-1.60 (m, 2H). LCMS (ESI) m/z: 459.0 $[M+H]^+$.

Example 1.3. Synthesis of (S)-1-Methyl-3-(trifluoromethyl)-N-(2-(2-(trifluoromethyl)pyridin-4-yl)-4,5,6,7-tetrahydro-2H-indazol-4-yl)-1H-pyrazole-5-carboxamide (I-4a) and (R)-1-Methyl-3-(trifluoromethyl)-N-(2-(2-(trifluoromethyl)pyridin-4-yl)-4,5,6,7-tetrahydro-2H-indazol-4-yl)-1H-pyrazole-5-carboxamide (I-4b)

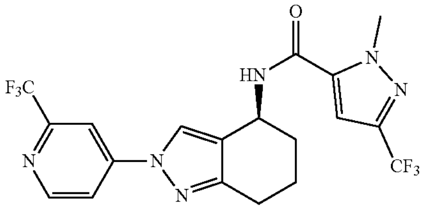

and

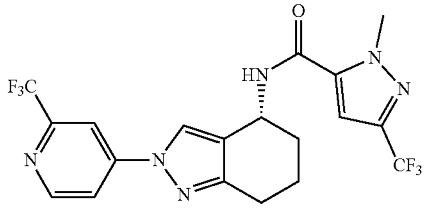

Step 1—Synthesis of (S)-2-(2-(Trifluoromethyl)pyridin-4-yl)-4,5,6,7-tetrahydro-2H-indazol-4-amine and (R)-2-(2-(Trifluoromethyl)pyridin-4-yl)-4,5,6,7-tetrahydro-2H-indazol-4-amine

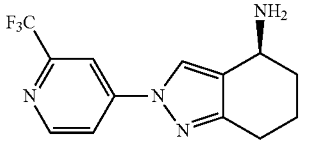

and

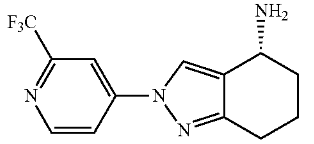

2-(2-(Trifluoromethyl)pyridin-4-yl)-4,5,6,7-tetrahydro-2H-indazol-4-amine (1 g, 3.5 mmol) was separated by using chiral SFC (DAICEL CHIRALPAK IF (250 mm*30 mm, 10 μm); Supercritical heptane/EtOH+0.1% $NH_3 \cdot H_2O$=80/20; 60 mL/min) to afford (S)-2-(2-(trifluoromethyl)pyridin-4-yl)-4,5,6,7-tetrahydro-2H-indazol-4-amine (357 mg, first peak) and (R)-2-(2-(trifluoromethyl)pyridin-4-yl)-4,5,6,7-tetrahydro-2H-indazol-4-amine (350 mg, second peak) both as white solids.

Step 2—Synthesis of (S)-1-Methyl-3-(trifluoromethyl)-N-(2-(2-(trifluoromethyl)pyridin-4-yl)-4,5,6,7-tetrahydro-2H-indazol-4-yl)-1H-pyrazole-5-carboxamide (I-4a)

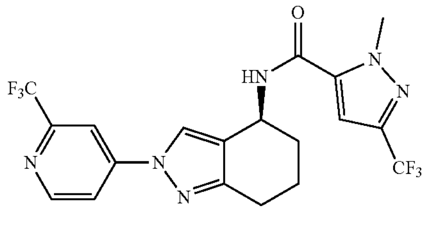

To a solution of (4S)-2-[2-(trifluoromethyl)-4-pyridyl]-4,5,6,7-tetrahydroindazol-4-amine (80 mg, 283 μmol), 1-methyl-3-(trifluoromethyl)-1H-pyrazole-5-carboxylic acid (66 mg, 340 μmol) and DIEA (0.15 mL, 850 μmol) in DCM (3 mL) was added HATU (129 mg, 340 μmol). The reaction mixture was stirred at 25° C. for 1 h. The reaction was diluted with $H_2O$ (30 mL), and then extracted with DCM (30 mL×2). The combined organic layers were washed with brine (20 mL×2), dried over anhydrous $Na_2SO_4$, filtered and concentrated in vacuo. The residue was purified by reverse phase chromatography (acetonitrile 40-80%/0.225% formic acid in water) to give the title compound (40 mg, 46%) as a white solid. $^1$H NMR (400 MHz, DMSO-$d_6$) δ 8.97 (d, J=8.0 Hz, 1H), 8.76 (d, J=5.6 Hz, 1H), 8.74 (s, 1H), 8.26 (s, 1H), 8.11 (d, J=4.0 Hz, 1H), 7.40 (s, 1H), 5.19-5.13 (m, 1H), 4.20 (s, 3H), 2.77-2.67 (m, 2H), 2.07-1.98 (m, 2H), 1.85-1.65 (m, 2H). LCMS (ESI) m/z: 459.0 $[M+H]^+$.

Example 1.4. Synthesis of (S)—N,1-Dimethyl-3-(trifluoromethyl)-N-(2-(2-(trifluoromethyl)pyridin-4-yl)-4,5,6,7-tetrahydro-2H-indazol-4-yl)-1H-pyrazole-5-carboxamide (I-37a)

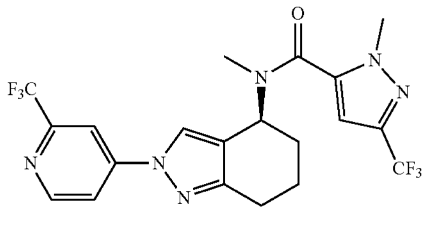 [SMILES: CN(C(=O)c1cc(C(F)(F)F)nn1C)[C@H]1CCCc2nn(-c3ccnc(C(F)(F)F)c3)cc21]

To a solution of 2-methyl-5-(trifluoromethyl)-N-[(4S)-2-[2-(trifluoromethyl)-4-pyridyl]-4,5,6,7-tetrahydroindazol-4-yl]pyrazole-3-carboxamide (50 mg, 109.1 μmol), dimethyl sulfate (28 mg, 218.2 μmol) in THE (5 mL) was added KOH (18 mg, 327.3 μmol). The reaction mixture was stirred at 60° C. for 1 h. After cooling to room temperature, the reaction was diluted with $H_2O$ (10 mL), and then extracted with EtOAc (30 mL×2). The combined organic layers were washed with brine (20 mL), dried over anhydrous $Na_2SO_4$, filtered and concentrated in vacuo. The residue was purified by reverse phase chromatography (acetonitrile 55-85%/

0.225% formic acid in water) to give the title compound (30 mg, 58%) as a white solid. $^1$H NMR (400 MHz, DMSO-$d_6$) δ 8.96-8.39 (m, 2H), 8.23 (s, 1H), 8.09 (d, J=4.4 Hz, 1H), 7.04 (s, 1H), 6.20-4.48 (m, 1H), 4.01 (s, 3H), 2.84 (s, 3H), 2.81-2.61 (m, 2H), 2.15-1.94 (m, 2H), 1.91-1.60 (m, 2H). LCMS (ESI) m/z: 473.1 $[M+H]^+$.

Example 1.5. Synthesis of (rac)-1-Methyl-3-(trifluoromethyl)-N-(2-(2-(trifluoromethyl)pyridin-4-yl)-4,5,6,7-tetrahydropyrazolo[1,5-a]pyridin-4-yl)-1H-pyrazole-5-carboxamide (I-42)

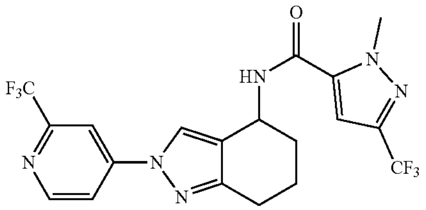 [SMILES: Cn1nc(C(F)(F)F)cc1C(=O)NC1CCCc2nn(-c3ccnc(C(F)(F)F)c3)cc21]

Step 1—Synthesis of Methyl 3-(2-(trifluoromethyl)pyridin-4-yl)-1-((2-(trimethylsilyl)ethoxy)methyl)-1H-pyrazole-5-carboxylate

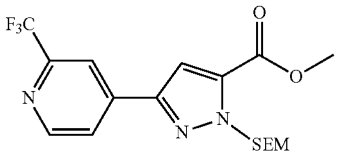 [SMILES: COC(=O)c1cc(-c2ccnc(C(F)(F)F)c2)nn1COCC[Si](C)(C)C]

To a solution of methyl 5-bromo-2-(2-trimethylsilylethoxymethyl)pyrazole-3-carboxylate (4.2 g, 12.5 mmol, prepared according to the procedure described in WO2022/034568), 4-(4,4,5,5-tetramethyl-1,3,2-dioxaborolan-2-yl)-2-(trifluoromethyl)pyridine (4.1 g, 15.0 mmol), $K_3PO_4$ (8.0 g, 37.6 mmol) in dioxane (100 mL) and $H_2O$ (10 mL) was added Pd(dppf)$Cl_2$ (916 mg, 1.3 mmol). The reaction mixture was stirred at 80° C. for 16 h under a nitrogen atmosphere. After cooling to room temperature, the mixture was diluted with $H_2O$ (100 mL) and extracted with ethyl acetate (50 mL×2). The combined organic layers were washed with brine (50 mL×2), dried over anhydrous $Na_2SO_4$, filtered and concentrated in vacuo. The residue was purified by silica gel chromatography (solvent gradient: 0-10% EtOAc in petroleum ether) to give the title compound (4.8 g, 92%) as a yellow solid. LCMS (ESI) m/z: 402.2 $[M+H]^+$.

Step 2—Synthesis of Methyl 3-(2-(trifluoromethyl)pyridin-4-yl)-1H-pyrazole-5-carboxylate

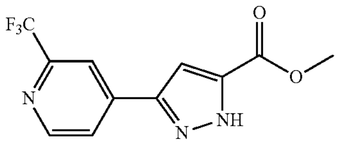 [SMILES: COC(=O)c1cc(-c2ccnc(C(F)(F)F)c2)n[nH]1]

To a solution of methyl 3-(2-(trifluoromethyl)pyridin-4-yl)-1-((2-(trimethylsilyl)ethoxy)methyl)-1H-pyrazole-5-carboxylate (2 g, 5 mmol) in DCM (10 mL) was added TFA (6.00 mL, 80.8 mmol). The mixture was stirred at room temperature for 2 h. The mixture was concentrated in vacuo to give the title compound (1.3 g, crude) as yellow oil that was used without further purification. LCMS (ESI) m/z: 272.1 $[M+H]^+$.

Step 3—Synthesis of Methyl 1-(4-ethoxy-4-oxobutyl)-3-(2-(trifluoromethyl)pyridin-4-yl)-1H-pyrazole-5-carboxylate

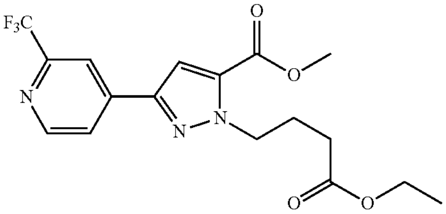 [SMILES: CCOC(=O)CCCn1nc(-c2ccnc(C(F)(F)F)c2)cc1C(=O)OC]

To a solution of methyl 3-(2-(trifluoromethyl)pyridin-4-yl)-1H-pyrazole-5-carboxylate (1.3 g, 3.7 mmol), $PPh_3$ (3.8 g, 14.4 mmol) and ethyl 4-hydroxybutanoate (1.28 g, 9.7 mmol) in THF (20 mL) was added DIAD (1.96 mL, 9.7 mmol). The reaction mixture was stirred at 80° C. for 16 h under a nitrogen atmosphere. After cooling to room temperature, the mixture was diluted with $H_2O$ (30 mL) and extracted with ethyl acetate (30 mL×2). The combined organic layers were washed with brine (50 mL×2), dried over anhydrous $Na_2SO_4$, filtered and concentrated in vacuo. The residue was purified by silica gel chromatography (solvent gradient: 0-25% EtOAc in petroleum ether) to give the title compound (1.2 g, 72%) as a yellow solid. $^1$H NMR (400 MHz, DMSO-$d_6$) δ 8.79 (d, J=5.2 Hz, 1H), 8.28 (s, 1H), 8.14 (d, J=5.2 Hz, 1H), 7.80 (s, 1H), 4.61 (t, J=6.8 Hz, 2H), 3.98 (q, J=6.8 Hz, 2H), 3.81 (s, 3H), 2.33 (t, J=7.2 Hz, 2H), 2.13-2.03 (m, 2H), 1.12 (t, J=7.2 Hz, 3H).

Step 4—Synthesis of Ethyl 4-oxo-2-(2-(trifluoromethyl)pyridin-4-yl)-4,5,6,7-tetrahydropyrazolo[1,5-a]pyridine-5-carboxylate

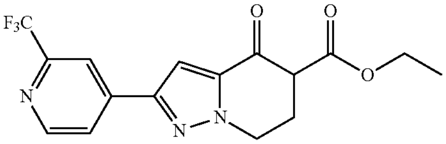 [SMILES: CCOC(=O)C1CCn2nc(-c3ccnc(C(F)(F)F)c3)cc2C1=O]

To a solution of methyl 1-(4-ethoxy-4-oxobutyl)-3-(2-(trifluoromethyl)pyridin-4-yl)-1H-pyrazole-5-carboxylate (1.2 g, 2.5 mmol) in toluene (20 mL) was added potassium 2-methylpropan-2-olate (4.2 mL, 1.8 M, 7.5 mmol) at 0° C. The reaction mixture was stirred at 90° C. for 16 h under a nitrogen atmosphere. After cooling to room temperature, the mixture was diluted with water (10 mL) and added aq. HCl (1M, 10 mL). The solution was adjusted to pH 6, then extracted with ethyl acetate (30 mL×2). The combined organic layers were washed with brine (10 mL), dried over anhydrous $Na_2SO_4$, filtered and concentrated in vacuo. The residue was purified by silica gel chromatography (solvent gradient: 0-25% EtOAc in petroleum ether) to give the title compound (0.8 g, 56%) as colorless oil. LCMS (ESI) m/z: 354.1 [M+H]+.

Step 5—Synthesis of 2-(2-(Trifluoromethyl)pyridin-4-yl)-6,7-dihydropyrazolo[1,5-a]pyridin-4(5H)-one

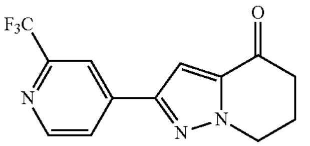 [SMILES: O=C1CCCn2nc(-c3ccnc(C(F)(F)F)c3)cc21]

To a solution of ethyl 4-oxo-2-(2-(trifluoromethyl)pyridin-4-yl)-4,5,6,7-tetrahydropyrazolo[1,5-a]pyridine-5-carboxylate (0.8 g, 2.5 μmol) was added conc. HCl (10 mL, 12 M). The reaction mixture was stirred at 100° C. for 16 h under a nitrogen atmosphere. After cooling to room temperature, the mixture was diluted with water (30 mL) and extracted with ethyl acetate (30 mL×2). The combined organic layers were washed with brine (10 mL), dried over anhydrous $Na_2SO_4$, filtered and concentrated in vacuo to give the title compound (0.6 g, crude) as a yellow solid that was used without further purification. LCMS (ESI) m/z: 282.1 [M+H]+.

Step 6—Synthesis of (rac)-2-(2-(Trifluoromethyl)pyridin-4-yl)-6,7-dihydropyrazolo[1,5-a]pyridin-4(5H)-one (I-42)

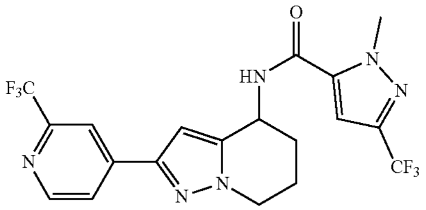 [SMILES: Cn1nc(C(F)(F)F)cc1C(=O)NC1CCCn2nc(-c3ccnc(C(F)(F)F)c3)cc21]

Following the procedure described in Example 1.2 using 2-(2-(trifluoromethyl)pyridin-4-yl)-6,7-dihydropyrazolo[1,5-a]pyridin-4(5H)-one, the title compound was obtained as a white solid after purification by reverse phase chromatography (acetonitrile 51%-81%/0.225% formic acid in water). $^1H$ NMR (400 MHz, DMSO-$d_6$) δ 9.17 (d, J=8.0 Hz, 1H), 8.74 (d, J=4.8 Hz, 1H), 8.20 (s, 1H), 8.07 (d, J=4.8 Hz, 1H), 7.39 (s, 1H), 7.05 (s, 1H), 5.40-5.23 (m, 1H), 4.29-4.12 (m, 5H), 2.25-2.05 (m, 3H), 1.95-1.76 (m, 1H). LCMS (ESI) m/z: 459.0 [M+H]+.

Example 1.6. Synthesis of (S)-1-Methyl-3-(trifluoromethyl)-N-(2-(2-(trifluoromethyl)pyridin-4-yl)-4,5,6,7-tetrahydropyrazolo[1,5-a]pyridin-4-yl)-1H-pyrazole-5-carboxamide (I-42a) and (R)-1-Methyl-3-(trifluoromethyl)-N-(2-(2-(trifluoromethyl)pyridin-4-yl)-4,5,6,7-tetrahydropyrazolo[1,5-a]pyridin-4-yl)-1H-pyrazole-5-carboxamide(I-42b)

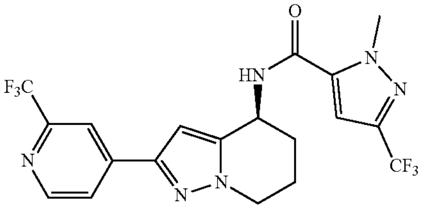

and

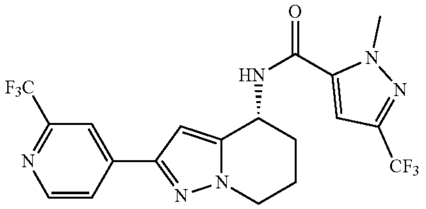

2-(2-(trifluoromethyl)pyridin-4-yl)-6,7-dihydropyrazolo[1,5-a]pyridin-4(5H)-one (200 mg, 510 μmol) was separated by using chiral SFC (DAICEL CHIRALCEL OJ (250 mm*30 mm, 10 μm); Supercritical $CO_2$/EtOH+0.1% $NH_3 \cdot H_2O$=65/35; 60 mL/min) to afford (S)-1-methyl-3-(trifluoromethyl)-N-(2-(2-(trifluoromethyl)pyridin-4-yl)-4,5,6,7-tetrahydropyrazolo[1,5-a]pyridin-4-yl)-1H-pyrazole-5-carboxamide (64 mg, first peak) and (R)-1-methyl-3-(trifluoromethyl)-N-(2-(2-(trifluoromethyl)pyridin-4-yl)-4,5,6,7-tetrahydropyrazolo[1,5-a]pyridin-4-yl)-1H-pyrazole-5-carboxamide (70 mg, second peak) both as white solid. First peak: (I-42a): $^1H$ NMR (400 MHz, DMSO-$d_6$) δ 9.17 (d, J=8.0 Hz, 1H), 8.74 (d, J=4.8 Hz, 1H), 8.20 (s, 1H), 8.07 (d, J=4.8 Hz, 1H), 7.39 (s, 1H), 7.05 (s, 1H), 5.40-5.23 (m, 1H), 4.29-4.12 (m, 5H), 2.25-2.05 (m, 3H), 1.95-1.76 (m, 1H). LCMS (ESI) m/z: 459.0 [M+H]+. Second peak: (I-42b): $^1H$ NMR (400 MHz, DMSO-$d_6$) δ 9.17 (d, J=8.0 Hz, 1H), 8.74 (d, J=4.8 Hz, 1H), 8.20 (s, 1H), 8.07 (d, J=4.8 Hz, 1H), 7.39 (s, 1H), 7.05 (s, 1H), 5.40-5.23 (m, 1H), 4.29-4.12 (m, 5H), 2.25-2.05 (m, 3H), 1.95-1.76 (m, 1H). LCMS (ESI) m/z: 459.0 [M+H]+.

Example 1.7. Synthesis of (rac)-3-Chloro-N-(2-(2-ethoxypyridin-4-yl)-4,5,6,7-tetrahydro-2H-indazol-4-yl)-5-(trifluoromethyl)benzamide (I-14)

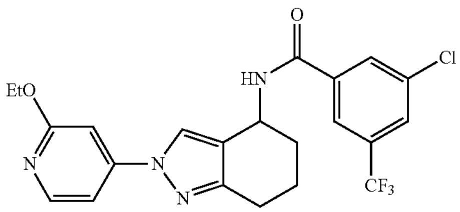 [SMILES: CCOc1cc(-n2cc3c(n2)CCCC3NC(=O)c2cc(Cl)cc(C(F)(F)F)c2)ccn1]

Step 1—Synthesis of 2-Ethoxy-4-iodopyridine

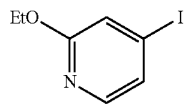

To a solution of 2-ethoxypyridin-4-amine (5 g, 36.2 mmol), $NaNO_2$ (3.8 g, 54.3 mmol) in conc. HCl (50 mL, 12 M) and $H_2O$ (25 mL) was added 12 (10 g, 39.8 mmol) at 0° C. The reaction mixture was stirred at 0° C. for 1 h under a nitrogen atmosphere. The mixture was quenched with sat. aq. $Na_2S_2O_3$ (20 mL), and water (20 mL) was added. The mixture was extracted with EtOAc (50 mL×2). The combined organic layers were washed with brine (50 mL×2), dried over anhydrous $Na_2SO_4$, filtered and concentrated in vacuo. The crude residue was purified by silica gel chromatography (solvent gradient: 0-20% EtOAc in petroleum ether) to give the title compound (1.7 g, 31%) as a yellow solid. LCMS (ESI) m/z: 250.0 $[M+H]^+$.

Step 2—Synthesis of 2-(2-Ethoxypyridin-4-yl)-2,5,6,7-tetrahydro-4H-indazol-4-one

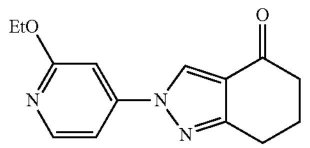 [SMILES: CCOc1cc(-n2cc3c(n2)CCCC3=O)ccn1]

To a solution of 2-ethoxy-4-iodopyridine (750 mg, 3.0 mmol), 2,5,6,7-tetrahydro-4H-indazol-4-one (492 mg, 3.6 mmol) and $Cs_2CO_3$ (1.96 g, 6.0 mmol) in DMSO (10 mL) was added CuI (115 mg, 602.3 μmol). The reaction mixture was stirred at 120° C. for 1 h under a nitrogen atmosphere. After cooling to room temperature, the reaction was diluted with water (50 mL), and the mixture was extracted with EtOAc (50 mL×2). The combined organic layers were washed with brine (50 mL×3), dried over anhydrous $Na_2SO_4$, filtered and concentrated in vacuo. The crude residue was purified by silica gel chromatography (solvent gradient: 0-55% EtOAc in petroleum ether) to give the title compound (0.25 g, 32%) as a yellow solid. $^1H$ NMR (400 MHz, DMSO-$d_6$) δ 9.19 (s, 1H), 8.23 (d, J=6.0 Hz, 1H), 7.59-7.47 (m, 1H), 7.30 (d, J=1.6 Hz, 1H), 4.34 (q, J=7.2 Hz, 2H), 2.91-2.80 (m, 2H), 2.49-2.45 (m, 2H), 2.16-1.96 (m, 2H), 1.33 (t, J=7.2 Hz, 3H). LCMS (ESI) m/z: 258.1 $[M+H]^+$.

Step 3—Synthesis of (rac)-3-Chloro-N-(2-(2-ethoxypyridin-4-yl)-4,5,6,7-tetrahydro-2H-indazol-4-yl)-5-(trifluoromethyl)benzamide (I-14)

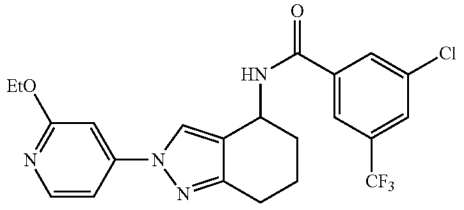 [SMILES: CCOc1cc(-n2cc3c(n2)CCCC3NC(=O)c2cc(Cl)cc(C(F)(F)F)c2)ccn1]

Following the procedure described in Example 1.2 using 2-(2-ethoxypyridin-4-yl)-2,5,6,7-tetrahydro-4H-indazol-4-one, the title compound was obtained as a white solid after purification by reverse phase chromatography (acetonitrile 38%-68%/0.225% formic acid in water). $^1H$ NMR (400 MHz, DMSO-$d_6$) δ 9.10 (d, J=8.0 Hz, 1H), 8.57 (s, 1H), 8.28 (s, 1H), 8.23 (s, 1H), 8.15 (d, J=5.6 Hz, 1H), 8.07 (s, 1H), 7.46-7.39 (m, 1H), 7.17 (s, 1H), 5.23-5.15 (m, 1H), 4.31 (q, J=7.2 Hz, 2H), 2.71-2.64 (m, 2H), 2.06-1.94 (m, 2H), 1.81-1.68 (m, 2H), 1.31 (t, J=7.2 Hz, 3H). LCMS (ESI) m/z: 465.0 $[M+H]^+$.

Example 1.8. Synthesis of (rac)-1-Methyl-3-(trifluoromethyl)-N-(2-(2-(trifluoromethyl)pyridin-4-yl)-4,5,6,7-tetrahydro-2H-indazol-5-yl)-1H-pyrazole-5-carboxamide (I-63)

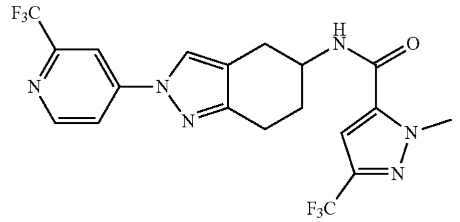 [SMILES: Cn1nc(C(F)(F)F)cc1C(=O)NC1CCc2nn(-c3ccnc(C(F)(F)F)c3)cc2C1]

Step 1—Synthesis of tert-Butyl (Z)-(3-((dimethylamino)methylene)-4-oxocyclohexyl)carbamate

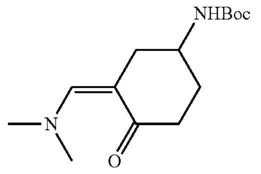 [SMILES: CN(C)/C=C1/CC(NC(=O)OC(C)(C)C)CCC1=O]

To a solution of tert-butyl N-(4-oxocyclohexyl) carbamate (5.00 mL, 23.4 mmol) was added DMF-DMA (5.5 mL, 37.6 mmol). The reaction mixture was stirred at 100° C. for 16 h under a nitrogen atmosphere. After cooling to room temperature, the reaction was diluted with water (50 mL), and the mixture was extracted with EtOAc (30 mL×2). The combined organic layers were washed with brine (20 mL×3), dried over anhydrous $Na_2SO_4$, filtered and concentrated in vacuo to give the title compound (4.6 g, crude) as a yellow solid that was used without further purification.

Step 2—Synthesis of tert-Butyl N-(4,5,6,7-tetrahydro-2H-indazol-5-yl)carbamate

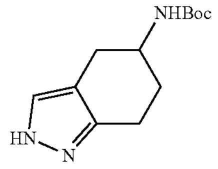 [SMILES: CC(C)(C)OC(=O)NC1CCc2n[nH]cc2C1]

To a solution of N-[(3Z)-3-(dimethylaminomethylene)-4-oxo-cyclohexyl]carbamate (4.6 g, 17.1 mmol) in EtOH (50 mL) was added $N_2H_4 \cdot H_2O$ (1.92 mL, 165.25 mmol). The mixture was stirred at room temperature for 16 h. The reaction mixture was concentrated in vacuo. The crude residue was purified by silica gel chromatography (solvent gradient: 0-50% EtOAc in petroleum ether) to give the title compound (1.6 g, 35%) as a yellow solid. $^1H$ NMR (400 MHz, $CDCl_3$) δ 12.28 (s, 1H), 7.26 (s, 1H), 6.90 (d, J=7.2 Hz, 1H), 3.59-3.56 (m, 1H), 2.74-2.68 (m, 2H), 2.61-2.54 (m, 1H), 2.38-2.23 (m, 1H), 1.96-1.85 (m, 1H), 1.72-1.53 (m, 1H), 1.40 (s, 9H).

Step 3—Synthesis of (rac)-tert-Butyl (2-(2-(trifluoromethyl)pyridin-4-yl)-4,5,6,7-tetrahydro-2H-indazol-5-yl)carbamate

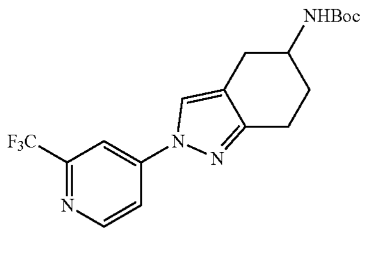 [SMILES: CC(C)(C)OC(=O)NC1CCc2nn(-c3ccnc(C(F)(F)F)c3)cc2C1]

To a solution of tert-butyl N-(4,5,6,7-tetrahydro-2H-indazol-5-yl)carbamate (0.8 g, 3.4 mmol), 4-iodo-2-(trifluoromethyl)pyridine (1 g, 3.7 mmol) and $Cs_2CO_3$ (2.20 g, 6.7 mmol) in DMSO (10 mL) was added CuI (32 mg, 168.6 μmol). The reaction mixture was stirred at 120° C. for 5 h for microwave under a nitrogen atmosphere. After cooling to room temperature, the reaction was diluted with water (50 mL), and the mixture was extracted with EtOAc (50 mL×2). The combined organic layers were washed with brine (50 mL×3), dried over anhydrous $Na_2SO_4$, filtered and concentrated in vacuo. The crude residue was purified by silica gel chromatography (solvent gradient: 0-55% EtOAc in petroleum ether) to give the title compound (0.56 g, mixture) as a yellow solid. LCMS (ESI) m/z: 383.1 $[M+H]^+$.

Step 4—Synthesis of (rac)-2-(2-(Trifluoromethyl)pyridin-4-yl)-4,5,6,7-tetrahydro-2H-indazol-5-amine hydrochloride

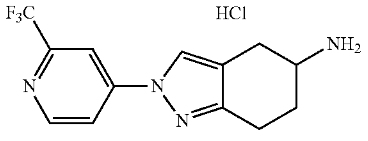 [SMILES: NC1CCc2nn(-c3ccnc(C(F)(F)F)c3)cc2C1 ; Cl]

To a solution of (rac)-tert-butyl N-[2-[2-(trifluoromethyl)-4-pyridyl]-4,5,6,7-tetrahydroindazol-5-yl]carbamate (280 mg, 732.26 μmol) in HCl/dioxane (10 mL, 2 M) was stirred at 25° C. for 2 h. The mixture was concentrated in vacuo to give the title compound (195 mg, crude) as yellow oil which was used without further purification. LCMS (ESI) m/z: 283.1 $[M+H]^+$.

Step 5—Synthesis of (rac)-1-Methyl-3-(trifluoromethyl)-N-(2-(2-(trifluoromethyl)pyridin-4-yl)-4,5,6,7-tetrahydro-2H-indazol-5-yl)-1H-pyrazole-5-carboxamide (I-64)

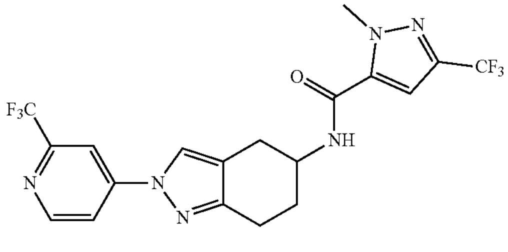 [SMILES: Cn1nc(C(F)(F)F)cc1C(=O)NC1CCc2nn(-c3ccnc(C(F)(F)F)c3)cc2C1]

Following the procedure described in Example 1.1 using 2-(2-(trifluoromethyl)pyridin-4-yl)-4,5,6,7-tetrahydro-2H-indazol-5-amine HCl, the title compound (mixture) was obtained as a white solid after purification by reverse phase chromatography (acetonitrile 59%-79%/0.225% formic acid in water). $^1H$ NMR (400 MHz, DMSO-$d_6$) δ 8.85-8.74 (m, 1H), 8.72-8.64 (m, 1H), 8.61 (s, 0.6H), 8.22 (d, J=2.0 Hz, 0.6H), 8.10-8.04 (m, 1H), 7.95 (d, J=2.0 Hz, 0.4H), 7.73 (s, 0.4H), 7.38-7.35 (m, 1H), 4.36-4.11 (m, 4H), 3.27-3.04 (m, 1H), 3.03-2.72 (m, 2H), 2.68-2.52 (m, 1H), 2.16-2.00 (m, 1H), 1.97-1.78 (m, 1H). LCMS (ESI) m/z: 459.1 $[M+H]^+$.

Example 1.9. Synthesis of (rac)-N-(2-(2-Cyclopropylpyridin-4-yl)-4,5,6,7-tetrahydropyrazolo[1,5-a]pyridin-4-yl)-1-methyl-3-(trifluoromethyl)-1H-pyrazole-5-carboxamide (I-65)

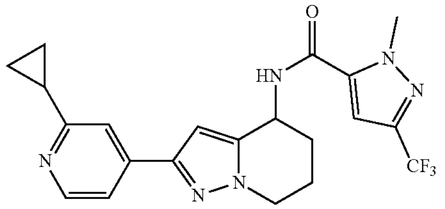

Step 1—Synthesis of Methyl 3-(2-cyclopropylpyridin-4-yl)-1-((2-(trimethylsilyl)ethoxy)methyl)-1H-pyrazole-5-carboxylate

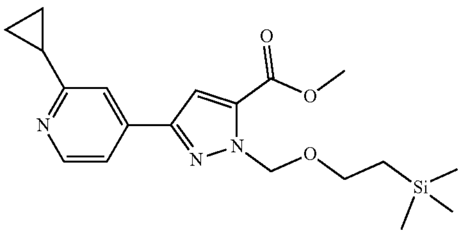 [SMILES: COC(=O)c1cc(-c2ccnc(C3CC3)c2)nn1COCC[Si](C)(C)C]

To a solution of 5-bromo-2-(2-trimethylsilylethoxymethyl)pyrazole-3-carboxylate (5 g, 14.9 mmol), 2-cyclopropyl-4-(4,4,5,5-tetramethyl-1,3,2-dioxaborolan-2-yl)pyridine (2.9 g, 17.9 mmol, prepared according to the procedure in WO2019/211463), $K_3PO_4$ (9.50 g, 44.7 mmol) in dioxane (50 mL) and $H_2O$ (5 mL) was added Pd(dppf)$Cl_2$ (545 mg, 745.7 μmol). The reaction mixture was stirred at 100° C. for 2 h under a nitrogen atmosphere. After cooling to room temperature, the mixture was diluted with water (30 mL) and extracted with ethyl acetate (50 mL×2). The combined organic layers were washed with brine (20 mL), dried over anhydrous $Na_2SO_4$, filtered, and concentrated in vacuo. The residue was purified by silica gel chromatography (solvent gradient: 0-20% EtOAc in petroleum ether) to give the title compound (5 g, 90%) as a yellow solid. LCMS (ESI) m/z: 374.2 $[M+H]^+$.

Step 2—Synthesis of Methyl 3-(2-cyclopropylpyridin-4-yl)-1H-pyrazole-5-carboxylate

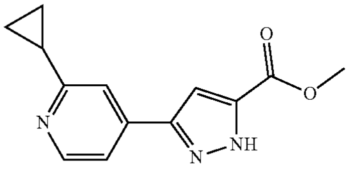 [SMILES: COC(=O)c1cc(-c2ccnc(C3CC3)c2)n[nH]1]

To a solution of methyl 5-(2-cyclopropyl-4-pyridyl)-2-(2-trimethylsilylethoxymethyl)pyrazole-3-carboxylate (5 g, 13.4 mmol) in DCM (20 mL) was added TFA (8 mL, 80.8 mmol). The mixture was stirred at room temperature for 2 h. The mixture was concentrated in vacuo to give the title compound (2.3 g, crude) as yellow oil that was used without further purification. LCMS (ESI) m/z: 244.1 $[M+H]^+$.

Step 3—Synthesis of Methyl 3-(2-cyclopropylpyridin-4-yl)-1-(4-ethoxy-4-oxobutyl)-1H-pyrazole-5-carboxylate

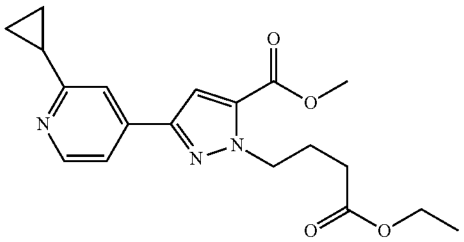 [SMILES: CCOC(=O)CCCn1nc(-c2ccnc(C3CC3)c2)cc1C(=O)OC]

To a solution of methyl 3-(2-cyclopropyl-4-pyridyl)-1H-pyrazole-5-carboxylate (1 g, 4.1 mmol), ethyl 4-bromobutanoate (882 mg, 4.5 mmol) in MeCN (10 mL) was $K_2CO_3$ (1.42 g, 10.3 mmol). The reaction mixture was stirred at 80° C. for 3 h. After cooling to room temperature, the mixture was diluted with water (30 mL) and extracted with ethyl acetate (30 mL×2). The combined organic layers were washed with brine (20 mL), dried over anhydrous $Na_2SO_4$, filtered, and concentrated in vacuo. The residue was purified by silica gel chromatography (solvent gradient: 0-50% EtOAc in petroleum ether) to give the title compound (1 g, 68%) as a yellow solid. $^1H$ NMR (400 MHz, DMSO-$d_6$) δ 8.41 (d, J=5.2 Hz, 1H), 7.74 (s, 1H), 7.58 (s, 1H), 7.56-7.51 (m, 1H), 4.59 (t, J=4.0, 6.8 Hz, 2H), 3.98 (q, J=4.0, 6.8 Hz, 2H), 3.87 (s, 3H), 2.32 (t, J=6.8 Hz, 2H), 2.22-2.02 (m, 3H), 1.23 (t, J=6.8 Hz, 2H), 0.98-0.91 (m, 4H). LCMS (ESI) m/z: 358.1 $[M+H]^+$.

Step 4—Synthesis of (rac)-N-(2-(2-Cyclopropylpyridin-4-yl)-4,5,6,7-tetrahydropyrazolo[1,5-a]pyridin-4-yl)-1-methyl-3-(trifluoromethyl)-1H-pyrazole-5-carboxamide (I-65)

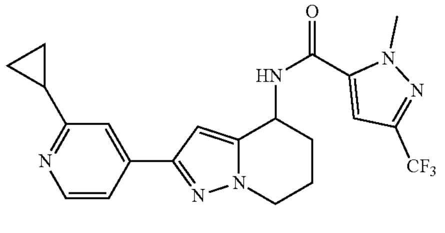 [SMILES: Cn1nc(C(F)(F)F)cc1C(=O)NC1CCCn2nc(-c3ccnc(C4CC4)c3)cc21]

Following the procedure described in Example 1.5 using methyl 3-(2-cyclopropylpyridin-4-yl)-1-(4-ethoxy-4-oxobutyl)-1H-pyrazole-5-carboxylate, the title compound (mixture) was obtained as a white solid after purification by reverse phase chromatography (acetonitrile 20%-60%/0.225% formic acid in water). $^1H$ NMR (400 MHz, DMSO-$d_6$) δ 9.16 (d, J=8.4 Hz, 1H), 8.38 (d, J=5.2 Hz, 1H), 7.71-7.64 (m, 1H), 7.58-7.49 (m, 1H), 7.42-7.35 (m, 1H), 6.89-6.83 (m, 1H), 5.36-5.25 (m, 1H), 4.26-4.19 (m, 4H), 4.18-4.07 (m, 1H), 2.27-2.00 (m, 4H), 1.93-1.77 (m, 1H), 1.05-0.85 (m, 4H). LCMS (ESI) m/z: 431.1 $[M+H]^+$.

Example 1.10. Synthesis of (S)-1-Methyl-3-(trifluoromethyl)-N-(2-(2-(trifluoromethyl)pyridin-4-yl)-2,4,5,6-tetrahydrocyclopenta[c]pyrazol-4-yl)-1H-pyrazole-5-carboxamide (I-1a) and (R)-1-Methyl-3-(trifluoromethyl)-N-(2-(2-(trifluoromethyl)pyridin-4-yl)-2,4,5,6-tetrahydrocyclopenta[c]pyrazol-4-yl)-1H-pyrazole-5-carboxamide (I-1b)

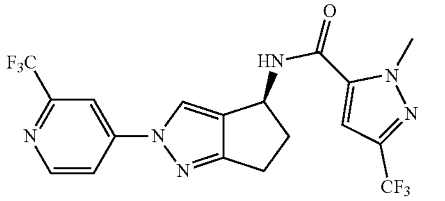

and

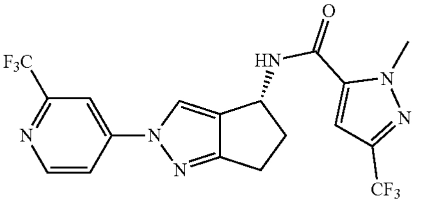

A mixture of 2-methyl-5-(trifluoromethyl)-N-[2-[2-(trifluoromethyl)-4-pyridyl]-5,6-dihydro-4H-cyclopenta[c]pyrazol-4-yl]pyrazole-3-carboxamide (100 mg, 225.1 μmol) was separated by using chiral SFC (DAICEL CHIRALCEL OJ (250 mm*30 mm, 10 μm); Supercritical $CO_2$/EtOH+0.1% $NH_3 \cdot H_2O$=70/30; 80 mL/min) to afford (R)-1-methyl-3-(trifluoromethyl)-N-(2-(2-(trifluoromethyl)pyridin-4-yl)-2,4,5,6-tetrahydrocyclopenta[c]pyrazol-4-yl)-1H-pyrazole-5-carboxamide (49 mg, first peak) and (S)-1-methyl-3-(trifluoromethyl)-N-(2-(2-(trifluoromethyl)pyridin-4-yl)-2,4,5,6-tetrahydrocyclopenta[c]pyrazol-4-yl)-1H-pyrazole-5-carboxamide (34 mg, second peak) both as white solid. First peak: (I-1a): $^1$H NMR (400 MHz, DMSO-$d_6$) 9.03 (d, J=7.6 Hz, 1H), 8.76 (d, J=6.0 Hz, 1H), 8.66 (s, 1H), 8.28 (d, J=2.0 Hz, 1H), 8.14-8.10 (m, 1H), 7.35 (s, 1H), 5.38-5.32 (m, 1H), 4.18 (s, 3H), 2.98-2.89 (m, 1H), 2.89-2.73 (m, 2H), 2.42-2.31 (m, 1H). LCMS (ESI) m/z: 445.0 $[M+H]^+$. Second peak: (I-1b): $^1$H NMR (400 MHz, DMSO-$d_6$) 9.03 (d, J=7.6 Hz, 1H), 8.76 (d, J=6.0 Hz, 1H), 8.66 (s, 1H), 8.28 (d, J=2.0 Hz, 1H), 8.14-8.10 (m, 1H), 7.35 (s, 1H), 5.38-5.32 (m, 1H), 4.18 (s, 3H), 2.98-2.89 (m, 1H), 2.89-2.73 (m, 2H), 2.42-2.31 (m, 1H). LCMS (ESI) m/z: 445.0 $[M+H]^+$.

Example 1.11. Synthesis of (S)-1-Methyl-3-(trifluoromethyl)-N-(2-(2-(trifluoromethyl)pyridin-4-yl)-2,4,5,6,7,8-hexahydrocyclohepta[c]pyrazol-4-yl)-1H-pyrazole-5-carboxamide (I-45a) and (R)-1-Methyl-3-(trifluoromethyl)-N-(2-(2-(trifluoromethyl)pyridin-4-yl)-2,4,5,6,7,8-hexahydrocyclohepta[c]pyrazol-4-yl)-1H-pyrazole-5-carboxamide (I-45b)

Step 1—Synthesis of 3-(2-(2-(trifluoromethyl)pyridin-4-yl)hydrazinyl)cyclohept-2-en-1-one

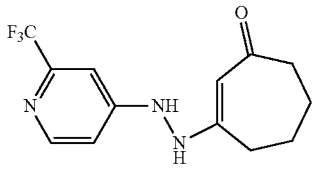 [SMILES: O=C1C=C(NNc2ccnc(C(F)(F)F)c2)CCCC1]

To a solution of [2-(trifluoromethyl)-4-pyridyl]hydrazine (3 g, 16.94 mmol) in EtOH (15 mL) and $H_2O$ (15 mL) was added cycloheptane-1,3-dione (2.14 g, 16.9 mmol) at 0° C. The mixture was stirred at 25° C. for 3 h. The reaction mixture was concentrated in vacuo and diluted with water (50 mL) and extracted with ethyl acetate (50 mL×2). The combined organic layers were washed with brine (50 mL), dried over anhydrous $Na_2SO_4$, filtered and concentrated in vacuo. The crude residue was purified by silica gel chromatography (solvent gradient: 0-30% EtOAc in petroleum ether) to give the title compound (2.4 g, 49.7%) as a brown solid. LCMS (ESI) m/z: 286.1 $[M+H]^+$.

Step 2—Synthesis of 2-(2-(Trifluoromethyl)pyridin-4-yl)-5,6,7,8-tetrahydrocyclohepta[c]pyrazol-4(2H)-one

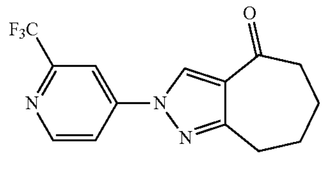 [SMILES: O=C1CCCCc2nn(-c3ccnc(C(F)(F)F)c3)cc21]

To a solution of 3-[2-[2-(trifluoromethyl)-4-pyridyl]hydrazino]cyclohept-2-en-1-one (2.4 g, 8.4 mmol) in THF (20 mL) was added DMF-DMA (3.2 mL, 25.2 mmol). The mixture was stirred at 70° C. for 16 h. After cooling to room temperature, the reaction was concentrated in vacuo and diluted with ethyl acetate (50 mL×2). The combined organic phase was washed with brine (50 mL×3), dried over anhydrous $Na_2SO_4$, filtered and concentrated in vacuo. The crude residue was purified by silica gel chromatography (solvent gradient: 0-30% EtOAc in petroleum ether) to give the title compound (350 mg, 14%) as a yellow solid. $^1$H NMR (400 MHz, DMSO-$d_6$) δ 9.34 (s, 1H), 8.85 (d, J=5.6 Hz, 1H), 8.43 (d, J=2.0 Hz, 1H), 8.25 (d, J=5.6 Hz, 1H), 3.07-3.01 (m, 2H), 2.74-2.69 (m, 2H), 1.96-1.85 (m, 4H). LCMS (ESI) m/z: 296.1 $[M+H]^+$.

Step 3—Synthesis of (rac)-2-(2-(Trifluoromethyl)pyridin-4-yl)-2,4,5,6,7,8-hexahydrocyclohepta[c]pyrazol-4-amine

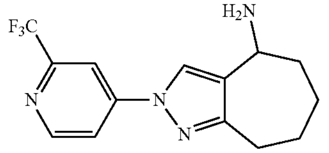 [SMILES: NC1CCCCc2nn(-c3ccnc(C(F)(F)F)c3)cc21]

To a solution of 2-(2-(trifluoromethyl)pyridin-4-yl)-5,6,7,8-tetrahydrocyclohepta[c]pyrazol-4(2H)-one (460 mg, 1.2 mmol) in MeOH (10 mL) was added $NH_4OAc$ (1.28 g, 5.0 mmol) and $NaBH_3CN$ (320 mg, 5.0 mmol). The mixture was stirred at room temperature for 16 h. The mixture was concentrated in vacuo. The crude residue was purified by silica gel chromatography (solvent gradient: 0-100% EtOAc in petroleum ether) to give the title compound (0.32 g, 70%) as a white solid. LCMS (ESI) m/z: 297.1 $[M+H]^+$.

Step 4—Synthesis of (rac)-1-Methyl-3-(trifluoromethyl)-N-(2-(2-(trifluoromethyl)pyridin-4-yl)-2,4,5,6,7,8-hexahydrocyclohepta[c]pyrazol-4-yl)-1H-pyrazole-5-carboxamide

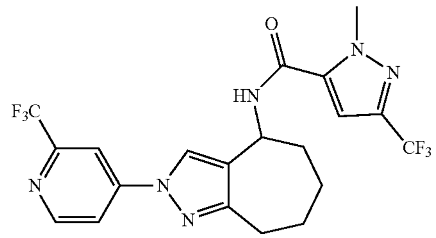

To a solution of 2-[2-(trifluoromethyl)-4-pyridyl]-5,6,7,8-tetrahydro-4H-cyclohepta[c]pyrazol-4-amine (260 mg, 781.4 μmol), 1-methyl-3-(trifluoromethyl)-1H-pyrazole-5-carboxylic acid (182 mg, 937.6 μmol) and DIEA (0.45 mL, 3.13 mmol) in DCM (5 mL) was added HATU (356 mg, 937.6 μmol). The reaction mixture was stirred at 25° C. for 1 h. The reaction was diluted with $H_2O$ (30 mL), and then extracted with DCM (30 mL×2). The combined organic layers were washed with brine (20 mL×2), dried over anhydrous $Na_2SO_4$, filtered and concentrated in vacuo. The residue was purified by reverse phase chromatography (acetonitrile 65-95%/0.225% formic acid in water) to give the title compound (160 mg, 43%) as a white solid. LCMS (ESI) m/z: 473.2 $[M+H]^+$.

Step 5—Synthesis of (S)-1-Methyl-3-(trifluoromethyl)-N-(2-(2-(trifluoromethyl)pyridin-4-yl)-2,4,5,6,7,8-hexahydrocyclohepta[c]pyrazol-4-yl)-1H-pyrazole-5-carboxamide (I-45a) and (R)-1-Methyl-3-(trifluoromethyl)-N-(2-(2-(trifluoromethyl)pyridin-4-yl)-2,4,5,6,7,8-hexahydrocyclohepta[c]pyrazol-4-yl)-1H-pyrazole-5-carboxamide (I-45b)

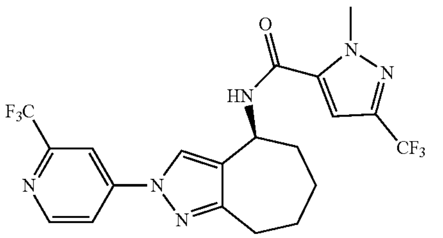

and

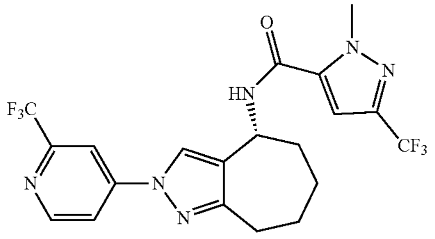 [SMILES: Cn1nc(C(F)(F)F)cc1C(=O)NC1CCCCc2nn(-c3ccnc(C(F)(F)F)c3)cc21]

A mixture of 2-methyl-5-(trifluoromethyl)-N-[2-[2-(trifluoromethyl)-4-pyridyl]-5,6,7,8-tetrahydro-4H-cyclohepta[c]pyrazol-4-yl]pyrazole-3-carboxamide (150 mg, 211.7 μmol) was separated by using chiral SFC (DAICEL CHIRALPAK AS (250 mm*30 mm, 10 μm); Supercritical $CO_2$/EtOH+0.1% $NH_3 \cdot H_2O$=90/10; 150 mL/min) to afford (R)-1-methyl-3-(trifluoromethyl)-N-(2-(2-(trifluoromethyl)pyridin-4-yl)-2,4,5,6,7,8-hexahydrocyclohepta[c]pyrazol-4-yl)-1H-pyrazole-5-carboxamide (58 mg, first peak) and (S)-1-methyl-3-(trifluoromethyl)-N-(2-(2-(trifluoromethyl)pyridin-4-yl)-2,4,5,6,7,8-hexahydrocyclohepta[c]pyrazol-4-yl)-1H-pyrazole-5-carboxamide (16 mg, second peak) both as white solid. First peak: (I-45b): $^1$H NMR (400 MHz, DMSO-$d_6$) δ 8.99 (d, J=8.0 Hz, 1H), 8.14 (d, J=6.4 Hz, 1H), 8.57 (s, 1H), 8.23 (d, J=4.0 Hz, 1H), 8.14-8.10 (m, 1H), 7.51 (s, 1H), 5.11-5.03 (m, 1H), 4.16 (s, 3H), 3.03-2.93 (m, 1H), 2.79-2.65 (m, 1H), 2.10-2.00 (m, 1H), 1.92-1.71 (m, 4H), 1.56-1.42 (m, 1H). LCMS (ESI) m/z: 473.1 $[M+H]^+$. Second peak: (I-45a): $^1$H NMR (400 MHz, DMSO-$d_6$) δ 8.99 (d, J=8.0 Hz, 1H), 8.14 (d, J=6.4 Hz, 1H), 8.57 (s, 1H), 8.23 (d, J=4.0 Hz, 1H), 8.14-8.10 (m, 1H), 7.51 (s, 1H), 5.11-5.03 (m, 1H), 4.16 (s, 3H), 3.03-2.93 (m, 1H), 2.79-2.65 (m, 1H), 2.10-2.00 (m, 1H), 1.92-1.71 (m, 4H), 1.56-1.42 (m, 1H). LCMS (ESI) m/z: 473.1 $[M+H]^+$.

Example 1.12. Synthesis of (rac)-1-Methyl-N-(2-(2-oxo-1,2-dihydropyridin-4-yl)-4,5,6,7-tetrahydro-2H-indazol-4-yl)-3-(trifluoromethyl)-1H-pyrazole-5-carboxamide (I-35)

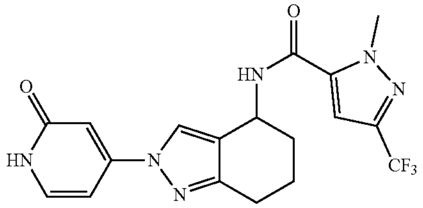 [SMILES: Cn1nc(C(F)(F)F)cc1C(=O)NC1CCCc2nn(-c3cc[nH]c(=O)c3)cc21]

To a solution of N-(2-(2-methoxypyridin-4-yl)-4,5,6,7-tetrahydro-2H-indazol-4-yl)-1-methyl-3-(trifluoromethyl)-1H-pyrazole-5-carboxamide (150 mg, 356.8 μmol) in acetonitrile (5 mL) was added TMSI (194.3 μL, 1.4 mmol). The reaction mixture was stirred at 65° C. for 2 h. After cooling to room temperature, the mixture was diluted with water (30 mL), $NaHCO_3$ (5 mL) was added to the mixture and extracted with ethyl acetate (30 mL×2). The combined organic layers were washed with brine (20 mL), dried over anhydrous $Na_2SO_4$, filtered, and concentrated in vacuo. The residue was purified by reverse phase chromatography (acetonitrile 35-65%/0.225% formic acid in water) to give the title compound (80 mg, 55%) as yellow oil. $^1$H NMR (400 MHz, DMSO-$d_6$) δ 11.56 (s, 1H), 8.92 (d, J=7.6 Hz, 1H), 8.46 (s, 1H), 7.46 (d, J=7.6 Hz, 1H), 7.39 (s, 1H), 6.80-6.75 (m, 1H), 6.66 (d, J=1.6 Hz, 1H), 5.25-5.01 (m, 1H), 4.19 (s, 3H), 2.76-2.71 (m, 2H), 2.05-1.95 (m, 2H), 1.84-1.61 (m, 2H). LCMS (ESI) m/z: 407.1$[M+H]^+$.

Example 1.13. Synthesis of Additional Exemplary Compounds

Compounds of the present disclosure, such as a compound of a formula included in any one of Tables 2-6, may be synthesized according to one of the general routes outlined in Examples 1.1 to 1.12 or by various other methods generally known in the art.

TABLE 2

Selected compounds of the present disclosure.

| Compound No. | Structure | Analytical data | Separation conditions |
|---|---|---|---|
| I-36 | 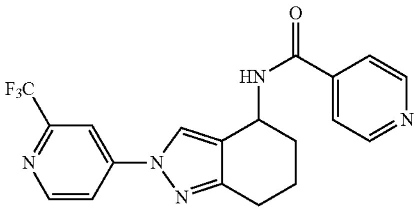 [SMILES: O=C(NC1CCCc2nn(-c3ccnc(C(F)(F)F)c3)cc21)c1ccncc1] (rac)-N-(2-(2-(Trifluoromethyl)pyridin-4-yl)-4,5,6,7-tetrahydro-2H-indazol-4-yl)isonicotinamide | LCMS (ESI) m/z: 388.0 $[M + H]^+$. $^1$H NMR (400 MHz, DMSO-$d_6$) δ 9.07 (d, J = 8.0 Hz, 1H), 8.78-8.73 (m, 4H), 8.30-8.28 (d, J = 2.0 Hz, 1H), 8.15-8.10 (m, 1H), 7.87-7.82 (m, 2H), 5.36-5.13 (m, 1H), 2.86-2.63 (m, 2H), 2.07-2.00 (m, 2H), 1.89-1.60 (m, 2H). | acetonitrile 0-20%/ 0.225% formic acid in water |

TABLE 2-continued

| Selected compounds of the present disclosure. | | | |
|---|---|---|---|
| Compound No. | Structure | Analytical data | Separation conditions |
| I-29 | 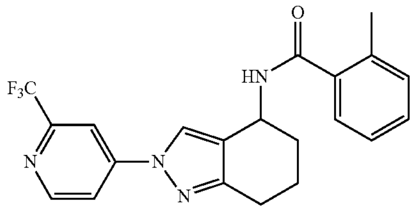 [SMILES: Cc1ccccc1C(=O)NC1CCCc2nn(-c3ccnc(C(F)(F)F)c3)cc21] (rac)-2-Methyl-N-(2-(2-(trifluoromethyl)pyridin-4-yl)-4,5,6,7-tetrahydro-2H-indazol-4-yl)benzamide | LCMS (ESI) m/z: 401.0 $[M+H]^+$. $^1H$ NMR (400 MHz, DMSO-$d_6$) δ 8.77 (d, J = 5.2 Hz, 1H), 8.74 (s, 1H), 8.55 (d, J = 8.4 Hz, 1H), 8.31 (d, J = 2.0 Hz, 1H), 8.19-8.09 (m, 1H), 7.42 (d, J = 8.0 Hz, 1H), 7.36-7.29 (m, 1H), 7.27-7.19 (m, 2H), 5.22-5.11 (m, 1H), 2.78-2.61 (m, 2H), 2.39 (s, 3H), 2.10-1.95 (m, 2H), 1.85-1.61 (m, 2H). | acetonitrile 0-49%/ 0.225% formic acid in water |
| I-24 | 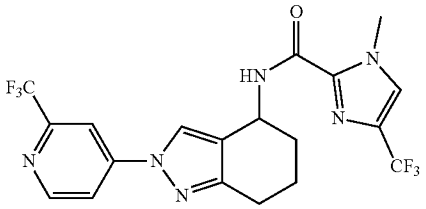 (rac)-1-Methyl-4-(trifluoromethyl)-N-(2-(2-(trifluoromethyl)pyridin-4-yl)-4,5,6,7-tetrahydro-2H-indazol-4-yl)-1H-imidazole-2-carboxamide | LCMS (ESI) m/z: 459.0 $[M+H]^+$. $^1H$ NMR (400 MHz, DMSO-$d_6$) δ 8.86 (d, J = 8.0 Hz, 1H), 8.75 (d, J = 5.6 Hz, 1H), 8.68 (s, 1H), 8.28 (d, J = 2.0 Hz, 1H), 8.16-8.10 (m, 1H), 8.07 (s, 1H), 5.20-5.10 (m, 1H), 4.04 (s, 3H), 2.82-2.60 (m, 2H), 2.11-1.68 (m, 4H). | acetonitrile 0-61%/ 0.225% formic acid in water |
| I-22 | 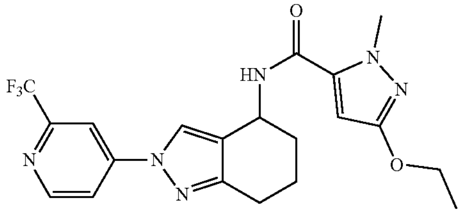 [SMILES: CCOc1cc(C(=O)NC2CCCc3nn(-c4ccnc(C(F)(F)F)c4)cc32)n(C)n1] (rac)-3-Ethoxy-1-methyl-N-(2-(2-(trifluoromethyl)pyridin-4-yl)-4,5,6,7-tetrahydro-2H-indazol-4-yl)-1H-pyrazole-5-carboxamide | LCMS (ESI) m/z: 435.1 $[M+H]^+$. $^1H$ NMR (400 MHz, DMSO-$d_6$) δ 8.76 (d, J = 5.2 Hz, 1H), 8.74 (s, 1H), 8.66 (d, J = 7.6 Hz, 1H), 8.31 (d, J = 7.6 Hz, 1H), 8.15-8.10 (m, 1H), 6.35 (s, 1H), 5.19-5.11 (m, 1H), 4.07 (q, J = 7.2 Hz, 2H), 3.96 (s, 3H), 2.76-2.63 (m, 2H), 2.12-1.93 (m, 2H), 1.85-1.61 (m, 2H), 1.28 (t, J = 7.2 Hz, 2H). | acetonitrile 0-54%/ 0.225% formic acid in water |
| I-12 | 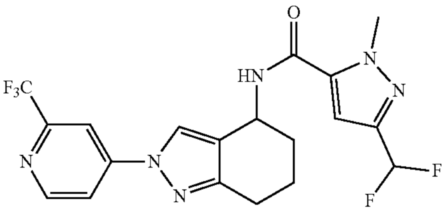 [SMILES: Cn1nc(C(F)F)cc1C(=O)NC1CCCc2nn(-c3ccnc(C(F)(F)F)c3)cc21] (rac)-3-(Difluoromethyl)-1-methyl-N-(2-(2-(trifluoromethyl)pyridin-4-yl)-4,5,6,7-tetrahydro-2H-indazol-4-yl)-1H-pyrazole-5-carboxamide | LCMS (ESI) m/z: 441.2 $[M+H]^+$. $^1H$ NMR (400 MHz, DMSO-$d_6$) δ 8.91 (d, J = 8.0 Hz, 1H), 8.77 (d, J = 5.2 Hz, 1H), 8.75 (s, 1H), 8.28 (d, J = 2.0 Hz, 1H), 8.14-8.10 (m, 1H), 7.22 (s, 1H), 7.02 (t, J = 80.0 Hz, 1H), 5.22-5.13 (m, 1H), 4.16 (s, 3H), 2.81-2.66 (m, 2H), 2.10-1.95 (m, 2H), 1.86-1.65 (m, 2H). | acetonitrile 49%-79%/ 0.225% formic acid in water |

TABLE 2-continued

Selected compounds of the present disclosure.

| Compound No. | Structure | Analytical data | Separation conditions |
|---|---|---|---|
| I-19 | 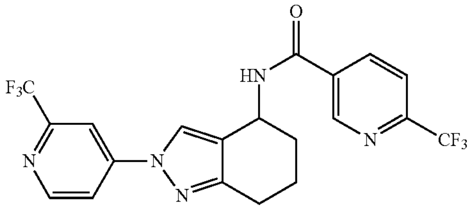 (rac)-6-(Trifluoromethyl)-N-(2-(2-(trifluoromethyl)pyridin-4-yl)-4,5,6,7-tetrahydro-2H-indazol-4-yl)nicotinamide | LCMS (ESI) m/z: 456.2 $[M + H]^+$. $^1H$ NMR (400 MHz, DMSO-$d_6$) δ 9.25-9.19 (m, 2H), 8.80 (s, 1H), 8.77 (d, J = 8.0 Hz, 1H), 8.55-8.50 (m, 1H), 8.27 (d, J = 2.0 Hz, 1H), 8.14-8.10 (m, 1H), 8.08 (d, J = 8.0 Hz, 1H), 5.29-5.21 (m, 1H), 2.82-2.70 (m, 2H), 2.12-2.01 (m, 2H), 1.89-1.64 (m, 2H). | acetonitrile 50%-80%/ 0.225% formic acid in water |
| I-9a | 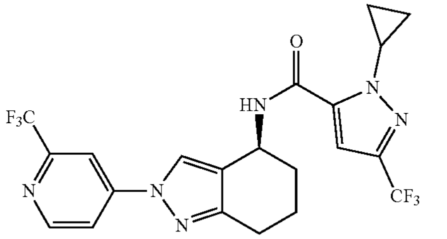 [SMILES: O=C(N[C@H]1CCCc2nn(-c3ccnc(C(F)(F)F)c3)cc21)c1cc(C(F)(F)F)nn1C1CC1] (S)-1-Cyclopropyl-3-(trifluoromethyl)-N-(2-(2-(trifluoromethyl)pyridin-4-yl)-4,5,6,7-tetrahydro-2H-indazol-4-yl)-1H-pyrazole-5-carboxamide | LCMS (ESI) m/z: 485.2 $[M + H]^+$. $^1H$ NMR (400 MHz, DMSO-$d_6$) δ 8.98 (d, J = 8.0 Hz, 1H), 8.79-8.75 (m, 2H), 8.28 (d, J = 2.0 Hz, 1H), 8.15-8.09 (m, 1H), 7.35 (s, 1H), 5.23-5.16 (m, 1H), 4.67-4.58 (m, 1H), 2.76-2.69 (m, 2H), 2.08-1.98 (m, 2H), 1.86-1.67 (m, 2H), 1.22-1.14 (m, 2H), 1.11-1.03 (m, 2H). | acetonitrile 50%-80%/ 0.225% formic acid in water |
| I-17 | 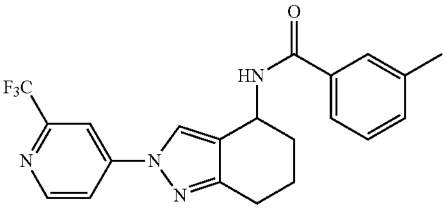 [SMILES: Cc1cccc(C(=O)NC2CCCc3nn(-c4ccnc(C(F)(F)F)c4)cc32)c1] (rac)-3-Methyl-N-(2-(2-(trifluoromethyl)pyridin-4-yl)-4,5,6,7-tetrahydro-2H-indazol-4-yl)benzamide | LCMS (ESI) m/z: 401.1 $[M + H]^+$. $^1H$ NMR (400 MHz, DMSO-$d_6$) δ 8.75 (d, J = 5.6 Hz, 1H), 8.73 (s, 1H), 8.68 (d, J = 8.0 Hz, 1H), 8.30 (d, J = 2.0 Hz, 1H), 8.14-8.13 (m, 1H), 7.76 (s, 1H), 7.74-7.68 (m, 1H), 7.36-7.31 (m, 2H), 5.27-5.18 (m, 1H), 2.77-2.66 (m, 2H), 2.35 (s, 3H), 2.09-1.95 (m, 2H), 1.85-1.66 (m, 2H). | acetonitrile 0%-35%/ 0.225% formic acid in water |
| I-4 | 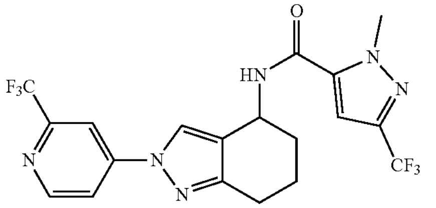 [SMILES: Cn1nc(C(F)(F)F)cc1C(=O)NC1CCCc2nn(-c3ccnc(C(F)(F)F)c3)cc21] (rac)-1-Methyl-3-(trifluoromethyl)-N-(2-(2-(trifluoromethyl)pyridin-4-yl)-4,5,6,7-tetrahydro-2H-indazol-4-yl)-1H-pyrazole-5-carboxamide | LCMS (ESI) m/z: 459.1 $[M + H]^+$. $^1H$ NMR (400 MHz, DMSO-$d_6$) δ 8.97 (d, J = 8.0 Hz, 1H), 8.76 (d, J = 5.6 Hz, 1H), 8.74 (s, 1H), 8.27 (d, J = 2.0 Hz, 1H), 8.14-8.09 (m, 1H), 7.40 (s, 1H), 5.25-5.09 (m, 1H), 4.20 (s, 3H), 2.84-2.63 (m, 2H), 2.13-1.97 (m, 2H), 1.87-1.60 (m, 2H). | acetonitrile 51%-81%/ 0.225% formic acid in water |

TABLE 2-continued

| Compound No. | Structure | Analytical data | Separation conditions |
|---|---|---|---|
| Selected compounds of the present disclosure. | | | |
| I-20 | 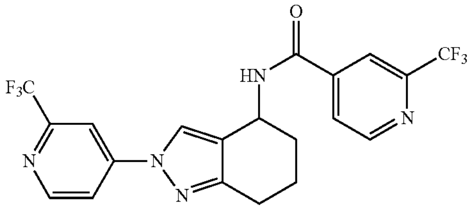 [SMILES: O=C(NC1CCCc2nn(-c3ccnc(C(F)(F)F)c3)cc21)c1ccnc(C(F)(F)F)c1] (rac)-2-(Trifluoromethyl)-N-(2-(2-(trifluoromethyl)pyridin-4-yl)-4,5,6,7-tetrahydro-2H-indazol-4-yl)isonicotinamide | LCMS (ESI) m/z: 456.0 $[M + H]^+$. $^1H$ NMR (400 MHz, DMSO-$d_6$) δ 9.31 (d, J = 8.0 Hz, 1H), 8.96 (d, J = 4.8 Hz, 1H), 8.78 (s, 1H), 8.76 (d, J = 5.6 Hz, 1H), 8.35 (s, 1H), 8.27 (d, J = 1.6 Hz, 1H), 8.16 (d, J = 5.2 Hz, 1H), 8.13-8.09 (m, 1H), 5.28-5.20 (m, 1H), 2.79-2.68 (m, 2H), 2.08-2.02 (m, 2H), 1.87-1.69 (m, 2H). | acetonitrile 50%-80%/ 0.225% formic acid in water |
| I-23 | 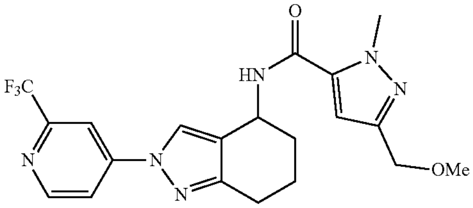 [SMILES: COCc1cc(C(=O)NC2CCCc3nn(-c4ccnc(C(F)(F)F)c4)cc32)n(C)n1] (rac)-3-(Methoxymethyl)-1-methyl-N-(2-(2-(trifluoromethyl)pyridin-4-yl)-4,5,6,7-tetrahydro-2H-indazol-4-yl)-1H-pyrazole-5-carboxamide | LCMS (ESI) m/z: 435.0 $[M + H]^+$. $^1H$ NMR (400 MHz, DMSO-$d_6$) δ 8.78-8.72 (m, 3H), 8.29 (d, J = 1.6 Hz, 1H), 8.14-8.11 (m, 1H), 6.92 (s, 1H), 5.19-5.12 (m, 1H), 4.32 (s, 2H), 4.08 (s, 3H), 3.24 (s, 3H), 2.80-2.62 (m, 2H), 2.10-1.95 (m, 2H), 1.83-1.62 (m, 2H). | acetonitrile 43%-73%/ 0.225% formic acid in water |
| I-21 | 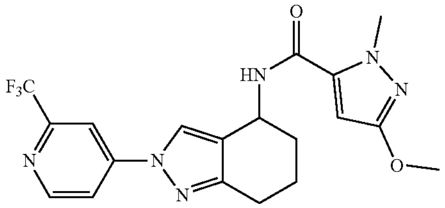 [SMILES: COc1cc(C(=O)NC2CCCc3nn(-c4ccnc(C(F)(F)F)c4)cc32)n(C)n1] (rac)-3-Methoxy-1-methyl-N-(2-(2-(trifluoromethyl)pyridin-4-yl)-4,5,6,7-tetrahydro-2H-indazol-4-yl)-1H-pyrazole-5-carboxamide | LCMS (ESI) m/z: 421.0 $[M + H]^+$. $^1H$ NMR (400 MHz, DMSO-$d_6$) δ 8.81-8.60 (m, 3H), 8.29 (d, J = 2.0 Hz, 1H), 8.18-8.04 (m, 1H), 6.36 (s, 1H), 5.22-5.08 (m, 1H), 3.97 (s, 3H), 3.75 (s, 3H), 2.85-2.58 (m, 2H), 2.13-1.91 (m, 2H), 1.86-1.60 (m, 2H). | acetonitrile 40-80%/ 0.225% formic acid in water |
| I-31 | 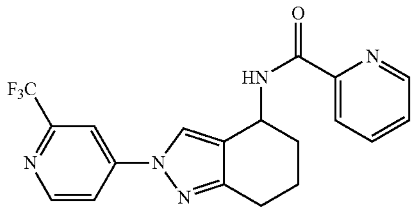 [SMILES: O=C(NC1CCCc2nn(-c3ccnc(C(F)(F)F)c3)cc21)c1ccccn1] (rac)-N-(2-(2-(Trifluoromethyl)pyridin-4-yl)-4,5,6,7-tetrahydro-2H-indazol-4-yl)picolinamide | LCMS (ESI) m/z: 388.0 $[M + H]^+$. $^1H$ NMR (400 MHz, DMSO-$d_6$) δ 8.85 (d, J = 8.4 Hz, 1H), 8.73 (d, J = 5.2 Hz, 1H), 8.70 (s, 1H), 8.66-8.62 (m, 1H), 8.28 (d, J = 2.0 Hz, 1H), 8.14-8.09 (m, 2H), 8.05-7.99 (m, 1H), 7.64-7.60 (m, 1H), 5.26-5.18 (m, 1H), 2.79-2.63 (m, 2H), 2.07-1.98 (m, 2H), 1.89-1.74 (m, 2H). | acetonitrile 40-80%/ 0.225% formic acid in water |

TABLE 2-continued

Selected compounds of the present disclosure.

| Compound No. | Structure | Analytical data | Separation conditions |
|---|---|---|---|
| I-11 | 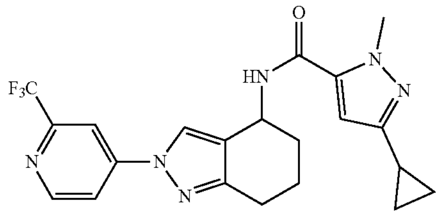 [SMILES: Cn1nc(C2CC2)cc1C(=O)NC1CCCc2nn(-c3ccnc(C(F)(F)F)c3)cc21] (rac)-3-Cyclopropyl-1-methyl-N-(2-(2-(trifluoromethyl)pyridin-4-yl)-4,5,6,7-tetrahydro-2H-indazol-4-yl)-1H-pyrazole-5-carboxamide | LCMS (ESI) m/z: 431.1 $[M + H]^+$. $^1H$ NMR (400 MHz, DMSO-$d_6$) δ 8.75 (d, J = 5.2 Hz, 1H), 8.60 (d, J = 8.0 Hz, 1H), 8.28 (d, J = 2.0 Hz, 1H), 8.18-8.09 (m, 1H), 6.62 (s, 1H), 5.23-5.05 (m, 1H), 4.01 (s, 3H), 2.80-2.76 (m, 1H), 2.07-1.94 (m, 2H), 1.88-1.77 (m, 1H), 0.92-0.80 (m, 2H), 0.63-0.52 (m, 2H). | acetonitrile 40-80%/ 0.225% formic acid in water |
| I-13 | 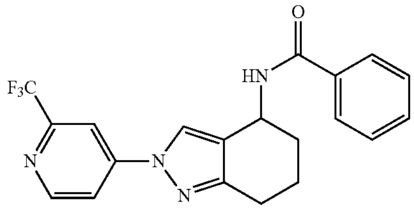 [SMILES: O=C(NC1CCCc2nn(-c3ccnc(C(F)(F)F)c3)cc21)c1ccccc1] (rac)-N-(2-(2-(Trifluoromethyl)pyridin-4-yl)-4,5,6,7-tetrahydro-2H-indazol-4-yl)benzamide | LCMS (ESI) m/z: 387.0 $[M + H]^+$. $^1H$ NMR (400 MHz, DMSO-$d_6$) δ 8.79-8.68 (m, 3H), 8.30 (d, J = 2.0 Hz, 1H), 8.17-8.11 (m, 1H), 7.95-7.90 (m, 2H), 7.57-7.41 (m, 3H), 5.31-5.16 (m, 1H), 2.81-2.62 (m, 2H), 2.12-1.93 (m, 2H), 1.87-1.60 (m, 2H). | acetonitrile 39-69%/ 0.05% $NH_3H_2O$ + 10 mM $NH_4HCO_3$ in water |
| I-16 | 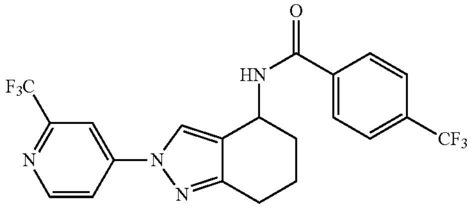 [SMILES: O=C(NC1CCCc2nn(-c3ccnc(C(F)(F)F)c3)cc21)c1ccc(C(F)(F)F)cc1] (rac)-4-(Trifluoromethyl)-N-(2-(2-(trifluoromethyl)pyridin-4-yl)-4,5,6,7-tetrahydro-2H-indazol-4-yl)benzamide | LCMS (ESI) m/z: 455.0 $[M + H]^+$. $^1H$ NMR (400 MHz, DMSO-$d_6$) δ 9.00 (d, J = 8.0 Hz, 1H), 8.80-8.72 (m, 2H), 8.28 (d, J = 2.0 Hz, 1H), 8.12 (m, 3H), 7.86 (d, J = 8.4 Hz, 2H), 5.28-5.18 (m, 1H), 2.74-2.66 (m, 2H), 2.10-1.99 (m, 2H), 1.85-1.68 (m, 2H). | acetonitrile 40%-80%/ 0.225% formic acid in water |
| I-32 | 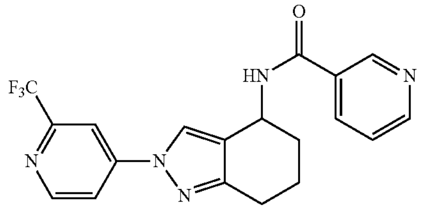 [SMILES: O=C(NC1CCCc2nn(-c3ccnc(C(F)(F)F)c3)cc21)c1cccnc1] (rac)-N-(2-(2-(Trifluoromethyl)pyridin-4-yl)-4,5,6,7-tetrahydro-2H-indazol-4-yl)nicotinamide | LCMS (ESI) m/z: 388.0 $[M + H]^+$. $^1H$ NMR (400 MHz, DMSO-$d_6$) δ 9.01 (d, J = 8.0 Hz, 1H), 8.82-8.71 (m, 2H), 8.28 (s, 1H), 8.14-8.08 (m, 3H), 7.85 (d, J = 8.0 Hz, 2H), 5.28-5.18 (m, 1H), 2.76-2.66 (m, 2H), 2.10-1.99 (m, 2H), 1.85-1.68 (m, 2H). | acetonitrile 40%-80%/ 0.225% formic acid in water |
| I-26 | 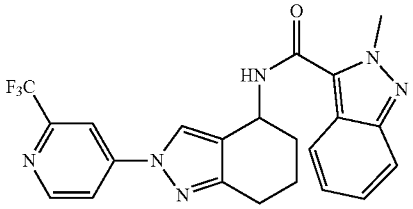 [SMILES: Cn1nc2ccccc2c1C(=O)NC1CCCc2nn(-c3ccnc(C(F)(F)F)c3)cc21] (rac)-2-Methyl-N-(2-(2-(trifluoromethyl)pyridin-4-yl)-4,5,6,7-tetrahydro-2H-indazol-4-yl)-2H-indazole-3-carboxamide | LCMS (ESI) m/z: 441.0 $[M + H]^+$. $^1H$ NMR (400 MHz, DMSO-$d_6$) δ 8.93 (d, J = 7.6 Hz, 1H), 8.83 (s, 1H), 8.77 (d, J = 6.4 Hz, 1H), 8.29 (s, 1H), 8.15 (d, J = 4.4 Hz, 1H), 7.79 (d, J = 8.4 Hz, 1H), 7.67 (d, J = 8.4 Hz, 1H), 7.35-7.25 (m, 1H), 7.23-7.13 (m, 1H), 5.28-5.18 (m, 1H), 4.35 (s, 3H), 2.76-2.66 (m, 2H), 2.10-1.97 (m, 2H), 1.89-1.71 (m, 2H). | acetonitrile 40%-80%/ 0.225% formic acid in water |

TABLE 2-continued

Selected compounds of the present disclosure.

| Compound No. | Structure | Analytical data | Separation conditions |
|---|---|---|---|
| I-10 | 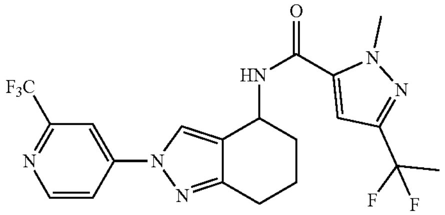 [SMILES: Cn1nc(C(C)(F)F)cc1C(=O)NC1CCCc2nn(-c3ccnc(C(F)(F)F)c3)cc21] (rac)-3-(1,1-Difluoroethyl)-1-methyl-N-(2-(2-(trifluoromethyl)pyridin-4-yl)-4,5,6,7-tetrahydro-2H-indazol-4-yl)-1H-pyrazole-5-carboxamide | LCMS (ESI) m/z: 455.7 $[M + H]^+$. $^1H$ NMR (400 MHz, DMSO-$d_6$) δ 8.88 (d, J = 8.0 Hz, 1H), 8.76 (d, J = 5.6 Hz, 1H), 8.73 (s, 1H), 8.28 (d, J = 2.0 Hz, 1H), 8.14-8.10 (m, 1H), 7.19 (s, 1H), 5.18-5.12 (m, 1H), 4.15 (s, 3H), 2.74-2.66 (m, 2H), 2.07-1.92 (m, 5H), 1.84-1.66 (m, 2H). | acetonitrile 55-85%/ 0.225% formic acid in water |
| I-7 | 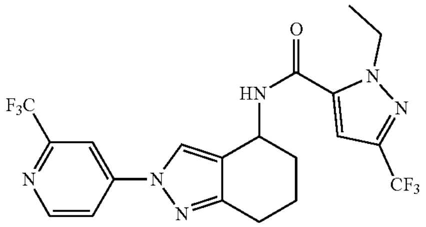 [SMILES: CCn1nc(C(F)(F)F)cc1C(=O)NC1CCCc2nn(-c3ccnc(C(F)(F)F)c3)cc21] (rac)-1-Ethyl-3-(trifluoromethyl)-N-(2-(2-(trifluoromethyl)pyridin-4-yl)-4,5,6,7-tetrahydro-2H-indazol-4-yl)-1H-pyrazole-5-carboxamide | LCMS (ESI) m/z: 473.0 $[M + H]^+$. $^1H$ NMR (400 MHz, DMSO-$d_6$) δ 8.99 (d, J = 8.0 Hz, 1H), 8.81-8.75 (m, 2H), 8.28 (d, J = 2.0 Hz, 1H), 8.19-8.09 (m, 1H), 7.41 (s, 1H), 5.24-5.11 (m, 1H), 4.74-4.61 (m, 2H), 2.81-2.67 (m, 2H), 2.13-1.99 (m, 2H), 1.85-1.63 (m, 2H), 1.41 (t, J = 7.2 Hz, 1H). | acetonitrile 40-80%/ 0.225% formic acid in water |
| I-8 | 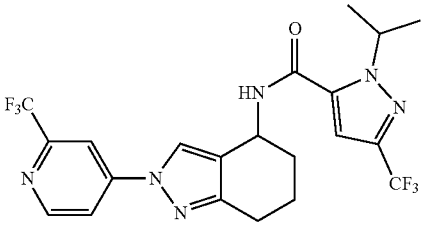 [SMILES: CC(C)n1nc(C(F)(F)F)cc1C(=O)NC1CCCc2nn(-c3ccnc(C(F)(F)F)c3)cc21] (rac)-1-Isopropyl-3-(trifluoromethyl)-N-(2-(2-(trifluoromethyl)pyridin-4-yl)-4,5,6,7-tetrahydro-2H-indazol-4-yl)-1H-pyrazole-5-carboxamide | LCMS (ESI) m/z: 487.6 $[M + H]^+$. $^1H$ NMR (400 MHz, DMSO-$d_6$) δ 8.96 (d, J = 8.0 Hz, 1H), 8.79-8.73 (m, 2H), 8.27 (d, J = 2.0 Hz, 1H), 8.14-8.09 (m, 1H), 7.35 (s, 1H), 5.68-5.59 (m, 1H), 5.21-5.12 (m, 1H), 2.76-2.64 (m, 2H), 2.09-1.96 (m, 2H), 1.85-1.65 (m, 2H), 1.47-1.41 (m, 6H). | acetonitrile 55-95%/ 0.225% formic acid in water |
| I-49a | 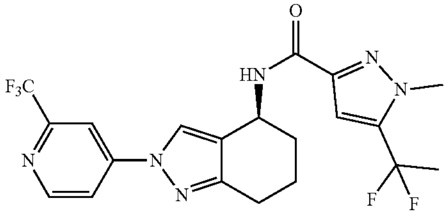 [SMILES: Cn1nc(C(=O)N[C@H]2CCCc3nn(-c4ccnc(C(F)(F)F)c4)cc32)cc1C(C)(F)F] (S)-1-Methyl-3-(trifluoromethyl)-N-(2-(2-(trifluoromethyl)pyridin-4-yl)-4,5,6,7-tetrahydrobenzo[b]thiophen-7-yl)-1H-pyrazole-5-carboxamide | LCMS (ESI) m/z: 455.1 $[M + H]^+$. $^1H$ NMR (400 MHz, DMSO-$d_6$) δ 8.74 (d, J = 5.6 Hz, 1H), 8.67 (s, 1H), 8.44 (d, J = 8.4 Hz, 1H), 8.29 (d, J = 2.0 Hz, 1H), 8.14-8.10 (m, 1H), 7.10 (s, 1H), 5.22-5.14 (m, 1H), 3.98 (s, 3H), 2.82-2.58 (m, 2H), 2.20-2.05 (m, 3H), 2.04-1.88 (m, 2H), 1.83-1.70 (m, 2H). | acetonitrile 65-95%/ 0.225% formic acid in water |

TABLE 2-continued

| Compound No. | Structure | Analytical data | Separation conditions |
|---|---|---|---|
| I-112a | 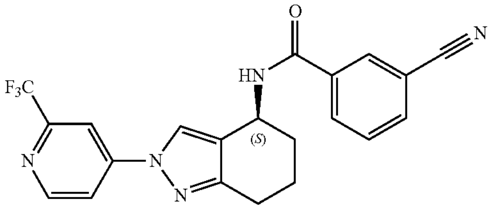 (S)-3-Cyano-N-(2-(2-(trifluoromethyl)pyridin-4-yl)-4,5,6,7-tetrahydro-2H-indazol-4-yl)benzamide | LCMS (ESI) m/z: 412.0 $[M + H]^+$. $^1H$ NMR (400 MHz, DMSO-$d_6$) δ 8.98 (d, J = 8.0 Hz, 1H), 8.81-8.72 (m, 2H), 8.41-8.34 (m, 1H), 8.29 (d, J = 2.0 Hz, 1H), 8.26-8.22 (m, 1H), 8.15-8.11 (m, 1H), 8.05-8.01 (m, 1H), 7.76-7.72 (m, 1H), 5.26-5.18 (m, 1H), 2.83-2.65 (m, 2H), 2.14-1.95 (m, 2H), 1.90-1.61 (m, 2H). | acetonitrile 50%-80%/0.225% formic acid in water |
| I-2a | 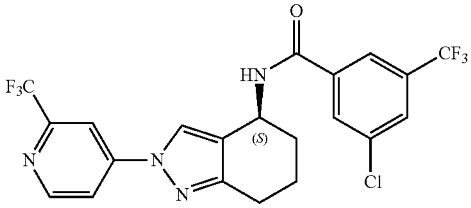 (S)-3-Chloro-5-(trifluoromethyl)-N-(2-(2-(trifluoromethyl)pyridin-4-yl)-4,5,6,7-tetrahydro-2H-indazol-4-yl)benzamide | LCMS (ESI) m/z: 488.9 $[M + H]^+$. $^1H$ NMR (400 MHz, DMSO-$d_6$) δ 9.14 (d, J = 8.0 Hz, 1H), 8.84-8.67 (m, 2H), 8.29 (s, 1H), 8.26 (d, J = 1.6 Hz, 1H), 8.24 (s, 1H), 8.14-8.10 (m, 1H), 8.09-8.07 (m, 1H), 5.27-5.19 (m, 1H), 2.79-2.65 (m, 2H), 2.09-1.98 (m, 2H), 1.85-1.66 (m, 2H). | acetonitrile 70%-100%/0.225% formic acid in water |
| I-25 | 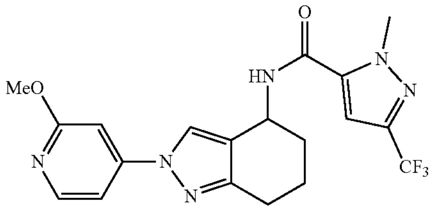 [SMILES: COc1cc(-n2cc3c(n2)CCCC3NC(=O)c2cc(C(F)(F)F)nn2C)ccn1] (rac)-N-(2-(2-Methoxypyridin-4-yl)-4,5,6,7-tetrahydro-2H-indazol-4-yl)-1-methyl-3-(trifluoromethyl)-1H-pyrazole-5-carboxamide | LCMS (ESI) m/z: 421.1 $[M + H]^+$. $^1H$ NMR (400 MHz, DMSO-$d_6$) δ 8.94 (d, J = 8.0 Hz, 1H), 8.55 (s, 1H), 8.17 (d, J = 6.0 Hz, 1H), 7.51-8.42 (m, 1H), 7.39 (s, 1H), 7.51-7.42 (m, 1H), 7.21-7.17 (m, 1H), 4.19 (s, 3H), 3.87 (s, 3H), 2.71-2.65 (m, 2H), 2.03-1.96 (m, 2H), 1.80-1.65 (m, 2H). | acetonitrile 30%-50%/0.225% formic acid in water |
| I-1 | 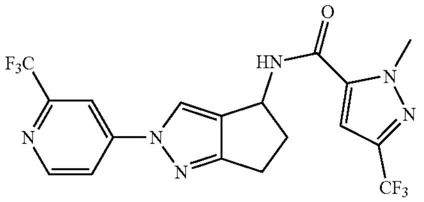 (rac)-1-Methyl-3-(trifluoromethyl)-N-(2-(2-(trifluoromethyl)pyridin-4-yl)-2,4,5,6-tetrahydrocyclopenta[c]pyrazol-4-yl)-1H-pyrazole-5-carboxamide | LCMS (ESI) m/z: 445.0 $[M + H]^+$. $^1H$ NMR (400 MHz, DMSO-$d_6$) δ 9.03 (d, J = 7.6 Hz, 1H), 8.76 (d, J = 5.6 Hz, 1H), 8.65 (s, 1H), 8.27 (d, J = 1.6 Hz, 1H), 8.13-8.08 (m, 1H), 7.35 (s, 1H), 5.48-5.22 (m, 1H), 4.18 (s, 3H), 2.98-2.89 (m, 1H), 2.86-2.73 (m, 2H), 2.42-2.31 (m, 1H). | acetonitrile 39-69%/0.05% $NH_3H_2O$ + 10 mM $NH_4HCO_3$ in water |

TABLE 2-continued

| Selected compounds of the present disclosure. | | | |
|---|---|---|---|
| Compound No. | Structure | Analytical data | Separation conditions |
| I-45 | 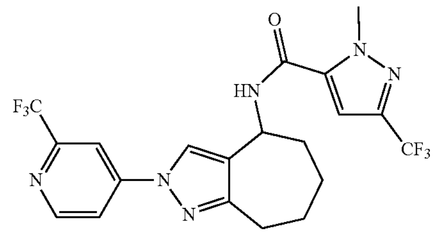 [SMILES: Cn1nc(C(F)(F)F)cc1C(=O)NC1CCCCc2nn(-c3ccnc(C(F)(F)F)c3)cc21] (rac)-1-Methyl-3-(trifluoromethyl)-N-(2-(2-(trifluoromethyl)pyridin-4-yl)-2,4,5,6,7,8-hexahydrocyclohepta[c]pyrazol-4-yl)-1H-pyrazole-5-carboxamide | LCMS (ESI) m/z: 473.6 $[M + H]^+$. $^1H$ NMR (400 MHz, DMSO-$d_6$) δ 8.99 (d, J = 8.4 Hz, 1H), 8.75 (d, J = 5.6 Hz, 1H), 8.57 (s, 1H), 8.24 (s, 1H), 8.12 (d, J = 5.6 Hz, 1H), 7.51 (s, 1H), 5.12-5.03 (m, 1H), 4.16 (s, 3H), 3.05-2.93 (m, 1H), 2.79-2.68 (m, 1H), 2.11-1.99 (m, 1H), 1.93-1.70 (m, 4H), 1.55-1.43 (m, 1H). | acetonitrile 55%-95%/0.225% formic acid in water |
| I-53a | 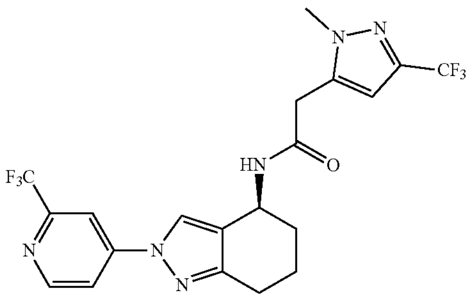 [SMILES: Cn1nc(C(F)(F)F)cc1CC(=O)N[C@H]1CCCc2nn(-c3ccnc(C(F)(F)F)c3)cc21] (S)-2-(1-Methyl-3-(trifluoromethyl)-1H-pyrazol-5-yl)-N-(2-(2-(trifluoromethyl)pyridin-4-yl)-4,5,6,7-tetrahydro-2H-indazol-4-yl)acetamide | LCMS (ESI) m/z: 473.1 $[M + H]^+$. $^1H$ NMR (400 MHz, DMSO-$d_6$) δ 8.78 (d, J = 5.6 Hz, 1H), 8.70 (s, 1H), 8.60 (d, J = 8.0 Hz, 1H), 8.27 (d, J = 2.0 Hz, 1H), 8.11 (m, 1H), 6.59 (s, 1H), 5.10-4.80 (m, 1H), 3.86 (s, 3H), 3.69 (s, 2H), 2.77-2.63 (m, 2H), 2.05-1.89 (m, 2H), 1.85-1.57 (m, 2H) | acetonitrile 53%-83%/0.225% formic acid in water |

TABLE 3

| Selected compounds of the present disclosure. | | | |
|---|---|---|---|
| Compound No. | Structure | Analytical data | Separation conditions |
| I-30 | 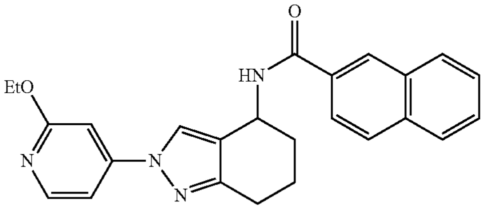 [SMILES: CCOc1cc(-n2cc3c(n2)CCCC3NC(=O)c2ccc3ccccc3c2)ccn1] (rac)-N-(2-(2-Ethoxypyridin-4-yl)-4,5,6,7-tetrahydro-2H-indazol-4-yl)-2-naphthamide | LCMS (ESI) m/z: 413.1 $[M + H]^+$. $^1H$ NMR (400 MHz, DMSO-$d_6$) δ 8.88 (d, J = 8.0 Hz, 1H), 8.54 (d, J = 16.8 Hz, 2H), 8.14 (d, J = 5.6 Hz, 1H), 8.05-7.94 (m, 4H), 7.66-7.54 (m, 2H), 7.48-7.43 (m, 1H), 7.19 (d, J = 1.2 Hz, 1H), 5.29-5.22 (m, 1H), 4.31 (q, J = 7.2 Hz, 2H), 2.73-2.66 (m, 2H), 2.11-2.02 (m, 2H), 1.82-1.72 (m, 2H), 1.30 (t, J = 7.2, Hz 3H). | acetonitrile 50%-90%/0.225% formic acid in water |

TABLE 3-continued

| Selected compounds of the present disclosure. | | | |
|---|---|---|---|
| Compound No. | Structure | Analytical data | Separation conditions |
| I-28 | 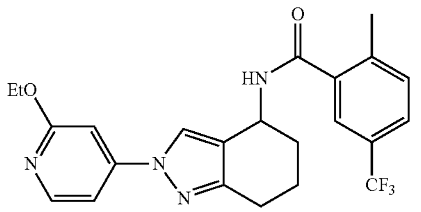 [SMILES: CCOc1cc(-n2cc3c(n2)CCCC3NC(=O)c2cc(C(F)(F)F)ccc2C)ccn1] (rac)-N-(2-(2-Ethoxypyridin-4-yl)-4,5,6,7-tetrahydro-2H-indazol-4-yl)-2-methyl-5-(trifluoromethyl)benzamide | LCMS (ESI) m/z: 445.1 $[M + H]^+$. $^1H$ NMR (400 MHz, DMSO-$d_6$) 8.81 (d, J = 8.0 Hz, 1H), 8.58 (s, 1H), 8.16 (d, J = 6.0 Hz, 1H), 7.73-7.64 (m, 2H), 7.51-7.42 (m, 2H), 7.20 (d, J = 1.2 Hz, 1H), 5.19-5.10 (m, 1H), 4.32 (q, J = 7.2 Hz, 2H), 271-2.61 (m, 2H), 2.45 (s, 3H), 2.06-1.93 (m, 2H), 1.82-1.63 (m, 2H), 1.32 (t, J = 7.2 Hz, 3H). | acetonitrile 50%-90%/ 0.225% formic acid in water |
| I-55 | 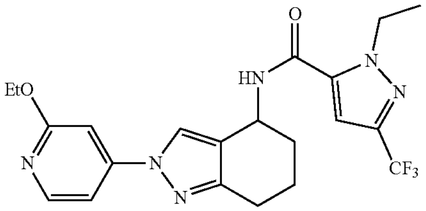 [SMILES: CCOc1cc(-n2cc3c(n2)CCCC3NC(=O)c2cc(C(F)(F)F)nn2CC)ccn1] (rac)-N-(2-(2-Ethoxypyridin-4-yl)-4,5,6,7-tetrahydro-2H-indazol-4-yl)-1-ethyl-3-(trifluoromethyl)-1H-pyrazole-5-carboxamide | LCMS (ESI) m/z: 449.1 $[M + H]^+$. $^1H$ NMR (400 MHz, DMSO-$d_6$) δ 8.94 (d, J = 8.0 Hz, 1H), 8.55 (s, 1H), 8.15 (d, J = 6.0 Hz, 1H), 7.44 (d, J = 5.6 Hz, 1H), 7.38 (s, 1H), 7.18 (s, 1H), 5.20-5.11 (m, 1H), 4.70-4.59 (m, 2H), 4.32 (q, J = 6.8 Hz, 1H), 2.69-2.67 (m, 2H), 2.03-1.96 (m, 2H), 1.82-1.63 (m, 2H), 1.39 (t, J = 7.2 Hz, 3H), 1.31 (t, J = 6.8 Hz, 3H). | acetonitrile 53%-83%/ 0.225% formic acid in water |
| I-15 | 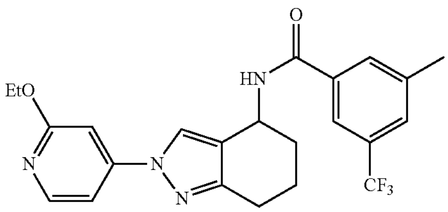 [SMILES: CCOc1cc(-n2cc3c(n2)CCCC3NC(=O)c2cc(C)cc(C(F)(F)F)c2)ccn1] (rac)-N-(2-(2-Ethoxypyridin-4-yl)-4,5,6,7-tetrahydro-2H-indazol-4-yl)-3-methyl-5-(trifluoromethyl)benzamide | LCMS (ESI) m/z: 445.1 $[M + H]^+$. $^1H$ NMR (400 MHz, DMSO-$d_6$) δ 8.94 (d, J = 8.0 Hz, 1H), 8.55 (s, 1H), 8.14 (d, J = 5.6 Hz, 1H), 8.05 (s, 2H), 7.72 (s, 1H), 7.48-7.41 (m, 1H), 7.18 (d, J = 1.6 Hz, 1H), 5.24-5.15 (m, 1H), 4.31 (q, J = 7.2 Hz, 2H), 2.73-2.64 (m, 2H), 2.45 (s, 3H), 2.08-1.94 (m, 2H), 1.83-1.66 (m, 2H), 1.31 (t, J = 7.2 Hz, 3H). | acetonitrile 50%-90%/ 0.225% formic acid in water |
| I-18 | 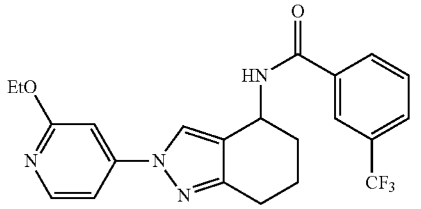 [SMILES: CCOc1cc(-n2cc3c(n2)CCCC3NC(=O)c2cccc(C(F)(F)F)c2)ccn1] (rac)-N-(2-(2-Ethoxypyridin-4-yl)-4,5,6,7-tetrahydro-2H-indazol-4-yl)-3-(trifluoromethyl)benzamide | LCMS (ESI) m/z: 431.1 $[M + H]^+$. $^1H$ NMR (400 MHz, DMSO-$d_6$) δ 9.01 (d, J = 8.0 Hz, 1H), 8.56 (s, 1H), 8.27 (s, 1H), 8.23 (d, J = 8.0 Hz, 1H), 8.14 (d, J = 5.6 Hz, 1H), 7.91 (d, J = 7.6 Hz, 1H), 7.76-7.69 (m, 1H), 7.45 (d, J = 3.6 Hz, 1H), 7.18 (d, J = 1.6 Hz, 1H), 5.27-5.15 (m, 1H), 4.31 (q, J = 7.2 Hz, 2H), 2.75-2.65 (m, 2H), 2.07-1.95 (m, 2H), 1.84-1.67 (m, 2H), 1.31 (t, J = 7.2 Hz, 3H). | acetonitrile 50%-90%/ 0.225% formic acid in water |

TABLE 3-continued

| Compound No. | Structure | Analytical data | Separation conditions |
|---|---|---|---|
| | Selected compounds of the present disclosure. | | |
| I-25 | 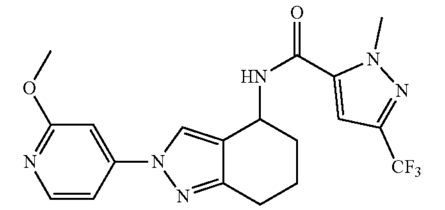 [SMILES: COc1cc(-n2cc3c(n2)CCCC3NC(=O)c2cc(C(F)(F)F)nn2C)ccn1] (rac)-N-(2-(2-Methoxypyridin-4-yl)-4,5,6,7-tetrahydro-2H-indazol-4-yl)-1-methyl-3-(trifluoromethyl)-1H-pyrazole-5-carboxamide | LCMS (ESI) m/z: 421.1 $[M + H]^+$. $^1H$ NMR (400 MHz, DMSO-$d_6$) δ 8.94 (d, J = 8.0 Hz, 1H), 8.55 (s, 1H), 8.18 (d, J = 5.6 Hz, 1H), 7.48-7.44 (m, 1H), 7.39 (s, 1H), 7.19 (d, J = 1.6 Hz, 1H), 5.19-5.05 (m, 1H), 4.19 (s, 3H), 3.87 (s, 3H), 2.73-2.65 (m, 2H), 2.05-1.94 (m, 2H), 1.84-1.63 (m, 2H). | acetonitrile 49%-79%/ 0.225% formic acid in water |
| I-39 | 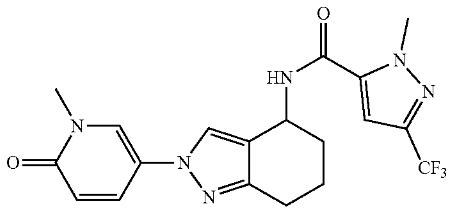 [SMILES: Cn1nc(C(F)(F)F)cc1C(=O)NC1CCCc2nn(-c3ccc(=O)n(C)c3)cc21] (rac)-1-Methyl-N-(2-(1-methyl-6-oxo-1,6-dihydropyridin-3-yl)-4,5,6,7-tetrahydro-2H-indazol-4-yl)-3-(trifluoromethyl)-1H-pyrazole-5-carboxamide | LCMS (ESI) m/z: 421.2 $[M + H]^+$. $^1H$ NMR (400 MHz, DMSO-$d_6$) δ 8.90 (d, J = 8.0 Hz, 1H), 8.21 (d, J = 2.8 Hz, 1H), 8.09 (s, 1H), 7.93-7.86 (m, 1H), 7.41 (s, 1H), 6.48 (d, J = 10.0 Hz, 1H), 5.15-5.08 (m, 1H), 4.18 (s, 3H), 3.48-3.46 (s, 3H), 2.66-2.62 (m, 2H), 2.03-1.95 (m, 2H), 1.81-1.65 (m, 2H). | acetonitrile 50%-80%/ 0.225% formic acid in water |
| I-38 | 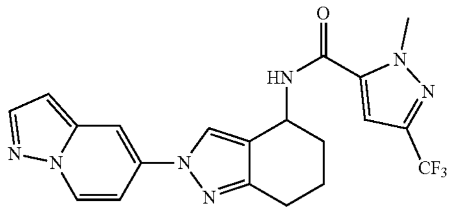 [SMILES: Cn1nc(C(F)(F)F)cc1C(=O)NC1CCCc2nn(-c3ccn4nccc4c3)cc21] (rac)-1-Methyl-N-(2-(pyrazolo[1,5-a]pyridin-5-yl)-4,5,6,7-tetrahydro-2H-indazol-4-yl)-3-(trifluoromethyl)-1H-pyrazole-5-carboxamide | LCMS (ESI) m/z: 430.1 $[M + H]^+$. $^1H$ NMR (400 MHz, DMSO-$d_6$) δ 8.95 (d, J = 8.0 Hz, 1H), 8.75 (d, J = 7.6 Hz, 1H), 8.51 (s, 1H), 8.04 (d, J = 2.4 Hz, 1H), 8.00 (d, J = 2.0 Hz, 1H), 7.50-7.44 (m, 1H), 7.41 (s, 1H), 6.60 (d, J = 2.0 Hz, 1H), 5.29-5.04 (m, 1H), 4.20 (s, 3H), 2.77-2.66 (m, 2H), 2.05-1.95 (m, 2H), 1.88-1.65 (m, 2H). | acetonitrile 53-83%/ 0.025 FA in water |
| I-34 | 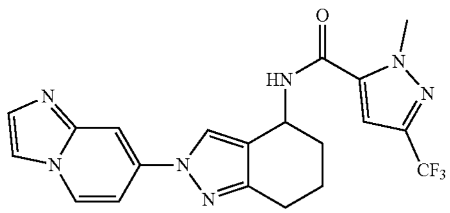 [SMILES: Cn1nc(C(F)(F)F)cc1C(=O)NC1CCCc2nn(-c3ccn4ccnc4c3)cc21] (rac)-N-(2-(Imidazo[1,2-a]pyridin-7-yl)-4,5,6,7-tetrahydro-2H-indazol-4-yl)-1-methyl-3-(trifluoromethyl)-1H-pyrazole-5-carboxamide | LCMS (ESI) m/z: 430.4 $[M + H]^+$. $^1H$ NMR (400 MHz, DMSO-$d_6$) δ 8.94 (d, J = 8.0 Hz, 1H), 8.61 (d, J = 7.2 Hz, 1H), 8.54 (s, 1H), 7.94-7.90 (m, 2H), 7.57-7.55 (m, 1H), 7.54-7.50 (m, 1H), 7.42-7.40 (m, 1H), 5.19-5.12 (m, 1H), 4.20 (s, 3H), 2.74-2.65 (m, 2H), 2.07-1.95 (m, 2H), 1.85-1.61 (m, 2H). | acetonitrile 15-55%/ 0.225% formic acid in water |

TABLE 3-continued

Selected compounds of the present disclosure.

| Compound No. | Structure | Analytical data | Separation conditions |
|---|---|---|---|
| I-25 | 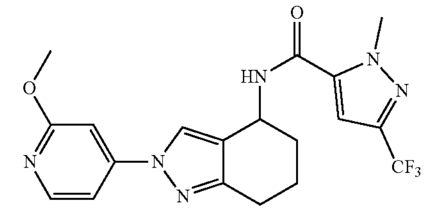 [SMILES: COc1cc(-n2cc3c(n2)CCCC3NC(=O)c2cc(C(F)(F)F)nn2C)ccn1] (rac)-N-(2-(2-Methoxypyridin-4-yl)-4,5,6,7-tetrahydro-2H-indazol-4-yl)-1-methyl-3-(trifluoromethyl)-1H-pyrazole-5-carboxamide | LCMS (ESI) m/z: 421.1 $[M + H]^+$. $^1H$ NMR (400 MHz, DMSO-$d_6$) δ 8.94 (d, J = 8.0 Hz, 1H), 8.55 (s, 1H), 8.18 (d, J = 5.6 Hz, 1H), 7.48-7.44 (m, 1H), 7.39 (s, 1H), 7.19 (d, J = 1.6 Hz, 1H), 5.19-5.05 (m, 1H), 4.19 (s, 3H), 3.87 (s, 3H), 2.73-2.65 (m, 2H), 2.05-1.94 (m, 2H), 1.84-1.63 (m, 2H). | acetonitrile 49-79%/ 0.225% formic acid in water |
| I-40 | 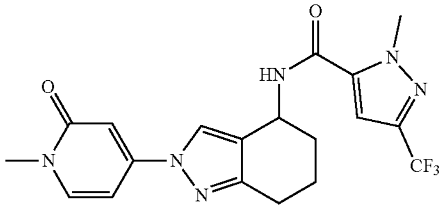 [SMILES: Cn1nc(C(F)(F)F)cc1C(=O)NC1CCCc2nn(-c3ccn(C)c(=O)c3)cc21] (rac)-1-Methyl-N-(2-(1-methyl-2-oxo-1,2-dihydropyridin-4-yl)-4,5,6,7-tetrahydro-2H-indazol-4-yl)-3-(trifluoromethyl)-1H-pyrazole-5-carboxamide | LCMS (ESI) m/z: 421.1 $[M + H]^+$. $^1H$ NMR (400 MHz, DMSO-$d_6$) δ 8.92 (d, J = 8.0 Hz, 1H), 8.46 (s, 1H), 7.79 (d, J = 7.2 Hz, 1H), 7.39 (s, 1H), 7.38 (s, 1H), 7.18 (s, 1H), 6.83-6.80 (m, 1H), 6.73 (d, J = 2.4 Hz, 1H), 5.14-5.09 (m, 1H), 4.19 (s, 3H), 3.41 (s, 3H), 2.72-2.63 (m, 2H), 2.02-1.96 (m, 2H), 1.81-1.63 (m, 2H). | acetonitrile 36-66%/ 0.225% formic acid in water |

TABLE 4

Selected compound of the present disclosure.

| Compound No. | Structure | Analytical data | Separation conditions |
|---|---|---|---|
| I-33 | 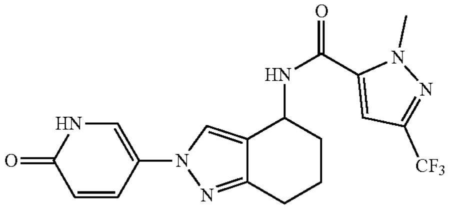 [SMILES: Cn1nc(C(F)(F)F)cc1C(=O)NC1CCCc2nn(-c3ccc(=O)[nH]c3)cc21] (rac)-1-Methyl-N-(2-(6-oxo-1,6-dihydropyridin-3-yl)-4,5,6,7-tetrahydro-2H-indazol-4-yl)-3-(trifluoromethyl)-1H-pyrazole-5-carboxamide | LCMS (ESI) m/z: 407.1 $[M + H]^+$. $^1H$ NMR (400 MHz, DMSO-$d_6$) δ 8.88 (d, J = 8.0 Hz, 1H), 8.14 (s, 1H), 7.94-7.89 (m, 1H), 7.84 (s, 1H), 7.40 (s, 1H), 6.47 (d, J = 9.6 Hz, 1H), 5.20-5.02 (m, 1H), 4.18 (s, 3H), 2.71-2.58 (m, 2H), 2.06-1.93 (m, 2H), 1.85-1.60 (m, 2H). | acetonitrile 30%-60%/ 0.225% formic acid in water |

TABLE 5

| Compound No. | Structure | Analytical data | Separation conditions |
|---|---|---|---|
| I-52 | 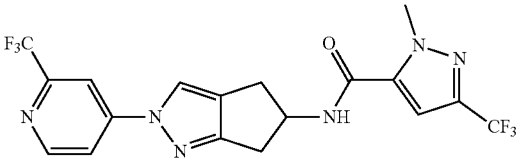 [SMILES: Cn1nc(C(F)(F)F)cc1C(=O)NC1Cc2cn(-c3ccnc(C(F)(F)F)c3)nc2C1] (rac)-1-Methyl-3-(trifluoromethyl)-N-(2-(2-(trifluoromethyl)pyridin-4-yl)-2,4,5,6-tetrahydrocyclopenta[c]pyrazol-5-yl)-1H-pyrazole-5-carboxamide | LCMS (ESI) m/z: 445.0 $[M + H]^+$. $^1H$ NMR (400 MHz, DMSO-$d_6$) δ 9.06 (d, J = 7.2 Hz, 1H), 8.76 (d, J = 5.6 Hz, 1H), 8.53 (s, 1H), 8.22 (d, J = 2.0 Hz, 1H), 8.10-8.04 (m, 1H), 7.35 (s, 1H), 5.13-4.89 (m, 1H), 4.15 (s, 3H), 3.24-3.10 (m, 2H), 2.89-2.67 (m, 2H). | acetonitrile 54%-84%/ 0.225% formic acid in water |
| I-62 | 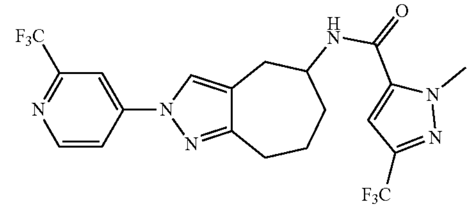 (rac)-1-Methyl-3-(trifluoromethyl)-N-(2-(2-(trifluoromethyl)pyridin-4-yl)-2,4,5,6,7,8-hexahydrocyclohepta[c]pyrazol-5-yl)-1H-pyrazole-5-carboxamide | LCMS (ESI) m/z: 473.1 $[M + H]^+$. $^1H$ NMR (400 MHz, DMSO-$d_6$) δ 8.75 (d, J = 5.6 Hz, 1H), 8.71-8.66 (m, 1H), 8.63 (s, 1H), 8.21-8.17 (m, 1H), 8.06-8.01 (m, 1H), 7.37-7.33 (m, 1H), 4.12 (s, 3H), 3.91-3.77 (m, 1H), 2.98-2.88 (m, 2H), 2.73-2.62 (m, 2H), 2.20-1.96 (m, 2H), 1.91-1.77 (m, 1H), 1.56-1.42 (m, 1H). | acetonitrile 60%-90%/ 0.225% formic acid in water |
| I-57 | 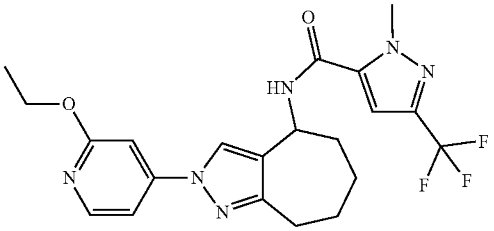 [SMILES: CCOc1cc(-n2cc3c(n2)CCCCC3NC(=O)c2cc(C(F)(F)F)nn2C)ccn1] (rac)-N-(2-(2-Ethoxypyridin-4-yl)-4,5,6,7-tetrahydro-2H-indazol-4-yl)-2-methyl-5-(trifluoromethyl)benzamide | LCMS (ESI) m/z: 449.0 $[M + H]^+$. $^1H$ NMR (400 MHz, DMSO-$d_6$) δ 8.94 (d, J = 8.0 Hz, 1H), 8.39 (s, 1H), 8.13 (d, J = 5.6 Hz, 1H), 7.50 (s, 1H), 7.45-7.41 (m, 1H), 7.19 (d, J = 1.6 Hz, 1H), 5.08-4.98 (m, 1H), 4.31 (q, J = 7.2 Hz, 2H), 4.15 (s, 3H), 3.02-2.86 (m, 1H), 2.79-2.61 (m, 1H), 2.18-1.97 (m, 1H), 1.92-1.61 (m, 4H), 1.56-1.38 (m, 1H), 1.31 (t, J = 7.2 Hz, 3H). | acetonitrile 49%-79%/ 0.225% formic acid in water |
| I-59 | 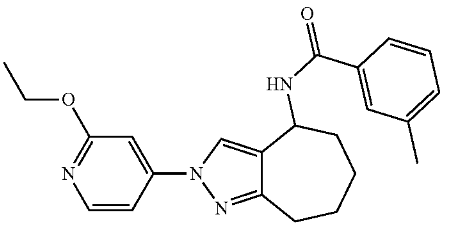 (rac)-N-(2-(2-Ethoxypyridin-4-yl)-2,4,5,6,7,8-hexahydrocyclohepta[c]pyrazol-4-yl)-3-methylbenzamide | LCMS (ESI) m/z: 391.1 $[M + H]^+$. $^1H$ NMR (400 MHz, DMSO-$d_6$) δ 8.63 (d, J = 8.0 Hz, 1H), 8.35 (s, 1H), 8.13 (d, J = 5.6 Hz, 1H), 7.84-7.68 (m, 2H), 7.45-7.41 (m, 1H), 7.39-7.31 (m, 2H), 7.18 (d, J = 1.6 Hz, 1H), 5.13-5.09 (m, 1H), 4.31 (q, J = 7.2 Hz, 2H), 3.06-2.89 (m, 1H), 2.82-2.62 (m, 1H), 2.38 (s, 3H), 2.11-1.95 (m, 1H), 1.90-1.64 (m, 4H), 1.61-1.41 (m, 1H), 1.31 (t, J = 7.2 Hz, 3H). | acetonitrile 48%-68%/ 0.225% formic acid in water |

Selected compounds of the present disclosure.

TABLE 5-continued

Selected compounds of the present disclosure.

| Compound No. | Structure | Analytical data | Separation conditions |
|---|---|---|---|
| I-61 | 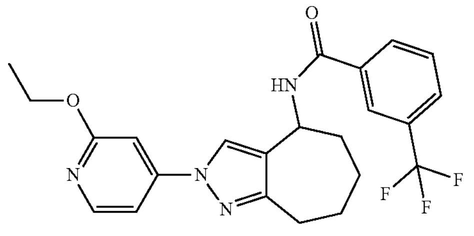 [SMILES: CCOc1cc(-n2cc3c(n2)CCCCC3NC(=O)c2cccc(C(F)(F)F)c2)ccn1] (rac)-N-(2-(2-Ethoxypyridin-4-yl)-2,4,5,6,7,8-hexahydrocyclohepta[c]pyrazol-4-yl)-3-(trifluoromethyl)benzamide | LCMS (ESI) m/z: 445.1 $[M + H]^+$. $^1H$ NMR (400 MHz, DMSO-$d_6$) δ 8.99 (d, J = 8.0 Hz, 1H), 8.40 (s, 1H), 8.33-8.23 (m, 2H), 8.13 (d, J = 5.6 Hz, 1H), 7.92 (d, J = 7.6 Hz, 1H), 7.78-7.72 (m, 1H), 7.45-7.41 (m, 1H), 7.20 (d, J = 1.6 Hz, 1H), 5.24-4.99 (m, 1H), 4.31 (q, J = 7.2 Hz, 2H), 3.00-2.96 (m, 1H), 2.82-2.61 (m, 1H), 2.18-1.94 (m, 1H), 1.93-1.65 (m, 4H), 1.62-1.40 (m, 1H), 1.30 (t, J = 7.2 Hz, 3H). | acetonitrile 49%-79%/0.225% formic acid in water |

TABLE 6

Selected compound of the present disclosure.

| Compound No. | Structure | Analytical data | Separation conditions |
|---|---|---|---|
| I-65 | 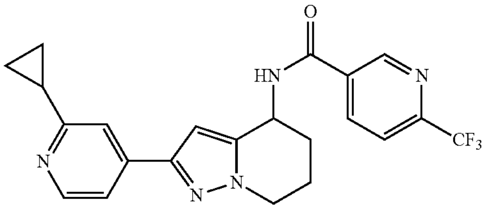 (rac)-N-(2-(2-Cyclopropylpyridin-4-yl)-4,5,6,7-tetrahydropyrazolo[1,5-a]pyridin-4-yl)-6-(trifluoromethyl)nicotinamide | LCMS (ESI) m/z: 428.0 $[M + H]^+$. $^1H$ NMR (400 MHz, DMSO-$d_6$) δ 9.40 (d, J = 8.4 Hz, 1H), 9.23 (s, 1H), 8.58-8.50 (m, 1H), 8.40 (d, J = 4.8 Hz, 1H), 8.08 (d, J = 8.4 Hz, 1H), 7.71 (s, 1H), 7.60 (s, 1H), 6.94 (m, 1H), 5.51-5.33 (m, 1H), 4.31-4.08 (m, 2H), 2.33-2.06 (m, 4H), 1.99-1.78 (m, 1H), 1.14-0.90 (m, 4H). | acetonitrile 15%-55%/0.225% formic acid in water |

Example 1.14. Synthesis of (S)-3-Chloro-5-methyl-N-(2-(2-(trifluoromethyl)pyridin-4-yl)-2,4,5,6-tetrahydrocyclopenta[c]pyrazol-4-yl)benzamide (I-129a)

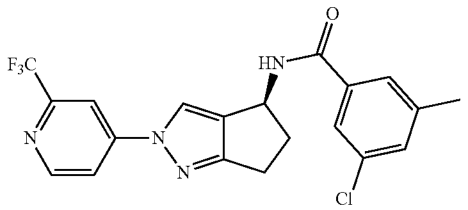 [SMILES: Cc1cc(Cl)cc(C(=O)N[C@H]2CCc3nn(-c4ccnc(C(F)(F)F)c4)cc32)c1]

Step 1—Synthesis of 4-Hydrazinyl-2-(trifluoromethyl)pyridine HCl salt

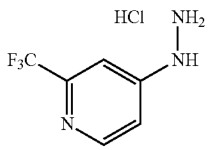

To a solution of 4-chloro-2-(trifluoromethyl)pyridine (500 g, 2.75 mol) in i-PrOH (5 L) was added $N_2H_4$—$H_2O$ (450 mL, 85%, 7.96 mol). The mixture was stirred at 110° C. for 60 h. After cooling to room temperature, HCl/EtOH (10 M, 2 L) was added to the reaction mixture to adjust pH to 4 to precipitate out the excess hydrazine as hydrochloride salt. The mixture was filtered and to the filtrate was added HCl/EtOH (10 M, 1 L) to adjust pH to 1, the mixture was filtered to obtain the solid, which was further dried in vacuo to yield the title compound (688 g, crude) as a white solid which was used without further purification. LCMS (ESI) m/z: 178.1 $[M+H]^+$.

Step 2—Synthesis of 3-(2-(2-(Trifluoromethyl)pyridin-4-yl)hydrazinyl)cyclopent-2-en-1-one

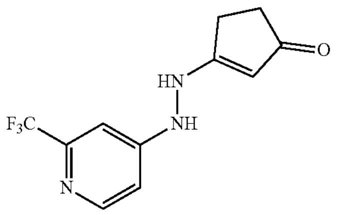 [SMILES: O=C1C=C(NNc2ccnc(C(F)(F)F)c2)CC1]

To a solution of [2-(trifluoromethyl)-4-pyridyl]hydrazine HCl salt (600 g, 2.09 mol) in $H_2O$ (1 L) was added KOAc (615 g, 6.3 mol) at 0° C. The mixture was stirred at 25° C. for 1 h, then to this mixture was dropwise added a solution of cyclopentane-1,3-dione (216 g, 2.09 mol) in EtOH (2 L). The mixture was heated to 60° C. for 16 h. After cooling to room temperature, the reaction mixture was concentrated in vacuo. The crude residue was triturated with THE and EtOAc to give the title compound (960 g, crude) as black oil which was used without further purification. LCMS (ESI) m/z: 317.1 $[M+H]^+$.

Step 3—Synthesis of 2-(2-(Trifluoromethyl)pyridin-4-yl)-5,6-dihydrocyclopenta[c]pyrazol-4(2H)-one

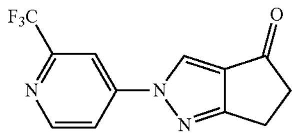 [SMILES: O=C1CCc2nn(-c3ccnc(C(F)(F)F)c3)cc21]

To a solution of 3-[2-[2-(trifluoromethyl)-4-pyridyl]hydrazino]cyclopent-2-en-1-one (960 g, 3.5 mol) in THE (6 L) was added DMF-DMA (615 mL, 4.5 mol). The mixture was stirred at 70° C. for 16 h. After cooling to room temperature, volatiles were removed under reduced pressure and residue was taken in ethyl acetate (2 L). The organic phase was washed with brine (500 mL×2), dried over anhydrous $Na_2SO_4$, filtered and concentrated in vacuo. The crude was dissolved in ethanol (300 mL) at 0° C., then acetone (300 mL) was added to induce a yellow solid precipitation. The cloudy solution was filtered to yield the title compound (280 g, 28%) as a yellow solid. $^1H$ NMR (400 MHz, DMSO-$d_6$) δ 9.27 (s, 1H), 8.87 (d, J=5.6 Hz, 1H), 8.38 (d, J=1.6 Hz, 1H), 8.27-8.16 (m, 1H), 3.09-3.03 (m, 2H), 3.00-2.92 (m, 2H). LCMS (ESI) m/z: 268.1 $[M+H]^+$.

Step 4—Synthesis of (R,E)-2-Methyl-N-(2-(2-(trifluoromethyl)pyridin-4-yl)-5,6-dihydrocyclopenta[c]pyrazol-4(2H-ylidene)propane-2-sulfinamide

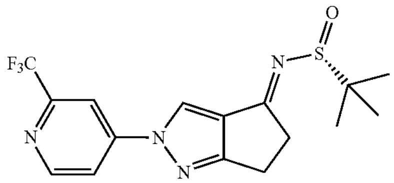 [SMILES: CC(C)(C)[S@@](=O)/N=C1\CCc2nn(-c3ccnc(C(F)(F)F)c3)cc21]

To a solution of 2-[2-(trifluoromethyl)-4-pyridyl]-5,6-dihydrocyclopenta[c]pyrazol-4-one (270 g, 1.03 mol) and (R)-2-methylpropane-2-sulfinamide (621 g, 5.13 mol) in THE (2 L) was added Ti(i-PrO)$_4$ (1.06 L, 3.59 mmol). The reaction mixture was stirred at 70° C. for 16 h under a nitrogen atmosphere. After cooling to room temperature, the mixture was quenched with $H_2O$ (2 L) and filtered. The filtrate was extracted with ethyl acetate (1 L×2). Combined organic layers were washed with brine (1 L×2), dried over anhydrous $Na_2SO_4$, filtered and concentrated in vacuo to give the title compound (370 g, crude) as a yellow solid which was used without further purification. LCMS (ESI) m/z: 371.1 $[M+H]^+$.

Step 5—Synthesis of (R)-2-Methyl-N—((S)-2-(2-(trifluoromethyl)pyridin-4-yl)-2,4,5,6-tetrahydrocyclopenta[c]pyrazol-4-yl)propane-2-sulfinamide

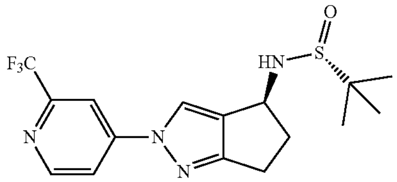 [SMILES: CC(C)(C)[S@@](=O)N[C@H]1CCc2nn(-c3ccnc(C(F)(F)F)c3)cc21]

To a solution of (R,E)-2-methyl-N-(2-(2-(trifluoromethyl)pyridin-4-yl)-5,6-dihydrocyclopenta[c]pyrazol-4(2H)-ylidene)propane-2-sulfinamide (370 g, 0.98 mol) in THE (2 L) was added $NaBH_4$ (59 g, 1.58 mol) in portions at 0° C. The reaction mixture was stirred at 25° C. for 1 h before it was quenched with sat. $NH_4Cl$ (500 mL), and water (500 mL). The mixture was extracted with EtOAc (1.5 L×2). Combined organic layers were washed with brine (500 mL×2), dried over anhydrous $Na_2SO_4$, filtered and concentrated in vacuo. The crude residue was purified on silica gel chromatography (solvent gradient: 0-20% THE in MTBE) to give 200 g crude material which was further purified by trituration with (petroleum ether/ethyl acetate=10/1, 500 mL) to give the title compound (62 g, 19%) as a yellow solid. LCMS (ESI) m/z: 373.1 $[M+H]^+$.

Step 6—Synthesis of (S)-2-(2-(Trifluoromethyl)pyridin-4-yl)-2,4,5,6-tetrahydrocyclopenta[c]pyrazol-4-amine hydrochloride

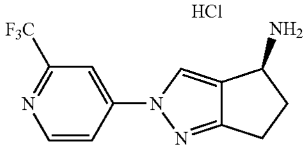

To a solution of (R)-2-methyl-N-[(4S)-2-[2-(trifluoromethyl)-4-pyridyl]-5,6-dihydro-4H-cyclopenta[c]pyrazol-4-yl]propane-2-sulfinamide (62 g, 368 mmol) in dioxane (50 mL) was added hydrochloride in dioxane (2 M, 500 mL). The mixture was stirred at room temperature for 16 h. The mixture was concentrated in vacuo, the resulting residue was triturated with acetonitrile (200 mL) to give the title compound (67.7 g, crude) as a yellow solid which was used without further purification. LCMS (ESI) m/z: 269.1 $[M+H]^+$.

Step 7—Synthesis of (S)-3-Chloro-5-methyl-N-(2-(2-(trifluoromethyl)pyridin-4-yl)-2,4,5,6-tetrahydrocyclopenta[c]pyrazol-4-yl)benzamide

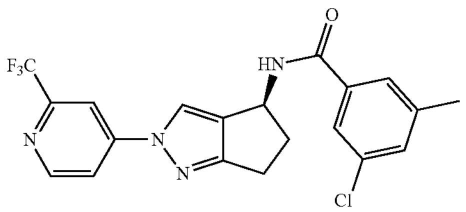

To a solution of (4S)-2-[2-(trifluoromethyl)-4-pyridyl]-5,6-dihydro-4H-cyclopenta[c]pyrazol-4-amine hydrochloride (40 mg, 149.1 μmol), 3-chloro-5-methyl-benzoic acid (33 mg, 193.8 μmol) and DIEA (0.1 mL, 300 μmol) in DCM (5 mL) was added HATU (68 mg, 220.8 μmol) at 25° C. and the reaction mixture was stirred for 1 h. The reaction was diluted with $H_2O$ (30 mL), and then extracted with DCM (30 mL×2). The combined organic layers were washed with brine (20 mL×2), dried over anhydrous $Na_2SO_4$, filtered and concentrated in vacuo. The residue was purified by RP-HPLC (acetonitrile 56-86%/0.225% formic acid in water) to give compound I-129a (7 mg, 10%) as a white solid. $^1H$ NMR (400 MHz, DMSO-$d_6$) δ 8.90 (d, J=7.2 Hz, 1H), 8.75 (d, J=5.6 Hz, 1H), 8.64 (s, 1H), 8.28 (d, J=2.0 Hz, 1H), 8.13-8.09 (m, 1H), 7.73 (s, 1H), 7.68 (s, 1H), 7.45 (s, 1H), 5.42-5.35 (m, 1H), 2.98-2.90 (m, 1H), 2.86-2.72 (m, 2H), 2.42-2.37 (m, 1H), 2.36 (s, 3H). LCMS (ESI) m/z: 421.0 $[M+H]^+$.

Example 1.15. Synthesis of (S)-3-Ethyl-5-fluoro-N-(2-(2-(trifluoromethyl)pyridin-4-yl)-2,4,5,6-tetrahydrocyclopenta[c]pyrazol-4-yl)benzamide (I-127a)

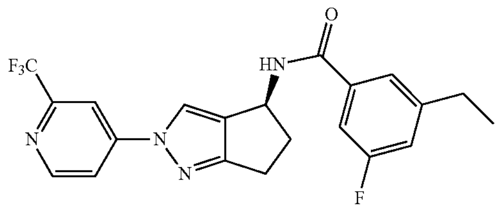 [SMILES: CCc1cc(F)cc(C(=O)N[C@H]2CCc3nn(-c4ccnc(C(F)(F)F)c4)cc32)c1]

Following the procedure described in Example 1.14 and using 3-ethyl-5-fluorobenzoic acid in step 7, compound I-127a was obtained as a white solid (36 mg, 58%) after purification of RP-HPLC (acetonitrile 45%-75%/0.225% formic acid in water). $^1H$ NMR (400 MHz, DMSO-$d_6$) δ 8.86 (d, J=7.6 Hz, 1H), 8.75 (d, J=5.6 Hz, 1H), 8.64 (s, 1H), 8.28 (d, J=2.0 Hz, 1H), 8.13-8.09 (m, 1H), 7.61 (s, 1H), 7.49 (d, J=10.0 Hz, 1H), 7.25 (d, J=9.6 Hz, 1H), 5.43-5.35 (m, 1H), 2.97-2.75 (m, 3H), 2.66 (q, J=7.6 Hz, 2H), 2.43-2.35 (m, 1H), 1.20 (t, J=7.6 Hz, 3H). LCMS (ESI) m/z: 419.0 $[M+H]^+$.

Example 1.16. Synthesis of (S)—N-(2-(2-(1,1-Difluoroethyl)pyridin-4-yl)-2,4,5,6-tetrahydrocyclopenta[c]pyrazol-4-yl)-1-methyl-3-(trifluoromethyl)-1H-pyrazole-5-carboxamide (I-77a)

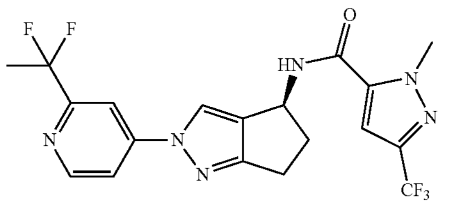 [SMILES: Cn1nc(C(F)(F)F)cc1C(=O)N[C@H]1CCc2nn(-c3ccnc(C(C)(F)F)c3)cc21]

Following the procedure described in Example 1.14, using 4-chloro-2-(1,1-difluoroethyl)pyridine in step 1 and 1-methyl-3-(trifluoromethyl)-1H-pyrazole-5-carboxylic acid in step 7, compound I-77a was obtained as a white solid (31 mg, 36%) after purification of RP-HPLC (acetonitrile 42%-82%/0.225% formic acid in water). $^1H$ NMR (400 MHz, DMSO-$d_6$) δ 9.02 (d, J=7.2 Hz, 1H), 8.66 (d, J=5.6 Hz, 1H), 8.61 (s, 1H), 8.08 (d, J=2.0 Hz, 1H), 7.98-7.39 (m, 1H), 7.35 (s, 1H), 5.42-5.29 (m, 1H), 4.18 (s, 3H), 2.99-2.71 (m, 3H), 2.43-2.27 (m, 1H), 2.02 (t, J=19.2 Hz, 3H). LCMS (ESI) m/z: 441.0 $[M+H]^+$.

Example 1.17. Synthesis of (S)-3-Cyano-N-(2-(2-(trifluoromethyl)pyridin-4-yl)-4,5,6,7-tetrahydropyrazolo[1,5-a]pyridin-4-yl)benzamide (I-128a)

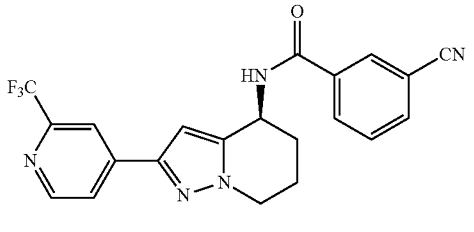 [SMILES: N#Cc1cccc(C(=O)N[C@H]2CCCn3nc(-c4ccnc(C(F)(F)F)c4)cc32)c1]

Step 1—Synthesis of Methyl 3-bromo-1-(4-methoxy-4-oxobutyl)-1H-pyrazole-5-carboxylate

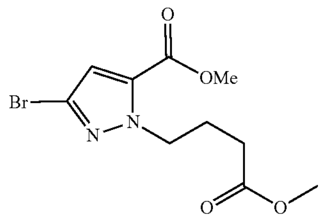 [SMILES: COC(=O)CCCn1nc(Br)cc1C(=O)OC]

To a solution of methyl 3-bromo-1H-pyrazole-5-carboxylate (1 kg, 4.98 mol), methyl 4-bromobutanoate (1.06 kg, 5.85 mol) in MeCN (5 L) was added DBU (1.1 L, 7.32 mol) at 0° C. The reaction mixture was stirred at 80° C. for 1 h under a nitrogen atmosphere. After cooling to room temperature, the mixture was quenched with HCl (3 M, 2 L), diluted with $H_2O$ (2 L), and extracted with ethyl acetate (2 L×2). The combined organic layers were washed with brine (1 L×2), dried over anhydrous $Na_2SO_4$, filtered and concentrated in vacuo to give the title compound (1.56 kg, crude) as brown oil which was used in the next step without further purifications. $^1H$ NMR (400 MHz, $CDCl_3$) δ 6.74 (s, 1H), 4.54 (t, J=6.8 Hz, 2H), 3.82 (s, 3H), 3.60 (s, 3H), 2.29 (t, J=6.8 Hz, 2H), 2.14-2.04 (m, 2H). LCMS (ESI) m/z: 329.1 $[M+Na]^+$.

Step 2—Synthesis of Potassium 2-bromo-5-(methoxycarbonyl)-6,7-dihydropyrazolo[1,5-a]pyridin-4-olate

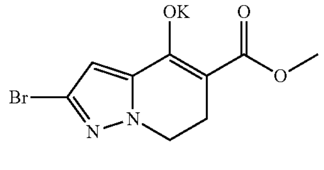

To a solution of methyl 3-bromo-1-(4-methoxy-4-oxobutyl)-1H-pyrazole-5-carboxylate (1.56 kg, 5.11 mol) in toluene (5 L) was added t-BuOK (860 g, 7.67 mol). The mixture was stirred at 90° C. for 14 h. After cooling to room temperature, the reaction mixture was filtered and the solid was further dried under vacuum to provide the title compound (1.5 kg, crude) as a yellow solid which was used without further purifications. LCMS (ESI) m/z: 272.9 $[M-K+2H]^+$.

Step 3—Synthesis of 2-Bromo-6,7-dihydropyrazolo [1,5-a]pyridin-4(5H)-one

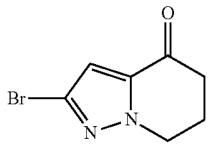 [SMILES: O=C1CCCn2nc(Br)cc21]

Potassium 2-bromo-5-(methoxycarbonyl)-6,7-dihydropyrazolo[1,5-a]pyridin-4-olate (1.5 kg, 4.82 mol) was dissolved in aq. HCl (12 M, 3 L). The mixture was stirred at 100° C. for 12 h. After cooling to room temperature, the reaction mixture was quenched with NaOH (6 M, 5 L) at 0° C., the mixture was adjusted to pH=9, then extracted with ethyl acetate (2 L×3). The combined organic layers were washed with brine (1 L×2), dried over anhydrous $Na_2SO_4$, filtered and concentrated in vacuo to give the title compound (1 kg, crude) as a brown oil which was used without further purifications. $^1H$ NMR (400 MHz, DMSO-$d_6$) δ 6.94 (s, 1H) 4.32 (t, J=6.0 Hz, 2H), 2.66 (t, J=6.8 Hz, 2H), 2.31-2.22 (m, 2H). LCMS (ESI) m/z: 214.9 $[M+H]^+$.

Step 4—Synthesis of (S,E)-N-(2-Bromo-6,7-dihydropyrazolo[1,5-a]pyridin-4(5H)-ylidene)-2-methylpropane-2-sulfinamide

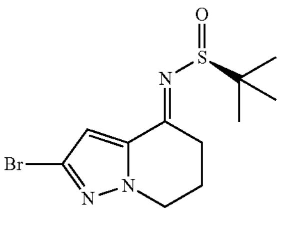 [SMILES: CC(C)(C)[S@](=O)/N=C1\CCCn2nc(Br)cc21]

To a solution of 2-bromo-6,7-dihydropyrazolo[1,5-a]pyridin-4(5H)-one (600 g, 2.91 mol), (S)-2-methylpropane-2-sulfinamide (880 g, 7.26 mol) in THE (3 L) was added $Ti(i-PrO)_4$ (1.06 L, 3.59 mol). The reaction mixture was stirred at 70° C. for 16 h under a nitrogen atmosphere. After cooling to room temperature, the mixture was quenched with $H_2O$ (3 L), and then filtered. The filtrate was extracted with ethyl acetate (2 L×2). The combined organic layers were washed with brine (1 L×2), dried over anhydrous $Na_2SO_4$, filtered and concentrated in vacuo to give the title compound (800 g, crude) as a yellow solid which was used without further purification. $^1H$ NMR (400 MHz, $CDCl_3$) δ 6.73 (s, 1H), 4.29-4.22 (m, 2H), 3.36-3.26 (m, 1H), 3.20-3.11 (m, 1H), 2.28-2.20 (m, 2H), 1.29 (s, 9H). LCMS (ESI) m/z: 318.1 $[M+H]^+$.

Step 5—Synthesis of (S)—N—((S)-2-Bromo-4,5,6,7-tetrahydropyrazolo[1,5-a]pyridin-4-yl)-2-methylpropane-2-sulfinamide

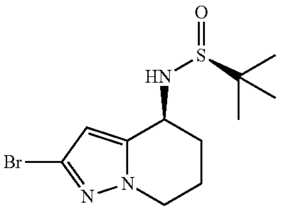 [SMILES: CC(C)(C)[S@](=O)N[C@H]1CCCn2nc(Br)cc21]

To a solution of (S,E)-N-(2-bromo-6,7-dihydropyrazolo[1,5-a]pyridin-4(5H)-ylidene)-2-methylpropane-2-sulfinamide (800 g, 2.51 mol) in THE (3 L) was added $NaBH_4$ (117 g, 3.09 mol) in portions at 0° C., then the mixture was stirred at 25° C. for 1 h under a nitrogen atmosphere. The mixture was quenched with sat. $NH_4Cl$ (2 L) and water (500 mL). The mixture was extracted with EtOAc (1 L×2). The combined organic layers were washed with brine (500 mL×2), dried over anhydrous $Na_2SO_4$, filtered and concentrated in vacuo to give the title compound (700 g, crude) as a brown oil which was used without further purification. $^1H$ NMR (400 MHz, $CDCl_3$) δ 6.43 (s, 1H), 4.62-4.53 (m, 1H), 4.13-4.06 (m, 2H), 2.22-2.12 (m, 2H), 2.01-1.87 (m, 2H), 1.23 (s, 9H). LCMS (ESI) m/z: 321.9 $[M+H]^+$.

Step 6—Synthesis of (S)-2-Methyl-N—((S)-2-(2-(trifluoromethyl)pyridin-4-yl)-4,5,6,7-tetrahydropyrazolo[1,5-a]pyridin-4-yl)propane-2-sulfinamide

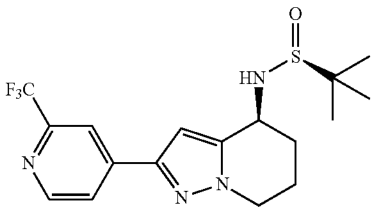 [SMILES: CC(C)(C)[S@](=O)N[C@H]1CCCn2nc(-c3ccnc(C(F)(F)F)c3)cc21]

To a solution of (S)—N—((S)-2-bromo-4,5,6,7-tetrahydropyrazolo[1,5-a]pyridin-4-yl)-2-methylpropane-2-sulfinamide (700 g, 2.17 mol), [2-(trifluoromethyl)-4-pyridyl] boronic acid (525 g, 2.45 mol) and $K_3PO_4$ (1.42 kg, 6.42 mol) in dioxane (5 L) and $H_2O$ (500 mL) was added $Pd(dppf)Cl_2$ (35 g, 42.25 mmol), then the mixture was stirred at 85° C. for 16 h under a nitrogen atmosphere. After cooling to room temperature, the reaction mixture was concentrated in vacuo, diluted with water (2 L) and extracted with ethyl acetate (2 L×2). The combined organic layers were washed with brine (500 mL), dried over anhydrous $Na_2SO_4$, filtered and concentrated in vacuo to give the crude residue which was triturated with petroleum ether/ethyl acetate (10:1, 1 L) to give the title compound (300 g, 35%) as a brown solid. $^1H$ NMR (400 MHz, DMSO-$d_6$) δ 8.75 (d, J=5.2 Hz, 1H), 8.09 (s, 1H), 7.99 (d, J=4.8 Hz, 1H), 7.06 (s, 1H), 5.91 (d, J=8.4 Hz, 1H), 4.56-4.44 (m, 1H), 4.23-4.02 (m, 2H), 2.20-1.92 (m, 3H), 1.86-1.74 (m, 1H), 1.16 (s, 9H). LCMS (ESI) m/z: 387.1 $[M+H]^+$.

Step 7—Synthesis of (S)-2-(2-(Trifluoromethyl)pyridin-4-yl)-4,5,6,7-tetrahydropyrazolo[1,5-a]pyridin-4-amine hydrochloride

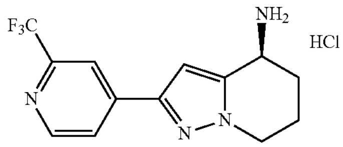 [SMILES: N[C@H]1CCCn2nc(-c3ccnc(C(F)(F)F)c3)cc21 ; Cl]

(S)-2-methyl-N—((S)-2-(2-(trifluoromethyl)pyridin-4-yl)-4,5,6,7-tetrahydropyrazolo[1,5-a]pyridin-4-yl)propane-2-sulfinamide (300 g, 0.74 mol) was added to a solution of HCl in dioxane (2 M, 1 L). The mixture was stirred at room temperature for 16 h. The mixture was filtered and the solid was washed with MeCN (500 mL) to give the title compound (305 g, crude) as a yellow solid which was used without further purification. $^1$H NMR (400 MHz, DMSO-$d_6$) δ 8.97 (s, 3H), 8.79 (d, J=5.2 Hz, 1H), 8.09 (s, 1H), 7.98 (d, J=4.8 Hz, 1H), 7.26 (s, 1H), 4.65-4.59 (m, 1H), 4.29-4.10 (m, 2H), 2.32-2.19 (m, 2H), 2.02-1.95 (m, 2H). LCMS (ESI) m/z: 283.1 [M+H]$^+$.

Step 8—Synthesis of (S)-3-Cyano-N-(2-(2-(trifluoromethyl)pyridin-4-yl)-4,5,6,7-tetrahydropyrazolo[1,5-a]pyridin-4-yl)benzamide

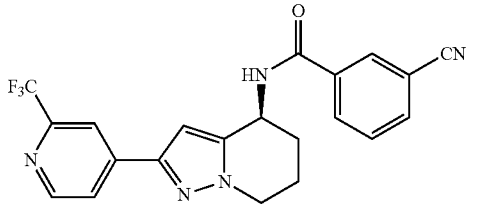 [SMILES: N#Cc1cccc(C(=O)N[C@H]2CCCn3nc(-c4ccnc(C(F)(F)F)c4)cc32)c1]

To a solution of (S)-3-cyano-N-(2-(2-(trifluoromethyl)pyridin-4-yl)-4,5,6,7-tetrahydropyrazolo [1,5-a]pyridin-4-yl)benzamide hydrochloride (50 mg, 0.18 mmol), 3-cyanobenzoic acid (31 mg, 0.21 mmol) and DIPEA (0.1 mL, 0.54 mmol) in DCM (2 mL) was added HATU (80 mg, 0.21 mmol). The reaction mixture was stirred at 25° C. for 1 h. The mixture was diluted with $H_2O$ (10 mL) and extracted with DCM (10 mL×2). The combined organic layers were washed with brine (10 mL×2), dried over anhydrous $Na_2SO_4$, filtered and concentrated in vacuo. The residue was purified by RP-HPLC (acetonitrile 40-70%/0.225% formic acid in water) to give compound I-128a (36 mg, 58%) as a white solid. $^1$H NMR (400 MHz, DMSO-$d_6$) δ 9.18 (d, J=8.0 Hz, 1H), 8.74 (d, J=5.2 Hz, 1H), 8.35 (s, 1H), 8.25-8.18 (m, 2H), 8.13-8.00 (m, 2H), 7.75-7.72 (m, 1H), 7.06 (s, 1H), 5.41-5.33 (m, 1H), 4.29-4.12 (m, 2H), 2.25-2.05 (m, 3H), 1.89-1.82 (m, 1H). LCMS (ESI) m/z: 412.0 [M+H]$^+$.

Example 1.18. Synthesis of (S)-2,6-Dimethoxy-N-(2-(2-(trifluoromethyl)pyridin-4-yl)-4,5,6,7-tetrahydropyrazolo[1,5-a]pyridin-4-yl)isonicotinamide (I-124a)

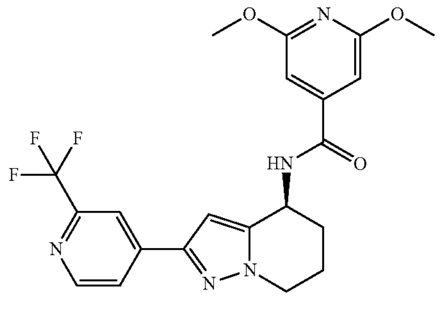 [SMILES: COc1cc(C(=O)N[C@H]2CCCn3nc(-c4ccnc(C(F)(F)F)c4)cc32)cc(OC)n1]

Following the procedure described in Example 1.17 and using 2,6-dimethoxyisonicotinic acid in step 8, compound I-124a was obtained as a white solid (51 mg, 32%) after purification of RP-HPLC (acetonitrile 40%-70%/0.225% formic acid in water). $^1$H NMR (400 MHz, DMSO-$d_6$) δ 9.10 (d, J=8.4 Hz, 1H), 8.73 (d, J=5.2 Hz, 1H), 8.21 (s, 1H), 8.11-8.06 (m, 1H), 7.02 (s, 1H), 6.83 (s, 2H), 5.37-5.30 (m, 1H), 4.28-4.09 (m, 2H), 3.89 (s, 6H), 2.26-2.17 (m, 1H), 2.16-2.04 (m, 2H), 1.90-1.79 (m, 1H). LCMS (ESI) m/z: 448.0 [M+H]$^+$.

Example 1.19. Synthesis of (S)-4-Methyl-2-(trifluoromethyl)-N-(2-(2-(trifluoromethyl)pyridin-4-yl)-4,5,6,7-tetrahydropyrazolo[1,5-a]pyridin-4-yl)oxazole-5-carboxamide (I-125a)

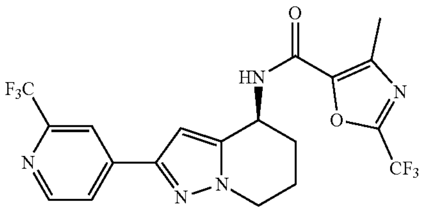 [SMILES: Cc1nc(C(F)(F)F)oc1C(=O)N[C@H]1CCCn2nc(-c3ccnc(C(F)(F)F)c3)cc21]

Step 1—Synthesis of 4-Methyl-2-(trifluoromethyl)oxazole-5-carboxylic acid

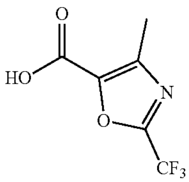

To a solution of benzyl 4-methyl-2-(trifluoromethyl)oxazole-5-carboxylate (100 mg, 350.6 μmol) in EtOAc (5 mL) was added Pd/C (38 mg, 35.1 μmol). The reaction mixture was stirred at 25° C. for 1 h under a hydrogen atmosphere (15 psi). The mixture was diluted with ethyl acetate (20 mL), filtered and concentrated in vacuo to give the title compound (40 mg, crude) as a yellow solid.

Step 2—Synthesis of (S)-4-Methyl-2-(trifluoromethyl)-N-(2-(2-(trifluoromethyl)pyridin-4-yl)-4,5,6,7-tetrahydropyrazolo[1,5-a]pyridin-4-yl)oxazole-5-carboxamide

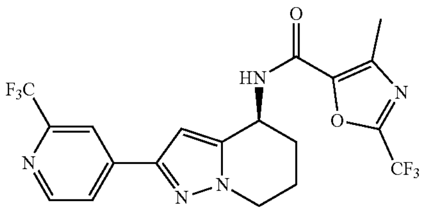 [SMILES: Cc1nc(C(F)(F)F)oc1C(=O)N[C@H]1CCCn2nc(-c3ccnc(C(F)(F)F)c3)cc21]

Following the procedure described in Example 1.17 and using 4-methyl-2-(trifluoromethyl)oxazole-5-carboxylic acid in step 8, compound I-125a was obtained as a white solid (17.6 mg, 20%) after purification of RP-HPLC (acetonitrile 55%-85%/0.225% formic acid in water). $^1$H NMR (400 MHz, DMSO-$d_6$) δ 9.32 (d, J=8.4 Hz, 1H), 8.74 (d, J=5.2 Hz, 1H), 8.20 (s, 1H), 8.07 (d, J=5.2 Hz, 1H), 7.03 (s, 1H), 5.58-5.18 (m, 1H), 4.27-4.20 m, 1H), 4.18-4.01 (m, 1H), 2.51-2.51 (m, 3H), 2.30-2.17 (m, 1H), 2.13-2.00 (m, 2H), 1.99-1.81 (m, 1H). LCMS (ESI) m/z: 460.1 [M+H]$^+$.

Example 1.20. Synthesis of (S)-1-Methyl-3-(trifluoromethyl)-N-(2-(2-(trifluoromethyl)pyridin-4-yl)-5,6,7,8-tetrahydro-[1,2,4]triazolo[1,5-a]pyridin-8-yl)-1H-pyrazole-5-carboxamide (I-86a)

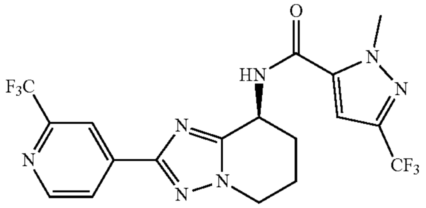

Following the procedure described in Example 1.17, ethyl 3-bromo-1H-1,2,4-triazole-5-carboxylate was used in step 1 and 1-methyl-3-(trifluoromethyl)-1H-pyrazole-5-carboxylic acid was used in step 8, compound I-86a was obtained as a white solid (10 mg, 23%) after purification by RP-HPLC (acetonitrile 33%-63%/0.225% formic acid in water). $^1$H NMR (400 MHz, DMSO-$d_6$) δ 9.28 (d, J=8.0 Hz, 1H), 8.87 (d, J=5.2 Hz, 1H), 8.24 (s, 1H), 8.21 (d, J=5.6 Hz, 1H), 7.33 (s, 1H), 5.43-5.33 (m, 1H), 4.31-4.25 (m, 2H), 4.19 (s, 3H), 2.25-2.20 (m, 2H), 2.17-2.06 (m, 1H), 2.04-1.96 (m, 1H). LCMS (ESI) m/z: 460.1 [M+H]$^+$.

Example 1.21. Synthesis of (S)—N-(2-(2-Cyclopropylpyridin-4-yl)-4,5,6,7-tetrahydrobenzo[d]oxazol-4-yl)-1-methyl-3-(trifluoromethyl)-1H-pyrazole-5-carboxamide (I-121a)

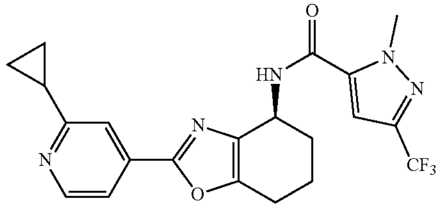

Step 1—Synthesis of 2-(2-Cyclopropylpyridin-4-yl)-6,7-dihydrobenzo[d]oxazol-4(5H)-one

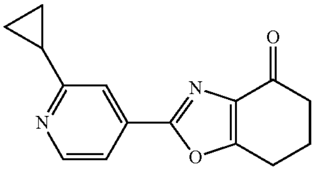 [SMILES: O=C1CCCc2oc(-c3ccnc(C4CC4)c3)nc21]

To a mixture of 2-diazocyclohexane-1,3-dione (1.8 g, 13.03 mmol, prepared according to the procedure in WO2021/178780) and 2-cyclopropylpyridine-4-carbonitrile (3.76 g, 26.06 mmol) was added $Rh_2(OAc)_4$ (58 mg, 130.3 μmol). The reaction mixture was stirred at 60° C. for 16 h under a nitrogen atmosphere. After cooling to room temperature, the reaction was diluted with water (20 mL), extracted with EtOAc (50 mL×2). The combined organic layers were washed with brine (20 mL×2), dried over anhydrous $Na_2SO_4$, filtered and concentrated in vacuo. The crude residue was purified by silica gel chromatography (solvent gradient: 0-50% EtOAc in petroleum ether) to give the title compound (0.86 g, 26%) as a yellow solid. $^1$H NMR (400 MHz, DMSO-$d_6$) δ 8.60 (d, J=5.2 Hz, 1H), 7.87 (s, 1H), 7.68-7.64 (m, 1H), 3.12-3.07 (m, 2H), 2.56-2.51 (m, 2H), 2.34-2.15 (m, 3H), 1.05-0.94 (m, 4H). LCMS (ESI) m/z: 255.0 [M+H]$^+$.

Step 2—Synthesis of (S)—N-(2-(2-Cyclopropylpyridin-4-yl)-4,5,6,7-tetrahydrobenzo[d]oxazol-4-yl)-1-methyl-3-(trifluoromethyl)-1H-pyrazole-5-carboxamide Following the procedure described in Example 1.14, 2-(2-cyclopropylpyridin-4-yl)-6,7-dihydrobenzo[d]oxazol-4(5H)-one was used in step 4 and 1-methyl-3-(trifluoromethyl)-1H-pyrazole-5-carboxylic acid was used in step 7, compound I-121a was obtained as a white solid (61 mg, 51%) after purification by RP-HPLC (acetonitrile 22%-52%/0.225% formic acid in water). $^1$H NMR (400 MHz, DMSO-$d_6$) δ 8.97 (d, J=8.0 Hz, 1H), 8.55 (d, J=5.2 Hz, 1H), 7.83 (s, 1H), 7.65 (d, J=4.8 Hz, 1H), 7.37 (s, 1H), 5.15-5.11 (m, 1H), 4.19 (s, 3H), 2.87-2.71 (m, 2H), 2.31-2.23 (m, 1H), 2.04-1.80 (m, 4H), 1.07-0.95 (m, 4H). LCMS (ESI) m/z: 432.1 [M+H]$^+$.

Example 1.22. Synthesis of (S)-1-Methyl-N-(2-(5-methyl-2-(trifluoromethyl)pyridin-4-yl)-4,5,6,7-tetrahydropyrazolo[1,5-a]pyridin-4-yl)-3-(trifluoromethyl)-1H-pyrazole-5-carboxamide (I-122a)

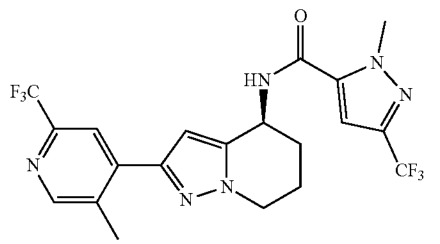 [SMILES: Cc1cnc(C(F)(F)F)cc1-c1cc2n(n1)CCC[C@@H]2NC(=O)c1cc(C(F)(F)F)nn1C]

Following the procedure described in Example 1.17, (5-methyl-4-(4,4,5,5-tetramethyl-1,3,2-dioxaborolan-2-yl)-2-(trifluoromethyl)pyridine (prepared according to the procedure in WO2022/034568) was used in step 6 and 1-methyl-3-(trifluoromethyl)-1H-pyrazole-5-carboxylic acid was used in step 8. Compound I-122a was obtained as a white solid (10 mg, 15%) after purification of RP-HPLC (acetonitrile 51%-81%/0.225% formic acid in water). $^1$H NMR (400 MHz, DMSO-$d_6$) δ 9.16 (d, J=8.4 Hz, 1H), 8.65 (s, 1H), 8.05 (s, 1H), 7.38 (s, 1H), 6.87 (s, 1H), 5.40-5.30 (m, 1H), 4.29-4.20 (m, 2H), 4.19 (s, 3H), 2.59 (s, 3H), 2.25-2.06 (m, 3H), 1.94-1.78 (m, 1H). LCMS (ESI) m/z: 473.0 $[M+H]^+$.

Example 1.23. Synthesis of (S)—N-(2-(2-Methoxypyridin-4-yl)-5,6,7,8-tetrahydro-4H-pyrazolo[1,5-a]azepin-4-yl)-1-methyl-3-(trifluoromethyl)-1H-pyrazole-5-carboxamide (I-126a)

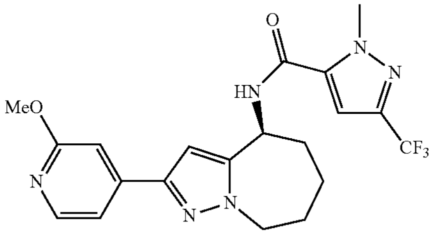 [SMILES: COc1cc(-c2cc3n(n2)CCCC[C@@H]3NC(=O)c2cc(C(F)(F)F)nn2C)ccn1]

Following the procedure described in Example 1.17 with methyl 5-bromopentanoate used in step 1, (2-methoxypyridin-4-yl)boronic acid used in step 6 and 1-methyl-3-(trifluoromethyl)-1H-pyrazole-5-carboxylic acid was used in step 7. Compound I-126a was obtained as a white solid (60 mg, 31%) after purification by RP-HPLC (acetonitrile 30%-60%/0.225% formic acid in water). $^1$H NMR (400 MHz, DMSO-$d_6$) 6.9.20 (d, J=7.6 Hz, 1H), 8.12 (d, J=5.2 Hz, 1H), 7.53 (s, 1H), 7.36 (d, J=5.2 Hz, 1H), 7.15 (s, 1H), 6.79 (s, 1H), 5.24-5.19 (m, 1H), 4.49-4.42 (m 1H), 4.34-4.24 (m, 1H), 4.14 (s, 3H), 3.85 (s, 3H), 2.06-1.98 (m, 1H), 1.97-1.88 (m, 2H), 1.85-1.76 (m, 2H), 1.63-1.49 (m, 1H). LCMS (ESI) m/z: 435.2 $[M+H]^+$.

Example 1.24. Synthesis of (S)-1-Methyl-3-(trifluoromethyl)-N-(2-(2-(trifluoromethyl)pyridin-4-yl)-5,6-dihydro-4H-pyrrolo[1,2-b]pyrazol-4-yl)-1H-pyrazole-5-carboxamide & (R)-1-Methyl-3-(trifluoromethyl)-N-(2-(2-(trifluoromethyl)pyridin-4-yl)-5,6-dihydro-4H-pyrrolo[1,2-b]pyrazol-4-yl)-1H-pyrazole-5-carboxamide (I-123a and I-123b)

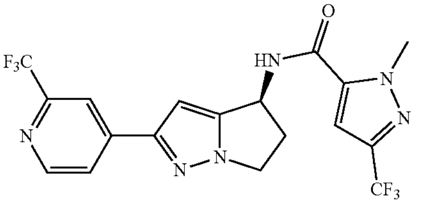

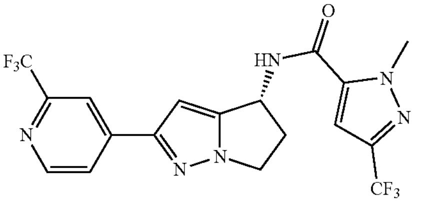

Step 1—Synthesis of Methyl 3-bromo-1-(3-methoxy-3-oxopropyl)-1H-pyrazole-5-carboxylate

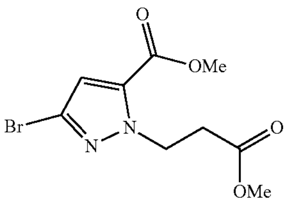 [SMILES: COC(=O)CCn1nc(Br)cc1C(=O)OC]

To a solution of methyl 3-bromo-1H-pyrazole-5-carboxylate (50 g, 243.89 mmol) and methyl 3-bromopropanoate (48.9 g, 292.67 mmol) in MeCN (500 mL) was added TEA (102 mL, 731.67 mmol). The reaction mixture was stirred at 80° C. for 16 h under a nitrogen atmosphere. After cooling to room temperature, the mixture was diluted with $H_2O$ (500 mL), extracted with ethyl acetate (500 mL×2). The combined organic layers were washed with brine (200 mL×2), dried over anhydrous $Na_2SO_4$, filtered and concentrated in vacuo. The residue was purified by silica gel chromatography (solvent gradient: 0-10% EtOAc in petroleum ether) to give the title compound (29 g, 41%) as a yellow solid. $^1$H NMR (400 MHz, DMSO-$d_6$) δ 7.01 (s, 1H), 4.71 (t, J=6.8 Hz, 2H), 3.84 (s, 3H), 3.58 (s, 3H), 2.87 (t, J=6.8 Hz, 2H). LCMS (ESI) m/z: 291.0 $[M+H]^+$.

Step 2—Synthesis of Methyl 1-(3-methoxy-3-oxopropyl)-3-(2-(trifluoromethyl)pyridin-4-yl)-1H-pyrazole-5-carboxylate

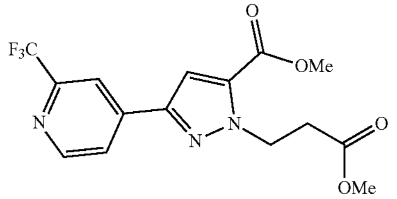 [SMILES: COC(=O)CCn1nc(-c2ccnc(C(F)(F)F)c2)cc1C(=O)OC]

To a solution of methyl 3-bromo-1-(3-methoxy-3-oxopropyl)-1H-pyrazole-5-carboxylate (16 g, 54.96 mmol), [2-(trifluoromethyl)-4-pyridyl]boronic acid (13.64 g, 71.45 mmol), $K_3PO_4$ (35 g, 164.89 mmol) in dioxane (160 mL) and $H_2O$ (16 mL) was added Pd(dppf)$Cl_2$ (4.02 g, 5.05 mmol). The reaction mixture was stirred at 85° C. for 16 h under a nitrogen atmosphere. After cooling to room temperature, the mixture was diluted with $H_2O$ (300 mL), extracted with ethyl acetate (800 mL×2). The combined organic layers were washed with brine (200 mL×2), dried over anhydrous $Na_2SO_4$, filtered and concentrated in vacuo. The residue was purified by silica gel chromatography (solvent gradient: 0-10% EtOAc in petroleum ether) to give the title compound (17.2 g, 88%) as a yellow solid. $^1$H NMR (400 MHz, DMSO-$d_6$) δ 8.80 (d, J=5.2 Hz, 1H), 8.27 (s, 1H), 8.13 (d, J=5.2 Hz, 1H), 7.79 (s, 1H), 4.82 (t, J=6.8 Hz, 2H), 3.89 (s, 3H), 3.60 (s, 3H), 2.96 (t, J=6.8 Hz, 2H). LCMS (ESI) m/z: 358.1 $[M+H]^+$.

Step 3—Synthesis of Sodium 5-(methoxycarbonyl)-2-(2-(trifluoromethyl)pyridin-4-yl)-6H-pyrrolo[1,2-b]pyrazol-4-olate

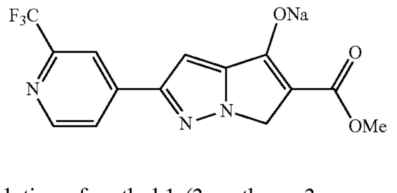

To a solution of methyl 1-(3-methoxy-3-oxopropyl)-3-(2-(trifluoromethyl)pyridin-4-yl)-1H-pyrazole-5-carboxylate (16 g, 44.78 mmol) in toluene (120 mL) was added NaOMe (16.59 mL, 5.4 M in MeOH, 89.56 mmol) at 0° C. The reaction mixture was stirred at 80° C. for 2 h under a nitrogen atmosphere. After cooling to room temperature, the mixture was filtered and the solid was further dried under vacuum to provide the title compound (16 g, crude) as a white solid which was used without further purifications. LCMS (ESI) m/z: 326.0 $[M-Na+2H]^+$.

Step 4—Synthesis of 1-Methyl-3-(trifluoromethyl)-N-(2-(2-(trifluoromethyl)pyridin-4-yl)-5,6-dihydro-4H-pyrrolo[1,2-b]pyrazol-4-yl)-1H-pyrazole-5-carboxamide

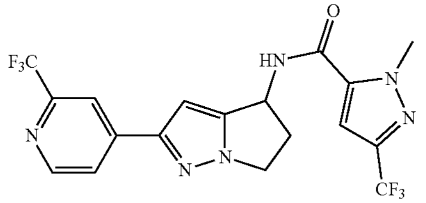

Following the procedure described in Example 1.17 and sodium 5-(methoxycarbonyl)-2-(2-(trifluoromethyl)pyridin-4-yl)-6H-pyrrolo[1,2-b]pyrazol-4-olate was used in step 3, the title compound was obtained as a white solid (180 mg, 54%) after purification of RP-HPLC (acetonitrile 35%-65%/0.225% formic acid in water).

Step 5—Synthesis of (S)-1-Methyl-3-(trifluoromethyl)-N-(2-(2-(trifluoromethyl)pyridin-4-yl)-5,6-dihydro-4H-pyrrolo[1,2-b]pyrazol-4-yl)-1H-pyrazole-5-carboxamide & (R)-1-Methyl-3-(trifluoromethyl)-N-(2-(2-(trifluoromethyl)pyridin-4-yl)-5,6-dihydro-4H-pyrrolo[1,2-b]pyrazol-4-yl)-1H-pyrazole-5-carboxamide

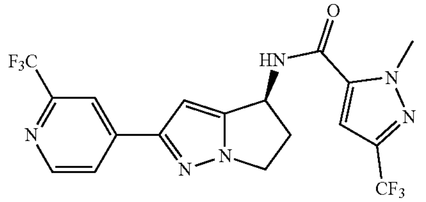

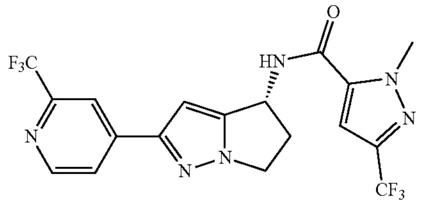 [SMILES: Cn1nc(C(F)(F)F)cc1C(=O)NC1CCn2nc(-c3ccnc(C(F)(F)F)c3)cc21]

(S)- and (R)-1-Methyl-3-(trifluoromethyl)-N-(2-(2-(trifluoromethyl)pyridin-4-yl)-5,6-dihydro-4H-pyrrolo[1,2-b]pyrazol-4-yl)-1H-pyrazole-5-carboxamide (120 mg, 405.1 μmol) was separated by the following method: chiral SFC (DAICEL CHIRALCEL OJ (250 mm*30 mm, 10 μm); supercritical $CO_2$/EtOH+0.1% $NH_3 \cdot H_2O$=65/35; 80 mL/min), affording (S)-1-methyl-3-(trifluoromethyl)-N-(2-(2-(trifluoromethyl)pyridin-4-yl)-5,6-dihydro-4H-pyrrolo[1,2-b]pyrazol-4-yl)-1H-pyrazole-5-carboxamide (76 mg, first peak) and (R)-1-methyl-3-(trifluoromethyl)-N-(2-(2-(trifluoromethyl)pyridin-4-yl)-5,6-dihydro-4H-pyrrolo[1,2-b]pyrazol-4-yl)-1H-pyrazole-5-carboxamide (37 mg, second peak). Both as white solid. First peak: (I-123a): $^1$H NMR (400 MHz, DMSO-$d_6$) δ 9.22 (d, J=7.6 Hz, 1H), 8.75 (d, J=4.8 Hz, 1H), 8.20 (s, 1H), 8.07 (d, J=5.2 Hz, 1H), 7.34 (s, 1H), 7.02 (s, 1H), 5.61-5.46 (m, 1H), 4.44-4.31 (m, 1H), 4.28-4.21 (m, 1H), 4.18 (s, 3H), 3.12-2.99 (m, 1H), 2.59-

2.52 (m, 1H). LCMS (ESI) m/z: 445.1 $[M+H]^+$. Second peak: (I-123b): $^1H$ NMR (400 MHz, DMSO-$d_6$) δ 9.22 (d, J=7.6 Hz, 1H), 8.75 (d, J=4.8 Hz, 1H), 8.20 (s, 1H), 8.07 (d, J=5.2 Hz, 1H), 7.34 (s, 1H), 7.02 (s, 1H), 5.61-5.46 (m, 1H), 4.44-4.31 (m, 1H), 4.28-4.21 (m, 1H), 4.18 (s, 3H), 3.12-2.99 (m, 1H), 2.59-2.52 (m, 1H). LCMS (ESI) m/z: 445.0 $[M+H]^+$.

Example 1.25. Synthesis of (S)-3,5-Difluoro-N-(2-(2-(trifluoromethyl)pyridin-4-yl)-5,6-dihydro-4H-pyrrolo[1,2-b]pyrazol-4-yl)benzamide & (R)-3,5-Difluoro-N-(2-(2-(trifluoromethyl)pyridin-4-yl)-5,6-dihydro-4H-pyrrolo[1,2-b]pyrazol-4-yl)benzamide (I-120a and I-120b)

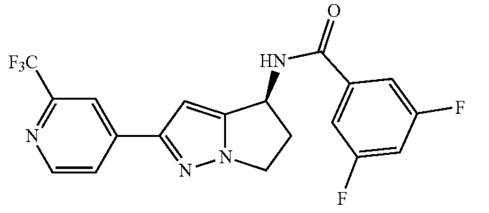

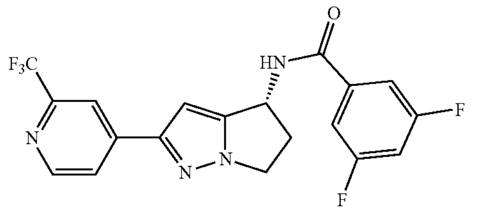

Step 1—Synthesis of 3,5-Difluoro-N-(2-(2-(trifluoromethyl)pyridin-4-yl)-5,6-dihydro-4H-pyrrolo[1,2-b]pyrazol-4-yl)benzamide

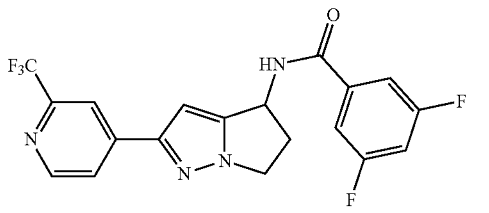 [SMILES: O=C(NC1CCn2nc(-c3ccnc(C(F)(F)F)c3)cc21)c1cc(F)cc(F)c1]

Following the procedure described in Example 1.14 and 3,5-difluorobenzoic acid was used in step 7, the title compound (100 mg) was obtained as a white solid after purification by flash column chromatography (solvent gradient: 0-20% EtOAc in petroleum ether).

Step 2—Synthesis of (S)-3,5-Difluoro-N-(2-(2-(trifluoromethyl)pyridin-4-yl)-5,6-dihydro-4H-pyrrolo[1,2-b]pyrazol-4-yl)benzamide & (R)-3,5-Difluoro-N-(2-(2-(trifluoromethyl)pyridin-4-yl)-5,6-dihydro-4H-pyrrolo[1,2-b]pyrazol-4-yl)benzamide

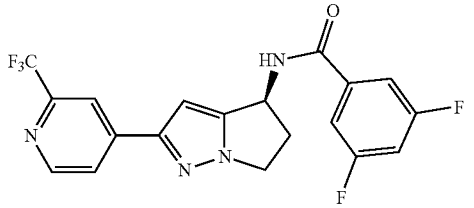

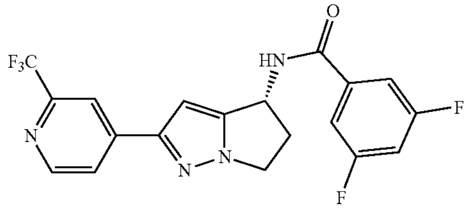

(S) and (R)-3,5-difluoro-N-(2-(2-(trifluoromethyl)pyridin-4-yl)-5,6-dihydro-4H-pyrrolo[1,2-b]pyrazol-4-yl)benzamide (100 mg, 245 μmol) was separated by the following conditions: chiral SFC (DAICEL CHIRALCEL OJ (250 mm*30 mm, 10 μm); supercritical $CO_2$/EtOH+0.1% $NH_3 \cdot H_2O$=75/25; 70 mL/min), affording (S)-3,5-difluoro-N-(2-(2-(trifluoromethyl)pyridin-4-yl)-5,6-dihydro-4H-pyrrolo[1,2-b]pyrazol-4-yl)benzamide (47 mg, first peak) and (R)-3,5-difluoro-N-(2-(2-(trifluoromethyl)pyridin-4-yl)-5,6-dihydro-4H-pyrrolo[1,2-b]pyrazol-4-yl)benzamide (43 mg, second peak) both as white solid. First peak: (I-120a): $^1H$ NMR (400 MHz, DMSO-$d_6$) δ 9.20 (d, J=7.6 Hz, 1H), 8.74 (d, J=5.2 Hz, 1H), 8.20 (s, 1H), 8.11-8.03 (m, 1H), 7.65-7.56 (m, 2H), 7.54-7.45 (m, 1H), 7.01 (s, 1H), 5.61-5.50 (m, 1H), 4.44-4.35 (m, 1H), 4.29-4.19 (m, 1H), 3.11-3.00 (m, 1H), 2.60-2.53 (m, 1H). LCMS (ESI) m/z: 409.0 $[M+H]^+$. Second peak (I-120b): $^1H$ NMR (400 MHz, DMSO-$d_6$) δ 9.20 (d, J=7.6 Hz, 1H), 8.74 (d, J=5.2 Hz, 1H), 8.20 (s, 1H), 8.11-8.03 (m, 1H), 7.65-7.56 (m, 2H), 7.54-7.45 (m, 1H), 7.01 (s, 1H), 5.61-5.50 (m, 1H), 4.44-4.35 (m, 1H), 4.29-4.19 (m, 1H), 3.11-3.00 (m, 1H), 2.60-2.53 (m, 1H). LCMS (ESI) m/z: 409.0 $[M+H]^+$.

Example 1.26. Synthesis of (S)-1-Methyl-3-(trifluoromethyl)-N-(2-(2-(trifluoromethyl)pyridin-4-yl)-4,5,6,7-tetrahydrobenzo[d]oxazol-7-yl)-1H-pyrazole-5-carboxamide (I-83a)

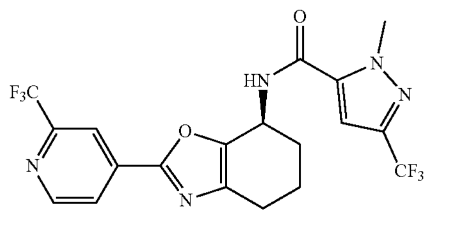 [SMILES: Cn1nc(C(F)(F)F)cc1C(=O)N[C@H]1CCCc2nc(-c3ccnc(C(F)(F)F)c3)oc21]

Step 1—Synthesis of N-(3-Oxocyclohex-1-en-1-yl)-2-(trifluoromethyl)isonicotinamide

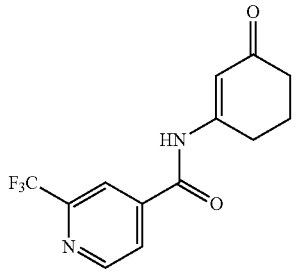 [SMILES: O=C1C=C(NC(=O)c2ccnc(C(F)(F)F)c2)CCC1]

To a solution of 2-(trifluoromethyl)pyridine-4-carboxylic acid (5 g, 26.16 mmol), 3-aminocyclohex-2-en-1-one (3.49 g, 31.40 mmol), DIEA (13.7 mL, 78.49 mmol) in DMF (50 mL) was added HATU (15 g, 39.24 mmol) and the mixture was stirred at 25° C. for 16 h. The reaction was diluted with water (100 mL), extracted with ethyl acetate (60 mL×3), the combined organic layers were washed with brine (50 mL×3), dried over anhydrous $Na_2SO_4$, filtered and concentrated in vacuo. The crude residue was purified by silica gel chromatography (solvent gradient: 0-60% EtOAc in petroleum ether) to give the title compound (3.5 g, 20%) as yellow oil. H NMR (400 MHz, $CDCl_3$) δ 9.28 (s, 1H), 8.88 (d, J=4.8 Hz, 1H), 8.12 (s, 1H), 7.99-7.90 (m, 2H), 6.72 (s, 1H), 2.75 (t, J=6.4 Hz, 2H), 2.39 (t, J=6.4 Hz, 2H), 2.13-2.04 (m, 2H). LCMS (ESI) m/z: 285.1 $[M+H]^+$.

Step 2—Synthesis of N-(2-Bromo-3-oxocyclohex-1-en-1-yl)-2-(trifluoromethyl)isonicotinamide

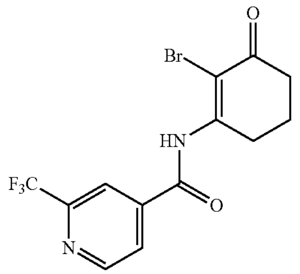 [SMILES: O=C1CCCC(NC(=O)c2ccnc(C(F)(F)F)c2)=C1Br]

To a solution of N-(3-oxocyclohexen-1-yl)-2-(trifluoromethyl)pyridine-4-carboxamide (3.5 g, 11.26 mmol) in DMF (30 mL) was added NBS (2.4 g, 13.51 mmol) and the mixture was stirred at 25° C. for 2 h. The reaction was diluted with water (50 mL), extracted with ethyl acetate (50 mL×3), the combined organic layers were washed with brine (50 mL×3), dried over anhydrous $Na_2SO_4$, filtered and concentrated in vacuo. The crude residue was purified by silica gel chromatography (solvent gradient: 0-60% EtOAc in petroleum ether) to give the title compound (3 g, 73%) as a yellow solid. $^1$H NMR (400 MHz, $CDCl_3$) δ 9.00 (d, J=5.2 Hz, 1H), 8.77 (s, 1H), 8.13 (s, 1H), 7.92-7.86 (m, 1H), 3.39 (t, J=6.4 Hz, 2H), 2.68 (t, J=6.4 Hz, 2H), 2.19-2.16 (m, 2H). LCMS (ESI) m/z: 363.0 $[M+H]^+$.

Step 3—Synthesis of 2-(2-(Trifluoromethyl)pyridin-4-yl)-5,6-dihydrobenzo[d]oxazol-7(4H)-one

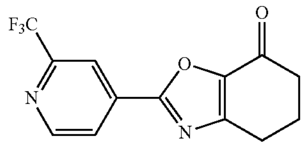 [SMILES: O=C1CCCc2nc(-c3ccnc(C(F)(F)F)c3)oc21]

To a solution of N-(2-bromo-3-oxo-cyclohexen-1-yl)-2-(trifluoromethyl)pyridine-4-carboxamide (3 g, 6.20 mmol), $Cs_2CO_3$ (6.06 g, 18.59 mmol) and N,N-dimethylglycine hydrochloride (259 mg, 1.86 mmol) in dioxane (30 mL) was added CuI (118 mg, 619.6 μmol). The mixture was stirred at 85° C. for 16 h under a nitrogen atmosphere. After cooling to room temperature, the reaction was quenched with water (50 mL), extracted with ethyl acetate (50 mL×2), the combined organic layers were washed with brine (100 mL), dried over anhydrous $Na_2SO_4$, filtered and concentrated in vacuo. The crude residue was purified by silica gel chromatography (solvent gradient: 0-30% EtOAc in petroleum ether) to give the title compound (1.4 g, 80%) as a white solid. $^1$H NMR (400 MHz, $CDCl_3$) δ 8.92 (d, J=4.8 Hz, 1H), 8.40 (s, 1H), 8.19 (d, J=4.8 Hz, 1H), 3.01 (t, J=5.2 Hz, 2H), 2.71 (t, J=6.0 Hz, 2H), 2.34-2.62 (m, 2H). LCMS (ESI) m/z: 283.0 $[M+H]^+$.

Step 4—Synthesis of (S,E)-2-Methyl-N-(2-(2-(trifluoromethyl)pyridin-4-yl)-5,6-dihydrobenzo[d]oxazol-7(4H)-ylidene)propane-2-sulfinamide

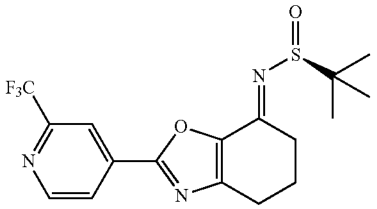 [SMILES: CC(C)(C)[S@](=O)/N=C1\CCCc2nc(-c3ccnc(C(F)(F)F)c3)oc21]

To a solution of 2-[2-(trifluoromethyl)-4-pyridyl]-5,6-dihydro-4H-1,3-benzoxazol-7-one (1.4 g, 4.96 mmol), (S)-2-methylpropane-2-sulfinamide (6 g, 49.61 mmol) in THE (20 mL) was added $Ti(i-PrO)_4$ (14 mL, 49.61 mmol). The mixture was stirred at 75° C. for 16 h. After cooling to room temperature, the mixture was quenched with $H_2O$ (50 mL) and filtered. The filtrate was extracted with ethyl acetate (50 mL×2). The combined layers were washed with brine (50 mL×3), dried over anhydrous $Na_2SO_4$, filtered and concentrated in vacuo to give the title compound (2.5 g, crude) as a brown solid which was used without further purification. LCMS (ESI) m/z: 386.1 $[M+H]^+$.

Step 5—Synthesis of (S)-2-Methyl-N—((S)-2-(2-(trifluoromethyl)pyridin-4-yl)-4,5,6,7-tetrahydrobenzo[d]oxazol-7-yl)propane-2-sulfinamide

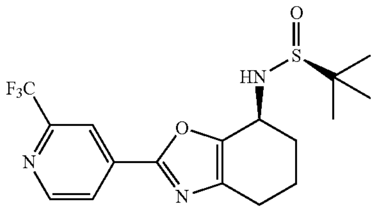 [SMILES: CC(C)(C)[S@](=O)N[C@H]1CCCc2nc(-c3ccnc(C(F)(F)F)c3)oc21]

To a solution of (S,E)-2-methyl-N-(2-(2-(trifluoromethyl)pyridin-4-yl)-5,6-dihydrobenzo[d]oxazol-7(4H)-ylidene)propane-2-sulfinamide (2.5 g, 6.49 mmol) in THE (30 mL) was added $NaBH_4$ (736 mg, 19.46 mmol) at 0° C. The mixture was stirred at 0° C. for 2 h. The reaction was quenched with sat. aq. $NH_4Cl$ (20 mL) and extracted with EtOAc (50 mL×2). The combined organic layers were washed with brine (30 mL×2), dried over anhydrous $Na_2SO_4$, filtered and concentrated in vacuo. The crude residue was purified by silica gel chromatography (solvent gradient: 0-30% EtOAc in petroleum ether) to give the title compound (1.5 g, 60%) as a yellow solid. LCMS (ESI) m/z: 388.1 $[M+H]^+$.

Step 6—Synthesis of (S)-2-(2-(Trifluoromethyl)pyridin-4-yl)-4,5,6,7-tetrahydrobenzo[d]oxazol-7-amine hydrochloride

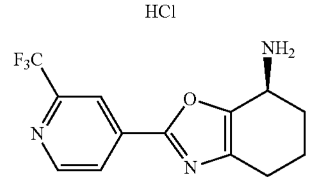 [SMILES: Cl ; N[C@H]1CCCc2nc(-c3ccnc(C(F)(F)F)c3)oc21]

To a solution of (S)-2-methyl-N—((S)-2-(2-(trifluoromethyl)pyridin-4-yl)-4,5,6,7-tetrahydrobenzo[d]oxazol-7-yl)propane-2-sulfinamide (1.5 g, 3.85 mmol) in dioxane (5 mL) was added hydrochloride in dioxane (2M, 20 mL). The mixture was stirred at 25° C. for 16 h. The mixture was concentrated in vacuo to give the title compound (1.5 g, crude) as a yellow solid which was used without further purification. LCMS (ESI) m/z: 284.2 $[M+H]^+$.

Step 7—Synthesis of (S)-1-Methyl-3-(trifluoromethyl)-N-(2-(2-(trifluoromethyl)pyridin-4-yl)-4,5,6,7-tetrahydrobenzo[d]oxazol-7-yl)-1H-pyrazole-5-carboxamide

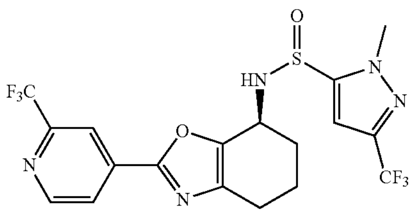 [SMILES: Cn1nc(C(F)(F)F)cc1S(=O)N[C@H]1CCCc2nc(-c3ccnc(C(F)(F)F)c3)oc21]

To a solution of (S)-2-(2-(trifluoromethyl)pyridin-4-yl)-4,5,6,7-tetrahydrobenzo[d]oxazol-7-amine hydrochloride salt (1.00 g, 3.13 mmol), DIEA (2.72 mL, 15.64 mmol), and 2-methyl-5-(trifluoromethyl)pyrazole-3-carboxylic acid (728 mg, 3.75 mmol) in DCM (10 mL) was added HATU (1.43 g, 3.75 mmol). The mixture was stirred at 25° C. for 3 h. The reaction was diluted with $H_2O$ (50 mL), extracted with DCM (50 mL×2). The combined organic layers were washed with brine (30 mL×2), dried over anhydrous $Na_2SO_4$, filtered and concentrated in vacuo. The residue was purified by RP-HPLC (acetonitrile 52%-82%/0.225% formic acid in water) to give the title compound (100 mg, 73% ee) as a white solid. LCMS (ESI) m/z: 460.2 $[M+H]^+$.

Step 8—Purification of (S)-1-Methyl-3-(trifluoromethyl)-N-(2-(2-(trifluoromethyl)pyridin-4-yl)-4,5,6,7-tetrahydrobenzo[d]oxazol-7-yl)-1H-pyrazole-5-carboxamide

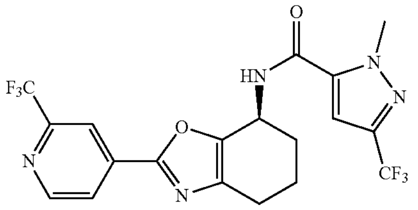 [SMILES: Cn1nc(C(F)(F)F)cc1C(=O)N[C@H]1CCCc2nc(-c3ccnc(C(F)(F)F)c3)oc21]

(S)-1-methyl-3-(trifluoromethyl)-N-(2-(2-(trifluoromethyl)pyridin-4-yl)-4,5,6,7-tetrahydrobenzo[d]oxazol-7-yl)-1H-pyrazole-5-carboxamide (100 mg, 218 μmol) was separated by using chiral SFC (DAICEL CHIRALCEL AS (250 mm*30 mm, 10 μm); Supercritical $CO_2$/EtOH+0.1% $NH_3 \cdot H_2O$=85/15; 60 mL/min) to afford(S)-1-methyl-3-(trifluoromethyl)-N-(2-(2-(trifluoromethyl)pyridin-4-yl)-4,5,6,7-tetrahydrobenzo[d]oxazol-7-yl)-1H-pyrazole-5-carboxamide (75 mg, first peak) and (R)-1-methyl-3-(trifluoromethyl)-N-(2-(2-(trifluoromethyl)pyridin-4-yl)-4,5,6,7-tetrahydrobenzo[d]oxazol-7-yl)-1H-pyrazole-5-carboxamide (15 mg, second peak) both as white solid. First peak: (I-83a): $^1H$ NMR (400 MHz, DMSO-$d_6$) δ 9.13 (d, J=8.0 Hz, 1H), 8.92 (d, J=4.8 Hz, 1H), 8.22 (s, 1H), 8.18 (d, J=5.2 Hz, 1H), 7.37 (s, 1H), 5.37-5.29 (m, 1H), 4.19 (s, 3H), 2.70-2.58 (m, 2H), 2.13-2.04 (m, 1H), 2.01-1.83 (m, 3H). LCMS (ESI) m/z: 460.2 $[M+H]^+$.

Example 1.27. Synthesis of (S)-1-Methyl-3-(trifluoromethyl)-N-(2-(2-(trifluoromethyl)pyridin-4-yl)-5,6-dihydro-4H-pyrrolo[1,2-b]pyrazol-4-yl)-1H-1,2,4-triazole-5-carboxamide (I-314a)

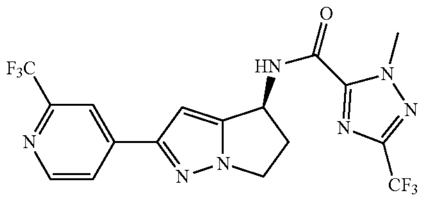 [SMILES: Cn1nc(C(F)(F)F)nc1C(=O)N[C@H]1CCn2nc(-c3ccnc(C(F)(F)F)c3)cc21]

Step 1—Synthesis of 3,5-Dibromo-1-(but-3-en-1-yl)-1H-pyrazole

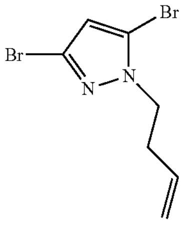

To a solution of 3,5-dibromo-1H-pyrazole (100 g, 442.73 mmol) in acetonitrile (600 mL) was added 4-bromobut-1-ene (49.4 mL, 487.01 mmol) and $K_2CO_3$ (184 g, 1.33 mol). The mixture was stirred at 60° C. for 16 h. After cooling to room temperature, the mixture was filtered and concentrated in vacuo to give the title compound (120 g, crude) as a yellow solid which was used without further purification. $^1H$ NMR (400 MHz, DMSO-$d_6$) δ 6.63 (s, 1H), 5.80-5.70 (m, 1H), 5.13-4.89 (m, 2H), 4.17 (t, J=7.2 Hz, 2H), 2.53-2.47 (s, 2H).

Step 2—Synthesis of 2-Bromo-4-methylene-5,6-dihydro-4H-pyrrolo[1,2-b]pyrazole

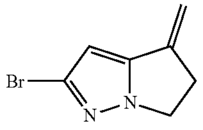

To a solution of 3,5-dibromo-1-but-3-enyl-pyrazole (120 g, 428.63 mmol), $PPh_3$ (22.5 g, 85.73 mmol) and TEA (179 mL, 1.29 mol) in acetonitrile (1.2 L) was added $Pd(OAc)_2$ (9.6 g, 42.86 mmol), then the mixture was stirred at 80° C. for 16 h under a nitrogen atmosphere. After cooling to room temperature, the reaction mixture was concentrated in vacuo. The crude residue was purified by silica gel chromatography (solvent gradient: 0-10% EtOAc in petroleum ether) to give the title compound (60 g, 71%) as a yellow solid. $^1H$ NMR (400 MHz, DMSO-$d_6$) δ 6.51 (s, 1H), 5.48-5.42 (m, 1H), 5.20-2.14 (m, 1H), 4.21 (t, J=6.4 Hz, 2H), 3.21-3.15 (m, 2H). LCMS (ESI) m/z: 198.9 $[M+H]^+$.

Step 3—Synthesis of 2-Bromo-5,6-dihydro-4H-pyrrolo[1,2-b]pyrazol-4-one

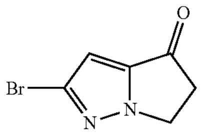

To a solution of 2-bromo-4-methylene-5,6-dihydropyrrolo[1,2-b]pyrazole (60 g, 300.75 mmol), NaIO4 (344 g, 1.61 mol) in THF (600 mL) and $H_2O$ (300 mL) was added $K_2OsO_4 \cdot 2H_2O$ (14.8 g, 40.19 mmol) at 0° C. The reaction was stirred at 25° C. for 16 h. The mixture was filtered, and the filtrate was quenched with sat. $Na_2S_2O_3$ (200 mL). The mixture was extracted with EtOAc (200 mL×2). Combined organic layers were washed with brine (200 mL×2), dried over anhydrous $Na_2SO_4$, filtered and concentrated in vacuo. The crude residue was purified by silica gel chromatography (solvent gradient: 0-10% EtOAc in petroleum ether) to give the title compound (45 g, 75%) as a yellow solid. $^1H$ NMR (400 MHz, DMSO-$d_6$) δ 6.93 (s, 1H), 4.47 (t, J=5.6 Hz, 2H), 3.16 (t, J=5.6 Hz, 2H). LCMS (ESI) m/z: 200.9 $[M+H]^+$.

Step 4—Synthesis of (R,E)-N-(2-Bromo-5,6-dihydro-4H-pyrrolo[1,2-b]pyrazol-4-ylidene)-2-methylpropane-2-sulfinamide

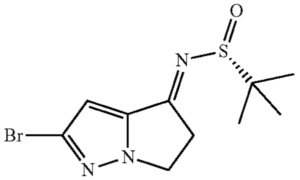 [SMILES: CC(C)(C)[S@@](=O)/N=C1\CCn2nc(Br)cc21]

To a solution of 2-bromo-5,6-dihydropyrrolo[1,2-b]pyrazol-4-one (57 g, 283.55 mmol) and (R)-2-methylpropane-2-sulfinamide (171.83 g, 1.42 mol) in THE (600 mL) was added $Ti(i\text{-}PrO)_4$ (418 mL, 1.42 mol). The reaction mixture was stirred at 70° C. for 16 h under a nitrogen atmosphere. After cooling to room temperature, the mixture was quenched with $H_2O$ (1 L) and filtered. The filtrate was extracted with ethyl acetate (300 mL×2). Combined organic layers were washed with brine (200 mL×2), dried over anhydrous $Na_2SO_4$, filtered and concentrated in vacuo to give the title compound (80 g, crude) as a yellow solid which was used without further purification. LCMS (ESI) m/z: 249.7 $[M-56]^+$.

Step 5—Synthesis of (R)—N-(2-Bromo-5,6-dihydro-4H-pyrrolo[1,2-b]pyrazol-4-yl)-2-methylpropane-2-sulfinamide

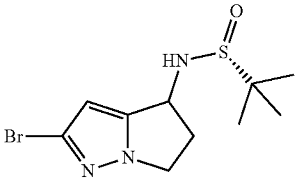 [SMILES: CC(C)(C)[S@@](=O)NC1CCn2nc(Br)cc21]

To a solution of (R,E)-N-(2-bromo-5,6-dihydro-4H-pyrrolo[1,2-b]pyrazol-4-ylidene)-2-methylpropane-2-sulfinamide (80 g, 262.98 mmol) in THE (800 mL) was added $NaBH_4$ (20 g, 528.68 mmol) in portions at 0° C. The reaction mixture was stirred at 25° C. for 2 h and then quenched with sat. $NH_4Cl$ (200 mL) and water (200 mL). The mixture was extracted with EtOAc (300 mL×2). Combined organic layers were washed with brine (300 mL×2), dried over anhydrous $Na_2SO_4$, filtered and concentrated in vacuo. The crude residue was purified on silica gel chromatography (solvent gradient: 0-10% EtOAc in petroleum ether) to give the title compound (35 g, mixture) as a yellow solid. LCMS (ESI) m/z: 308.1 $[M+H]^+$.

Step 6—Synthesis of (R)-2-Methyl-N—((S)-2-(2-(trifluoromethyl)pyridin-4-yl)-5,6-dihydro-4H-pyrrolo[1,2-b]pyrazol-4-yl)propane-2-sulfinamide

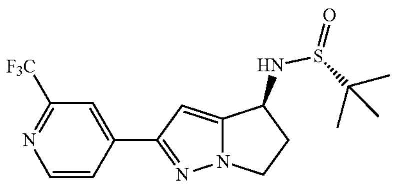 [SMILES: CC(C)(C)[S@@](=O)N[C@H]1CCn2nc(-c3ccnc(C(F)(F)F)c3)cc21]

To a solution of (R)—N-(2-bromo-5,6-dihydro-4H-pyrrolo[1,2-b]pyrazol-4-yl)-2-methylpropane-2-sulfinamide (35 g, 114.293 mmol), 4-(4,4,5,5-tetramethyl-1,3,2-dioxaborolan-2-yl)-2-(trifluoromethyl)pyridine (37 g, 137.13 mmol) and $K_3PO_4$ (72.8 g, 342.86 mmol) in dioxane (400 mL) and $H_2O$ (40 mL) was added Pd(dppf)$Cl_2$ (8.4 g, 11.41 mmol), then the mixture was stirred at 85° C. for 16 h under a nitrogen atmosphere. After cooling to room temperature, the mixture was diluted with $H_2O$ (200 mL), extracted with EtOAc (200 mL×2). The combined organic layers were washed with brine (300 mL), dried over anhydrous $Na_2SO_4$, filtered and concentrated in vacuo. The crude residue was purified on silica gel chromatography (solvent gradient: 0-10% EtOAc in petroleum ether) to give 15 g crude material which was further purified by trituration with (petroleum ether/ethyl acetate=3/1, 50 mL) to give the title compound (11 g, 26%) as a yellow solid. LCMS (ESI) m/z: 373.1 $[M+H]^+$.

Step 7—Synthesis of (S)-2-(2-(Trifluoromethyl)pyridin-4-yl)-5,6-dihydro-4H-pyrrolo[1,2-b]pyrazol-4-amine hydrochloride salt

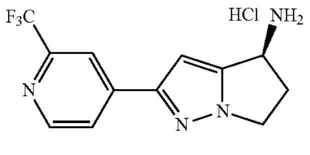 [SMILES: Cl ; N[C@H]1CCn2nc(-c3ccnc(C(F)(F)F)c3)cc21]

To a solution of (R)-2-methyl-N-[(4S)-2-[2-(trifluoromethyl)-4-pyridyl]-5,6-dihydro-4H-pyrrolo[1,2-b]pyrazol-4-yl]propane-2-sulfinamide (11 g, 29.55 mmol) in dioxane (20 mL) was added hydrochloride in dioxane (2M, 50 mL). The mixture was stirred at room temperature for 3 h. The mixture was concentrated in vacuo, the resulting residue was triturated with acetonitrile (30 mL) to give the title compound (8 g, crude) as a yellow solid which was used without further purification. $^1H$ NMR (400 MHz, DMSO-$d_6$) δ 8.78 (d, J=5.2 Hz, 4H), 8.19 (s, 1H), 8.09 (d, J=5.0 Hz, 1H), 7.05 (s, 1H), 4.89-4.78 (m, 1H), 4.40 (m, 1H), 4.23 m, 1H), 3.08-2.96 (m, 1H), 2.59 (m, 1H). LCMS (ESI) m/z: 269.1 $[M+H]^+$.

Step 8—Synthesis of 5-Bromo-3-(trifluoromethyl)-1H-1,2,4-triazole

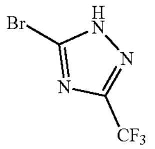

To a solution of 3-(trifluoromethyl)-1H-1,2,4-triazol-5-amine (100 g, 657.56 mmol) in $H_2O$ (800 mL) and $H_2SO_4$ (70 mL, 1.31 mol) was slowly added an aqueous solution of $NaNO_2$ (68 g, 986.32 mmol in 800 mL $H_2O$) at 0° C. over 30 minutes. Then an aqueous solution of CuBr (28.28 g, 197.28 mmol) and KBr (133 g, 1.12 mol) in 800 mL $H_2O$ was added at 0° C. The mixture was stirred at 25° C. for 16 h under a nitrogen atmosphere. The mixture was adjusted to pH 7 with $NaHCO_3$ (100 g). The mixture was concentrated in vacuo and filtered and the filtrate purified by RP-HPLC (acetonitrile 24%-54%/0.225% formic acid in water) to afford the title compound (26 g, 18%) as a black solid. LCMS (ESI) m/z: 215.8 $[M+H]^+$.

Step 9—Synthesis of 5-Bromo-1-methyl-3-(trifluoromethyl)-1H-1,2,4-triazole

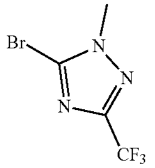

To a solution of 5-bromo-3-(trifluoromethyl)-1H-1,2,4-triazole (13 g, 68.07 mmol) in THF (150 mL) was added NaH (3.27 g, 81.68 mmol, 60% in mineral oil) dropwise at 0° C., the mixture was stirred at 0° C. for 0.5 h, then MeI (4.66 mL, 74.88 mmol) was added and the reaction mixture was stirred at 25° C. for 16 h. The reaction was quenched with sat. $NH_4Cl$ (50 mL) and diluted with $H_2O$ (50 mL), then extracted with EtOAc (50 mL×2). The combined organic layers were washed with brine (50 mL), dried over anhydrous $Na_2SO_4$, filtered and concentrated in vacuo to give the title compound (12.8 g, crude) as a yellow oil which was used without further purification. LCMS (ESI) m/z: 229.9 $[M+H]^+$.

Step 10—Synthesis of Methyl 2-methyl-5-(trifluoromethyl)-1,2,4-triazole-3-carboxylate

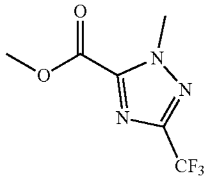

To a solution of 5-bromo-1-methyl-3-(trifluoromethyl)-1,2,4-triazole (12.8 g, 55.66 mmol) in DMF (50 mL) and MeOH (50 mL) was added KOAc (16.4 g, 166.97 mmol) and Pd(dppf)$Cl_2$ (4.07 g, 5.57 mmol). Then the mixture was stirred at 80° C. for 16 h under a CO atmosphere of 50 psi. After cooling to room temperature, the mixture was concentrated in vacuo and diluted with $H_2O$ (100 mL), extracted with EtOAc (100 mL×2). The combined organic layers were washed with brine (100 mL×3), dried over anhydrous $Na_2SO_4$, filtered and concentrated in vacuo. The crude was purified by RP-HPLC (acetonitrile 20%-50%/0.225% formic acid in water) to afford the title compound (3.46 g, 35%) as a black solid. $^1$H NMR (400 MHz, DMSO-$d_6$) δ 4.19 (s, 3H), 3.93 (s, 3H). LCMS (ESI) m/z: 210.0 [M+H]$^+$.

Step 11—Synthesis of (S)-1-Methyl-3-(trifluoromethyl)-N-(2-(2-(trifluoromethyl)pyridin-4-yl)-5,6-dihydro-4H-pyrrolo[1,2-b]pyrazol-4-yl)-1H-1,2,4-triazole-5-carboxamide

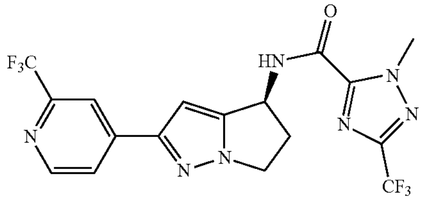 [SMILES: Cn1nc(C(F)(F)F)nc1C(=O)N[C@H]1CCn2nc(-c3ccnc(C(F)(F)F)c3)cc21]

To a solution of methyl 2-methyl-5-(trifluoromethyl)-1,2,4-triazole-3-carboxylate (300 mg, 1.43 mmol) in THE (10 mL) was added (4S)-2-[2-(trifluoromethyl)-4-pyridyl]-5,6-dihydro-4H-pyrrolo[1,2-b]pyrazol-4-amine hydrochloride (437 mg, 1.43 mmol) and DABAL-$Me_3$ (919 mg, 3.59 mmol). The mixture was stirred at 70° C. for 16 h under a nitrogen atmosphere. After cooling to room temperature, the mixture was filtered and concentrated in vacuo. The crude was purified by RP-HPLC (acetonitrile 22%-55%/0.225% formic acid in water) to afford the title compound (0.35 g, 58%) as a white solid. $^1$H NMR (400 MHz, DMSO-$d_6$) δ 9.81 (d, J=2.0 Hz, 1H), 8.74 (d, J=5.2 Hz, 1H), 8.19 (s, 1H), 8.09-8.05 (m, 1H), 6.99 (s, 1H), 5.58-5.52 (m, 1H), 4.41-4.38 (m, 1H), 4.25 (s, 3H), 4.22-4.16 (m, 1H), 3.09-2.98 (m, 1H), 2.69-2.60 (m, 1H). LCMS (ESI) m/z: 446.0 [M+H]$^+$.

Example 1.28. Synthesis of (S)—N-(2-(5-Fluoro-2-(trifluoromethyl)pyridin-4-yl)-5,6-dihydro-4H-pyrrolo[1,2-b]pyrazol-4-yl)-2-methoxyisonicotinamide (I-145a)

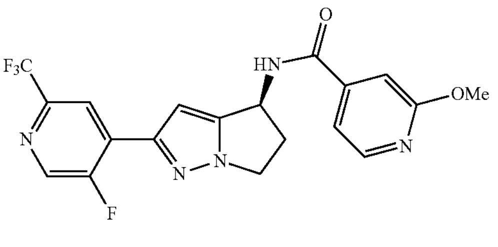 [SMILES: COc1cc(C(=O)N[C@H]2CCn3nc(-c4cc(C(F)(F)F)ncc4F)cc32)ccn1]

Step 1—Synthesis of (R)—N—((S)-2-Bromo-5,6-dihydro-4H-pyrrolo[1,2-b]pyrazol-4-yl)-2-methylpropane-2-sulfinamide

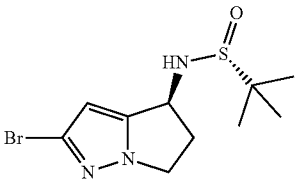 [SMILES: CC(C)(C)[S@@](=O)N[C@H]1CCn2nc(Br)cc21]

Crude (R,E)-N-(2-bromo-5,6-dihydro-4H-pyrrolo[1,2-b]pyrazol-4-ylidene)-2-methylpropane-2-sulfinamide (15 g, 52.35 mmol) was purified by RP-HPLC (acetonitrile 55%-85%/0.225% formic acid in water) to give the title compound (2.8 g, 25%) as yellow oil. LCMS (ESI) m/z: 306.2 [M+H]$^+$.

Step 2—Synthesis of (R)—N—((S)-2-(5-Fluoro-2-(trifluoromethyl)pyridin-4-yl)-5,6-dihydro-4H-pyrrolo[1,2-b]pyrazol-4-yl)-2-methylpropane-2-sulfinamide

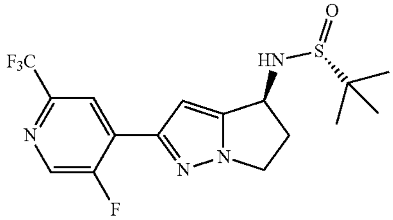 [SMILES: CC(C)(C)[S@@](=O)N[C@H]1CCn2nc(-c3cc(C(F)(F)F)ncc3F)cc21]

To a solution of (R)—N—((S)-2-bromo-5,6-dihydro-4H-pyrrolo[1,2-b]pyrazol-4-yl)-2-methylpropane-2-sulfinamide (400 mg, 13.31 mmol), (5-fluoro-2-(trifluoromethyl)pyridin-4-yl)boronic acid (546 mg, 79.94 mmol), $K_3PO_4$ (1.4 g, 6.53 mmol) in dioxane (10 mL) was added Xphos-Pd G2 (103 mg, 130.62 mmol). The reaction mixture was stirred at 80° C. for 16 h under a nitrogen atmosphere. After cooling to room temperature, (5-fluoro-2-(trifluoromethyl)pyridin-4-yl)boronic acid (546 mg, 79.9 mmol), $K_3PO_4$ (1.4 g, 6.5 mmol) and Xphos-Pd G2 (103 mg, 130.6 mmol) was added to the mixture. The reaction was stirred at 80° C. for another 16 h under a nitrogen atmosphere. After cooling to room temperature, the mixture was diluted with $H_2O$ (60 mL), extracted with ethyl acetate (50 mL×2). The combined organic layers were washed with brine (50 mL×2), dried over anhydrous $Na_2SO_4$, filtered and concentrated in vacuo. The residue was purified by silica gel chromatography (solvent gradient: 0-40% EtOAc in petroleum ether) to give the title compound (150 mg, 29%) as a yellow solid. LCMS (ESI) m/z: 391.1 [M+H]$^+$.

Step 3—Synthesis of (S)-2-(5-Fluoro-2-(trifluoromethyl)pyridin-4-yl)-5,6-dihydro-4H-pyrrolo[1,2-b]pyrazol-4-amine hydrochloride salt

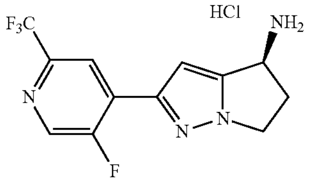 [SMILES: Cl ; N[C@H]1CCn2nc(-c3cc(C(F)(F)F)ncc3F)cc21]

To a solution of (R)—N—((S)-2-(5-fluoro-2-(trifluoromethyl)pyridin-4-yl)-5,6-dihydro-4H-pyrrolo[1,2-b]pyrazol-4-yl)-2-methylpropane-2-sulfinamide (150 mg, 384.2 μmol) in dioxane (2 mL) was added hydrochloric acid in dioxane (2M, 10 mL) and stirred at room temperature for 2 h. The mixture was concentrated in vacuo to give the title compound (100 mg, crude) as yellow solid which was used without further purification. LCMS (ESI) m/z: 286.9 $[M+H]^+$.

Step 4—Synthesis of (S)—N-(2-(5-Fluoro-2-(trifluoromethyl)pyridin-4-yl)-5,6-dihydro-4H-pyrrolo[1,2-b]pyrazol-4-yl)-2-methoxyisonicotinamide

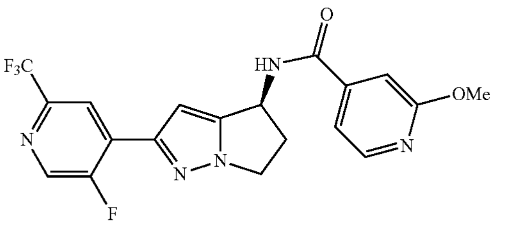 [SMILES: COc1cc(C(=O)N[C@H]2CCn3nc(-c4cc(C(F)(F)F)ncc4F)cc32)ccn1]

To a solution of (S)-2-(5-fluoro-2-(trifluoromethyl)pyridin-4-yl)-5,6-dihydro-4H-pyrrolo[1,2-b]pyrazol-4-amine hydrochloride salt (50 mg, 155.0 μmol), 2-methoxyisonicotinic acid (28 mg, 185.9 μmol) and DIEA (0.1 mL, 774.7 μmol) in DCM (2 mL) was added HATU (75 mg, 185.9 μmol). The mixture was stirred at 25° C. for 2 h. The reaction was diluted with $H_2O$ (30 mL), extracted with DCM (30 mL×2). The combined organic layers were washed with brine (20 mL×2), dried over anhydrous $Na_2SO_4$, filtered and concentrated in vacuo. The residue was purified by reverse phase chromatography (acetonitrile 50%-80%/0.225% formic acid in water) to give the title compound (17.9 mg, 27%) as a white solid. I-145a $^1H$ NMR (400 MHz, DMSO-$d_6$) δ 9.26 (d, J=7.6 Hz, 1H), 8.85 (d, J=2.4 Hz, 1H), 8.52-8.06 (m, 2H), 7.43-7.33 (m, 1H), 7.22 (s, 1H), 6.78 (d, J=3.2 Hz, 1H), 5.61-5.49 (m, 1H), 4.47-4.36 (m, 1H), 4.31-4.22 (m, 1H), 3.89 (s, 3H), 3.11-3.01 (m, 1H), 2.61-2.55 (m, 1H). LCMS (ESI) m/z: 422.1 $[M+H]^+$.

Example 1.29. Synthesis of (S)-3-(Trifluoromethyl)-N-(2-(2-(trifluoromethyl)pyridin-4-yl)-5,6-dihydro-4H-pyrrolo[1,2-b]pyrazol-4-yl)bicyclo[1.1.1]pentane-1-carboxamide (I-138a)

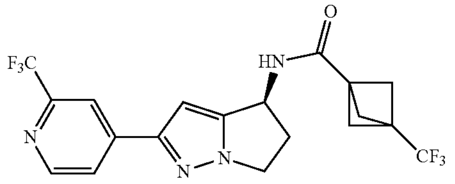 [SMILES: O=C(N[C@H]1CCn2nc(-c3ccnc(C(F)(F)F)c3)cc21)C12CC(C(F)(F)F)(C1)C2]

Step 1—Synthesis of Methyl 3-bromo-1-(3-methoxy-3-oxopropyl)-1H-pyrazole-5-carboxylate

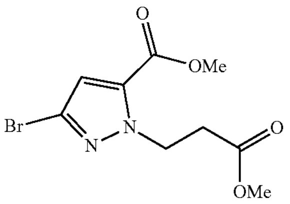 [SMILES: COC(=O)CCn1nc(Br)cc1C(=O)OC]

To a solution of methyl 3-bromo-1H-pyrazole-5-carboxylate (50 g, 243.89 mmol) and methyl 3-bromopropanoate (48.9 g, 292.7 mmol) in MeCN (500 mL) was added TEA (102 mL, 731.7 mmol). The reaction mixture was stirred at 80° C. for 16 h under a nitrogen atmosphere. After cooling to room temperature, the mixture was diluted with $H_2O$ (500 mL), extracted with ethyl acetate (500 mL×2). The combined organic layers were washed with brine (200 mL×2), dried over anhydrous $Na_2SO_4$, filtered and concentrated in vacuo. The residue was purified by silica gel chromatography (solvent gradient: 0-10% EtOAc in petroleum ether) to give the title compound (29 g, 41%) as a yellow solid. $^1H$ NMR (400 MHz, DMSO-$d_6$) δ 7.01 (s, 1H), 4.71 (t, J=6.8 Hz, 2H), 3.84 (s, 3H), 3.58 (s, 3H), 2.87 (t, J=6.8 Hz, 2H). LCMS (ESI) m/z: 291.0 $[M+H]^+$.

Step 2—Synthesis of Methyl 1-(3-methoxy-3-oxopropyl)-3-(2-(trifluoromethyl)pyridin-4-yl)-1H-pyrazole-5-carboxylate

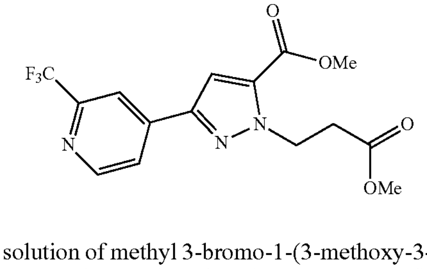

To a solution of methyl 3-bromo-1-(3-methoxy-3-oxopropyl)-1H-pyrazole-5-carboxylate (16 g, 55.0 mmol), [2-(trifluoromethyl)-4-pyridyl]boronic acid (13.64 g, 71.45 mmol), $K_3PO_4$ (35 g, 164.9 mmol) in dioxane (160 mL) and $H_2O$ (16 mL) was added Pd(dppf)$Cl_2$ (4.02 g, 5.1 mmol). The reaction mixture was stirred at 85° C. for 16 h under a nitrogen atmosphere. After cooling to room temperature, the mixture was diluted with $H_2O$ (300 mL), extracted with ethyl acetate (800 mL×2). The combined organic layers were washed with brine (200 mL×2), dried over anhydrous $Na_2SO_4$, filtered and concentrated in vacuo. The residue was purified by silica gel chromatography (solvent gradient: 0-10% EtOAc in petroleum ether) to give the title compound (17.2 g, 88%) as a yellow solid. $^1H$ NMR (400 MHz, DMSO-$d_6$) δ 8.80 (d, J=5.2 Hz, 1H), 8.27 (s, 1H), 8.13 (d, J=5.2 Hz, 1H), 7.79 (s, 1H), 4.82 (t, J=6.8 Hz, 2H), 3.89 (s, 3H), 3.60 (s, 3H), 2.96 (t, J=6.8 Hz, 2H). LCMS (ESI) m/z: 358.1 $[M+H]^+$.

Step 3—Synthesis of Sodium 5-(methoxycarbonyl)-2-(2-(trifluoromethyl)pyridin-4-yl)-6H-pyrrolo[1,2-b]pyrazol-4-olate

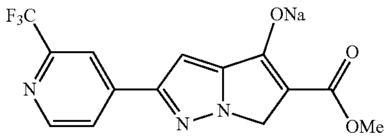

To a solution of methyl 1-(3-methoxy-3-oxopropyl)-3-(2-(trifluoromethyl)pyridin-4-yl)-1H-pyrazole-5-carboxylate (16 g, 44.8 mmol) in toluene (120 mL) was added NaOMe (16.59 mL, 5.4 M in MeOH, 89.6 mmol) at 0° C. The reaction mixture was stirred at 80° C. for 2 h under a nitrogen atmosphere. After cooling to room temperature, the mixture was filtered and the solid was further dried under vacuum to provide the title compound (16 g, crude) as a white solid which was used without further purifications. LCMS (ESI) m/z: 326.0 $[M-Na+2H]^+$.

Step 4—Synthesis of 2-(2-(Trifluoromethyl)pyridin-4-yl)-5,6-dihydro-4H-pyrrolo[1,2-b]pyrazol-4-one

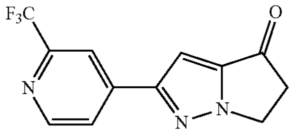

To a solution of methyl 4-oxo-2-(2-(trifluoromethyl)pyridin-4-yl)-5,6-dihydro-4H-pyrrolo[1,2-b]pyrazole-5-carboxylate (14 g, 43.0 mmol) was added conc. HCl (30 mL, 12M). The reaction mixture was stirred at 100° C. for 16 h under a nitrogen atmosphere. After cooling to room temperature, the reaction was adjusted to pH=8 with sat. $NaHCO_3$ (100 mL) and extracted with ethyl acetate (100 mL×2). The combined organic phase was washed with brine (50 mL×2), dried over anhydrous $Na_2SO_4$, filtered and concentrated in vacuo. The residue was purified by silica gel chromatography (solvent gradient: 0-40% EtOAc in petroleum ether) to give the title compound (9.8 g, 85%) as a white solid. $^1H$ NMR (400 MHz, DMSO-$d_6$) δ 8.83 (d, J=5.2 Hz, 1H), 8.31 (s, 1H), 8.19 (d, J=5.2 Hz, 1H), 7.62 (s, 1H), 4.59 (t, J=5.6 Hz, 2H), 3.25 (t, J=5.6 Hz, 2H). LCMS (ESI) m/z: 267.9 $[M+H]^+$.

Step 5—Synthesis of (R,E)-2-Methyl-N-(2-(2-(trifluoromethyl)pyridin-4-yl)-5,6-dihydro-4H-pyrrolo[1,2-b]pyrazol-4-ylidene)propane-2-sulfinamide

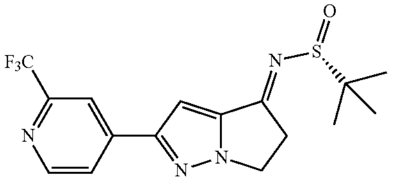 [SMILES: CC(C)(C)[S@@](=O)/N=C1\CCn2nc(-c3ccnc(C(F)(F)F)c3)cc21]

To a solution of 2-(2-(trifluoromethyl)pyridin-4-yl)-5,6-dihydro-4H-pyrrolo[1,2-b]pyrazol-4-one (6.15 g, 23.02 mmol), (R)-2-methylpropane-2-sulfinamide (13.95 g, 115.08 mmol) in THE (60 mL) was added $Ti(i\text{-}PrO)_4$ (34 mL, 115.08 mmol). The reaction mixture was stirred at 75° C. for 16 h under a nitrogen atmosphere. After cooling to room temperature, the mixture was quenched with $H_2O$ (200 mL), and then filtered. The filtrate was extracted with ethyl acetate (300 mL×2). The combined organic layers were washed with brine (100 mL), dried over anhydrous $Na_2SO_4$, filtered and concentrated in vacuo. The residue was purified by silica gel chromatography (solvent gradient: 0-40% EtOAc in petroleum ether) to give the title compound (6.45 g, 76%) as a white solid. LCMS (ESI) m/z: 371.1 $[M+H]^+$.

Step 6—Synthesis of (R)-2-Methyl-N-(2-(2-(trifluoromethyl)pyridin-4-yl)-5,6-dihydro-4H-pyrrolo[1,2-b]pyrazol-4-yl)propane-2-sulfinamide

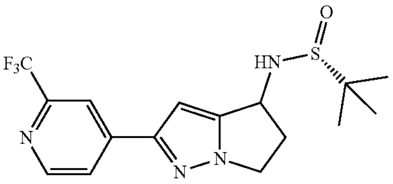 [SMILES: CC(C)(C)[S@@](=O)NC1CCn2nc(-c3ccnc(C(F)(F)F)c3)cc21]

To a solution of (R,E)-2-methyl-N-(2-(2-(trifluoromethyl)pyridin-4-yl)-5,6-dihydro-4H-pyrrolo[1,2-b]pyrazol-4-ylidene)propane-2-sulfinamide (6.45 g, 17.4 mmol) in THE (60 mL) at 0° C. was added $NaBH_4$ (1.98 g, 52.2 mmol) and stirred at 25° C. for 2 h. The mixture was quenched with sat. aq. $NH_4Cl$ (50 mL). The mixture was extracted with EtOAc (200 mL×2). The combined organic layers were washed with brine (150 mL×2), dried over anhydrous $Na_2SO_4$, filtered and concentrated in vacuo. The crude residue was purified by silica gel chromatography (solvent gradient: 0-70% EtOAc in petroleum ether) to give the title compound (2.89 g, 45%) as a yellow solid. LCMS (ESI) m/z: 373.1 $[M+H]^+$.

Step 7—Synthesis of 2-(2-(Trifluoromethyl)pyridin-4-yl)-5,6-dihydro-4H-pyrrolo[1,2-b]pyrazol-4-amine hydrochloride salt

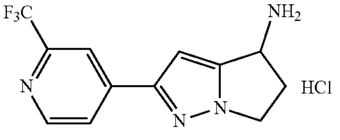 [SMILES: NC1CCn2nc(-c3ccnc(C(F)(F)F)c3)cc21 ; Cl]

To a solution of (R)-2-methyl-N-(2-(2-(trifluoromethyl) pyridin-4-yl)-5,6-dihydro-4H-pyrrolo[1,2-b]pyrazol-4-yl) propane-2-sulfinamide (2.89 g, 7.8 mmol) in dioxane (10 mL) was added hydrochloric acid in dioxane (2M, 50 mL). The mixture was stirred at room temperature for 2 h. The mixture was concentrated in vacuo to give the title compound (2.6 g, crude) as yellow oil which was used without purification. LCMS (ESI) m/z: 283.2 [M+H]+.

Step 8—Synthesis of 3-(Trifluoromethyl)-N-(2-(2-(trifluoromethyl)pyridin-4-yl)-5,6-dihydro-4H-pyrrolo[1,2-b]pyrazol-4-yl)bicyclo[1.1.1]pentane-1-carboxamide

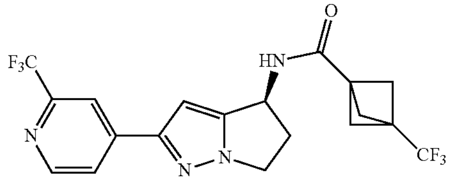 [SMILES: O=C(N[C@H]1CCn2nc(-c3ccnc(C(F)(F)F)c3)cc21)C12CC(C(F)(F)F)(C1)C2]

To a solution of 2-(2-(trifluoromethyl)pyridin-4-yl)-5,6-dihydro-4H-pyrrolo[1,2-b]pyrazol-4-amine hydrochloride salt (150 mg, 0.44 mmol), 3-(trifluoromethyl)bicyclo[1.1.1]pentane-1-carboxylic acid (80 mg, 447.4 μmol) and DIEA (0.4 mL, 2.30 mmol) in DCM (3 mL) was added HATU (200 mg, 0.53 mmol). The reaction mixture was stirred at 25° C. for 1 h. The reaction was diluted with $H_2O$ (30 mL), and then extracted with DCM (30 mL×2). The combined organic layers were washed with brine (20 mL×2), dried over anhydrous $Na_2SO_4$, filtered and concentrated in vacuo. The residue was purified by silica gel chromatography (solvent gradient: 0-40% EtOAc in petroleum ether) to give the title compound (100 mg, 36%) as a white solid. LCMS (ESI) m/z: 431.1 [M+H]+.

Step 9—Synthesis of (S)-3-(Trifluoromethyl)-N-(2-(2-(trifluoromethyl)pyridin-4-yl)-5,6-dihydro-4H-pyrrolo[1,2-b]pyrazol-4-yl)bicyclo[1.1.1]pentane-1-carboxamide & (R)-3-(Trifluoromethyl)-N-(2-(2-(trifluoromethyl)pyridin-4-yl)-5,6-dihydro-4H-pyrrolo[1,2-b]pyrazol-4-yl)bicyclo[1.1.1]pentane-1-carboxamide

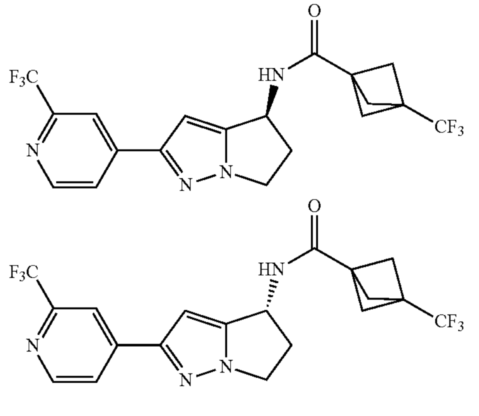

3-(Trifluoromethyl)-N-(2-(2-(trifluoromethyl)pyridin-4-yl)-5,6-dihydro-4H-pyrrolo[1,2-b]pyrazol-4-yl)bicyclo[1.1.1]pentane-1-carboxamide (100 mg, 232 μmol) was separated by the following conditions: chiral SFC (DAICEL CHIRALCEL OJ (250 mm*30 mm, 10 μm); supercritical $CO_2$/EtOH+0.1% $NH_3{\cdot}H_2O$=80/20; 80 mL/min), affording (S)-3-(trifluoromethyl)-N-(2-(2-(trifluoromethyl)pyridin-4-yl)-5,6-dihydro-4H-pyrrolo[1,2-b]pyrazol-4-yl)bicyclo[1.1.1]pentane-1-carboxamide (40 mg, first peak) and (R)-3-(trifluoromethyl)-N-(2-(2-(trifluoromethyl)pyridin-4-yl)-5,6-dihydro-4H-pyrrolo[1,2-b]pyrazol-4-yl)bicyclo[1.1.1]pentane-1-carboxamide (20 mg, second peak) both as white solid. First peak: (I-138a): $^1$H NMR (400 MHz, DMSO-$d_6$) δ 8.74 (d, J=5.2 Hz, 1H), 8.61 (d, J=8.0 Hz, 1H), 8.20 (s, 1H), 8.12-8.05 (m, 1H), 6.96 (s, 1H), 5.38-5.30 (m, 1H), 4.36-4.28 (m, 1H), 4.21-4.13 (m, 1H), 2.99-2.93 (m, 1H), 2.41-2.35 (m, 1H), 2.18 (s, 6H). LCMS (ESI) m/z: 431.1 [M+H]+. Second peak: $^1$H NMR (400 MHz, DMSO-$d_6$) δ 8.74 (d, J=5.2 Hz, 1H), 8.61 (d, J=8.0 Hz, 1H), 8.20 (s, 1H), 8.12-8.05 (m, 1H), 6.96 (s, 1H), 5.38-5.30 (m, 1H), 4.36-4.28 (m, 1H), 4.21-4.13 (m, 1H), 2.99-2.93 (m, 1H), 2.41-2.35 (m, 1H), 2.18 (s, 6H). LCMS (ESI) m/z: 431.1 [M+H]+.

Example 1.30. Synthesis of (S)-3-Cyano-N-(2-(2-(1,1-difluoroethyl)pyridin-4-yl)-2,4,5,6-tetrahydrocyclopenta[c]pyrazol-4-yl)benzamide (I-274a)

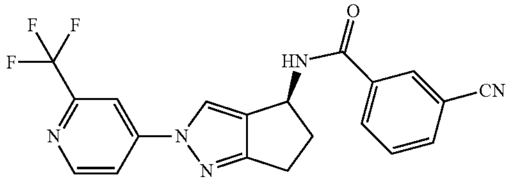 [SMILES: N#Cc1cccc(C(=O)N[C@H]2CCc3nn(-c4ccnc(C(F)(F)F)c4)cc32)c1]

Step 1—Synthesis of 2-(2-(1,1-Difluoroethyl)pyridin-4-yl)-5,6-dihydrocyclopenta[c]pyrazol-4(2H)-one

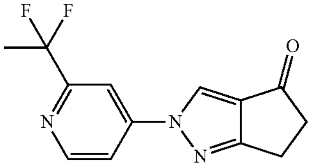 [SMILES: CC(F)(F)c1cc(-n2cc3c(n2)CCC3=O)ccn1]

To a solution of 4-bromo-2-(1,1-difluoroethyl)pyridine (1.5 g, 6.76 mmol), 5,6-dihydrocyclopenta[c]pyrazol-4(2H)-one (990 mg, 8.11 mmol, prepared according to the procedure in WO2012/008999), $K_3PO_4$ (4.30 g, 20.27 mmol) in dioxane (15 mL) was added t-BuXPhos-Pd G3 (464 mg, 675.6 μmol). The reaction was stirred at 100° C. for 16 h under a nitrogen atmosphere. After cooling to room temperature, the reaction was diluted with $H_2O$ (30 mL), extracted with ethyl acetate (50 mL×2). The combined organic layers were washed with brine (50 mL×2), dried over anhydrous $Na_2SO_4$, filtered and concentrated in vacuo. The crude residue was purified by silica gel chromatography (solvent gradient: 0-50% EtOAc in petroleum ether) to give the title compound (400 mg, 22%) as a white solid. $^1$H NMR (400 MHz, $CDCl_3$) δ 8.75 (d, J=5.6 Hz, 1H), 8.31 (s, 1H), 8.03 (d, J=2.0 Hz, 1H), 7.76-7.73 (m, 1H), 3.19-3.13 (m, 2H), 3.10-3.03 (m, 2H), 2.07 (t, J=18.8 Hz, 3H). LCMS (ESI) m/z: 264.0 [M+H]+.

Step 2—Synthesis of (S)-3-Cyano-N-(2-(2-(1,1-difluoroethyl)pyridin-4-yl)-2,4,5,6-tetrahydrocyclopenta[c]pyrazol-4-yl)benzamide

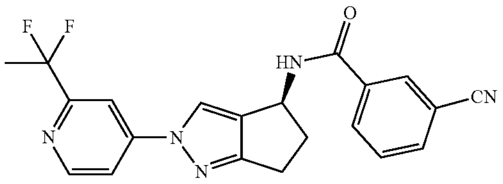 [SMILES: CC(F)(F)c1cc(-n2cc3c(n2)CC[C@@H]3NC(=O)c2cccc(C#N)c2)ccn1]

Following the procedure described in Example 1.26, 2-(2-(1,1-difluoroethyl)pyridin-4-yl)-5,6-dihydrocyclopenta[c]pyrazol-4(2H)-one was used in step 4, and (S)-2-(2-(1,1-difluoroethyl)pyridin-4-yl)-2,4,5,6-tetrahydrocyclopenta[c]pyrazol-4-amine hydrochloride salt was used in step 7, the title compound (16.4 mg, 28%) was obtained as a white solid after purification of RP-HPLC (acetonitrile 44%-74%/0.225% formic acid in water). I-274a: $^1$H NMR (400 MHz, $CDCl_3$) δ 8.64 (d, J=5.6 Hz, 1H), 8.09 (s, 1H), 8.04 (d, J=8.0 Hz, 1H), 7.97 (s, 1H), 7.92 (d, J=2.0 Hz, 1H), 7.80 (d, J=7.6 Hz, 1H), 7.68-7.64 (m, 1H), 7.62-7.57 (m, 1H), 6.48 (d, J=6.4 Hz, 1H), 5.53-5.46 (m, 1H), 3.12-3.00 (m, 2H), 2.96-2.86 (m, 1H), 2.46-2.37 (m, 1H), 2.05 (t, J=18.8 Hz, 3H). LCMS (ESI) m/z: 394.2 $[M+H]^+$.

Example 1.31. Synthesis of (S)-3-Cyano-N-(2-(2-(trifluoromethyl)pyridin-4-yl)-5,6,7,8-tetrahydro-4H-cyclohepta[d]oxazol-4-yl)benzamide (I-160a)

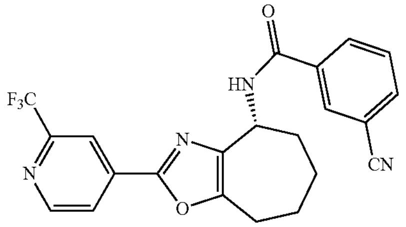 [SMILES: N#Cc1cccc(C(=O)N[C@@H]2CCCCc3oc(-c4ccnc(C(F)(F)F)c4)nc32)c1]

Step 1—Synthesis of 2-(2-(Trifluoromethyl)pyridin-4-yl)-5,6,7,8-tetrahydro-4H-cyclohepta[d]oxazol-4-one

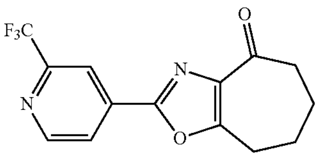 [SMILES: O=C1CCCCc2oc(-c3ccnc(C(F)(F)F)c3)nc21]

To a solution of 2-(trifluoromethyl)isonicotinonitrile (30 g, 174.32 mmol) and $Rh_2(Oac)_4$ (771 mg, 1.74 mmol) was added 2-diazocyclohexane-1,3-dione (45 g, 239.14 mmol) dropwise at 60° C. The reaction mixture was stirred at 60° C. for 4 h under a nitrogen atmosphere. After cooling to room temperature, the crude residue was purified by silica gel chromatography (solvent gradient: 0-40% ethyl acetate in petroleum ether) to give the title compound (6.6 g, 13%) as a yellow solid. LCMS (ESI) m/z: 297.0 $[M+H]^+$.

Step 2—Synthesis of 2-(2-(Trifluoromethyl)pyridin-4-yl)-5,6,7,8-tetrahydro-4H-cyclohepta[d]oxazol-4-ol

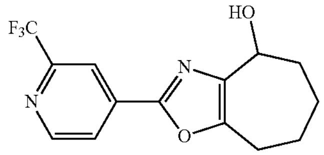 [SMILES: OC1CCCCc2oc(-c3ccnc(C(F)(F)F)c3)nc21]

To a solution of 2-(2-(trifluoromethyl)pyridin-4-yl)-5,6,7,8-tetrahydro-4H-cyclohepta[d]oxazol-4-one (6 g, 20.25 mmol) in THE (20 mL) was added $NaBH_4$ (2.32 g, 61.33 mmol) at 0° C. The reaction mixture was stirred at 25° C. for 1 h and quenched with sat. $NH_4Cl$ (50 mL). The mixture was extracted with EtOAc (50 mL×2). Combined organic layers were washed with brine (30 mL×2), dried over anhydrous $Na_2SO_4$, filtered and concentrated in vacuo. The crude was purified by silica gel chromatography (solvent gradient: 0-35% ethyl acetate in petroleum ether) to give the title compound (530 mg, 9%) as a white solid. LCMS (ESI) m/z: 299.1 $[M+H]^+$.

Step 3—Synthesis of 4-Azido-2-(2-(trifluoromethyl)pyridin-4-yl)-5,6,7,8-tetrahydro-4H-cyclohepta[d]oxazole

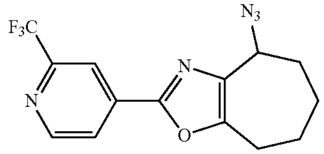

To a solution of 2-(2-(trifluoromethyl)pyridin-4-yl)-5,6,7,8-tetrahydro-4H-cyclohepta[d]oxazol-4-ol (530 mg, 1.78 mmol) and DBU (400 μL, 2.67 mmol) in toluene (5 mL) was added DPPA (570 μL, 2.67 mmol) at 0° C. and the reaction mixture was stirred at 25° C. for 2 h. The reaction mixture was diluted with ethyl acetate (30 mL), washed with $NaHCO_3$ (10 mL) and brine (10 mL), dried over anhydrous $Na_2SO_4$, filtered and concentrated in vacuo. The crude was purified by silica gel chromatography (solvent gradient: 0-10% ethyl acetate in petroleum ether) to give the title compound (170 mg, 30%) as a white solid. LCMS (ESI) m/z: 324.1 $[M+H]^+$.

Step 4—Synthesis of 2-(2-(Trifluoromethyl)pyridin-4-yl)-5,6,7,8-tetrahydro-4H-cyclohepta[d]oxazol-4-amine

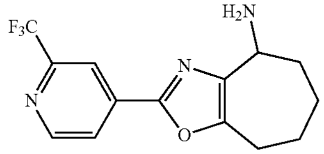 [SMILES: NC1CCCCc2oc(-c3ccnc(C(F)(F)F)c3)nc21]

To a solution of 4-azido-2-(2-(trifluoromethyl)pyridin-4-yl)-5,6,7,8-tetrahydro-4H-cyclohepta[d]oxazole (170 mg, 525.8 μmol) in THE (3 mL) with $H_2O$ (1 mL) was added $PPh_3$ (138 mg, 525.8 μmol). The reaction mixture was stirred at 60° C. for 1 h under a nitrogen atmosphere. After cooling to room temperature, the mixture was diluted with $H_2O$ (5 mL), extracted with ethyl acetate (10 mL×2). Dried over anhydrous $Na_2SO_4$, filtered and concentrated in vacuo. The crude was purified by silica gel chromatography (solvent gradient: 0-60% ethyl acetate in petroleum ether) to give the title compound (150 mg, 96%) as a white solid. LCMS (ESI) m/z: 298.1 $[M+H]^+$.

Step 5—Synthesis of 3-Cyano-N-(2-(2-(trifluoromethyl)pyridin-4-yl)-5,6,7,8-tetrahydro-4H-cyclohepta[d]oxazol-4-yl)benzamide

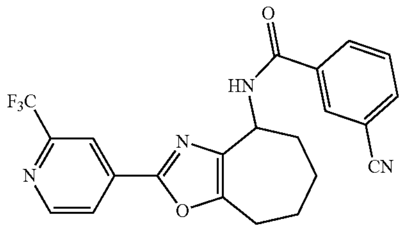

To a solution of 2-(2-(trifluoromethyl)pyridin-4-yl)-5,6,7,8-tetrahydro-4H-cyclohepta[d]oxazol-4-amine (150 mg, 604.6 μmol), 3-cyanobenzoic acid (89 mg, 604.6 μmol) and DIEA (260 μL, 1.51 mmol) in DCM (2 mL) was added HATU (230 mg, 605.5 μmol). The reaction mixture was stirred at 25° C. for 2 h. The reaction was diluted with $H_2O$ (10 mL), then extracted with DCM (10 mL×2). The combined organic layers were washed with brine (10 mL×2), dried over anhydrous $Na_2SO_4$, filtered and concentrated in vacuo. The crude was purified by silica gel chromatography (solvent gradient: 0-30% ethyl acetate in petroleum ether) to give the title compound (160 mg, 74%) as a white solid. LCMS (ESI) m/z: 427.1 $[M+H]^+$.

Step 6—Synthesis of (S)-3-Cyano-N-(2-(2-(trifluoromethyl)pyridin-4-yl)-5,6,7,8-tetrahydro-4H-cyclohepta[d]oxazol-4-yl)benzamide & (R)-3-Cyano-N-(2-(2-(trifluoromethyl)pyridin-4-yl-5,6,7,8-tetrahydro-4H-cyclohepta[d]oxazol-4-yl)benzamide

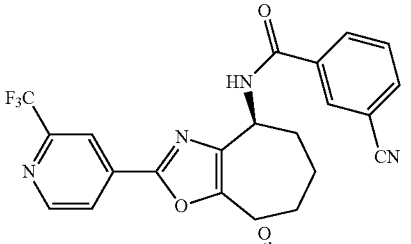

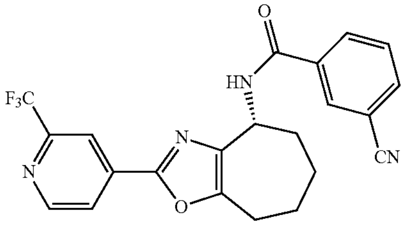

3-Cyano-N-(2-(2-(trifluoromethyl)pyridin-4-yl)-5,6,7,8-tetrahydro-4H-cyclohepta[d]oxazol-4-yl)benzamide (160 mg, 375.24 μmol) was separated by the following conditions: chiral SFC (DAICEL CHIRALCEL AD (250 mm*30 mm, 10 μm); supercritical $CO_2$/EtOH+0.1% $NH_3 \cdot H_2O$=70/30; 80 mL/min), affording (S)-3-cyano-N-(2-(2-(trifluoromethyl)pyridin-4-yl)-5,6,7,8-tetrahydro-4H-cyclohepta[d]oxazol-4-yl)benzamide (64 mg, first peak) and (R)-3-cyano-N-(2-(2-(trifluoromethyl)pyridin-4-yl)-5,6,7,8-tetrahydro-4H-cyclohepta[d]oxazol-4-yl)benzamide (65 mg, second peak) both as white solid. First peak: (I-160a): $^1H$ NMR (400 MHz, DMSO-$d_6$) δ 8.90 (d, J=4.8 Hz, 1H), 8.85 (d, J=7.6 Hz, 1H), 8.30 (s, 1H), 8.19 (d, J=8.0 Hz, 1H), 8.17 (s, 1H), 8.13 (d, J=4.8 Hz, 1H), 8.01 (d, J=7.6 Hz, 1H), 7.74-7.69 (m, 1H), 5.27-5.21 (m, 1H), 3.04-2.94 (m, 2H), 2.14-2.05 (m, 1H), 1.99-1.86 (m, 3H), 1.83-1.68 (m, 2H). LCMS (ESI) m/z: 427.1 $[M+H]^+$. Second peak (I-160b): $^1H$ NMR (400 MHz, DMSO-$d_6$) δ 8.90 (d, J=4.8 Hz, 1H), 8.85 (d, J=7.6 Hz, 1H), 8.30 (s, 1H), 8.19 (d, J=8.0 Hz, 1H), 8.17 (s, 1H), 8.13 (d, J=4.8 Hz, 1H), 8.01 (d, J=7.6 Hz, 1H), 7.74-7.69 (m, 1H), 5.27-5.21 (m, 1H), 3.04-2.94 (m, 2H), 2.14-2.05 (m, 1H), 1.99-1.86 (m, 3H), 1.83-1.68 (m, 2H). LCMS (ESI) m/z: 427.2 $[M+H]^+$.

Example 1.32. Synthesis of (S)-1-Methyl-N-(1-methyl-2-(2-(trifluoromethyl)pyridin-4-yl)-4,5,6,7-tetrahydro-1H-benzo[d]imidazol-4-yl)-3-(trifluoromethyl)-1H-pyrazole-5-carboxamide (I-247a)

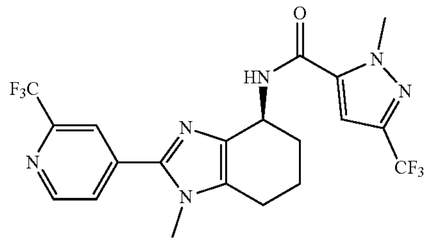 [SMILES: Cn1nc(C(F)(F)F)cc1C(=O)N[C@H]1CCCc2c1nc(-c1ccnc(C(F)(F)F)c1)n2C]

Step 1—Synthesis of 1-Methyl-1,5,6,7-tetrahydro-4H-benzo[d]imidazol-4-one

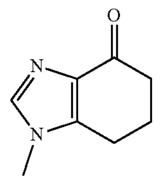

To a mixture of 1,5,6,7-tetrahydro-4H-benzo[d]imidazol-4-one (1.2 g, 8.81 mmol, prepared according to the procedure in Example 1 of EP3608321) in THE (10 mL) was added NaH (388 mg, 9.70 mmol, 60% in mineral oil), the mixture was stirred at 0° C. for 0.5 h, then $CH_3I$ (1.25 g, 8.81 mmol) was added. The reaction mixture was stirred at 20° C. for 16 h under a nitrogen atmosphere. The reaction mixture was quenched with MeOH (0.5 mL), then concentrated in vacuo, the crude was purified by silica gel chromatography (solvent gradient: 0-10% EtOAc in petroleum ether) to give the title compound (1.3 g, 98%) as a white solid. $^1H$ NMR (400 MHz, DMSO-$d_6$) δ 7.70 (s, 1H), 3.59 (s, 3H), 2.79 (t, J=6.0 Hz, 2H), 2.37 (t, J=6.0 Hz, 2H), 2.11-2.00 (m, 2H). LCMS (ESI) m/z: 151.2 $[M+H]^+$.

Step 2—Synthesis of 2-Bromo-1-methyl-1,5,6,7-tetrahydro-4H-benzo[d]imidazol-4-one

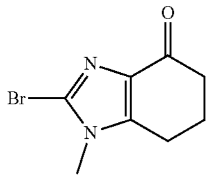

To a solution of 2-bromo-1-methyl-1,5,6,7-tetrahydro-4H-benzo[d]imidazol-4-one (700 mg, 3.06 mmol) in DMF (10 mL) was added NBS (3.85 g, 21.64 mmol) and the reaction mixture was stirred at 50° C. for 16 h under a nitrogen atmosphere. After cooling to room temperature, the mixture was diluted with $H_2O$ (30 mL), extracted with ethyl acetate (30 mL×2). The combined organic layers were washed with brine (30 mL×2), dried over anhydrous $Na_2SO_4$, filtered and concentrated in vacuo. The residue was purified by RP-HPLC (acetonitrile 0-16%/0.225% formic acid in water) to give the title compound (700 mg, 35%) as a yellow solid. $^1H$ NMR (400 MHz, DMSO-$d_6$) δ 3.53 (s, 3H), 2.81 (t, J=6.4 Hz, 2H), 2.38 (t, J=6.4 Hz, 2H), 2.06 (m, 2H). LCMS (ESI) m/z: 229.0 $[M+H]^+$.

Step 3—Synthesis of 1-Methyl-2-(2-(trifluoromethyl)pyridin-4-yl)-1,5,6,7-tetrahydro-4H-benzo[d]imidazol-4-one

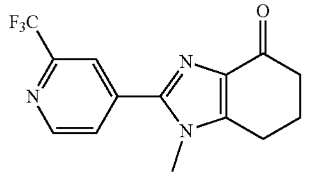 [SMILES: Cn1c(-c2ccnc(C(F)(F)F)c2)nc2c1CCCC2=O]

To a solution of 2-bromo-1-methyl-1,5,6,7-tetrahydro-4H-benzo[d]imidazol-4-one (700 mg, 3.06 mmol), (2-(trifluoromethyl)pyridin-4-yl)boronic acid (670 mg, 3.51 mmol), $K_3PO_4$ (1.55 g, 7.31 mmol) in dioxane (10 mL) was added Pd(dppf)$Cl_2$ (21 mg, 29.25 μmol). The reaction mixture was stirred at 80° C. for 16 h under a nitrogen atmosphere. After cooling to room temperature, the mixture was diluted with $H_2O$ (30 mL), extracted with ethyl acetate (30 mL×2). The combined organic layers were washed with brine (20 mL), dried over anhydrous $Na_2SO_4$, filtered and concentrated in vacuo. The crude was purified by silica gel chromatography (solvent gradient: 0-5% methanol in DCM) to give the title compound (800 mg, 93%) as a yellow solid. LCMS (ESI) m/z: 296.1 $[M+H]^+$.

Step 4—(S)-1-Methyl-N-(1-methyl-2-(2-(trifluoromethyl)pyridin-4-yl)-4,5,6,7-tetrahydro-1H-benzo[d]imidazol-4-yl)-3-(trifluoromethyl)-1H-pyrazole-5-carboxamide

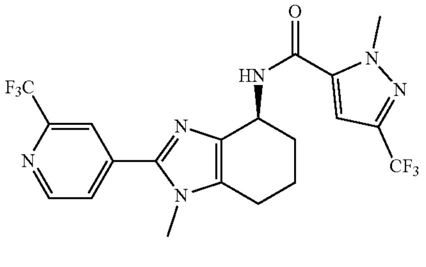 [SMILES: Cn1nc(C(F)(F)F)cc1C(=O)N[C@H]1CCCc2c1nc(-c1ccnc(C(F)(F)F)c1)n2C]

Following the procedure described in Example 1.26, 1-methyl-2-(2-(trifluoromethyl)pyridin-4-yl)-1,5,6,7-tetrahydro-4H-benzo[d]imidazol-4-one was used in step 2, (S)-1-methyl-2-(2-(trifluoromethyl)pyridin-4-yl)-4,5,6,7-tetrahydro-1H-benzo[d]imidazol-4-amine hydrochloride salt was used in step 7, the title compound (62.1 mg, 22%) was obtained as a white solid after purification of (acetonitrile 45%-75%/0.225% formic acid in water). I-247a: $^1H$ NMR (400 MHz, DMSO-$d_6$) δ 8.87 (d, J=8.0 Hz, 1H), 8.84 (d, J=5.2 Hz, 1H), 8.10 (s, 1H), 8.05-7.95 (m, 1H), 7.39 (s, 1H), 5.15-5.04 (m, 1H), 4.18 (s, 3H), 3.76 (s, 3H), 2.73-2.58 (m, 2H), 2.03-1.90 (m, 2H), 1.90-1.75 (m, 2H). LCMS (ESI) m/z: 473.1 $[M+H]^+$.

Example 1.33. Synthesis of (S)-3-Cyano-N-(6,6-dimethyl-2-(2-(trifluoromethyl)pyridin-4-yl)-4,5,6,7-tetrahydropyrazolo[1,5-a]pyridin-4-yl)benzamide (I-220a)

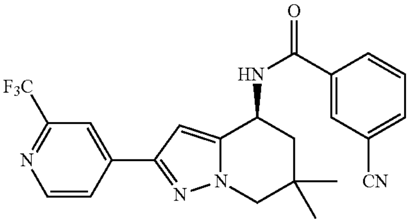 [SMILES: CC1(C)C[C@H](NC(=O)c2cccc(C#N)c2)c2cc(-c3ccnc(C(F)(F)F)c3)nn2C1]

Step 1—Synthesis of tert-Butyl 4-(3,5-dibromo-1H-pyrazol-1-yl)-3,3-dimethylbutanoate

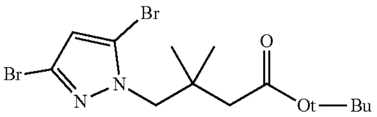

To a solution of tert-butyl 4-hydroxy-3,3-dimethyl-butanoate (11.5 g, 61.1 mmol, prepared according to the procedure in WO2020/077217), 3,5-dibromo-1H-pyrazole (13.80 g, 61.1 mmol) and $PPh_3$ (19 g, 73.3 mmol) in THF (150 mL) was added DIAD (14.2 mL, 73.3 mmol) at 0° C. The mixture was stirred at 25° C. for 16 h. The reaction was diluted with $H_2O$ (100 mL), extracted with EtOAc (100 mL×2) and the combined organic layers were washed with brine (100 mL), dried over anhydrous $Na_2SO_4$, filtered and concentrated in vacuo. The crude residue was purified on silica gel chromatography (solvent gradient: 0-5% EtOAc in petroleum ether) to give the title compound (14.8 g, 64%) as a yellow solid. $^1H$ NMR (400 MHz, $CDCl_3$) δ 7.27 (s, 1H), 6.29 (s, 1H), 4.14 (s, 2H), 2.27 (s, 2H), 1.47 (s, 9H), 1.08 (s, 6H).

Step 2—Synthesis of 2-Bromo-6,6-dimethyl-6,7-dihydropyrazolo[1,5-a]pyridin-4(5H)-one

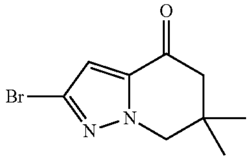

To a solution of tert-butyl 4-(3,5-dibromopyrazol-1-yl)-3,3-dimethyl-butanoate (15 g, 37.87 mmol) in toluene (150 mL) was added n-BuLi (2.5M, 13.63 mL, 42.5 mmol) dropwise at −78° C., after addition, the resulting solution was warmed to 25° C. and stirred for 2 h. The reaction was quenched with sat. $NH_4Cl$ (50 mL) and diluted with $H_2O$ (100 mL). The mixture was extracted with EtOAc (100 mL×2). Combined organic layers were washed with brine (100 mL×2), dried over anhydrous $Na_2SO_4$, filtered and concentrated in vacuo. The crude residue was purified by silica gel chromatography (solvent gradient: 0-20% EtOAc in petroleum ether) to give the title compound (7.6 g, 51%) as colorless oil. $^1H$ NMR (400 MHz, DMSO-$d_6$) δ 6.38 (s, 1H), 4.03 (s, 2H), 2.10 (s, 2H), 0.94 (s, 6H). LCMS (ESI) m/z: 243.1 $[M+H]^+$.

Step 3—Synthesis of (S)-3-Cyano-N-(6,6-dimethyl-2-(2-(trifluoromethyl)pyridin-4-yl)-4,5,6,7-tetrahydropyrazolo[1,5-a]pyridin-4-yl)benzamide

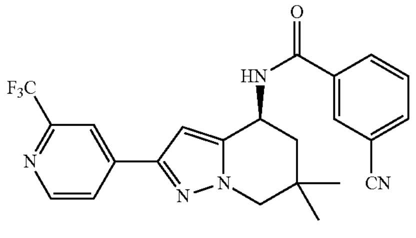 [SMILES: CC1(C)C[C@H](NC(=O)c2cccc(C#N)c2)c2cc(-c3ccnc(C(F)(F)F)c3)nn2C1]

Following the procedure described in Example 1.28 and 2-bromo-6,6-dimethyl-6,7-dihydropyrazolo[1,5-a]pyridin-4(5H)-one was used in step 3, (S)-6,6-dimethyl-2-(2-(trifluoromethyl)pyridin-4-yl)-4,5,6,7-tetrahydropyrazolo[1,5-a]pyridin-4-amine hydrochloride salt was used in step 4, the title compound (58 mg, 31%) was obtained as a white solid after purification of (acetonitrile 30%-60%/0.225% formic acid in water). I-220a: $^1H$ NMR (400 MHz, DMSO-$d_6$) δ 9.18 (d, J=8.4 Hz, 1H), 8.73 (d, J=5.2 Hz, 1H), 8.33 (s, 1H), 8.25-8.19 (m, 2H), 8.10-8.02 (m, 2H), 7.76-7.72 (m, 1H), 7.09 (s, 1H), 5.43-5.34 (m, 1H), 4.06 (d, J=13.2 Hz, 1H), 3.87 (d, J=13.2 Hz, 1H), 2.01-1.95 (m, 1H), 1.77 (m, 1H), 1.17 (s, 3H), 1.08 (s, 3H). LCMS (ESI) m/z: 440.1 $[M+H]^+$.

Example 1.34. Synthesis of (S)—N-(6,6-Dimethyl-2-(2-(trifluoromethyl)pyridin-4-yl)-4,5,6,7-tetrahydropyrazolo[1,5-a]pyridin-4-yl)-1-methyl-3-(trifluoromethyl)-1H-pyrazole-5-carboxamide (I-219a)

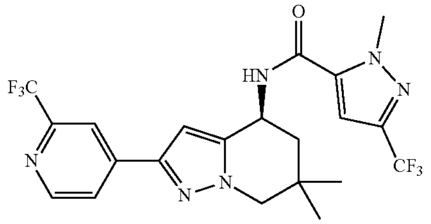 [SMILES: Cn1nc(C(F)(F)F)cc1C(=O)N[C@H]1CC(C)(C)Cn2nc(-c3ccnc(C(F)(F)F)c3)cc21]

Following the procedure described in Example 1.28, 1-methyl-3-(trifluoromethyl)-1H-pyrazole-5-carboxylic acid was used in step 4, the title compound (38 mg, 18%) was obtained as a white solid after purification of (acetonitrile 30%-60%/0.225% formic acid in water). I-219a: $^1H$ NMR (400 MHz, DMSO-$d_6$) δ 9.18 (d, J=8.8 Hz, 1H), 8.74 (d, J=5.2 Hz, 1H), 8.20 (s, 1H), 8.07 (d, J=4.8 Hz, 1H), 7.37 (s, 1H), 7.09 (s, 1H), 5.36-5.27 (m, 1H), 4.21 (s, 3H), 4.05 (d, J=12.8 Hz, 1H), 3.86 (d, J=12.8 Hz, 1H), 1.99-1.93 (m, 1H), 1.79-1.70 (m, 1H), 1.17 (s, 3H), 1.07 (s, 3H). LCMS (ESI) m/z: 487.1 $[M+H]^+$.

Example 1.35. Synthesis of (S)-3-(Difluoromethyl)-1-methyl-N-(2-(2-(trifluoromethyl)pyridin-4-yl)-5,6-dihydro-4H-pyrrolo[1,2-b]pyrazol-4-yl)-1H-1,2,4-triazole-5-carboxamide (I-155a)

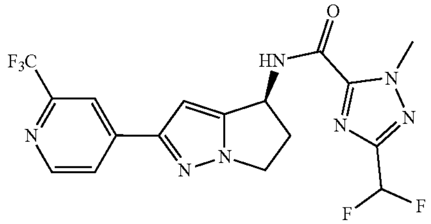 [SMILES: Cn1nc(C(F)F)nc1C(=O)N[C@H]1CCn2nc(-c3ccnc(C(F)(F)F)c3)cc21]

Step 1—Synthesis of 5-Bromo-3-(((tert-butyldiphenylsilyl)oxy)methyl)-1-methyl-1H-1,2,4-triazole

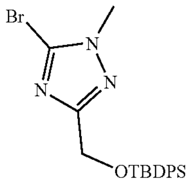

To a solution of (5-bromo-1-methyl-1H-1,2,4-triazol-3-yl)methanol (500 mg, 2.60 mmol, prepared according to the procedure in US2021/0130303) and imidazole (355 mg, 5.21 mmol) in DCM (5 mL) was added TBDPSCl (733 μL, 2.86 mmol). The reaction mixture was stirred at 25° C. for 16 h under a nitrogen atmosphere. The reaction was diluted with $H_2O$ (20 mL), then extracted with DCM (10 mL×2).

Combined organic layers were washed with brine (10 mL), dried over anhydrous $Na_2SO_4$, filtered and concentrated in vacuo. The crude residue was purified by silica gel chromatography (solvent gradient: 0-10% ethyl acetate in petroleum ether) to give the title compound (600 mg, 54%) as a colorless oil. $^1$H NMR (400 MHz, $CDCl_3$) δ 7.84-7.66 (m, 4H), 7.50-7.31 (m, 6H), 4.71 (s, 2H), 3.83 (s, 3H), 1.08 (s, 9H).

Step 2—Synthesis of Methyl 3-(((tert-butyldiphenylsilyl)oxy)methyl)-1-methyl-1H-1,2,4-triazole-5-carboxylate

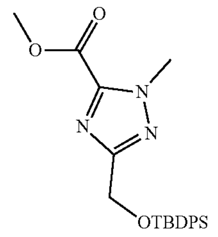

To a solution of 5-bromo-3-(((tert-butyldiphenylsilyl)oxy)methyl)-1-methyl-1H-1,2,4-triazole (600 mg, 1.39 mmol) and KOAc (410 mg, 4.18 mmol) in MeOH (5 mL) and DMF (5 mL) was added Pd(dppf)$Cl_2$ (102 mg, 139.4 μmol). The mixture was stirred at 80° C. for 16 h under a CO atmosphere. The mixture was concentrated in vacuo, the resulting residue was triturated with 30% ethyl acetate in petroleum ether (10 mL) to give the title compound (570 mg, crude) as a yellow solid which was used without further purification. $^1$H NMR (400 MHz, $CDCl_3$) δ 7.79-7.68 (m, 4H), 7.46-7.33 (m, 6H), 4.80 (s, 2H), 4.20 (s, 3H), 4.00 (s, 3H), 1.07 (s, 9H).

Step 3—Synthesis of (S)-3-(((tert-Butyldiphenylsilyl)oxy)methyl)-1-methyl-N-(2-(2-(trifluoromethyl)pyridin-4-yl)-5,6-dihydro-4H-pyrrolo[1,2-b]pyrazol-4-yl)-1H-1,2,4-triazole-5-carboxamide

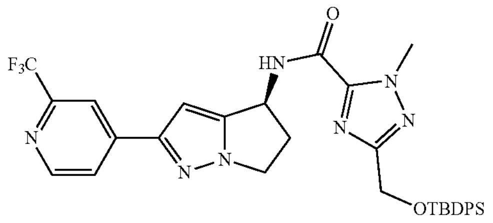

To a solution of methyl 3-(((tert-butyldiphenylsilyl)oxy)methyl)-1-methyl-1H-1,2,4-triazole-5-carboxylate (560 mg, 1.37 mmol) and (S)-2-(2-(trifluoromethyl)pyridin-4-yl)-5,6-dihydro-4H-pyrrolo[1,2-b]pyrazol-4-amine hydrochloride (800 mg, 2.63 mmol) in THF (8 mL) was added DABAL-$Me_3$ (1.05 g, 4.10 mmol). The reaction mixture was stirred at 70° C. for 60 h under a nitrogen atmosphere. After cooling to room temperature, the mixture was diluted with $H_2O$ (10 mL), and extracted with ethyl acetate (10 mL×2). The combined organic layers were washed with brine (10 mL×2), dried over anhydrous $Na_2SO_4$, filtered and concentrated in vacuo. The crude residue was purified by silica gel chromatography (solvent gradient: 0-40% ethyl acetate in petroleum ether) to give the title compound (370 mg, 42%) as a white solid. $^1$H NMR (400 MHz, DMSO-$d_6$) δ 9.51 (d, J=8.0 Hz, 1H), 8.74 (d, J=4.8 Hz, 1H), 8.20 (s, 1H), 8.07 (d, J=4.8 Hz, 1H), 7.66-7.60 (m, 4H), 7.47-7.41 (m, 6H), 6.99 (s, 1H), 5.63-5.45 (m, 1H), 4.69 (s, 2H), 4.45-4.32 (m, 1H), 4.24-4.17 (m, 1H), 4.13 (s, 3H), 3.07-2.96 (m, 1H), 2.67-2.63 (m, 1H), 0.98 (s, 9H). LCMS (ESI) m/z: 646.1 [M+H]$^+$.

Step 4—Synthesis of (S)-3-(Hydroxymethyl)-1-methyl-N-(2-(2-(trifluoromethyl)pyridin-4-yl)-5,6-dihydro-4H-pyrrolo[1,2-b]pyrazol-4-yl)-1H-1,2,4-triazole-5-carboxamide

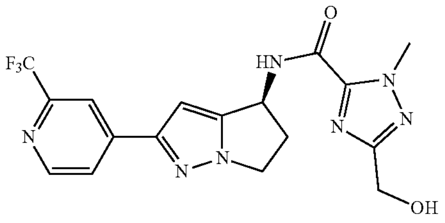 [SMILES: Cn1nc(CO)nc1C(=O)N[C@H]1CCn2nc(-c3ccnc(C(F)(F)F)c3)cc21]

To a solution of (S)-3-(((tert-butyldiphenylsilyl)oxy)methyl)-1-methyl-N-(2-(2-(trifluoromethyl)pyridin-4-yl)-5,6-dihydro-4H-pyrrolo[1,2-b]pyrazol-4-yl)-1H-1,2,4-triazole-5-carboxamide (370 mg, 572.98 μmol) in dioxane (2 mL) was added hydrochloride in dioxane (2M, 5 mL). The mixture was stirred at room temperature for 48 h. The mixture was concentrated in vacuo, the resulting residue was triturated with acetonitrile (10 mL) to give the title compound (220 mg, crude) as a white solid which was used without further purification. $^1$H NMR (400 MHz, DMSO-$d_6$) δ 9.54 (d, J=8.4 Hz, 1H), 8.73 (d, J=5.2 Hz, 1H), 8.18 (s, 1H), 8.05 (d, J=5.2 Hz, 1H), 6.95 (s, 1H), 5.55-5.42 (m, 1H), 4.47-4.31 (m, 3H), 4.27-4.04 (m, 4H), 3.07-2.92 (m, 1H), 2.66-2.58 (m, 1H). LCMS (ESI) m/z: 408.0 [M+H]$^+$.

Step 5—Synthesis of (S)-3-Formyl-1-methyl-N-(2-(2-(trifluoromethyl)pyridin-4-yl)-5,6-dihydro-4H-pyrrolo[1,2-b]pyrazol-4-yl)-1H-1,2,4-triazole-5-carboxamide

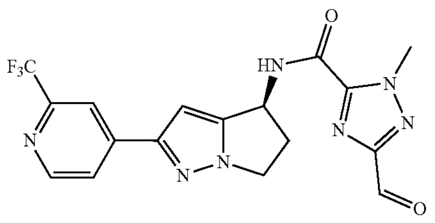 [SMILES: Cn1nc(C=O)nc1C(=O)N[C@H]1CCn2nc(-c3ccnc(C(F)(F)F)c3)cc21]

To a solution of DMSO (384 μL, 4.91 mmol) in DCM (5 mL) was added oxalyl dichloride (215 μL, 2.45 mmol) at −40° C., the mixture was stirred at the same temperature for another 5 minutes, then (S)-3-(hydroxymethyl)-1-methyl-N-(2-(2-(trifluoromethyl)pyridin-4-yl)-5,6-dihydro-4H-pyrrolo[1,2-b]pyrazol-4-yl)-1H-1,2,4-triazole-5-carboxamide (100 mg, 245.49 mol) in DCM (5 mL) was added within 2 minutes. The mixture was stirred at −40° C. for 15 minutes and TEA (1.35 mL, 9.82 mmol) was added. After another 20 minutes the reaction was warmed up to room temperature.

The mixture was diluted with $H_2O$ (10 mL), extracted with ethyl acetate (10 mL×2). The combined organic layers were washed with brine (10 mL), dried over anhydrous $Na_2SO_4$, filtered and concentrated in vacuo to give the title compound (110 mg, crude) as a yellow solid which was used without further purification. $^1H$ NMR (400 MHz, DMSO-$d_6$) δ 9.86 (s, 1H), 9.49-9.28 (m, 1H), 8.74 (d, J=4.4 Hz, 1H), 8.19 (s, 1H), 8.06 (d, J=4.4 Hz, 1H), 6.97 (s, 1H), 5.59-5.51 (m, 1H), 4.44-4.33 (m, 1H), 4.32-4.15 (m, 4H), 2.92-2.88 (m, 1H), 2.62-2.60 (m, 1H). LCMS (ESI) m/z: 406.0 $[M+H]^+$.

Step 6—Synthesis of (S)-3-(Difluoromethyl)-1-methyl-N-(2-(2-(trifluoromethyl)pyridin-4-yl)-5,6-dihydro-4H-pyrrolo[1,2-b]pyrazol-4-yl)-1H-1,2,4-triazole-5-carboxamide

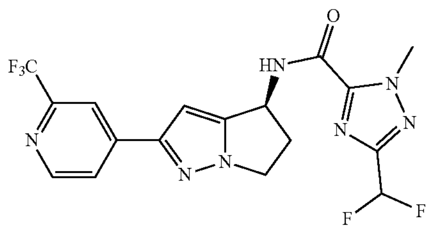 [SMILES: Cn1nc(C(F)F)nc1C(=O)N[C@H]1CCn2nc(-c3ccnc(C(F)(F)F)c3)cc21]

To a solution of (S)-3-formyl-1-methyl-N-(2-(2-(trifluoromethyl)pyridin-4-yl)-5,6-dihydro-4H-pyrrolo[1,2-b]pyrazol-4-yl)-1H-1,2,4-triazole-5-carboxamide (110 mg, 271.4 mol in DCM (4 mL) added DAST (72 μL, 542.8 μmol) at 0° C. The reaction mixture was stirred at 25° C. for 1 h. The reaction was diluted with $H_2O$ (5 mL), and then extracted with DCM (5 mL×2). The combined organic layers were washed with brine (10 mL), dried over anhydrous $Na_2SO_4$, filtered and concentrated in vacuo. The residue was purified by RP-HPLC (acetonitrile 25%-55%/0.225% formic acid in water) to give the title compound (10.45 mg, 9%) as a white solid. I-155a $^1H$ NMR (400 MHz, DMSO-$d_6$) δ 9.73 (d, J=8.0 Hz, 1H), 8.74 (d, J=5.2 Hz, 1H), 8.19 (s, 1H), 8.06 (d, J=5.2 Hz, 1H), 7.13 (t, J=12.8 Hz, 1H), 6.98 (s, 1H), 5.65-5.46 (m, 1H), 4.43-4.36 (m, 1H), 4.24-4.16 (m, 4H), 3.07-2.97 (m, 1H), 2.66-2.59 (m, 1H). LCMS (ESI) m/z: 428.1 $[M+H]^+$.

Example 1.36. Synthesis of (S)-1-Methyl-3-(trifluoromethyl)-N-(2-(2-(trifluoromethyl)pyridin-4-yl)-6,7-dihydro-5H-cyclopenta[d]pyrimidin-7-yl)-1H-pyrazole-5-carboxamide (I-46a)

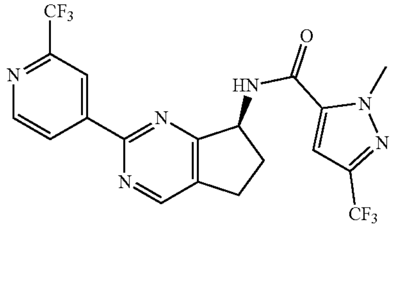 [SMILES: Cn1nc(C(F)(F)F)cc1C(=O)N[C@H]1CCc2cnc(-c3ccnc(C(F)(F)F)c3)nc21]

Step 1—Synthesis of 2-(2-(Trifluoromethyl)pyridin-4-yl)-6,7-dihydro-5H-cyclopenta[d]pyrimidine

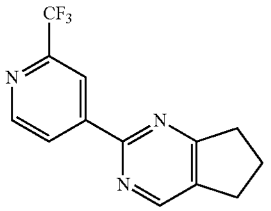 [SMILES: FC(F)(F)c1cc(-c2ncc3c(n2)CCC3)ccn1]

To a mixture of 2-chloro-6,7-dihydro-5H-cyclopenta[d]pyrimidine (5.67 g, 36.7 mmol), (2-(trifluoromethyl)pyridin-4-yl)boronic acid (8.40 g, 44.0 mmol), $K_2CO_3$ (15.21 g, 110.0 mmol) in dioxane (80 mL) and $H_2O$ (15 mL) was added Pd(dppf)$Cl_2$ (1.34 g, 1.8 mmol). The reaction mixture was stirred at 80° C. for 16 h under a nitrogen atmosphere. After cooling to room temperature, the reaction mixture was diluted with $H_2O$ (30 mL), extracted with EtOAc (50 mL×2). The combined organic layers were washed with brine (50 mL), dried over anhydrous $Na_2SO_4$, filtered and concentrated in vacuo. The crude residue was purified by silica gel chromatography (solvent gradient: 0-20% EtOAc in petroleum ether) to give the title compound (8.4 g, 86.3%) as a yellow solid. $^1H$ NMR (400 MHz, $CDCl_3$) δ 8.85 (d, J=4.8 Hz, 1H), 8.72 (s, 1H), 8.66 (s, 1H), 8.52-8.47 (m, 1H), 3.12 (t, J=8.0 Hz, 2H), 3.05 (t, J=7.6 Hz, 2H), 2.30-2.20 (m, 2H). LCMS (ESI) m/z: 266.0 $[M+H]^+$.

Step 2—Synthesis of 2-(2-(Trifluoromethyl)pyridin-4-yl)-6,7-dihydro-5H-cyclopenta[d]pyrimidine 1-oxide

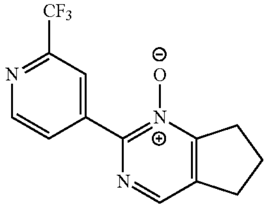 [SMILES: [O-][n+]1c(-c2ccnc(C(F)(F)F)c2)ncc2c1CCC2]

To a solution of 2-(2-(trifluoromethyl)pyridin-4-yl)-6,7-dihydro-5H-cyclopenta[d]pyrimidine (4 g, 15.1 mmol) in DCM (50 mL) was added m-CPBA (7.8 g, 45.2 mmol). The mixture was stirred at 25° C. for 48 h. The reaction mixture was diluted with $H_2O$ (50 mL), quenched with sat. $NaHCO_3$ (50 mL), extracted with DCM (50 mL×2). The combined organic layers were washed with brine (100 mL), dried over anhydrous $Na_2SO_4$, filtered and concentrated in vacuo to give the title compound (4 g, crude) as yellow oil which was used without further purification. LCMS (ESI) m/z: 282.0 $[M+H]^+$.

Step 3—Synthesis of 2-(2-(Trifluoromethyl)pyridin-4-yl)-6,7-dihydro-5H-cyclopenta[d]pyrimidin-7-yl acetate

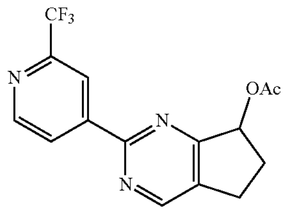 [SMILES: CC(=O)OC1CCc2cnc(-c3ccnc(C(F)(F)F)c3)nc21]

To a solution of 2-(2-(trifluoromethyl)pyridin-4-yl)-6,7-dihydro-5H-cyclopenta[d]pyrimidine 1-oxide (4.00 g, 14.22 mmol) was added $Ac_2O$ (30 mL). The mixture was stirred at 110° C. for 6 h. After cooling to room temperature, the reaction mixture was concentrated in vacuo. The crude residue was purified by silica gel chromatography (solvent gradient: 0-8% EtOAc in petroleum ether) to give the title compound (2.0 g, 53.3%) as a yellow solid. $^1H$ NMR (400 MHz, $CDCl_3$) δ 8.87 (d, J=5.2 Hz, 1H), 8.82 (s, 1H), 8.72 (s, 1H), 8.52 (d, J=4.8 Hz, 1H), 6.28-6.18 (m, 1H), 3.23-3.15 (m, 1H), 3.06-2.96 (m, 1H), 2.79-2.69 (m, 1H), 2.19 (s, 3H), 2.18-2.13 (m, 1H). LCMS (ESI) m/z: 324.1 $[M+H]^+$.

Step 4—Synthesis of 2-(2-(Trifluoromethyl)pyridin-4-yl)-6,7-dihydro-5H-cyclopenta[d]pyrimidin-7-ol

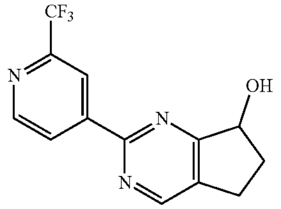 [SMILES: OC1CCc2cnc(-c3ccnc(C(F)(F)F)c3)nc21]

To a solution of 2-(2-(trifluoromethyl)pyridin-4-yl)-6,7-dihydro-5H-cyclopenta[d]pyrimidin-7-yl acetate (0.7 g, 2.17 mmol) in THF (4 mL) and $H_2O$ (1 mL) was added $LiOH \cdot H_2O$ (272 mg, 6.50 mmol). The mixture was stirred at 25° C. for 2 h. The reaction mixture was diluted with $H_2O$ (30 mL), extracted with EtOAc (20 mL×2). The combined organic layers were washed with brine (20 mL), dried over anhydrous $Na_2SO_4$, filtered and concentrated in vacuo to give the title compound (0.6 g, crude) as yellow oil which was used without further purification. LCMS (ESI) m/z: 282.1 $[M+H]^+$.

Step 5—Synthesis of 2-(2-(Trifluoromethyl)pyridin-4-yl)-5,6-dihydro-7H-cyclopenta[d]pyrimidin-7-one

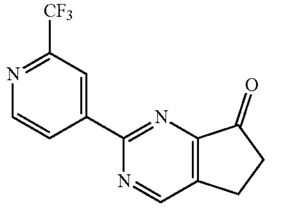 [SMILES: O=C1CCc2cnc(-c3ccnc(C(F)(F)F)c3)nc21]

To a solution of 2-(2-(trifluoromethyl)pyridin-4-yl)-6,7-dihydro-5H-cyclopenta[d]pyrimidin-7-ol (0.6 g, 2.13 mmol) in DCM (6 mL) was added DMP (2.71 g, 6.40 mmol). The mixture was stirred at 25° C. for 2 h. The reaction mixture was diluted with quenched with sat. $NaHCO_3$ (30 mL), and then extracted with DCM (20 mL×2). The combined organic layers were washed with brine (20 mL), dried over anhydrous $Na_2SO_4$, filtered and concentrated in vacuo. The crude residue was purified by silica gel chromatography (solvent gradient: 0-30% EtOAc in petroleum ether) to give the title compound (0.18 g, 30%) as a black solid. $^1H$ NMR (400 MHz, $CDCl_3$) δ 9.31 (s, 1H), 8.91 (d, J=5.2 Hz, 1H), 8.81 (s, 1H), 8.66-8.61 (m, 1H), 3.36-3.31 (m, 2H), 2.94-2.89 (m, 2H). LCMS (ESI) m/z: 280.1 $[M+H]^+$.

Step 6—Synthesis of 2-(2-(Trifluoromethyl)pyridin-4-yl)-6,7-dihydro-5H-cyclopenta[d]pyrimidin-7-amine

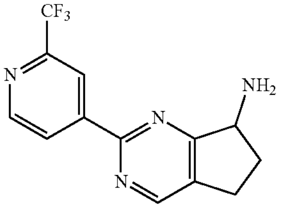 [SMILES: NC1CCc2cnc(-c3ccnc(C(F)(F)F)c3)nc21]

To a solution of 2-(2-(trifluoromethyl)pyridin-4-yl)-5,6-dihydro-7H cyclopenta[d]pyrimidin-7-one (120 mg, 429.8 μmol) in MeOH (3 mL) was added $NH_4OAc$ (331 mg, 4.30 mmol). The reaction was stirred 0.5 h at room temperature, then $NaBH_3CN$ (81 mg, 1.29 mmol) was added and the mixture stirred at 40° C. for 16 h. After cooling to room temperature, the reaction mixture was diluted with $H_2O$ (30 mL), and then extracted with EtOAc (20 mL×2). The combined organic layers were washed with brine (20 mL), dried over anhydrous $Na_2SO_4$, filtered and concentrated in vacuo to give the title compound (0.12 g, crude) as black oil which was used without further purification. LCMS (ESI) m/z: 281.1 $[M+H]^+$.

Step 7—Synthesis of 1-Methyl-3-(trifluoromethyl)-N-(2-(2-(trifluoromethyl)pyridin-4-yl)-6,7-dihydro-5H-cyclopenta[d]pyrimidin-7-yl)-1H-pyrazole-5-carboxamide

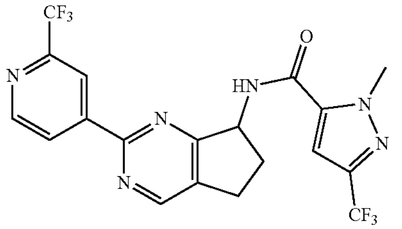 [SMILES: Cn1nc(C(F)(F)F)cc1C(=O)NC1CCc2cnc(-c3ccnc(C(F)(F)F)c3)nc21]

Following the procedure described in Example 1.26 and 2-(2-(trifluoromethyl)pyridin-4-yl)-6,7-dihydro-5H-cyclopenta[d]pyrimidin-7-amine was used in step 7, the title compound (48 mg, 28%) was obtained as a white solid after purification of RP-HPLC (acetonitrile 40-70%/0.225% formic acid in water).

Step 8—Synthesis of (S)-1-Methyl-3-(trifluoromethyl)-N-(2-(2-(trifluoromethyl)pyridin-4-yl)-6,7-dihydro-5H-cyclopenta[d]pyrimidin-7-yl)-1H-pyrazole-5-carboxamide & (R)-1-Methyl-3-(trifluoromethyl)-N-(2-(2-(trifluoromethyl)pyridin-4-yl)-6,7-dihydro-5H-cyclopenta[d]pyrimidin-7-yl)-1H-pyrazole-5-carboxamide

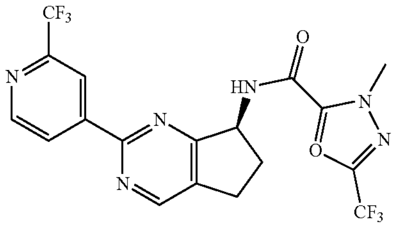

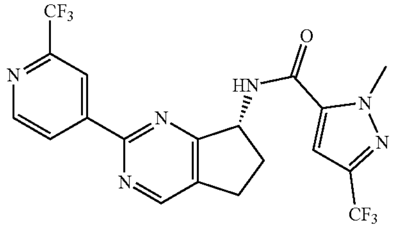

1-Methyl-3-(trifluoromethyl)-N-(2-(2-(trifluoromethyl) pyridin-4-yl)-6,7-dihydro-5H-cyclopenta[d]pyrimidin-7-yl)-1H-pyrazole-5-carboxamide (38 mg, 83 μmol) was separated by the following conditions: chiral SFC (DAICEL CHIRALPAK AS (250 mm*30 mm, 10 μm); supercritical $CO_2$/EtOH (0.1% $NH_3 \cdot H_2O$=60/40; 30 mL/min), affording (S)-1-methyl-3-(trifluoromethyl)-N-(2-(2-(trifluoromethyl) pyridin-4-yl)-6,7-dihydro-5H-cyclopenta[d]pyrimidin-7-yl)-1H-pyrazole-5-carboxamide (3.22 mg, first peak) and (R)-1-methyl-3-(trifluoromethyl)-N-(2-(2-(trifluoromethyl) pyridin-4-yl)-6,7-dihydro-5H-cyclopenta[d]pyrimidin-7-yl)-1H-pyrazole-5-carboxamide (5.82 mg, second peak) both as white solid. First peak: (I-46a): $^1$H NMR (400 MHz, DMSO-$d_6$) δ 9.21 (d, J=8.0 Hz, 1H), 8.97 (s, 1H), 8.96 (d, J=5.2 Hz, 1H), 8.61 (s, 1H), 8.56-8.53 (m, 1H), 7.34 (s, 1H), 5.60-5.52 (m, 1H), 4.19 (s, 3H), 3.18-3.10 (m, 1H), 3.07-2.97 (m, 1H), 2.65-2.59 (m, 1H), 2.12-2.02 (m, 1H). LCMS (ESI) m/z: 457.0 $[M+H]^+$. Second peak (I-46b): $^1$H NMR (400 MHz, DMSO-$d_6$) δ 9.21 (d, J=8.0 Hz, 1H), 8.97 (s, 1H), 8.95 (d, J=5.2 Hz, 1H), 8.60 (s, 1H), 8.54 (m, 1H), 7.33 (s, 1H), 5.60-5.52 (m, 1H), 4.18 (s, 3H), 3.18-3.09 (m, 1H), 3.07-2.97 (m, 1H), 2.65-2.58 (m, 1H), 2.11-2.03 (m, 1H). LCMS (ESI) m/z: 457.1 $[M+H]^+$.

Example 1.37. Synthesis of (S)-1-Methyl-3-(trifluoromethyl)-N-(2-(2-(trifluoromethyl)pyridin-4-yl)-4,5,6,7-tetrahydro-1H-indol-7-yl)-1H-pyrazole-5-carboxamide (I-89a)

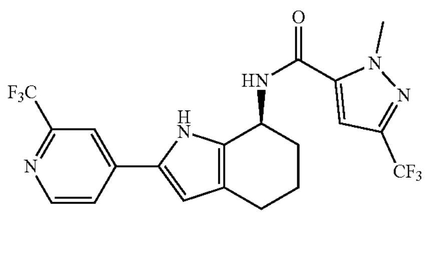 [SMILES: Cn1nc(C(F)(F)F)cc1C(=O)N[C@H]1CCCc2cc(-c3ccnc(C(F)(F)F)c3)[nH]c21]

Step 1—Synthesis of 3-Chloro-7-oxo-4,5,6,7-tetrahydro-1H-indole-2-carboxylic acid

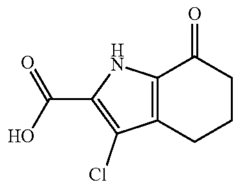 [SMILES: O=C(O)c1[nH]c2c(c1Cl)CCCC2=O]

To a solution of 7-oxo-4,5,6,7-tetrahydro-1H-indole-2-carboxylic acid (3 g, 16.74 mmol, prepared according to the procedure in EP2460794) in DMF (60 mL) was added NCS (2.68 g, 20.09 mmol) at 0° C. The mixture was stirred at 60° C. for 16 h under a nitrogen atmosphere. After cooling to room temperature, the reaction was diluted with water (50 mL), extracted with ethyl acetate (50 mL×2). The combined organic layers were washed with brine (50 mL×2), dried over anhydrous $Na_2SO_4$, filtered and concentrated in vacuo. The mixture was concentrated in vacuo to give the title compound (3 g, crude) as a yellow solid which was used without further purification. LCMS (ESI) m/z: 213.8 $[M+H]^+$.

Step 2—Synthesis of 2-Bromo-3-chloro-1,4,5,6-tetrahydro-7H-indol-7-one

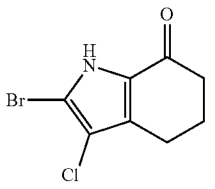 [SMILES: O=C1CCCc2c1[nH]c(Br)c2Cl]

To a solution of 3-chloro-7-oxo-4,5,6,7-tetrahydro-1H-indole-2-carboxylic acid (3 g, 14.04 mmol) and $NaHCO_3$ (1.77 g, 21.07 mmol) in DMF (30 mL) was added NBS (2.50 g, 14.04 mmol) at 0° C. The mixture was stirred at 25° C. for 2 h. The reaction mixture was diluted with water (50 mL), extracted with ethyl acetate (50 mL×2). The combined organic layers were washed with brine (50 mL×3), dried over anhydrous $Na_2SO_4$, filtered and concentrated in vacuo. The mixture was concentrated in vacuo to give the title compound (3.2 g, crude) as a yellow solid which was used without further purification. LCMS (ESI) m/z: 247.9 $[M+H]^+$.

Step 3—Synthesis of 3-Chloro-2-(2-(trifluoromethyl)pyridin-4-yl)-1,4,5,6-tetrahydro-7H-indol-7-one

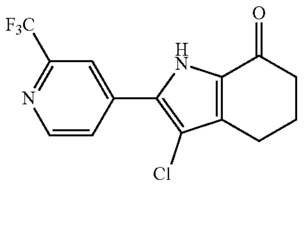 [SMILES: O=C1CCCc2c1[nH]c(-c1ccnc(C(F)(F)F)c1)c2Cl]

To a solution of 2-bromo-3-chloro-1,4,5,6-tetrahydro-7H-indol-7-one (3.2 g, 7.73 mmol), (2-(trifluoromethyl)pyridin-4-yl)boronic acid (1.48 g, 7.73 mmol), $K_3PO_4$ (4.92 g, 23.18 mmol) in dioxane (30 mL) and $H_2O$ (3 mL) was added Pd(dppf)$Cl_2$ (565 mg, 0.77 mmol). The reaction mixture was stirred at 80° C. for 1 h under a nitrogen atmosphere. After cooling to room temperature, the mixture was diluted with $H_2O$ (60 mL), extracted with ethyl acetate (50 mL×2). The combined organic layers were washed with brine (50 mL×2), dried over anhydrous $Na_2SO_4$, filtered and concentrated in vacuo. The residue was purified by silica gel chromatography (solvent gradient: 0-30% EtOAc in petroleum ether) to give the title compound (430 mg, 18%) as a yellow solid. $^1$H NMR (400 MHz, DMSO-$d_6$) δ 12.91 (s, 1H), 8.84 (d, J=5.2 Hz, 1H), 8.36 (d, J=1.2 Hz, 1H), 8.22-8.15 (m, 1H), 2.71-2.66 (m, 2H), 2.54 (s, 2H), 2.13-2.03 (m, 2H). LCMS (ESI) m/z: 315.0 [M+H]$^+$.

Step 4—Synthesis of 2-(2-(Trifluoromethyl)pyridin-4-yl)-1,4,5,6-tetrahydro-7H-indol-7-one

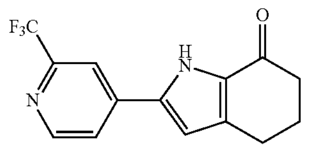 [SMILES: O=C1CCCc2cc(-c3ccnc(C(F)(F)F)c3)[nH]c21]

To a solution of 3-chloro-2-(2-(trifluoromethyl)pyridin-4-yl)-1,4,5,6-tetrahydro-7H-indol-7-one (300 mg, 953.32 μmol) in MeOH (5 mL) was added Pd/C (10%) (300 mg, 281.9 μmol). The reaction was stirred at 25° C. for 2 h under a hydrogen atmosphere (15 psi). The mixture was filtered and concentrated in vacuo to give the title compound (150 mg, crude) as yellow solid which was used without further purification. LCMS (ESI) m/z: 281.1 [M+H]$^+$.

Step 5—Synthesis of (S)-1-Methyl-3-(trifluoromethyl)-N-(2-(2-(trifluoromethyl)pyridin-4-yl)-4,5,6,7-tetrahydro-1H-indol-7-yl)-1H-pyrazole-5-carboxamide

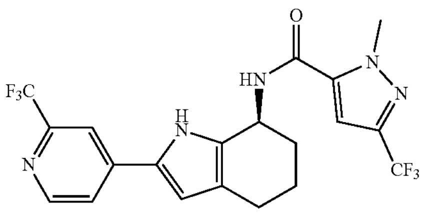 [SMILES: Cn1nc(C(F)(F)F)cc1C(=O)N[C@H]1CCCc2cc(-c3ccnc(C(F)(F)F)c3)[nH]c21]

Following the procedure described in Example 1.26 and 2-(2-(trifluoromethyl)pyridin-4-yl)-1,4,5,6-tetrahydro-7H-indol-7-one was used in step 4, (S)-2-(2-(trifluoromethyl)pyridin-4-yl)-4,5,6,7-tetrahydro-1H-indol-7-amine hydrochloride salt was used in step 7, the title compound (62.1 mg, 22%) was obtained as a white solid after purification of RP-HPLC (acetonitrile 58-88%/0.225% formic acid in water). I-89a $^1$H NMR (400 MHz, DMSO-$d_6$) δ 11.53 (d, J=1.6 Hz, 1H), 9.05 (d, J=8.0 Hz, 1H), 8.56 (d, J=5.6 Hz, 1H), 8.08 (d, J=1.2 Hz, 1H), 7.88-7.82 (m, 1H), 7.46 (s, 1H), 6.82 (d, J=2.4 Hz, 1H), 5.29-5.10 (m, 1H), 4.21 (s, 3H), 2.60-2.52 (m, 1H), 2.49-2.41 (m, 1H), 2.01-1.82 (m, 2H), 1.82-1.66 (m, 2H). LCMS (ESI) m/z: 458.2 [M+H]$^+$.

Example 1.38. Synthesis of (S)—N-(2-(2-Cyclopropyl-5-fluoropyridin-4-yl)-4,5,6,7-tetrahydrobenzo[d]oxazol-4-yl)-1-methyl-3-(trifluoromethyl)-1H-1,2,4-triazole-5-carboxamide (I-191a)

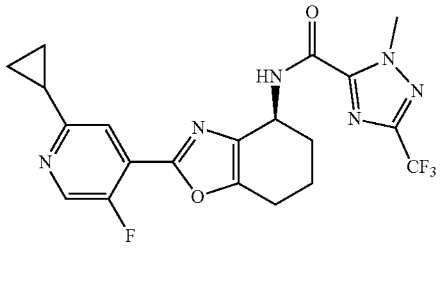 [SMILES: Cn1nc(C(F)(F)F)nc1C(=O)N[C@H]1CCCc2oc(-c3cc(C4CC4)ncc3F)nc21]

Step 1—Synthesis of 2-Cyclopropyl-5-fluoro isonicotinonitrile

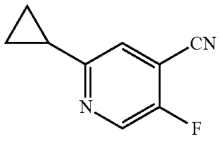 [SMILES: N#Cc1cc(C2CC2)ncc1F]

To a solution of 2-bromo-5-fluoroisonicotinonitrile (33 g, 164.2 mmol), cyclopropylboronic acid (36 g, 419.1 mmol), $K_3PO_3$ (106 g, 499.4 mmol), P(Cy)$_3$ (9.24 g, 32.9 mmol) in toluene (300 mL) and $H_2O$ (30 mL) was added Pd(OAc)$_2$ (3.7 g, 16.5 mmol). The reaction mixture was stirred at 100° C. for 3 h under a nitrogen atmosphere. After cooling to room temperature, the reaction was diluted with $H_2O$ (300 mL), extracted with ethyl acetate (200 mL×2). The combined organic layers were washed with brine (100 mL×2), dried over anhydrous $Na_2SO_4$, filtered and concentrated in vacuo. The crude residue was purified by silica gel chromatography (solvent gradient: 0-50% EtOAc in petroleum ether) to give the title compound (18.3 g, 68%) as a white solid. $^1$H NMR (400 MHz, DMSO-$d_6$) δ 8.72 (s, 1H), 7.91 (d, J=4.8 Hz, 1H), 2.27-2.14 (m, 1H), 1.07-0.98 (m, 2H), 0.95-0.82 (m, 2H). LCMS (ESI) m/z: 163.1 [M+H]$^+$.

Step 2—Synthesis of 2-(2-Cyclopropyl-5-fluoropyridin-4-yl)-6,7-dihydrobenzo[d]oxazol-4(5H)-one

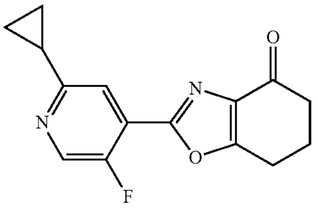 [SMILES: O=C1CCCc2oc(-c3cc(C4CC4)ncc3F)nc21]

To a mixture of 2-bromo-5-fluoroisonicotinonitrile (17 g, 104.8 mmol) and $Rh_2(OAc)_4$ (2.32 g, 10.5 mmol) at 60° C. was added 2-diazocyclohexane-1,3-dione (72.4 g, 524.2 mmol) dropwise. The reaction mixture was stirred at 60° C. for 4 h under a nitrogen atmosphere. After cooling to room temperature, the crude residue was purified by silica gel chromatography (solvent gradient: 0-35% ethyl acetate in petroleum ether) to give the title compound (5.8 g, 28%) as a yellow solid. LCMS (ESI) m/z: 273.1 [M+H]$^+$.

Step 3—Synthesis of (S)-2-(2-Cyclopropyl-5-fluoropyridin-4-yl)-4,5,6,7-tetrahydrobenzo[d]oxazol-4-amine hydrochloride salt

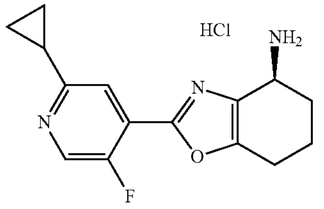 [SMILES: N[C@H]1CCCc2oc(-c3cc(C4CC4)ncc3F)nc21 ; Cl]

Following the procedure described in Example 1.26 and 2-(2-cyclopropyl-5-fluoropyridin-4-yl)-6,7-dihydrobenzo[d]oxazol-4(5H)-one was used in step 4, (S)—N—((S)-2-(2-cyclopropyl-5-fluoropyridin-4-yl)-4,5,6,7-tetrahydrobenzo[d]oxazol-4-yl)-2-methylpropane-2-sulfinamide hydrochloride salt was used in step 7, the title compound (150 mg, crude) was obtained as a yellow solid. LCMS (ESI) m/z: 274.1 [M+H]$^+$.

Step 4—Synthesis of (S)—N-(2-(2-Cyclopropyl-5-fluoropyridin-4-yl)-4,5,6,7-tetrahydrobenzo[d]oxazol-4-yl)-1-methyl-3-(trifluoromethyl)-1H-1,2,4-triazole-5-carboxamide

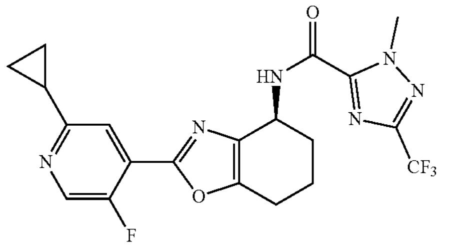 [SMILES: Cn1nc(C(F)(F)F)nc1C(=O)N[C@H]1CCCc2oc(-c3cc(C4CC4)ncc3F)nc21]

To a solution of methyl 2-methyl-5-(trifluoromethyl)-1,2,4-triazole-3-carboxylate (300 mg, 1.43 mmol) in THE (10 mL) was added (S)—N—((S)-2-(2-cyclopropyl-5-fluoropyridin-4-yl)-4,5,6,7-tetrahydrobenzo[d]oxazol-4-yl)-2-methylpropane-2-sulfinamide hydrochloride salt (150 mg, 50.9 μmol) and DABAL-$Me_3$ (460 mg, 1.78 mmol). The mixture was stirred at 70° C. for 16 h under a nitrogen atmosphere. After cooling to room temperature, the mixture was filtered and concentrated in vacuo. The residue was purified by RP-HPLC (acetonitrile 38%-68%/0.225% formic acid in water) to give the title compound (51.4 mg, 21%) as white solid. I-191a: $^1$H NMR (400 MHz, DMSO-$d_6$) δ 9.40 (d, J=8.4 Hz, 1H), 8.57 (d, J=2.4 Hz, 1H), 7.87 (d, J=6.0 Hz, 1H), 5.19-5.12 (m, 1H), 4.25 (s, 3H), 2.75 (s, 2H), 2.32-2.25 (m, 1H), 2.11-2.04 (m, 1H), 2.04-1.97 (m, 1H), 1.97-1.83 (m, 2H), 0.99-0.93 (m, 2H), 0.93-0.88 (m, 2H). LCMS (ESI) m/z: 451.2 [M+H]$^+$.

Example 1.39. Synthesis of (S)—N-(2-(2-Cyclopropyl-5-fluoropyridin-4-yl)-4,5,6,7-tetrahydrobenzo[d]oxazol-7-yl)-1-methyl-3-(trifluoromethyl)-1H-pyrazole-5-carboxamide (I-166a)

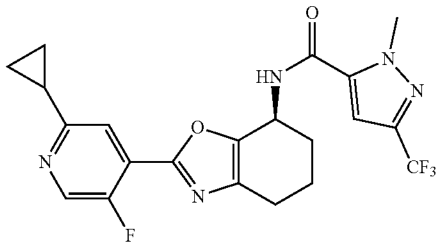 [SMILES: Cn1nc(C(F)(F)F)cc1C(=O)N[C@H]1CCCc2nc(-c3cc(C4CC4)ncc3F)oc21]

Step 1—Synthesis of (S)—N—((S)-2-(2-Bromo-5-fluoropyridin-4-yl)-4,5,6,7-tetrahydrobenzo[d]oxazol-7-yl)-2-methylpropane-2-sulfinamide

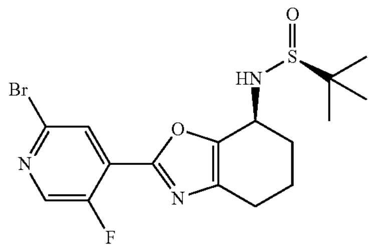 [SMILES: CC(C)(C)[S@](=O)N[C@H]1CCCc2nc(-c3cc(Br)ncc3F)oc21]

Following the procedure described in Example 1.26 and 2-bromo-5-fluoroisonicotinic acid was used in step 1, (S,E)-N-(2-(2-bromo-5-fluoropyridin-4-yl)-5,6-dihydrobenzo[d]oxazol-7(4H)-ylidene)-2-methylpropane-2-sulfinamide was used in step 5, the title compound (4.8 g, 60%) was obtained as a white solid after purification of silica gel chromatography (solvent gradient: 0-50% EtOAc in petroleum ether). LCMS (ESI) m/z: 414.2 [M+H]$^+$.

Step 2—Synthesis of (S)—N—((S)-2-(2-Cyclopropyl-5-fluoropyridin-4-yl)-4,5,6,7-tetrahydrobenzo[d]oxazol-7-yl)-2-methylpropane-2-sulfinamide

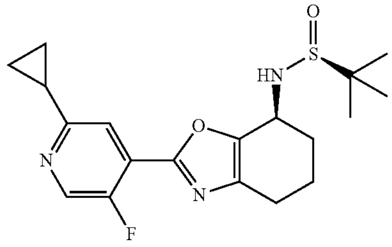 [SMILES: CC(C)(C)[S@](=O)N[C@H]1CCCc2nc(-c3cc(C4CC4)ncc3F)oc21]

To a solution of (S)—N—((S)-2-(2-bromo-5-fluoropyridin-4-yl)-4,5,6,7-tetrahydrobenzo[d]oxazol-7-yl)-2-methylpropane-2-sulfinamide (500 mg, 1.20 mmol), cyclopropylboronic acid (124 mg, 1.44 mmol), dicyclohexylphosphorylcyclohexane (71 mg, 240.2 mol), $K_3PO_4$ (1.53 g, 7.21 mmol) in toluene (6 mL) and $H_2O$ (0.6 mL) was added $Pd(OAc)_2$ (54 mg, 240.2 μmol). The reaction mixture was stirred at 100° C. for 16 h under a nitrogen atmosphere. After cooling to room temperature, the reaction was diluted with $H_2O$ (30 mL), and then extracted with EtOAc (30 mL×2). The combined organic layers were washed with brine (20 mL×2), dried over anhydrous $Na_2SO_4$, filtered and concentrated in vacuo. The crude residue was purified by silica gel chromatography (solvent gradient: 0-35% ethyl acetate in petroleum ether) to give the title compound to give the title compound (200 mg, 44%) as a white solid. LCMS (ESI) m/z: 378.1 $[M+H]^+$.

Step 3—Synthesis of (S)—N-(2-(2-Cyclopropyl-5-fluoropyridin-4-yl)-4,5,6,7-tetrahydrobenzo[d]oxazol-7-yl)-1-methyl-3-(trifluoromethyl)-1H-pyrazole-5-carboxamide

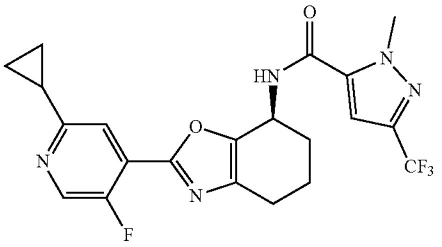 [SMILES: Cn1nc(C(F)(F)F)cc1C(=O)N[C@H]1CCCc2nc(-c3cc(C4CC4)ncc3F)oc21]

Following the procedure described in Example 1.26 and (S)—N—((S)-2-(2-bromo-5-fluoropyridin-4-yl)-4,5,6,7-tetrahydrobenzo[d]oxazol-7-yl)-2-methylpropane-2-sulfinamide was used in step 6, (S)-2-(2-cyclopropyl-5-fluoropyridin-4-yl)-4,5,6,7-tetrahydrobenzo[d]oxazol-7-amine hydrochloride salt was used in step 7, the title compound (25 mg, 15%) was obtained as a white solid after purification of RP-HPLC (acetonitrile 53%-83%/0.225% formic acid in water). I-166a: $^1H$ NMR (400 MHz, DMSO-$d_6$) δ 9.12 (d, J=8.0 Hz, 1H), 8.56 (d, J=2.8 Hz, 1H), 7.86 (d, J=6.0 Hz, 1H), 7.36 (s, 1H), 5.33-5.29 (m, 1H), 4.18 (s, 3H), 2.67-2.58 (m, 2H), 2.33-2.25 (m, 1H), 2.10-2.02 (m, 1H), 2.00-1.83 (m, 3H), 0.98-0.94 (m, 2H), 0.91-0.88 (m, 2H). LCMS (ESI) m/z: 450.2 $[M+H]^+$.

Example 1.40. Synthesis of (S)-1-Methyl-3-(trifluoromethyl)-N-(2-(2-(trifluoromethyl)thiazol-5-yl)-4,5,6,7-tetrahydropyrazolo[1,5-a]pyridin-4-yl)-1H-pyrazole-5-carboxamide (I-41a)

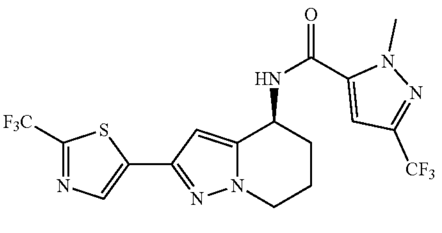

Step 1—Synthesis of (S)-(4-(1-Methyl-3-(trifluoromethyl)-1H-pyrazole-5-carboxamido)-4,5,6,7-tetrahydropyrazolo[1,5-a]pyridin-2-yl)boronic acid

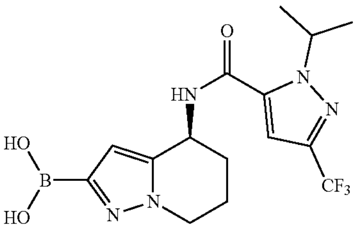 [SMILES: CC(C)n1nc(C(F)(F)F)cc1C(=O)N[C@H]1CCCn2nc(B(O)O)cc21]

To a solution of 4,4,5,5-tetramethyl-2-(4,4,5,5-tetramethyl-1,3,2-dioxaborolan-2-yl)-1,3,2-dioxaborolane (1.72 g, 6.76 mmol), (S)—N-(2-bromo-4,5,6,7-tetrahydropyrazolo[1,5-a]pyridin-4-yl)-1-methyl-3-(trifluoromethyl)-1H-pyrazole-5-carboxamide (0.53 g, 1.35 mmol) and KOAc (663 mg, 6.76 mmol) in dioxane (15 mL) was added $Pd(dppf)Cl_2$ (98 mg, 135.1 μmol) and the mixture was stirred at 100° C. for 16 h under a nitrogen atmosphere. After cooling to room temperature, the reaction mixture was filtered and concentrated in vacuo to give the title compound (2.5 g, crude) as black oil which was used without further purification. LCMS (ESI) m/z: 358.1 $[M+H]^+$.

Step 2—Synthesis of (S)-1-Methyl-3-(trifluoromethyl)-N-(2-(2-(trifluoromethyl)thiazol-5-yl)-4,5,6,7-tetrahydropyrazolo[1,5-a]pyridin-4-yl)-1H-pyrazole-5-carboxamide

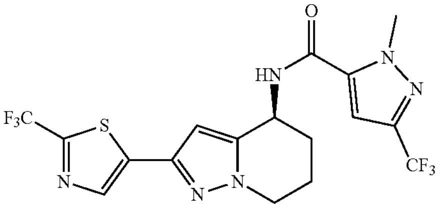

To a solution of 5-bromo-2-(trifluoromethyl)thiazole (117 mg, 504.1 μmol), (S)-(4-(1-methyl-3-(trifluoromethyl)-1H-pyrazole-5-carboxamido)-4,5,6,7-tetrahydropyrazolo[1,5-a]pyridin-2-yl)boronic acid (100 mg, 168.0 μmol), $K_3PO_4$ (107 mg, 504.1 μmol) in dioxane (4 mL) and $H_2O$ (0.8 mL) was added $Pd(dppf)Cl_2$ (13 mg, 16.8 μmol), and the mixture was stirred at 80° C. for 2 h under a nitrogen atmosphere. After cooling to room temperature, the mixture was diluted with water (20 mL) and extracted with ethyl acetate (15 mL×2). The combined organic layers were washed with brine (20 mL), dried over anhydrous $Na_2SO_4$, filtered and concentrated in vacuo. The residue was purified by RP-HPLC (acetonitrile 55%-85%/0.225% formic acid in water) to give the title compound (12 mg, 15%) as a white solid. I-41a: $^1H$ NMR (400 MHz, DMSO-$d_6$) δ 9.18 (d, J=8.4 Hz, 1H), 8.46 (d, J=0.8 Hz, 1H), 7.39 (s, 1H), 6.83 (s, 1H), 5.34-5.27 (m, 1H), 4.20 (s, 3H), 4.20-4.15 (m, 1H), 4.14-4.06 (m, 1H), 2.25-2.15 (m, 1H), 2.15-2.01 (m, 2H), 1.89-1.78 (m, 1H). LCMS (ESI) m/z: 465.1 $[M+H]^+$.

Example 1.41. Synthesis of (S)—N-(2-(2-(1,1-Difluoroethyl)pyridin-4-yl)-5,6-dihydro-4H-pyrrolo[1,2-b]pyrazol-4-yl)-1-methyl-3-(trifluoromethyl)-1H-1,2,4-triazole-5-carboxamide (I-146a)

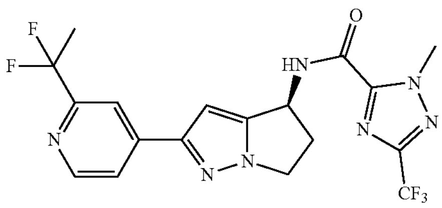

Step 1—Synthesis of (S)-2-Bromo-5,6-dihydro-4H-pyrrolo[1,2-b]pyrazol-4-amine hydrochloride salt

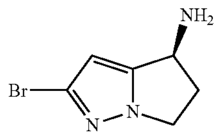

To a solution of (R)—N—((S)-2-bromo-5,6-dihydro-4H-pyrrolo[1,2-b]pyrazol-4-yl)-2-methylpropane-2-sulfinamide (0.8 g, 2.61 mmol) in dioxane (5 mL) was added hydrochloride in dioxane (2M, 20 mL). The mixture was stirred at 25° C. for 2 h. The mixture was concentrated in vacuo to give the title compound (520 mg, crude) as a yellow solid which was used without further purification. LCMS (ESI) m/z: 202.1 $[M+H]^+$.

Step 2—Synthesis of (S)—N-(2-Bromo-5,6-dihydro-4H-pyrrolo[1,2-b]pyrazol-4-yl)-1-methyl-3-(trifluoromethyl)-1H-1,2,4-triazole-5-carboxamide

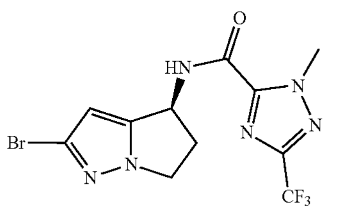 [SMILES: Cn1nc(C(F)(F)F)nc1C(=O)N[C@H]1CCn2nc(Br)cc21]

To a solution of methyl 2-methyl-5-(trifluoromethyl)-1,2,4-triazole-3-carboxylate (700 mg, 3.35 mmol) in THE (10 mL) was added (S)-2-bromo-5,6-dihydro-4H-pyrrolo[1,2-b]pyrazol-4-amine hydrochloride salt (520 mg, 2.57 mmol) and DABAL-$Me_3$ (1.32 g, 5.15 mmol). The mixture was stirred at 70° C. for 16 h under a nitrogen atmosphere. After cooling to room temperature, the mixture was diluted with $H_2O$ (10 mL), extracted with ethyl acetate (20 mL×2). The combined organic layers were washed with brine (10 mL×2), dried over anhydrous $Na_2SO_4$, filtered and concentrated in vacuo. The crude residue was purified by silica gel chromatography (solvent gradient: 0-40% ethyl acetate in petroleum ether) to give the title compound (563 mg, 57%) as a white solid. LCMS (ESI) m/z: 379.0 $[M+H]^+$.

Step 3—Synthesis of (S)—N-(2-(2-(1,1-Difluoroethyl)pyridin-4-yl)-5,6-dihydro-4H-pyrrolo[1,2-b]pyrazol-4-yl)-1-methyl-3-(trifluoromethyl)-1H-1,2,4-triazole-5-carboxamide

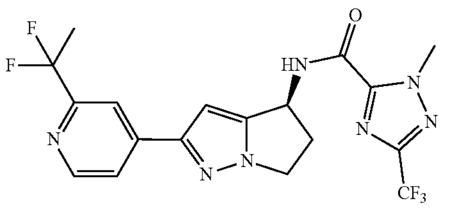 [SMILES: Cn1nc(C(F)(F)F)nc1C(=O)N[C@H]1CCn2nc(-c3ccnc(C(C)(F)F)c3)cc21]

To a solution of (S)—N-(2-bromo-5,6-dihydro-4H-pyrrolo[1,2-b]pyrazol-4-yl)-1-methyl-3-(trifluoromethyl)-1H-1,2,4-triazole-5-carboxamide (100 mg, 263.8 μmol), (2-(1,1-difluoroethyl)pyridin-4-yl)boronic acid (99 mg, 527.5 μmol), $K_3PO_4$ (224 mg, 1.06 mmol) in dioxane (4 mL) and $H_2O$ (1 mL) was added Pd(dppf)$Cl_2$ (13 mg, 16.8 μmol), and the mixture was stirred at 80° C. for 2 h under a nitrogen atmosphere. After cooling to room temperature, the mixture was diluted with water (20 mL) and extracted with ethyl acetate (10 mL×2). The combined organic layers were washed with brine (20 mL), dried over anhydrous $Na_2SO_4$, filtered and concentrated in vacuo. The residue was purified by RP-HPLC (acetonitrile 38%-68%/0.225% formic acid in water) to give the title compound (17.5 mg, 15%) as a white solid. I-146a: $^1$H NMR (400 MHz, DMSO-$d_6$) δ 9.79 (d, J=7.6 Hz, 1H), 8.64 (d, J=5.2 Hz, 1H), 8.03 (s, 1H), 7.89 (d, J=4.8 Hz, 1H), 6.90 (s, 1H), 5.59-5.51 (m, 1H), 4.43-4.34 (m, 1H), 4.26 (s, 3H), 4.23-4.15 (m, 1H), 3.09-2.96 (m, 1H), 2.65-2.59 (m, 1H), 2.02 (t, J=19.2 Hz, 3H). LCMS (ESI) m/z: 442.1 $[M+H]^+$.

Example 1.42. Synthesis of (S)—N-(2-(2-Cyclopropyl-5-fluoropyridin-4-yl)-5,6-dihydro-4H-pyrrolo[1,2-b]pyrazol-4-yl)-1-methyl-3-(trifluoromethyl)-1H-pyrazole-5-carboxamide (I-154a)

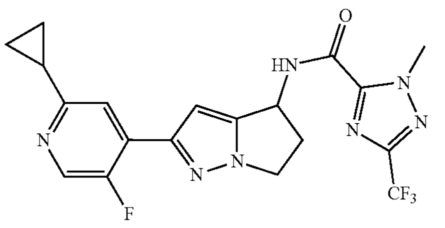

Step 1—Synthesis of 4-Chloro-2-cyclopropyl-5-fluoropyridine

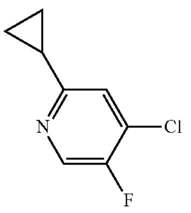 [SMILES: Fc1cnc(C2CC2)cc1Cl]

To a solution of 2-bromo-4-chloro-5-fluoropyridine (5 g, 23.76 mmol), cyclopropylboronic acid (2.04 g, 23.76 mmol), $K_3PO_4$ (15.13 g, 71.28 mmol) in dioxane (100 mL) was added Pd(dppf)$Cl_2$ (1.55 g, 2.38 mmol). The reaction mixture was stirred at 100° C. for 16 h under a nitrogen atmosphere. After cooling to room temperature, the mixture was diluted with $H_2O$ (100 mL), extracted with ethyl acetate (50 mL×2). The combined organic layers were washed with brine (50 mL×2), dried over anhydrous $Na_2SO_4$, filtered and concentrated in vacuo. The residue was purified by silica gel chromatography (solvent gradient: 100% petroleum ether) to give the title compound (750 mg, 18%) as a white solid. $^1$H NMR (400 MHz, DMSO-$d_6$) δ 8.50 (d, J=1.2 Hz, 1H), 7.65 (d, J=5.6 Hz, 1H), 2.20-2.08 (m, 1H), 1.00-0.93 (m, 2H), 0.91-0.86 (m, 2H). LCMS (ESI) m/z: 172.0 [M+H]$^+$.

Step 2—Synthesis of ((S)-4-(((R)-tert-Butylsulfinyl) amino)-5,6-dihydro-4H-pyrrolo[1,2-b]pyrazol-2-yl) boronic acid

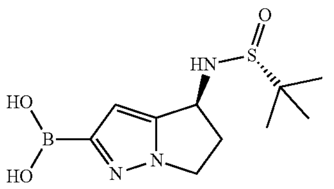 [SMILES: CC(C)(C)[S@@](=O)N[C@H]1CCn2nc(B(O)O)cc21]

To a solution of (R)—N—((S)-2-bromo-5,6-dihydro-4H-pyrrolo[1,2-b]pyrazol-4-yl)-2-methylpropane-2-sulfinamide (400 mg, 1.31 mmol), B(pin)$_2$ (1.66 g, 6.53 mmol), KOAc (384 mg, 3.92 mmol) in dioxane (6 mL) was added Pd(dppf) $Cl_2$ (192 mg, 261.3 μmol). The reaction mixture was stirred at 100° C. for 16 h under a nitrogen atmosphere. After cooling to room temperature, the mixture was filtered and concentrated in vacuo to give the title compound (320 mg, crude) as a black oil which was used without further purification. LCMS (ESI) m/z: 272.1 [M+H]$^+$.

Step 3—Synthesis of (R)—N—((S)-2-(2-Cyclopropyl-5-fluoropyridin-4-yl)-5,6-dihydro-4H-pyrrolo[1, 2-b]pyrazol-4-yl)-2-methylpropane-2-sulfinamide

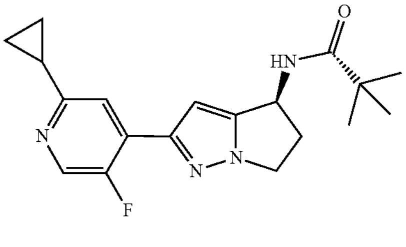

To a solution of ((S)-4-(((R)-tert-butylsulfinyl)amino)-5, 6-dihydro-4H-pyrrolo[1,2-b]pyrazol-2-yl)boronic acid (320 mg, 780.1 μmol), 4-chloro-2-cyclopropyl-5-fluoropyridine (120 mg, 699.3 μmol), $K_3PO_4$ (445.32 mg, 2.10 mmol) in dioxane (3 mL) was added Pd(dppf)$Cl_2$ (52 mg, 69.9 μmol). The reaction mixture was stirred at 100° C. for 16 h under a nitrogen atmosphere. After cooling to room temperature, the mixture was diluted with $H_2O$ (50 mL), extracted with ethyl acetate (50 mL×2). The combined organic layers were washed with brine (50 mL×2), dried over anhydrous $Na_2SO_4$, filtered and concentrated in vacuo. The residue was purified by silica gel chromatography (solvent gradient: 0-20% ethyl acetate in petroleum ether) to give the title compound (750 mg, 18%) as a white solid. LCMS (ESI) m/z: 363.1 [M+H]$^+$.

Step 4—Synthesis of (S)-2-(2-Cyclopropyl-5-fluoropyridin-4-yl)-5,6-dihydro-4H-pyrrolo[1,2-b]pyrazol-4-amine hydrochloride salt

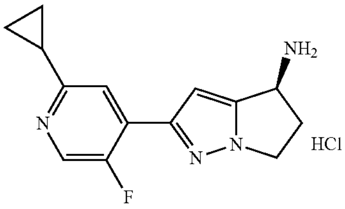 [SMILES: N[C@H]1CCn2nc(-c3cc(C4CC4)ncc3F)cc21 ; Cl]

To a solution of (R)—N—((S)-2-(2-cyclopropyl-5-fluoropyridin-4-yl)-5,6-dihydro-4H-pyrrolo[1,2-b]pyrazol-4-yl)-2-methylpropane-2-sulfinamide (80 mg, 220.71 μmol) in dioxane (2 mL) was added hydrochloric acid in dioxane (2M, 5 mL). The mixture was stirred at room temperature for 2 h. The mixture was concentrated in vacuo to give the title compound (100 mg, crude) as a yellow solid which was used without further purification. LCMS (ESI) m/z: 259.1 [M+H]$^+$.

Step 5—Synthesis of (S)—N-(2-(2-Cyclopropyl-5-fluoropyridin-4-yl)-5,6-dihydro-4H-pyrrolo[1,2-b] pyrazol-4-yl)-1-methyl-3-(trifluoromethyl)-1H-pyrazole-5-carboxamide

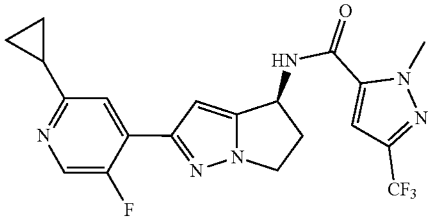 [SMILES: Cn1nc(C(F)(F)F)cc1C(=O)N[C@H]1CCn2nc(-c3cc(C4CC4)ncc3F)cc21]

To a solution of (S)-2-(2-cyclopropyl-5-fluoropyridin-4-yl)-5,6-dihydro-4H-pyrrolo[1,2-b]pyrazol-4-amine hydrochloride salt (60 mg, 203.6 μmol), 1-methyl-3-(trifluoromethyl)-1H-pyrazole-5-carboxylic acid (47 mg, 244.3 μmol) and DIEA (0.2 mL, 1.02 mmol) in DCM (2 mL) was added HATU (93 mg, 244.3 μmol). The reaction mixture was stirred at 25° C. for 2 h. The reaction was diluted with $H_2O$ (30 mL), and then extracted with DCM (30 mL×2). The combined organic layers were washed with brine (20 mL×2), dried over anhydrous $Na_2SO_4$, filtered and concentrated in vacuo. The residue was purified by RP-HPLC (acetonitrile 45%-75%/0.225% formic acid in water) to give the title compound (30.1 mg, 34%) as a white solid. I-154a $^1$H NMR (400 MHz, DMSO-$d_6$) δ 9.21 (d, J=7.6 Hz, 1H), 8.41 (d, J=2.4 Hz, 1H), 7.79 (d, J=6.4 Hz, 1H), 7.34 (s, 1H), 6.65 (d, J=3.2 Hz, 1H), 5.58-5.48 (m, 1H), 4.42-4.34 (m, 1H), 4.28-4.20 (m, 1H), 4.17 (s, 3H), 3.10-3.01 (m, 1H), 2.57-2.52 (m, 1H), 2.22-2.15 (m, 1H), 0.97-0.91 (m, 2H), 0.91-0.86 (m, 2H). LCMS (ESI) m/z: 435.1 [M+H]$^+$.

Example 1.43. Synthesis of (S)—N-(2-(2-(Hydroxymethyl)pyridin-4-yl)-4,5,6,7-tetrahydropyrazolo[1,5-a]pyridin-4-yl)-1-methyl-3-(trifluoromethyl)-1H-pyrazole-5-carboxamide (I-322a)

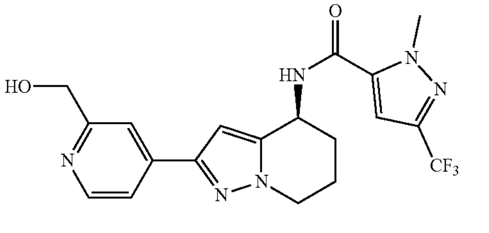

Step 1—Synthesis of Methyl (S)-4-(4-(1-methyl-3-(trifluoromethyl)-1H-pyrazole-5-carboxamido)-4,5,6,7-tetrahydropyrazolo[1,5-a]pyridin-2-yl)picolinate

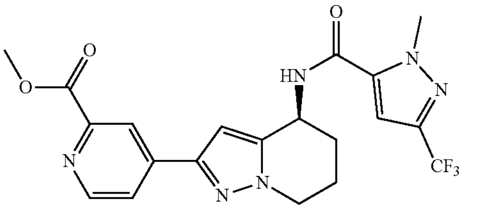 [SMILES: COC(=O)c1cc(-c2cc3n(n2)CCC[C@@H]3NC(=O)c2cc(C(F)(F)F)nn2C)ccn1]

To a solution of N-[(4S)-2-bromo-4,5,6,7-tetrahydropyrazolo[1,5-a]pyridin-4-yl]-2-methyl-5-(trifluoromethyl) pyrazole-3-carboxamide (140 mg, 359.5 μmol), (2-methoxycarbonyl-4-pyridyl)boronic acid (78 mg, 431.4 μmol), $K_3PO_4$ (229 mg, 1.08 mmol) in dioxane (3 mL) and $H_2O$ (3 mL) was added Pd(dppf)$Cl_2$ (26 mg, 35.9 μmol). The reaction mixture was stirred at 100° C. for 3 h under a nitrogen atmosphere. After cooling to room temperature, the mixture was diluted with $H_2O$ (30 mL), extracted with ethyl acetate (30 mL×2). The combined organic layers were washed with brine (20 mL×2), dried over anhydrous $Na_2SO_4$, filtered and concentrated in vacuo. The residue was purified by silica gel chromatography (solvent gradient: 0-20% ethyl acetate in petroleum ether) to give the title compound (56 mg, 34%) as a white solid. LCMS (ESI) m/z: 449.1 $[M+H]^+$.

Step 2—Synthesis of (S)—N-(2-(2-(Hydroxymethyl)pyridin-4-yl)-4,5,6,7-tetrahydropyrazolo[1,5-a]pyridin-4-yl)-1-methyl-3-(trifluoromethyl)-1H-pyrazole-5-carboxamide

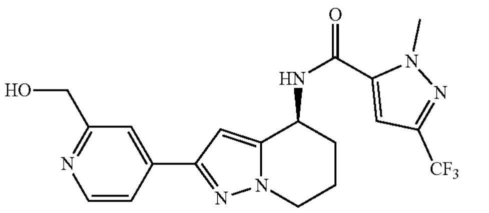

To a solution of methyl 4-[(4S)-4-[[2-methyl-5-(trifluoromethyl)pyrazole-3-carbonyl]amino]-4,5,6,7-tetrahydropyrazolo[1,5-a]pyridin-2-yl]pyridine-2-carboxylate (56 mg, 124.9 μmol) in THE (30 mL) was added $NaBH_4$ (60 mg, 1.59 mmol) and the mixture was stirred at 25° C. for 2 h. The reaction was quenched with sat. $NH_4Cl$ (5 mL) and diluted with $H_2O$ (20 mL). The mixture was extracted with EtOAc (20 mL×2). Combined organic layers were washed with brine (20 mL×2), dried over anhydrous $Na_2SO_4$, filtered and concentrated in vacuo. The residue was purified by RP-HPLC (acetonitrile 35%-65%/0.05% $NH_3H_2O$+10 mM $NH_4HCO_3$ in water) to give the title compound (5 mg, 11%) as a white solid. I-322a: $^1$H NMR (400 MHz, DMSO-$d_6$) δ 9.15 (d, J=8.4 Hz, 1H), 8.45 (d, J=5.2 Hz, 1H), 7.86 (s, 1H), 7.60 (dd, J=1.2, 5.2 Hz, 1H), 7.39 (s, 1H), 6.82 (s, 1H), 5.43 (t, J=6.0 Hz, 1H), 5.35-5.30 (m, 1H), 4.57 (d, J=5.6 Hz, 2H), 4.28-4.23 (m, 1H), 4.21 (s, 3H), 4.16-4.11 (m, 1H), 2.23-2.05 (m, 3H), 1.91-1.80 (m, 1H). LCMS (ESI) m/z: 421.1 $[M+H]^+$.

Example 1.44. Synthesis of (S)-1-Methyl-3-(trifluoromethyl)-N-(2-(6-(trifluoromethyl)pyridazin-4-yl)-4,5,6,7-tetrahydropyrazolo[1,5-a]pyridin-4-yl)-1H-pyrazole-5-carboxamide (I-307a)

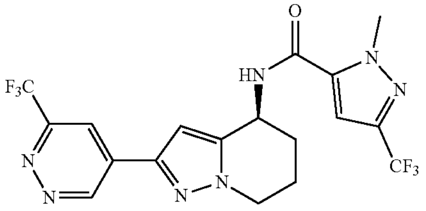

Step 1—Synthesis of (S)—N-(2-(5-Fluoro-2-(trifluoromethyl)pyridin-4-yl)-4,5,6,7-tetrahydropyrazolo[1,5-a]pyridin-4-yl)-5-methoxy-2,6-naphthyridin-1-amine

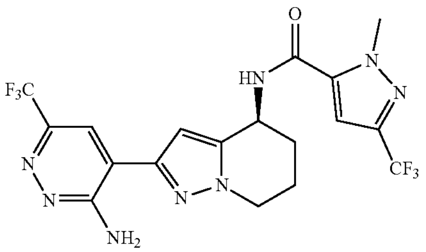 [SMILES: Cn1nc(C(F)(F)F)cc1C(=O)N[C@H]1CCCn2nc(-c3cc(C(F)(F)F)nnc3N)cc21]

To a solution of 4-bromo-6-(trifluoromethyl)pyridazin-3-amine (122 mg, 504.1 mol, prepared according to the procedure in WO2014/184234), (S)-(4-(1-methyl-3-(trifluoromethyl)-1H-pyrazole-5-carboxamido)-4,5,6,7-tetrahydropyrazolo[1,5-a]pyridin-2-yl)boronic acid (100 mg, 168.0 μmol), $K_3PO_4$ (107 mg, 504.1 μmol) in dioxane (4 mL) and $H_2O$ (0.8 mL) was added Pd(dppf)$Cl_2$ (13 mg, 16.8 μmol), and the mixture was stirred at 80° C. for 2 h under a nitrogen atmosphere. After cooling to room temperature, the mixture was diluted with water (20 mL) and extracted with ethyl acetate (20 mL×2). The combined organic layers were washed with brine (10 mL), dried over anhydrous $Na_2SO_4$, filtered and concentrated in vacuo. The residue was purified by RP-HPLC (acetonitrile 40%-70%/0.225% formic acid in water) to give the title compound (78 mg, 79%) as a white solid. LCMS (ESI) m/z: 475.1 $[M+H]^+$.

Step 2—Synthesis of (S)-1-Methyl-3-(trifluoromethyl)-N-(2-(6-(trifluoromethyl)pyridazin-4-yl)-4,5,6,7-tetrahydropyrazolo[1,5-a]pyridin-4-yl)-1H-pyrazole-5-carboxamide

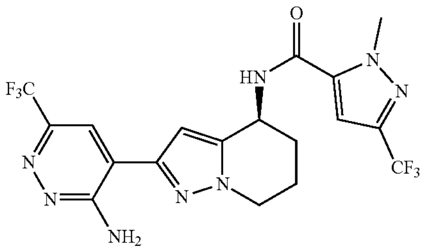 [SMILES: Cn1nc(C(F)(F)F)cc1C(=O)N[C@H]1CCCn2nc(-c3cc(C(F)(F)F)nnc3N)cc21]

To a solution of N-[(4S)-2-[3-amino-6-(trifluoromethyl)pyridazin-4-yl]-4,5,6,7-tetrahydropyrazolo[1,5-a]pyridin-4-yl]-2-methyl-5-(trifluoromethyl)pyrazole-3-carboxamide (78 mg, 164.4 μmol) in THF (5 mL) was added tert-butyl nitrite (40 μL, 328.9 μmol). The reaction mixture was stirred at 60° C. for 2 h under a nitrogen atmosphere. After cooling to room temperature, the mixture was diluted with $H_2O$ (20 mL), extracted with ethyl acetate (20 mL×2). The combined organic layers were washed with brine (20 mL×2), dried over anhydrous $Na_2SO_4$, filtered and concentrated in vacuo. The residue was purified by reverse phase chromatography (acetonitrile 45%-75%/0.225% formic acid in water) to give the title compound (5 mg, 7%) as a white solid. $^1H$ NMR (400 MHz, DMSO-$d_6$) δ 9.90 (d, J=1.6 Hz, 1H), 9.20 (d, J=8.4 Hz, 1H), 8.46 (d, J=2.0 Hz, 1H), 7.38 (s, 1H), 7.22 (s, 1H), 5.38-5.29 (m, 1H), 4.33-4.25 (m, 1H), 4.21 (s, 3H), 4.19-4.14 (m, 1H), 2.27-2.19 (m, 1H), 2.19-2.08 (m, 2H), 1.91-1.80 (m, 1H). LCMS (ESI) m/z: 460.2 $[M+H]^+$.

Example 1.45. Synthesis of (S)-1-Methyl-N-(2-(2-(1-methylcyclopropyl)pyridin-4-yl)-2,4,5,6-tetrahydrocyclopenta[c]pyrazol-4-yl)-3-(trifluoromethyl)-1H-pyrazole-5-carboxamide (I-75a)

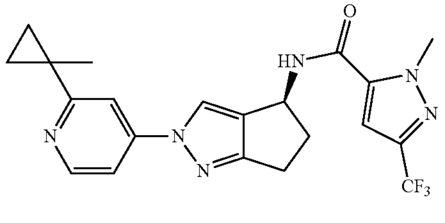 [SMILES: Cn1nc(C(F)(F)F)cc1C(=O)N[C@H]1CCc2nn(-c3ccnc(C4(C)CC4)c3)cc21]

Step 1—Synthesis of 1-Methyl-N-(2-(2-(1-methylcyclopropyl)pyridin-4-yl)-2,4,5,6-tetrahydrocyclopenta[c]pyrazol-4-yl)-3-(trifluoromethyl)-1H-pyrazole-5-carboxamide

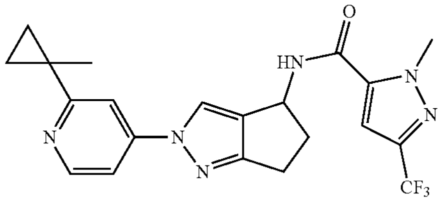 [SMILES: Cn1nc(C(F)(F)F)cc1C(=O)NC1CCc2nn(-c3ccnc(C4(C)CC4)c3)cc21]

Following the procedure described in Example 1.31 and 4-bromo-2-(1-methylcyclopropyl)pyridine was used in step 1 and 2-(2-(1-methylcyclopropyl)pyridin-4-yl)-2,4,5,6-tetrahydrocyclopenta[c]pyrazol-4-amine hydrochloride salt was used in step 2, the title compound (120 mg, 39%) was obtained as a white solid after purification of silica gel chromatography (solvent gradient: 0-30% EtOAc in petroleum ether). LCMS (ESI) m/z: 409.0 $[M+H]^+$.

Step 2—Synthesis of (S)-1-Methyl-N-(2-(2-(1-methylcyclopropyl)pyridin-4-yl)-2,4,5,6-tetrahydrocyclopenta[c]pyrazol-4-yl)-3-(trifluoromethyl)-1H-pyrazole-5-carboxamide & (R)-1-Methyl-N-(2-(2-(1-methylcyclopropyl)pyridin-4-yl)-2,4,5,6-tetrahydrocyclopenta[c]pyrazol-4-yl)-3-(trifluoromethyl)-1H-pyrazole-5-carboxamide

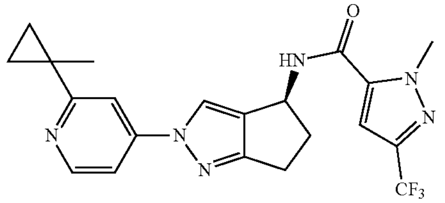

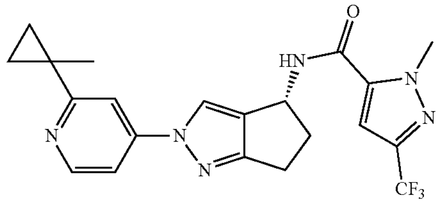

1-Methyl-N-(2-(2-(1-methylcyclopropyl)pyridin-4-yl)-2,4,5,6-tetrahydrocyclopenta[c]pyrazol-4-yl)-3-(trifluoromethyl)-1H-pyrazole-5-carboxamide (120 mg, 279 μmol) was separated by using chiral SFC (DAICEL CHIRALCEL OJ (250 mm*30 mm, 10 μm); Supercritical $CO_2$/EtOH+0.1% $NH_3 \cdot H_2O$=55/45; 60 mL/min) to afford (S)-1-methyl-N-(2-(2-(1-methylcyclopropyl)pyridin-4-yl)-2,4,5,6-tetrahydrocyclopenta[c]pyrazol-4-yl)-3-(trifluoromethyl)-1H-pyrazole-5-carboxamide (16.4 mg, first peak) and (R)-1-methyl-N-(2-(2-(1-methylcyclopropyl)pyridin-4-yl)-2,4,5,6-tetrahydrocyclopenta[c]pyrazol-4-yl)-3-(trifluoromethyl)-1H-pyrazole-5-carboxamide (25.1 mg, second peak) both as white solid. First peak: (I-75a): $^1H$ NMR (400 MHz, DMSO-$d_6$) δ 9.02 (d, J=7.2 Hz, 1H), 8.54 (s, 1H), 8.42 (d, J=5.6 Hz, 1H), 7.70 (d, J=2.0 Hz, 1H), 7.61-7.52 (m, 1H), 7.37 (s, 1H), 5.42-5.31 (m, 1H), 4.18 (s, 3H), 2.99-2.70 (m, 3H), 2.39-2.27 (m, 1H), 1.50 (s, 3H), 1.20 (d, J=3.6 Hz, 2H), 0.82 (d, J=3.2 Hz, 2H). LCMS (ESI) m/z: 431.2 [M+H]$^+$. Second peak (I-75b): $^1$H NMR (400 MHz, DMSO-$d_6$) δ 9.02 (d, J=7.6 Hz, 1H), 8.54 (s, 1H), 8.42 (d, J=5.6 Hz, 1H), 7.70 (d, J=2.0 Hz, 1H), 7.59-7.51 (m, 1H), 7.37 (s, 1H), 5.46-5.25 (m, 1H), 4.18 (s, 3H), 2.95-2.71 (m, 3H), 2.37-2.29 (m, 1H), 1.51 (s, 3H), 1.29-1.15 (m, 2H), 0.82 (d, J=2.8 Hz, 2H). LCMS (ESI) m/z: 431.3 [M+H]$^+$.

Example 1.46. Synthesis of (S)-3-Cyano-5-fluoro-N-(2-(2-(trifluoromethyl)pyridin-4-yl)-5,6-dihydro-4H-pyrrolo[1,2-b]pyrazol-4-yl)benzamide (I-323a)

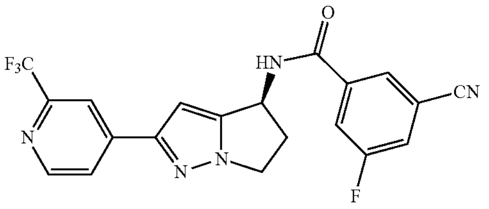 [SMILES: N#Cc1cc(F)cc(C(=O)N[C@H]2CCn3nc(-c4ccnc(C(F)(F)F)c4)cc32)c1]

Step 1—Synthesis of 3-Cyano-5-fluoro-N-(2-(2-(trifluoromethyl)pyridin-4-yl)-5,6-dihydro-4H-pyrrolo[1,2-b]pyrazol-4-yl)benzamide

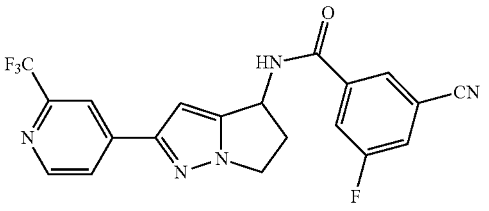 [SMILES: N#Cc1cc(F)cc(C(=O)NC2CCn3nc(-c4ccnc(C(F)(F)F)c4)cc32)c1]

Following the procedure described in Example 1.26 and 2-(2-(trifluoromethyl)pyridin-4-yl)-5,6-dihydro-4H-pyrrolo[1,2-b]pyrazol-4-amine hydrochloride salt was used in step 7, the title compound (110 mg, 60%) was obtained as a white solid after purification of silica gel chromatography (solvent gradient: 0-40% EtOAc in petroleum ether). LCMS (ESI) m/z: 416.1 [M+H]$^+$.

Step 2—Synthesis of (S)-3-Cyano-5-fluoro-N-(2-(2-(trifluoromethyl)pyridin-4-yl)-5,6-dihydro-4H-pyrrolo[1,2-b]pyrazol-4-yl)benzamide & (R)-3-Cyano-5-fluoro-N-(2-(2-(trifluoromethyl)pyridin-4-yl)-5,6-dihydro-4H-pyrrolo[1,2-b]pyrazol-4-yl)benzamide

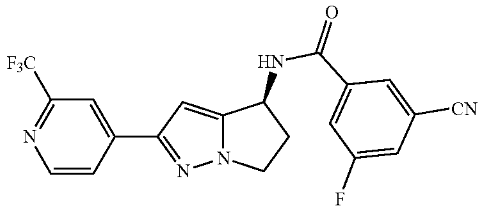

-continued

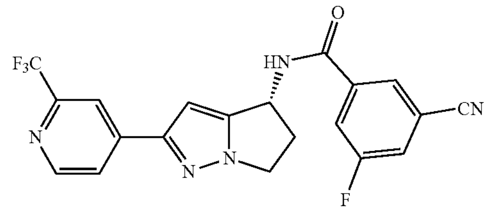

3-Cyano-5-fluoro-N-(2-(2-(trifluoromethyl)pyridin-4-yl)-5,6-dihydro-4H-pyrrolo[1,2-b]pyrazol-4-yl)benzamide (110 mg, 265 μmol) was separated by using chiral SFC (DAICEL CHIRALCEL OJ (250 mm*30 mm, 10 μm); Supercritical $CO_2$/EtOH+0.1% $NH_3 \cdot H_2O$=80/20; 70 mL/min) to afford (S)-3-cyano-5-fluoro-N-(2-(2-(trifluoromethyl)pyridin-4-yl)-5,6-dihydro-4H-pyrrolo[1,2-b]pyrazol-4-yl)benzamide (22.2 mg, first peak) and (R)-3-cyano-5-fluoro-N-(2-(2-(trifluoromethyl)pyridin-4-yl)-5,6-dihydro-4H-pyrrolo[1,2-b]pyrazol-4-yl)benzamide (26.7 mg, second peak) both as white solid. First peak: (I-323a): $^1$H NMR (400 MHz, DMSO-$d_6$) δ 9.31 (d, J=7.6 Hz, 1H), 8.75 (d, J=5.2 Hz, 1H), 8.20 (d, J=1.2 Hz, 2H), 8.15-7.98 (m, 3H), 7.02 (s, 1H), 5.62-5.50 (m, 1H), 4.44-4.35 (m, 1H), 4.29-4.20 (m, 1H), 3.12-3.00 (m, 1H), 2.60-2.53 (m, 1H). LCMS (ESI) m/z: 416.2 [M+H]$^+$. Second peak (I-323b): $^1$H NMR (400 MHz, DMSO-$d_6$) δ 9.32 (d, J=7.2 Hz, 1H), 8.76 (d, J=5.2 Hz, 1H), 8.20 (s, 2H), 8.14-8.02 (m, 3H), 7.03 (s, 1H), 5.66-5.49 (m, 1H), 4.46-4.34 (m, 1H), 4.30-4.18 (m, 1H), 3.14-3.01 (m, 1H), 2.61-2.53 (m, 1H). LCMS (ESI) m/z: 416.2 [M+H]$^+$.

Example 1.47. Synthesis of (S)-3-(Trifluoromethyl)-N-(2-(2-(trifluoromethyl)pyridin-4-yl)-5,6-dihydro-4H-pyrrolo[1,2-b]pyrazol-4-yl)benzamide (I-289a)

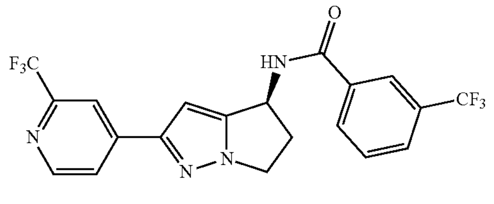 [SMILES: O=C(N[C@H]1CCn2nc(-c3ccnc(C(F)(F)F)c3)cc21)c1cccc(C(F)(F)F)c1]

Step 1—Synthesis of 3-(Trifluoromethyl)-N-(2-(2-(trifluoromethyl)pyridin-4-yl)-5,6-dihydro-4H-pyrrolo[1,2-b]pyrazol-4-yl)benzamide

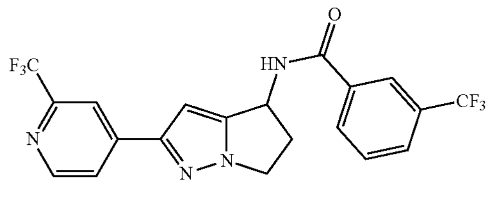 [SMILES: O=C(NC1CCn2nc(-c3ccnc(C(F)(F)F)c3)cc21)c1cccc(C(F)(F)F)c1]

Following the procedure described in Example 1.26 and 2-(2-(trifluoromethyl)pyridin-4-yl)-5,6-dihydro-4H-pyrrolo[1,2-b]pyrazol-4-amine hydrochloride salt was used in step 7, the title compound (150 mg, 77%) was obtained as a white solid after purification of silica gel chromatography (solvent gradient: 0-40% EtOAc in petroleum ether). LCMS (ESI) m/z: 441.1 [M+H]$^+$.

Step 2—Synthesis of (R)-3-(Trifluoromethyl)-N-(2-(2-(trifluoromethyl)pyridin-4-yl)-5,6-dihydro-4H-pyrrolo[1,2-b]pyrazol-4-yl)benzamide & (S)-3-(Trifluoromethyl)-N-(2-(2-(trifluoromethyl)pyridin-4-yl)-5,6-dihydro-4H-pyrrolo[1,2-b]pyrazol-4-yl)benzamide

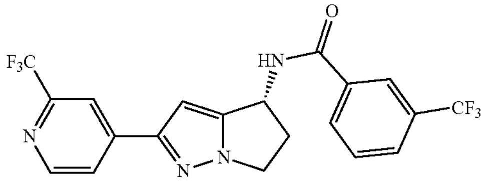

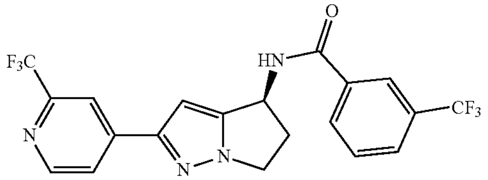

3-(Trifluoromethyl)-N-(2-(2-(trifluoromethyl)pyridin-4-yl)-5,6-dihydro-4H-pyrrolo[1,2-b]pyrazol-4-yl)benzamide (150 mg, 341 μmol) was separated by using chiral SFC DAICEL CHIRALPAK AS (250 mm*30 mm, 10 μm); Supercritical $CO_2$/EtOH+0.1% $NH_3 \cdot H_2O$=80/20; 70 mL/min) to afford (R)-1-methyl-N-(2-(5-methyl-2-(trifluoromethyl)pyridin-4-yl)-5,6,7,8-tetrahydro-4H-pyrazolo[1,5-a]azepin-4-yl)-3-(trifluoromethyl)-1H-pyrazole-5-carboxamide (20.0 mg, first peak) and (S)-3-(trifluoromethyl)-N-(2-(2-(trifluoromethyl)pyridin-4-yl)-5,6-dihydro-4H-pyrrolo[1,2-b]pyrazol-4-yl)benzamide (59.0 mg, second peak) both as white solids. First peak (I-289b): $^1$H NMR (400 MHz, DMSO-$d_6$) δ 9.31 (d, J=7.6 Hz, 1H), 8.74 (d, J=5.2 Hz, 1H), 8.31-8.17 (m, 3H), 8.10-8.05 (m, 1H), 7.94 (d, J=8.0 Hz, 1H), 7.78-7.15 (m, 1H), 7.03 (s, 1H), 5.67-5.55 (m, 1H), 4.47-4.35 (m, 1H), 4.31-4.16 (m, 1H), 3.14-2.99 (m, 1H), 2.61-2.54 (m, 1H). LCMS (ESI) m/z: 441.2 [M+H]$^+$. Second peak: (I-289a): $^1$H NMR (400 MHz, DMSO-$d_6$) δ 9.31 (d, J=7.6 Hz, 1H), 8.74 (d, J=5.2 Hz, 1H), 8.28-8.15 (m, 3H), 8.12-8.03 (m, 1H), 7.94 (d, J=8.0 Hz, 1H), 7.81-7.70 (m, 1H), 7.03 (s, 1H), 5.65-5.56 (m, 1H), 4.48-4.34 (m, 1H), 4.31-4.18 (m, 1H), 3.14-3.00 (m, 1H), 2.61-2.53 (m, 1H). LCMS (ESI) m/z: 441.2 [M+H]$^+$.

Example 1.48. Synthesis of (S)-3-Cyano-N-(2-(2-(trifluoromethyl)pyridin-4-yl)-5,6-dihydro-4H-pyrrolo[1,2-b]pyrazol-4-yl)benzamide (I-342a)

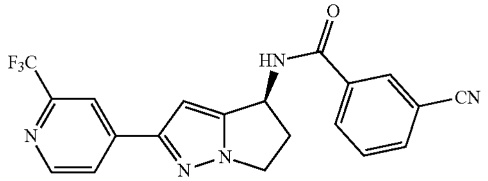 [SMILES: N#Cc1cccc(C(=O)N[C@H]2CCn3nc(-c4ccnc(C(F)(F)F)c4)cc32)c1]

Step 1—Synthesis of 3-Cyano-N-(2-(2-(trifluoromethyl)pyridin-4-yl)-5,6-dihydro-4H-pyrrolo[1,2-b]pyrazol-4-yl)benzamide

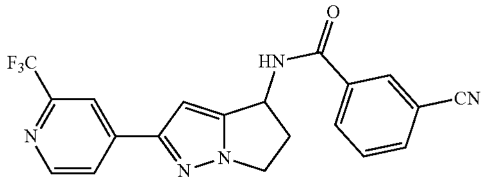

Following the procedure described in Example 1.26 and 2-(2-(trifluoromethyl)pyridin-4-yl)-5,6-dihydro-4H-pyrrolo[1,2-b]pyrazol-4-amine hydrochloride salt and 3-cyanobenzoic acid were used in step 7, the title compound (100 mg, 57%) was obtained as a white solid after purification of silica gel chromatography (solvent gradient: 0-40% EtOAc in petroleum ether). LCMS (ESI) m/z: 398.1 [M+H]$^+$.

Step 2—Synthesis of (S)-3-Cyano-N-(2-(2-(trifluoromethyl)pyridin-4-yl)-5,6-dihydro-4H-pyrrolo[1,2-b]pyrazol-4-yl)benzamide & (R)-3-Cyano-N-(2-(2-(trifluoromethyl)pyridin-4-yl)-5,6-dihydro-4H-pyrrolo[1,2-b]pyrazol-4-yl)benzamide

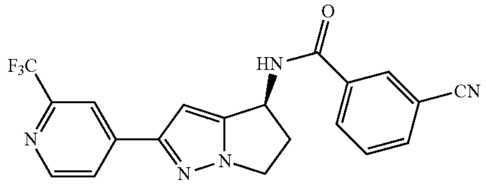

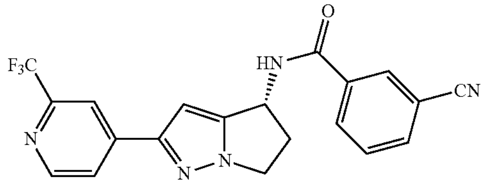

3-Cyano-N-(2-(2-(trifluoromethyl)pyridin-4-yl)-5,6-dihydro-4H-pyrrolo[1,2-b]pyrazol-4-yl)benzamide (100 mg, 252 μmol) was separated by using chiral SFC (DAICEL CHIRALCEL OJ (250 mm*30 mm, 10 μm); Supercritical $CO_2$/EtOH+0.1% $NH_3 \cdot H_2O$=70/30; 70 mL/min) to afford (S)-3-cyano-N-(2-(2-(trifluoromethyl)pyridin-4-yl)-5,6-dihydro-4H-pyrrolo[1,2-b]pyrazol-4-yl)benzamide (42.7 mg, first peak) and (R)-3-cyano-N-(2-(2-(trifluoromethyl)pyridin-4-yl)-5,6-dihydro-4H-pyrrolo[1,2-b]pyrazol-4-yl)benzamide (37.4 mg, second peak) both as white solids. First peak: (I-342a): $^1$H NMR (400 MHz, DMSO-$d_6$) δ 9.24 (d, J=7.6 Hz, 1H), 8.74 (d, J=5.2 Hz, 1H), 8.33-8.29 (m, 1H), 8.23-8.16 (m, 2H), 8.12-7.98 (m, 2H), 7.75-7.70 (m, 1H), 7.02 (s, 1H), 5.63-5.53 (m, 1H), 4.48-4.32 (m, 1H), 4.29-4.15 (m, 1H), 3.14-2.96 (m, 1H), 2.60-2.52 (m, 1H). LCMS (ESI) m/z: 398.0 [M+H]$^+$. Second peak (I-342b): $^1$H NMR (400 MHz, DMSO-$d_6$) δ 9.25 (d, J=7.2 Hz, 1H), 8.74 (d, J=5.2 Hz, 1H), 8.31 (s, 1H), 8.22-8.15 (m, 2H), 8.09-8.00 (m, 2H), 7.75-7.70 (m, 1H), 7.02 (s, 1H), 5.68-5.44 (m, 1H), 4.44-4.35 (m, 1H), 4.29-4.19 (m, 1H), 3.13-2.98 (m, 1H), 2.61-2.53 (m, 1H). LCMS (ESI) m/z: 398.1 [M+H]$^+$.

Example 1.49. Synthesis of (S)-3-Cyano-5-(trifluoromethyl)-N-(2-(2-(trifluoromethyl)pyridin-4-yl)-5,6-dihydro-4H-pyrrolo[1,2-b]pyrazol-4-yl)benzamide (I-288a)

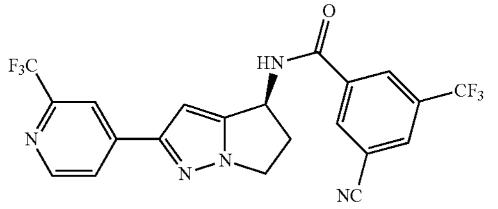 [SMILES: N#Cc1cc(C(=O)N[C@H]2CCn3nc(-c4ccnc(C(F)(F)F)c4)cc32)cc(C(F)(F)F)c1]

Step 1—Synthesis of 3-Cyano-5-(trifluoromethyl)-N-(2-(2-(trifluoromethyl)pyridin-4-yl)-5,6-dihydro-4H-pyrrolo[1,2-b]pyrazol-4-yl)benzamide

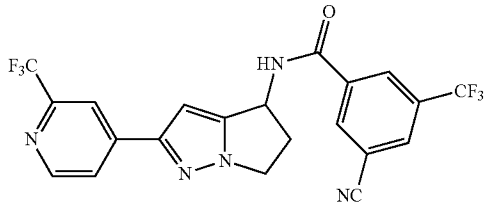 [SMILES: N#Cc1cc(C(=O)NC2CCn3nc(-c4ccnc(C(F)(F)F)c4)cc32)cc(C(F)(F)F)c1]

Following the procedure described in Example 1.26 and 2-(2-(trifluoromethyl)pyridin-4-yl)-5,6-dihydro-4H-pyrrolo[1,2-b]pyrazol-4-amine hydrochloride salt and 3-cyano-5-(trifluoromethyl)benzoic acid were used in step 7, the title compound (150 mg, 77%) was obtained as a white solid after purification of RP-HPLC (acetonitrile 45-75%/0.225% formic acid in water). LCMS (ESI) m/z: 466.1 $[M+H]^+$.

Step 2—Synthesis of (S)-3-Cyano-5-(trifluoromethyl)-N-(2-(2-(trifluoromethyl)pyridin-4-yl)-5,6-dihydro-4H-pyrrolo[1,2-b]pyrazol-4-yl)benzamide & (R)-3-Cyano-5-(trifluoromethyl)-N-(2-(2-(trifluoromethyl)pyridin-4-yl)-5,6-dihydro-4H-pyrrolo[1,2-b]pyrazol-4-yl)benzamide

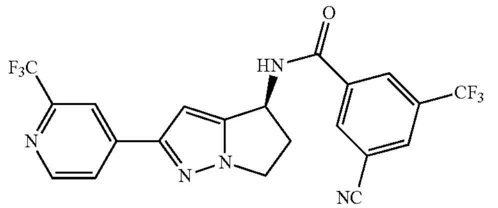

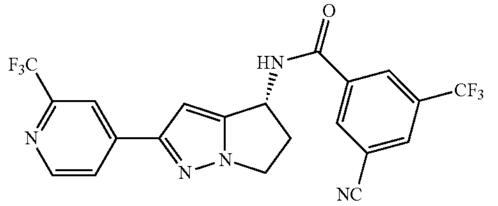

3-Cyano-5-(trifluoromethyl)-N-(2-(2-(trifluoromethyl)pyridin-4-yl)-5,6-dihydro-4H-pyrrolo[1,2-b]pyrazol-4-yl)benzamide (90 mg, 193 μmol) was separated by using chiral SFC (DAICEL CHIRALCEL OJ (250 mm*30 mm, 10 μm); Supercritical $CO_2$/EtOH+0.1% $NH_3 \cdot H_2O$=85/15; 70 mL/min) to afford (S)-3-cyano-5-(trifluoromethyl)-N-(2-(2-(trifluoromethyl)pyridin-4-yl)-5,6-dihydro-4H-pyrrolo[1,2-b]pyrazol-4-yl)benzamide (28.8 mg, first peak) and (R)-3-cyano-5-(trifluoromethyl)-N-(2-(2-(trifluoromethyl)pyridin-4-yl)-5,6-dihydro-4H-pyrrolo[1,2-b]pyrazol-4-yl)benzamide (22.3 mg, second peak) both as white solids. First peak: (I-288a): $^1H$ NMR (400 MHz, DMSO-$d_6$) δ 9.45 (d, J=7.6 Hz, 1H), 8.75 (d, J=5.2 Hz, 1H), 8.60 (d, J=11.2 Hz, 2H), 8.51 (s, 1H), 8.20 (s, 1H), 8.11-8.04 (m, 1H), 7.04 (s, 1H), 5.63-5.56 (m, 1H), 4.46-4.35 (m, 1H), 4.31-4.18 (m, 1H), 3.16-3.00 (m, 1H), 2.62-2.54 (m, 1H). LCMS (ESI) m/z: 466.2 $[M+H]^+$. Second peak (I-288b): $^1H$ NMR (400 MHz, DMSO-$d_6$) δ 9.45 (d, J=7.6 Hz, 1H), 8.75 (d, J=5.2 Hz, 1H), 8.60 (d, J=11.2 Hz, 2H), 8.51 (s, 1H), 8.20 (s, 1H), 8.07 (d, J=5.2 Hz, 1H), 7.04 (s, 1H), 5.62-5.56 (m, 1H), 4.46-4.34 (m, 1H), 4.32-4.21 (m, 1H), 3.19-3.00 (m, 1H), 2.61-2.54 (m, 1H). LCMS (ESI) m/z: 466.2 $[M+H]^+$.

Example 1.50. Synthesis of (S)-3-Cyano-5-methoxy-N-(2-(2-(trifluoromethyl)pyridin-4-yl)-5,6-dihydro-4H-pyrrolo[1,2-b]pyrazol-4-yl)benzamide (I-258a)

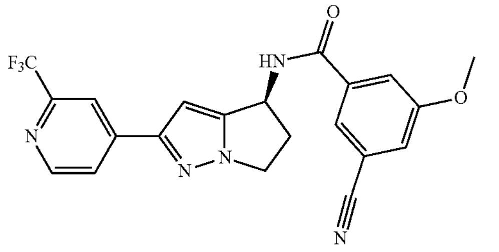 [SMILES: COc1cc(C#N)cc(C(=O)N[C@H]2CCn3nc(-c4ccnc(C(F)(F)F)c4)cc32)c1]

Step 1—Synthesis of 3-Cyano-5-(trifluoromethyl)-N-(2-(2-(trifluoromethyl)pyridin-4-yl)-5,6-dihydro-4H-pyrrolo[1,2-b]pyrazol-4-yl)benzamide

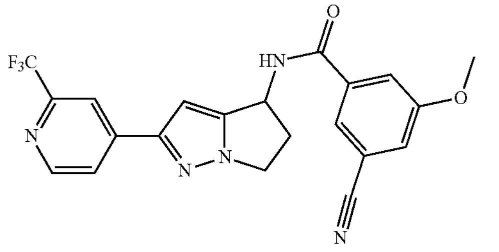 [SMILES: COc1cc(C#N)cc(C(=O)NC2CCn3nc(-c4ccnc(C(F)(F)F)c4)cc32)c1]

Following the procedure described in Example 1.26 and 2-(2-(trifluoromethyl)pyridin-4-yl)-5,6-dihydro-4H-pyrrolo[1,2-b]pyrazol-4-amine hydrochloride salt and 3-cyano-5-methoxybenzoic acid were used in step 7, the title compound (100 mg, 48%) was obtained as a white solid after purification of RP-HPLC (acetonitrile 30-60%/0.225% formic acid in water). LCMS (ESI) m/z: 428.1 $[M+H]^+$.

Step 2—Synthesis of (S)-3-Cyano-5-methoxy-N-(2-(2-(trifluoromethyl)pyridin-4-yl)-5,6-dihydro-4H-pyrrolo[1,2-b]pyrazol-4-yl)benzamide & (R)-3-Cyano-5-methoxy-N-(2-(2-(trifluoromethyl)pyridin-4-yl)-5,6-dihydro-4H-pyrrolo[1,2-b]pyrazol-4-yl)benzamide

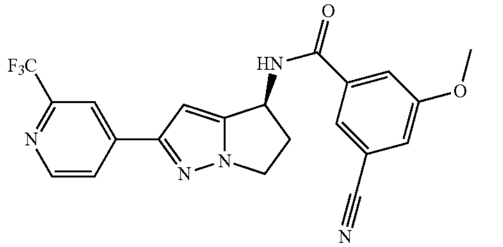

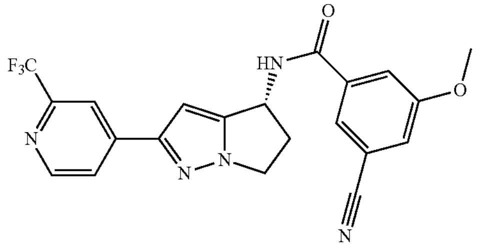

3-Cyano-5-(trifluoromethyl)-N-(2-(2-(trifluoromethyl)pyridin-4-yl)-5,6-dihydro-4H-pyrrolo[1,2-b]pyrazol-4-yl)benzamide (100 mg, 234 μmol) was separated by using chiral SFC (DAICEL CHIRALCEL OJ (250 mm*30 mm, 10 μm); Supercritical $CO_2$/EtOH+0.1% $NH_3 \cdot H_2O$=60/40; 70 mL/min) to afford (S)-3-cyano-5-methoxy-N-(2-(2-(trifluoromethyl)pyridin-4-yl)-5,6-dihydro-4H-pyrrolo[1,2-b]pyrazol-4-yl)benzamide (25 mg, first peak) and (R)-3-cyano-5-methoxy-N-(2-(2-(trifluoromethyl)pyridin-4-yl)-5,6-dihydro-4H-pyrrolo[1,2-b]pyrazol-4-yl)benzamide (40 mg, second peak) both as white solids. First peak: (I-258a): $^1H$ NMR (400 MHz, DMSO-$d_6$) δ 9.24 (d, J=7.6 Hz, 1H), 8.75 (d, J=5.2 Hz, 1H), 8.21 (s, 1H), 8.10-8.06 (m, 1H), 7.90 (s, 1H), 7.76-7.72 (m, 1H), 7.68-7.65 (m, 1H), 7.03 (s, 1H), 5.61-5.55 (m, 1H), 4.50-4.39 (m, 1H), 4.35-4.21 (m, 1H), 3.88 (s, 3H), 3.15-3.02 (m, 1H), 2.62-2.54 (m, 1H). LCMS (ESI) m/z: 428.2 $[M+H]^+$. Second peak (I-258b): $^1H$ NMR (400 MHz, DMSO-$d_6$) δ 9.24 (d, J=7.6 Hz, 1H), 8.75 (d, J=5.2 Hz, 1H), 8.21 (s, 1H), 8.10-8.06 (m, 1H), 7.90 (s, 1H), 7.76-7.72 (m, 1H), 7.68-7.65 (m, 1H), 7.03 (s, 1H), 5.61-5.55 (m, 1H), 4.50-4.39 (m, 1H), 4.35-4.21 (m, 1H), 3.88 (s, 3H), 3.15-3.02 (m, 1H), 2.62-2.54 (m, 1H). LCMS (ESI) m/z: 428.2 $[M+H]^+$.

Example 1.51. Synthesis of (S)-3-Cyano-4-fluoro-N-(2-(2-(trifluoromethyl)pyridin-4-yl)-5,6-dihydro-4H-pyrrolo[1,2-b]pyrazol-4-yl)benzamide (I-266a)

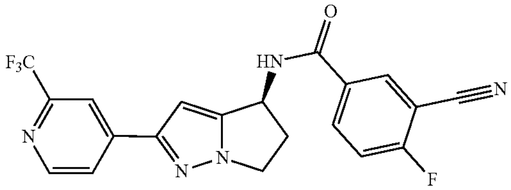 [SMILES: N#Cc1cc(C(=O)N[C@H]2CCn3nc(-c4ccnc(C(F)(F)F)c4)cc32)ccc1F]

Step 1—Synthesis of 3-Cyano-4-fluoro-N-(2-(2-(trifluoromethyl)pyridin-4-yl)-5,6-dihydro-4H-pyrrolo[1,2-b]pyrazol-4-yl)benzamide

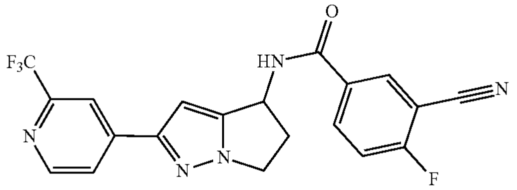 [SMILES: N#Cc1cc(C(=O)NC2CCn3nc(-c4ccnc(C(F)(F)F)c4)cc32)ccc1F]

Following the procedure described in Example 1.26 and 2-(2-(trifluoromethyl)pyridin-4-yl)-5,6-dihydro-4H-pyrrolo[1,2-b]pyrazol-4-amine hydrochloride salt and 3-cyano-4-fluorobenzoic acid were used in step 7, the title compound (100 mg, 49%) was obtained as a white solid after purification of RP-HPLC (acetonitrile 30-60%/0.225% formic acid in water). LCMS (ESI) m/z: 416.2 $[M+H]^+$.

Step 2—Synthesis of (S)-3-Cyano-4-fluoro-N-(2-(2-(trifluoromethyl)pyridin-4-yl)-5,6-dihydro-4H-pyrrolo[1,2-b]pyrazol-4-yl)benzamide & (R)-3-Cyano-4-fluoro-N-(2-(2-(trifluoromethyl)pyridin-4-yl)-5,6-dihydro-4H-pyrrolo[1,2-b]pyrazol-4-yl)benzamide

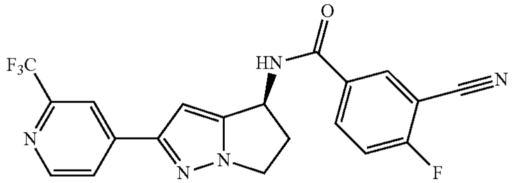

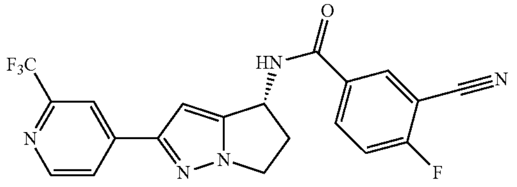

3-Cyano-4-fluoro-N-(2-(2-(trifluoromethyl)pyridin-4-yl)-5,6-dihydro-4H-pyrrolo[1,2-b]pyrazol-4-yl)benzamide (100 mg, 241 μmol) was separated by using chiral SFC (DAICEL CHIRALCEL OJ (250 mm*30 mm, 10 μm); Supercritical $CO_2$/EtOH+0.1% $NH_3 \cdot H_2O$=70/30; 65 mL/min) to afford (S)-3-cyano-4-fluoro-N-(2-(2-(trifluoromethyl)pyridin-4-yl)-5,6-dihydro-4H-pyrrolo[1,2-b]pyrazol-4-yl)benzamide (17 mg, first peak) and (R)-3-cyano-4-fluoro-N-(2-(2-(trifluoromethyl)pyridin-4-yl)-5,6-dihydro-4H-pyrrolo[1,2-b]pyrazol-4-yl)benzamide (30 mg, second peak) both as white solids. First peak: (I-266a): $^1H$ NMR (400 MHz, DMSO-$d_6$) δ 9.24 (d, J=7.6 Hz, 1H), 8.75 (d, J=5.2 Hz, 1H), 8.42 (dd, J=2.4, 6.2 Hz, 1H), 8.32-8.26 (m, 1H), 8.20 (s, 1H), 8.07 (d, J=6.0 Hz, 1H), 7.70-7.65 (m, 1H), 7.02 (s, 1H), 5.60-5.52 (m, 1H), 4.43-4.35 (m, 1H), 4.30-4.20 (m, 1H), 3.12-3.01 (m, 1H), 2.60-2.54 (m, 1H). LCMS (ESI) m/z: 416.2 $[M+H]^+$. Second peak (I-266b): $^1H$ NMR (400 MHz, DMSO-$d_6$) δ 9.24 (d, J=7.6 Hz, 1H), 8.75 (d, J=5.2 Hz, 1H), 8.42 (dd, J=2.4, 6.2 Hz, 1H), 8.32-8.26 (m, 1H), 8.20 (s, 1H), 8.07 (d, J=6.0 Hz, 1H), 7.70-7.65 (m, 1H), 7.02 (s, 1H), 5.60-5.52 (m, 1H), 4.43-4.35 (m, 1H), 4.30-4.20 (m, 1H), 3.12-3.01 (m, 1H), 2.60-2.54 (m, 1H). LCMS (ESI) m/z: 416.1 $[M+H]^+$.

Example 1.52. Synthesis of (S)-3-Cyano-5-methyl-N-(2-(2-(trifluoromethyl)pyridin-4-yl)-5,6-dihydro-4H-pyrrolo[1,2-b]pyrazol-4-yl)benzamide (I-334a)

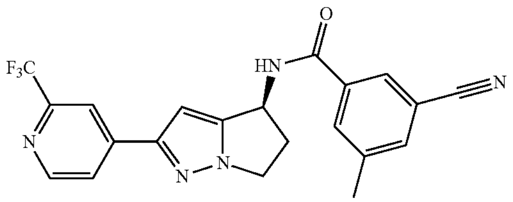 [SMILES: Cc1cc(C#N)cc(C(=O)N[C@H]2CCn3nc(-c4ccnc(C(F)(F)F)c4)cc32)c1]

Step 1—Synthesis of 3-Cyano-5-methyl-N-(2-(2-(trifluoromethyl)pyridin-4-yl)-5,6-dihydro-4H-pyrrolo[1,2-b]pyrazol-4-yl)benzamide

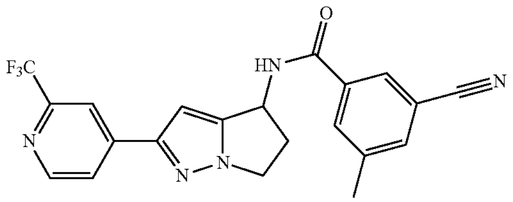 [SMILES: Cc1cc(C#N)cc(C(=O)NC2CCn3nc(-c4ccnc(C(F)(F)F)c4)cc32)c1]

Following the procedure described in Example 1.26 and 2-(2-(trifluoromethyl)pyridin-4-yl)-5,6-dihydro-4H-pyrrolo[1,2-b]pyrazol-4-amine hydrochloride salt and 3-cyano-5-methylbenzoic acid were used in step 7, the title compound (102 mg, 43%) was obtained as a white solid after purification of RP-HPLC (acetonitrile 36-66%/0.225% formic acid in water). LCMS (ESI) m/z: 412.2 $[M+H]^+$.

Step 2—Synthesis of (S)-3-Cyano-5-methyl-N-(2-(2-(trifluoromethyl)pyridin-4-yl)-5,6-dihydro-4H-pyrrolo[1,2-b]pyrazol-4-yl)benzamide & (R)-3-Cyano-5-methyl-N-(2-(2-(trifluoromethyl)pyridin-4-yl)-5,6-dihydro-4H-pyrrolo[1,2-b]pyrazol-4-yl)benzamide

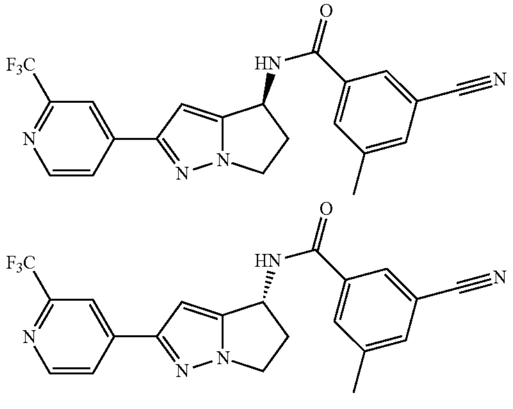

3-Cyano-4-fluoro-N-(2-(2-(trifluoromethyl)pyridin-4-yl)-5,6-dihydro-4H-pyrrolo[1,2-b]pyrazol-4-yl)benzamide (102 mg, 241 μmol) was separated by using chiral SFC (DAICEL CHIRALCEL OJ (250 mm*30 mm, 10 μm); Supercritical $CO_2$/EtOH+0.1% $NH_3 \cdot H_2O$=70/30; 65 mL/min) to afford (S)-3-cyano-5-methyl-N-(2-(2-(trifluoromethyl)pyridin-4-yl)-5,6-dihydro-4H-pyrrolo[1,2-b]pyrazol-4-yl)benzamide (41 mg, first peak) and (R)-3-cyano-5-methyl-N-(2-(2-(trifluoromethyl)pyridin-4-yl)-5,6-dihydro-4H-pyrrolo[1,2-b]pyrazol-4-yl)benzamide (34 mg, second peak) both as white solids. First peak: (I-334a): $^1$H NMR (400 MHz, DMSO-$d_6$) δ 9.20 (d, J=7.6 Hz, 1H), 8.75 (d, J=5.2 Hz, 1H), 8.20 (s, 1H), 8.10 (s, 1H), 8.07 (d, J=4.8 Hz, 1H), 8.03 (s, 1H), 7.87 (s, 1H), 7.01 (s, 1H), 5.59-5.55 (m, 1H), 4.50-4.33 (m, 1H), 4.30-4.19 (m, 1H), 3.11-2.99 (m, 1H), 2.62-2.51 (m, 1H), 2.41 (s, 3H). LCMS (ESI) m/z: 412.2 $[M+H]^+$.

Second peak (I-334b): $^1$H NMR (400 MHz, DMSO-$d_6$) δ 9.20 (d, J=7.6 Hz, 1H), 8.75 (d, J=5.2 Hz, 1H), 8.20 (s, 1H), 8.10 (s, 1H), 8.07 (d, J=4.8 Hz, 1H), 8.03 (s, 1H), 7.87 (s, 1H), 7.01 (s, 1H), 5.59-5.55 (m, 1H), 4.50-4.33 (m, 1H), 4.30-4.19 (m, 1H), 3.11-2.99 (m, 1H), 2.62-2.51 (m, 1H), 2.41 (s, 3H). LCMS (ESI) m/z: 412.2 $[M+H]^+$.

Example 1.53. Synthesis of (S)-3,5-Difluoro-N-(2-(2-(trifluoromethyl)pyridin-4-yl)-5,6,7,8-tetrahydro-[1,2,4]triazolo[1,5-a]pyridin-8-yl)benzamide (I-234a)

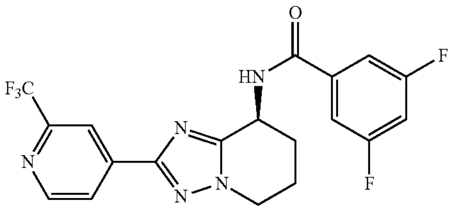 [SMILES: O=C(N[C@H]1CCCn2nc(-c3ccnc(C(F)(F)F)c3)nc21)c1cc(F)cc(F)c1]

Step 1—Synthesis of 2-(2-(Trifluoromethyl)pyridin-4-yl)-6,7-dihydro-[1,2,4]triazolo[1,5-a]pyridin-8(5H)-one

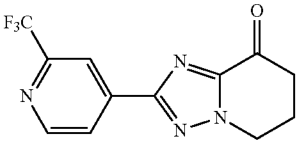

To a solution of 2-bromo-6,7-dihydro-[1,2,4]triazolo[1,5-a]pyridin-8(5H)-one (3 g, 13.9 mmol), (2-(trifluoromethyl)pyridin-4-yl)boronic acid (2.5 g, 10.5 mmol), $K_3PO_4$ (4.65 g, 22.32 mmol) in dioxane (50 mL) and $H_2O$ was added Pd(dppf)$Cl_2$ (200 mg, 2.92 mmol). The reaction mixture was stirred at 80° C. for 16 h under a nitrogen atmosphere. After cooling to room temperature, the mixture was diluted with $H_2O$ (50 mL), extracted with ethyl acetate (50 mL×2). The combined organic layers were washed with brine (50 mL), dried over anhydrous $Na_2SO_4$, filtered and concentrated in vacuo. The crude was purified by silica gel chromatography (solvent gradient: 0-5% methanol in DCM) to give the title compound (2.5 g, 64%) as a yellow solid. LCMS (ESI) m/z: 283.1 $[M+H]^+$.

Step 2—Synthesis of 3,5-Difluoro-N-(2-(2-(trifluoromethyl)pyridin-4-yl)-5,6,7,8-tetrahydro-[1,2,4]triazolo[1,5-a]pyridin-8-yl)benzamide

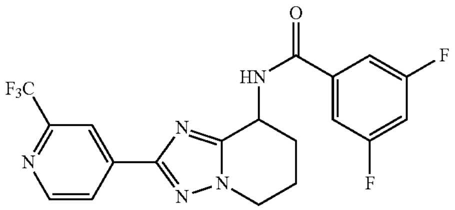

Following the procedure described in Example 1.26 and 2-(2-(trifluoromethyl)pyridin-4-yl)-6,7-dihydro-[1,2,4]triazolo[1,5-a]pyridin-8(5H)-one was used in step 4, 2-(2-(trifluoromethyl)pyridin-4-yl)-5,6,7,8-tetrahydro-[1,2,4]triazolo[1,5-a]pyridin-8-amine hydrochloride and 3,5-difluorobenzoic acid were used in step 7, the title compound (200 mg, 76%) was obtained as a white solid after purification of RP-HPLC (acetonitrile 45%-75%/0.225% formic acid in water). LCMS (ESI) m/z: 424.1 $[M+H]^+$.

Step 2—Synthesis of (R)-3,5-Difluoro-N-(2-(2-(trifluoromethyl)pyridin-4-yl)-5,6,7,8-tetrahydro-[1,2,4]triazolo[1,5-a]pyridin-8-yl)benzamide & (S)-3,5-Difluoro-N-(2-(2-(trifluoromethyl)pyridin-4-yl)-5,6,7,8-tetrahydro-[1,2,4]triazolo[1,5-a]pyridin-8-yl)benzamide

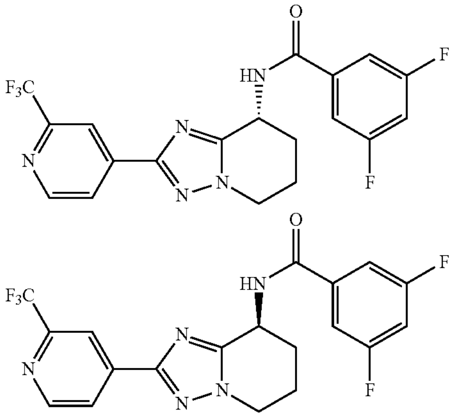

3,5-Difluoro-N-(2-(2-(trifluoromethyl)pyridin-4-yl)-5,6,7,8-tetrahydro-[1,2,4]triazolo[1,5-a]pyridin-8-yl)benzamide (200 mg, 472 μmol) was separated by using chiral SFC (DAICEL CHIRALCEL AS (250 mm*30 mm, 10 μm); Supercritical $CO_2$/EtOH+0.1% $NH_3 \cdot H_2O$=80/20; 70 mL/min) to afford (R)-3,5-difluoro-N-(2-(2-(trifluoromethyl)pyridin-4-yl)-5,6,7,8-tetrahydro-[1,2,4]triazolo[1,5-a]pyridin-8-yl)benzamide (80.1 mg, first peak) and (S)-3,5-difluoro-N-(2-(2-(trifluoromethyl)pyridin-4-yl)-5,6,7,8-tetrahydro-[1,2,4]triazolo[1,5-a]pyridin-8-yl)benzamide (51.2 mg, second peak) both as white solid. First peak (I-234b): $^1H$ NMR (400 MHz, DMSO-$d_6$) δ 9.28 (d, J=8.0 Hz, 1H), 8.86 (d, J=5.2 Hz, 1H), 8.24 (s, 1H), 8.21 (d, J=5.2 Hz, 1H), 7.65-7.57 (m, 2H), 7.56-7.48 (m, 1H), 5.48-5.35 (m, 1H), 4.34-4.22 (m, 2H), 2.30-2.08 (m, 3H), 2.07-1.95 (m, 1H). LCMS (ESI) m/z: 424.2 $[M+H]^+$. Second peak: (I-234a): $^1H$ NMR (400 MHz, DMSO-$d_6$) δ 9.27 (d, J=8.0 Hz, 1H), 8.86 (d, J=5.2 Hz, 1H), 8.24 (s, 1H), 8.21 (d, J=5.2 Hz, 1H), 7.64-7.57 (m, 2H), 7.56-7.46 (m, 1H), 5.50-5.33 (m, 1H), 4.37-4.21 (m, 2H), 2.30-2.10 (m, 3H), 2.07-1.93 (m, 1H). LCMS (ESI) m/z: 424.2 $[M+H]^+$.

Example 1.54. Synthesis of (S)-4-Methyl-2-(trifluoromethyl)-N-(2-(2-(trifluoromethyl)pyridin-4-yl)-5,6,7,8-tetrahydro-[1,2,4]triazolo[1,5-a]pyridin-8-yl)oxazole-5-carboxamide (I-216a)

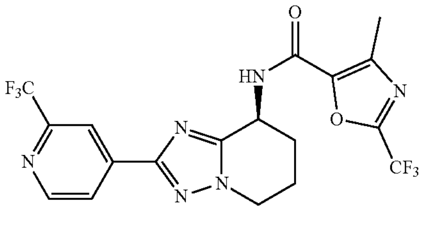 [SMILES: Cc1nc(C(F)(F)F)oc1C(=O)N[C@H]1CCCn2nc(-c3ccnc(C(F)(F)F)c3)nc21]

Step 1—Synthesis of 4-Methyl-2-(trifluoromethyl)-N-(2-(2-(trifluoromethyl)pyridin-4-yl)-5,6,7,8-tetrahydro-[1,2,4]triazolo[1,5-a]pyridin-8-yl)oxazole-5-carboxamide

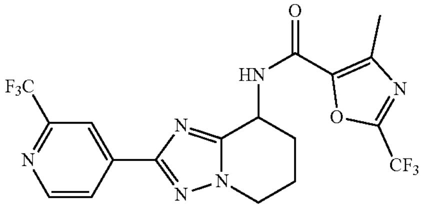 [SMILES: Cc1nc(C(F)(F)F)oc1C(=O)NC1CCCn2nc(-c3ccnc(C(F)(F)F)c3)nc21]

Following the procedure described in Example 1.26 and 2-(2-(trifluoromethyl)pyridin-4-yl)-5,6,7,8-tetrahydro-[1,2,4]triazolo[1,5-a]pyridin-8-amine hydrochloride and 4-methyl-2-(trifluoromethyl)oxazole-5-carboxylic acid were used in step 7, the title compound (170 mg, 53%) was obtained as a white solid after purification of silica gel chromatography (solvent gradient: 0-40% EtOAc in petroleum ether). LCMS (ESI) m/z: 461.1 $[M+H]^+$.

Step 2—Synthesis of (S)-4-Methyl-2-(trifluoromethyl)-N-(2-(2-(trifluoromethyl)pyridin-4-yl)-5,6,7,8-tetrahydro-[1,2,4]triazolo[1,5-a]pyridin-8-yl)oxazole-5-carboxamide & (R)-4-Methyl-2-(trifluoromethyl)-N-(2-(2-(trifluoromethyl)pyridin-4-yl)-5,6,7,8-tetrahydro-[1,2,4]triazolo[1,5-a]pyridin-8-yl)oxazole-5-carboxamide

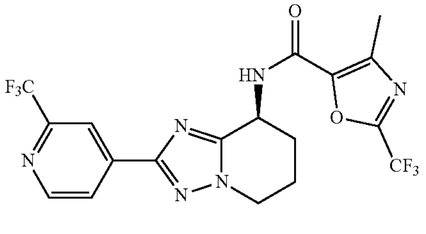

-continued

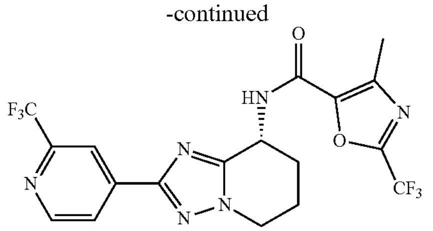

4-Methyl-2-(trifluoromethyl)-N-(2-(2-(trifluoromethyl)pyridin-4-yl)-5,6,7,8-tetrahydro-[1,2,4]triazolo[1,5-a]pyridin-8-yl)oxazole-5-carboxamide (170 mg, 369 μmol) was separated by using chiral SFC (DAICEL CHIRALCEL AD (250 mm*30 mm, 10 μm); Supercritical $CO_2$/EtOH+0.1% $NH_3 \cdot H_2O$=80/20; 150 mL/min) to afford (S)-4-methyl-2-(trifluoromethyl)-N-(2-(2-(trifluoromethyl)pyridin-4-yl)-5,6,7,8-tetrahydro-[1,2,4]triazolo[1,5-a]pyridin-8-yl)oxazole-5-carboxamide (50.5 mg, first peak) and (R)-4-methyl-2-(trifluoromethyl)-N-(2-(2-(trifluoromethyl)pyridin-4-yl)-5,6,7,8-tetrahydro-[1,2,4]triazolo[1,5-a]pyridin-8-yl)oxazole-5-carboxamide (56.7 mg, second peak) both as white solids. First peak: (I-216a): $^1$H NMR (400 MHz, DMSO-$d_6$) δ 9.38 (d, J=8.4 Hz, 1H), 8.86 (d, J=5.2 Hz, 1H), 8.23 (s, 1H), 8.20 (d, J=5.2 Hz, 1H), 5.44-5.33 (m, 1H), 4.34-4.17 (m, 2H), 2.49 (s, 3H), 2.28-2.08 (m, 3H), 2.07-1.96 (m, 1H). LCMS (ESI) m/z: 461.2 $[M+H]^+$. Second peak (I-216b): $^1$H NMR (400 MHz, DMSO-$d_6$) δ 9.38 (d, J=8.4 Hz, 1H), 8.86 (d, J=5.2 Hz, 1H), 8.23 (s, 1H), 8.20 (d, J=5.2 Hz, 1H), 5.44-5.35 (m, 1H), 4.34-4.16 (m, 2H), 2.49 (s, 3H), 2.29-2.09 (m, 3H), 2.07-1.98 (m, 1H). LCMS (ESI) m/z: 461.2 $[M+H]^+$.

Example 1.55. Synthesis of (S)-6-(Trifluoromethyl)-N-(2-(2-(trifluoromethyl)pyridin-4-yl)-5,6,7,8-tetrahydro-[1,2,4]triazolo[1,5-a]pyridin-8-yl)pyrazine-2-carboxamide (I-215a)

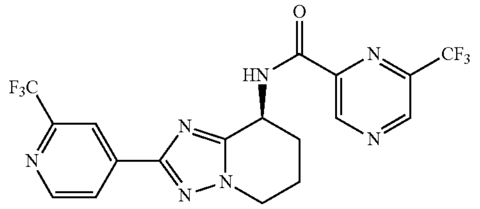 [SMILES: O=C(N[C@H]1CCCn2nc(-c3ccnc(C(F)(F)F)c3)nc21)c1cncc(C(F)(F)F)n1]

Step 1—Synthesis of 6-(Trifluoromethyl)-N-(2-(2-(trifluoromethyl)pyridin-4-yl)-5,6,7,8-tetrahydro-[1,2,4]triazolo[1,5-a]pyridin-8-yl)pyrazine-2-carboxamide

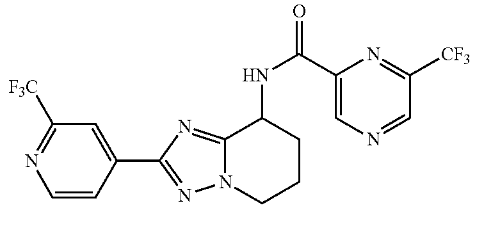

Following the procedure described in Example 1.26 2-(2-(trifluoromethyl)pyridin-4-yl)-5,6,7,8-tetrahydro-[1,2,4]triazolo[1,5-a]pyridin-8-amine hydrochloride and 6-(trifluoromethyl)pyrazine-2-carboxylic acid were used in step 7, the title compound (180 mg, 47%) was obtained as a white solid after purification of silica gel chromatography (solvent gradient: 0-40% EtOAc in petroleum ether). LCMS (ESI) m/z: 458.1 $[M+H]^+$.

Step 2—Synthesis of (S)-6-(Trifluoromethyl)-N-(2-(2-(trifluoromethyl)pyridin-4-yl)-5,6,7,8-tetrahydro-[1,2,4]triazolo[1,5-a]pyridin-8-yl)pyrazine-2-carboxamide & (R)-6-(Trifluoromethyl)-N-(2-(2-(trifluoromethyl)pyridin-4-yl)-5,6,7,8-tetrahydro-[1,2,4]triazolo[1,5-a]pyridin-8-yl)pyrazine-2-carboxamide

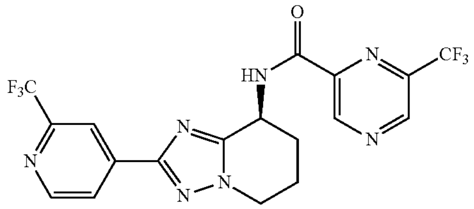

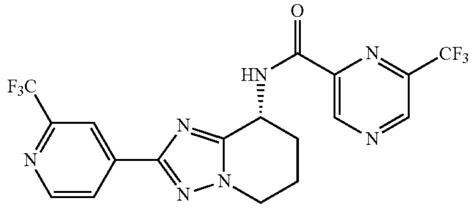

6-(Trifluoromethyl)-N-(2-(2-(trifluoromethyl)pyridin-4-yl)-5,6,7,8-tetrahydro-[1,2,4]triazolo[1,5-a]pyridin-8-yl)pyrazine-2-carboxamide (180 mg, 394 μmol) was separated by using chiral SFC (DAICEL CHIRALCEL OJ (250 mm*30 mm, 10 μm); Supercritical $CO_2$/EtOH+0.1% $NH_3 \cdot H_2O$=92.5/7.5; 150 mL/min) to afford (S)-6-(trifluoromethyl)-N-(2-(2-(trifluoromethyl)pyridin-4-yl)-5,6,7,8-tetrahydro-[1,2,4]triazolo[1,5-a]pyridin-8-yl)pyrazine-2-carboxamide (43.9 mg, first peak) and (R)-6-(trifluoromethyl)-N-(2-(2-(trifluoromethyl)pyridin-4-yl)-5,6,7,8-tetrahydro-[1,2,4]triazolo[1,5-a]pyridin-8-yl)pyrazine-2-carboxamide (55.6 mg, second peak) both as white solids. First peak: (I-215a): $^1$H NMR (400 MHz, DMSO-$d_6$) δ 9.60 (d, J=8.8 Hz, 1H), 9.54 (s, 1H), 9.43 (s, 1H), 8.85 (d, J=5.2 Hz, 1H), 8.22 (s, 1H), 8.19 (d, J=5.2 Hz, 1H), 5.48 (d, J=5.6 Hz, 1H), 4.37-4.28 (m, 1H), 4.25-4.15 (m, 1H), 2.29-2.19 (m, 2H), 2.19-2.05 (m, 2H). LCMS (ESI) m/z: 458.2 $[M+H]^+$. Second peak (I-215b): $^1$H NMR (400 MHz, DMSO-$d_6$) δ 9.60 (d, J=8.8 Hz, 1H), 9.54 (s, 1H), 9.43 (s, 1H), 8.85 (d, J=5.2 Hz, 1H), 8.22 (s, 1H), 8.19 (d, J=5.2 Hz, 1H), 5.55-5.38 (m, 1H), 4.37-4.27 (m, 1H), 4.25-4.15 (m, 1H), 2.29-2.19 (m, 2H), 2.14 (d, J=6.8 Hz, 2H). LCMS (ESI) m/z: 458.2 $[M+H]^+$.

Example 1.56. Synthesis of (S)-2-Methoxy-N-(2-(2-(trifluoromethyl)pyridin-4-yl)-5,6,7,8-tetrahydro-[1,2,4]triazolo[1,5-a]pyridin-8-yl)isonicotinamide (I-214a)

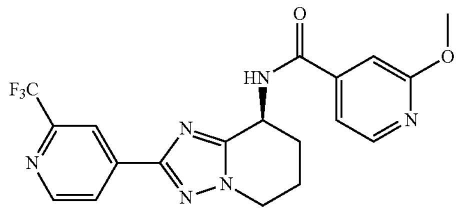 [SMILES: COc1cc(C(=O)N[C@H]2CCCn3nc(-c4ccnc(C(F)(F)F)c4)nc32)ccn1]

Step 1—Synthesis of 2-Methoxy-N-(2-(2-(trifluoromethyl)pyridin-4-yl)-5,6,7,8-tetrahydro-[1,2,4]triazolo[1,5-a]pyridin-8-yl)isonicotinamide

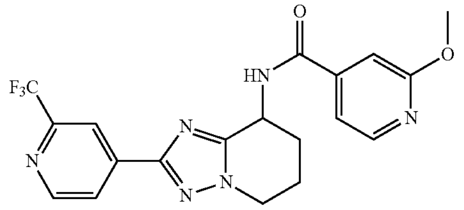 [SMILES: COc1cc(C(=O)NC2CCCn3nc(-c4ccnc(C(F)(F)F)c4)nc32)ccn1]

Following the procedure described in Example 1.26 and 2-(2-(trifluoromethyl)pyridin-4-yl)-5,6,7,8-tetrahydro-[1,2,4]triazolo[1,5-a]pyridin-8-amine hydrochloride and 6-(trifluoromethyl)pyrazine-2-carboxylic acid were used in step 7, the title compound (200 mg, 57%) was obtained as a white solid after purification of silica gel chromatography (solvent gradient: 0-40% EtOAc in petroleum ether). LCMS (ESI) m/z: 419.1pre $[M+H]^+$.

Step 2—Synthesis of (S)-2-Methoxy-N-(2-(2-(trifluoromethyl)pyridin-4-yl)-5,6,7,8-tetrahydro-[1,2,4]triazolo[1,5-a]pyridin-8-yl)isonicotinamide & (R)-2-Methoxy-N-(2-(2-(trifluoromethyl)pyridin-4-yl)-5,6,7,8-tetrahydro-[1,2,4]triazolo[1,5-a]pyridin-8-yl)isonicotinamide

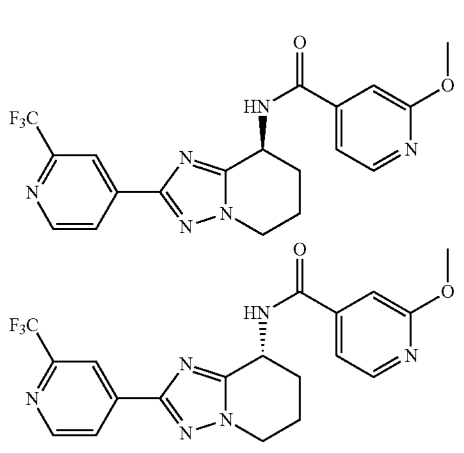

2-Methoxy-N-(2-(2-(trifluoromethyl)pyridin-4-yl)-5,6,7,8-tetrahydro-[1,2,4]triazolo[1,5-a]pyridin-8-yl)isonicotinamide (200 mg, 478 μmol) was separated by using chiral SFC (DAICEL CHIRALCEL OJ (250 mm*30 mm, 10 μm); Supercritical $CO_2$/EtOH+0.1% $NH_3 \cdot H_2O$=85/15; 150 mL/min) to afford (S)-2-methoxy-N-(2-(2-(trifluoromethyl)pyridin-4-yl)-5,6,7,8-tetrahydro-[1,2,4]triazolo[1,5-a]pyridin-8-yl)isonicotinamide (40.6 mg, first peak) and (R)-2-methoxy-N-(2-(2-(trifluoromethyl)pyridin-4-yl)-5,6,7,8-tetrahydro-[1,2,4]triazolo[1,5-a]pyridin-8-yl) isonicotinamide (51.1 mg, second peak) both as white solids. First peak: (I-214a): $^1$H NMR (400 MHz, DMSO-$d_6$) δ 9.32 (d, J=8.0 Hz, 1H), 8.86 (d, J=5.2 Hz, 1H), 8.32 (d, J=5.2 Hz, 1H), 8.23 (s, 1H), 8.20 (d, J=5.2 Hz, 1H), 7.41-7.36 (m, 1H), 7.22 (s, 1H), 5.47-5.36 (m, 1H), 4.34-4.18 (m, 2H), 3.89 (s, 3H), 2.29-2.09 (m, 3H), 2.09-1.91 (m, 1H). LCMS (ESI) m/z: 419.1 $[M+H]^+$. Second peak (I-214b): $^1$H NMR (400 MHz, DMSO-$d_6$) δ 9.32 (d, J=8.4 Hz, 1H), 8.86 (d, J=5.2 Hz, 1H), 8.32 (d, J=5.2 Hz, 1H), 8.23 (s, 1H), 8.20 (d, J=5.2 Hz, 1H), 7.43-7.36 (m, 1H), 7.22 (s, 1H), 5.49-5.35 (m, 1H), 4.33-4.22 (m, 2H), 3.89 (s, 3H), 2.29-2.11 (m, 3H), 2.07-1.95 (m, 1H). LCMS (ESI) m/z: 419.2 $[M+H]^+$.

Example 1.57. Synthesis of (S)—N-(2-(2-Cyclopropylpyridin-4-yl)-5,6,7,8-tetrahydro-[1,2,4]triazolo[1,5-a]pyridin-8-yl)-1-methyl-3-(trifluoromethyl)-1H-pyrazole-5-carboxamide (I-201a)

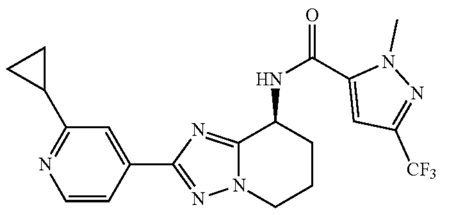

Step 1—Synthesis of N-(2-(2-Cyclopropylpyridin-4-yl)-5,6,7,8-tetrahydro-[1,2,4]triazolo[1,5-a]pyridin-8-yl)-1-methyl-3-(trifluoromethyl)-1H-pyrazole-5-carboxamide

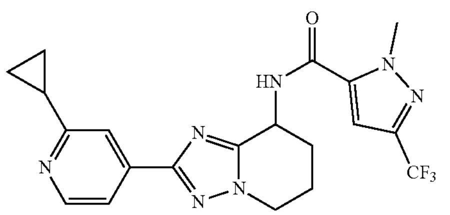

Following the procedure described in Example 1.52 and (2-cyclopropylpyridin-4-yl)boronic acid in step 1, 2-(2-cyclopropylpyridin-4-yl)-5,6,7,8-tetrahydro-[1,2,4]triazolo[1,5-a]pyridin-8-amine hydrochloride salt and 6-(trifluoromethyl)pyrazine-2-carboxylic acid were used in step 2, the title compound (45 mg, 38%) was obtained as a white solid after purification of RP-HPLC (acetonitrile 26%-56%/0.225% formic acid in water). LCMS (ESI) m/z: 419.1 $[M+H]^+$.

Step 2—Synthesis of (S)—N-(2-(2-Cyclopropylpyridin-4-yl)-5,6,7,8-tetrahydro-[1,2,4]triazolo[1,5-a]pyridine-8-yl)-1-methyl-3-(trifluoromethyl)-1H-pyrazole-5-carboxamide

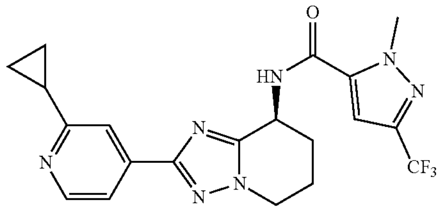

N-(2-(2-Cyclopropylpyridin-4-yl)-5,6,7,8-tetrahydro-[1,2,4]triazolo[1,5-a]pyridin-8-yl)-1-methyl-3-(trifluoromethyl)-1H-pyrazole-5-carboxamide (45 mg, 104 μmol) was separated by using chiral SFC (DAICEL CHIRALCEL OJ (250 mm*30 mm, 10 μm)); Supercritical $CO_2$/EtOH+0.1% $NH_3 \cdot H_2O$=75/25; 80 mL/min) to afford (S)—N-(2-(2-cyclopropylpyridin-4-yl)-5,6,7,8-tetrahydro-[1,2,4]triazolo[1,5-a]pyridin-8-yl)-1-methyl-3-(trifluoromethyl)-1H-pyrazole-5-carboxamide (15 mg, first peak) and I—N-(2-(2-cyclopropylpyridin-4-yl)-5,6,7,8-tetrahydro-[1,2,4]triazolo[1,5-a]pyridin-8-yl)-1-methyl-3-(trifluoromethyl)-1H-pyrazole-5-carboxamide (7 mg, second peak) both as white solids. First peak: (I-201a): $^1$H NMR (400 MHz, DMSO-$d_6$) δ 9.28 (d, J=8.0 Hz, 1H), 8.46 (d, J=4.4 Hz, 1H), 7.81 (s, 1H), 7.62 (d, J=3.6 Hz, 1H), 7.33 (s, 1H), 5.37 (s, 1H), 4.24 (s, 2H), 4.19 (s, 3H), 2.25-2.11 (m, 4H), 2.05-1.92 (m, 1H), 0.94 (s, 4H). LCMS (ESI) m/z: 432.3 $[M+H]^+$. Second peak (I-201b): $^1$H NMR (400 MHz, DMSO-$d_6$) δ 9.28 (d, J=8.0 Hz, 1H), 8.46 (d, J=4.4 Hz, 1H), 7.81 (s, 1H), 7.62 (d, J=3.6 Hz, 1H), 7.33 (s, 1H), 5.37 (s, 1H), 4.24 (s, 2H), 4.19 (s, 3H), 2.25-2.11 (m, 4H), 2.05-1.92 (m, 1H), 0.94 (s, 4H). LCMS (ESI) m/z: 432.3 $[M+H]^+$.

Example 1.58. Synthesis of (S)—N-(2-(2-Methoxypyridin-4-yl)-5,6,7,8-tetrahydro-[1,2,4]triazolo[1,5-a]pyridin-8-yl)-1-methyl-3-(trifluoromethyl)-1H-pyrazole-5-carboxamide (I-260a)

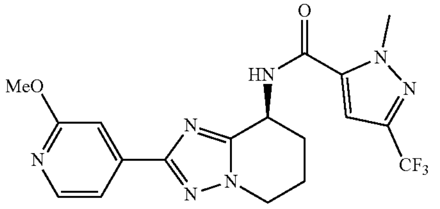 [SMILES: COc1cc(-c2nc3n(n2)CCC[C@@H]3NC(=O)c2cc(C(F)(F)F)nn2C)ccn1]

Step 1—(S)—N-(2-(2-Methoxypyridin-4-yl)-5,6,7,8-tetrahydro-[1,2,4]triazolo[1,5-a]pyridin-8-yl)-1-methyl-3-(trifluoromethyl)-1H-pyrazole-5-carboxamide

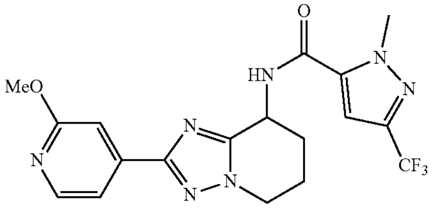 [SMILES: COc1cc(-c2nc3n(n2)CCCC3NC(=O)c2cc(C(F)(F)F)nn2C)ccn1]

Following the procedure described in Example 1.52 and (2-methoxypyridin-4-yl)boronic acid was used in step 1, 2-(2-methoxypyridin-4-yl)-5,6,7,8-tetrahydro-[1,2,4]triazolo[1,5-a]pyridin-8-amine hydrochloride salt and 6-(trifluoromethyl)pyrazine-2-carboxylic acid were used in step 2, the title compound (40 mg, 35%) was obtained as a white solid after purification of RP-HPLC (acetonitrile 30%-60%/0.225% formic acid in water). LCMS (ESI) m/z: 422.1 $[M+H]^+$.

Step 2—Synthesis of (S)—N-(2-(2-Methoxypyridin-4-yl)-5,6,7,8-tetrahydro-[1,2,4]triazolo[1,5-a]pyridin-8-yl)-1-methyl-3-(trifluoromethyl)-1H-pyrazole-5-carboxamide

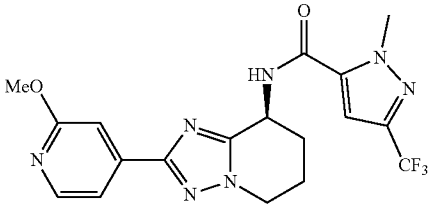 [SMILES: COc1cc(-c2nc3n(n2)CCC[C@@H]3NC(=O)c2cc(C(F)(F)F)nn2C)ccn1]

(S)—N-(2-(2-Methoxypyridin-4-yl)-5,6,7,8-tetrahydro-[1,2,4]triazolo[1,5-a]pyridin-8-yl)-1-methyl-3-(trifluoromethyl)-1H-pyrazole-5-carboxamide (40 mg, 95 μmol) was separated by using chiral SFC (DAICEL CHIRALCEL OJ (250 mm*30 mm, 10 μm)); Supercritical $CO_2$/EtOH+0.1% $NH_3 \cdot H_2O$=60/40; 80 mL/min) to afford (S)—N-(2-(2-methoxypyridin-4-yl)-5,6,7,8-tetrahydro-[1,2,4]triazolo[1,5-a]pyridin-8-yl)-1-methyl-3-(trifluoromethyl)-1H-pyrazole-5-carboxamide (8.8 mg, first peak) and (R)—N-(2-(2-methoxypyridin-4-yl)-5,6,7,8-tetrahydro-[1,2,4]triazolo[1,5-a]pyridin-8-yl)-1-methyl-3-(trifluoromethyl)-1H-pyrazole-5-carboxamide (6.8 mg, second peak) both as white solids. First peak: (I-260a): $^1$H NMR (400 MHz, DMSO-$d_6$) δ 9.28 (d, J=8.0 Hz, 1H), 8.25 (d, J=5.2 Hz, 1H), 7.51 (dd, J=1.2, 5.2 Hz, 1H), 7.33 (s, 1H), 7.25 (s, 1H), 5.43-5.29 (m, 1H), 4.28-4.23 (m, 2H), 4.19 (s, 3H), 3.88 (s, 3H), 2.28-2.08 (m, 3H), 2.03-1.92 (m, 1H). LCMS (ESI) m/z: 422.1 $[M+H]^+$.

Example 1.59. Synthesis of (S)-1-Methyl-3-(trifluoromethyl)-N-(2-(2-(trifluoromethyl)pyridin-4-yl)-6,7,8,9-tetrahydro-5H-cyclohepta[b]pyridin-5-yl)-1H-pyrazole-5-carboxamide & (R)-1-Methyl-3-(trifluoromethyl)-N-(2-(2-(trifluoromethyl)pyridin-4-yl)-6,7,8,9-tetrahydro-5H-cyclohepta[b]pyridin-5-yl)-1H-pyrazole-5-carboxamide (I-136a and I-136b)

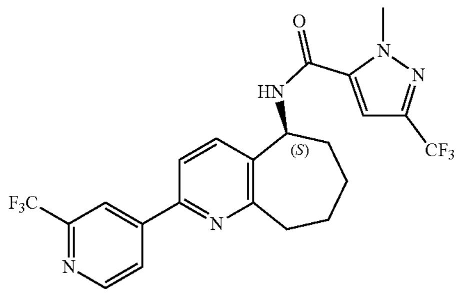

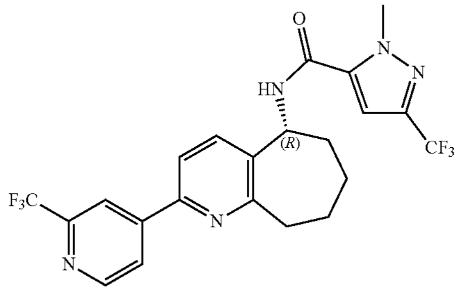

Step 1—Synthesis of 1-Methyl-3-(trifluoromethyl)-N-(2-(2-(trifluoromethyl)pyridin-4-yl)-6,7,8,9-tetrahydro-5H-cyclohepta[b]pyridin-5-yl)-1H-pyrazole-5-carboxamide

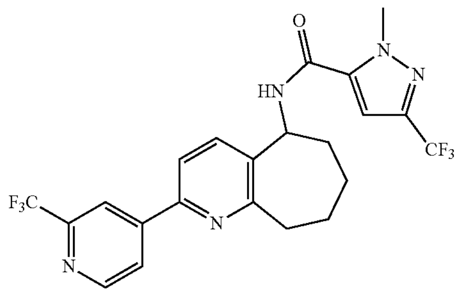 [SMILES: Cn1nc(C(F)(F)F)cc1C(=O)NC1CCCCc2nc(-c3ccnc(C(F)(F)F)c3)ccc21]

Following the procedure described in Example 1.32 and (2-chloro-6,7,8,9-tetrahydro-5H-cyclohepta[b]pyridin-5-one, prepared according to the procedure in WO2023/250480) was used in step 3, 2-(2-(trifluoromethyl)pyridin-4-yl)-6,7,8,9-tetrahydro-5H-cyclohepta[b]pyridin-5-amine hydrochloride salt and 6-(trifluoromethyl)pyrazine-2-carboxylic acid were used in step 4, the title compound (101 mg, 40%) was obtained as a white solid after purification of RP-HPLC (acetonitrile 62%-92%/0.225% formic acid in water). LCMS (ESI) m/z: 422.1 $[M+H]^+$.

Step 2—Synthesis of (S)-1-Methyl-3-(trifluoromethyl)-N-(2-(2-(trifluoromethyl)pyridin-4-yl)-6,7,8,9-tetrahydro-5H-cyclohepta[b]pyridin-5-yl)-1H-pyrazole-5-carboxamide & (R)-1-Methyl-3-(trifluoromethyl)-N-(2-(2-(trifluoromethyl)pyridin-4-yl)-6,7,8,9-tetrahydro-5H-cyclohepta[b]pyridin-5-yl)-1H-pyrazole-5-carboxamide

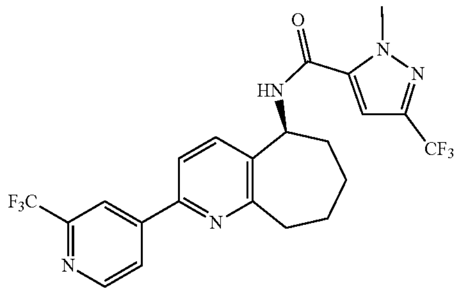

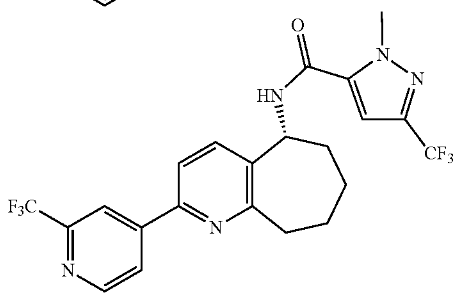

1-Methyl-3-(trifluoromethyl)-N-(2-(2-(trifluoromethyl)pyridin-4-yl)-6,7,8,9-tetrahydro-5H-cyclohepta[b]pyridin-5-yl)-1H-pyrazole-5-carboxamide (101 mg, 208 μmol) was separated by using chiral SFC (DAICEL CHIRALCEL IG (250 mm*30 mm, 10 μm)); Supercritical $CO_2$/EtOH+0.1% $NH_3 \cdot H_2O$=85/15; 80 mL/min) to afford (S)-1-methyl-3-(trifluoromethyl)-N-(2-(2-(trifluoromethyl)pyridin-4-yl)-6,7,8,9-tetrahydro-5H-cyclohepta[b]pyridin-5-yl)-1H-pyrazole-5-carboxamide (33 mg, first peak) and (R)-1-methyl-3-(trifluoromethyl)-N-(2-(2-(trifluoromethyl)pyridin-4-yl)-6,7,8,9-tetrahydro-5H-cyclohepta[b]pyridin-5-yl)-1H-pyrazole-5-carboxamide (36 mg, second peak) both as white solids. First peak: I-136* $^1H$ NMR (400 MHz, DMSO-$d_6$) δ 9.21 (d, J=7.2 Hz, 1H), 8.87 (d, J=5.2 Hz, 1H), 8.49 (s, 1H), 8.35 (d, J=4.8 Hz, 1H), 8.06 (d, J=8.0 Hz, 1H), 7.76 (d, J=8.0 Hz, 1H), 7.58 (s, 1H), 5.29-5.23 (m, 1H), 4.11 (s, 3H), 3.20 (s, 2H), 2.10-1.89 (m, 4H), 1.83-1.71 (m, 1H), 1.46-1.36 (m, 1H). LCMS (ESI) m/z: 484.1 $[M+H]^+$. Second peak: I-136** $^1H$ NMR (400 MHz, DMSO-$d_6$) δ 9.21 (d, J=7.6 Hz, 1H), 8.87 (d, J=5.2 Hz, 1H), 8.49 (s, 1H), 8.35 (d, J=5.2 Hz, 1H), 8.06 (d, J=8.0 Hz, 1H), 7.75 (d, J=8.0 Hz, 1H), 7.58 (s, 1H), 5.29-5.23 (m, 1H), 4.11 (s, 3H), 3.20 (s, 2H), 2.10-1.89 (m, 4H), 1.83-1.71 (m, 1H), 1.46-1.36 (m, 1H). LCMS (ESI) m/z: 484.1 $[M+H]^+$.

Example 1.60. Synthesis of (S)-6-(Trifluoromethyl)-N-(3-(2-(trifluoromethyl)pyridin-4-yl)-6,7-dihydro-5H-cyclopenta[c]pyridin-5-yl)pyrazine-2-carboxamide (I-197a)

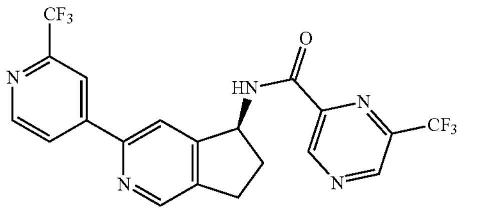 [SMILES: O=C(N[C@H]1CCc2cnc(-c3ccnc(C(F)(F)F)c3)cc21)c1cncc(C(F)(F)F)n1]

Step 1—Synthesis of 3-(2-(Trifluoromethyl)pyridin-4-yl)-6,7-dihydro-5H-cyclopenta[c]pyridin-5-one

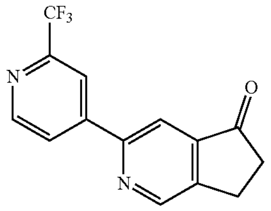 [SMILES: O=C1CCc2cnc(-c3ccnc(C(F)(F)F)c3)cc21]

To a solution of 3-chloro-6,7-dihydro-5H-cyclopenta[c]pyridin-5-one (2 g, 11.9 mmol), (2-(trifluoromethyl)pyridin-4-yl)boronic acid (2.6 g, 11.5 mmol), $K_3PO_4$ (4.65 g, 22.32 mmol) in dioxane (30 mL) and $H_2O$ (3 mL) was added $Pd(dppf)Cl_2$ (300 mg, 4.45 mmol). The reaction mixture was stirred at 80° C. for 16 h under a nitrogen atmosphere. After cooling to room temperature, the mixture was diluted with $H_2O$ (50 mL), extracted with ethyl acetate (50 mL×2). The combined organic layers were washed with brine (50 mL), dried over anhydrous $Na_2SO_4$, filtered and concentrated in vacuo. The crude was purified by silica gel chromatography (solvent gradient: 0-40% EtOAc in petroleum ether) to give the title compound (1.85 g, 56%) as a yellow solid. LCMS (ESI) m/z: 278.1 $[M+H]^+$.

Step 2—Synthesis of 6-(Trifluoromethyl)-N-(3-(2-(trifluoromethyl)pyridin-4-yl)-6,7-dihydro-5H-cyclopenta[c]pyridin-5-yl)pyrazine-2-carboxamide

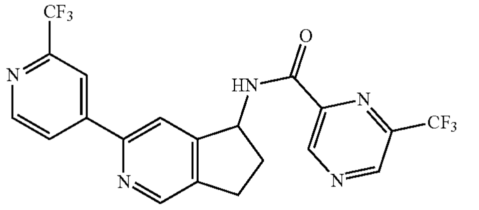 [SMILES: O=C(NC1CCc2cnc(-c3ccnc(C(F)(F)F)c3)cc21)c1cncc(C(F)(F)F)n1]

Following the procedure described in Example 1.26 and 3-(2-(trifluoromethyl)pyridin-4-yl)-6,7-dihydro-5H-cyclopenta[c]pyridin-5-one was used in step 4, 3-(2-(trifluoromethyl)pyridin-4-yl)-6,7-dihydro-5H-cyclopenta[c]pyridin-5-amine hydrochloride salt and 6-(trifluoromethyl)pyrazine-2-carboxylic acid were used in step 7, the title compound (180 mg, 89%) was obtained as a white solid after purification of silica gel chromatography (solvent gradient: 0-40% EtOAc in petroleum ether). LCMS (ESI) m/z: 454.1 $[M+H]^+$.

Step 3—Synthesis of (R)-6-(Trifluoromethyl)-N-(3-(2-(trifluoromethyl)pyridin-4-yl)-6,7-dihydro-5H-cyclopenta[c]pyridin-5-yl)pyrazine-2-carboxamide & (S)-6-(Trifluoromethyl)-N-(3-(2-(trifluoromethyl)pyridin-4-yl)-6,7-dihydro-5H-cyclopenta[c]pyridin-5-yl)pyrazine-2-carboxamide

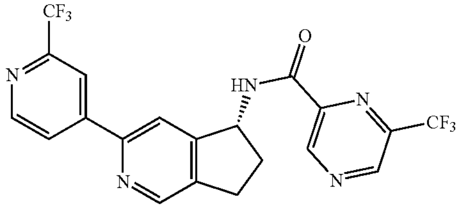

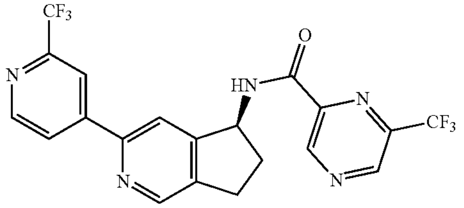

6-(Trifluoromethyl)-N-(3-(2-(trifluoromethyl)pyridin-4-yl)-6,7-dihydro-5H-cyclopenta[c]pyridin-5-yl)pyrazine-2-carboxamide (135 mg, 298 μmol) was separated by using chiral SFC (DAICEL CHIRALCEL AS (250 mm*30 mm, 10 μm); Supercritical $CO_2$/EtOH+0.1% $NH_3 \cdot H_2O$=85/15; 100 mL/min) to afford (R)-6-(trifluoromethyl)-N-(3-(2-(trifluoromethyl)pyridin-4-yl)-6,7-dihydro-5H-cyclopenta[c]pyridin-5-yl)pyrazine-2-carboxamide (63.6 mg, first peak) and (S)-6-(trifluoromethyl)-N-(3-(2-(trifluoromethyl)pyridin-4-yl)-6,7-dihydro-5H-cyclopenta[c]pyridin-5-yl)pyrazine-2-carboxamide (61.2 mg, second peak) both as white solids. First peak (I-197b): $^1H$ NMR (400 MHz, DMSO-$d_6$) δ 9.56 (s, 1H), 9.50 (d, J=8.8 Hz, 1H), 9.42 (s, 1H), 8.83 (d, J=5.2 Hz, 1H), 8.72 (s, 1H), 8.50 (d, J=0.8 Hz, 1H), 8.41-8.34 (m, 1H), 8.15 (s, 1H), 5.85-5.65 (m, 1H), 3.18-3.08 (m, 1H), 3.06-2.93 (m, 1H), 2.60-2.52 (m, 1H), 2.30-2.18 (m, 1H). LCMS (ESI) m/z: 454.2 $[M+H]^+$. Second peak: (I-197a): $^1H$ NMR (400 MHz, DMSO-$d_6$) δ 9.56 (s, 1H), 9.50 (d, J=8.7 Hz, 1H), 9.42 (s, 1H), 8.84 (d, J=5.2 Hz, 1H), 8.72 (s, 1H), 8.50 (d, J=0.8 Hz, 1H), 8.41-8.34 (m, 1H), 8.15 (s, 1H), 5.81-5.66 (m, 1H), 3.18-3.08 (m, 1H), 3.05-2.94 (m, 1H), 2.60-2.52 (m, 1H), 2.30-2.18 (m, 1H). LCMS (ESI) m/z: 454.2 $[M+H]^+$.

Example 1.61. Synthesis of (S)-2-Methoxy-N-(3-(2-(trifluoromethyl)pyridin-4-yl)-6,7-dihydro-5H-cyclopenta[c]pyridin-5-yl)isonicotinamide (I-196a)

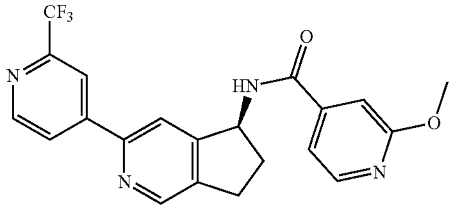 [SMILES: COc1cc(C(=O)N[C@H]2CCc3cnc(-c4ccnc(C(F)(F)F)c4)cc32)ccn1]

Step 1—Synthesis of 2-Methoxy-N-(3-(2-(trifluoromethyl)pyridin-4-yl)-6,7-dihydro-5H-cyclopenta[c]pyridin-5-yl)isonicotinamide

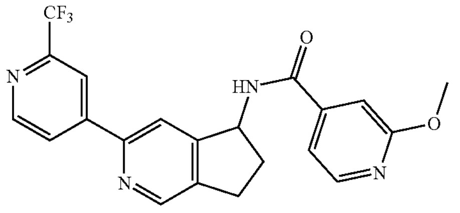

Following the procedure described in Example 1.26 and 3-(2-(trifluoromethyl)pyridin-4-yl)-6,7-dihydro-5H-cyclopenta[c]pyridin-5-amine hydrochloride salt and 2-methoxyisonicotinic acid were used in step 7, the title compound (170 mg, 92%) was obtained as a white solid after purification of silica gel chromatography (solvent gradient: 0-40% EtOAc in petroleum ether). LCMS (ESI) m/z: 415.1 [M+H]+.

Step 2—Synthesis of (S)-2-Methoxy-N-(3-(2-(trifluoromethyl)pyridin-4-yl)-6,7-dihydro-5H-cyclopenta[c]pyridin-5-yl)isonicotinamide & (R)-2-Methoxy-N-(3-(2-(trifluoromethyl)pyridin-4-yl)-6,7-dihydro-5H-cyclopenta[c]pyridin-5-yl)isonicotinamide

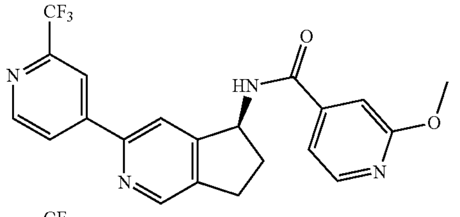

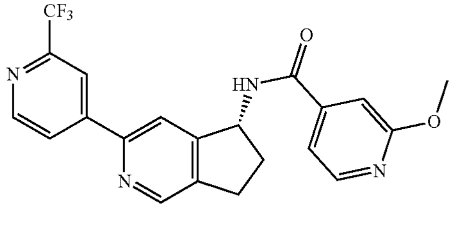 [SMILES: COc1cc(C(=O)NC2CCc3cnc(-c4ccnc(C(F)(F)F)c4)cc32)ccn1]

2-Methoxy-N-(3-(2-(trifluoromethyl)pyridin-4-yl)-6,7-dihydro-5H-cyclopenta[c]pyridin-5-yl)isonicotinamide (170 mg, 410 μmol) was separated by using chiral SFC (DAICEL CHIRALCEL OJ (250 mm*30 mm, 10 μm); Supercritical $CO_2$/EtOH+0.1% $NH_3 \cdot H_2O$=80/20; 80 mL/min) to afford (S)-2-methoxy-N-(3-(2-(trifluoromethyl) pyridin-4-yl)-6,7-dihydro-5H-cyclopenta[c]pyridin-5-yl) isonicotinamide (70.5 mg, first peak) and (R)-2-methoxy-N-(3-(2-(trifluoromethyl)pyridin-4-yl)-6,7-dihydro-5H-cyclopenta[c]pyridin-5-yl)isonicotinamide (72.4 mg, second peak) both as white solids. First peak: (I-196a): $^1H$ NMR (400 MHz, DMSO-$d_6$) δ 9.14 (d, J=8.0 Hz, 1H), 8.85 (d, J=5.2 Hz, 1H), 8.72 (s, 1H), 8.53 (s, 1H), 8.44-8.38 (m, 1H), 8.31 (d, J=5.2 Hz, 1H), 8.19 (s, 1H), 7.47-7.05 (m, 1H), 7.29 (s, 1H), 5.72-5.57 (m, 1H), 3.89 (s, 3H), 3.16-3.07 (m, 1H), 3.04-2.92 (m, 1H), 2.62-2.56 (m, 1H), 2.12-1.94 (m, 1H). LCMS (ESI) m/z: 415.2 [M+H]+. Second peak (I-196b): $^1H$ NMR (400 MHz, DMSO-$d_6$) δ 9.14 (d, J=8.0 Hz, 1H), 8.85 (d, J=5.2 Hz, 1H), 8.72 (s, 1H), 8.53 (s, 1H), 8.44-8.36 (m, 1H), 8.31 (d, J=5.2 Hz, 1H), 8.19 (s, 1H), 7.48-7.40 (m, 1H), 7.29 (s, 1H), 5.70-5.59 (m, 1H), 3.89 (s, 3H), 3.16-3.07 (m, 1H), 3.05-2.92 (m, 1H), 2.62-2.54 (m, 1H), 2.14-1.95 (m, 1H). LCMS (ESI) m/z: 415.2 [M+H]+.

Example 1.62. Synthesis of (S)-4-Methyl-2-(trifluoromethyl)-N-(3-(2-(trifluoromethyl)pyridin-4-yl)-6,7-dihydro-5H-cyclopenta[c]pyridin-5-yl)oxazole-5-carboxamide (I-192a)

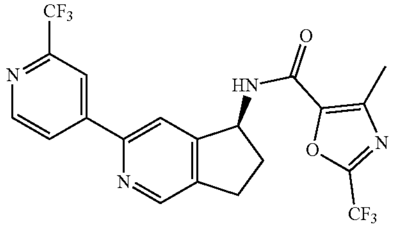 [SMILES: Cc1nc(C(F)(F)F)oc1C(=O)N[C@H]1CCc2cnc(-c3ccnc(C(F)(F)F)c3)cc21]

Step 1—Synthesis of 4-Methyl-2-(trifluoromethyl)-N-(3-(2-(trifluoromethyl)pyridin-4-yl)-6,7-dihydro-5H-cyclopenta[c]pyridin-5-yl)oxazole-5-carboxamide

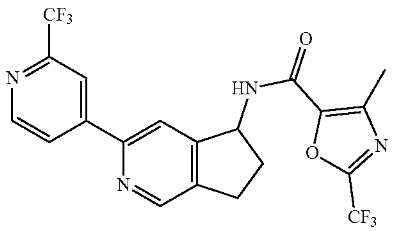 [SMILES: Cc1nc(C(F)(F)F)oc1C(=O)NC1CCc2cnc(-c3ccnc(C(F)(F)F)c3)cc21]

Following the procedure described in Example 1.26 and 3-(2-(trifluoromethyl)pyridin-4-yl)-6,7-dihydro-5H-cyclopenta[c]pyridin-5-amine hydrochloride salt and 4-methyl-2-(trifluoromethyl)oxazole-5-carboxylic acid were used in step 4, the title compound 180 mg, 83%) was obtained as a white solid after purification of silica gel chromatography (solvent gradient: 0-40% EtOAc in petroleum ether). LCMS (ESI) m/z: 457.2 [M+H]+.

Step 2—Synthesis of (S)-4-Methyl-2-(trifluoromethyl)-N-(3-(2-(trifluoromethyl)pyridin-4-yl)-6,7-dihydro-5H-cyclopenta[c]pyridin-5-yl)oxazole-5-carboxamide & (R)-4-Methyl-2-(trifluoromethyl)-N-(3-(2-(trifluoromethyl)pyridin-4-yl)-6,7-dihydro-5H-cyclopenta[c]pyridin-5-yl)oxazole-5-carboxamide

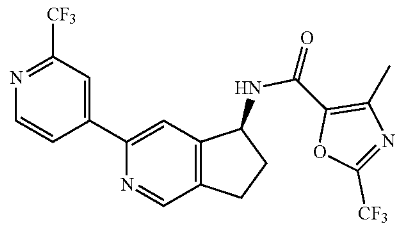

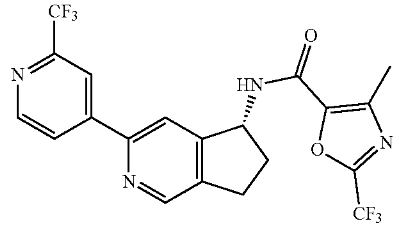

4-Methyl-2-(trifluoromethyl)-N-(3-(2-(trifluoromethyl)pyridin-4-yl)-6,7-dihydro-5H-cyclopenta[c]pyridin-5-yl)oxazole-5-carboxamide (170 mg, 410 μmol) was separated by using chiral SFC (DAICEL CHIRALCEL OJ (250 mm*30 mm, 10 μm); Supercritical $CO_2$/i-PrOH+0.1% $NH_3 \cdot H_2O$=80/15; 80 mL/min) to afford (S)-4-methyl-2-(trifluoromethyl)-N-(3-(2-(trifluoromethyl)pyridin-4-yl)-6,7-dihydro-5H-cyclopenta[c]pyridin-5-yl)oxazole-5-carboxamide (64.0 mg, first peak) and (R)-4-methyl-2-(trifluoromethyl)-N-(3-(2-(trifluoromethyl)pyridin-4-yl)-6,7-dihydro-5H-cyclopenta[c]pyridin-5-yl)oxazole-5-carboxamide (60.0 mg, second peak) both as white solids. First peak: (I-192a): $^1$H NMR (400 MHz, DMSO-$d_6$) δ 9.27 (d, J=8.4 Hz, 1H), 8.85 (d, J=5.2 Hz, 1H), 8.71 (s, 1H), 8.53 (s, 1H).

), 8.41 (d, J=5.2 Hz, 1H), 8.19 (s, 1H), 5.71-5.57 (m, 1H), 3.16-3.05 (m, 1H), 3.03-2.91 (m, 1H), 2.61-2.52 (m, 1H), 2.51 (s, 3H), 2.19-2.02 (m, 1H). LCMS (ESI) m/z: 457.2 $[M+H]^+$. Second peak (I-192b): $^1$H NMR (400 MHz, DMSO-$d_6$) δ 9.27 (d, J=8.4 Hz, 1H), 8.86 (d, J=5.2 Hz, 1H), 8.71 (s, 1H), 8.53 (s, 1H), 8.41 (d, J=5.2 Hz, 1H), 8.19 (s, 1H), 5.76-5.51 (m, 1H), 3.19-3.06 (m, 1H), 3.04-2.91 (m, 1H), 2.59-2.53 (m, 1H), 2.51 (s, 3H), 2.17-2.01 (m, 1H). LCMS (ESI) m/z: 457.1 $[M+H]^+$.

Example 1.63. Synthesis of (S)-2-(1,1-Difluoroethyl)-N-(2-(2-(trifluoromethyl)pyridin-4-yl)-5,6-dihydro-4H-pyrrolo[1,2-b]pyrazol-4-yl)isonicotinamide (I-528a)

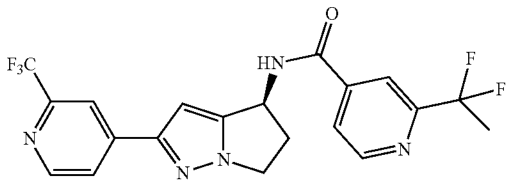 [SMILES: CC(F)(F)c1cc(C(=O)N[C@H]2CCn3nc(-c4ccnc(C(F)(F)F)c4)cc32)ccn1]

Step 1—Synthesis of 2-(2-(Trifluoromethyl)pyridin-4-yl)-5,6-dihydro-4H-pyrrolo[1,2-b]pyrazol-4-one

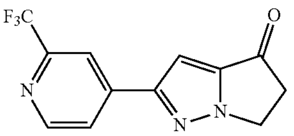 [SMILES: O=C1CCn2nc(-c3ccnc(C(F)(F)F)c3)cc21]

To a solution of 2-bromo-5,6-dihydro-4H-pyrrolo[1,2-b]pyrazol-4-one (50 g, 248.7 mmol), $K_3PO_4$ (159 g, 746.2 mmol), 4-(4,4,5,5-tetramethyl-1,3,2-dioxaborolan-2-yl)-2-(trifluoromethyl)-pyridine (102 g, 373.2 mmol) in dioxane (500 mL) and $H_2O$ (50 mL) was added Pd(dppf)$Cl_2$ (9.4 g, 12.5 mmol). The reaction vessel was evacuated and back-filled with $N_2$ three times, then stirred at 100° C. for 16 h under a nitrogen atmosphere. After cooling to room temperature, the reaction was diluted with $H_2O$ (300 mL) then extracted with ethyl acetate (300 mL×2). The combined organic layers were washed with brine (200 mL×2), dried over anhydrous $Na_2SO_4$, filtered and concentrated in vacuo. The crude residue was purified by silica gel chromatography (solvent gradient: 0-25% ethyl acetate in hexanes) to give the title compound (58 g, 87%) as a white solid. $^1$H NMR (400 MHz, DMSO-$d_6$) δ 8.82 (d, J=5.2 Hz, 1H), 8.30 (s, 1H), 8.18 (d, J=5.2 Hz, 1H), 7.61 (s, 1H), 4.58 (t, J=5.6 Hz, 2H), 3.25 (t, J=5.6 Hz, 2H). LCMS (ESI) m/z: 267.9 $[M+H]^+$.

Step 2—Synthesis of (R)-2-(2-(Trifluoromethyl)pyridin-4-yl)-5,6-dihydro-4H-pyrrolo[1,2-b]pyrazol-4-ol

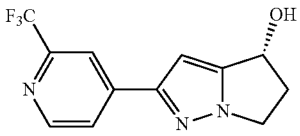 [SMILES: O[C@@H]1CCn2nc(-c3ccnc(C(F)(F)F)c3)cc21]

To a mixture of 2-(2-(trifluoromethyl)pyridin-4-yl)-5,6-dihydro-4H-pyrrolo[1,2-b]pyrazol-4-one (10 g, 37.4 mmol) in DCM (100 mL) was added TEA (15.6 mL, 112.3 mmol), formic acid (4.9 mL, 131.0 mmol) at 0° C., then RuCl[(R,R)-Tsdpen](mesitylene) (1.18 g, 1.9 mmol) was added and the mixture was stirred at room temperature for 3 h. The reaction mixture was filtered and concentrated. The residue was purified by silica gel chromatography (solvent gradient: 0-30% EtOAc in hexanes) to give the title compound (6.7 g, 67%) as a yellow solid. $^1$H NMR (400 MHz, DMSO-$d_6$) δ 8.75 (d, J=5.2 Hz, 1H), 8.19 (s, 1H), 8.07 (dd, J=1.2, 5.2 Hz, 1H), 6.98 (s, 1H), 5.74 (d, J=6.0 Hz, 1H), 5.18-5.13 (m, 1H), 4.29-4.31 (m, 1H), 4.09-4.11 (m, 1H), 2.95-2.83 (m, 1H), 2.40-2.26 (m, 1H). LCMS (ESI) m/z: 270.0 $[M+H]^+$.

Step 3—Synthesis of (S)-4-Azido-2-(2-(trifluoromethyl)pyridin-4-yl)-5,6-dihydro-4H-pyrrolo[1,2-b]pyrazole

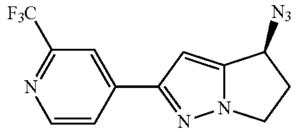 [SMILES: [N-]=[N+]=N[C@H]1CCn2nc(-c3ccnc(C(F)(F)F)c3)cc21]

To a mixture of (R)-2-(2-(trifluoromethyl)pyridin-4-yl)-5,6-dihydro-4H-pyrrolo[1,2-b]pyrazol-4-ol (6.7 g, 24.9 mmol) in toluene (100 mL) was added DBU (5.6 mL, 37.3 mmol) at 0° C., then DPPA (8.1 mL, 37.33 mmol) was added. The reaction vessel was evacuated and backfilled with $N_2$ three times, then stirred at room temperature for 6 h under a nitrogen atmosphere. The reaction mixture was filtered and concentrated in vacuo. The residue was purified by silica gel chromatography (solvent gradient: 0-10% EtOAc in hexanes) to give the title compound (7.2 g, 99%) as a yellow solid. $^1$H NMR (400 MHz, DMSO-$d_6$) δ 8.77 (d, J=5.2 Hz, 1H), 8.22 (s, 1H), 8.09 (dd, J=1.2, 5.2 Hz, 1H), 7.20 (s, 1H), 5.38-5.32 (m, 1H), 4.39-4.28 (m, 1H), 4.20-4.23 (m, 1H), 3.08-2.89 (m, 1H), 2.55-2.51 (m, 1H). LCMS (ESI) m/z: 294.9 [M+H]$^+$.

Step 4—Synthesis of (S)-2-(2-(Trifluoromethyl)pyridin-4-yl)-5,6-dihydro-4H-pyrrolo[1,2-b]pyrazol-4-amine HCl salt

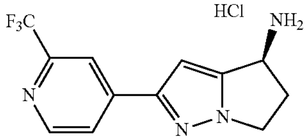 [SMILES: Cl ; N[C@H]1CCn2nc(-c3ccnc(C(F)(F)F)c3)cc21]

To a mixture of (S)-4-azido-2-(2-(trifluoromethyl)pyridin-4-yl)-5,6-dihydro-4H-pyrrolo[1,2-b]pyrazole (7.3 g, 24.8 mmol) in THE (90 mL) and $H_2O$ (15 mL) was added $PPh_3$ (9.76 g, 37.2 mmol). The reaction vessel was evacuated and backfilled with $N_2$ twice, then stirred at 60° C. for 4 h under a nitrogen atmosphere. After cooling to room temperature, the reaction was diluted with $H_2O$ (50 mL), and the solution was adjusted to pH=3 with HCl (1M, 30 mL). The mixture was exacted with ethyl acetate (60 mL) and the aqueous phase was washed with ethyl acetate (50 mL×2). The aqueous phase was lyophilized to afford the title compound (7.5 g, HCl salt) as a yellow solid which was used without further purification. $^1$H NMR (400 MHz, DMSO-$d_6$) δ 8.94 (s, 3H), 8.77 (d, J=5.2 Hz, 1H), 8.17 (s, 1H), 8.07 (d, J=4.8 Hz, 1H), 7.06 (s, 1H), 4.85-4.80 (s, 1H), 4.49-4.35 (m, 1H), 4.23 (m, 1H), 3.13-2.92 (m, 1H), 2.71-2.55 (m, 1H). LCMS (ESI) m/z: 269.1 [M+H]$^+$.

Step 5—Synthesis of (S)-2-(1,1-Difluoroethyl)-N-(2-(2-(trifluoromethyl)pyridin-4-yl)-5,6-dihydro-4H-pyrrolo[1,2-b]pyrazol-4-yl)isonicotinamide

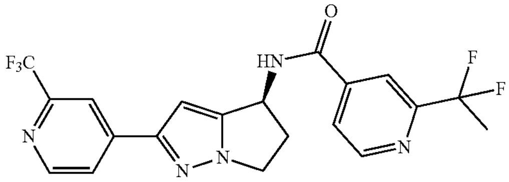 [SMILES: CC(F)(F)c1cc(C(=O)N[C@H]2CCn3nc(-c4ccnc(C(F)(F)F)c4)cc32)ccn1]

Following the procedure described in Example 1.26, (S)-2-(2-(trifluoromethyl)pyridin-4-yl)-5,6-dihydro-4H-pyrrolo[1,2-b]pyrazol-4-amine HCl salt and 2-(1,1-difluoroethyl)isonicotinic acid were used in step 7, the title compound (85 mg, 54%) was obtained as a white solid after purification of RP-HPLC (Column: 58-Phenomenex Gemini NX C18 150×40 mm, 5 μm; mobile phase: acetonitrile 50%-80%/0.225% formic acid in water). I-528a: $^1$H NMR (400 MHz, DMSO-$d_6$) δ 9.51 (d, J=7.6 Hz, 1H), 8.84 (d, J=5.2 Hz, 1H), 8.74 (d, J=5.2 Hz, 1H), 8.20 (s, 1H), 8.13 (s, 1H), 8.07 (d, J=4.8 Hz, 1H), 7.96 (d, J=4.8 Hz, 1H), 7.03 (s, 1H), 5.64-5.57 (m, 1H), 4.40 (m, 1H), 4.28-4.21 (m 1H), 3.12-3.03 (m, 1H), 2.57 (d, J=5.4 Hz, 1H), 2.08-1.97 (m, 3H). LCMS (ESI) m/z: 438.1 [M+H]$^+$.

Example 1.64. Synthesis of (S)—N-(2-(5-Fluoro-2-(trifluoromethyl)pyridin-4-yl)-5,6-dihydro-4H-pyrrolo[1,2-b]pyrazol-4-yl)spiro[2.3]hexane-5-carboxamide (I-522a)

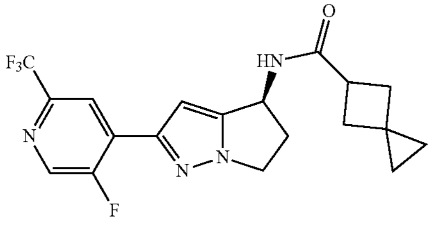 [SMILES: O=C(N[C@H]1CCn2nc(-c3cc(C(F)(F)F)ncc3F)cc21)C1CC2(CC2)C1]

Step 1—Synthesis of tert-Butyl (S)-(2-bromo-5,6-dihydro-4H-pyrrolo[1,2-b]pyrazol-4-yl)carbamate

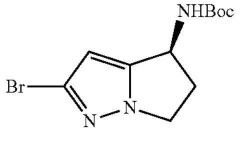 [SMILES: CC(C)(C)OC(=O)N[C@H]1CCn2nc(Br)cc21]

To a solution of (4S)-2-bromo-5,6-dihydro-4H-pyrrolo[1,2-b]pyrazol-4-amine hydrochloride salt (5 g, 21.0 mmol) in THE (50 mL) was added TEA (14.6 mL, 104.9 mmol) and $Boc_2O$ (7.2 mL, 31.3 mmol) and the mixture was stirred at 25° C. for 2 h. The reaction was diluted with water (50 mL), extracted with ethyl acetate (50 mL×2), the combined organic layers were washed with brine (50 mL), dried over anhydrous $Na_2SO_4$, filtered and concentrated in vacuo. The crude residue was purified by silica gel chromatography (solvent gradient: 0-25% EtOAc in hexanes) to give the title compound (4.9 g, 78%) as a white solid. $^1$H NMR (400 MHz, DMSO-$d_6$) δ 7.49 (d, J=7.6 Hz, 1H), 6.16 (s, 1H), 5.02-4.94 (m, 1H), 4.21-4.14 (m, 1H), 4.04-3.97 (m, 1H), 2.87-2.78 (m, 1H), 2.31-2.21 (m, 1H), 1.39 (s, 9H).

Step 2—Synthesis of tert-Butyl (S)-(2-(5-fluoro-2-(trifluoromethyl)pyridin-4-yl)-5,6-dihydro-4H-pyrrolo[1,2-b]pyrazol-4-yl)carbamate

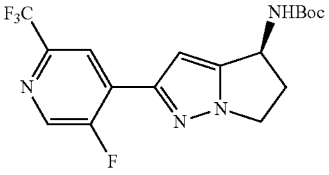 [SMILES: CC(C)(C)OC(=O)N[C@H]1CCn2nc(-c3cc(C(F)(F)F)ncc3F)cc21]

To a solution of tert-butyl (S)-(2-bromo-5,6-dihydro-4H-pyrrolo[1,2-b]pyrazol-4-yl)carbamate (1.2 g, 4.0 mmol), (5-fluoro-2-(trifluoromethyl)pyridin-4-yl)boronic acid (1 g, 4.79 mmol), $K_3PO_4$ (2.1 g, 9.9 mmol) in dioxane (20 mL) was added X-Phos Pd $G_2$ (260 mg, 330.5 mol). The reaction vessel was evacuated and backfilled with $N_2$ three times, then stirred at 80° C. for 16 h under a nitrogen atmosphere. After cooling to room temperature, the reaction was diluted with water (30 mL), extracted with ethyl acetate (30 mL×2), the combined organic layers were washed with brine (20 mL×2), dried over anhydrous $Na_2SO_4$, filtered and concentrated in vacuo. The crude residue was purified by silica gel chromatography (solvent gradient: 0-25% EtOAc in hexanes) to give the title compound (720 mg, 56%) as a white solid. $^1$H NMR (400 MHz, DMSO-$d_6$) δ 8.84 (d, J=2.4 Hz, 1H), 8.30 (d, J=5.6 Hz, 1H), 7.56 (d, J=8.0 Hz, 1H), 6.68 (d, J=3.6 Hz, 1H), 5.12-5.01 (m, 1H), 4.36-4.28 (m, 1H), 4.19-4.15 (m, 1H), 2.97-2.87 (m, 1H), 2.43-2.33 (m, 1H), 1.41 (s, 9H). LCMS (ESI) m/z: 387.1 $[M+H]^+$.

Step 3—Synthesis of (S)-2-(5-Fluoro-2-(trifluoromethyl)pyridin-4-yl)-5,6-dihydro-4H-pyrrolo[1,2-b]pyrazol-4-amine HCl salt

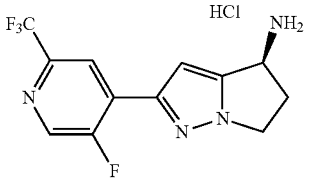 [SMILES: Cl ; N[C@H]1CCn2nc(-c3cc(C(F)(F)F)ncc3F)cc21]

A solution of tert-butyl (S)-(2-(5-fluoro-2-(trifluoromethyl)pyridin-4-yl)-5,6-dihydro-4H-pyrrolo[1,2-b]pyrazol-4-yl)carbamate (720 mg, 1.9 mmol) in HCl/dioxane (2M, 10 mL) was stirred at room temperature for 3 h. The mixture was concentrated in vacuo to give the title compound (600 mg, crude) as a yellow solid which was used without further purification. LCMS (ESI) m/z: 287.1 $[M+H]^+$.

Step 4—Synthesis of (S)—N-(2-(5-Fluoro-2-(trifluoromethyl)pyridin-4-yl)-5,6-dihydro-4H-pyrrolo[1,2-b]pyrazol-4-yl)spiro[2.3]hexane-5-carboxamide

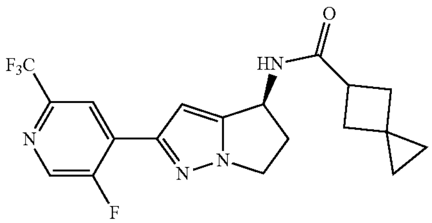 [SMILES: O=C(N[C@H]1CCn2nc(-c3cc(C(F)(F)F)ncc3F)cc21)C1CC2(CC2)C1]

Following the procedure described in Example 1.26, (S)-2-(5-fluoro-2-(trifluoromethyl)pyridin-4-yl)-5,6-dihydro-4H-pyrrolo[1,2-b]pyrazol-4-amine HCl salt and spiro[2.3]hexane-5-carboxylic acid were used in step 7 the title compound (55 mg, 58%) was obtained as a white solid after purification of RP-HPLC (Column: 51-Welch Xtimate C18 100×40 mm, 3 m; mobile phase: acetonitrile 54%-84%/0.225% formic acid in water). I-522a: $^1$H NMR (400 MHz, DMSO-$d_6$) δ 8.83 (d, J=2.0 Hz, 1H), 8.39 (d, J=7.2 Hz, 1H), 8.30 (d, J=5.6 Hz, 1H), 6.69 (d, J=3.2 Hz, 1H), 5.36-5.29 (m, 1H), 4.38-4.31 (m, 1H), 4.23-4.16 (m, 1H), 3.18-3.10 (m, 1H), 3.00-2.93 (m, 1H), 2.42-2.35 (m, 3H), 2.09-2.02 (m, 2H), 0.46-0.41 (m, 2H), 0.31-0.36 (m, 2H). LCMS (ESI) m/z: 395.1 [M+H]+

Example 1.65. Synthesis of (S)—N-(2-(2-Cyclopropyl-5-fluoropyridin-4-yl)-5,6-dihydro-4H-pyrrolo[1,2-b]pyrazol-4-yl)-1-methyl-3-(trifluoromethyl)-1H-1,2,4-triazole-5-carboxamide (I-483a)

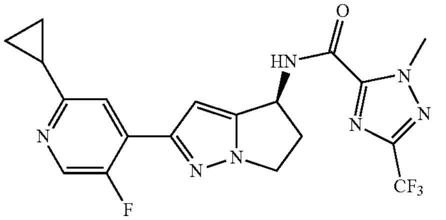

Step 1—Synthesis of 4-Chloro-2-cyclopropyl-5-fluoropyridine

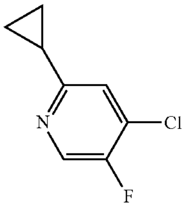 [SMILES: Fc1cnc(C2CC2)cc1Cl]

To a solution of 2-bromo-4-chloro-5-fluoropyridine (5 g, 23.8 mmol), cyclopropylboronic acid (2.04 g, 23.8 mmol), $K_3PO_4$ (15.13 g, 71.28 mmol) in dioxane (100 mL) was added Pd(dtbpf)$Cl_2$ (1.55 g, 2.4 mmol). The reaction mixture was evacuated and backfilled with $N_2$ three times, then stirred at 100° C. for 16 h under a nitrogen atmosphere. After cooling to room temperature, the mixture was diluted with $H_2O$ (50 mL) and extracted with ethyl acetate (50 mL×2). The combined organic layers were washed with brine (50 mL×2), dried over anhydrous $Na_2SO_4$, filtered and concentrated in vacuo. The residue was purified by silica gel chromatography (100% hexanes) to give the title compound (750 mg, 18%) as a white solid. $^1H$ NMR (400 MHz, DMSO-$d_6$) δ 8.50 (d, J=1.2 Hz, 1H), 7.65 (d, J=5.6 Hz, 1H), 2.20-2.08 (m, 1H), 1.00-0.93 (m, 2H), 0.91-0.86 (m, 2H). LCMS (ESI) m/z: 172.0 $[M+H]^+$.

Step 2—Synthesis of ((S)-4-(((R)-tert-Butylsulfinyl) amino)-5,6-dihydro-4H-pyrrolo[1,2-b]pyrazol-2-yl) boronic acid

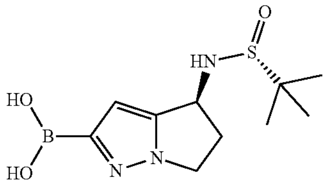 [SMILES: CC(C)(C)[S@@](=O)N[C@H]1CCn2nc(B(O)O)cc21]

To a solution of (R)—N—((S)-2-bromo-5,6-dihydro-4H-pyrrolo[1,2-b]pyrazol-4-yl)-2-methylpropane-2-sulfinamide (400 mg, 1.30 mmol), $B_2pin_2$ (1.66 g, 6.5 mmol), KOAc (384 mg, 3.9 mmol) in dioxane (6 mL) was added Pd(dppf)$Cl_2$ (192 mg, 261.3 μmol). The reaction mixture was evacuated and backfilled with $N_2$ three times, then stirred at 100° C. for 3 h under a nitrogen atmosphere. After cooling to room temperature, the mixture was filtered and concentrated in vacuo to give the title compound (320 mg, crude) as a black oil which was used without further purification. LCMS (ESI) m/z: 272.1 $[M+H]^+$.

Step 3—Synthesis of (R)—N—((S)-2-(2-Cyclopropyl-5-fluoropyridin-4-yl)-5,6-dihydro-4H-pyrrolo[1,2-b]pyrazol-4-yl)-2-methylpropane-2-sulfinamide

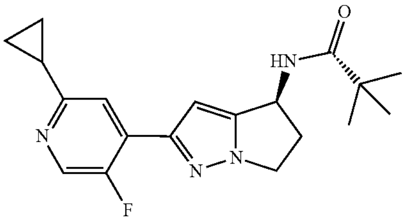

To a solution of ((S)-4-(((R)-tert-butylsulfinyl)amino)-5,6-dihydro-4H-pyrrolo[1,2-b]pyrazol-2-yl)boronic acid (320 mg, 780.1 μmol), 4-chloro-2-cyclopropyl-5-fluoropyridine (120 mg, 699.3 μmol), $K_3PO_4$ (445.32 mg, 2.1 mmol) in dioxane (3 mL) was added Pd(dppf)$Cl_2$ (52 mg, 69.9 μmol). The reaction mixture was evacuated and backfilled with $N_2$ three times, then stirred at 100° C. for 16 h under a nitrogen atmosphere. After cooling to room temperature, the mixture was diluted with $H_2O$ (50 mL) and extracted with ethyl acetate (50 mL×2). The combined organic layers were washed with brine (50 mL×2), dried over anhydrous $Na_2SO_4$, filtered and concentrated in vacuo. The residue was purified by silica gel chromatography (solvent gradient: 0-20% ethyl acetate in hexanes) to give the title compound (750 mg, 18%) as a white solid. LCMS (ESI) m/z: 363.1 $[M+H]^+$.

Step 4—Synthesis of (S)-2-(2-Cyclopropyl-5-fluoropyridin-4-yl)-5,6-dihydro-4H-pyrrolo[1,2-b]pyrazol-4-amine hydrochloride salt

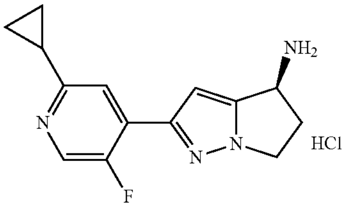 [SMILES: N[C@H]1CCn2nc(-c3cc(C4CC4)ncc3F)cc21 ; Cl]

To a solution of (R)—N—((S)-2-(2-cyclopropyl-5-fluoropyridin-4-yl)-5,6-dihydro-4H-pyrrolo[1,2-b]pyrazol-4-yl)-2-methylpropane-2-sulfinamide (80 mg, 220.7 μmol) in dioxane (2 mL) was added HCl/dioxane (2M, 5 mL). The mixture was stirred at room temperature for 2 h, concentrated in vacuo and the resulting residue triturated with acetonitrile (20 mL) to give the title compound (100 mg, crude) as a yellow solid which was used without further purification. LCMS (ESI) m/z: 259.1 $[M+H]^+$.

Step 5—Synthesis of Lithium 1-methyl-3-(trifluoromethyl)-1H-1,2,4-triazole-5-carboxylate

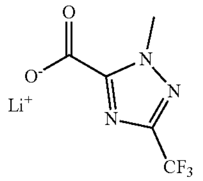

To a solution of methyl 1-methyl-3-(trifluoromethyl)-1H-1,2,4-triazole-5-carboxylate (150 mg, 717.3 μmol) in THE (3 mL), MeOH (3 mL) and $H_2O$ (1 mL) was added LiOH·$H_2O$ (90 mg, 2.2 mmol). The mixture was stirred at 25° C. for 2 h. The reaction mixture was lyophilized in vacuo to give the title compound (120 mg, crude) as a yellow solid which was used without further purification.

Step 6—Synthesis of (S)—N-(2-(2-Cyclopropyl-5-fluoropyridin-4-yl)-5,6-dihydro-4H-pyrrolo[1,2-b]pyrazol-4-yl)-1-methyl-3-(trifluoromethyl)-1H-1,2,4-triazole-5-carboxamide

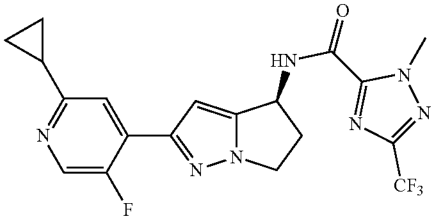

To a solution of (S)-2-(2-cyclopropyl-5-fluoropyridin-4-yl)-5,6-dihydro-4H-pyrrolo[1,2-b]pyrazol-4-amine hydrochloride salt (40 mg, 135.7 μmol), lithium 1-methyl-3-(trifluoromethyl)-1H-1,2,4-triazole-5-carboxylate (30 mg, 164.1 μmol) and DIEA (0.12 mL, 678.5 umol) in DMF (2 mL) was added HATU (62 mg, 162.8 μmol). The reaction mixture was stirred at 25° C. for 2 h. The reaction was diluted with $H_2O$ (30 mL) and then extracted with ethyl acetate (30 mL×2). The combined organic layers were washed with brine (20 mL×2), dried over anhydrous $Na_2SO_4$, filtered and concentrated in vacuo. The residue was purified by RP-HPLC (Column: C18 150×30 mm; mobile phase: acetonitrile 50%-80%/0.225% formic acid in water) to give the title compound (2.4 mg, 4%) as a white solid. I-483a: $^1$H NMR (400 MHz, DMSO-$d_6$) δ 9.77 (d, J=8.0 Hz, 1H), 8.40 (d, J=2.4 Hz, 1H), 7.79 (d, J=6.0 Hz, 1H), 6.61 (d, J=3.2 Hz, 1H), 5.66-5.43 (m, 1H), 4.45-4.35 (m, 1H), 4.24 (s, 3H), 4.23-4.17 (m, 1H), 3.06-3.00 (m, 1H), 2.66-2.60 (m, 1H), 2.22-2.15 (m, 1H), 0.97-0.91 (m, 2H), 0.91-0.85 (m, 2H). LCMS (ESI) m/z: 436.1 $[M+H]^+$.

Example 1.66. Synthesis of (S)—N-(2-(5-Fluoro-2-(trifluoromethyl)pyridin-4-yl)-4,5,6,7-tetrahydrobenzo[d]oxazol-4-yl)-3-(trifluoromethyl)benzamide (I-554a)

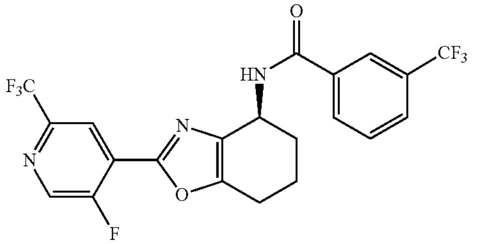 [SMILES: O=C(N[C@H]1CCCc2oc(-c3cc(C(F)(F)F)ncc3F)nc21)c1cccc(C(F)(F)F)c1]

Step 1—Synthesis of 5-Fluoro-2-(trifluoromethyl)isonicotinic acid

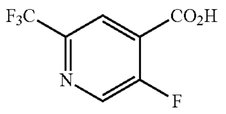

To a solution of 5-fluoro-2-(trifluoromethyl)pyridine (30 g, 30.3 mmol) in THE (225 mL) was added LDA (2M, 180 mL) dropwise at −70° C. within 15 min. After addition, the mixture was stirred at this temperature for 60 min, then dry $CO_2$ gas was added at −70° C. The resulting mixture was stirred at −70° C. for another 2 h. The reaction was quenched with sat. aq. $NH_4Cl$ (100 mL), then warmed to room temperature. The reaction mixture was diluted with water (200 ml) and adjusted to pH=5 with HCl (2M, 100 mL), then extracted with ethyl acetate (200 mL×2). The combined organic layers were washed with brine (100 mL×2), dried over anhydrous $Na_2SO_4$, filtered and concentrated in vacuo to give the title compound (37 g, crude) as a black oil which was used without purification. $^1$H NMR (400 MHz, DMSO-$d_6$) δ 8.63 (s, 1H), 7.85 (d, J=5.2 Hz, 1H). LCMS (ESI) m/z: 210.0 $[M+H]^+$.

Step 2—Synthesis of 5-Fluoro-2-(trifluoromethyl)isonicotinamide

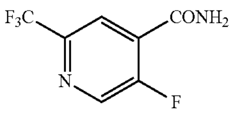 [SMILES: NC(=O)c1cc(C(F)(F)F)ncc1F]

To a solution of 5-fluoro-2-(trifluoromethyl)isonicotinic acid (4.3 g, 20.6 mmol), DIEA (11 mL, 63.2 mmol) in DMF (50 mL) was added HATU (9.4 g, 24.7 mmol) and stirred for 20 min, then $NH_4Cl$ (3.3 g, 61.7 mmol) was added and the mixture was stirred at 25° C. for 16 h. The reaction was diluted with water (50 mL), extracted with ethyl acetate (50 mL×3), the combined organic layers were washed with brine (50 mL×3), dried over anhydrous $Na_2SO_4$, filtered and concentrated in vacuo. The crude residue was purified by silica gel chromatography (solvent gradient: 0-30% EtOAc in hexanes) to give the title compound (3.1 g, 72%) as a green oil. LCMS (ESI) m/z: 209.0 $[M+H]^+$.

Step 3—Synthesis of 5-Fluoro-2-(trifluoromethyl)isonicotinonitrile

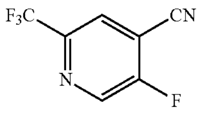 [SMILES: N#Cc1cc(C(F)(F)F)ncc1F]

To a solution of 5-fluoro-2-(trifluoromethyl)isonicotinamide (2.7 g, 13.0 mmol), TEA (4.8 mL, 34.5 mmol) in DCM (80 mL) was added TFAA (2.4 mL, 17.3 mmol) at 0° C. and the mixture was stirred at 25° C. for 3 h. The reaction was quenched with sat. aq. $NaHCO_3$ (50 mL), extracted with dichloromethane (50 mL×2), the combined organic layers were washed with brine (50 mL), dried over anhydrous $Na_2SO_4$, filtered and concentrated in vacuo. The crude residue was purified by silica gel chromatography (solvent gradient: 0-15% EtOAc in hexanes) to give the title compound (1.3 g, 53%) as a yellow oil. $^1$H NMR (400 MHz, $CDCl_3$) δ 8.83 (s, 1H), 7.97 (d, J=4.4 Hz, 1H).

Step 4—Synthesis of 2-(5-Fluoro-2-(trifluoromethyl)pyridin-4-yl)-6,7-dihydrobenzo[d]oxazol-4(5H)-one

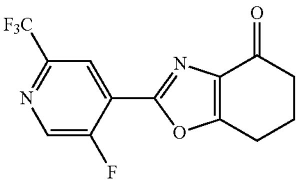 [SMILES: O=C1CCCc2oc(-c3cc(C(F)(F)F)ncc3F)nc21]

To a solution of 5-fluoro-2-(trifluoromethyl)isonicotinonitrile (1.3 g, 6.84 mmol), $Rh_2(OAc)_4$ (90 mg, 203.6 μmol) in fluorobenzene (30 mL) was added 2-diazocyclohexane-1,3-dione (1.4 g, 10.4 mmol), the reaction vessel was evacuated and backfilled with $N_2$ three times, then stirred at 60° C. for 3 h under a nitrogen atmosphere. After cooling to room temperature, the mixture was filtered and concentrated in vacuo. The crude residue was purified by silica gel chromatography (solvent gradient: 0-20% EtOAc in hexanes) to give the title compound (250 mg, 12%) as a yellow solid. $^1H$ NMR (400 MHz, $CDCl_3$) δ 8.76 (d, J=1.6 Hz, 1H), 8.52 (d, J=5.2 Hz, 1H), 3.16-3.13 (m, 2H), 2.72-2.51 (m, 2H), 2.50-2.34 (m, 2H). LCMS (ESI) m/z: 301.0 $[M+H]^+$.

Step 5—Synthesis of (S,E)-N-(2-(5-Fluoro-2-(trifluoromethyl)pyridin-4-yl)-6,7-dihydrobenzo[d]oxazol-4(5H)-ylidene)-2-methylpropane-2-sulfinamide

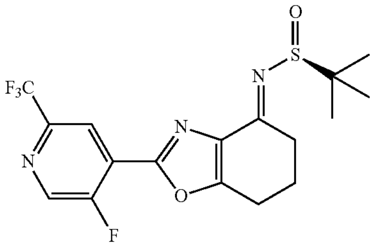 [SMILES: CC(C)(C)[S@](=O)/N=C1\CCCc2oc(-c3cc(C(F)(F)F)ncc3F)nc21]

To a solution of 2-(5-fluoro-2-(trifluoromethyl)pyridin-4-yl)-6,7-dihydrobenzo[d]oxazol-4(5H)-one (200 mg, 666.2 μmol) and (S)-2-methylpropane-2-sulfinamide (640 mg, 5.3 mmol) in THF (5 mL) was added $Ti(i\text{-}PrO)_4$ (1.7 mL, 5.8 mmol). The reaction vessel was evacuated and backfilled with $N_2$ twice, then stirred at 70° C. for 16 h under a nitrogen atmosphere. After cooling to room temperature, the mixture was quenched with $H_2O$ (30 mL) and filtered. The filtrate was extracted with ethyl acetate (20 mL×2) and the combined organic layers were washed with brine (20 mL×2), dried over anhydrous $Na_2SO_4$, filtered and concentrated in vacuo to give the title compound (300 mg, crude) as a black oil which was used without further purification. LCMS (ESI) m/z: 404.1 $[M+H]^+$.

Step 6—Synthesis of (S)—N—((S)-2-(5-Fluoro-2-(trifluoromethyl)pyridin-4-yl)-4,5,6,7-tetrahydrobenzo[d]oxazol-4-yl)-2-methylpropane-2-sulfinamide

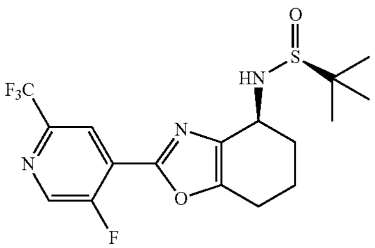 [SMILES: CC(C)(C)[S@](=O)N[C@H]1CCCc2oc(-c3cc(C(F)(F)F)ncc3F)nc21]

To a solution of (S,E)-N-(2-(5-fluoro-2-(trifluoromethyl)pyridin-4-yl)-6,7-dihydrobenzo[d]oxazol-4(5H)-ylidene)-2-methylpropane-2-sulfinamide (300 mg, 743.7 μmol) in THF (8 mL) was added $NaBH_4$ (16 mg, 476.1 μmol) in portions at 0° C. and stirred at 25° C. for 2 h. The mixture was quenched with sat. $NH_4Cl$ (20 mL) and extracted with ethyl acetate (30 mL). The combined organic layers were washed with brine (30 mL×2), dried over anhydrous $Na_2SO_4$, filtered and concentrated in vacuo. The crude residue was purified on silica gel chromatography (solvent gradient: 0-30% EtOAc in hexanes) to give the title compound (140 mg, 49%) as a yellow solid. LCMS (ESI) m/z: 406.1 $[M+H]^+$.

Step 7—Synthesis of (S)-2-(5-Fluoro-2-(trifluoromethyl)pyridin-4-yl)-4,5,6,7-tetrahydrobenzo[d]oxazol-4-amine HCl salt

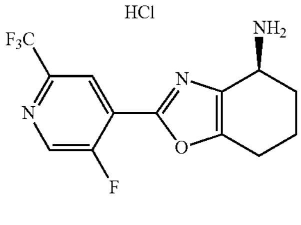 [SMILES: Cl ; N[C@H]1CCCc2oc(-c3cc(C(F)(F)F)ncc3F)nc21]

To a solution of (S)—N—((S)-2-(5-fluoro-2-(trifluoromethyl)pyridin-4-yl)-4,5,6,7-tetrahydrobenzo[d]oxazol-4-yl)-2-methylpropane-2-sulfinamide (140 mg, 345.3 mmol) in DCM (1 mL) was added HCl/dioxane (2M, 3 mL). The reaction was stirred at room temperature for 3 h. The mixture was concentrated in vacuo and the resulting residue was triturated with acetonitrile (20 mL) to give the title compound (130 mg, crude) as a yellow solid which was used without further purification. LCMS (ESI) m/z: 302.1 $[M+H]^+$.

Step 8—Synthesis of (S)—N-(2-(5-Fluoro-2-(trifluoromethyl)pyridin-4-yl)-4,5,6,7-tetrahydrobenzo[d]oxazol-4-yl)-3-(trifluoromethyl)benzamide

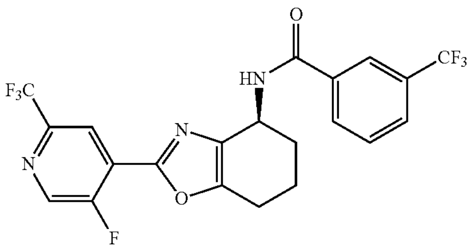 [SMILES: O=C(N[C@H]1CCCc2oc(-c3cc(C(F)(F)F)ncc3F)nc21)c1cccc(C(F)(F)F)c1]

To a solution of (S)-2-(5-fluoro-2-(trifluoromethyl)pyridin-4-yl)-4,5,6,7-tetrahydrobenzo[d]oxazol-4-amine HCl salt (130 mg, 385.0 μmol), DIEA (0.5 mL, 2.6 mmol), and 3-(trifluoromethyl)benzoic acid (80 mg, 426.1 μmol) in DMF (4 mL) was added HATU (160 mg, 420.8 μmol). The mixture was stirred at 25° C. for 3 h. The reaction was diluted with $H_2O$ (20 mL) and extracted with ethyl acetate (20 mL×2). The combined organic layers were washed with brine (30 mL), dried over anhydrous $Na_2SO_4$, filtered and concentrated in vacuo. The residue was purified by RP-HPLC (Column: 57-Phenomenex Gemini NX C18 150×30 mm, 5 m; mobile phase: acetonitrile 52%-82%/0.225% formic acid in water) to give the title compound (60 mg, 86% ee) as a white solid. LCMS (ESI) m/z: 474.2 $[M+H]^+$.

Step 9—Purification of (S)—N-(2-(5-Fluoro-2-(trifluoromethyl)pyridin-4-yl)-4,5,6,7-tetrahydrobenzo[d]oxazol-4-yl)-3-(trifluoromethyl)benzamide

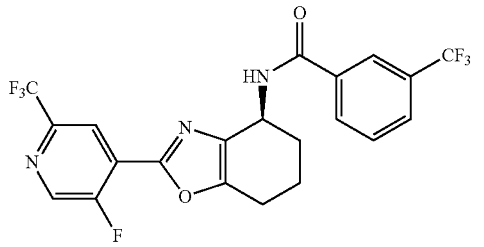 [SMILES: O=C(N[C@H]1CCCc2oc(-c3cc(C(F)(F)F)ncc3F)nc21)c1cccc(C(F)(F)F)c1]

(S)—N-(2-(5-fluoro-2-(trifluoromethyl)pyridin-4-yl)-4,5,6,7-tetrahydrobenzo[d]oxazol-4-yl)-3-(trifluoromethyl)benzamide (60 mg, 127 μmol) was separated by chiral SFC (DAICEL CHIRALCEL OJ (250 mm*30 mm, 10 μm); Supercritical $CO_2$/EtOH+0.1% $NH_3 \cdot H_2O$=10/90; 80 mL/min) to afford (S)—N-(2-(5-fluoro-2-(trifluoromethyl)pyridin-4-yl)-4,5,6,7-tetrahydrobenzo[d]oxazol-4-yl)-3-(trifluoromethyl)benzamide (42 mg, first peak) as a white solid. First peak: I-554a: $^1H$ NMR (400 MHz, DMSO-$d_6$) δ 9.06 (d, J=8.0 Hz, 1H), 9.01 (d, J=2.0 Hz, 1H), 8.34 (d, J=5.6 Hz, 1H), 8.25 (s, 1H), 8.21 (d, J=8.0 Hz, 1H), 7.92 (d, J=7.6 Hz, 1H), 7.76-7.70 (m, 1H), 5.29-5.20 (m, 1H), 2.91-2.76 (m, 2H), 2.09-1.88 (m, 4H). LCMS (ESI) m/z: 474.2 $[M+H]^+$.

Example 1.67. Synthesis of (S)—N-(2-(5-Fluoro-2-(trifluoromethyl)pyridin-4-yl)-4,5,6,7-tetrahydrobenzo[d]oxazol-7-yl)-1-methyl-3-(trifluoromethyl)-1H-pyrazole-5-carboxamide (I-514a)

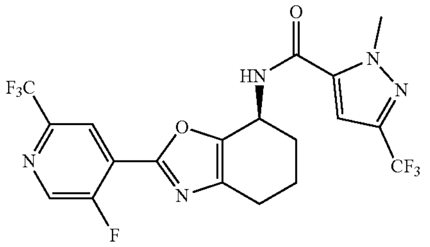 [SMILES: Cn1nc(C(F)(F)F)cc1C(=O)N[C@H]1CCCc2nc(-c3cc(C(F)(F)F)ncc3F)oc21]

Step 1—Synthesis of N-(3-Oxocyclohex-1-en-1-yl)-2-(trifluoromethyl)isonicotinamide

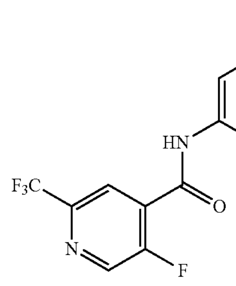

To a solution of 5-fluoro-2-(trifluoromethyl)pyridine-4-carboxylic acid (37 g, 168.4 mmol), 3-aminocyclohex-2-en-1-one (19.7 g, 177.0 mmol), DIEA (92 mL, 177.0 mmol) in DMF (250 mL) was added HATU (81 g, 213.0 mmol) and the mixture was stirred at 25° C. for 16 h. The reaction was diluted with water (500 mL), extracted with ethyl acetate (300 mL×3), the combined organic layers washed with brine (300 mL×3), dried over anhydrous $Na_2SO_4$, filtered and concentrated in vacuo. The crude residue was purified by RP-HPLC (Column: 50-Welch Xtimate C18 150×40 mm, 5 μm; mobile phase: acetonitrile 25%-55%/0.225% formic acid in water) to give the title compound (12 g, 29%) as yellow solid. LCMS (ESI) m/z: 303.1 $[M+H]^+$.

Step 2—Synthesis of N-(2-Bromo-3-oxocyclohex-1-en-1-yl)-5-fluoro-2-(trifluoromethyl)isonicotinamide

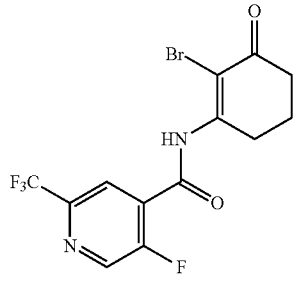 [SMILES: O=C1CCCC(NC(=O)c2cc(C(F)(F)F)ncc2F)=C1Br]

To a solution of 5-fluoro-N-(3-oxocyclohexen-1-yl)-2-(trifluoromethyl)pyridine-4-carboxamide (12 g, 39.7 mmol) in DMF (100 mL) was added NBS (7.6 g, 42.7 mmol) and the mixture was stirred at 25° C. for 2 h. The reaction was diluted with water (100 mL), extracted with ethyl acetate (100 mL×2), the combined organic layers washed with brine (50 mL×4), dried over anhydrous $Na_2SO_4$, filtered and concentrated in vacuo. The crude residue was purified by RP-HPLC (Column: 50-Welch Xtimate C18 150×40 mm, 5 m; mobile phase: acetonitrile 35%-65%/0.225% formic acid in water) to give the title compound (2 g, 12%) as a yellow solid. LCMS (ESI) m/z: 381.0 $[M+H]^+$.

Step 3—Synthesis of 2-(5-Fluoro-2-(trifluoromethyl)pyridin-4-yl)-5,6-dihydrobenzo[d]oxazol-7(4H)-one

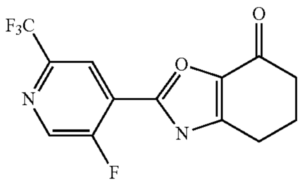

To a solution of N-(2-bromo-3-oxo-cyclohexen-1-yl)-5-fluoro-2-(trifluoromethyl)pyridine-4-carboxamide (2 g, 5.3 mmol), $Cs_2CO_3$ (5.1 g, 15.7 mmol) and N,N-dimethylglycine hydrochloride (220 mg, 1.6 mmol) in dioxane (30 mL) was added CuI (100 mg, 525.2 μmol). The reaction vessel was evacuated and backfilled with $N_2$ three times, then stirred at 85° C. for 16 h under a nitrogen atmosphere. After cooling to room temperature, the reaction was diluted with water (50 mL), extracted with ethyl acetate (50 mL×2), the combined organic layers washed with brine (100 mL), dried over anhydrous $Na_2SO_4$, filtered and concentrated in vacuo. The crude residue was purified by silica gel chromatography (solvent gradient: 0-50% EtOAc in hexanes) to give the title compound (146 mg, 9%) as a white solid. $^1$H NMR (400 MHz, $CDCl_3$) δ 9.10 (d, J=1.6 Hz, 1H), 8.42 (d, J=5.6 Hz, 1H), 2.96-2.92 (m, 2H), 2.65-2.62 (m, 2H), 2.21-2.15 (m, 2H). LCMS (ESI) m/z: 301.0 [M+H]$^+$.

Step 4—Synthesis of (S)—N-(2-(5-Fluoro-2-(trifluoromethyl)pyridin-4-yl)-4,5,6,7-tetrahydrobenzo[d]oxazol-7-yl)-1-methyl-3-(trifluoromethyl)-1H-pyrazole-5-carboxamide

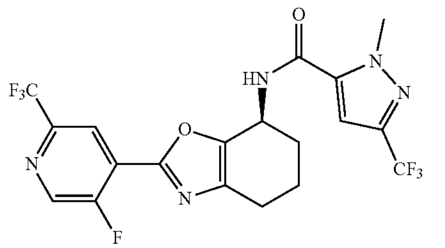 [SMILES: Cn1nc(C(F)(F)F)cc1C(=O)N[C@H]1CCCc2nc(-c3cc(C(F)(F)F)ncc3F)oc21]

Following the procedure described in Example 1.66, 2-(5-fluoro-2-(trifluoromethyl)pyridin-4-yl)-5,6-dihydrobenzo[d]oxazol-7(4H)-one was used in step 5, (S)-2-(5-fluoro-2-(trifluoromethyl)pyridin-4-yl)-4,5,6,7-tetrahydrobenzo[d]oxazol-7-amine hydrochloride salt was used in step 8, the title compound (20 mg, 71% ee) was obtained as a white solid after purification of RP-HPLC (Column: C18 150×30 mm; mobile phase: acetonitrile 58%-88%/0.225% formic acid in water). LCMS (ESI) m/z: 478.0 [M+H]$^+$.

Step 5—Purification of (S)-1-Methyl-3-(trifluoromethyl)-N-(2-(2-(trifluoromethyl)pyridin-4-yl)-4,5,6,7-tetrahydrobenzo[d]oxazol-7-yl)-1H-pyrazole-5-carboxamide

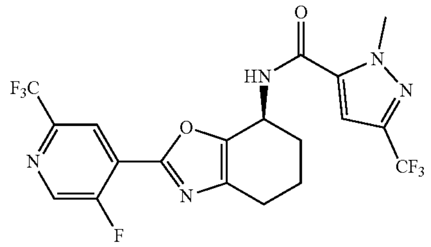 [SMILES: Cn1nc(C(F)(F)F)cc1C(=O)N[C@H]1CCCc2nc(-c3cc(C(F)(F)F)ncc3F)oc21]

(S)-1-methyl-3-(trifluoromethyl)-N-(2-(2-(trifluoromethyl)pyridin-4-yl)-4,5,6,7-tetrahydrobenzo[d]oxazol-7-yl)-1H-pyrazole-5-carboxamide (20 mg, 42 μmol) was separated by chiral SFC (DAICEL CHIRALCEL AS (250 mm*30 mm, 10 μm); Supercritical $CO_2$/EtOH+0.1% $NH_3 \cdot H_2O$=85/15; 60 mL/min) to afford (S)-1-methyl-3-(trifluoromethyl)-N-(2-(2-(trifluoromethyl)pyridin-4-yl)-4,5,6,7-tetrahydrobenzo[d]oxazol-7-yl)-1H-pyrazole-5-carboxamide (1.9 mg, first peak) as a white solid. First peak: I-514a: $^1$H NMR (400 MHz, DMSO-$d_6$) δ 9.13 (d, J=8.0 Hz, 1H), 9.01 (s, 1H), 8.33 (d, J=5.2 Hz, 1H), 7.35 (s, 1H), 5.37-5.31 (m, 1H), 4.18 (s, 3H), 2.71-2.61 (m, 2H), 2.09-1.87 (m, 4H). LCMS (ESI) m/z: 478.0 [M+H]$^+$.

Example 1.68. Synthesis of (1R,2S)-2-(Trifluoromethyl)-N—((S)-2-(2-(trifluoromethyl)pyridin-4-yl)-5,6-dihydro-4H-pyrrolo[1,2-b]pyrazol-4-yl)cyclopropane-1-carboxamide & (1R,2R)-2-(Trifluoromethyl)-N—((S)-2-(2-(trifluoromethyl)pyridin-4-yl)-5,6-dihydro-4H-pyrrolo[1,2-b]pyrazol-4-yl)cyclopropane-1-carboxamide (I-487^ and I-488^)

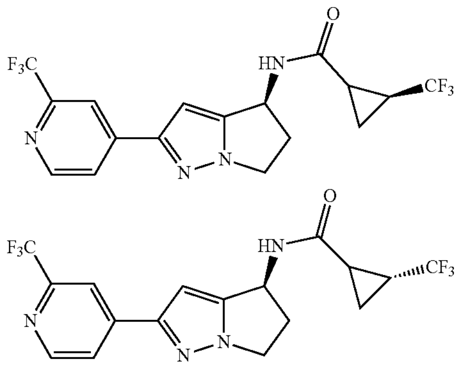

Following the procedure described in Example 1.26, (S)-2-(2-(trifluoromethyl)pyridin-4-yl)-5,6-dihydro-4H-pyrrolo[1,2-b]pyrazol-4-amine HCl salt and 2-(trifluoromethyl)cyclopropane-1-carboxylic acid were used in step 7, (1R,2S)-2-(trifluoromethyl)-N—((S)-2-(2-(trifluoromethyl)pyridin-4-yl)-5,6-dihydro-4H-pyrrolo[1,2-b]pyrazol-4-yl)cyclopropane-1-carboxamide (58 mg, first peak) and (1R,2R)-2-(trifluoromethyl)-N—((S)-2-(2-(trifluoromethyl)pyridin-4-yl)-5,6-dihydro-4H-pyrrolo[1,2-b]pyrazol-4-yl)cyclopropane-1-carboxamide (17 mg, second peak) were obtained both as white solids after purification of RP-HPLC (Column: C18 150×30 mm; mobile phase: acetonitrile 40%-70%/0.225% formic acid in water). First peak: I-487^: $^1$H NMR (400 MHz, DMSO-$d_6$) δ 8.89-8.85 (m, 1H), 8.74 (d, J=4.8 Hz, 1H), 8.18 (d, J=6.0 Hz, 1H), 8.06 (t, J=5.6 Hz, 1H), 6.95-6.82 (m, 1H), 5.37-5.29 (m, 1H), 4.35-4.27 (m, 1H), 4.20-4.14 (m, 1H), 3.01-2.89 (m, 1H), 2.39-2.31 (m, 1H), 2.18-2.08 (m, 1H), 2.03-1.96 (m, 1H), 1.48-1.40 (m, 1H), 1.25-1.15 (m, 1H). LCMS (ESI) m/z: 405.2 [M+H]$^+$. Second peak: I-488^: $^1$H NMR (400 MHz, DMSO-$d_6$) δ 9.06-9.02 (m, 1H), 8.75 (d, J=5.2 Hz, 1H), 8.20 (s, 1H), 8.10-8.04 (m, 1H), 6.99 (d, J=16.8 Hz, 1H), 5.37-5.29 (m, 1H), 4.39-4.29 (m, 1H), 4.24-4.14 (m, 1H), 3.02-2.94 (m, 1H), 2.41-2.36 (m, 1H), 2.24-2.15 (m, 1H), 2.07-2.00 (m, 1H), 1.24-1.18 (m, 2H). LCMS (ESI) m/z: 405.2 [M+H]$^+$.

Example 1.69. Synthesis of (S)—N-(2-(5-Fluoro-2-(trifluoromethyl)pyridin-4-yl)-5,6-dihydro-4H-pyrrolo[1,2-b]pyrazol-4-yl)-1-methyl-3-(trifluoromethyl)-1H-1,2,4-triazole-5-carboxamide (I-548a)

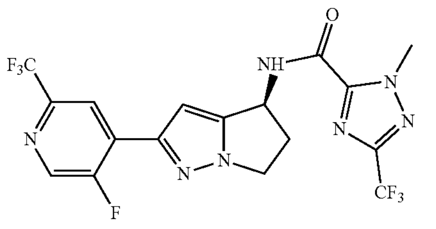

Step 1—Synthesis of (S)—N-(2-Bromo-5,6-dihydro-4H-pyrrolo[1,2-b]pyrazol-4-yl)-1-methyl-3-(trifluoromethyl)-1H-1,2,4-triazole-5-carboxamide

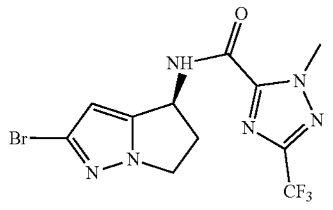 [SMILES: Cn1nc(C(F)(F)F)nc1C(=O)N[C@H]1CCn2nc(Br)cc21]

To a solution of DABCO (294 mg, 2.6 mmol) in THE (10 mL) was added $AlMe_3$ (2.7 mL, 5.4 mmol) at 0° C. under a nitrogen atmosphere and the mixture was stirred at 0° C. for 4 h, then (S)-2-bromo-5,6-dihydro-4H-pyrrolo[1,2-b]pyrazol-4-amine HCl salt (400 mg, 1.5 mmol) and 1-methyl-3-(trifluoromethyl)-1H-1,2,4-triazole-5-carboxylate (365 mg, 1.8 mmol) were added to the solution. The mixture was stirred at 70° C. for 16 h under a nitrogen atmosphere. After cooling to room temperature, the mixture was filtered and concentrated in vacuo. The crude residue was purified by silica gel chromatography (solvent gradient: 0-50% EtOAc in hexanes) to give the title compound (414 mg, 75%) as a yellow solid. $^1$H NMR (400 MHz, DMSO-$d_6$) δ 9.72 (d, J=8.0 Hz, 1H), 6.24 (s, 1H), 5.47-5.40 (m, 1H), 4.33-4.25 (m, 1H), 4.22 (s, 3H), 4.09-4.05 (m, 1H), 2.99-2.88 (m, 1H), 2.59-2.51 (m, 1H). LCMS (ESI) m/z: 381.2 $[M+H]^+$.

Step 2—Synthesis of (S)—N-(2-(5-Fluoro-2-(trifluoromethyl)pyridin-4-yl)-5,6-dihydro-4H-pyrrolo[1,2-b]pyrazol-4-yl)-1-methyl-3-(trifluoromethyl)-1H-1,2,4-triazole-5-carboxamide

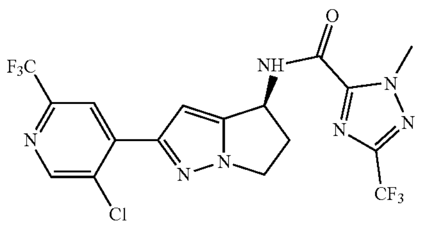 [SMILES: Cn1nc(C(F)(F)F)nc1C(=O)N[C@H]1CCn2nc(-c3cc(C(F)(F)F)ncc3Cl)cc21]

To a solution of (S)—N-(2-bromo-5,6-dihydro-4H-pyrrolo[1,2-b]pyrazol-4-yl)-1-methyl-3-(trifluoromethyl)-1H-1,2,4-triazole-5-carboxamide (414 mg, 1.1 mmol), (5-fluoro-2-(trifluoromethyl)pyridin-4-yl)boronic acid (685 mg, 3.3 mmol), $K_3PO_4$ (927 mg, 4.4 mmol) in dioxane (10 mL) was added and X-Phos Pd G2 (86 mg, 109.2 μmol). The reaction vessel was evacuated and backfilled with $N_2$ three times, then stirred at 80° C. for 16 h under a nitrogen atmosphere. After cooling to room temperature, the mixture was filtered and concentrated in vacuo. The crude material was purified by RP-HPLC (Column: Xtimate C18 100*30 mm*3 μm; mobile phase: acetonitrile 55%-85%/0.225% formic acid in water) to afford the title compound (124 mg, 24%) as a white solid. I-548a: $^1$H NMR (400 MHz, DMSO-$d_6$) δ 9.80 (d, J=8.0 Hz, 1H), 8.85 (d, J=2.4 Hz, 1H), 8.32 (d, J=5.6 Hz, 1H), 6.76 (d, J=3.6 Hz, 1H), 5.56-5.50 (m, 1H), 4.41-4.43 (m, 1H), 4.29-4.21 (m, 4H), 3.10-2.99 (m, 1H), 2.69-2.63 (m, 1H). LCMS (ESI) m/z: 464.0 $[M+H]^+$.

Example 1.70. Synthesis of (S)—N-(2-(2-Cyclopropylpyridin-4-yl)-4,5,6,7-tetrahydrobenzo[d]oxazol-4-yl)-3-(difluoromethyl)-1-(trifluoromethyl)-1H-pyrazole-4-carboxamide (I-505a)

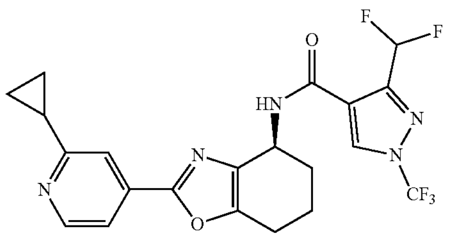 [SMILES: O=C(N[C@H]1CCCc2oc(-c3ccnc(C4CC4)c3)nc21)c1cn(C(F)(F)F)nc1C(F)F]

Step 1—Synthesis of Ethyl 1-(bromodifluoromethyl)-3-(difluoromethyl)-1H-pyrazole-4-carboxylate

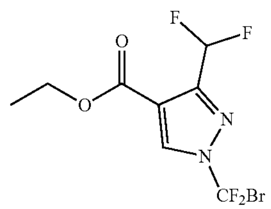

To a solution of ethyl 3-(difluoromethyl)-1H-pyrazole-4-carboxylate (5 g, 26.3 mmol) in THE (50 mL) was added NaH (760 mg, 31.7 mmol, 60% in mineral oil) at 0° C. and stirred at 0° C. for 30 minutes, then dibromodifluoromethane (8.3 g, 39.6 mmol) was added and the mixture stirred at room temperature for 16 h under a nitrogen atmosphere. The mixture was quenched with sat. aq. $NH_4Cl$ (20 mL) and diluted with $H_2O$ (50 mL) and extracted with ethyl acetate (50 mL×2). The combined organic layers were washed with brine (50 mL×2), dried over anhydrous $Na_2SO_4$, filtered and concentrated in vacuo. The residue was purified by RP-HPLC (Column: Xtimate C18 150*40 mm*10 μm; mobile phase: acetonitrile 50%-80%/0.225% formic acid in water) to give the title compound (1.2 g, 14%) as a white solid. LCMS (ESI) m/z: 319.1 $[M+H]^+$.

Step 2—Synthesis of Ethyl 3-(difluoromethyl)-1-(trifluoromethyl)-1H-pyrazole-4-carboxylate

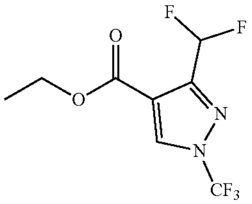 [SMILES: CCOC(=O)c1cn(C(F)(F)F)nc1C(F)F]

To a solution of ethyl 1-(bromodifluoromethyl)-3-(difluoromethyl)-1H-pyrazole-4-carboxylate (1 g, 3.1 mmol) in DCM (10 mL) was dropwise added $AgBF_4$ (1.80 g, 9.4 mmol) at −70° C. After addition, the mixture was stirred at room temperature for 2 h, then further $AgBF_4$ (610 mg, 3.1 mmol) was added at −70° C. and the resulting mixture was stirred at room temperature for 16 h. The mixture was diluted with $H_2O$ (50 mL) and extracted with ethyl acetate (30 mL×2). The combined organic layers were washed with brine (30 mL×2), dried over anhydrous $Na_2SO_4$, filtered and concentrated in vacuo to give the title compound (700 mg, crude) as a yellow oil which was used without further purification. $^1$H NMR (400 MHz, DMSO-$d_6$) δ 9.32 (s, 1H), 7.32 (t, J=12.8 Hz, 1H), 4.30 (q, J=7.2 Hz, 2H), 1.30 (t, J=7.2 Hz, 3H). LCMS (ESI) m/z: 259.0 $[M+H]^+$.

Step 3—Synthesis of 3-(Difluoromethyl)-1-(trifluoromethyl)-1H-pyrazole-4-carboxylic acid

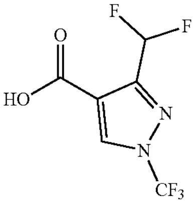 [SMILES: O=C(O)c1cn(C(F)(F)F)nc1C(F)F]

To a solution of ethyl 3-(difluoromethyl)-1-(trifluoromethyl)-1H-pyrazole-4-carboxylate (200 mg, 774.8 μmol) in THE (2 mL) and $H_2O$ (2 mL) was added $LiOH{\cdot}H_2O$ (55 mg, 2.3 mmol) and the mixture was stirred at 25° C. for 3 h. The reaction mixture was diluted with water (10 ml), and the solution was adjusted to pH=5 with HCl (1M, 5 mL) and extracted with ethyl acetate (20 mL×2). The combined organic layers were washed with brine (20 mL×2), dried over anhydrous $Na_2SO_4$, filtered and concentrated in vacuo to give the title compound (150 mg, crude) as a brown solid which was used without purification. LCMS (ESI) m/z: 231.0 $[M+H]^+$.

Step 4—Synthesis of (S)—N-(2-(2-Cyclopropylpyridin-4-yl)-4,5,6,7-tetrahydrobenzo[d]oxazol-4-yl)-3-(difluoromethyl)-1-(trifluoromethyl)-1H-pyrazole-4-carboxamide

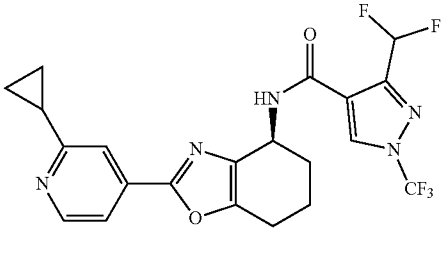 [SMILES: O=C(N[C@H]1CCCc2oc(-c3ccnc(C4CC4)c3)nc21)c1cn(C(F)(F)F)nc1C(F)F]

Following the procedure described in Example 1.26, (S)-2-(2-cyclopropylpyridin-4-yl)-4,5,6,7-tetrahydrobenzo[d]oxazol-4-amine HCl salt and 3-(difluoromethyl)-1-(trifluoromethyl)-1H-pyrazole-4-carboxylic acid were used in step 7, the title compound (46 mg, 26%) was obtained as a white solid after purification of RP-HPLC (Column: C18 150×30 mm; mobile phase: acetonitrile 36%-67%/0.225% formic acid in water). I-505a: $^1$H NMR (400 MHz, DMSO-$d_6$) δ 9.09 (s, 1H), 8.83 (d, J=8.0 Hz, 1H), 8.58 (d, J=5.2 Hz, 1H), 7.86 (s, 1H), 7.73 (d, J=5.2 Hz, 1H), 7.47 (t, J=13.2 Hz, 1H), 5.12 (s, 1H), 2.83-2.78 (m, 2H), 2.33-2.27 (m, 1H), 2.01-1.84 (m, 4H), 1.12-1.02 (m, 4H). LCMS (ESI) m/z: 394.1 $[M+H]^+$.

Example 1.71. Synthesis of (R)—N-(2-(2-(1,1-Difluoroethyl)pyridin-4-yl)-4,5,6,7-tetrahydrobenzo[d]oxazol-4-yl)-3-fluorobenzamide & (S)—N-(2-(2-(1,1-Difluoroethyl)pyridin-4-yl)-4,5,6,7-tetrahydrobenzo[d]oxazol-4-yl)-5-(trifluoromethyl)nicotinamide (I-508a and I-508b)

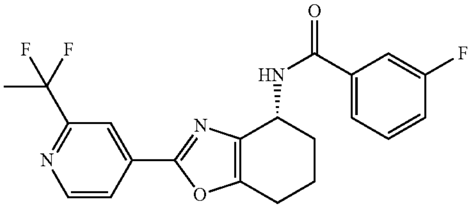

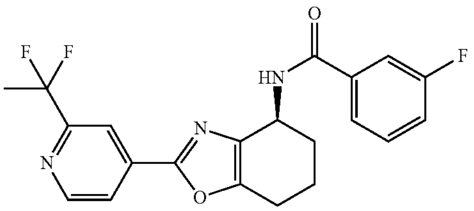

Step 1—Synthesis of Ethyl 2-(2-(1,1-difluoroethyl) isonicotinamido)cyclohex-1-ene-1-carboxylate

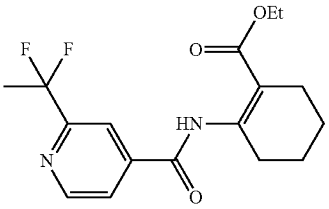 [SMILES: CCOC(=O)C1=C(NC(=O)c2ccnc(C(C)(F)F)c2)CCCC1]

To a solution of 2-(1,1-difluoroethyl)isonicotinic acid (13 g, 69.5 mmol, prepared according to the procedure in WO2023/039505), ethyl 2-aminocyclohex-1-ene-1-carboxylate (14 g, 83.3 mmol), DIEA (36 mL, 208.4 mmol) in DCM (100 mL) was added HATU (34 g, 89.4 mmol) and the mixture was stirred at room temperature for 16 h. The reaction was diluted with water (100 mL), extracted with DCM (80 mL×3), the combined organic layers washed with brine (50 mL×3), dried over anhydrous $Na_2SO_4$, filtered and concentrated in vacuo. The crude residue was purified by silica gel chromatography (solvent gradient: 0-50% EtOAc in hexanes) to give the title compound (22 g, 93%) as a yellow solid. LCMS (ESI) m/z: 339.1 $[M+H]^+$.

Step 2—Synthesis of Ethyl 3-bromo-2-(2-(1,1-difluoroethyl)isonicotinamido)cyclohex-1-ene-1-carboxylate

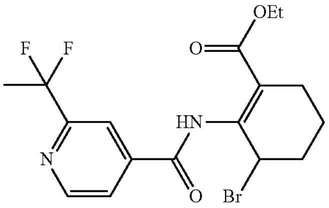 [SMILES: CCOC(=O)C1=C(NC(=O)c2ccnc(C(C)(F)F)c2)C(Br)CCC1]

To a solution of ethyl 2-(2-(1,1-difluoroethyl)isonicotinamido)cyclohex-1-ene-1-carboxylate (20 g, 59.1 mmol) in DMF (200 mL) was added NBS (11.5 g, 65.0 mmol) and the mixture was stirred at 50° C. for 12 h. After cooling to room temperature, the reaction was diluted with water (200 mL), extracted with ethyl acetate (100 mL×3), the combined organic layers washed with brine (50 mL×5), dried over anhydrous $Na_2SO_4$, filtered and concentrated in vacuo. The crude residue was purified by silica gel chromatography (solvent gradient: 0-30% EtOAc in hexanes) to give the title compound (17 g, 68%) as a yellow solid. LCMS (ESI) m/z: 417.0 $[M+H]^+$.

Step 3—Synthesis of (rac)-2-(2-(1,1-Difluoroethyl) pyridin-4-yl)-4,5,6,7-tetrahydrobenzo[d]oxazole-4-carboxylic acid

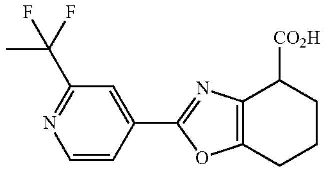 [SMILES: CC(F)(F)c1cc(-c2nc3c(o2)CCCC3C(=O)O)ccn1]

To a solution of ethyl 3-bromo-2-(2-(1,1-difluoroethyl) isonicotinamido)cyclohex-1-ene-1-carboxylate (17 g, 40.7 mmol) in MeOH (100 mL) was added KOH (4.5 g, 80.4 mmol). The mixture was stirred at 70° C. for 2 h. After cooling to room temperature, the reaction mixture was concentrated in vacuo and the crude residue was purified by RP-HPLC (Column: C18 150×40 mm; mobile phase: acetonitrile 30%-60%/0.225% formic acid in water) to give the title compound (6.0 g, 47%) as a gray solid. $^1H$ NMR (400 MHz, DMSO-$d_6$) δ 8.81 (d, J=4.8 Hz, 1H), 8.04 (s, 1H), 7.99 (d, J=5.2 Hz, 1H), 3.65-3.60 (m, 1H), 2.81-2.69 (m, 2H), 2.09-1.98 (m, 5H), 1.96-1.82 (m, 2H). LCMS (ESI) m/z: 309.1 $[M+H]^+$.

Step 4—Synthesis of (rac)-Benzyl (2-(2-(1,1-difluoroethyl)pyridin-4-yl)-4,5,6,7-tetrahydrobenzo[d] oxazol-4-yl)carbamate

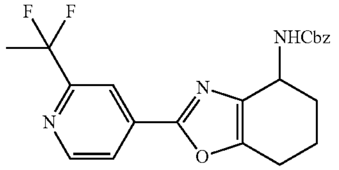 [SMILES: CC(F)(F)c1cc(-c2nc3c(o2)CCCC3NC(=O)OCc2ccccc2)ccn1]

To a solution of 2-(2-(1,1-difluoroethyl)pyridin-4-yl)-4,5,6,7-tetrahydrobenzo[d]oxazole-4-carboxylic acid (6.0 g, 19.5 mmol), DIEA (6.8 mL, 39.0 mmol), DPPA (8.5 mL, 39.4 mmol) in toluene (40 mL) was added BnOH (10 mL, 96.5 mmol). The mixture was evacuated and backfilled with $N_2$ three times, then stirred at 100° C. for 4 h under a nitrogen atmosphere. After cooling to room temperature, the mixture was concentrated in vacuo and the residue was purified by RP-HPLC (Column: 50-Welch Xtimate C18 150×40 mm, 5 m; mobile phase: acetonitrile 55%-85%/0.225% formic acid in water) to give the title compound (1.25 g, 15%) as a white solid. LCMS (ESI) m/z: 414.1 $[M+H]^+$.

Step 5—Synthesis of (rac)-2-(2-(1,1-Difluoroethyl) pyridin-4-yl)-4,5,6,7-tetrahydrobenzo[d]oxazol-4-amine

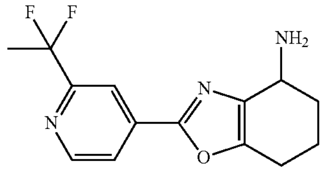 [SMILES: CC(F)(F)c1cc(-c2nc3c(o2)CCCC3N)ccn1]

To a solution of benzyl (2-(2-(1,1-difluoroethyl)pyridin-4-yl)-4,5,6,7-tetrahydrobenzo[d]oxazol-4-yl)carbamate (1.25 g, 3.0 mmol) in EtOH (20 mL) was added Pd/C (1.3 g, 1.2 mmol, 10% w/w). The mixture was evacuated and backfilled with $H_2$ three times, then stirred at room temperature for 16 h under $H_2$ atmosphere (15 psi). The mixture was filtered and concentrated in vacuo to give the title compound (800 mg, crude) as a yellow oil which was used without further purification. LCMS (ESI) m/z: 280.0 $[M+H]^+$.

Step 6—Synthesis of (rac)-Benzyl (2-(2-(1,1-difluoroethyl)pyridin-4-yl)-4,5,6,7-tetrahydrobenzo[d]oxazol-4-yl)carbamate

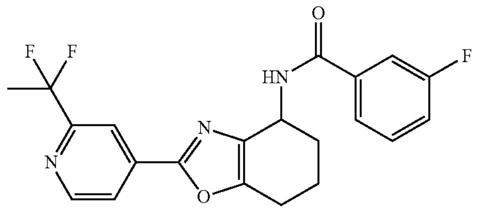 [SMILES: CC(F)(F)c1cc(-c2nc3c(o2)CCCC3NC(=O)c2cccc(F)c2)ccn1]

Following the procedure described in Example 1.26, 2-(2-(1,1-difluoroethyl)pyridin-4-yl)-4,5,6,7-tetrahydrobenzo[d]oxazol-4-amine and 3-fluorobenzoic acid were used in step 7, the title compound (70 mg, 40%) was obtained as a white solid after purification of RP-HPLC (Column: 58-Phenomenex Gemini NX C18 150×40 mm, 5 m; acetonitrile 50%-80%/0.225% formic acid in water).

Step 7—Synthesis of (R)—N-(2-(2-(1,1-Difluoroethyl)pyridin-4-yl)-4,5,6,7-tetrahydrobenzo[d]oxazol-4-yl)-3-fluorobenzamide & (S)—N-(2-(2-(1,1-Difluoroethyl)pyridin-4-yl)-4,5,6,7-tetrahydrobenzo[d]oxazol-4-yl)-5-(trifluoromethyl)nicotinamide

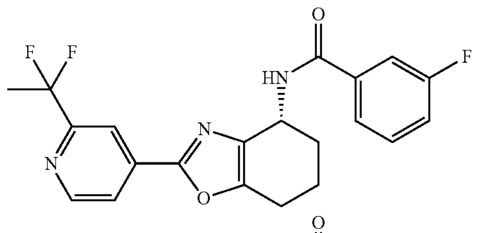

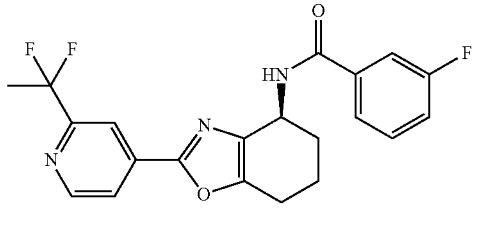

N-(2-(2-(1,1-difluoroethyl)pyridin-4-yl)-4,5,6,7-tetrahydrobenzo[d]oxazol-4-yl)-3-fluorobenzamide (70 mg, 174.4 μmol) was separated by chiral SFC (DAICEL CHIRALPAK AS (250 mm*30 mm, 10 μm); Supercritical $CO_2$/EtOH+0.1% $NH_3 \cdot H_2O$=70/30; 150 mL/min) to afford (R)—N-(2-(2-(1,1-difluoroethyl)pyridin-4-yl)-4,5,6,7-tetrahydrobenzo[d]oxazol-4-yl)-3-fluorobenzamide (18 mg, first peak) and (S)—N-(2-(2-(1,1-difluoroethyl)pyridin-4-yl)-4,5,6,7-tetrahydrobenzo[d]oxazol-4-yl)-3-fluorobenzamide (15 mg, second peak) both as white solids. First peak: I-508b: $^1$H NMR (400 MHz, DMSO-$d_6$) δ 8.84 (d, J=8.4 Hz, 1H), 8.81 (d, J=4.8 Hz, 1H), 8.05 (s, 1H), 8.02 (d, J=5.2 Hz, 1H), 7.76 (d, J=8.0 Hz, 1H), 7.73-7.67 (m, 1H), 7.56-7.48 (m, 1H), 7.42-7.38 (m, 1H), 5.23-5.15 (m, 1H), 2.86-2.72 (m, 2H), 2.09-1.96 (m, 5H), 1.94-1.79 (m, 2H). LCMS (ESI) m/z: 402.2 $[M+H]^+$. Second peak: I-508a: $^1$H NMR (400 MHz, DMSO-$d_6$) δ 8.84 (d, J=8.0 Hz, 1H), 8.81 (d, J=5.2 Hz, 1H), 8.06 (s, 1H), 8.03-8.00 (m, 1H), 7.76 (d, J=8.0 Hz, 1H), 7.72-7.68 (m, 1H), 7.54-7.51 (m, 1H), 7.42-7.36 (m, 1H), 5.22-5.16 (m, 1H), 2.86-2.73 (m, 2H), 2.08-1.97 (m, 5H), 1.94-1.82 (m, 2H). LCMS (ESI) m/z: 402.2 $[M+H]^+$.

Example 1.72. Synthesis of (S)—N-(2-(2-(1,1-Difluoroethyl)pyridin-4-yl)-4,5,6,7-tetrahydrobenzo[d]oxazol-4-yl)-5-(trifluoromethyl)nicotinamide & (R)—N-(2-(2-(1,1-Difluoroethyl)pyridin-4-yl)-4,5,6,7-tetrahydrobenzo[d]oxazol-4-yl)-5-(trifluoromethyl)nicotinamide (I-533a and I-533b)

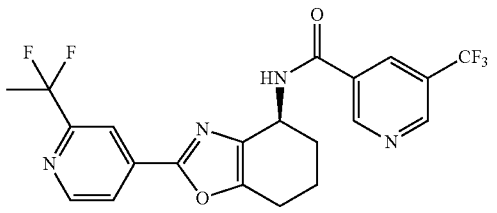

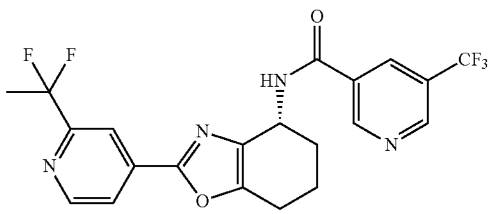

Step 1—Synthesis of (rac)-N-(2-(2-(1,1-Difluoroethyl)pyridin-4-yl)-4,5,6,7-tetrahydrobenzo[d]oxazol-4-yl)-5-(trifluoromethyl)nicotinamide

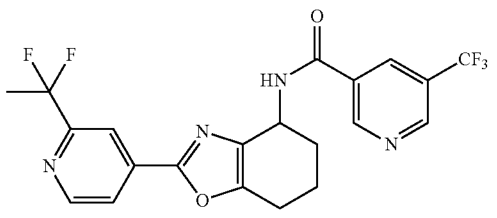

Following the procedure described in Example 1.26, 2-(2-(1,1-difluoroethyl)pyridin-4-yl)-4,5,6,7-tetrahydrobenzo[d]oxazol-4-amine and 5-(trifluoromethyl)nicotinic acid were used in step 7, the title compound (115 mg, 47%) was obtained as a white solid after purification of RP-HPLC (Column: 58-Phenomenex Gemini NX C18 150×40 mm, 5 m; mobile phase: acetonitrile 50%-80%/0.225% formic acid in water).

Step 2—Synthesis of (S)—N-(2-(2-(1,1-Difluoroethyl)pyridin-4-yl)-4,5,6,7-tetrahydrobenzo[d]oxazol-4-yl)-3-fluorobenzamide & (R)—N-(2-(2-(1,1-Difluoroethyl)pyridin-4-yl)-4,5,6,7-tetrahydrobenzo[d]oxazol-4-yl)-5-(trifluoromethyl)nicotinamide

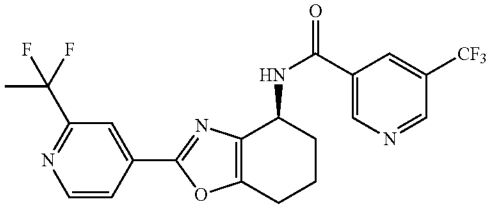

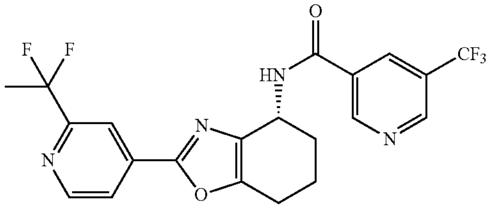 [SMILES: CC(F)(F)c1cc(-c2nc3c(o2)CCCC3NC(=O)c2cncc(C(F)(F)F)c2)ccn1]

N-(2-(2-(1,1-Difluoroethyl)pyridin-4-yl)-4,5,6,7-tetrahydrobenzo[d]oxazol-4-yl)-5-(trifluoromethyl)nicotinamide (115 mg, 254.2 μmol) was separated by chiral SFC (DAICEL CHIRALPAK AD (250 mm*30 mm, 10 μm); Supercritical $CO_2$/EtOH+0.1% $NH_3 \cdot H_2O$=70/30; 150 mL/min) to afford (S)—N-(2-(2-(1,1-difluoroethyl)pyridin-4-yl)-4,5,6,7-tetrahydrobenzo[d]oxazol-4-yl)-3-fluorobenzamide (41.25 mg, first peak) and (R)—N-(2-(2-(1,1-difluoroethyl)pyridin-4-yl)-4,5,6,7-tetrahydrobenzo[d]oxazol-4-yl)-5-(trifluoromethyl)nicotinamide (36.53 mg, second peak) both as white solids. First peak: I-533a: $^1$H NMR (400 MHz, DMSO-$d_6$) δ=9.32 (d, J=1.2 Hz, 1H), 9.22 (d, J=7.6 Hz, 1H), 9.14 (d, J=1.2 Hz, 1H), 8.82 (d, J=5.2 Hz, 1H), 8.63 (s, 1H), 8.06 (s, 1H), 8.04-7.99 (m, 1H), 5.27-5.19 (m, 1H), 2.90-2.76 (m, 2H), 2.09-1.97 (m, 5H), 1.97-1.86 (m, 2H). LCMS (ESI) m/z: 453.1 $[M+H]^+$. Second peak: I-533b: $^1$H NMR (400 MHz, DMSO-$d_6$) δ=9.32 (s, 1H), 9.22 (d, J=7.6 Hz, 1H), 9.14 (s, 1H), 8.82 (d, J=5.2 Hz, 1H), 8.63 (s, 1H), 8.06 (s, 1H), 8.02 (d, J=4.8 Hz, 1H), 5.26-5.19 (m, 1H), 2.91-2.74 (m, 2H), 2.09-1.97 (m, 5H), 1.97-1.86 (m, 2H). LCMS (ESI) m/z: 453.1 $[M+H]^+$.

Example 1.73. Synthesis of (R)—N-(2-(2-(1,1-Difluoroethyl)pyridin-4-yl)-4,5,6,7-tetrahydrobenzo[d]oxazol-4-yl)-5-fluoronicotinamide & (S)—N-(2-(2-(1,1-Difluoroethyl)pyridin-4-yl)-4,5,6,7-tetrahydrobenzo[d]oxazol-4-yl)-5-fluoronicotinamide (I-544a and I-544b)

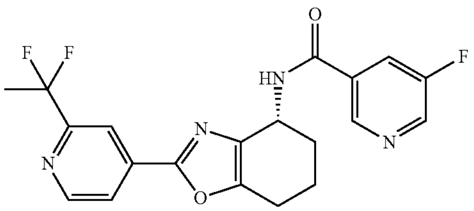 [SMILES: CC(F)(F)c1cc(-c2nc3c(o2)CCCC3NC(=O)c2cncc(F)c2)ccn1]

-continued

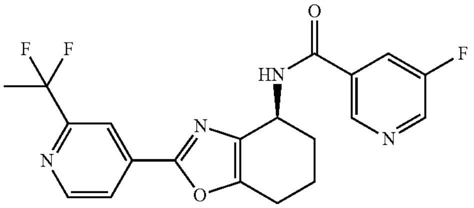

Step 1—Synthesis of (rac)-N-(2-(2-(1,1-difluoroethyl)pyridin-4-yl)-4,5,6,7-tetrahydrobenzo[d]oxazol-4-yl)-5-fluoronicotinamide

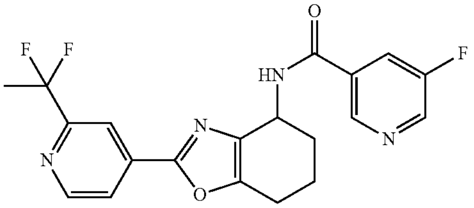

Following the procedure described in Example 1.26, 2-(2-(1,1-difluoroethyl)pyridin-4-yl)-4,5,6,7-tetrahydrobenzo[d]oxazol-4-amine and were used in step 7, the title compound (115 mg, 44%) was obtained as a white solid after purification of RP-HPLC (Column: 58-Phenomenex Gemini NX C18 150×40 mm, 5 m; mobile phase: acetonitrile 45%-75%/0.225% formic acid in water).

Step 2—Synthesis of (R)—N-(2-(2-(1,1-Difluoroethyl)pyridin-4-yl)-4,5,6,7-tetrahydrobenzo[d]oxazol-4-yl)-5-fluoronicotinamide & (S)—N-(2-(2-(1,1-Difluoroethyl)pyridin-4-yl)-4,5,6,7-tetrahydrobenzo[d]oxazol-4-yl)-5-fluoronicotinamide

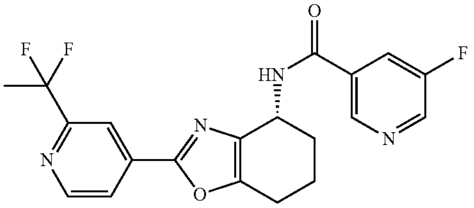

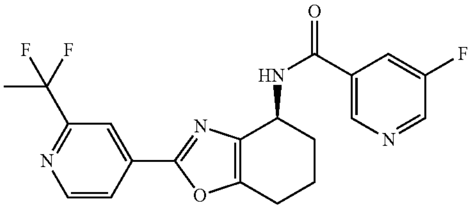

N-(2-(2-(1,1-Difluoroethyl)pyridin-4-yl)-4,5,6,7-tetrahydrobenzo[d]oxazol-4-yl)-5-fluoronicotinamide (115 mg, 285.8 μmol) was separated by chiral SFC (REGIS (R,R) WHELK-O1 (250 mm*25 mm, 10 μm); Supercritical $CO_2$/EtOH+0.1% $NH_3 \cdot H_2O$=60/40; 150 mL/min) to afford (R)—N-(2-(2-(1,1-difluoroethyl)pyridin-4-yl)-4,5,6,7-tetrahydrobenzo[d]oxazol-4-yl)-5-fluoronicotinamide (35 mg, first peak) and (S)—N-(2-(2-(1,1-difluoroethyl)pyridin-4-yl)-4,5,6,7-tetrahydrobenzo[d]oxazol-4-yl)-5-fluoronicotinamide (31 mg, second peak) both as white solids. First peak: I-544b: $^1$H NMR (400 MHz, DMSO-$d_6$) δ 9.06 (d, J=8.0 Hz, 1H), 8.93 (s, 1H), 8.82 (d, J=4.8 Hz, 1H), 8.75 (d, J=2.8 Hz, 1H), 8.17-8.10 (m, 1H), 8.06 (s, 1H), 8.03 (d, J=4.8 Hz, 1H), 5.25-5.15 (m, 1H), 2.89-2.74 (m, 2H), 2.09-1.97 (m, 5H), 1.96-1.84 (m, 2H). LCMS (ESI) m/z: 403.1 [M+H]$^+$. Second peak: I-544a: $^1$H NMR (400 MHz, DMSO-$d_6$) δ=9.06 (d, J=7.6 Hz, 1H), 8.93 (s, 1H), 8.82 (d, J=5.2 Hz, 1H), 8.75 (d, J=2.8 Hz, 1H), 8.16-8.11 (m, 1H), 8.06 (s, 1H), 8.02 (d, J=5.2 Hz, 1H), 5.24-5.18 (m, 1H), 2.88-2.75 (m, 2H), 2.08-1.97 (m, 5H), 1.96-1.84 (m, 2H). LCMS (ESI) m/z: 403.1 [M+H]$^+$.

Example 1.74. Synthesis of (S)—N-(2-(2-(1,1-Difluoroethyl)pyridin-4-yl)-4,5,6,7-tetrahydrobenzo[d]oxazol-4-yl)-1-(difluoromethyl)-5-(trifluoromethyl)-1H-pyrazole-3-carboxamide & (R)—N-(2-(2-(1,1-Difluoroethyl)pyridin-4-yl)-4,5,6,7-tetrahydrobenzo[d]oxazol-4-yl)-1-(difluoromethyl)-5-(trifluoromethyl)-1H-pyrazole-3-carboxamide (I-534a and I-534b)

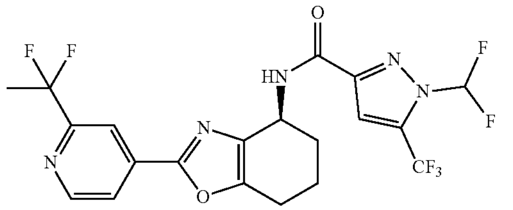

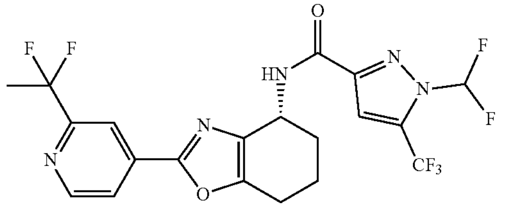

Step 1—Synthesis of (rac)-N-(2-(2-(1,1-Difluoroethyl)pyridin-4-yl)-4,5,6,7-tetrahydrobenzo[d]oxazol-4-yl)-1-(difluoromethyl)-5-(trifluoromethyl)-1H-pyrazole-3-carboxamide

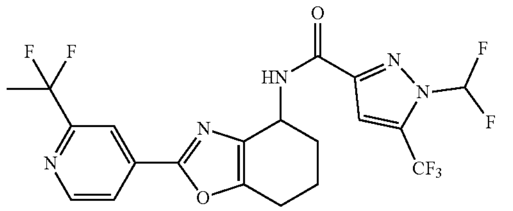 [SMILES: CC(F)(F)c1cc(-c2nc3c(o2)CCCC3NC(=O)c2cc(C(F)(F)F)n(C(F)F)n2)ccn1]

Following the procedure described in Example 1.26, 2-(2-(1,1-difluoroethyl)pyridin-4-yl)-4,5,6,7-tetrahydrobenzo[d]oxazol-4-amine and 1-(difluoromethyl)-5-(trifluoromethyl)-1H-pyrazole-3-carboxylic acid were used in step 7, the title compound (60 mg, 24%) was obtained as a white solid after purification of RP-HPLC (Column: 58-Phenomenex Gemini NX C18 150×40 mm, 5 m; mobile phase: acetonitrile 55%-85%/0.225% formic acid in water).

Step 2—Synthesis of (S)—N-(2-(2-(1,1-Difluoroethyl)pyridin-4-yl)-4,5,6,7-tetrahydrobenzo[d]oxazol-4-yl)-1-(difluoromethyl)-5-(trifluoromethyl)-1H-pyrazole-3-carboxamide & (R)—N-(2-(2-(1,1-Difluoroethyl)pyridin-4-yl)-4,5,6,7-tetrahydrobenzo[d]oxazol-4-yl)-1-(difluoromethyl)-5-(trifluoromethyl)-1H-pyrazole-3-carboxamide

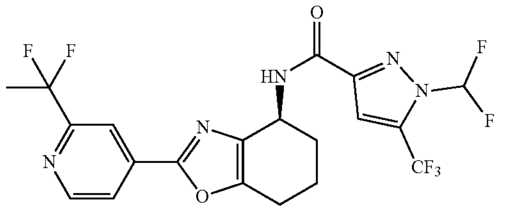

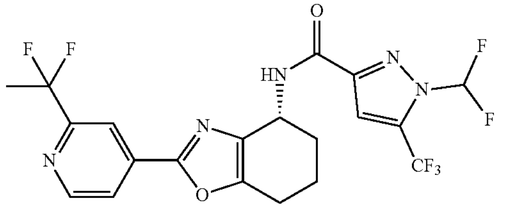

A mixture of N-(2-(2-(1,1-difluoroethyl)pyridin-4-yl)-4,5,6,7-tetrahydrobenzo[d]oxazol-4-yl)-1-(difluoromethyl)-5-(trifluoromethyl)-1H-pyrazole-3-carboxamide (60 mg, 122.4 μmol) was separated by chiral SFC (Daicel ChiralPak IG (250*30 mm, 10 um); Supercritical $CO_2$/EtOH+0.1% $NH_3 \cdot H_2O$=20/80; 65 mL/min) to afford (S)—N-(2-(2-(1,1-difluoroethyl)pyridin-4-yl)-4,5,6,7-tetrahydrobenzo[d]oxazol-4-yl)-1-(difluoromethyl)-5-(trifluoromethyl)-1H-pyrazole-3-carboxamide (42.37 mg, first peak) and (R)—N-(2-(2-(1,1-difluoroethyl)pyridin-4-yl)-4,5,6,7-tetrahydrobenzo[d]oxazol-4-yl)-1-(difluoromethyl)-5-(trifluoromethyl)-1H-pyrazole-3-carboxamide (39.00 mg, second peak) both as white solids. First peak: I-534a: $^1$H NMR (400 MHz, DMSO-$d_6$) δ 8.99 (d, J=8.0 Hz, 1H), 8.82 (d, J=4.8 Hz, 1H), 8.25-7.95 (m, 3H), 7.70 (s, 1H), 5.23-5.17 (m, 1H), 2.85-2.71 (m, 2H), 2.09-1.98 (m, 5H), 1.93-1.84 (m, 2H). Second peak: I-534b: $^1$H NMR (400 MHz, DMSO-$d_6$) δ 8.99 (d, J=8.0 Hz, 1H), 8.82 (d, J=4.8 Hz, 1H), 8.25-7.95 (m, 3H), 7.70 (s, 1H), 5.23-5.17 (m, 1H), 2.85-2.71 (m, 2H), 2.09-1.98 (m, 5H), 1.93-1.84 (m, 2H). LCMS (ESI) m/z: 492.2 [M+H]$^+$.

Example 1.75. Synthesis of (S)—N-(2-(2-(1,1-Difluoroethyl)pyridin-4-yl)-4,5,6,7-tetrahydrobenzo[d]oxazol-4-yl)-3-(difluoromethyl)-1-(trifluoromethyl)-1H-pyrazole-4-carboxamide & (R)—N-(2-(2-(1,1-Difluoroethyl)pyridin-4-yl)-4,5,6,7-tetrahydrobenzo[d]oxazol-4-yl)-3-(difluoromethyl)-1-(trifluoromethyl)-1H-pyrazole-4-carboxamide (I-535a and I-535b)

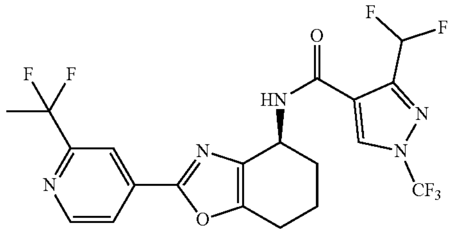

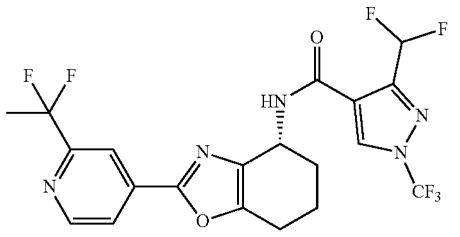

Step 1—Synthesis of (rac)-N-(2-(2-(1,1-Difluoroethyl)pyridin-4-yl)-4,5,6,7-tetrahydrobenzo[d]oxazol-4-yl)-3-(difluoromethyl)-1-(trifluoromethyl)-1H-pyrazole-4-carboxamide

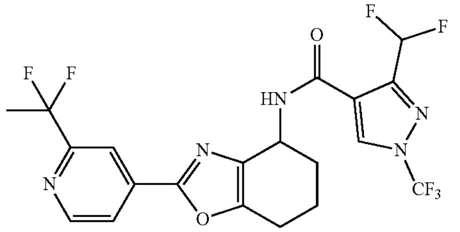 [SMILES: CC(F)(F)c1cc(-c2nc3c(o2)CCCC3NC(=O)c2cn(C(F)(F)F)nc2C(F)F)ccn1]

Following the procedure described in Example 1.26, 2-(2-(1,1-difluoroethyl)pyridin-4-yl)-4,5,6,7-tetrahydrobenzo[d]oxazol-4-amine and 3-(difluoromethyl)-1-(trifluoromethyl)-1H-pyrazole-4-carboxylic acid were used in step 7, the title compound (60 mg, 26%) was obtained as a white solid after purification of RP-HPLC (Column: 58-Phenomenex Gemini NX C18 150×40 mm, 5 m; mobile phase: acetonitrile 55%-85%/0.225% formic acid in water).

Step 2—Synthesis of (S)—N-(2-(2-(1,1-Difluoroethyl)pyridin-4-yl)-4,5,6,7-tetrahydrobenzo[d]oxazol-4-yl)-3-(difluoromethyl)-1-(trifluoromethyl)-1H-pyrazole-4-carboxamide & (R)—N-(2-(2-(1,1-Difluoroethyl)pyridin-4-yl)-4,5,6,7-tetrahydrobenzo[d]oxazol-4-yl)-3-(difluoromethyl)-1-(trifluoromethyl)-1H-pyrazole-4-carboxamide

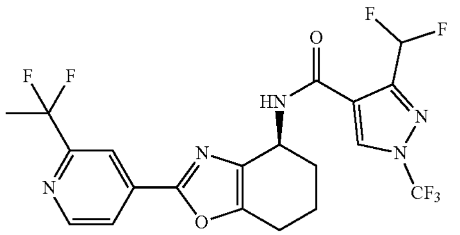

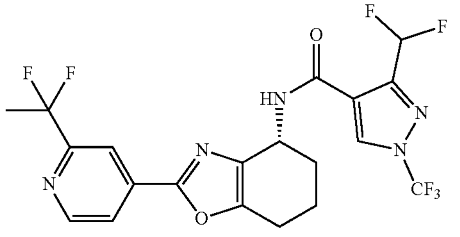

A mixture of N-(2-(2-(1,1-difluoroethyl)pyridin-4-yl)-4,5,6,7-tetrahydrobenzo[d]oxazol-4-yl)-3-(difluoromethyl)-1-(trifluoromethyl)-1H-pyrazole-4-carboxamide (60 mg, 122.4 μmol) was separated by chiral SFC (Daicel ChiralPak IG (250*30 mm, 10 μm); Supercritical $CO_2$/EtOH+0.1% $NH_3 \cdot H_2O$=30/70; 80 mL/min) to afford (S)—N-(2-(2-(1,1-difluoroethyl)pyridin-4-yl)-4,5,6,7-tetrahydrobenzo[d]oxazol-4-yl)-3-(difluoromethyl)-1-(trifluoromethyl)-1H-pyrazole-4-carboxamide (30 mg, first peak) and (R)—N-(2-(2-(1,1-difluoroethyl)pyridin-4-yl)-4,5,6,7-tetrahydrobenzo[d]oxazol-4-yl)-1-(difluoromethyl)-5-(trifluoromethyl)-1H-pyrazole-3-carboxamide (18.58 mg, second peak) both as white solids. First peak: I-535a: $^1H$ NMR (400 MHz, DMSO-$d_6$) δ 9.10 (s, 1H), 8.85-8.82 (m, 2H), 8.06 (s, 1H), 8.02 (d, J=5.2 Hz, 1H), 7.63-7.32 (m, 1H), 5.13 (d, J=4.8 Hz, 1H), 2.90-2.74 (m, 2H), 2.09-1.84 (m, 7H). Second peak: I-535b: $^1H$ NMR (400 MHz, DMSO-$d_6$) δ9.10 (s, 1H), 8.85-8.82 (m, 2H), 8.06 (s, 1H), 8.02 (d, J=5.2 Hz, 1H), 7.63-7.32 (m, 1H), 5.13 (d, J=4.8 Hz, 1H), 2.90-2.74 (m, 2H), 2.09-1.84 (m, 7H). LCMS (ESI) m/z: 492.2 $[M+H]^+$.

Example 1.76. Synthesis of (R)—N-(2-(2-(1,1-Difluoroethyl)pyridin-4-yl)-4,5,6,7-tetrahydrobenzo[d]oxazol-4-yl)-1,3-bis(trifluoromethyl)-1H-pyrazole-4-carboxamide & (S)—N-(2-(2-(1,1-Difluoroethyl)pyridin-4-yl)-4,5,6,7-tetrahydrobenzo[d]oxazol-4-yl)-1,3-bis(trifluoromethyl)-1H-pyrazole-4-carboxamide (I-545a and I-545b)

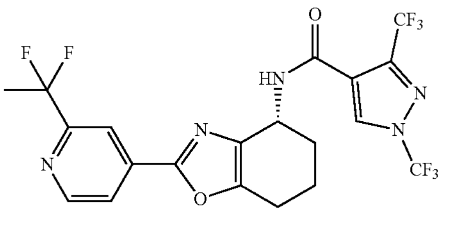

-continued

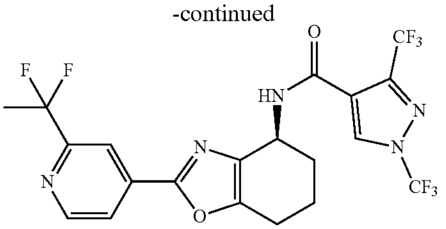

Step 1—Synthesis of (rac)-N-(2-(2-(1,1-difluoroethyl)pyridin-4-yl)-4,5,6,7-tetrahydrobenzo[d]oxazol-4-yl)-1,3-bis(trifluoromethyl)-1H-pyrazole-4-carboxamide

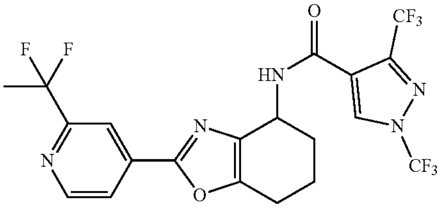

Following the procedure described in Example 1.26, 2-(2-(1,1-difluoroethyl)pyridin-4-yl)-4,5,6,7-tetrahydrobenzo[d]oxazol-4-amine was used in step 7, the title compound (55 mg, 26%) was obtained as a white solid after purification of RP-HPLC (Column: 58-Phenomenex Gemini NX C18 150×40 mm, 5 m; mobile phase: acetonitrile 55%-85%/0.225% formic acid in water).

Step 2—Synthesis of (R)—N-(2-(2-(1,1-Difluoroethyl)pyridin-4-yl)-4,5,6,7-tetrahydrobenzo[d]oxazol-4-yl)-1,3-bis(trifluoromethyl)-1H-pyrazole-4-carboxamide & (S)—N-(2-(2-(1,1-Difluoroethyl)pyridin-4-yl)-4,5,6,7-tetrahydrobenzo[d]oxazol-4-yl)-1,3-bis(trifluoromethyl)-1H-pyrazole-4-carboxamide

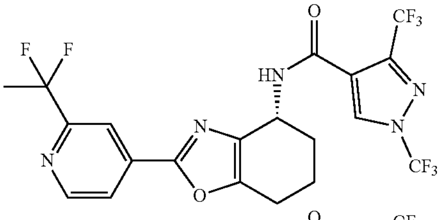

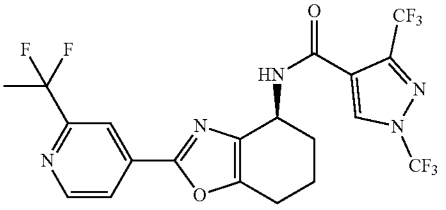

A mixture of N-(2-(2-(1,1-difluoroethyl)pyridin-4-yl)-4,5,6,7-tetrahydrobenzo[d]oxazol-4-yl)-1,3-bis(trifluoromethyl)-1H-pyrazole-4-carboxamide (55 mg, 108.1 μmol) was separated by chiral SFC AS (250 mm*30 mm, 10 μm); Supercritical $CO_2$/EtOH+0.1% $NH_3 \cdot H_2O$=30/70; 80 mL/min) to afford (R)—N-(2-(2-(1,1-difluoroethyl)pyridin-4-yl)-4,5,6,7-tetrahydrobenzo[d]oxazol-4-yl)-1,3-bis(trifluoromethyl)-1H-pyrazole-4-carboxamide (25.56 mg, first peak) and (S)—N-(2-(2-(1,1-difluoroethyl)pyridin-4-yl)-4,5,6,7-tetrahydrobenzo[d]oxazol-4-yl)-1,3-bis(trifluoromethyl)-1H-pyrazole-4-carboxamide (25.34 mg, second peak) both as white solids. First peak: I-545b: $^1$H NMR (400 MHz, DMSO-$d_6$) δ 9.19 (s, 1H), 8.86 (d, J=7.6 Hz, 1H), 8.83 (d, J=4.8 Hz, 1H), 8.07 (s, 1H), 8.01 (d, J=4.4 Hz, 1H), 5.13-5.10 (m, 1H), 2.88-2.72 (m, 2H), 2.09-1.84 (m, 7H). LCMS (ESI) m/z: 492.2 $[M+H]^+$. Second peak: I-545a: $^1$H NMR (400 MHz, DMSO-$d_6$) δ 9.19 (s, 1H), 8.86 (d, J=7.6 Hz, 1H), 8.83 (d, J=4.8 Hz, 1H), 8.07 (s, 1H), 8.01 (d, J=4.4 Hz, 1H), 5.13-5.10 (m, 1H), 2.88-2.72 (m, 2H), 2.09-1.84 (m, 7H). LCMS (ESI) m/z: 492.2 $[M+H]^+$.

Example 1.77. Synthesis of (S)—N-(2-(2-Cyclopropylpyridin-4-yl)-4,5,6,7-tetrahydrobenzo[d]oxazol-4-yl)-1,3-bis(trifluoromethyl)-1H-pyrazole-4-carboxamide & (S)—N-(2-(2-Cyclopropylpyridin-4-yl)-4,5,6,7-tetrahydrobenzo[d]oxazol-4-yl)-1,5-bis(trifluoromethyl)-1H-pyrazole-4-carboxamide (I-519a and I-530a)

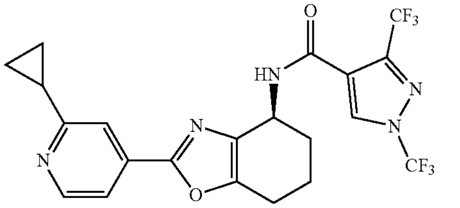

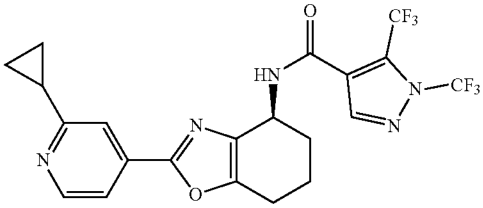

Step 1—Synthesis of (S)—N-(2-(2-Cyclopropylpyridin-4-yl)-4,5,6,7-tetrahydrobenzo[d]oxazol-4-yl)-1,3-bis(trifluoromethyl)-1H-pyrazole-4-carboxamide & (S)—N-(2-(2-Cyclopropylpyridin-4-yl)-4,5,6,7-tetrahydrobenzo[d]oxazol-4-yl)-1,5-bis(trifluoromethyl)-1H-pyrazole-4-carboxamide

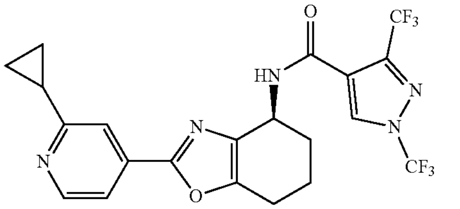

-continued

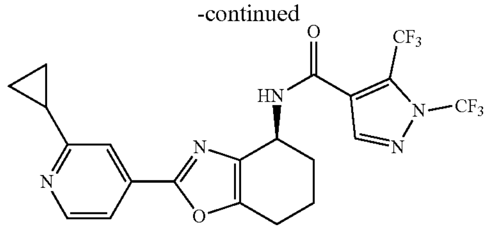

Following the procedure described in Example 1.26, (S)—N-(2-(2-cyclopropylpyridin-4-yl)-4,5,6,7-tetrahydrobenzo[d]oxazol-4-yl)-1,3-bis(trifluoromethyl)-1H-pyrazole-4-carboxamide HCl salt and acid (mixture, prepared according to the procedure in J. Med. Chem., 2021, 64, 16159) were used in step 7, the title compound (50 mg, mixture) was obtained as a white solid after purification of RP-HPLC (Column: 58-Phenomenex Gemini NX C18 150×40 mm, 5 m; mobile phase: acetonitrile 45%-75%/0.225% formic acid in water). The mixture was separated by chiral SFC (Daicel ChiralPak AS (250 mm*30 mm, 10 um); Supercritical $CO_2$/EtOH+0.1% $NH_3 \cdot H_2O$=18/82; 150 mL/min) to afford (S)—N-(2-(2-cyclopropylpyridin-4-yl)-4,5,6,7-tetrahydrobenzo[d]oxazol-4-yl)-1,3-bis(trifluoromethyl)-1H-pyrazole-4-carboxamide (23 mg, first peak) and (S)—N-(2-(2-cyclopropylpyridin-4-yl)-4,5,6,7-tetrahydrobenzo[d]oxazol-4-yl)-1,5-bis(trifluoromethyl)-1H-pyrazole-4-carboxamide (3.15 mg, second peak) both as white solids. First peak: I-519a: $^1H$ NMR (400 MHz, DMSO-$d_6$) δ 9.19 (s, 1H), 8.85 (d, J=8.0 Hz, 1H), 8.53 (d, J=5.2 Hz, 1H), 7.80 (s, 1H), 7.60 (dd, J=1.6, 5.2 Hz, 1H), 7.22-6.92 (m, 1H), 5.16-5.03 (m, 1H), 2.86-2.71 (m, 2H), 2.28-2.20 (m, 1H), 2.02-1.81 (m, 4H), 1.02-0.94 (m, 4H). LCMS (ESI) m/z: 486.2 $[M+H]^+$. Second peak: I-530a: $^1H$ NMR (400 MHz, DMSO-$d_6$) δ 9.18 (d, J=8.0 Hz, 1H), 8.53 (d, J=5.2 Hz, 1H), 8.39 (s, 1H), 7.80 (s, 1H), 7.59 (dd, J=1.6, 5.2 Hz, 1H), 5.09-5.03 (m, 1H), 2.81-2.73 (m, 2H), 2.28-2.20 (m, 1H), 1.98-1.82 (m, 4H), 1.01-0.94 (m, 4H). LCMS (ESI) m/z: 486.2 $[M+H]^+$.

Example 1.78. Synthesis of (S)-1,3-Bis(trifluoromethyl)-N-(2-(2-(trifluoromethyl)pyridin-4-yl)-4,5,6,7-tetrahydrobenzo[d]oxazol-4-yl)-1H-pyrazole-4-carboxamide & (S)-1,5-Bis(trifluoromethyl)-N-(2-(2-(trifluoromethyl)pyridin-4-yl)-4,5,6,7-tetrahydrobenzo[d]oxazol-4-yl)-1H-pyrazole-4-carboxamide (I-520a and I-531a)

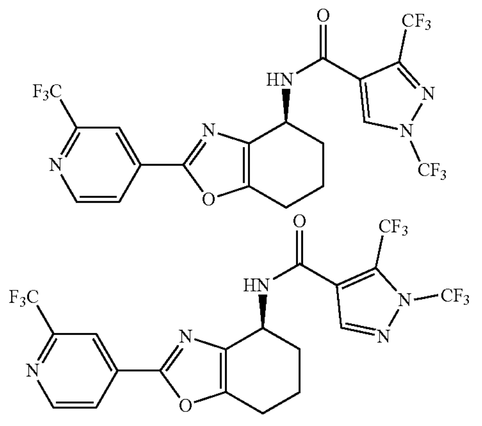

Step 1—Synthesis of (S)-1,3-Bis(trifluoromethyl)-N-(2-(2-(trifluoromethyl)pyridin-4-yl)-4,5,6,7-tetrahydrobenzo[d]oxazol-4-yl)-1H-pyrazole-4-carboxamide & (S)-1,5-Bis(trifluoromethyl)-N-(2-(2-(trifluoromethyl)pyridin-4-yl)-4,5,6,7-tetrahydrobenzo[d]oxazol-4-yl)-1H-pyrazole-4-carboxamide

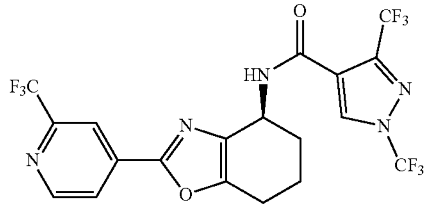

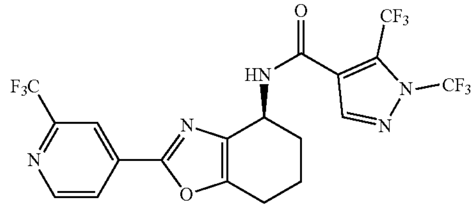

Following the procedure described in Example 1.26, (S)-2-(2-(trifluoromethyl)pyridin-4-yl)-4,5,6,7-tetrahydrobenzo[d]oxazol-4-amine HCl salt was used in step 7, the title compound (55 mg, mixture) was obtained as a white solid after purification of RP-HPLC (Column: 58-Phenomenex Gemini NX C18 150×40 mm, 5 m; mobile phase: acetonitrile 60%-90%/0.225% formic acid in water). The mixture was separated by chiral SFC (Daicel ChiralPak AD (250 mm*30 mm, 10 μm); Supercritical $CO_2$/EtOH+0.1% $NH_3 \cdot H_2O$=10/90; 150 mL/min) to afford (S)-1,3-bis(trifluoromethyl)-N-(2-(2-(trifluoromethyl)pyridin-4-yl)-4,5,6,7-tetrahydrobenzo[d]oxazol-4-yl)-1H-pyrazole-4-carboxamide (35.44 mg, first peak) and (S)-1,5-bis(trifluoromethyl)-N-(2-(2-(trifluoromethyl)pyridin-4-yl)-4,5,6,7-tetrahydrobenzo[d]oxazol-4-yl)-1H-pyrazole-4-carboxamide (11.7 mg, second peak) both as white solids. First peak: I-520a: $^1H$ NMR (400 MHz, DMSO-$d_6$) δ 9.19 (s, 1H), 8.93 (d, J=4.8 Hz, 1H), 8.88 (d, J=8.0 Hz, 1H), 8.22 (s, 1H), 8.18 (dd, J=1.2, 5.2 Hz, 1H), 5.15-5.08 (m, 1H), 2.89-2.73 (m, 2H), 2.07 (s, 1H), 2.03-1.82 (m, 4H). LCMS (ESI) m/z: 514.2 $[M+H]^+$. Second peak: I-531a: $^1H$ NMR (400 MHz, DMSO-$d_6$) δ 9.19 (d, J=8.0 Hz, 1H), 8.93 (d, J=4.8 Hz, 1H), 8.39 (s, 1H), 8.23 (s, 1H), 8.18 (dd, J=1.2, 5.2 Hz, 1H), 5.12-5.07 (m, 1H), 2.83-2.76 (m, 2H), 2.01-1.82 (m, 4H). LCMS (ESI) m/z: 514.2 $[M+H]^+$.

Example 1.79. Synthesis of (S)-1,3-Bis(trifluoromethyl)-N-(2-(2-(trifluoromethyl)pyridin-4-yl)-5,6-dihydro-4H-pyrrolo[1,2-b]pyrazol-4-yl)-1H-pyrazole-4-carboxamide & (S)-1,5-Bis(trifluoromethyl)-N-(2-(2-(trifluoromethyl)pyridin-4-yl)-5,6-dihydro-4H-pyrrolo[1,2-b]pyrazol-4-yl)-1H-pyrazole-4-carboxamide (I-521a and I-532a)

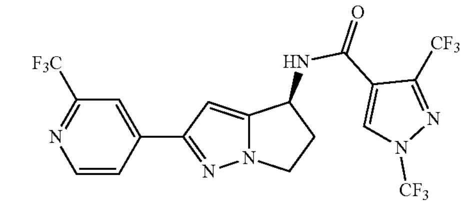

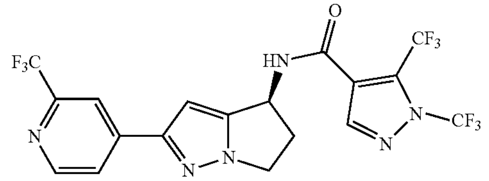

Step 1—Synthesis of (S)-1,3-Bis(trifluoromethyl)-N-(2-(2-(trifluoromethyl)pyridin-4-yl)-5,6-dihydro-4H-pyrrolo[1,2-b]pyrazol-4-yl)-1H-pyrazole-4-carboxamide & (S)-1,5-Bis(trifluoromethyl)-N-(2-(2-(trifluoromethyl)pyridin-4-yl)-5,6-dihydro-4H-pyrrolo[1,2-b]pyrazol-4-yl)-1H-pyrazole-4-carboxamide

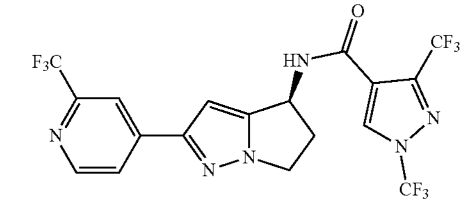

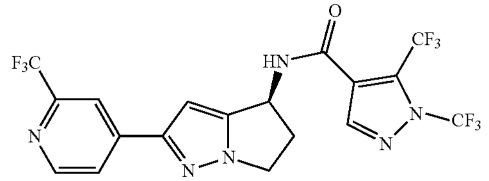

Following the procedure described in Example 1.26, (S)-2-(2-(trifluoromethyl)pyridin-4-yl)-5,6-dihydro-4H-pyrrolo[1,2-b]pyrazol-4-amine HCl salt was used in step 7, the title compound (55 mg, mixture) was obtained as a white solid after purification of RP-HPLC (Column: 58-Phenomenex Gemini NX C18 150×40 mm, 5 m; mobile phase: acetonitrile 55%-85%/0.225% formic acid in water). The mixture was separated was separated by using chiral SFC AD (250 mm*30 mm, 10 μm); Supercritical $CO_2$/EtOH+0.1% $NH_3 \cdot H_2O$=10/90; 150 mL/min) to afford (S)-1,3-bis(trifluoromethyl)-N-(2-(2-(trifluoromethyl)pyridin-4-yl)-5,6-dihydro-4H-pyrrolo[1,2-b]pyrazol-4-yl)-1H-pyrazole-4-carboxamide (12.51 mg, first peak) and (S)-1,5-bis(trifluoromethyl)-N-(2-(2-(trifluoromethyl)pyridin-4-yl)-5,6-dihydro-4H-pyrrolo[1,2-b]pyrazol-4-yl)-1H-pyrazole-4-carboxamide (10.07 mg, second peak) both as white solids. First peak: I-521a: $^1$H NMR (400 MHz, DMSO-$d_6$) δ 9.19 (s, 1H), 9.13 (d, J=7.6 Hz, 1H), 8.75 (d, J=5.2 Hz, 1H), 8.20 (s, 1H), 8.07 (dd, J=0.8, 5.2 Hz, 1H), 7.00 (s, 1H), 5.52-5.47 (m, 1H), 4.40-4.34 (m, 1H), 4.27-4.21 (m, 1H), 3.10-3.02 (m, 1H), 2.49-2.43 (m, 1H). LCMS (ESI) m/z: 499.0 $[M+H]^+$. Second peak: I-532a: $^1$H NMR (400 MHz, DMSO-$d_6$) δ 9.44 (d, J=7.6 Hz, 1H), 8.75 (d, J=5.2 Hz, 1H), 8.41 (s, 1H), 8.20 (s, 1H), 8.08 (dd, J=0.8, 5.2 Hz, 1H), 6.99 (s, 1H), 5.52-5.47 (m, 1H), 4.40-4.34 (m, 1H), 4.27-4.21 (m, 1H), 3.10-3.02 (m, 1H), 2.49-2.42 (m, 1H). LCMS (ESI) m/z: 499.0 $[M+H]^+$.

Example 1.80. Synthesis of (S)-1,3-Bis(trifluoromethyl)-N-(2-(2-(trifluoromethyl)pyridin-4-yl)-4,5,6,7-tetrahydropyrazolo[1,5-a]pyridin-4-yl)-1H-pyrazole-4-carboxamide & (S)-1,5-Bis(trifluoromethyl)-N-(2-(2-(trifluoromethyl)pyridin-4-yl)-4,5,6,7-tetrahydropyrazolo[1,5-a]pyridin-4-yl)-1H-pyrazole-4-carboxamide (I-338a and I-529a)

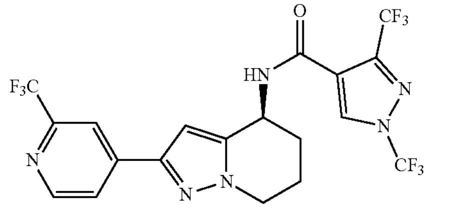

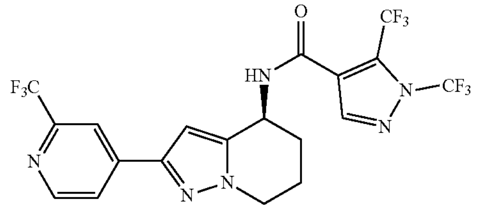

Step 1—Synthesis of (S)-1,3-Bis(trifluoromethyl)-N-(2-(2-(trifluoromethyl)pyridin-4-yl)-4,5,6,7-tetrahydropyrazolo[1,5-a]pyridin-4-yl)-1H-pyrazole-4-carboxamide & (S)-1,5-Bis(trifluoromethyl)-N-(2-(2-(trifluoromethyl)pyridin-4-yl)-4,5,6,7-tetrahydropyrazolo[1,5-a]pyridin-4-yl)-1H-pyrazole-4-carboxamide

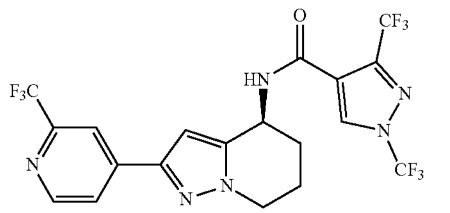

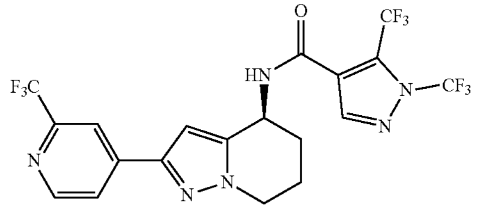

Following the procedure described in Example 1.26, (S)-2-(2-(trifluoromethyl)pyridin-4-yl)-4,5,6,7-tetrahydro-pyrazolo[1,5-a]pyridin-4-amine HCl salt was used in step 7, the title compound (63 mg, mixture) was obtained as a white solid after purification of RP-HPLC (Column: 58-Phenomenex Gemini NX C18 150×40 mm, 5 m; mobile phase: acetonitrile 55%-85%/0.225% formic acid in water). The mixture was separated by using chiral SFC AD (250 mm*30 mm, 10 μm); Supercritical $CO_2$/EtOH+0.1% $NH_3 \cdot H_2O$=20/80; 150 mL/min) to afford (S)-1,3-bis(trifluoromethyl)-N-(2-(2-(trifluoromethyl)pyridin-4-yl)-4,5,6,7-tetrahydropyrazolo[1,5-a]pyridin-4-yl)-1H-pyrazole-4-carboxamide (23.6 mg, first peak) and (S)-1,5-bis(trifluoromethyl)-N-(2-(2-(trifluoromethyl)pyridin-4-yl)-4,5,6,7-tetrahydropyrazolo[1,5-a]pyridin-4-yl)-1H-pyrazole-4-carboxamide (13 mg, second peak) both as white solids. First peak: I-338a: $^1$H NMR (400 MHz, DMSO-$d_6$) δ 9.22 (s, 1H), 9.07 (d, J=8.0 Hz, 1H), 8.75 (d, J=5.2 Hz, 1H), 8.18 (s, 1H), 8.05 (d, J=4.8 Hz, 1H), 7.02 (s, 1H), 5.33-5.25 (m, 1H), 4.28-4.14 (m, 2H), 2.25-2.03 (m, 3H), 1.85-1.75 (m, 1H). LCMS (ESI) m/z: 513.2 [M+H]$^+$. Second peak: I-529a: $^1$H NMR (400 MHz, DMSO-$d_6$) δ 9.38 (d, J=8.0 Hz, 1H), 8.77 (d, J=5.2 Hz, 1H), 8.45 (s, 1H), 8.18 (s, 1H), 8.06 (d, J=5.2 Hz, 1H), 7.02 (s, 1H), 5.32-5.25 (m, 1H), 4.26-4.12 (m, 2H), 2.21-2.05 (m, 3H), 1.84-1.74 (m, 1H). LCMS (ESI) m/z: 513.2 [M+H]$^+$.

Example 1.81. Synthesis of (S)-3-(Trifluoromethyl)-N-(2-(2-(trifluoromethyl)pyridin-4-yl)-6,7,8,9-tetrahydro-5H-cyclohepta[b]pyridin-5-yl)benzamide & (R)-3-(Trifluoromethyl)-N-(2-(2-(trifluoromethyl)pyridin-4-yl)-6,7,8,9-tetrahydro-5H-cyclohepta[b]pyridin-5-yl)benzamide (I-339a and I-339b)

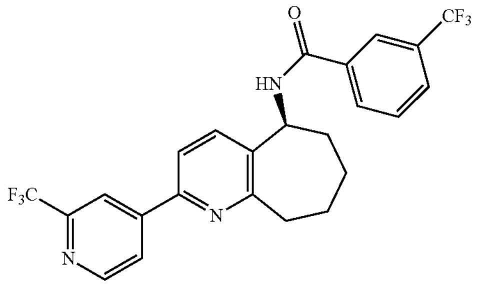

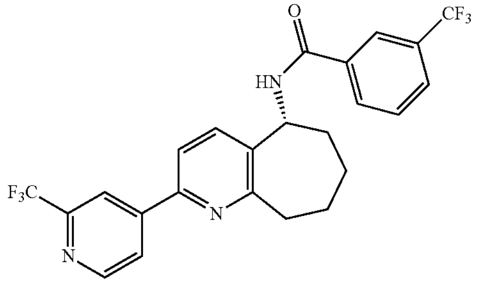

Step 1—Synthesis of N-(2-(2-(1,1-Difluoroethyl)pyridin-4-yl)-4,5,6,7-tetrahydrobenzo[d]oxazol-4-yl)-1,3-bis(trifluoromethyl)-1H-pyrazole-4-carboxamide

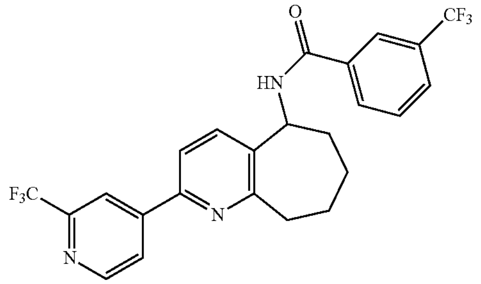

Following the procedure described in Example 1.26, 2-(2-(trifluoromethyl)pyridin-4-yl)-6,7,8,9-tetrahydro-5H-cyclohepta[b]pyridin-5-amine HCl salt and 3-(trifluoromethyl)benzoic acid were used in step 7, the title compound (80 mg, 36%) was obtained as a white solid after purification of RP-HPLC (Column: Welch Xtimate C18 150*30 mm*5 μm; mobile phase: acetonitrile 55%-85%/0.225% formic acid in water).

Step 2—Synthesis of (S)-3-(Trifluoromethyl)-N-(2-(2-(trifluoromethyl)pyridin-4-yl)-6,7,8,9-tetrahydro-5H-cyclohepta[b]pyridin-5-yl)benzamide & (R)-3-(Trifluoromethyl)-N-(2-(2-(trifluoromethyl)pyridin-4-yl)-6,7,8,9-tetrahydro-5H-cyclohepta[b]pyridin-5-yl)benzamide

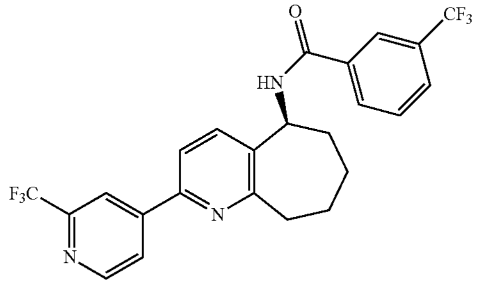

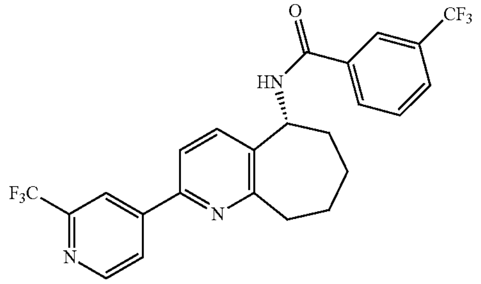 [SMILES: O=C(NC1CCCCc2nc(-c3ccnc(C(F)(F)F)c3)ccc21)c1cccc(C(F)(F)F)c1]

A mixture of 3-(trifluoromethyl)-N-(2-(2-(trifluoromethyl)pyridin-4-yl)-6,7,8,9-tetrahydro-5H-cyclohepta[b]pyridin-5-yl)benzamide (80 mg, 167 μmol) was separated by chiral SFC (DAICEL CHIRALCEL OJ (250 mm*30 mm, 10 μm); Supercritical $CO_2$/i-PrOH+0.1% $NH_3 \cdot H_2O$=80/15; 80 mL/min) to afford (S)-3-(trifluoromethyl)-N-(2-(2-(trifluoromethyl)pyridin-4-yl)-6,7,8,9-tetrahydro-5H-cyclohepta

[b]pyridin-5-yl)benzamide (18 mg, first peak) and (R)-3-(trifluoromethyl)-N-(2-(2-(trifluoromethyl)pyridin-4-yl)-6,7,8,9-tetrahydro-5H-cyclohepta[b]pyridin-5-yl)benzamide (29 mg, second peak) both as white solids. First peak: I-339a: $^1$H NMR (400 MHz, DMSO-$d_6$) δ 9.28 (d, J=7.4 Hz, 1H), 8.87 (d, J=5.2 Hz, 1H), 8.49 (s, 1H), 8.36-8.31 (m, 2H), 8.27 (d, J=7.8 Hz, 1H), 8.07 (d, J=8.2 Hz, 1H), 7.96 (d, J=7.8 Hz, 1H), 7.80-7.76 (m, 1H), 7.72 (d, J=8.2 Hz, 1H), 5.35-5.29 (m, 1H), 3.23-3.19 (m, 2H), 2.11-1.91 (m, 4H), 1.84-1.75 (m, 1H), 1.47-1.36 (m, 1H). LCMS (ESI) m/z: 480.1 $[M+H]^+$. Second peak I-339b: $^1$H NMR (400 MHz, DMSO-$d_6$) δ 9.28 (d, J=7.4 Hz, 1H), 8.87 (d, J=5.2 Hz, 1H), 8.49 (s, 1H), 8.36-8.31 (m, 2H), 8.27 (d, J=7.8 Hz, 1H), 8.07 (d, J=8.2 Hz, 1H), 7.96 (d, J=7.8 Hz, 1H), 7.80-7.76 (m, 1H), 7.72 (d, J=8.2 Hz, 1H), 5.35-5.28 (m, 1H), 3.24-3.18 (m, 2H), 2.12-1.91 (m, 4H), 1.84-1.74 (m, 1H), 1.48-1.37 (m, 1H). LCMS (ESI) m/z: 480.1 $[M+H]^+$.

Compounds in the table below were synthesized according to one of the general routes outlined in the Examples above or by various other methods generally known in the art.

| Compound No. | Structure | Analytical data | Separation conditions |
|---|---|---|---|
| I-177a | 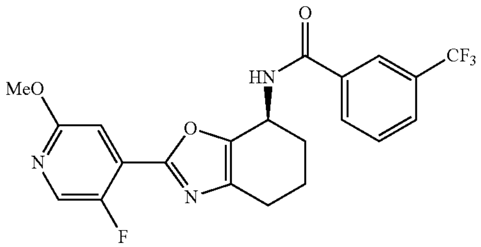 [SMILES: COc1cc(-c2nc3c(o2)[C@@H](NC(=O)c2cccc(C(F)(F)F)c2)CCC3)c(F)cn1] (S)-N-(2-(5-Fluoro-2-methoxypyridin-4-yl)-4,5,6,7-tetrahydrobenzo[d]oxazol-7-yl)-3-(trifluoromethyl)benzamide | LCMS (ESI) m/z: 436.1 $[M + H]^+$. $^1$H NMR (400 MHz, DMSO-$d_6$) δ 9.17 (d, J = 7.6 Hz, 1H), 8.34 (d, J = 2.4 Hz, 1H), 8.24-8.18 (m, 2H), 7.92 (d, J = 8.0 Hz, 1H), 7.76-7.70 (m, 1H), 7.25 (d, J = 4.8 Hz, 1H), 5.42-5.32 (m, 1H), 3.86 (s, 3H), 2.67-2.53 (m, 2H), 2.10-1.83 (m, 4H). | acetonitrile 40%-70%/0.225% formic acid in water |
| I-176a | 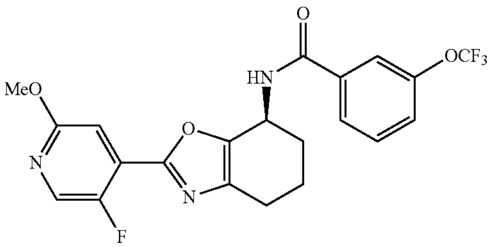 (S)-N-(2-(5-Fluoro-2-methoxypyridin-4-yl)-4,5,6,7-tetrahydrobenzo[d]oxazol-7-yl)-3-(trifluoromethoxy)benzamide | LCMS (ESI) m/z: 452.1 $[M + H]^+$. $^1$H NMR (400 MHz, DMSO-$d_6$) δ 9.09 (d, J = 7.6 Hz, 1H), 8.35 (d, J = 2.4 Hz, 1H), 7.94 (d, J = 7.6 Hz, 1H), 7.84 (s, 1H), 7.66-7.60 (m, 1H), 7.59-7.55 (m, 1H), 7.25 (d, J = 4.8 Hz, 1H), 5.38-5.32 (m, 1H), 3.87 (s, 3H), 2.68-2.57 (m, 2H), 2.13-1.84 (m, 4H). | acetonitrile 40%-70%/0.225% formic acid in water |
| I-175a | 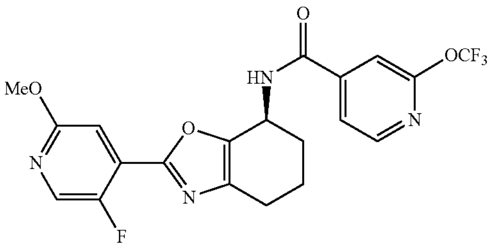 1-Methyl-4-(trifluoromethyl)-N-(2-(2-(trifluoromethyl)pyridin-4-yl)-4,5,6,7-tetrahydro-2H-indazol-4-yl)-1H-imidazole-2-carboxamide | LCMS (ESI) m/z: 453.1 $[M + H]^+$. $^1$H NMR (400 MHz, DMSO-$d_6$) δ 9.31 (d, J = 7.6 Hz, 1H), 8.52 (d, J = 5.2 Hz, 1H), 8.36 (d, J = 2.4 Hz, 1H), 7.85-7.81 (m, 1H), 7.66 (s, 1H), 7.26 (d, J = 5.2 Hz, 1H), 5.38-5.30 (m, 1H), 3.87 (s, 3H), 2.67-2.55 (m, 2H), 2.11-1.84 (m, 4H). | acetonitrile 40%-70%/0.225% formic acid in water |
| I-174a | 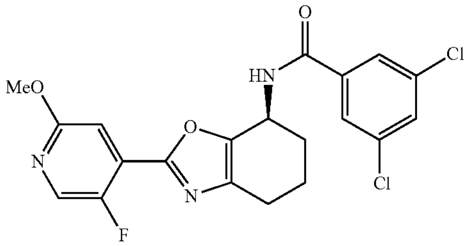 [SMILES: COc1cc(-c2nc3c(o2)[C@@H](NC(=O)c2cc(Cl)cc(Cl)c2)CCC3)c(F)cn1] (S)-3,5-Dichloro-N-(2-(5-fluoro-2-methoxypyridin-4-yl)-4,5,6,7-tetrahydrobenzo[d]oxazol-7-yl)benzamide | LCMS (ESI) m/z: 436.0 $[M + H]^+$. $^1$H NMR (400 MHz, DMSO-$d_6$) δ 9.12 (d, J = 7.6 Hz, 1H), 8.34 (d, J = 2.0 Hz, 1H), 7.90 (d, J = 2.0 Hz, 2H), 7.82-7.79 (m, 1H), 7.25 (d, J = 4.8 Hz, 1H), 5.35-5.28 (m, 1H), 3.86 (s, 3H), 2.69-2.54 (m, 2H), 2.07-1.80 (m, 4H) | acetonitrile 35%-65%/0.225% formic acid in water |

-continued

| Compound No. | Structure | Analytical data | Separation conditions |
|---|---|---|---|
| I-173a | 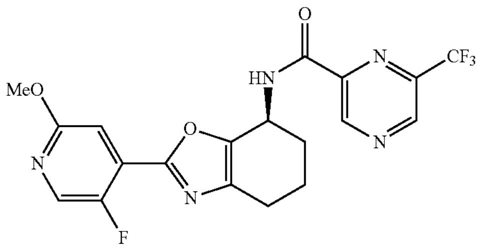 [SMILES: COc1cc(-c2nc3c(o2)[C@@H](NC(=O)c2cncc(C(F)(F)F)n2)CCC3)c(F)cn1]<br>(S)-N-(2-(5-Fluoro-2-methoxypyridin-4-yl)-4,5,6,7-tetrahydrobenzo[d]oxazol-7-yl)-3-(trifluoromethyl)benzamide | LCMS (ESI) m/z: 438.1 $[M + H]^+$. $^1$H NMR (400 MHz, DMSO-$d_6$) δ 9.51-9.38 (m, 3H), 8.34 (s, 1H), 7.23 (d, J = 4.4 Hz, 1H), 5.41 (d, J = 6.0 Hz, 1H), 3.86 (s, 3H), 2.59-2.60 (m, 2H), 2.13-1.80 (m, 4H). | acetonitrile 35%-65%/ 0.225% formic acid in water |
| I-168a | 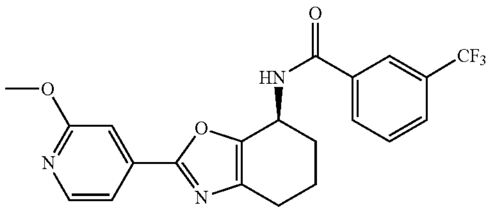 [SMILES: COc1cc(-c2nc3c(o2)[C@@H](NC(=O)c2cccc(C(F)(F)F)c2)CCC3)ccn1]<br>(S)-N-(2-(2-Methoxypyridin-4-yl)-4,5,6,7-tetrahydrobenzo[d]oxazol-7-yl)-3-(trifluoromethyl)benzamide | LCMS (ESI) m/z: 418.0 $[M + H]^+$. $^1$H NMR (400 MHz, DMSO-$d_6$) δ 9.18 (d, J = 7.6 Hz, 1H), 8.30 (d, J = 5.6 Hz, 1H), 8.27-8.18 (m, 2H), 7.92 (d, J = 7.6 Hz, 1H), 7.75-7.71 (m, 1H), 7.46 (dd, J = 1.2, 5.6 Hz, 1H), 7.21 (s, 1H), 5.43-5.29 (m, 1H), 3.89 (s, 3H), 2.69-2.54 (m, 2H), 2.13-1.79 (m, 4H). | acetonitrile 51%-81%/ 0.225% formic acid in water |
| I-135a | 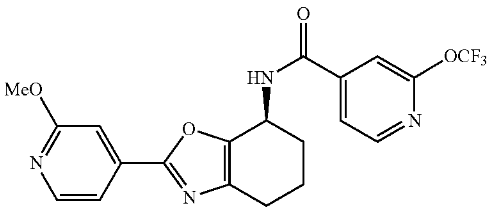 [SMILES: COc1cc(-c2nc3c(o2)[C@@H](NC(=O)c2ccnc(OC(F)(F)F)c2)CCC3)ccn1]<br>(S)-N-(2-(2-Methoxypyridin-4-yl)-4,5,6,7-tetrahydrobenzo[d]oxazol-7-yl)-2-(trifluoromethoxy)isonicotinamide | LCMS (ESI) m/z: 435.5 $[M + H]^+$. $^1$H NMR (400 MHz, DMSO-$d_6$) δ 9.30 (d, J = 7.6 Hz, 1H), 8.52 (d, J = 5.2 Hz, 1H), 8.30 (d, J = 5.2 Hz, 1H), 7.85 (dd, J = 1.2, 5.2 Hz, 1H), 7.67 (s, 1H), 7.46 (dd, J = 1.2, 5.2 Hz, 1H), 7.22 (s, 1H), 5.40-5.23 (m, 1H), 3.89 (s, 3H), 2.65-2.54 (m, 2H), 2.14-2.03 (m, 1H), 2.01-1.89 (m, 2H), 1.89-1.80 (m, 1H). | acetonitrile 45%-75%/ 0.225% formic acid in water |
| I-151a | 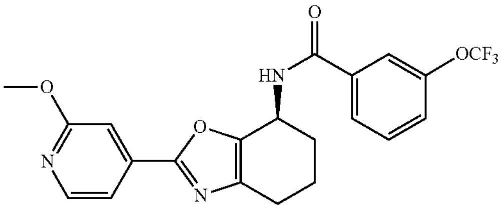<br>(S)-N-(2-(2-Methoxypyridin-4-yl)-4,5,6,7-tetrahydrobenzo[d]oxazol-7-yl)-3-(trifluoromethoxy)benzamide | LCMS (ESI) m/z: 434.1 $[M + H]^+$. $^1$H NMR (400 MHz, DMSO-$d_6$) δ 9.30 (d, J = 7.6 Hz, 1H), 8.30 (d, J = 5.2 Hz, 1H), 7.96 (d, J = 7.6 Hz, 1H), 7.86 (s, 1H), 7.66-7.60 (m, 1H), 7.59-7.53 (m, 1H), 7.46 (dd, J = 1.2, 5.2 Hz, 1H), 7.21 (s, 1H), 5.51-5.21 (m, 1H), 3.89 (s, 3H), 2.70-2.55 (m, 2H), 2.13-1.78 (m, 4H). | acetonitrile 52%-82%/ 0.225% formic acid in water |
| I-143a | 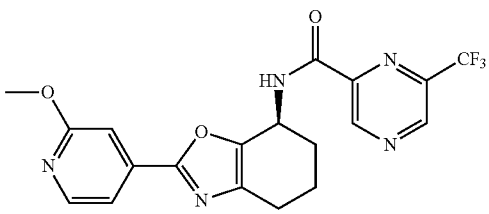 [SMILES: COc1cc(-c2nc3c(o2)[C@@H](NC(=O)c2cncc(C(F)(F)F)n2)CCC3)ccn1]<br>(S)-N-(2-(2-Methoxypyridin-4-yl)-4,5,6,7-tetrahydrobenzo[d]oxazol-7-yl)-6-(trifluoromethyl)pyrazine-2-carboxamide | LCMS (ESI) m/z: 420.1 $[M + H]^+$. $^1$H NMR (400 MHz, DMSO-$d_6$) δ 9.51 (s, 1H), 9.46 (d, J = 8.2 Hz, 1H), 9.40 (s, 1H), 8.29 (d, J = 5.2 Hz, 1H), 7.44 (dd, J = 1.6, 5.2 Hz, 1H), 7.19 (s, 1H), 5.47-5.36 (m, 1H), 3.88 (s, 3H), 2.64-2.55 (m, 2H), 2.16-2.05 (m, 1H), 2.05-1.95 (m, 2H), 1.92-1.78 (m, 1H). | acetonitrile 50%-80%/ 0.225% formic acid in water |

-continued

| Compound No. | Structure | Analytical data | Separation conditions |
|---|---|---|---|
| I-150a | 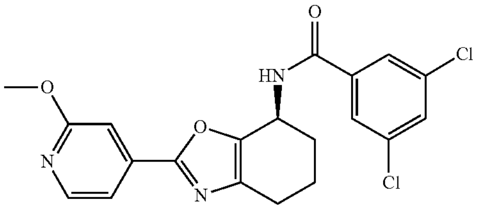 [SMILES: COc1cc(-c2nc3c(o2)[C@@H](NC(=O)c2cc(Cl)cc(Cl)c2)CCC3)ccn1] (S)-3,5-Dichloro-N-(2-(2-methoxypyridin-4-yl)-4,5,6,7-tetrahydrobenzo[d]oxazol-7-yl)benzamide | LCMS (ESI) m/z: 418.0 [M + H]$^+$. $^1$H NMR (400 MHz, DMSO-$d_6$) δ 9.12 (d, J = 7.6 Hz, 1H), 8.30 (d, J = 5.6 Hz, 1H), 7.93 (d, J = 2.0 Hz, 2H), 7.84-7.80 (m, 1H), 7.46 (dd, J = 1.2, 5.2 Hz, 1H), 7.22 (s, 1H), 5.40-5.23 (m, 1H), 3.89 (s, 3H), 2.69-2.54 (m, 2H), 2.13-1.77 (m, 4H). | acetonitrile 55%-85%/ 0.225% formic acid in water |
| I-171a | 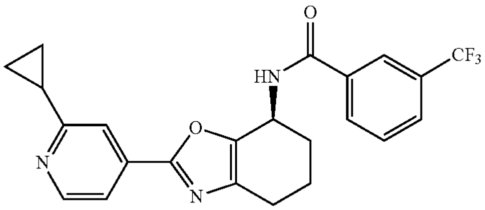 (S)-N-(2-(2-Cyclopropylpyridin-4-yl)-4,5,6,7-tetrahydrobenzo[d]oxazol-7-yl)-3-(trifluoromethyl)benzamide | LCMS (ESI) m/z: 428.2 [M + H]$^+$. $^1$H NMR (400 MHz, DMSO-$d_6$) δ 9.20 (d, J = 7.6 Hz, 1H), 8.51 (d, J = 5.2 Hz, 1H), 8.26 (s, 1H), 8.23 (d, J = 8.0 Hz, 1H), 7.93 (d, J = 8.0 Hz, 1H), 7.80 (s, 1H), 7.76-7.73 (m, 1H), 7.59 (dd, J = 1.2, 5.2 Hz, 1H), 5.47-5.30 (m, 1H), 2.66-2.53 (m, 2H), 2.27-2.21 (m, 1H), 2.13-2.04 (m, 1H), 2.02-1.90 (m, 2H), 1.90-1.82 (m, 1H), 0.99-0.88 (m, 4H). | acetonitrile 27%-57%/ 0.225% formic acid in water |
| I-170a | 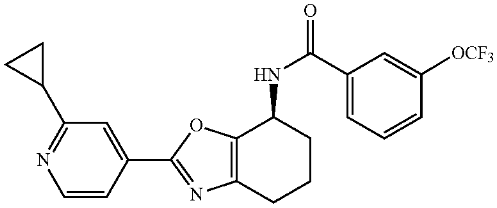 [SMILES: O=C(N[C@H]1CCCc2nc(-c3ccnc(C4CC4)c3)oc21)c1cccc(OC(F)(F)F)c1] (S)-N-(2-(2-Cyclopropylpyridin-4-yl)-4,5,6,7-tetrahydrobenzo[d]oxazol-7-yl)-3-(trifluoromethoxy)benzamide | LCMS (ESI) m/z: 444.2 [M + H]$^+$. $^1$H NMR (400 MHz, DMSO-$d_6$) δ 9.11 (d, J = 7.6 Hz, 1H), 8.51 (d, J = 4.4 Hz, 1H), 7.97 (d, J = 7.6 Hz, 1H), 7.87 (s, 1H), 7.80 (s, 1H), 7.66-7.61 (m, 1H), 7.60-7.55 (m, 2H), 5.39-5.33 (m, 1H), 2.65-2.54 (m, 2H), 2.28-2.21 (m, 1H), 2.11-2.03 (m, 1H), 2.02-1.90 (m, 2H), 1.89-1.82 (m, 1H), 1.00-0.93 (m, 4H). | acetonitrile 35%-65%/ 0.225% formic acid in water |
| I-169a | 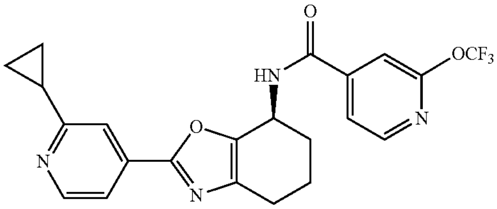 (S)-N-(2-(2-Cyclopropylpyridin-4-yl)-4,5,6,7-tetrahydrobenzo[d]oxazol-7-yl)-2-(trifluoromethoxy)isonicotinamide | LCMS (ESI) m/z: 445.2 [M + H]$^+$. $^1$H NMR (400 MHz, DMSO-$d_6$) δ 9.33 (d, J = 7.6 Hz, 1H), 8.54-8.50 (m, 2H), 7.86 (dd, J = 1.2, 5.2 Hz, 1H), 7.80 (s, 1H), 7.68 (s, 1H), 7.59 (dd, J = 1.6, 5.2 Hz, 1H), 5.40-5.28 (m, 1H), 2.64-2.52 (m, 2H), 2.29-2.21 (m, 1H), 2.14-2.03 (m, 1H), 2.02-1.90 (m, 2H), 1.89-1.78 (m, 1H), 1.01-0.90 (m, 4H). | acetonitrile 27%-57%/ 0.225% formic acid in water |
| I-153a | 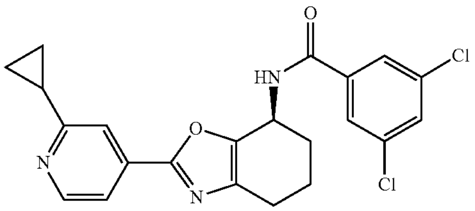 [SMILES: O=C(N[C@H]1CCCc2nc(-c3ccnc(C4CC4)c3)oc21)c1cc(Cl)cc(Cl)c1] (S)-3,5-Dichloro-N-(2-(2-cyclopropylpyridin-4-yl)-4,5,6,7-tetrahydrobenzo[d]oxazol-7-yl)benzamide | LCMS (ESI) m/z: 428.2 [M + H]$^+$. $^1$H NMR (400 MHz, DMSO-$d_6$) δ 9.15 (d, J = 7.6 Hz, 1H), 8.52 (d, J = 5.2 Hz, 1H), 7.94 (d, J = 2.0 Hz, 2H), 7.83 (t, J = 2.0 Hz, 1H), 7.80 (s, 1H), 7.59 (dd, J = 1.6, 5.2 Hz, 1H), 5.36-5.30 (m, 1H), 2.65-2.54 (m, 2H), 2.28-2.21 (m, 1H), 2.11-2.02 (m, 1H), 2.00-1.89 (m, 2H), 1.88-1.79 (m, 1H), 0.98-0.92 (m, 4H). | acetonitrile 25%-65%/ 0.225% formic acid in water |

-continued

| Compound No. | Structure | Analytical data | Separation conditions |
|---|---|---|---|
| I-152a | 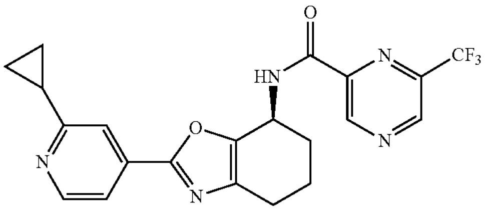 [SMILES: O=C(N[C@H]1CCCc2nc(-c3ccnc(C4CC4)c3)oc21)c1cncc(C(F)(F)F)n1] (S)-N-(2-(2-Cyclopropylpyridin-4-yl)-4,5,6,7-tetrahydrobenzo[d]oxazol-7-yl)-6-(trifluoromethyl)pyrazine-2-carboxamide | LCMS (ESI) m/z: 430.2 [M + H]$^+$. $^1$H NMR (400 MHz, DMSO-$d_6$) δ 9.52 (s, 1H), 9.49 (d, J = 8.4 Hz, 1H), 9.41 (s, 1H), 8.51 (d, J = 5.2 Hz, 1H), 7.78 (s, 1H), 7.57 (dd, J = 1.6, 5.2 Hz, 1H), 5.45-5.39 (m, 1H), 2.64-2.55 (m, 2H), 2.27-2.20 (m, 1H), 2.16-2.07 (m, 1H), 2.05-1.95 (m, 2H), 1.91-1.81 (m, 1H), 0.98-0.91 (m, 4H). | acetonitrile 24%-54%/0.225% formic acid in water |
| I-180a | 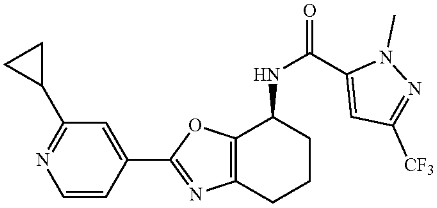 [SMILES: Cn1nc(C(F)(F)F)cc1C(=O)N[C@H]1CCCc2nc(-c3ccnc(C4CC4)c3)oc21] (S)-N-(2-(2-Cyclopropylpyridin-4-yl)-4,5,6,7-tetrahydrobenzo[d]oxazol-7-yl)-1-methyl-3-(trifluoromethyl)-1H-pyrazole-5-carboxamide | LCMS (ESI) m/z: 432.2 [M + H]$^+$. $^1$H NMR (400 MHz, DMSO-$d_6$) δ 9.12 (d, J = 8.0 Hz, 1H), 8.53 (d, J = 4.8 Hz, 1H), 7.80 (s, 1H), 7.60 (dd, J = 1.6, 5.2 Hz, 1H), 7.38 (s, 1H), 5.36-5.24 (m, 1H), 4.19 (s, 3H), 2.66-2.52 (m, 2H), 2.28-2.21 (m, 1H), 2.11-2.01 (m, 1H), 1.98-1.75 (m, 3H), 1.02-0.91 (m, 4H). | acetonitrile 39%-69%/0.225% formic acid in water |
| I-184a | 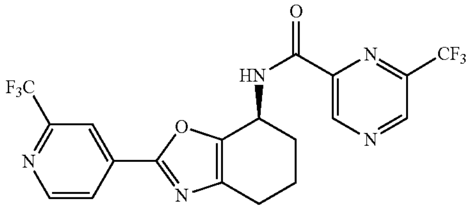 [SMILES: O=C(N[C@H]1CCCc2nc(-c3ccnc(C(F)(F)F)c3)oc21)c1cncc(C(F)(F)F)n1] (S)-6-(Trifluoromethyl)-N-(2-(2-(trifluoromethyl)pyridin-4-yl)-4,5,6,7-tetrahydrobenzo[d]oxazol-7-yl)pyrazine-2-carboxamide | LCMS (ESI) m/z: 458.1 [M + H]$^+$. $^1$H NMR (400 MHz, DMSO-$d_6$) δ 9.52 (s, 1H), 9.52 (d, J = 8.4 Hz, 1H), 9.42 (s, 1H), 8.91 (d, J = 5.2 Hz, 1H), 8.28-8.10 (m, 2H), 5.61-5.25 (m, 1H), 2.70-2.61 (m, 1H), 2.16-1.96 (m, 2H), 1.89-1.73 (m, 1H). | acetonitrile 37%-67%/0.225% formic acid in water |
| I-185a | 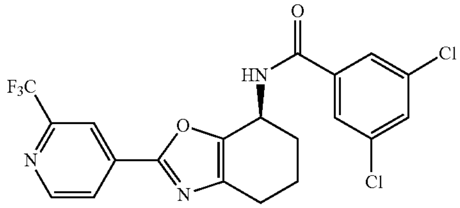 [SMILES: O=C(N[C@H]1CCCc2nc(-c3ccnc(C(F)(F)F)c3)oc21)c1cc(Cl)cc(Cl)c1] (S)-3,5-Dichloro-N-(2-(2-(trifluoromethyl)pyridin-4-yl)-4,5,6,7-tetrahydrobenzo[d]oxazol-7-yl)benzamide | LCMS (ESI) m/z: 455.0 [M + H]$^+$. $^1$H NMR (400 MHz, DMSO-$d_6$) δ 9.16 (d, J = 7.6 Hz, 1H), 8.92 (d, J = 5.2 Hz, 1H), 8.23 (s, 1H), 8.19 (d, J = 5.2 Hz, 1H), 7.93 (d, J = 2.0 Hz, 2H), 7.86-7.82 (m, 1H), 5.37-5.33 (m, 1H), 2.70-2.56 (m, 2H), 2.10-2.03 (m, 1H), 1.99-1.82 (m, 3H). | acetonitrile 43%-73%/0.225% formic acid in water |
| I-186a | 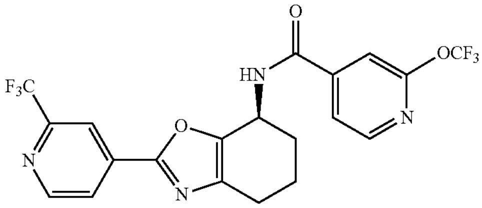 [SMILES: O=C(N[C@H]1CCCc2nc(-c3ccnc(C(F)(F)F)c3)oc21)c1ccnc(OC(F)(F)F)c1] (S)-2-(Trifluoromethoxy)-N-(2-(2-(trifluoromethyl)pyridin-4-yl)-4,5,6,7-tetrahydrobenzo[d]oxazol-7-yl)isonicotinamide | LCMS (ESI) m/z: 473.1 [M + H]$^+$. $^1$H NMR (400 MHz, DMSO-$d_6$) δ 9.34 (d, J = 7.6 Hz, 1H), 8.92 (d, J = 5.2 Hz, 1H), 8.53 (d, J = 5.2 Hz, 1H), 8.22 (s, 1H), 8.19 (d, J = 5.2 Hz, 1H), 7.86 (m, J = 1.2, 5.2 Hz, 1H), 7.68 (s, 1H), 5.43-5.33 (m, 1H), 2.72-2.55 (m, 2H), 2.07 (d, J = 5.2 Hz, 1H), 2.02-1.82 (m, 3H). | acetonitrile 43%-73%/0.225% formic acid in water |

-continued

| Compound No. | Structure | Analytical data | Separation conditions |
|---|---|---|---|
| I-187a | 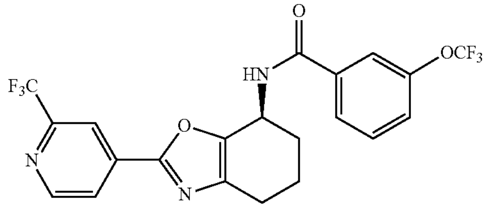 [SMILES: O=C(N[C@H]1CCCc2nc(-c3ccnc(C(F)(F)F)c3)oc21)c1cccc(OC(F)(F)F)c1] (S)-3-(Trifluoromethoxy)-N-(2-(2-(trifluoromethyl)pyridin-4-yl)-4,5,6,7-tetrahydrobenzo[d]oxazol-7-yl)benzamide | LCMS (ESI) m/z: 472.1 [M + H]$^+$. $^1$H NMR (400 MHz, DMSO-$d_6$) δ 9.13 (d, J = 7.6 Hz, 1H), 8.91 (d, J = 5.2 Hz, 1H), 8.22 (s, 1H), 8.19 (d, J = 5.2 Hz, 1H), 7.97 (d, J = 7.6 Hz, 1H), 7.87 (s, 1H), 7.67-7.55 (m, 2H), 5.38-5.37 (m, 1H), 2.72-2.58 (m, 2H), 2.11-1.86 (m, 4H). | acetonitrile 41%-71%/ 0.225% formic acid in water |
| I-188a | 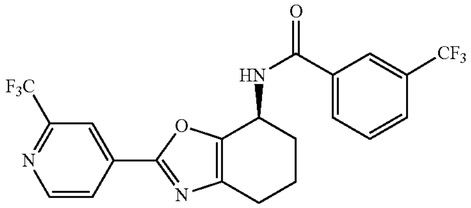 [SMILES: O=C(N[C@H]1CCCc2nc(-c3ccnc(C(F)(F)F)c3)oc21)c1cccc(C(F)(F)F)c1] (S)-3-(Trifluoromethyl)-N-(2-(2-(trifluoromethyl)pyridin-4-yl)-4,5,6,7-tetrahydrobenzo[d]oxazol-7-yl)benzamide | LCMS (ESI) m/z: 456.1 [M + H]$^+$. $^1$H NMR (400 MHz, DMSO-$d_6$) δ 9.21 (d, J = 7.6 Hz, 1H), 8.91 (d, J = 5.2 Hz, 1H), 8.26-8.16 (m, 4H), 7.93 (d, J = 7.6 Hz, 1H), 7.77-7.72 (m, 1H), 5.44-5.36 (m, 1H), 2.69-2.56 (m, 2H), 2.10-1.85 (m, 4H). | acetonitrile 40%-70%/ 0.225% formic acid in water |
| I-164a | 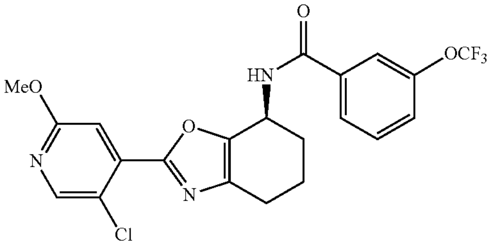 (S)-N-(2-(5-Chloro-2-methoxypyridin-4-yl)-4,5,6,7-tetrahydrobenzo[d]oxazol-7-yl)-3-(trifluoromethoxy)benzamide | LCMS (ESI) m/z: 468.0 [M + H]$^+$. $^1$H NMR (400 MHz, DMSO-$d_6$) δ 9.08 (d, J = 7.6 Hz, 1H), 8.41 (s, 1H), 7.94 (d, J = 7.6 Hz, 1H), 7.84 (s, 1H), 7.68-7.53 (m, 2H), 7.29 (s, 1H), 5.38-5.33 (m, 1H), 3.89 (s, 3H), 2.64-2.59 (m, 2H), 2.12-1.89 (m, 4H). | acetonitrile 50%-80%/ 0.225% formic acid in water |
| I-163a | 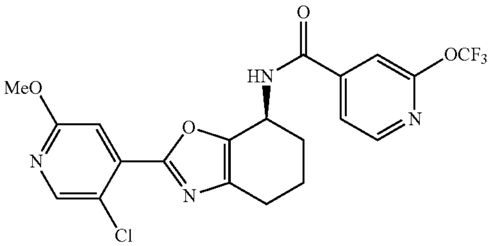 [SMILES: COc1cc(-c2nc3c(o2)[C@@H](NC(=O)c2ccnc(OC(F)(F)F)c2)CCC3)c(Cl)cn1] 1-Ethyl-3-(trifluoromethyl)-N-(2-(2-(trifluoromethyl)pyridin-4-yl)-4,5,6,7-tetrahydro-2H-indazol-4-yl)-1H-pyrazole-5-carboxamide | LCMS (ESI) m/z: 469.1 [M + H]$^+$. $^1$H NMR (400 MHz, DMSO-$d_6$) δ 9.31 (d, J = 7.6 Hz, 1H), 8.52 (d, J = 4.8 Hz, 1H), 8.41 (s, 1H), 7.83 (d, J = 5.2 Hz, 1H), 7.65 (s, 1H), 7.30 (s, 1H), 5.39-5.31 (m, 1H), 3.89 (s, 3H), 2.65-2.59 (m, 2H), 2.15-1.82 (m, 4H). | acetonitrile 53%-83%/ 0.225% formic acid in water |

-continued

| Compound No. | Structure | Analytical data | Separation conditions |
|---|---|---|---|
| I-162a | 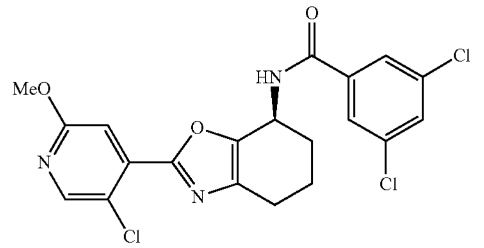 (S)-3,5-Dichloro-N-(2-(5-chloro-2-methoxypyridin-4-yl)-4,5,6,7-tetrahydrobenzo[d]oxazol-7-yl)benzamide | LCMS (ESI) m/z: 452.1 $[M + H]^+$. $^1H$ NMR (400 MHz, DMSO-$d_6$) δ 9.12 (d, J = 7.6 Hz, 1H), 8.41 (s, 1H), 7.91 (d, J = 2.0 Hz, 2H), 7.86-7.79 (m, 1H), 7.30 (s, 1H), 5.36-5.29 (m, 1H), 3.89 (s, 3H), 2.64-2.59 (m, 2H), 2.09-1.83 (m, 4H). | acetonitrile 58%-88%/ 0.225% formic acid in water |
| I-161a | 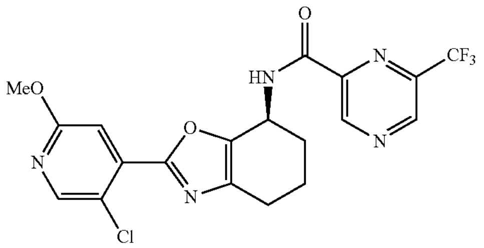 [SMILES: COc1cc(-c2nc3c(o2)[C@@H](NC(=O)c2cncc(C(F)(F)F)n2)CCC3)c(Cl)cn1] (S)-N-(2-(5-Chloro-2-methoxypyridin-4-yl)-4,5,6,7-tetrahydrobenzo[d]oxazol-7-yl)-6-(trifluoromethyl)pyrazine-2-carboxamide | LCMS (ESI) m/z: 454.1 $[M + H]^+$. $^1H$ NMR (400 MHz, DMSO-$d_6$) δ 9.49 (s, 1H), 8.44 (d, J = 8.4 Hz, 2H), 9.39 (s, 3H), 8.40 (s, 1H), 7.27 (s, 1H), 5.45-5.37 (m, 1H), 3.88 (s, 3H), 2.64-2.56 (m, 2H), 2.17-2.08 (m, 1H), 2.06-1.94 (m, 2H), 1.91-1.76 (m, 1H). | acetonitrile 53%-83%/ 0.225% formic acid in water |
| I-167a | 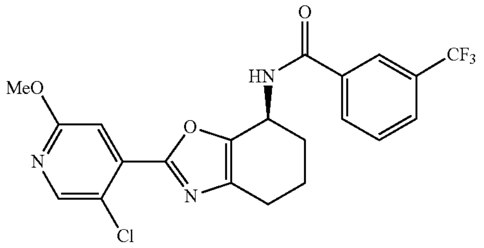 [SMILES: COc1cc(-c2nc3c(o2)[C@@H](NC(=O)c2cccc(C(F)(F)F)c2)CCC3)c(Cl)cn1] (S)-N-(2-(5-Chloro-2-methoxypyridin-4-yl)-4,5,6,7-tetrahydrobenzo[d]oxazol-7-yl)-3-(trifluoromethyl)benzamide | LCMS (ESI) m/z: 452.1 $[M + H]^+$. $^1H$ NMR (400 MHz, DMSO-$d_6$) δ 9.17 (d, J = 8.0 Hz, 1H), 8.41 (s, 1H), 8.26-8.16 (m, 2H), 7.92 (d, J = 8.0 Hz, 1H), 7.75-7.70 (m, 1H), 7.29 (s, 1H), 5.41-5.34 (m, 1H), 3.89 (s, 3H), 2.67-2.58 (m, 2H), 2.13-1.84 (m, 4H). | acetonitrile 55%-85%/ 0.225% formic acid in water |
| I-156a | 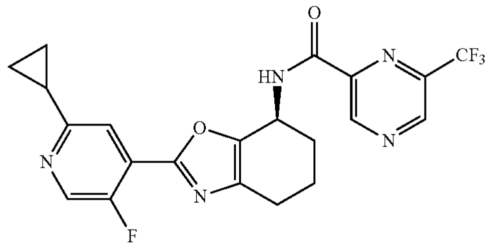 [SMILES: O=C(N[C@H]1CCCc2nc(-c3cc(C4CC4)ncc3F)oc21)c1cncc(C(F)(F)F)n1] (S)-2-(1-Methyl-3-(trifluoromethyl)-1H-pyrazol-5-yl)-N-(2-(2-(trifluoromethyl)pyridin-4-yl)-4,5,6,7-tetrahydro-2H-indazol-4-yl)acetamide | LCMS (ESI) m/z: 448.2 $[M + H]^+$. $^1H$ NMR (400 MHz, DMSO-$d_6$) δ 9.50 (s, 1H), 9.48 (d, J = 8.4 Hz, 1H), 9.40 (s, 1H), 8.54 (d, J = 2.4 Hz, 1H), 7.84 (d, J = 5.6 Hz, 1H), 5.51-5.36 (m, 1H), 2.68-2.58 (m, 2H), 2.30-2.22 (m, 1H), 2.16-2.07 (m, 1H), 2.07-1.94 (m, 2H), 1.92-1.80 (m, 1H), 0.98-0.92 (m, 2H), 0.92-0.86 (m, 2H). | acetonitrile 48%-78%/ 0.225% formic acid in water |

-continued

| Compound No. | Structure | Analytical data | Separation conditions |
|---|---|---|---|
| I-157a | 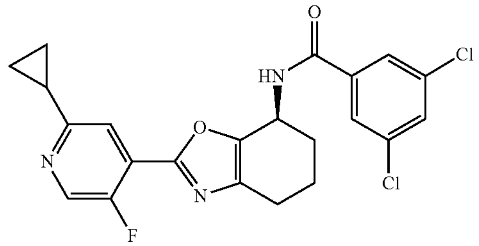 [SMILES: O=C(N[C@H]1CCCc2nc(-c3cc(C4CC4)ncc3F)oc21)c1cc(Cl)cc(Cl)c1] (S)-3,5-Dichloro-N-(2-(2-cyclopropyl-5-fluoropyridin-4-yl)-4,5,6,7-tetrahydrobenzo[d]oxazol-7-yl)benzamide | LCMS (ESI) m/z: 446.1 $[M + H]^+$. $^1H$ NMR (400 MHz, DMSO-$d_6$) δ 9.15 (d, J = 7.6 Hz, 1H), 8.56 (d, J = 2.4 Hz, 1H), 7.92 (d, J = 2.0 Hz, 2H), 7.87 (d, J = 6.0 Hz, 1H), 7.84-7.82 (m, 1H), 5.36-5.31 (m, 1H), 2.68-2.58 (m, 2H), 2.31-2.26 (m, 1H), 2.10-2.03 (m, 1H), 1.99-1.84 (m, 3H), 0.96 (m, 2H), 0.93-0.88 (m, 2H). | acetonitrile 60%-90%/0.225% formic acid in water |
| I-158a | 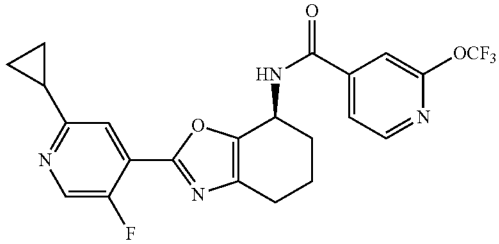 [SMILES: O=C(N[C@H]1CCCc2nc(-c3cc(C4CC4)ncc3F)oc21)c1ccnc(OC(F)(F)F)c1] (S)-N-(2-(2-Cyclopropyl-5-fluoropyridin-4-yl)-4,5,6,7-tetrahydrobenzo[d]oxazol-7-yl)-2-(trifluoromethoxy)isonicotinamide | LCMS (ESI) m/z: 463.2 $[M + H]^+$. $^1H$ NMR (400 MHz, DMSO-$d_6$) δ 9.34 (d, J = 7.6 Hz, 1H), 8.55 (d, J = 2.4 Hz, 1H), 8.52 (d, J = 5.2 Hz, 1H), 7.87-7.83 (m, 2H), 7.66 (s, 1H), 5.35 (d, J = 6.8 Hz, 1H), 2.69-2.58 (m, 2H), 2.30-2.24 (m, 1H), 2.12-2.04 (m, 1H), 2.02-1.86 (m, 3H), 0.98-0.93 (m, 2H), 0.92-0.87 (m, 2H). | acetonitrile 52-82%/0.225% formic acid in water |
| I-159a | 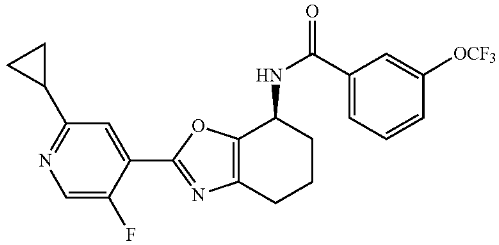 [SMILES: O=C(N[C@H]1CCCc2nc(-c3cc(C4CC4)ncc3F)oc21)c1cccc(OC(F)(F)F)c1] (S)-N-(2-(2-Cyclopropyl-5-fluoropyridin-4-yl)-4,5,6,7-tetrahydrobenzo[d]oxazol-7-yl)-3-(trifluoromethoxy)benzamide | LCMS (ESI) m/z: 462.2 $[M + H]^+$. $^1H$ NMR (400 MHz, DMSO-$d_6$) δ 9.11 (d, J = 7.6 Hz, 1H), 8.55 (d, J = 2.0 Hz, 1H), 7.95 (d, J = 8.0 Hz, 1H), 7.85 (d, J = 5.6 Hz, 2H), 7.64-7.60 (m, 1H), 7.57 (d, J = 8.4 Hz, 1H), 5.37-5.35 (m, 1H), 2.68-2.59 (m, 2H), 2.30-2.24 (m, 1H), 2.11-2.06 (m, 1H), 2.02-1.85 (m, 3H), 0.97-0.93 (m, 2H), 0.90-0.87 (m, 2H). | acetonitrile 56%-86%/0.225% formic acid in water |
| I-165a | 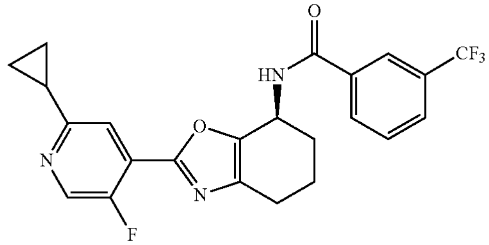 [SMILES: O=C(N[C@H]1CCCc2nc(-c3cc(C4CC4)ncc3F)oc21)c1cccc(C(F)(F)F)c1] (S)-N-(2-(2-Cyclopropyl-5-fluoropyridin-4-yl)-4,5,6,7-tetrahydrobenzo[d]oxazol-7-yl)-3-(trifluoromethyl)benzamide | LCMS (ESI) m/z: 446.2 $[M + H]^+$. $^1H$ NMR (400 MHz, DMSO-$d_6$) δ 9.20 (d, J = 8.0 Hz, 1H), 8.56 (d, J = 2.4 Hz, 1H), 8.24 (s, 1H), 8.21 (d, J = 7.6 Hz, 1H), 7.93 (d, J = 8.0 Hz, 1H), 7.87 (d, J = 6.0 Hz, 1H), 7.76-7.72 (m, 1H), 5.41-5.37 (m, 1H), 2.69-2.60 (m, 2H), 2.31-2.25 (m, 1H), 2.12-2.05 (m, 1H), 2.03-1.85 (m, 3H), 0.98-0.94 (m, 2H), 0.91-0.88 (m, 2H). | acetonitrile 54%-84%/0.225% formic acid in water |

-continued

| Compound No. | Structure | Analytical data | Separation conditions |
|---|---|---|---|
| I-200a | 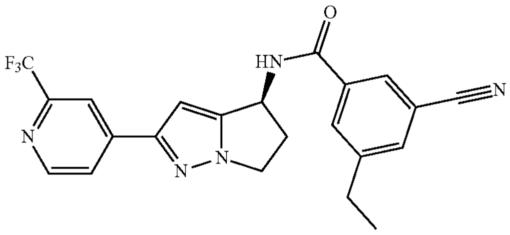 [SMILES: CCc1cc(C#N)cc(C(=O)N[C@H]2CCn3nc(-c4ccnc(C(F)(F)F)c4)cc32)c1] (S)-3-Cyano-5-ethyl-N-(2-(2-(trifluoromethyl)pyridin-4-yl)-5,6-dihydro-4H-pyrrolo[1,2-b]pyrazol-4-yl)benzamide | LCMS (ESI) m/z: 426.0 $[M + H]^+$. $^1H$ NMR (400 MHz, DMSO-$d_6$) δ 9.19 (d, J = 7.6 Hz, 1H), 8.74 (d, J = 5.2 Hz, 1H), 8.19 (s, 1H), 8.12 (s, 1H), 8.09-8.04 (m, 2H), 7.90 (s, 1H), 7.01 (s, 1H), 5.62-5.54 (m, 1H), 4.48-4.16 (m, 2H), 3.10-3.01 (m, 1H), 2.72 (q, J = 7.6 Hz, 3H), 2.60-2.53 (m, 1H), 1.21 (t, J = 7.6 Hz, 3H). | acetonitrile 46%-76%/ 0.225% formic acid in water |
| I-198a | 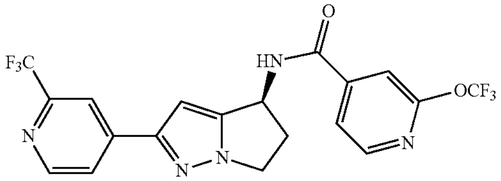 [SMILES: O=C(N[C@H]1CCn2nc(-c3ccnc(C(F)(F)F)c3)cc21)c1ccnc(OC(F)(F)F)c1] (S)-2-(Trifluoromethoxy)-N-(2-(2-(trifluoromethyl)pyridin-4-yl)-5,6-dihydro-4H-pyrrolo[1,2-b]pyrazol-4-yl)isonicotinamide | LCMS (ESI) m/z: 458.0 $[M + H]^+$. $^1H$ NMR (400 MHz, DMSO-$d_6$) δ 9.44 (d, J = 7.6 Hz, 1H), 8.75 (d, J = 5.2 Hz, 1H), 8.55 (d, J = 5.2 Hz, 1H), 8.20 (s, 1H), 8.07 (d, J = 5.2 Hz, 1H), 7.84 (dd, J = 1.2, 5.2 Hz, 1H), 7.66 (s, 1H), 7.03 (s, 1H), 5.61-5.52 (m, 1H), 4.47-4.15 (m, 2H), 3.11-3.02 (m, 1H), 2.62-2.53 (m, 1H). | acetonitrile 46%-76%/ 0.225% formic acid in water |
| I-147a | 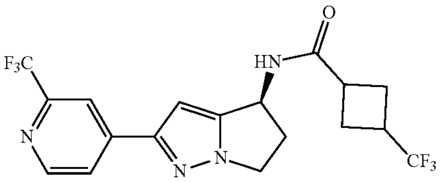 (S)-3-(Trifluoromethyl)-N-(2-(2-(trifluoromethyl)pyridin-4-yl)-5,6-dihydro-4H-pyrrolo[1,2-b]pyrazol-4-yl)cyclobutane-1-carboxamide | LCMS (ESI) m/z: 419.1 $[M + H]^+$. $^1H$ NMR (400 MHz, DMSO-$d_6$) δ 8.74 (d, J = 5.2 Hz, 1H), 8.50 (d, J = 8.0 Hz, 1H), 8.19 (s, 1H), 8.07 (d, J = 5.2 Hz, 1H), 6.94 (s, 1H), 5.35-5.28 (m, 1H), 4.36-4.26 (m, 1H), 4.20-4.15 (m, 1H), 3.19-3.11 (m, 1H), 3.01-2.92 (m, 2H), 2.37-2.31 (m, 1H), 2.26-2.21 (m, 3H). | acetonitrile 42%-72%/ 0.225% formic acid in water |
| I-224a | 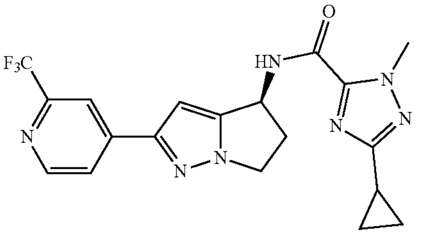 [SMILES: Cn1nc(C2CC2)nc1C(=O)N[C@H]1CCn2nc(-c3ccnc(C(F)(F)F)c3)cc21] (S)-3-Cyclopropyl-1-methyl-N-(2-(2-(trifluoromethyl)pyridin-4-yl)-5,6-dihydro-4H-pyrrolo[1,2-b]pyrazol-4-yl)-1H-1,2,4-triazole-5-carboxamide | LCMS (ESI) m/z: 418.2 $[M + H]^+$. $^1H$ NMR (400 MHz, DMSO-$d_6$) δ 9.38 (d, J = 8.4 Hz, 1H), 8.74 (d, J = 5.2 Hz, 1H), 8.19 (s, 1H), 8.06 (d, J = 4.8 Hz, 1H), 6.98 (s, 1H), 5.55-5.43 (m, 1H), 4.44-4.34 (m, 1H), 4.22-4.13 (m, 1H), 4.07 (s, 3H), 3.07-2.93 (m, 1H), 2.65-2.55 (m, 1H), 2.02-1.92 (m, 1H), 0.95-0.88 (m, 2H), 0.86-0.78 (m, 2H). | acetonitrile 28%-28%/ 0.225% formic acid in water |
| I-225a | 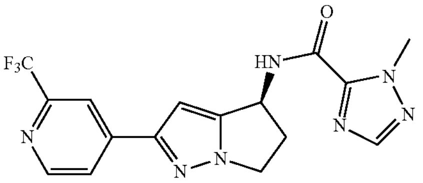 [SMILES: Cn1ncnc1C(=O)N[C@H]1CCn2nc(-c3ccnc(C(F)(F)F)c3)cc21] (S)-N-(2-(5-Fluoro-2-methoxypyridin-4-yl)-5,6,7,8-tetrahydro-4H-pyrazolo[1,5-a]azepin-4-yl)-1-methyl-3-(trifluoromethyl)-1H-pyrazole-5-carboxamide | LCMS (ESI) m/z: 378.1 $[M + H]^+$. $^1H$ NMR (400 MHz, DMSO-$d_6$) δ 9.52 (d, J = 7.6 Hz, 1H), 8.74 (d, J = 5.2 Hz, 1H), 8.19 (s, 1H), 8.09-8.02 (m, 2H), 6.96 (s, 1H), 5.58-5.52 (m, 1H), 4.46-4.35 (m, 1H), 4.24-4.18 (m, 1H), 4.17 (s, 3H), 3.07-2.97 (m, 1H), 2.67-2.62 (m, 1H). | acetonitrile 30%-70%/ 0.225% formic acid in water |

-continued

| Compound No. | Structure | Analytical data | Separation conditions |
|---|---|---|---|
| I-221a | 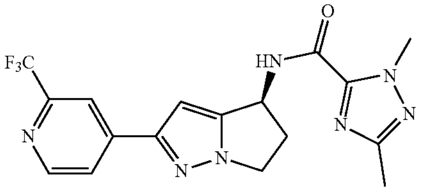 [SMILES: Cc1nc(C(=O)N[C@H]2CCn3nc(-c4ccnc(C(F)(F)F)c4)cc32)n(C)n1] (S)-1,3-Dimethyl-N-(2-(2-(trifluoromethyl)pyridin-4-yl)-5,6-dihydro-4H-pyrrolo[1,2-b]pyrazol-4-yl)-1H-1,2,4-triazole-5-carboxamide | LCMS (ESI) m/z: 392.2 $[M + H]^+$. $^1H$ NMR (400 MHz, DMSO-$d_6$) δ 9.50 (d, J = 8.4 Hz, 1H), 8.74 (d, J = 5.2 Hz, 1H), 8.19 (s, 1H), 8.06 (d, J = 4.8 Hz, 1H), 6.96 (s, 1H), 5.55-5.47 (m, 1H), 4.43-4.35 (m, 1H), 4.19 (m, 1H), 4.09 (s, 3H), 3.05-2.94 (m, 1H), 2.67-2.59 (m, 1H), 2.27 (s, 3H). | acetonitrile 20%-50%/ 0.225% formic acid in water |
| I-210a | 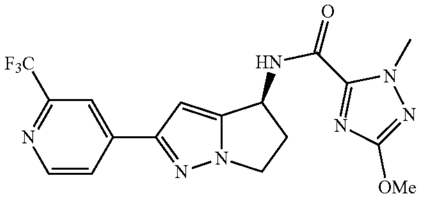 [SMILES: COc1nc(C(=O)N[C@H]2CCn3nc(-c4ccnc(C(F)(F)F)c4)cc32)n(C)n1] (S)-3-Methoxy-1-methyl-N-(2-(2-(trifluoromethyl)pyridin-4-yl)-5,6-dihydro-4H-pyrrolo[1,2-b]pyrazol-4-yl)-1H-1,2,4-triazole-5-carboxamide | LCMS (ESI) m/z: 408.2 $[M + H]^+$. $^1H$ NMR (400 MHz, DMSO-$d_6$) δ 9.46 (d, J = 8.0 Hz, 1H), 8.74 (d, J = 5.2 Hz, 1H), 8.19 (s, 1H), 8.06 (d, J = 5.2 Hz, 1H), 6.97 (s, 1H), 5.53-5.48 (m, 1H), 4.42-4.36 (m, 1H), 4.22-4.16 (m, 1H), 4.05 (s, 3H), 3.89 (s, 3H), 3.06-2.95 (m, 1H), 2.65-2.57 (m, 1H). | acetonitrile 35%-65%/ 0.225% formic acid in water |
| I-207a | 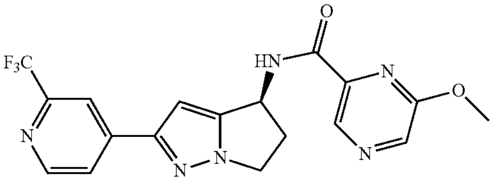 [SMILES: COc1cncc(C(=O)N[C@H]2CCn3nc(-c4ccnc(C(F)(F)F)c4)cc32)n1] (S)-6-Methoxy-N-(2-(2-(trifluoromethyl)pyridin-4-yl)-5,6-dihydro-4H-pyrrolo[1,2-b]pyrazol-4-yl)pyrazine-2-carboxamide | LCMS (ESI) m/z: 405.1 $[M + H]^+$. $^1H$ NMR (400 MHz, DMSO-$d_6$) δ 9.29 (d, J = 8.4 Hz, 1H), 8.76 (s, 1H), 8.74 (d, J = 5.2 Hz, 1H), 8.52 (s, 1H), 8.20 (s, 1H), 8.07 (d, J = 5.2 Hz, 1H), 6.99 (s, 1H), 5.69-5.62 (m, 1H), 4.46-4.38 (m, 1H), 4.27-4.18 (m, 1H), 4.03 (s, 3H), 3.10-2.99 (m, 1H), 2.68-2.62 (m, 1H). | acetonitrile 42%-72%/ 0.225% formic acid in water |
| I-331a | 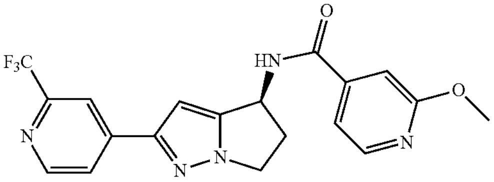 [SMILES: COc1cc(C(=O)N[C@H]2CCn3nc(-c4ccnc(C(F)(F)F)c4)cc32)ccn1] (S)-2-Methoxy-N-(2-(2-(trifluoromethyl)pyridin-4-yl)-5,6-dihydro-4H-pyrrolo[1,2-b]pyrazol-4-yl)isonicotinamide | LCMS (ESI) m/z: 404.2 $[M + H]^+$. $^1H$ NMR (400 MHz, DMSO-$d_6$) δ 9.27 (d, J = 8.0 Hz, 1H), 8.74 (d, J = 5.2 Hz, 1H), 8.31 (d, J = 5.6 Hz, 1H), 8.20 (s, 1H), 8.08-8.06 (m, 1H), 7.40-7.37 (m, 1H), 7.22 (s, 1H), 7.01 (s, 1H), 5.60-5.53 (m, 1H), 4.42-4.35 (m, 1H), 4.29-4.16 (m, 1H), 3.89 (s, 3H), 3.12-2.96 (m, 1H), 2.61-2.53 (m, 1H). | Prep-HPLC: acetonitrile 42%-72%/0.225% formic acid in water. Prep-SFC: chiral SFC (DAICEL CHIRALCEL OJ (250 mm * 30 mm, 10 μm); Supercritical $CO_2$/EtOH + 0.1% $NH_3$•$H_2O$ = 70/30; 80 mL/min |
| I-291a | 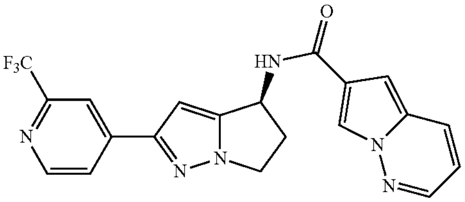 [SMILES: O=C(N[C@H]1CCn2nc(-c3ccnc(C(F)(F)F)c3)cc21)c1cc2cccnn2c1] (S)-N-(2-(2-(Trifluoromethyl)pyridin-4-yl)-5,6-dihydro-4H-pyrrolo[1,2-b]pyrazol-4-yl)pyrrolo[1,2-b]pyridazine-6-carboxamide | LCMS (ESI) m/z: 413.0 $[M + H]^+$. $^1H$ NMR (400 MHz, DMSO-$d_6$) δ 8.87 (d, J = 7.6 Hz, 1H), 8.74 (d, J = 5.2 Hz, 1H), 8.30 (s, 1H), 8.26-8.18 (m, 2H), 8.13-7.99 (m, 2H), 7.07 (s, 1H), 6.96 (s, 1H), 6.77-6.69 (m, 1H), 5.66-5.54 (m, 1H), 4.46-4.34 (m, 1H), 4.29-4.16 (m, 1H), 3.14-2.97 (m, 1H), 2.60-2.52 (m, 1H). | acetonitrile 37%-67%/ 0.225% formic acid in water |

-continued

| Compound No. | Structure | Analytical data | Separation conditions |
|---|---|---|---|
| I-236a | 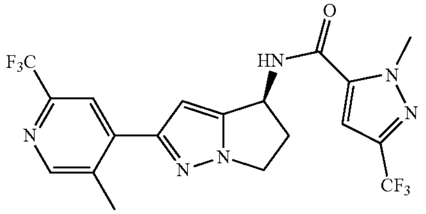 (S)-1-Methyl-N-(2-(5-methyl-2-(trifluoromethyl)pyridin-4-yl)-5,6-dihydro-4H-pyrrolo[1,2-b]pyrazol-4-yl)-3-(trifluoromethyl)-1H-pyrazole-5-carboxamide | LCMS (ESI) m/z: 459.2 [M + H]+. $^1$H NMR (400 MHz, DMSO-$d_6$) δ 9.24 (d, J = 7.6 Hz, 1H), 8.66 (s, 1H), 8.07 (s, 1H), 7.35 (s, 1H), 6.84 (s, 1H), 5.68-5.47 (m, 1H), 4.45-4.35 (m, 1H), 4.30-4.21 (m, 1H), 4.18 (s, 3H), 3.13-2.99 (m, 1H), 2.60 (s, 3H), 2.53 (s, 1H). | acetonitrile 50%-80%/ 0.225% formic acid in water |
| I-254a | 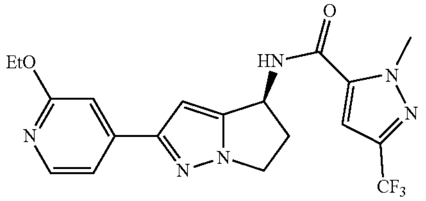 (S)-N-(2-(2-Ethoxypyridin-4-yl)-5,6-dihydro-4H-pyrrolo[1,2-b]pyrazol-4-yl)-1-methyl-3-(trifluoromethyl)-1H-pyrazole-5-carboxamide | LCMS (ESI) m/z: 421.1 [M + H]+. $^1$H NMR (400 MHz, DMSO-$d_6$) δ 9.22 (d, J = 7.6 Hz, 1H), 8.13 (d, J = 5.6 Hz, 1H), 7.37 (dd, J = 1.2, 5.2 Hz, 1H), 7.34 (s, 1H), 7.13 (s, 1H), 6.81 (s, 1H), 5.55-5.48 (m, 1H), 4.32 (q, J = 7.2 Hz, 2H), 4.23-4.19 (m, 1H), 4.18 (s, 3H), 3.07-2.98 (m, 1H), 2.49-2.44 (m, 1H), 1.32 (t, J = 7.2 Hz, 3H). | acetonitrile 38%-68%/ 0.225% formic acid in water |
| I-310a | 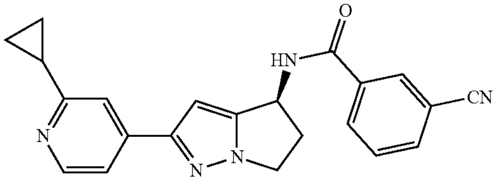 [SMILES: N#Cc1cccc(C(=O)N[C@H]2CCn3nc(-c4ccnc(C5CC5)c4)cc32)c1] (S)-3-Cyano-N-(2-(2-cyclopropylpyridin-4-yl)-5,6-dihydro-4H-pyrrolo[1,2-b]pyrazol-4-yl)benzamide | LCMS (ESI) m/z: 370.2 [M + H]+. $^1$H NMR (400 MHz, DMSO-$d_6$) δ 9.24 (d, J = 7.6 Hz, 1H), 8.35 (d, J = 5.2 Hz, 1H), 8.34-8.30 (m, 1H), 8.20 (d, J = 8.0 Hz, 1H), 8.03 (d, J = 7.6 Hz, 1H), 7.75-7.70 (m, 1H), 7.66 (s, 1H), 7.48 (dd, J = 1.6, 5.2 Hz, 1H), 6.79 (s, 1H), 5.57-5.52 (m, 1H), 4.40-4.31 (m, 1H), 4.25-4.17 (m, 1H), 3.08-3.01 (m, 1H), 2.53 (m, 1H), 2.15-2.07 (m, 1H), 0.95-0.90 (m, 4H). | Prep-HPLC: acetonitrile 25%-55%/ 0.225% formic acid in water. Prep-SFC: chiral SFC (DAICEL CHIRALCEL OD (250 mm * 30 mm, 10 μm); Supercritical $CO_2$/ EtOH + 0.1% $NH_3$•$H_2O$ = 65/35; 80 mL/min |
| I-218a | 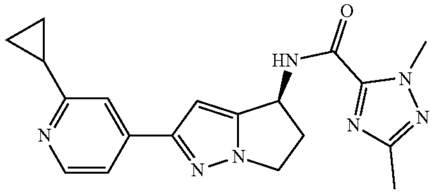 (S)-N-(2-(2-Cyclopropylpyridin-4-yl)-5,6-dihydro-4H-pyrrolo[1,2-b]pyrazol-4-yl)-1,3-dimethyl-1H-1,2,4-triazole-5-carboxamide | LCMS (ESI) m/z: 408.1 [M + H]+. $^1$H NMR (400 MHz, DMSO-$d_6$) δ 9.80 (s, 1H), 8.15 (d, J = 5.2 Hz, 1H), 7.39-7.35 (m, 1H), 7.14 (s, 1H), 6.77 (s, 1H), 5.57-5.51 (m, 1H), 4.44-4.30 (m, 1H), 4.25 (s, 3H), 4.21-4.09 (m, 1H), 3.86 (s, 3H), 3.08-2.95 (m, 1H), 2.64-2.58 (m, 1H). | Prep-HPLC: acetonitrile 20%-50%/ 0.05% $NH_3H_2O$ + 10 mM $NH_4HCO_3$ in water. Prep-SFC: chiral SFC (DAICEL CHIRALCEL OD (250 mm * 30 mm, 10 μm); Supercritical $CO_2$/ EtOH + 0.1% $NH_3$•$H_2O$ = 50/50; 80 mL/min |
| I-172a | 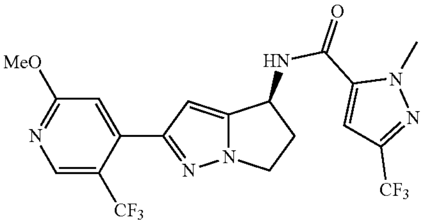 [SMILES: COc1cc(-c2cc3n(n2)CC[C@@H]3NC(=O)c2cc(C(F)(F)F)nn2C)c(C(F)(F)F)cn1] (S)-N-(2-(2-Methoxy-5-(trifluoromethyl)pyridin-4-yl)-5,6-dihydro-4H-pyrrolo[1,2-b]pyrazol-4-yl)-1-methyl-3-(trifluoromethyl)-1H-pyrazole-5-carboxamide | LCMS (ESI) m/z: 475.3 [M + H]+. $^1$H NMR (400 MHz, DMSO-$d_6$) δ 9.21 (d, J = 7.6 Hz, 1H), 8.62 (s, 1H), 7.33 (s, 1H), 7.11 (s, 1H), 6.52 (s, 1H), 5.58-5.50 (m, 1H), 4.40-.4.34 (m, 1H), 4.26-4.19 (m, 1H), 4.16 (s, 3H), 3.96 (s, 3H), 3.08-3.03 (m, 1H), 2.57-2.52 (m, 1H). | acetonitrile 44%-74%/ 0.225% formic acid in water. |

-continued

| Compound No. | Structure | Analytical data | Separation conditions |
|---|---|---|---|
| I-237a | 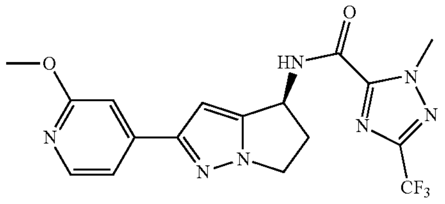 (S)-N-(2-(2-Methoxypyridin-4-yl)-5,6-dihydro-4H-pyrrolo[1,2-b]pyrazol-4-yl)-1-methyl-3-(trifluoromethyl)-1H-1,2,4-triazole-5-carboxamide | LCMS (ESI) m/z: 408.1 $[M + H]^+$. $^1$H NMR (400 MHz, DMSO-$d_6$) δ 9.80 (s, 1H), 8.15 (d, J = 5.2 Hz, 1H), 7.39-7.35 (m, 1H), 7.14 (s, 1H), 6.77 (s, 1H), 5.57-5.51 (m, 1H), 4.44-4.30 (m, 1H), 4.25 (s, 3H), 4.21-4.09 (m, 1H), 3.86 (s, 3H), 3.08-2.95 (m, 1H), 2.64-2.58 (m, 1H). | Prep-HPLC: acetonitrile 40%-70%/0.225% formic acid in water. Prep-SFC: chiral SFC (DAICEL CHIRALCEL OD (250 mm * 30 mm, 10 μm); Supercritical $CO_2$/EtOH + 0.1% $NH_3$•$H_2O$ = 65/35; 80 mL/min |
| I-253a | 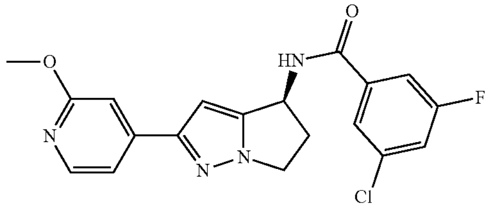 [SMILES: COc1cc(-c2cc3n(n2)CC[C@@H]3NC(=O)c2cc(F)cc(Cl)c2)ccn1] (S)-3-Chloro-5-fluoro-N-(2-(2-methoxypyridin-4-yl)-5,6-dihydro-4H-pyrrolo[1,2-b]pyrazol-4-yl)benzamide | LCMS (ESI) m/z: 387.1 $[M + H]^+$. $^1$H NMR (400 MHz, DMSO-$d_6$) δ 9.22 (d, J = 7.6 Hz, 1H), 8.15 (d, J = 5.6 Hz, 1H), 7.82 (s, 1H), 7.73-7.64 (m, 2H), 7.39-7.37 (m, 1H), 7.15 (s, 1H), 6.80 (s, 1H), 5.57-5.50 (m, 1H), 4.39-4.31 (m, 1H), 4.23-4.16 (m, 1H), 3.86 (s, 3H), 3.14-2.94 (m, 1H), 2.55 (s, 1H). | Prep-HPLC: acetonitrile 45%-75%/0.225% formic acid in water. Prep-SFC: chiral SFC (DAICEL CHIRALCEL AS (250 mm * 30 mm, 10 μm); Supercritical $CO_2$/EtOH + 0.1% $NH_3$•$H_2O$ = 60/40; 80 mL/min |
| I-286a | 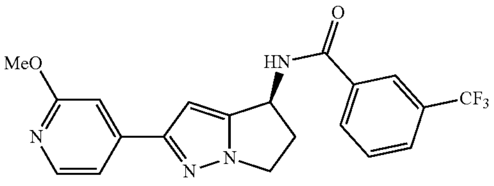 [SMILES: COc1cc(-c2cc3n(n2)CC[C@@H]3NC(=O)c2cccc(C(F)(F)F)c2)ccn1] (S)-N-(2-(2-Methoxypyridin-4-yl)-5,6-dihydro-4H-pyrrolo[1,2-b]pyrazol-4-yl)-3-(trifluoromethyl)benzamide | LCMS (ESI) m/z: 403.1 $[M + H]^+$. $^1$H NMR (400 MHz, DMSO-$d_6$) δ 9.29 (d, J = 8.0 Hz, 1H), 8.24 (s, 1H), 8.20 (d, J = 8.0 Hz, 1H), 8.15 (d, J = 5.2 Hz, 1H), 7.93 (d, J = 8.0 Hz, 1H), 7.77-7.72 (m, 1H), 7.38 (m, 1H), 7.15 (s, 1H), 6.81 (s, 1H), 5.62-5.56 (m, 1H), 4.36 (m, 1H), 4.20 (m, 1H), 3.86 (s, 3H), 3.11-2.99 (m, 1H), 2.57-2.51 (m, 1H). | Prep-HPLC: acetonitrile 35%-65%/0.225% formic acid in water. Prep-SFC: chiral SFC (DAICEL CHIRALCEL OJ (250 mm * 30 mm, 10 μm); Supercritical $CO_2$/EtOH + 0.1% $NH_3$•$H_2O$ = 50/50, 80 mL/min) |
| I-240a | 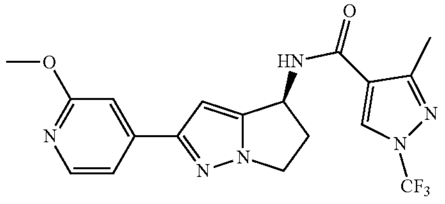 (S)-N-(2-(2-Methoxypyridin-4-yl)-5,6-dihydro-4H-pyrrolo[1,2-b]pyrazol-4-yl)-3-methyl-1-(trifluoromethyl)-1H-pyrazole-4-carboxamide | LCMS (ESI) m/z: 407.1 $[M + H]^+$. $^1$H NMR (400 MHz, DMSO-$d_6$) δ 8.84 (s, 1H), 8.76 (d, J = 7.6 Hz, 1H), 8.15 (d, J = 5.2 Hz, 1H), 7.39-7.36 (m, 1H), 7.14 (s, 1H), 6.78 (s, 1H), 5.51-5.44 (m, 1H), 4.36-4.29 (m, 1H), 4.23-4.15 (m, 1H), 3.86 (s, 3H), 3.08-2.96 (m, 1H), 2.44 (s, 3H), 2.43-2.37 (m, 1H). | Prep-HPLC: acetonitrile 35%-65%/0.225% formic acid in water. Prep-SFC chiral SFC (DAICEL CHIRALCEL OD (250 mm * 30 mm, 10 μm); Supercritical $CO_2$/EtOH + 0.1% $NH_3$•$H_2O$ = 75/25, 80 mL/min) |
| I-285a | 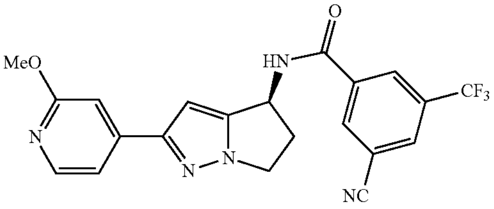 [SMILES: COc1cc(-c2cc3n(n2)CC[C@@H]3NC(=O)c2cc(C#N)cc(C(F)(F)F)c2)ccn1] (S)-3-Cyano-N-(2-(2-methoxypyridin-4-yl)-5,6-dihydro-4H-pyrrolo[1,2-b]pyrazol-4-yl)-5-(trifluoromethyl)benzamide | LCMS (ESI) m/z: 428.1 $[M + H]^+$. $^1$H NMR (400 MHz, DMSO-$d_6$) δ 9.44 (d, J = 7.6 Hz, 1H), 8.62 (s, 1H), 8.58 (s, 1H), 8.50 (s, 1H), 8.15 (d, J = 5.2 Hz, 1H), 7.38 (d, J = 5.2 Hz, 1H), 7.15 (s, 1H), 6.81 (s, 1H), 5.62-5.53 (m, 1H), 4.41-4.32 (m, 1H), 4.27-4.16 (m, 1H), 3.86 (s, 3H), 3.12-3.00 (m, 1H), 2.58-2.52 (m, 1H). | Prep-HPLC: acetonitrile 38%-68%/0.225% formic acid in water. Prep-SFC: chiral SFC (DAICEL CHIRALCEL OJ (250 mm * 30 mm, 10 μm); Supercritical $CO_2$/EtOH + 0.1% $NH_3$•$H_2O$ = 50/50, 80 mL/min) |

-continued

| Compound No. | Structure | Analytical data | Separation conditions |
|---|---|---|---|
| I-255a | 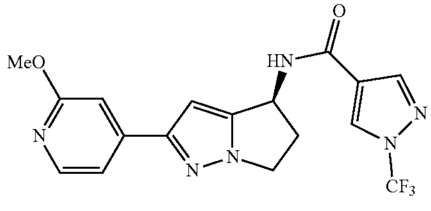 [SMILES: COc1cc(-c2cc3n(n2)CC[C@@H]3NC(=O)c2cnn(C(F)(F)F)c2)ccn1] (S)-N-(2-(2-Methoxypyridin-4-yl)-5,6-dihydro-4H-pyrrolo[1,2-b]pyrazol-4-yl)-1-(trifluoromethyl)-1H-pyrazole-4-carboxamide | LCMS (ESI) m/z: 393.1 [M + H]$^+$. $^1$H NMR (400 MHz, DMSO-$d_6$) δ 9.22 (d, J = 7.6 Hz, 1H), 8.15 (d, J = 5.6 Hz, 1H), 7.82 (s, 1H), 7.73-7.64 (m, 2H), 7.39-7.37 (m, 1H), 7.15 (s, 1H), 6.80 (s, 1H), 5.57-5.50 (m, 1H), 4.39-4.31 (m, 1H), 4.23-4.16 (m, 1H), 3.86 (s, 3H), 3.14-2.94 (m, 1H), 2.55 (s, 1H). | Prep-HPLC: acetonitrile 30%-60%/0.225% formic acid in water. Prep-SFC: chiral SFC (DAICEL CHIRALCEL OD (250 mm * 30 mm, 10 μm); Supercritical $CO_2$/ EtOH + 0.1% $NH_3$•$H_2O$ = 65/35, 80 mL/min) |
| I-230a | 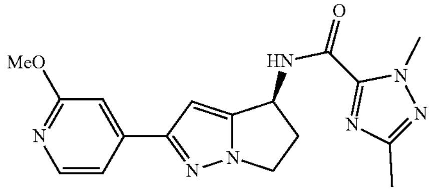 [SMILES: COc1cc(-c2cc3n(n2)CC[C@@H]3NC(=O)c2nc(C)nn2C)ccn1] (S)-N-(2-(2-Methoxypyridin-4-yl)-5,6-dihydro-4H-pyrrolo[1,2-b]pyrazol-4-yl)-1,3-dimethyl-1H-1,2,4-triazole-5-carboxamide | LCMS (ESI) m/z: 354.2 [M + H]$^+$. $^1$H NMR (400 MHz, DMSO-$d_6$) δ 9.48 (d, J = 8.4 Hz, 1H), 8.14 (d, J = 5.6 Hz, 1H), 7.37 (dd, J = 1.2, 5.2 Hz, 1H), 7.13 (s, 1H), 6.73 (s, 1H), 5.54-5.45 (m, 1H), 4.41-4.31 (m, 1H), 4.20-4.11 (m, 1H), 4.09 (s, 3H), 3.85 (s, 3H), 3.02-2.92 (m, 1H), 2.62-2.54 (m, 1H), 2.26 (s, 3H). | acetonitrile 21%-51%/ 0.225% formic acid in water. |
| I-306a | 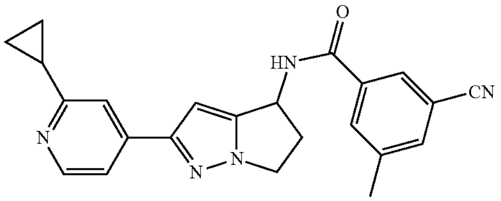 [SMILES: Cc1cc(C#N)cc(C(=O)NC2CCn3nc(-c4ccnc(C5CC5)c4)cc32)c1] 3-Cyano-N-(2-(2-cyclopropylpyridin-4-yl)-5,6-dihydro-4H-pyrrolo[1,2-b]pyrazol-4-yl)-5-methylbenzamide | LCMS (ESI) m/z: 384.2 [M + H]$^+$. $^1$H NMR (400 MHz, DMSO-$d_6$) δ 9.18 (d, J = 8.0 Hz, 1H), 8.36 (d, J = 5.2 Hz, 1H), 8.11 (s, 1H), 8.03 (s, 1H), 7.87 (s, 1H), 7.66 (s, 1H), 7.48 (d, J = 4.8 Hz, 1H), 6.78 (s, 1H), 5.60-5.52 (m, 1H), 4.40-4.32 (m, 1H), 4.25-4.15 (m, 1H), 3.07-3.00 (m, 1H), 2.64-2.61 (m, 1H), 2.41 (s, 3H), 2.14-2.08 (m, 1H), 0.95-0.90 (m, 4H). | Prep-HPLC: acetonitrile 20-50%/0.225% formic acid in water. Prep-SFC: chiral SFC (ODDAICEL CHIRALCEL OD (250 mm * 30 mm, 10 μm); Supercritical $CO_2$/ EtOH + 0.1% $NH_3$•$H_2O$ = 65/35; 80 mL/min) |
| I-300a | 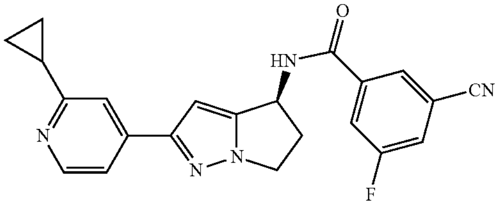 [SMILES: N#Cc1cc(F)cc(C(=O)N[C@H]2CCn3nc(-c4ccnc(C5CC5)c4)cc32)c1] (S)-3-Cyano-N-(2-(2-cyclopropylpyridin-4-yl)-5,6-dihydro-4H-pyrrolo[1,2-b]pyrazol-4-yl)-5-fluorobenzamide | LCMS (ESI) m/z: 388.1 [M + H]$^+$. $^1$H NMR (400 MHz, DMSO-$d_6$) δ 9.30 (d, J = 7.6 Hz, 1H), 8.36 (d, J = 4.8 Hz, 1H), 8.20 (s, 1H), 8.12-8.07 (m, 1H), 8.06-8.00 (m, 1H), 7.66 (s, 1H), 7.48 (dd, J = 1.2, 4.8 Hz, 1H), 6.79 (s, 1H), 5.59-5.51 (m, 1H), 4.41-4.31 (m, 1H), 4.26-4.13 (m, 1H), 3.08-3.01 (m, 1H), 2.63-2.59 (m, 1H), 2.14-2.07 (m, 1H), 0.96-0.90 (m, 4H). | Prep-HPLC: acetonitrile 20-50%/0.225% formic acid in water. Prep-SFC: Chiral SFC (DAICEL CHIRALPAK IG (250 mm * 30 mm, 10 μm); Supercritical $CO_2$/ EtOH + 0.1% $NH_3$•$H_2O$ = 60/40; 80 mL/min |
| I-279a | 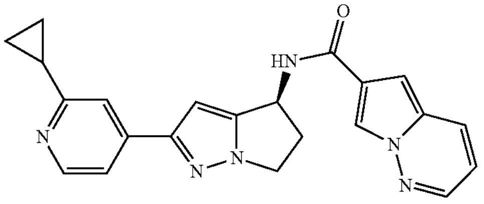 [SMILES: O=C(N[C@H]1CCn2nc(-c3ccnc(C4CC4)c3)cc21)c1cc2cccnn2c1] (S)-N-(2-(2-Cyclopropylpyridin-4-yl)-5,6-dihydro-4H-pyrrolo[1,2-b]pyrazol-4-yl)pyrrolo[1,2-b]pyridazine-6-carboxamide | LCMS (ESI) m/z: 385.2 [M + H]$^+$. $^1$H NMR (400 MHz, DMSO-$d_6$) δ 8.86 (d, J = 7.6 Hz, 1H), 8.35 (d, J = 5.2 Hz, 1H), 8.30 (d, J = 1.2 Hz, 1H), 8.23 (dd, J = 1.6, 4.0 Hz, 1H), 8.02 (dd, J = 1.2, 9.2 Hz, 1H), 7.67 (s, 1H), 7.48 (dd, J = 1.6, 5.2 Hz, 1H), 6.97 (d, J = 1.6 Hz, 1H), 6.78 (s, 1H), 6.74-6.70 (m, 1H), 5.61-5.56 (m, 1H), 4.41-4.34 (m, 1H), 4.23-4.15 (m, 1H), 3.08-2.98 (m, 1H), 2.57-2.51 (m, 1H), 2.14-2.06 (m, 1H), 0.95-0.89 (m, 4H). | Prep-HPLC: acetonitrile 3-33%/0.225% formic acid in water. Prep-SFC: chiral SFC DAICEL CHIRALPAK AS (250 mm * 30 mm, 10 μm); Supercritical $CO_2$/ EtOH + 0.1% $NH_3$•$H_2O$ = 55/45; 80 mL/min |

-continued

| Compound No. | Structure | Analytical data | Separation conditions |
|---|---|---|---|
| I-292a | 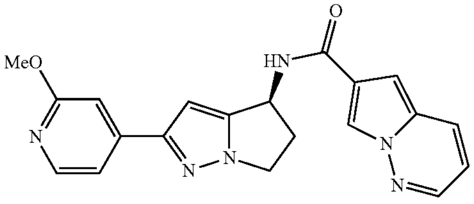 [SMILES: COc1cc(-c2cc3n(n2)CC[C@@H]3NC(=O)c2cc3cccnn3c2)ccn1] (S)-N-(2-(2-Methoxypyridin-4-yl)-5,6-dihydro-4H-pyrrolo[1,2-b]pyrazol-4-yl)pyrrolo[1,2-b]pyridazine-6-carboxamide | LCMS (ESI) m/z: 375.1 $[M + H]^+$. $^1H$ NMR (400 MHz, DMSO-$d_6$) δ 8.86 (d, J = 8.0 Hz, 1H), 8.30 (d, J = 1.6 Hz, 1H), 8.23 (dd, J = 1.6, 4.4 Hz, 1H), 8.14 (d, J = 5.6 Hz, 1H), 8.02 (dd, J = 1.6, 9.2 Hz, 1H), 7.38 (dd, J = 1.2, 5.2 Hz, 1H), 7.15 (s, 1H), 6.98-6.94 (m, 1H), 6.78 (s, 1H), 6.75-6.70 (m, 1H), 5.61-5.54 (m, 1H), 4.40-4.32 (m, 1H), 4.23-4.15 (m, 1H), 3.85 (s, 3H), 3.29-3.26 (m, 1H), 3.08-2.97 (m, 1H). | acetonitrile 50%-80%/ 0.225% formic acid in water |
| I-301a | 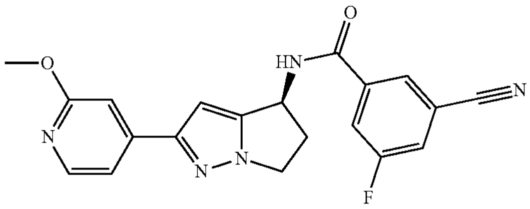 [SMILES: COc1cc(-c2cc3n(n2)CC[C@@H]3NC(=O)c2cc(F)cc(C#N)c2)ccn1] (S)-3-Cyano-5-fluoro-N-(2-(2-methoxypyridin-4-yl)-5,6-dihydro-4H-pyrrolo[1,2-b]pyrazol-4-yl)benzamide | LCMS (ESI) m/z: 378.2 $[M + H]^+$. $^1H$ NMR (400 MHz, DMSO-$d_6$) δ 9.29 (d, J = 7.6 Hz, 1H), 8.22-8.18 (m, 1H), 8.15 (d, J = 5.2 Hz, 1H), 8.11-8.07 (m, 1H), 8.02 (s, 1H), 7.14 (s, 1H), 6.79 (s, 1H), 5.59-5.51 (m, 1H), 4.38-4.32 (m, 1H), 4.24-4.18 (m, 1H), 3.86 (s, 3H), 3.09-2.99 (m, 1H). | Prep-HPLC: acetonitrile 25-75%/0.225% formic acid in water. Prep-SFC: chiral SFC DAICEL CHIRALCEL OD (250 mm * 30 mm, 10 μm); Supercritical $CO_2$/ EtOH + 0.1% $NH_3$•$H_2O$ = 75/25; 150 mL/min) |
| I-257a | 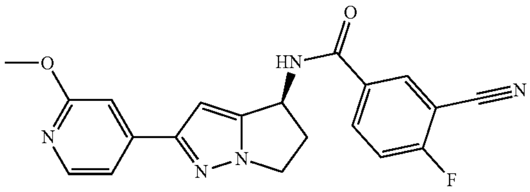 [SMILES: COc1cc(-c2cc3n(n2)CC[C@@H]3NC(=O)c2ccc(F)c(C#N)c2)ccn1] (S)-3-Cyano-4-fluoro-N-(2-(2-methoxypyridin-4-yl)-5,6-dihydro-4H-pyrrolo[1,2-b]pyrazol-4-yl)benzamide | LCMS (ESI) m/z: 378.1 $[M + H]^+$. $^1H$ NMR (400 MHz, DMSO-$d_6$) δ$^1$H NMR (400 MHz, DMSO-$d_6$) δ 9.22 (d, J = 7.6 Hz, 1H), 8.42 (dd, J = 2.0, 6.4 Hz, 1H), 8.29-8.24 (m, 1H), 8.14 (d, J = 5.2 Hz, 1H), 7.71-7.62 (m, 1H), 7.39-8.35 (m, 1H), 7.14 (s, 1H), 6.79 (s, 1H), 5.59-5.52 (m, 1H), 4.37-4.31 (m, 1H), 4.25-4.15 (m, 1H), 3.85 (s, 3H), 3.09-2.98 (m, 1H), 2.58 (s, 1H). | Prep-HPLC: acetonitrile 20-60%/0.225% formic acid in water. Prep-SFC: chiral SFC DAICEL CHIRALCEL AD (250 mm * 30 mm, 10 μm); Supercritical $CO_2$/ EtOH + 0.1% $NH_3$•$H_2O$ = 50/50; 80 mL/min) |
| I-243a | 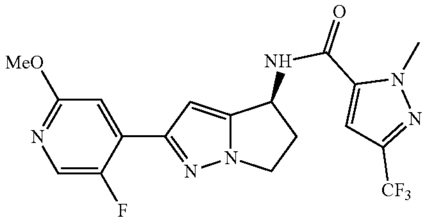 [SMILES: COc1cc(-c2cc3n(n2)CC[C@@H]3NC(=O)c2cc(C(F)(F)F)nn2C)c(F)cn1] (S)-N-(2-(5-Fluoro-2-methoxypyridin-4-yl)-5,6-dihydro-4H-pyrrolo[1,2-b]pyrazol-4-yl)-1-methyl-3-(trifluoromethyl)-1H-pyrazole-5-carboxamide | LCMS (ESI) m/z: 425.2 $[M + H]^+$. $^1H$ NMR (400 MHz, DMSO-$d_6$) δ 9.22 (d, J = 7.2 Hz, 1H), 8.22 (d, J = 2.4 Hz, 1H), 7.34 (s, 1H), 7.23 (d, J = 4.8 Hz, 1H), 6.66 (d, J = 3.2 Hz, 1H), 5.56-5.47 (m, 1H), 4.41-4.35 (m, 1H), 4.27-4.21 (m, 1H), 4.17 (s, 3H), 3.85 (s, 3H), 3.07-3.03 (m, 1H), 2.60-2.58 (m, 1H). | Prep-HPLC: acetonitrile 45-75%/0.225% formic acid in water. Prep-SFC: chiral SFC DAICEL CHIRALCEL OJ (250 mm * 30 mm, 10 μm); Supercritical $CO_2$/ EtOH + 0.1% $NH_3$•$H_2O$ = 40/60; 80 mL/min) |
| I-205a | 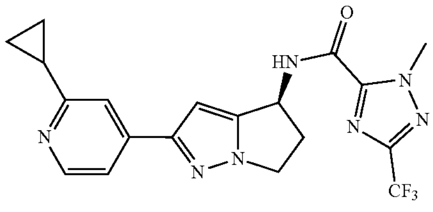 (S)-N-(2-(2-Cyclopropylpyridin-4-yl)-5,6-dihydro-4H-pyrrolo[1,2-b]pyrazol-4-yl)-1-methyl-3-(trifluoromethyl)-1H-1,2,4-triazole-5-carboxamide | LCMS (ESI) m/z: 418.2 $[M + H]^+$. $^1H$ NMR (400 MHz, DMSO-$d_6$) δ 9.78 (d, J = 8.4 Hz, 1H), 8.35 (d, J = 5.2 Hz, 1H), 7.70 (d, J = 8.0 Hz, 1H), 7.65 (s, 1H), 7.48-7.46 (m, 1H), 7.36 (d, J = 8.0 Hz, 1H), 7.27 (s, 1H), 6.76 (s, 1H), 5.58-5.50 (m, 1H), 4.42-4.31 (m, 1H), 4.25 (s, 3H), 4.21-4.12 (m, 1H), 3.04-3.97 (s, 1H), 2.65-2.56 (m, 1H), 2.14-2.06 (s, 1H), 0.96-0.89 (m, 4H). | acetonitrile 40%-70%/ 0.225% formic acid in water. |

-continued

| Compound No. | Structure | Analytical data | Separation conditions |
|---|---|---|---|
| I-261a | 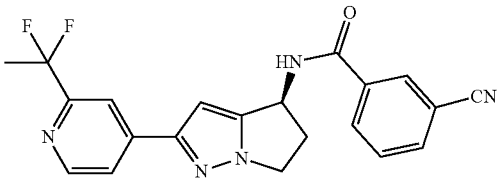 [SMILES: CC(F)(F)c1cc(-c2cc3n(n2)CC[C@@H]3NC(=O)c2cccc(C#N)c2)ccn1] (S)-3-Cyano-N-(2-(2-(1,1-difluoroethyl)pyridin-4-yl)-5,6-dihydro-4H-pyrrolo[1,2-b]pyrazol-4-yl)benzamide | LCMS (ESI) m/z: 394.1 $[M + H]^+$. $^1H$ NMR (400 MHz, DMSO-$d_6$) δ 9.24 (d, J = 7.6 Hz, 1H), 8.64 (d, J = 5.2 Hz, 1H), 8.31 (s, 1H), 8.23-8.17 (m, 1H), 8.06-8.00 (m, 2H), 7.89 (d, J = 5.6 Hz, 1H), 7.75-7.70 (m, 1H), 6.93 (s, 1H), 5.60-5.55 (m, 1H), 4.43-4.33 (m, 1H), 4.28-4.18 (m, 1H), 3.11-3.00 (m, 1H), 2.60-2.54 (m, 1H), 2.01 (t, J = 19.2 Hz, 3H). | Prep-HPLC: acetonitrile 33%-63%/0.225% formic acid in water. Prep-SFC: chiral SFC (DAICEL CHIRALCEL OJ (250 mm * 30 mm, 10 μm); Supercritical $CO_2$/ EtOH + 0.1% $NH_3$•$H_2O$ = 60/40, 80 mL/min |
| I-206a | 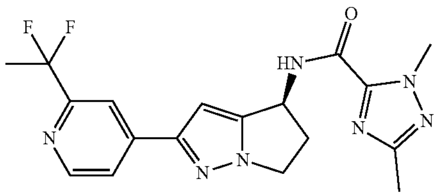 [SMILES: Cc1nc(C(=O)N[C@H]2CCn3nc(-c4ccnc(C(C)(F)F)c4)cc32)n(C)n1] (S)-N-(2-(2-(1,1-Difluoroethyl)pyridin-4-yl)-5,6-dihydro-4H-pyrrolo[1,2-b]pyrazol-4-yl)-1,3-dimethyl-1H-1,2,4-triazole-5-carboxamide | LCMS (ESI) m/z: 388.2 $[M + H]^+$. $^1H$ NMR (400 MHz, DMSO-$d_6$) δ 9.49 (d, J = 8.0 Hz, 1H), 8.63 (d, J = 5.2 Hz, 1H), 8.02 (s, 1H), 7.88 (d, J = 5.2 Hz, 1H), 6.87 (s, 1H), 5.55-5.46 (m, 1H), 4.42-4.33 (m, 1H), 4.21-4.13 (m, 1H), 4.09 (s, 3H), 3.04-2.94 (m, 1H), 2.68-2.56 (m, 1H), 2.26 (s, 3H), 2.01 (t, J = 19.2 Hz, 3H). | Prep-HPLC: acetonitrile 27%-57%/0.225% formic acid in water. Prep-SFC: chiral SFC (DAICEL CHIRALCEL OJ (250 mm * 30 mm, 10 μm); Supercritical $CO_2$/ EtOH + 0.1% $NH_3$•$H_2O$ = 60/40, 80 mL/min |
| I-142a | 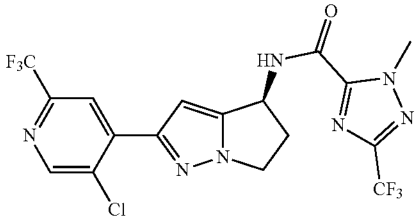 (S)-N-(2-(5-Chloro-2-(trifluoromethyl)pyridin-4-yl)-5,6-dihydro-4H-pyrrolo[1,2-b]pyrazol-4-yl)-1-methyl-3-(trifluoromethyl)-1H-1,2,4-triazole-5-carboxamide | LCMS (ESI) m/z: 480.2 $[M + H]^+$. $^1H$ NMR (400 MHz, DMSO-$d_6$) δ 9.81 (d, J = 8.0 Hz, 1H), 8.89 (s, 1H), 8.29 (s, 1H), 6.99 (s, 1H), 5.63-5.55 (m, 1H), 4.48-4.39 (m, 1H), 4.27-4.22 (m, 4H), 3.10-3.01 (m, 1H), 2.69-2.66 (m, 1H). | acetonitrile 50%-80%/ 0.225% formic acid in water. |
| I-141a | 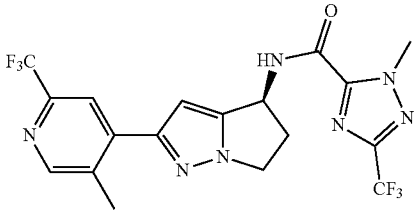 [SMILES: Cc1cnc(C(F)(F)F)cc1-c1cc2n(n1)CC[C@@H]2NC(=O)c1nc(C(F)(F)F)nn1C] (S)-1-Methyl-N-(2-(5-methyl-2-(trifluoromethyl)pyridin-4-yl)-5,6-dihydro-4H-pyrrolo[1,2-b]pyrazol-4-yl)-3-(trifluoromethyl)-1H-1,2,4-triazole-5-carboxamide | LCMS (ESI) m/z: 460.3 $[M + H]^+$. $^1H$ NMR (400 MHz, DMSO-$d_6$) δ 9.81 (d, J = 8.0 Hz, 1H), 8.89 (s, 1H), 8.29 (s, 1H), 6.99 (s, 1H), 5.62-5.54 (m, 1H), 4.48-4.39 (m, 1H), 4.27-4.22 (m, 4H), 3.10-3.01 (m, 1H), 2.69-2.66 (m, 1H). | acetonitrile 50%-80%/ 0.225% formic acid in water. |
| I-144a | 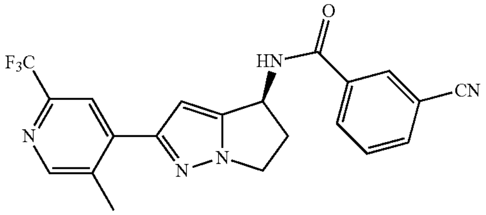 [SMILES: Cc1cnc(C(F)(F)F)cc1-c1cc2n(n1)CC[C@@H]2NC(=O)c1cccc(C#N)c1] (S)-3-Cyano-N-(2-(5-methyl-2-(trifluoromethyl)pyridin-4-yl)-5,6-dihydro-4H-pyrrolo[1,2-b]pyrazol-4-yl)benzamide | LCMS (ESI) m/z: 412.1 $[M + H]^+$. $^1H$ NMR (400 MHz, DMSO-$d_6$) δ 9.25 (d, J = 7.6 Hz, 1H), 8.66 (s, 1H), 8.32 (s, 1H), 8.24-8.17 (m, 1H), 8.07 (s, 1H), 8.05-8.01 (m, 1H), 7.75-7.70 (m, 1H), 6.83 (s, 1H), 5.65-5.58 (m, 1H), 4.43-4.40 (m, 1H), 4.27-4.25 (m, 1H), 3.10-3.05 (m, 1H), 2.60 (s, 3H), 2.59-2.53 (m, 1H). | acetonitrile 35%-65%/ 0.225% formic acid in water. |

-continued

| Compound No. | Structure | Analytical data | Separation conditions |
|---|---|---|---|
| I-233a | 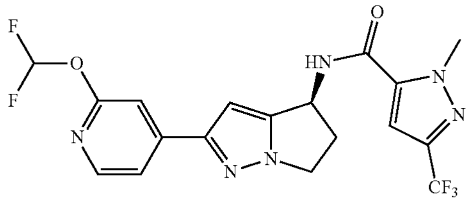 [SMILES: Cn1nc(C(F)(F)F)cc1C(=O)N[C@H]1CCn2nc(-c3ccnc(OC(F)F)c3)cc21] (S)-N-(2-(2-(Difluoromethoxy)pyridin-4-yl)-5,6-dihydro-4H-pyrrolo[1,2-b]pyrazol-4-yl)-1-methyl-3-(trifluoromethyl)-1H-pyrazole-5-carboxamide | LCMS (ESI) m/z: 443.2 [M + H]+. $^1$H NMR (400 MHz, DMSO-$d_6$) δ 9.23 (d, J = 7.6 Hz, 1H), 8.25 (d, J = 5.2 Hz, 1H), 7.91-7.54 (m, 2H), 7.40 (s, 1H), 7.34 (s, 1H), 6.90 (s, 1H), 5.56-5.49 (m, 1H), 4.39-4.32 (m, 1H), 4.26-4.19 (m, 1H), 4.18 (s, 3H), 3.08-3.01 (m, 1H), 2.55-2.52 (m, 1H). | acetonitrile 35%-65%/ 0.225% formic acid in water. |
| I-140a | 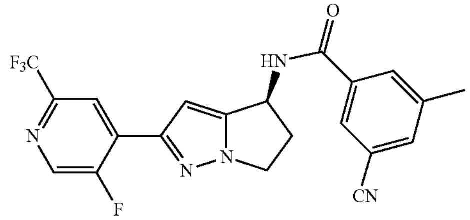 [SMILES: Cc1cc(C#N)cc(C(=O)N[C@H]2CCn3nc(-c4cc(C(F)(F)F)ncc4F)cc32)c1] (S)-N-(2-(5-Fluoro-2-(trifluoromethyl)pyridin-4-yl)-5,6-dihydro-4H-pyrrolo[1,2-b]pyrazol-4-yl)-3-(trifluoromethyl)benzamide | LCMS (ESI) m/z: 430.1 [M + H]+. $^1$H NMR (400 MHz, DMSO-$d_6$) δ.19 (d, J = 7.2 Hz, 1H), 8.85 (d, J = 2.4 Hz, 1H), 8.33 (d, J = 5.6 Hz, 1H), 8.10 (s, 1H), 8.03 (s, 1H), 7.86 (s, 1H), 6.79 (d, J = 3.6 Hz, 1H), 5.61-5.51 (m, 1H), 4.47-4.37 (m, 1H), 4.32-4.21 (m, 1H), 3.12-3.02 (m, 1H), 2.61-2.55 (m, 1H), 2.41 (s, 3H). | acetonitrile 50%-80%/ 0.225% formic acid in water. |
| I-139a | 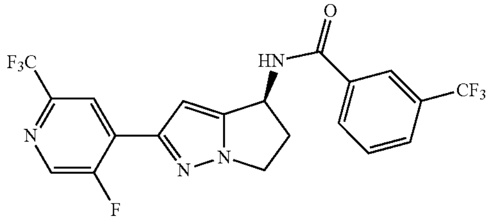 [SMILES: O=C(N[C@H]1CCn2nc(-c3cc(C(F)(F)F)ncc3F)cc21)c1cccc(C(F)(F)F)c1] (S)-N-(2-(5-Fluoro-2-(trifluoromethyl)pyridin-4-yl)-5,6-dihydro-4H-pyrrolo[1,2-b]pyrazol-4-yl)-3-(trifluoromethyl)benzamide | LCMS (ESI) m/z: 459.0 [M + H]+. $^1$H NMR (400 MHz, DMSO-$d_6$) δ 9.30 (d, J = 7.6 Hz, 1H), 8.85 (d, J = 2.4 Hz, 1H), 8.33 (d, J = 5.6 Hz, 1H), 8.27-8.15 (m, 2H), 7.93 (d, J = 7.6 Hz, 1H), 7.80-7.67 (m, 1H), 6.80 (d, J = 3.6 Hz, 1H), 5.65-5.54 (m, 1H), 4.45-4.38 (m, 1H), 4.33-4.24 (m, 1H), 3.13-3.03 (m, 1H), 2.65-2.55 (m, 1H). | acetonitrile 65%-95%/ 0.225% formic acid in water. |
| I-308a | 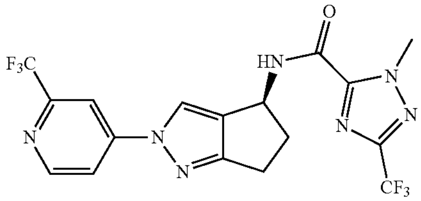 [SMILES: Cn1nc(C(F)(F)F)nc1C(=O)N[C@H]1CCc2nn(-c3ccnc(C(F)(F)F)c3)cc21] (S)-1-Methyl-3-(trifluoromethyl)-N-(2-(2-(trifluoromethyl)pyridin-4-yl)-2,4,5,6-tetrahydrocyclopenta[c]pyrazol-4-yl)-1H-1,2,4-triazole-5-carboxamide | LCMS (ESI) m/z: 446.1 [M + H]+. $^1$H NMR (400 MHz, DMSO-$d_6$) δ 9.59 (d, J = 7.6 Hz, 1H), 8.75 (d, J = 5.4 Hz, 1H), 8.64 (s, 1H), 8.27 (d, J = 2.0 Hz, 1H), 8.13-8.08 (m, 1H), 5.43-5.29 (m, 1H), 4.25 (s, 3H), 3.05-2.92 (m, 1H), 2.89-2.60 (m, 3H). | acetonitrile 50%-80%/ 0.225% formic acid in water |
| I-337a | 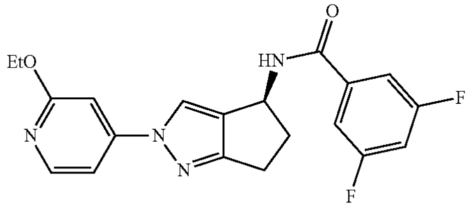 (S)-N-(2-(2-Ethoxypyridin-4-yl)-2,4,5,6-tetrahydrocyclopenta[c]pyrazol-4-yl)-3,5-difluorobenzamide | LCMS (ESI) m/z: 385.1 [M + H]+. $^1$H NMR (400 MHz, DMSO-$d_6$) δ 8.97 (d, J = 7.2 Hz, 1H), 8.45 (s, 1H), 8.16 (d, J = 6.0 Hz, 1H), 7.67-7.55 (m, 2H), 7.51-7.38 (m, 2H), 7.17 (s, 1H), 5.42-5.31 (m, 1H), 4.33 (q, J = 7.2 Hz, 2H), 2.97-2.87 (m, 1H), 2.86-2.70 (m, 2H), 2.38-2.31 (m, 1H), 1.32 (t, J = 7.2 Hz, 3H). | acetonitrile 35%-65%/ 0.225% formic acid in water |

-continued

| Compound No. | Structure | Analytical data | Separation conditions |
|---|---|---|---|
| I-332a | 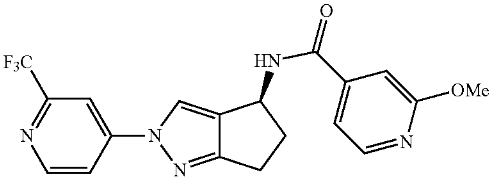 [SMILES: COc1cc(C(=O)N[C@H]2CCc3nn(-c4ccnc(C(F)(F)F)c4)cc32)ccn1] (S)-2-Methoxy-N-(2-(2-(trifluoromethyl)pyridin-4-yl)-2,4,5,6-tetrahydrocyclopenta[c]pyrazol-4-yl)isonicotinamide | LCMS (ESI) m/z: 404.2 $[M + H]^+$. $^1H$ NMR (400 MHz, DMSO-$d_6$) δ 9.05 (d, J = 7.2 Hz, 1H), 8.75 (d, J = 5.6 Hz, 1H), 8.66 (s, 1H), 8.36-8.19 (m, 2H), 8.11 (dd, J = 1.6, 5.6 Hz, 1H), 7.39 (dd, J = 1.2, 5.2 Hz, 1H), 7.23 (s, 1H), 5.50-5.24 (m, 1H), 3.88 (s, 3H), 2.98-2.90 (m, 1H), 2.86-2.72 (m, 2H), 2.45-2.34 (m, 1H). | acetonitrile 36%-66%/ 0.225% formic acid in water |
| I-190a | 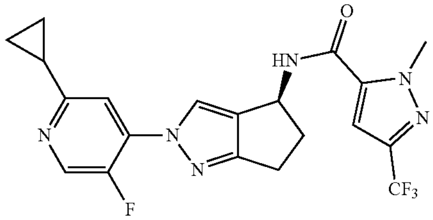 (S)-N-(2-(2-Cyclopropyl-5-fluoropyridin-4-yl)-2,4,5,6-tetrahydrocyclopenta[c]pyrazol-4-yl)-1-methyl-3-(trifluoromethyl)-1H-pyrazole-5-carboxamide | LCMS (ESI) m/z: 432.3 $[M + H]^+$. $^1H$ NMR (400 MHz, DMSO-$d_6$) δ 9.01 (d, J = 7.2 Hz, 1H), 8.53 (d, J = 3.6 Hz, 1H), 8.11 (d, J = 1.2 Hz, 1H), 7.82 (d, J = 6.4 Hz, 1H), 7.35 (s, 1H), 5.35-5.29 (m, 1H), 4.16 (s, 3H), 2.98-2.75 (m, 3H), 2.39-2.32 (m, 1H), 2.25-2.17 (m, 1H), 0.99-0.94 (m, 2H), 0.92-0.90 (m, 2H). | acetonitrile 30%-60%/ 0.225% formic acid in water |
| I-235a | 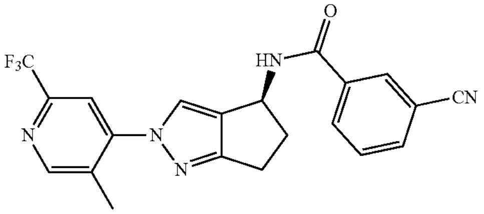 [SMILES: Cc1cnc(C(F)(F)F)cc1-n1cc2c(n1)CC[C@@H]2NC(=O)c1cccc(C#N)c1] (S)-3-Cyano-N-(2-(5-methyl-2-(trifluoromethyl)pyridin-4-yl)-2,4,5,6-tetrahydrocyclopenta[c]pyrazol-4-yl)benzamide | LCMS (ESI) m/z: 412.2 $[M + H]^+$. $^1H$ NMR (400 MHz, DMSO-$d_6$) δ 9.02 (d, J = 7.2 Hz, 1H), 8.75 (s, 1H), 8.32 (s, 1H), 8.25 (s, 1H), 8.20 (d, J = 8.0 Hz, 1H), 8.01 (d, J = 7.6 Hz, 1H), 7.96 (s, 1H), 7.74-7.67 (m, 1H), 5.45-5.37 (m, 1H), 3.00-2.91 (m, 1H), 2.90-2.73 (m, 2H), 2.55 (s, 3H), 2.43-2.35 (m, 1H). | acetonitrile 42%-72%/ 0.225% formic acid in water |
| I-336a | 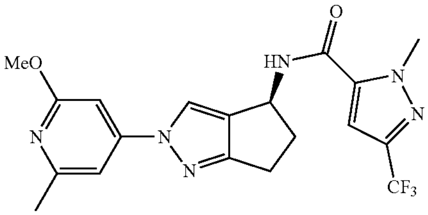 [SMILES: COc1cc(-n2cc3c(n2)CC[C@@H]3NC(=O)c2cc(C(F)(F)F)nn2C)cc(C)n1] (S)-N-(2-(2-Methoxy-6-methylpyridin-4-yl)-2,4,5,6-tetrahydrocyclopenta[c]pyrazol-4-yl)-1-methyl-3-(trifluoromethyl)-1H-pyrazole-5-carboxamide | LCMS (ESI) m/z: 421.2 $[M + H]^+$. $^1H$ NMR (400 MHz, DMSO-$d_6$) δ 9.01 (d, J = 7.6 Hz, 1H), 8.42 (s, 1H), 7.35 (d, J = 2.4 Hz, 1H),, 7.00 (s, 1H), 5.36-5.28 (m, 1H), 4.18 (s, 3H), 3.85 (s, 3H), 2.87-2.71 (m, 1H), 2.41 (s, 3H), 2.35-2.31 (m, 1H). | acetonitrile 55%-88%/ 0.225% formic acid in water |

-continued

| Compound No. | Structure | Analytical data | Separation conditions |
|---|---|---|---|
| I-304a | 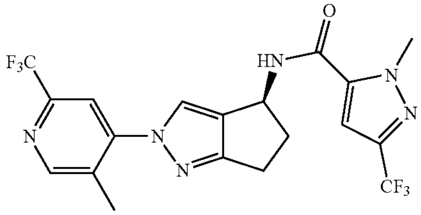 [SMILES: Cc1cnc(C(F)(F)F)cc1-n1cc2c(n1)CC[C@@H]2NC(=O)c1cc(C(F)(F)F)nn1C] (S)-1-Methyl-N-(2-(5-methyl-2-(trifluoromethyl)pyridin-4-yl)-2,4,5,6-tetrahydrocyclopenta[c]pyrazol-4-yl)-3-(trifluoromethyl)-1H-pyrazole-5-carboxamide | LCMS (ESI) m/z: 459.2 $[M + H]^+$. $^1H$ NMR (400 MHz, DMSO-$d_6$) δ 9.02 (d, J = 7.2 Hz, 1H), 8.76 (s, 1H), 8.25 (s, 1H), 7.96 (s, 1H), 7.36 (s, 1H), 5.40-5.33 (m, 1H), 4.17 (s, 3H), 2.98-2.73 (m, 3H), 2.55 (s, 3H), 2.40-2.32 (m, 1H). | acetonitrile 55%-85%/0.225% formic acid in water |
| I-246a | 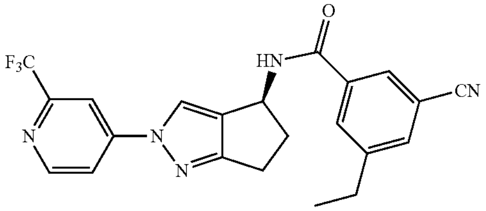 [SMILES: CCc1cc(C#N)cc(C(=O)N[C@H]2CCc3nn(-c4ccnc(C(F)(F)F)c4)cc32)c1] (S)-3-Cyano-5-ethyl-N-(2-(2-(trifluoromethyl)pyridin-4-yl)-2,4,5,6-tetrahydrocyclopenta[c]pyrazol-4-yl)benzamide | LCMS (ESI) m/z: 426.2 $[M + H]^+$. $^1H$ NMR (400 MHz, DMSO-$d_6$) δ 9.00 (d, J = 7.2 Hz, 1H), 8.76 (d, J = 5.6 Hz, 1H), 8.66 (s, 1H), 8.28 (d, J = 1.6 Hz, 1H), 8.15-8.09 (m, 2H), 8.06 (s, 1H), 7.89 (s, 1H), 5.43-5.36 (m, 1H), 2.99-2.91 (m, 1H), 2.89-2.76 (m, 2H), 2.71 (q, J = 7.6 Hz, 2H), 2.43-2.36 (m, 1H), 1.21 (t, J = 7.6 Hz, 3H). | acetonitrile 46%-76%/0.225% formic acid in water |
| I-259a | 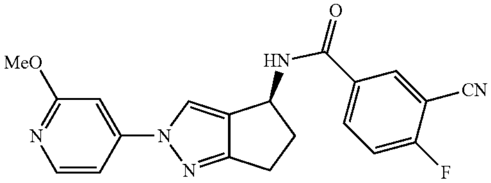 [SMILES: COc1cc(-n2cc3c(n2)CC[C@@H]3NC(=O)c2ccc(F)c(C#N)c2)ccn1] (S)-3-Cyano-4-fluoro-N-(2-(2-methoxypyridin-4-yl)-2,4,5,6-tetrahydrocyclopenta[c]pyrazol-4-yl)benzamide | LCMS (ESI) m/z: 378.1 $[M + H]^+$. $^1H$ NMR (400 MHz, DMSO-$d_6$) δ 9.01 (d, J = 7.6 Hz, 1H), 8.46 (s, 1H), 8.42 (dd, J = 2.4, 6.0 Hz, 1H), 8.30-8.24 (m, 1H), 8.17 (d, J = 5.2 Hz, 1H), 7.67-7.63 (m, 1H), 7.46 (dd, J = 2.0, 6.0 Hz, 1H), 7.19 (d, J = 1.2 Hz, 1H), 5.40-5.34 (m, 1H), 3.87 (s, 3H), 2.96-2.87 (m, 1H), 2.85-2.70 (m, 2H), 2.38-2.30 (m, 1H). | acetonitrile 32%-62%/0.225% formic acid in water |
| I-267a | 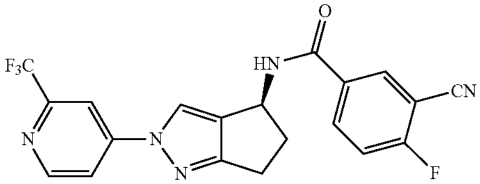 [SMILES: N#Cc1cc(C(=O)N[C@H]2CCc3nn(-c4ccnc(C(F)(F)F)c4)cc32)ccc1F] (S)-3-Cyano-4-fluoro-N-(2-(2-(trifluoromethyl)pyridin-4-yl)-2,4,5,6-tetrahydrocyclopenta[c]pyrazol-4-yl)benzamide | LCMS (ESI) m/z: 416.1 $[M + H]^+$. $^1H$ NMR (400 MHz, DMSO-$d_6$) δ 9.03 (d, J = 7.2 Hz, 1H), 8.76 (d, J = 5.6 Hz, 1H), 8.66 (s, 1H), 8.42 (dd, J = 2.4, 6.4 Hz, 1H), 8.31-8.25 (m, 2H), 8.11 (dd, J = 2.0, 5.2 Hz, 1H), 7.69-7.64 (m, 1H), 5.41-5.34 (m, 1H), 2.99-2.91 (m, 1H), 2.89-2.74 (m, 2H), 2.43-2.35 (m, 1H). | acetonitrile 45%-75%/0.225% formic acid in water |
| I-335a | 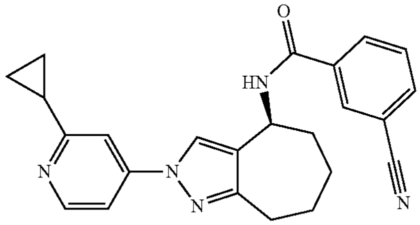 [SMILES: N#Cc1cccc(C(=O)N[C@H]2CCCCc3nn(-c4ccnc(C5CC5)c4)cc32)c1] (S)-3-Cyano-N-(2-(2-cyclopropylpyridin-4-yl)-2,4,5,6,7,8-hexahydrocyclohepta[c]pyrazol-4-yl)benzamide | LCMS (ESI) m/z: 398.2 $[M + H]^+$. $^1H$ NMR (400 MHz, DMSO-$d_6$) δ 8.96 (d, J = 8.0 Hz, 1H), 8.42 (s, 1H), 8.39 (s, 1H), 8.36 (d, J = 5.6 Hz, 1H), 8.25 (d, J = 8.0 Hz, 1H), 8.03 (d, J = 7.6 Hz, 1H), 7.75-7.69 (m, 2H), 7.58-7.52 (m, 1H), 5.17-5.10 (m, 1H), 3.00-2.94 (m, 1H), 2.78-2.69 (m, 2H), 2.16-2.11 (m, 1H), 2.07-1.99 (m, 1H), 1.88-1.84 (m, 2H), 1.82-1.75 (m, 1H), 1.58-1.50 (m, 1H), 1.02-0.92 (m, 4H). | acetonitrile 13%-43%/0.225% formic acid in water. |

-continued

| Compound No. | Structure | Analytical data | Separation conditions |
|---|---|---|---|
| I-343a | 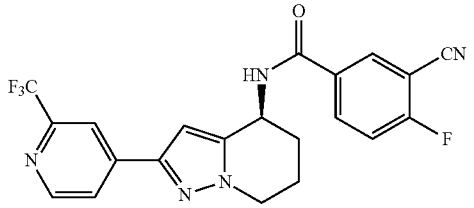 [SMILES: N#Cc1cc(C(=O)N[C@H]2CCCn3nc(-c4ccnc(C(F)(F)F)c4)cc32)ccc1F] (S)-3-Cyano-4-fluoro-N-(2-(2-(trifluoromethyl)pyridin-4-yl)-4,5,6,7-tetrahydropyrazolo[1,5-a]pyridin-4-yl)benzamide | LCMS (ESI) m/z: 430.2 $[M + H]^+$. $^1H$ NMR (400 MHz, DMSO-$d_6$) δ 9.18 (d, J = 8.4 Hz, 1H), 8.74 (d, J = 4.8 Hz, 1H), 8.45 (dd, J = 2.4, 6.0 Hz, 1H), 8.35-8.26 (m, 1H), 8.19 (s, 1H), 8.07 (d, J = 5.2 Hz, 1H), 7.72-6.65 (m, 1H), 7.05 (s, 1H), 5.40-5.31 (m, 1H), 4.30-4.09 (m, 2H), 2.27-2.18 (m, 1H), 2.18-2.02 (m, 2H), 1.92-1.75 (m, 1H). | acetonitrile 37%-78%/ 0.225% formic acid in water |
| I-330a | 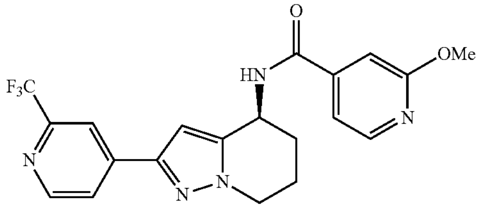 [SMILES: COc1cc(C(=O)N[C@H]2CCCn3nc(-c4ccnc(C(F)(F)F)c4)cc32)ccn1] (S)-2-Methoxy-N-(2-(2-(trifluoromethyl)pyridin-4-yl)-4,5,6,7-tetrahydropyrazolo[1,5-a]pyridin-4-yl)isonicotinamide | LCMS (ESI) m/z: 418.2 $[M + H]^+$. $^1H$ NMR (400 MHz, DMSO-$d_6$) δ 9.19 (d, J = 8.4 Hz, 1H), 8.73 (d, J = 4.8 Hz, 1H), 8.31 (d, J = 5.2 Hz, 1H), 8.21 (s, 1H), 8.08 (dd, J = 1.2, 5.2 Hz, 1H), 7.42 (dd, J = 1.2, 5.2 Hz, 1H), 7.27 (s, 1H), 7.04 (s, 1H), 5.40-5.31 (m, 1H), 4.29-4.24 (m, 1H), 4.18-4.10 (m, 1H), 3.89 (s, 3H), 2.26-2.18 (m, 1H), 2.17-2.04 (m, 2H), 1.91-1.81 (m, 1H). | acetonitrile 35%-65%/ 0.225% formic acid in water |
| I-213a | 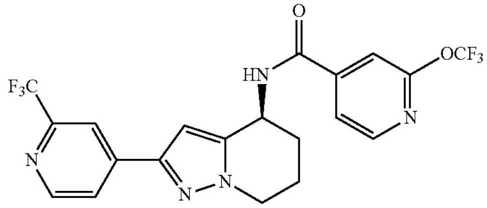 [SMILES: O=C(N[C@H]1CCCn2nc(-c3ccnc(C(F)(F)F)c3)cc21)c1ccnc(OC(F)(F)F)c1] (S)-2-(Trifluoromethoxy)-N-(2-(2-(trifluoromethyl)pyridin-4-yl)-4,5,6,7-tetrahydropyrazolo[1,5-a]pyridin-4-yl)isonicotinamide | LCMS (ESI) m/z: 472.2 $[M + H]^+$. $^1H$ NMR (400 MHz, DMSO-$d_6$) δ 9.38 (d, J = 8.4 Hz, 1H), 8.74 (d, J = 5.2 Hz, 1H), 8.55 (d, J = 5.2 Hz, 1H), 8.19 (s, 1H), 8.10-8.05 (m, 1H), 7.87 (dd, J = 1.2, 5.2 Hz, 1H), 7.69 (s, 1H), 7.07 (s, 1H), 5.43-5.30 (m, 1H), 4.32-4.20 (m, 1H), 4.18-4.13 (m, 1H), 2.27-2.04 (m, 3H), 1.93-1.79 (m, 1H). | acetonitrile 50%-80%/ 0.225% formic acid in water |
| I-295a | 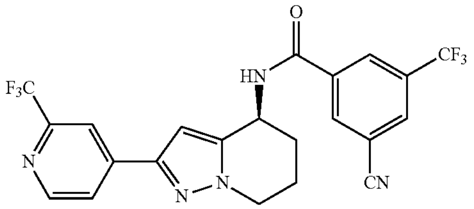 (S)-3-Cyano-5-(trifluoromethyl)-N-(2-(2-(trifluoromethyl)pyridin-4-yl)-4,5,6,7-tetrahydropyrazolo[1,5-a]pyridin-4-yl)benzamide | LCMS (ESI) m/z: 480.2 $[M + H]^+$. $^1H$ NMR (400 MHz, DMSO-$d_6$) δ 9.40 (d, J = 8.0 Hz, 1H), 8.74 (d, J = 5.2 Hz, 1H), 8.65 (s, 1H), 8.59 (s, 1H), 8.54 (s, 1H), 8.19 (s, 1H), 8.07 (d, J = 4.8 Hz, 1H), 7.08 (s, 1H), 5.44-5.35 (m, 1H), 4.30-4.15 (m, 2H), 2.27-2.07 (m, 3H), 1.93-1.82 (m, 1H). | acetonitrile 52%-82%/ 0.225% formic acid in water |
| I-333a | 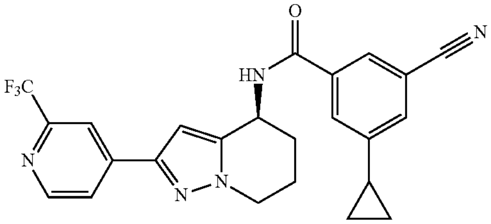 [SMILES: N#Cc1cc(C(=O)N[C@H]2CCCn3nc(-c4ccnc(C(F)(F)F)c4)cc32)cc(C2CC2)c1] (S)-3-Cyano-5-cyclopropyl-N-(2-(2-(trifluoromethyl)pyridin-4-yl)-4,5,6,7-tetrahydropyrazolo[1,5-a]pyridin-4-yl)benzamide | LCMS (ESI) m/z: 452.1 $[M + H]^+$. $^1H$ NMR (400 MHz, DMSO-$d_6$) δ 9.12 (d, J = 6.0 Hz, 1H), 8.74 (d, J = 5.2 Hz, 1H), 8.20 (s, 1H), 8.11-8.06 (m, 2H), 7.93-7.89 (m, 1H), 7.78-7.74 (m, 1H), 7.05 (s, 1H), 5.42-5.30 (m, 1H), 4.32-4.22 (m, 1H), 4.20-4.07 (m, 1H), 2.30-2.21 (m, 1H), 2.17-2.04 (m, 3H), 1.92-1.76 (m, 1H), 1.12-1.01 (m, 2H), 0.91-0.82 (m, 2H). | acetonitrile 52%-82%/ 0.225% formic acid in water |

-continued

| Compound No. | Structure | Analytical data | Separation conditions |
|---|---|---|---|
| I-325a | 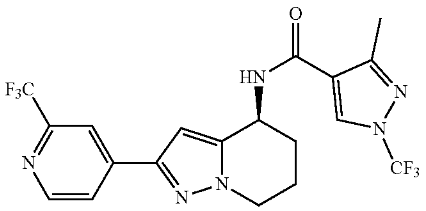 [SMILES: Cc1nn(C(F)(F)F)cc1C(=O)N[C@H]1CCCn2nc(-c3ccnc(C(F)(F)F)c3)cc21] (S)-3-Methyl-1-(trifluoromethyl)-N-(2-(2-(trifluoromethyl)pyridin-4-yl)-4,5,6,7-tetrahydropyrazolo[1,5-a]pyridin-4-yl)-1H-pyrazole-4-carboxamide | LCMS (ESI) m/z: 459.1 $[M + H]^+$. $^1H$ NMR (400 MHz, DMSO-$d_6$) δ 8.87 (s, 1H), 8.76-8.70 (m, 2H), 8.19 (s, 1H), 8.07 (d, J = 5.2 Hz, 1H), 7.02 (s, 1H), 5.33-5.26 (m, 1H), 4.28-4.20 (m, 1H), 4.20-4.11 (m, 1H), 2.47 (s, 3H), 2.25-2.16 (m, 1H), 2.16-2.04 (m, 2H), 1.85-1.73 (m, 1H). | acetonitrile 30%-60%/ 0.225% formic acid in water |
| I-341a | 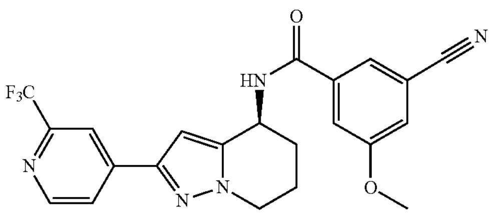 (S)-3-Cyano-5-methoxy-N-(2-(2-(trifluoromethyl)pyridin-4-yl)-4,5,6,7-tetrahydropyrazolo[1,5-a]pyridin-4-yl)benzamide | LCMS (ESI) m/z: 442.1 $[M + H]^+$. $^1H$ NMR (400 MHz, DMSO-$d_6$) δ 9.15 (d, J = 8.4 Hz, 1H), 8.74 (d, J = 5.2 Hz, 1H), 8.20 (s, 1H), 8.10-8.06 (m, 1H), 7.94-7.91 (m, 1H), 7.77 (dd, J = 1.6, 2.4 Hz, 1H), 7.65 (dd, J = 1.2, 2.4 Hz, 1H), 7.05 (s, 1H), 5.42-5.33 (m, 1H), 4.32-4.21 (m, 1H), 4.20-4.09 (m, 1H), 3.88 (s, 3H), 2.28-2.19 (m, 1H), 2.18-2.04 (m, 2H), 1.92-1.79 (m, 1H). | acetonitrile 49%-79%/ 0.225% formic acid in water |
| I-327a | 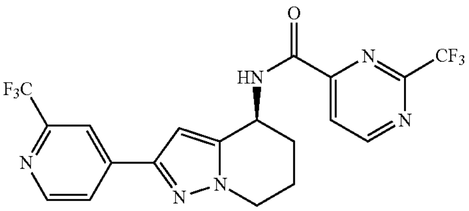 [SMILES: O=C(N[C@H]1CCCn2nc(-c3ccnc(C(F)(F)F)c3)cc21)c1ccnc(C(F)(F)F)n1] (S)-2-(Trifluoromethyl)-N-(2-(2-(trifluoromethyl)pyridin-4-yl)-4,5,6,7-tetrahydropyrazolo[1,5-a]pyridin-4-yl)pyrimidine-4-carboxamide | LCMS (ESI) m/z: 457.1 $[M + H]^+$. $^1H$ NMR (400 MHz, DMSO-$d_6$) δ 9.57 (d, J = 8.8 Hz, 1H), 9.35 (d, J = 5.2 Hz, 1H), 8.73 (d, J = 4.8 Hz, 1H), 8.37 (d, J = 5.2 Hz, 1H), 8.18 (s, 1H), 8.07-8.04 (m, 1H), 7.00 (s, 1H), 5.45-5.38 (m, 1H), 4.31-4.24 (m, 1H), 4.15-4.07 (m, 1H), 2.26-2.20 (m, 1H), 2.13-2.04 (m, 3H). | acetonitrile 42%-72%/ 0.225% formic acid in water |
| I-328a | 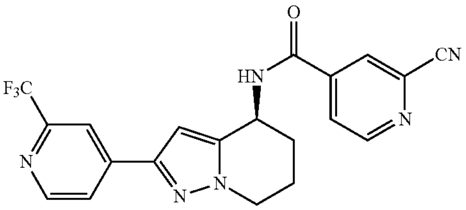 [SMILES: N#Cc1cc(C(=O)N[C@H]2CCCn3nc(-c4ccnc(C(F)(F)F)c4)cc32)ccn1] (S)-2-Cyano-N-(2-(2-(trifluoromethyl)pyridin-4-yl)-4,5,6,7-tetrahydropyrazolo[1,5-a]pyridin-4-yl)isonicotinamide | LCMS (ESI) m/z: 413.2 $[M + H]^+$. $^1H$ NMR (400 MHz, DMSO-$d_6$) δ 9.44 (d, J = 8.4 Hz, 1H), 8.95 (d, J = 4.8 Hz, 1H), 8.75 (d, J = 5.2 Hz, 1H), 8.44 (s, 1H), 8.19 (s, 1H), 8.15 (dd, J = 1.6, 5.2 Hz, 1H), 8.09-8.02 (m, 1H), 7.08 (s, 1H), 5.41-5.34 (m, 1H), 4.30-4.22 (m, 1H), 4.21-4.13 (m, 1H), 2.26-2.08 (m, 3H), 1.91-1.83 (m, 1H). | acetonitrile 30%-60%/ 0.225% formic acid in water |
| I-320a | 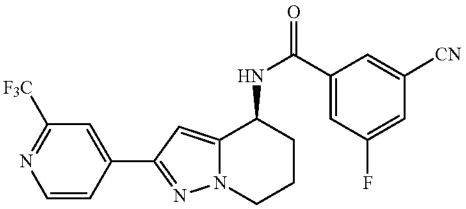 [SMILES: N#Cc1cc(F)cc(C(=O)N[C@H]2CCCn3nc(-c4ccnc(C(F)(F)F)c4)cc32)c1] (S)-3-Cyano-5-fluoro-N-(2-(2-(trifluoromethyl)pyridin-4-yl)-4,5,6,7-tetrahydropyrazolo[1,5-a]pyridin-4-yl)benzamide | LCMS (ESI) m/z: 430.1 $[M + H]^+$. $^1H$ NMR (400 MHz, DMSO-$d_6$) δ 9.26 (d, J = 8.0 Hz, 1H), 8.74 (d, J = 5.2 Hz, 1H), 8.23 (s, 1H), 8.19 (s, 1H), 8.15-8.03 (m, 3H), 7.06 (s, 1H), 5.41-5.31 (m, 1H), 4.29-4.22 (m, 1H), 4.21-4.10 (m, 1H), 2.27-2.19 (m, 1H), 2.18-2.04 (m, 2H), 1.91-1.81 (m, 1H). | acetonitrile 36%-46%/ 0.225% formic acid in water |

-continued

| Compound No. | Structure | Analytical data | Separation conditions |
|---|---|---|---|
| I-321a | 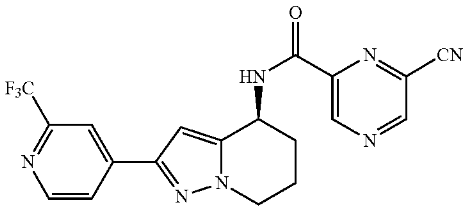 [SMILES: N#Cc1cncc(C(=O)N[C@H]2CCCn3nc(-c4ccnc(C(F)(F)F)c4)cc32)n1]<br>(S)-6-Cyano-N-(2-(2-(trifluoromethyl)pyridin-4-yl)-4,5,6,7-tetrahydropyrazolo[1,5-a]pyridin-4-yl)pyrazine-2-carboxamide | LCMS (ESI) m/z: 414.1 $[M + H]^+$. $^1H$ NMR (400 MHz, DMSO-$d_6$) δ 9.26 (d, J = 8.0 Hz, 1H), 8.74 (d, J = 5.2 Hz, 1H), 8.23 (s, 1H), 8.19 (s, 1H), 8.15-8.03 (m, 3H), 7.06 (s, 1H), 5.41-5.31 (m, 1H), 4.29-4.22 (m, 1H), 4.21-4.10 (m, 1H), 2.27-2.19 (m, 1H), 2.18-2.04 (m, 2H), 1.91-1.81 (m, 1H). | acetonitrile 36%-46%/ 0.225% formic acid in water |
| I-278a | 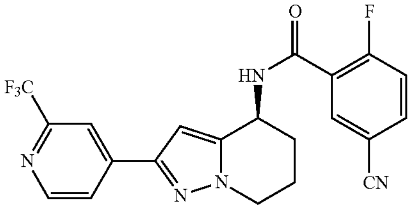 [SMILES: N#Cc1ccc(F)c(C(=O)N[C@H]2CCCn3nc(-c4ccnc(C(F)(F)F)c4)cc32)c1]<br>(S)-5-Cyano-2-fluoro-N-(2-(2-(trifluoromethyl)pyridin-4-yl)-4,5,6,7-tetrahydropyrazolo[1,5-a]pyridin-4-yl)benzamide | LCMS (ESI) m/z: 430.2 $[M + H]^+$. $^1H$ NMR (400 MHz, DMSO-$d_6$) δ 9.15 (d, J = 8.4 Hz, 1H), 8.76 (d, J = 4.8 Hz, 1H), 8.21-8.16 (m, 2H), 8.10-8.05 (m, 2H), 7.60-7.54 (m, 1H), 7.07 (s, 1H), 5.36-5.27 (m, 1H), 4.29-4.20 (m, 1H), 4.19-4.09 (m, 1H), 2.24-2.05 (m, 3H), 1.89-1.79 (m, 1H) | acetonitrile 45%-75%/ 0.225% formic acid in water |
| I-282a | 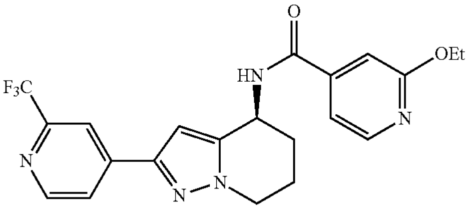 [SMILES: CCOc1cc(C(=O)N[C@H]2CCCn3nc(-c4ccnc(C(F)(F)F)c4)cc32)ccn1]<br>(S)-2-Ethoxy-N-(2-(2-(trifluoromethyl)pyridin-4-yl)-4,5,6,7-tetrahydropyrazolo[1,5-a]pyridin-4-yl)isonicotinamide | LCMS (ESI) m/z: 430.2 $[M + H]^+$. $^1H$ NMR (400 MHz, DMSO-$d_6$) δ 9.18 (d, J = 8.4 Hz, 1H), 8.73 (d, J = 5.2 Hz, 1H), 8.29 (d, J = 5.2 Hz, 1H), 8.21 (s, 1H), 8.08 (d, J = 4.8 Hz, 1H), 7.39 (m, 1H), 7.24 (s, 1H), 7.04 (s, 1H), 5.41-5.29 (m, 1H), 4.33 (q, J = 7.2 Hz, 2H), 4.29-4.21 (m, 1H), 4.18-4.09 (m, 1H), 2.27-2.18 (m, 1H), 2.17-2.05 (m, 2H), 1.91-1.80 (m, 1H), 1.32 (t, J = 7.2 Hz, 3H). | acetonitrile 45%-75%/ 0.225% formic acid in water |
| I-245a | 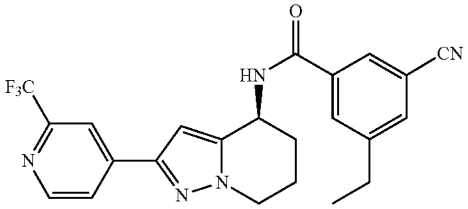 [SMILES: CCc1cc(C#N)cc(C(=O)N[C@H]2CCCn3nc(-c4ccnc(C(F)(F)F)c4)cc32)c1]<br>(S)-3-Cyano-5-ethyl-N-(2-(2-(trifluoromethyl)pyridin-4-yl)-4,5,6,7-tetrahydropyrazolo[1,5-a]pyridin-4-yl)benzamide | LCMS (ESI) m/z: 440.2 $[M + H]^+$. $^1H$ NMR (400 MHz, DMSO-$d_6$) δ 9.15 (d, J = 8.4 Hz, 1H), 8.74 (d, J = 5.2 Hz, 1H), 8.21 (s, 1H), 8.16 (s, 1H), 8.11-8.05 (m, 2H), 7.91 (s, 1H), 7.05 (s, 1H), 5.42-5.34 (m, 1H), 4.31-4.11 (m, 2H), 2.72 (q, J = 7.6 Hz, 2H), 2.28-2.19 (m, 1H), 2.18-2.05 (m, 2H), 1.92-1.79 (m, 1H), 1.22 (t, J = 7.6 Hz, 3H). | acetonitrile 52%-82%/ 0.225% formic acid in water |
| I-290a | 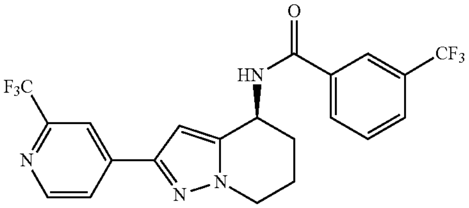 [SMILES: O=C(N[C@H]1CCCn2nc(-c3ccnc(C(F)(F)F)c3)cc21)c1cccc(C(F)(F)F)c1]<br>(S)-3-(Trifluoromethyl)-N-(2-(2-(trifluoromethyl)pyridin-4-yl)-4,5,6,7-tetrahydropyrazolo[1,5-a]pyridin-4-yl)benzamide | LCMS (ESI) m/z: 455.1 $[M + H]^+$. $^1H$ NMR (400 MHz, DMSO-$d_6$) δ 9.25 (d, J = 8.4 Hz, 1H), 8.73 (d, J = 5.2 Hz, 1H), 8.28-8.21 (m, 3H), 8.09-8.08 (m, 1H), 7.94 (d, J = 8.0 Hz, 1H), 7.78-7.73 (m, 1H), 7.06 (s, 1H), 5.43-5.40 (m, 1H), 4.28-4.24 (m, 1H), 4.19-4.16 (m, 1H), 2.48-2.12 (m, 3H), 1.92-1.89 (m, 1H). | acetonitrile 50%-80%/ 0.225% formic acid in water |

-continued

| Compound No. | Structure | Analytical data | Separation conditions |
|---|---|---|---|
| I-326a | 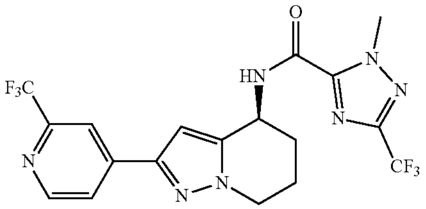 (S)-1-Methyl-3-(trifluoromethyl)-N-(2-(2-(trifluoromethyl)pyridin-4-yl)-4,5,6,7-tetrahydropyrazolo[1,5-a]pyridin-4-yl)-1H-1,2,4-triazole-5-carboxamide | LCMS (ESI) m/z: 474.1 $[M + H]^+$. $^1H$ NMR (400 MHz, DMSO-$d_6$) δ 9.66 (d, J = 8.8 Hz, 1H), 8.74 (d, J = 4.8 Hz, 1H), 8.18 (s, 1H), 8.06 (d, J = 5.2 Hz, 1H), 7.02 (s, 1H), 5.43-5.24 (m, 1H), 4.29 (s, 3H), 4.28-4.21 (m, 1H), 4.14-4.03 (m, 1H), 2.30-2.19 (m, 1H), 2.15-1.97 (m, 3H). | acetonitrile 56%-86%/ 0.225% formic acid in water |
| I-195a | 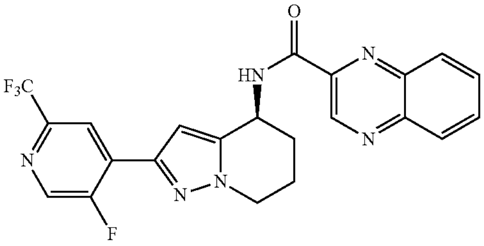 [SMILES: O=C(N[C@H]1CCCn2nc(-c3cc(C(F)(F)F)ncc3F)cc21)c1cnc2ccccc2n1] (S)-N-(2-(5-Fluoro-2-(trifluoromethyl)pyridin-4-yl)-4,5,6,7-tetrahydropyrazolo[1,5-a]pyridin-4-yl)quinoxaline-2-carboxamide | LCMS (ESI) m/z: 457.1 $[M + H]^+$. $^1H$ NMR (400 MHz, DMSO-$d_6$) δ 9.59-9.51 (m, 2H), 8.82 (d, J = 2.0 Hz, 1H), 8.33-8.29 (m, 1H), 8.24-8.17 (m, 2H), 8.03-7.96 (m, 2H), 6.81 (d, J = 3.6 Hz, 1H), 5.54-5.43 (m, 1H), 4.36-4.27 (m, 1H), 4.24-4.14 (m, 1H), 2.34-2.25 (m, 1H), 2.20-2.07 (m, 3H). | acetonitrile 40%-70%/ 0.225% formic acid in water |
| I-199a | 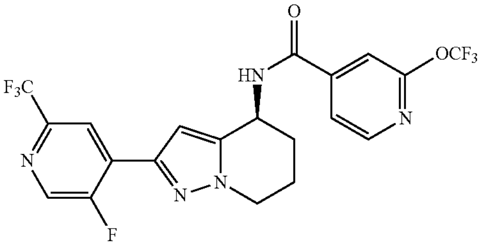 [SMILES: O=C(N[C@H]1CCCn2nc(-c3cc(C(F)(F)F)ncc3F)cc21)c1ccnc(OC(F)(F)F)c1] (S)-N-(2-(5-Fluoro-2-(trifluoromethyl)pyridin-4-yl)-4,5,6,7-tetrahydropyrazolo[1,5-a]pyridin-4-yl)-2-(trifluoromethoxy)isonicotinamide | LCMS (ESI) m/z: 490.0 $[M + H]^+$. $^1H$ NMR (400 MHz, DMSO-$d_6$) δ 9.36 (d, J = 8.0 Hz, 1H), 8.84 (d, J = 2.4 Hz, 1H), 8.54 (d, J = 5.2 Hz, 1H), 8.31 (d, J = 5.6 Hz, 1H), 7.86 (dd, J = 1.2, 5.2 Hz, 1H), 7.68 (s, 1H), 6.84 (d, J = 3.6 Hz, 1H), 5.45-5.25 (m, 1H), 4.37-4.12 (m, 2H), 2.31-2.02 (m, 3H), 1.97-1.84 (m, 1H). | acetonitrile 50%-80%/ 0.225% formic acid in water |
| I-204a | 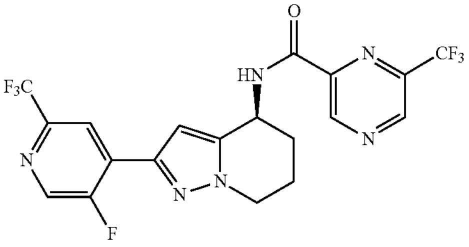 [SMILES: O=C(N[C@H]1CCCn2nc(-c3cc(C(F)(F)F)ncc3F)cc21)c1cncc(C(F)(F)F)n1] (S)-N-(2-(5-Fluoro-2-(trifluoromethyl)pyridin-4-yl)-4,5,6,7-tetrahydropyrazolo[1,5-a]pyridin-4-yl)-6-(trifluoromethyl)pyrazine-2-carboxamide | LCMS (ESI) m/z: 475.2 $[M + H]^+$. $^1H$ NMR (400 MHz, DMSO-$d_6$) δ 9.53 (s, 1H), 9.48 (d, J = 8.8 Hz, 1H), 9.41 (s, 1H), 8.82 (s, 1H), 8.30 (d, J = 5.6 Hz, 1H), 6.77 (d, J = 3.2 Hz, 1H), 5.51-5.40 (m, 1H), 4.34-4.27 (m, 1H), 4.20-4.09 (m, 1H), 2.30-2.21 (m, 1H), 2.14-2.04 (m, 3H). | acetonitrile 52%-82%/ 0.225% formic acid in water |

-continued

| Compound No. | Structure | Analytical data | Separation conditions |
|---|---|---|---|
| I-203a | 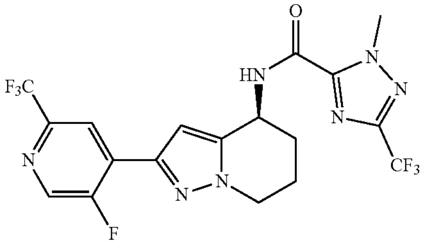 [SMILES: Cn1nc(C(F)(F)F)nc1C(=O)N[C@H]1CCCn2nc(-c3cc(C(F)(F)F)ncc3F)cc21] (S)-N-(2-(5-Fluoro-2-(trifluoromethyl)pyridin-4-yl)-4,5,6,7-tetrahydropyrazolo[1,5-a]pyridin-4-yl)-1-methyl-3-(trifluoromethyl)-1H-1,2,4-triazole-5-carboxamide | LCMS (ESI) m/z: 478.3 $[M + H]^+$. $^1H$ NMR (400 MHz, DMSO-$d_6$) δ 9.62 (d, J = 8.8 Hz, 1H), 8.84 (d, J = 2.4 Hz, 1H), 8.31 (d, J = 5.6 Hz, 1H), 6.80 (d, J = 3.2 Hz, 1H), 5.42-5.26 (m, 1H), 4.26 (s, 3H), 4.25-4.23 (m, 1H), 4.19-4.06 (m, 1H), 2.30-2.18 (m, 1H), 2.17-1.95 (m, 3H). | acetonitrile 43%-73%/ 0.225% formic acid in water |
| I-202a | 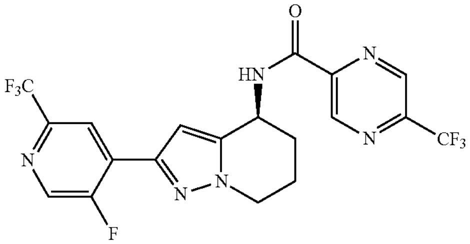 [SMILES: O=C(N[C@H]1CCCn2nc(-c3cc(C(F)(F)F)ncc3F)cc21)c1cnc(C(F)(F)F)cn1] (S)-N-(2-(5-Fluoro-2-(trifluoromethyl)pyridin-4-yl)-4,5,6,7-tetrahydropyrazolo[1,5-a]pyridin-4-yl)-5-(trifluoromethyl)pyrazine-2-carboxamide | LCMS (ESI) m/z: 475.1 $[M + H]^+$. $^1H$ NMR (400 MHz, DMSO-$d_6$) δ 9.66-9.61 (m, 1H), 9.42 (s, 1H), 9.27 (s, 1H), 8.83 (d, J = 2.0 Hz, 1H), 8.30 (d, J = 5.6 Hz, 1H), 6.76 (d, J = 3.2 Hz, 1H), 5.54-5.32 (m, 1H), 4.38-4.26 (m, 1H), 4.22-4.06 (m, 1H), 2.31-2.04 (m, 4H). | acetonitrile 52%-82%/ 0.225% formic acid in water |
| I-302a | 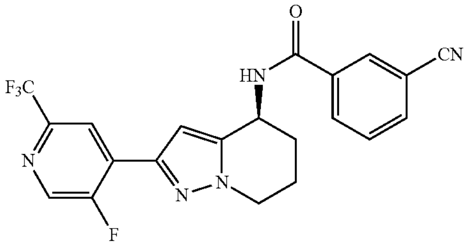 [SMILES: N#Cc1cccc(C(=O)N[C@H]2CCCn3nc(-c4cc(C(F)(F)F)ncc4F)cc32)c1] (S)-3-Cyano-N-(2-(5-fluoro-2-(trifluoromethyl)pyridin-4-yl)-4,5,6,7-tetrahydropyrazolo[1,5-a]pyridin-4-yl)benzamide | LCMS (ESI) m/z: 430.1 $[M + H]^+$. $^1H$ NMR (400 MHz, DMSO-$d_6$) δ 9.19 (d, J = 8.4 Hz, 1H), 8.85 (d, J = 2.0 Hz, 1H), 8.39-8.30 (m, 2H), 8.23 (d, J = 7.6 Hz, 1H), 8.04 (d, J = 7.6 Hz, 1H), 7.79-7.63 (m, 1H), 6.83 (d, J = 3.5 Hz, 1H), 5.46-5.33 (m, 1H), 4.36-4.16 (m, 2H), 2.26-2.07 (m, 3H), 1.99-1.84 (m, 1H). | acetonitrile 43%-73%/ 0.225% formic acid in water |
| I-209a | 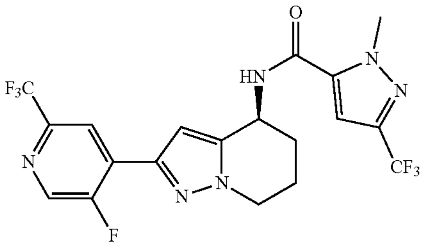 [SMILES: Cn1nc(C(F)(F)F)cc1C(=O)N[C@H]1CCCn2nc(-c3cc(C(F)(F)F)ncc3F)cc21] (S)-N-(2-(5-Fluoro-2-(trifluoromethyl)pyridin-4-yl)-4,5,6,7-tetrahydropyrazolo[1,5-a]pyridin-4-yl)-1-methyl-3-(trifluoromethyl)-1H-pyrazole-5-carboxamide | LCMS (ESI) m/z: 477.2 $[M + H]^+$. $^1H$ NMR (400 MHz, DMSO-$d_6$) δ 9.16 (d, J = 8.0 Hz, 1H), 8.85 (d, J = 2.4 Hz, 1H), 8.31 (d, J = 5.6 Hz, 1H), 7.37 (s, 1H), 6.83 (d, J = 3.2 Hz, 1H), 5.40-5.27 (m, 1H), 4.35-4.20 (m, 2H), 4.19 (s, 3H), 2.28-2.19 (m, 1H), 2.19-2.03 (m, 2H), 1.96-1.80 (m, 1H). | acetonitrile 52%-82%/ 0.225% formic acid in water |

-continued

| Compound No. | Structure | Analytical data | Separation conditions |
|---|---|---|---|
| I-182a | 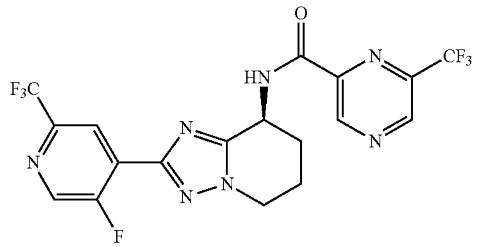 (S)-N-(2-(5-Fluoro-2-(trifluoromethyl)pyridin-4-yl)-5,6,7,8-tetrahydro-[1,2,4]triazolo[1,5-a]pyridin-8-yl)-6-(trifluoromethyl)pyrazine-2-carboxamide | LCMS (ESI) m/z: 476.2 [M + H]$^+$. $^1$H NMR (400 MHz, DMSO-$d_6$) δ 9.60 (d, J = 8.8 Hz, 1H), 9.53 (s, 1H), 9.43 (s, 1H), 8.94 (d, J = 2.0 Hz, 1H), 8.30 (d, J = 5.6 Hz, 1H), 5.55-5.43 (m, 1H), 4.41-4.30 (m, 1H), 4.28-4.16 (m, 1H), 2.31-2.20 (m, 2H), 2.20-2.09 (m, 2H). | acetonitrile 37%-67%/ 0.225% formic acid in water |
| I-305a | 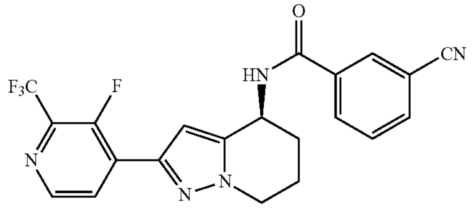 [SMILES: N#Cc1cccc(C(=O)N[C@H]2CCCn3nc(-c4ccnc(C(F)(F)F)c4F)cc32)c1] (S)-3-Cyano-N-(2-(5-fluoro-2-(trifluoromethyl)pyridin-4-yl)-4,5,6,7-tetrahydropyrazolo[1,5-a]pyridin-4-yl)benzamide | LCMS (ESI) m/z: 430.1 [M + H]$^+$. $^1$H NMR (400 MHz, DMSO-$d_6$) δ 9.18 (d, J = 8.0 Hz, 1H), 8.57 (d, J = 4.8 Hz, 1H), 8.34 (t, J = 1.2 Hz, 1H), 8.29-8.17 (m, 2H), 8.06-8.01 (m, 1H), 7.75-7.70 (m, 1H), 6.80 (d, J = 3.6 Hz, 1H), 5.45-5.28 (m, 1H), 4.41-4.10 (m, 2H), 2.30-2.06 (m, 3H), 2.00-1.84 (m, 1H). | acetonitrile 50%-80%/ 0.225% formic acid in water |
| I-303a | 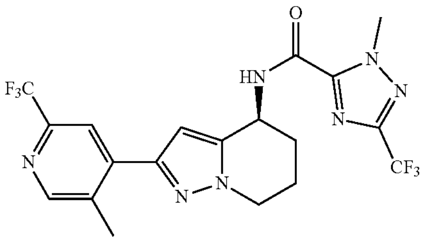 [SMILES: Cc1cnc(C(F)(F)F)cc1-c1cc2n(n1)CCC[C@@H]2NC(=O)c1nc(C(F)(F)F)nn1C] (S)-1-Methyl-N-(2-(5-methyl-2-(trifluoromethyl)pyridin-4-yl)-4,5,6,7-tetrahydropyrazolo[1,5-a]pyridin-4-yl)-3-(trifluoromethyl)-1H-1,2,4-triazole-5-carboxamide | LCMS (ESI) m/z: 474.2 [M + H]$^+$. $^1$H NMR (400 MHz, DMSO-$d_6$) δ 9.63 (d, J = 8.8 Hz, 1H), 8.65 (s, 1H), 8.04 (s, 1H), 6.84 (s, 1H), 5.43-5.26 (m, 1H), 4.28 (s, 3H), 4.27-4.21 (m, 1H), 4.19-4.07 (m, 1H), 2.60 (s, 3H), 2.28-2.01 (m, 4H). | acetonitrile 46%-76%/ 0.225% formic acid in water |
| I-181a | 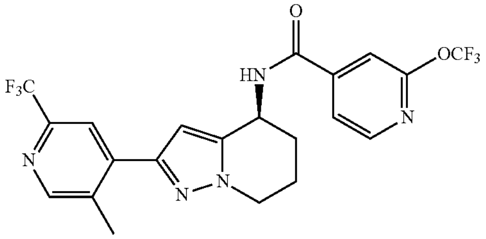 [SMILES: Cc1cnc(C(F)(F)F)cc1-c1cc2n(n1)CCC[C@@H]2NC(=O)c1ccnc(OC(F)(F)F)c1] (S)-N-(2-(5-Methyl-2-(trifluoromethyl)pyridin-4-yl)-4,5,6,7-tetrahydropyrazolo[1,5-a]pyridin-4-yl)-2-(trifluoromethoxy)isonicotinamide | LCMS (ESI) m/z: 486.2 [M + H]$^+$. $^1$H NMR (400 MHz, DMSO-$d_6$) δ 9.36 (d, J = 8.4 Hz, 1H), 8.65 (s, 1H), 8.54 (d, J = 5.2 Hz, 1H), 8.05 (s, 1H), 7.87 (d, J = 5.2 Hz, 1H), 7.69 (s, 1H), 6.89 (s, 1H), 5.43-5.34 (m, 1H), 4.30-4.15 (m, 2H), 2.59 (s, 3H), 2.27-2.03 (m, 3H), 1.94-1.81 (m, 1H). | acetonitrile 50%-80%/ 0.225% formic acid in water |

-continued

| Compound No. | Structure | Analytical data | Separation conditions |
|---|---|---|---|
| I-179a | 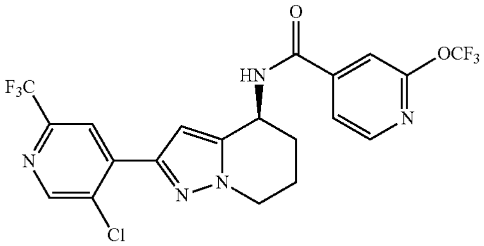 [SMILES: O=C(N[C@H]1CCCn2nc(-c3cc(C(F)(F)F)ncc3Cl)cc21)c1ccnc(OC(F)(F)F)c1] (S)-N-(2-(5-Chloro-2-(trifluoromethyl)pyridin-4-yl)-4,5,6,7-tetrahydropyrazolo[1,5-a]pyridin-4-yl)-2-(trifluoromethoxy)isonicotinamid | LCMS (ESI) m/z: 506.2 $[M + H]^+$. $^1H$ NMR (400 MHz, DMSO-$d_6$) δ 9.38 (d, J = 8.0 Hz, 1H), 8.88 (s, 1H), 8.54 (d, J = 5.2 Hz, 1H), 8.26 (s, 1H), 7.87-7.83 (m, 1H), 7.67 (s, 1H), 7.05 (s, 1H), 5.43-5.36 (m, 1H), 4.32-4.17 (m, 2H), 2.28-2.08 (m, 3H), 1.95-1.85 (m, 1H). | acetonitrile 73%-46%/ 0.225% formic acid in water |
| I-284a | 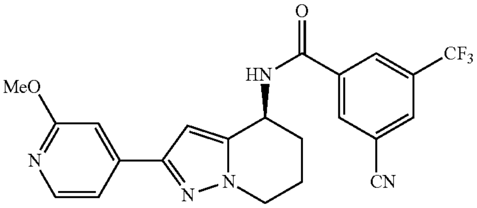 [SMILES: COc1cc(-c2cc3n(n2)CCC[C@@H]3NC(=O)c2cc(C#N)cc(C(F)(F)F)c2)ccn1] (S)-3-Cyano-N-(2-(2-methoxypyridin-4-yl)-4,5,6,7-tetrahydropyrazolo[1,5-a]pyridin-4-yl)-5-(trifluoromethyl)benzamide | LCMS (ESI) m/z: 442.1 $[M + H]^+$. $^1H$ NMR (400 MHz, DMSO-$d_6$) δ 9.38 (d, J = 8.4 Hz, 1H), 8.64 (s, 1H), 8.58 (s, 1H), 8.53 (s, 1H), 8.14 (d, J = 5.6 Hz, 1H), 7.38 (dd, J = 1.6, 5.6 Hz, 1H), 7.16 (s, 1H), 6.87 (s, 1H), 5.40-5.33 (m, 1H), 4.25-4.11 (m, 2H), 3.85 (s, 3H), 2.27-2.18 (m, 1H), 2.17-2.03 (m, 2H), 1.91-1.81 (m, 1H). | acetonitrile 41%-71%/ 0.225% formic acid in water |
| I-287a | 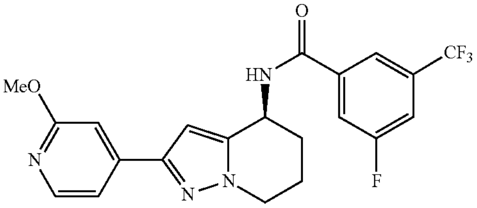 [SMILES: COc1cc(-c2cc3n(n2)CCC[C@@H]3NC(=O)c2cc(F)cc(C(F)(F)F)c2)ccn1] (S)-3-Fluoro-N-(2-(2-methoxypyridin-4-yl)-4,5,6,7-tetrahydropyrazolo[1,5-a]pyridin-4-yl)-5-(trifluoromethyl)benzamide | $^1H$ NMR (400 MHz, DMSO-$d_6$) δ 9.29 (d, J = 8.4 Hz, 1H), 8.18-8.11 (m, 2H), 8.06 (d, J = 9.6 Hz, 1H), 7.94 (d, J = 8.4 Hz, 1H), 7.38 (d, J = 5.6 Hz, 1H), 7.16 (s, 1H), 6.86 (s, 1H), 5.40-5.32 (m, 1H), 4.25-4.09 (m, 2H), 3.85 (s, 3H), 2.25-2.17 (m, 1H), 2.17-2.04 (m, 2H), 1.91-1.81 (m, 1H). | acetonitrile 45%-75%/ 0.225% formic acid in water |
| I-344a | 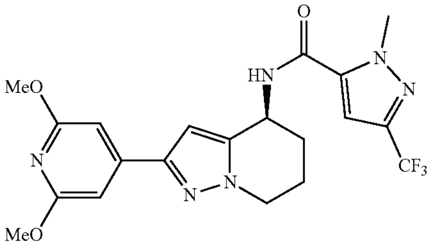 [SMILES: COc1cc(-c2cc3n(n2)CCC[C@@H]3NC(=O)c2cc(C(F)(F)F)nn2C)cc(OC)n1] (S)-3-Cyano-5-fluoro-N-(2-(2-methoxypyridin-4-yl)-4,5,6,7-tetrahydropyrazolo[1,5-a]pyridin-4-yl)benzamide | LCMS (ESI) m/z: 451.1 $[M + H]^+$. $^1H$ NMR (400 MHz, DMSO-$d_6$) δ 9.13 (d, J = 8.4 Hz, 1H), 7.37 (s, 1H), 6.80 (s, 1H), 6.75 (s, 2H), 5.33-5.24 (m, 1H), 4.23-4.16 (m, 4H), 4.14-4.07 (m, 1H), 3.85 (s, 6H), 2.23-2.15 (m, 1H), 2.14-1.99 (m, 2H), 1.95-1.75 (m, 1H). | acetonitrile 40%-80%/ 0.225% formic acid in water |

-continued

| Compound No. | Structure | Analytical data | Separation conditions |
|---|---|---|---|
| I-313a | 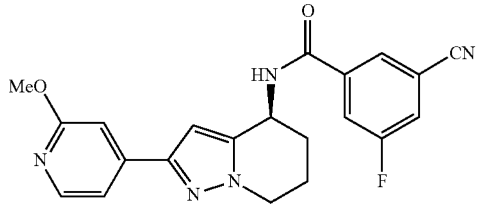 [SMILES: COc1cc(-c2cc3n(n2)CCC[C@@H]3NC(=O)c2cc(F)cc(C#N)c2)ccn1] (S)-3-Cyano-5-fluoro-N-(2-(2-methoxypyridin-4-yl)-4,5,6,7-tetrahydropyrazolo[1,5-a]pyridin-4-yl)benzamide | LCMS (ESI) m/z: 392.2 $[M + H]^+$. $^1H$ NMR (400 MHz, DMSO-$d_6$) δ 9.21 (d, J = 8.0 Hz, 1H), 8.22 (s, 1H), 8.14 (d, J = 5.2 Hz, 1H), 8.10-8.03 (m, 2H), 7.39-7.35 (m, 1H), 7.15 (s, 1H), 6.84 (s, 1H), 5.36-5.32 (m, 1H), 4.23-4.13 (m, 2H), 3.85 (s, 3H), 2.22-2.10 (m, 3H), 1.85-1.82 (m, 1H). | acetonitrile 34%-64%/0.225% formic acid in water |
| I-262a | 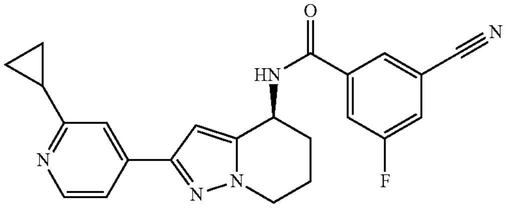 [SMILES: N#Cc1cc(F)cc(C(=O)N[C@H]2CCCn3nc(-c4ccnc(C5CC5)c4)cc32)c1] (S)-2-(Trifluoromethoxy)-N-(2-(2-(trifluoromethyl)pyridin-4-yl)-4,5,6,7-tetrahydropyrazolo[1,5-a]pyridin-4-yl)isonicotinamid | LCMS (ESI) m/z: 402.2 $[M + H]^+$. $^1H$ NMR (400 MHz, DMSO-$d_6$) δ 9.25 (d, J = 8.2 Hz, 1H), 8.36 (d, J = 5.2 Hz, 1H), 8.24 (s, 1H), 8.13-8.06 (m, 2H), 7.67 (s, 1H), 7.49 (dd, J = 1.6, 5.2 Hz, 1H), 6.84 (s, 1H), 5.39-5.30 (m, 1H), 4.26-4.19 (m, 1H), 4.17-4.09 (m, 1H), 2.28-2.19 (m, 1H), 2.17-2.03 (m, 3H), 1.93-1.79 (m, 1H), 0.97-0.90 (m, 4H). | acetonitrile 17%-47%/0.225% formic acid in water |
| I-281a | 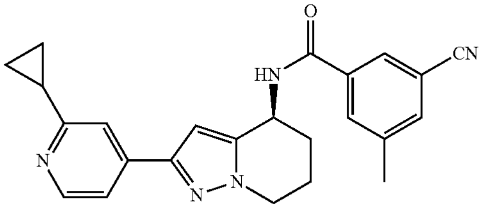 [SMILES: Cc1cc(C#N)cc(C(=O)N[C@H]2CCCn3nc(-c4ccnc(C5CC5)c4)cc32)c1] (S)-3-Cyano-N-(2-(2-cyclopropylpyridin-4-yl)-4,5,6,7-tetrahydropyrazolo[1,5-a]pyridin-4-yl)-5-methylbenzamide TFA salt | LCMS (ESI) m/z: 398.2 $[M + H]^+$. 9.13 (d, J = 8.4 Hz, 1H), 8.51 (d, J = 6.0 Hz, 1H), 8.14 (s, 1H), 8.07 (s, 1H), 7.92-7.77 (m, 3H), 7.04 (s, 1H), 5.41-5.34 (m, 1H), 4.29-4.23 (m, 1H), 4.21-4.15 (m, 1H), 2.53-2.51 (m, 1H), 2.42 (s, 3H), 2.27-2.20 (m, 2H), 2.17-2.07 (m, 2H), 1.93-1.84 (m, 1H), 1.14 (m, 4H). | acetonitrile 9%-39%/0.075% TFA acid in water |
| I-252a | 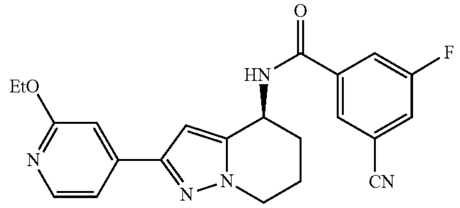 (S)-3-Cyano-N-(2-(2-ethoxypyridin-4-yl)-4,5,6,7-tetrahydropyrazolo[1,5-a]pyridin-4-yl)-5-fluorobenzamide | LCMS (ESI) m/z: 406.2 $[M + H]^+$. $^1H$ NMR (400 MHz, DMSO-$d_6$) δ 9.23 (d, J = 8.4 Hz, 1H), 8.22 (s, 1H), 8.12 (d, J = 5.2 Hz, 1H), 8.11-8.03 (m, 2H), 7.36 (dd, J = 1.2, 5.6 Hz, 1H), 7.13 (s, 1H), 6.86 (s, 1H), 5.36-5.28 (m, 1H), 4.29 (q, J = 6.8 Hz, 2H), 4.24-4.17 (m, 1H), 4.16-4.08 (m, 1H), 2.25-2.17 (m, 1H), 2.16-2.03 (m, 2H), 1.90-1.77 (m, 1H), 1.31 (t, J = 6.8 Hz, 3H). | acetonitrile 33%-63%/0.225% formic acid in water |
| I-222a | 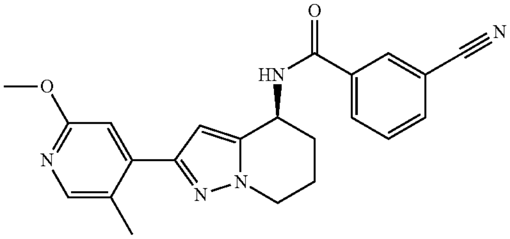 [SMILES: COc1cc(-c2cc3n(n2)CCC[C@@H]3NC(=O)c2cccc(C#N)c2)c(C)cn1] (S)-3-Cyano-N-(2-(2-methoxy-5-methylpyridin-4-yl)-4,5,6,7-tetrahydropyrazolo[1,5-a]pyridin-4-yl)benzamide | LCMS (ESI) m/z: 388.2 $[M + H]^+$. $^1H$ NMR (400 MHz, DMSO-$d_6$) δ 9.15 (d, J = 8.0 Hz, 1H), 8.33 (s, 1H), 8.21 (d, J = 8.0 Hz, 1H), 8.04-8.00 (m, 2H), 7.74-7.67 (m, 1H), 7.00 (s, 1H), 6.66 (s, 1H), 5.43-5.31 (m, 1H), 4.26-4.11 (m, 2H), 3.82 (s, 3H), 2.38 (s, 3H), 2.25-2.20 (m, 1H), 2.17-2.02 (m, 2H), 1.91-1.81 (m, 1H). 1.31 (t, J = 6.8 Hz, 3H). | acetonitrile 40%-70%/0.05% $NH_3H_2O$ + 10 mM $NH_4HCO_3$ in water |

-continued

| Compound No. | Structure | Analytical data | Separation conditions |
|---|---|---|---|
| I-239a | 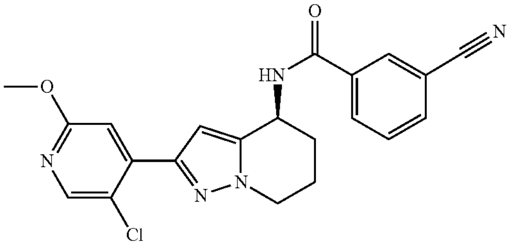 [SMILES: COc1cc(-c2cc3n(n2)CCC[C@@H]3NC(=O)c2cccc(C#N)c2)c(Cl)cn1] (S)-N-(2-(5-Chloro-2-methoxypyridin-4-yl)-4,5,6,7-tetrahydropyrazolo[1,5-a]pyridin-4-yl)-3-cyanobenzamide | LCMS (ESI) m/z: 408.1 $[M+H]^+$. $^1H$ NMR (400 MHz, DMSO-$d_6$) δ9.18 (d, J = 8.0 Hz, 1H), 8.32 (s, 1H), 8.26 (s, 1H), 8.21 (d, J = 8.0 Hz, 1H), 8.02 (d, J = 7.8 Hz, 1H), 7.73-7.68 (m, 1H), 7.18 (s, 1H), 6.82 (s, 1H), 5.44-5.32 (m, 1H), 4.29-4.12 (m, 2H), 3.86 (s, 3H), 2.30-2.03 (m, 3H), 1.98-1.82 (m, 1H). | acetonitrile 20%-50%/ 0.225% formic acid in water. |
| I-193a | 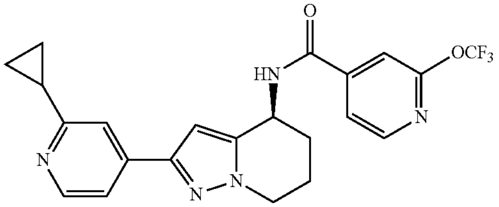 [SMILES: O=C(N[C@H]1CCCn2nc(-c3ccnc(C4CC4)c3)cc21)c1ccnc(OC(F)(F)F)c1] (S)-N-(2-(2-Cyclopropylpyridin-4-yl)-4,5,6,7-tetrahydropyrazolo[1,5-a]pyridin-4-yl)-2-(trifluoromethoxy)isonicotinamide | LCMS (ESI) m/z: 444.3 $[M+H]^+$. $^1H$ NMR (400 MHz, DMSO-$d_6$) δ 9.38 (d, J = 8.4 Hz, 1H), 8.56 (d, J = 4.8 Hz, 1H), 8.47 (d, J = 5.2 Hz, 1H), 7.88-7.87 (m, 1H), 7.79-7.76 (m, 2H), 7.69 (s, 1H), 7.02 (s, 1H), 5.40-5.34 (m, 1H), 4.27-4.16 (m, 2H), 2.23-2.12 (m, 4H), 1.92-1.79 (m, 1H), 1.18-1.08 (m, 4H). | acetonitrile 20%-50%/ 0.225% formic acid in water |
| I-309* | 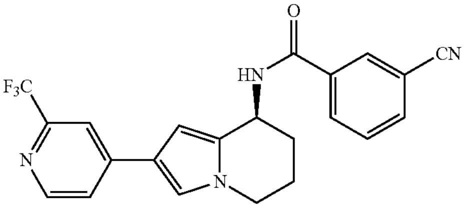 [SMILES: N#Cc1cccc(C(=O)N[C@H]2CCCn3cc(-c4ccnc(C(F)(F)F)c4)cc32)c1] (S)-3-Cyano-N-(2-(2-(trifluoromethyl)pyridin-4-yl)-5,6,7,8-tetrahydroindolizin-8-yl)benzamide | LCMS (ESI) m/z: 411.1 $[M+H]^+$. $^1H$ NMR (400 MHz, DMSO-$d_6$) δ 9.06 (d, J = 8.0 Hz, 1H), 8.54 (d, J = 5.2 Hz, 1H), 8.36 (s, 1H), 8.23 (d, J = 8.0 Hz, 1H), 8.02 (d, J = 8.0 Hz, 1H), 7.94 (s, 1H), 7.77 (d, J = 4.8 Hz, 1H), 7.73-7.68 (m, 1H), 7.65 (s, 1H), 6.63 (s, 1H), 5.32-5.24 (m, 1H), 4.08-4.00 (m, 1H), 3.99-3.91 (m, 1H), 2.19-2.03 (m, 2H), 1.96-1.93 (m, 1H), 1.83-1.73 (m, 1H). | acetonitrile 44%-74%/ 0.225% formic acid in water |
| I-315a | 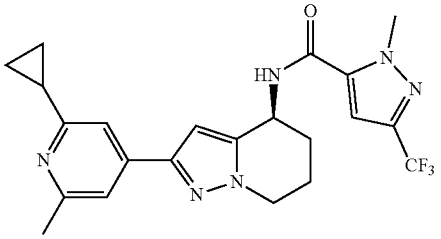 [SMILES: Cc1cc(-c2cc3n(n2)CCC[C@@H]3NC(=O)c2cc(C(F)(F)F)nn2C)cc(C2CC2)n1] (S)-N-(2-(2-Cyclopropyl-6-methylpyridin-4-yl)-4,5,6,7-tetrahydropyrazolo[1,5-a]pyridin-4-yl)-1-methyl-3-(trifluoromethyl)-1H-pyrazole-5-carboxamide | LCMS (ESI) m/z: 445.1 $[M+H]^+$. $^1H$ NMR (400 MHz, DMSO-$d_6$) δ 9.14 (d, J = 8.4 Hz, 1H), 8.12 (d, J = 1.2 Hz, 1H), 7.69 (d, J = 1.2 Hz, 1H), 7.38 (s, 1H), 6.71 (s, 1H), 5.33-5.23 (m, 1H), 4.20 (s, 3H), 4.18-4.01 (m, 2H), 2.25-2.15 (m, 1H), 2.15-2.02 (m, 2H), 1.88-1.75 (m, 1H). | acetonitrile 57%-87%/ 0.225% formic acid in water |
| I-117a | 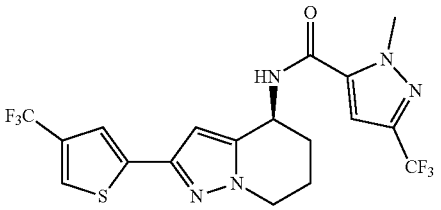 [SMILES: Cn1nc(C(F)(F)F)cc1C(=O)N[C@H]1CCCn2nc(-c3cc(C(F)(F)F)cs3)cc21] (S)-3-Cyano-N-(2-(2-methoxy-5-methylpyridin-4-yl)-4,5,6,7-tetrahydropyrazolo[1,5-a]pyridin-4-yl)benzamide | LCMS (ESI) m/z: 464.0 $[M+H]^+$. $^1H$ NMR (400 MHz, DMSO-$d_6$) δ 9.14 (d, J = 8.4 Hz, 1H), 8.12 (d, J = 1.2 Hz, 1H), 7.69 (d, J = 1.2 Hz, 1H), 7.38 (s, 1H), 6.71 (s, 1H), 5.33-5.23 (m, 1H), 4.20 (s, 3H), 4.18-4.01 (m, 2H), 2.25-2.15 (m, 1H), 2.15-2.02 (m, 2H), 1.88-1.75 (m, 1H). | acetonitrile 57%-87%/ 0.225% formic acid in water |

-continued

| Compound No. | Structure | Analytical data | Separation conditions |
|---|---|---|---|
| I-317a | 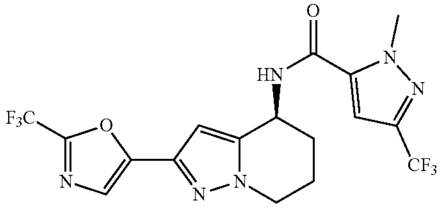 [SMILES: Cn1nc(C(F)(F)F)cc1C(=O)N[C@H]1CCCn2nc(-c3cnc(C(F)(F)F)o3)cc21]<br>(S)-1-Methyl-3-(trifluoromethyl)-N-(2-(2-(trifluoromethyl)oxazol-5-yl)-4,5,6,7-tetrahydropyrazolo[1,5-a]pyridin-4-yl)-1H-pyrazole-5-carboxamide | LCMS (ESI) m/z: 449.1 $[M + H]^+$. $^1H$ NMR (400 MHz, DMSO-$d_6$) δ 9.15 (d, J = 8.4 Hz, 1H), 7.81 (s, 1H), 7.37 (s, 1H), 6.69 (s, 1H), 5.34-5.25 (m, 1H), 4.27-4.08 (m, 5H), 2.27-2.17 (m, 1H), 2.17-2.02 (m, 2H), 1.90-1.79 (m, 1H). | acetonitrile 36%-66%/ 0.225% formic acid in water |
| I-316a | 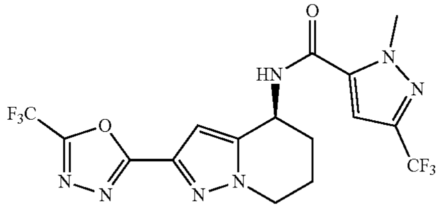 [SMILES: Cn1nc(C(F)(F)F)cc1C(=O)N[C@H]1CCCn2nc(-c3nnc(C(F)(F)F)o3)cc21]<br>(S)-1-Methyl-3-(trifluoromethyl)-N-(2-(5-(trifluoromethyl)-1,3,4-oxadiazol-2-yl)-4,5,6,7-tetrahydropyrazolo[1,5-a]pyridin-4-yl)-1H-pyrazole-5-carboxamide | LCMS (ESI) m/z: 450.1 $[M + H]^+$. $^1H$ NMR (400 MHz, DMSO-$d_6$) δ 9.17 (d, J = 8.4 Hz, 1H), 7.37 (s, 1H), 6.96 (s, 1H), 5.36-5.28 (m, 1H), 4.34-4.26 (m, 1H), 4.25-4.19 (m, 1H), 4.18 (s, 3H), 2.28-2.19 (m, 1H), 2.19-2.05 (m, 2H), 1.93-1.83 (m, 1H). | acetonitrile 45%-75%/ 0.225% formic acid in water |
| I-324a | 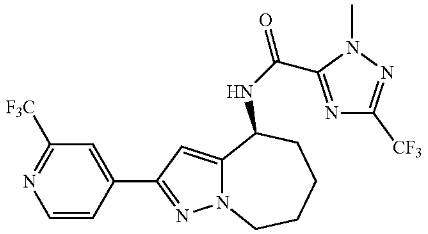<br>(S)-1-Methyl-3-(trifluoromethyl)-N-(2-(2-(trifluoromethyl)pyridin-4-yl)-5,6,7,8-tetrahydro-4H-pyrazolo[1,5-a]azepin-4-yl)-1H-1,2,4-triazole-5-carboxamide | LCMS (ESI) m/z: 474.1 $[M + H]^+$. $^1H$ NMR (400 MHz, DMSO-$d_6$) δ 9.81 (d, J = 8.2 Hz, 1H), 8.71 (d, J = 4.4 Hz, 1H), 8.12 (s, 1H), 8.01 (d, J = 4.8 Hz, 1H), 6.91 (s, 1H), 5.20 (d, J = 2.4 Hz, 1H), 4.60-4.45 (m, 1H), 4.37-4.27 (m, 1H), 4.23 (s, 3H), 2.06-1.80 (m, 5H), 1.59-1.46 (m, 1H). | acetonitrile 54%-84%/ 0.225% formic acid in water |
| I-319a | 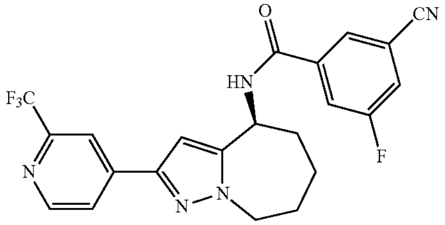 [SMILES: N#Cc1cc(F)cc(C(=O)N[C@H]2CCCCn3nc(-c4ccnc(C(F)(F)F)c4)cc32)c1]<br>(S)-3-Cyano-5-fluoro-N-(2-(2-(trifluoromethyl)pyridin-4-yl)-5,6,7,8-tetrahydro-4H-pyrazolo[1,5-a]azepin-4-yl)benzamide | LCMS (ESI) m/z: 444.1 $[M + H]^+$. $^1H$ NMR (400 MHz, DMSO-$d_6$) δ 9.29 (d, J = 7.6 Hz, 1H), 8.73 (d, J = 5.2 Hz, 1H), 8.31 (s, 1H), 8.17 (s, 1H), 8.12 (d, J = 8.4 Hz, 2H), 8.07 (d, J = 4.8 Hz, 1H), 7.00 (s, 1H), 5.33-5.24 (m, 1H), 4.58-4.52 (m, 1H), 4.40-4.30 (m, 1H), 2.06-1.92 (m, 3H), 1.91-1.80 (m, 2H), 1.64-1.51 (m, 1H). | acetonitrile 36%-66%/ 0.225% formic acid in water |
| I-329a | 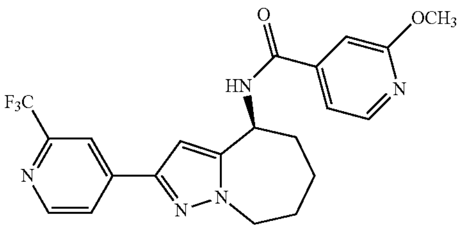 [SMILES: COc1cc(C(=O)N[C@H]2CCCCn3nc(-c4ccnc(C(F)(F)F)c4)cc32)ccn1]<br>(S)-2-Methoxy-N-(2-(2-(trifluoromethyl)pyridin-4-yl)-5,6,7,8-tetrahydro-4H-pyrazolo[1,5-a]azepin-4-yl)isonicotinamide | LCMS (ESI) m/z: 432.1 $[M + H]^+$. $^1H$ NMR (400 MHz, DMSO-$d_6$) δ 9.24 (d, J = 8.0 Hz, 1H), 8.72 (d, J = 5.2 Hz, 1H), 8.34-8.32 (m, 1H), 8.19-8.17 (s, 1H), 8.08-8.05 (m, 1H), 7.47-7.44 (m, 1H), 7.36-7.34 (m, 1H), 6.95 (s, 1H), 5.31-5.24 (m, 1H), 4.57-4.50 (m, 1H), 4.38-4.30 (m, 1H), 3.92 (s, 3H), 2.05-1.92 (m, 3H), 1.87-1.80 (m, 2H), 1.62-1.51 (m, 1H). | acetonitrile 36%-66%/ 0.225% formic acid in water |

-continued

| Compound No. | Structure | Analytical data | Separation conditions |
|---|---|---|---|
| I-263a | 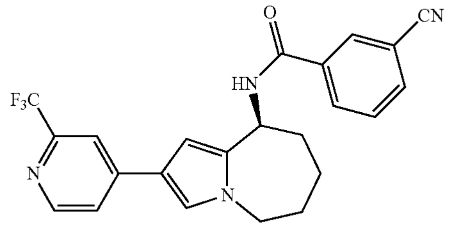 [SMILES: N#Cc1cccc(C(=O)N[C@H]2CCCCn3cc(-c4ccnc(C(F)(F)F)c4)cc32)c1] (S)-3-Cyano-N-(2-(2-(trifluoromethyl)pyridin-4-yl)-6,7,8,9-tetrahydro-5H-pyrrolo[1,2-a]azepin-9-yl)benzamide | LCMS (ESI) m/z: 425.1 [M + H]$^+$. $^1$H NMR (400 MHz, DMSO-$d_6$) δ 9.02 (d, J = 8.0 Hz, 1H), 8.53 (d, J = 5.2 Hz, 1H), 8.42 (s, 1H), 8.25 (d, J = 8.0 Hz, 1H), 8.04 (d, J = 7.6 Hz, 1H), 7.88 (s, 1H), 7.76-7.70 (m, 2H), 7.66 (d, J = 2.0 Hz, 1H), 6.57 (d, J = 1.2 Hz, 1H), 5.26-5.15 (m, 1H), 4.25-4.19 (m, 1H), 4.08-3.97 (m, 1H), 1.97 (s, 1H), 1.94-1.81 (m, 3H), 1.79-1.66 (m, 1H), 1.64-1.48 (m, 1H). | acetonitrile 45%-75%/ 0.225% formic acid in water |
| I-277a | 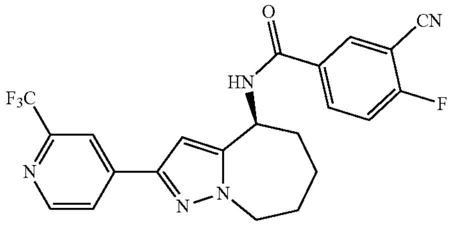 [SMILES: N#Cc1cc(C(=O)N[C@H]2CCCCn3nc(-c4ccnc(C(F)(F)F)c4)cc32)ccc1F] (S)-3-Cyano-4-fluoro-N-(2-(2-(trifluoromethyl)pyridin-4-yl)-5,6,7,8-tetrahydro-4H-pyrazolo[1,5-a]azepin-4-yl)benzamide | LCMS (ESI) m/z: 444.1 [M + H]$^+$. $^1$H NMR (400 MHz, DMSO-$d_6$) δ 9.19 (d, J = 8.0 Hz, 1H), 8.73 (d, J = 5.2 Hz, 1H), 8.58-8.51 (m, 1H), 8.38-8.30 (m, 1H), 8.17 (s, 1H), 8.06 (d, J = 5.2 Hz, 1H), 7.73-7.65 (m, 1H), 6.98 (s, 1H), 5.31-5.25 (m, 1H), 4.60-4.52 (m, 1H), 4.38-4.32 (m, 1H), 2.09-1.92 (m, 3H), 1.90-1.78 (m, 2H), 1.64-1.52 (m, 1H). | acetonitrile 50%-80%/ 0.225% formic acid in water |
| I-244a | 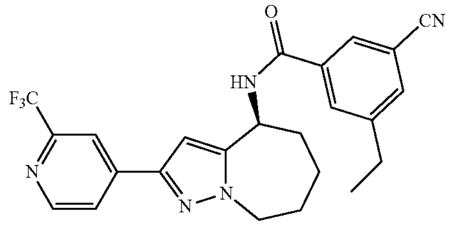 [SMILES: CCc1cc(C#N)cc(C(=O)N[C@H]2CCCCn3nc(-c4ccnc(C(F)(F)F)c4)cc32)c1] (S)-3-Cyano-5-ethyl-N-(2-(2-(trifluoromethyl)pyridin-4-yl)-5,6,7,8-tetrahydro-4H-pyrazolo[1,5-a]azepin-4-yl)benzamide | LCMS (ESI) m/z: 454.2 [M + H]$^+$. $^1$H NMR (400 MHz, DMSO-$d_6$) δ 9.18 (d, J = 7.6 Hz, 1H), 8.72 (d, J = 5.2 Hz, 1H), 8.26 (s, 1H), 8.18 (s, 1H), 8.10 (s, 1H), 8.07 (d, J = 4.8 Hz, 1H), 7.93 (s, 1H), 6.98 (s, 1H), 5.32-5.25 (m, 1H), 4.58-4.50 (m, 1H), 4.40-4.31 (m, 1H), 2.75 (d, J = 7.6 Hz, 2H), 2.06-1.92 (m, 3H), 1.88-1.82 (m, 2H), 1.64-1.50 (m, 1H), 1.24 (t, J = 7.6 Hz, 3H). | acetonitrile 52%-82%/ 0.225% formic acid in water |
| I-283a | 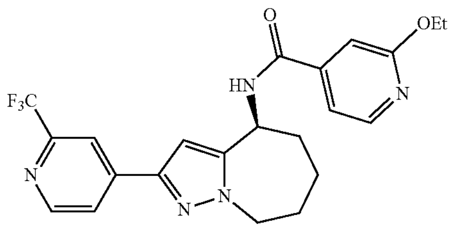 [SMILES: CCOc1cc(C(=O)N[C@H]2CCCCn3nc(-c4ccnc(C(F)(F)F)c4)cc32)ccn1] (S)-2-Ethoxy-N-(2-(2-(trifluoromethyl)pyridin-4-yl)-5,6,7,8-tetrahydro-4H-pyrazolo[1,5-a]azepin-4-yl)isonicotinamide | LCMS (ESI) m/z: 446.2 [M + H]$^+$. $^1$H NMR (400 MHz, DMSO-$d_6$) δ 9.21 (d, J = 8.0 Hz, 1H), 8.72 (d, J = 4.8 Hz, 1H), 8.30 (d, J = 5.2 Hz, 1H), 8.18 (s, 1H), 8.07 (d, J = 5.2 Hz, 1H), 7.42 (dd, J = 1.2, 5.2 Hz, 1H), 7.33 (s, 1H), 6.94 (s, 1H), 5.31-5.23 (m, 1H), 4.70-4.49 (m, 1H), 4.40-4.30 (m, 3H), 2.07-1.91 (m, 3H), 1.87-1.78 (m, 2H), 1.62-1.50 (m, 1H), 1.34 (t, J = 6.8 Hz, 3H). | acetonitrile 50%-80%/ 0.225% formic acid in water |

-continued

| Compound No. | Structure | Analytical data | Separation conditions |
|---|---|---|---|
| I-272* | 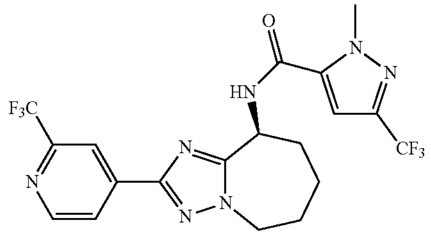 [SMILES: Cn1nc(C(F)(F)F)cc1C(=O)N[C@H]1CCCCn2nc(-c3ccnc(C(F)(F)F)c3)nc21] (S)-1-Methyl-3-(trifluoromethyl)-N-(2-(2-(trifluoromethyl)pyridin-4-yl)-6,7,8,9-tetrahydro-5H-[1,2,4]triazolo[1,5-a]azepin-9-yl)-1H-pyrazole-5-carboxamide | LCMS (ESI) m/z: 474.2 [M + H]$^+$. $^1$H NMR (400 MHz, DMSO-$d_6$) δ 9.28 (d, J = 8.0 Hz, 1H), 8.86 (d, J = 4.8 Hz, 1H), 8.21 (s, 1H), 8.16 (dd, J = 0.8, 4.8 Hz, 1H), 7.47 (s, 1H), 5.46-5.38 (m, 1H), 4.61-4.53 (m, 1H), 4.45 (m, 1H), 4.16 (s, 3H), 2.11-2.02 (m, 1H), 2.01-1.89 (m, 4H), 1.73-1.62 (m, 1H). | acetonitrile 57%-87%/ 0.225% formic acid in water. |
| I-265a | 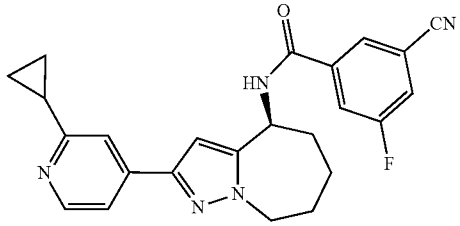 [SMILES: N#Cc1cc(F)cc(C(=O)N[C@H]2CCCCn3nc(-c4ccnc(C5CC5)c4)cc32)c1] (S)-3-Cyano-N-(2-(2-cyclopropylpyridin-4-yl)-5,6,7,8-tetrahydro-4H-pyrazolo[1,5-a]azepin-4-yl)-5-fluorobenzamide | LCMS (ESI) m/z: 416.2 [M + H]$^+$. $^1$H NMR (400 MHz, DMSO-$d_6$) δ 9.27 (d, J = 7.6 Hz, 1H), 8.35-8.30 (m, 2H), 8.12-8.10 (m, 2H), 7.64 (s, 1H), 7.48-7.46 (m, 1H), 6.78 (s, 1H), 5.29-5.24 (m, 1H), 4.52-4.28 (m, 2H), 2.13-2.10 (m, 1H), 1.95-1.93 (m, 1H), 1.87-1.84 (m, 4H), 1.64-1.55 (m, 1H), 0.95-0.88 (m, 4H). | acetonitrile 22%-55%/ 0.225% formic acid in water |
| I-312a | 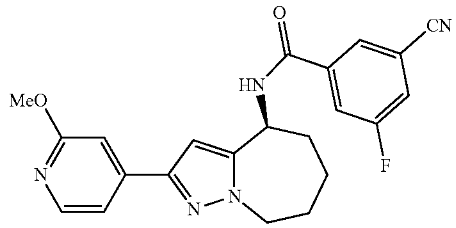 [SMILES: COc1cc(-c2cc3n(n2)CCCC[C@@H]3NC(=O)c2cc(F)cc(C#N)c2)ccn1] (S)-3-Cyano-5-fluoro-N-(2-(2-methoxypyridin-4-yl)-5,6,7,8-tetrahydro-4H-pyrazolo[1,5-a]azepin-4-yl)benzamide | LCMS (ESI) m/z: 406.2 [M + H]$^+$. $^1$H NMR (400 MHz, DMSO-$d_6$) δ 9.24 (d, J = 8.0 Hz, 1H), 8.29 (s, 1H), 8.13-4.09 (m, 3H), 7.37-7.36 (m, 1H), 7.15 (s, 1H), 6.81 (s, 1H), 5.27-5.24 (m, 1H), 4.52-4.47 (m, 1H), 4.33-4.27 (m, 1H), 3.85 (s, 3H), 2.04-1.82 (m, 5H), 1.65-1.50 (m, 1H). | acetonitrile 35%-65%/ 0.225% formic acid in water |
| I-183a | 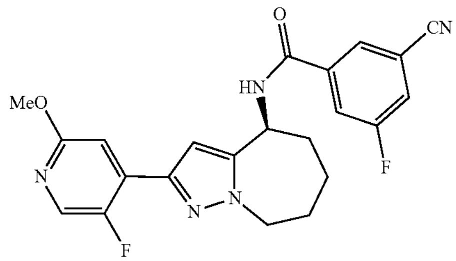 [SMILES: COc1cc(-c2cc3n(n2)CCCC[C@@H]3NC(=O)c2cc(F)cc(C#N)c2)c(F)cn1] (S)-3-Cyano-5-fluoro-N-(2-(5-fluoro-2-methoxypyridin-4-yl)-5,6,7,8-tetrahydro-4H-pyrazolo[1,5-a]azepin-4-yl)benzamide | LCMS (ESI) m/z: 424.1 [M + H]$^+$. $^1$H NMR (400 MHz, DMSO-$d_6$) δ 9.25 (d, J = 7.6 Hz, 1H), 8.27 (d, J = 1.6 Hz, 1H), 8.18 (d, J = 2.8 Hz, 1H), 8.13-8.05 (m, 2H), 7.21 (d, J = 5.2 Hz, 1H), 6.64 (d, J = 3.6 Hz, 1H), 5.33-5.26 (m, 1H), 4.57-4.49 (m, 1H), 4.39-4.31(m, 1H), 3.84 (s, 3H), 2.05-1.81 (m, 5H), 1.63-1.56 (m, 1H). | Prep-HPLC: acetonitrile 57%-87%/0.225% formic acid in water. Prep-SFC: chiral SFC (DIACEL CHIRALCEL OJ (250 mm * 30 mm, 10 μm); Supercritical $CO_2$/ EtOH + 0.1% $NH_3$•$H_2O$ = 75/25; 70 mL/min) |

-continued

| Compound No. | Structure | Analytical data | Separation conditions |
|---|---|---|---|
| I-311a | 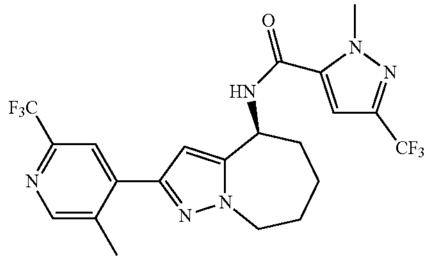 [SMILES: Cc1cnc(C(F)(F)F)cc1-c1cc2n(n1)CCCC[C@@H]2NC(=O)c1cc(C(F)(F)F)nn1C] (S)-1-Methyl-N-(2-(5-methyl-2-(trifluoromethyl)pyridin-4-yl)-5,6,7,8-tetrahydro-4H-pyrazolo[1,5-a]azepin-4-yl)-3-(trifluoromethyl)-1H-pyrazole-5-carboxamide | LCMS (ESI) m/z: 487.3 $[M + H]^+$. $^1H$ NMR (400 MHz, DMSO-$d_6$) δ 9.20 (d, J = 8.0 Hz, 1H), 8.64 (s, 1H), 8.02 (s, 1H), 7.52 (s, 1H), 6.82 (s, 1H), 5.30-5.22 (m, 1H), 4.59-4.49 (m, 1H), 4.42-4.31 (m, 1H), 4.14 (s, 3H), 2.59 (s, 3H), 2.07-1.98 (m, 1H), 1.98-1.90 (m, 2H), 1.90-1.78 (m, 2H), 1.67-1.52 (m, 1H). | Prep-HPLC: acetonitrile 57%-87%/0.225% formic acid in water. Prep-SFC: chiral SFC (DAICEL CHIRALCEL AS (250 mm * 30 mm, 10 μm); Supercritical $CO_2$/EtOH + 0.1% $NH_3$•$H_2O$ = 75/25; 70 mL/min) |
| I-280a | 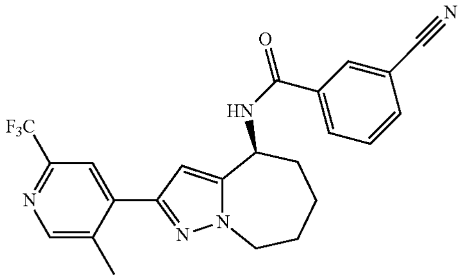 [SMILES: Cc1cnc(C(F)(F)F)cc1-c1cc2n(n1)CCCC[C@@H]2NC(=O)c1cccc(C#N)c1] (S)-3-Cyano-N-(2-(5-methyl-2-(trifluoromethyl)pyridin-4-yl)-5,6,7,8-tetrahydro-4H-pyrazolo[1,5-a]azepin-4-yl)benzamide | LCMS (ESI) m/z: 440.2 $[M + H]^+$. $^1H$ NMR (400 MHz, DMSO-$d_6$) δ 9.20 (d, J = 7.6 Hz, 1H), 8.64 (s, 1H), 8.42 (s, 1H), 8.25 (d, J = 8.0 Hz, 1H), 8.10-7.99 (m, 2H), 7.74 (t, J = 8.0 Hz, 1H), 6.82 (s, 1H), 5.37-5.30 (m, 1H), 4.62-4.52 (m, 1H), 4.44-4.33 (m, 1H), 2.59 (s, 3H), 2.09-2.01 (m, 1H), 2.00-1.84 (m, 4H), 1.71-1.48 (m, 1H). | Prep-HPLC: acetonitrile 48%-78%/0.225% formic acid in water. Prep-SFC: chiral SFC (DAICEL CHIRALPAK AD (250 mm * 30 mm, 10 μm); Supercritical $CO_2$/i-PrOH + 0.1% $NH_3$•$H_2O$ = 70/30; 80 mL/min) |
| I-256a | 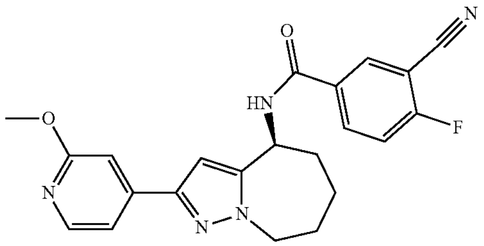 [SMILES: COc1cc(-c2cc3n(n2)CCCC[C@@H]3NC(=O)c2ccc(F)c(C#N)c2)ccn1] (S)-3-Cyano-4-fluoro-N-(2-(2-methoxypyridin-4-yl)-5,6,7,8-tetrahydro-4H-pyrazolo[1,5-a]azepin-4-yl)benzamide | LCMS (ESI) m/z: 406.2 $[M + H]^+$. $^1H$ NMR (400 MHz, DMSO-$d_6$) δ 9.19 (d, J = 8.0 Hz, 1H), 8.57-8.52 (m, 1H), 8.36-8.30 (m, 1H), 8.13 (d, J = 5.4 Hz, 1H), 7.71-7.65 (m, 1H), 7.36 (dd, J = 1.2, 5.6 Hz, 1H), 7.15 (s, 1H), 6.80 (s, 1H), 5.33-5.28 (m, 1H), 4.52-4.46 (m, 1H), 4.36-4.24 (m, 1H), 3.85 (s, 3H), 2.04-1.80 (m, 5H), 1.65-1.49 (m, 1H). | Prep-HPLC: acetonitrile 35%-65%/0.225% formic acid in water. Prep-SFC: chiral SFC (DAICEL CHIRALCEL OJ (250 mm * 30 mm, 10 μm); Supercritical $CO_2$/EtOH + 0.1% $NH_3$•$H_2O$ = 50/50, 80 mL/min |
| I-212a | 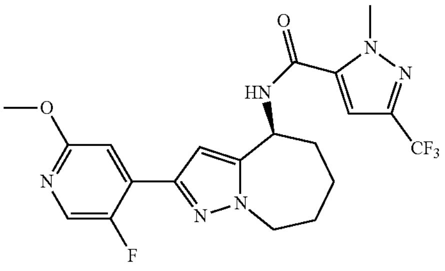 [SMILES: COc1cc(-c2cc3n(n2)CCCC[C@@H]3NC(=O)c2cc(C(F)(F)F)nn2C)c(F)cn1] (S)-N-(2-(5-Fluoro-2-methoxypyridin-4-yl)-5,6,7,8-tetrahydro-4H-pyrazolo[1,5-a]azepin-4-yl)-1-methyl-3-(trifluoromethyl)-1H-pyrazole-5-carboxamide | LCMS (ESI) m/z: 453.1 $[M + H]^+$. $^1H$ NMR (400 MHz, DMSO-$d_6$) δ 9.21 (d, J = 8.0 Hz, 1H), 8.18 (d, J = 2.4 Hz, 1H), 7.49 (s, 1H), 7.21 (d, J = 5.2 Hz, 1H), 6.64 (d, J = 3.2 Hz, 1H), 5.30-5.24 (m, 1H), 4.59-4.45 (m, 1H), 4.38-4.29 (m, 1H), 4.13 (s, 3H), 3.84 (s, 3H), 2.03-1.79 (m, 5H), 1.65-1.49 (m, 1H). | Prep-HPLC: acetonitrile 58%-88%/0.225% formic acid in water. Prep-SFC: chiral SFC (DAICEL CHIRALCEL OJ (250 mm * 30 mm, 10 μm); Supercritical $CO_2$/iPrOH + 0.1% $NH_3$•$H_2O$ = 75/25, 80 mL/min |

-continued

| Compound No. | Structure | Analytical data | Separation conditions |
|---|---|---|---|
| I-273a | 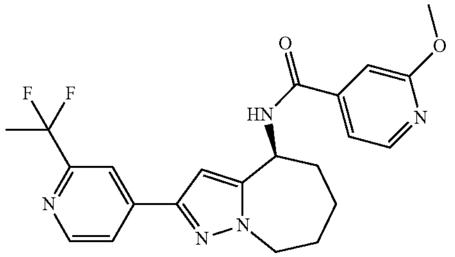 [SMILES: COc1cc(C(=O)N[C@H]2CCCCn3nc(-c4ccnc(C(C)(F)F)c4)cc32)ccn1] (S)-N-(2-(5-Fluoro-2-methoxypyridin-4-yl)-5,6,7,8-tetrahydro-4H-pyrazolo[1,5-a]azepin-4-yl)-1-methyl-3-(trifluoromethyl)-1H-pyrazole-5-carboxamide | LCMS (ESI) m/z: 428.1 $[M + H]^+$. $^1H$ NMR (400 MHz, DMSO-$d_6$) δ 9.23 (d, J = 8.0 Hz, 1H), 8.62 (d, J = 5.2 Hz, 1H), 8.33 (d, J = 5.2 Hz, 1H), 8.02 (s, 1H), 7.89 (d, J = 4.8 Hz, 1H), 7.49-7.43 (m, 1H), 7.34 (s, 1H), 6.87 (s, 1H), 5.31-5.23 (m, 1H), 4.55-4.51 (m, 1H), 4.36-4.31 (m, 1H), 3.92 (s, 3H), 1.95 (d, J = 19.2 Hz, 1H), 1.99-1.89 (m, 3H), 1.89-1.79 (m, 2H), 1.66-1.48 (m, 1H). | Prep-HPLC: acetonitrile 33%-63%/0.225% formic acid in water. Prep-SFC: chiral SFC (DAICEL CHIRALCEL OJ (250 mm * 30 mm, 10 μm); Supercritical $CO_2$/EtOH + 0.1% $NH_3$•$H_2O$ = 75/25, 80 mL/min |
| I-194a | 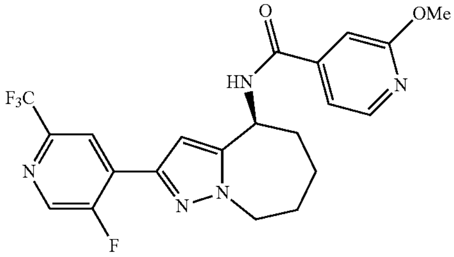 [SMILES: COc1cc(C(=O)N[C@H]2CCCCn3nc(-c4cc(C(F)(F)F)ncc4F)cc32)ccn1] (S)-N-(2-(5-Fluoro-2-(trifluoromethyl)pyridin-4-yl)-5,6,7,8-tetrahydro-4H-pyrazolo[1,5-a]azepin-4-yl)-2-methoxyisonicotinamide | LCMS (ESI) m/z: 450.2 $[M + H]^+$. $^1H$ NMR (400 MHz, DMSO-$d_6$) δ 9.27 (d, J = 8.0 Hz, 1H), 8.82 (d, J = 2.0 Hz, 1H), 8.32 (m, 2H), 7.42 (dd, J = 1.2, 5.2 Hz, 1H), 7.28 (s, 1H), 6.70 (d, J = 3.2 Hz, 1H), 5.36-5.28 (m, 1H), 4.62-4.53 (m, 1H), 4.44-4.36 (m, 1H), 3.92 (s, 3H), 2.05-1.81 (m, 5H), 1.65-1.50 (m, 1H). | Prep-HPLC: acetonitrile 45%-75%/0.225% formic acid in water. Prep-SFC: chiral SFC (DAICEL CHIRALCEL OJ (250 mm * 30 mm, 10 μm); Supercritical $CO_2$/EtOH + 0.1% $NH_3$•$H_2O$ = 70/30, 80 mL/min |
| I-268* | 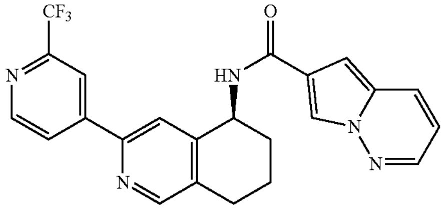 [SMILES: O=C(N[C@H]1CCCc2cnc(-c3ccnc(C(F)(F)F)c3)cc21)c1cc2cccnn2c1] (S)-N-(3-(2-(Trifluoromethyl)pyridin-4-yl)-5,6,7,8-tetrahydroisoquinolin-5-yl)pyrrolo[1,2-b]pyridazine-6-carboxamide | LCMS (ESI) m/z: 438.2 $[M + H]^+$. $^1H$ NMR (400 MHz, DMSO-$d_6$) δ 8.82 (d, J = 5.2 Hz, 1H), 8.74 (d, J = 8.4 Hz, 1H), 8.60 (s, 1H), 8.44 (s, 1H), 8.35 (d, J = 1.2 Hz, 1H), 8.27-8.24 (m, 1H), 8.22 (dd, J = 2.0, 4.4 Hz, 1H), 8.04-8.00 (m, 2H), 7.00 (d, J = 1.1 Hz, 1H), 7.35-6.67 (m, 1H), 5.33-5.26 (m, 1H), 2.90-2.85 (m, 2H), 2.09-1.97 (m, 2H), 1.92-1.83 (m, 2H). | acetonitrile 38%-68%/0.225% formic acid in water |
| I-270* | 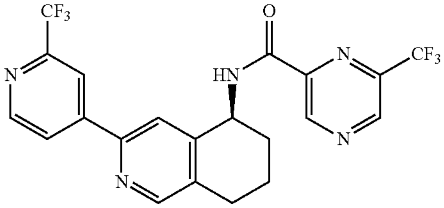 [SMILES: O=C(N[C@H]1CCCc2cnc(-c3ccnc(C(F)(F)F)c3)cc21)c1cncc(C(F)(F)F)n1] (S)-6-(Trifluoromethyl)-N-(3-(2-(trifluoromethyl)pyridin-4-yl)-5,6,7,8-tetrahydroisoquinolin-5-yl)pyrazine-2-carboxamide | LCMS (ESI) m/z: 468.2 $[M + H]^+$. $^1H$ NMR (400 MHz, DMSO-$d_6$) δ 9.55 (s, 1H), 9.44 (d, J = 8.8 Hz, 1H), 9.41 (s, 1H), 8.81 (d, J = 5.2 Hz, 1H), 8.58 (s, 1H), 8.43 (s, 1H), 8.31-8.27 (m, 1H), 8.04 (s, 1H), 5.38-5.28 (m, 1H), 2.92-2.82 (m, 2H), 2.13-1.95 (m, 3H), 1.92-1.79 (m, 1H). | acetonitrile 60%-90%/0.225% formic acid in water |

-continued

| Compound No. | Structure | Analytical data | Separation conditions |
| --- | --- | --- | --- |
| I-271* | 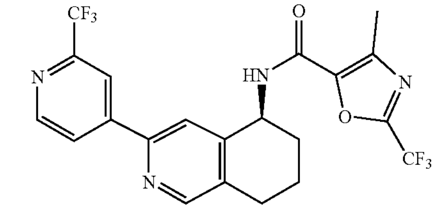 [SMILES: Cc1nc(C(F)(F)F)oc1C(=O)N[C@H]1CCCc2cnc(-c3ccnc(C(F)(F)F)c3)cc21] (S)-4-Methyl-2-(trifluoromethyl)-N-(3-(2-(trifluoromethyl)pyridin-4-yl)-5,6,7,8-tetrahydroisoquinolin-5-yl)oxazole-5-carboxamide | LCMS (ESI) m/z: 471.2 [M + H]$^+$. $^1$H NMR (400 MHz, DMSO-$d_6$) δ 9.24 (d, J = 8.4 Hz, 1H), 8.84 (d, J = 5.2 Hz, 1H), 8.58 (s, 1H), 8.47 (s, 1H), 8.35 (d, J = 5.2 Hz, 1H), 8.08 (s, 1H), 5.32-5.18 (m, 1H), 2.90-2.79 (m, 1H), 2.51 (s, 3H), 2.06-1.94 (m, 2H), 1.94-1.77 (m, 2H). | acetonitrile 60%-90%/ 0.225% formic acid in water |
| I-276a | 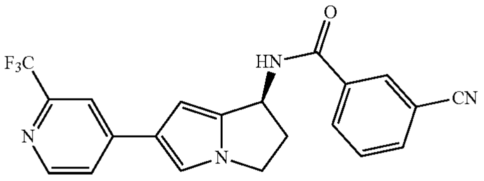 [SMILES: N#Cc1cccc(C(=O)N[C@H]2CCn3cc(-c4ccnc(C(F)(F)F)c4)cc32)c1] 3-Cyano-N-(6-(2-(trifluoromethyl)pyridin-4-yl)-2,3-dihydro-1H-pyrrolizin-1-yl)benzamide | LCMS (ESI) m/z: 397.2 [M + H]$^+$. $^1$H NMR (400 MHz, DMSO-$d_6$) δ 9.11 (d, J = 8.0 Hz, 1H), 8.83 (d, J = 5.2 Hz, 1H), 8.59 (s, 1H), 8.47 (s, 1H), 8.32 (dd, J = 1.2, 4.8 Hz, 1H), 8.29 (d, J = 5.6 Hz, 1H), 8.07 (s, 1H), 7.42 (dd, J = 1.6, 5.2 Hz, 1H), 7.27 (s, 1H), 5.29-5.22 (m, 1H), 3.88 (s, 3H), 2.90-2.83 (m, 2H), 2.07-1.93 (m, 2H), 1.91-1.81 (m, 2H) | Prep-HPLC: acetonitrile 45%-75%/ 0.225% formic acid in water. Prep-HPLC: chiral SFC (DAICEL CHIRALCEL OJ (250 mm * 30 mm, 10 μm); Supercritical $CO_2$/EtOH + 0.1% $NH_3$•$H_2O$ = 75/25, 70 mL/min |
| I-269* | 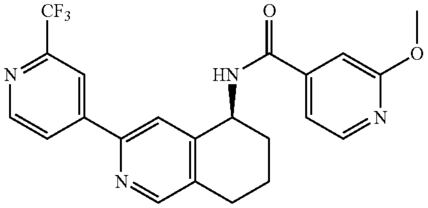 [SMILES: COc1cc(C(=O)N[C@H]2CCCc3cnc(-c4ccnc(C(F)(F)F)c4)cc32)ccn1] (S)-2-Methoxy-N-(3-(2-(trifluoromethyl)pyridin-4-yl)-5,6,7,8-tetrahydroisoquinolin-5-yl)isonicotinamide | LCMS (ESI) m/z: 429.1 [M + H]$^+$. $^1$H NMR (400 MHz, DMSO-$d_6$) δ 9.11 (d, J = 8.0 Hz, 1H), 8.83 (d, J = 5.2 Hz, 1H), 8.59 (s, 1H), 8.47 (s, 1H), 8.32 (dd, J = 1.2, 4.8 Hz, 1H), 8.29 (d, J = 5.6 Hz, 1H), 8.07 (s, 1H), 7.42 (dd, J = 1.6, 5.2 Hz, 1H), 7.27 (s, 1H), 5.29-5.22 (m, 1H), 3.88 (s, 3H), 2.90-2.83 (m, 2H), 2.07-1.93 (m, 2H), 1.91-1.81 (m, 2H) | acetonitrile 38%-68%/ 0.225% formic acid in water |
| I-134a | 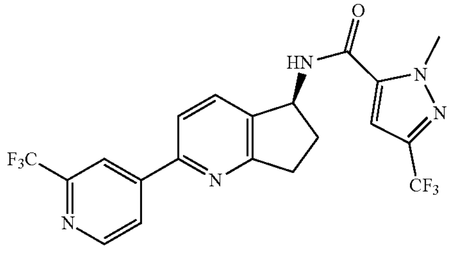 [SMILES: Cn1nc(C(F)(F)F)cc1C(=O)N[C@H]1CCc2nc(-c3ccnc(C(F)(F)F)c3)ccc21] (S)-1-Methyl-3-(trifluoromethyl)-N-(2-(2-(trifluoromethyl)pyridin-4-yl)-6,7-dihydro-5H-cyclopenta[b]pyridin-5-yl)-1H-pyrazole-5-carboxamide | LCMS (ESI) m/z: 456.2 [M + H]$^+$. $^1$H NMR (400 MHz, DMSO-$d_6$) δ 9.10 (d, J = 8.0 Hz, 1H), 8.88 (d, J = 5.2 Hz, 1H), 8.51 (s, 1H), 8.38 (d, J = 4.4 Hz, 1H), 8.12 (d, J = 8.0 Hz, 1H), 7.88 (d, J = 8.4 Hz, 1H), 7.37 (s, 1H), 5.63-5.51 (m, 1H), 4.19 (s, 3H), 3.15-3.02 (m, 2H), 2.62-2.55 (m, 1H), 2.13-2.03 (m, 1H). | Prep-HPLC: acetonitrile 53%-83%/0.225% formic acid in water. Prep-SFC: chiral SFC (DAICEL CHIRALCEL OJ (250 mm * 30 mm, 10 μm); supercritical $CO_2$/ EtOH + 0.1% $NH_3$•$H_2O$ = 70/30; 80 mL/min |
| I-133a | 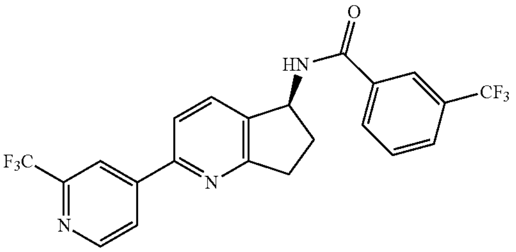 [SMILES: O=C(N[C@H]1CCc2nc(-c3ccnc(C(F)(F)F)c3)ccc21)c1cccc(C(F)(F)F)c1] (S)-3-(Trifluoromethyl)-N-(2-(2-(trifluoromethyl)pyridin-4-yl)-6,7-dihydro-5H-cyclopenta[b]pyridin-5-yl)benzamide | LCMS (ESI) m/z: 452.1 [M + H]$^+$. $^1$H NMR (400 MHz, DMSO-$d_6$) δ 9.17 (d, J = 8.4 Hz, 1H), 8.88 (d, J = 5.2 Hz, 1H), 8.51 (s, 1H), 8.38 (d, J = 5.2 Hz, 1H), 8.26 (s, 1H), 8.23 (d, J = 8.0 Hz, 1H), 8.12 (d, J = 8.0 Hz, 1H), 7.93 (d, J = 7.6 Hz, 1H), 7.87 (d, J = 8.4 Hz, 1H), 7.78-7.73 (m, 1H), 5.70-5.62 (m, 1H), 3.19-3.14 (m, 1H), 3.13-3.06 (m, 1H), 2.63-2.67 (m, 1H), 2.18-2.08 (m, 1H). | Prep-HPLC: acetonitrile 50%-80%/0.225% formic acid in water. Prep-SFC: chiral SFC (DAICEL CHIRALCEL OJ (250 mm * 30 mm, 10 μm); supercritical $CO_2$/ EtOH + 0.1% $NH_3$•$H_2O$ = 80/20; 80 mL/min |

-continued

| Compound No. | Structure | Analytical data | Separation conditions |
|---|---|---|---|
| I-149* | 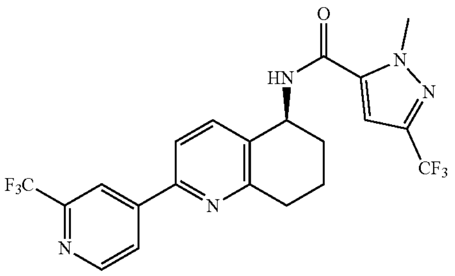 [SMILES: Cn1nc(C(F)(F)F)cc1C(=O)N[C@H]1CCCc2nc(-c3ccnc(C(F)(F)F)c3)ccc21] (S)-3-(Trifluoromethyl)-N-(2-(2-(trifluoromethyl)pyridin-4-yl)-6,7-dihydro-5H-cyclopenta[b]pyridin-5-yl)benzamide | LCMS (ESI) m/z: 470.1 $[M + H]^+$. $^1H$ NMR (400 MHz, DMSO-$d_6$) δ 9.04 (d, J = 6.0 Hz, 1H), 8.88 (s, 1H), 8.48 (s, 1H), 8.36 (s, 1H), 8.08 (d, J = 6.4 Hz, 1H), 7.82 (d, J = 5.6 Hz, 1H), 7.36 (s, 1H), 5.30-5.24 (m, 1H), 4.20 (s, 3H), 3.05-2.97 (m, 2H), 2.08-2.02 (m, 2H), 1.91-1.86 (s, 2H). | acetonitrile 60%-90%/ 0.225% formic acid in water. |
| I-148* | 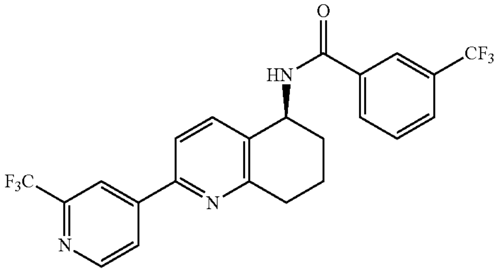 [SMILES: O=C(N[C@H]1CCCc2nc(-c3ccnc(C(F)(F)F)c3)ccc21)c1cccc(C(F)(F)F)c1] (S)-3-(Trifluoromethyl)-N-(2-(2-(trifluoromethyl)pyridin-4-yl)-5,6,7,8-tetrahydroquinolin-5-yl)benzamide | LCMS (ESI) m/z: 466.0 $[M + H]^+$. $^1H$ NMR (400 MHz, DMSO-$d_6$) δ 9.14 (d, J = 8.4 Hz, 1H), 8.87 (d, J = 5.2 Hz, 1H), 8.48 (s, 1H), 8.35 (d, J = 5.2 Hz, 1H), 8.29-8.20 (m, 2H), 8.08 (d, J = 8.0 Hz, 1H), 7.92 (d, J = 7.6 Hz, 1H), 7.80 (d, J = 8.0 Hz, 1H), 7.77-7.74 (m, 1H), 5.37-5.33 (m, 1H), 3.04-2.97 (m, 2H), 2.15-2.00 (m, 2H), 1.99-1.82 (m, 2H). | acetonitrile 60%-90%/ 0.225% formic acid in water. |
| I-223a | 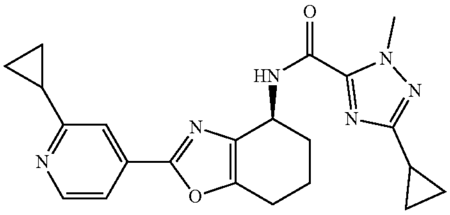 [SMILES: Cn1nc(C2CC2)nc1C(=O)N[C@H]1CCCc2oc(-c3ccnc(C4CC4)c3)nc21] (S)-3-Cyclopropyl-N-(2-(2-cyclopropylpyridin-4-yl)-4,5,6,7-tetrahydrobenzo[d]oxazol-4-yl)-1-methyl-1H-1,2,4-triazole-5-carboxamide | LCMS (ESI) m/z: 405.2 $[M + H]^+$. $^1H$ NMR (400 MHz, DMSO-$d_6$) δ 8.89 (d, J = 8.4 Hz, 1H), 8.51 (d, J = 5.2 Hz, 1H), 7.79 (s, 1H), 7.58 (d, J = 6.8 Hz, 1H), 5.15-5.06 (m, 1H), 4.07 (s, 3H), 2.73 (s, 2H), 2.29-2.21 (m, 1H), 2.08-2.01 (m, 1H), 2.00-1.92 (m, 2H), 1.92-1.77 (m, 2H), 0.99-0.93 (m, 4H), 0.92-0.89 (m, 2H), 0.85-0.78 (m, 2H). | acetonitrile 25%-55%/ 0.225% formic acid in water |
| I-227a | 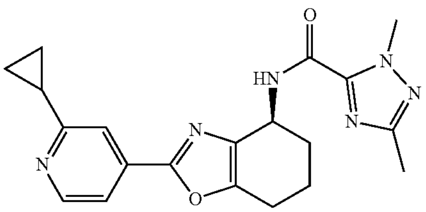 [SMILES: Cc1nc(C(=O)N[C@H]2CCCc3oc(-c4ccnc(C5CC5)c4)nc32)n(C)n1] (S)-N-(2-(2-Cyclopropylpyridin-4-yl)-4,5,6,7-tetrahydrobenzo[d]oxazol-4-yl)-1,3-dimethyl-1H-1,2,4-triazole-5-carboxamide | LCMS (ESI) m/z: 379.2 $[M + H]^+$. $^1H$ NMR (400 MHz, DMSO-$d_6$) δ 8.97 (d, J = 8.4 Hz, 1H), 8.51 (d, J = 5.2 Hz, 1H), 7.79 (s, 1H), 7.57 (dd, J = 1.2, 4.8 Hz, 1H), 5.16-5.07 (m, 1H), 4.10 (s, 3H), 2.73 (s, 2H), 2.25 (s, 3H), 2.25-2.20 (m, 1H), 2.10-1.81 (m, 4H), 1.01-0.91 (m, 4H). | acetonitrile 20%-50%/ 0.225% formic acid in water |

-continued

| Compound No. | Structure | Analytical data | Separation conditions |
|---|---|---|---|
| I-238a | 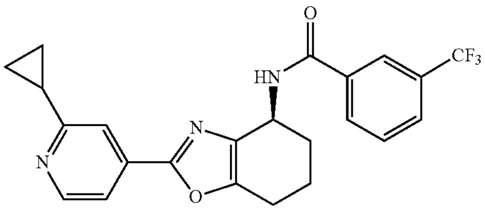 [SMILES: O=C(N[C@H]1CCCc2oc(-c3ccnc(C4CC4)c3)nc21)c1cccc(C(F)(F)F)c1] (S)-N-(2-(2-Cyclopropylpyridin-4-yl)-4,5,6,7-tetrahydrobenzo[d]oxazol-4-yl)-3-(trifluoromethyl)benzamide | LCMS (ESI) m/z: 428.2 $[M + H]^+$. $^1H$ NMR (400 MHz, DMSO-$d_6$) δ 9.04 (d, J = 8.0 Hz, 1H), 8.51 (d, J = 5.2 Hz, 1H), 8.26 (s, 1H), 8.22 (d, J = 8.0 Hz, 1H), 7.92 (d, J = 7.6 Hz, 1H), 7.80 (s, 1H), 7.75-7.72 (m, 1H), 7.59 (m, 1H), 5.24-5.17 (m, 1H), 2.86-2.73 (m, 2H), 2.30-2.17 (m, 1H), 2.06-1.95 (m, 2H), 1.95-1.82 (m, 2H), 0.99-0.93 (m, 4H) | acetonitrile 25%-55%/ 0.225% formic acid in water |
| I-242a | 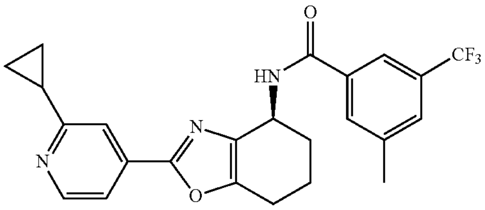 [SMILES: Cc1cc(C(=O)N[C@H]2CCCc3oc(-c4ccnc(C5CC5)c4)nc32)cc(C(F)(F)F)c1] (S)-N-(2-(2-Cyclopropylpyridin-4-yl)-4,5,6,7-tetrahydrobenzo[d]oxazol-4-yl)-3-methyl-5-(trifluoromethyl)benzamide | LCMS (ESI) m/z: 442.2 $[M + H]^+$. $^1H$ NMR (400 MHz, DMSO-$d_6$) δ 8.99 (d, J = 8.0 Hz, 1H), 8.55 (d, J = 5.2 Hz, 1H), 8.04 (s, 2H), 7.84 (s, 1H), 7.74 (s, 1H), 7.67 (d, J = 4.4 Hz, 1H), 5.24-5.17 (m, 1H), 2.85-2.74 (m, 2H), 2.45 (s, 3H), 2.31-2.22 (m, 1H), 2.07-1.96 (m, 2H), 1.95-1.82 (m, 2H), 1.06-0.98 (m, 4H). | acetonitrile 45%-75%/ 0.225% formic acid in water. |
| I-228a | 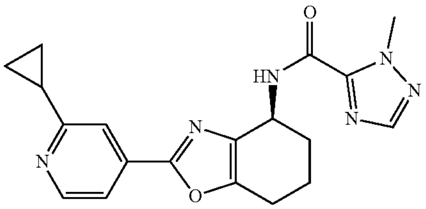 [SMILES: Cn1ncnc1C(=O)N[C@H]1CCCc2oc(-c3ccnc(C4CC4)c3)nc21] (S)-N-(2-(2-Cyclopropylpyridin-4-yl)-4,5,6,7-tetrahydrobenzo[d]oxazol-4-yl)-1-methyl-1H-1,2,4-triazole-5-carboxamide | LCMS (ESI) m/z: 365.2 $[M + H]^+$. $^1H$ NMR (400 MHz, DMSO-$d_6$) δ 9.12 (d, J = 8.0 Hz, 1H), 8.61 (d, J = 5.6 Hz, 1H), 8.06 (s, 1H), 7.89 (s, 1H), 7.83 (d, J = 5.2 Hz, 1H), 5.19-5.11 (m, 1H), 4.17 (s, 3H), 2.79-2.71 (m, 2H), 2.37-2.30 (m, 1H), 2.11-1.97 (m, 2H), 1.95-1.83 (m, 2H), 1.17-1.09 (m, 4H). | acetonitrile 20%-50%/ 0.225% formic acid in water |
| I-137a | 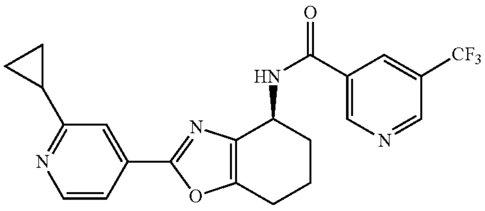 (S)-N-(2-(2-Cyclopropylpyridin-4-yl)-4,5,6,7-tetrahydrobenzo[d]oxazol-4-yl)-5-(trifluoromethyl)nicotinamide | LCMS (ESI) m/z: 429.2 $[M + H]^+$. $^1H$ NMR (400 MHz, DMSO-$d_6$) δ 9.34 (s, 1H), 9.21 (d, J = 8.0 Hz, 1H), 9.15 (s, 1H), 8.63 (s, 1H), 8.53 (d, J = 5.2 Hz, 1H), 7.81 (s, 1H), 7.61 (d, J = 5.2 Hz, 1H), 5.24-5.18 (m, 1H), 2.84-2.72 (m, 2H), 2.29-2.22 (m, 1H), 2.08-1.99 (m, 2H), 1.96-1.85 (m, 2H), 1.00-0.95 (m, 4H). | acetonitrile 40%-70%/ 0.225% formic acid in water |
| I-130a | 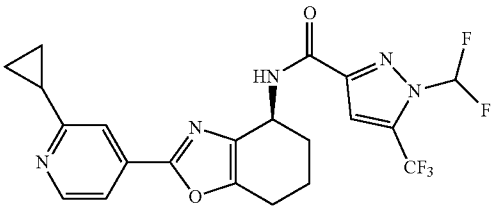 [SMILES: O=C(N[C@H]1CCCc2oc(-c3ccnc(C4CC4)c3)nc21)c1cc(C(F)(F)F)n(C(F)F)n1] (S)-N-(2-(2-Cyclopropylpyridin-4-yl)-4,5,6,7-tetrahydrobenzo[d]oxazol-4-yl)-1-(difluoromethyl)-5-(trifluoromethyl)-1H-pyrazole-3-carboxamide | LCMS (ESI) m/z: 468.0 $[M + H]^+$. $^1H$ NMR (400 MHz, DMSO-$d_6$) δ 8.99 (d, J = 8.4 Hz, 1H), 8.54 (d, J = 5.2 Hz, 1H), 8.09 (t, J = 19.2 Hz, 1H), 7.82 (s, 1H), 7.69 (s, 1H), 7.66 (d, J = 5.2 Hz, 1H), 5.17 (d, J = 6.0 Hz, 1H), 2.79-2.74 (m, 2H), 2.30-2.23 (m, 1H), 2.09-1.96 (m, 2H), 1.93-1.84 (m, 2H), 1.05-0.98 (m, 4H). | acetonitrile 42%-72%/ 0.225% formic acid in water |

-continued

| Compound No. | Structure | Analytical data | Separation conditions |
|---|---|---|---|
| I-132a | 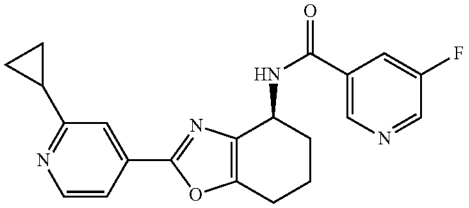 (S)-N-(2-(2-Cyclopropylpyridin-4-yl)-4,5,6,7-tetrahydrobenzo[d]oxazol-4-yl)-5-fluoronicotinamide | LCMS (ESI) m/z: 379.2 $[M + H]^+$. $^1H$ NMR (400 MHz, DMSO-$d_6$) δ 9.05 (d, J = 7.6 Hz, 1H), 8.93 (s, 1H), 8.75 (d, J = 2.8 Hz, 1H), 8.53 (d, J = 5.2 Hz, 1H), 8.17-8.10 (m, 1H), 7.82 (s, 1H), 7.66-7.58 (m, 1H), 5.24-5.15 (m, 1H), 2.86-2.74 (m, 2H), 2.28-2.21 (m, 1H), 2.10-1.98 (m, 2H), 1.94-1.83 (m, 2H), 1.02-0.95 (m, 4H). | acetonitrile 28%-58%/0.225% formic acid in water |
| I-131a | 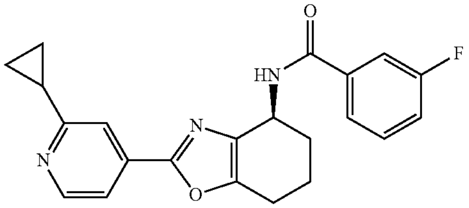 (S)-N-(2-(2-Cyclopropylpyridin-4-yl)-4,5,6,7-tetrahydrobenzo[d]oxazol-4-yl)-3-fluorobenzamide | LCMS (ESI) m/z: 378.2 $[M + H]^+$. $^1H$ NMR (400 MHz, DMSO-$d_6$) δ 8.84 (d, J = 8.0 Hz, 1H), 8.54 (d, J = 5.0 Hz, 1H), 7.83 (s, 1H), 7.76 (d, J = 8.0 Hz, 1H), 7.73-7.68 (m, 1H), 7.68-7.62 (m, 1H), 7.56-7.48 (m, 1H), 7.42-7.36 (m, 1H), 5.22-5.16 (m, 1H), 2.84-2.71 (m, 2H), 2.30-2.22 (m, 1H), 2.07-1.96 (m, 2H), 1.95-1.83 (m, 2H), 1.04-0.96 (m, 4H). | acetonitrile 28%-58%/0.225% formic acid in water |
| I-229a | 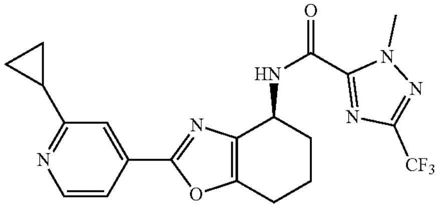 [SMILES: Cn1nc(C(F)(F)F)nc1C(=O)N[C@H]1CCCc2oc(-c3ccnc(C4CC4)c3)nc21] (S)-N-(2-(2-Cyclopropylpyridin-4-yl)-4,5,6,7-tetrahydrobenzo[d]oxazol-4-yl)-1-methyl-3-(trifluoromethyl)-1H-1,2,4-triazole-5-carboxamide | LCMS (ESI) m/z: 433.2 $[M + H]^+$. $^1H$ NMR (400 MHz, DMSO-$d_6$) δ 9.40 (d, J = 8.4 Hz, 1H), 8.51 (d, J = 5.2 Hz, 1H), 7.80 (s, 1H), 7.59-7.56 (m, 1H), 5.29-4.98 (m, 1H), 4.25 (s, 3H), 2.74 (s, 2H), 2.31-2.18 (m, 1H), 2.13-1.80 (m, 4H), 1.06-0.88 (m, 4H). | acetonitrile 43%-73%/0.225% formic acid in water |
| I-232a | 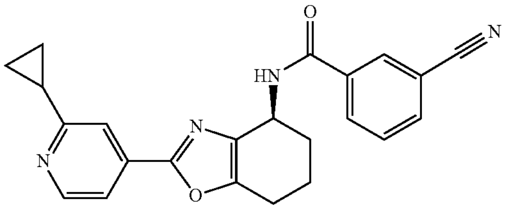 [SMILES: N#Cc1cccc(C(=O)N[C@H]2CCCc3oc(-c4ccnc(C5CC5)c4)nc32)c1] (S)-3-Cyano-N-(2-(2-cyclopropylpyridin-4-yl)-4,5,6,7-tetrahydrobenzo[d]oxazol-4-yl)benzamide | LCMS (ESI) m/z: 385.2 $[M + H]^+$. $^1H$ NMR (400 MHz, DMSO-$d_6$) δ 8.98 (d, J = 8.0 Hz, 1H), 8.53 (d, J = 5.2 Hz, 1H), 8.33 (s, 1H), 8.22 (d, J = 8.0 Hz, 1H), 8.02 (d, J = 7.6 Hz, 1H), 7.83 (s, 1H), 7.72-7.68 (m, 1H), 7.63 (d, J = 5.2 Hz, 1H), 5.25-5.14 (m, 1H), 2.89-2.71 (m, 2H), 2.31-2.19 (m, 1H), 2.08-1.83 (m, 4H), 1.03-0.96 (m, 4H). | acetonitrile 25%-55%/0.225% formic acid in water |
| I-231a | 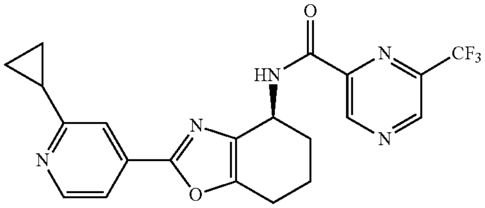 [SMILES: O=C(N[C@H]1CCCc2oc(-c3ccnc(C4CC4)c3)nc21)c1cncc(C(F)(F)F)n1] (S)-3-Cyano-N-(2-(2-cyclopropylpyridin-4-yl)-4,5,6,7-tetrahydrobenzo[d]oxazol-4-yl)benzamide | LCMS (ESI) m/z: 430.2 $[M + H]^+$. $^1H$ NMR (400 MHz, DMSO-$d_6$) δ 9.51 (s, 1H), 9.40 (s, 1H), 9.23 (d, J = 8.4 Hz, 1H), 8.52 (d, J = 5.2 Hz, 1H), 7.81 (s, 1H), 7.63-7.60 (m, 1H), 5.35-5.18 (m, 1H), 2.80-2.75 (s, 2H), 2.30-2.19 (m, 1H), 2.13-1.88 (m, 4H), 1.01-0.95 (m, 4H). | acetonitrile 22%-55%/0.225% formic acid in water. |

-continued

| Compound No. | Structure | Analytical data | Separation conditions |
|---|---|---|---|
| I-241a | 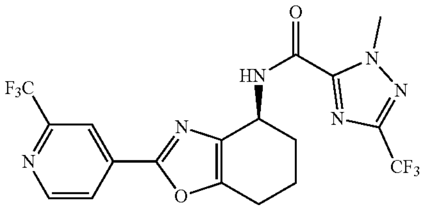 [SMILES: Cn1nc(C(F)(F)F)nc1C(=O)N[C@H]1CCCc2oc(-c3ccnc(C(F)(F)F)c3)nc21] (S)-1-Methyl-3-(trifluoromethyl)-N-(2-(2-(trifluoromethyl)pyridin-4-yl)-4,5,6,7-tetrahydrobenzo[d]oxazol-4-yl)-1H-1,2,4-triazole-5-carboxamide | LCMS (ESI) m/z: 461.1 $[M + H]^+$. $^1H$ NMR (400 MHz, DMSO-$d_6$) δ 9.41 (d, J = 8.4 Hz, 1H), 8.91 (d, J = 5.2 Hz, 1H), 8.21 (s, 1H), 8.18 (d, J = 5.2 Hz, 1H), 5.35-4.99 (m, 1H), 4.26 (s, 3H), 2.77 (s, 2H), 2.14-1.84 (m, 4H). | acetonitrile 55%-85%/ 0.225% formic acid in water |
| I-296a | 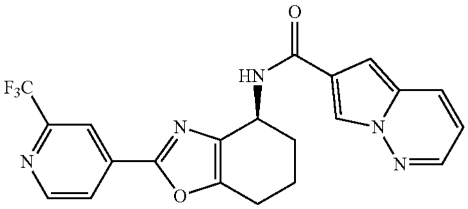 (S)-N-(2-(2-(Trifluoromethyl)pyridin-4-yl)-4,5,6,7-tetrahydrobenzo[d]oxazol-4-yl)pyrrolo[1,2-b]pyridazine-6-carboxamide | LCMS (ESI) m/z: 428.1 $[M + H]^+$. $^1H$ NMR (400 MHz, DMSO-$d_6$) δ 8.91 (d, J = 4.8 Hz, 1H), 8.59 (d, J = 8.4 Hz, 1H), 8.32 (d, J = 1.2 Hz, 1H), 8.26-8.15 (m, 3H), 8.00 (m, 1H), 7.02-6.96 (m, 1H), 6.71 (m, 1H), 5.27-5.16 (m, 1H), 2.90-2.73 (m, 2H), 2.10-1.79 (m, 4H). | acetonitrile 40%-70%/ 0.225% formic acid in water |
| I-297a | 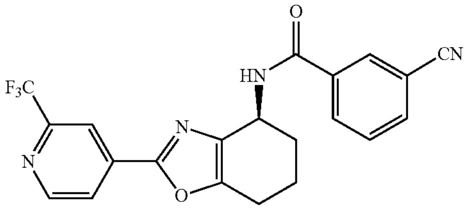 [SMILES: N#Cc1cccc(C(=O)N[C@H]2CCCc3oc(-c4ccnc(C(F)(F)F)c4)nc32)c1] (S)-3-Cyano-N-(2-(2-(trifluoromethyl)pyridin-4-yl)-4,5,6,7-tetrahydrobenzo[d]oxazol-4-yl)benzamide | LCMS (ESI) m/z: 413.1 $[M + H]^+$. $^1H$ NMR (400 MHz, DMSO-$d_6$) δ 9.01-8.96 (m, 1H), 8.93-8.88 (m, 1H), 8.33 (s, 1H), 8.24-8.17 (m, 3H), 8.05-7.97 (m, 1H), 7.74-7.67 (m, 1H), 5.25-5.16 (m, 1H), 2.90-2.74 (m, 2H), 2.09-1.98 (m, 2H), 1.96-1.85 (m, 2H). | acetonitrile 40%-70%/ 0.225% formic acid in water |
| I-298a | 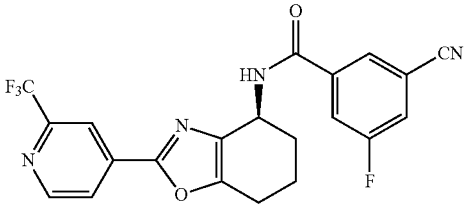 [SMILES: N#Cc1cc(F)cc(C(=O)N[C@H]2CCCc3oc(-c4ccnc(C(F)(F)F)c4)nc32)c1] (S)-3-Cyano-5-fluoro-N-(2-(2-(trifluoromethyl)pyridin-4-yl)-4,5,6,7-tetrahydrobenzo[d]oxazol-4-yl)benzamide | LCMS (ESI) m/z: 431.1 $[M + H]^+$. $^1H$ NMR (400 MHz, DMSO-$d_6$) δ 9.08-9.01 (m, 1H), 8.92 (d, J = 4.8 Hz, 1H), 8.23-8.17 (m, 3H), 8.10-8.03 (m, 2H), 5.25-5.15 (m, 1H), 2.92-2.74 (m, 2H), 2.09-1.98 (m, 2H), 1.96-1.83 (m, 2H). | acetonitrile 40%-70%/ 0.225% formic acid in water |
| I-299a | 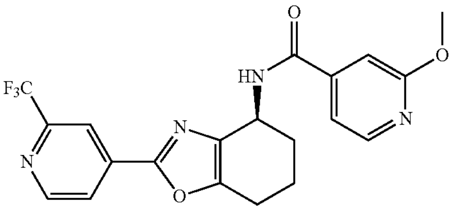 [SMILES: COc1cc(C(=O)N[C@H]2CCCc3oc(-c4ccnc(C(F)(F)F)c4)nc32)ccn1] (S)-3-Cyano-5-fluoro-N-(2-(2-(trifluoromethyl)pyridin-4-yl)-4,5,6,7-tetrahydrobenzo[d]oxazol-4-yl)benzamide | LCMS (ESI) m/z: 419.1 $[M + H]^+$. $^1H$ NMR (400 MHz, DMSO-$d_6$) δ 9.00 (d, J = 7.6 Hz, 1H), 8.94-8.89 (m, 1H), 8.29 (d, J = 5.4 Hz, 1H), 8.24-8.17 (m, 2H), 7.40-7.46 (m, 1H), 7.23 (s, 1H), 5.24-5.15 (m, 1H), 3.88 (s, 3H), 2.88-2.74 (m, 2H), 2.06-1.97 (m, 2H), 1.95-1.83 (m, 2H). | acetonitrile 40%-70%/ 0.225% formic acid in water |

-continued

| Compound No. | Structure | Analytical data | Separation conditions |
|---|---|---|---|
| I-251a | 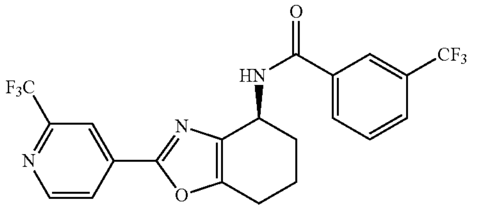 [SMILES: O=C(N[C@H]1CCCc2oc(-c3ccnc(C(F)(F)F)c3)nc21)c1cccc(C(F)(F)F)c1] (S)-3-(Trifluoromethyl)-N-(2-(2-(trifluoromethyl)pyridin-4-yl)-4,5,6,7-tetrahydrobenzo[d]oxazol-4-yl)benzamide | LCMS (ESI) m/z: 456.2 $[M + H]^+$. $^1H$ NMR (400 MHz, DMSO-$d_6$) δ 9.06 (d, J = 8.0 Hz, 1H), 8.91 (d, J = 5.2 Hz, 1H), 8.25 (s, 1H), 8.24-8.17 (m, 3H), 7.92 (d, J = 7.6 Hz, 1H), 7.76-7.70 (m, 1H), 5.27-5.20 (m, 1H), 2.89-2.76 (m, 2H), 2.08-1.98 (m, 2H), 1.96-1.83 (m, 2H). | acetonitrile 55%-85%/ 0.225% formic acid in water |
| I-250a | 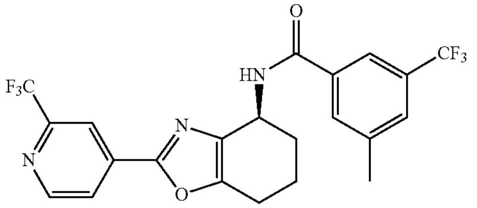 [SMILES: Cc1cc(C(=O)N[C@H]2CCCc3oc(-c4ccnc(C(F)(F)F)c4)nc32)cc(C(F)(F)F)c1] (S)-3-Methyl-5-(trifluoromethyl)-N-(2-(2-(trifluoromethyl)pyridin-4-yl)-4,5,6,7-tetrahydrobenzo[d]oxazol-4-yl)benzamide | LCMS (ESI) m/z: 370.2 $[M + H]^+$. $^1H$ NMR (400 MHz, DMSO-$d_6$) δ 8.99 (d, J = 8.0 Hz, 1H), 8.91 (d, J = 5.2 Hz, 1H), 8.22 (s, 1H), 8.19 (d, J = 5.2 Hz, 1H), 8.04 (s, 2H), 7.74 (s, 1H), 5.26-5.19 (m, 1H), 2.89-2.76 (m, 2H), 2.45 (s, 3H), 2.10-1.98 (m, 2H), 1.95-1.83 (m, 2H). | acetonitrile 55%-85%/ 0.225% formic acid in water |
| I-211a | 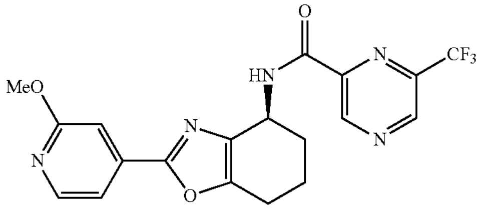 [SMILES: COc1cc(-c2nc3c(o2)CCC[C@@H]3NC(=O)c2cncc(C(F)(F)F)n2)ccn1] (S)-N-(2-(2-Methoxypyridin-4-yl)-4,5,6,7-tetrahydrobenzo[d]oxazol-4-yl)-6-(trifluoromethyl)pyrazine-2-carboxamide | LCMS (ESI) m/z: 420.1 $[M + H]^+$. $^1H$ NMR (400 MHz, DMSO-$d_6$) δ 9.50 (s, 1H), 9.39 (s, 1H), 9.21 (d, J = 8.4 Hz, 1H), 8.29 (d, J = 5.2 Hz, 1H), 7.46 (d, J = 5.6 Hz, 1H), 7.20 (s, 1H), 5.33-5.16 (m, 1H), 3.89 (s, 3H), 2.79-2.73 (m, 2H), 2.08-1.87 (m, 4H). | acetonitrile 35%-65%/ 0.225% formic acid in water |
| I-249a | 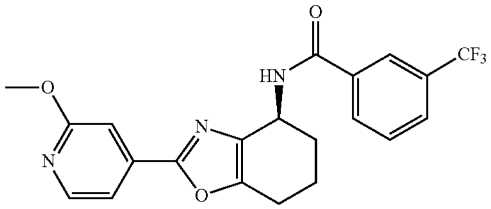 [SMILES: COc1cc(-c2nc3c(o2)CCC[C@@H]3NC(=O)c2cccc(C(F)(F)F)c2)ccn1] (S)-N-(2-(2-Methoxypyridin-4-yl)-4,5,6,7-tetrahydrobenzo[d]oxazol-4-yl)-3-(trifluoromethyl)benzamide | LCMS (ESI) m/z: 418.4 $[M + H]^+$. $^1H$ NMR (400 MHz, DMSO-$d_6$) δ 9.03 (d, J = 8.0 Hz, 1H), 8.30 (d, J = 5.6 Hz, 1H), 8.25 (s, 1H), 8.21 (d, J = 8.0 Hz, 1H), 7.91 (d, J = 7.6 Hz, 1H), 7.76-7.69 (m, 1H), 7.50-7.45 (m, 1H), 7.21 (s, 1H), 5.23-5.15 (m, 1H), 3.89 (s, 3H), 2.86-2.70 (m, 2H), 2.09-1.95 (m, 2H), 1.95-1.82 (m, 2H). | acetonitrile 55%-85%/ 0.225% formic acid in water |
| I-248a | 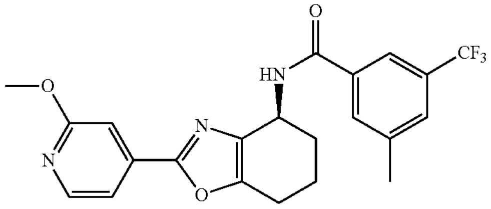 [SMILES: COc1cc(-c2nc3c(o2)CCC[C@@H]3NC(=O)c2cc(C)cc(C(F)(F)F)c2)ccn1] (S)-N-(2-(2-Methoxypyridin-4-yl)-4,5,6,7-tetrahydrobenzo[d]oxazol-4-yl)-3-(trifluoromethyl)benzamide | LCMS (ESI) m/z: 432.1 $[M + H]^+$. $^1H$ NMR (400 MHz, DMSO-$d_6$) δ 8.97 (d, J = 8.0 Hz, 1H), 8.30 (d, J = 5.4 Hz, 1H), 8.04 (s, 2H), 7.73 (s, 1H), 7.47 (dd, J = 1.2, 5.6 Hz, 1H), 7.21 (s, 1H), 5.23-5.11 (m, 1H), 3.89 (s, 3H), 2.85-2.69 (m, 2H), 2.44 (s, 3H), 2.04-1.84 (m, 4H). | acetonitrile 35%-65%/ 0.225% formic acid in water |

-continued

| Compound No. | Structure | Analytical data | Separation conditions |
|---|---|---|---|
| I-275a | 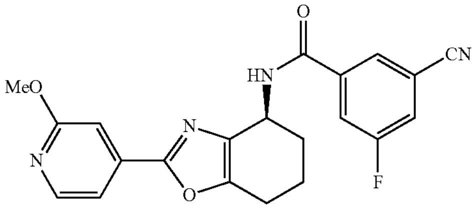 (S)-N-(2-(2-Methoxypyridin-4-yl)-4,5,6,7-tetrahydrobenzo[d]oxazol-4-yl)-3-methyl-5-(trifluoromethyl)benzamide | LCMS (ESI) m/z: 393.0 $[M + H]^+$. $^1H$ NMR (400 MHz, DMSO-$d_6$) δ 9.03 (d, J = 7.6 Hz, 1H), 8.30 (d, J = 5.2 Hz, 1H), 8.22-8.20 (m, 1H), 8.09-8.03 (m, 2H), 7.47 (dd, J = 1.6, 5.2 Hz, 1H), 7.22 (s, 1H), 5.19-5.13 (m, 1H), 3.89 (s, 3H), 2.85-2.74 (m, 2H), 2.04-1.96 (m, 2H), 1.93-1.84 (m, 2H). | acetonitrile 50%-80%/ 0.225% formic acid in water |
| I-293a | 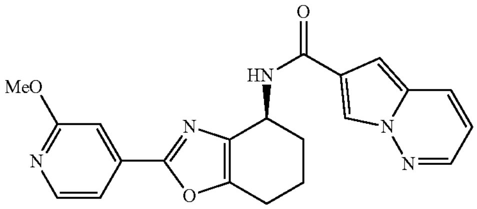 [SMILES: COc1cc(-c2nc3c(o2)CCC[C@@H]3NC(=O)c2cc3cccnn3c2)ccn1] (S)-N-(2-(2-Methoxypyridin-4-yl)-4,5,6,7-tetrahydrobenzo[d]oxazol-4-yl)pyrrolo[1,2-b]pyridazine-6-carboxamide | LCMS (ESI) m/z: 390.1 $[M + H]^+$. $^1H$ NMR (400 MHz, DMSO-$d_6$) δ 8.57 (d, J = 8.4 Hz, 1H), 8.33-8.31 (m, 1H), 8.30 (d, J = 5.2 Hz, 1H), 8.22 (dd, J = 1.6, 4.4 Hz, 1H), 8.02-7.98 (m, 1H), 7.49-4.46 (m, 1H), 7.21 (s, 1H), 6.99-6.97 (m, 1H), 6.73-6.68 (m, 1H), 5.21-5.15 (m, 1H), 3.89 (s, 3H), 2.81-2.74 (m, 2H), 2.07-1.94 (m, 2H), 1.93-1.81 (m, 2H). | acetonitrile 27%-57%/ 0.225% formic acid in water |
| I-294a | 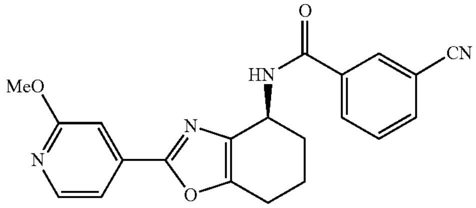 [SMILES: COc1cc(-c2nc3c(o2)CCC[C@@H]3NC(=O)c2cccc(C#N)c2)ccn1] (S)-3-Cyano-N-(2-(2-methoxypyridin-4-yl)-4,5,6,7-tetrahydrobenzo[d]oxazol-4-yl)benzamide | LCMS (ESI) m/z: 374.9 $[M + H]^+$. $^1H$ NMR (400 MHz, DMSO-$d_6$) δ 8.96 (d, J = 7.6 Hz, 1H), 8.33-8.31 (m, 1H), 8.30 (d, J = 5.6 Hz, 1H), 8.23-8.19 (m, 1H), 8.03-8.00 (m, 1H), 7.73-7.67 (m, 1H), 7.47 (dd, J = 1.6, 5.6 Hz, 1H), 7.22 (s, 1H), 5.20-5.14 (m, 1H), 3.89 (s, 3H), 2.82-2.74 (m, 2H), 2.04-1.95 (m, 2H), 1.94-1.84 (m, 2H). | acetonitrile 30%-60%/ 0.225% formic acid in water |
| I-189a | 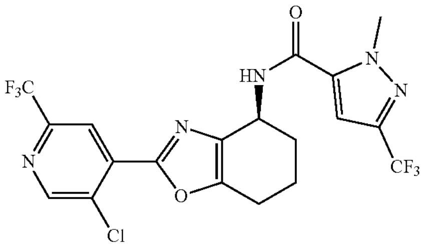 (S)-N-(2-(2-Cyclopropylpyridin-4-yl)-4,5,6,7-tetrahydrobenzo[d]oxazol-4-yl)-1-methyl-1H-1,2,4-triazole-5-carboxamide | LCMS (ESI) m/z: 494.0 $[M + H]^+$. $^1H$ NMR (400 MHz, DMSO-$d_6$) δ 9.04 (s, 1H), 8.99 (d, J = 8.0 Hz, 1H), 8.33 (s, 1H), 7.36 (s, 1H), 5.25-5.09 (m, 1H), 4.18 (s, 3H), 2.91-2.73 (m, 2H), 2.07-1.84 (m, 4H). | acetonitrile 54%-84%/ 0.225% formic acid in water |
| I-178a | 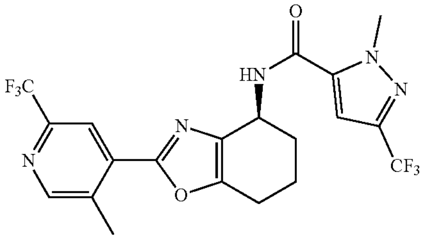 [SMILES: Cc1cnc(C(F)(F)F)cc1-c1nc2c(o1)CCC[C@@H]2NC(=O)c1cc(C(F)(F)F)nn1C] (S)-1-Methyl-N-(2-(5-methyl-2-(trifluoromethyl)pyridin-4-yl)-4,5,6,7-tetrahydrobenzo[d]oxazol-4-yl)-3-(trifluoromethyl)-1H-pyrazole-5-carboxamide | LCMS (ESI) m/z: 474.1 $[M + H]^+$. $^1H$ NMR (400 MHz, DMSO-$d_6$) δ 8.97 (d, J = 8.0 Hz, 1H), 8.82 (s, 1H), 8.19 (s, 1H), 7.36 (s, 1H), 5.25-5.09 (m, 1H), 4.18 (s, 3H), 2.91-2.74 (m, 2H), 2.71 (s, 3H), 2.08-1.81 (m, 4H). | acetonitrile 54%-84%/ 0.225% formic acid in water |

-continued

| Compound No. | Structure | Analytical data | Separation conditions |
|---|---|---|---|
| I-217a | 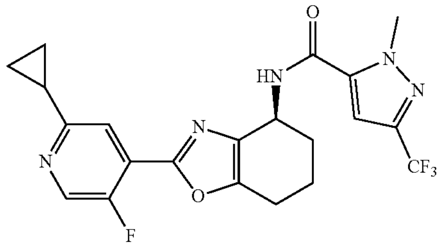 [SMILES: Cn1nc(C(F)(F)F)cc1C(=O)N[C@H]1CCCc2oc(-c3cc(C4CC4)ncc3F)nc21] (S)-N-(2-(2-Cyclopropyl-5-fluoropyridin-4-yl)-4,5,6,7-tetrahydrobenzo[d]oxazol-4-yl)-1-methyl-3-(trifluoromethyl)-1H-pyrazole-5-carboxamide | LCMS (ESI) m/z: 450.2 $[M + H]^+$. $^1H$ NMR (400 MHz, DMSO-$d_6$) δ 8.98 (d, J = 7.6 Hz, 1H), 8.58 (d, J = 2.4 Hz, 1H), 7.89 (d, J = 5.6 Hz, 1H), 7.38 (s, 1H), 5.20-5.12 (m, 1H), 4.19 (s, 3H), 2.84-2.76 (m, 2H), 2.31-2.24 (m, 1H), 2.08 (s, 1H), 2.05-1.80 (m, 4H), 1.03-0.87 (m, 4H). | acetonitrile 37%-67%/0.225% formic acid in water |
| I-208a | 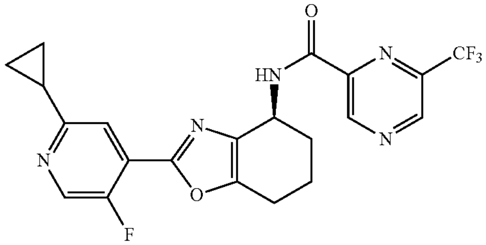 [SMILES: O=C(N[C@H]1CCCc2oc(-c3cc(C4CC4)ncc3F)nc21)c1cncc(C(F)(F)F)n1] (S)-N-(2-(2-Cyclopropyl-5-fluoropyridin-4-yl)-4,5,6,7-tetrahydrobenzo[d]oxazol-4-yl)-6-(trifluoromethyl)pyrazine-2-carboxamide | LCMS (ESI) m/z: 448.2 $[M + H]^+$. $^1H$ NMR (400 MHz, DMSO-$d_6$) δ 9.51 (s, 1H), 9.40 (s, 1H), 9.23 (d, J = 8.4 Hz, 1H), 8.56 (d, J = 2.4 Hz, 1H), 7.87 (d, J = 6.0 Hz, 1H), 5.29-5.22 (m, 1H), 2.86-2.71 (m, 2H), 2.30-2.23 (m, 1H), 2.11-1.88 (m, 4H), 0.98-0.86 (m, 4H). | acetonitrile 40%-70%/0.225% formic acid in water |
| I-523a | 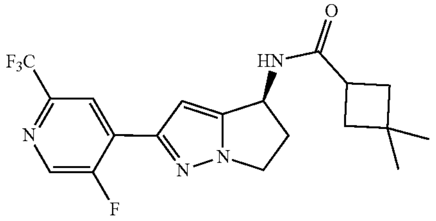 [SMILES: CC1(C)CC(C(=O)N[C@H]2CCn3nc(-c4cc(C(F)(F)F)ncc4F)cc32)C1] (S)-N-(2-(5-Fluoro-2-(trifluoromethyl)pyridin-4-yl)-5,6-dihydro-4H-pyrrolo[1,2-b]pyrazol-4-yl)-3,3-dimethylcyclobutane-1-carboxamide | LCMS (ESI) m/z: 397.1 $[M + H]^+$. $^1H$ NMR (400 MHz, DMSO-$d_6$) δ 8.84 (d, J = 2.4 Hz, 1H), 8.33-8.29 (m, 2H), 6.67 (d, J = 3.6 Hz, 1H), 5.33-5.26 (m, 1H), 4.37-4.29 (m, 1H), 4.22-4.15 (m, 1H), 2.98-2.90 (m, 2H), 2.39-2.31 (m, 1H), 1.97-1.90 (m, 2H), 1.84-1.77 (m, 2H), 1.12-1.04 (m, 6H). | Column: 52-Welch Xtimate C18 150 × 30 mm, 5 μm; mobile phase: acetonitrile 37%-67%/0.225% formic acid in water. |
| I-524a | 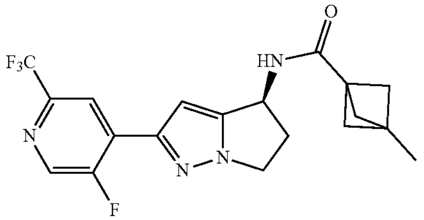 [SMILES: CC12CC(C(=O)N[C@H]3CCn4nc(-c5cc(C(F)(F)F)ncc5F)cc43)(C1)C2] (S)-N-(2-(5-Fluoro-2-(trifluoromethyl)pyridin-4-yl)-5,6-dihydro-4H-pyrrolo[1,2-b]pyrazol-4-yl)-3-methylbicyclo[1.1.1]pentane-1-carboxamide | LCMS (ESI) m/z: 395.2 $[M + H]^+$. $^1H$ NMR (400 MHz, DMSO-$d_6$) δ 9.09 (d, J = 7.6 Hz, 1H), 8.35 (d, J = 2.4 Hz, 1H), 7.94 (d, J = 7.6 Hz, 1H), 7.84 (s, 1H), 7.66-7.60 (m, 1H), 7.59-7.55 (m, 1H), 7.25 (d, J = 4.8 Hz, 1H), 5.38-5.32 (m, 1H), 3.87 (s, 3H), 2.68-2.57 (m, 2H), 2.13-1.84 (m, 4H). | Column: 51-Welch Xtimate C18 100 × 40 mm, 3 μm; mobile phase: acetonitrile 37%-67%/0.225% formic acid in water |

-continued

| Compound No. | Structure | Analytical data | Separation conditions |
|---|---|---|---|
| I-525a | 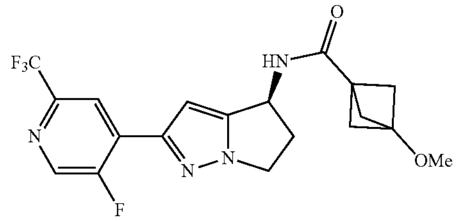 [SMILES: COC12CC(C(=O)N[C@H]3CCn4nc(-c5cc(C(F)(F)F)ncc5F)cc43)(C1)C2] (S)-N-(2-(5-Fluoro-2-(trifluoromethyl)pyridin-4-yl)-5,6-dihydro-4H-pyrrolo[1,2-b]pyrazol-4-yl)-3-methoxybicyclo[1.1.1]pentane-1-carboxamide | LCMS (ESI) m/z: 411.1 [M + H]$^+$. $^1$H NMR (400 MHz, DMSO-$d_6$) δ 8.84 (d, J = 2.0 Hz, 1H), 8.44 (d, J = 7.6 Hz, 1H), 8.31 (d, J = 5.6 Hz, 1H), 6.68 (d, J = 3.6 Hz, 1H), 5.36-5.30 (m, 1H), 4.39-4.31 (m, 1H), 4.23-4.16 (m, 1H), 3.18 (s, 3H), 3.00-2.90 (m, 1H), 2.46-2.37 (m, 1H), 2.02 (s, 6H). | Column: 51-Welch Xtimate C18 100 x 40 mm, 3 μm; mobile phase: acetonitrile 35%-65%/0.225% formic acid in water |
| I-526a | 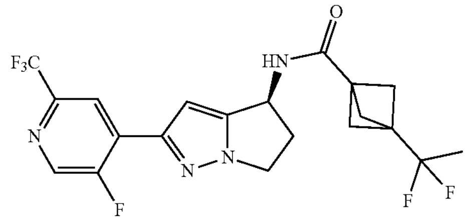 [SMILES: CC(F)(F)C12CC(C(=O)N[C@H]3CCn4nc(-c5cc(C(F)(F)F)ncc5F)cc43)(C1)C2] (S)-3-(1,1-Difluoroethyl)-N-(2-(5-fluoro-2-(trifluoromethyl)pyridin-4-yl)-5,6-dihydro-4H-pyrrolo[1,2-b]pyrazol-4-yl)bicyclo[1.1.1]pentane-1-carboxamide | LCMS (ESI) m/z: 445.1 [M + H]$^+$. $^1$H NMR (400 MHz, DMSO-$d_6$) δ 8.85 (d, J = 2.4 Hz, 1H), 8.51 (d, J = 7.6 Hz, 1H), 8.31 (d, J = 5.6 Hz, 1H), 6.70 (d, J = 3.2 Hz, 1H), 5.36-5.30 (m, 1H), 4.40-4.33 (m, 1H), 4.23-4.16 (m, 1H), 3.01-2.92 (m, 1H), 2.46-2.39 (m, 1H), 2.10-1.99 (m, 6H), 1.60-1.50 (m, 3H). | Column: 51-Welch Xtimate C18 100 x 40 mm, 3 μm; mobile phase: acetonitrile 42%-72%/0.225% formic acid in water |
| I-527a | 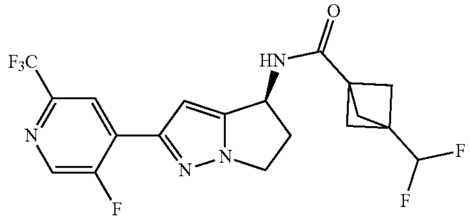 [SMILES: O=C(N[C@H]1CCn2nc(-c3cc(C(F)(F)F)ncc3F)cc21)C12CC(C(F)F)(C1)C2] (S)-3-(Difluoromethyl)-N-(2-(5-fluoro-2-(trifluoromethyl)pyridin-4-yl)-5,6-dihydro-4H-pyrrolo[1,2-b]pyrazol-4-yl)bicyclo[1.1.1]pentane-1-carboxamide | LCMS (ESI) m/z: 431.1 [M + H]$^+$. $^1$H NMR (400 MHz, DMSO-$d_6$) δ 8.84 (d, J = 2.0 Hz, 1H), 8.51 (d, J = 7.6 Hz, 1H), 8.31 (d, J = 5.6 Hz, 1H), 6.70 (d, J = 3.2 Hz, 1H), 6.21-5.91 (m, 1H), 5.36-5.29 (m, 1H), 4.40-4.32 (m, 1H), 4.24-4.16 (m, 1H), 3.01-2.92 (m, 1H), 2.46-2.38 (m, 1H), 2.01 (s, 6H). | Column: 51-Welch Xtimate C18 100 x 40 mm, 3 μm; mobile phase: acetonitrile 40%-70%/0.225% formic acid in water |
| I-539a | 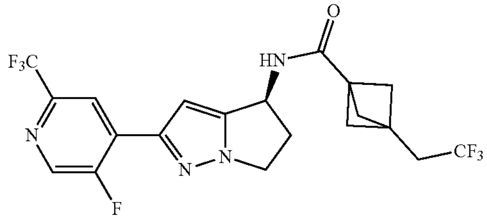 [SMILES: O=C(N[C@H]1CCn2nc(-c3cc(C(F)(F)F)ncc3F)cc21)C12CC(CC(F)(F)F)(C1)C2] (S)-N-(2-(2-Methoxypyridin-4-yl)-4,5,6,7-tetrahydrobenzo[d]oxazol-7-yl)-3-(trifluoromethyl)benzamide | LCMS (ESI) m/z: 463.1 [M + H]$^+$. $^1$H NMR (400 MHz, DMSO-$d_6$) δ 8.84 (d, J = 2.4 Hz, 1H), 8.39 (d, J = 8.0 Hz, 1H), 8.31 (d, J = 5.6 Hz, 1H), 6.68 (d, J = 3.6 Hz, 1H), 5.34-5.29 (m, 1H), 4.36-4.32 (m, 1H), 4.23-4.16 (m, 1H), 2.99-2.90 (m, 1H), 2.58-2.51 (m, 2H), 2.46-2.36 (m, 1H), 1.96 (s, 6H). | Column: 58-Phenomenex Gemini NX C18 150 x 40 mm, 5 μm; mobile phase: acetonitrile 54%-84%/0.225% formic acid in water |

-continued

| Compound No. | Structure | Analytical data | Separation conditions |
|---|---|---|---|
| I-540a | 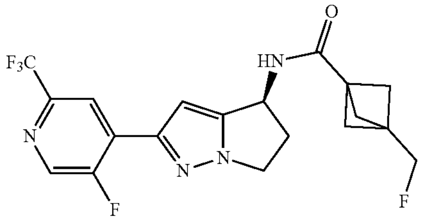 [SMILES: O=C(N[C@H]1CCn2nc(-c3cc(C(F)(F)F)ncc3F)cc21)C12CC(CF)(C1)C2] (S)-N-(2-(5-Fluoro-2-(trifluoromethyl)pyridin-4-yl)-5,6-dihydro-4H-pyrrolo[1,2-b]pyrazol-4-yl)-3-(fluoromethyl)bicyclo[1.1.1]pentane-1-carboxamide | LCMS (ESI) m/z: 413.1 $[M + H]^+$. $^1H$ NMR (400 MHz, DMSO-$d_6$) δ 8.84 (d, J = 2.0 Hz, 1H), 8.42 (d, J = 7.6 Hz, 1H), 8.31 (d, J = 5.6 Hz, 1H), 6.69 (d, J = 3.2 Hz, 1H), 5.36-5.30 (m, 1H), 4.46 (s, 1H), 4.38-4.33 (m, 2H), 4.24-4.16 (m, 1H), 3.01-2.91 (m, 1H), 2.46-2.37 (m, 1H), 1.92 (s, 6H). | Column: 58-Phenomenex Gemini NX C18 150 × 40 mm, 5 μm; mobile phase: acetonitrile 45%-75%/0.225% formic acid in water |
| I-546a | 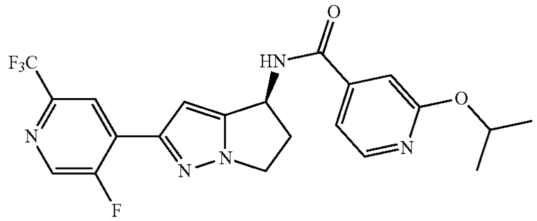 [SMILES: CC(C)Oc1cc(C(=O)N[C@H]2CCn3nc(-c4cc(C(F)(F)F)ncc4F)cc32)ccn1] (S)-N-(2-(5-Fluoro-2-(trifluoromethyl)pyridin-4-yl)-5,6-dihydro-4H-pyrrolo[1,2-b]pyrazol-4-yl)-2-isopropoxyisonicotinamide | LCMS (ESI) m/z: 450.1 $[M + H]^+$. $^1H$ NMR (400 MHz, DMSO-$d_6$) δ 9.22 (d, J = 7.2 Hz, 1H), 8.85 (d, J = 2.4 Hz, 1H), 8.33 (d, J = 5.6 Hz, 1H), 8.27 (d, J = 5.2 Hz, 1H), 7.34-7.31 (m, 1H), 7.15 (s, 1H), 6.78 (d, J = 3.6 Hz, 1H), 5.57-5.51 (m, 1H), 5.29-5.22 (m, 1H), 4.45-4.38 (m 1H), 4.30-4.22 (m, 1H), 3.10-3.01 (m, 1H), 2.60-2.54 (m, 1H), 1.30-1.27 (m, 6H). | Column: 58-Phenomenex Gemini NX C18 150 × 40 mm, 5 μm; mobile phase: acetonitrile 60%-90%/0.225% formic acid in water |
| I-547a | 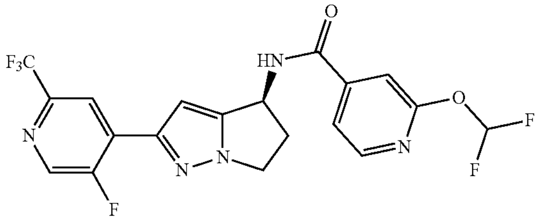 [SMILES: O=C(N[C@H]1CCn2nc(-c3cc(C(F)(F)F)ncc3F)cc21)c1ccnc(OC(F)F)c1] (S)-2-(Difluoromethoxy)-N-(2-(5-fluoro-2-(trifluoromethyl)pyridin-4-yl)-5,6-dihydro-4H-pyrrolo[1,2-b]pyrazol-4-yl)isonicotinamide | LCMS (ESI) m/z: 458.0 $[M + H]^+$. $^1H$ NMR (400 MHz, DMSO-$d_6$) δ 9.38 (d, J = 7.2 Hz, 1H), 8.86 (d, J = 2.4 Hz, 1H), 8.42 (d, J = 4.8 Hz, 1H), 8.33 (d, J = 5.6 Hz, 1H), 7.93-7.55 (m, 2H), 7.47 (s, 1H), 6.80 (d, J = 3.2 Hz, 1H), 5.59-5.53 (m, 1H), 4.46-4.39 (m, 1H), 4.31-4.24 (m, 1H), 3.12-3.03 (m, 1H), 2.61-2.54 (m, 1H). | Column: 58-Phenomenex Gemini NX C18 150 × 40 mm, 5 μm; mobile phase: acetonitrile 55%-85%/0.225% formic acid in water |
| I-318a | 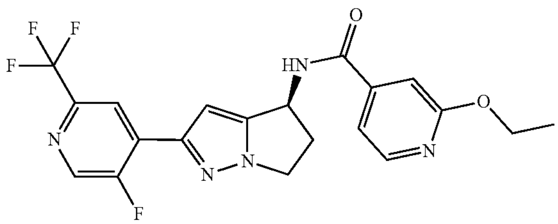 [SMILES: CCOc1cc(C(=O)N[C@H]2CCn3nc(-c4cc(C(F)(F)F)ncc4F)cc32)ccn1] (S)-2-Ethoxy-N-(2-(5-fluoro-2-(trifluoromethyl)pyridin-4-yl)-5,6-dihydro-4H-pyrrolo[1,2-b]pyrazol-4-yl)isonicotinamide | LCMS (ESI) m/z: 436.2 $[M + H]^+$. $^1H$ NMR (400 MHz, DMSO-$d_6$) δ 9.23 (d, J = 7.6 Hz, 1H), 8.84 (d, J = 2.0 Hz, 1H), 8.32 (d, J = 5.6 Hz, 1H), 8.28 (d, J = 5.2 Hz, 1H), 7.35 (d, J = 5.2 Hz, 1H), 7.20 (s, 1H), 6.78 (d, J = 3.2 Hz, 1H), 5.59-5.51 (m, 1H), 4.40-4.42 (m, 1H), 4.33 (q, J = 7.2 Hz, 2H), 4.29-4.22 (m, 1H), 3.12-3.02 (m, 1H), 2.63-2.54 (m, 1H), 1.31 (t, J = 6.8 Hz, 3H). | Column: 50-Welch Xtimate C18 150 × 40 mm, 5 μm; mobile phase: acetonitrile 45%-75%/0.225% formic acid in water |

-continued

| Compound No. | Structure | Analytical data | Separation conditions |
|---|---|---|---|
| I-552a | 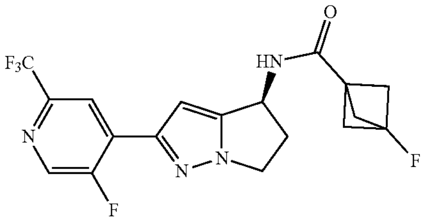 [SMILES: O=C(N[C@H]1CCn2nc(-c3cc(C(F)(F)F)ncc3F)cc21)C12CC(F)(C1)C2] (S)-3-Fluoro-N-(2-(5-fluoro-2-(trifluoromethyl)pyridin-4-yl)-5,6-dihydro-4H-pyrrolo[1,2-b]pyrazol-4-yl)bicyclo[1.1.1]pentane-1-carboxamide | LCMS (ESI) m/z: 445.2 [M + H]$^+$. $^1$H NMR (400 MHz, DMSO-$d_6$) δ 8.84 (d, J = 2.4 Hz, 1H), 8.36 (d, J = 8.0 Hz, 1H), 8.31 (d, J = 6.0 Hz, 1H), 6.68 (d, J = 3.6 Hz, 1H), 6.22-5.90 (m, 1H), 5.34-5.28 (m, 1H), 4.39-4.32 (m, 1H), 4.22-4.15 (m, 1H), 2.99-2.89 (m, 1H), 2.45-2.37 (m, 1H), 2.09-1.98 (m, 2H), 1.91 (s, 6H). | Column: 58-Phenomenex Gemini NX C18 150 × 40 mm, 5 μm; mobile phase: acetonitrile 50%-80%/0.225% formic acid in water |
| I-536a | 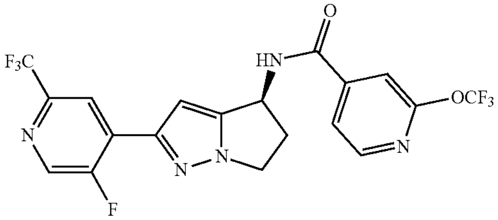 (S)-N-(2-(5-Fluoro-2-(trifluoromethyl)pyridin-4-yl)-5,6-dihydro-4H-pyrrolo[1,2-b]pyrazol-4-yl)-2-(trifluoromethoxy)isonicotinamide | LCMS (ESI) m/z: 476.1 [M + H]$^+$. $^1$H NMR (400 MHz, DMSO-$d_6$) δ 9.44 (d, J = 7.2 Hz, 1H), 8.84 (s, 1H), 8.53 (d, J = 4.8 Hz, 1H), 8.32 (d, J = 4.8 Hz, 1H), 7.83 (d, J = 4.4 Hz, 1H), 7.66 (s, 1H), 6.80 (s, 1H), 5.59-5.51 (m, 1H), 4.50-4.35 (m, 1H), 4.33-4.21 (m, 1H), 3.15-3.01(m, 1H), 2.63-2.52(m, 1H). | Column: 58-Phenomenex Gemini NX C18 150 × 40 mm, 5 μm; mobile phase: acetonitrile 55%-85%/0.225% formic acid in water |
| I-558a | 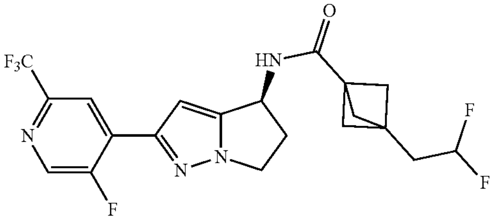 [SMILES: O=C(N[C@H]1CCn2nc(-c3cc(C(F)(F)F)ncc3F)cc21)C12CC(CC(F)F)(C1)C2] (S)-3-(2,2-Difluoroethyl)-N-(2-(5-fluoro-2-(trifluoromethyl)pyridin-4-yl)-5,6-dihydro-4H-pyrrolo[1,2-b]pyrazol-4-yl)bicyclo[1.1.1]pentane-1-carboxamide | LCMS (ESI) m/z: 428.2 [M + H]$^+$. $^1$H NMR (400 MHz, DMSO-$d_6$) δ 9.20 (d, J = 7.6 Hz, 1H), 8.51 (d, J = 5.2 Hz, 1H), 8.26 (s, 1H), 8.23 (d, J = 8.0 Hz, 1H), 7.93 (d, J = 8.0 Hz, 1H), 7.80 (s, 1H), 7.76-7.73 (m, 1H), 7.59 (dd, J = 1.2, 5.2 Hz, 1H), 5.47-5.30 (m, 1H), 2.66-2.53 (m, 2H), 2.27-2.21 (m, 1H), 2.13-2.04 (m, 1H), 2.02-1.90 (m, 2H), 1.90-1.82 (m, 1H), 0.99-0.88 (m, 4H). | Column: 58-Phenomenex Gemini NX C18 150 × 40 mm, 5 μm; mobile phase: acetonitrile 50%-80%/0.225% formic acid in water |
| I-549a | 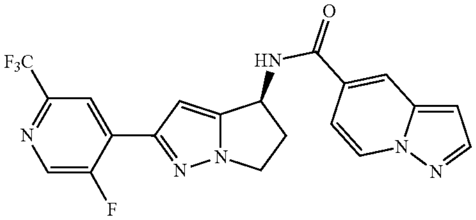 [SMILES: O=C(N[C@H]1CCn2nc(-c3cc(C(F)(F)F)ncc3F)cc21)c1ccn2nccc2c1] (S)-N-(2-(2-Cyclopropylpyridin-4-yl)-4,5,6,7-tetrahydrobenzo[d]oxazol-7-yl)-3-(trifluoromethoxy)benzamide | LCMS (ESI) m/z: 431.1 [M + H]$^+$. $^1$H NMR (400 MHz, DMSO-$d_6$) δ 9.23 (d, J = 7.6 Hz, 1H), 8.84 (d, J = 1.6 Hz, 1H), 8.77 (d, J = 7.2 Hz, 1H), 8.33 (d, J = 6.0 Hz, 1H), 8.28 (s, 1H), 8.09 (d, J = 2.0 Hz, 1H), 7.33-7.28 (m, 1H), 6.83 (d, J = 1.6 Hz, 1H), 6.79 (d, J = 3.6 Hz, 1H), 5.62-5.55 (m, 1H), 4.48-4.41 (m, 1H), 4.32-4.24 (m, 1H), 3.13-3.04 (m, 1H), 2.65-2.56 (m, 1H). | Column: 58-Phenomenex Gemini NX C18 150 × 40 mm, 5 μm; mobile phase: acetonitrile 45%-75%/0.225% formic acid in water |
| I-493a | 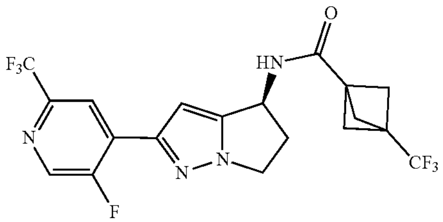 [SMILES: O=C(N[C@H]1CCn2nc(-c3cc(C(F)(F)F)ncc3F)cc21)C12CC(C(F)(F)F)(C1)C2] (S)-N-(2-(5-Fluoro-2-(trifluoromethyl)pyridin-4-yl)-5,6-dihydro-4H-pyrrolo[1,2-b]pyrazol-4-yl)-3-(trifluoromethyl)bicyclo[1.1.1]pentane-1-carboxamide | LCMS (ESI) m/z: 449.1 [M + H]$^+$. $^1$H NMR (400 MHz, DMSO-$d_6$) δ 8.86 (d, J = 2.4 Hz, 1H), 8.61 (d, J = 7.6 Hz, 1H), 8.32 (d, J = 5.6 Hz, 1H), 6.71 (d, J = 3.6 Hz, 1H), 5.34-5.30 (m, 1H), 4.36-4.38 (m, 1H), 4.21-4.23 (m, 1H), 2.96-2.98 (m, 1H), 2.40-2.42 (m, 1H), 2.18 (s, 6H). | Column: 52-Welch Xtimate C18 150 × 30 mm, 5 μm; mobile phase: acetonitrile 43%-73%/0.225% formic acid in water |

-continued

| Compound No. | Structure | Analytical data | Separation conditions |
|---|---|---|---|
| I-129a | 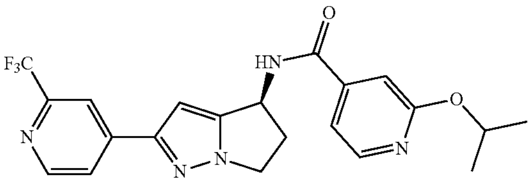 [SMILES: CC(C)Oc1cc(C(=O)N[C@H]2CCn3nc(-c4ccnc(C(F)(F)F)c4)cc32)ccn1] (S)-2-Isopropoxy-N-(2-(2-(trifluoromethyl)pyridin-4-yl)-5,6-dihydro-4H-pyrrolo[1,2-b]pyrazol-4-yl)isonicotinamide | LCMS (ESI) m/z: 432.2 $[M + H]^+$. $^1H$ NMR (400 MHz, DMSO-$d_6$) δ 9.21 (d, J = 7.6 Hz, 1H), 8.74 (d, J = 5.2 Hz, 1H), 8.28 (d, J = 5.2 Hz, 1H), 8.20 (s, 1H), 8.07 (d, J = 5.2 Hz, 1H), 7.32-7.28 (m, 1H), 7.15 (s, 1H), 7.00 (s, 1H), 5.55-5.50 (m, 1H), 5.26 (d, J = 6.0 Hz, 1H), 4.36-4.38 (m, 1H), 4.29-4.14 (m, 1H), 3.08-2.96 (m, 1H), 2.59-2.53 (m, 1H), 1.27-1.29 (m, 6H). | Prep silica gel chromatography: (solvent gradient: 0-25% EtOAc in hexanes) |
| I-264a | 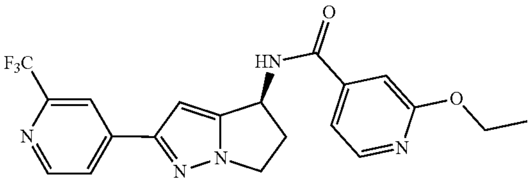 [SMILES: CCOc1cc(C(=O)N[C@H]2CCn3nc(-c4ccnc(C(F)(F)F)c4)cc32)ccn1] (S)-N-(2-(2-Cyclopropyl-5-fluoropyridin-4-yl)-5,6-dihydro-4H-pyrrolo[1,2-b]pyrazol-4-yl)-1-methyl-3-(trifluoromethyl)-1H-pyrazole-5-carboxamide | LCMS (ESI) m/z: 418.1 $[M + H]^+$. $^1H$ NMR (400 MHz, DMSO-$d_6$) δ 9.23 (d, J = 8.0 Hz, 1H), 8.74 (d, J = 4.8 Hz, 1H), 8.28 (d, J = 5.2 Hz, 1H), 8.20 (s, 1H), 8.07 (d, J = 5.2 Hz, 1H), 7.36 (d, J = 6.0 Hz, 1H), 7.20 (s, 1H), 7.01 (s, 1H), 5.60-5.51 (m, 1H), 4.41-4.30 (m, 3H), 4.26-4.20 (m, 1H), 3.10-2.99 (m, 1H), 2.62-2.55 (m, 1H), 1.31 (t, J = 7.2 Hz, 3H). | Column: 52-Welch Xtimate C18 150 × 30 mm, 5 μm; mobile phase: acetonitrile 35%-65%/0.225% formic acid in water |
| I-489a | 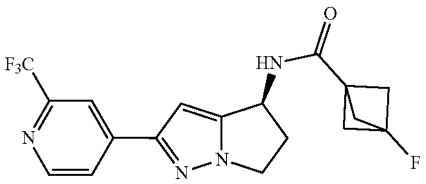 [SMILES: O=C(N[C@H]1CCn2nc(-c3ccnc(C(F)(F)F)c3)cc21)C12CC(F)(C1)C2] (S)-3-Fluoro-N-(2-(2-(trifluoromethyl)pyridin-4-yl)-5,6-dihydro-4H-pyrrolo[1,2-b]pyrazol-4-yl)bicyclo[1.1.1]pentane-1-carboxamide | LCMS (ESI) m/z: 381.1 $[M + H]^+$. $^1H$ NMR (400 MHz, DMSO-$d_6$) δ 8.74 (d, J = 5.2 Hz, 1H), 8.57 (d, J = 8.0 Hz, 1H), 8.20 (s, 1H), 8.08 (d, J = 4.8 Hz, 1H), 6.96 (s, 1H), 5.41-5.30 (m, 1H), 4.36-4.27 (m, 1H), 4.22-4.13 (m, 1H), 3.00-2.90 (m, 1H), 2.43-2.35 (m, 1H), 2.28 (d, J = 2.4 Hz, 6H). | Column: 58-Phenomenex Gemini NX C18 150 × 40 mm, 5 μm; mobile phase: acetonitrile 45%-75%/0.225% formic acid in water |
| I-491a | 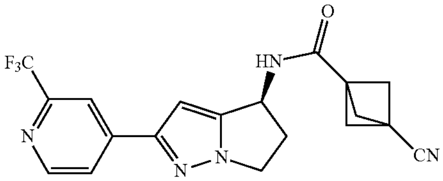 [SMILES: N#CC12CC(C(=O)N[C@H]3CCn4nc(-c5ccnc(C(F)(F)F)c5)cc43)(C1)C2] (S)-3-Cyano-N-(2-(2-(trifluoromethyl)pyridin-4-yl)-5,6-dihydro-4H-pyrrolo[1,2-b]pyrazol-4-yl)bicyclo[1.1.1]pentane-1-carboxamide | LCMS (ESI) m/z: 388.2 $[M + H]^+$. $^1H$ NMR (400 MHz, DMSO-$d_6$) δ 8.74 (d, J = 5.2 Hz, 1H), 8.60 (d, J = 8.0 Hz, 1H), 8.20 (s, 1H), 8.07 (d, J = 5.2 Hz, 1H), 6.94 (s, 1H), 5.34-5.28 (m, 1H), 4.34-4.28 (m, 1H), 4.19-4.13 (m, 1H), 2.98-2.89 (m, 1H), 2.43 (s, 6H), 2.40-2.32 (m, 1H). | Column: 58-Phenomenex Gemini NX C18 150 × 40 mm, 5 μm; mobile phase: acetonitrile 40%-70%/0.225% formic acid in water |
| I-550a | 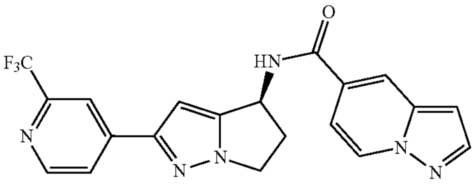 (S)-N-(2-(2-(Trifluoromethyl)pyridin-4-yl)-5,6-dihydro-4H-pyrrolo[1,2-b]pyrazol-4-yl)pyrazolo[1,5-a]pyridine-5-carboxamide | LCMS (ESI) m/z: 413.1 $[M + H]^+$. $^1H$ NMR (400 MHz, DMSO-$d_6$) δ 9.23 (d, J = 7.6 Hz, 1H), 8.78 (d, J = 7.6 Hz, 1H), 8.74 (d, J = 5.2 Hz, 1H), 8.28 (d, J = 0.8 Hz, 1H), 8.21 (s, 1H), 8.12-8.09 (m, 1H), 8.08 (d, J = 5.2 Hz, 1H), 7.31 (dd, J = 1.6, 7.2 Hz, 1H), 7.03 (s, 1H), 6.83 (d, J = 1.6 Hz, 1H), 5.69-5.47 m, 1H), 4.46-4.36 (mz, 1H), 4.30-4.20 (m, 1H), 3.13-3.02 (mz, 1H), 2.61-2.54 (m, 1H). | Column: 52-Welch Xtimate C18 150 × 30 mm, 5 μm; mobile phase: acetonitrile 40%-70%/0.225% formic acid in water |

-continued

| Compound No. | Structure | Analytical data | Separation conditions |
| --- | --- | --- | --- |
| I-490a | 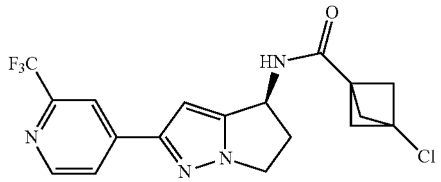 (S)-3-Chloro-N-(2-(2-(trifluoromethyl)pyridin-4-yl)-5,6-dihydro-4H-pyrrolo[1,2-b]pyrazol-4-yl)bicyclo[1.1.1]pentane-1-carboxamide | LCMS (ESI) m/z: 397.2 $[M + H]^+$. $^1H$ NMR (400 MHz, DMSO-$d_6$) δ 8.74 (d, J = 5.2 Hz, 1H), 8.55 (d, J = 8.0 Hz, 1H), 8.20 (s, 1H), 8.07 (d, J = 5.2 Hz, 1H), 6.95 (s, 1H), 5.41-5.22 (m, 1H), 4.40-4.23 (m, 1H), 4.21-4.09 (m, 1H), 3.01-2.89 (m, 1H), 2.36 (s, 6H), 2.34-2.29 (m, 1H). | Column: 58-Phenomenex Gemini NX C18 150 × 40 mm, 5 μm; mobile phase: acetonitrile 35%-75%/0.225% formic acid in water |
| I-226a | 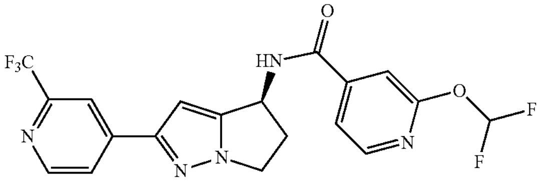 [SMILES: O=C(N[C@H]1CCn2nc(-c3ccnc(C(F)(F)F)c3)cc21)c1ccnc(OC(F)F)c1] (S)-2-(Difluoromethoxy)-N-(2-(2-(trifluoromethyl)pyridin-4-yl)-5,6-dihydro-4H-pyrrolo[1,2-b]pyrazol-4-yl)isonicotinamide | LCMS (ESI) m/z: 440.1 $[M + H]^+$. $^1H$ NMR (400 MHz, DMSO-$d_6$) δ 9.38 (d, J = 7.6 Hz, 1H), 8.75 (d, J = 5.2 Hz, 1H), 8.43 (d, J = 5.2 Hz, 1H), 8.20 (s, 1H), 8.07 (d, J = 5.2 Hz, 1H), 7.94-7.54 (m, 2H), 7.47 (s, 1H), 7.02 (s, 1H), 5.61-5.53 (m, 1H), 4.43-4.35 (m, 1H), 4.28-4.19 (m, 1H), 3.11-3.00(m, 1H), 2.60-2.54 (m, 1H). | Column: 58-Phenomenex Gemini NX C18 150 × 40 mm, 5 μm; mobile phase: acetonitrile 50%-80%/0.225% formic acid in water |
| I-583a | 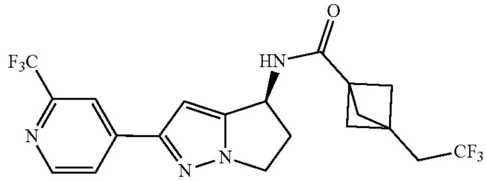 [SMILES: O=C(N[C@H]1CCn2nc(-c3ccnc(C(F)(F)F)c3)cc21)C12CC(CC(F)(F)F)(C1)C2] (S)-3-(2,2,2-Trifluoroethyl)-N-(2-(2-(trifluoromethyl)pyridin-4-yl)-5,6-dihydro-4H-pyrrolo[1,2-b]pyrazol-4-yl)bicyclo[1.1.1]pentane-1-carboxamide | LCMS (ESI) m/z: 445.2 $[M + H]^+$. $^1H$ NMR (400 MHz, DMSO-$d_6$) δ 8.74 (d, J = 5.2 Hz, 1H), 8.38 (d, J = 8.0 Hz, 1H), 8.20 (s, 1H), 8.07 (d, J = 4.8 Hz, 1H), 6.93 (s, 1H), 5.39-5.28 (m, 1H), 4.36-4.27 (m, 1H), 4.19-4.11 (m, 1H), 2.97-2.88 (m, 1H), 2.54 (s, 2H), 2.43-2.35 (m, 1H), 1.96 (s, 6H). | Column: 58-Phenomenex Gemini NX C18 150 × 40 mm, 5 μm; mobile phase: acetonitrile 55%-85%/0.225% formic acid in water |
| I-556a | 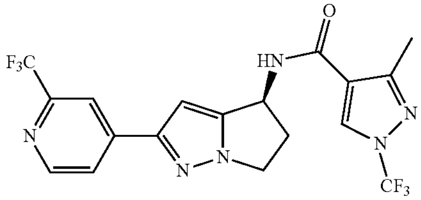 [SMILES: Cc1nn(C(F)(F)F)cc1C(=O)N[C@H]1CCn2nc(-c3ccnc(C(F)(F)F)c3)cc21] (S)-3-Fluoro-5-methoxy-N-(2-(2-(trifluoromethyl)pyridin-4-yl)-5,6-dihydro-4H-pyrrolo[1,2-b]pyrazol-4-yl)benzamide | LCMS (ESI) m/z: 445.1 $[M + H]^+$. $^1H$ NMR (400 MHz, DMSO-$d_6$) δ 8.84 (s, 1H), 8.81-8.72 (m, 2H), 8.20 (s, 1H), 8.07 (d, J = 4.4 Hz, 1H), 7.00 (s, 1H), 5.53-5.46 (m, 1H), 4.40-4.32 (m, 1H), 4.27-4.19 (m, 1H), 3.08-2.98 (m, 1H), 2.47-2.46 (m, 1H), 2.45 (s, 3H). | Prep-HPLC: Column: 57-Phenomenex Gemini NX C18 150 × 30 mm, phase: 5 μm; mobile phase: acetonitrile 20%-50%/0.225% formic acid in water. Prep-SFC: chiral SFC (DAICEL CHIRALCEL OJ (250 mm * 25 mm, 10 um); Supercritical $CO_2$/EtOH + 0.1% $NH_3$•$H_2O$ = 85/15; 80 mL/min) |
| I-484a | 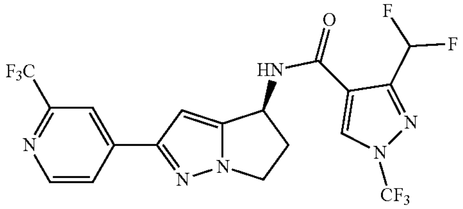 [SMILES: O=C(N[C@H]1CCn2nc(-c3ccnc(C(F)(F)F)c3)cc21)c1cn(C(F)(F)F)nc1C(F)F] (S)-3-(Difluoromethyl)-1-(trifluoromethyl)-N-(2-(2-(trifluoromethyl)pyridin-4-yl)-5,6-dihydro-4H-pyrrolo[1,2-b]pyrazol-4-yl)-1H-pyrazole-4-carboxamide | LCMS (ESI) m/z: 481.1 $[M + H]^+$. $^1H$ NMR (400 MHz, DMSO-$d_6$) δ 9.10 (d, J = 7.6 Hz, 1H), 9.07 (s, 1H), 8.75 (d, J = 5.2 Hz, 1H), 8.19 (s, 1H), 8.07 (dd, J = 0.8, 5.2 Hz, 1H), 7.45 (t, J = 13.2 Hz, 1H), 7.00 (s, 1H), 5.54-5.48 (m, 1H), 4.40-4.34 (m, 1H), 4.27-4.21 (m, 1H), 3.10-3.01 (m, 1H), 2.49-2.44 (m, 1H) | Column: 52-Welch Xtimate C18 150 × 30 mm, 5 μm; mobile phase: acetonitrile 45%-75%/0.225% formic acid in water. |

-continued

| Compound No. | Structure | Analytical data | Separation conditions |
|---|---|---|---|
| I-571a | 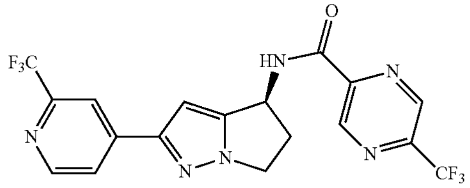 [SMILES: O=C(N[C@H]1CCn2nc(-c3ccnc(C(F)(F)F)c3)cc21)c1cnc(C(F)(F)F)cn1] (S)-5-(Trifluoromethyl)-N-(2-(2-(trifluoromethyl)pyridin-4-yl)-5,6-dihydro-4H-pyrrolo[1,2-b]pyrazol-4-yl)pyrazine-2-carboxamide | LCMS (ESI) m/z: 443.1 [M + H]$^+$. $^1$H NMR (400 MHz, DMSO-$d_6$) δ 9.82 (d, J = 8.8 Hz, 1H), 9.39 (s, 1H), 9.26 (s, 1H), 8.74 (d, J = 5.2 Hz, 1H), 8.19 (s, 1H), 8.06 (d, J = 5.2 Hz, 1H), 6.98 (s, 1H), 5.68-5.61 (m, 1H), 4.47-4.38 (m, 1H), 4.26-4.18 (m, 1H), 3.10-3.00 (m, 1H), 2.64-2.55 (m, 1H). | Column: 57-Phenomenex Gemini NX C18 150 × 30 mm, 5 μm; mobile phase: acetonitrile 45%-75%/0.225% formic acid in water. |
| I-572a | 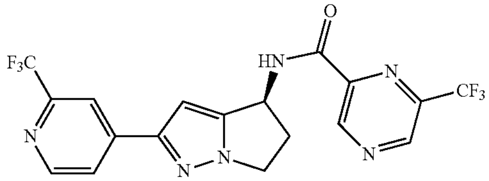 [SMILES: O=C(N[C@H]1CCn2nc(-c3ccnc(C(F)(F)F)c3)cc21)c1cncc(C(F)(F)F)n1] (S)-6-(Trifluoromethyl)-N-(2-(2-(trifluoromethyl)pyridin-4-yl)-5,6-dihydro-4H-pyrrolo[1,2-b]pyrazol-4-yl)pyrazine-2-carboxamide | LCMS (ESI) m/z: 443.1 [M + H]$^+$. $^1$H NMR (400 MHz, DMSO-$d_6$) δ 9.64 (d, J = 8.4 Hz, 1H), 9.51 (s, 1H), 9.42 (s, 1H), 8.74 (d, J = 5.2 Hz, 1H), 8.20 (s, 1H), 8.07 (d, J = 4.0 Hz, 1H), 7.01 (s, 1H), 5.70-5.63 (m, 1H), 4.46-4.39 (m, 1H), 4.27-4.17 (m, 1H), 3.12-3.00 (m, 1H), 2.67-2.60 (m, 1H). | Column: 58-Phenomenex Gemini NX C18 150 × 40 mm, 5 μm; mobile phase: acetonitrile 50%-80%/0.225% formic acid in water. |
| I-573a | 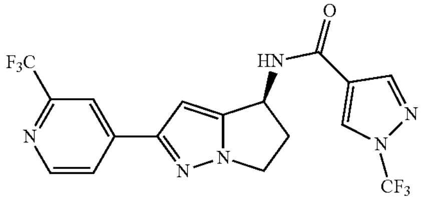 [SMILES: O=C(N[C@H]1CCn2nc(-c3ccnc(C(F)(F)F)c3)cc21)c1cnn(C(F)(F)F)c1] (S)-1-(Trifluoromethyl)-N-(2-(2-(trifluoromethyl)pyridin-4-yl)-5,6-dihydro-4H-pyrrolo[1,2-b]pyrazol-4-yl)-1H-pyrazole-4-carboxamide | LCMS (ESI) m/z: 431.1 [M + H]$^+$. $^1$H NMR (400 MHz, DMSO-$d_6$) δ 9.02-8.93 (m, 2H), 8.75 (d, J = 5.2 Hz, 1H), 8.33 (s, 1H), 8.20 (s, 1H), 8.07 (d, J = 4.8 Hz, 1H), 7.01 (s, 1H), 5.58-5.50 (m, 1H), 4.42-4.33 (m, 1H), 4.27-4.19 (m, 1H), 3.10-3.00 (m, 1H), 2.49-2.42 (m, 1H). | Column: 58-Phenomenex Gemini NX C18 150 × 40 mm, 5 μm; mobile phase: acetonitrile 45%-75%/0.225% formic acid in water. |
| I-567a | 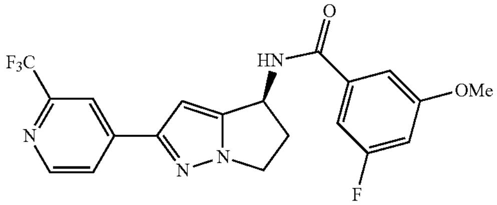 [SMILES: COc1cc(F)cc(C(=O)N[C@H]2CCn3nc(-c4ccnc(C(F)(F)F)c4)cc32)c1] (S)-3-Fluoro-5-methoxy-N-(2-(2-(trifluoromethyl)pyridin-4-yl)-5,6-dihydro-4H-pyrrolo[1,2-b]pyrazol-4-yl)benzamide | LCMS (ESI) m/z: 421.2 [M + H]$^+$. $^1$H NMR (400 MHz, DMSO-$d_6$) δ 9.10 (d, J = 7.6 Hz, 1H), 8.74 (d, J = 4.8 Hz, 1H), 8.20 (s, 1H), 8.07 (d, J = 4.8 Hz, 1H), 7.31 (s, 1H), 7.30-7.26 (m, 1H), 7.06-7.02 (m, 1H), 7.00 (s, 1H), 5.59-5.53 (m, 1H), 4.42-4.36 (m, 1H), 4.26-4.19 (m, 1H), 3.82 (s, 3H), 3.10-2.99 (m, 1H), 2.60-2.52 (m, 1H). | Column: 20-Welch Xtimate C18 250 × 50 mm, 5 μm; mobile phase: acetonitrile 60%-90%/0.225% formic acid in water. |
| I-568a | 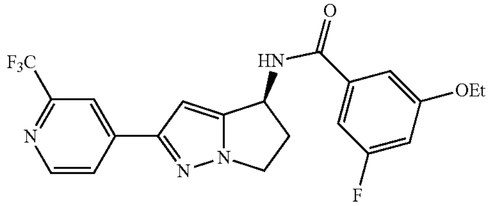 [SMILES: CCOc1cc(F)cc(C(=O)N[C@H]2CCn3nc(-c4ccnc(C(F)(F)F)c4)cc32)c1] (S)-3-Ethoxy-5-fluoro-N-(2-(2-(trifluoromethyl)pyridin-4-yl)-5,6-dihydro-4H-pyrrolo[1,2-b]pyrazol-4-yl)benzamide | LCMS (ESI) m/z: 435.2 [M + H]$^+$. $^1$H NMR (400 MHz, DMSO-$d_6$) δ 9.08 (d, J = 7.6 Hz, 1H), 8.74 (d, J = 4.8 Hz, 1H), 8.20 (s, 1H), 8.07 (d, J = 4.8 Hz, 1H), 7.30 (s, 1H), 7.26 (d, J = 9.2 Hz, 1H), 7.05-6.98 (m, 2H), 5.60-5.52 (m, 1H), 4.43-4.35 (m, 1H), 4.27-4.19 (m, 1H), 4.08 (q, J = 7.2 Hz, 2H), 3.08-2.99 (m, 1H), 2.59-2.52 (m, 1H), 1.33 (t, J = 7.2 Hz, 3H). | Column: 57-Phenomenex Gemini NX C18 150 × 30 mm, 5 μm; mobile phase: acetonitrile 20%-50%/0.225% formic acid in water. |

-continued

| Compound No. | Structure | Analytical data | Separation conditions |
| --- | --- | --- | --- |
| I-569a | 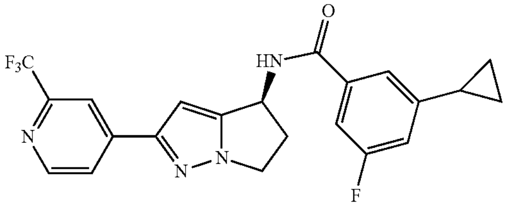 [SMILES: O=C(N[C@H]1CCn2nc(-c3ccnc(C(F)(F)F)c3)cc21)c1cc(F)cc(C2CC2)c1] (S)-3-Cyclopropyl-5-fluoro-N-(2-(2-(trifluoromethyl)pyridin-4-yl)-5,6-dihydro-4H-pyrrolo[1,2-b]pyrazol-4-yl)benzamide | LCMS (ESI) m/z: 431.2 [M + H]$^+$. $^1$H NMR (400 MHz, DMSO-$d_6$) δ 9.07 (d, J = 8.0 Hz, 1H), 8.74 (d, J = 5.2 Hz, 1H), 8.20 (s, 1H), 8.07 (d, J = 5.2 Hz, 1H), 7.46-7.40 (m, 2H), 7.13 (d, J = 10.0 Hz, 1H), 7.00 (s, 1H), 5.59-5.54 (m, 1H), 4.42-4.36 (m, 1H), 4.26-4.19 (m, 1H), 3.10-2.98 (m, 1H), 2.58-2.52 (m, 1H), 2.05-1.96 (m, 1H), 1.04-0.97 (m, 2H), 0.79-0.72 (m, 2H). | Column: 52-Welch Xtimate C18 150 × 30 mm, 5 μm; mobile phase: acetonitrile 60%-90%/0.225% formic acid in water. |
| I-570a | 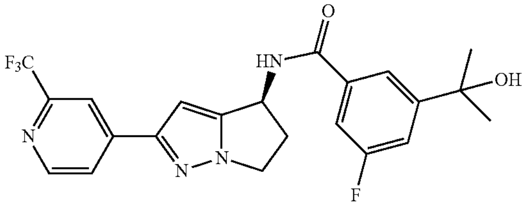 [SMILES: CC(C)(O)c1cc(F)cc(C(=O)N[C@H]2CCn3nc(-c4ccnc(C(F)(F)F)c4)cc32)c1] (S)-3-Fluoro-5-(2-hydroxypropan-2-yl)-N-(2-(2-(trifluoromethyl)pyridin-4-yl)-5,6-dihydro-4H-pyrrolo[1,2-b]pyrazol-4-yl)benzamide | LCMS (ESI) m/z: 449.2 [M + H]$^+$. $^1$H NMR (400 MHz, DMSO-$d_6$) δ 9.13 (d, J = 7.6 Hz, 1H), 8.74 (d, J = 5.2 Hz, 1H), 8.20 (s, 1H), 8.07 (d, J = 4.8 Hz, 1H), 7.85 (s, 1H), 7.53-7.50 (m, 1H), 7.48-7.41 (m, 1H), 7.01 (s, 1H), 5.64-5.51 (m, 1H), 4.43-4.36 (m, 1H), 4.26-4.20 (m, 1H), 3.09-3.00 (m, 1H), 2.60-2.53 (m, 1H), 1.44 (s, 6H). | Column: 20-Welch Xtimate C18 250 × 50 mm, 5 μm; mobile phase: acetonitrile 60%-90%/0.225% formic acid in water. |
| I-494a | 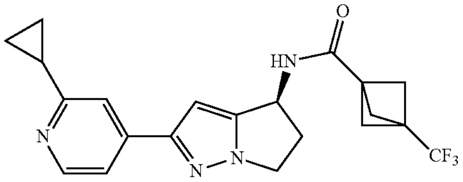 [SMILES: O=C(N[C@H]1CCn2nc(-c3ccnc(C4CC4)c3)cc21)C12CC(C(F)(F)F)(C1)C2] (S)-N-(2-(2-Cyclopropylpyridin-4-yl)-5,6-dihydro-4H-pyrrolo[1,2-b]pyrazol-4-yl)-3-(trifluoromethyl)bicyclo[1.1.1]pentane-1-carboxamide | LCMS (ESI) m/z: 403.1 [M + H]$^+$. $^1$H NMR (400 MHz, DMSO-$d_6$) δ 8.61 (d, J = 8.0 Hz, 1H), 8.35 (d, J = 5.2 Hz, 1H), 7.66 (s, 1H), 7.47 (dd, J = 1.6, 5.2 Hz, 1H), 6.72 (s, 1H), 5.54-5.08 (m, 1H), 4.34-4.24 (m, 1H), 4.17-4.07 (m, 1H), 2.99-2.89 (m, 1H), 2.39-2.31 (m, 1H), 2.17 (s, 6H), 2.13-2.07 (m, 1H), 0.97-0.87 (m, 4H). | Column: 58-Phenomenex Gemini NX C18 150 × 40 mm, 5 μm; mobile phase: acetonitrile 20%-50%/0.225% formic acid in water. |
| I-555a | 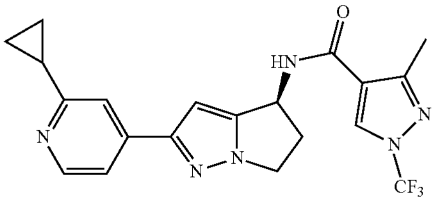 [SMILES: Cc1nn(C(F)(F)F)cc1C(=O)N[C@H]1CCn2nc(-c3ccnc(C4CC4)c3)cc21] (S)-N-(2-(2-Cyclopropylpyridin-4-yl)-5,6-dihydro-4H-pyrrolo[1,2-b]pyrazol-4-yl)-3-methyl-1-(trifluoromethyl)-1H-pyrazole-4-carboxamide | LCMS (ESI) m/z: 417.2 [M + H]$^+$. $^1$H NMR (400 MHz, DMSO-$d_6$) δ 8.84 (s, 1H), 8.77 (d, J = 7.6 Hz, 1H), 8.36 (d, J = 5.2 Hz, 1H), 7.66 (s, 1H), 7.48 (dd, J = 1.2, 4.8 Hz, 1H), 6.77 (s, 1H), 5.52-5.45 (m, 1H), 4.37-4.28 (m, 1H), 4.23-4.15 (m, 1H), 3.07-2.97 (m, 1H), 2.45 (s, 3H), 2.44-2.39 (m, 1H), 2.15-2.07 (m, 1H), 0.96-0.90 (m, 4H). | Column: 58-Phenomenex Gemini NX C18 150 × 40 mm, 5 μm; mobile phase: acetonitrile 20%-50%/0.225% formic acid in water. |
| I-541a | 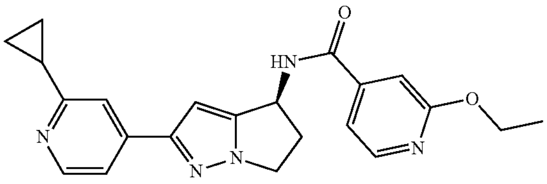 [SMILES: CCOc1cc(C(=O)N[C@H]2CCn3nc(-c4ccnc(C5CC5)c4)cc32)ccn1] (S)-N-(2-(2-Cyclopropylpyridin-4-yl)-5,6-dihydro-4H-pyrrolo[1,2-b]pyrazol-4-yl)-2-ethoxyisonicotinamide | LCMS (ESI) m/z: 390.2 [M + H]$^+$. $^1$H NMR (400 MHz, DMSO-$d_6$) δ 9.25 (d, J = 7.6 Hz, 1H), 8.61 (d, J = 6.4 Hz, 1H), 8.29 (d, J = 5.2 Hz, 1H), 8.09 (dd, J = 1.6, 6.4 Hz, 1H), 7.88 (d, J = 1.2 Hz, 1H), 7.35 (dd, J = 1.2, 5.2 Hz, 1H), 7.19 (s, 2H), 5.60-5.50 (m, 1H), 4.45-4.39 (m, 1H), 4.36-4.30 (m, 2H), 4.29-4.24 (m, 1H), 3.08-3.02 (m, 1H), 2.64-2.56 (m, 1H), 2.35-2.30 (m, 1H), 1.38-1.33 (m, 2H), 1.33-1.29 (m, 3H), 1.27-1.23 (m, 2H). | Column: 58-Phenomenex Gemini NX C18 150 × 40 mm, 5 μm; mobile phase: acetonitrile 20%-50%/0.225% formic acid in water. |

-continued

| Compound No. | Structure | Analytical data | Separation conditions |
|---|---|---|---|
| I-542a | 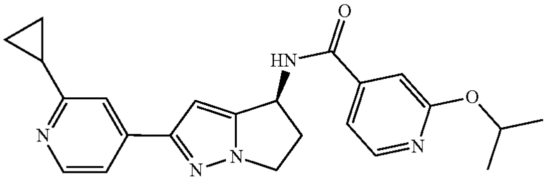 [SMILES: CC(C)Oc1cc(C(=O)N[C@H]2CCn3nc(-c4ccnc(C5CC5)c4)cc32)ccn1] (S)-N-(2-(2-Cyclopropylpyridin-4-yl)-5,6-dihydro-4H-pyrrolo[1,2-b]pyrazol-4-yl)-2-isopropoxyisonicotinamide | LCMS (ESI) m/z: 404.3 $[M+H]^+$. $^1H$ NMR (400 MHz, DMSO-$d_6$) δ 9.22 (d, J = 7.6 Hz, 1H), 8.61 (d, J = 6.4 Hz, 1H), 8.29 (d, J = 5.2 Hz, 1H), 8.09 (d, J = 6.4 Hz, 1H), 7.88 (d, J = 1.2 Hz, 1H), 7.32 (dd, J = 1.2, 5.2 Hz, 1H), 7.19 (s, 1H), 7.15 (s, 1H), 5.60-5.41 (m, 1H), 5.32-5.20 (m, 1H), 4.48-4.37 (m, 1H), 4.30-4.23 (m, 1H), 3.09-3.00 (m, 1H), 2.64-2.55 (m, 1H), 2.35-2.30 (m, 1H), 1.38-1.31 (m, 2H), 1.29 (dd, J = 1.6, 6.0 Hz, 6H), 1.28-1.23 (m, 2H). | Column: 58-Phenomenex Gemini NX C18 150 × 40 mm, 5 μm; mobile phase: acetonitrile 30%-60%/0.225% formic acid in water. |
| I-543a | 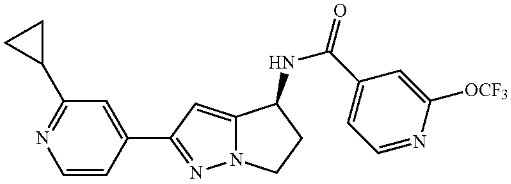 [SMILES: O=C(N[C@H]1CCn2nc(-c3ccnc(C4CC4)c3)cc21)c1ccnc(OC(F)(F)F)c1] (S)-N-(2-(2-Cyclopropylpyridin-4-yl)-5,6-dihydro-4H-pyrrolo[1,2-b]pyrazol-4-yl)-2-(trifluoromethoxy)isonicotinamide | LCMS (ESI) m/z: 430.2 $[M+H]^+$. $^1H$ NMR (400 MHz, DMSO-$d_6$) δ 9.43 (d, J = 7.6 Hz, 1H), 8.54 (d, J = 5.2 Hz, 1H), 8.36 (d, J = 5.2 Hz, 1H), 7.84 (dd, J = 1.2, 5.2 Hz, 1H), 7.66 (s, 2H), 7.48 (dd, J = 1.6, 5.2 Hz, 1H), 6.80 (s, 1H), 5.61-5.47 (m, 1H), 4.39-4.32 (m, 1H), 4.24-4.17 (m, 1H), 3.08-3.01 (m, 1H), 2.58-2.54 (m, 1H), 2.14-2.07 (m, 1H), 0.97-0.91 (m, 4H). | Column: 58-Phenomenex Gemini NX C18 150 × 40 mm, 5 μm; mobile phase: acetonitrile 20%-50%/0.225% formic acid in water. |
| I-584a | 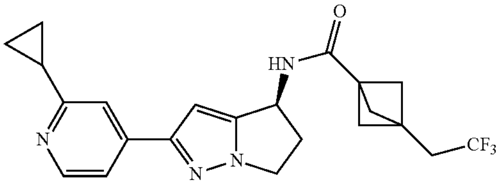 [SMILES: O=C(N[C@H]1CCn2nc(-c3ccnc(C4CC4)c3)cc21)C12CC(CC(F)(F)F)(C1)C2] (S)-N-(2-(2-Cyclopropylpyridin-4-yl)-5,6-dihydro-4H-pyrrolo[1,2-b]pyrazol-4-yl)-3-(2,2,2-trifluoroethyl)bicyclo[1.1.1]pentane-1-carboxamide | LCMS (ESI) m/z: 445.2 $[M+H]^+$. $^1H$ NMR (400 MHz, DMSO-$d_6$) δ 8.40-8.32 (m, 2H), 7.67 (s, 1H), 7.50 (d, J = 4.8 Hz, 1H), 6.72 (s, 1H), 5.36-5.27 (m, 1H), 4.32-4.24 (m, 1H), 4.15-4.08 (m, 1H), 2.96-2.87 (m, 1H), 2.58-2.52 (m, 2H), 2.38-2.32 (m, 1H), 2.15-2.09 (m, 1H), 1.95 (s, 6H), 0.98-0.91 (m, 4H). | Column: 58-Phenomenex Gemini NX C18 150 × 40 mm, 5 μm; mobile phase: acetonitrile 20%-50%/0.225% formic acid in water. |
| I-492a | 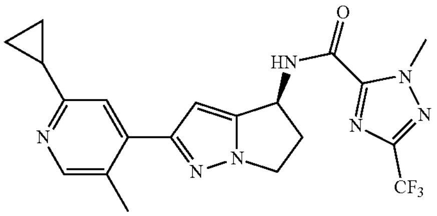 [SMILES: Cc1cnc(C2CC2)cc1-c1cc2n(n1)CC[C@@H]2NC(=O)c1nc(C(F)(F)F)nn1C] (S)-N-(2-(2-Cyclopropyl-5-methylpyridin-4-yl)-5,6-dihydro-4H-pyrrolo[1,2-b]pyrazol-4-yl)-1-methyl-3-(trifluoromethyl)-1H-1,2,4-triazole-5-carboxamide | LCMS (ESI) m/z: 432.3 $[M+H]^+$. $^1H$ NMR (400 MHz, DMSO-$d_6$) δ 9.78 (d, J = 8.0 Hz, 1H), 8.24 (s, 1H), 7.49 (s, 1H), 6.60 (s, 1H), 5.57-5.55 (m, 1H), 4.44-4.34 (m, 1H), 4.25 (s, 3H), 4.16-4.18 (m, 1H), 3.08-2.96 (m, 1H), 2.67-2.58 (m, 1H), 2.41 (s, 3H), 2.12-2.03 (m, 1H), 0.91-0.85 (m, 4H). | Column: 50-Welch Xtimate C18 150 × 40 mm, 5 μm; mobile phase: acetonitrile 15%-45%/0.225% formic acid in water. |
| I-537a | 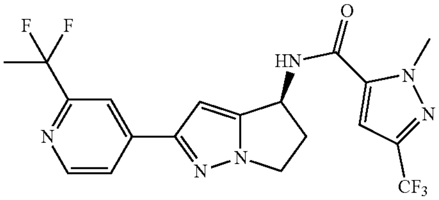 (S)-N-(2-(2-(1,1-Difluoroethyl)pyridin-4-yl)-5,6-dihydro-4H-pyrrolo[1,2-b]pyrazol-4-yl)-1-methyl-3-(trifluoromethyl)-1H-pyrazole-5-carboxamide | LCMS (ESI) m/z: 418.2 $[M+H]^+$. $^1H$ NMR (400 MHz, DMSO-$d_6$) δ 9.22 (d, J = 7.6 Hz, 1H), 8.64 (d, J = 5.2 Hz, 1H), 8.03 (s, 1H), 7.89 (d, J = 4.8 Hz, 1H), 7.34 (s, 1H), 6.93 (s, 1H), 5.60-5.45 (m, 1H), 4.40-4.32 (m, 1H), 4.27-4.20 (m, 1H), 4.18 (s, 3H), 3.09-3.00 (m, 1H), 2.57-2.52 (m, 1H), 2.01 (t, J = 19.2 Hz, 3H). | Column: 58-Phenomenex Gemini NX C18 150 × 40 mm, 5 μm; mobile phase: acetonitrile 50%-80%/0.225% formic acid in water. |

-continued

| Compound No. | Structure | Analytical data | Separation conditions |
|---|---|---|---|
| I-538a | 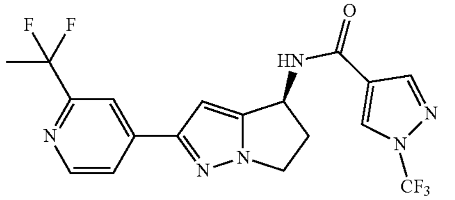 [SMILES: CC(F)(F)c1cc(-c2cc3n(n2)CC[C@@H]3NC(=O)c2cnn(C(F)(F)F)c2)ccn1] (S)-N-(2-(2-(1,1-Difluoroethyl)pyridin-4-yl)-5,6-dihydro-4H-pyrrolo[1,2-b]pyrazol-4-yl)-1-(trifluoromethyl)-1H-pyrazole-4-carboxamide | LCMS (ESI) m/z: 427.2 [M + H]$^+$. $^1$H NMR (400 MHz, DMSO-d$_6$) δ 8.97 (d, J = 8.0 Hz, 1H), 8.96 (s, 1H), 8.64 (d, J = 5.2 Hz, 1H), 8.33 (s, 1H), 8.03 (s, 1H), 7.89 (dd, J = 1.2, 5.2 Hz, 1H), 6.92 (s, 1H), 5.63-5.44 (m, 1H), 4.42-4.31 (m, 1H), 4.28-4.16 (m, 1H), 3.11-2.99 (m, 1H), 2.48-2.43 (m, 1H), 2.01 (t, J = 19.2 Hz, 3H). | Column: 58-Phenomenex Gemini NX C18 150 × 40 mm, 5 μm; mobile phase: acetonitrile 40%-70%/0.225% formic acid in water. |
| I-559a | 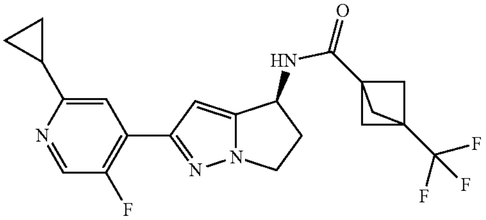 [SMILES: O=C(N[C@H]1CCn2nc(-c3cc(C4CC4)ncc3F)cc21)C12CC(C(F)(F)F)(C1)C2] (S)-N-(2-(2-Cyclopropyl-5-fluoropyridin-4-yl)-5,6-dihydro-4H-pyrrolo[1,2-b]pyrazol-4-yl)-3-(trifluoromethyl)bicyclo[1.1.1]pentane-1-carboxamide | LCMS (ESI) m/z: 421.2 [M + H]$^+$. $^1$H NMR (400 MHz, DMSO-d$_6$) δ 8.59 (d, J = 7.6 Hz, 1H), 8.41 (d, J = 2.8 Hz, 1H), 7.79 (d, J = 6.0 Hz, 1H), 6.56 (d, J = 3.6 Hz, 1H), 5.37-5.29 (m, 1H), 4.37-4.29 (m, 1H), 4.22-4.13 (m, 1H), 3.01-2.91 (m, 1H), 2.43-2.35 (m, 1H), 2.18 (s, 6H), 0.97-0.91 (m, 2H), 0.91-0.85 (m, 2H). | Column: 58-Phenomenex Gemini NX C18 150 × 40 mm, 5 μm; mobile phase: acetonitrile 50%-80%/0.225% formic acid in water |
| I-560a | 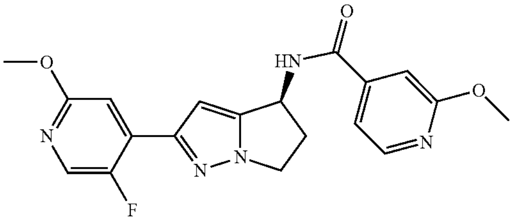 (S)-N-(2-(5-Fluoro-2-methoxypyridin-4-yl)-5,6-dihydro-4H-pyrrolo[1,2-b]pyrazol-4-yl)-2-methoxyisonicotinamide | LCMS (ESI) m/z: 384.2 [M + H]$^+$. $^1$H NMR (400 MHz, DMSO-d$_6$) δ 9.21 (d, J = 7.6 Hz, 1H), 8.30 (d, J = 5.2 Hz, 1H), 8.20 (d, J = 2.8 Hz, 1H), 7.38 (d, J = 5.2 Hz, 1H), 7.26-7.19 (m, 2H), 6.63 (d, J = 3.6 Hz, 1H), 5.60-5.48 (m, 1H), 4.41-4.36 (m, 1H), 4.25-4.19 (m, 1H), 3.89 (s, 3H), 3.85 (s, 3H), 3.12-2.99 (m, 1H), 2.59-2.54 (m, 1H). 2.58-2.53 (m, 1H) | Column: 40-WePure Biotech XP tC18 150 × 30 mm, 7 μm; mobile phase: acetonitrile 35%-65%/0.225% formic acid in water. |
| I-574a | 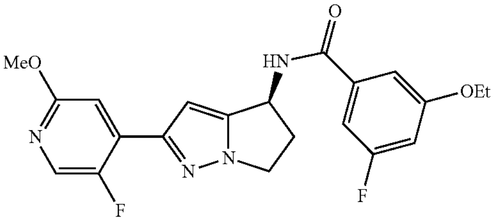 [SMILES: CCOc1cc(F)cc(C(=O)N[C@H]2CCn3nc(-c4cc(OC)ncc4F)cc32)c1] (S)-3-Ethoxy-5-fluoro-N-(2-(5-fluoro-2-methoxypyridin-4-yl)-5,6-dihydro-4H-pyrrolo[1,2-b]pyrazol-4-yl)benzamide | LCMS (ESI) m/z: 415.2 [M + H]$^+$. $^1$H NMR (400 MHz, DMSO-d$_6$) δ 9.05 (d, J = 7.6 Hz, 1H), 8.21 (d, J = 2.8 Hz, 1H), 7.30 (s, 1H), 7.28-7.21 (m, 2H), 7.04-6.98 (m, 1H), 6.62 (d, J = 3.2 Hz, 1H), 5.57-5.49 (m, 1H), 4.42-4.34 (m, 1H), 4.26-4.18 (m, 1H), 4.08 (q, J = 6.8 Hz, 2H), 3.85 (s, 3H), 3.09-2.99 (m, 1H), 2.58-2.53 (m, 1H), 1.33 (t, J = 7.2 Hz, 3H). | Column: 50-Welch Xtimate C18 150 × 40 mm, 5 μm; mobile phase: acetonitrile 50%-80%/0.225% formic acid in water. |
| I-575a | 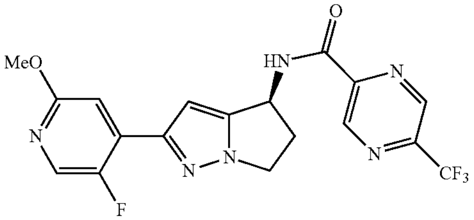 [SMILES: COc1cc(-c2cc3n(n2)CC[C@@H]3NC(=O)c2cnc(C(F)(F)F)cn2)c(F)cn1] (S)-N-(2-(5-Fluoro-2-methoxypyridin-4-yl)-5,6-dihydro-4H-pyrrolo[1,2-b]pyrazol-4-yl)-5-(trifluoromethyl)pyrazine-2-carboxamide | LCMS (ESI) m/z: 423.3 [M + H]$^+$. $^1$H NMR (400 MHz, DMSO-d$_6$) δ 9.79 (d, J = 8.0 Hz, 1H), 9.39 (s, 1H), 9.25 (s, 1H), 8.20 (d, J = 2.8 Hz, 1H), 7.22 (d, J = 5.2 Hz, 1H), 6.59 (d, J = 3.6 Hz, 1H), 5.66-5.60 (m, 1H), 4.45-4.39 (m, 1H), 4.25-4.19 (m, 1H), 3.84 (s, 3H), 3.09-3.01 (m, 1H), 2.68-2.63 (m, 1H). | Column: 58-Phenomenex Gemini NX C18 150 × 40 mm, 5 μm; mobile phase: acetonitrile 40%-70%/0.225% formic acid in water. |

-continued

| Compound No. | Structure | Analytical data | Separation conditions |
|---|---|---|---|
| I-576a | 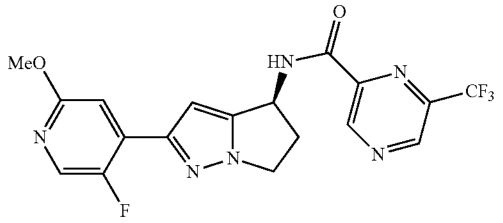 [SMILES: COc1cc(-c2cc3n(n2)CC[C@@H]3NC(=O)c2cncc(C(F)(F)F)n2)c(F)cn1] (S)-N-(2-(5-Fluoro-2-methoxypyridin-4-yl)-5,6-dihydro-4H-pyrrolo[1,2-b]pyrazol-4-yl)-6-(trifluoromethyl)pyrazine-2-carboxamide | LCMS (ESI) m/z: 423.2 $[M + H]^+$. $^1H$ NMR (400 MHz, DMSO-$d_6$) δ 9.61 (d, J = 8.4 Hz, 1H), 9.50 (s, 1H), 9.41 (s, 1H), 8.21 (d, J = 2.8 Hz, 1H), 7.22 (d, J = 5.2 Hz, 1H), 6.62 (d, J = 3.6 Hz, 1H), 5.69-5.63 (m, 1H), 4.45-4.39 (m, 1H), 4.25-4.19 (m, 1H), 3.85 (s, 3H), 3.09-3.02 (m, 1H), 2.66-2.58 (m, 1H). | Column: 58-Phenomenex Gemini NX C18 150 × 40 mm, 5 μm; mobile phase: acetonitrile 48%-78%/0.225% formic acid in water. |
| I-577a | 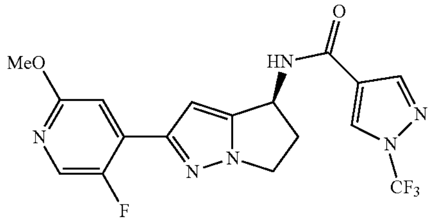 [SMILES: COc1cc(-c2cc3n(n2)CC[C@@H]3NC(=O)c2cnn(C(F)(F)F)c2)c(F)cn1] (S)-N-(2-(5-Fluoro-2-methoxypyridin-4-yl)-5,6-dihydro-4H-pyrrolo[1,2-b]pyrazol-4-yl)-1-(trifluoromethyl)-1H-pyrazole-4-carboxamide | LCMS (ESI) m/z: 411.1 $[M + H]^+$. $^1H$ NMR (400 MHz, DMSO-$d_6$) δ 8.99-8.94 (m, 2H), 8.32 (s, 1H), 8.21 (d, J = 2.8 Hz, 1H), 7.22 (d, J = 5.2 Hz, 1H), 6.63 (d, J = 3.6 Hz, 1H), 5.53-5.47 (m, 1H), 4.41-4.37 (m, 1H), 4.26-4.19 (m, 1H), 3.85 (s, 3H), 3.09-3.00 (m, 1H), 2.49-2.41 (m, 1H). | Column: 58-Phenomenex Gemini NX C18 150 × 40 mm, 5 μm; mobile phase: acetonitrile 43%-73%/0.225% formic acid in water. |
| I-172a | 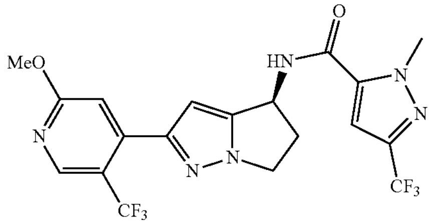 [SMILES: COc1cc(-c2cc3n(n2)CC[C@@H]3NC(=O)c2cc(C(F)(F)F)nn2C)c(C(F)(F)F)cn1] (S)-N-(2-(2-Methoxy-5-(trifluoromethyl)pyridin-4-yl)-5,6-dihydro-4H-pyrrolo[1,2-b]pyrazol-4-yl)-1-methyl-3-(trifluoromethyl)-1H-pyrazole-5-carboxamide | LCMS (ESI) m/z: 475.2 $[M + H]^+$. $^1H$ NMR (400 MHz, DMSO-$d_6$) δ 9.22 (d, J = 7.6 Hz, 1H), 8.62 (s, 1H), 7.34 (s, 1H), 7.11 (s, 1H), 6.52 (s, 1H), 5.54-5.50 (m, 1H), 4.37 (m, 1H), 4.26-4.19 (m, 1H), 4.16 (s, 3H), 3.95 (s, 3H), 3.10-3.00 (m, 1H), 2.58-2.52 (m, 1H). | Column: 50-Welch Xtimate C18 150 × 40 mm, 5 μm; mobile phase: acetonitrile 45%-75%/0.225% formic acid in water. |
| I-578a | 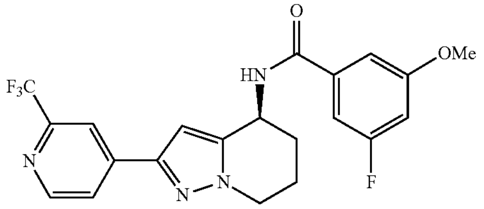 (S)-3-Fluoro-5-methoxy-N-(2-(2-(trifluoromethyl)pyridin-4-yl)-4,5,6,7-tetrahydropyrazolo[1,5-a]pyridin-4-yl)benzamide | LCMS (ESI) m/z: 435.2 $[M + H]^+$. $^1H$ NMR (400 MHz, DMSO-$d_6$) δ 8.75 (d, J = 5.2 Hz, 1H), 8.52 (d, J = 8.4 Hz, 1H), 8.19 (s, 1H), 8.08 (dd, J = 1.2, 5.2 Hz, 1H), 6.91 (s, 1H), 5.16-5.09 (m, 1H), 4.26-4.18 (m, 1H), 4.15-4.07 (m, 1H), 2.21 (s, 6H), 2.18-2.12 (m, 1H), 2.01 (td, J = 5.6, 11.2 Hz, 2H), 1.77-1.66 (m, 1H). | Column: 58-Phenomenex Gemini NX C18 150 × 40 mm, 5 μm; mobile phase: acetonitrile 55%-85%/0.225% formic acid in water. |

-continued

| Compound No. | Structure | Analytical data | Separation conditions |
| --- | --- | --- | --- |
| I-497a | 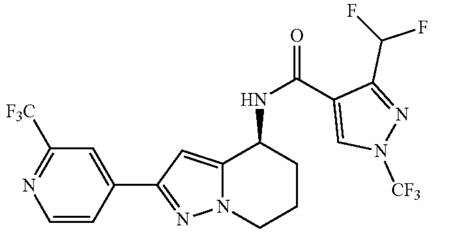 (S)-3-(Difluoromethyl)-1-(trifluoromethyl)-N-(2-(2-(trifluoromethyl)pyridin-4-yl)-4,5,6,7-tetrahydropyrazolo[1,5-a]pyridin-4-yl)-1H-pyrazole-4-carboxamide | LCMS (ESI) m/z: 495.2 [M + H]$^+$. $^1$H NMR (400 MHz, DMSO-$d_6$) δ 9.11 (s, 1H), 9.04 (d, J = 8.4 Hz, 1H), 8.75 (d, J = 4.8 Hz, 1H), 8.18 (s, 1H), 8.05 (d, J = 4.8 Hz, 1H), 7.47 (t, J = 13.2 Hz, 1H), 7.02 (s, 1H), 5.35-5.27 (m, 1H), 4.28-4.13 (m, 2H), 2.25-2.04 (m, 3H), 1.86-1.75 (m, 1H). | Column: 52-Welch Xtimate C18 150 × 30 mm, 5 μm; mobile phase: acetonitrile 45%-75%/0.225% formic acid in water. |
| I-579a | 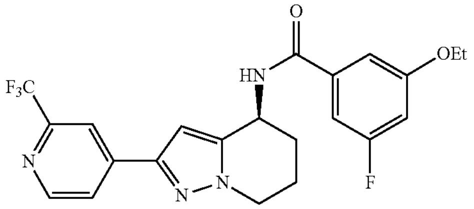 (S)-3-Fluoro-5-methoxy-N-(2-(2-(trifluoromethyl)pyridin-4-yl)-4,5,6,7-tetrahydropyrazolo[1,5-a]pyridin-4-yl)benzamide | LCMS (ESI) m/z: 449.1 [M + H]$^+$. $^1$H NMR (400 MHz, DMSO-$d_6$) δ 9.01 (d, J = 8.0 Hz, 1H), 8.73 (d, J = 5.2 Hz, 1H), 8.21 (s, 1H), 8.08 (d, J = 5.2 Hz, 1H), 7.34 (s, 1H), 7.29 (d, J = 9.6 Hz, 1H), 7.04-7.00 (m, 2H), 5.40-5.31 (m, 1H), 4.29-4.22 (m, 1H), 4.18-4.12 (m, 1H), 4.10 (q, J = 7.2 Hz, 2H), (m, 2H), 2.26-2.19 (m, 1H), 2.16-2.14 (m, 2H), 1.90-1.80 (m, 1H), 1.33 (t, J = 7.2 Hz, 3H). | Column: 58-Phenomenex Gemini NX C18 150 × 40 mm, 5 μm; mobile phase: acetonitrile 55%-85%/0.225% formic acid in water. |
| I-580a | 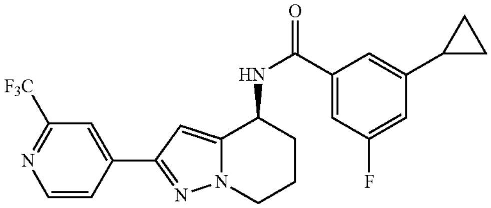 [SMILES: O=C(N[C@H]1CCCn2nc(-c3ccnc(C(F)(F)F)c3)cc21)c1cc(F)cc(C2CC2)c1] (S)-3-Cyclopropyl-5-fluoro-N-(2-(2-(trifluoromethyl)pyridin-4-yl)-4,5,6,7-tetrahydropyrazolo[1,5-a]pyridin-4-yl)benzamide | LCMS (ESI) m/z: 445.2 [M + H]$^+$. $^1$H NMR (400 MHz, DMSO-$d_6$) δ 9.01 (d, J = 8.0 Hz, 1H), 8.73 (d, J = 5.2 Hz, 1H), 8.21 (s, 1H), 8.09 (d, J = 5.2 Hz, 1H), 7.52-7.40 (m, 2H), 7.16-7.10 (m, 1H), 7.03 (s, 1H), 5.39-5.31 (m, 1H), 4.31-4.22 (m, 1H), 4.18-4.09 (m, 1H), 2.26-2.18 (m, 1H), 2.17-2.06 (m, 2H), 2.04-1.97 (m, 1H), 1.90-1.80 (m, 1H), 1.05-0.97 (m, 2H), 0.82-0.73 (m, 2H). | Column: 58-Phenomenex Gemini NX C18 150 × 40 mm, 5 μm; mobile phase: acetonitrile 60%-90%/0.225% formic acid in water. |
| I-581a | 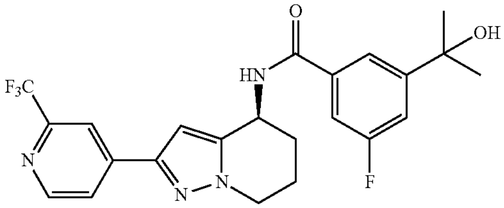 [SMILES: CC(C)(O)c1cc(F)cc(C(=O)N[C@H]2CCCn3nc(-c4ccnc(C(F)(F)F)c4)cc32)c1] (S)-3-Cyclopropyl-5-fluoro-N-(2-(2-(trifluoromethyl)pyridin-4-yl)-4,5,6,7-tetrahydropyrazolo[1,5-a]pyridin-4-yl)benzamide | LCMS (ESI) m/z: 463.1 [M + H]$^+$. $^1$H NMR (400 MHz, DMSO-$d_6$) δ 9.05 (d, J = 8.0 Hz, 1H), 8.73 (d, J = 5.2 Hz, 1H), 8.21 (s, 1H), 8.08 (d, J = 4.8 Hz, 1H), 7.88 (s, 1H), 7.57 (d, J = 9.2 Hz, 1H), 7.45 (d, J = 10.0 Hz, 1H), 7.03 (s, 1H), 5.44-5.29 (m, 1H), 4.33-4.22 (m, 1H), 4.19-4.08 (m, 1H), 2.30-2.04 (m, 3H), 1.94-1.82 (m, 1H), 1.45 (s, 6H). | Column: 58-Phenomenex Gemini NX C18 150 × 40 mm, 5 μm; mobile phase: acetonitrile 40%-70%/0.225% formic acid in water. |
| I-582a | 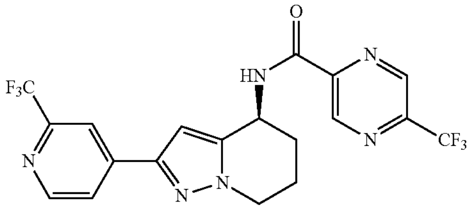 [SMILES: O=C(N[C@H]1CCCn2nc(-c3ccnc(C(F)(F)F)c3)cc21)c1cnc(C(F)(F)F)cn1] (S)-5-(Trifluoromethyl)-N-(2-(2-(trifluoromethyl)pyridin-4-yl)-4,5,6,7-tetrahydropyrazolo[1,5-a]pyridin-4-yl)pyrazine-2-carboxamide | LCMS (ESI) m/z: 457.1 [M + H]$^+$. $^1$H NMR (400 MHz, DMSO-$d_6$) δ 9.63 (d, J = 8.8 Hz, 1H), 9.44 (s, 1H), 9.29 (s, 1H), 8.72 (d, J = 5.2 Hz, 1H), 8.16 (s, 1H), 8.04 (d, J = 5.2 Hz, 1H), 6.98 (s, 1H), 5.49-5.33 (m, 1H), 4.32-4.22 (m, 1H), 4.15-4.05 (m, 1H), 2.28-2.21 (m, 1H), 2.16-2.04 (m, 3H). | Column: 58-Phenomenex Gemini NX C18 150 × 40 mm, 5 μm; mobile phase: acetonitrile 45%-75%/0.225% formic acid in water |

-continued

| Compound No. | Structure | Analytical data | Separation conditions |
|---|---|---|---|
| I-501a | 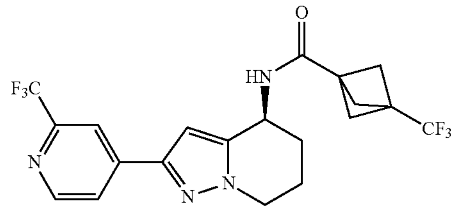 [SMILES: O=C(N[C@H]1CCCn2nc(-c3ccnc(C(F)(F)F)c3)cc21)C12CC(C(F)(F)F)(C1)C2] (S)-3-(Trifluoromethyl)-N-(2-(2-(trifluoromethyl)pyridin-4-yl)-4,5,6,7-tetrahydropyrazolo[1,5-a]pyridin-4-yl)bicyclo[1.1.1]pentane-1-carboxamide | LCMS (ESI) m/z: 445.1 $[M + H]^+$. $^1H$ NMR (400 MHz, DMSO-$d_6$) δ 8.75 (d, J = 5.2 Hz, 1H), 8.51 (d, J = 8.4 Hz, 1H), 8.19 (s, 1H), 8.08 (dd, J = 1.2, 5.2 Hz, 1H), 6.91 (s, 1H), 5.15-5.10 (m, 1H), 4.26-4.18 (m, 1H), 4.15-4.05 (m, 1H), 2.21 (s, 6H), 2.18-2.12 (m, 1H), 2.07-1.96 (m, 2H), 1.78-1.67 (m, 1H). | Column: 40-WePure Biotech XP tC18 150 × 30 mm, 7 μm; mobile phase: acetonitrile 60%-90%/0.225% formic acid in water. |
| I-496a | 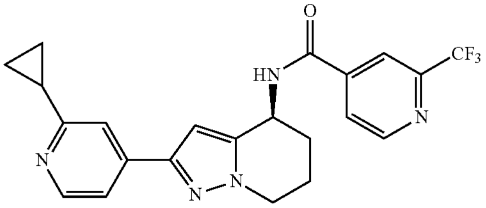 (S)-N-(2-(2-Cyclopropylpyridin-4-yl)-4,5,6,7-tetrahydropyrazolo[1,5-a]pyridin-4-yl)-2-(trifluoromethyl)isonicotinamide | LCMS (ESI) m/z: 428.2 $[M + H]^+$. $^1H$ NMR (400 MHz, DMSO-$d_6$) δ 9.49 (d, J = 8.0 Hz, 1H), 8.96 (d, J = 5.2 Hz, 1H), 8.36-8.32 (m, 2H), 8.17 (d, J = 4.8 Hz, 1H), 7.95 (s, 1H), 7.66 (s, 1H), 7.47 (dd, J = 1.2, 5.2 Hz, 1H), 6.85 (s, 1H), 5.43-5.34 (m, 1H), 4.26-4.10 (m, 2H), 2.89 (s, 1H), 2.73 (s, 1H), 2.25-2.07 (m, 4H), 1.92-1.82 (m, 1H), 0.95-0.89 (m, 4H). | Column: 52-Welch Xtimate C18 150 × 30 mm, 5 μm; mobile phase: acetonitrile 40%-80%/0.225% formic acid in water. |
| I-499a | 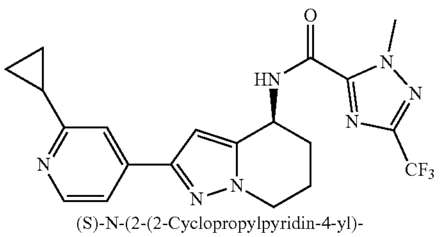 (S)-N-(2-(2-Cyclopropylpyridin-4-yl)-4,5,6,7-tetrahydropyrazolo[1,5-a]pyridin-4-yl)-1-methyl-3-(trifluoromethyl)-1H-1,2,4-triazole-5-carboxamide | LCMS (ESI) m/z: 432.1 $[M + H]^+$. $^1H$ NMR (400 MHz, DMSO-$d_6$) δ 9.63 (s, 1H), 8.34 (d, J = 5.2 Hz, 1H), 7.64 (s, 1H), 7.46-7.40 (m, 1H), 6.77 (s, 1H), 5.35-5.24 (m, 1H), 4.27 (s, 3H), 4.24-4.17 (m, 1H), 4.10-4.00 (m, 1H), 2.29-2.16 (m, 1H), 2.14-1.96 (m, 4H), 0.97-0.88 (m, 4H). | Prep-silica gel chromatography: solvent gradient: 0-25% ethyl acetate in hexanes. |
| I-495a | 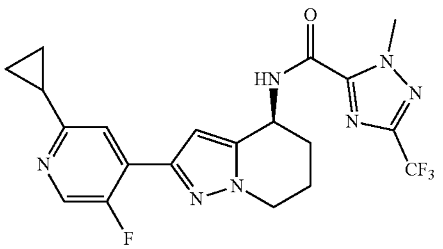 [SMILES: Cn1nc(C(F)(F)F)nc1C(=O)N[C@H]1CCCn2nc(-c3cc(C4CC4)ncc3F)cc21] (S)-N-(2-(2-Cyclopropyl-5-fluoropyridin-4-yl)-4,5,6,7-tetrahydropyrazolo[1,5-a]pyridin-4-yl)-1-methyl-3-(trifluoromethyl)-1H-1,2,4-triazole-5-carboxamide | LCMS (ESI) m/z: 450.1 $[M + H]^+$. $^1H$ NMR (400 MHz, DMSO-$d_6$) δ 9.61 (d, J = 8.8 Hz, 1H), 8.40 (d, J = 2.8 Hz, 1H), 8.13 (s, 1H), 7.78 (d, J = 6.4 Hz, 1H), 6.65 (d, J = 3.6 Hz, 1H), 5.48-5.18 (m, 1H), 4.26 (s, 3H), 4.24-4.20 (m, 1H), 4.14-4.06 (m, 1H), 2.28-2.14 (m, 2H), 2.14-1.92 (m, 3H), 0.97-0.90 (m, 2H), 0.90-0.81 (m, 2H). | Column: C18 150 × 30 mm; mobile phase: acetonitrile 48%-78%/0.225% formic acid in water. |

-continued

| Compound No. | Structure | Analytical data | Separation conditions |
|---|---|---|---|
| I-498a | 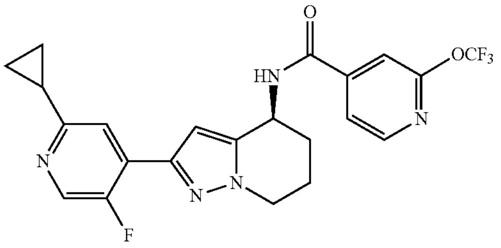 [SMILES: O=C(N[C@H]1CCCn2nc(-c3cc(C4CC4)ncc3F)cc21)c1ccnc(OC(F)(F)F)c1] (S)-N-(2-(2-Cyclopropyl-5-fluoropyridin-4-yl)-4,5,6,7-tetrahydropyrazolo[1,5-a]pyridin-4-yl)-2-(trifluoromethoxy)isonicotinamide | LCMS (ESI) m/z: 420.1 $[M + H]^+$. $^1H$ NMR (400 MHz, DMSO-$d_6$) δ 9.37 (d, J = 8.0 Hz, 1H), 8.54 (d, J = 5.2 Hz, 1H), 8.40 (d, J = 2.8 Hz, 1H), 7.86 (dd, J = 1.2, 5.2 Hz, 1H), 7.79 (d, J = 6.0 Hz, 1H), 7.68 (s, 1H), 6.69 (d, J = 3.6 Hz, 1H), 5.41-5.33 (m, 1H), 4.30-4.12 (m, 2H), 2.28-2.05 (m, 4H), 1.96-1.82 (m, 1H), 0.97-0.90 (m, 2H), 0.90-0.84 (m, 2H). | Column: C18 150 × 40 mm; mobile phase: acetonitrile 50%-80%/0.225% formic acid in water. |
| I-500a | 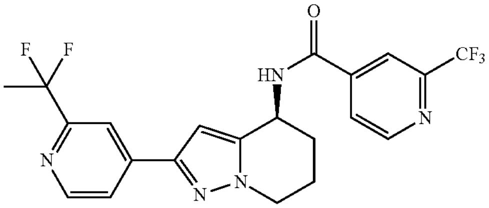 [SMILES: CC(F)(F)c1cc(-c2cc3n(n2)CCC[C@@H]3NC(=O)c2ccnc(C(F)(F)F)c2)ccn1] (S)-N-(2-(2-(1,1-Difluoroethyl)pyridin-4-yl)-4,5,6,7-tetrahydropyrazolo[1,5-a]pyridin-4-yl)-2-(trifluoromethyl)isonicotinamide | LCMS (ESI) m/z: 452.1 $[M + H]^+$. $^1H$ NMR (400 MHz, DMSO-$d_6$) δ 9.49 9.49 (d, J = 8.0 Hz, 1H), 8.97 (d, J = 5.2 Hz, 1H), 8.63 (d, J = 4.8 Hz, 1H), 8.33 (s, 1H), 8.17 (d, J = 4.8 Hz, 1H), 8.03 (s, 1H), 7.90 (d, J = 5.2 Hz, 1H), 7.01 (s, 1H), 5.47-5.31 (m, 1H), 4.30-4.21 (m, 1H), 4.20-4.11 (m, 1H), 2.28-2.08 (m, 3H), 2.01 (t, J = 19.2 Hz, 3H), 1.92-1.84 (m, 1H). | Column: Welch Xtimate C18 150 * 30 mm * 5 um; mobile phase: acetonitrile 40%-70%/0.225% formic acid in water. |
| I-551a | 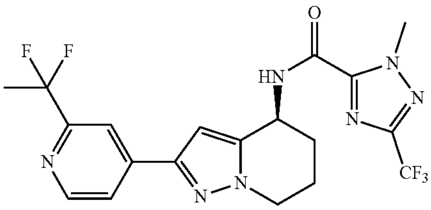 (S)-N-(2-(2-(1,1-Difluoroethyl)pyridin-4-yl)-4,5,6,7-tetrahydropyrazolo[1,5-a]pyridin-4-yl)-1-methyl-3-(trifluoromethyl)-1H-1,2,4-triazole-5-carboxamide | LCMS (ESI) m/z: 456.1 $[M + H]^+$. $^1H$ NMR (400 MHz, DMSO-$d_6$) δ 9.62 (d, J = 8.8 Hz, 1H), 8.63 (d, J = 4.8 Hz, 1H), 8.01 (s, 1H), 7.88 (d, J = 4.8 Hz, 1H), 6.93 (s, 1H), 5.37-5.27 (m, 1H), 4.28 (s, 3H), 4.26-4.21 (m, 1H), 4.11-4.04 (m, 1H), 2.10 (s, 2H), 2.06-1.95 (m, 5H). | Column: 58-Phenomenex Gemini NX C18 150 × 40 mm, 5 μm; mobile phase: acetonitrile 55%-85%/0.225% formic acid in water. |
| I-518a | 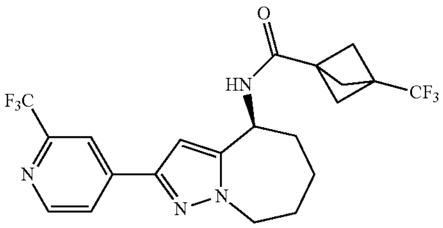 [SMILES: O=C(N[C@H]1CCCCn2nc(-c3ccnc(C(F)(F)F)c3)cc21)C12CC(C(F)(F)F)(C1)C2] (S)-N-(2-(2-(1,1-Difluoroethyl)pyridin-4-yl)-4,5,6,7-tetrahydropyrazolo[1,5-a]pyridin-4-yl)-1-methyl-3-(trifluoromethyl)-1H-1,2,4-triazole-5-carboxamide | LCMS (ESI) m/z: 456.1 $[M + H]^+$. $^1H$ NMR (400 MHz, DMSO-$d_6$) δ 8.75 (d, J = 5.2 Hz, 1H), 8.55 (d, J = 8.0 Hz, 1H), 8.13 (s, 1H), 8.04 (d, J = 4.8 Hz, 1H), 6.74 (s, 1H), 5.10-5.02 (m, 1H), 4.46-4.48 (m, 1H), 4.36-4.23 (m, 1H), 2.27 (s, 6H), 1.99-1.88 (m, 2H), 1.85-1.72 (m, 3H), 1.60-1.48 (m, 1H). | silica gel chromatography (solvent gradient: 0-30% ethyl acetate in hexanes). |

-continued

| Compound No. | Structure | Analytical data | Separation conditions |
|---|---|---|---|
| I-557a | 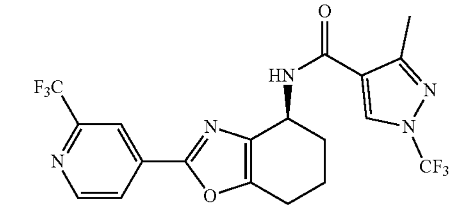 [SMILES: Cc1nn(C(F)(F)F)cc1C(=O)N[C@H]1CCCc2oc(-c3ccnc(C(F)(F)F)c3)nc21] (S)-3-Methyl-1-(trifluoromethyl)-N-(2-(2-(trifluoromethyl)pyridin-4-yl)-4,5,6,7-tetrahydrobenzo[d]oxazol-4-yl)-1H-pyrazole-4-carboxamide | LCMS (ESI) m/z: 460.1 $[M + H]^+$. $^1H$ NMR (400 MHz, DMSO-$d_6$) δ 8.93 (d, J = 5.2 Hz, 1H), 8.85 (s, 1H), 8.53 (d, J = 8.0 Hz, 1H), 8.22 (s, 1H), 8.19 (d, J = 4.8 Hz, 1H), 5.16-5.10 (m, 1H), 2.87-2.74 (m, 2H), 2.45 (s, 3H), 2.01-1.80 (m, 4H). | Prep-HPLC: Column: 40-WePure Biotech XP tC18 150 × 30 mm, 7 μm; mobile phase: acetonitrile 57%-87%/0.225% formic acid in water. Prep-SFC: chiral SFC (DAICEL CHIRALCEL AD (250 mm * 25 mm, 10 um); Supercritical $CO_2$/EtOH + 0.1% $NH_3$•$H_2O$ = 80/20; 150 mL/min). |
| I-507a | 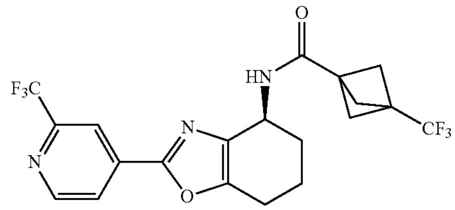 [SMILES: O=C(N[C@H]1CCCc2oc(-c3ccnc(C(F)(F)F)c3)nc21)C12CC(C(F)(F)F)(C1)C2] (S)-3-(Trifluoromethyl)-N-(2-(2-(trifluoromethyl)pyridin-4-yl)-4,5,6,7-tetrahydrobenzo[d]oxazol-4-yl)bicyclo[1.1.1]pentane-1-carboxamide | LCMS (ESI) m/z: 446.1 $[M + H]^+$. $^1H$ NMR (400 MHz, DMSO-$d_6$) δ 8.93 (d, J = 5.2 Hz, 1H), 8.36 (d, J = 8.0 Hz, 1H), 8.22 (s, 1H), 8.19 (d, J = 4.8 Hz, 1H), 5.00-4.90 (m, 1H), 2.86-2.70 (m, 2H), 2.18 (s, 6H), 2.00-1.83 (m, 3H), 1.76-1.72 (m, 1H). | Prep silica gel chromatography: (solvent gradient: 0-30% ethyl acetate in hexanes). |
| I-506a | 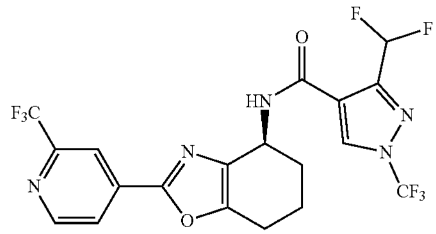 [SMILES: O=C(N[C@H]1CCCc2oc(-c3ccnc(C(F)(F)F)c3)nc21)c1cn(C(F)(F)F)nc1C(F)F] (S)-3-(Difluoromethyl)-1-(trifluoromethyl)-N-(2-(2-(trifluoromethyl)pyridin-4-yl)-4,5,6,7-tetrahydrobenzo[d]oxazol-4-yl)-1H-pyrazole-4-carboxamide | LCMS (ESI) m/z: 496.2 $[M + H]^+$. $^1H$ NMR (400 MHz, DMSO-$d_6$) δ 9.10 (s, 1H), 8.93 (d, J = 4.8 Hz, 1H), 8.83 (d, J = 8.0 Hz, 1H), 8.22 (s, 1H), 8.19 (d, J = 4.8 Hz, 1H), 7.47 (t, J = 13.2 Hz, 1H), 5.15-5.12 (m, 1H), 2.90-2.75 (m, 2H), 2.07 (s, 1H), 2.03-1.83 (m, 4H). | Column: 52-Welch Xtimate C18 150 × 30 mm; mobile phase: acetonitrile 50%-80%/0.225% formic acid in water. |
| I-208b | 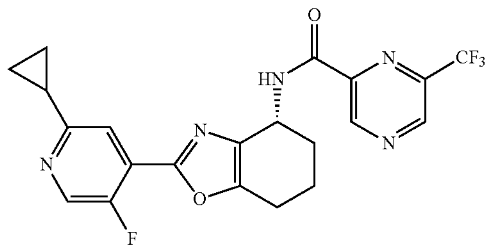 [SMILES: O=C(N[C@@H]1CCCc2oc(-c3cc(C4CC4)ncc3F)nc21)c1cncc(C(F)(F)F)n1] (R)-N-(2-(2-Cyclopropyl-5-fluoropyridin-4-yl)-4,5,6,7-tetrahydrobenzo[d]oxazol-4-yl)-6-(trifluoromethyl)pyrazine-2-carboxamide | LCMS (ESI) m/z: 448.2 $[M + H]^+$. $^1H$ NMR (400 MHz, DMSO-$d_6$) δ 9.51 (s, 1H), 9.40 (s, 1H), 9.23 (d, J = 8.4 Hz, 1H), 8.56 (d, J = 2.4 Hz, 1H), 7.87 (d, J = 6.0 Hz, 1H), 5.30-5.21 (m, 1H), 2.80-2.75 (m, 2H), 2.31-2.24 (m, 1H), 2.10-1.88 (m, 4H), 0.98-0.88 (m, 4H). | Prep-TLC ($SiO_2$, Hexanes/Ethyl acetate: 1/1). |

-continued

| Compound No. | Structure | Analytical data | Separation conditions |
|---|---|---|---|
| I-515a | 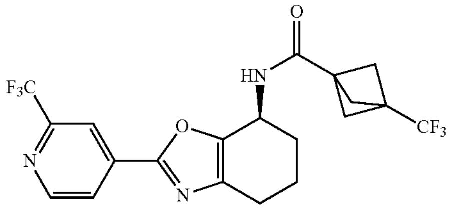 [SMILES: O=C(N[C@H]1CCCc2nc(-c3ccnc(C(F)(F)F)c3)oc21)C12CC(C(F)(F)F)(C1)C2]<br>(S)-3-Methyl-1-(trifluoromethyl)-N-(2-(2-(trifluoromethyl)pyridin-4-yl)-4,5,6,7-tetrahydrobenzo[d]oxazol-4-yl)-1H-pyrazole-4-carboxamide | LCMS (ESI) m/z: 446.2 $[M + H]^+$. $^1H$ NMR (400 MHz, DMSO-$d_6$) δ 8.93 (d, J = 5.2 Hz, 1H), 8.51 (d, J = 8.0 Hz, 1H), 8.20 (s, 1H), 8.18-8.15 (m, 1H), 5.22-5.01 (m, 1H), 2.62-2.54 (m, 2H), 2.19 (s, 6H), 2.00-1.87 (m, 2H), 1.85-1.75 (m, 2H). | Prep-HPLC: Column: 58-Phenomenex Gemini NX C18 150 x 40 mm, 5 μm; mobile phase: acetonitrile 55%-85%/0.225% formic acid in water. Prep-SFC: chiral SFC (DAICEL CHIRALCEL AD (250 mm * 25 mm, 10 um); Supercritical $CO_2$/EtOH + 0.1% $NH_3$•$H_2O$ = 80/20; 150 mL/min). |
| I-553a | 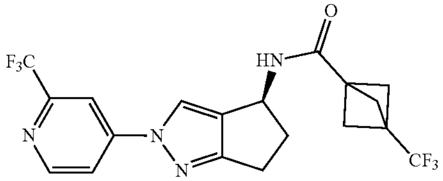 [SMILES: O=C(N[C@H]1CCc2nn(-c3ccnc(C(F)(F)F)c3)cc21)C12CC(C(F)(F)F)(C1)C2]<br>(S)-3-(Trifluoromethyl)-N-(2-(2-(trifluoromethyl)pyridin-4-yl)-2,4,5,6-tetrahydrocyclopenta[c]pyrazol-4-yl)bicyclo[1.1.1]pentane-1-carboxamide | LCMS (ESI) m/z: 431.1 $[M + H]^+$. $^1H$ NMR (400 MHz, DMSO-$d_6$) δ 8.76 (d, J = 5.6 Hz, 1H), 8.62 (s, 1H), 8.40 (d, J = 7.2 Hz, 1H), 8.29 (d, J = 2.0 Hz, 1H), 8.17 (s, 1H), 8.11-8.05 (m, 1H), 5.21-5.11 (m, 1H), 2.96-2.84 (m, 1H), 2.80-2.68 (m, 2H), 2.28-2.20 (m, 1H), 2.17 (s, 6H), 2.08 (s, 1H). | Column: 52-Welch Xtimate C18 150 x 30 mm, 5 μm; mobile phase: acetonitrile 52%-82%/0.225% formic acid in water. |
| I-561a | 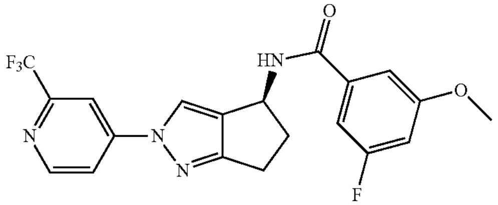<br>(S)-3-Fluoro-5-methoxy-N-(2-(2-(trifluoromethyl)pyridin-4-yl)-2,4,5,6-tetrahydrocyclopenta[c]pyrazol-4-yl)benzamide | LCMS (ESI) m/z: 421.1 $[M + H]^+$. $^1H$ NMR (400 MHz, DMSO-$d_6$) δ 8.89 (d, J = 7.6 Hz, 1H), 8.75 (d, J = 5.6 Hz, 1H), 8.65 (s, 1H), 8.28 (d, J = 1.6 Hz, 1H), 8.14-8.09 (m, 1H), 7.46-7.41 (m, 2H), 7.14-7.08 (m, 1H), 5.43-5.32 (m, 1H), 3.82 (s, 3H), 2.95-2.90 (m, 1H), 2.86-2.76 (m, 2H), 2.42-2.34 (m, 1H). | Column: 52-Welch Xtimate C18 150 x 30 mm, 5 μm; mobile phase: acetonitrile 45%-75%/0.225% formic acid in water. |
| I-562a | 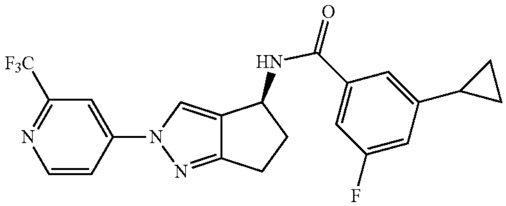 [SMILES: O=C(N[C@H]1CCc2nn(-c3ccnc(C(F)(F)F)c3)cc21)c1cc(F)cc(C2CC2)c1]<br>(S)-3-Cyclopropyl-5-fluoro-N-(2-(2-(trifluoromethyl)pyridin-4-yl)-2,4,5,6-tetrahydrocyclopenta[c]pyrazol-4-yl)benzamide | LCMS (ESI) m/z: 431.2 $[M + H]^+$. $^1H$ NMR (400 MHz, DMSO-$d_6$) δ 8.86 (d, J = 7.6 Hz, 1H), 8.75 (d, J = 5.6 Hz, 1H), 8.65 (s, 1H), 8.28 (d, J = 1.6 Hz, 1H), 8.14-8.09 (m, 1H), 7.46-7.41 (m, 2H), 7.14-7.08 (m, 1H), 5.43-5.36 (m, 1H), 2.99-2.90 (m, 1H), 2.87-2.76 (m, 2H), 2.42-2.35 (m, 1H), 2.03-1.97 (m, 1H), 1.03-0.98 (m, 2H), 0.78-0.74 (m, 2H). | Column: 52-Welch Xtimate C18 150 x 30 mm, 5 μm; mobile phase: acetonitrile 60%-90%/0.225% formic acid in water. |
| I-563a | 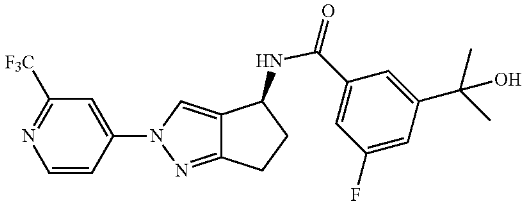 [SMILES: CC(C)(O)c1cc(F)cc(C(=O)N[C@H]2CCc3nn(-c4ccnc(C(F)(F)F)c4)cc32)c1]<br>(S)-3-Fluoro-5-(2-hydroxypropan-2-yl)-N-(2-(2-(trifluoromethyl)pyridin-4-yl)-2,4,5,6-tetrahydrocyclopenta[c]pyrazol-4-yl)benzamide | LCMS (ESI) m/z: 449.1 $[M + H]^+$. $^1H$ NMR (400 MHz, DMSO-$d_6$) δ 8.90 (d, J = 7.2 Hz, 1H), 8.75 (d, J = 5.6 Hz, 1H), 8.66 (s, 1H), 8.28 (s, 1H), 8.12 (d, J = 4.8 Hz, 1H), 7.84 (s, 1H), 7.53 (d, J = 10.4 Hz, 1H), 7.43 (d, J = 9.6 Hz, 1H), 5.45-5.37 (m, 1H), 2.97-2.91 (m, 1H), 2.86-2.75 (m, 2H), 2.44-2.38 (m, 1H), 1.44 (s, 6H). | Column: 58-Phenomenex Gemini NX C18 150 x 40 mm, 5 μm; mobile phase: acetonitrile 50%-80%/0.225% formic acid in water. |

-continued

| Compound No. | Structure | Analytical data | Separation conditions |
|---|---|---|---|
| I-564a | 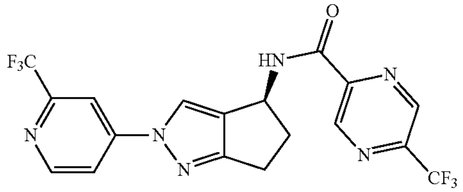 [SMILES: O=C(N[C@H]1CCc2nn(-c3ccnc(C(F)(F)F)c3)cc21)c1cnc(C(F)(F)F)cn1] (S)-5-(Trifluoromethyl)-N-(2-(2-(trifluoromethyl)pyridin-4-yl)-2,4,5,6-tetrahydrocyclopenta[c]pyrazol-4-yl)pyrazine-2-carboxamide | LCMS (ESI) m/z: 443.1 $[M + H]^+$. $^1H$ NMR (400 MHz, DMSO-$d_6$) δ 9.53 (d, J = 7.6 Hz, 1H), 9.38 (s, 1H), 9.24 (s, 1H), 8.75 (d, J = 5.2 Hz, 1H), 8.65 (s, 1H), 8.27 (s, 1H), 8.15-8.06 (m, 1H), 5.51-5.39 (m, 1H), 3.03-2.93 (m, 1H), 2.88-2.73 (m, 2H), 2.57-2.53 (m, 1H). | Prep silica gel chromatography: (solvent gradient: 0-40% EtOAc in hexanes). |
| I-565a | 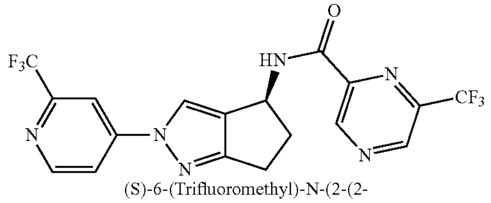 (S)-6-(Trifluoromethyl)-N-(2-(2-(trifluoromethyl)pyridin-4-yl)-2,4,5,6-tetrahydrocyclopenta[c]pyrazol-4-yl)pyrazine-2-carboxamide | LCMS (ESI) m/z: 443.1 $[M + H]^+$. $^1H$ NMR (400 MHz, DMSO-$d_6$) δ 9.50 (s, 1H), 9.43-9.34 (m, 2H), 8.75 (d, J = 5.6 Hz, 1H), 8.67 (s, 1H), 8.28 (d, J = 2.0 Hz, 1H), 8.12-8.10 (m, 1H), 5.54-5.42 (m, 1H), 3.06-2.93 (m, 1H), 2.90-2.72 (m, 2H), 2.59-2.52 (m, 1H). | Column: 57-Phenomenex Gemini NX C18 150 × 30 mm, 5 μm; mobile phase: acetonitrile 40%-70%/0.225% formic acid in water. |
| I-566a | 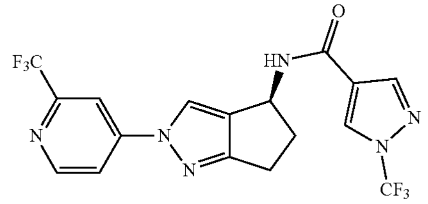 (S)-1-(Trifluoromethyl)-N-(2-(2-(trifluoromethyl)pyridin-4-yl)-2,4,5,6-tetrahydrocyclopenta[c]pyrazol-4-yl)-1H-pyrazole-4-carboxamide | LCMS (ESI) m/z: 431.1 $[M + H]^+$. $^1H$ NMR (400 MHz, DMSO-$d_6$) δ 8.95 (s, 1H), 8.76 (d, J = 5.6 Hz, 2H), 8.66 (s, 1H), 8.32 (s, 1H), 8.28 (d, J = 1.6 Hz, 1H), 8.12-8.10 (m, 1H), 5.41-5.31 (m, 1H), 2.99-2.88 (m, 1H), 2.87-2.72 (m, 2H), 2.38-2.31 (m, 1H). | Column: 58-Phenomenex Gemini NX C18 150 × 40 mm, 5 μm; mobile phase: acetonitrile 50%-80%/0.225% formic acid in water. |

Example 2. Biological Assays

Example 2.1. FLIPR TI/K Flux Assay

HEK293 cells stably expressing human, KCNT1 were cultured in DMEM, 10% FBS, 100 U/mL penicillin-streptomycin and 0.8 g/mL puromycin for selection purposes. One day before the assay, cells were detached using TrypLE™ Express and counted using a cell counter. Only cells with >85% viability were used for the assay. Cells were resuspended in culture media and seeded at 20,000 cells per well at 301 per well in a 384-well plate. The cells were incubated overnight at 37° C., 5% (v/v) $CO_2$.

On the day of the assay, the reagents were prepared following the FLIPR® Potassium Assay Kit manual: prepare 2× dye solution, dilute the dye with assay buffer (20 mM HEPES in 1× HBSS, PH7.4), addition of probenecid to a final concentration of 5 mM, and vortexed vigorously for 1-2 minutes. The cell plate was flicked to remove medium and tapped on paper towels to remove excess media. The assay buffer and 2× dye solution were mixed 1:1 and added to each well for a total volume of 201 per well. The cell plate was moved to a plate shaker, agitated at 600 rpm for two minutes, and then incubated at 25° C. for one hour.

The compounds were prepared in DMSO and transferred to a 384-well compound plate (PP, low binding), referred to as a source plate. Reference agonist (300 nM) compound and test inhibitor (10 mM) compounds were added to the compound plate and a 4-fold serial dilution was performed in DMSO. Using an ECHO dispenser, compounds were dispensed at 90 nL/well from the source plate to a 384-well compound plate (PP, low binding). After the dispensing was complete, 30 L/well assay buffer was added to the compound plate and mixed for two minutes on a plate shaker. The cell plate, compound plate, and tips were loaded into the FLIPR instrument, and a transfer of 10 μl of 3× compound to the cell plate was initiated. The treated cell plate was kept at in the dark at 25° C. for 30 minutes. Chloride-free stimulation buffer containing 4× 2 mM Tl+ and 4×$EC_{80}$ of agonist Loxapine was loaded into a 384-well compound plate (PP, low binding). After the 30-minute incubation, the cell plate, compound plate containing stimulation buffer, and FLIPR tips were loaded into the FLIPR instrument. After a baseline read, the FLIPR initiates a transfer of 10 μL of stimulation buffer containing Loxapine to the cell plate. The plate was read for 160 sec with 1 second interval reads to obtain the data.

The normalized fluorescence reading (RFU) was calculated as shown follow, while Fmax and Fmin stand for maximum and minimum of signal during defined time window. The $IC_{50}$ was calculated by fitting % inhibition against log of compound concentrations with Hill equation using XLfit.

$$\% \text{ Inhibition} = \left(1 - \frac{(RFU \text{ compound} - RFU \text{ low control})}{(RFU \text{ high control} - RFU \text{ low control})}\right) * 100\%$$

Results are presented in Table 7.

TABLE 7

| Compound No. | IC50 |
|---|---|
| I-1 | A |
| I-1a | A |
| I-1b | D |
| I-2a | A |
| I-3a | C |
| I-4 | A |
| I-4a | A |
| I-4b | D |
| I-5a | A |
| I-6* | C |
| I-6** | D |
| I-7 | A |
| I-8 | A |
| I-9a | A |
| I-10 | A |
| I-11 | B |
| I-12 | A |
| I-13 | A |
| I-14 | A |
| I-15 | A |
| I-16 | A |
| I-17 | A |
| I-18 | A |
| I-19 | B |
| I-20 | A |
| I-21 | D |
| I-22 | B |
| I-23 | D |
| I-24 | C |
| I-25 | B |
| I-26 | B |
| I-27 | D |
| I-28 | B |
| I-29 | D |
| I-30 | C |
| I-31 | D |
| I-32 | D |
| I-33 | D |
| I-34 | D |
| I-35 | D |
| I-36 | D |
| I-37a | D |
| I-38 | D |
| I-39 | D |
| I-40 | D |
| I-41a | A |
| I-42 | A |
| I-42a | A |
| I-42b | D |
| I-43* | D |
| I-43** | D |
| I-44a | A |
| I-45 | A |
| I-45a | A |
| I-45b | D |
| I-46a | B |
| I-46b | D |
| I-48a | A |
| I-49a | D |
| I-50a | A |
| I-51 | D |
| I-52 | A |
| I-52* | C |
| I-52** | A |
| I-53a | D |
| I-55 | A |
| I-56a | A |
| I-56b | C |
| I-57 | A |

TABLE 7-continued

| Compound No. | IC50 |
|---|---|
| I-58a | A |
| I-58b | C |
| I-59 | A |
| I-60a | A |
| I-60b | C |
| I-61 | A |
| I-62 | A |
| I-62* | A |
| I-62** | B |
| I-63 | A |
| I-63* | A |
| I-63** | A |
| I-64 | A |
| I-64a | A |
| I-64b | C |
| I-65 | A |
| I-66a | A |
| I-67* | A |
| I-68a | A |
| I-68b | C |
| I-69a | A |
| I-69b | D |
| I-70a | A |
| I-70b | D |
| I-71a | A |
| I-71b | C |
| I-72a | A |
| I-72b | D |
| I-73a | A |
| I-73b | C |
| I-74a | A |
| I-74b | D |
| I-75a | A |
| I-76a | D |
| I-77a | A |
| I-77b | C |
| I-78a | A |
| I-78b | D |
| I-79a | A |
| I-80a | C |
| I-80b | D |
| I-81a | A |
| I-82a | A |
| I-83* | A |
| I-84a | A |
| I-86a | A |
| I-87a | C |
| I-87b | D |
| I-88a | D |
| I-89a | D |
| I-90a | B |
| I-91a | A |
| I-91b | D |
| I-92a | A |
| I-92b | D |
| I-93a | A |
| I-93b | D |
| I-94a | A |
| I-94b | D |
| I-95a | A |
| I-95b | D |
| I-96a | D |
| I-96b | D |
| I-97a | A |
| I-97b | D |
| I-98a | A |
| I-98b | D |
| I-99a | A |
| I-99b | C |
| I-100a | A |
| I-100b | D |
| I-102a | A |
| I-103a | A |
| I-103b | D |
| I-104a | C |
| I-104b | D |
| I-105a | A |
| I-105b | D |

TABLE 7-continued

| Compound No. | IC50 |
|---|---|
| I-106a | A |
| I-106b | D |
| I-109a | A |
| I-109b | D |
| I-110a | A |
| I-111a | A |
| I-112a | A |
| I-113a | B |
| I-116a | A |
| I-117a | A |
| I-118a | A |
| I-120a | A |
| I-121a | A |
| I-122a | A |
| I-123a | A |
| I-123b | B |
| I-124a | A |
| I-125a | A |
| I-126a | A |
| I-127a | A |
| I-127b | A |
| I-128a | A |
| I-129a | A |
| I-130a | A |
| I-131a | A |
| I-132a | A |
| I-133a | A |
| I-134a | A |
| I-135a | A |
| I-136* | B |
| I-136** | C |
| I-137a | A |
| I-138a | A |
| I-139a | A |
| I-140a | A |
| I-141a | A |
| I-142a | A |
| I-143a | D |
| I-144a | A |
| I-145a | A |
| I-146a | A |
| I-147^ | A |
| I-148* | A |
| I-148** | C |
| I-149* | A |
| I-149** | A |
| I-150a | A |
| I-151a | A |
| I-152a | A |
| I-153a | A |
| I-154a | A |
| I-155a | A |
| I-156a | A |
| I-157a | A |
| I-158a | A |
| I-159a | A |
| I-160a | A |
| I-160b | A |
| I-161a | B |
| I-162a | A |
| I-163a | A |
| I-164a | A |
| I-165a | A |
| I-166a | A |
| I-167a | A |
| I-168a | A |
| I-169a | A |
| I-170a | A |
| I-171a | A |
| I-172a | A |
| I-172b | D |
| I-173a | B |
| I-174a | A |
| I-175a | A |
| I-176a | A |
| I-177a | A |
| I-178a | A |
| I-179a | A |

TABLE 7-continued

| Compound No. | IC50 |
|---|---|
| I-180a | A |
| I-181a | A |
| I-182a | C |
| I-183a | A |
| I-184a | A |
| I-185a | A |
| I-186a | A |
| I-187a | A |
| I-188a | A |
| I-189a | A |
| I-190a | A |
| I-191a | A |
| I-192a | B |
| I-193a | A |
| I-194a | A |
| I-195a | A |
| I-196a | C |
| I-197a | D |
| I-198a | A |
| I-199a | A |
| I-200a | A |
| I-201a | A |
| I-202a | A |
| I-203a | A |
| I-204a | A |
| I-205a | A |
| I-206a | D |
| I-207a | A |
| I-208a | A |
| I-209a | A |
| I-210a | A |
| I-211a | A |
| I-212a | A |
| I-213a | A |
| I-214a | A |
| I-215a | A |
| I-216a | A |
| I-217a | A |
| I-218a | B |
| I-219a | D |
| I-220a | B |
| I-221a | A |
| I-222a | A |
| I-223a | A |
| I-224a | A |
| I-225a | D |
| I-226a | A |
| I-227a | D |
| I-228a | D |
| I-229a | A |
| I-230a | D |
| I-231a | A |
| I-232a | A |
| I-233a | A |
| I-234a | A |
| I-235a | A |
| I-236a | A |
| I-237a | A |
| I-238a | A |
| I-239a | A |
| I-240a | A |
| I-241a | A |
| I-242a | A |
| I-243a | A |
| I-244a | A |
| I-245a | A |
| I-246a | A |
| I-247a | D |
| I-248a | A |
| I-249a | A |
| I-250a | A |
| I-251a | A |
| I-252a | A |
| I-253a | A |
| I-254a | A |
| I-255a | A |
| I-256a | A |
| I-257a | A |

TABLE 7-continued

| Compound No. | IC50 |
|---|---|
| I-258a | A |
| I-259a | A |
| I-260a | B |
| I-261a | A |
| I-262a | A |
| I-263a | A |
| I-264a | A |
| I-265a | A |
| I-266a | A |
| I-267a | A |
| I-268* | D |
| I-269* | D |
| I-270* | D |
| I-271* | C |
| I-272* | A |
| I-273a | A |
| I-274a | A |
| I-275a | A |
| I-276a | A |
| I-277a | A |
| I-278a | A |
| I-279a | A |
| I-280a | A |
| I-281a | A |
| I-282a | A |
| I-283a | A |
| I-284a | A |
| I-285a | A |
| I-286a | A |
| I-287a | A |
| I-288a | A |
| I-289a | A |
| I-290a | A |
| I-291a | A |
| I-292a | A |
| I-293a | B |
| I-294a | A |
| I-295a | A |
| I-296a | A |
| I-297a | A |
| I-298a | A |
| I-299a | A |
| I-300a | A |
| I-301a | A |
| I-302a | A |
| I-303a | A |
| I-304a | A |
| I-305a | B |
| I-306a | A |
| I-307a | C |
| I-308a | A |
| I-309* | A |
| I-310a | A |
| I-311a | A |
| I-311b | D |
| I-312a | A |
| I-313a | A |
| I-314a | A |
| I-315a | A |
| I-316a | C |
| I-317a | C |
| I-318a | A |
| I-319a | A |
| I-320a | A |
| I-321a | A |
| I-322a | D |
| I-323a | A |
| I-324a | A |
| I-325a | A |
| I-326a | A |
| I-327a | A |
| I-328a | A |
| I-329a | A |
| I-330a | A |
| I-331a | A |
| I-332a | A |
| I-333a | A |
| I-334a | A |

TABLE 7-continued

| Compound No. | IC50 |
|---|---|
| I-335a | A |
| I-336a | C |
| I-337a | A |
| I-338a | A |
| I-339* | B |
| I-339** | D |
| I-340a | D |
| I-341a | A |
| I-342a | A |
| I-343a | A |
| I-344a | D |
| I-347a | A |
| I-348a | A |
| I-349a | A |
| I-350a | A |
| I-351a | A |
| I-352a | A |
| I-353b | C |
| I-354a | A |
| I-355a | A |
| I-356a | B |
| I-357a | A |
| I-358a | A |
| I-359a | A |
| I-360a | A |
| I-360b | D |
| I-361a | A |
| I-361b | D |
| I-362a | A |
| I-363a | A |
| I-364a | A |
| I-365a | B |
| I-366a | A |
| I-367a | A |
| I-368a | D |
| I-369a | A |
| I-369b | D |
| I-370a | A |
| I-371a | A |
| I-372a | A |
| I-372b | C |
| I-373a | A |
| I-373b | A |
| I-375a | D |
| I-376a | A |
| I-376b | D |
| I-377a | A |
| I-378a | A |
| I-379a | A |
| I-380^ | D |
| I-381a | A |
| I-382a | A |
| I-383a | D |
| I-383b | D |
| I-384a | A |
| I-384b | A |
| I-385a | A |
| I-385b | B |
| I-386a | D |
| I-387a | A |
| I-388a | A |
| I-389a | A |
| I-390a | A |
| I-391a | A |
| I-392a | A |
| I-393* | D |
| I-393** | D |
| I-394a | B |
| I-395a | D |
| I-396a | A |
| I-397a | D |
| I-398a | A |
| I-399a | A |
| I-400a | A |
| I-401a | D |
| I-402a | A |
| I-403a | A |
| I-404a | A |

TABLE 7-continued

| Compound No. | IC50 |
|---|---|
| I-405a | A |
| I-406a | B |
| I-407a | B |
| I-408a | A |
| I-409a | A |
| I-410a | A |
| I-411a | A |
| I-412a | D |
| I-413a | D |
| I-414a | A |
| I-415a | A |
| I-416a | B |
| I-417a | A |
| I-418a | A |
| I-419a | A |
| I-420a | A |
| I-421a | A |
| I-422a | D |
| I-423a | D |
| I-424a | A |
| I-425a | D |
| I-426a | A |
| I-427a | A |
| I-427b | D |
| I-428a | A |
| I-429a | A |
| I-430* | C |
| I-430** | D |
| I-431a | A |
| I-432a | A |
| I-433a | D |
| I-434a | A |
| I-435a | D |
| I-436a | D |
| I-437a | A |
| I-438a | D |
| I-439a | A |
| I-440a | C |
| I-441a | A |
| I-442a | A |
| I-443a | A |
| I-444a | C |
| I-445a | A |
| I-446a | A |
| I-447a | A |
| I-447b | A |
| I-448a | A |
| I-449a | A |
| I-450a | A |
| I-450a | A |
| I-451a | A |
| I-452a | B |
| I-452b | D |
| I-453a | D |
| I-453b | D |
| I-454a | A |
| I-455a | A |
| I-456a | A |
| I-457a | A |
| I-458a | A |
| I-459a | A |
| I-460a | D |
| I-461a | A |
| I-462a | A |
| I-463 | D |
| I-464 | D |
| I-465* | A |
| I-465** | A |
| I-466* | A |
| I-466** | C |
| I-467* | A |
| I-467** | C |
| I-468* | A |
| I-468** | A |
| I-469* | A |
| I-469** | A |
| I-470b | A |
| I-471b | C |

TABLE 7-continued

| Compound No. | IC50 |
|---|---|
| I-472b | D |
| I-473** | D |
| I-474b | D |
| I-475b | D |
| I-476b | B |
| I-477 | A |
| I-478 | A |
| I-479* | A |
| I-479** | B |
| I-480b | C |
| I-481b | B |
| I-482b | C |
| I-483a | A |
| I-484a | A |
| I-485b | A |
| I-486b | B |
| I-487^ | A |
| I-488^ | A |
| I-489a | A |
| I-490a | A |
| I-491a | C |
| I-492a | A |
| I-493a | A |
| I-494a | A |
| I-495a | A |
| I-496a | A |
| I-497a | A |
| I-498a | A |
| I-499a | A |
| I-500a | A |
| I-501a | A |
| I-502b | D |
| I-503b | D |
| I-504b | D |
| I-505a | A |
| I-506a | A |
| I-507a | A |
| I-508a | A |
| I-508b | D |
| I-509b | D |
| I-510b | D |
| I-511b | D |
| I-512b | D |
| I-513b | D |
| I-514a | A |
| I-515a | A |
| I-516b | C |
| I-517b | C |
| I-518a | A |
| I-519a | A |
| I-520a | A |
| I-521a | A |
| I-522a | A |
| I-523a | A |
| I-524a | A |
| I-525a | A |
| I-526a | A |
| I-527a | A |
| I-528a | A |
| I-529a | A |
| I-530a | A |
| I-531a | A |
| I-532a | A |
| I-533a | A |
| I-534* | A |
| I-535* | A |
| I-536a | A |
| I-537a | A |
| I-538a | A |
| I-539a | A |
| I-540a | A |
| I-541a | A |
| I-542a | A |
| I-543a | A |
| I-544a | A |
| I-545a | A |
| I-546a | A |
| I-547a | A |

TABLE 7-continued

| Compound No. | IC50 |
|---|---|
| I-548a | A |
| I-549a | A |
| I-550a | A |
| I-551a | A |
| I-552a | A |
| I-553a | A |
| I-554a | A |
| I-555a | A |
| I-556a | A |
| I-557a | A |
| I-558a | A |
| I-559a | A |
| I-560a | A |
| I-561a | A |
| I-562a | A |
| I-563a | A |
| I-564a | A |
| I-565a | A |
| I-566a | A |
| I-567a | A |
| I-568a | A |
| I-569a | A |
| I-570a | A |
| I-571a | A |
| I-572a | A |
| I-573a | A |
| I-574a | A |
| I-575a | A |
| I-576a | A |
| I-577a | A |
| I-578a | A |
| I-579a | A |
| I-580a | A |
| I-581a | A |
| I-582a | A |
| I-583a | A |
| I-584a | A |

*single enantiomer of unknown configuration

**single enantiomer of unknown configuration that is different from an enantiomer designated *

^mixture of diastereomers

In Table 7, "A" indicates an IC50 of ≤250 nM; "B" indicates an IC50 of >250 nM and ≤500 nM; "C" indicates an IC50 of >500 nM and ≤1000 nM; and "D" indicates an IC50 of >1000 nM.

The invention claimed is:

1. A compound of formula I':

I'

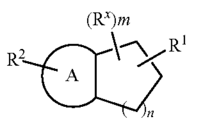

or a pharmaceutically acceptable salt thereof, wherein:

Ring A is

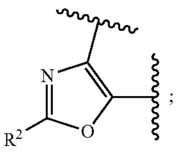

$R^1$ is selected from

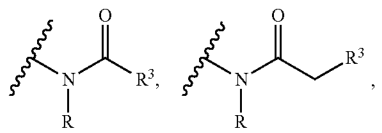

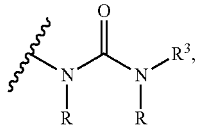

and

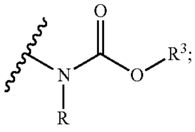

$R^2$ is a 5- to 6-membered heteroaryl ring having 1-3 heteroatoms independently selected from nitrogen, oxygen, and sulfur or a 9- to 10-membered heteroaryl ring having 1-4 heteroatoms independently selected from nitrogen, oxygen, and sulfur, wherein $R^2$ is substituted with 0-3 instances of $R^y$;

$R^3$ is selected from $C_{1-6}$ aliphatic, a 3- to 6-membered saturated or partially unsaturated carbocyclic ring, a 5- to 7-membered bridged bicyclic carbocyclic ring, a 6- to 8-membered spirocyclic carbocyclic ring, phenyl, a 10-membered aryl ring, a 5- to 6-membered heteroaryl ring having 1-3 heteroatoms independently selected from nitrogen, oxygen, and sulfur, and an 8- to 10-membered heteroaryl ring having 1-4 heteroatoms independently selected from nitrogen, oxygen, and sulfur, wherein $R^3$ is substituted with 0-4 instances of $R^z$;

each $R^x$ is selected from optionally substituted $C_{1-6}$ aliphatic, —N(R)$_2$, and —OR;

each $R^y$ is independently selected from oxo, —CN, —N(R)$_2$, —OR, —$CO_2$R, or an optionally substituted group selected from $C_{1-4}$ aliphatic and a 3- to 7-membered saturated or partially unsaturated carbocyclic ring;

each $R^z$ is independently selected from —CN, halogen, —OR, —$SO_2$R, and an optionally substituted group selected from $C_{1-6}$ aliphatic, phenyl, and a 3- to 7-membered saturated or partially unsaturated carbocyclic ring;

each R is independently selected from hydrogen or an optionally substituted group selected from $C_{1-6}$ aliphatic, phenyl, a 3- to 7-membered saturated or partially unsaturated carbocyclic ring, a 3- to 7-membered saturated or partially unsaturated heterocyclic ring having 1-3 heteroatoms independently selected from nitrogen, oxygen, and sulfur, and a 5- to 6-membered heteroaryl ring having 1-4 heteroatoms independently selected from nitrogen, oxygen, and sulfur;

m is 0-2; and n is 1-3.

2. The compound according to claim 1, wherein the compound is a compound of formula I-i-i or formula I-j-i:

I-i-i

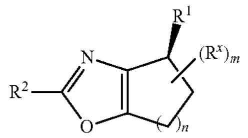

-continued

I-j-i

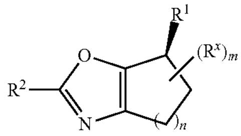

or a pharmaceutically acceptable salt thereof.

3. The compound according to claim 1, wherein the compound is a compound of formula III-i, formula III-j, formula IV-e, formula III-i-i, formula III-j-i, or formula IV-e-i:

III-i

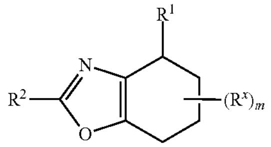

III-j

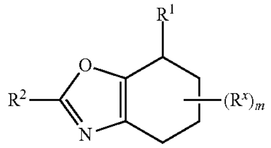

IV-e

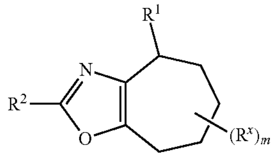

III-i-i

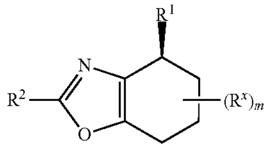

III-j-i

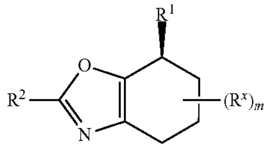

IV-e-i

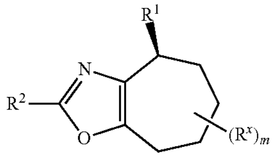

or a pharmaceutically acceptable salt thereof.

4. The compound according to claim 3, wherein $R^1$ is

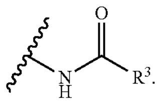

5. The compound according to claim 4, wherein $R^2$ is a 6-membered heteroaryl ring having 1-2 nitrogen atoms, wherein $R^2$ is substituted with 0-2 instances of $R^y$.

6. The compound according to claim 5, wherein $R^2$ is selected from

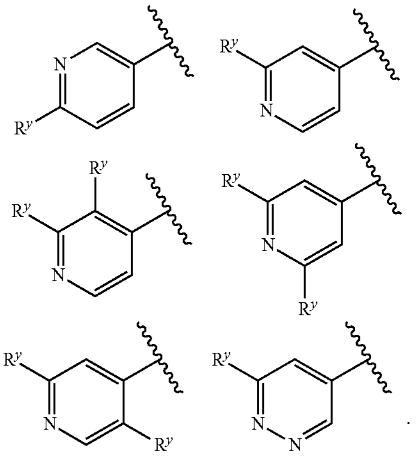

7. The compound according to claim 6, wherein each $R^y$ is independently selected from fluoro, chloro,

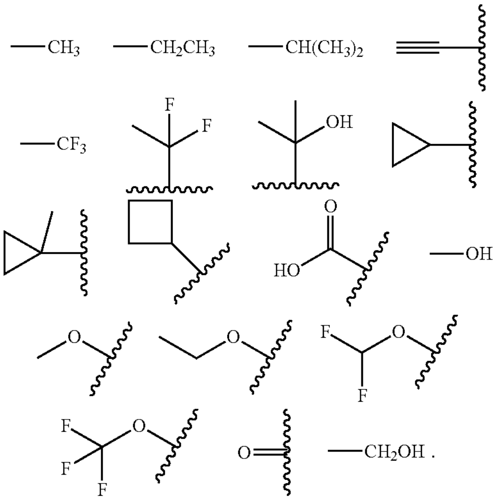

8. The compound according to claim 7, wherein $R^2$ is selected from

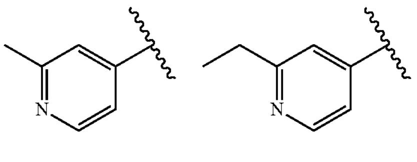

-continued

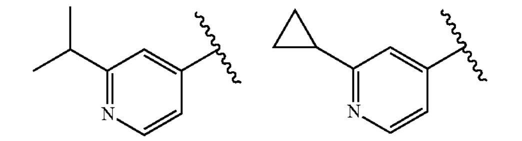
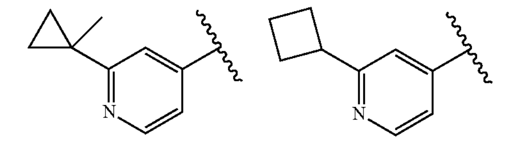
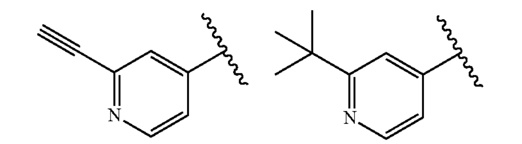
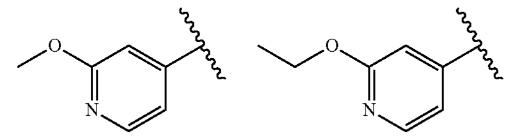
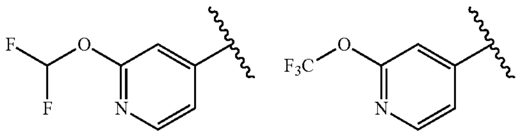
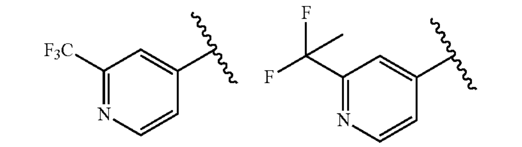
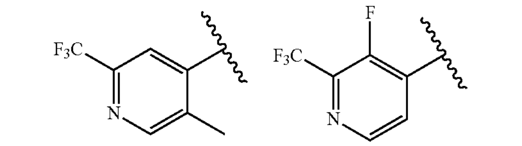
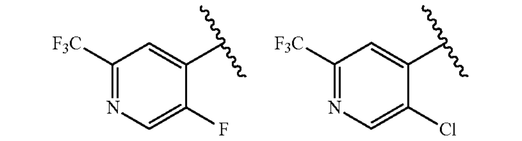
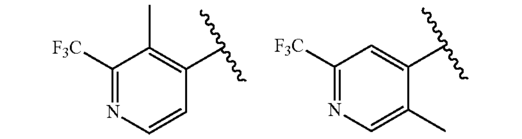
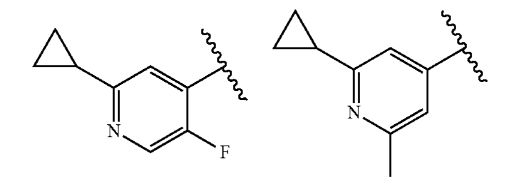
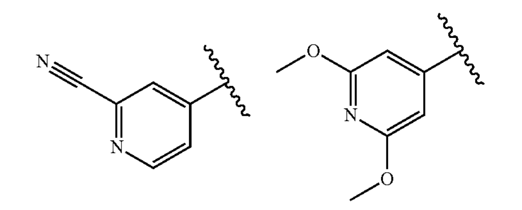

-continued

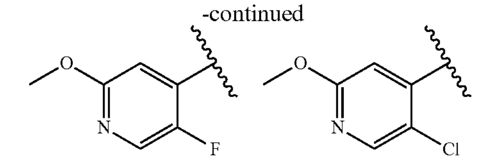
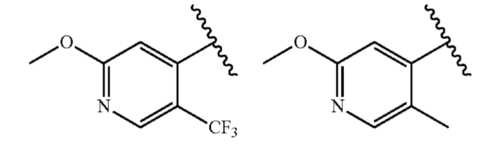
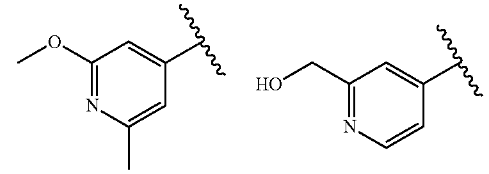
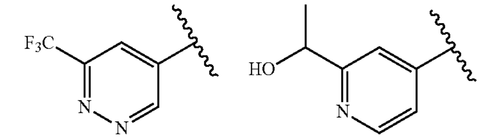
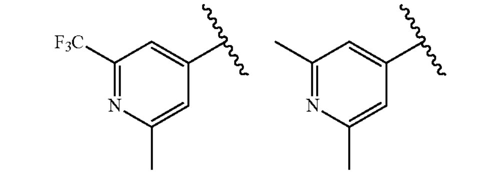
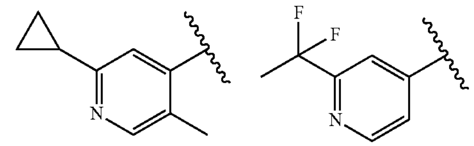

.

9. The compound according to claim 4, wherein $R^3$ is a 5- to 6-membered heteroaryl ring having 1-3 heteroatoms independently selected from nitrogen, oxygen, and sulfur.

10. The compound according to claim 9, wherein $R^3$ is a 5-membered heteroaryl ring having 1-3 heteroatoms independently selected from nitrogen, oxygen, and sulfur.

11. The compound according to claim 10, wherein $R^3$ is a 5-membered heteroaryl ring having 1-2 heteroatoms independently selected from nitrogen, oxygen, and sulfur.

12. The compound according to claim 4, wherein $R^3$ is selected from

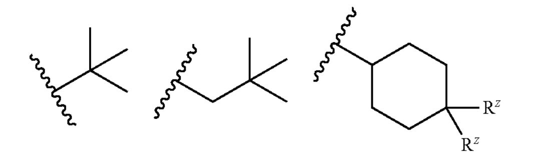
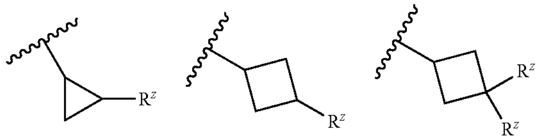
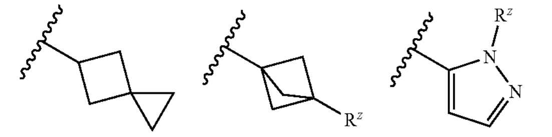

-continued
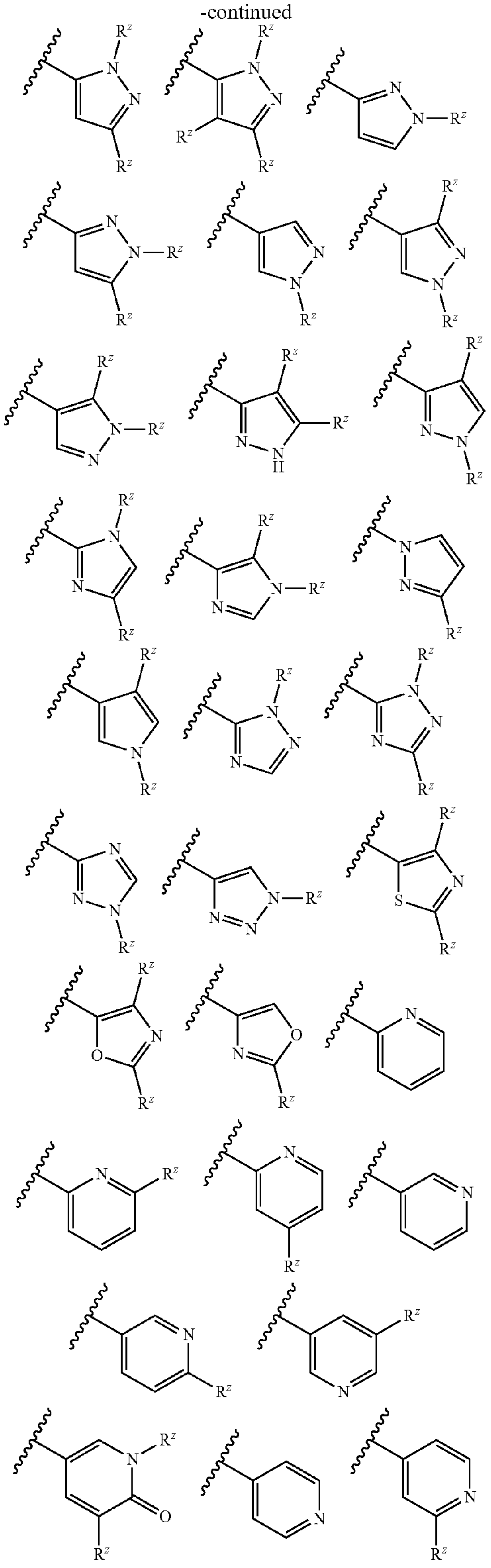
-continued
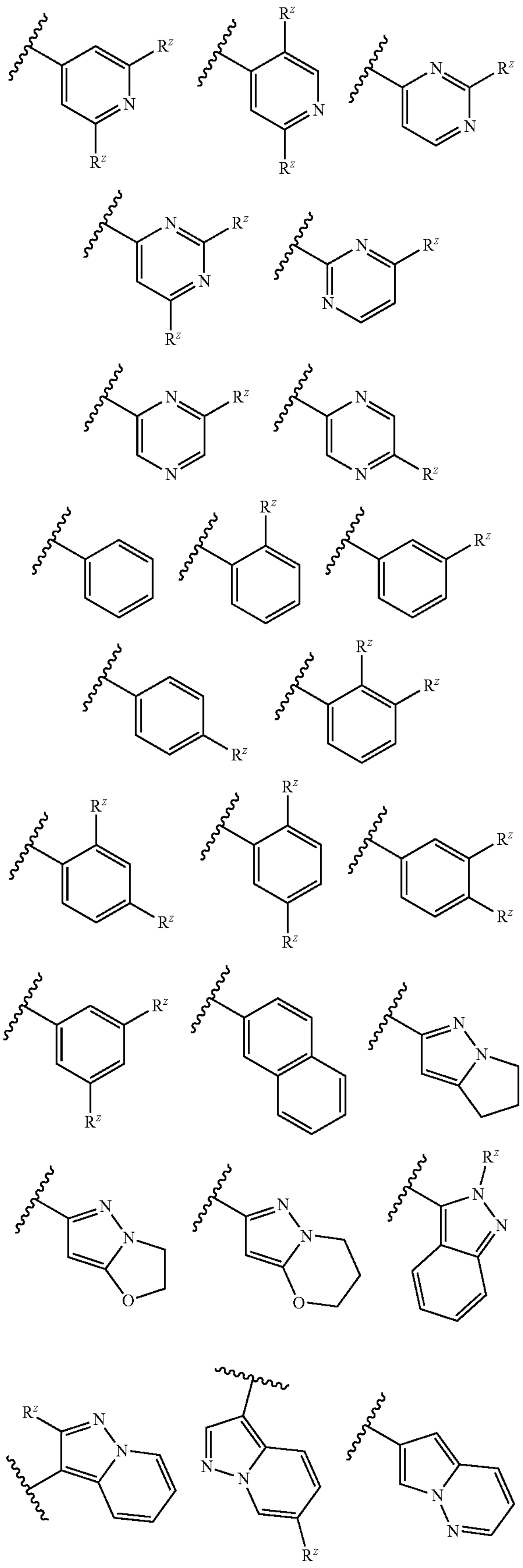

-continued
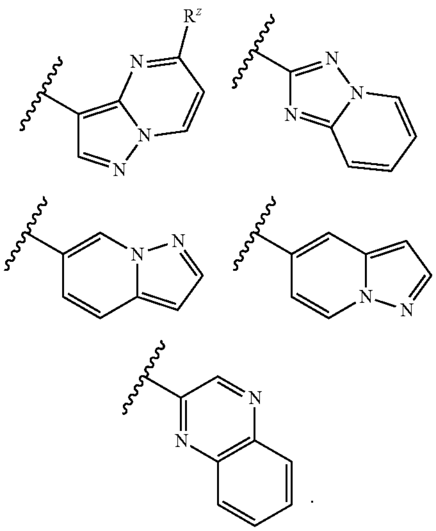
13. The compound according to claim 12, wherein at least one $R^z$ is $-CF_3$ or $-CN$.
14. The compound according to claim 12, wherein each $R^z$ is independently selected from $-CH_3$, $-CH_2CH_3$, $-CH(CH_3)_2$, cyclopropyl, $-F$, $-Cl$, $-CN$, $-CF_3$, $-CHF_2$, $-CF_2CH_3$, $-CH_2CN$, $-CH_2OCH_3$, $-OCH_3$, $-OCH_2CH_3$, and $-SO_2CH_3$.
15. The compound according to claim 12, wherein $R^3$ is selected
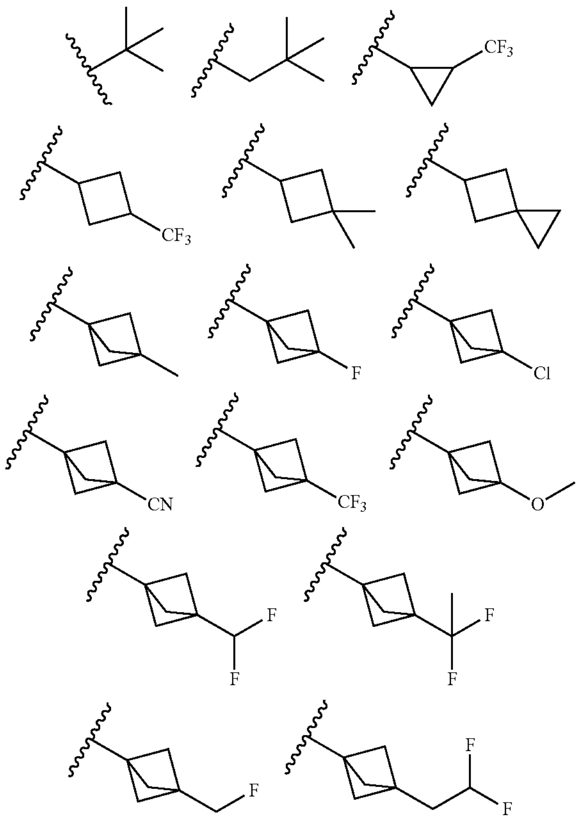
-continued
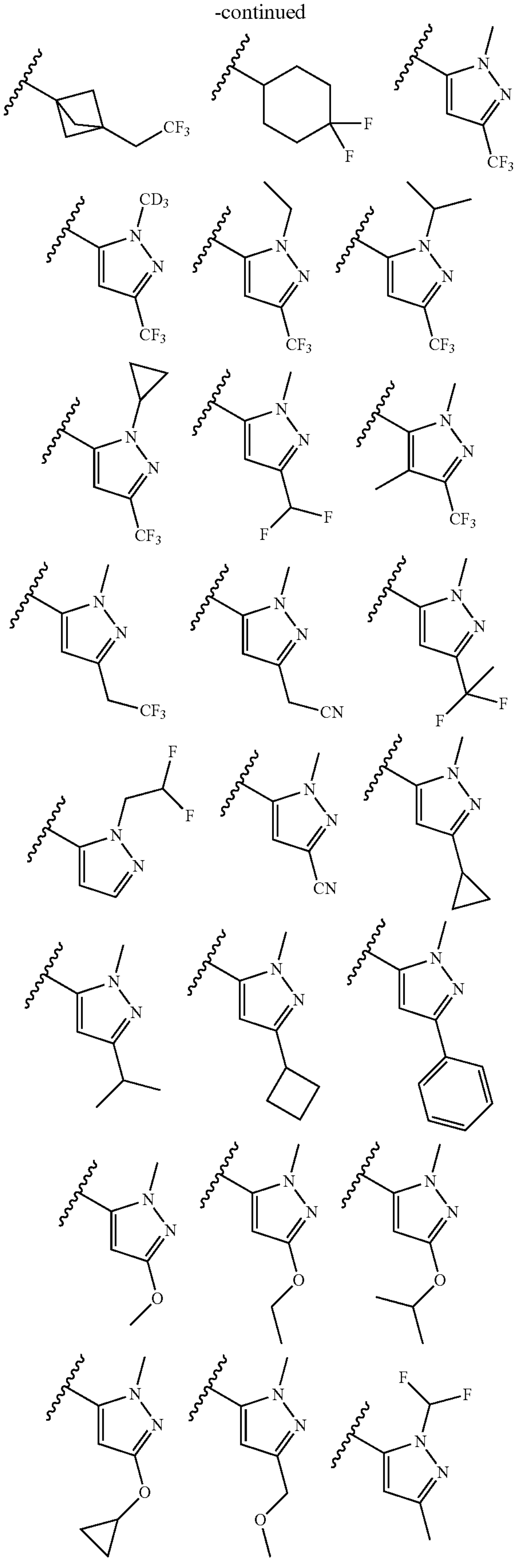

-continued
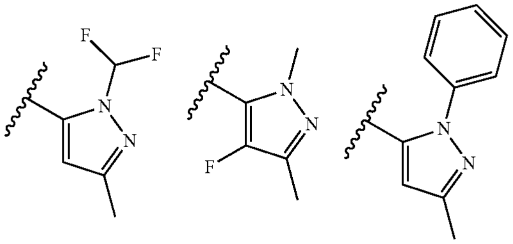
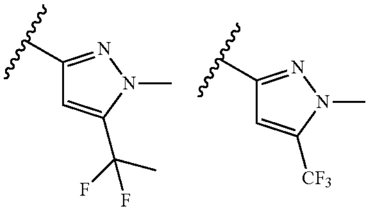
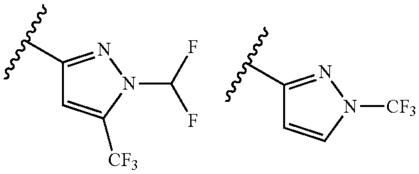
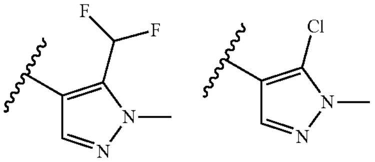
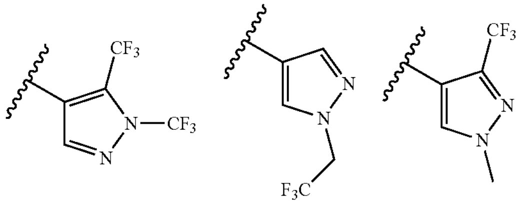
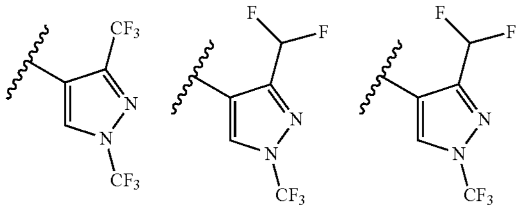
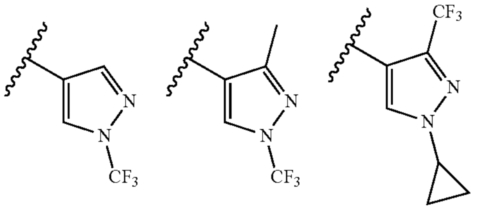
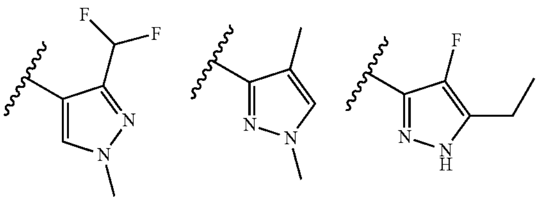
-continued
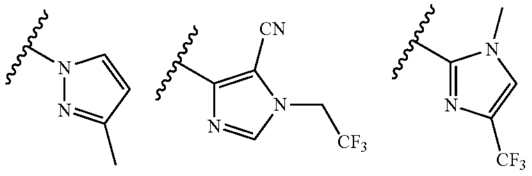
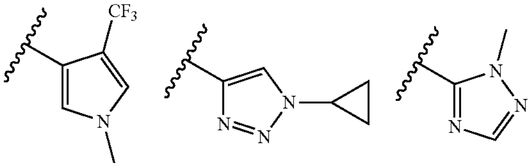
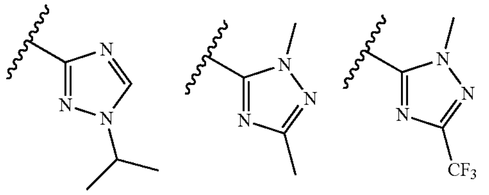
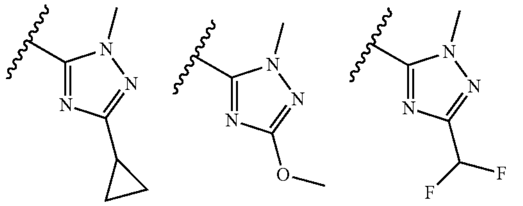
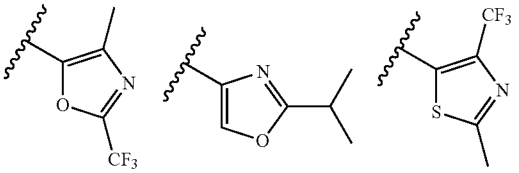
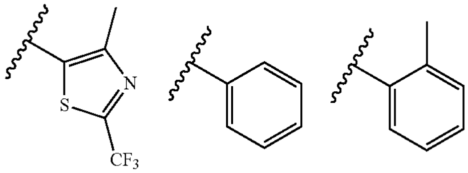
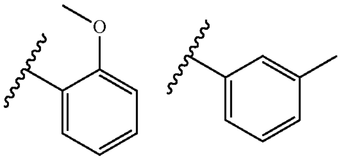
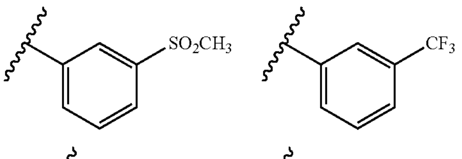
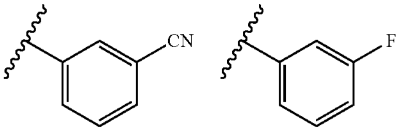
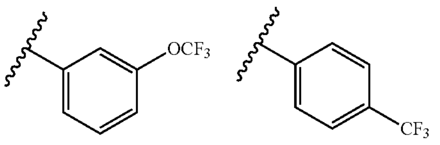

-continued
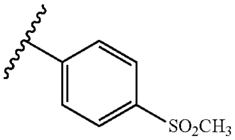
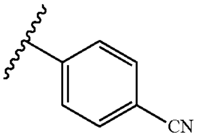
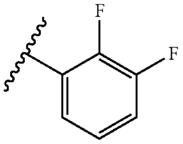
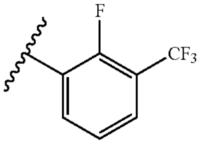
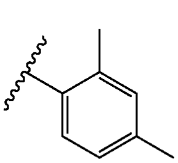
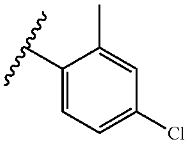
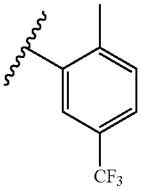
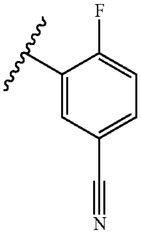
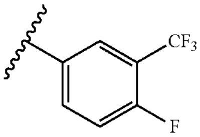
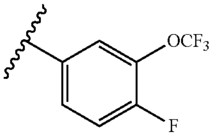
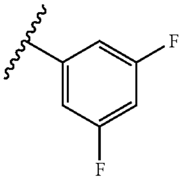
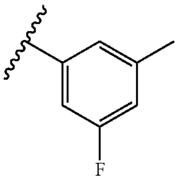
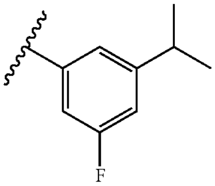
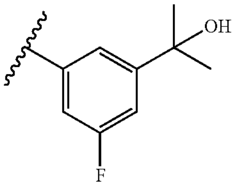
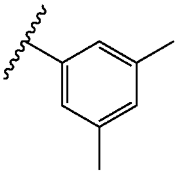
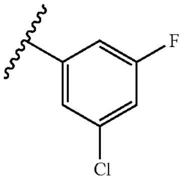
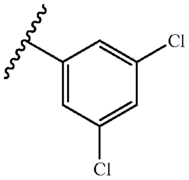
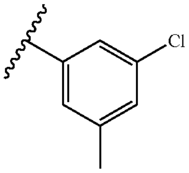
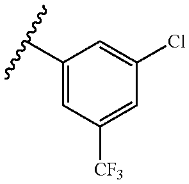
-continued
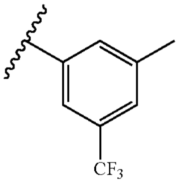
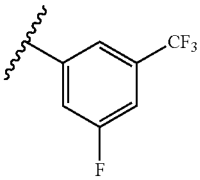
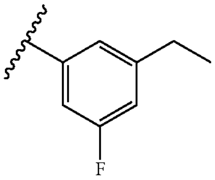
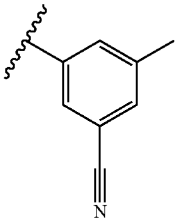
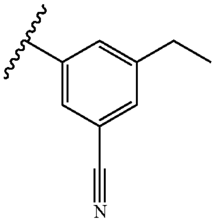
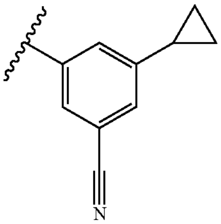
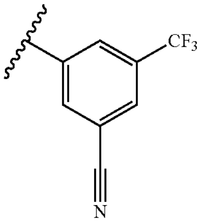
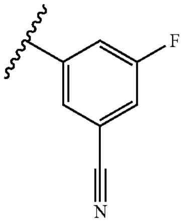
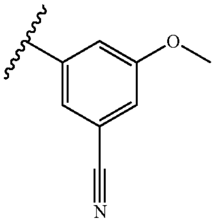
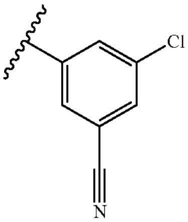
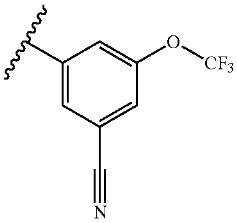
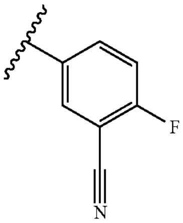
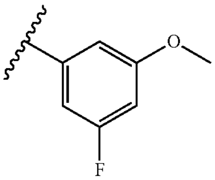
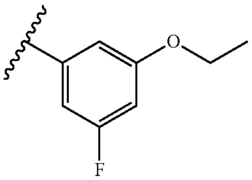
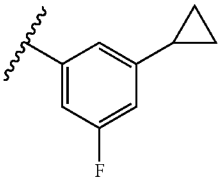
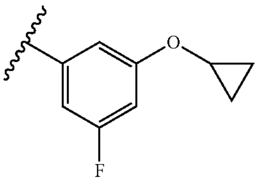

-continued
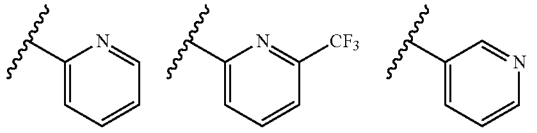
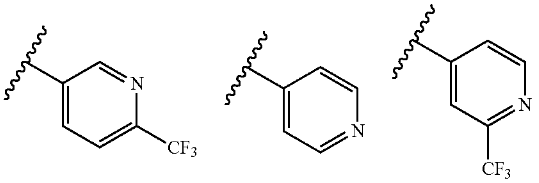
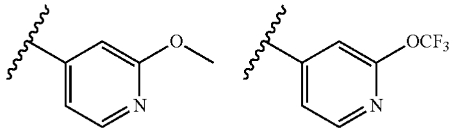
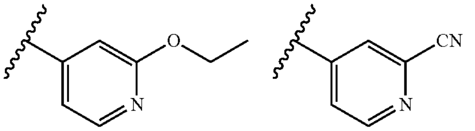
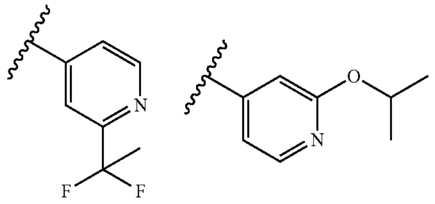
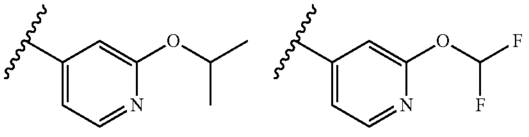
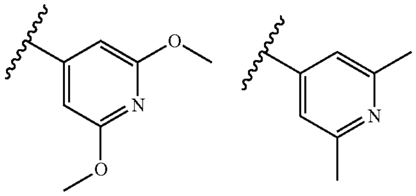
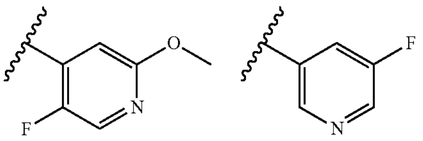
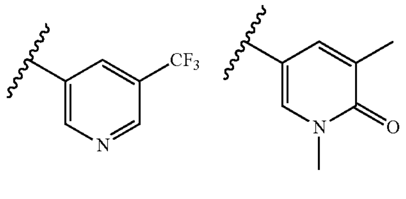
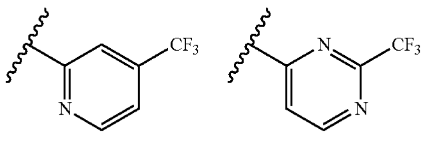
-continued
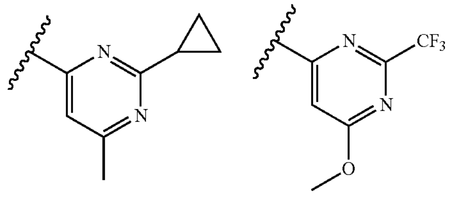
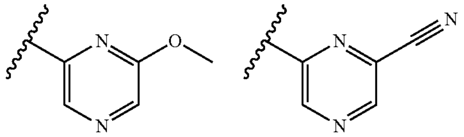
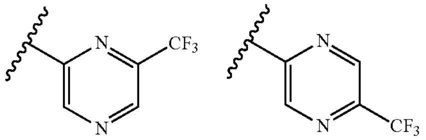
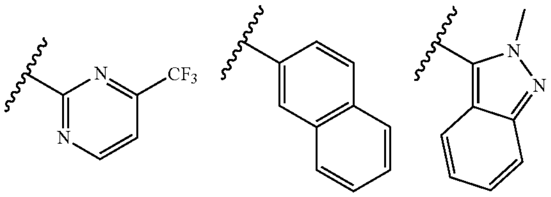
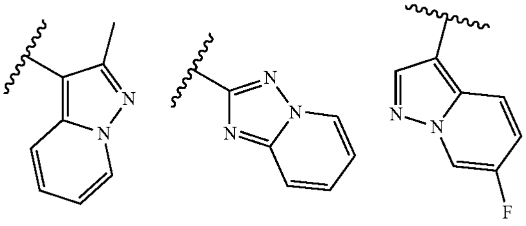
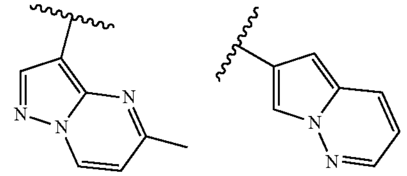
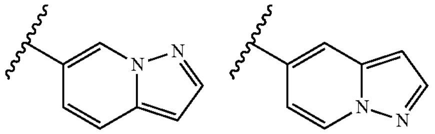
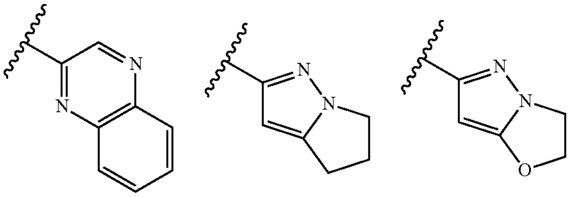
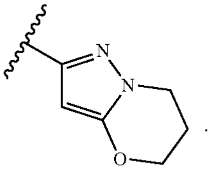
16. A pharmaceutical composition comprising a compound according to claim 1, or a pharmaceutically acceptable salt thereof, and one or more pharmaceutically acceptable excipients, carriers, or diluents.
17. The compound according to claim 1, wherein the compound is selected from -continued
I-83
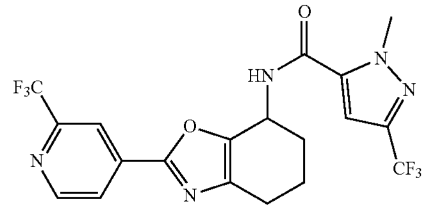
I-83a
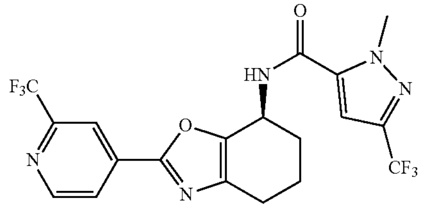
I-83b
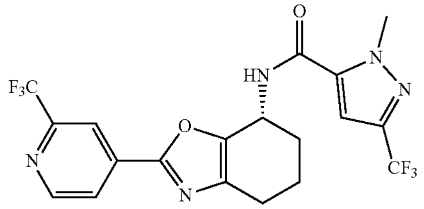
I-84
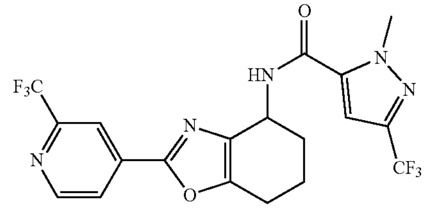
I-84a
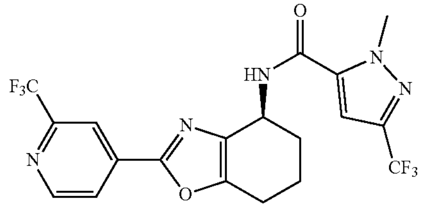
I-84b
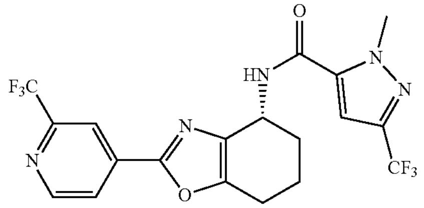
I-121
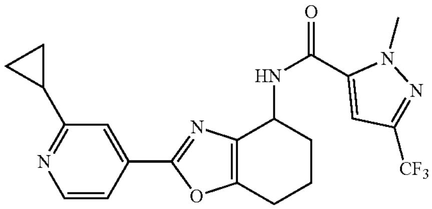
I-121a
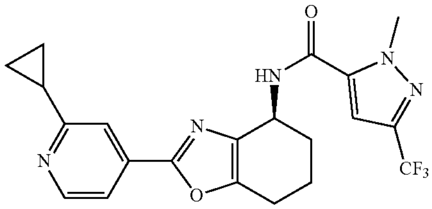
I-121b
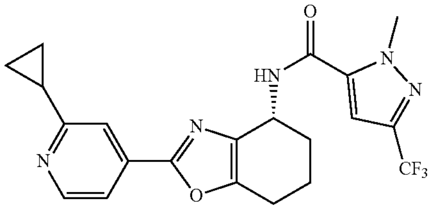
I-130
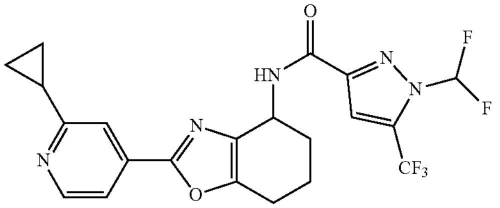
I-130a
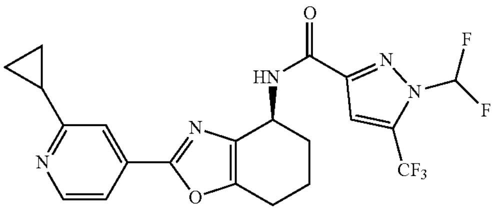
I-130b
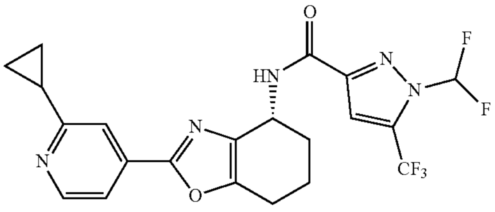
I-131
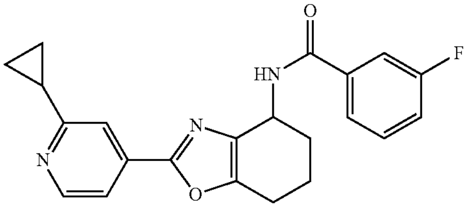
I-131a
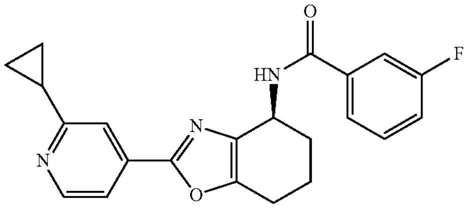

I-131b
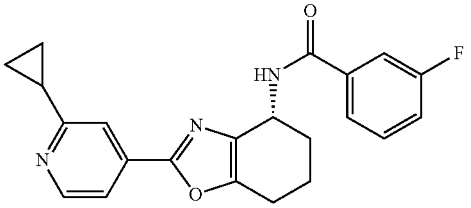
I-132
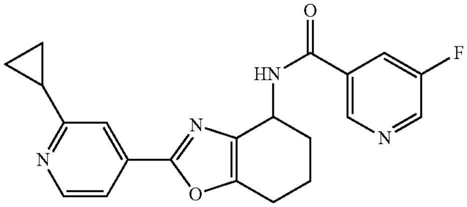
I-132a
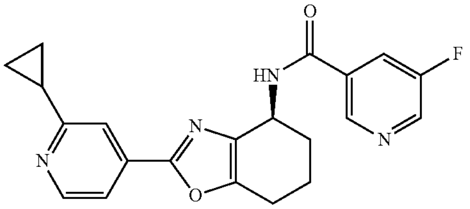
I-132b
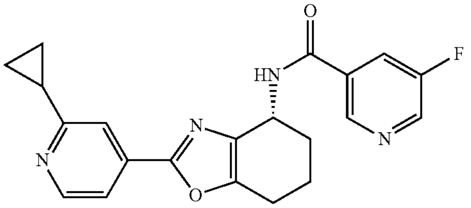
I-135
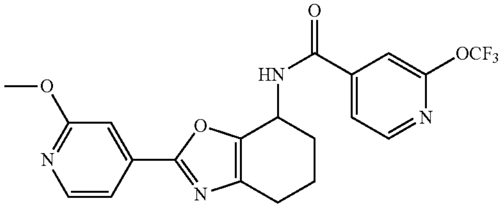
I-135a
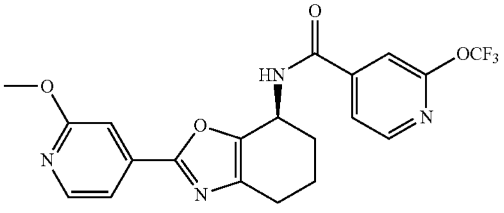
I-135b
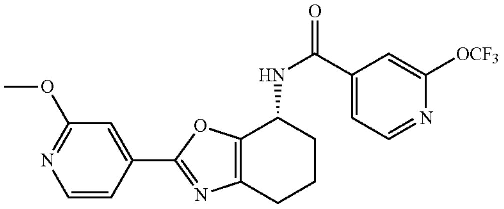
I-137
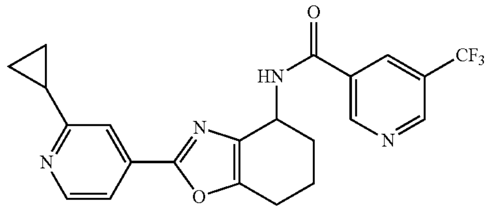
I-137a
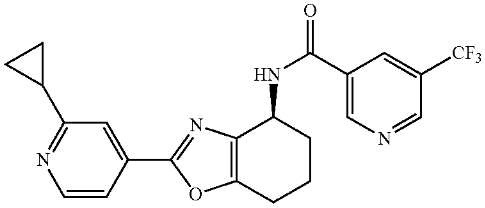
I-137b
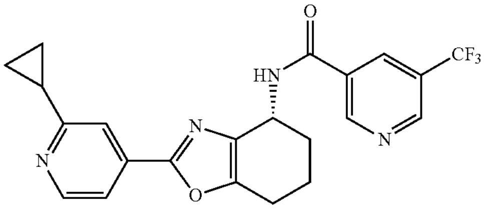
I-143
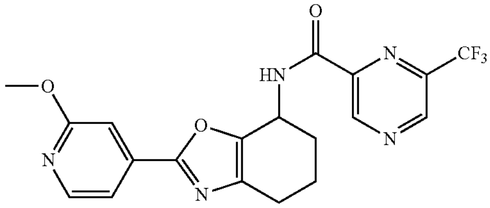
I-143a
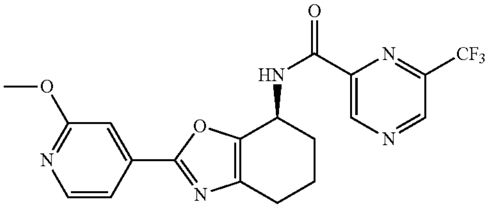
I-143b
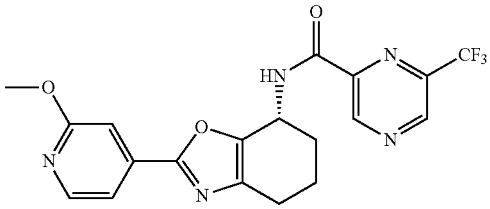
I-150
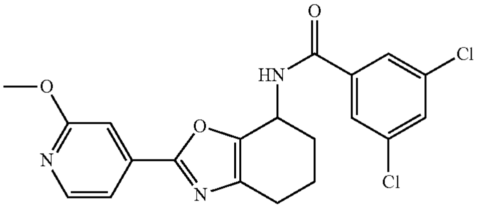

-continued
I-150a
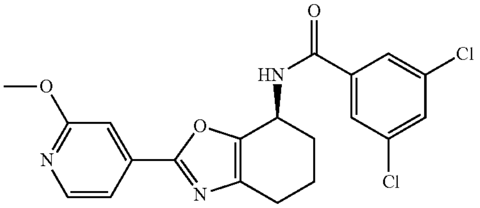
I-150b
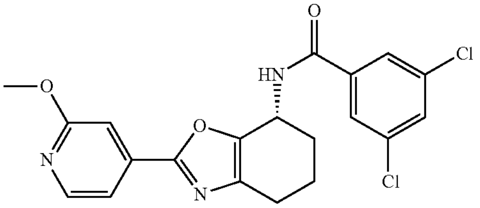
I-151
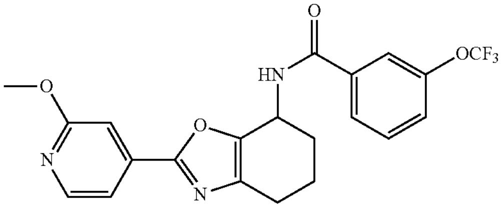
I-151a
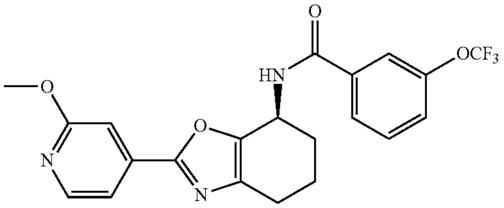
I-151b
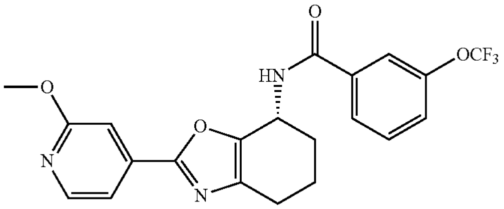
I-152
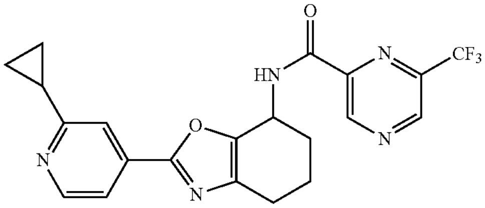
I-152a
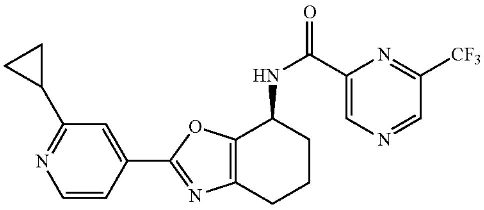
-continued
I-152b
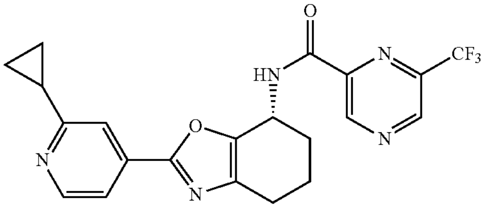
I-153
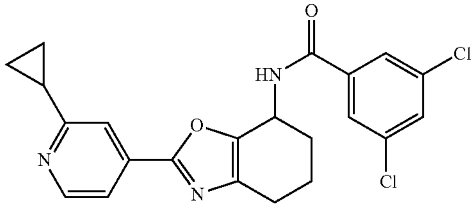
I-153a
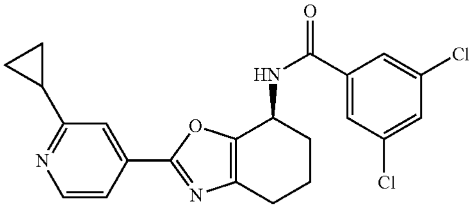
I-153b
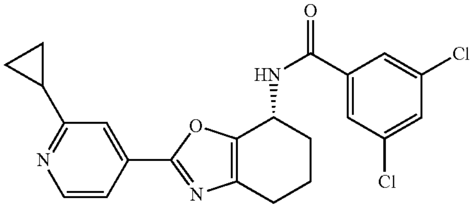
I-156
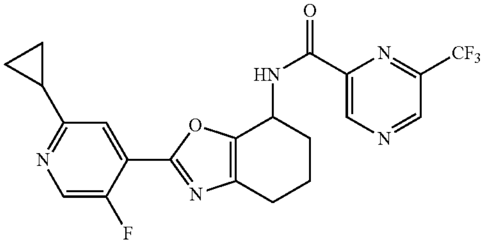
I-156a
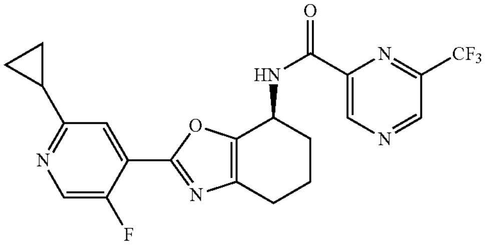

-continued
I-156b
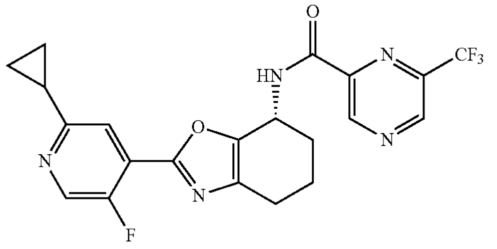
I-157
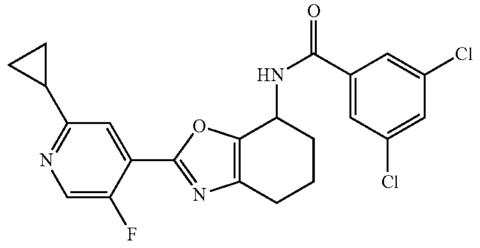
I-157a
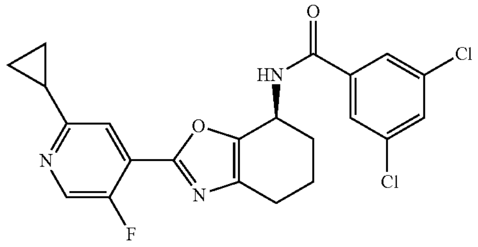
I-157b
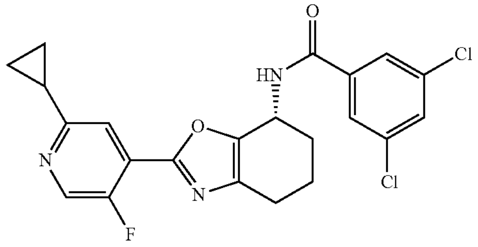
I-158
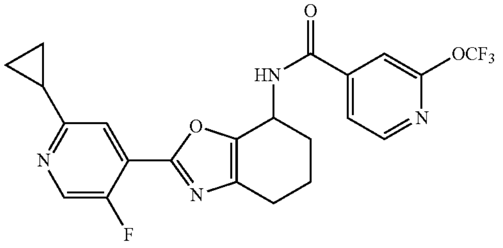
I-158a
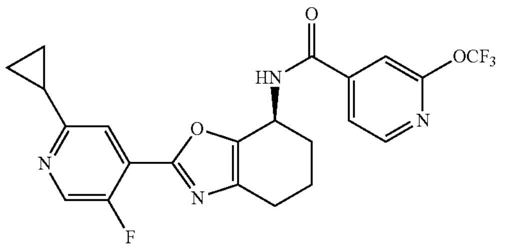
-continued
I-158b
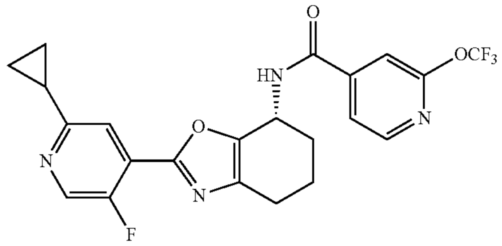
I-159
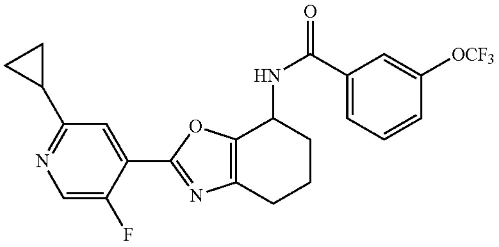
I-159a
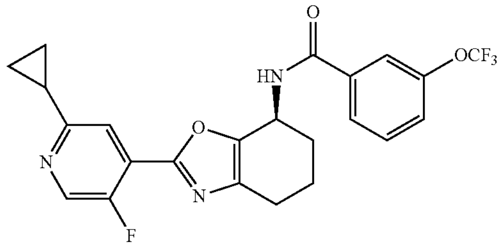
I-159b
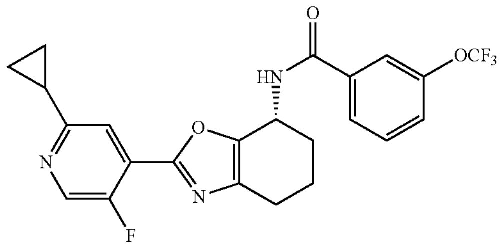
I-160
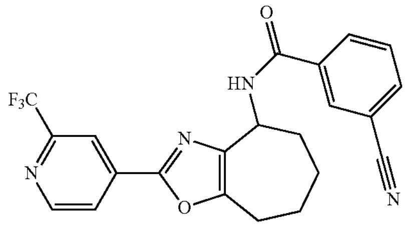
I-160a
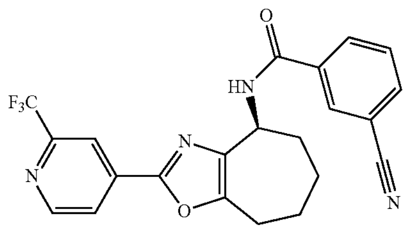

I-160b
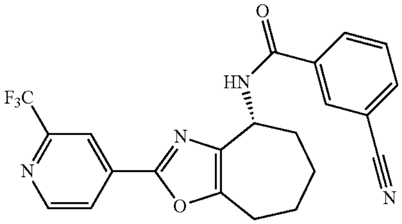
I-161
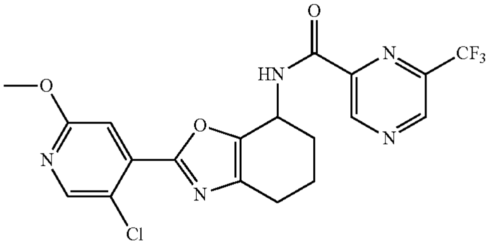
I-161a
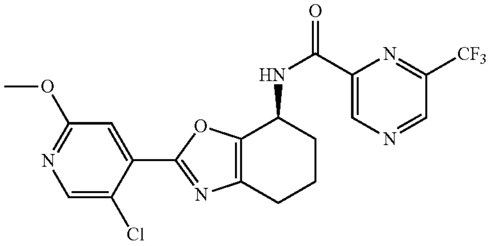
I-161b
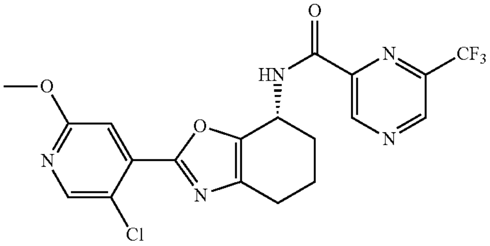
I-162
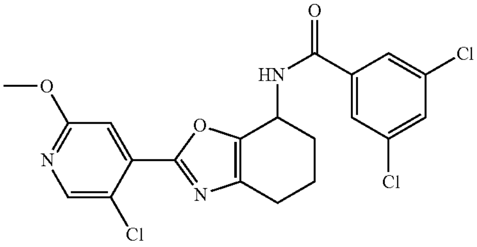
I-162a
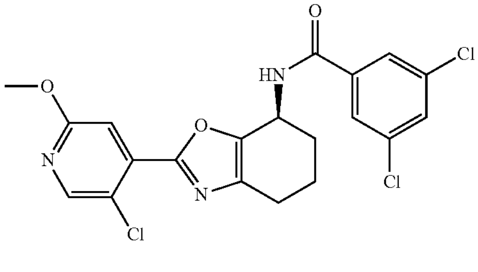
I-162b
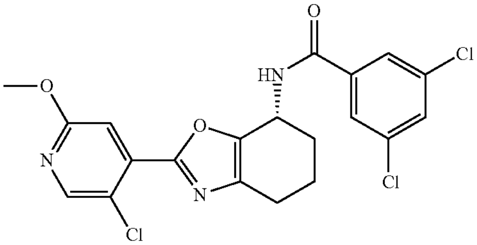
I-163
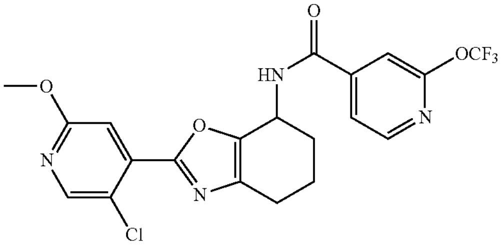
I-163a
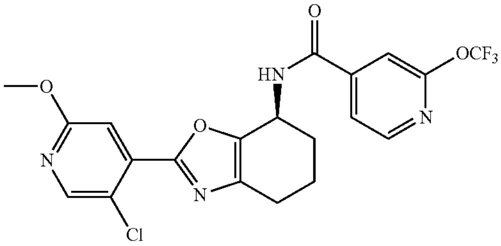
I-163b
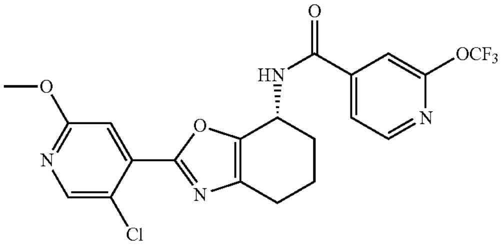
I-164
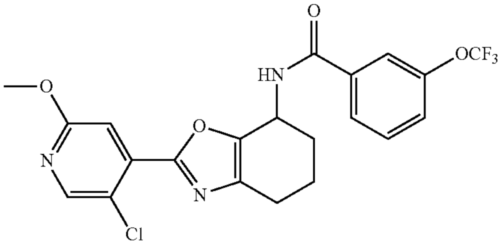
I-164a
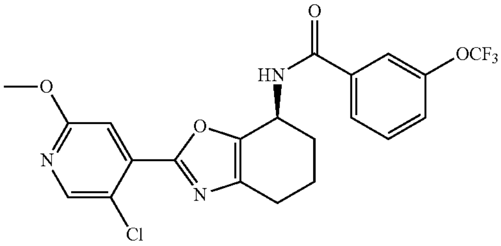

-continued
I-164b
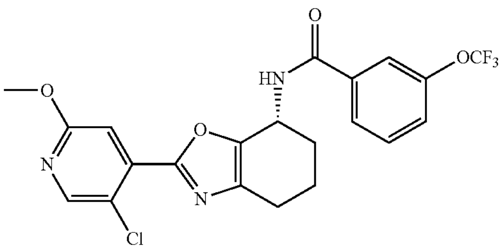
I-165
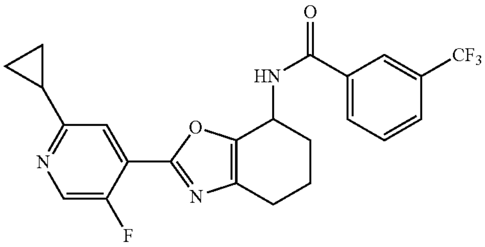
I-165a
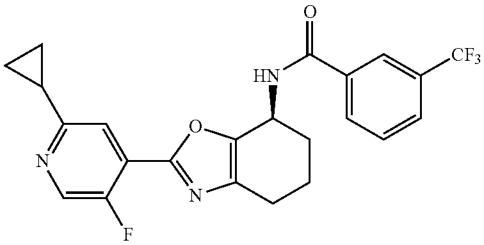
I-165b
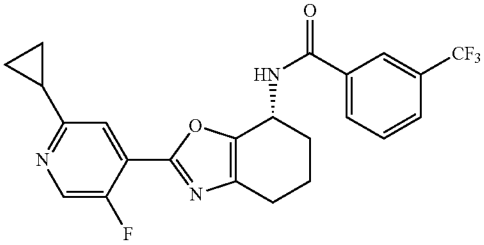
I-166
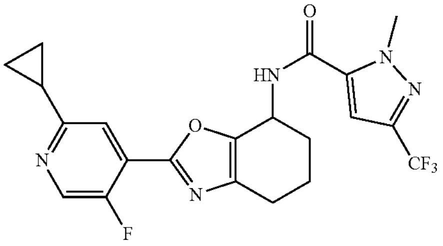
I-166a
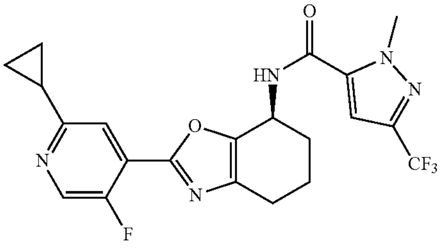
-continued
I-166b
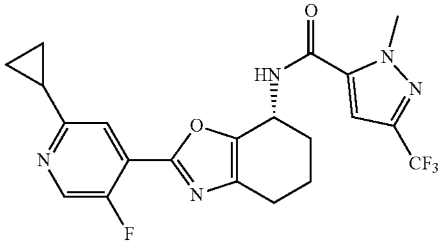
I-167
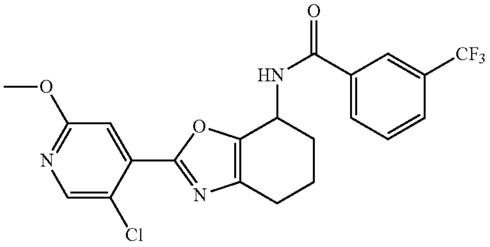
I-167a
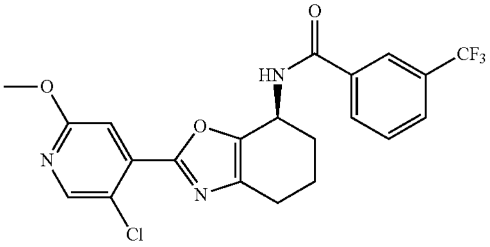
I-167b
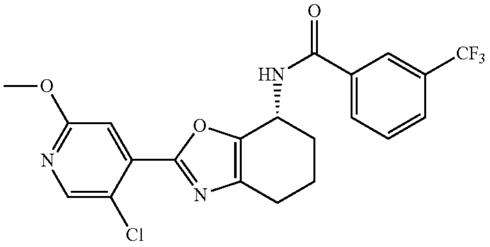
I-168
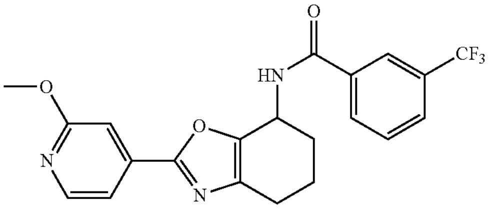
I-168a
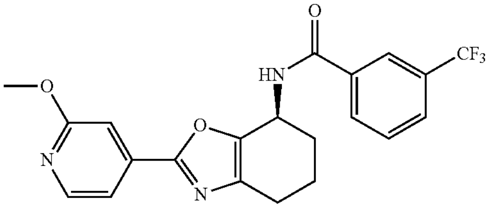

-continued
I-168b
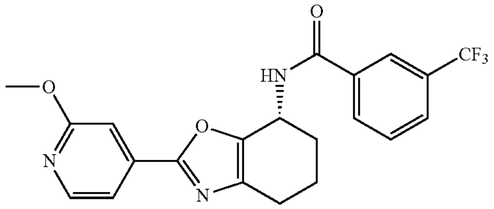
I-169
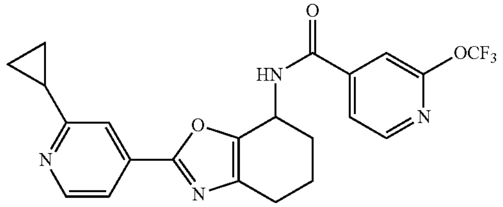
I-169a
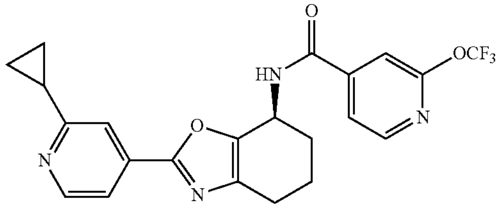
I-169b
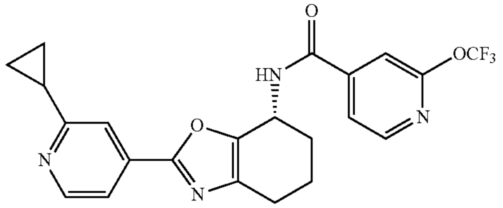
I-170
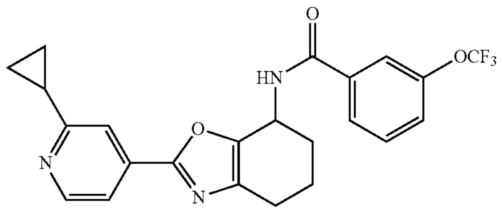
I-170a
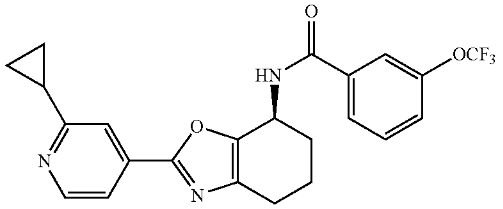
I-170b
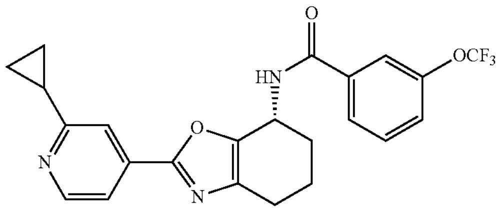
-continued
I-171
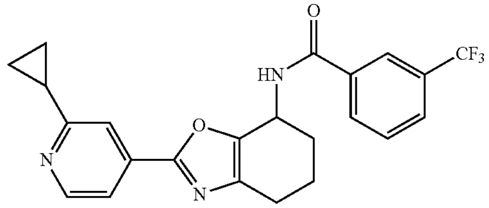
I-171a
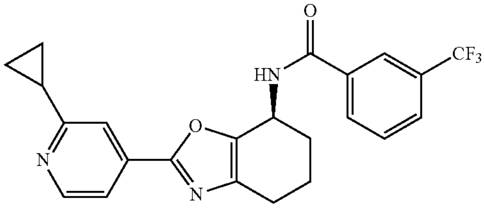
I-171b
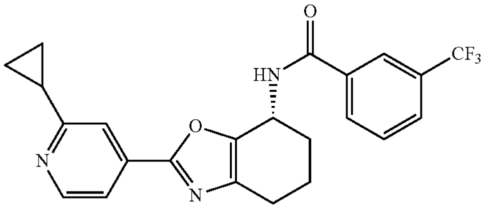
I-173
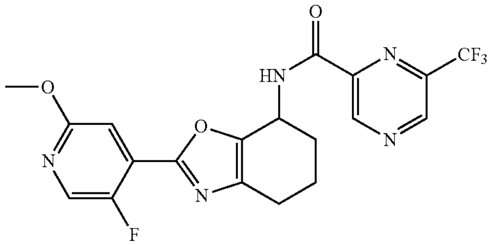
I-173a
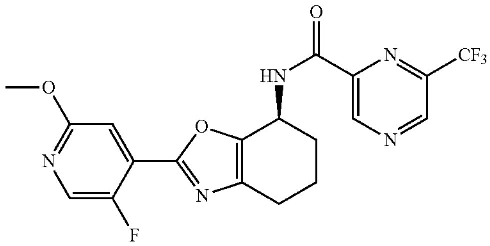
I-173b
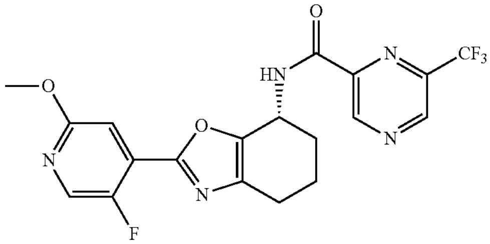

I-174
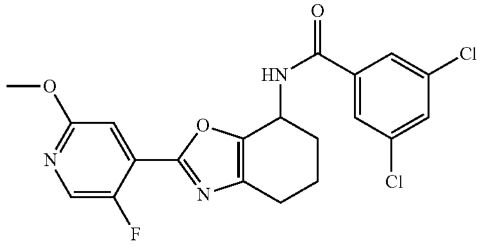
I-174a
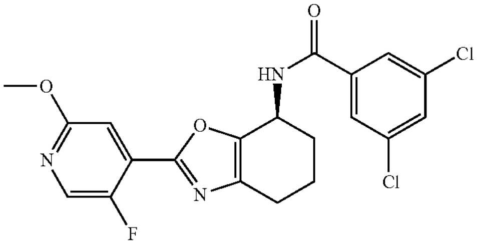
I-174b
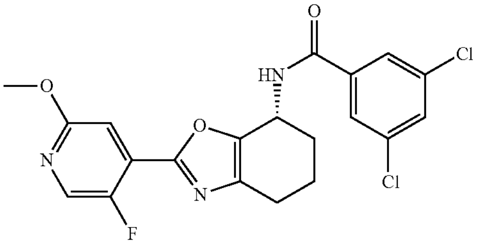
I-175
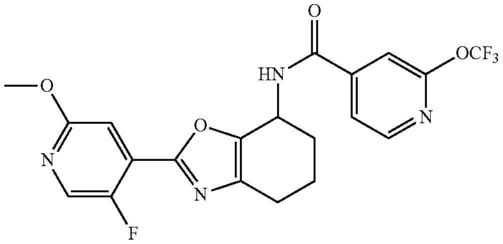
I-175a
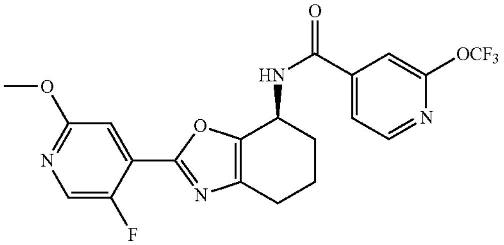
I-175b
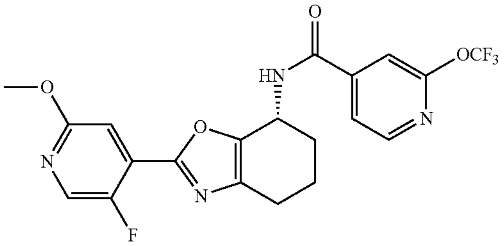
I-176
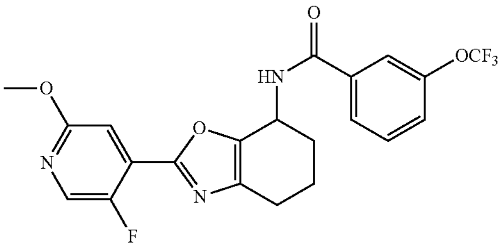
I-176a
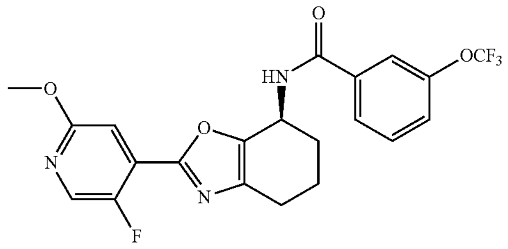
I-176b
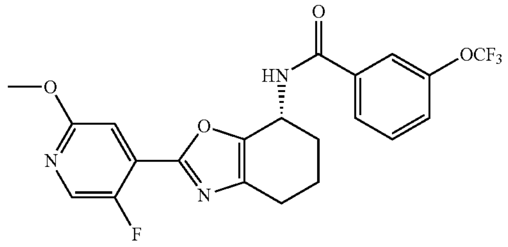
I-177
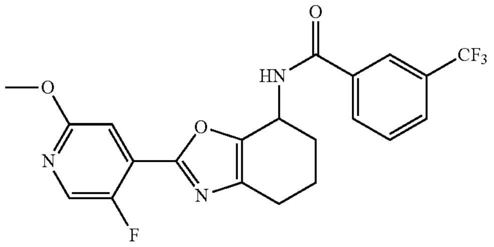
I-177a
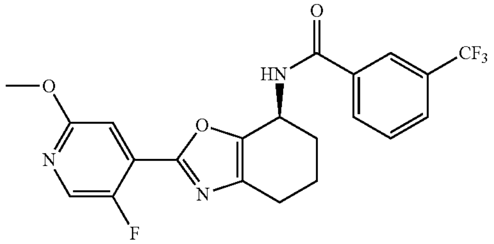
I-177b
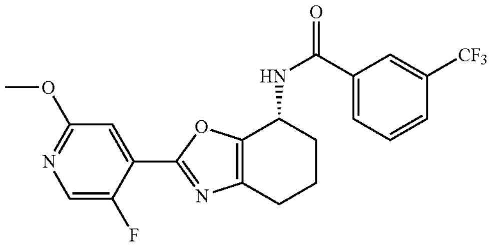

-continued
I-178
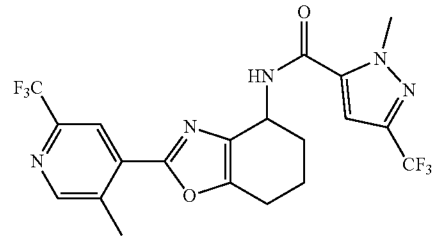
I-178a
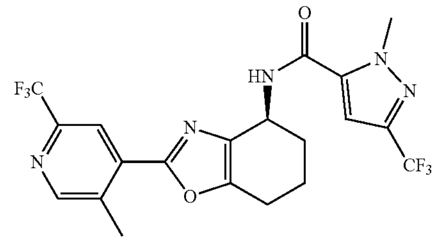
I-178b
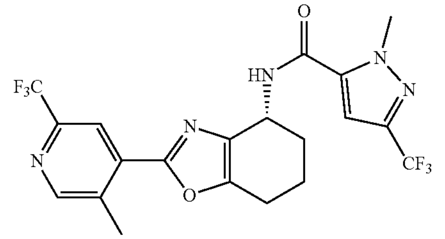
I-180
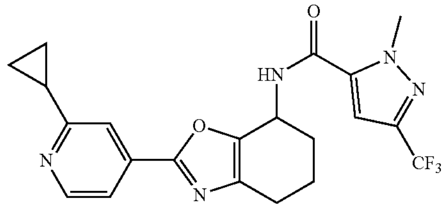
I-180a
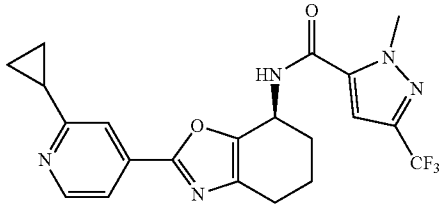
I-180b
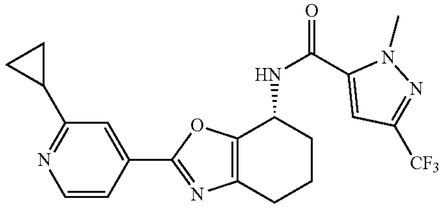
-continued
I-184
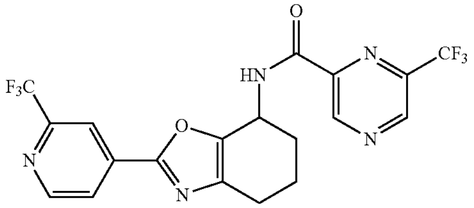
I-184a
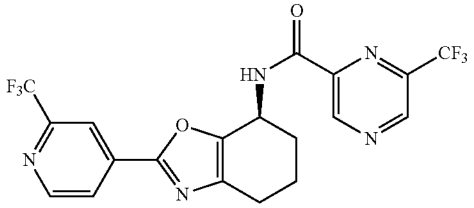
I-184b
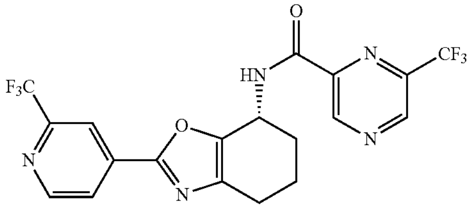
I-185
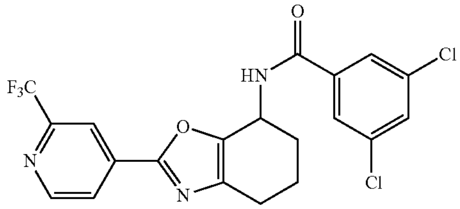
I-185a
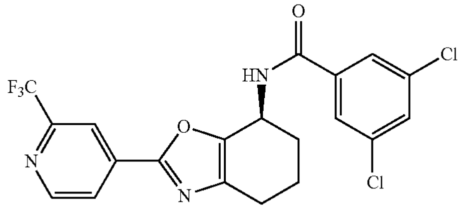
I-185b
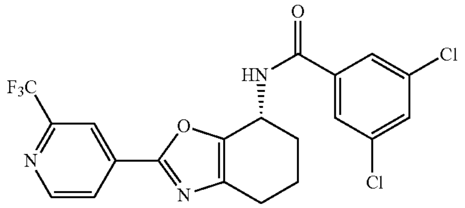
I-186
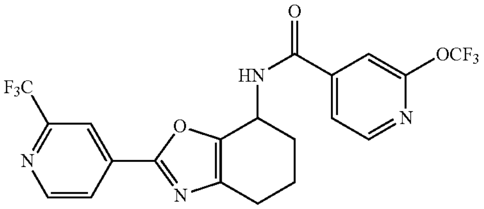

-continued
I-186a
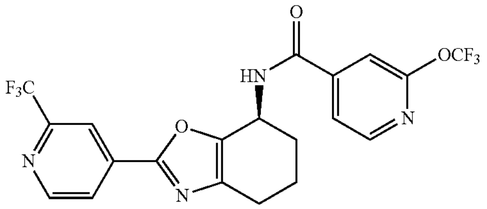
I-186b
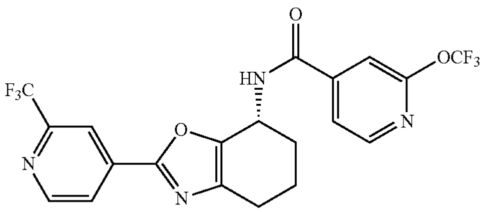
I-187
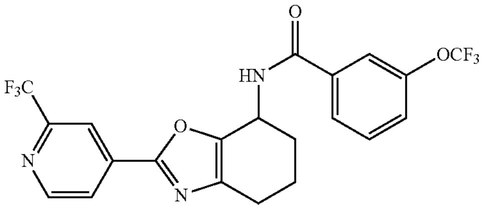
I-187a
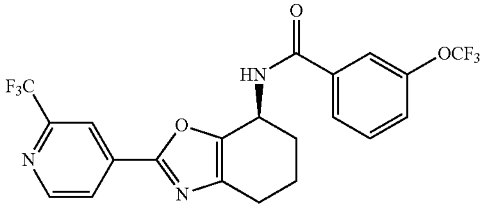
I-187b
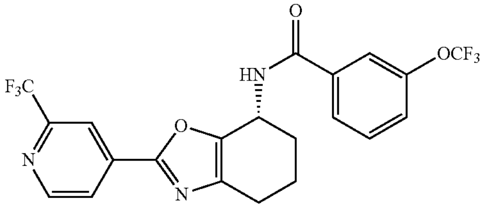
I-188
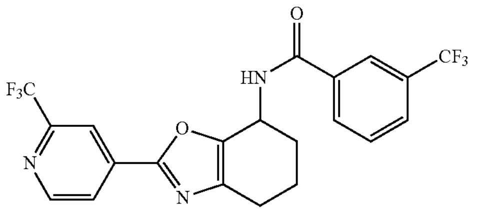
I-188a
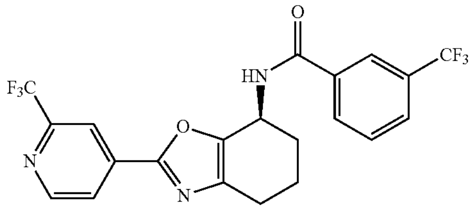
-continued
I-188b
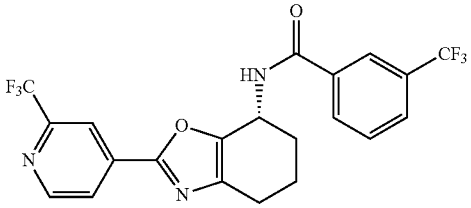
I-189
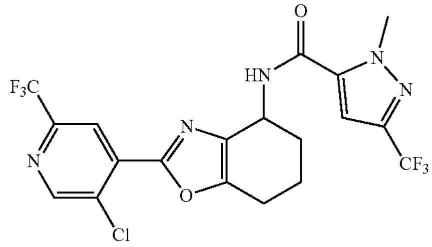
I-189a
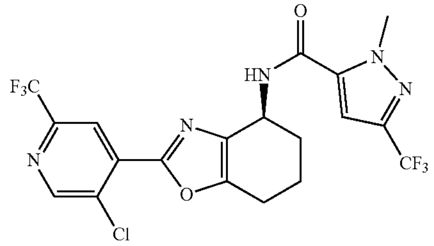
I-189b
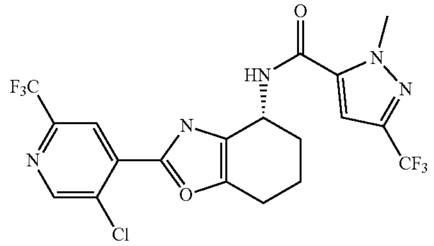
I-191
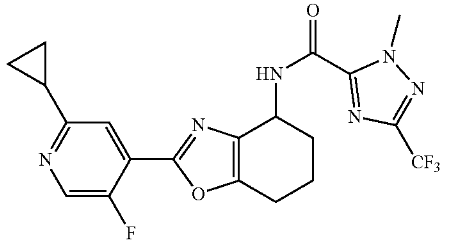
I-191a
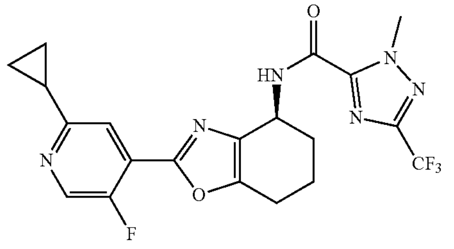

-continued
I-191b
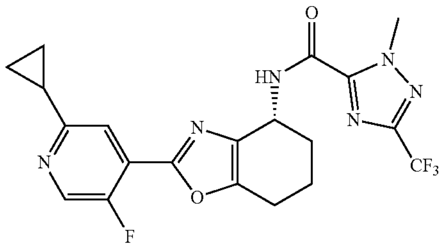
I-208
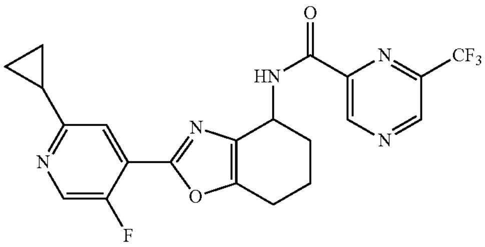
I-208a
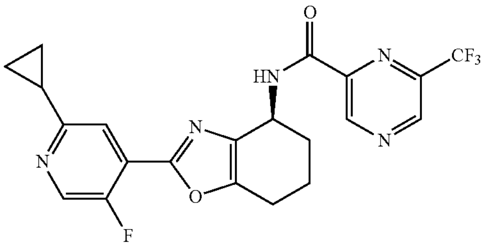
I-208b
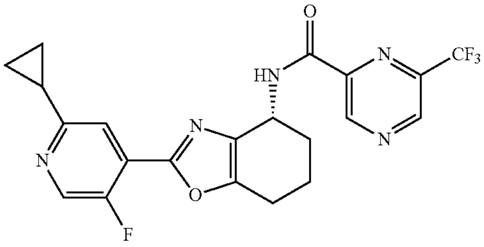
I-211
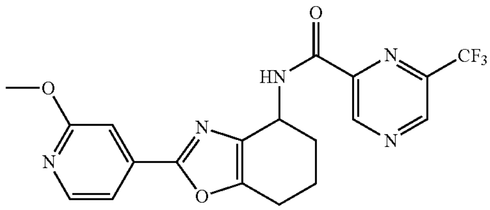
I-211a
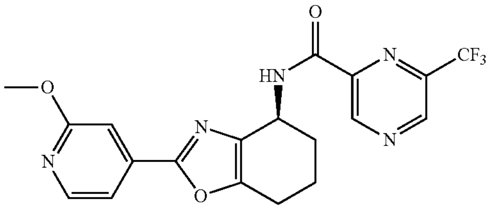
-continued
I-211b
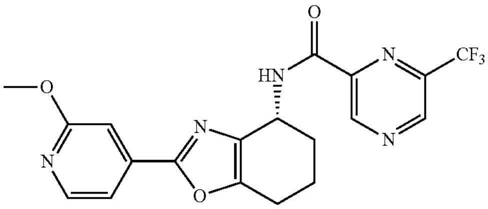
I-217
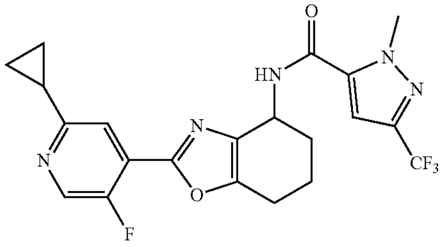
I-217a
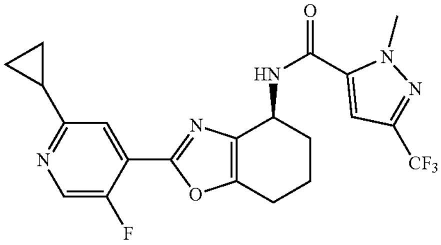
I-217b
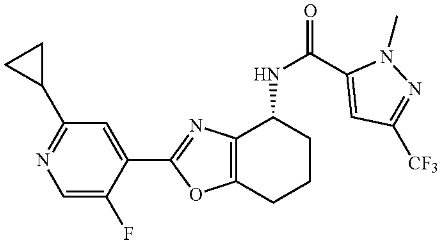
I-223
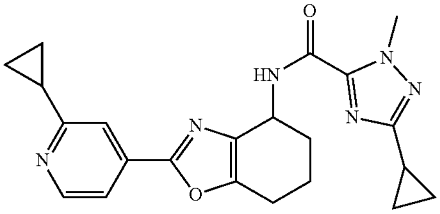
I-223a
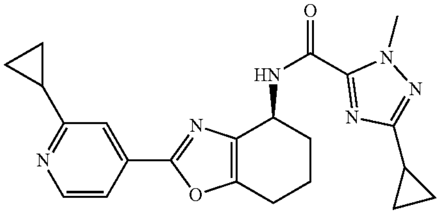
I-223b
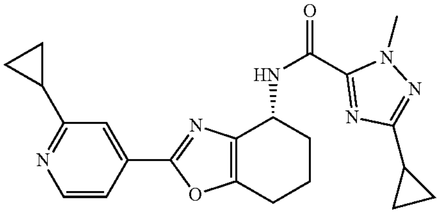

-continued
I-227
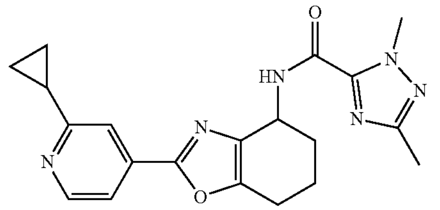
I-227a
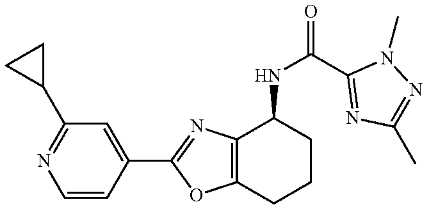
I-227b
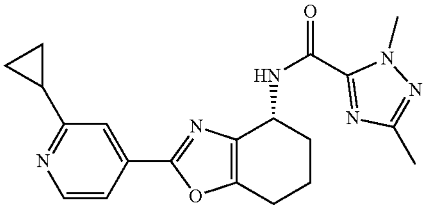
I-228
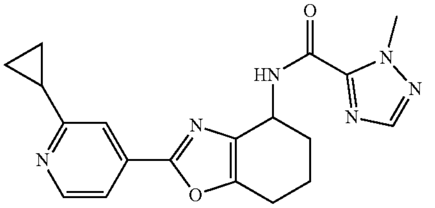
I-228a
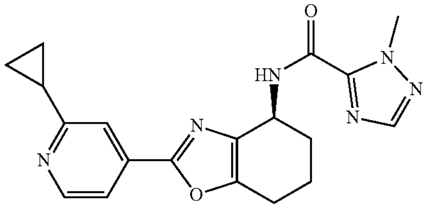
I-228b
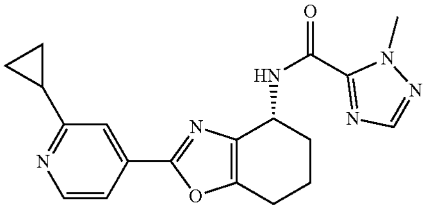
I-229
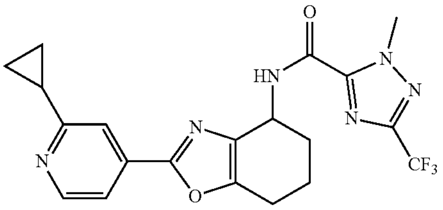
-continued
I-229a
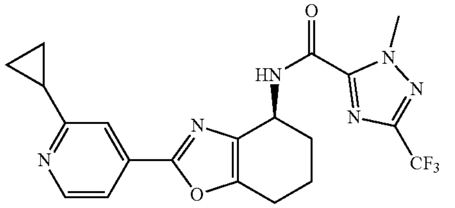
I-229b
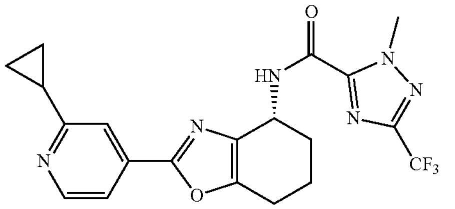
I-231
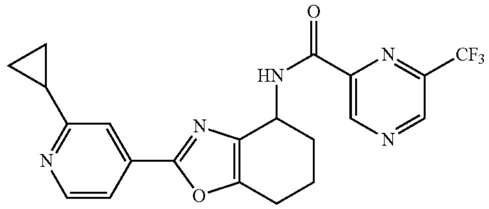
I-231a
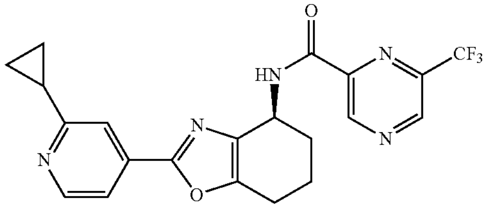
I-231b
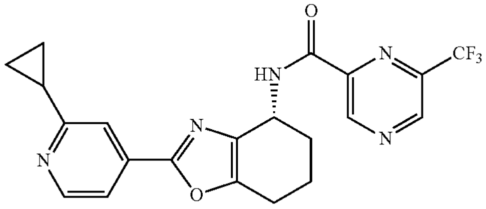
I-232
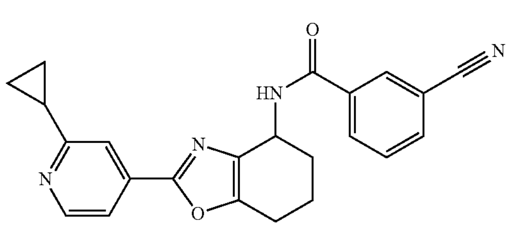
I-232a
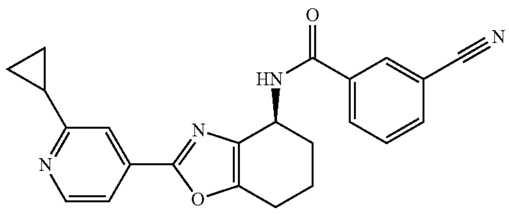

-continued
I-232b
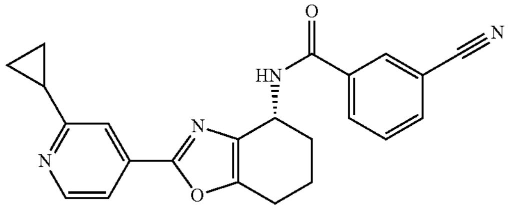
I-238
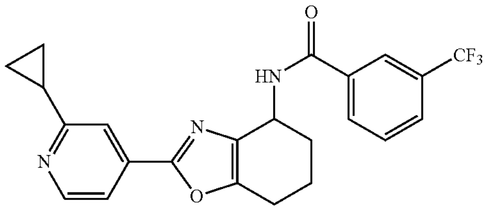
I-238a
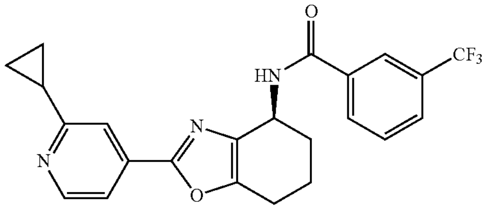
I-238b
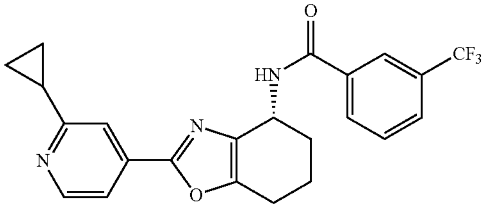
I-241
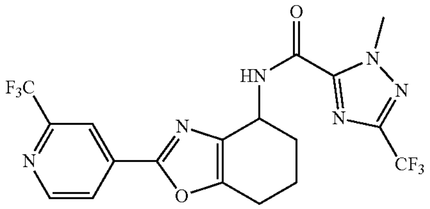
I-241a
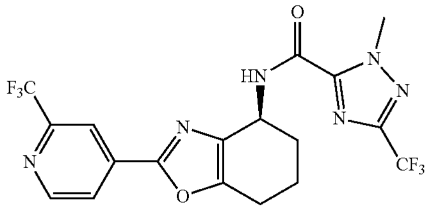
I-241b
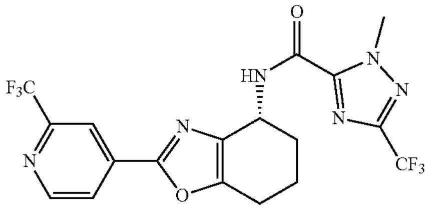
-continued
I-242
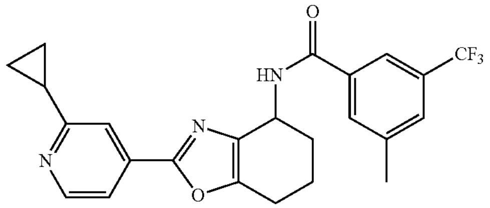
I-242a
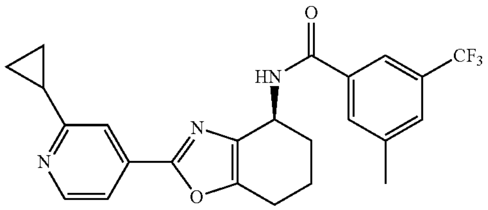
I-242b
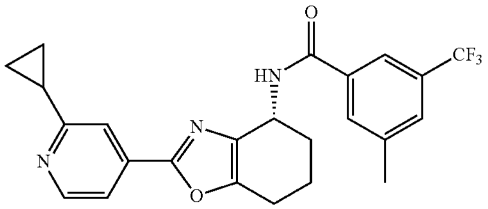
I-248
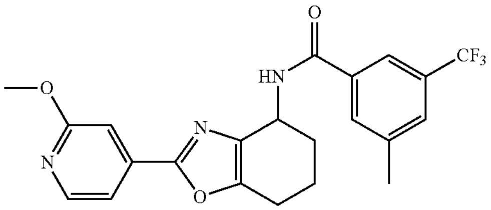
I-248a
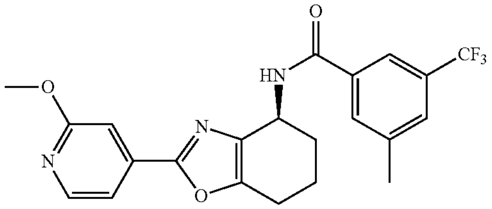
I-248b
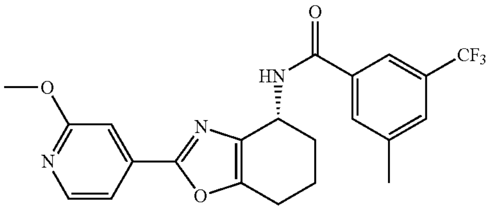
I-249
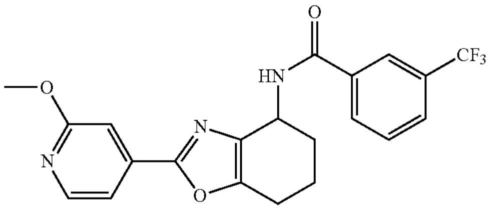

-continued
I-249a
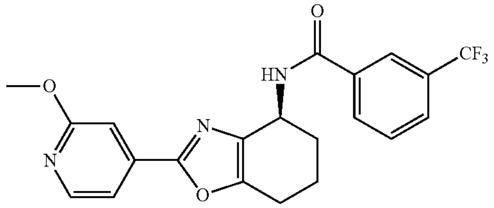
I-249b
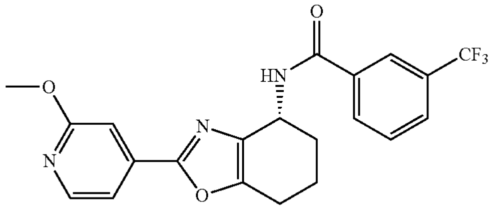
I-250
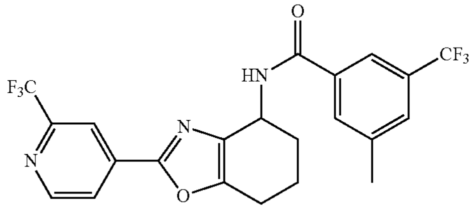
I-250a
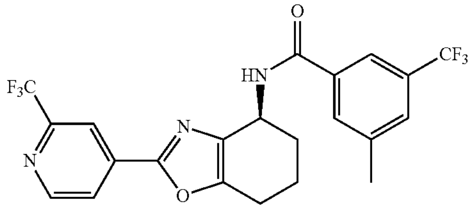
I-250b
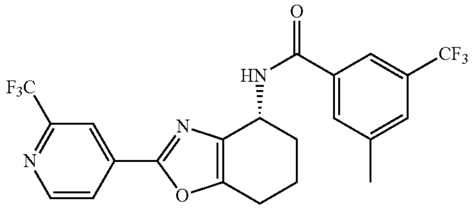
I-251
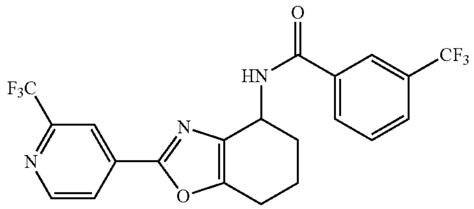
I-251a
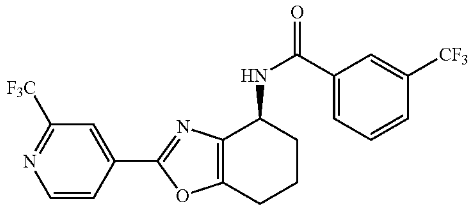
-continued
I-251b
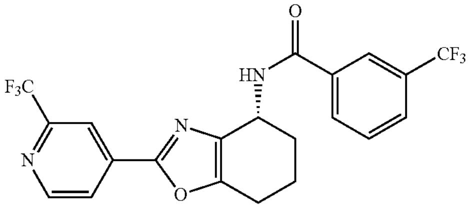
I-275
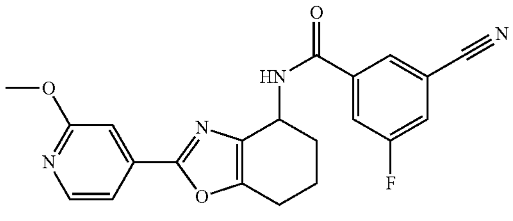
I-275a
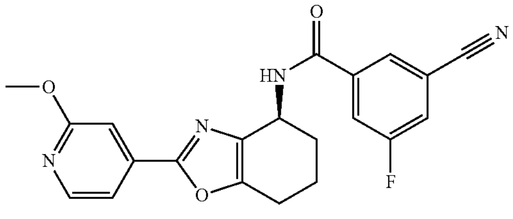
I-275b
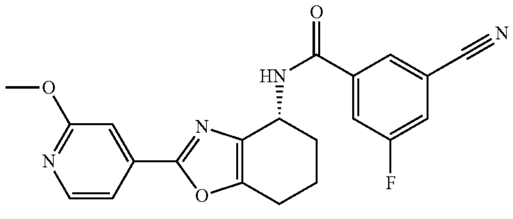
I-293
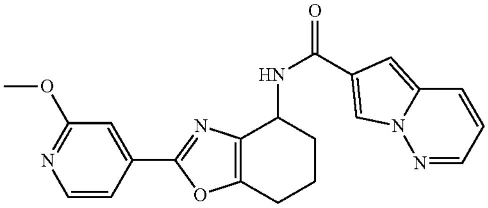
I-293a
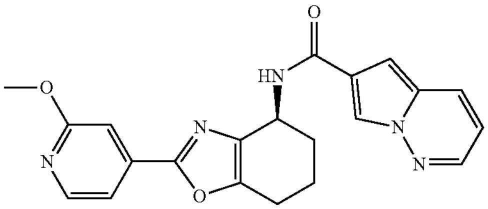
I-293b
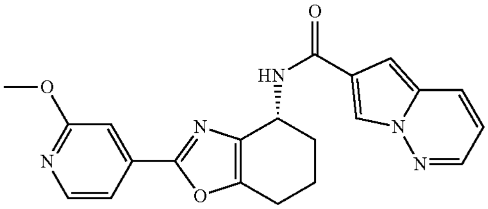

-continued
I-294
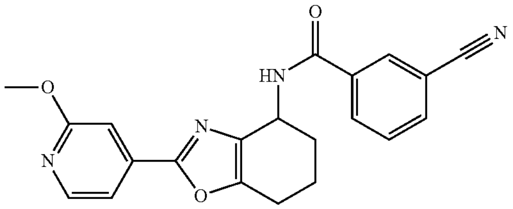
I-294a
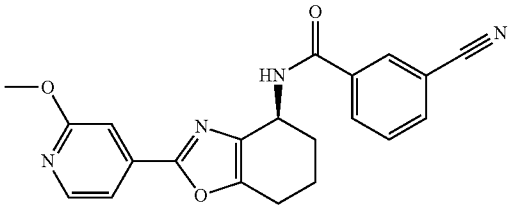
I-294b
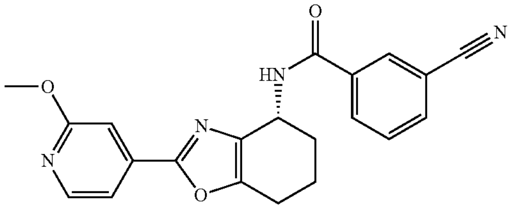
I-296
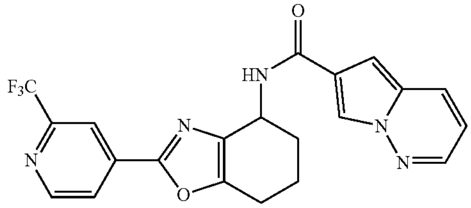
I-296a
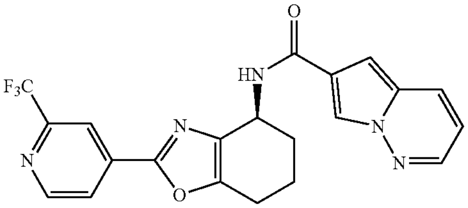
I-296b
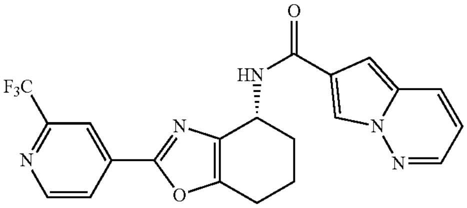
I-297
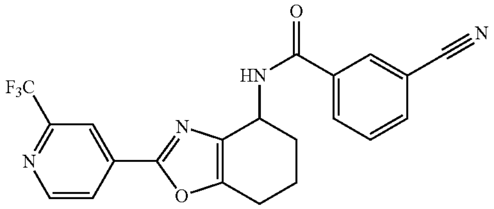
-continued
I-297a
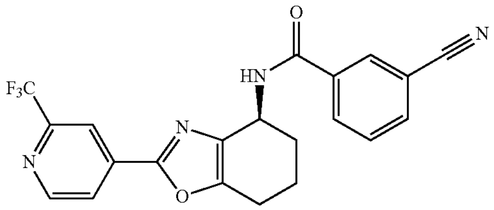
I-297b
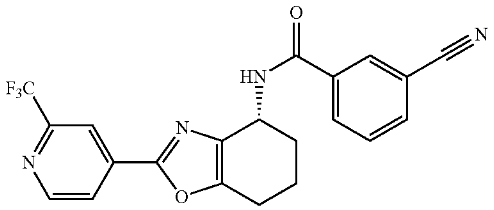
I-298
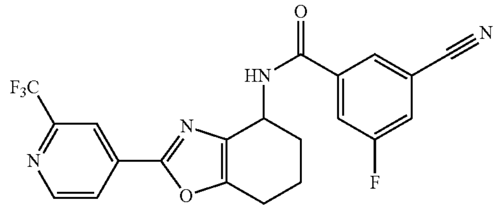
I-298a
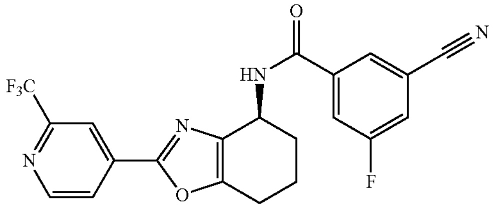
I-298b
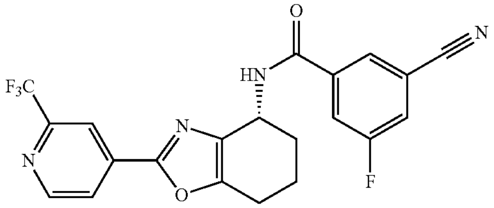
I-299
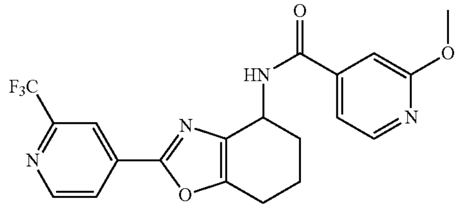
I-299a
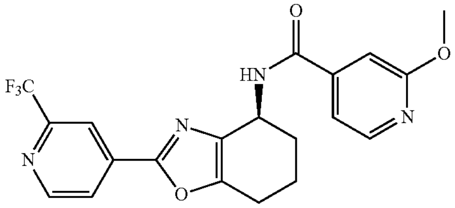

-continued
I-299b
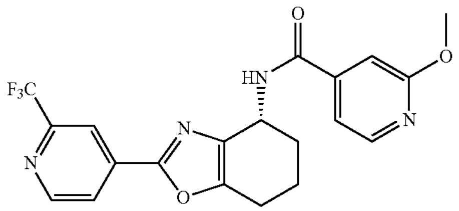
I-428
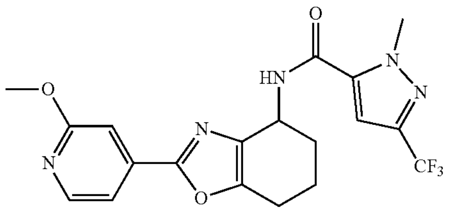
I-428a
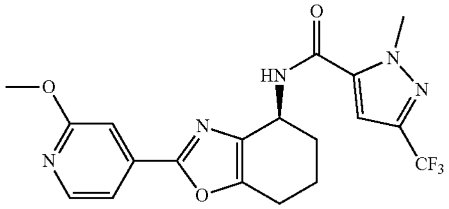
I-428b
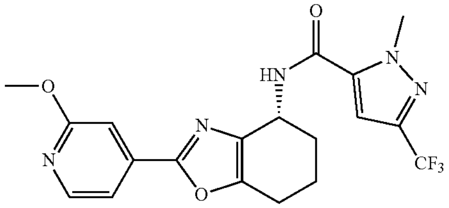
I-471
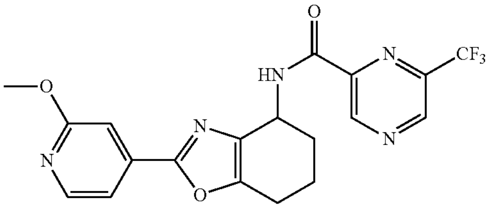
I-471a
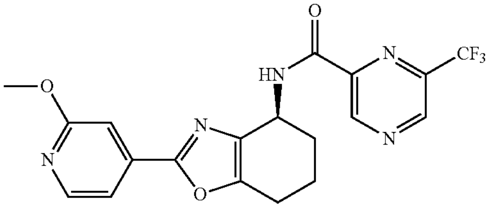
I-471b
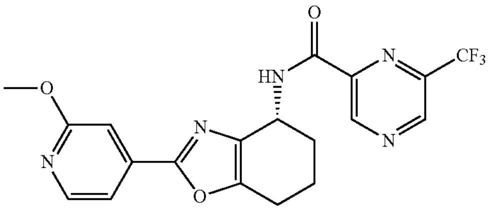
-continued
I-477
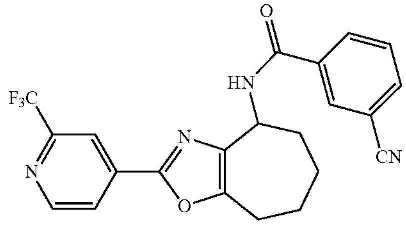
I-477a
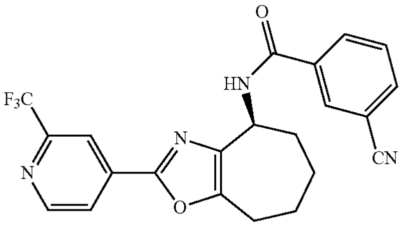
I-477b
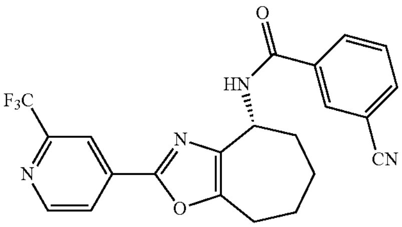
I-503
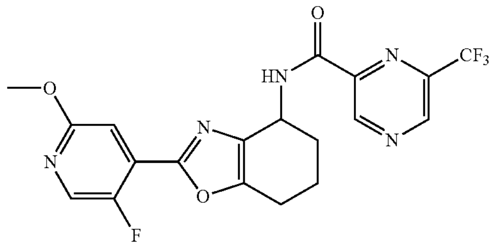
I-503a
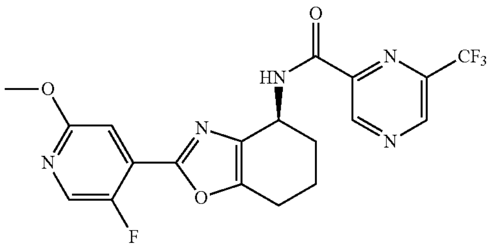
I-503b
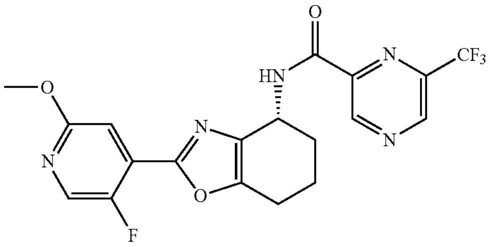

-continued
I-504
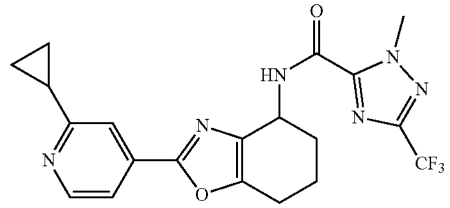
I-504a
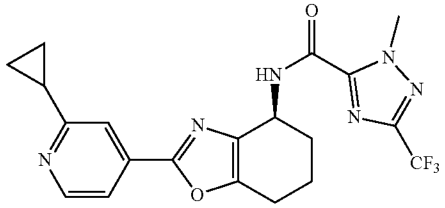
I-504b
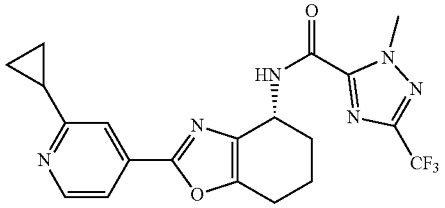
I-505
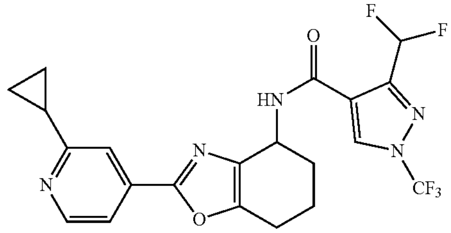
I-505a
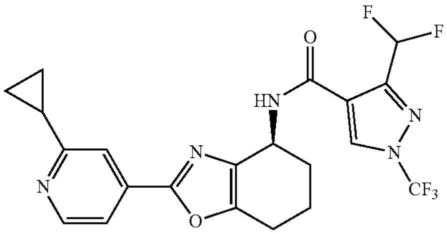
I-505b
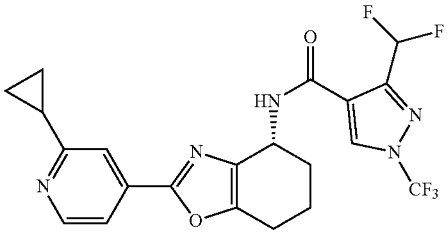
-continued
I-506
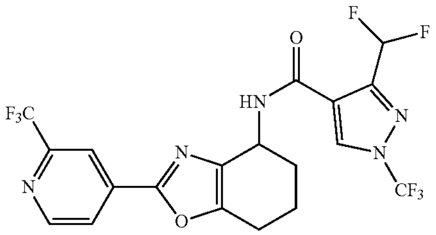
I-506a
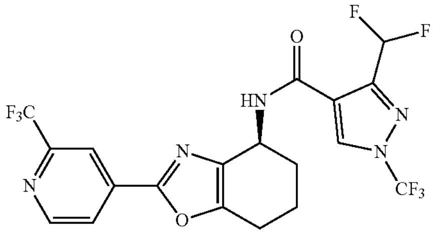
I-506b
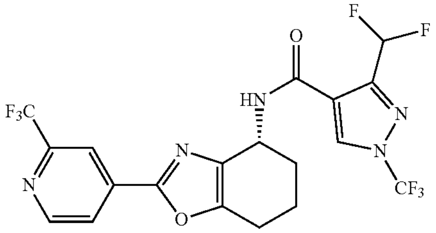
I-507
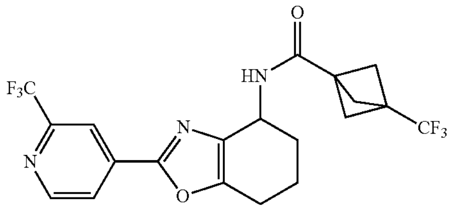
I-507a
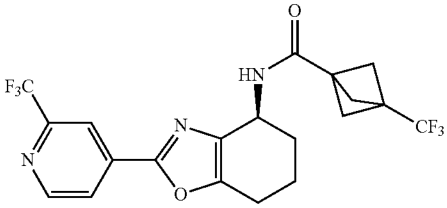
I-507b
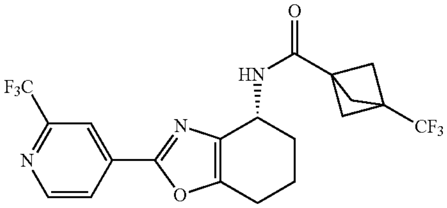
I-508
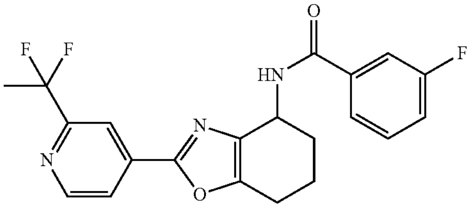

-continued
I-508a
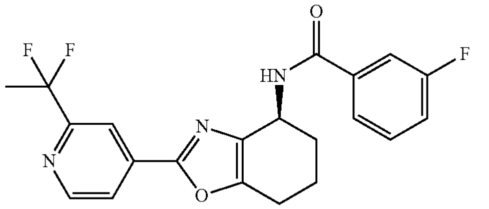
I-508b
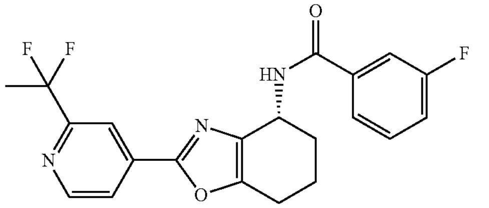
I-509
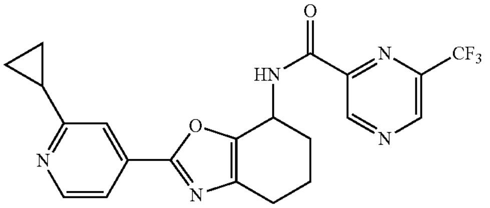
I-509a
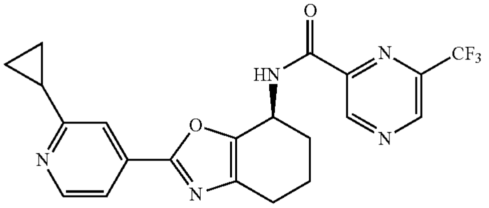
I-509b
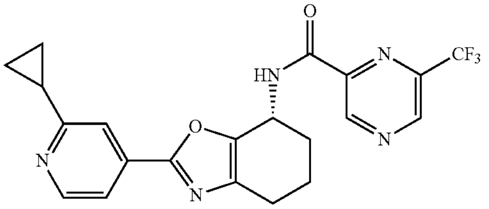
I-510
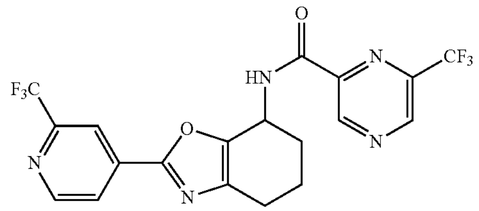
I-510a
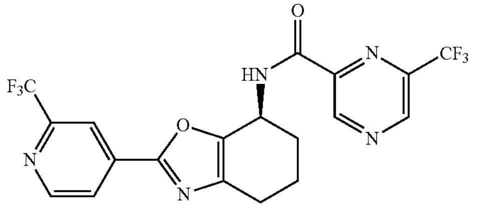
-continued
I-510b
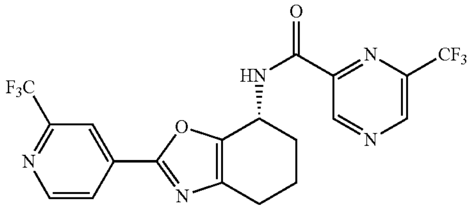
I-511
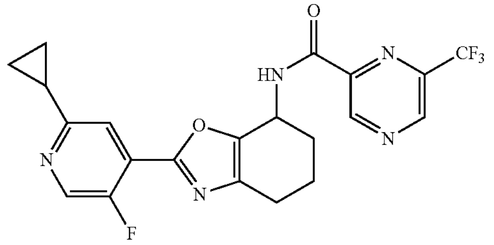
I-511a
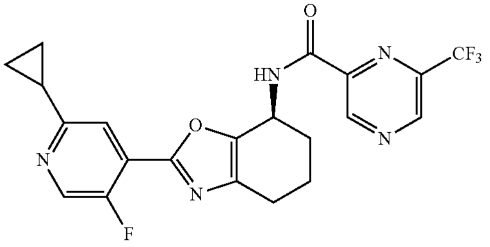
I-511b
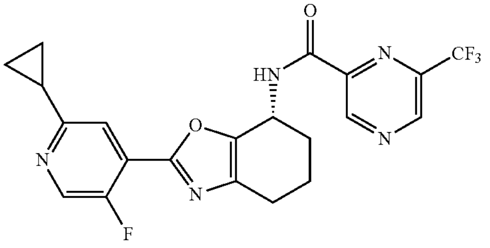
I-512
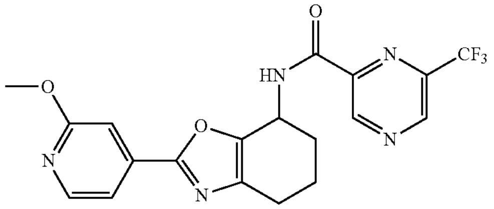
I-512a
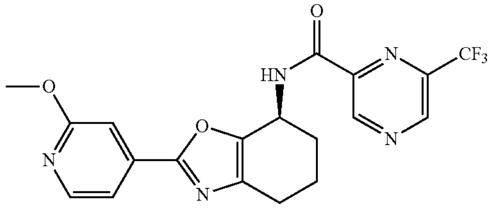
I-512b
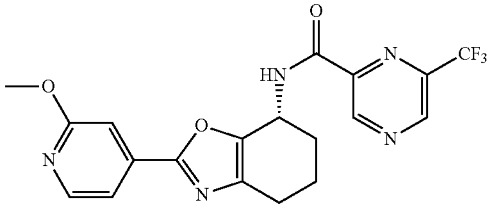

-continued
I-513
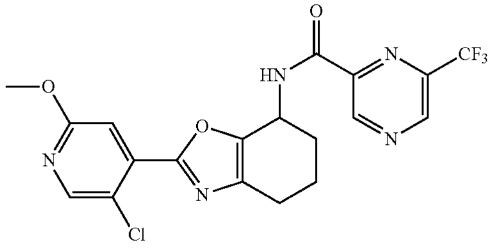
I-513a
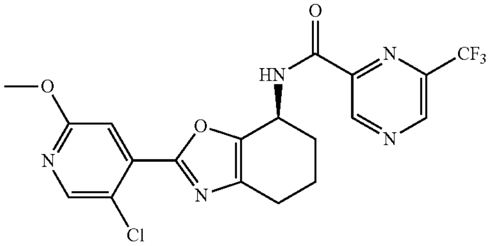
I-513b
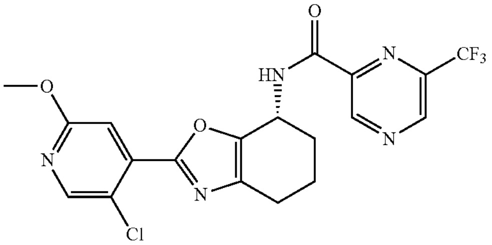
I-514
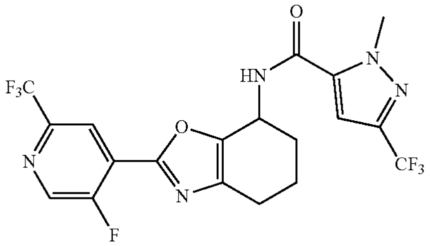
I-514a
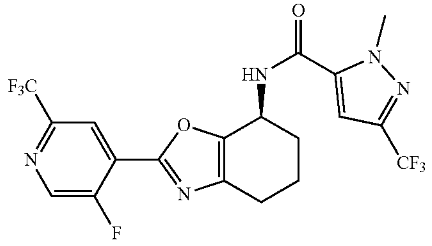
I-514b
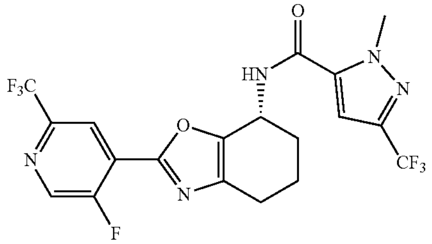
-continued
I-515
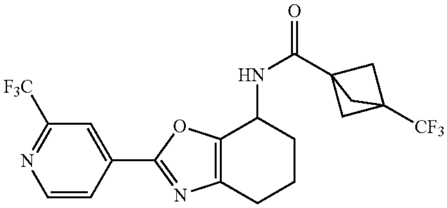
I-515a
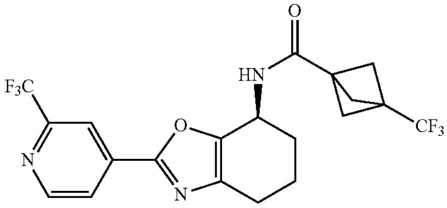
I-515b
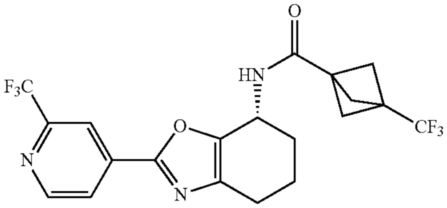
I-519
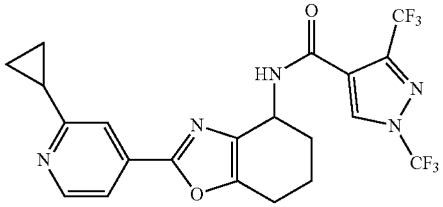
I-519a
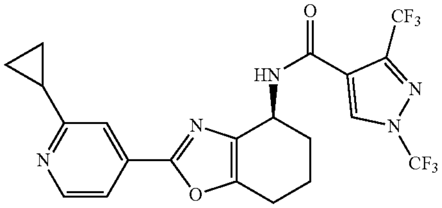
I-519b
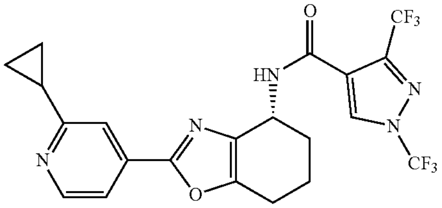
I-520
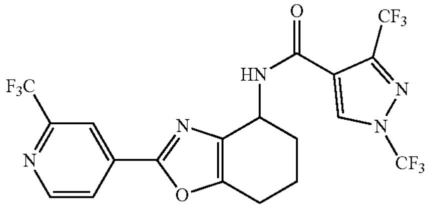

-continued
I-520a
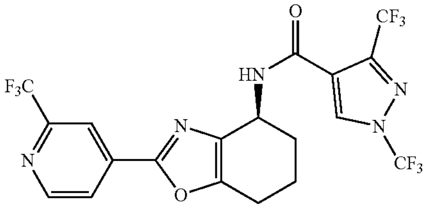
I-520b
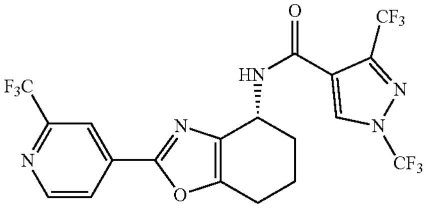
I-530
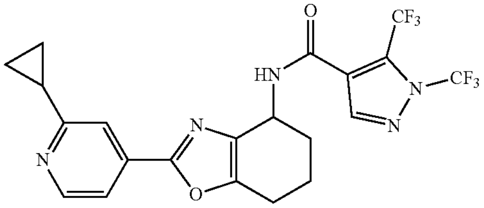
I-530a
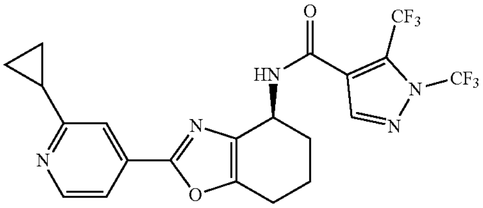
I-530b
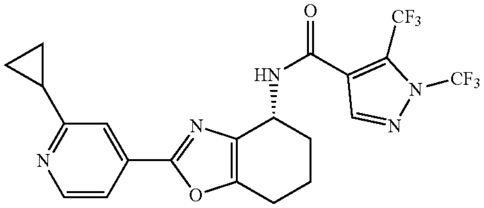
I-531
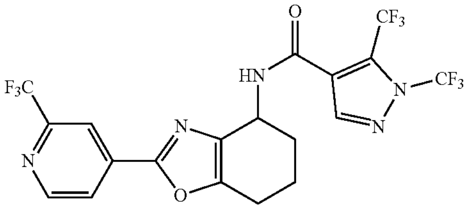
I-531a
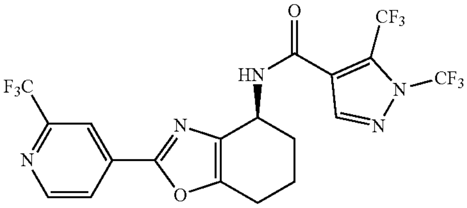
-continued
I-531b
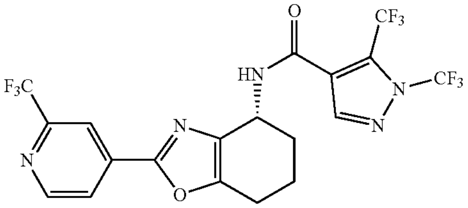
I-533
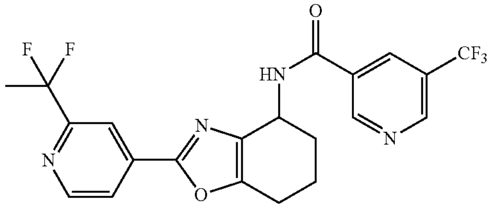
I-533a
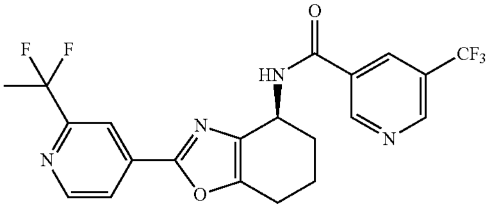
I-533b
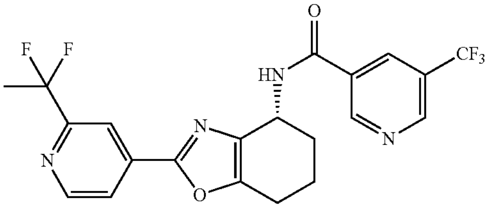
I-534
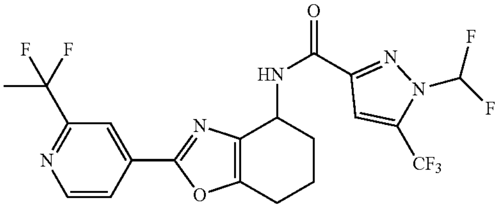
I-534a
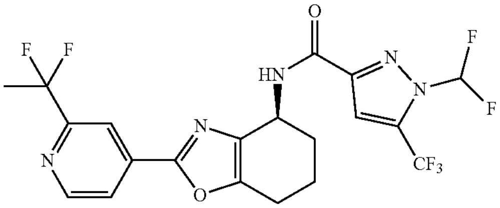
I-534b
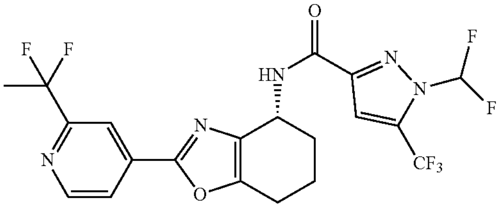

-continued
I-535
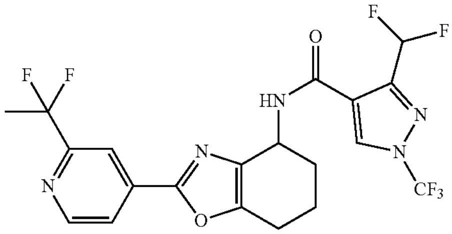
I-535a
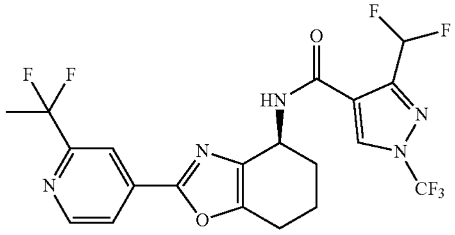
I-535b
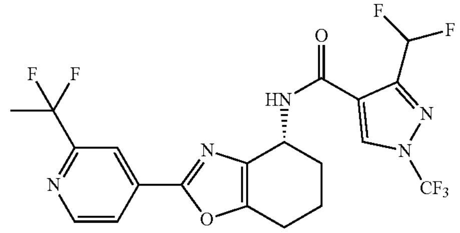
I-544
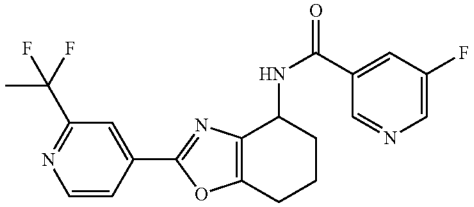
I-544a
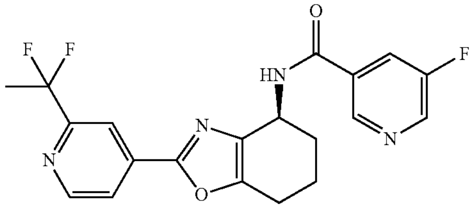
I-544b
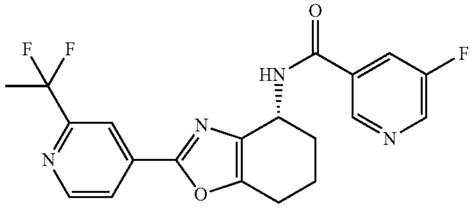
I-545
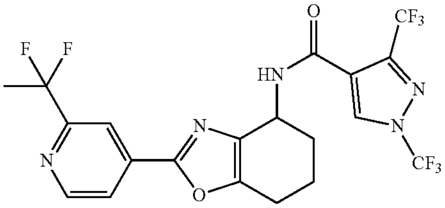
-continued
I-545a
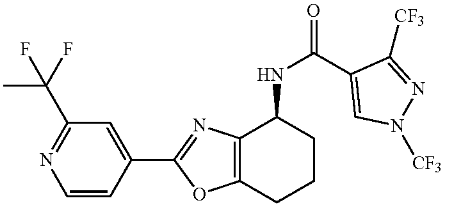
I-545b
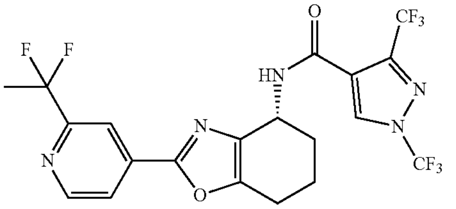
I-554
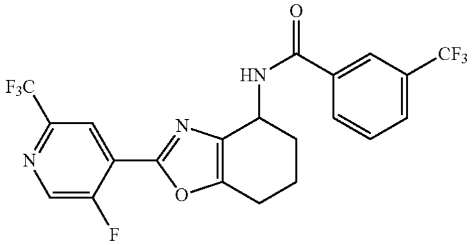
I-554a
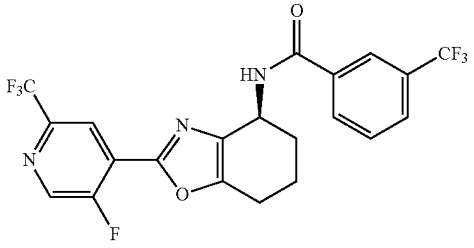
I-554b
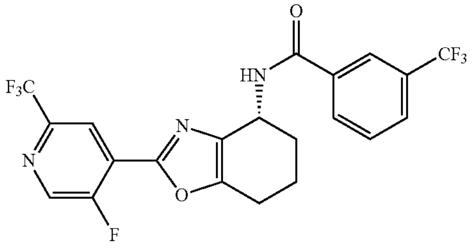
I-557
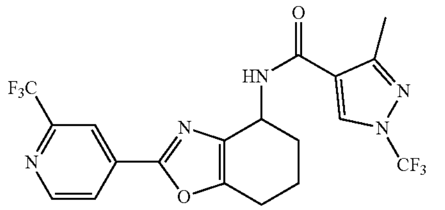
I-557a
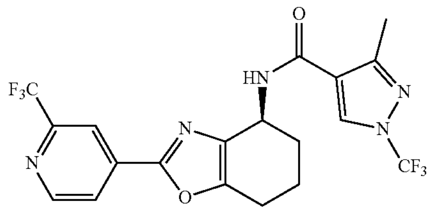

-continued
I-557b
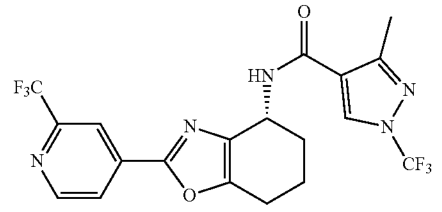
or a pharmaceutically acceptable salt thereof.
18. The compound according to claim 1, wherein the compound is selected from
I-84a
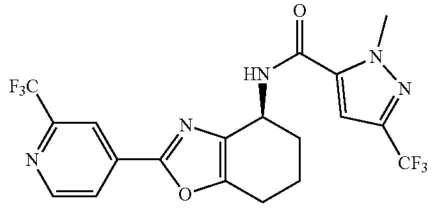
I-121a
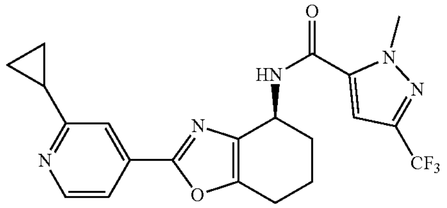
I-130a
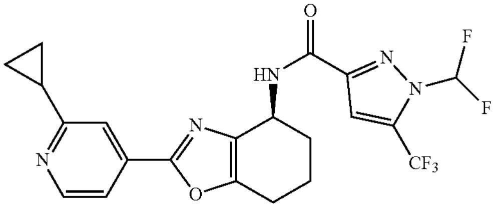
I-131a
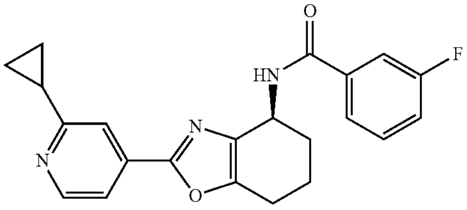
I-132a
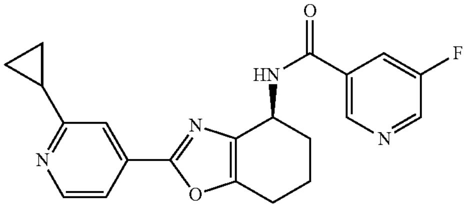
-continued
I-135a
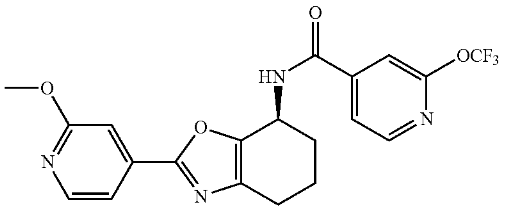
I-137a
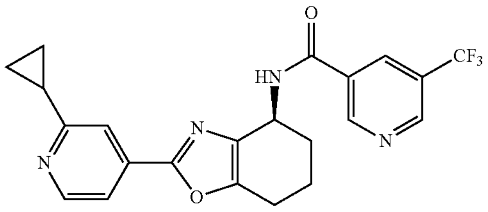
I-150a
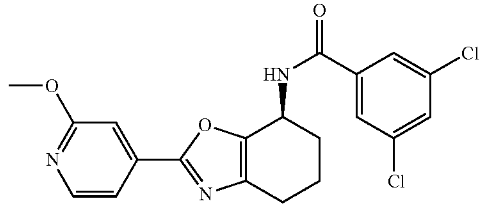
I-151a
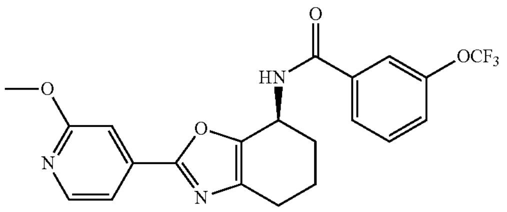
I-152a
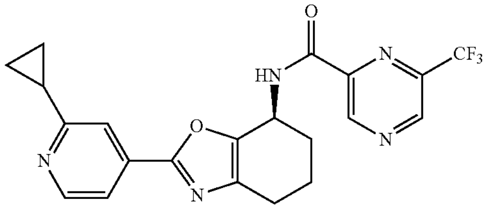
I-153a
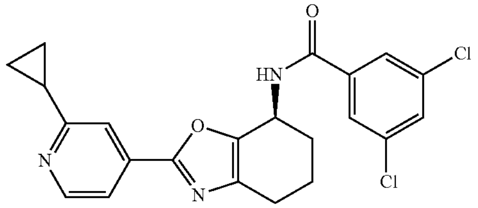
I-156a
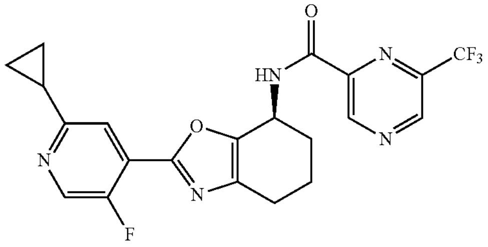

-continued
I-157a
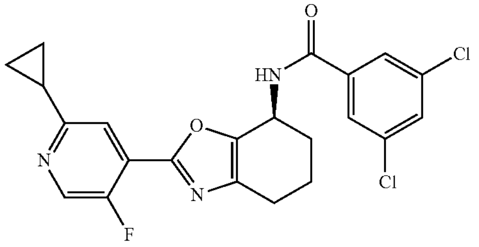
I-158a
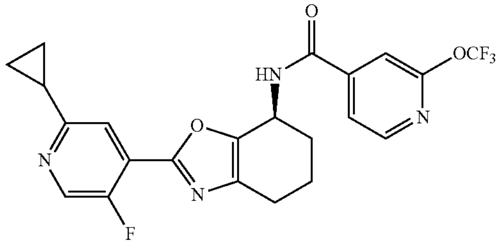
I-159a
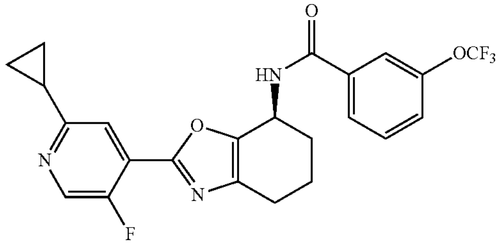
I-162a
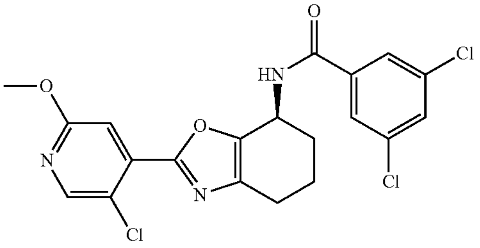
I-163a
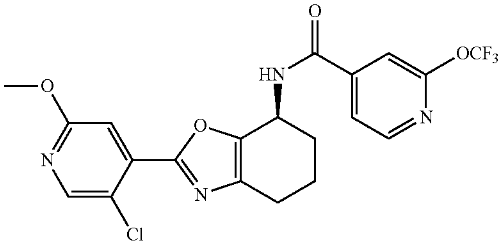
I-164a
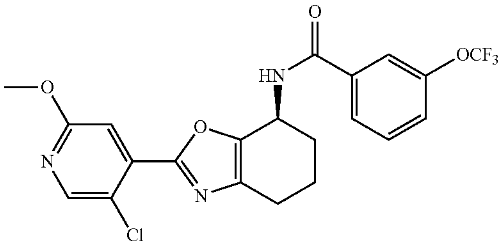
-continued
I-165a
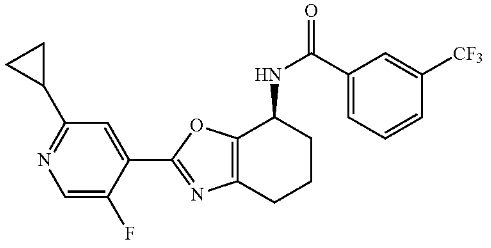
I-166a
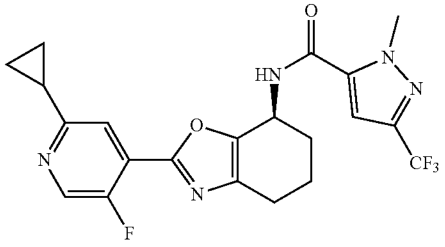
I-167a
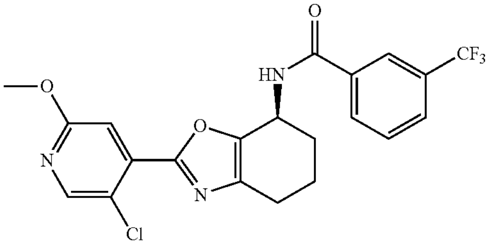
I-168a
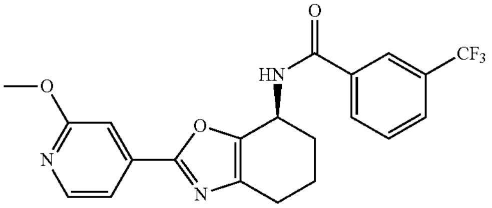
I-169a
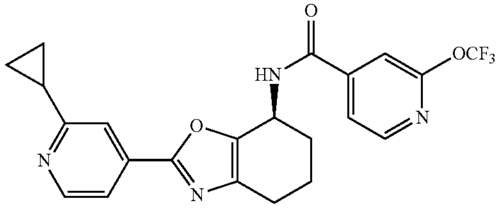
I-170a
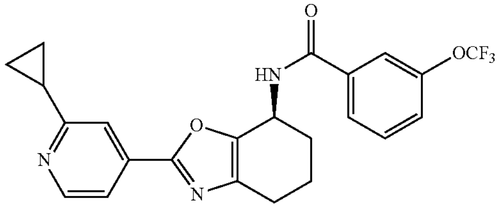

-continued
I-171a
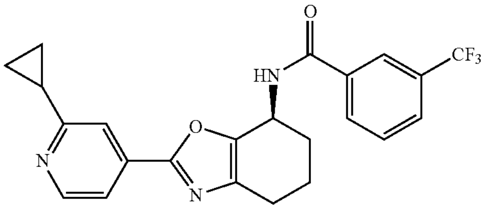
I-174a
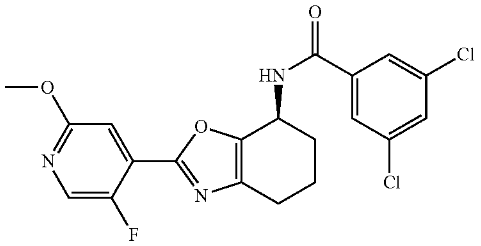
I-175a
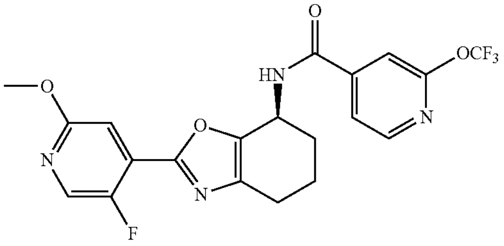
I-176a
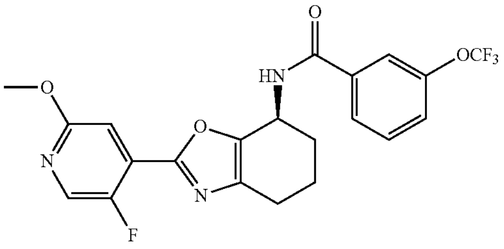
I-177a
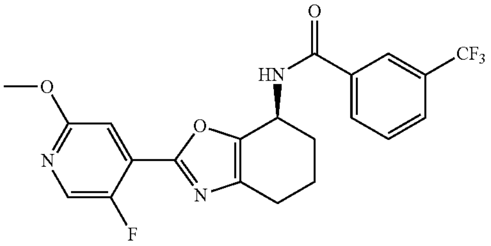
I-178a
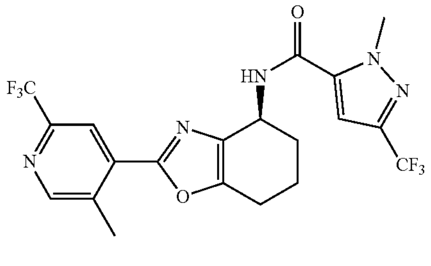
-continued
I-180a
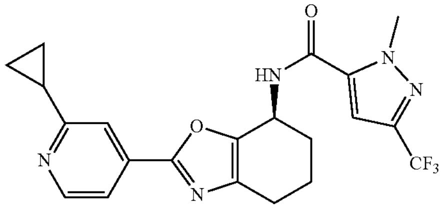
I-184a
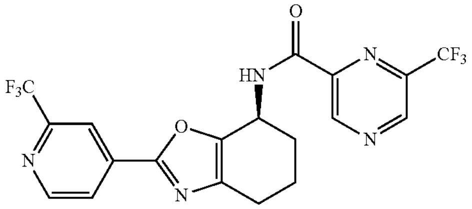
I-185a
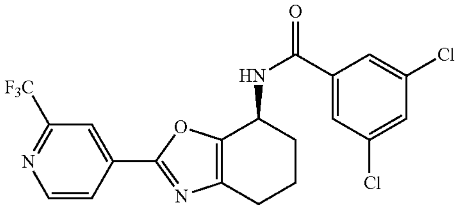
I-186a
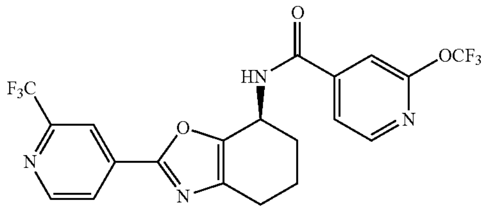
I-187a
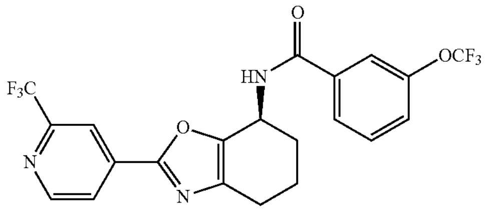
I-188a
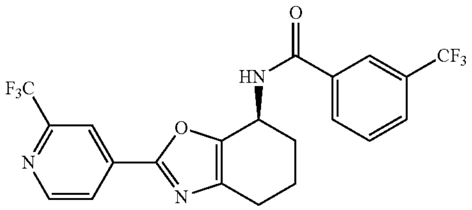
I-189a
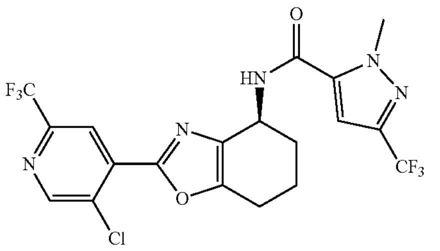

-continued
I-191a
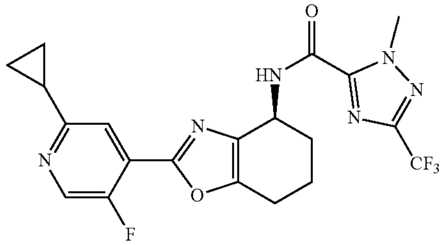
I-208a
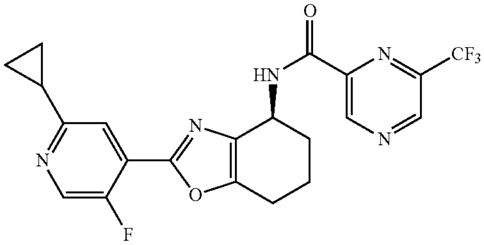
I-211a
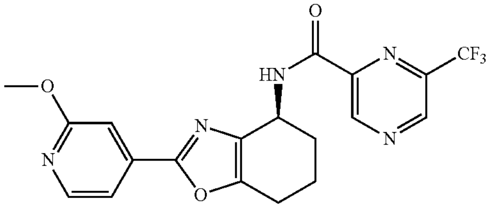
I-217a
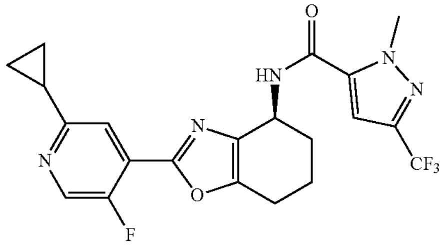
I-223a
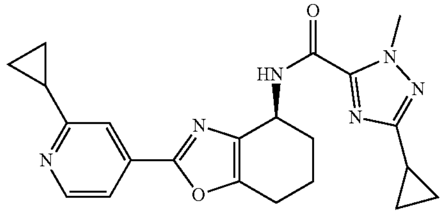
I-229a
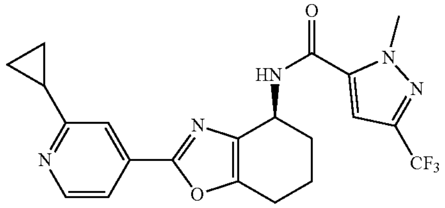
I-231a
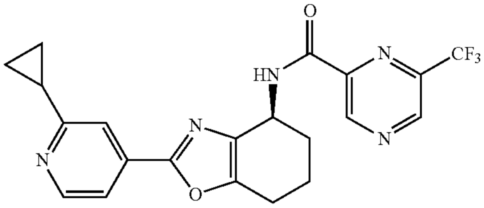
-continued
I-232a
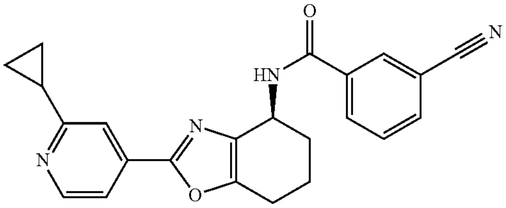
I-238a
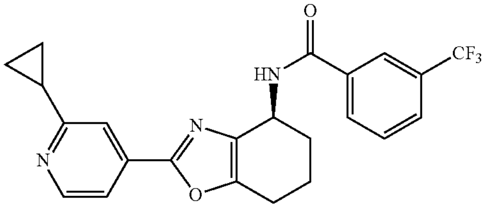
I-241a
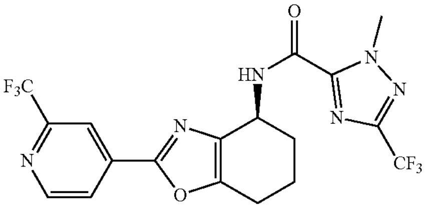
I-242a
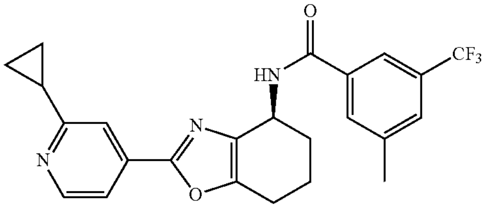
I-248a
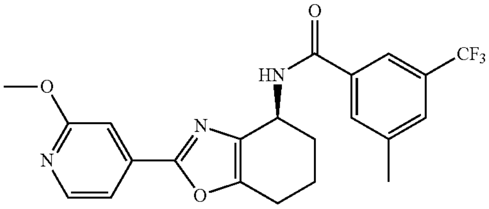
I-249a
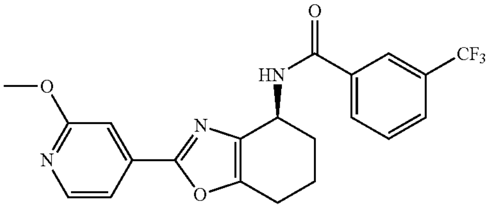
I-250a
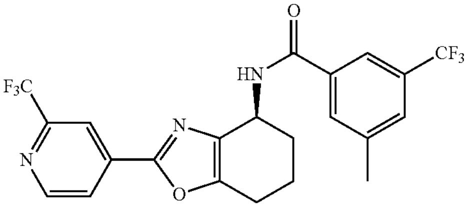

-continued
I-251a
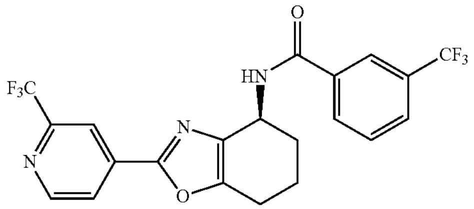
I-275a
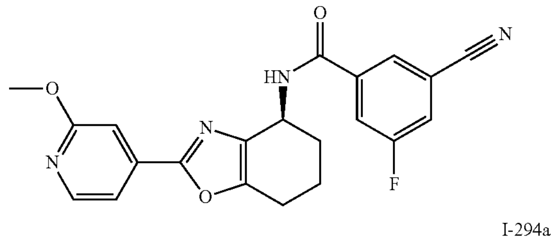
I-294a
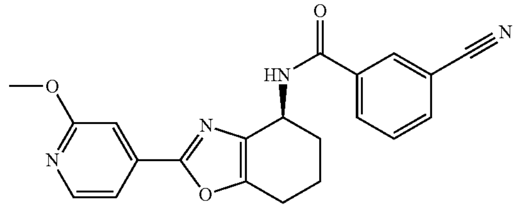
I-296a
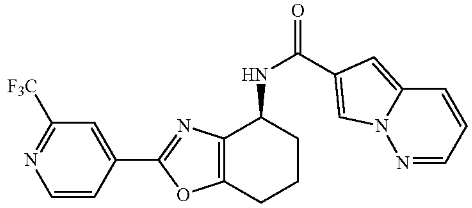
I-297a
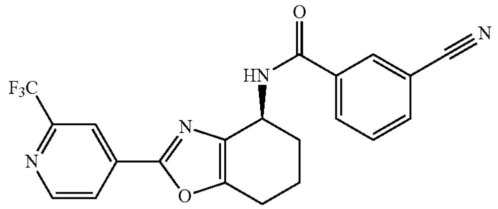
I-298a
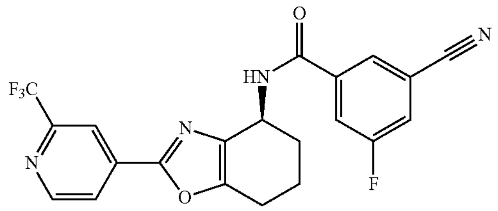
I-299a
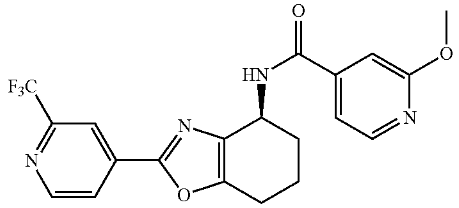
-continued
I-428a
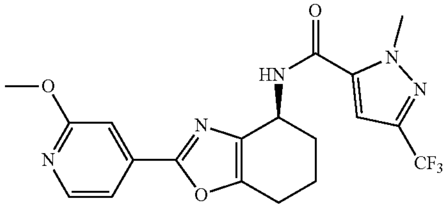
I-477a
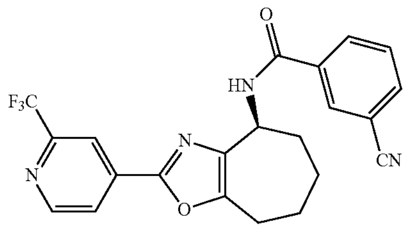
I-505a
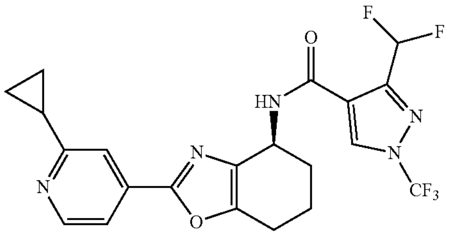
I-506a
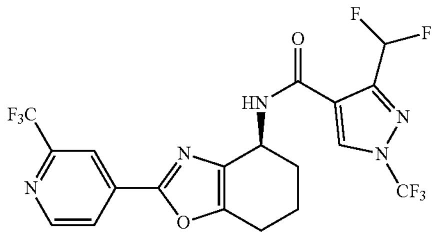
I-507a
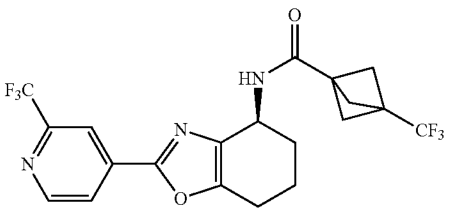
I-508a
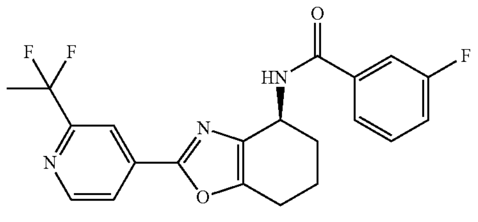
I-514a
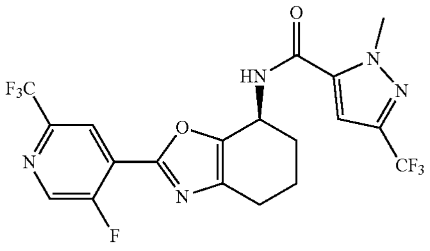

-continued
I-515a
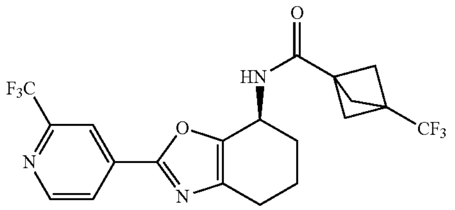
I-519a
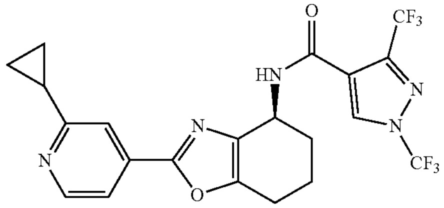
I-520a
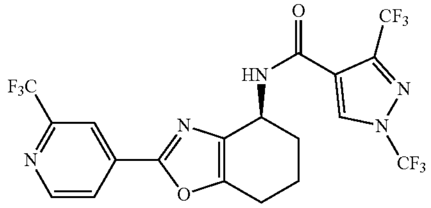
I-530a
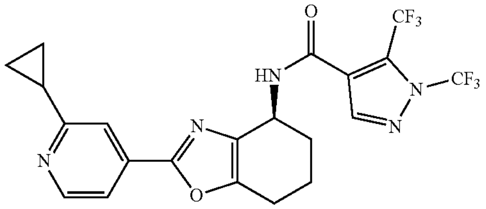
I-531a
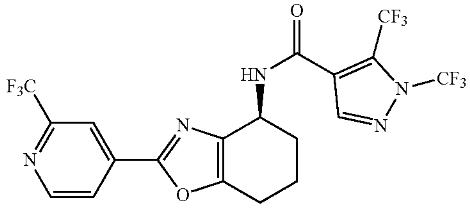
I-533a
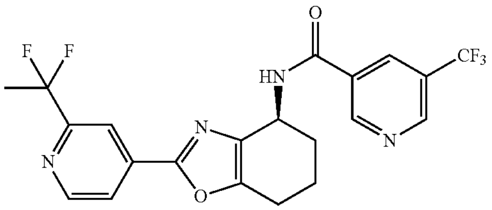
I-544a
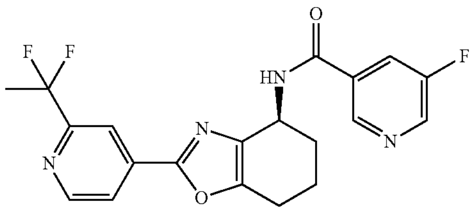
-continued
I-545a
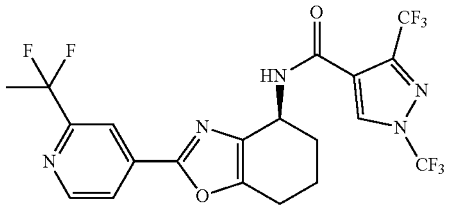
I-554a
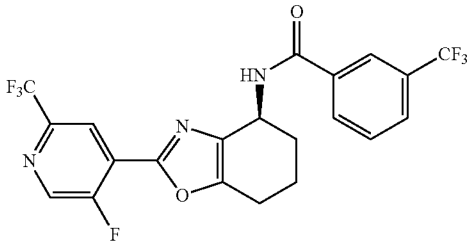
I-557a
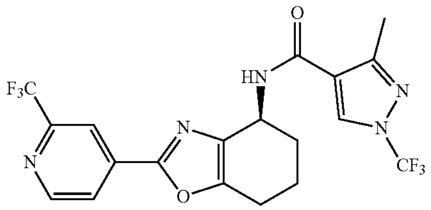
or a pharmaceutically acceptable salt thereof.
19. The compound according to claim 18, wherein the compound is
I-121a
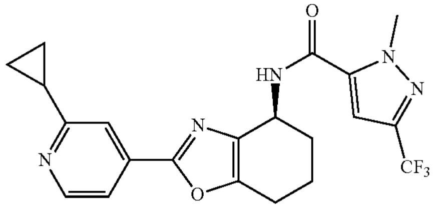
or a pharmaceutically acceptable salt thereof.
20. The compound according to claim 18, wherein the compound is
I-506a
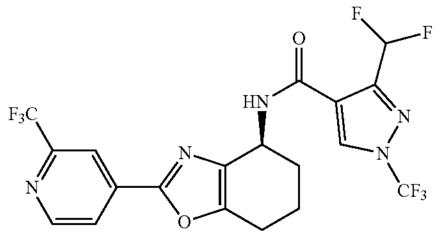
or a pharmaceutically acceptable salt thereof.

21. The compound according to claim 18, wherein the compound is

I-176a

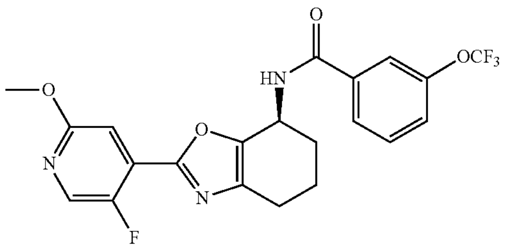

or a pharmaceutically acceptable salt thereof.

22. The compound according to claim 18, wherein the compound is

I-158a

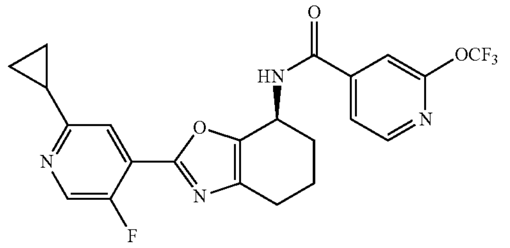

or a pharmaceutically acceptable salt thereof.

23. The compound according to claim 18, wherein the compound is

I-275a

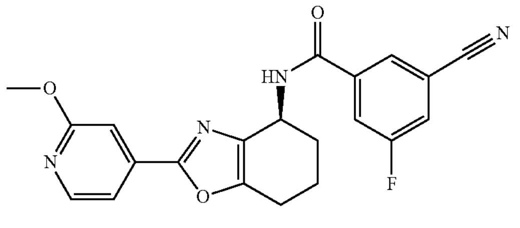

or a pharmaceutically acceptable salt thereof.

24. A pharmaceutical composition comprising a compound according to claim 17, or a pharmaceutically acceptable salt thereof, and one or more pharmaceutically acceptable excipients, carriers, or diluents.

25. A pharmaceutical composition comprising a compound according to claim 18, or a pharmaceutically acceptable salt thereof, and one or more pharmaceutically acceptable excipients, carriers, or diluents.

26. The pharmaceutical composition according to claim 16, wherein the composition comprises the compound I-121a

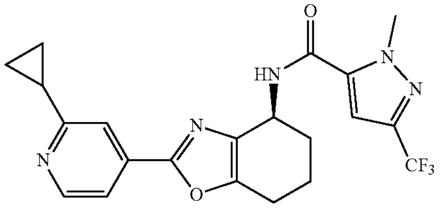

or a pharmaceutically acceptable salt thereof.

27. The pharmaceutical composition according to claim 16, wherein the composition comprises the compound I-506a

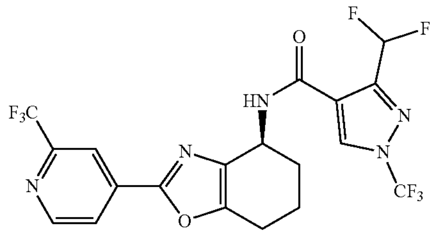

or a pharmaceutically acceptable salt thereof.

28. The pharmaceutical composition according to claim 16, wherein the composition comprises the compound I-176a

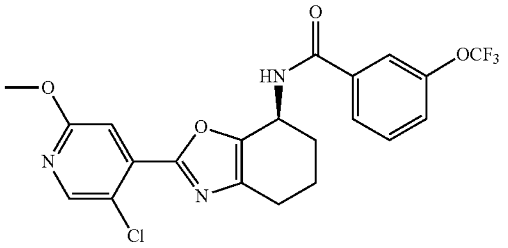

or a pharmaceutically acceptable salt thereof.

29. The pharmaceutical composition according to claim 16, wherein the composition comprises the compound I-158a

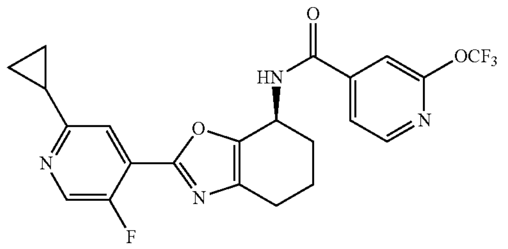

or a pharmaceutically acceptable salt thereof.

30. The pharmaceutical composition according to claim 16, wherein the composition comprises the compound
I-275a
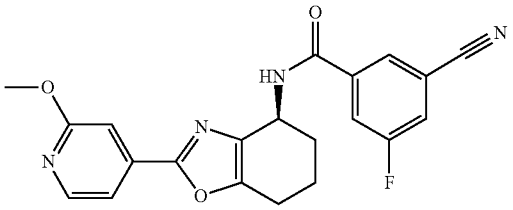
or a pharmaceutically acceptable salt thereof.
* * * * *